US012678507B2

(12) United States Patent
Jin et al.

(10) Patent No.: US 12,678,507 B2
(45) Date of Patent: Jul. 14, 2026

(54) PROTEIN TYROSINE KINASE 6 (PTK6) DEGRADATION / DISRUPTION COMPOUNDS AND METHODS OF USE

(71) Applicant: Icahn School of Medicine at Mount Sinai, New York, NY (US)

(72) Inventors: Jian Jin, New York, NY (US); Hanna Irie, New York, NY (US); Jing Liu, New York, NY (US); Yan Xiong, New York, NY (US); Jessica Byerly, New York, NY (US); Shannon Tomita, New York, NY (US); Jianping Hu, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 1400 days.

(21) Appl. No.: 17/256,516

(22) PCT Filed: Jul. 3, 2019

(86) PCT No.: PCT/US2019/040507
§ 371 (c)(1),
(2) Date: Dec. 28, 2020

(87) PCT Pub. No.: WO2020/010204
PCT Pub. Date: Jan. 9, 2020

(65) Prior Publication Data
US 2023/0070613 A1 Mar. 9, 2023

Related U.S. Application Data

(60) Provisional application No. 62/694,118, filed on Jul. 5, 2018.

(51) Int. Cl.
*A61P 35/00* (2006.01)
*A61K 45/06* (2006.01)
(Continued)

(52) U.S. Cl.
CPC ............ *A61K 47/545* (2017.08); *A61K 45/06* (2013.01); *A61P 35/00* (2018.01); *C07D 401/14* (2013.01); *C07D 403/02* (2013.01); *C07D 417/14* (2013.01)

(58) Field of Classification Search
CPC ....... A61K 47/545; A61K 45/06; A61P 35/00; C07D 401/14; C07D 403/02; C07D 417/14
See application file for complete search history.

(56) References Cited

U.S. PATENT DOCUMENTS 5,691,147 A 11/1997 Draetta et al.
8,377,937 B2 2/2013 Bencsik et al.
(Continued)

FOREIGN PATENT DOCUMENTS

CN 102822165 12/2012
CN 103189067 7/2013
(Continued)

OTHER PUBLICATIONS

Toure et al., Catalytic in vivo protein knockdown by small-molecule PROTACs, Angew. Chem. Int. Ed, 55, pp. 1966-1973 (Year: 2016).*
(Continued)

*Primary Examiner* — Jeffrey S Lundgren
*Assistant Examiner* — Alexander K. Showalter
(74) *Attorney, Agent, or Firm* — Fish & Richardson P.C.

(57) ABSTRACT

Disclosed herein are protein tyrosine kinase 6 (PTK6) degradation/disruption compounds including a PTK6 ligand, a degradation/disruption tag, and a linker, and methods of using such compounds in the treatment of FTK6-mediated diseases.

1 Claim, 13 Drawing Sheets

(51) Int. Cl.

| | |
|---|---|
| ***A61K 47/54*** | (2017.01) |
| ***C07D 401/14*** | (2006.01) |
| ***C07D 403/02*** | (2006.01) |
| ***C07D 417/14*** | (2006.01) |

(56) References Cited

U.S. PATENT DOCUMENTS

| | | | |
|---|---|---|---|
| 8,648,096 | B2 | 2/2014 | Muller et al. |
| 9,809,603 | B1 | 11/2017 | Jacques |
| 9,822,094 | B2 | 11/2017 | Man et al. |
| 12,465,648 | B2 | 11/2025 | Jin et al. |
| 2002/0098161 | A1 | 7/2002 | Uhrich |
| 2004/0063773 | A1 | 4/2004 | Tang et al. |
| 2011/0172107 | A1 | 7/2011 | Katz et al. |
| 2011/0196150 | A1 | 8/2011 | Man et al. |
| 2014/0031325 | A1 | 1/2014 | Bartlett et al. |
| 2014/0356322 | A1 | 12/2014 | Crews et al. |
| 2015/0119435 | A1 | 4/2015 | Crews et al. |
| 2015/0274738 | A1 | 10/2015 | Gray et al. |
| 2015/0291562 | A1 | 10/2015 | Crew et al. |
| 2016/0045504 | A1 | 2/2016 | Grembecka et al. |
| 2017/0008904 | A1 | 1/2017 | Crew et al. |
| 2017/0114098 | A1 | 4/2017 | Aivado et al. |
| 2017/0121321 | A1 | 5/2017 | Crews et al. |
| 2017/0224685 | A1 | 8/2017 | Duncan et al. |
| 2017/0283807 | A1 | 10/2017 | Mounir et al. |
| 2018/0072741 | A1 | 3/2018 | Vechorkin et al. |
| 2018/0086767 | A1 | 3/2018 | Fesik et al. |
| 2018/0134684 | A1 | 5/2018 | Bradner et al. |
| 2018/0186800 | A1 | 7/2018 | Yamamoto et al. |
| 2019/0092768 | A1 | 3/2019 | Gray et al. |
| 2019/0255041 | A1 | 8/2019 | Jin et al. |
| 2019/0336503 | A1 | 11/2019 | Jin et al. |
| 2019/0367525 | A1 | 12/2019 | Ioannidis et al. |
| 2020/0338070 | A1 | 10/2020 | Jin et al. |
| 2020/0399266 | A1 | 12/2020 | Jin et al. |
| 2021/0261538 | A1 | 8/2021 | Jin et al. |
| 2021/0283261 | A1 | 9/2021 | Jin et al. |
| 2021/0355140 | A1 | 11/2021 | Shunatona et al. |
| 2021/0395244 | A1 | 12/2021 | Jin et al. |
| 2022/0054488 | A1 | 2/2022 | Jin et al. |
| 2023/0022524 | A1 | 1/2023 | Jin et al. |
| 2023/0167106 | A1 | 6/2023 | Jin et al. |
| 2023/0391765 | A1 | 12/2023 | Jin et al. |

FOREIGN PATENT DOCUMENTS

| | | | | |
|---|---|---|---|---|
| CN | 104736569 | | 6/2015 | |
| CN | 105085620 | | 11/2015 | |
| CN | 105175284 | | 12/2015 | |
| CN | 108137507 | | 6/2018 | |
| CN | 109071552 | | 12/2018 | |
| CN | 109790143 | | 5/2019 | |
| CN | 112778303 | | 5/2021 | |
| JP | 2007-512364 | | 5/2007 | |
| JP | 2008-525526 | | 7/2008 | |
| JP | 2009-542721 | | 12/2009 | |
| JP | 2009-542723 | | 12/2009 | |
| JP | 2010-532386 | | 10/2010 | |
| JP | 2010-532387 | | 10/2010 | |
| JP | 2015-508414 | | 3/2015 | |
| JP | 2016-540811 | | 12/2016 | |
| JP | 2017-513862 | | 6/2017 | |
| JP | 2018-502097 | | 1/2018 | |
| JP | 2018-526430 | | 9/2018 | |
| JP | 2019-514883 | | 5/2020 | |
| JP | 2021-511342 | | 5/2021 | |
| MX | 2018000471 | | 4/2018 | |
| MX | 2018000360 | | 6/2018 | |
| WO | WO 2008/109104 | | 9/2008 | |
| WO | WO 2012/142504 | A1 | 10/2012 | |
| WO | WO 2014/100719 | | 6/2014 | |
| WO | WO 2015/101293 | | 7/2015 | |
| WO | WO 2015/104677 | | 7/2015 | |
| WO | WO 2015/192123 | | 12/2015 | |
| WO | WO 2016/073956 | | 5/2016 | |
| WO | WO 2016/105518 | | 6/2016 | |
| WO | WO 2016/106518 | | 7/2016 | |
| WO | WO 2016/115480 | | 7/2016 | |
| WO | WO 2016/149668 | | 9/2016 | |
| WO | WO 2016/168992 | | 10/2016 | |
| WO | WO 2016/174130 | | 11/2016 | |
| WO | WO 2016/197032 | | 12/2016 | |
| WO | WO 2016/208595 | | 12/2016 | |
| WO | WO 2017/011371 | | 1/2017 | |
| WO | WO 2017/011590 | | 1/2017 | |
| WO | WO 2017/024317 | | 2/2017 | |
| WO | WO 2017/024319 | | 2/2017 | |
| WO | WO-2017046036 | A1 * | 3/2017 | ........... C07D 417/14 |
| WO | WO 2017/079267 | | 5/2017 | |
| WO | WO 2017/147700 | | 9/2017 | |
| WO | WO 2017/147701 | | 9/2017 | |
| WO | WO 2017/185031 | | 10/2017 | |
| WO | WO 2017/197051 | | 11/2017 | |
| WO | WO 2017/197055 | | 11/2017 | |
| WO | WO 2018/049152 | A1 | 3/2018 | |
| WO | WO 2018/049200 | | 3/2018 | |
| WO | WO 2018/098280 | | 5/2018 | |
| WO | WO 2018/106870 | | 6/2018 | |
| WO | WO 2018/117177 | | 6/2018 | |
| WO | WO 2018/119441 | | 6/2018 | |
| WO | WO 2018/144649 | | 8/2018 | |
| WO | WO 2019/084030 | | 5/2019 | |
| WO | WO 2019/090198 | A1 | 5/2019 | |
| WO | WO 2019/222380 | | 11/2019 | |
| WO | WO 2019/246570 | | 12/2019 | |
| WO | WO 2020/252043 | | 12/2020 | |
| WO | WO 2021/021904 | | 2/2021 | |
| WO | WO 2021/057872 | | 4/2021 | |
| WO | WO 2023/006063 | | 2/2023 | |

OTHER PUBLICATIONS

Zeng et al., Discovery of novel imidazo[1,2-a]pyrazin-8-amines as Brk/PTK6 inhibitors, Bioorg. & Med. Chem. Lett., 21, pp. 5870-5875 (Year: 2011).*

International Preliminary Report on Patentability Chapter II in International Appln. No. PCT/US2022/050929, mailed on Jun. 21, 2024, 6 pages.

International Preliminary Report on Patentability in International Appln. No. PCT/US2022/013225, mailed on Aug. 3, 2023, 21 pages.

Office Action in Australian Appln. No. 2019288740, mailed on Jun. 13, 2024, 4 pages.

Office Action in Chinese Appln. No. 202080049386.9, mailed on Sep. 4, 2024, 14 pages (with Machine translation).

Office Action in European Appln. No. 17877800.7, mailed Mar. 6, 2024, 6 pages.

Ishoey et al., "Translation Termination Factor GSPT1 is a Phenotypically Relevant Off-Target of Heterobifunctional Phthalimide Degraders," ACS Chemical Biology, Jan. 22, 2018, 13(3):553-560.

Office Action in Chinese Appln. No. 202080049386.9, mailed on Feb. 2, 2024, 23 pages (with Machine translation).

Office Action in Chinese Appln. No. 201980054694.8, mailed on Sep. 1, 2023, 21 pages (with Machine translation).

EP Extended European Search Report in European Appln. No. 19821826.5, dated May 3, 2022, 10 pages.

Fisher et al., "Targeted protein degradation and the enzymology of degraders," Current Opinion in Chemical Biology, 2018, 44:47-55.

U.S. Appl. No. 16/926,418, filed Jul. 10, 2020, Jian Jin.

U.S. Appl. No. 16/467,888, filed Jun. 7, 2019, Jian Jin.

U.S. Appl. No. 16/977,654, filed Sep. 2, 2020, Jian Jin.

U.S. Appl. No. 17/938,502, filed Oct. 6, 2022, Jian Jin.

U.S. Appl. No. 17/254,345, filed Dec. 21, 2020, Jian Jin.

U.S. Appl. No. 17/336,059, filed Jun. 1, 2021, Jian Jin.

AU Office Action in Australian Appln. No. 2022201488, dated Feb. 14, 2023, 6 pages.

CN Office Action in Chinese Appln. No. 201980030599.4, dated Jan. 5, 2023, 13 pages (with English Translation).

(56) References Cited

OTHER PUBLICATIONS

EP Extended European Search Report in European Appln. No. 20802303.6, dated Dec. 23, 2022, 6 pages.
EP Office Action in European Appln. No. 17863645.2, dated Nov. 11, 2022, 6 pages.
Fioravanti et al., "Six years (2012-2018) of researches on catalytic EZH2 inhibitors: The boom of the 2-pyridone compounds," Manuscript, The Chemical Record, 2018, 18(12):1818-1832.
Kumar et al., "EZH2 Inhibitor GSK126 for Cancer Treatment: Metabolism, drug transporter and rat pharmacokinetic studies," Medical Research Archives, 2015, Issue 3, 31 pages.
PCT Invitation to Pay Additional Fees in International Appln. No. PCT/US2022/050929, dated Feb. 6, 2023, 3 pages.
Stazi et al., "EZH2 inhibitors: a patent review (2014-2016)," Expert Opinion on Therapeutic Patents, 2017, 27(7):797-813.
CN Office Action in Chinese Appln. No. 201780081246.8, dated Mar. 4, 2023, 16 pages (with English Translation).
EP Office Action in European Appln. No. 17877800.7, Apr. 13, 2023, 7 pages.
EP Office Action in European Appln. No. 19763958.6, dated May 10, 2023, 4 pages.
EP Office Action in European Appln. No. 19821826.5, dated Apr. 12, 2023, 4 pages.
JP Office Action in Japanese Appln. No. 2020-546159, dated May 9, 2023, 14 pages (with English Translation).
JP Office Action in Japanese Appln. No. 2020-570728, dated Jun. 27, 2023, 11 pages (with English Translation).
JP Office Action in Japanese Appln. No. 2021-500187, dated Jul. 4, 2023, 12 pages (with English Translation).
PCT International Preliminary Report on Patentability in International Appln. No. PCT/US2021/055574, dated May 4, 2023, 8 pages.
PCT International Search Report and Written Opinion in International Appln. No. PCT/US2022/050929, dated Apr. 7, 2023, 13 pages.
Popow et al., "Highly selective PTK2 proteolysis targeting chimeras to probe focal adhesion kinase scaffolding functions," Journal of Medicinal Chemistry, 2019, 62(5):2508-2520.
Wang et al., "Discovery of potent 2-Aryl-6,7-dihydro-5H-pyrrolo[1,2-a] imidazoles as WDR5-WIN-site inhibitors using fragment-based methods and structure-based design," Journal of Medicinal Chemistry, 2018, 61(13):5623-5642.
Wei et al., "Discovery of a first-in-class mitogen-activated protein kinase kinase 1/2 degrader," Journal of Medicinal Chemistry, 2019, 62(23):10897-10911.
Xue et al., "Protein degradation through covalent inhibitor-based PROTACs," Chemical Communications, 2020, 56(10):1521-1524.
Karaman et al., "A quantitative analysis of kinase inhibitor selectivity," Nature biotechnology, Jan. 2008, 26(1):127-132.
Office Action in Japanese Appln. No. 2021-565854, mailed on May 7, 2024, 6 pages (with English translation).
PCT International Search Report and Written Opinion in International Appln. No. PCT/US2022/013225, dated Jun. 6, 2022, 24 pages.
EP Office Action in European Appln. No. 17877800.7, dated May 24, 2022, 6 pages.
Herrera-Montavez et al., "MEK1/2-Targeting PROTACs Promote the Collateral Degradation of CRAF in KRAS Mutant Cells," bioRxiv, Jun. 2023, retrieved from URL<https://doi.org/10.1101/2023.06.15.545136]>, 28 pages.
Abramovich et al., "Hox regulation of normal and leukemic hematopoietic stem cells," Curr. Opin. Hematol., May 2005, 12(3):210-216.
Addie et al., "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases," J. Med. Chem., Mar. 2013, 56(5):2059-2073.
Aguilar et al., "Discovery of 4-((3'R,4'S,5'R)-6"-Chloro-4'-(3-chloro-2-fluorophenyl)1'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development," Journal of Medicinal Chemistry, Mar. 2017, 60(7):2819-2839.
Alinari et al., "Selective inhibition of protein arginine methyltransferase 5 blocks initiation and maintenance of B-cell transformation," Blood, Apr. 2015, 125(16):2530-2543.
Alzabin et al., "Hematopoietic progenitor kinase 1 is a critical component of prostaglandin E2-mediated suppression of the anti-tumor immune response," Cancer Immunol. Immunother., 2010, 59:419-429.
Alzabin et al., "Hematopoietic Progenitor Kinase 1 is a Negative Regulator of Dendritic Cell Activation," J Immunol, 2009, 182:6187-6194.
Anders et al., "Differential expression analysis for sequence count data," Genome Biol., 2010 11:R106.
Armstrong et al., "MLL translocations specify a distinct gene expression profile that distinguishes a unique leukemia," Nat Genet., Jan. 2002, 30:41-47.
Artinger et al., "An MLL-dependent network sustains hematopoiesis," Proc. Natl. Acad. Sci. USA, Jul. 2013, 110(29):12000-12005.
Asiaban et al., "Cell-Based Ligand Discovery for the ENL YEATS Domain," ACS Chem. Biol., Apr. 2020, 15(4):895-903.
AU Notice of Allowance in Australian Appln. No. 2017348322, dated Dec. 14, 2021, 3 pages.
AU Office Action in Australian Appln. No. 2017348322, dated Dec. 10, 2020, 7 pages.
AU Office Action in Australian Appln. No. 2017348322, dated Sep. 27, 2021, 2 pages.
Ayton et al., "Molecular mechanisms of leukemogenesis mediated by MLL fusion proteins," Oncogene, Oct. 2001, 20:5695-5707.
Bachman et al., "EZH2 Expression is Associated With High Proliferation Rate and Aggressive Tumor Subgroups in Cutaneous Melanoma and Cancers of the Endometrium, Prostate, and Breast," J. Clin. Oncol., 2006, 24(2):268-273.
Bai et al., "Targeted degradation of BET proteins in triple-negative breast cancer," Cancer Res., May 1, 2017, 77(9):2476-2487.
Basiorka et al. "Lenalidomide Stabilizes the Erythropoietin Receptor by Inhibiting the E3 Ubiquitin Ligase RNF41," Cancer Res., Apr. 2016, 76:3531-3540.
Bennett et al., "The Role of Nuclear Receptor-Binding SET Domain Family Histone Lysine Methyltransferases in Cancer," Cold Spring Harb. Perspect. Med., Jun. 2017, 7(6):a026708.
Berge et al., "Pharmaceutical Salts," Journal of Pharmaceutical Science, 1997, 66:1-19.
Bilsland et al., "Behavioral and neurochemical alterations in mice deficient in anaplastic lymphoma kinase suggest therapeutic potential for psychiatric indications," Neuropsychopharmacology, 2008, 33:685-700.
Biondi et al., "Biological and therapeutic aspects of infant leukemia. ," Blood, Jul. 2000, 96:24-33.
Biswas et al., "Function of leukemogenic mixed lineage leukemia 1 (MLL) fusion proteins through distinct partner protein complexes," Proc. Natl. Acad. Sci. USA, Sep. 2011, 108(38):15751-15756.
Bitoun et al., "The mixed-lineage leukemia fusion partner 10 AF4 stimulates RNA polymerase II transcriptional elongation and mediates coordinated chromatin remodeling," Human Molecular Genetics, Jan. 2007, 16:92-106.
Blake et al., "Discovery and preclinical pharmacology of a selective ATP-competitive Akt inhibitor (GDC-0068) for the treatment of human tumors," J. Med. Chem., Sep. 2012, 55(18):8110-8127.
Bolshan et al., "Synthesis, optimization, and evaluation of novel small molecules as antagonists of WDR5-MLL interaction," ACS Medicinal Chemistry Letters, Mar. 2013, 4(3):353-357.
Bondeson et al., "Catalytic in vivo protein knockdown by small-molecule PROTACs," Nature Chemical Biology, 2015, 11(8):611-617.
Bondeson et al., "Lessons in PROTAC design from selective degradation with a promiscuous warhead," Cell Chem. Biol., Jan. 2018, 25:78-87e5.
Bottcher et al., "Fragment-based discovery of a chemical probe for the PWWP1 domain of NSD3," Nat. Chem. Biol., Aug. 2019, 15:822-829.

(56) References Cited

OTHER PUBLICATIONS

Bourdi et al., "Safety Assessment of Metarrestin in Dogs: A Clinical Candidate Targeting a Subnuclear Structure Unique to Metastatic Cancer Cell," Regul. Toxicol. Pharmacol., Aug. 2020, 116:104716.
Bracken et al., "*EZH2* is downstream of the pRB-E2F pathway, essential for proliferation and amplified in cancer," EMBO J., 2003, 22(20)5323-5335.
Bradley et al., "EZH2 Inhibitor Efficacy in Non-Hodgkin's Lymphoma Does Not Require Suppression of H3K27 Monomethylation," Chem. Biol., 2014, 21(11):1463-1475.
Brand et al., "Homolog-selective degradation as a strategy to probe the function of CDK6 in AML," Cell Chem. Biol., Feb. 2019, 26(2):300-306e9.
Brauer et al., "Building a better understanding of the intracellular tyrosine kinase PTK6—BRK by BRK," Biochim. Biophys. Acta., Aug. 2010, 1806:66-73.
Braun et al., "Coordinated Splicing of Regulatory Detained Introns within Oncogenic Transcripts Creates an Exploitable Vulnerability in Malignant Glioma," Cancer Cell, Oct. 2017, 32(4):411-426.
Brooun et al., "Polycomb repressive complex 2 structure with inhibitor reveals a mechanism of activation and drug resistance," Nat. Commun., Apr. 28, 2016, 7:11384, 12 pages.
Browne et al., "Regulation of peptide-chain elongation in mammalian cells," Eur. J. Biochem., Nov. 2002, 269:5360-5368.
Buckley et al., "HaloPROTACS: use of small molecule PROTACs to induce degradation of HaloTag fusion proteins," ACS Chemical Biology, Aug. 2015, 10(8):1831-1837.
Buckley et al., "Small-molecule control of intracellular protein levels through modulation of the ubiquitin proteasome system," Angew Chem. Int. Ed. Engl., 2014, 53(9):2312-2330.
Buckley et al., "Small-molecule inhibitors of the interaction between the E3 ligase VHL and HIF1α," Angew Chem Int. Ed. Engl., 2012, 51(46):11463-11467.
Buckley et al., "Targeting the von Hippel-Lindau E3 ubiquitin ligase using small molecules to disrupt the VHL/HIF-1α interaction," Journal of the American Chemical Society, 2012, 134(10):4465-4468.
Burkhart et al., "Cellular mechanisms of tumour suppression by the retinoblastoma gene," Nature Reviews Cancer, 2008, 8(9):671-682.
Burnet, "The concept of immunological surveillance," Progress Exp. Tumor Res., 1970, 13:1-27.
Burslem et al., "Small-molecule modulation of protein homeostasis," Chem. Rev., Aug. 2017, 117(17):11269-11301.
Burslem et al., "The advantages of targeted protein degradation over inhibition: An RTK case study," Cell Chem. Biol., Jan. 2018, 25:67-77e3.
Cai et al., "Subunit composition and substrate specificity of a MOF-containing histone acetyltransferase distinct from the male-specific lethal (MSL) complex," The Journal of Biological Chemistry, Feb. 2010, 285(7):4268-4272.
Cai et al., "ZFX Mediates Non-canonical Oncogenic Functions of the Androgen Receptor Splice Variant 7 in Castrate-Resistant Prostate Cancer," 2018, Mol. Cell 72, 341-354 e346.
Campbell et al., "EPZ011989, A Potent, OrallyAvailable EZH2 Inhibitor with Robust in Vivo Activity," ACS Med. Chem. Lett., 2015, 6(5):491-495.
Cao et al., "Regulation and functional role of eEF1A2 in pancreatic carcinoma," Biochem. Biophys. Res. Commun., 2009, 380(1):11-16.
Cao et al., "Role of Histone H3 Lysine 27 Methylation in Polycomb-Group Silencing," Science, 2002, 298(5595):1039-1043.
Cao et al., "Targeting MLL1 H3K4 methyltransferase activity in mixed-lineage leukemia," Molecular Cell, Jan. 2014, 53(2):247-261.
Cappuzzo et al., "Erlotinib as maintenance treatment in advanced non-small-cell lung cancer: a multicentre, randomised, placebo-controlled phase 3 study," Lancet Oncol., Jun. 2010, 11:521-529.
Cardenas et al., "Enantioselective Synthesis of Pyrrolopyrirnidine Scaffolds through Cation-Directed Nucleophilic Aromatic Substitution," Org. Lett., Mar. 2018, 20:2037-2041.
Carugo et al., "In vivo functional platform targeting patient-derived xenografts identifies WDR5-Myc association as a critical determinant of pancreatic cancer," Cell Reports, Jun. 2016, 16(1):133-147.
Castro et al., "Breast tumor kinase and extracellular signal-regulated kinase 5 mediate Met receptor signaling to cell migration in breast cancer cells," Breast Cancer Research, 2010, 12:R60, 15 pages.
Chamberlain et al., "Structure of the human Cereblon-DDBI-lenalidomide complex reveals basis for responsiveness to thalidomide analogs," Nat. Struct. Mol. Biol., 2014, 21(9):803-809.
Chang et al., "EZH2 promotes expansion of breast tumor initiating cells through activation of RAFI-β-catenin signaling, " Cancer Cell, 2011, 19(1):86-100.
Chan-Penebre et al., "A selective inhibitor of PRMT5 with in vivo and in vitro potency in MCL models," Nature Chemical Biology, Apr. 2015, 11:432-437.
Chau et al., "An Anatomical Site and Genetic-Base Prognostic Model for Patients With Nuclear Protein in Testis (NUT) Midline Carcinoma: Analysis of 124 Patients," JNCI Cancer Spectr 4, 2020, pkz094 2020.
Chawade et al., "Normalyzer: a tool for rapid evaluation of normalization methods for omics data sets," J. Proteome. Res., 2014, 13:3114-31202014.
Chen et al., "Design, synthesis, and initial evaluation of affinity-based small molecular probe for detection of WDR5," Bioorganic Chemistry, Feb. 2018, 76:380-385.
Chen et al., "Gene expression profiling of WDR5 regulated genes in bladder cancer," Genomics Data, Sep. 2015, 5:27-29.
Chen et al., "PTK6 promotes hepatocellular carcinoma cell proliferation and invasion," Am. J. Transl. Res., Oct. 2016, (10):4354-4361.
Chen et al., "Upregulated WDR5 promotes proliferation, self-renewal and chemoresistance in bladder cancer via mediating H3K4 trimethylation," Scientific Reports, Feb. 2015, 5: 12 pages.
Chi et al., "Covalent histone modifications—miswritten, misinterpreted and mis-erased in human cancers," Nat. Rev. Cancer, 2010, 10:457-469.
Choi et al., "EML4-ALK mutations in lung cancer that confer resistance to ALK inhibitors," N. Engl. J. Med., Oct. 2010, 363(18):1734-1739.
Choi et al., "Identification of novel isoforms of the EML4-ALK transforming gene in non-small cell lung cancer," Cancer Res., Jul. 2008, 68(13):4971-4976.
Christott et al., "Discovery of a Selective Inhibitor for the YEATS Domains of ENL/AF9.," SLAS Discov., 2019, 24:133-141.
Chung et al., "Cbx8 acts non-canonically with Wdr5 to promote mammary tumorigenesis," Cell Reports, Jul. 2016, 16(2):472-486.
Clinicaltrials.gov [online], "Metarrestin (ML-246) in Subjects with Metastatic Solid Tumors," Jan. 10, 2020, retrieved on Mar. 16, 2022, retrieved from URL<https://clinicaltrials.gov/ct2/show/NCT04222413>, 12 pages.
CN Office Action in Chinese Appln. No. 201780081246.8, dated Dec. 2, 2021, 18 pages (with English Translation).
CN Office Action in Chinese Appln. No. 201780081246.8, dated Jun. 4, 2021, 19 pages (with English Translation).
CN Office Action in Chinese Appln. No. 201780085879.6, dated Jan. 5, 2022, 18 pages (with English Translation).
Corthay, "Does the immune system naturally protect against cancer?" Front. Immunol., May 2014, 5(197):1-8.
Cromm et al., "Addressing kinase-independent functions of Fak via PROTAC-mediated degradation," J. Am. Chem. Soc., Nov. 2018, 140(49):17019-17026.
Cromm et al., "Targeted protein degradation: from chemical biology to drug discovery," Cell Chem. Biol., Sep. 2017, 24(9):1181-1190.
Czermin et al., "*Drosophila* enhancer of Zeste/ESC complexes have a histone H3 methyltransferase activity that marks chromosomal Polycomb sites," Cell, 2002, 111(2):185-196.
Dai et al., "WDR5 expression is prognostic of breast cancer outcome," PLoS One, Sep. 2015, 10: 15 pages.
Davies et al., "Monoacidic Inhibitors of the Kelch-like ECH-Associated Protein 1: Nuclear Factor Erythroid 2-Related Factor 2 (KEAPI :NRF2) Protein-Protein Interaction with High Cell Potency Identified by Fragment-Based Discovery," Journal of Medicinal Chemistry, Apr. 2016, 59(8):3991-4006.

(56) References Cited

OTHER PUBLICATIONS

Dawson et al., "Inhibition of BET recruitment to chromatin as an effective treatment for MLL-fusion leukaemia," Nature, 2011, 478:529-533.
Deng et al., "Protein arginine methyltransferase 5 functions as an epigenetic activator of the androgen receptor to promote prostate cancer cell growth," Oncogene, 2017, 36:1223-1231.
Derry et al., "Altered localization and activity of the intracellular tyrosine kinase BRK/Sik in prostate tumor cells," Oncogene, Jul. 2003, 22:4212-4220.
Deshpande et al., "Chromatin modifications as therapeutic targets in MLL-rearranged leukemia," Trends Immunol., Nov. 2012, 33(11):563-570.
Dias et al., "Structural analysis of the KANSLI/WDR5/KANSL2 complex reveals that WDR5 is required for efficient assembly and chromatin targeting of the NSL complex," Genes & Development, May 2014, 28(9):929-942.
Douglass, Jr. et al., "A comprehensive mathematical model for three-body binding equilibria," J. Am. Chem. Soc., Apr. 2013, 135(16):6092-6099.
Du et al., "FOXC1, a target of polycomb, inhibits metastasis of breast cancer cells," Breast Cancer Res. Treat., 2012, 131(1):65-73.
Duanmin et al., "eEF1A2 protein expression correlates with lymph node metastasis and decreased survival in pancreatic ductal adenocarcinoma," Hepatogastroenterology, Jun. 2013, 60(124):870-875.
Dumble et al., "Discovery of novel AKT inhibitors with enhanced anti-tumor effects in combination with the MEK inhibitor," PloS One, Jun. 2014, 9(6), 11 pages.
EA Office Action in Eurasian Appln. No. 201991071, dated Jun. 10, 2020, 4 pages (with English translation).
Ee et al., "An embryonic stem cell-specific NuRD complex functions through interaction with WDR5," Stem Cell Reports, Jun. 2017, 8(6): 9 pages.
EP Extended European Search Report in European Appln. No. 17863645.2, dated Aug. 6, 2020, 10 pages.
EP Extended European Search Report in European Appln. No. 17877800.7, dated Feb. 19, 2021, 9 pages.
EP Extended European Search Report in European Appln. No. 19757825.5, dated Jan. 26, 2022, 14 pages.
EP Extended European Search Report in European Appln. No. 19763958.6, dated Dec. 8, 2021, 12 pages.
EP Extended European Search Report in European Appln. No. 19830269.7, dated Mar. 7, 2022, 6 pages.
EP Office Action in European Appln. No. 17863645.2, dated Apr. 6, 2021, 7 pages.
EP Office Action in European Appln. No. 17863645.2, dated Mar. 11, 2022, 5 pages.
EP Office Action in European Appln. No. 19821826.5, dated Jan. 13, 2022, 4 pages.
EP Partial Supplementary Search Report in European Appln. No. 19757825.5, dated Oct. 18, 2021, 16 pages.
Erb et al. (2017). Transcription control by the ENL YEATS domain in acute leukaemia. Nature 543, 270-274.
Fabian et al., "A small molecule-kinase interaction map for clinical kinase inhibitors," Nat. Biotechnol., Mar. 2005, 23(3):329-336.
Fan et al., "A Kinase Inhibitor Targeted to mTORC1 Drives Regression in Glioblastoma," Cancer Cell, Mar. 2017, 31(3):424-435.
Fan et al., "BAHCC1 binds H3K27me3 via a conserved BAH module to mediate gene silencing and oncogenesis," Nature genetics, 2020, 52:1384-1396.
Fda.gov [online], "Data Standards Manual (Monographs)," Feb. 27, 2018, retrieved on Feb. 7, 2022, retrieved from URL <https://www.fda.gov/drugs/electronic-regulatory-submission-and-review/data-standards-manual-monographs>, 1 page.
Fda.gov [online], "Development & Approval Process | Drugs," Oct. 28, 2019, retrieved on Feb. 4, 2022, retrieved from URL <https://www.fda.gov/drugs/development-approval-process-drugs>, 4 pages.
Fei et al., "PROTAC and its Application in the Treatment of Cancer," Chemistry of Life, Aug. 2014, 34(4):549-554 (with English abstract).
Ferguson et al., "Kinase inhibitors: the road ahead," Nat. Rev. Drug Discov., May 2018, 17:353-377.
Ferrando et al., "Gene expression signatures in MLL-rearranged T-lineage and B-precursor acute leukemias: dominance of HOX dysregulation," Blood, Jul. 2003, 102(1):262-268.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study," The Lancet Oncology, 2015, 16(1):25-35.
Fischer et al., "Structure of the DDB1-CRBN E3 ubiquitin ligase in complex with thalidomide," Nature, Aug. 2014, 512(7512):49-53.
Frankowski et al., "Metarrestin, a perinucleolar compartment inhibitor, effectively suppresses metastasis," Science Translational Medicine, May 2018, 10(441), 13 pages.
Frost et al., "Potent and selective chemical probe of hypoxic signalling downstream of HIF-α hydroxylation via VHL inhibition," Nat. Commun., Nov. 2016, 7:13312, 12 pages.
Fujii et al., "Enhancer of Zeste Homologue 2 (EZH2) Down-regulates RUNX3 by Increasing Histone H3 Methylation," J. Biol. Chem., 2008, 283(25):17324-17332.
Fujii et al., "MEKERK pathway regulates EZH2 overexpression in association with aggressive breast cancer subtypes," Oncogene, 2011, 30(39):4118-4128.
Gadd et al., "A Children's Oncology Group and TARGET initiative exploring the genetic landscape of Wilms tumor," Nat. Genet., Oct. 2017, 49:1487-1494.
Galdeano et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities," J. Med. Chem., 2014, 57(20):8657-8663.
Gao et al., "ZLD1122, a novel EZH2 and EZH1 small molecular inhibitor, blocks H3K27 methylation and diffuse large B cell lymphoma cell growth," RSC Adv., 2016, 6:28512-28521.
Garapaty-Rao et al., "Identification of EZH2 and EZH1 small molecule inhibitors with selective impact on diffuse large B cell lymphoma cell growth," Chem. Biol., 2013, 20(11):1329-1339.
Garnar-Wortzel et al., "Chemical Inhibition of ENL/AF9 Yeats Domains in Acute Leukemia," ACS Central Science, Apr. 2021, 7(5):815-830.
Ge et al., "WDR5 high expression and its effect on tumorigenesis in leukemia," Oncotarget, Jun. 2016, 7(25):37740-37754.
Gehling et al., "Discovery, design, and synthesis of indole-based EZH2 inhibitors," Bioorg. Med. Chem. Lett., 2015, 25(17):3644-3649.
Genscript.com [online], "Gen Script Make Research Easy," available on or before Mar. 3, 2015, retrieved on Mar. 17, 2022, retrieved from URL<https://www.genscript.com/gRNAdatabase.html>.
Getlik et al., "Structure-based optimization of a small molecule antagonist of the interaction between WD repeat-containing protein 5 (WDR5) and mixed-lineage leukemia 1 (MLL1)," Journal of Medicinal Chemistry, Mar. 2016, 59(6):2478-2496.
Gillis et al., "Biochemical and biological characterization of lymphocyte regulatory molecules; V. Identification of an interleukin 2-producing human leukemia T cell line," The Journal of experimental medicine, Dec. 1980,152:1709-1719.
Github.com [online], "PreprocessCore," Oct. 26, 2021, retrieved on Mar. 17, 2022, retrieved from URL<Gihttps://github.com/bmbolstad/preprocessCore>, 1 pages.
Github.com [online], "ProteiNorm," Jul. 27, 2020, retrieved on Mar. 17, 2022, retrieved from URL <https://github.com/ByrumLab/proteiNorm>, 3 page.
Gluz et al., "Triplenegative breast cancer—current status and future directions," Ann. Oncol., 2009, 20(12):1913-1927.
Godin-Heymann et al., "The T790M 'gatekeeper' mutation in EGFR mediates resistance to low concentrations of an irreversible EGFR inhibitor," Mol. Cancer Ther., Apr. 2008, 7(4):874-879.

(56) References Cited

OTHER PUBLICATIONS

Gonzalez et al., "Downregulation of EZH2 decreases growth of estrogen receptor-negative invasive breast carcinoma and requires BRCA1," Oncogene, 2009, 28(6):843-853.
Gonzalez et al., "EZH2 expands breast stem cells through activation of NOTCH1 signaling," Proc. Natl. Acad. Sci. USA, 2014, 111(8):3098-3103.
Grabe et al., "C797S Resistance: The undruggable EGFR mutation in non-small cell lung cancer?" ACS Med. Chem. Lett., 2018, 9:779-782.
Grebien et al., "Pharmacological targeting of the Wdr5-MLL interaction in C/EBPα N-terminal leukemia," Nature Chemical Biology, Aug. 2015, 11(8): 11 pages.
Guarnaccia et al., "Moonlighting with WDR5: A cellular multitasker," Journal of Clinical Medicine, Feb. 2018, 7(2): 17 pages.
Gullà et al., "Protein arginine methyltransferase 5 has prognostic relevance and is a druggable target in multiple myeloma," Leukemia, 2018, 32:996-1002.
Haegebarth et al., "Protein tyrosine kinase 6 negatively regulates growth and promotes enterocyte differentiation in the small intestine," Mol. Cell Biol., Jul. 2006, 26:4949-4957.
Hallberg et al., "Mechanistic insight into ALK receptor tyrosine kinase in human cancer biology," Nature Reviews Cancer, Oct. 2013, 13:685-700.
Hamilton et al., "Targeting CDK4/6 in patients with cancer," Cancer Treatment Reviews, 2016, 45:129-138.
Han et al., "Discovery of ARD-69 as a Highly Potent Proteolysis Targeting Chimera (PROTAC) Degrader of Androgen Receptor (AR) for the Treatment of Prostate Cancer," Journal of Medicinal Chemistry, Jan. 2019, 62:941-964.
Harvey et al., "Brk protects breast cancer cells from autophagic cell death induced by loss of anchorage," The American Journal of Pathology, Sep. 2009, 175:1226-1234.
Harvey et al., "Use of RNA interference to validate Brk as a novel therapeutic target in breast cancer: Brk promotes breast carcinoma cell proliferation," Oncogene, Aug. 2003, 22:5006-5010.
He et al., "HIV-1 Tat and Host AFF4 Recruit Two Transcription Elongation Factors into a Bifunctional Complex for Coordinated Activation of HIV-I Transcription," Mol. Cell., May 2010, 38(3):428-438.
He et al., "Human Polymerase-Associated Factor complex (PAFc) connects the Super Elongation Complex (SEC) to RNA polymerase II on chromatin," Proc. Natl. Acad. Sci. USA, Sep. 2011, 108(36):E636-E645.
Heerding et al., "Identification of 4-(2-(4-amino-1,2,5-oxadiazol-3-yl)-l-ethyl-7-{[(3S)-3-piperidinylmethyl]oxy }-1H-imidazo[4,5-c]pyridin-4-yl)-2-methyl-3-butyn-2-ol (GSK690693), a novel inhibitor of AKT kinase," Journal of Medicinal Chemistry, Sep. 2008, 51(18):5663-5679.
Heidenreich et al., "Structure-Based Approach toward Identification of Inhibitory Fragments for Eleven-Nineteen-Leukemia Protein (ENL)," J. Med. Chem., Nov. 2018, 61(23):10929-10934.
Henning et al., "Degradation of Akt using protein-catalyzed capture agent," Journal of Peptide Science, 2016, 22:196-200.
Herbst et al., "Gefitinib—a novel targeted approach to treating cancer," Nat. Rev. Cancer, Dec. 2004, 4:956-965.
Hernandez et al., "The Kinase Activity of Hematopoietic Progenitor Kinase 1 is Essential for the Regulation of T Cell Function," Cell reports, Oct. 2018, 25:80-94.
Herrera-Abreu et al., "Early adaptation and acquired resistance to CDK4/6 inhibition in estrogen receptor-positive breast cancer," Cancer Research, 2016, 76(8):2301-2313.
Hess, "MLL: a histone methyltransferase disrupted in leukemia," Trends Mol. Med., Oct. 2004, 10(10):500-507.
Higa et al., "CUL4-DDB 1 ubiquitin ligase interacts with multiple WD40-repeat proteins and regulates histone methylation," Nature Cell Biology, Nov. 2006, 8(11):1277-1283.
Hirai et al., "MK-2206, an allosteric Akt inhibitor, enhances antitumor efficacy by standard chemotherapeutic agents or molecular targeted drugs in vitro and in vivo," Molecular Cancer Therapeutics, Jul. 2010, 9(7):1956-1967.
Hiroyuki et al., "The structure of bestatin," The Journal of Antibiotics, Jan. 1976, 29(1):100-101.
Hirsch et al., "Lung cancer: current therapies and new targeted treatments," Lancet, Jan. 2017, 389:299-311.
Holm et al., "Global H3K27 trimethylation and EZH2 abundance in breast tumor subtypes," Mol. Oncol., 2012, 6(5):494-506.
Hsu et al., "Recognition of histone acetylation by the GAS41 YEATS domain promotes H2A.Z deposition in non-small cell lung cancer," Genes Dev., 2018, 32:58-69.
Hu et al., "Human HPK1, a novel human hematopoietic progenitor kinase that activates the JNK/SAPK kinase cascade," Genes Dev., Sep. 1996, 10:2251-2264.
Hu et al., "Small Molecule Inhibitors of Protein Arginine Methyltransferases," Expert Opinion Investigational Drugs, 2016, 25:335-358.
Huang et al., "A Chemoproteomic Approach to Query the Degradable Kinome Using a Multi-kinase Degrader," Cell Chemical Biology, Jan. 2018, 25(1):88-99.
Huang et al., "Covalent inhibition of NSD1 histone methyltransferase," Nat. Chem. Biol, 2020, 16:1403-1410.
Huber et al., "Variance stabilization applied to microarray data calibration and to the quantification of differential expression," Bioinformatics, 2002, 18 Suppl 1:S96-104.
IN Office Action in Indian Appln. No. 201917020814, dated Jun. 23, 2021, 6 pages (with English Translation).
Irie et al., "PTK6 regulates IGF-1-induced anchorage-independent survival," PLoS One, Jul. 2010, 5(7):el1729.
Ito et al., "Identification of a primary target of thalidomide teratogenicity," Science, Mar. 2010, 327(5971):1345-1350.
Ito et al., "PTK6 Inhibition Suppresses Metastases of Triple-Negative Breast Cancer via SNAIL-Dependent E-Cadherin regulation," Cancer Res., Aug. 2016, 76:4406-4417.
Ito et al., "PTK6 regulates growth and survival of endocrine therapy-resistant ER+ breast cancer cells," NPJ Breast Cancer, Nov. 2017, 3:45.
Iwahara et al., "Molecular characterization of ALK, a receptor tyrosine kinase expressed specifically in the nervous system," Oncogene, Jan. 30, 1997, 14:439-449.
Jakobsson et al., "The dual methyltransferase METTL13 targets N terminus and Lys55 of eEF1A and modulates codon-specific translation rates," Nature Communications, Aug. 2018, 15 pages.
Jiang et al., "Development of dual and selective degraders of cyclin-dependent kinases 4 and 6," Angew. Chem. Int. Ed. Engl., May 2019, 58(19):6321-6326.
Jiang et al., "Targeting BRK-Positive Breast Cancers with Small-Molecule Kinase Inhibitors," Cancer Res., Jan. 2017, 77:175-186.
Jiao et al., "Structural basis of histone H3K27 trimethylation by an active polycomb repressive complex 2," Science, 2015, 350(6258):aac4383.
Jin et al., "Targeting methyltransferase PRMT5 eliminates leukemia stem cells in chronic myelogenous leukemia," The Journal of Clinical Investigation, Oct. 2016, 126:3961-3980.
JP Office Action in Japanese Appln. No. 2019-522841, dated Oct. 5, 2021, 14 pages (with English Translation).
JP Office Action in Japanese Appln. No. 2019-530811, dated Dec. 14, 2021, 4 pages (with English Translation).
Jude et al., "Unique and independent roles for MLL in adult hematopoietic stem cells and progenitors," Cell Stem Cell, Sep. 2007, 1(3):324-337.
Justin et al., "Structural basis of oncogenic histone H3K27M inhibition of human polycomb repressive complex 2," Nat. Commun., 2016, 7:11316.
Kanda et al., "Protein arginine methyltransferase 5 is associated with malignant phenotype and peritoneal metastasis in gastric cancer," International Journal of Oncology, Jun. 2016, 49:1195-1202.
Kanis et al., "A small molecule inhibitor of the perinucleolar compartment, ML246, attenuates growth and spread of ovarian cancer," Gynecol. Oncol. Res. Pract., 2018, 5:7.

(56) References Cited

OTHER PUBLICATIONS

Kanis et al., "Metarrestin: A novel compound active against ovarian cancer," Gynecol Oncol., Oct. 2015, 139(1):190.
Kaniskan et al., "Inhibitors of Protein Methyltransferases and Demethylases," Chem. Rev., 2018, 118(3):989-1068.
Kaniskan et al., "Selective inhibitors of protein methyltransferases," Journal of Medicinal Chemistry, 2015, 58:1596-1629.
Karatas et al., "Discovery of a highly potent, cell-permeable macrocyclic peptidomimetic (MM-589) targeting the WD repeat domain 5 protein (WDR5)-mixed lineage leukemia (MLL) protein-protein interaction," Journal of Medicinal Chemistry, Jun. 2017, 60(12):4818-4839.
Khalyfa et al., "Characterization of elongation factor-1A (eEF1A-1) and eEF1A-2/S1 protein expression in normal and *wasted* mice," Journal of Biological Chemistry, 2001, 276:22915-22922.
Kiefer et al., "HPKI, a hematopoietic protein kinase activating the SAPK/JNK pathway," EMBO J., Dec. 1996, 15(24):7013-7025.
Kim et al. "Targeted disruption of the EZH2-EED complex inhibits EZH2-dependent cancer" Nature Chemical Biology, 2013, 9:643-650.
Kim et al., "Targeting EZH2 in cancer," Nat. Med., 2016, 22(2):128-134.
Kleer et al., "EZH2 is a marker of aggressive breast cancer and promotes neoplastic transformation of breast epithelial cells," PNAS, 2003, 100(20):11606-11611.
Klein et al., "Yaf9 subunit of the NuA4 and SWRI complexes targets histone H3K27ac through its YEATS domain," Nucleic Acids Res., Jan. 2018, 46:421-430.
Knutson et al., "A selective inhibitor of EZH2 blocks H3K27 methylation and kills mutant lymphoma cells," Nat. Chem. Biol., 8(11):890-896.
Knutson et al., "Durable tumor regression in genetically altered malignant rhabdoid tumors by inhibition of methyltransferase EZH2," Proc. Natl. Acad. Sci. USA., 2013, 110(19):7922-7927.
Kobayashi et al., "EGFR mutation and resistance of non-small-cell lung cancer to gefitinib," N. Engl. J. Med., Feb. 2005, 352(8):786-792.
Koivunen et al., "*EML4-ALK* fusion gene and efficacy of an ALK kinase inhibitor in lung cancer," Clinical Cancer Research, Jul. 1, 2008, 14(13):4275-4283.
Konze et al., "An Orally Bioavailable Chemical Probe of the Lysine Methyltransferases EZH2 and EZHI," ACS Chem. Biol., 2013, 8(6):1324-1334.
Krause et al., "Tyrosine kinases as targets for cancer therapy," N. Engl. J. Med., Jul. 2005, 353(2):172-187.
Krivtsov et al., "*MLL* translocations, histone modifications and leukaemia stem-cell development," Nat. Rev. Cancer, Nov. 2007, 7:823-833.
Kryukov et al., "*MTAP* deletion confers enhanced dependency on the PRMT5 arginine methyltransferase in cancer cells," Science, 2016, 351(6278):1214-1218.
Kuenzi et al., "Polypharmacology-based ceritinib repurposing using integrated functional proteomics," Nat. Chem. Biol., Dec. 2017, 13(12):1222-1231.
Kung et al., "Design and Synthesis of Pyridone-Containing 3,4-Dihydroisoquinoline-1(2H)-ones as a Novel Class of Enhancer of Zeste Homolog 2 (EZH2) Inhibitors," J. Med. Chem., 2016, 59(18):8306-8325.
Kuzmichev et al., "Histone methyltransferase activity associated with a human multiprotein complex containing the Enhancer of Zeste protein," Genes Dev., 2002, 16(22):2893-2905.
Kwak et al., "Anaplastic lymphoma kinase inhibition in non-small-cell lung cancer," New England Journal of Medicine, Oct. 28, 2010, 363(18):1693-1703.
Lai et al., "Induced protein degradation: an emerging drug discovery paradigm," Nat. Rev. Drug Discov., Feb. 2017, 16(2):101-114.
Lai et al., "Modular PROTAC design for the degradation of oncogenic BCR-ABL,"Angewandte Chemie International Edition English, Jan. 2016, 55(2):807-810.
Lapierre et al., "Discovery of 3-(3-(4-(1-Aminocyclobutyl)phenyl)-5-phenyl-3H-imidazo[4,5-b]pyridin-2-yl)pyridin-2-amine (ARQ 092): An orally bioavailable, selective, and potent allosteric AKT inhibitor," Journal of Medicinal Chemistry, 2016, 59:6455-6469.
Lebraud et al., "Protein Degradation by In-Cell Self-Assembly of Proteolysis Targeting Chimeras," ACS Central Science, 2016, 2:927-934.
Li et al., "AF9 YEATS domain links histone acetylation to DOT1L-mediated H3K79 methylation," Cell, Oct. 2014, 159(3):558-571.
Li et al., "Discovery of MD-224 as a first-in-class, highly potent, and efficacious proteolysis targeting chimera Murine Double Minute 2 degrader capable of achieving complete and durable tumor regression," J. Med. Chem., 2019, 62(2):448-466.
Li et al., "Discovery of potent and noncovalent reversible EGFR kinase inhibitors of $EGFR^{L858R/T790M/C797S}$ ," ACS Med. Chem. Lett., Jun. 2019, 10(6):869-873.
Li et al., "High-affinity small molecular blockers of mixed lineage leukemia 1 (MLL1)-WDR5 interaction inhibit MILL1 complex H3K4 methyltransferase activity," European Journal of Medicinal Chemistry, Nov. 2016, 124:480-489.
Li et al., "Molecular Coupling of Histone Crotonylation and Active Transcription by AF9 YEATS Domain," Mol. Cell., Apr. 2016, 62(2):181-193.
Li et al., "RSEM: accurate transcript quantification from RNA-Seq data with or without a reference genome," Bmc Bioinformatics, 2011, 12:323.
Li et al., "Structure-based design and synthesis of small molecular inhibitors disturbing the interaction of MLL1-WDR5," European Journal of Medicinal Chemistry, Aug. 2016, 118:1-8.
Li et al., "Structure-guided development of YEATS domain inhibitors by targeting π-π-π stacking," Nat. Chem. Biol., Dec. 2018, 14:1140-1149.
Li et al., "The OncoPPi network of cancer-focused protein-protein interactions to inform biological insights and therapeutic strategies," Nat. Commun., Feb. 2017, 8:14356.
Li et al., "Understanding histone H3 lysine 36 methylation and its deregulation in disease," Cell. Mol. Life Sci., Aug. 2019, 76(15):2899-2916.
Li et al., "ZMYND11-MBTD1 induces leukemogenesis through hijacking NuA4/TIP60 acetyltransferase complex and a PWWP-mediated chromatin association mechanism," Nat. Commun., 2021, 12(1), 18 pages.
Lim et al., "CDK4/6 inhibitors: promising opportunities beyond breast cancer," Cancer Discovery, 2016, 6(7):697-699.
Lin et al., "AFF4, a component of the ELL/PTEFb elongation complex and a shared subunit of MLL chimeras, can link transcription elongation to leukemia," Mol. Cell., Feb. 2010, 37(3):429-437.
Lin et al., "Clinicopathologic features, patterns of recurrence, and survival among women with triple-negative breast cancer in the National Comprehensive Cancer Network," Cancer, 2012, 118(22):5463-5472.
Lin et al., "Targeting ALK: Precision Medicine Takes on Drug Resistance," Cancer Discovery, Feb. 2017, 7(2):137-155.
Ling et al., "Involvement of hematopoietic progenitor kinase 1 in T cell receptor signaling," The Journal of biological chemistry, Jun. 2001, 276:18908-18914.
Liou et al., "HPK1 is activated by lymphocyte antigen receptors and negatively regulates AP-1," Immunity, Apr. 2000, 12(4):399-408.
Liu et al., "Calcineurin is a common target of cyclophilin-cyclosporin A and FKBP-FK506 complexes," Cell, Aug. 1991, 66(4):807-815.
Liu et al., "Critical role of kinase activity of hematopoietic progenitor kinase 1 in anti-tumor immune surveillance," PloS one, Mar. 2019, 14:e02 12670.
Liu et al., "METTL13 Methylation of eEF1A Increases Translational Output to Promote Tumorigenesis," Cell, Jan. 2019, 176:491-504.e421.
Liu et al., "Widening Synthesis Bottlenecks: Realization of Ultrafast and Continuous-Flow Synthesis of High-Silica Zeolite SSZ-13 for NOx Removal," Angew. Chem., May 4, 2015, 127(19):5775-5779.
Losada et al., "Binding of *eEF1A2* to the RNA-dependent protein kinase PKR modulates its activity and promotes tumour cell survival," British Journal of Cancer, Nov. 2018, 119(11):1410-1420.

(56) References Cited

OTHER PUBLICATIONS

Lu et al., "Epigenetic Perturbations by Arg882-Mutated DNMT3A Potentiate Aberrant Stem Cell Gene-Expression Program and Acute Leukemia Development," Cancer Cell, 2016, 30:92-107.
Lu et al., "Hijacking the E3 ubiquitin ligase cereblon to efficiently target BRD4," Chemistry & Biology, Jun. 2015, 22(6):755-763.
Lu et al., "Targeting $EGFR^{L858R/T790M}$ and $EGFR^{L858R/T790M/C797S}$ resistance mutations in NSCLC: Current developments in medicinal chemistry," Med. Res. Rev., Jan. 2018, 38(5):1550-1581.
Mahara et al., "HIFI-α activation underlies a functional switch in the paradoxical role of Ezh2/PRC2 in breast cancer," PNAS, 2016, 113(26):E3735-E3744.
Mahmoud et al., "Discovery of 4-anilino α-carbolines as novel Brk inhibitors," Bioorganic & Medicinal Chemistry Letters, Apr. 2014, 24:1948-1951.
Majer et al., "A687V EZH2 is a gain-offunction mutation found in lymphoma patients," FEBS Lett., 2012, 586(19):3448-3451.
Maniaci et al., "Homo-PROTACs: bivalent small-molecule dimerizers of the VHL E3 ubiquitin ligase to induce self-degradation," Nature Communication, Oct. 2017, 8, 14 pages.
Manning et al., "AKT/PKB signaling: navigating the network," Cell, Apr. 2017, 169(3):381-405.
Marjon et al., "*MTAP* Deletions in Cancer Create Vulnerability to Targeting of the MAT2A/PRMT5/RIOK1 Axis," Cell Reports, Apr. 2016, 15:574-587.
Marschalek, "MLL Leukemia and Future Treatment Strategies," Arch. Pharm. Chem. Life Sci., Apr. 2015, 348(4):221-228.
Matsushime et al., "Identification and properties of an atypical catalytic subunit ($p34^{PSK-13}$/cdk4) for mammalian D type G1 cyclins," Cell, 1992, 71(2):323-334.
Mavrakis et al., "Disordered methionine metabolism in MTAP/CDKN2A-deleted cancers leads to dependence on PRMT5," Science, Feb. 2016, 351(6278): 1208-1213.
Mcalpine et al., "Abstract 4857: Discovery of PF-06855800, a SAM competitive PRMT5 inhibitor with potent antitumor activity," American Association for Cancer Research Annual Meeting, 2018, 78(13 Supplement), 4 pages.
McCabe et al., "EZH2 inhibition as a therapeutic strategy for lymphoma with EZH2-activating mutations," Nature, 2012, 492(7427):108-112.
McCabe et al., "Mutation of A677 in histone methyltransferase EZH2 in human B-cell lymphoma promotes hypertrimethylation of histone H3 on lysine 27 (H3K27)," Proc. Natl. Acad. Sci. USA, 2012, 109(8):2989-2994.
Meyer et al., "New insights to the *MLL* recombinome of acute leukemias," Leukemia, Aug. 2009, 23:1490-1499.
Meyer et al., "The *MLL* recombinome of acute leukemias in 2013," Leukemia, Nov. 2013, 27:2165-2176.
Meyer et al., "The MLL recombinome of acute leukemias," Leukemia, May 2006, 20:777-784.
Meyerson et al., "Identification of $G_1$ kinase activity for cdk6, a novel cyclin D partner," Molecular and Cellular Biology. 1994, 14(3):2077-2086.
Mi et al., "YEATS2 links histone acetylation to tumorigenesis of non-small cell lung cancer," Nat. Commun., Oct. 2017, 8:1088, 14 pages.
Migliori et al., "Symmetric dimethylation of H3R2 is a newly identified histone mark that supports euchromatin maintenance," Nature Structural and Molecular Biology, Feb. 2012, 19(2):136-144.
Miller et al., "COMPASS: a complex of proteins associated with atrithorax-related SET domain protein," Proceedings of the National Academy of Sciences, Nov. 2001, 98(23):12902-12907.
Mitchell et al., "Cloning and characterisation of cDNAs encoding a novel non-receptor tyrosine kinase, brk, expressed in human breast tumours," Oncogene, Aug. 1994, 9:2383-2390.
Mohan et al., "Licensed to elongate: a molecular mechanism for MLL-based leukaemogenesis," Nat. Rev. Cancer, Oct. 2010, 10:721-728.
Mohan et al., "Linking H3K79 trimethylation to Wnt signaling through a novel Dot1-containing complex (DotCom)," Genes Dev., 2010, 24:574-589.
Molander et al., "Efficient hydrolysis of organotrifluoroborates via silica gel and water," Journal of Organic Chemistry, Oct. 2009, 74(19):364-7369.
Morin et al., "Somatic mutations altering EZH2 (Y641) in follicular and diffuse large B-cell lymphomas of germinal-center origin," Nat. Genet., 2010, 42(2):181-185.
Morris et al., "*ALK*, the chromosome 2 gene locus altered by the t(2;5) in non-Hodgkin's lymphoma, encodes a novel neural receptor tyrosine kinase that is highly related to leukocyte tyrosine kinase (LTK)," Oncogene, Mar. 8, 1997, 14:2175-2188.
Morris et al., "Fusion of a kinase gene, *ALK*, to a nucleolar protein gene, *NPM*, in non-Hodgkin's lymphoma," Science, Mar. 4, 1994, 263(5151):1281-1284.
Moustakim et al., "Discovery of an MLLT1/3 YEATS Domain Chemical Probe," Angew. Chem. Int. Ed. Engl., Dec. 2018, 57(50):16302-16307.
Mueller et al., "A role for the MLL fusion partner ENL in transcriptional elongation and chromatin modification," Blood, Dec. 2007, 110(13):4445-4454.
Mueller et al., "Misguided Transcriptional Elongation Causes Mixed Lineage Leukemia," Plos Biol., Nov. 2009, 7(11):e1000249, 15 pages.
Müller et al., "Histone methyltransferase activity of a *Drosophila* Poly comb group repressor complex," Cell, 2002, 111(2):197-208.
MX Office Action in Mexican Appln. No. MX/a/2019/004950, dated Aug. 6, 2021, 6 pages (with English translation).
MX Office Action in Mexican Appln. No. MX/a/2019/004950, dated Nov. 23, 2021, 8 pages (with English Translation).
Nadeem Abbas et al., "Advances in targeting the epidermal growth factor receptor pathway by synthetic products and its regulation by epigenetic modulators as a therapy for glioblastoma," Cells, Apr. 2019, 8:350, 22 pages.
Neklesa et al., "Small-molecule hydrophobic tagging induced degradation of HaloTag fusion proteins," Nat. Chem. Biol., 2011, 7(8):538-543.
Ni et al., "Structural Insights into Interaction Mechanisms of Alternative Piperazine-urea YEATS Domain Binders in MLLTI," ACS Med. Chem. Lett., Dec. 2019, 10(12):1661-1666.
Nicholson et al., "EGFR and cancer prognosis," Eur. J. Cancer, Sep. 2001, 37(Supp. 4):9-15.
Noble et al., "Protein kinase inhibitors: insights into drug design from structure," Science, Mar. 2004, 303:1800-1805.
Odho et al., "Characterization of a novel WDR5-binding site that recruits RbBP5 through a conserved motif to enhance methylation of histone H3 lysine 4 by mixed lineage leukemia protein-1," Journal of Biological Chemistry, Oct. 2010, 285(43):32967-32976.
Ohoka et al., "In vivo knockdown of pathogenic proteins via specific and nongenetic inhibitor of apoptosis protein (IAP)-dependent protein erasers (SNIPERs)," Journal of Biological Chemistry, Mar. 2017, 292(11):4556-4570.
Okada et al., "hDOTIL links histone methylation to leukemogenesis," Cell, Apr. 2005, 121(2):167-178.
Okuhira et al., "Specific degradation of CRABP-II via cIAPI-mediated ubiquitylation induced by hybrid molecules that crosslink cIAP1 and the target protein," FEBS Lett., Apr. 2011, 585(8):1147-1152.
Olson et al., "Pharmacological perturbation of CDK9 using selective CDK9 inhibition or degradation," Nat. Chem. Biol., Feb. 2018, 14:163-170.
Ono et al., "PTK6 promotes cancer rnigration and invasion in pancreatic cancer cells dependent on ERK signaling," PLoS One, 2014, 9:e96060.
Ostrander et al., "Brk/PTK6 signaling in normal and cancer cell models," Curr. Opin. Phannacol., 2010, 10:662-669.
Ottis et al., "Proteolysis-targeting chimeras: induced protein degradation as a therapeutic strategy," ACS Chem. Biol., Mar. 2017, 12(4):892-898.
Paez et al., "*EGFR* mutations in lung cancer: correlation with clinical response to gefitinib therapy," Science, Jun. 2004, 304:1497-500.

(56) References Cited

OTHER PUBLICATIONS

Pao et al., "Acquired resistance of lung adenocarcinomas to gefitinib or erlotinib is associated with a second mutation in the EGFR kinase domain, " PLoS Med., Feb. 2005, 2(3):e73.
Papazimas et al., "A General Strategy for the Preparation of Thalidomide-Conjugate Linkers," Synlett, Aug. 23, 2017, 28:2881-2885.
Park et al., "Discovery of EGF receptor inhibitors that are selective for the d746-750/T790M/C797S mutant through structure-based *de novo* design," Angew. Chem. Int. Ed., Jun. 2017, 56(26):7634-7638.
Park et al., "PTK6 inhibition promotes apoptosis of Lapatinib-resistant $Her2^+$ breast cancer cells by inducing Bim," Breast Cancer Res, 2015, 17:86.
Patel et al., "A conserved arginine-containing motif crucial for the assembly and enzymatic activity of the mixed lineage leukemia protein-I core complex," The Journal of Biological Chemistry, Nov. 2008, 283(47):32162-32175.
Patel et al., "Recent updates on third generation EGFR inhibitors and emergence of fourth generation EGFR inhibitors to combat C797S resistance," Eur. J. Med. Chem., Dec. 2017, 142:32-47.
Patel et al., "Structure of WDR5 bound to mixed lineage leukemia protein-I peptide," The Journal of Biological Chemistry, Nov. 2008, 283(47):32158-32161.
PCT International Preliminary Report on Patentability in International Appln No. PCT/US2018/063847, dated Jun. 18, 2020, 8 pages.
PCT International Preliminary Report on Patentability in International Appln. No. PCT/US2019/019123, dated Aug. 27, 2020, 10 pages.
PCT International Preliminary Report on Patentability in International Appln. No. PCT/US2019/038560, dated Dec. 30, 2020, 9 pages.
PCT International Preliminary Report on Patentability in International Appln. No. PCT/US2019/040507, dated Jan. 5, 2021, 7 pages.
PCT International Preliminary Report on Patentability in International Appln. No. PCT/US2020/031527, dated Nov. 2, 2021, 8 pages.
PCT International Search Report and Written Opinion in International Appln. No. PCT/US2017/058718, dated Jan. 28, 2018, 8 pages.
PCT International Search Report and Written Opinion in International Appln. No. PCT/US2017/065027, dated Mar. 6, 2018, 8 pages.
PCT International Search Report and Written Opinion in International Appln. No. PCT/US2018/063847, dated Mar. 27, 2019, 11 pages.
PCT International Search Report and Written Opinion in International Appln. No. PCT/US2019/019123, dated Jun. 20, 2019, 15 pages.
PCT International Search Report and Written Opinion in International Appln. No. PCT/US2019/021014, dated Jun. 27, 2019, 11 pages.
PCT International Search Report and Written Opinion in International Appln. No. PCT/US2019/038560, dated Oct. 10, 2019, 12 pages.
PCT International Search Report and Written Opinion in International Appln. No. PCT/US2019/040507, dated Nov. 12, 2019, 10 pages.
PCT International Search Report and Written Opinion in International Appln. No. PCT/US2020/031527, dated Sep. 14, 2020, 11 pages.
PCT International Search Report and Written Opinion in International Appln. No. PCT/US2021/055574, dated Feb. 25, 2022, 11 pages.
PCT Invitation to Pay Additional Fees in International Appln. No. PCT/US2019/019123, dated Apr. 8, 2019, 3 pages.
PCT Invitation to Pay Additional Fees in International Appln. No. PCT/US2019/021014, dated Apr. 22, 2019, 2 pages.
PCT Invitation to Pay Additional Fees in International Appln. No. PCT/US2019/038560, dated Aug. 14, 2019, 2 pages.
PCT Invitation to Pay Additional Fees in International Appln. No. PCT/US2021/055574, dated Dec. 22, 2021, 2 pages.
Pellegrino et al., "EEF1A2 inactivates p53 by way of PI3K/AKT/mTOR-dependent stabilization of MDM4 in hepatocellular carcinoma," Hepatology, May 2014, 59(5):1886-1899.
Peng et al., "Protein tyrosine kinase 6 promotes ERBB2-induced rnammary gland tumorigenesis in the mouse," Cell Death Dis., 2015, 6:e1848.
Perlman et al., "*MLLT1* YEATS domain mutations in clinically distinctive Favourable Histology Wilms tumours," Nat. Commun., Dec. 2015, 6:10013, 10 pages.
Peters et al., "Alectinib versus Crizotinib in Untreated ALK Positive Non-Small-Cell Lung Cancer," New England Journal of Medicine, Aug. 31, 2017, 377(9):829-838.
Pettersson et al., "PROteolysis TArgeting Chimeras (PROTACs)—past, present and future," Drug Discov. Today Technol., Apr. 2019, 31:15-27.
Pieters et al., "A treatment protocol for infants younger than 1 year with acute lymphoblastic leukaemia (Interfant-99): an observational study and a multicentre randomised trial," Lancet, Jul. 2007, 370:240-250.
Prabhu et al., "Adapting AlphaLISA high throughput screen to discover a novel small-molecule inhibitor targeting protein arginine methyltransferase 5 in pancreatic and colorectal cancers," Oncotarget, May 2017, 8(25):39963-39977.
Prêtre et al., "Inhibition of Akt and other AGC kinases: A target for clinical cancer therapy?," Accepted Manuscript, Seminars in Cancer Biology, 2018, 48:70-77.
PubChem-CID-44631912, NIH, National Center for Biotechnology Information, Create Date: Mar. 8, 2010, 30 pages.
Pui et al., "Treating Childhood Acute Lymphoblastic Leukemia without Cranial Irradiation," N. Engl. J. Med., Jun. 2009, 360(26):2730-2741.
Pulford et al., "Detection of anaplastic lymphoma kinase (ALK) and nucleolar protein nucleophosmin (NPM)-ALK proteins in normal and neoplastic cells with the monoclonal antibody ALK1," Blood, Feb. 15, 1997, 89(4):1394-1404.
Qi et al., "Selective inhibition of Ezh2 by a small molecule inhibitor blocks tumor cells proliferation," Proc. Natl. Acad. Sci. USA, 2012, 109(52):21360-21365.
Quentmeier et al., "EZH2 Y641 mutations in follicular lymphoma," Leukemia, 2011, 25(4):726-729.
Raina et al., "PROTACinduced BET protein degradation as a therapy for castration-resistant prostate cancer," Proceedings of the National Academy of Sciences of the United States of America, Jun. 2016, 113(26):7124-7129.
Rao et al., "Hijacked in cancer: the KMT2 (MLL) family of methyltransferases," Nat. Rev. Cancer, Jun. 2015, 15:334-346.
Ren et al., "PHF19 promotes multiple myeloma tumorigenicity through PRC2 activation and broad H3K27me3 domain formation," Blood, 2019, 134:1176-1189.
Ren et al., "Polycomb protein EZH2 regulates tumor invasion via the transcriptional repression of the metastasis suppressor RKIP in breast and prostate cancer," Cancer Res., 2012, 72(12):3091-3104.
Ribas et al., "Cancer immunotherapy using checkpoint blockade," Science (New York, NY), Mar. 2018, 359(6382):1350-1355.
Rikova et al., "Global survey of phosphotyrosine signaling identifies oncogenic kinases in lung cancer," Cell, Dec. 14, 2007, 131(6):1190-1203.
Ritchie et al., "*limma* powers differential expression analyses for RNA-sequencing and microarray studies," Nucleic Acids Res., 2015, 43(7):e47.
Rodrik-Outmezguine et al., "Overcoming mTOR resistance mutations with a new-generation mTOR inhibitor," Nature, Jun. 2016, 534:272-276.
Roguev et al., "The *Saccharomyces cerevisiae* Set1 complex includes an ash2 homologue and methylates histone 3 lysine," The EMBO journal, Dec. 2001, 20(24):7137-7148.
Rosati et al., "*NUP98* is fused to the NSD3 gene in acute myeloid leukemia associated with t(8;11)(p11.2;p15), " Blood, 2002, 99:3857-3860.

(56) References Cited

OTHER PUBLICATIONS

Sakamoto et al., "Protacs: chimeric molecules that target proteins to the Skp1-Cullin-F box complex for ubiquitination and degradation," Proc. Natl. Acad. Sci. USA, Jul. 2001, 98(15):8554-8559.
Salami et al., "Waste disposal—An attractive strategy for cancer therapy," Science, Mar. 2017, 355:1163-1167.
Saura et al., "A first-in-human phase I study of the ATP-competitive AKT inhibitor ipatasertib demonstrates robust and safe targeting of AKT in patients with solid tumors," Cancer Discovery, Jan. 2017, 7(1):102-113.
Sauvageau et al., "Poly comb group proteins: multi-faceted regulators of somatic stem cells and cancer," Cell Stem Cell., 2010, 7(3):299-313.
Sawasdikosol et al., "Hematopoietic progenitor kinase 1 (HPKI) regulates prostaglandin $E_2$-induced fos gene transcription," Blood, May 2003, 101(9):3687-3689.
Sawasdikosol et al., "HPKI as a novel target for cancer immunotherapy," Immunologic Research, Dec. 2012, 54(1-3):262-265.
Sawasdikosol et al., "Prostaglandin $E_2$ activates HPK 1 kinase activity via a PKA-dependent pathway," The Journal of biological chemistry, Nov. 2007, 282(48):34693-34699.
Schapira et al., "Targeted protein degradation: expanding the toolbox," Nat. Rev. Drug Discov., Dec. 2019, 18(12):949-963.
Schmandt et al., "The BRK tyrosine kinase is expressed in high-grade serous carcinoma of the ovary," Cancer Biol. Ther., 2006, 5:1136-1141.
Schneider et al. "Characterization of EBV-genome negative 'null' and 'T' cell lines derived from children with acute lymphoblastic leukemia and leukemic transformed non-Hodgkin lymphoma," International Journal of Cancer, May 1977, 19(5): 621-626.
Schramm et al., "Novel BQCA- and TBPB-derived M1 receptor hybrid ligands: orthosteric carbachol differentially regulates partial agonism," ChemMedChem, Jul. 2019, 14(14):1349-1358.
Senisterra et al., "Small-molecule inhibition of MLL activity by disruption of its interaction with WDR5," Biochemical Journal, Jan. 2013, 449(1):151-159.
Seshacharyulu et al., "Targeting the EGFR signaling pathway in cancer therapy," Expert Opin. Ther. Targets, Jan. 2012, 16:15-31.
Shanle et al., "Association of Taf14 with acetylated histone H3 directs gene transcription and the DNA damage response," Genes Dev., 2015, 29:1795-1800.
Sharma et al., "Epidermal growth factor receptor mutations in lung cancer," Nat. Rev. Cancer, Mar. 2007, 7:169-181.
Shaw et al., "Ceritinib in ALK-rearranged non-small-cell lung cancer," New England Journal of Medicine, Mar. 27, 2014, 370(13):1189-1197.
Shen et al., "Identification of LEM-14 inhibitor of the oncoprotein NSD2," Biochem Biophys. Res. Commun., Jan. 2019, 508(1):102-108.
Shen et al., "NSD3-Short is an Adaptor Protein that Couples BRD4 to the CHD8 Chromatin Remodeler," Mol. Cell., Dec. 2015, 60(6):847-859.
Shen et al., "Structure-based design of 5-methylpyrimidopyridone derivatives as new wild-type sparing inhibitors of the epidermal growth factor receptor triple mutant ($EGFR^{L858R/T790M/C797S}$)," J. Med. Chem., Jul. 2019, 62:7302-7308.
Sherr et al., "Targeting CDK4 and CDK6: from discovery to therapy," Cancer Discovery, 2016, 6(4):353-367.
Shibata et al., "Development of protein degradation inducers of oncogenic BCR-ABL protein by conjugation of ABL kinase inhibitors and IAP ligands," Cancer Science, Aug. 2017, 108(8):1657-1666.
Shimizu et al., "The protein arginine methyltransferase 5 promotes malignant phenotype of hepatocellular carcinoma cells and is associated with adverse patient outcomes after curative hepatectomy," International Journal of Oncology, Jan. 2017, 50(2):381-386.
Shiota et al., "Hyperphosphorylation of a novel 80 kDa protein-tyrosine kinase similar to Ltk in a human 40 Ki-1 lymphoma cell line, AMS3," Oncogene, Jun. 1994, 9(6):1567-1574.
Shui et al., "Hematopoietic progenitor kinase 1 negatively regulates T-cell receptor signaling and T cell-mediated immune responses," Nature Immunology, Jan. 2007, 8(1):84-91.
Slany, "When epigenetics kills: MLL fusion proteins in leukemia," Hematol. Oncol., Mar. 2005, 23:1-9.
Sneeringer et al., "Coordinated activities of wild-type plus mutant EZH2 drive tumorassociated hypertrimethylation oflysine 27 on histone H3 (H3K27) in human B-cell lymphomas," Proc. Natl. Acad. Sci. USA, Dec. 7, 2010, 107(49): 20980-20985.
Soda et al., "Identification of the transforming *EML4-ALK* fusion gene in non-small-cell lung cancer," Nature, Aug. 2, 2007,448:561-566.
Solomon et al., "First-line crizotinib versus chemotherapy in *ALK*-positive lung cancer," New England Journal of Medicine, Dec. 4, 2014, 371(23):2167-2177.
Song et al., "Selective inhibition of EZH2 by ZLD1039 blocks H3K27methylation and leads to potent anti-tumor activity in breast cancer," Sci. Rep., 2016, 6:20864.
Song et al., "WDR5 interacts with mixed lineage leukemia (MLL) protein via the histone HJ-binding pocket," The Journal of Biological Chemistry, Dec. 2008, 283(50):35258-35264.
Soucy et al., "An inhibitor of NEDD8-activating enzyme as a new approach to treat cancer," Nature, Apr. 2009, 458:732-736.
Subramanian et al., "Gene set enrichment analysis: a knowledge-based approach for interpreting genome-wide expression profiles," Proc. Natl. Acad. Sci. USA, Sep. 2005, 102(43):15545-15550.
Suda et al., "The structure of bestatin," The Journal of Antibiotic, Jan. 1976, 29(1):100-101.
Sun et al., "Discovery of AMG 232, a potent, selective, and orally bioavailable MDM2-p53 inhibitor in clinical development," Journal of Medicinal Chemistry, Feb. 2014, 57(4):1454-1472.
Sun et al., "PROTAC-induced BTK degradation as a novel therapy for mutated BTK C481S induced ibrutinib-resistant B-cell malignancies," Cell Research, Jul. 2018, 28(7):779-781.
Sun et al., "Up-regulated WDR5 promotes gastric cancer formation by induced cyclin D1 expression," Journal of Cellular Biochemistry, Apr. 2018, 119(4): 28 pages.
Sun et al., "WDR5 supports an N-Myc transcriptional complex that drives a protumorigenic gene expression signature in neuroblastoma," Cancer Research, Dec. 2015 75(23):5143-5154.
Tahirovic et al., "Discovery of *N-alkyl* piperazine side chain based CXCR4 antagonists with improved drug-like properties," ACS Med. Chem. Lett., May 2018, 9(5):446-451.
Takeuchi et al., "KIF5B-ALK, a novel fusion oncokinase identified by an immunohistochemistry-based diagnostic system for ALK-positive lung cancer," Clinical Cancer Research, May 1, 2009, 15(9):3143-3149.
Tan et al., "A kinase-independent role for EGF receptor in autophagy initiation," Cell, Jan. 2015, 160(1-2):145-160.
Tan et al., "Next-generation epidermal growth factor receptor tyrosine kinase inhibitors in epidermal growth factor receptor-mutant non-small cell lung cancer," Lung Cancer, Mar. 2016, 93:59-68.
Tan et al., "PBK/AKT-mediated upregulation of WDR5 promotes colorectal cancer metastasis by directly targeting ZNF407," Cell Death and Disease, Mar. 2017, 8(3): 12 pages.
Taniguchi et al., "Silencing of Kruppel-like factor 2 by the histone methyltransferase EZH2 in human cancer," Oncogene, 2012, 31(15):1988-1994.
Tarighat et al., "The dual epigenetic role of PRMT5 in acute myeloid leukemia: gene activation and repression via histone arginine methylation," Leukemia, Nov. 2016, 30:789-799.
Thomas et al., "Interaction with WDR5 promotes target gene recognition and tumorigenesis by MYC," Molecular Cell, May 2015, 58(3):440-452.
Thomas et al., "The MYC-WDR5 nexus and cancer," Cancer Research, Oct. 2015, 75(19):4012- 4015.
Thress et al., "Acquired *EGFR* C797S mutation mediates resistance to AZD9291 in non-small cell lung cancer harboring *EGFR* T790M," Nat. Med., May 2015, 21:560-562.
Toure et al., "Small-Molecule PROTACS: New Approaches to Protein Degradation," Angewandte Chemie-International Edition, Feb. 2016, 55(6):1966-1973.

(56) References Cited

OTHER PUBLICATIONS

Trievel et al., "WDR5, a complexed protein," Nature Structural & Molecular Biology, Jul. 2009, 16(7):678-680.
Turner et al., "Palbociclib in hormone-receptor-positive advanced breast cancer," New England Journal of Medicine, 2015, 373(3):209-219.
Turner-Ivey et al., "Development of mammary hyperplasia, dysplasia, and invasive ductal carcinoma in transgenic mice expressing the 8p11 amplicon oncogene NSD3," Breast Cancer Res. Treat., Jul. 2017, 164(2):349-358.
Varambally et al., "The polycomb group protein EZH2 is involved in progression of prostate cancer," Nature, 2002, 419(6907):624-629.
Varfolomeev et al., "IAP antagonists induce autoubiquitination of c-IAPs, NF-κB activation, and TNFα-dependent apoptosis," Cell, Nov. 2007, 131(4):669-681.
Vassilev et al., "In vivo activation of the p53 pathway by small-molecule antagonists of MDM2," Science, Feb. 2004, 303(5659):844-848.
Verma et al., "Identification of Potent, Selective, Cell-Active Inhibitors of the Histone Lysine Methyltransferase EZH2," Acs Med. Chem. Lett., 2012, 3(12):1091-1096.
Vivanco et al., "A kinase-independent function of AKT promotes cancer cell survival," eLIFE, 2014, 3:e03751.
Vu et al., "Discovery of RG7112: a small-molecule MDM2 inhibitor in clinical development," ACS Medicinal Chemistry Letters, May 2013, 4(5):466-469.
Wakeling, "Use of pure antioestrogens to elucidate the mode of action of oestrogens," Biochemical Pharmacology, May 1995, 49(11):1545-1549.
Wan et al., "ENL links histone acetylation to oncogenic gene expression in acute myeloid leukaemia," Nature, Mar. 2017, 543:265-269.
Wan et al., "Impaired cell fate through gain-of-function mutations in a chromatin reader," Nature, Jan. 2020, 577:121-126.
Wang et al., "EAI045: The fourth-generation EGFR inhibitor overcoming T790M and C797S resistance," Cancer Lett., Jan. 2017, 385:51-54.
Wang et al., "MapSplice: accurate mapping of RNA-seq reads for splice junction discovery," Nucleic Acids Res., 2010, 38:e178.
Wang et al., "NUP98-NSD1 links H3K36 methylation to Hox-A gene activation and leukaemogenesis," Nat. Cell. Biol., Jul. 2007, 9(7):804-812.
Wang et al., "Polycomb genes, miRNA, and their deregulation in B-cell malignancies," Blood, 2015, 125(8):1217-1225.
Wei et al., "Protein arginine methylation of non-histone proteins and its role in diseases," Cell Cycle, 2014, 13(1):32-41.
Weisberg et al., "Smac mimetics: implications for enhancement of targeted therapies in leukemia," Leukemia, Dec. 2010, 24:2100-2109.
Weiss et al., "Anaplastic lymphoma kinase and leukocyte tyrosine kinase: functions and genetic interactions in learning, memory and adult neurogenesis," Pharmacology, Biochemistry and Behavior, Jan. 2012, 100(3):566-574.
Weiss et al., "The role of T3 surface molecules in the activation of human T cells: a two-stimulus requirement for IL 2 production reflects events occurring at a pre-translational level," Journal of Immunology, Aug. 1984, 133(1):123-128.
Wieduwilt et al., "The epidermal growth factor receptor family: biology driving targeted therapeutics," Cell. Mol. Life Sci., May 2008, 65(10):1566-1584.
Winter et al., "Phthalimide conjugation as a strategy for in vivo target protein degradation," Science, May 2015, 348(6241):1376-1381.
Wood et al., "Lack of the t(2;5) or other mutations resulting in expression of anaplastic lymphoma kinase catalytic domain in $CD30^+$ primary cutaneous lymphoproliferative disorders and Hodgkin's disease," Blood, Sep. 1, 1996, 88(5):1765-1770.
Wu et al., "Overexpression of WD repeat domain 5 associates with aggressive clinicopathological features and unfavorable prognosis in head neck squamous cell carcinoma," International Association of Oral Pathologists and the American Academy of Oral Pathology, Apr. 2018, 47(5): 27 pages.
Xie et al., "Pharmacological targeting of the pseudokinase Her3," Nature Chemical Biology, Dec. 2014, 10(12):1006-1012.
Xie et al., "WDR5 positively regulates p53 stability by inhibiting p53 ubiquitination," Biochemical and Biophysical Research Communications, May 2017, 487(2):333-338.
Xu et al., "eEF1A2 promotes cell migration, invasion and metastasis in pancreatic cancer by upregulating MMP-9 expression through Akt activation," Clin. Exp. Metastasis, May 2013, 30(7):933-944.
Xu et al., "Selective inhibition of EZH2 and EZH1 enzymatic activity by a small molecule suppresses *MLL*-rearranged leukemia," Blood, Jan. 2015, 125:346-357.
Xu et al., "Targeting EZH2 and PRC2 dependence as novel anticancer therapy," Exp. Hematol., 2015, 43(8):698-712.
Yang et al., "Structure-Activity Relationship Studies for Enhancer of Zeste Homologue 2 (EZH2) and Enhancer of Zeste Homologue 1 (EZHI) Inhibitors," J. Med. Chem., 2016, 59(16):7617-7633.
Yokoyama et al., "A Higher-Order Complex Containing AF4 and ENL Family Proteins with P-TEFb Facilitates Oncogenic and Physiologic MLL-Dependent Transcription," Cancer Cell, Feb. 2010, 17(2):198-212.
You et al., "Discovery of an AKT degrader with prolonged inhibition of downstream signaling," Cell Chemical Biology, 2020, 27(1):66-73.
Yu et al., "Altered *Hox* Expression and Segmental Identity in *Mll*-Mutant Mice," Nature, Nov. 1995, 378:505-508.
Yu et al., "Requirement for CDK4 kinase function in breast cancer," Cancer Cell, 2006, 9(1):23-32.
Yu et al., "Targeting AKT1-E17K and the PI3K/AKT pathway with an allosteric AKT inhibitor, ARQ 092," PLOS One, Oct. 2015, 10(10):e0140479.
Yun et al., "The T790M mutation in EGFR kinase causes drug resistance by increasing the affinity for ATP," Proc. Natl. Acad. Sci. USA, Feb. 2008, 105(6):2070-2075.
Zeng et al., "Discovery of novel imidazo[1,2-a]pyrazin-8-amines as Brk/PTK6 inhibitors," Bioorg. Med. Chem. Lett., Oct. 2011, 21(19):5870-5875.
Zengerle et al., "Selective Small Molecule Induced Degradation of the BET Bromodomain Protein BRD4," ACS Chemical Biology, Jun. 2015, 10(8):1770-1777.
Zhang et al., "Proteolysis targeting chimeras (PROTACs) of anaplastic lymphoma linase (ALK)," Eur. J. Med. Chem., May 2018, 151:304-314.
Zhang et al., "Structural Insights into Histone Crotonyl-Lysine Recognition by the AF9 YEATS Domain," Structure, Sep. 2016, 24(9):1606-1612.
Zhao et al., "PROTACs suppression of CDK4/6, crucial kinases for cell cycle regulation in cancer," Chem. Commun. (Camb)., 2019, 55:2704-2707.
Zhao et al., "The language of chromatin modification in human cancers," Nat. Rev. Cancer, Jul. 2021, 21:413-430.
Zheng et al., "PTK6 activation at the membrane regulates epithelial-mesenchymal transition in prostate cancer," Cancer Res., Sep. 2013, 73(17):5426-5437.
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry, 2018, 61(2):462-481.
Zuber et al., "RNAi screen identifies Brd4 as a therapeutic target in acute myeloid leukaemia," Nature, 2011, 478:524-528.
CN Office Action in Chinese Appln. No. 201780085879.6, dated Jun. 27, 2022, 15 pages (with English Translation).
JP Office Action in Japanese Appln. No. 2019-522841, dated Jul. 12, 2022, 8 pages (with English Translation).
Office Action in U.S. Appl. No. 16/970,305, mailed on Sep. 8, 2023, 22 pages.
Office Action in Chinese Appln. No. 202080049386.9, mailed on Feb. 13, 2025, 14 pages (with English translation).
Vaswani et al., "Identification of (R)-N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-

(56) References Cited

OTHER PUBLICATIONS

1205), a Potent and Selective Inhibitor of Histone Methyltransferase EZH2, Suitable for Phase I Clinical Trials for B-Cell Lymphomas," J Med Chem, Nov. 10, 2016, available online Oct. 28, 2016, 59(21):9928-9941.
Extended European Search Report in European Appln. No. 24222311.3, mailed on Mar. 31, 2025, 9 pages.
Degnan et al., "Discovery of Orally Active Isofuranones as Potent, Selective Inhibitors of Hematopoetic Progenitor Kinase 1," ACS Medicinal Chemistry Letters, Feb. 19, 2021, 12(3):443-450.
Extended European Search Report in European Appln. No. 22899400.0, mailed on Oct. 24, 2025, 7 pages.
Office Action in Canadian Appln. No. 3104298, mailed on Jul. 28, 2025, 4 pages.
Office Action in European Appln. No. 17877800.7, mailed on Dec. 1, 2025, 7 pages.
Office Action in European Appl. No. 24222311.3, mailed on Nov. 28, 2025, 4 pages.
U.S. Appl. No. 16/345,591, filed Apr. 26, 2019, Jian Jin.
U.S. Appl. No. 16/926,418 (U.S. Pat. No. 11,510,920), filed Jul. 10, 2020 (Nov. 29, 2022), Jian Jin.
U.S. Appl. No. 17/978,696, filed Nov. 1, 2022, Jian Jin.
U.S. Appl. No. 16/467,888 (U.S. Pat. No. 11,541,051) filed Jun. 7, 2019 (Jan. 3, 2023), Jian Jin.
U.S. Appl. No. 17/453,619, filed Nov. 4, 2021, Jian Jin.
U.S. Appl. No. 16/769,326, filed Jun. 3, 2020, Jian Jin.
U.S. Appl. No. 16/970,305, filed Aug. 14, 2020, Jian Jin.
U.S. Appl. No. 16/977,654 (U.S. Pat. No. 11,472,799) filed Sep. 2, 2020 (Oct. 18, 2022), Jian Jin.
U.S. Appl. No. 17/254,345 (U.S. Pat. No. 12,110,295) filed Dec. 21, 2020 (Oct. 8, 2024), Jian Jin.
U.S. Appl. No. 17/604,636, filed Oct. 18, 2021, Jian Jin.
U.S. Appl. No. 17/336,059 (U.S. Pat. No. 12,103,924) filed Jun. 1, 2021 (Oct. 1, 2024), Jian Jin.
U.S. Appl. No. 18/032,758, filed Apr. 19, 2023, Jian Jin.
U.S. Appl. No. 18/711,706, filed May 20, 2024, Jian Jin.

* cited by examiner 79-29 and 79-30:
Negative control compounds

PROTEIN TYROSINE KINASE 6 (PTK6) DEGRADATION / DISRUPTION COMPOUNDS AND METHODS OF USE

CROSS-REFERENCE TO RELATED APPLICATION

This application is a U.S. National Stage application, and claims priority of International Application No. PCT/US2019/040507, filed Jul. 3, 2019, which claims the benefit of U.S. Provisional Application Ser. No. 62/694,118, filed Jul. 5, 2018. The entire contents of the foregoing are incorporated by reference.

TECHNICAL FIELD

This disclosure relates to bivalent compounds (e.g., bi-functional small molecule compounds) which degrade and/or disrupt the protein tyrosine kinase 6 (PTK6, also known as breast tumor kinase or Brk) compositions comprising one or more of the bivalent compounds, and to methods of use thereof for the treatment of PTK6-mediated disease in a subject in need thereof. The disclosure also relates to methods for designing such bivalent compounds.

BACKGROUND OF THE INVENTION

PTK6, a member of a distinct family of non-receptor tyrosine kinases distantly related to Src kinases, is expressed in breast cancers and multiple other cancer types (Brauer and Tyner, 2010; Derry et al., 2003; Mitchell et al., 1994; Ostrander et al., 2010; Schmandt et al., 2006). PTK6 promotes oncogenic phenotypes including enhanced proliferation, enhanced anoikis resistance, regulation of autophagy, epithelial-mesenchymal transition, and migration/invasion, via kinase activity-dependent and/or independent mechanisms (Brauer and Tyner, 2010; Castro and Lange, 2010; Harvey and Crompton, 2003; Harvey et al., 2009; Ito et al., 2016; Ostrander et al., 2010; Park et al., 2015; Zheng et al., 2013). Unlike the distantly related src kinases, PTK6 lacks a myristylation sequence. Therefore, PTK6 exhibits a broader range of cellular localization that could impact its activities; PTK6 protein has been detected in the nucleus, cytosol, and membranes of cells (Derry et al., 2003).

PTK6 has a role in multiple cancer types, including prostate, pancreatic, bladder, ovarian, liver and cervical cancers. Specifically, down regulation of PTK6 expression (via siRNA/shRNA) in pancreatic and liver cancer cells were reported to impair their viability (Chen et al., 2016; Ono et al., 2014). In addition to its roles in cancer cell survival regulation, PTK6 promotes epithelial-mesenchymal transition (EMT), a developmental process often coopted by cancer cells to promote invasion/migration, chemotherapy resistance and metastases. We showed that PTK6 promotes EMT of triple negative breast cancer cells and enhances their capacity for invasion and metastases by regulating the stability of Snail, a transcription factor (Ito et al., 2016). shRNA-mediated downregulation of PTK6 expression inhibited 3D growth, migration and metastasis of triple negative breast cancer cells (Ito et al., 2016).

Reduction of PTK6 protein levels is unlikely to have major side effects on the host/patient. Genetically engineered PTK6 knockout mice are viable, reach maturity and reproduce normally. The only phenotype observed thus far is the hyperproliferation of cells in the small intestine, consistent with a role for PTK6 in enterocyte differentiation (Haegebarth et al., 2006). Crossing of these PTK6−/− mice with ErbB2 (Her2) transgenic mice that develop mammary gland tumors resulted in decreased lung metastases, again supporting a critical role for PTK6 protein in cancer metastases (Peng et al., 2015).

A few PTK6 inhibitors are known, including compound 21d (Zeng et al., 2011), compound 4f (Mahmoud et al., 2014), compound 1 (Yamamoto, 2016), XMU-MP-2 (Jiang et al., 2017), and compound 3s (Cardenas et al., 2018). Compound 21d was recently validated (Ito et al., 2017; Ito et al., 2016). Compound 21d treatment phenocopied the effects of PTK6 shRNA with respect to EMT regulation of TNBC cells. However, with respect to 3D growth, treatment with compound 21d did not consistently phenocopy the effects of shRNA for all cell lines evaluated. Indeed, kinase-independent oncogenic activities of PTK6 have been reported (Harvey and Crompton, 2003) and may account for these discrepancies and may limit the generalized utility of kinase inhibition as a therapeutic strategy. PTK6 degraders that reduce PTK6 protein levels would therefore more consistently phenocopy the effects of PTK6 knockdown via RNA interference and overcome kinase-independent activities of PTK6.

SUMMARY OF THE INVENTION

Unlike PTK6 inhibitors, which inhibit the kinase activity of PTK6, the PTK6 degradation/disruption compounds ("PTK6 degraders") disclosed herein bind and induce degradation of PTK6, thus eliminating any scaffolding functions of PTK6 in addition to the kinase activity of PTK6. The PTK6 degraders disclosed herein are bivalent compounds, including a PTK6 ligand conjugated to a degradation/disruption tag via a linker.

The PTK6 degraders disclosed herein offer a novel mechanism for treating PTK6-mediated diseases. In particular, the present PTK6 degraders have the ability to target PTK6 for degradation, as opposed to merely inhibit the kinase activity of PTK6.

In an aspect, this disclosure provides a method of treating PTK6-mediated diseases, the method including administering one or more PTK6 degraders to a subject who has an PTK6-mediated disease, the PTK6 degraders being bivalent compounds including a PTK6 ligand conjugated to a degradation/disruption tag via a linker. The PTK6-mediated disease can be a disease resulting from PTK6 expression. The PTK6-mediated disease can have elevated PTK6 expression relative to a wild-type tissue of the same species and tissue type. Non-limiting examples of PTK6-mediated diseases include breast cancer, ovarian cancer, prostate cancer, colon cancer, pancreatic cancer, bladder cancer, liver cancer, and cervical cancer.

The PTK6-mediated cancer can include, e.g., a relapsed cancer. The PTK6-mediated cancer can, e.g., be refractory to one or more previous treatments.

The present disclosure relates generally to bivalent compounds (e.g., bi-functional small molecule compounds) which degrade and/or disrupt PTK6, and to methods for the treatment of PTK6-mediated cancer (i.e., a cancer which depends on PTK6 protein; or cancer having elevated levels of PTK6, or PTK6 activity relative to a wild-type tissue of the same species and tissue type). Because the PTK6 degraders/disruptors have dual functions (kinase-activity inhibition plus protein degradation/disruption), the bivalent compounds of the present disclosure can be significantly more effective therapeutic agents than current PTK6 inhibitors, which inhibit the kinase activity of PTK6, but do not affect PTK6 protein levels. The present disclosure further provides methods for identifying PTK6 degraders/disruptors as described herein.

More specifically, the present disclosure provides a bivalent compound including an PTK6 ligand conjugated to a degradation/disruption tag via a linker.

In some aspects, the PTK6 degraders/disruptors have the form "PI-Linker-EL", as shown below:

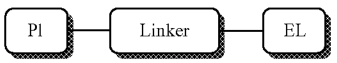

wherein PI (a ligand for a "protein of interest," i.e., the protein to be degraded) comprises an PTK6 ligand (e.g., an PTK6 kinase inhibitor), and EL (e.g., a ligand for an E3 ligase) comprises a degradation/disruption tag (e.g., E3 ligase ligand). Exemplary PTK6 ligands (PI), exemplary degradation/disruption tags (EL), and exemplary linkers (Linker) are illustrated below:

PTK6 Ligands

PTK6 Ligands include but are not limited to:

FORMULA 1

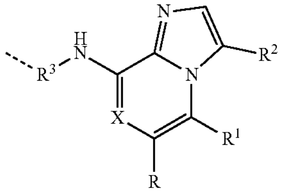

Wherein

R is selected from H, halo, or unsubstituted or optionally substituted $C_{1-8}$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_1$-$C_8$ alkyleneOR$^4$, $C_1$-$C_8$ alkyleneSR$^5$, $C_1$-$C_8$ alkylene NR$^6$R$^7$, $C_2$-$C_8$ alkenyl, $C_2$-$C_8$ alkynyl, OR$^4$, SR$^5$, and NR$^6$R$^7$;

R$^1$ is selected from H, $C_{1-8}$ alkyl, $C_1$-$C_8$ hydroxyalkyl, $C_1$-$C_8$ alkoxyalkyl, $C_3$-$C_{10}$ cycloalkyl, $C_3$-$C_{10}$ heterocyclyl, OR$^8$, SR$^9$, and NR$^{10}$R$^{11}$;

R$^2$ is selected from $C_6$-$C_{10}$ aryl or $C_5$-$C_{10}$ heteroaryl. R$^2$ is unsubstituted or optionally substituted with one or more of groups selected from halo, =O, =S, CN, $NO_2$, $C_{1-8}$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_1$-$C_8$ alkyleneOR$^{12}$, $C_1$-$C_8$ alkyleneSR$^3$, $C_1$-$C_8$ alkylene NR$^{14}$R$^{15}$, $C_2$-$C_8$ alkenyl, $C_2$-$C_8$ alkynyl, OR$^{12}$, SR$^{13}$, and NR$^{14}$R$^{15}$;

R$^3$ is selected from $C_6$-$C_{10}$ aryl or $C_8$-$C_{10}$ heteroaryl. R$^3$ is unsubstituted or substituted with one or more of groups selected from $C_1$-$C_8$ alkyl, $C_1$-$C_8$ haloalkyl, $C_1$-$C_8$ hydroxyalkyl, $C_1$-$C_8$ alkoxyalkyl, $C_3$-$C_{10}$ cycloalkyl, $C_3$-$C_{10}$ heterocyclyl, $C_2$-$C_8$ alkenyl, $C_2$-$C_8$ alkynyl, halo, CN, $NO_2$, =O, =S, R$^{16}$, OR$^{16}$, SR$^{17}$, $SO_2$R$^{18}$, NR$^{19}$R$^{20}$, C(O)R$^{16}$, C(O)OR$^{16}$, C(S)OR$^{16}$, C(O)NR$^{19}$R$^{20}$, C(S)NR$^{19}$R$^{20}$, NR$^{19}$C(O)R$^{16}$, NR$^{19}$C(O)OR$^{16}$, NR$^{19}$S(O)R$^{16}$, NR$^{19}$S(O)OR$^{16}$, S(O)R$^{16}$, S(O)OR$^{16}$, and S(O)ONR$^{19}$R$^{20}$;

R$^4$, R$^5$, R$^6$, R$^7$, R$^8$, R$^9$, R$^{10}$, R$^{11}$, R$^{12}$, R$^{13}$, R$^{14}$, R$^{15}$ are independently selected from H, $C_1$-$C_8$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, C(O)$C_1$-$C_8$ alkyl, C(O)$C_1$-$C_8$ haloalkyl, C(O)$C_1$-$C_8$ hydroxyalkyl, C(O)$C_3$-$C_{10}$ cycloalkyl, and C(O)$C_3$-$C_{10}$ heterocyclyl, or R$^6$ and R$^7$; R$^{10}$ and R$^{11}$; R$^{14}$ and R$^{15}$ together with the nitrogen atom to which they connected can independently form 3-10 membered heterocyclyl rings;

R$^{16}$, R$^{17}$, and R$^{18}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_8$ cycloalkyl, $C_3$-$C_7$ heterocycloalkyl, $C_6$-$C_{10}$ aryl, $C_5$-$C_{10}$ heteroaryl, C(O)$C_1$-$C_8$ alkyl, C(O)$C_1$-$C_8$ haloalkyl, C(O)$C_1$-$C_8$ hydroxyalkyl, C(O)$C_1$-$C_8$ alkoxyalkyl, C(O)$C_3$-$C_{10}$ cycloalkyl, C(O)$C_3$-$C_{10}$ heterocyclyl, C(O)$C_6$-$C_{10}$ aryl, C(O)$C_5$-$C_{10}$ heteroaryl, $C_1$-$C_8$ alkylene$C_3$-$C_{10}$ cycloalkyl, $C_1$-$C_8$ alkylene$C_3$-$C_{10}$ heterocycloalkyl, $C_1$-$C_8$ alkylene$C_6$-$C_{10}$ aryl, $C_1$-$C_8$ alkylene, and $C_5$-$C_{10}$ heteroaryl;

R$^{19}$ and R$^{20}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_{10}$ cycloalkyl, $C_3$-$C_{10}$ heterocycloalkyl, $C_6$-$C_{10}$ aryl, $C_5$-$C_{10}$ heteroaryl, C(O)$C_1$-$C_8$ alkyl, C(O)$C_1$-$C_8$ haloalkyl, C(O)$C_1$-$C_8$ hydroxyalkyl, C(O)$C_1$-$C_8$ alkoxyalkyl, C(O)$C_3$-$C_{10}$ cycloalkyl, C(O)$C_3$-$C_{10}$ heterocycloalkyl, C(O)$C_6$-$C_{10}$ aryl, C(O)$C_5$-$C_{10}$ heteroaryl, C(O)O$C_1$-$C_8$ alkyl, C(O)O$C_1$-$C_8$ haloalkyl, C(O)O$C_1$-$C_8$ hydroxyalkyl, C(O)O$C_1$-$C_8$ alkoxyalkyl, C(O)O$C_3$-$C_{10}$ cycloalkyl, C(O)O$C_3$-$C_{10}$ heterocyclyl, C(O)O$C_6$-$C_{10}$ aryl, C(O)O$C_5$-$C_{10}$ heteroaryl, C(O)N$C_1$-$C_8$ alkyl, C(O)N$C_1$-$C_8$ haloalkyl, C(O)N$C_1$-$C_8$ hydroxyalkyl, C(O)N$C_1$-$C_8$ alkoxyalkyl, C(O)N$C_3$-$C_{10}$ cycloalkyl, C(O)N$C_3$-$C_{10}$ heterocyclyl, C(O)N$C_6$-$C_{10}$ aryl, C(O)N$C_5$-$C_{10}$ heteroaryl, $SO_2C_1$-$C_8$ alkyl, $SO_2C_1$-$C_8$ haloalkyl, $SO_2C_1$-$C_8$ hydroxyalkyl, $SO_2C_1$-$C_8$ alkoxyalkyl, $SO_2C_3$-$C_{10}$ cycloalkyl, $SO_2C_3$-$C_{10}$ heterocyclyl, $SO_2C_6$-$C_{10}$ aryl, $SO_2C_5$-$C_{10}$ heteroaryl, $C_1$-$C_8$ alkylene$C_3$-$C_{10}$ cycloalkyl, $C_1$-$C_8$ alkylene$C_3$-$C_{10}$ heterocycloalkyl, $C_1$-$C_8$ alkylene$C_6$-$C_{10}$ aryl, $C_1$-$C_8$ alkylene$C_5$-$C_{10}$ heteroaryl, or R$^{19}$ and R$^{20}$ together with the nitrogen atom to which they connected can independently form 3-10 membered heterocyclyl rings; and X is selected from CH or N.

In some aspects of Formula 1, R is selected from H, halogen, optionally substituted $C_{1-3}$ alkyl, and optionally substituted $C_{1-3}$ alkoxy.

In some aspects of Formula 1, R is selected from H, F, $CH_3$, $CH_2F$, $CHF_2$, $CF_3$, $CH_2CH_3$, $CH_2CF_3$, i-Pr, c-Pr, $OCH_3$, $OCH_2F$, $OCHF_2$, $OCF_3$, $OCH_2CH_3$, $OCH_2CF_3$, Oi-Pr, and Oc-Pr.

In some aspects of Formula 1, R is selected from $CH_3$, $CF_3$, $CH_2CH_3$, $CH_2CF_3$, and c-Pr.

In some aspects of Formula 1, R is selected from $CH_3$, and c-Pr.

In some aspects of Formula 1, R is c-Pr.

In some aspects of Formula 1, R$^1$ is selected from H, halogen, optionally substituted $C_{1-3}$ alkyl, and optionally substituted $C_{1-3}$ alkoxy.

In some aspects of Formula 1, R$^1$ is selected from H, F, $CH_3$, $CH_2F$, $CHF_2$, $CF_3$, $CH_2CH_3$, $CH_2CF_3$, i-Pr, c-Pr, $OCH_3$, $OCH_2F$, $OCHF_2$, $OCF_3$, $OCH_2CH_3$, $OCH_2CF_3$, Oi-Pr, and Oc-Pr.

In some aspects of Formula 1, R$^1$ is selected from H, F, $CH_3$, and $CF_3$.

In some aspects of Formula 1, R$^1$ is H.

In some aspects of Formula 1, R$^2$ is selected from phenyl and 5-6 membered heteroaryl, which are optionally substituted with one or more of groups selected from halogen, optionally substituted $C_{1-3}$ alkyl, and optionally substituted $C_{1-3}$ alkoxy.

In some aspects of Formula 1, $R^2$ is 5-6 membered heteroaryl, which are optionally substituted with one or more of groups selected from halogen, optionally substituted $C_{1-3}$ alkyl, and optionally substituted $C_{1-3}$ alkoxy.

In some aspects of Formula 1, $R^2$ is selected from phenyl,

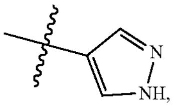

and

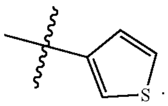

.

In some aspects of Formula 1, $R^2$ is

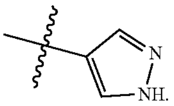

In some aspects of Formula 1, $R^3$ is selected from phenyl, and 5-6 membered heteroaryl, which are optionally substituted with one or more of groups selected from halogen, optionally substituted $C_{1-8}$ alkyl, and optionally substituted $C_{1-8}$ alkoxy, optionally substituted $C_{1-8}$ alkylene, optionally substituted 3-8 membered carbocyclyl, optionally substituted 4-8 membered heterocyclyl, optionally substituted aryl, optionally substituted 5-6 membered heteroaryl, —CO—, —C(O)—($C_{1-8}$ alkylene)-, —C(O)—NH($C_{1-8}$ alkylene)-, —C(O)—N($C_{1-8}$ alkylene)($C_{1-8}$ alkylene)-, —C(O)-(3-8 membered carbocyclyl)-, —C(O)-(4-8 membered heterocyclyl)-, —C(O)-(5-6 membered heteroaryl)-, —NH($C_{1-8}$ alkylene)-, —N($C_{1-8}$ alkylene)($C_{1-8}$ alkylene)-, —$CH_2$-(3-8 membered carbocyclyl)-, —$CH_2$-(4-8 membered heterocyclyl)-, and —$CH_2$-(5-6 membered heteroaryl)-.

In some aspects of Formula 1, $R^3$ is selected from phenyl, and 5-6 membered heteroaryl, which are optionally substituted with one or more of groups selected from F, Cl, $CH_3$, $CF_3$, $OCH_3$, $OCF_3$, $CH_2CH_3$, $CH_2CF_3$, $OCH_2CH_3$, $OCH_2CF_3$, i-Pr, c-Pr, i-PrO, c-PrO, —CO—, optionally substituted

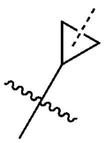

, optionally substituted

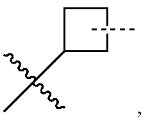

, optionally substituted

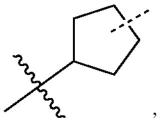

, optionally substituted

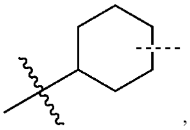

, optionally substituted

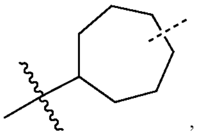

, optionally substitute

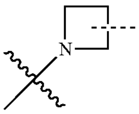

, optionally substituted

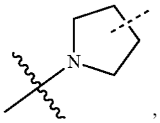

, optionally substituted

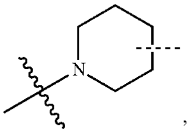

, optionally substituted

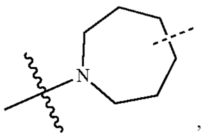

, optionally substituted
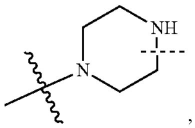
,
optionally substituted
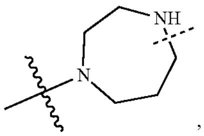
,
optionally substituted
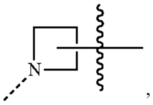
,
optionally substituted
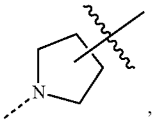
,
optionally substituted
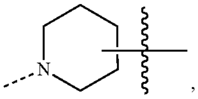
,
optionally substituted
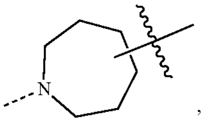
,
optionally substituted
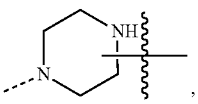
,
optionally substituted
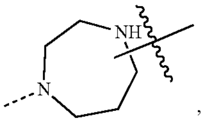
,
optionally substituted
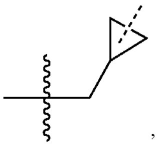
,
optionally substituted
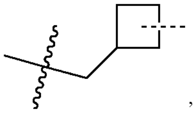
,
optionally substituted
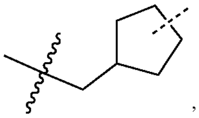
,
optionally substituted
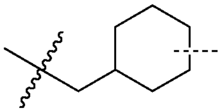
,
optionally substituted
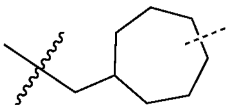
,
optionally substituted
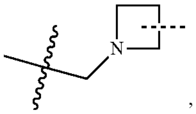
, optionally substituted
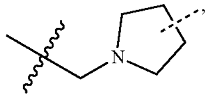
optionally substitute
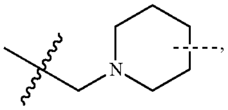
optionally substituted
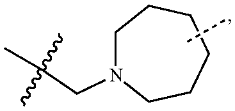
optionally substituted
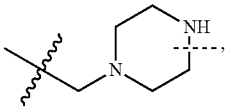
optionally substitute
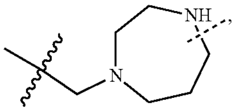
optionally substituted
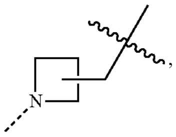
optionally substituted
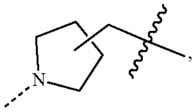
optionally substituted
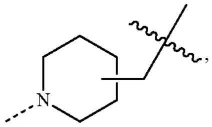
optionally substituted
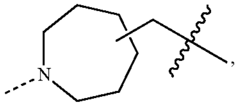
optionally substituted
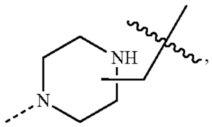
optionally substituted
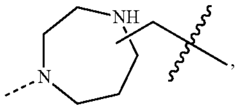
optionally substituted
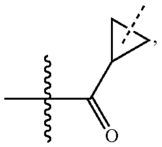
optionally substituted
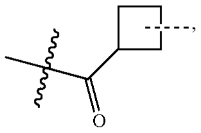
optionally substituted
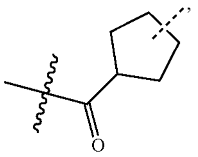

optionally substituted
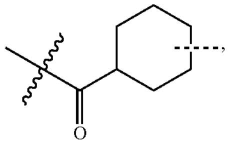
optionally substituted
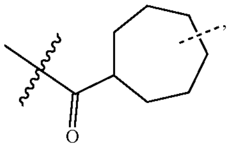
optionally substituted
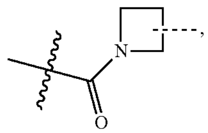
optionally substituted
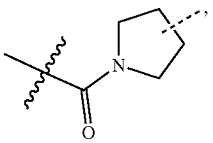
optionally substituted
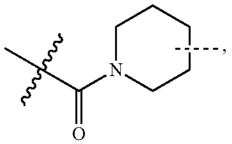
optionally substituted
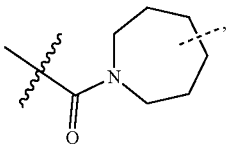
optionally substituted
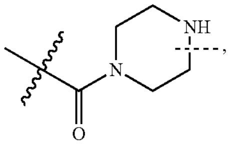
optionally substitute
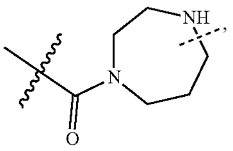
optionally substituted
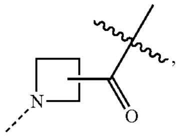
optionally substituted
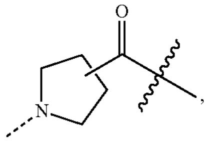
optionally substituted
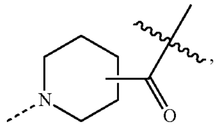
optionally substituted
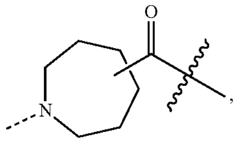
optionally substituted
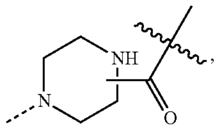
and optionally substituted
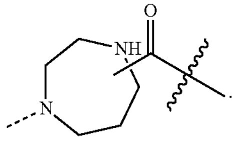

In some aspects of Formula 1, $R^3$ is selected from phenyl, thiophene, thiazole, isothiazole, pyrolyl, pyrazolyl, imidazolyl, pyridinyl, pyrimidinyl, and pyrazinyl, which are optionally substituted with one or more of groups selected from F, Cl, $CH_3$, $CF_3$, $OCH_3$, $OCF_3$, $CH_2CH_3$, $CH_2CF_3$, $OCH_2CH_3$, $OCH_2CF_3$, i-Pr, c-Pr, i-PrO, c-PrO, —CO—, optionally substituted,

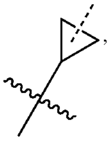, optionally substituted

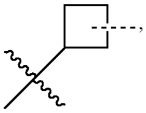, optionally substituted

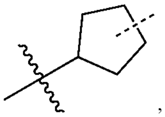, optionally substituted

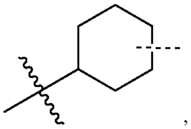, optionally substituted

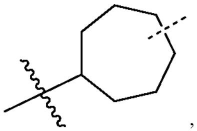, optionally substituted

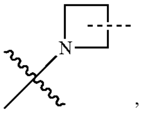, optionally substituted

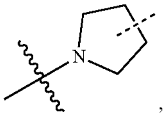, optionally substituted

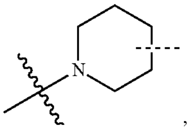, optionally substituted

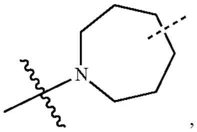, optionally substituted

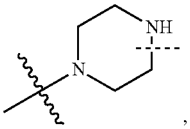, optionally substituted

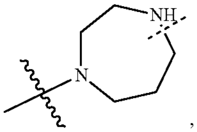, optionally substituted

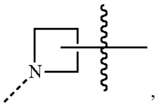, optionally substituted

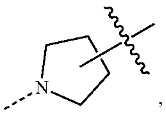, optionally substitute
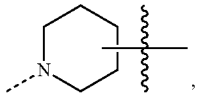
optionally substituted
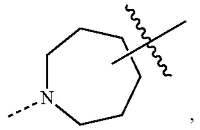
optionally substituted
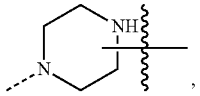
optionally substituted
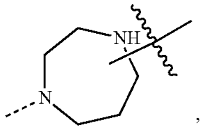
optionally substituted
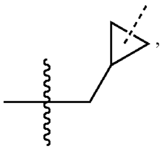
optionally substituted
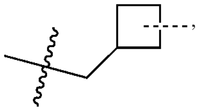
optionally substituted
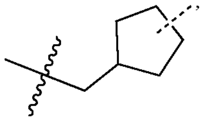
optionally substituted
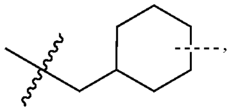
optionally substituted
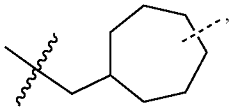
optionally substituted
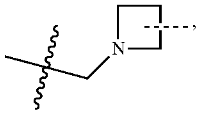
optionally substituted
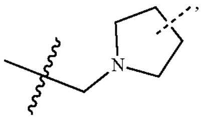
optionally substituted
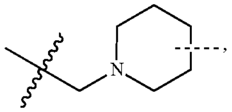
optionally substituted
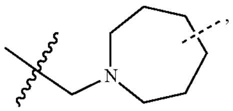
optionally substituted
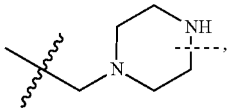

optionally substituted
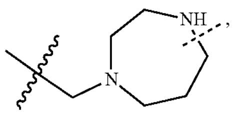
optionally substituted
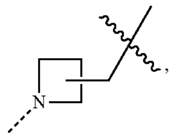
optionally substituted
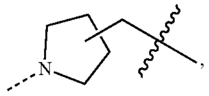
optionally substituted
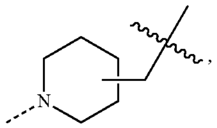
optionally substituted
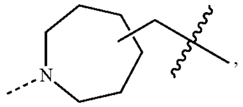
optionally substituted
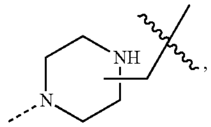
optionally substituted
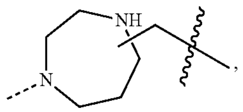
optionally substituted
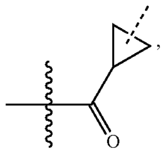
optionally substituted
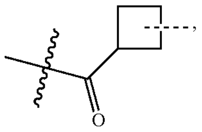
optionally substituted
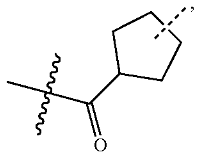
optionally substituted
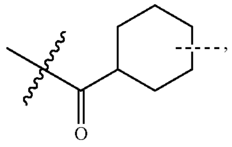
optionally substituted
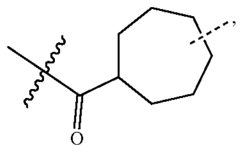
optionally substituted
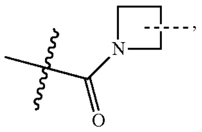

optionally substituted
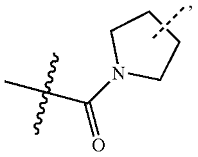
optionally substituted
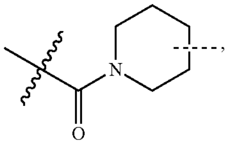
optionally substituted
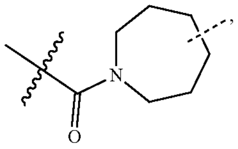
optionally substituted
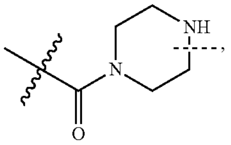
optionally substituted
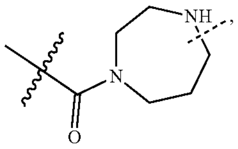
optionally substituted
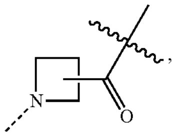
optionally substituted
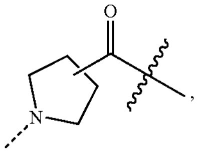
optionally substitute
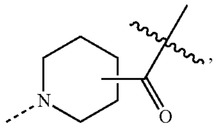
optionally substituted
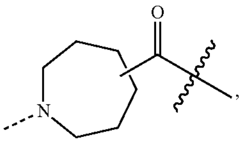
optionally substituted
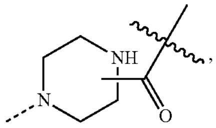
and optionally substituted
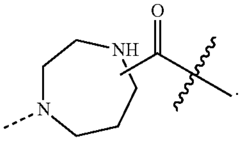
In some aspects of Formula 1, $R^3$ is selected from
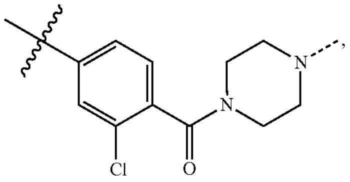
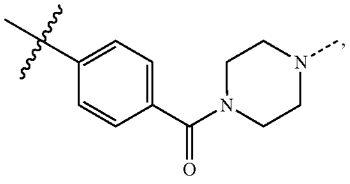

-continued
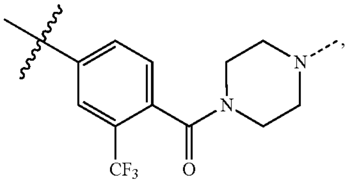
,
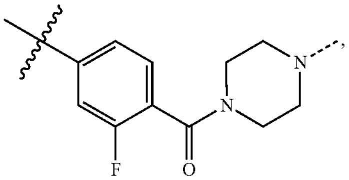
,
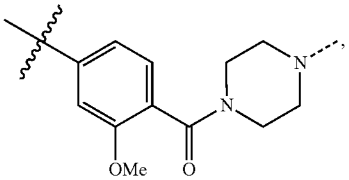
,
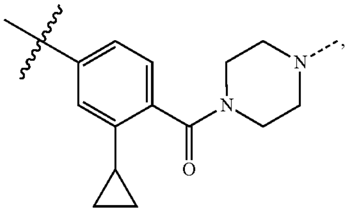
,
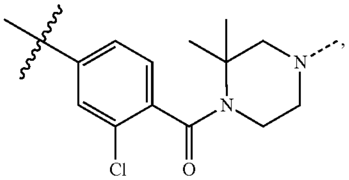
,
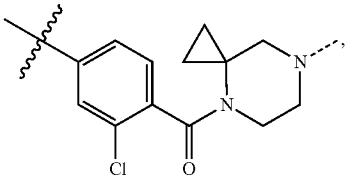
,
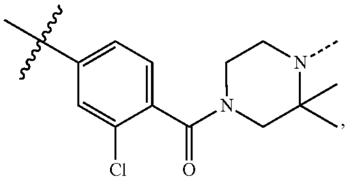
,
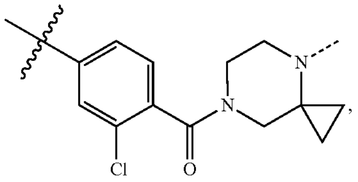
,
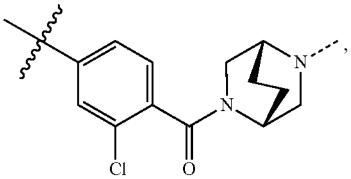
,
-continued
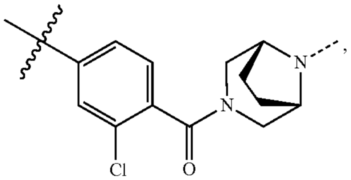
,
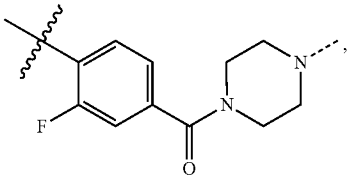
,
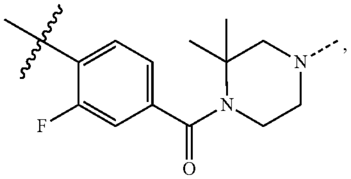
,
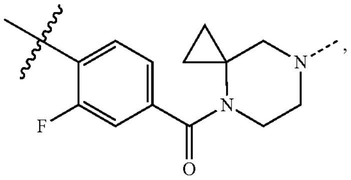
,
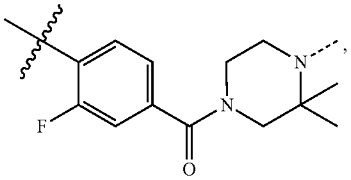
,
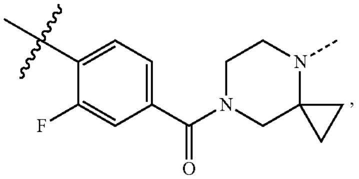
,
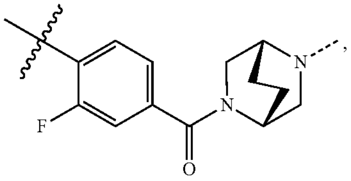
,
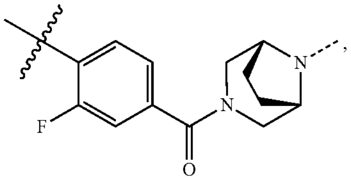
,
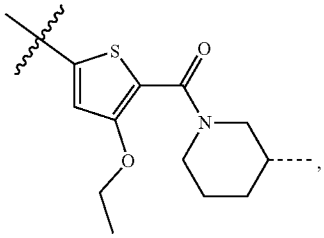
, -continued

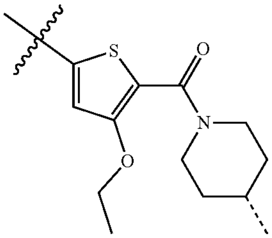

,

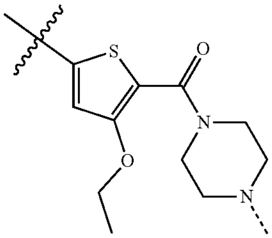

,

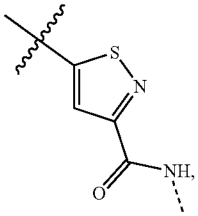

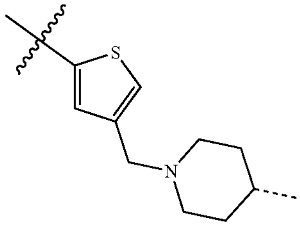

,

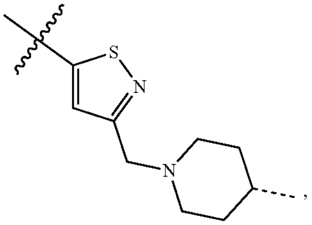

, and

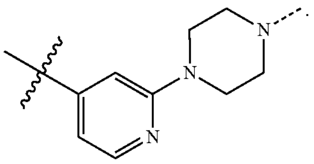

In some aspects of Formula 1, $R^3$ is selected from

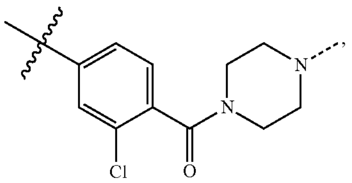

, and

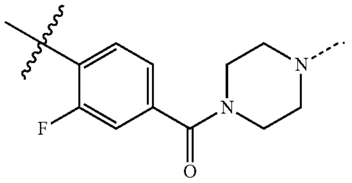

In some aspects of Formula 1, $R^3$ is

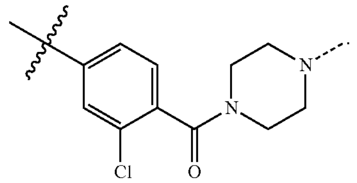

In some aspects of Formula 1, X is N.

PTK6 Ligands also include but are not limited to:

FORMULA 2

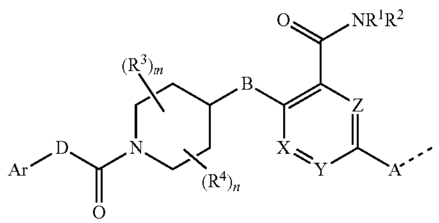

Wherein

X, Y and Z are independently selected from null, $CR^5$, and N, wherein $R^5$ is selected from hydrogen, halogen, or optionally substituted $C_{1-3}$ alkyl;

A is selected from null or —$R^6$—$R^7$—, wherein $R^6$ and $R^7$ are independently selected from null, $NR^8$, O, S, C(O), C(O)$NR^8$, $NR^8$C(O), $NR^8$C(O)$NR^9$, OC(O)$NR^9$, $NR^8$C(O)O, S(O), S(O)$NR^8$, $NR^8$S(O), $NR^8$S(O)$NR^9$, OS(O)$NR^9$, $NR^8$S(O)O, $S(O)_2$, $S(O)_2NR^8$, $NR^8S(O)_2$, $NR^8S(O)_2NR^9$, $OS(O)_2NR^9$, $NR^8S(O)_2O$, optionally substituted $C_1$-$C_8$ alkylene, optionally substituted $C_2$-$C_8$ alkenylene, optionally substituted $C_2$-$C_8$ alkynylene, optionally substituted 3-10 membered carbocyclyl, optionally substituted 4-10 membered heterocyclyl, optionally substituted aryl, and optionally substituted heteroaryl, wherein $R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$ alkyl, optionally substituted $C_1$-$C_8$alkylamino$C_1$-$C_8$ alkyl, optionally substituted 3-10 membered carbocyclyl$C_1$-$C_8$ alkyl, optionally substituted 4-10 membered heterocyclyl$C_1$-$C_8$alkyl, optionally substituted 3-10 membered carbocyclyl, optionally substituted 4-10 membered heterocyclyl, optionally substituted aryl, and optionally substituted heteroaryl, or $R^8$ and $R^9$ together with the atom to which they are connected form a 4-20 membered heterocyclyl ring;

B and D are independently selected from $CR^{10}R^{11}$, $NR^{10}$, O, SO, or $SO_2$, wherein $R^{10}$ and $R^{11}$ are independently selected from hydrogen, halogen, hydroxy, cyano, nitro, and optionally substituted $C_1$-$C_3$ alkyl, or $R^{10}$ and $R^{11}$ together with the atom to which they are connected form a 3-6 membered carbocyclyl rings or 4-6 membered heterocyclyl ring;

$R^1$ and $R^2$ are independently selected from hydrogen, and optionally substituted $C_1$-$C_3$ alkyl, or $R^1$ and $R^2$ together with the atom to which they are connected form a 4-6 membered heterocyclyl ring;

$R^3$ and $R^4$, at each occurrence, are independently selected from hydrogen, fluoro, hydroxyl, cyano, amino, nitro, optionally substituted $C_1$-$C_3$ alkyl, optionally substituted $C_1$-$C_3$ alkoxy, and optionally substituted $C_1$-$C_3$ alkylamino.

m and n are independently selected from 0, 1, 2, 3, and 4.

Ar is selected from aryl, and heteroaryl, which are optionally substituted with one or more substituents independently selected from hydrogen, halogen, oxo, CN, $NO_2$, $OR^{12}$, $SR^{12}$, $NR^{12}R^{13}$, $OCOR^{12}$, $OCO_2R^{12}$, $OCON(R^{12})R^{13}$, $COR^{12}$, $CO_2R^{12}$, $CON(R^{12})R^{13}$, $SOR^{12}$, $SO_2R^{12}$, $SO_2N(R^{12})R^{13}$, $NR^4CO_2R^{12}$, $NR^4COR^{12}$, $NR^4C(O)N(R^{12})R^3$, $NR^{14}SOR^{12}$, $NR^{14}SO_2R^{12}$, $NR^{14}SO_2N(R^{12})R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$ alkyl, optionally substituted $C_1$-$C_8$alkylamino$C_1$-$C_8$ alkyl, optionally substituted 4-10 membered heterocyclyl$C_1$-$C_8$alkyl, optionally substituted 3-10 membered carbocyclyl$C_1$-$C_8$ alkyl, optionally substituted 3-10 membered carbocyclyl, optionally substituted 4-10 membered heterocyclyl, optionally substituted aryl, and optionally substituted heteroaryl, wherein $R^{12}$, $R^{13}$, and $R^{14}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$ alkyl, optionally substituted $C_1$-$C_8$alkylamino$C_1$-$C_8$ alkyl, optionally substituted 3-10 membered carbocyclyl$C_1$-$C_8$ alkyl, optionally substituted 4-10 membered heterocyclyl$C_1$-$C_8$ alkyl, optionally substituted 3-10 membered carbocyclyl, optionally substituted 4-10 membered heterocyclyl, optionally substituted aryl, and optionally substituted heteroaryl, or $R^1$ and $R^{13}$, $R^1$ and $R^{14}$ together with the atom to which they are connected form a 4-20 membered heterocyclyl ring;

In some aspects of Formula 2, X, Y and Z are independently selected from CH, CF, and N.

In some aspects of Formula 2, X is N; Y and Z are independently selected from CH, CF, and N.

In some aspects of Formula 2, X is N; Y and Z are CH.

In some aspects of Formula 2, A is null or selected from optionally substituted 3-8 membered carbocyclyl, optionally substituted 4-8 membered heterocyclyl, optionally substituted 6 membered aryl, optionally substituted 5-6 membered heteroaryl, fused rings, bridged rings, and spiro rings.

In some aspects of Formula 2, A is null, phenyl, 4-8 membered heterocyclyl, and 5-6 membered heteroaryl, which are optionally substituted by F, OH, CN, $NO_2$, $NH_2$, optionally substituted $C_1$-$C_6$ alkyl, optionally substituted $C_1$-$C_6$ alkoxy, optionally substituted 3-10 membered carbocyclyl, optionally substituted 4-10 membered heterocyclyl, optionally substituted aryl, and optionally substituted heteroaryl.

In some aspects of Formula 2, A is null, phenyl, 4-8 membered heterocyclyl, and 5-6 membered heteroaryl, which are optionally substituted by F, OH, CN, $NO_2$, $NH_2$, $CH_3$, $CF_3$, i-Pr, and c-Pr.

In some aspects of Formula 2, A is

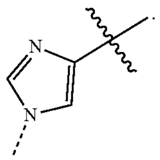

In some aspects of Formula 2, B and D are independently selected from $CH_2$, CHOH, $CHCH_3$, $C(CH_3)_2$,

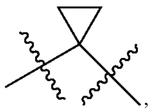

CHF, $CF_2$, O, NH, and $NCH_3$.

In some aspects of Formula 2, B is O.

In some aspects of Formula 2, D is $CH_2$.

In some aspects of Formula 2, $R^1$ and $R^2$ are independently selected from H, and optionally substituted $C_1$-$C_3$ alkyl, with the proviso that at least one of $R^1$ and $R^2$ is H.

In some aspects of Formula 2, $R^1$ and $R^2$ are independently selected from H, and $CH_3$, with the proviso that at least one of $R^1$ and $R^2$ is H.

In some aspects of Formula 2, $R^1$ and $R^2$ are H.

In some aspects of Formula 2, $R^3$ and $R^4$, at each occurrence, are independently selected from H, F, OH, CN, $NH_2$, $NO_2$, $CH_3$, $CH_2F$, $CHF_2$, $CF_3$, i-Pr, and c-Pr.

In some aspects of Formula 2, $R^3$ and $R^4$, at each occurrence, are independently selected from H, and F.

In some aspects of Formula 2, m and n are independently selected from 0, 1, and 2.

In some aspects of Formula 2, m and n are 1.

In some aspects of Formula 2, Ar is selected from aryl, and heteroaryl, which are optionally substituted with one or more substituents independently selected from H, F, =O, CN, $NO_2$, $CH_3$, $OCH_3$, $CH_2F$, $CHF_2$, $CF_3$, $OCH_2F$, $OCHF_2$, $OCF_3$, i-Pr, and c-Pr.

In some aspects of Formula 2, Ar is phenyl, which is optionally substituted with one or more substituents independently selected from H, F, =O, CN, $NO_2$, $CH_3$, $OCH_3$, $CH_2F$, $CHF_2$, $CF_3$, $OCH_2F$, $OCHF_2$, $OCF_3$, i-Pr, and c-Pr.

In some aspects of Formula 2, Ar is 4-$OCF_3$ substituted phenyl.

In some aspects, the PTK6 ligand may be a derivative of following compounds:

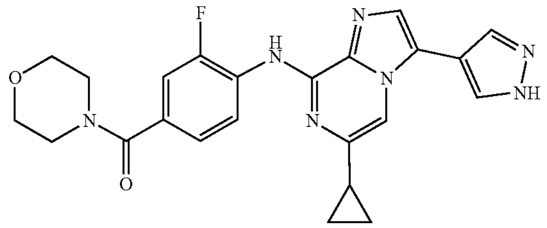
Compound 21d
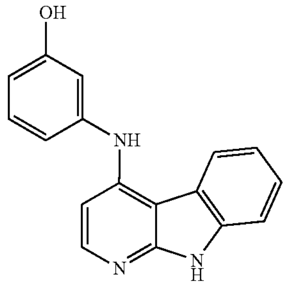
Compound 4f
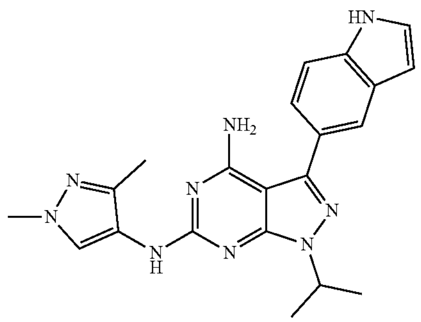
Compound 1
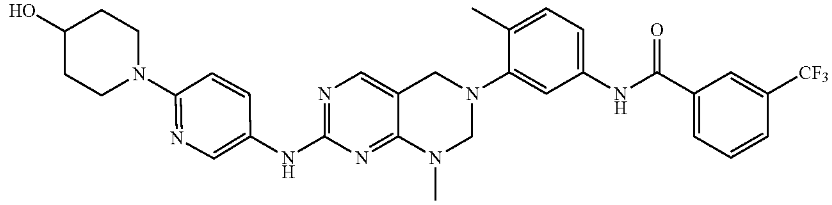
XMU-MP-2
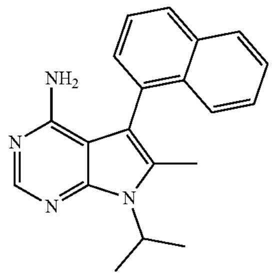
XMU-MP-2

-continued
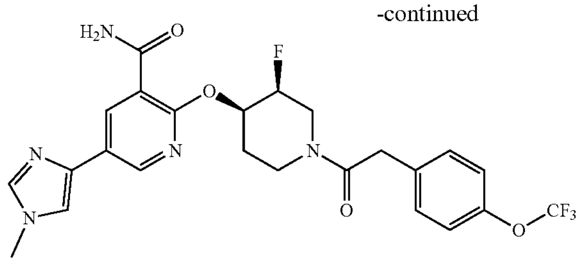
PF-6698840
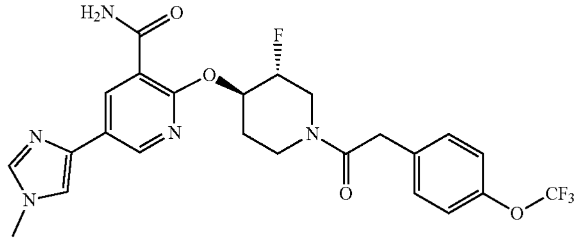
PF-6698840
In some aspects, the PTK6 ligand can be, e.g.:
FORMULA 2A
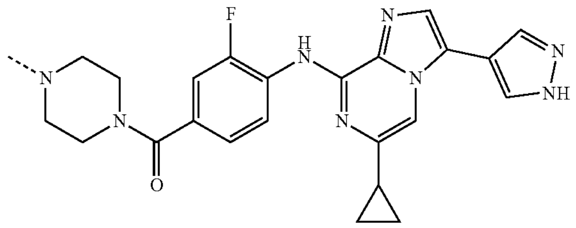
FORMULA 2B
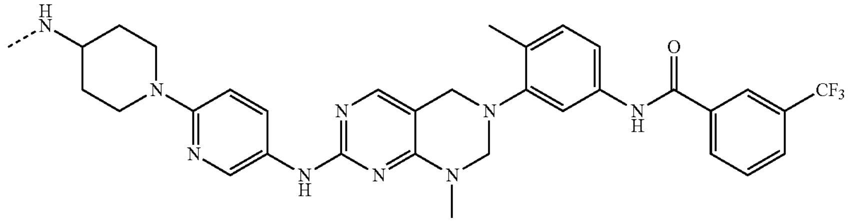
FORMULA 2C
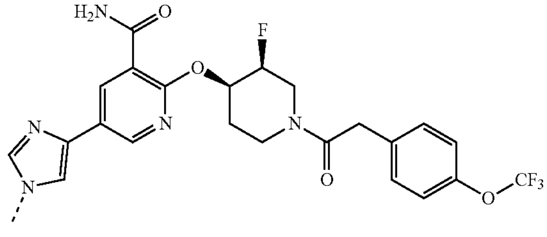
FORMULA 2D
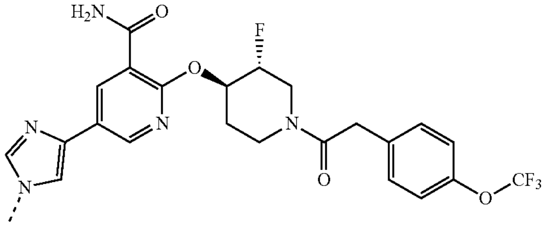

The PTK6 ligand can be bound to PTK6 and/or PTK6 mutant proteins.

Degradation/Disruption Tags

Degradation/Disruption Tags (EL) include but are not limited to:

FORMULA 3A

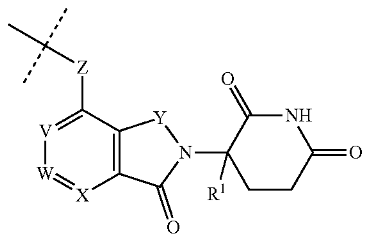

FORMULA 3B

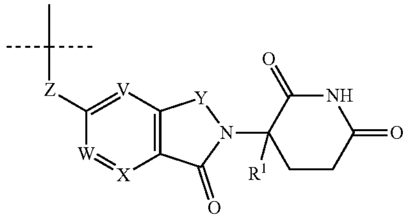

FORMULA 3C

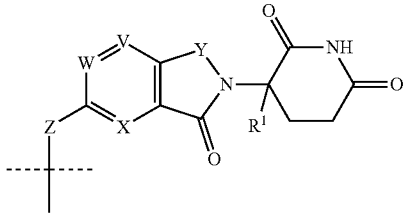

FORMULA 3D

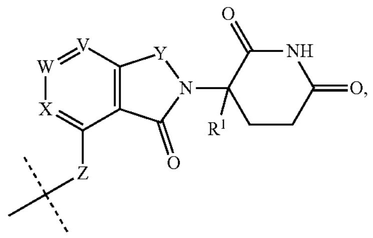

wherein

V, W, and X are independently selected from $CR^2$ and N;

Y is selected from CO, $CR^3R^4$, and N═N,

Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{10}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferly, Z is selected from null, $CH_2$, CH═CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

FORMULA 3A

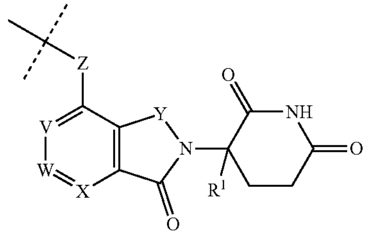

FORMULA 3B

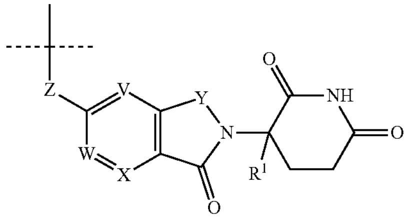

FORMULA 3C

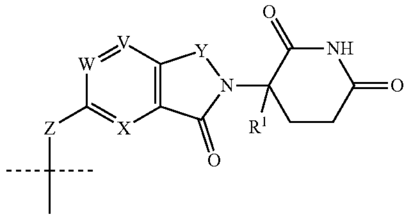

FORMULA 3D

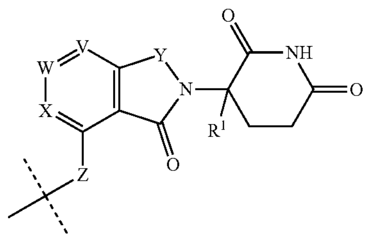

wherein

V, W, and X are independently $CR^2$ or N,

Y is CO or $CH_2$,

Z is $CH_2$, NH, or O, $R^1$ is hydrogen, methyl, or fluoro, and $R^2$ is hydrogen, halogen, or $C_1$-$C_8$ alkyl;

FORMULA 3E

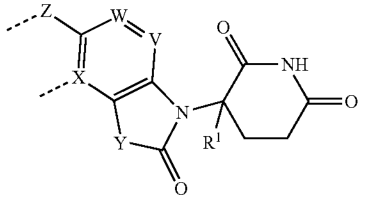

FORMULA 3F

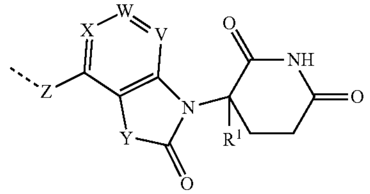

FORMULA 3G

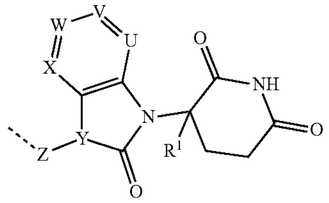

FORMULA 3H

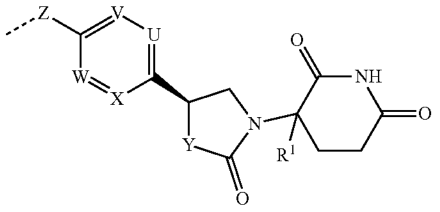

FORMULA 3I

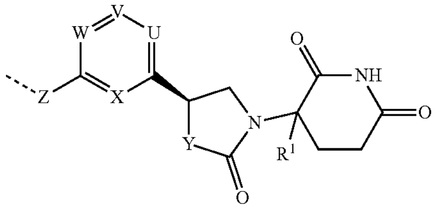

wherein

U, V, W, and X are independently selected from $CR^2$ and N;

Y is selected from $CR^3R^4$, $NR^3$ and O; preferly, Y is selected from $CH_2$, NH, $NCH_3$ and O;

Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferly, Z is selected from null, $CH_2$, CH═CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

FORMULA 4A

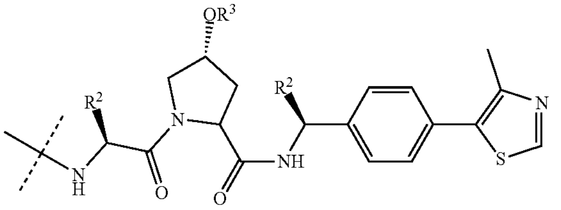

wherein $R^1$ and $R^2$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_1$-$C_8$ aminoalkyl, $C_1$-$C_8$ alkylaminoalkyl, $C_3$-$C_7$ cycloalkyl, $C_3$-$C_7$ heterocyclyl, $C_2$-$C_8$ alkenyl, or $C_2$-$C_8$ alkynyl;

$R^3$ is H, C(O)$C_1$-$C_8$ alkyl, C(O)$C_1$-$C_8$ alkoxyalkyl, C(O)$C_1$-$C_8$ haloalkyl, C(O)$C_1$-$C_8$ hydroxyalkyl, C(O)$C_1$-$C_8$ aminoalkyl, C(O)$C_1$-$C_8$ alkylaminoalkyl, C(O)$C_3$-$C_7$ cycloalkyl, C(O)$C_3$-$C_7$ heterocyclyl, C(O)$C_2$-$C_8$ alkenyl, C(O)$C_2$-$C_8$ alkynyl, C(O)O$C_1$-$C_8$ alkoxyalkyl, C(O)O$C_1$-$C_8$ haloalkyl, C(O)O$C_1$-$C_8$ hydroxyalkyl, C(O)O$C_1$-$C_8$ aminoalkyl, C(O)O$C_1$-$C_8$ alkylaminoalkyl, C(O)O$C_3$-$C_7$ cycloalkyl, C(O)O$C_3$-$C_7$ heterocyclyl, C(O)O$C_2$-$C_8$ alkenyl, C(O)O$C_2$-$C_8$ alkynyl, C(O)N$C_1$-$C_8$ alkoxyalkyl, C(O)N$C_1$-$C_8$ haloalkyl, C(O)N$C_1$-$C_8$ hydroxyalkyl, C(O)N$C_1$-$C_8$ aminoalkyl, C(O)N$C_1$-$C_8$ alkylaminoalkyl, C(O)N$C_3$-$C_7$ cycloalkyl, C(O)N$C_3$-$C_7$ heterocyclyl, C(O)N$C_2$-$C_8$ alkenyl, C(O)N$C_2$-$C_8$ alkynyl, $P(O)(OH)_2$, P(O)(O$C_1$-$C_8$ alkyl)$_2$, or P(O)(O$C_1$-$C_8$ aryl)$_2$,

FORMULA 4B

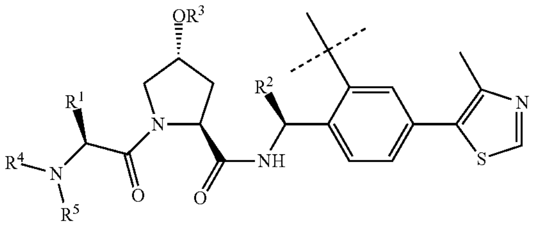

-continued

FORMULA 4C

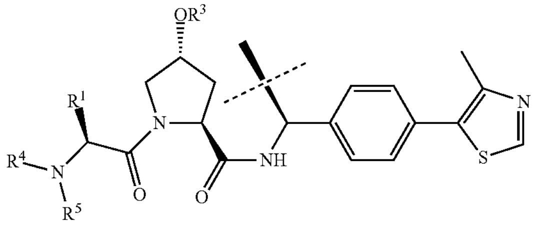

FORMULA 4D

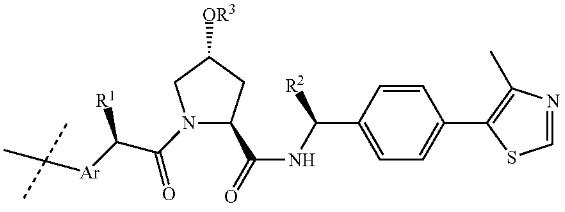

FORMULA 4E

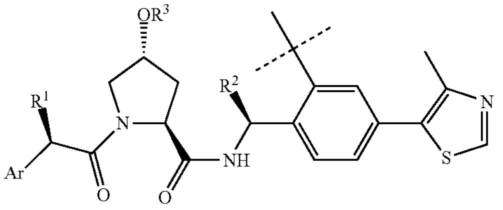

FORMULA 4F

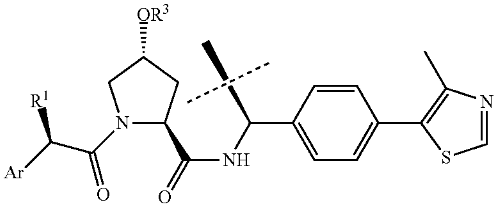

wherein $R^1$ and $R^2$ are independently selected from hydrogen, halogen, OH, $NH_2$, CN, optionally substituted $C_1$-$C_8$ alkyl, optionally substituted $C_1$-$C_8$alkoxy$C_1$-$C_8$ alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$ alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; (preferably, $R^1$ is selected from iso-propyl or tert-butyl; and $R^2$ is selected from hydrogen or methyl);

$R^3$ is hydrogen, optionally substituted C(O)$C_1$-$C_8$ alkyl, optionally substituted C(O)$C_1$-$C_8$alkoxy$C_1$-$C_8$ alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$ alkyl, optionally substituted C(O)$C_3$-$C_7$ cycloalkyl, optionally substituted C(O)(3-7 membered heterocyclyl), optionally substituted C(O)$C_2$-$C_8$ alkenyl, optionally substituted C(O)$C_2$-$C_8$ alkynyl, optionally substituted C(O)O$C_1$-$C_8$alkoxy$C_1$-$C_8$ alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$ aminoalkyl, optionally substituted C(O)O$C_1$-$C_8$alkylamino$C_1$-$C_8$ alkyl, optionally substituted C(O)O$C_3$-$C_7$ cycloalkyl, optionally substituted C(O)O(3-7 membered heterocyclyl), optionally substituted C(O)O$C_2$-$C_8$ alkenyl, optionally substituted C(O)O$C_2$-$C_8$ alkynyl, optionally substituted C(O)N$C_1$-$C_8$alkoxy$C_1$-$C_8$ alkyl, optionally substituted C(O)N$C_1$-$C_8$ haloalkyl, optionally substituted C(O)N$C_1$-$C_8$ hydroxyalkyl, optionally substituted C(O)N$C_1$-$C_8$ aminoalkyl, optionally substituted C(O)N$C_1$-$C_8$alkylamino$C_1$-$C_8$ alkyl, optionally substituted C(O)N$C_3$-$C_7$ cycloalkyl, optionally substituted C(O)N(3-7 membered heterocyclyl), optionally substituted C(O)N$C_2$-$C_8$ alkenyl, optionally substituted C(O)N$C_2$-$C_8$ alkynyl, optionally substituted $P(O)(OH)_2$, optionally substituted P(O)(O$C_1$-$C_8$ alkyl$)_2$, and optionally substituted P(O)(O$C_1$-$C_8$ aryl$)_2$; and $R^4$ and $R^5$ are independently selected from hydrogen, $COR^6$, $CO_2R^6$, $CONR^6R^7$, $SOR^6$, $SO_2R^6$, $SO_2NR^6R^7$, optionally substituted $C_1$-$C_8$ alkyl, optionally substituted $C_1$-$C_8$alkoxy$C_1$-$C_8$ alkyl, optionally substituted $C_1$-$C_8$alkylamino$C_1$-$C_8$ alkyl, optionally substituted 3-8 membered cycloalkyl, optionally substituted 3-8 membered heterocyclyl, optionally substituted aryl, and optionally substituted heteroaryl, wherein $R^6$ and $R^7$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$ alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl, or $R^4$ and $R^5$; $R^6$ and $R^7$ together with the atom to which they are connected form a 4-8 membered cycloalkyl or heterocyclyl ring;

Ar is selected from aryl and heteroaryl, each of which is optionally substituted with one or more substituents independently selected from F, Cl, CN, $NO_2$, $OR^8$, $NR^8R^9$, $COR^8$, $CO_2R^8$, $CONR^8R^9$, $SOR^8$, $SO_2R^8$, $SO_2NR^9R^{10}$, $NR^9COR^{10}$, $NR^8C(O)NR^9R^{10}$, $NR^9SOR^{10}$, $NR^9SO_2R^{10}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl, wherein $R^8$, $R^9$, and $R^{10}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl, or $R^8$ and $R^9$; $R^9$ and $R^{10}$ together with the atom to which they are connected form a 4-8 membered cycloalkyl or heterocyclyl ring.

FORMULA 5A

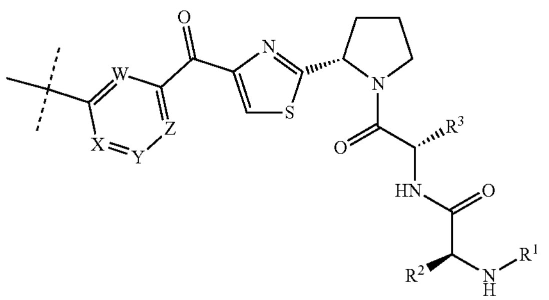

wherein $R^1$, $R^2$, $R^3$, and $R^4$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_3$-$C_2$ cycloalkyl, $C_3$-$C_7$ heterocyclyl, $C_2$-$C_8$ alkenyl, or $C_2$-$C_8$ alkynyl, and V, W, X, and Z are independently $CR^4$ or N.

And

FORMULA 5B

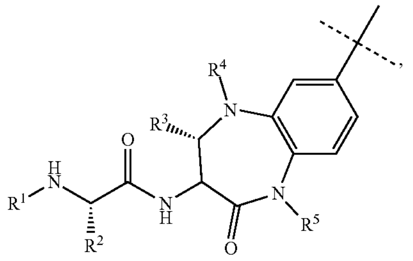

wherein $R^1$, $R^2$, and $R^3$ are independently selected from hydrogen, halogene, optionally substituted $C_1$-$C_8$ alkyl, optionally substituted $C_1$-$C_8$alkoxy$C_1$-$C_8$ alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl;

$R^4$ and $R^5$ are independently selected from hydrogen, $COR^6$, $CO_2R^6$, $CONR^6R^7$, $SOR_6$, $SO_2R^6$, $SO_2NR^6R^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$ alkyl, optionally substituted aryl-$C_1$-$C_8$alkyl, optionally substituted 3-8 membered cycloalkyl, optionally substituted 3-8 membered heterocyclyl, optionally substituted aryl, and optionally substituted heteroaryl, wherein $R^6$ and $R^7$ are independently selected from hydrogen, optionally substituted $C_1$-$C_8$ alkyl, optionally substituted $C_1$-$C_8$alkoxy$C_1$-$C_8$ alkyl, optionally substituted $C_1$-$C_8$alkylamino$C_1$-$C_8$ alkyl, optionally substituted 3-8 membered cycloalkyl, optionally substituted 3-8 membered heterocyclyl, optionally substituted aryl, and optionally substituted heteroaryl, or $R^6$ and $R^7$ together with the atom to which they are connected form a 4-8 membered cycloalkyl or heterocyclyl ring.

In some aspects, the degradation/disruption tag can be, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl) sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), FK506 (Liu et al., 1991) rapamycin (Fan et al., 2017; Rodrik-Outmezguine et al., 2016) and/or analogs thereof.

In some aspects, the degradation/disruption tag can be, e.g., one of the following structures:

FORMULA 6A

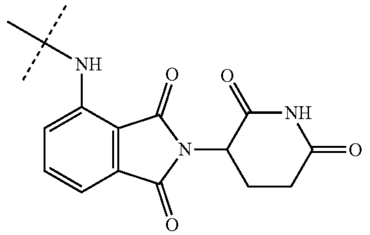

FORMULA 6B

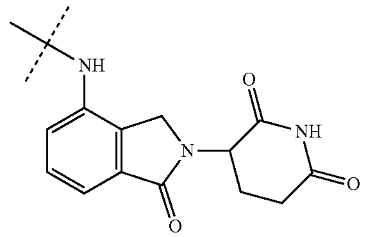

FORMULA 6C

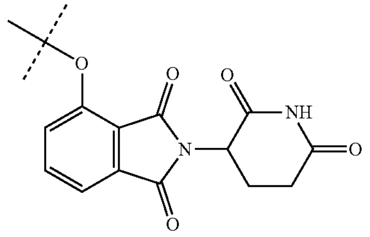

FORMULA 6D

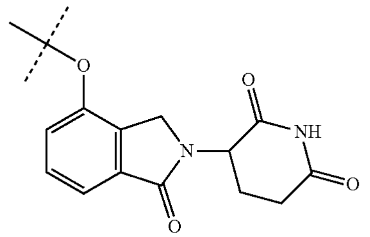

FORMULA 6E

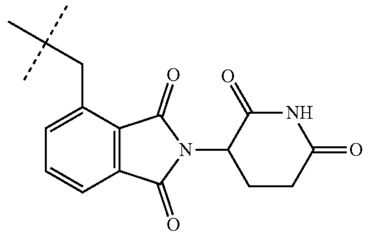

-continued
FORMULA 6F
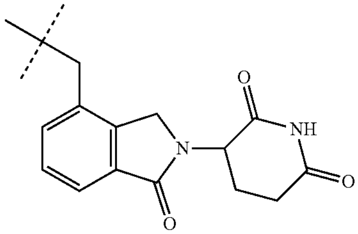
FORMULA 6G
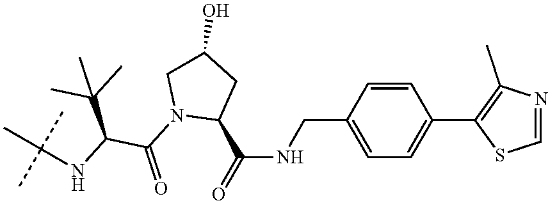
FORMULA 6H
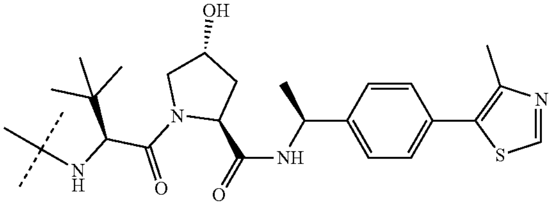
FORMULA 6I
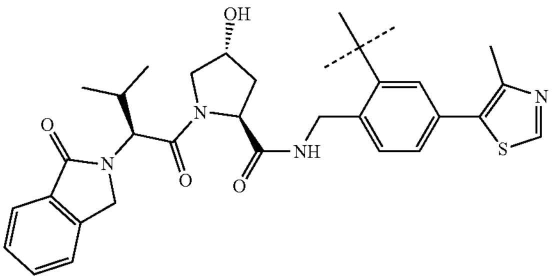
FORMULA 6J
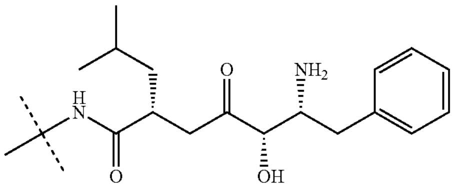
FORMULA 6K
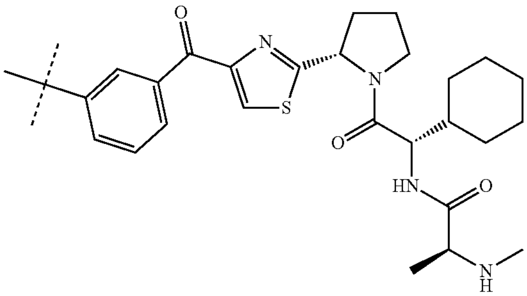
-continued
FORMULA 6L
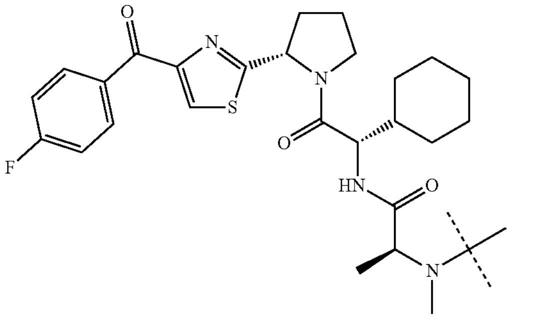
FORMULA 6M
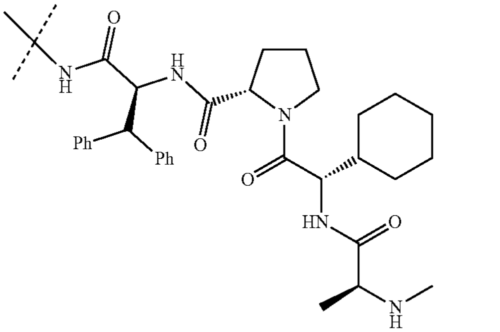
FORMULA 6N
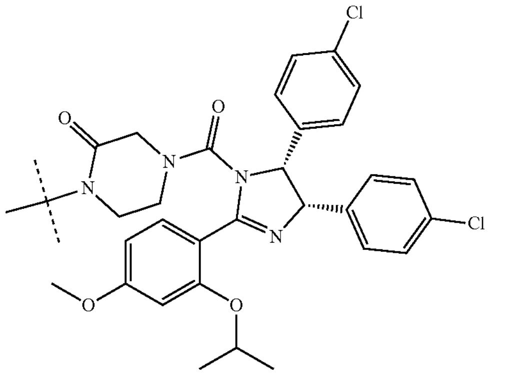
FORMULA 6O
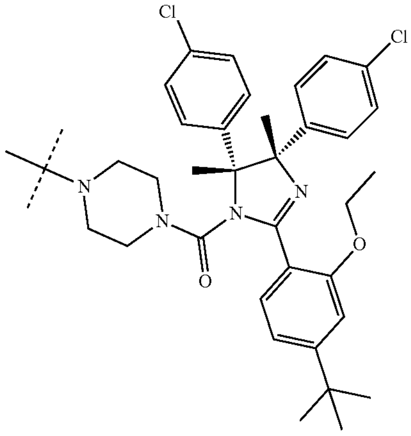

-continued
FORMULA 6P
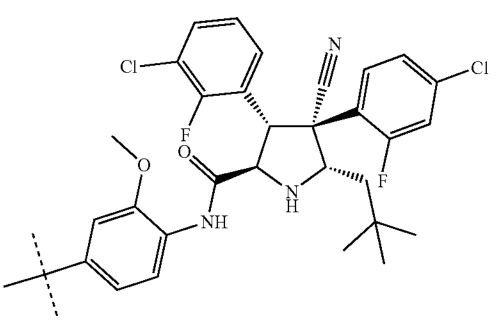
FORMULA 6Q
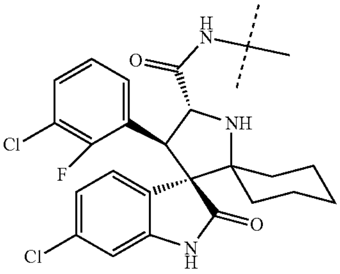
FORMULA 6R
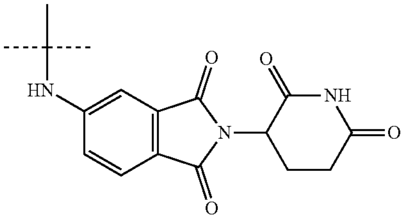
FORMULA 6S
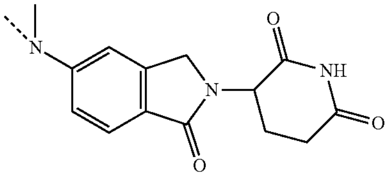
FORMULA 6T
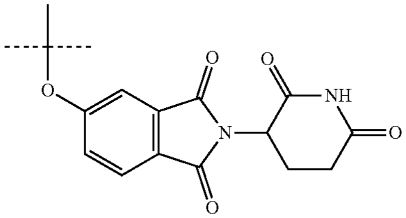
FORMULA 6U
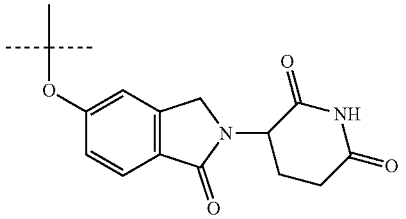
-continued
FORMULA 6V
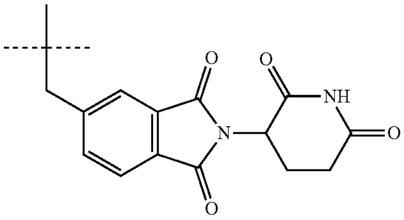
FORMULA 6W
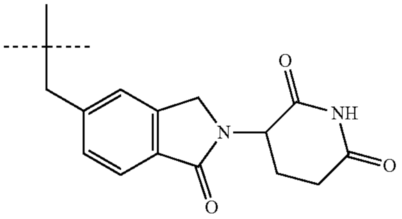
FORMULA 6X
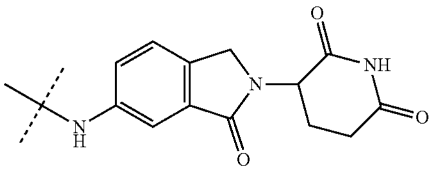
FORMULA 6Y
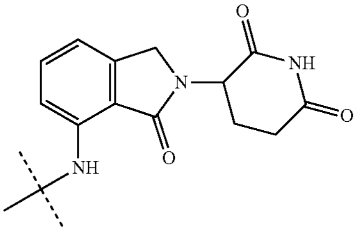
FORMULA 6Z
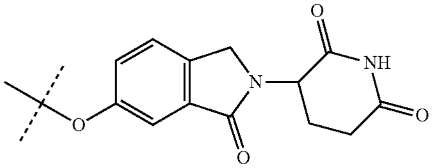
FORMULA 6AA
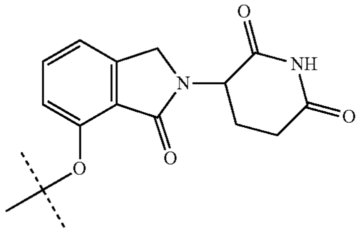
FORMULA 6AB
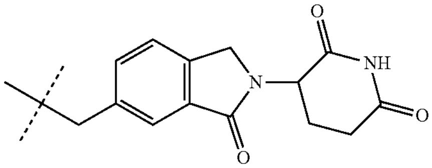

-continued
FORMULA 6AC
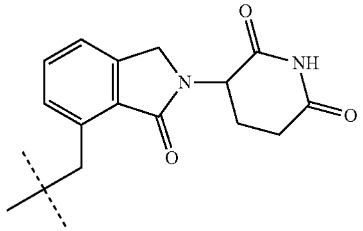
FORMULA 6AD
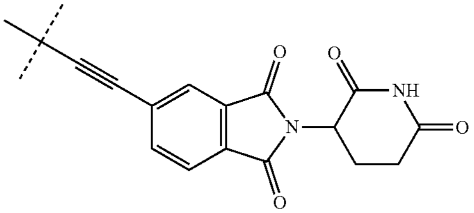
FORMULA 6AE
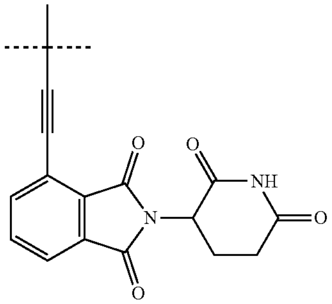
FORMULA 6AF
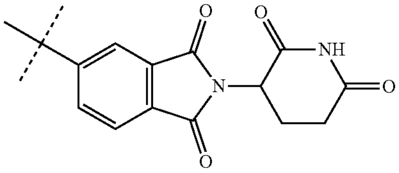
FORMULA 6AG
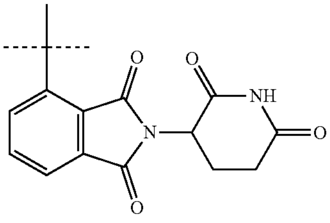
FORMULA 6AH
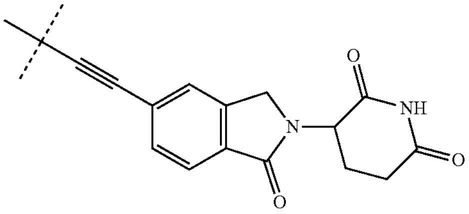
-continued
FORMULA 6AI
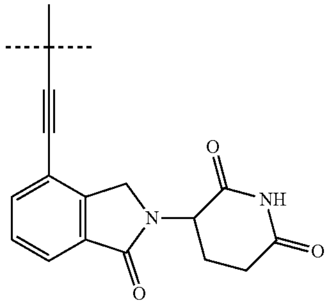
FORMULA 6AJ
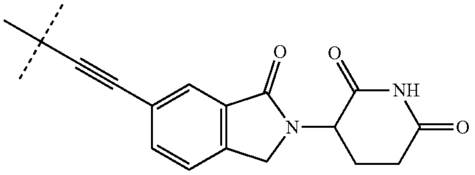
FORMULA 6AK
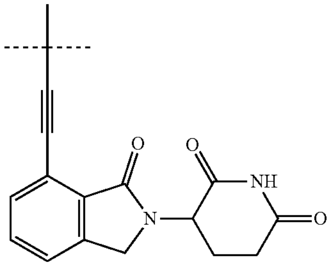
FORMULA 6AL
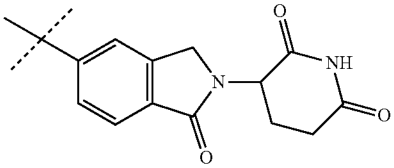
FORMULA 6AM
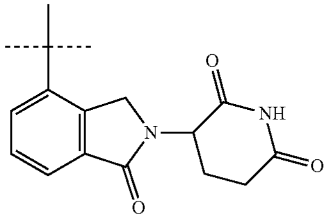
FORMULA 6AN
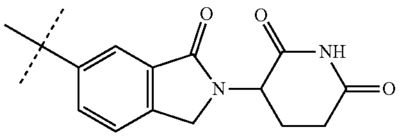
FORMULA 6AO
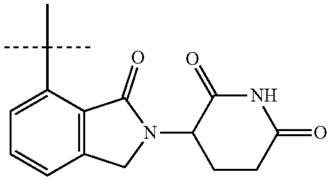

-continued
FORMULA 6AP
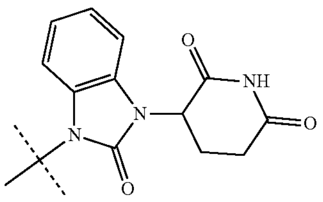
FORMULA 6AQ
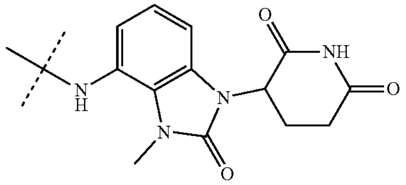
FORMULA 6AR
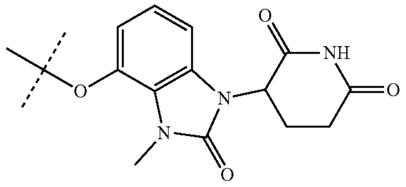
FORMULA 6AS
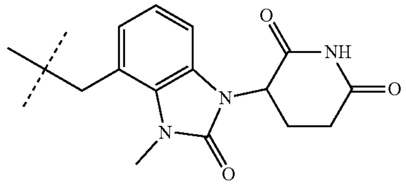
FORMULA 6AT
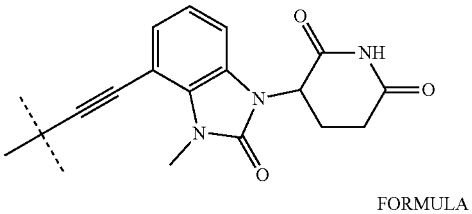
FORMULA 6AU
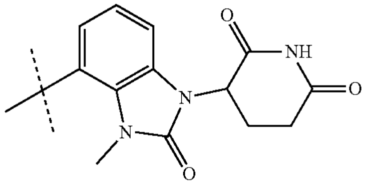
FORMULA 6AV
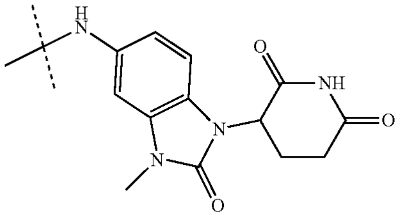
-continued
FORMULA 6AW
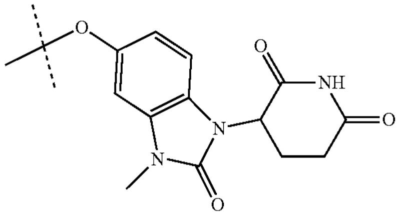
FORMULA 6AX
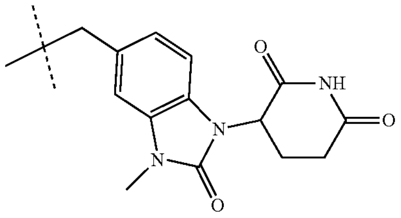
FORMULA 6AY
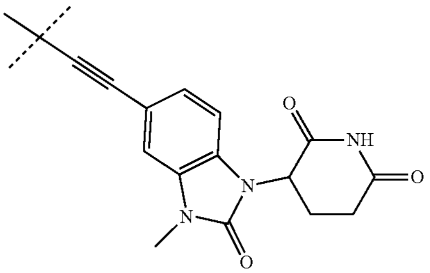
FORMULA 6AZ
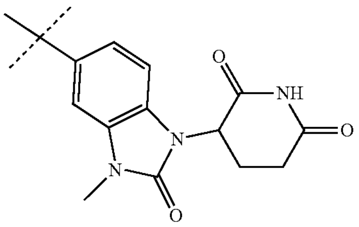
FORMULA 6BA
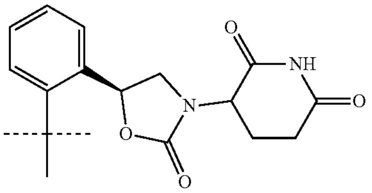
FORMULA 6BB
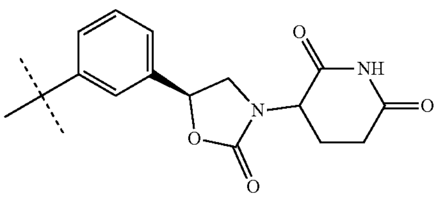

-continued
FORMULA 6BC
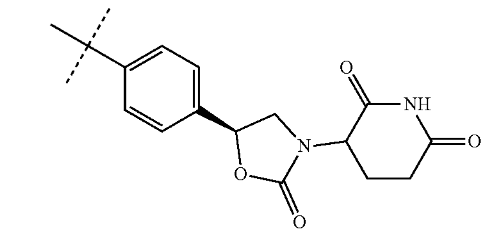
FORMULA 6BD
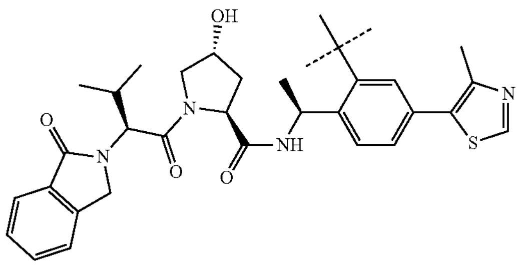
FORMULA 6BE
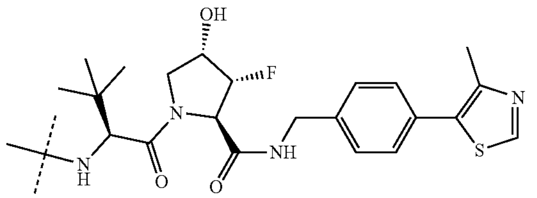
FORMULA 6BF
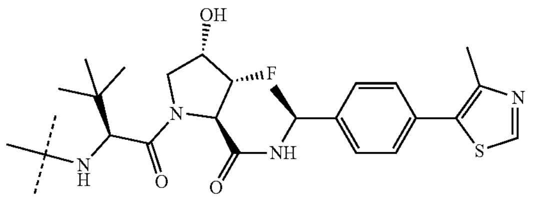
FORMULA 6BG
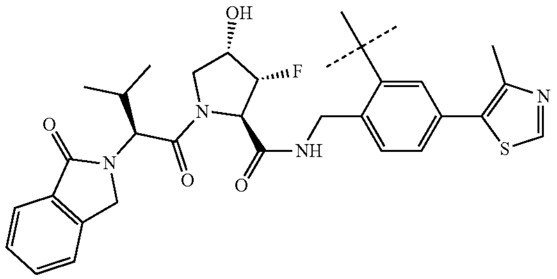
FORMULA 6BH
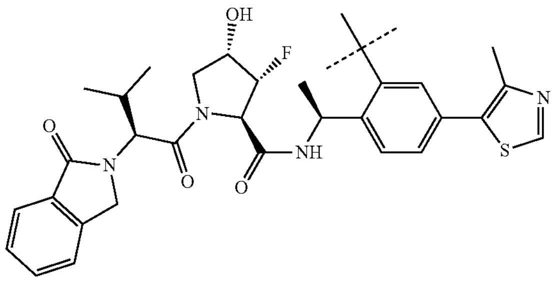
-continued
FORMULA 6BI
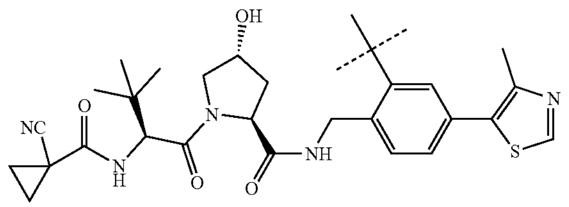
FORMULA 6BJ
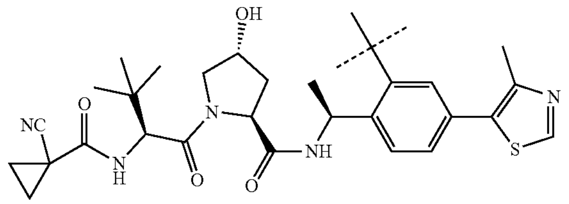
FORMULA 6BK
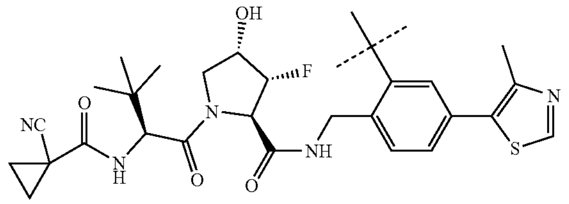
FORMULA 6BL
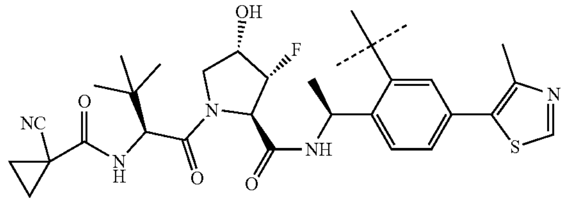
FORMULA 6BM
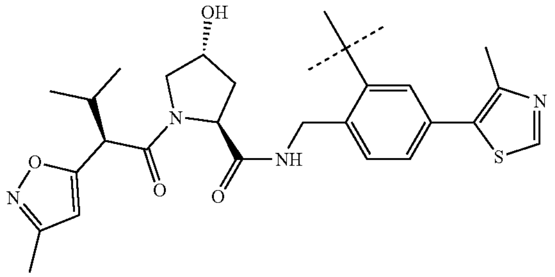
FORMULA 6BN
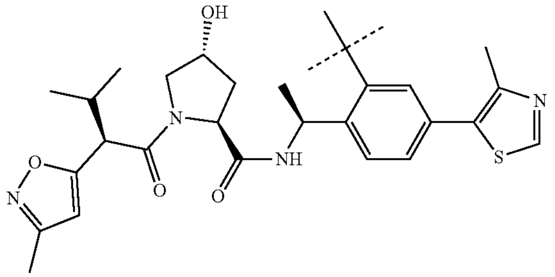

-continued
FORMULA 6BO
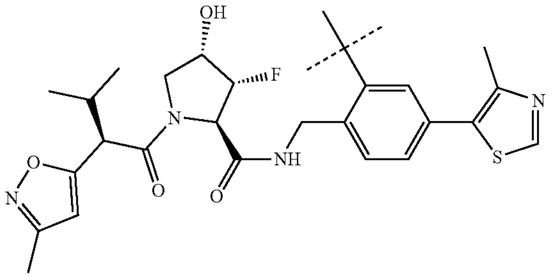
FORMULA 6BP
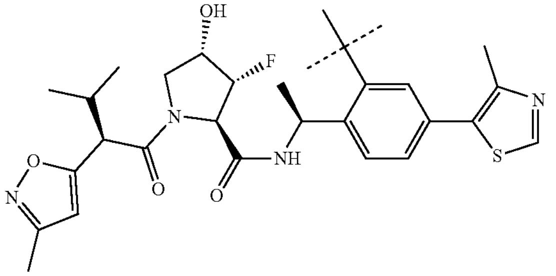
FORMULA 6BQ
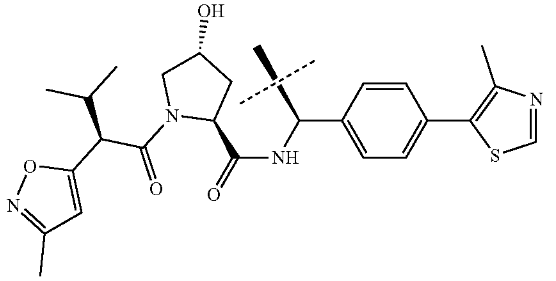
FORMULA 6BR
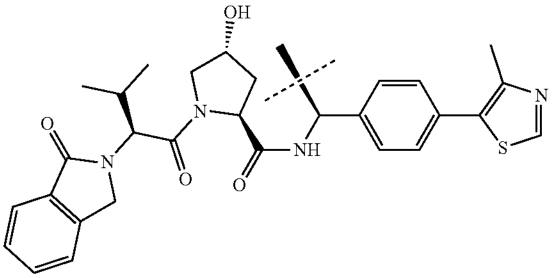
FORMULA 6BS
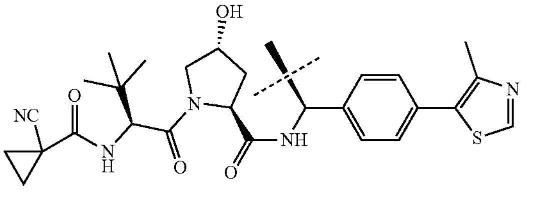
-continued
FORMULA 6BT
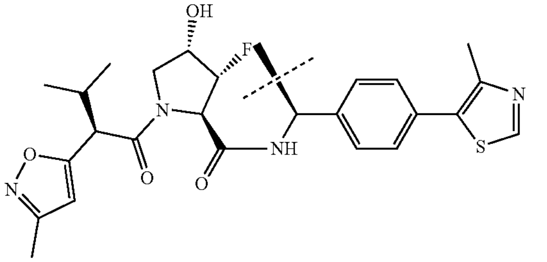
FORMULA 6BU
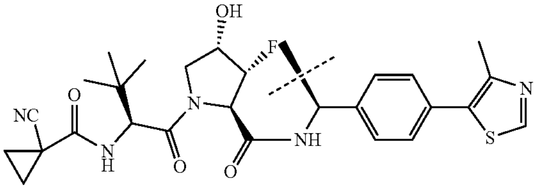
FORMULA 6BV
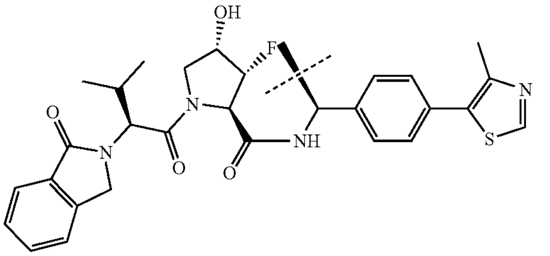
FORMULA 6BW
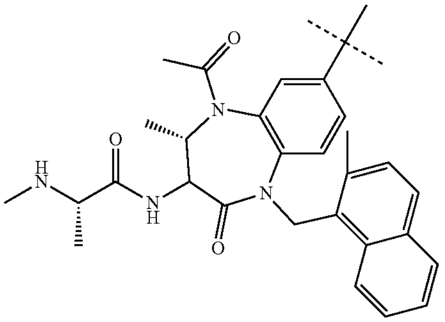
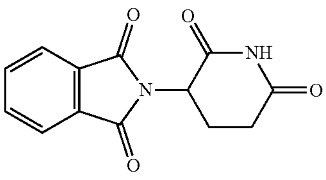
thalidomide
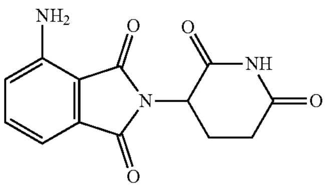
pomalidomide -continued
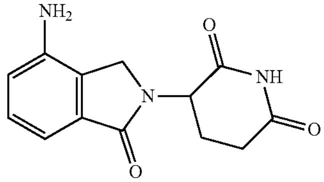
lenalidomide
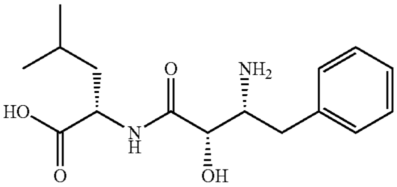
bestatin
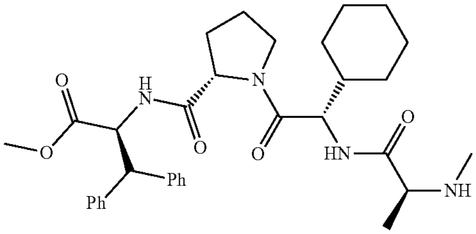
MVI
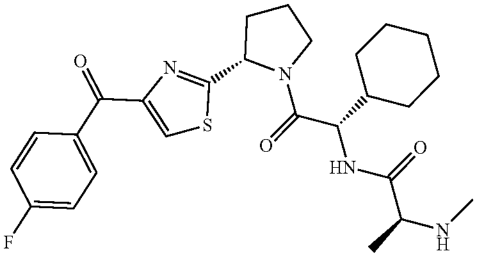
LCL161
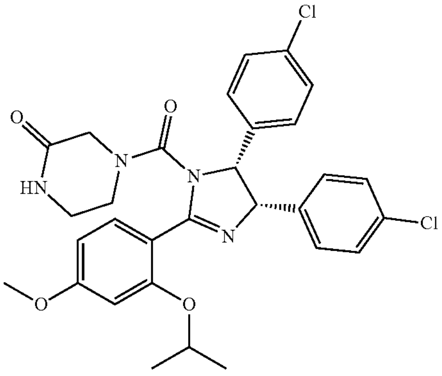
nutlin-3a
-continued
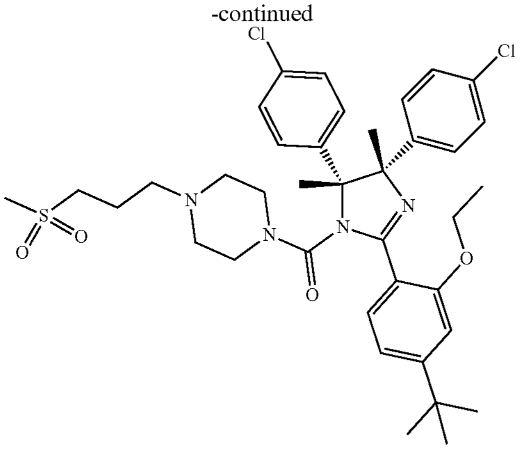
RG7112
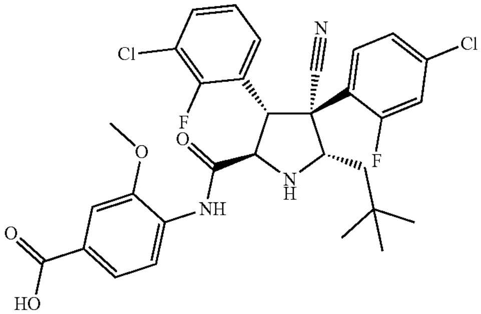
RG7338
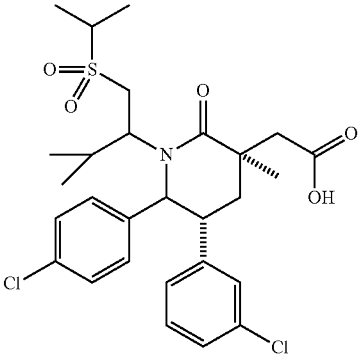
AMG232
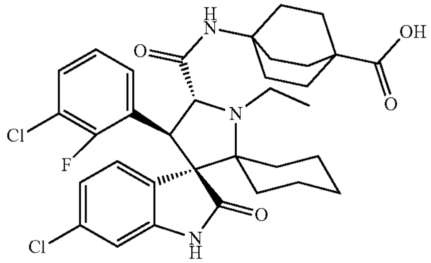
AA-115
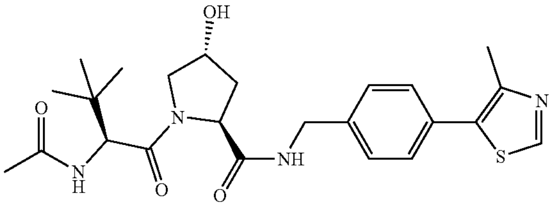
VH032

-continued

Compound W1

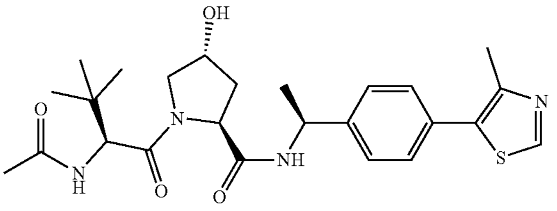

Compound W2

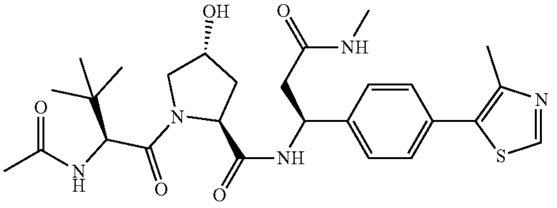

Compound W3

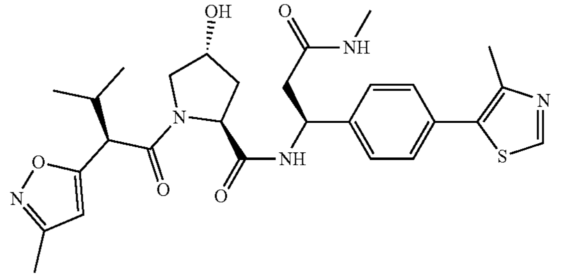

Compound W4

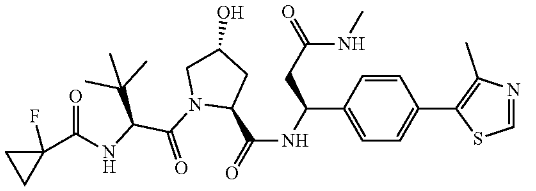

Compound W5

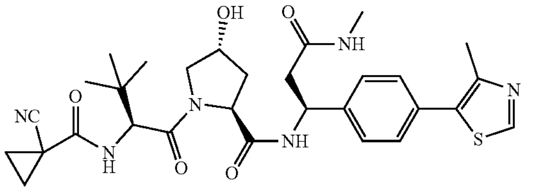

Compound W6

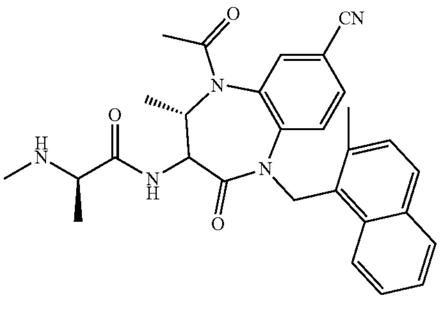

-continued

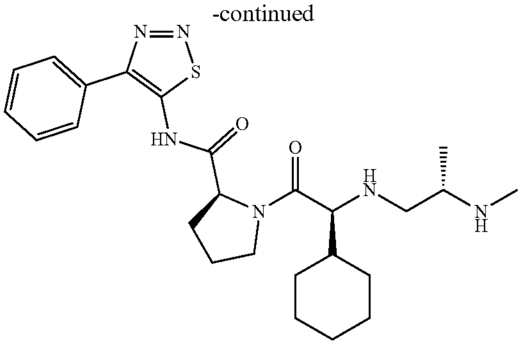

GDC-0152

Compound W7

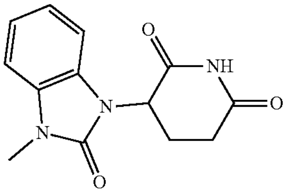

Compound W8

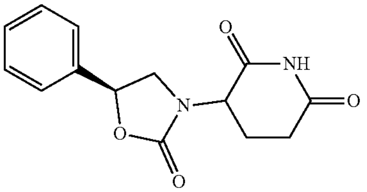

In some aspects, the degradation/disruption tag can bind to a ubiquitin ligase (e.g., an E3 ligase such as a cereblon E3 ligase, a VHL E3 ligase, a MDM2 ligase, a TRIM21 ligase, a TRIM24 ligase, a KEAP1 ligase and/or an LAP ligase) and/or serve as a hydrophobic group or a tag group that leads to PTK6 protein misfolding.

Linkers

In all of the above-described compounds, the PTK6 ligand is conjugated to the degradation/disruption tag through a linker. The linker can include, for example, acyclic or cyclic saturated or unsaturated carbon, ethylene glycol, amide, amino, ether, urea, carbamate, aromatic, heteroaromatic, heterocyclic and/or carbonyl containing groups with different lengths.

In some aspects, the linker can be a moiety of:

FORMULA 7

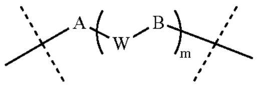

wherein

A, W and B, at each occurrence, are independently selected from null, or bivalent moiety selected from R'—R", R'COR", $R'CO_2R"$, $R'C(O)N(R^1)R^{41}$, $R'C(S)N(R^1)R"$, R'OR", R'OC(O)R", R'OC(O)OR", $R'OCON(R^1)R"$, R'SR", R'SOR", $R'SO_2R'$, $R'SO_2N(R^1)R"$, $R'N(R^1)R"$, $R'NR^1COR"$, $R'NR^1C(O)OR"$, $R'NR^1CON(R^2)R"$, $R'NR^1C(S)R"$, $R'NR^1S(O)R"$, $R'NR^1S(O)_2R"$, and $R'NR^1S(O)_2N(R^2)R"$, wherein R' and R" are independently selected from null, optionally substituted $R^{r}$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$ alkyl, optionally substituted $C_1$-$C_8$alkylamino$C_1$-$C_8$ alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$ alkylene, optionally substituted $C_1$-$C_8$alkylamino$C_1$-$C_8$ alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^{r}$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^1$ and $R^2$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl;

R' and R", $R^1$ and $R^2$, R' and $R^1$, R' and $R^2$, R" and $R^1$, $R^1$ and $R^2$ together with the atom to which they are connected form a 3-20 membered cycloalkyl or 4-20 membered heterocyclyl ring; and m is 0 to 15.

FORMULA 7A

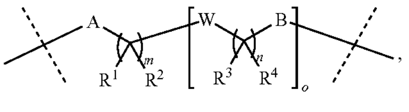

wherein $R^1$, $R^2$, $R^3$ and $R^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-8 membered heterocyclyl, optionally substituted aryl, and optionally substituted heteroaryl, or $R^1$ and $R^2$, $R^3$ and $R^4$ together with the atom to which they are connected form a 3-20 membered cycloalkyl or 4-20 membered heterocyclyl ring;

A, W and B, at each occurrence, are independently selected from null, or bivalent moiety selected from R'—R", R'COR", R'$CO_2$R", R'C(O)N($R^5$)R", R'C(S)N($R^5$)R", R'OR", R' OC(O)R", R'OC(O)OR", R'OCON$R^5$R", R'SR", R'SOR", R'$SO_2$R', R'$SO_2$N($R^5$)R", R'N($R^1$)R", R'N$R^5$COR", R'N$R^5$C(O)OR", R'N$R^5$CON($R^6$)R", R'N$R^5$C(S)R", R'N$R^5$S(O)R", R'N$R^5$S$(O)_2$R", and R'N$R^5$S$(O)_2$N($R^6$)R", wherein R' and R" are independently selected from null, optionally substituted $R^{r}$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$ alkyl, optionally substituted $C_1$-$C_8$alkylamino$C_1$-$C_8$ alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$ alkylene, optionally substituted $C_1$-$C_8$alkylamino$C_1$-$C_8$ alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^{r}$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_1$-$C_3$ spiro cycloalkyl, optionally substituted $C_3$-$C_{13}$ spiro heterocyclyl, optionally substituted aryl, and optionally substituted heteroaryl;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl;

R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;

n, at each occurrence, is 0 to 15; and is 0 to 15.

FORMULA 7B

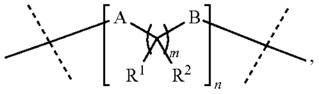

wherein $R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'—R", R'COR", R'$CO_2$R", R'C(O)N$R^3$R", R'C(S)N$R^3$R", R'OR", R'OC(O)R", R'OC(O)OR", R'OCON($R^3$)R", R'SR", R'SOR", R'$SO_2$R", R'$SO_2$N($R^3$)R", R'N($R^3$)R", R'N$R^3$COR", R'N$R^3$C(O)OR", R'N$R^3$CON($R^4$)R", R'N$R^3$C(S)R", R'N$R^3$S(O)R", R'N$R^3$S(O)$_2$R", and R'N$R^3$S(O)$_2$N($R^4$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$ alkyl, optionally substituted $C_1$-$C_8$alkylamino$C_1$-$C_8$ alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$ alkylene, optionally substituted $C_1$-$C_8$alkylamino$C_1$-$C_8$ alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^3$ and $R^4$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R' and $R^3$, R' and $R^4$ together with the atom to which they are connected form a 3-20 membered cycloalkyl or 4-20 membered heterocyclyl ring;

m, at each occurrence, is 0 to 15; and n is 0 to 15.

FORMULA 7C

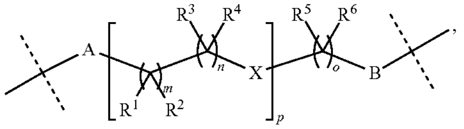

wherein

X is selected from O, NH, and $NR^7$;

$R^1$, $R^2$, $R^3$, $R^4$, $R^5$, and $R^6$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$alkylamino$C_1$-$C_8$ alkyl, optionally substituted 3-10 membered carbocyclyl, optionally substituted 3-8 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", R'$CO_2$R", R'C(O)N($R^8$)R", R'C(S)N($R^8$)R", R'OR", R'OC(O)R", R'OC(O)OR", R'OCON($R^8$)R", R'SR", R'SOR", R'$SO_2$R", R'$SO_2$N($R^8$)R", R'N($R^8$)R", R'N$R^8$COR", R'N$R^8$C(O)OR", R'N$R^8$CON($R^9$)R", R'N$R^8$C(S)R", R'N$R^8$S(O)R", R'N$R^8$S(O)$_2$R", and R'N$R^8$S(O)$_2$N($R^9$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$ alkyl, optionally substituted $C_1$-$C_8$alkylamino$C_1$-$C_8$ alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$ alkylene, optionally substituted $C_1$-$C_8$alkylamino$C_1$-$C_8$ alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^{r}$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^7$, $R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl;

R' and R", $R^8$ and $R^9$, R' and R", R' and $R^9$, R' and R", R" and $R^9$ together with the atom to which they are connected form a 3-20 membered cycloalkyl or 4-20 membered heterocyclyl ring;

m, at each occurrence, is 0 to 15;

n, at each occurrence, is 0 to 15;

is 0 to 15; and p is 0 to 15.

In some aspects of Formulae 7, 7A, 7B, and 7C, the linker moiety comprises a ring selected from the group consisting of a 3 to 13 membered ring, a 3 to 13 membered fused ring, a 3 to 13 membered bridged ring, and a 3 to 13 membered spiro ring.

In some aspects of Formulae 7, 7A, 7B, and 7C, the linker moiety comprises a ring selected from the group consisting of Formula C1, C2, C3, C4 and C5:

Formula C1

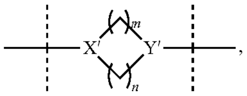

X' = N or CH
Y' = N or CH
m = 0-5
n = 0-5

Formula C2

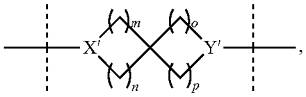

X' = N or CH
Y' = N or CH
m = 0-5
n = 0-5
o = 0-5
p = 0-5

-continued

Formula C3

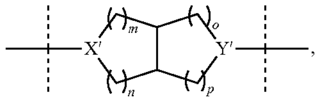

X' = N or CH
Y' = N or CH
m = 0-5
n = 0-5
o = 0-5
p = 0-5

Formula C4

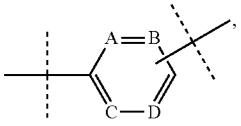

and

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N Formula C5

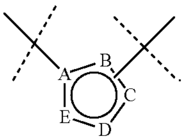

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3 alkyl), O, S In some aspects, the linker can also be a moiety of:

Formula A

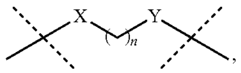

wherein X is C═O or $CH_2$,
Y is C═O or $CH_2$, and
n is 0-15;

Formula B

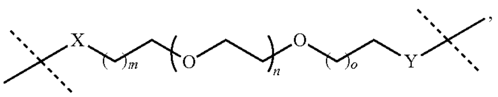

wherein X is C═O or $CH_2$,
Y is C═O or $CH_2$,
m is 0-15,
n is 0-6, and
is 0-15; or Formula C

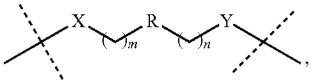

wherein

X is C═O or $CH_2$,

Y is C═O or $CH_2$,

R is —$CH_2$—, —$CF_2$—, —CH($C_{1-3}$ alkyl)-, —C($C_{1-3}$ alkyl)($C_{1-3}$ alkyl)-, —CH═CH—, —C($C_{1-3}$ alkyl)═C($C_{1-3}$ alkyl)-, —C≡C—, —O—, —NH—, —N($C_{1-3}$ alkyl)-, —C(O)NH—, —C(O)N($C_{1-3}$ alkyl)-, a 3-13 membered ring, a 3-13 membered fused ring, a 3-13 membered bridged ring, and/or a 3-13 membered spiro ring, m is 0-15, and n is 0-15.

In some aspects of Formula C, R is a 3-13 membered ring, a 3-13 membered fused ring, a 3-13 membered bridged ring, and/or a 3-13 membered spiro ring, one or more of which can contain one or more heteroatoms.

In some aspects of Formula C, R has a structure of

Formula C1

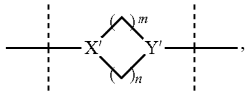,

X′ = N or CH
Y′ = N or CH
m = 0-5
n = 0-5

Formula C2

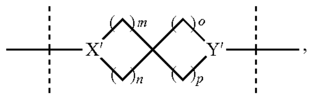,

X′ = N or CH
Y′ = N or CH
m = 0-5
n = 0-5
o = 0-5
p = 0-5

Formula C3

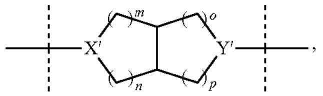,

X′ = N or CH
Y′ = N or CH
m = 0-5
n = 0-5
o = 0-5
p = 0-5

Formula C4

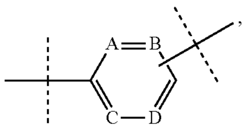, or

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N -continued Formula C5

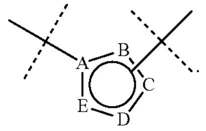

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH,C(C1-3 alkyl), N, NH,N(C1-3alkyl),O, S In some aspects, the bivalent compound is a compound selected from the following compounds, as identified in Table 1 below. YX39-86, YX39-89, YX39-90, YX39-91, YX39-92, YX39-93, YX39-94, YX39-96, YX39-97, YX39-98, YX39-99, YX39-100, YX39-101, YX39-102, YX39-103, YX39-104, YX39-105, YX39-106, YX39-107, YX39-127, YX39-128, YX39-129, YX44-158, YX44-172, YX44-184, YX49-7-2, YX49-8, YX49-9, YX49-10, YX49-11, YX49-24, YX49-99, YX49-100, YX49-101, YX49-102, YX59-122, YX69-5, YX69-157, YX69-158, YX69-159, YX69-182, YX69-183, YX69-184, YX79-3, YX79-4, YX79-5, YX79-6, YX79-10, YX79-11, YX79-12, YX79-13, YX79-14, YX79-15, YX79-16, YX79-17, YX79-18, YX79-19, YX79-20, YX79-21, YX79-22, YX79-23, YX79-24, YX79-25, YX79-29, YX79-30, YX79-34, YX79-35, YX79-36, YX79-37, YX79-38, YX79-39, YX79-40, YX79-41, YX79-42, YX79-43, YX79-56, YX79-57, YX79-58, YX79-59, YX79-60, YX79-61, YX79-62, YX79-63, YX79-64, YX79-65, YX79-66, YX79-67, YX79-68, YX79-69, YX79-70, YX79-86, YX79-87, YX79-88, YX79-89, YX79-90, YX79-91, YX79-92, YX79-93, YX79-94, YX79-95, YX79-967, YX79-97, YX79-131, YX79-132, YX79-133, YX79-134, YX79-135, YX79-136, YX79-137, YX79-138, YX79-139, YX79-140, YX79-141, YX79-142, YX79-143, YX79-144, YX79-145, YX79-146, YX79-147, YX79-148, YX79-149, YX79-150, YX79-151, YX79-152, YX79-153, YX79-154, YX79-155, YX79-156. YX79-157, YX79-158, YX79-159, YX79-160, YX79-161, YX79-162, YX79-164, YX79-165, JH077-29, JH077-30, JH077-31, JH077-32, JH077-33, JH077-34, JH077-35, JH077-35, JH077-36, JH077-37, JH077-38, JH077-39, JH077-40, JH077-41, JH077-47, JH077-48, JH077-49, JH077-51, JH077-52, JH077-53, JH077-54, JH077-55, JH077-56, JH077-57, JH077-58, JH077-65, JH077-66, JH077-67, JH077-68, JH077-69, JH077-70, JH077-71, JH077-72, JH077-73, JH077-74, JH077-75, JH077-76, JH077-76, JH077-77, JH077-78, JH077-79, JH077-80, JH077-81, JH077-82, JH077-83, JH077-84, JH077-85, JH077-86, JH077-87, JH077-88, JH077-89, JH077-90, JH077-91, JH077-92, JH077-93 examples 190-280, or analogs thereof.

In some aspects, this disclosure provides a method of treating PTK6-mediated cancers, the method including administering to a subject in need thereof one or more bivalent compounds including a PTK6 ligand conjugated to a degradation/disruption tag via a linker. The PTK6-mediated cancer can be a cancer resulting from (aberrant) PTK6 activation. The PTK6-mediated cancer can have elevated PTK6 expression relative to a wild-type tissue of the same species and tissue type. Non-limiting examples of PTK6- mediated diseases include breast cancer, ovarian cancer, prostate cancer, colon cancer, pancreatic cancer, bladder cancer, liver cancer, and cervical cancer.

The PTK6-mediated cancer can be a relapsed cancer. The PTK6-mediated cancer can have been refractory to one or more previous treatments by different therapies.

In any of the above-described methods, the bivalent compounds can be YX39-86, YX39-89, YX39-90, YX39-91, YX39-92, YX39-93, YX39-94, YX39-96, YX39-97, YX39-98, YX39-99, YX39-100, YX39-101, YX39-102, YX39-103, YX39-104, YX39-105, YX39-106, YX39-107, YX39-127, YX39-128, YX39-129, YX44-158, YX44-172, YX44-184, YX49-7-2, YX49-8, YX49-9, YX49-10, YX49-11, YX49-24, YX49-99, YX49-100, YX49-101, YX49-102, YX59-122, YX69-5, YX69-157, YX69-158, YX69-159, YX69-182, YX69-183, YX69-184, YX79-3, YX79-4, YX79-5, YX79-6, YX79-10, YX79-11, YX79-12, YX79-13, YX79-14, YX79-15, YX79-16, YX79-17, YX79-18, YX79-19, YX79-20, YX79-21, YX79-22, YX79-23, YX79-24, YX79-25, YX79-29, YX79-30, YX79-34, YX79-35, YX79-36, YX79-37, YX79-38, YX79-39, YX79-40, YX79-41, YX79-42, YX79-43, YX79-56, YX79-57, YX79-58, YX79-59, YX79-60, YX79-61, YX79-62, YX79-63, YX79-64, YX79-65, YX79-66, YX79-67, YX79-68, YX79-69, YX79-70, YX79-86, YX79-87, YX79-88, YX79-89, YX79-90, YX79-91, YX79-92, YX79-93, YX79-94, YX79-95, YX79-967, YX79-97, YX79-131, YX79-132, YX79-133, YX79-134, YX79-135, YX79-136, YX79-137, YX79-138, YX79-139, YX79-140, YX79-141, YX79-142, YX79-143, YX79-144, YX79-145, YX79-146, YX79-147, YX79-148, YX79-149, YX79-150, YX79-151, YX79-152, YX79-153, YX79-154, YX79-155, YX79-156. YX79-157, YX79-158, YX79-159, YX79-160, YX79-161, YX79-162, YX79-164, YX79-165, JH077-29, JH077-30, JH077-31, JH077-32, JH077-33, JH077-34, JH077-35, JH077-35, JH077-36, JH077-37, JH077-38, JH077-39, JH077-40, JH077-41, JH077-47, JH077-48, JH077-49, JH077-51, JH077-52, JH077-53, JH077-54, JH077-55, JH077-56, JH077-57, JH077-58, JH077-65, JH077-66, JH077-67, JH077-68, JH077-69, JH077-70, JH077-71, JH077-72, JH077-73, JH077-74, JH077-75, JH077-76, JH077-76, JH077-77, JH077-78, JH077-79, JH077-80, JH077-81, JH077-82, JH077-83, JH077-84, JH077-85, JH077-86, JH077-87, JH077-88, JH077-89, JH077-90, JH077-91, JH077-92, JH077-93 examples 190-280, or analogs thereof.

In some aspects of the methods described herein, the bivalent compounds can be administered, e.g., orally, parenterally, intradermally, subcutaneously, topically, and/or rectally.

Any of the above-described methods can further include treating a subject with one or more additional therapeutic regimens for treating cancer. The one or more additional therapeutic regimens for treating cancer can be, e.g., one or more of surgery, chemotherapy, radiation therapy, hormone therapy, or immunotherapy.

This disclosure additionally provides a method for identifying a bivalent compound which mediates degradation/disruption of PTK6, the method including providing a heterobifunctional test compound including a PTK6 ligand conjugated to a degradation/disruption tag via a linker, contacting the heterobifunctional test compound with a cell (e.g., a cancer cell such as a PTK6-mediated cancer cell) including a ubiquitin ligase and PTK6.

As used herein, the terms “about” and “approximately” are defined as being within plus or minus 10% of a given value or state, preferably within plus or minus 5% of said value or state. The terms “bivalent” and “bi-functional” are used interchangeably herein. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Figure 11:
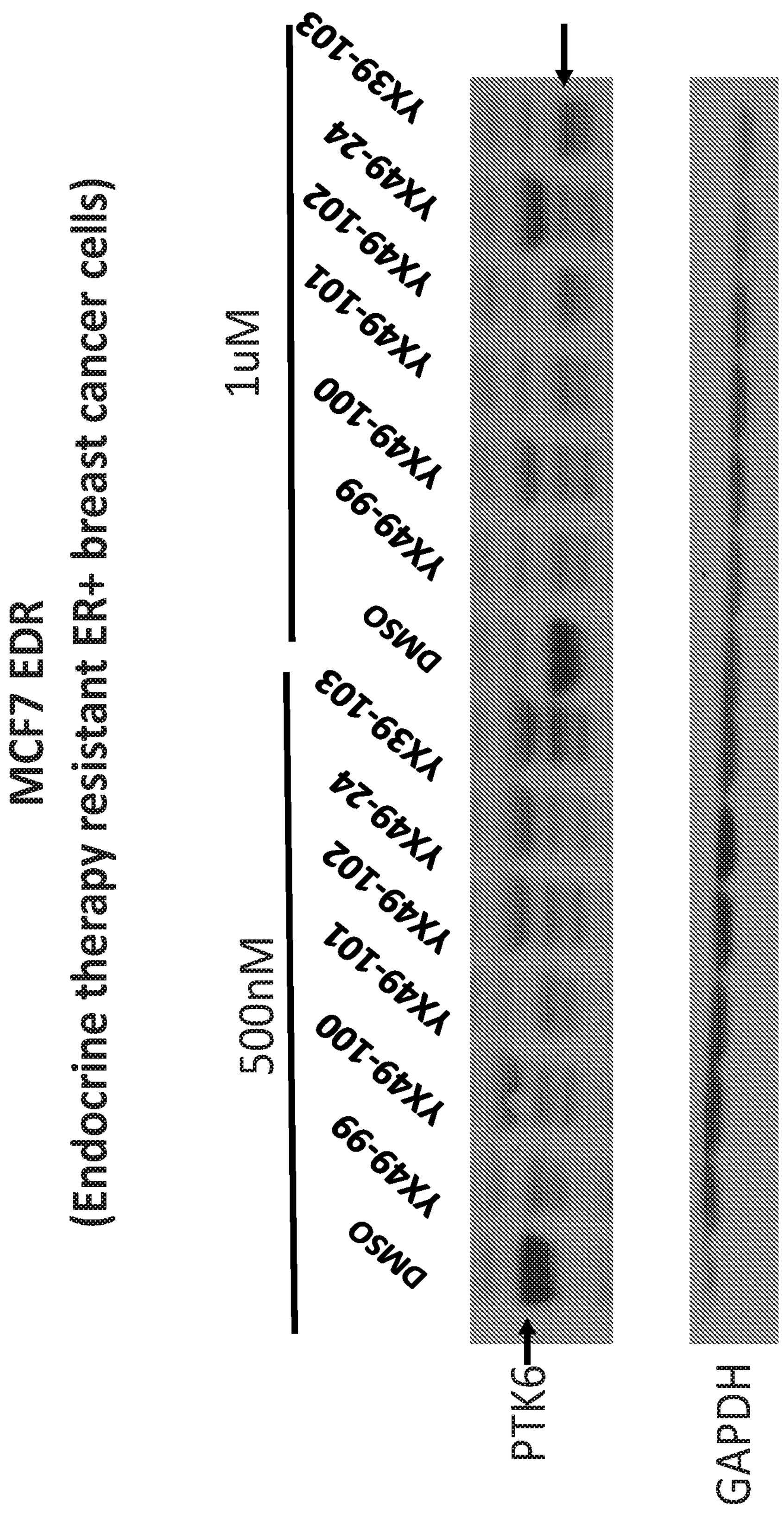

FIG. 11. PTK6 degraders suppress PTK6 expression in endocrine therapy-resistant ER+ breast cancer cells (MCF/EDR). MCF7EDR cells in monolayer cultures were treated with PTK6 degraders for 24 hours at the indicated concentrations. Cells were lysed and expression of PTK6 was assessed.

Figure 12A:
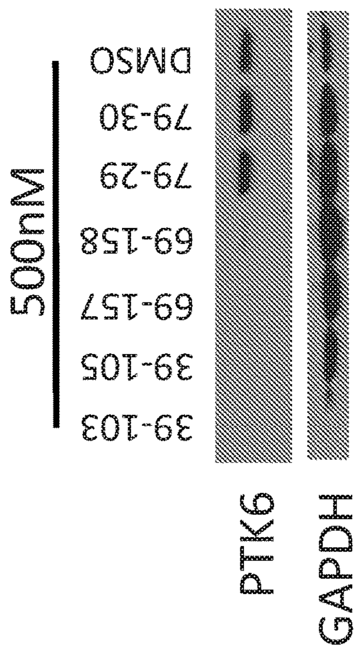
Figure 12B:
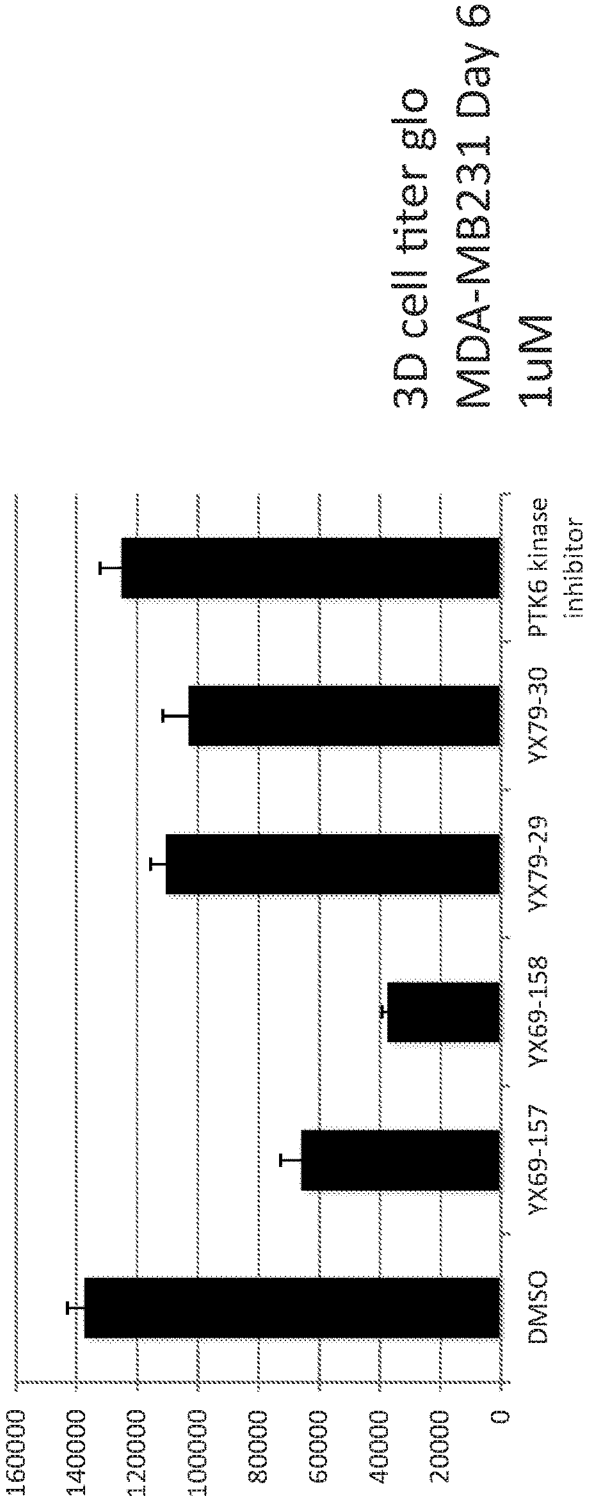

FIG. 12*a*. PTK6 degraders, but not kinase activity inhibitor, suppress viability in 3D cultures. Expression of PTK6 in cells treated with PTK6 degraders, negative control compounds or PTK6 kinase activity inhibitor was assessed after 24 hour treatment in monolayer cultures with 1 uM of compound. Cells were lysed and proteins were resolved and probed with anti-PTK6 antibody (Cell Signaling). FIG. 12*b*. MDA-MB231 triple negative breast cancer cells were seeded into 3D Matrigel cultures (4×10^3 cells/well) and treated with indicated PTK6 degraders, negative control compounds or PTK6 kinase activity inhibitor at 1 uM for 6 days with re-feeding of compound after 3 days in culture. Viability was assessed using 3D Cell Titer glo (Promega).

Figure 13:
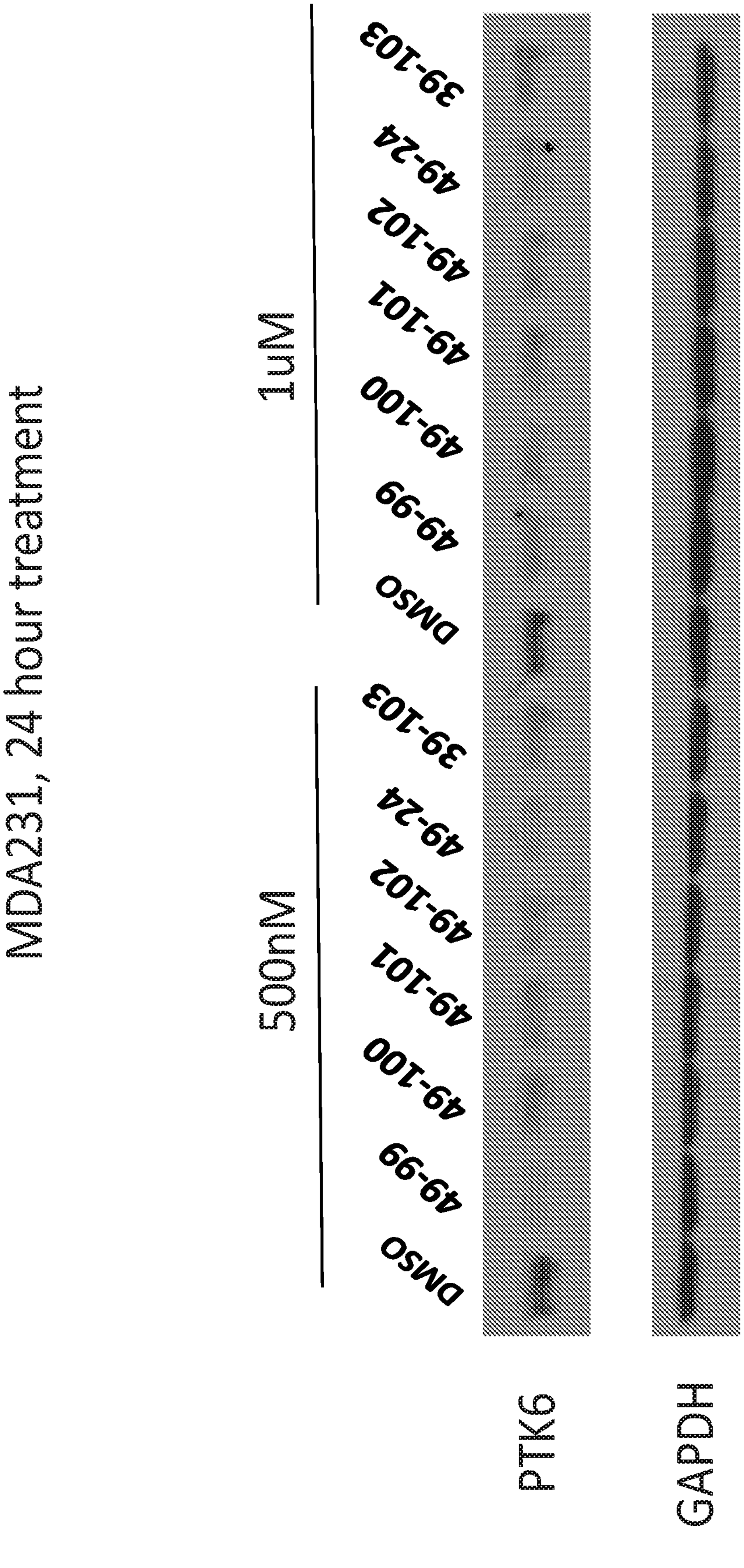

FIG. 13. PTK6 degraders suppress PTK6 expression. MDA-MB231 cells were treated with compounds (500 nM or 1 uM) for 24 hours in monolayer cultures. Cells were lysed and lysates were probed with anti-PTK6 antibody.

DETAILED DESCRIPTION

The present disclosure is based in part, on the discovery that novel heterobifunctional small molecules which degrade PTK6 and/or PTK6 mutant are useful in the treatment of PTK6-mediated diseases, particularly breast cancer, ovarian cancer, prostate cancer, colon cancer, pancreatic cancer, bladder cancer, liver cancer and cervical cancer.

Successful strategies for selective degradation/disruption of the target protein induced by a bifunctional small molecule include recruiting an E3 ubiquitin ligase and mimicking protein misfolding with a hydrophobic tag (Buckley and Crews, 2014). The bifunctional molecules have three moieties: one E3-binder moiety that binds an E3 ubiquitin ligase; one targeted protein-binder moiety that binds the protein target of interest; and a linker moiety that connects the E3-binder and the targeted protein-binder moieties (Buckley and Crews, 2014). The induced proximity leads to selective ubiquitination of the target followed by its degradation at the proteasome. Several types of high affinity small-molecule E3 ligase ligands have been identified/developed. They include (1) immunomodulatory drugs (IMiDs) such as thalidomide and pomalidomide, which bind cereblon (CRBN or CRL4CRBN), a component of a cullin-RING ubiquitin ligase (CRL) complex (Bondeson et al., 2015; Chamberlain et al., 2014; Fischer et al., 2014; Ito et al., 2010; Winter et al., 2015); (2) VHL-1, a hydroxyproline-containing ligand, which binds van Hippel-Lindau protein (VHL or CRL2VHL), a component of another CRL complex (Bondeson et al., 2015; Buckley et al., 2012a; Buckley et al., 2012b; Galdeano et al., 2014; Zengerle et al., 2015); (3) compound 7, which selectively binds KEAP1, a component of a CRL3 complex (Davies et al., 2016); (4) AMG232, which selectively binds MDM2, a heterodimeric RING E3 ligase (Sun et al., 2014); and (5) LCL161, which selectively binds IAP, a homodimeric RING E3 ligase (Ohoka et al., 2017; Okuhira et al., 2011; Shibata et al., 2017). The technology has been applied to degradation of several protein targets (Bondeson et al., 2015; Buckley et al., 2015; Lai et al., 2016; Lu et al., 2015; Winter et al., 2015; Zengerle et al., 2015), but not to degradation of PTK6 or PTK6 mutant proteins. In addition, a hydrophobic tagging approach, which utilizes a bulky and hydrophobic adamantyl group, has been developed to mimic protein misfolding, leading to the degradation of the target protein by proteasome (Buckley and Crews, 2014). This approach has been applied to selective degradation of the pseudokinase Her3 (Xie et al., 2014), but not to degradation of PTK6 or PTK6 mutant proteins.

As discussed in the following examples, this disclosure provides specific examples of novel PTK6 degraders/disruptors, and examines the effect of exemplary degraders/disruptors in inhibiting/disrupting PTK6 function, reducing PTK6 protein levels, and inhibiting cancer cell proliferation. The results indicate that these novel small molecules can be beneficial in treating human disease, especially breast cancer, ovarian cancer, prostate cancer, colon cancer, pancreatic cancer, bladder cancer, liver cancer and cervical cancer.

A number of selective small-molecule PTK6 kinase inhibitors, such as compound 21d (Zeng et al., 2011), compound 4f (Mahmoud et al., 2014), compound 1 (Yamamoto, 2016), XMU-MP-2 (Jiang et al., 2017), and compound 3s (Cardenas et al., 2018), have been reported.

Currently available small molecules targeting PTK6 focus on inhibition of the kinase activity of PTK6. In the present disclosure, a different approach is taken: to develop compounds that directly and selectively target not only the kinase activity of PTK6, but also its protein level. Strategies for inducing protein degradation include recruiting E3 ubiquitin ligases, mimicking protein misfolding with hydrophobic tags, and inhibiting chaperones. For example, a thalidomide-JQ1 bivalent compound has been used to hijack the cereblon E3 ligase, inducing highly selective BET protein degradation in vitro and in vivo and resulting in a demonstrated delay in leukemia progression in mice (Winter et al., 2015). Similarly, BET protein degradation has also been induced via another E3 ligase, VHL (Zengerle et al., 2015). Partial degradation of Her3 has been induced using an adamantane-modified compound (Xie et al., 2014). Such an approach, based on the use of bivalent small molecule compounds, permits more flexible regulation of protein levels in vitro and in vivo compared with techniques such as gene knockout or shRNA (short hairpin RNA) knockdown. Unlike gene knockout or shRNA knockdown, a small molecule approach further provides an opportunity to study dose and time dependency in a disease model through varying the concentrations and frequencies of administration of the relevant small molecule.

This disclosure includes all stereoisomers, geometric isomers, tautomers and isotopes of the structures depicted and compounds named herein. This disclosure also includes compounds described herein, regardless of how they are prepared, e.g., synthetically, through biological process (e.g., metabolism or enzyme conversion), or a combination thereof.

This disclosure includes pharmaceutically acceptable salts of the structures depicted and compounds named herein.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms. In some embodiments, the compound includes at least one fluorine atom. In some embodiments, the compound includes two or more fluorine atoms. In some embodiments, the compound includes 1-2, 1-3, 1-4, 1-5, or 1-6 fluorine atoms. In some embodiments, all of the hydrogen atoms in a compound can be replaced or substituted by fluorine atoms.

Degraders

In some aspects, the present disclosure provides bivalent compounds, also referred to herein as degraders, comprising an PTK6 ligand (or targeting moiety) conjugated to a degradation tag. Linkage of the PTK6 ligand to the degradation tag can be direct, or indirect via a linker.

As used herein, the terms "Protein tyrosine kinase 6 ligand", "breast tumor kinase ligand", "PTK6 ligand", "Brk ligand", or "PTK6 targeting moiety" are to be construed broadly, and encompass a wide variety of molecules ranging from small molecules to large proteins that associate with or bind to PTK6. The PTK6 ligand or targeting moiety can be, for example, a small molecule compound (i.e., a molecule of molecular weight less than about 1.5 kilodaltons (kDa)), a peptide or polypeptide, nucleic acid or oligonucleotide, carbohydrate such as oligosaccharides, or an antibody or fragment thereof.

The PTK6 ligand or targeting moiety can be a PTK6 kinase inhibitor (e.g., compound 21d (Zeng et al., 2011), compound 4f (Mahmoud et al., 2014), compound 1 (Yamamoto, 2016), XMU-MP-2 (Jiang et al., 2017), and compound 3s (Cardenas et al., 2018), and analogs thereof), which is capable of inhibiting the kinase activity of PTK6. As used herein, a "PTK6 kinase inhibitor" refers to an agent that restrains, retards, or otherwise causes inhibition of a physiological, chemical or enzymatic action or function and causes a decrease in binding of at least 5%. An inhibitor can also or alternately refer to a drug, compound, or agent that prevents or reduces the expression, transcription, or translation of a gene or protein. An inhibitor can reduce or prevent the function of a protein, e.g., by binding to or activating/inactivating another protein or receptor.

Exemplary PTK6 ligands include, but are not limited to, the compounds listed below:

Compound 21d

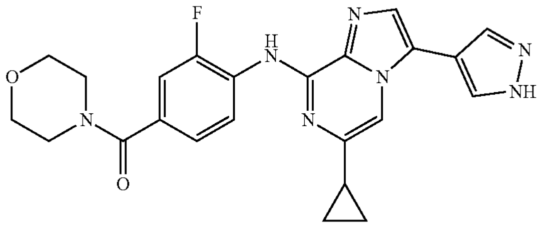

Compound 4f

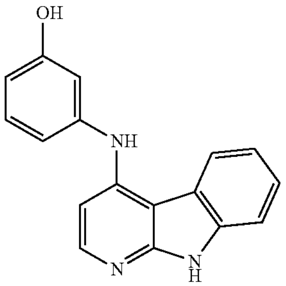

Compound 1

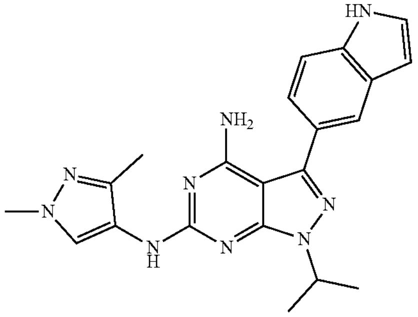

XMU-MP-2

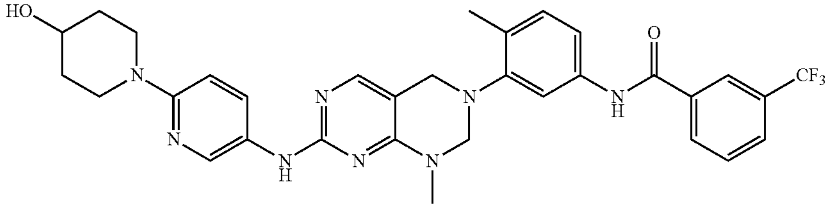

-continued

Compound 3s

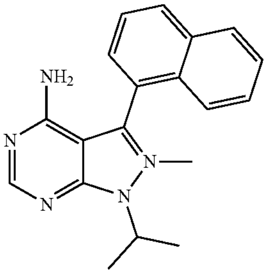

PF-6683324

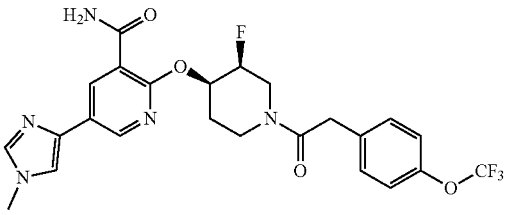

PF-6698840

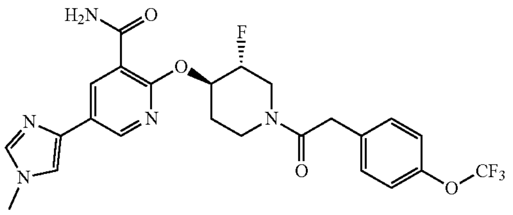

FORMULA 2A

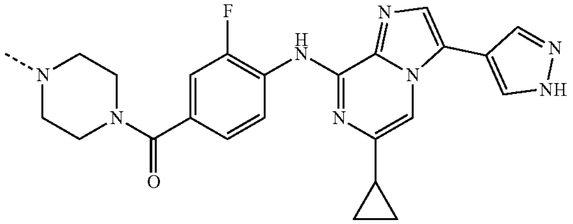

FORMULA 2B

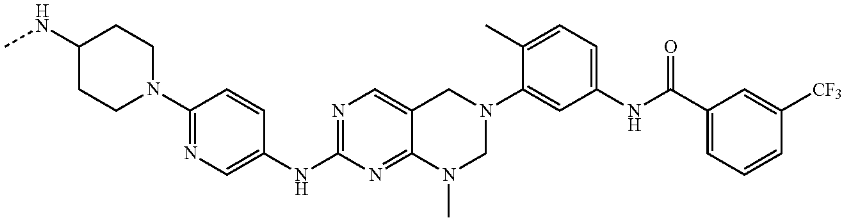

FORMULA 2C

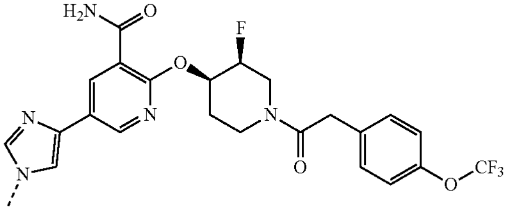

FORMULA 2D

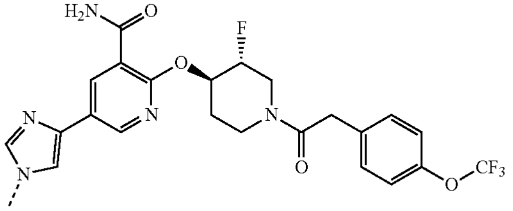

As used herein, the term "degradation/disruption tag" refers to a compound, which associates with or binds to an ubiquitin ligase for recruitment of the corresponding ubiquitination machinery to PTK6 or induces PTK6 protein misfolding and subsequent degradation at the proteasome or loss of function.

In some aspects, the degradation/disruption tags of the present disclosure include, e.g., pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), FK506 (Liu et al., 1991) rapamycin (Fan et al., 2017, Rodrik-Outmezguine et al., 2016), and/or analogs thereof.

As used herein, a "linker" is a bond, molecule, or group of molecules that binds two separate entities to one another. Linkers provide for optimal spacing of the two entities. The term "linker" in some aspects refers to any agent or molecule that bridges the PTK6 ligand to the degradation/disruption tag. One of ordinary skill in the art recognizes that sites on the PTK6 ligand or the degradation/disruption tag, which are not necessary for the function of the degraders of the present disclosure, are ideal sites for attaching a linker, provided that the linker, once attached to the conjugate of the present disclosures, does not interfere with the function of the PTK6 ligand, i.e., its ability to bind PTK6, or the function of the degradation/disruption tag, i.e., its ability to recruit a ubiquitin ligase.

The length of the linker of the bivalent compound can be adjusted to minimize the molecular weight of the disruptors/degraders and avoid the clash of the PTK6 ligand or targeting moiety with the ubiquitin ligase or induce PTK6 misfolding by the hydrophobic tag at the same time.

In some aspects, the degradation/disruption tags of the present disclosure include, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), FK506 (Liu et al., 1991) rapamycin (Fan et al., 2017; Rodrik-Outmezguine et al., 2016), and analogs thereof. The degradation/disruption tags can be attached to each portion of interest in the structure of a PTK6 ligand or targeting moiety (e.g., compound 21d (Zeng et al., 2011), compound 4f (Mahmoud et al., 2014), compound 1 (Yamamoto, 2016), XMU-MP-2 (Jiang et al., 2017), and compound 3s (Cardenas et al., 2018), and analogs thereof) with linkers of different types and lengths in order to generate effective bivalent compounds. In particular, attaching pomalidomide or VHL-1 to either portion of the molecule can recruit the cereblon E3 ligase or VHL E3 ligase to PTK6.

The bivalent compounds disclosed herein can selectively affect PTK6-mediated disease cells compared to WT (wild type) cells (i.e., an PTK6 degrader/disruptor able to kill or inhibit the growth of an PTK6-mediated disease cell while also having a relatively low ability to lyse or inhibit the growth of a WT cell), e.g., possess a $GI_{50}$ for one or more PTK6-mediated disease cells more than 1.5-fold lower, more than 2-fold lower, more than 2.5-fold lower, more than 3-fold lower, more than 4-fold lower, more than 5-fold lower, more than 6-fold lower, more than 7-fold lower, more than 8-fold lower, more than 9-fold lower, more than 10-fold lower, more than 15-fold lower, or more than 20-fold lower than its $GI_{50}$ for one or more WT cells, e.g., WT cells of the same species and tissue type as the PTK6-mediated disease cells.

Additional bivalent compounds (i.e., PTK6 degraders/disruptors) can be developed using the principles and methods disclosed herein. For example, other linkers, degradation/disruption tags, and PTK6 binding/inhibiting moieties (not limited to compound 21d (Zeng et al., 2011), compound 4f (Mahmoud et al., 2014), compound 1 (Yamamoto, 2016), XMU-MP-2 (Jiang et al., 2017), and compound 3s (Cardenas et al., 2018), and analogs thereof) can be synthesized and tested.

In some aspects, the PTK6 degraders/disruptors have the form "PI-Linker-EL", as shown below:

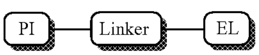

wherein PI (a ligand for a "protein of interest," i.e., the protein to be degraded) comprises an PTK6 ligand (e.g., an PTK6 kinase inhibitor), and EL (e.g., a ligand for an E3 ligase) comprises a degradation/disruption tag (e.g., E3 ligase ligand). Exemplary PTK6 ligands (PI), exemplary degradation/disruption tags (EL), and exemplary linkers (Linker) are illustrated below:

PTK6 Ligands

PTK6 Ligands include but are not limited to:

FORMULA 1

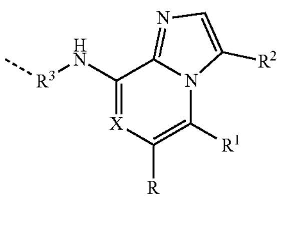

Wherein

R is selected from H, halo, or unsubstituted or optionally substituted $C_{1-8}$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_1$-$C_8$ alkyleneOR$^4$, $C_1$-$C_8$ alkyleneSR$^5$, $C_1$-$C_8$ alkylene NR$^6$R$^7$, $C_2$-$C_8$ alkenyl, $C_2$-$C_8$ alkynyl, OR$^4$, SR$^5$, NR$^6$R$^7$, R$^1$ is selected from H, $C_{1-8}$ alkyl, $C_1$-$C_8$ hydroxyalkyl, $C_1$-$C_8$ alkoxyalkyl, $C_3$-$C_{10}$ cycloalkyl, $C_3$-$C_{10}$ heterocyclyl, OR$^8$, SR$^9$, NR$^{10}$R$^{11}$, R$^2$ is selected from $C_6$-$C_{10}$ aryl or $C_5$-$C_{10}$ heteroaryl. R$^2$ is unsubstituted or optionally substituted with one or more of groups selected from halo, =O, =S, CN, $NO_2$, $C_{1-8}$ alkyl, $C_1$-$C_8$ haloalkyl, $C_1$-$C_8$ hydroxyalkyl, $C_3$-$C_{10}$ cycloalkyl, $C_3$-Cia heterocyclyl, $C_1$-$C_8$ alkyleneOR$^{12}$, $C_1$-$C_8$ alkyleneSR$^{13}$, $C_1$-$C_8$ alkylene NR$^{14}$R$^{15}$, $C_2$-$C_8$ alkenyl, $C_2$-$C_8$ alkynyl, OR", SR", NR$^{14}$R$^{15}$, R$^3$ is selected from $C_6$-$C_{10}$ aryl or $C_5$-$C_{10}$ heteroaryl. R$^3$ is unsubstituted or substituted with one or more of groups selected from $C_1$-$C_8$ alkyl, $C_1$-$C_8$ haloalkyl, $C_1$-$C_8$ hydroxyalkyl, $C_1$-$C_8$ alkoxyalkyl, $C_3$-$C_{10}$ cycloalkyl, $C_3$-$C_{10}$ heterocyclyl, $C_2$-$C_8$ alkenyl, $C_2$-$C_8$ alkynyl, halo, CN, $NO_2$, =O, =S, R$^{16}$, OR$^{16}$, SR$^{17}$, SO$_2$R$^{18}$, NR$^{19}$R$^{20}$, C(O)R$^{16}$, C(O)OR$^{16}$, C(S)OR$^{16}$, C(O)NR$^{19}$R$^{20}$, C(S)NR$^{19}$R$^{20}$, NR$^{19}$C(O)R$^{16}$, NR$^{19}$C(O)OR$^{16}$, NR$^{19}$S(O)R$^{16}$, NR$^{19}$S(O)OR$^{16}$, S(O)R$^{16}$, S(O)OR$^{16}$, and S(O)ONR$^{19}$R$^{20}$, R$^4$, R$^5$, R$^6$, R$^7$, R$^8$, R$^9$, R$^{10}$, R$^{11}$, R$^{12}$, R$^{13}$, R$^{14}$, R$^{15}$ are independently selected from H, $C_1$-$C_8$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, C(O)$C_1$-$C_8$ alkyl, C(O)$C_1$-$C_8$ haloalkyl, C(O)$C_1$-$C_8$ hydroxyalkyl, C(O)$C_3$-$C_{10}$ cycloalkyl, and C(O)$C_3$-$C_{10}$ heterocyclyl, or R$^6$ and R$^7$; R$^{10}$ and R$^{11}$; R$^{14}$ and R$^{15}$ together with the nitrogen atom to which they connected can independently form 3-10 membered heterocyclyl rings, R$^{16}$, R$^{17}$, and R$^{18}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_1$-$C_8$ cycloalkyl, $C_3$-$C_7$ heterocycloalkyl, $C_6$-$C_{10}$ aryl, $C_8$-$C_{10}$ heteroaryl, C(O)$C_1$-$C_8$ alkyl, C(O)$C_1$-$C_8$ haloalkyl, C(O)$C_1$-$C_8$ hydroxyalkyl, C(O)$C_1$-$C_8$ alkoxyalkyl, C(O)$C_3$-$C_{10}$ cycloalkyl, C(O)$C_3$-$C_{10}$ heterocyclyl, C(O)$C_6$-$C_{10}$ aryl, C(O)$C_8$-$C_{10}$ heteroaryl, $C_1$-$C_8$ alkylene$C_3$-$C_{10}$ cycloalkyl, $C_1$-$C_8$ alkylene$C_3$-$C_{10}$ heterocycloalkyl, $C_1$-$C_8$ alkylene$C_6$-$C_{10}$ aryl, $C_1$-$C_8$ alkylene, or $C_8$-$C_{10}$ heteroaryl, R$^{19}$ and R$^{20}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_{10}$ cycloalkyl, $C_3$-$C_{10}$ heterocycloalkyl, $C_6$-$C_{10}$ aryl, $C_5$-$C_{10}$ heteroaryl, C(O)$C_1$-$C_8$ alkyl, $C(O)C_1$-$C_8$ haloalkyl, $C(O)C_1$-$C_8$ hydroxyalkyl, $C(O)C_1$-$C_8$ alkoxyalkyl, $C(O)C_3$-$C_{10}$ cycloalkyl, C(O) $C_3$-$C_{10}$ heterocycloalkyl, $C(O)C_6$-$C_{10}$ aryl, $C(O)C_8$-$C_{10}$ heteroaryl, $C(O)OC_1$-$C_8$ alkyl, $C(O)OC_1$-$C_8$ haloalkyl, $C(O)OC_1$-$C_8$ hydroxyalkyl, $C(O)OC_1$-$C_8$ alkoxyalkyl, $C(O)OC_3$-$C_{10}$ cycloalkyl, $C(O)OC_3$-$C_{10}$ heterocyclyl, $C(O)OC_6$-$C_{10}$ aryl, $C(O)OC_5$-$C_{10}$ heteroaryl, $C(O)NC_1$-$C_8$ alkyl, $C(O)NC_1$-$C_8$ haloalkyl, $C(O)NC_1$-$C_8$ hydroxyalkyl, $C(O)NC_1$-$C_8$ alkoxyalkyl, $C(O)NC_3$-$C_{10}$ cycloalkyl, $C(O)NC_3$-$C_{10}$ heterocyclyl, $C(O)NC_6$-$C_{10}$ aryl, $C(O)NC_5$-$C_{10}$ heteroaryl, $SO_2C_1$-$C_8$ alkyl, $SO_2C_1$-$C_8$ haloalkyl, $SO_2C_1$-$C_8$ hydroxyalkyl, $SO_2C_1$-$C_8$ alkoxyalkyl, $SO_2C_3$-$C_{10}$ cycloalkyl, $SO_2C_3$-$C_{10}$ heterocyclyl, $SO_2C_6$-$C_{10}$ aryl, $SO_2C_5$-$C_{10}$ heteroaryl, $C_1$-$C_8$ alkylene$C_3$-$C_{10}$ cycloalkyl, $C_1$-$C_8$ alkylene$C_3$-$C_{10}$ heterocycloalkyl, $C_1$-$C_8$ alkylene$C_6$-$C_{10}$ aryl, $C_1$-$C_8$ alkylene$C_5$-$C_{10}$ heteroaryl, or $R^{19}$ and $R^{20}$ together with the nitrogen atom to which they connected can independently form 3-membered heterocyclyl rings, and X is selected from CH or N.

In some aspects of Formula 1, R is selected from H, halogen, optionally substituted $C_{1-3}$ alkyl, and optionally substituted $C_{1-3}$ alkoxy.

In some aspects of Formula 1, R is selected from H, F, $CH_3$, $CH_2F$, $CHF_2$, $CF_3$, $CH_2CH_3$, $CH_2CF_3$, i-Pr, c-Pr, $OCH_3$, $OCH_2F$, $OCHF_2$, $OCF_3$, $OCH_2CH_3$, $OCH_2CF_3$, Oi-Pr, and Oc-Pr.

In some aspects of Formula 1, R is selected from $CH_3$, $CF_3$, $CH_2CH$, $CH_2CF_3$, and c-Pr.

In some aspects of Formula 1, R is selected from $CH_3$, and c-Pr.

In some aspects of Formula 1, R is c-Pr.

In some aspects of Formula 1, $R^1$ is selected from H, halogen, optionally substituted $C_{1-3}$ alkyl, and optionally substituted $C_{1-3}$ alkoxy.

In some aspects of Formula 1, $R^1$ is selected from H, F, $CH_3$, $CH_2F$, $CHF_2$, $CF_3$, $CH_2CH_3$, $CH_2CF$, i-Pr, c-Pr, $OCH_3$, $OCH_2F$, $OCHF_2$, $OCF_3$, $OCH_2CH_3$, $OCH_2CF_3$, Oi-Pr, and Oc-Pr.

In some aspects of Formula 1, $R^1$ is selected from H, F, $CH_3$, and $CF_3$.

In some aspects of Formula 1, $R^1$ is H.

In some aspects of Formula 1, $R^2$ is selected from phenyl and 5-6 membered heteroaryl, which are optionally substituted with one or more of groups selected from halogen, optionally substituted $C_{1-3}$ alkyl, and optionally substituted $C_{1-3}$ alkoxy.

In some aspects of Formula 1, $R^2$ is 5-6 membered heteroaryl, which are optionally substituted with one or more of groups selected from halogen, optionally substituted $C_{1-3}$ alkyl, and optionally substituted $C_{1-3}$ alkoxy.

In some aspects of Formula 1, $R^2$ is selected from phenyl

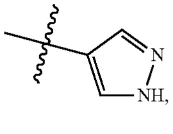

and

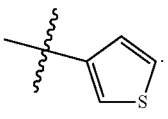

In some aspects of Formula 1, $R^2$ is NH

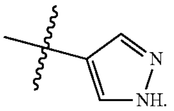 [SMILES: *c1cn[nH]c1]

In some aspects of Formula 1, $R^3$ is selected from phenyl, and 5-6 membered heteroaryl, which are optionally substituted with one or more of groups selected from halogen, optionally substituted $C_{1-8}$ alkyl, and optionally substituted $C_{1-8}$ alkoxy, optionally substituted $C_{1-8}$ alkylene, optionally substituted 3-8 membered carbocyclyl, optionally substituted 4-8 membered heterocyclyl, optionally substituted aryl, optionally substituted 5-6 membered heteroaryl, —CO—, —C(O)—($C_{1-8}$ alkylene)-, —C(O)—NH($C_{1-8}$ alkylene)-, —C(O)—N($C_{1-8}$ alkylene)($C_{1-8}$ alkylene)-, —C(O)-(3-8 membered carbocyclyl)-, —C(O)-(4-8 membered heterocyclyl)-, —C(O)-(5-6 membered heteroaryl)-, —NH($C_{1-8}$ alkylene)-, —N($C_{1-8}$ alkylene)($C_{1-8}$ alkylene)-, —$CH_2$-(3-8 membered carbocyclyl)-, —$CH_2$-(4-8 membered heterocyclyl)-, and —$CH_2$-(5-6 membered heteroaryl)-.

In some aspects of Formula 1, $R^3$ is selected from phenyl, and 5-6 membered heteroaryl, which are optionally substituted with one or more of groups selected from F, Cl, $CH_3$, $CF_3$, $OCH_3$, $OCF_3$, $CH_2CH_3$, $CH_2CF_3$, $OCH_2CH_3$, $OCH_2CF_3$, i-Pr, c-Pr, i-PrO, c-PrO, —CO—, optionally substituted

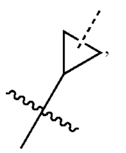

optionally substituted

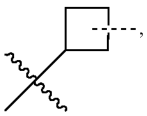

optionally substituted

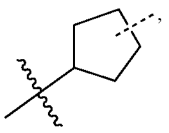

optionally substituted

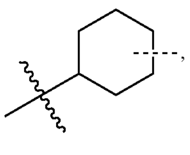

optionally substituted
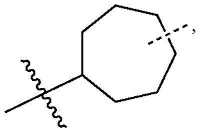
optionally substitute
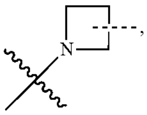
optionally substituted
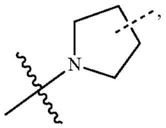
optionally substituted
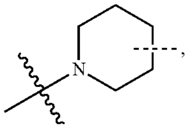
optionally substituted
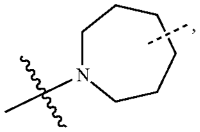
optionally substituted
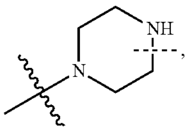
optionally substituted
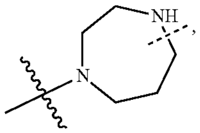
optionally substituted
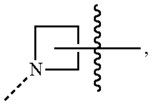
optionally substituted
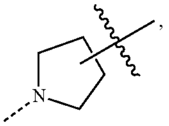
optionally substituted
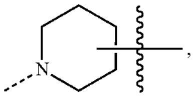
optionally substituted
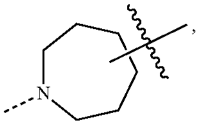
optionally substituted
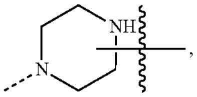
optionally substituted
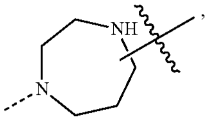
optionally substituted
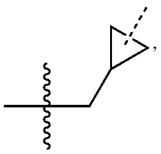

optionally substituted
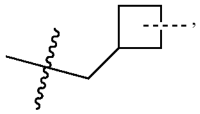
optionally substituted
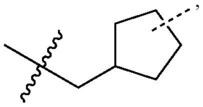
optionally substituted
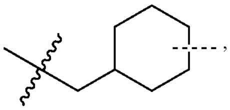
optionally substituted
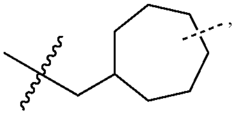
optionally substituted
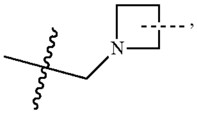
optionally substituted
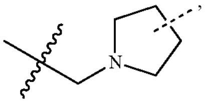
optionally substituted
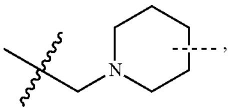
optionally substituted
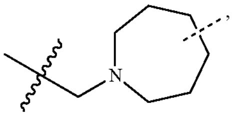
optionally substituted
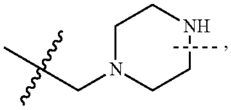
optionally substituted
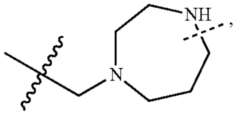
optionally substituted
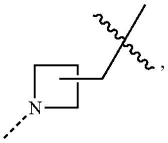
optionally substituted
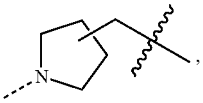
optionally substituted
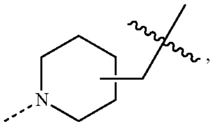
optionally substituted
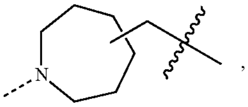

optionally substituted
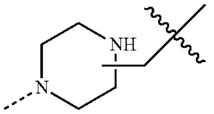
,
optionally substituted
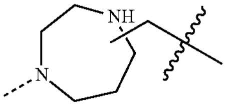
,
optionally substituted
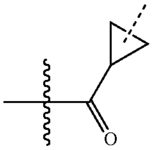
,
optionally substituted
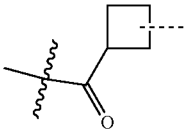
,
optionally substituted
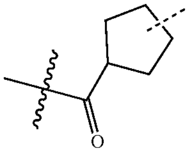
,
optionally substituted
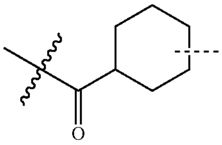
,
optionally substituted
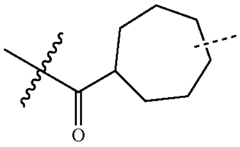
,
optionally substituted
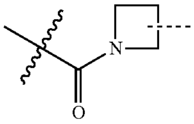
,
optionally substituted
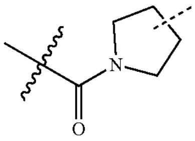
,
optionally substituted
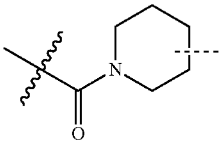
,
optionally substituted
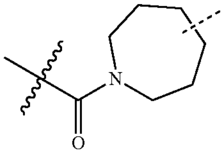
,
optionally substituted
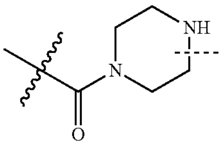
,
optionally substituted
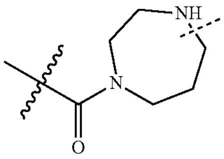
, optionally substituted

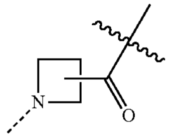 , optionally substituted

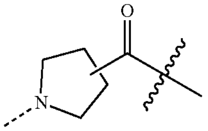 , optionally substituted

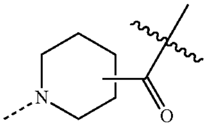 , optionally substituted

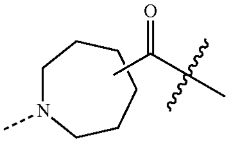 , optionally substituted

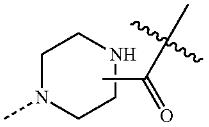 , and optionally substituted

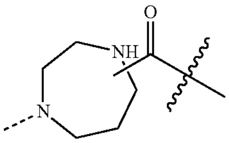 .

In some aspects of Formula 1, $R^3$ is selected from phenyl, thiophene, thiazole, isothiazole, pyrolyl, pyrazolyl, imidazolyl, pyridinyl, pyrimidinyl, and pyrazinyl, which are optionally substituted with one or more of groups selected from F, Cl, $CH_3$, $CF_3$, $OCH_3$, $OCF_3$, $CH_2CH_3$, $CH_2CF_3$, $OCH_2CH_3$, $OCH_2CF_3$, i-Pr, c-Pr, i-PrO, c-PrO, —CO—, optionally substituted

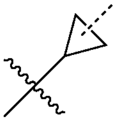 , optionally substituted

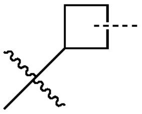 , optionally substituted

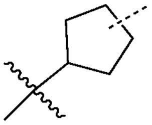 , optionally substituted

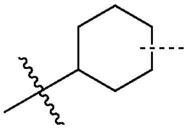 , optionally substituted

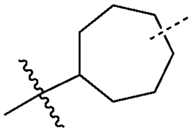 , optionally substituted

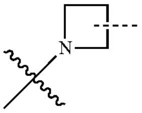 , optionally substituted

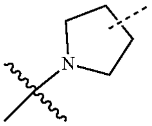 , optionally substituted
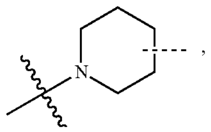
optionally substituted
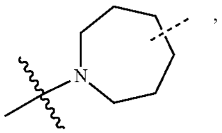
optionally substituted
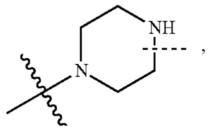
optionally substituted
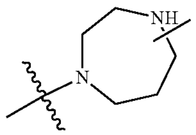
optionally substituted
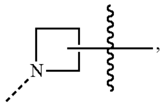
optionally substituted
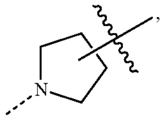
optionally substituted
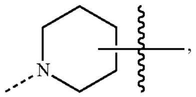
optionally substitute
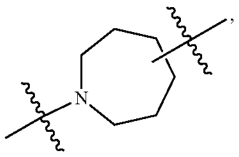
optionally substituted
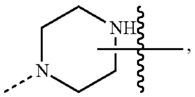
optionally substituted
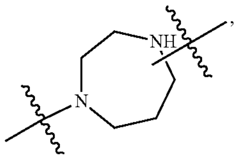
optionally substituted
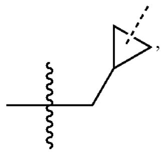
optionally substituted
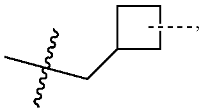
optionally substituted
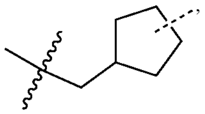
optionally substituted
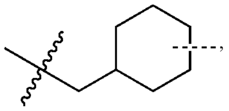

optionally substituted,
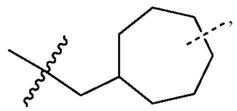
optionally substituted
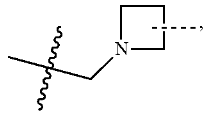
optionally substituted
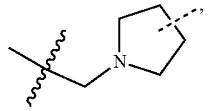
optionally substituted
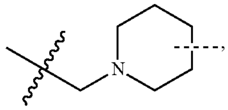
optionally substituted
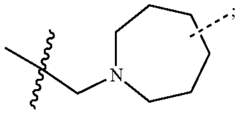
optionally substituted
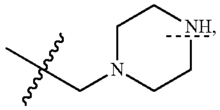
optionally substituted
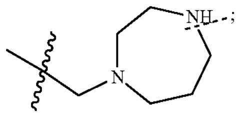
optionally substituted
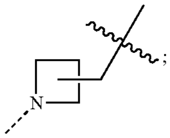
optionally substitute
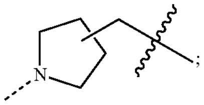
optionally substituted
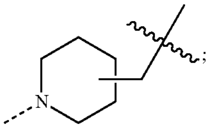
optionally substituted
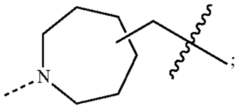
optionally substituted
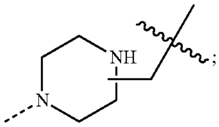
optionally substituted
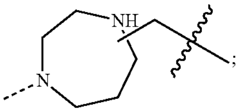
optionally substituted
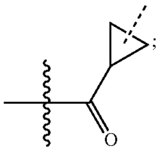

optionally substituted
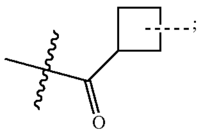
optionally substituted
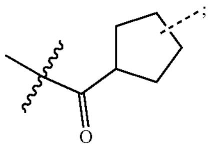
optionally substituted
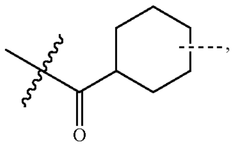
optionally substituted
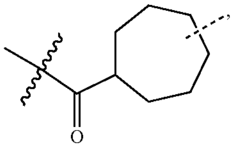
optionally substituted
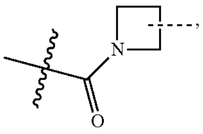
optionally substituted
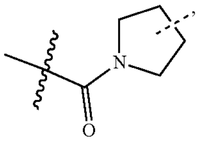
optionally substituted
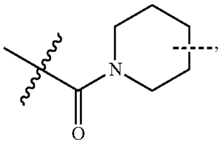
optionally substituted
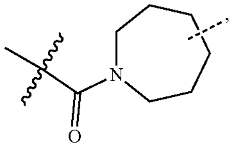
optionally substituted
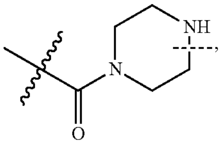
optionally substituted
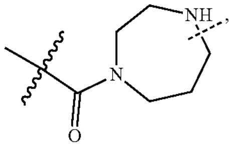
optionally substituted
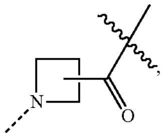
optionally substituted
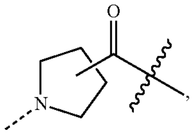
optionally substituted
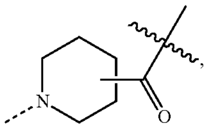

optionally substituted
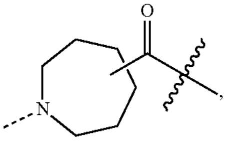
optionally substituted
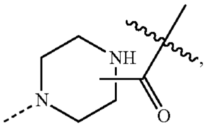
and optionally substituted
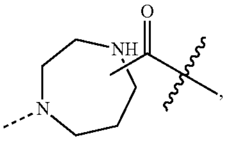
In some aspects of Formula 1, $R^3$ is selected from
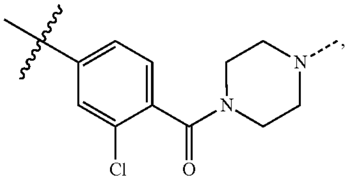
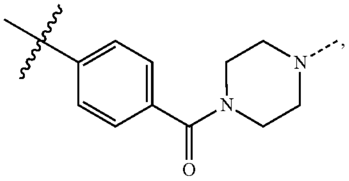
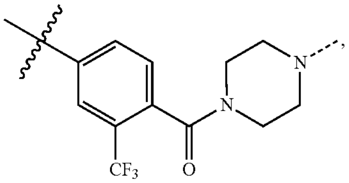
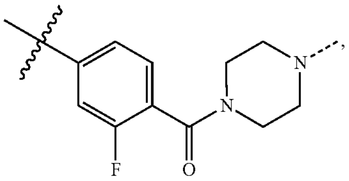
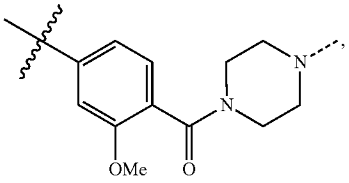
-continued
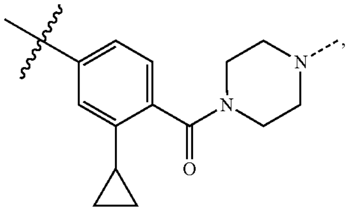
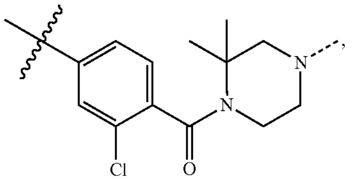
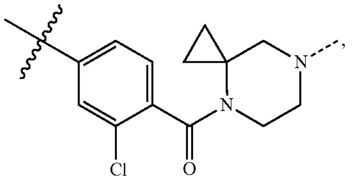
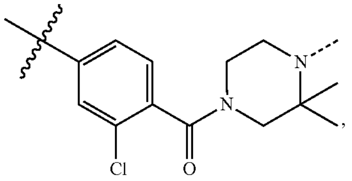
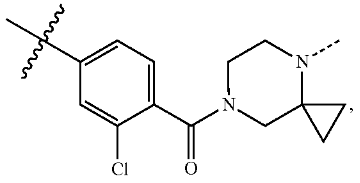
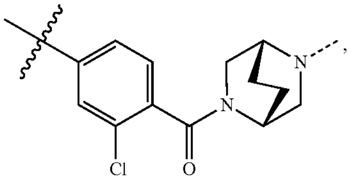
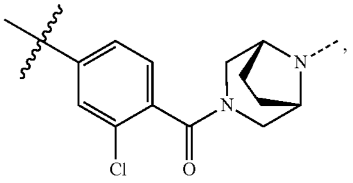
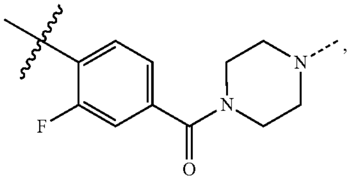
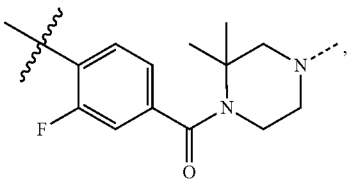

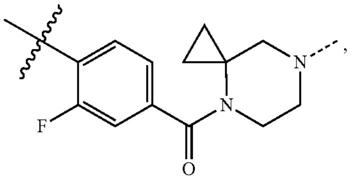
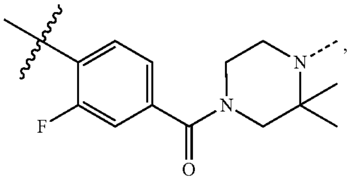
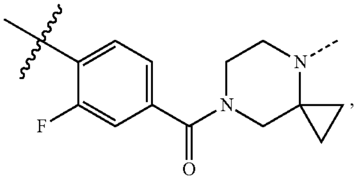
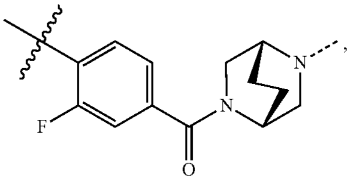
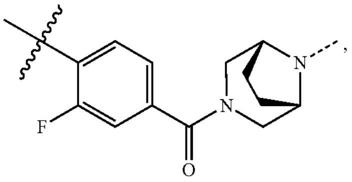
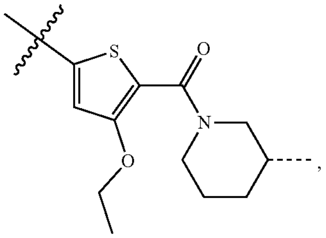
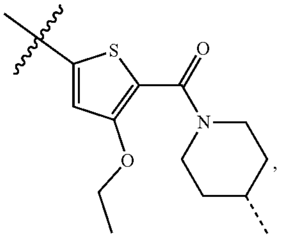
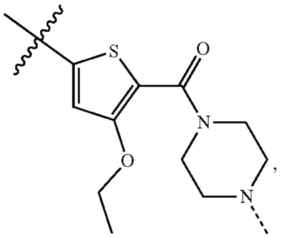
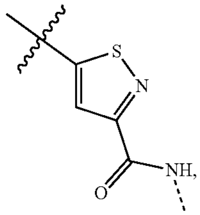
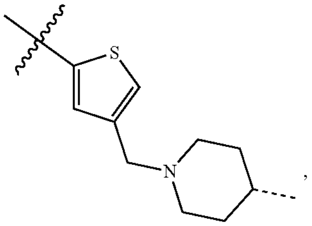
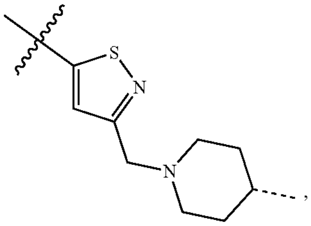
and
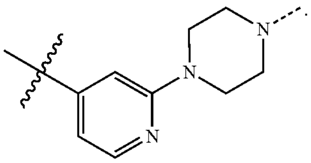
In some aspects of Formula 1, $R^3$ is selected from
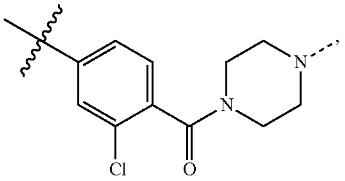
and
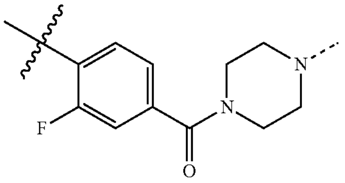
In some aspects of Formula 1, $R^3$ is
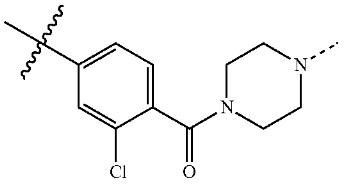
In some aspects of Formula 1, X is N.

PTK6 Ligands could also be:

FORMULA 2

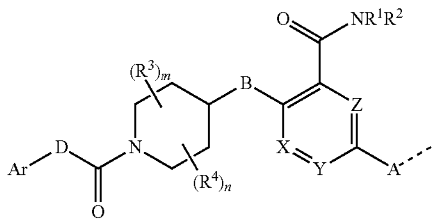

Wherein

X, Y and Z are independently selected from null, $CR^5$, and N, wherein $R^5$ is selected from hydrogen, halogen, or optionally substituted $C_{1-3}$ alkyl;

A is selected from null or —$R^6$—$R^7$—, wherein $R^6$ and $R^7$ are independently selected from null, $NR^8$, O, S, C(O), $C(O)NR^8$, $NR^8C(O)$, $NR^8C(O)NR^9$, $OC(O)NR^9$, NRC(O)O, S(O), $S(O)NR^9$, $NR^8S(O)$, $NR^8S(O)NR^9$, $OS(O)NR^9$, $NR^8S(O)O$, $S(O)_2$, $S(O)_2NR^8$, $NR^8S(O)_2$, $NR^8S(O)_2NR^9$, $OS(O)_2NR^9$, $NR^8S(O)_2O$, optionally substituted $C_1$-$C_8$ alkylene, optionally substituted $C_2$-$C_8$ alkenylene, optionally substituted $C_2$-$C_8$ alkynylene, optionally substituted 3-10 membered carbocyclyl, optionally substituted 4-10 membered heterocyclyl, optionally substituted aryl, and optionally substituted heteroaryl, wherein $R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$ alkyl, optionally substituted $C_1$-$C_8$alkylamino$C_1$-$C_8$ alkyl, optionally substituted 3-10 membered carbocyclyl$C_1$-$C_8$ alkyl, optionally substituted 4-10 membered heterocyclyl$C_1$-$C_8$ alkyl, optionally substituted 3-10 membered carbocyclyl, optionally substituted 4-10 membered heterocyclyl, optionally substituted aryl, and optionally substituted heteroaryl, or $R^8$ and $R^9$ together with the atom to which they are connected form a 4-20 membered heterocyclyl ring;

B and D are independently selected from $CR^{10}R^{11}$, $NR^{10}$, O, SO, or $SO_2$, wherein $R^{10}$ and $R^{11}$ are independently selected from hydrogen, halogen, hydroxy, cyano, nitro, and optionally substituted $C_1$-$C_3$ alkyl, or $R^{10}$ and $R^{11}$ together with the atom to which they are connected form a 3-6 membered carbocyclyl rings or 4-6 membered heterocyclyl ring;

$R^1$ and $R^2$ are independently selected from hydrogen, and optionally substituted $C_1$-$C_3$ alkyl, or $R^1$ and $R^2$ together with the atom to which they are connected form a 4-6 membered heterocyclyl ring;

$R^3$ and $R^4$, at each occurrence, are independently selected from hydrogen, fluoro, hydroxyl, cyano, amino, nitro, optionally substituted $C_1$-$C_3$ alkyl, optionally substituted $C_1$-$C_3$ alkoxy, and optionally substituted $C_1$-$C_3$ alkylamino.

m and n are independently selected from 0, 1, 2, 3, and 4.

Ar is selected from aryl, and heteroaryl, which are optionally substituted with one or more substituents independently selected from hydrogen, halogen, oxo, CN, $NO_2$, $OR^{12}$, $SR^{12}$, $NR^{12}R^{13}$, $OCOR^{12}$, $OCO_2R^{12}$, $OCON(R^{12})R^3$, $COR^{12}$, $CO_2R^{12}$, $CON(R^{12})R^{12}$, $SOR^{12}$, $SO_2R^{12}$, $SO_2N(R^{12})R^{13}$, $NR^{14}CO_2R^{12}$, $NR^{14}COR^{12}$, $NR^{14}C(O)N(R^{12})R^{13}$, $NR^{14}SOR^{12}$, $NR^{14}SO_2R^{12}$, $NR^{14}SO_2N(R^{12})R^3$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$ alkyl, optionally substituted $C_1$-$C_8$alkylamino$C_1$-$C_8$ alkyl, optionally substituted 4-10 membered heterocyclyl$C_1$-$C_8$ alkyl, optionally substituted 3-10 membered carbocyclyl$C_1$-$C_8$ alkyl, optionally substituted 3-membered carbocyclyl, optionally substituted 4-10 membered heterocyclyl, optionally substituted aryl, and optionally substituted heteroaryl, wherein $R^1$, $R^{13}$, and $R^1$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$ alkyl, optionally substituted $C_1$-$C_8$alkylamino$C_1$-$C_8$ alkyl, optionally substituted 3-10 membered carbocyclyl$C_1$-$C_8$ alkyl, optionally substituted 4-10 membered heterocyclyl$C_1$-$C_8$alkyl, optionally substituted 3-10 membered carbocyclyl, optionally substituted 4-10 membered heterocyclyl, optionally substituted aryl, and optionally substituted heteroaryl, or $R^{12}$ and $R^{13}$, $R^{12}$ and $R^{14}$ together with the atom to which they are connected form a 4-20 membered heterocyclyl ring;

In some aspects of Formula 2, X, Y and Z are independently selected from CH, CF, and N.

In some aspects of Formula 2, X is N; Y and Z are independently selected from CH, CF, and N.

In some aspects of Formula 2, X is N; Y and Z are CH.

In some aspects of Formula 2, A is null or selected from optionally substituted 3-8 membered carbocyclyl, optionally substituted 4-8 membered heterocyclyl, optionally substituted 6 membered aryl, optionally substituted 5-6 membered heteroaryl, fused rings, bridged rings, and spiro rings.

In some aspects of Formula 2, A is null, phenyl, 4-8 membered heterocyclyl, and 5-6 membered heteroaryl, which are optionally substituted by F, OH, CN, $NO_2$, $NH_2$, optionally substituted $C_1$-$C_6$ alkyl, optionally substituted $C_1$-$C_6$ alkoxy, optionally substituted 3-10 membered carbocyclyl, optionally substituted 4-10 membered heterocyclyl, optionally substituted aryl, and optionally substituted heteroaryl.

In some aspects of Formula 2, A is null, phenyl, 4-8 membered heterocyclyl, and 5-6 membered heteroaryl, which are optionally substituted by F, OH, CN, $NO_2$, $NH_2$, $CH_3$, $CF_3$, i-Pr, and c-Pr.

In some aspects of Formula 2, A is

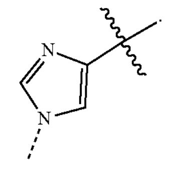

In some aspects of Formula 2, B and D are independently selected from $CH_2$, CHOH, $CHCH_3$, $C(CH_3)_2$,

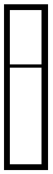

CHF, $CF_2$, O, NH, and $NCH_3$.

In some aspects of Formula 2, B is O.

In some aspects of Formula 2, D is $CH_2$.

In some aspects of Formula 2, $R^1$ and $R^2$ are independently selected from H, and optionally substituted $C_1$-$C_3$ alkyl, with the proviso that at least one of $R^1$ and $R^2$ is H.

In some aspects of Formula 2, $R^1$ and $R^2$ are independently selected from H, and $CH_3$, with the proviso that at least one of $R^1$ and $R^2$ is H.

In some aspects of Formula 2, $R^1$ and $R^2$ are H.

In some aspects of Formula 2, $R^3$ and $R^4$, at each occurrence, are independently selected from H, F, OH, CN, $NH_2$, $NO_2$, $CH_3$, $CF_3$, i-Pr, and c-Pr.

In some aspects of Formula 2, $R^3$ and $R^4$, at each occurrence, are independently selected from H, and F.

In some aspects of Formula 2, m and n are independently selected from 0, 1, and 2.

In some aspects of Formula 2, m and n are 1.

In some aspects of Formula 2, Ar is selected from aryl, and heteroaryl, which are optionally substituted with one or more substituents independently selected from H, F, =O, CN, $NO_2$, $CH_3$, $OCH_3$, $CH_2F$, $CHF_2$, $CF_3$, $OCH_2F$, $OCHF_2$, $OCF_3$, i-Pr, and c-Pr.

In some aspects of Formula 2, Ar is phenyl, which is optionally substituted with one or more substituents independently selected from H, F, =O, CN, $NO_2$, $CH_3$, $OCH_3$, $CH_2F$, $CHF_2$, $CF_3$, $OCH_2F$, $OCHF_2$, $OCF_3$, i-Pr, and c-Pr.

In some aspects of Formula 2, Ar is 4-$OCF_3$ substituted phenyl.

In some aspects, the PTK6 ligand can be derivatives of following compounds.

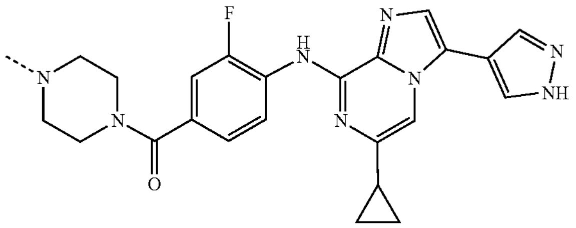

Formula 2A

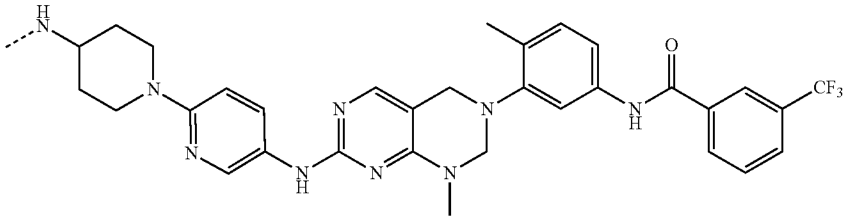

Formula 2B

In some aspects, the PTK6 ligand can be, e.g.:

FORMULA 2A

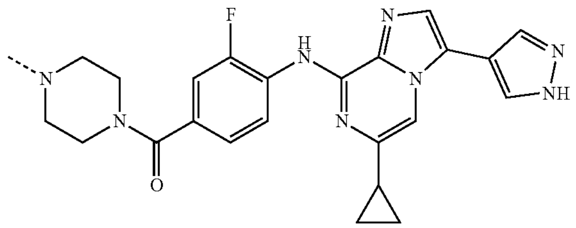

FORMULA 2B

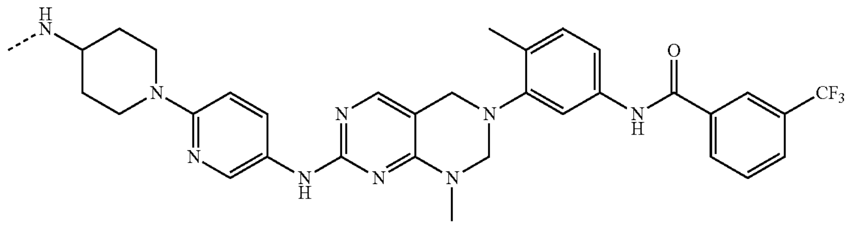

-continued

FORMULA 2C

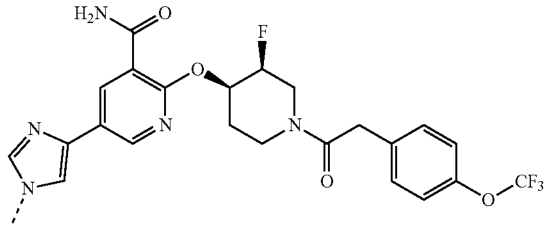

FORMULA 2D

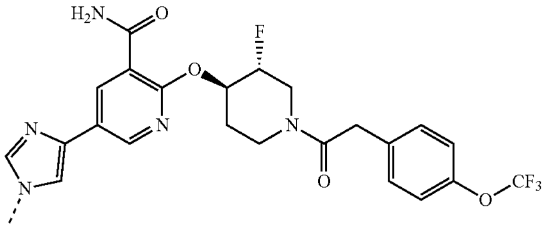

The PTK6 ligand can be bound to PTK6 and/or PTK6 mutant proteins.

Degradation/Disruption Tags

Degradation/Disruption Tags EL include but are not limited to:

FORMULA 3A

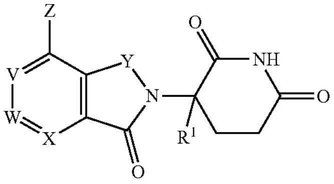

FORMULA 3B

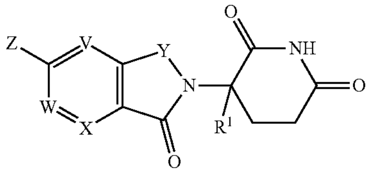

FORMULA 3C

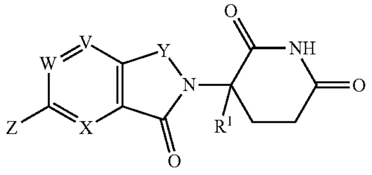

FORMULA 3D,

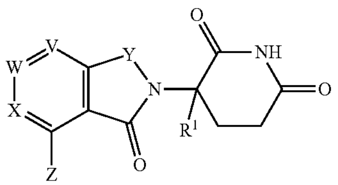

wherein

V, W, and X are independently selected from $CR^2$ and N;

Y is selected from CO, $CR^3R^4$, and N═N;

Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_3$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferly, Z is selected from null, $CH_2$, CH═CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

FORMULA 3A

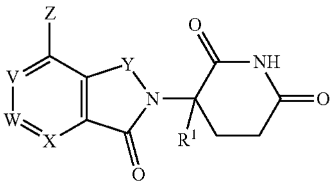

FORMULA 3B

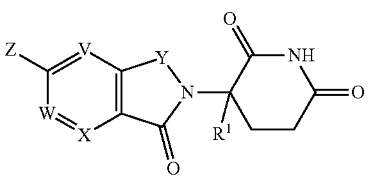

FORMULA 3C

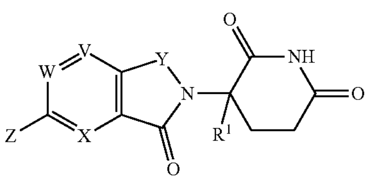

-continued

FORMULA 3D

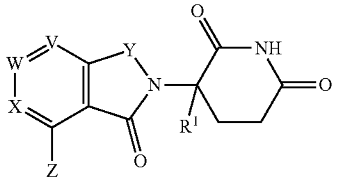

wherein

V, W, and X are independently $CR^2$ or N,

Y is CO or $CH_2$,

Z is $CH_2$, NH, or O, $R^1$ is hydrogen, methyl, or fluoro, and $R^2$ is hydrogen, halogen, or $C_1$-$C_5$ alkyl;

FORMULA 3E

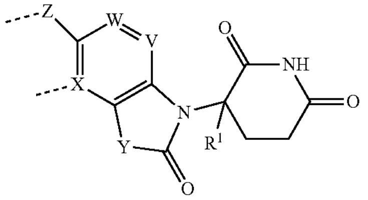

FORMULA 3F

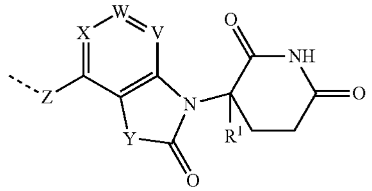

FORMULA 3G

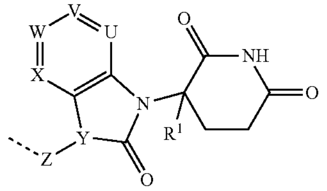

FORMULA 3H

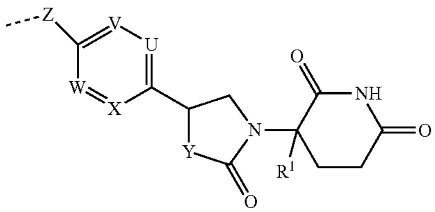

FORMULA 3I

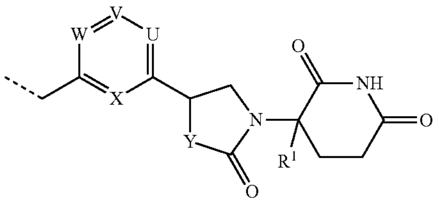

wherein

U, V, W, and X are independently selected from $CR^2$ and N;

Y is selected from $CR^3R^4$, $NR^3$ and O; preferably, Y is selected from $CH_2$, NH, $NCH_3$ and O;

Z is selected from null, CO, $CR^5R^6$, NR'', O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferly, Z is selected from null, $CH_2$, CH=CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

FORMULA 4A

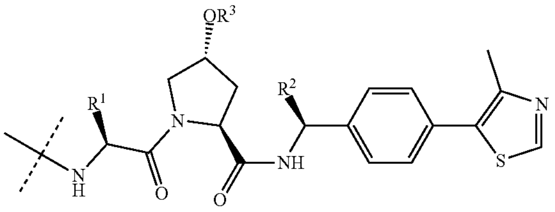

wherein $R^1$ and $R^2$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_1$-$C_8$ aminoalkyl, $C_1$-$C_8$ alkylaminoalkyl, $C_3$-$C_7$ cycloalkyl, $C_3$-$C_7$ heterocyclyl, $C_2$-$C_8$ alkenyl, or $C_2$-$C_8$ alkynyl;

$R^3$ is H, $C(O)C_1$-$C_8$ alkyl, $C(O)C_1$-$C_8$ alkoxyalkyl, $C(O)C_1$-$C_8$ haloalkyl, $C(O)C_1$-$C_8$ hydroxyalkyl, $C(O)C_1$-$C_8$ aminoalkyl, $C(O)C_1$-$C_8$ alkylaminoalkyl, $C(O)C_3$-$C_7$ cycloalkyl, $C(O)C_3$-$C_7$ heterocyclyl, $C(O)C_2$-$C_8$ alkenyl, $C(O)C_2$-$C_8$ alkynyl, $C(O)OC_1$-$C_8$ alkoxyalkyl, $C(O)OC_1$-$C_8$ haloalkyl, $C(O)OC_1$-$C_8$ hydroxyalkyl, $C(O)OC_1$-$C_8$ aminoalkyl, $C(O)OC_1$-$C_8$ alkylaminoalkyl, $C(O)OC_3$-$C_7$ cycloalkyl, $C(O)OC_3$-$C_7$ heterocyclyl, $C(O)OC_2$-$C_8$ alkenyl, $C(O)OC_2$-$C_8$ alkynyl, $C(O)NC_1$-$C_8$ alkoxyalkyl, $C(O)NC_1$-$C_8$ haloalkyl, $C(O)NC_1$-$C_8$ hydroxyalkyl, $C(O)NC_1$-$C_8$ aminoalkyl, $C(O)NC_1$-$C_8$ alkylaminoalkyl, $C(O)NC_3$-$C_7$ cycloalkyl, C(O)N$C_3$-$C_7$ heterocyclyl, C(O)N$C_2$-$C_8$ alkenyl, C(O)N$C_2$-$C_8$ alkynyl, $P(O)(OH)_2$, P(O)(O$C_1$-$C_8$ alkyl$)_2$, or P(O)(O$C_1$-$C_8$ aryl$)_2$.

FORMULA 4B

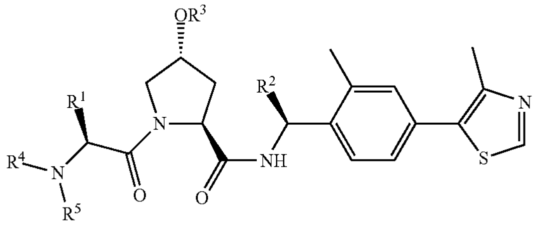

FORMULA 4C

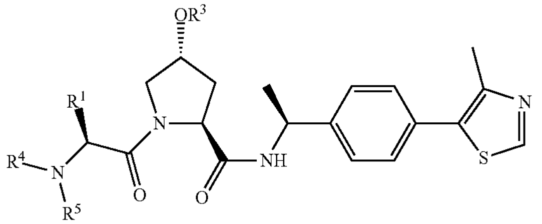

FORMULA 4D

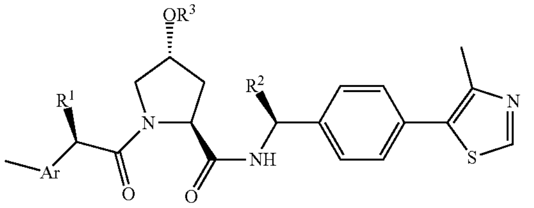

FORMULA 4E

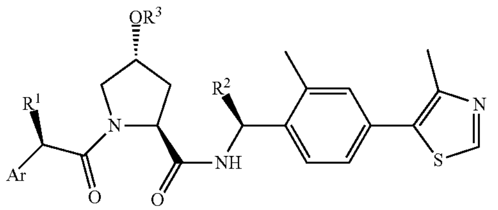

FORMULA 4F

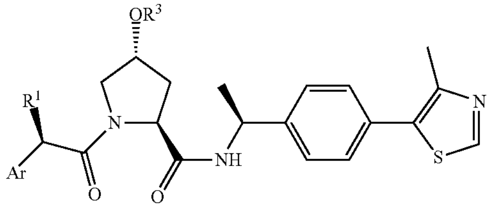

wherein $R^1$ and $R^2$ are independently selected from hydrogen, halogen, OH, $NH_2$, CN, optionally substituted $C_1$-$C_8$ alkyl, optionally substituted $C_1$-$C_8$alkoxy$C_1$-$C_8$ alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$ alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; (preferably, $R^1$ is selected from iso-propyl or tert-butyl; and $R^2$ is selected from hydrogen or methyl).

$R^3$ is hydrogen, optionally substituted C(O)$C_1$-$C_8$ alkyl, optionally substituted C(O)$C_1$-$C_8$alkoxy$C_1$-$C_8$ alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$ alkyl, optionally substituted C(O)$C_3$-$C_7$ cycloalkyl, optionally substituted C(O)(3-7 membered heterocyclyl), optionally substituted C(O)$C_2$-$C_8$ alkenyl, optionally substituted C(O)$C_2$-$C_8$ alkynyl, optionally substituted C(O)O$C_1$-$C_8$alkoxy$C_1$-$C_8$ alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$ aminoalkyl, optionally substituted C(O)O$C_1$-$C_8$alkylamino$C_1$-$C_8$ alkyl, optionally substituted C(O)O$C_3$-$C_7$ cycloalkyl, optionally substituted C(O)O(3-7 membered heterocyclyl), optionally substituted C(O)O$C_2$-$C_8$ alkenyl, optionally substituted C(O)O$C_2$-$C_8$ alkynyl, optionally substituted C(O)N$C_1$-$C_8$alkoxy$C_1$-$C_8$ alkyl, optionally substituted C(O)N$C_1$-$C_8$ haloalkyl, optionally substituted C(O)N$C_1$-$C_8$ hydroxyalkyl, optionally substituted C(O)N$C_1$-$C_8$ aminoalkyl, optionally substituted C(O)N$C_1$-$C_8$alkylamino$C_1$-$C_8$ alkyl, optionally substituted C(O)N$C_3$-$C_7$ cycloalkyl, optionally substituted C(O)N(3-7 membered heterocyclyl), optionally substituted C(O)N$C_2$-$C_8$ alkenyl, optionally substituted C(O)N$C_2$-$C_8$ alkynyl, optionally substituted $P(O)(OH)_2$, optionally substituted P(O)(O$C_1$-$C_8$ alkyl$)_2$, and optionally substituted P(O)(O$C_1$-$C_8$ aryl$)_2$; and $R^4$ and $R^5$ are independently selected from hydrogen, $COR^6$, $CO_2R^6$, $CONR^6R^7$, $SOR^6$, $SO_2R^6$, $SO_2NR^6R^7$, optionally substituted $C_1$-$C_8$ alkyl, optionally substituted $C_1$-$C_8$alkoxy$C_1$-$C_8$ alkyl, optionally substituted $C_1$-$C_8$alkylamino$C_1$-$C_8$ alkyl, optionally substituted 3-8 membered cycloalkyl, optionally substituted 3-8 membered heterocyclyl, optionally substituted aryl, and optionally substituted heteroaryl, wherein $R^6$ and $R^7$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$ alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl, or $R^4$ and $R^5$; $R^6$ and $R^7$ together with the atom to which they are connected form a 4-8 membered cycloalkyl or heterocyclyl ring;

Ar is selected from aryl and heteroaryl, each of which is optionally substituted with one or more substituents independently selected from F, Cl, CN, $NO_2$, $OR^8$, $NR^8R^9$, $COR^8$, $CO_2R^8$, $CONR^8R^9$, $SOR^8$, $SO_2R^8$, $SO_2NR^9R^{10}$, $NR^9COR^{10}$, $NR^8C(O)NR^9R^{10}$, $NR^9SOR^{10}$, $NR^9SO_2R^{10}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_8$alkyl, optionally substituted $C_3$-$C_2$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl, wherein $R^8$, $R^9$, and $R^{10}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl, or $R^8$ and $R^9$; $R^9$ and $R^{10}$ together with the atom to which they are connected form a 4-8 membered cycloalkyl or heterocyclyl ring.

FORMULA 5A

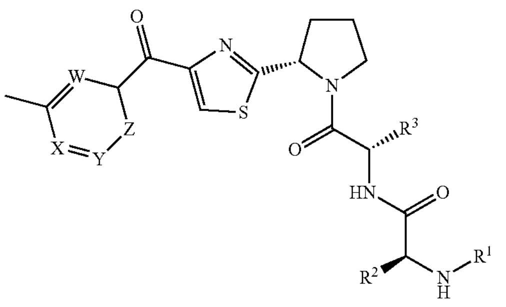

wherein $R^1$, $R^2$, $R^3$, and $R^4$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_3$-$C_7$ cycloalkyl, $C_3$-$C_7$ heterocyclyl, $C_2$-$C_8$ alkenyl, or $C_2$-$C_8$ alkynyl, and V, W, X, and Z are independently $CR^4$ or N.

And

FORMULA 5B,

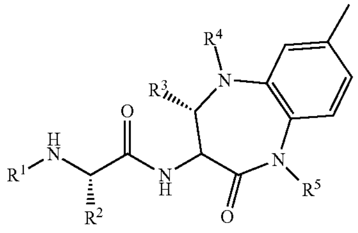

wherein $R^1$, $R^2$, and $R^3$ are independently selected from hydrogen, halogene, optionally substituted $C_1$-$C_8$ alkyl, optionally substituted $C_1$-$C_8$alkoxy$C_1$-$C_8$ alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl;

$R^4$ and $R^5$ are independently selected from hydrogen, $COR^6$, $CO_2R^6$, $CONR^6R^7$, $SOR^6$, $SO_2R^6$, $SO_2NR^6R^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$ alkyl, optionally substituted aryl-$C_1$-$C_8$alkyl, optionally substituted 3-8 membered cycloalkyl, optionally substituted 3-8 membered heterocyclyl, optionally substituted aryl, and optionally substituted heteroaryl, wherein $R^6$ and $R^7$ are independently selected from hydrogen, optionally substituted $C_1$-$C_8$ alkyl, optionally substituted $C_1$-$C_8$alkoxy$C_1$-$C_8$ alkyl, optionally substituted $C_1$-$C_8$alkylamino$C_1$-$C_8$ alkyl, optionally substituted 3-8 membered cycloalkyl, optionally substituted 3-8 membered heterocyclyl, optionally substituted aryl, and optionally substituted heteroaryl, or $R^6$ and $R^7$ together with the atom to which they are connected form a 4-8 membered cycloalkyl or heterocyclyl ring.

In some aspects, the degradation/disruption tag can be, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl) sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), FK506 (Liu et al., 1991) rapamycin (Fan et al., 2017; Rodrik-Outmezguine et al., 2016), and/or analogs thereof.

In some aspects, the degradation/disruption tag can be, e.g., one of the following structures:

FORMULA 6A

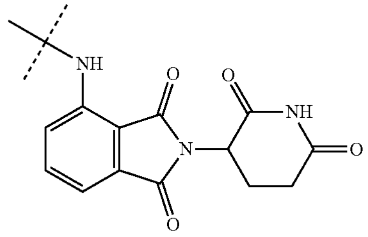

FORMULA 6B

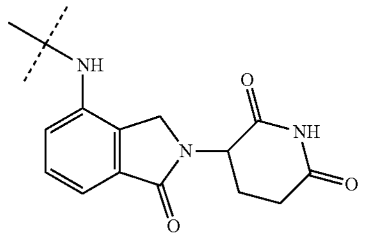

FORMULA 6C

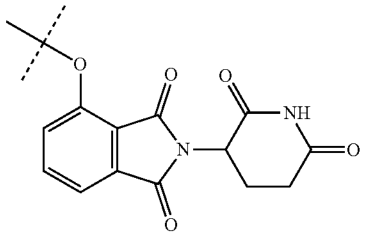

FORMULA 6D

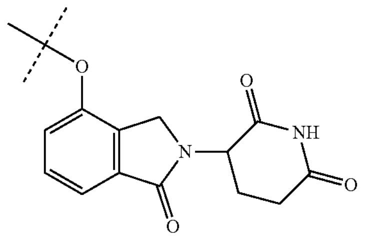

-continued
FORMULA 6E
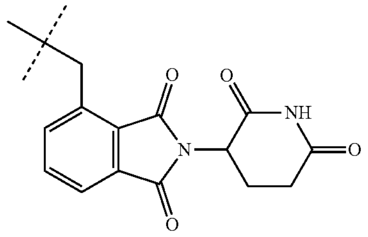
FORMULA 6F
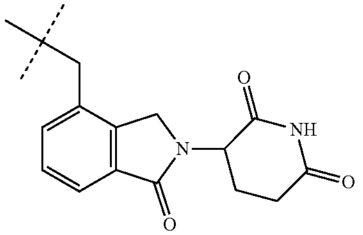
FORMULA 6G
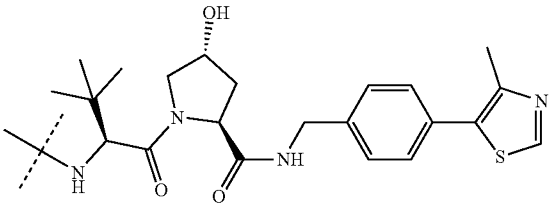
FORMULA 6H
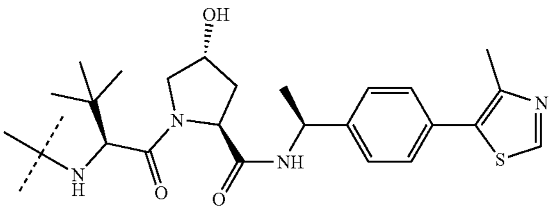
FORMULA 6I
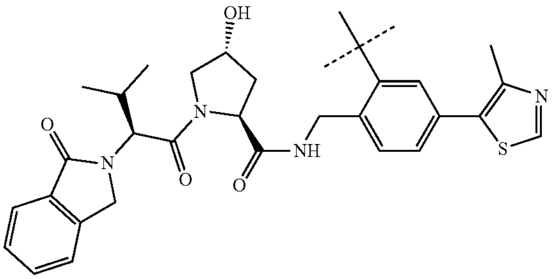
FORMULA 6J
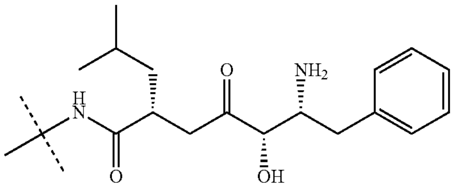
-continued
FORMULA 6K
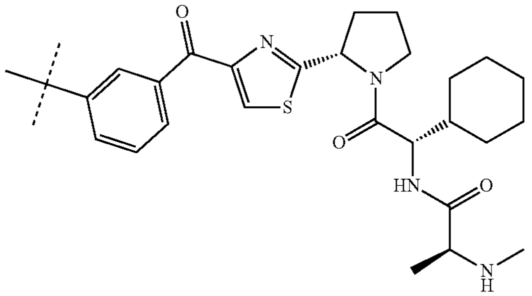
FORMULA 6L
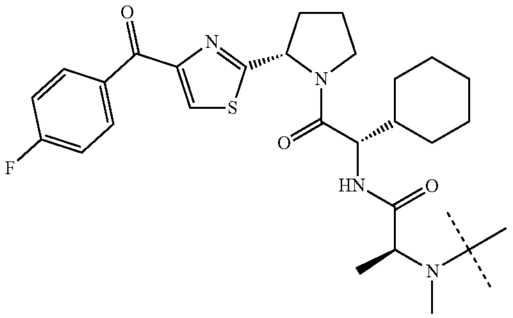
FORMULA 6M
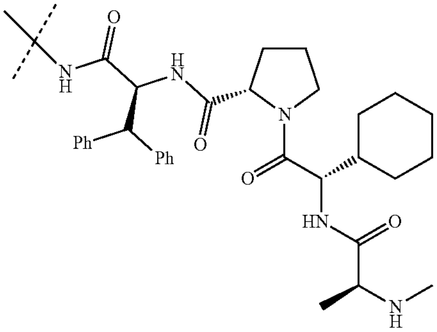
FORMULA 6N
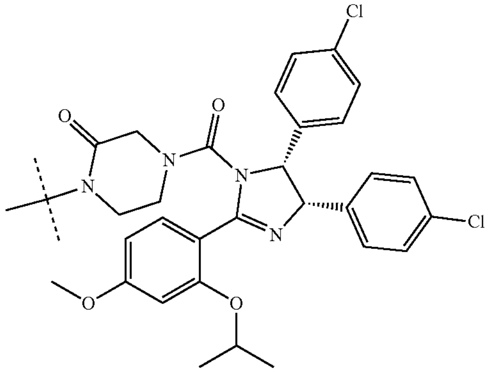

-continued
FORMULA 6O
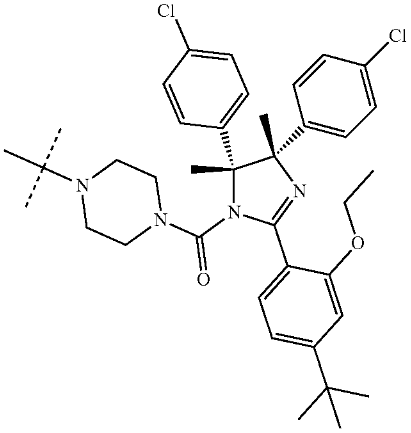
FORMULA 6P
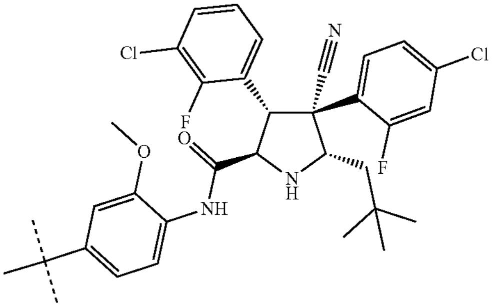
FORMULA 6Q
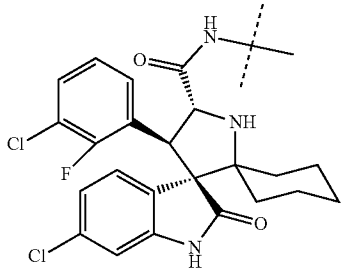
FORMULA 6R
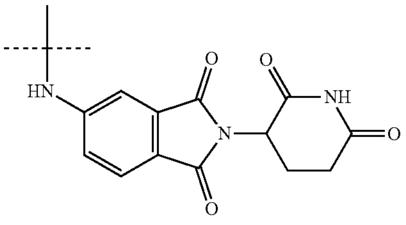
FORMULA 6S
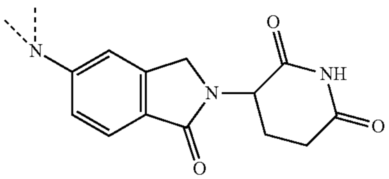
-continued
FORMULA 6T
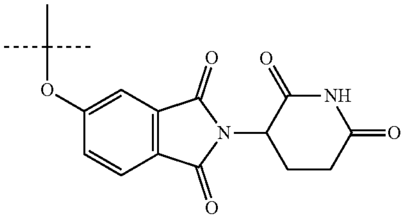
FORMULA 6U
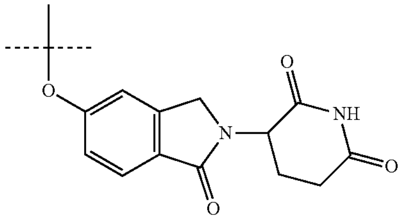
FORMULA 6V
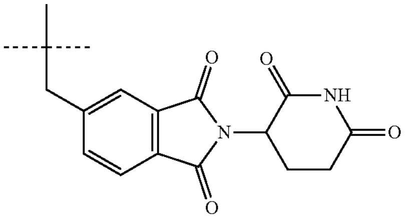
FORMULA 6W
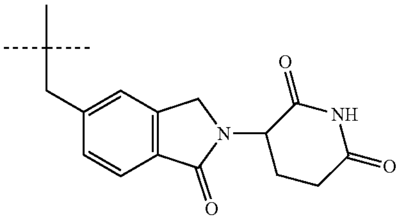
FORMULA 6X
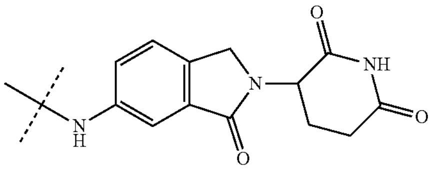
FORMULA 6Y
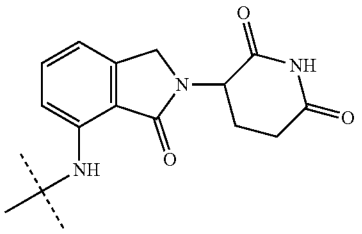
FORMULA 6Z
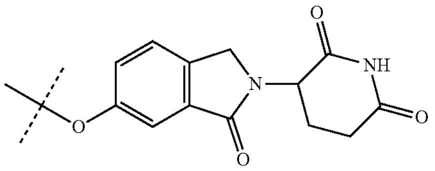

-continued
FORMULA 6AA
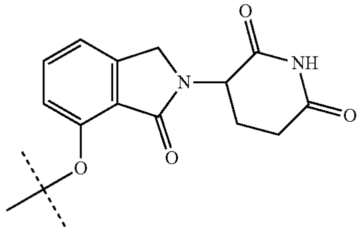
FORMULA 6AB
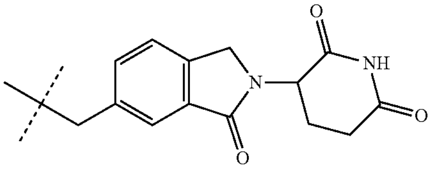
FORMULA 6AC
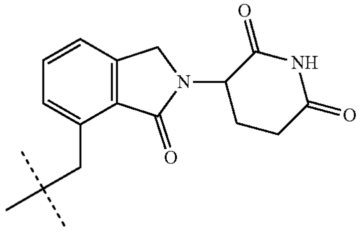
FORMULA 6AD
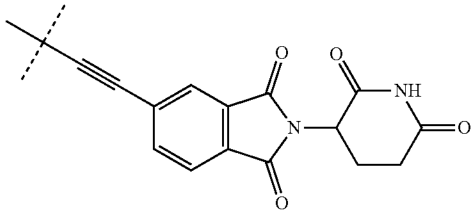
FORMULA 6AE
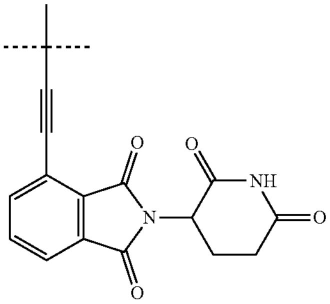
FORMULA 6AF
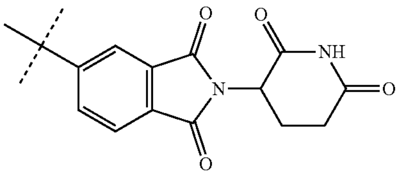
FORMULA 6AG
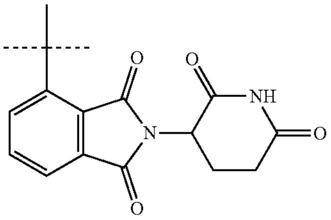
-continued
FORMULA 6AH
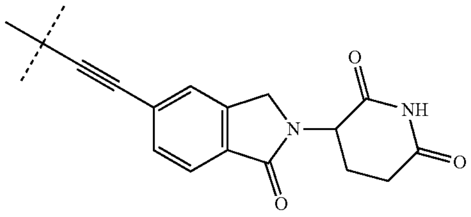
FORMULA 6AI
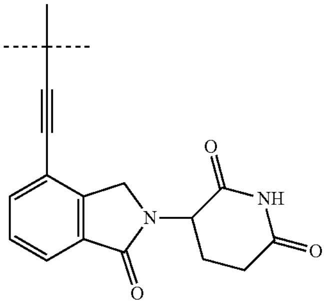
FORMULA 6AJ
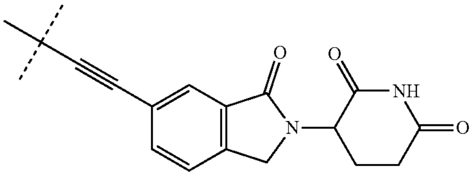
FORMULA 6AK
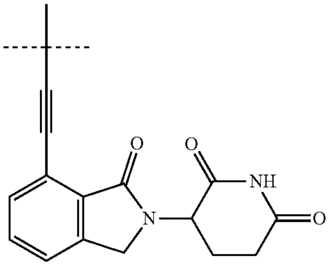
FORMULA 6AL
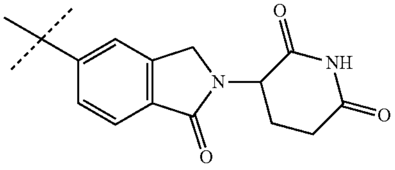
FORMULA 6AM
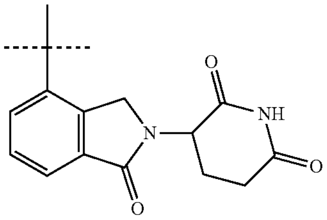
FORMULA 6AN
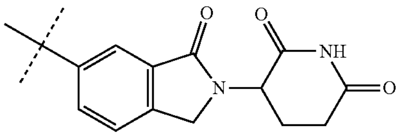

-continued
FORMULA 6AO
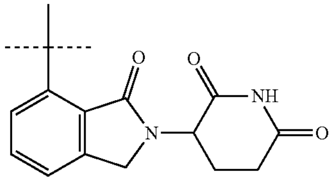
FORMULA 6AP
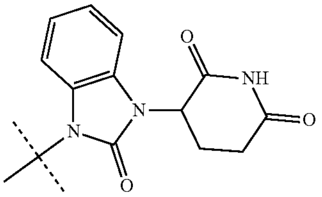
FORMULA 6AQ
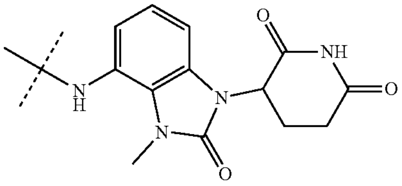
FORMULA 6AR
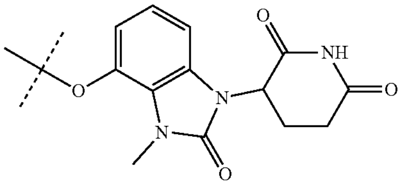
FORMULA 6AS
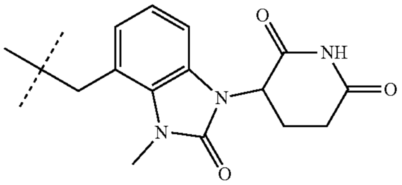
FORMULA 6AT
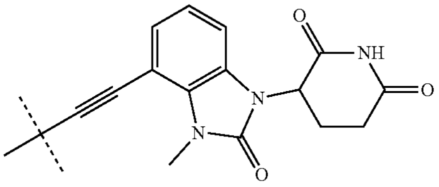
FORMULA 6AU
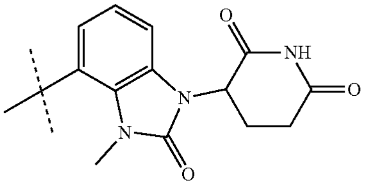
FORMULA 6AV
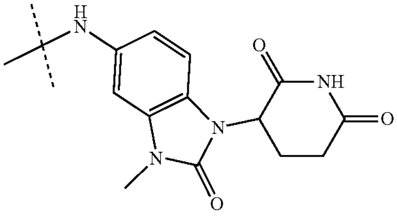
-continued
FORMULA 6AW
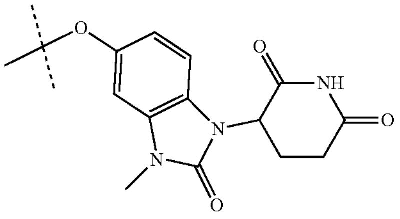
FORMULA 6AX
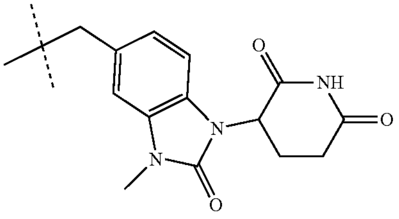
FORMULA 6AY
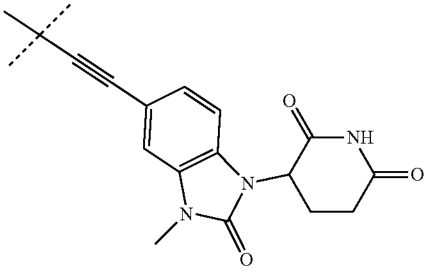
FORMULA 6AZ
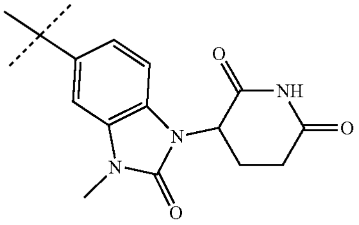
FORMULA 6BA
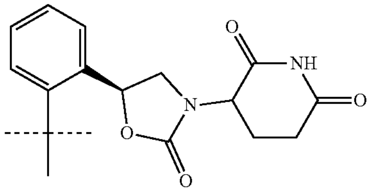
FORMULA 6BB
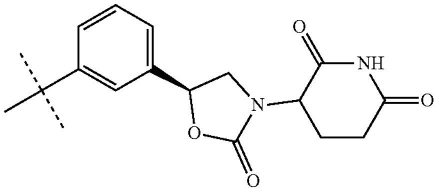

FORMULA 6BC
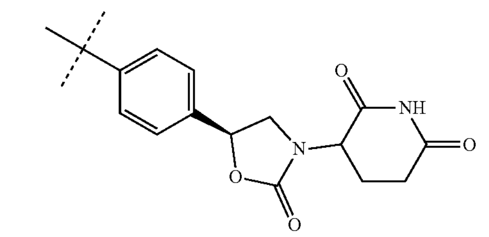
FORMULA 6BD
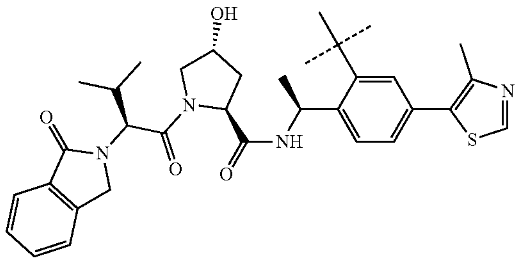
FORMULA 6BE
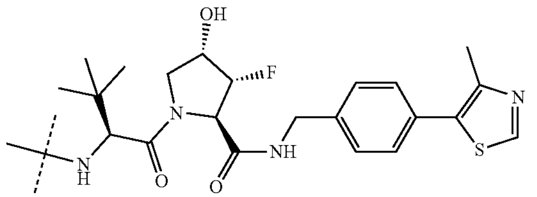
FORMULA 6BF
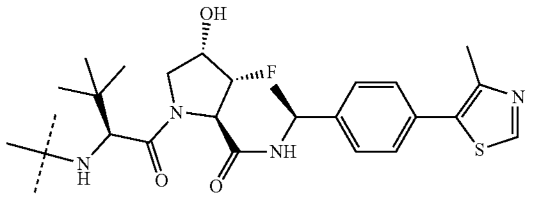
FORMULA 6BG
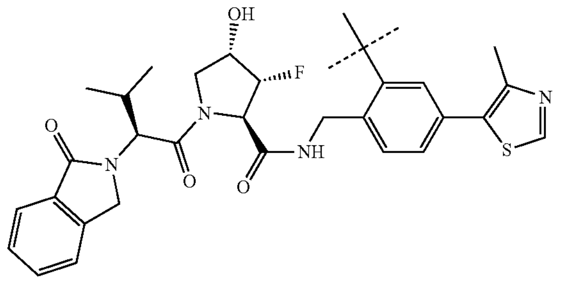
FORMULA 6BH
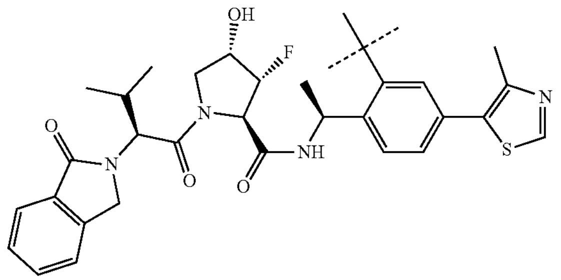
FORMULA 6BI
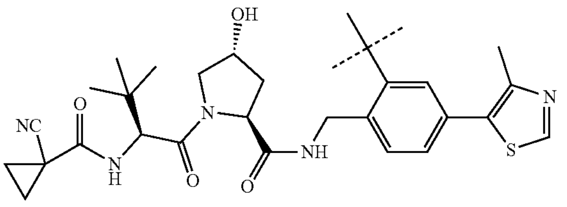
FORMULA 6BJ
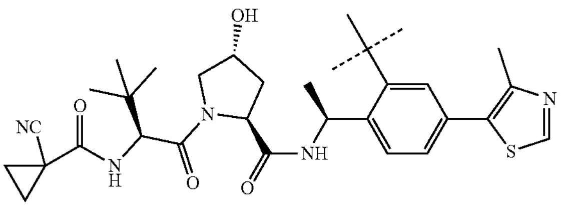
FORMULA 6BK
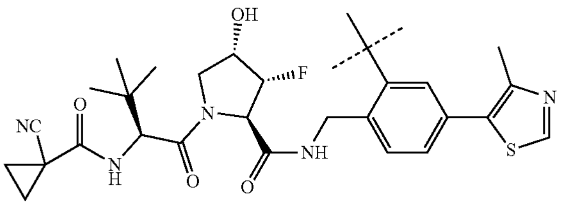
FORMULA 6BL
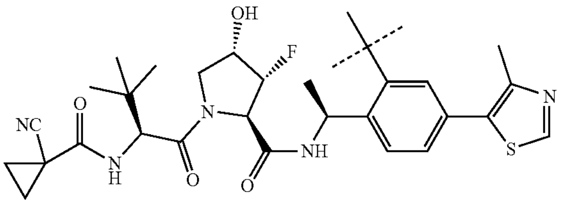
FORMULA 6BM
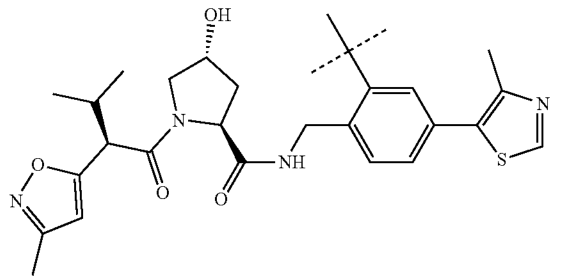
FORMULA 6BN
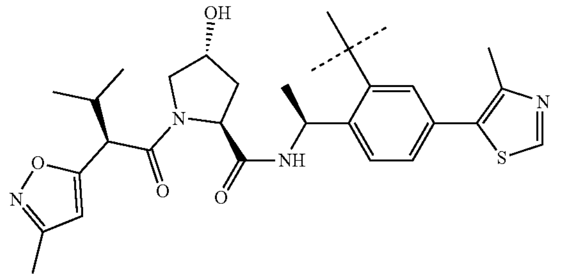

-continued
FORMULA 6BO
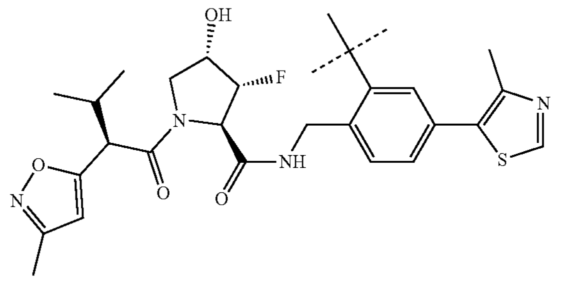
FORMULA 6BP
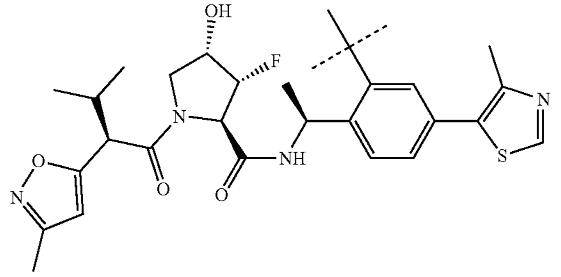
FORMULA 6BQ
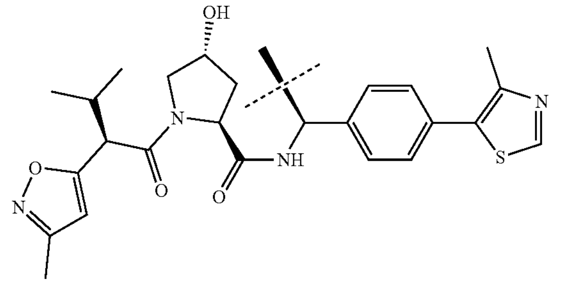
FORMULA 6BR
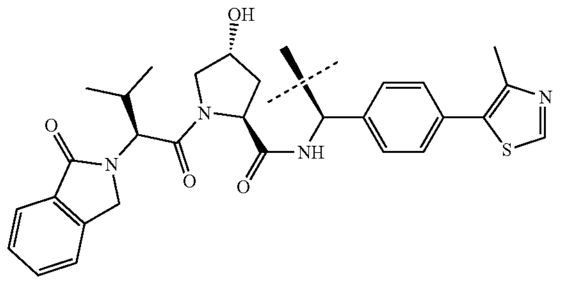
FORMULA 6BS
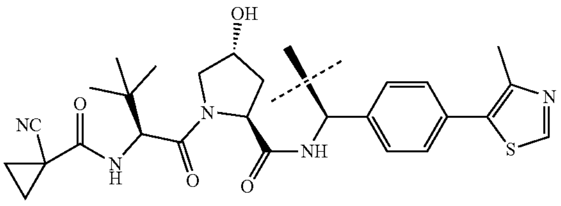
-continued
FORMULA 6BT
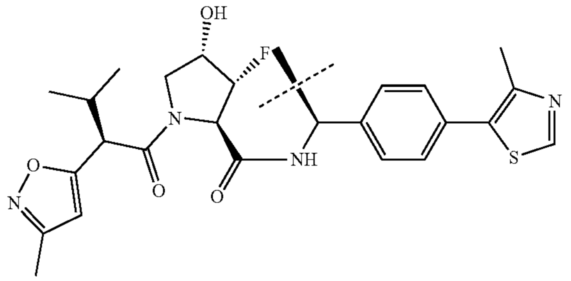
FORMULA 6BU
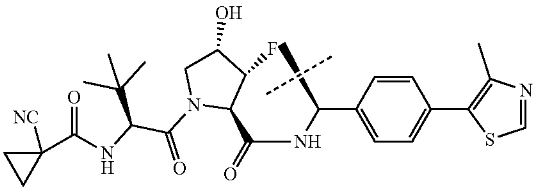
FORMULA 6BV
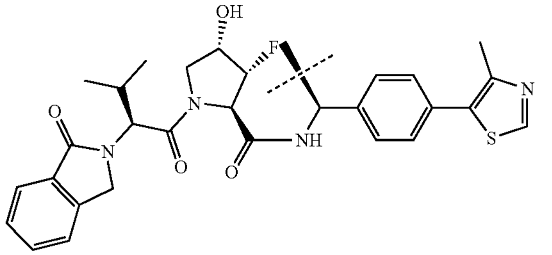
FORMULA 6BW
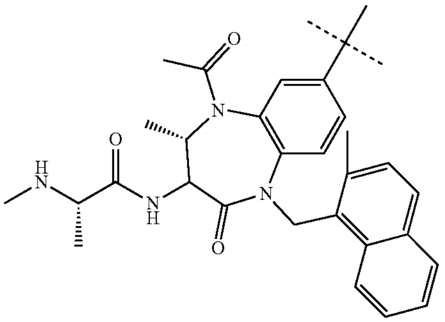
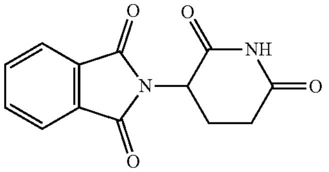
thalidomide
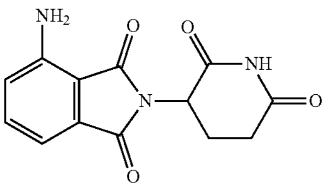
pomalidomide -continued
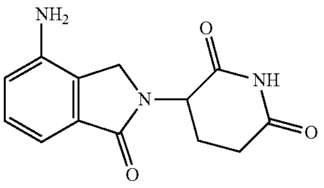
lenalidomide
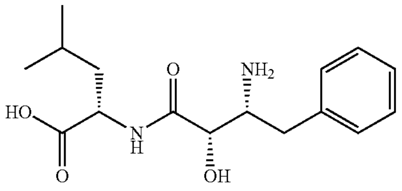
bestatin
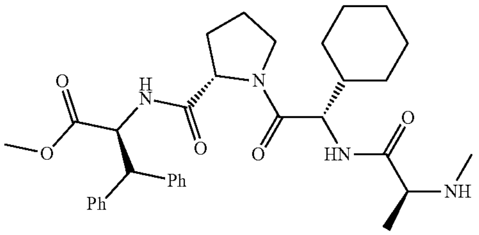
MVI
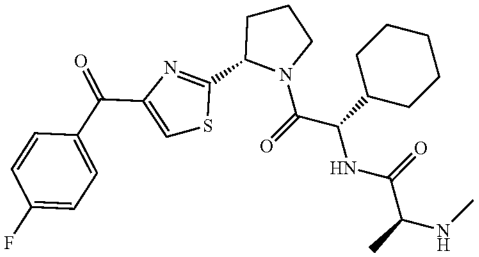
LCL161
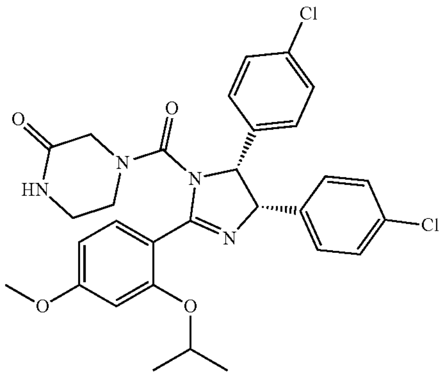
nutlin-3a
-continued
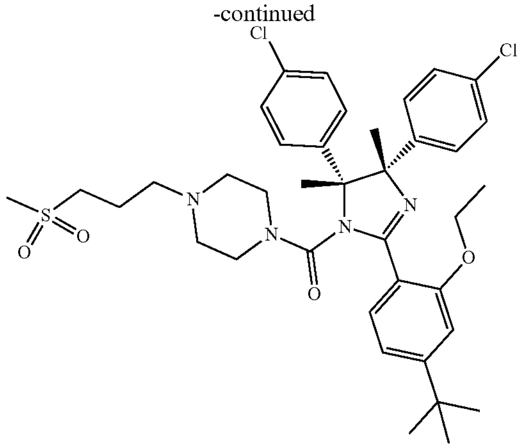
RG7112
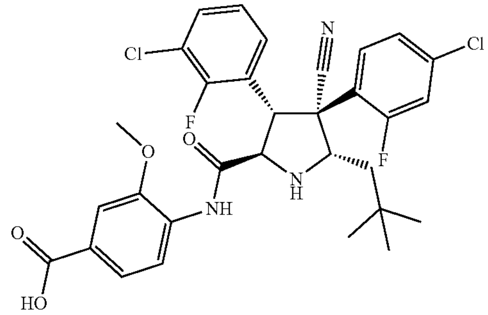
RG7338
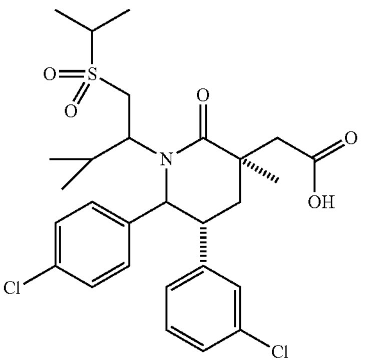
AMG232
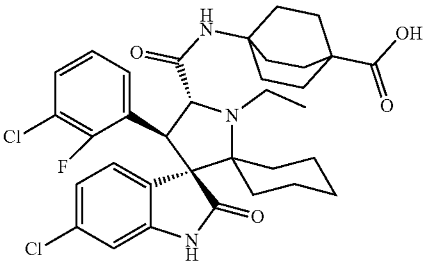
AA-115
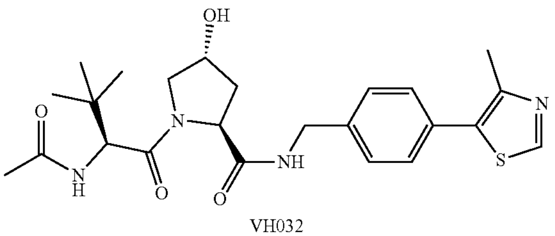
VH032

-continued

Compound W1

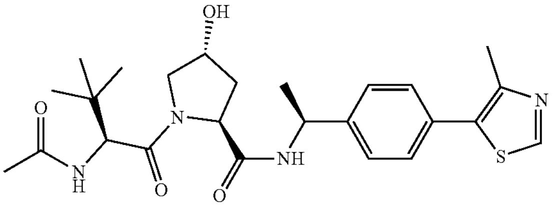

Compound W2

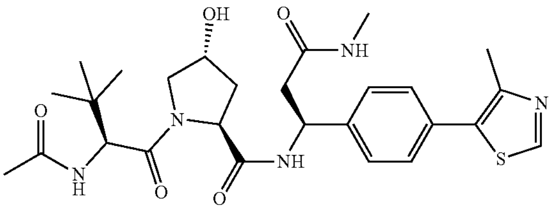

Compound W3

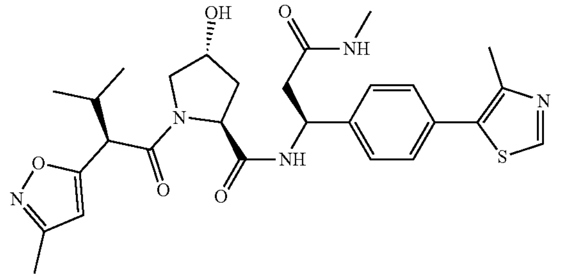

Compound W4

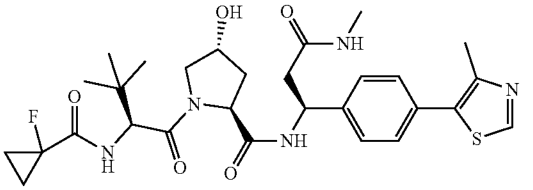

Compound W5

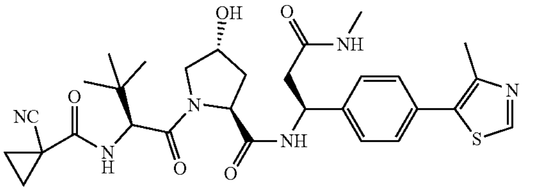

Compound W6

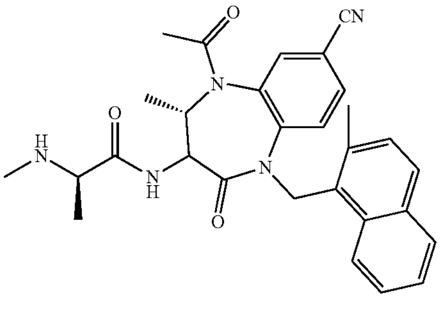

-continued

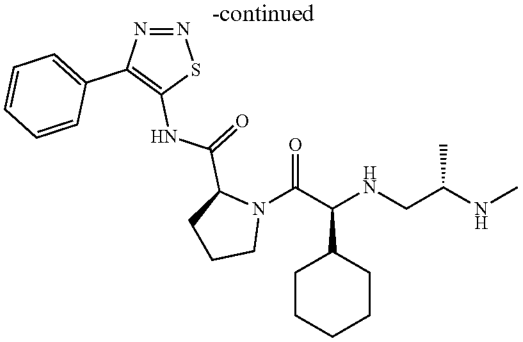

GDC-0152

Compound W7

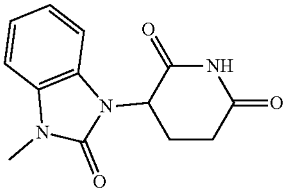

Compound W8

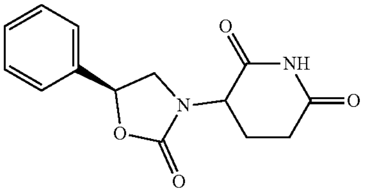

In some aspects, the degradation/disruption tag can bind to a ubiquitin ligase (e.g., an E3 ligase such as a cereblon E3 ligase, a VHL E3 ligase, a MDM2 ligase, a TRIM21 ligase, a TRIM24 ligase, a KEAP1 E3 ligase and/or an IAP ligase) and/or serve as a hydrophobic group or a tag that leads to PTK6 protein misfolding.

Linkers

In all of the above-described compounds, the PTK6 ligand is conjugated to the degradation/disruption tag through a linker. The linker can include, for example, acyclic or cyclic saturated or unsaturated carbon, ethylene glycol, amide, amino, ether, urea, carbamate, aromatic, heteroaromatic, heterocyclic and/or carbonyl containing groups with different lengths.

In some aspects, the linker can be a moiety of:

FORMULA 7

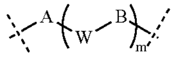

wherein

A, W and B, at each occurrence, are independently selected from null, or bivalent moiety selected from R'—R", R'COR", R'$CO_2$R", R'C(O)N($R^1$)R", R'C(S)N($R^1$)R", R'OR", R'OC(O)R", R'OC(O)OR", R'OCON($R^1$)R", R'SR", R'SOR", R'$SO_2$R", R'$SO_2$N($R^1$)R", R'N($R^1$)R", R'N$R^1$COR", R'N$R^1$C(O)OR", R'N$R^1$CON($R^2$)R", R'N$R^{1C}$(S)R", R'N$R^1$S(O)R", R'N$R^1$S$(O)_2$R", and R'N$R^1$S$(O)_2$N($R^2$)R", wherein R' and R" are independently selected from null, optionally substituted $R^{r}$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$ alkyl, optionally substituted $C_1$-$C_8$alkylamino$C_1$-$C_8$ alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$ alkylene, optionally substituted $C_1$-$C_8$alkylamino$C_1$-$C_8$ alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^{r}$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl:

$R^1$ and $R^2$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl;

R' and R", $R^1$ and $R^2$, R' and $R^1$, R' and $R^2$, R" and $R^1$, R" and $R^2$ together with the atom to which they are connected form a 3-20 membered cycloalkyl or 4-20 membered heterocyclyl ring; and m is 0 to 15.

FORMULA 7A,

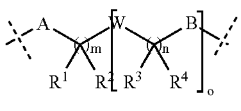

wherein $R^1$, $R^2$, $R^3$ and $R^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-8 membered heterocyclyl, optionally substituted aryl, and optionally substituted heteroaryl, or $R^1$ and $R^2$, $R^3$ and $R^4$ together with the atom to which they are connected form a 3-20 membered cycloalkyl or 4-20 membered heterocyclyl ring;

A, W and B, at each occurrence, are independently selected from null, or bivalent moiety selected from R'—R", R'COR", R'$CO_2$R", R'C(O)N($R^5$)R", R'C(S)N($R^5$)R", R'OR", R'OC(O)R", R'OC(O)OR", R'OCON$R^5$R", R'SR", R'SOR", R'$SO_2$R", R'$SO_2$N($R^5$)R", R'N($R^5$)R", R'N$R^5$COR", R'N$R^5$C(O)OR", R'N$R^5$CON($R^6$)R", R'N$R^5$C(S)R", R'N$R^5$S(O)R", R'N$R^5$S(O)$_2$R", and R'N$R^5$S(O)$_2$N($R^6$)R", wherein R' and R" are independently selected from null, optionally substituted $R^{r}$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$ alkyl, optionally substituted $C_1$-$C_8$alkylamino$C_1$-$C_8$ alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$ alkylene, optionally substituted $C_1$-$C_8$alkylamino$C_1$-$C_8$ alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^{r}$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl;

R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;

n, at each occurrence, is 0 to 15; and is 0 to 15.

FORMULA 7B,

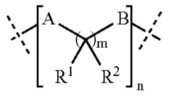

wherein $R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'—R", R'COR", R'$CO_2$R", R'C(O)N$R^3$R", R'C(S)N$R^3$R", R'OR", R'OC(O)R", R'OC(O)OR", R'OCON($R^3$)R", R'SR", R'SOR", R'$SO_2$R", R'$SO_2$N($R^3$)R", R'N($R^3$)R", R'N$R^3$COR", R'N$R^3$C(O)OR", R'N$R^3$CON($R^4$)R", R'N$R^3$C(S)R", R'N$R^3$S(O)R", R'N$R^3$S$(O)_2$R", and R'N$R^3$S$(O)_2$N($R^4$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$ alkyl, optionally substituted $C_1$-$C_8$alkylamino$C_1$-$C_8$ alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$ alkylene, optionally substituted $C_1$-$C_8$alkylamino$C_1$-$C_8$ alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^3$ and $R^4$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R" and $R^3$, R" and $R^4$ together with the atom to which they are connected form a 3-20 membered cycloalkyl or 4-20 membered heterocyclyl ring;

m, at each occurrence, is 0 to 15; and n is 0 to 15.

FORMULA 7C,

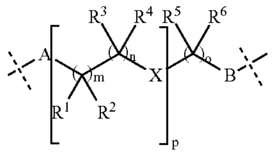

wherein

X is selected from O, NH, and N$R^7$;

$R^1$, $R^2$, $R^3$, $R^4$, $R^5$, and $R^6$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$alkylamino$C_1$-$C_8$ alkyl, optionally substituted 3-10 membered carbocyclyl, optionally substituted 3-8 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", R'$CO_2$R", R'C(O)N($R^8$)R", R'C(S)N($R^8$)R", R'OR", R'OC(O)R", R'OC(O)OR", R'OCON($R^8$)R", R'SR", R'SOR", R'$SO_2$R", R'$SO_2$N($R^8$)R", R'N($R^8$)R", R'N$R^8$COR", R'N$R^8$C(O)OR", R'N$R^8$CON($R^9$)R", R'N$R^8$C(S)R", R'N$R^8$S(O)R", R'N$R^8$S$(O)_2$R", and R'N$R^8$$(O)_2$N($R^9$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$ alkyl, optionally substituted $C_1$-$C_8$alkylamino$C_1$-$C_8$ alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$ alkylene, optionally substituted $C_1$-$C_8$alkylamino$C_1$-$C_8$ alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^7$, $R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl;

R' and R", $R^8$ and $R^9$, R' and $R^8$, R" and $R^9$, R" and $R^8$, R" and $R^9$ together with the atom to which they are connected form a 3-20 membered cycloalkyl or 4-20 membered heterocyclyl ring;

m, at each occurrence, is 0 to 15;

n, at each occurrence, is 0 to 15;

is 0 to 15; and p is 0 to 15.

In some aspects of Formulae 7, 7A, 7B, and 7C, the linker moiety comprises a ring selected from the group consisting of a 3 to 13 membered ring, a 3 to 13 membered fused ring, a 3 to 13 membered bridged ring, and a 3 to 13 membered spiro ring.

In some aspects of Formulae 7, 7A, 7B, and 7C, the linker moiety comprises a ring selected from the group consisting of Formula C1, C2, C3, C4 and C5:

Formula C1

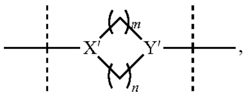

X' = N or CH
Y' = N or CH
m = 0-5
n = 0-5

Formula C2

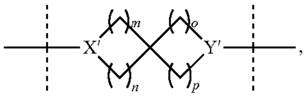

X' = N or CH
Y' = N or CH
m = 0-5
n = 0-5
o = 0-5
p = 0-5

Formula C3

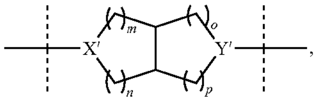

X' = N or CH
Y' = N or CH
m = 0-5
n = 0-5
o = 0-5
p = 0-5

-continued

Formula C4

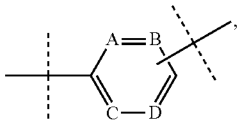

and

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N Formula C5

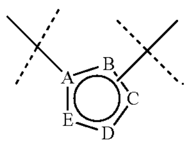

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3 alkyl), O, S In some aspects, the linker can also be a moiety of:

Formula A,

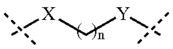

wherein X is C═O or $CH_2$,
Y is C═O or $CH_2$, and
n is 0-15:

Formula B,

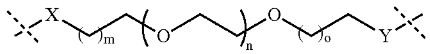

wherein X is C═O or $CH_2$,
Y is C═O or $CH_2$,
m is 0-15,
n is 0-6, and
is 0-15; or Formula C,

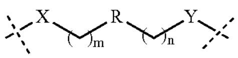

wherein

X is C═O or $CH_2$,

Y is C═O or $CH_2$,

R is —$CH_2$—, —$CF_2$—, —CH($C_{1-3}$ alkyl)-, —C($C_{1-3}$ alkyl)($C_{1-3}$ alkyl)-, —CH═CH—, —C($C_{1-3}$ alkyl)═C($C_{1-3}$ alkyl)-, —C≡C—, —O—, —NH—, —N($C_{1-3}$ alkyl)-, —C(O)NH—, —C(O)N($C_{1-3}$ alkyl)-, a 3-13 membered ring, a 3-13 membered fused ring, a 3-13 membered bridged ring, and/or a 3-13 membered spiro ring, m is 0-15, and n is 0-15.

In some aspects of Formula C, R is a 3-13 membered ring, a 3-13 membered fused ring, a 3-13 membered bridged ring, and/or a 3-13 membered spiro ring, one or more of which can contain one or more heteroatoms.

In some aspects of Formula C, R has a structure of:

Formula C1

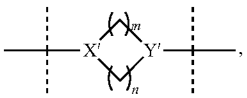

X′ = N or CH
Y′ = N or CH
m = 0-5
n = 0-5

Formula C2

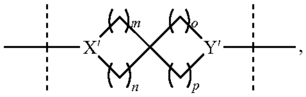

X′ = N or CH
Y′ = N or CH
m = 0-5
n = 0-5
o = 0-5
p = 0-5

Formula C3

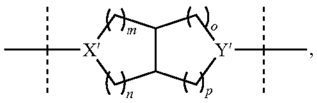

X′ = N or CH
Y′ = N or CH
m = 0-5
n = 0-5
o = 0-5
p = 0-5

Formula C4

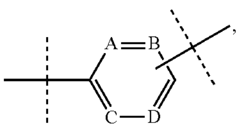

or

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N Formula C5

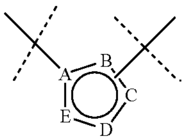

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3 alkyl), O, S Synthesis and Testing of Bivalent Compounds The binding affinity of novel synthesized bivalent compounds (i.e., PTK6 degraders/disruptors) can be assessed using standard biophysical assays known in the art (e.g., isothermal titration calorimetry (ITC), surface plasmon resonance (SPR)). Cellular assays can then be used to assess the bivalent compound's ability to induce PTK6 degradation and inhibit cancer cell proliferation. Besides evaluating a bivalent compound's induced changes in the protein expression of PTK6 or PTK6 mutant proteins, enzymatic activity can also be assessed. Assays suitable for use in any or all of these steps are known in the art, and include, e.g., Western blotting, quantitative mass spectrometry (MS) analysis, flow cytometry, enzymatic inhibition, ITC, SPR, cell growth inhibition and xenograft and PDX models. Suitable cell lines for use in any or all of these steps are known in the art and include, cancer cell lines: 1) Breast (MDA-MB231, MCF7, UACC893, $HCC_{1954}$, T47D, BT474, ZR751); 2) Ovarian (DOV-13, HeyC2, OV2008, OvCAR5); 3) Pancreatic (PANC-1, BxP3, Capan1, Hs766T, MIAPaCa2); 4) Prostate (PC-3, DU145). Suitable mouse models for use in any or all of these steps are known in the art and include, patient-derived xenograft models of triple negative breast cancer.

By way of non-limiting example, detailed synthesis protocols are described in the Examples for specific exemplary PTK6 degraders/disruptors.

Pharmaceutically acceptable isotopic variations of the compounds disclosed herein are contemplated and can be synthesized using conventional methods known in the art or methods corresponding to those described in the Examples (substituting appropriate reagents with appropriate isotopic variations of those reagents). Specifically, an isotopic variation is a compound in which at least one atom is replaced by an atom having the same atomic number, but an atomic mass different from the atomic mass usually found in nature. Useful isotopes are known in the art and include, for example, isotopes of hydrogen, carbon, nitrogen, oxygen, phosphorus, sulfur, fluorine, and chlorine. Exemplary isotopes thus include, e.g., $^{2}H$, $^{3}H$, $^{13}C$, $^{14}C$, $^{15}N$, $^{17}O$, $^{18}O$, $^{32}P$, $^{35}S$, $^{18}F$, and $^{36}Cl$.

Isotopic variations (e.g., isotopic variations containing $^{2}H$) can provide therapeutic advantages resulting from greater metabolic stability, e.g., increased in vitro half-life or reduced dosage requirements. In addition, certain isotopic variations (particularly those containing a radioactive isotope) can be used in drug or substrate tissue distribution studies. The radioactive isotopes tritium ($^{3}H$) and carbon-14 ($^{14}C$) are particularly useful for this purpose in view of their ease of incorporation and ready means of detection.

Pharmaceutically acceptable solvates of the compounds disclosed herein are contemplated. A solvate can be generated, e.g., by substituting a solvent used to crystallize a compound disclosed herein with an isotopic variation (e.g., $D_2O$ in place of $H_2O$, $d_6$-acetone in place of acetone, or $d_6$-DMSO in place of DMSO).

Pharmaceutically acceptable fluorinated variations of the compounds disclosed herein are contemplated and can be synthesized using conventional methods known in the art or methods corresponding to those described in the Examples (substituting appropriate reagents with appropriate fluorinated variations of those reagents). Specifically, a fluorinated variation is a compound in which at least one hydrogen atom is replaced by a fluoro atom. Fluorinated variations can provide therapeutic advantages resulting from greater metabolic stability, e.g., increased in vivo half-life or reduced dosage requirements.

Pharmaceutically acceptable prodrugs of the compounds disclosed herein are contemplated and can be synthesized using conventional methods known in the art or methods corresponding to those described in the Examples (e.g., converting hydroxyl groups or carboxylic acid groups to ester groups). As used herein, a "prodrug" refers to a compound that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

Characterization of Exemplary PTK6 Degraders/Disruptors

Figure 1:
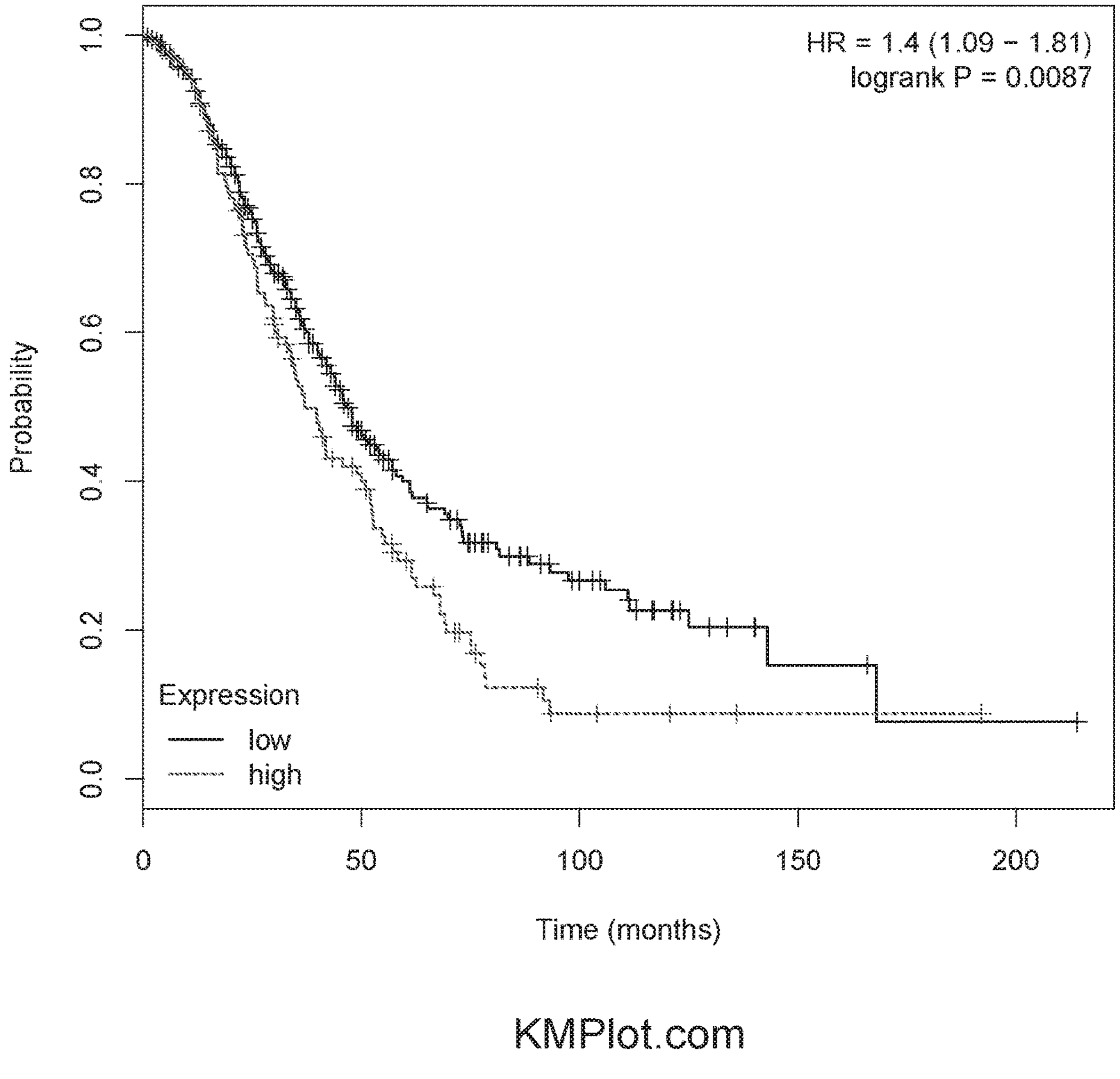
FIG. 1. Kaplan-Meier curves showing prognostic significance of high PTK6 transcript expression based on analysis using KMPlot.com. Higher expression of PTK6 is associated with poorer survival for patients with ovarian cancer, stage 2/3.
Figure 2:
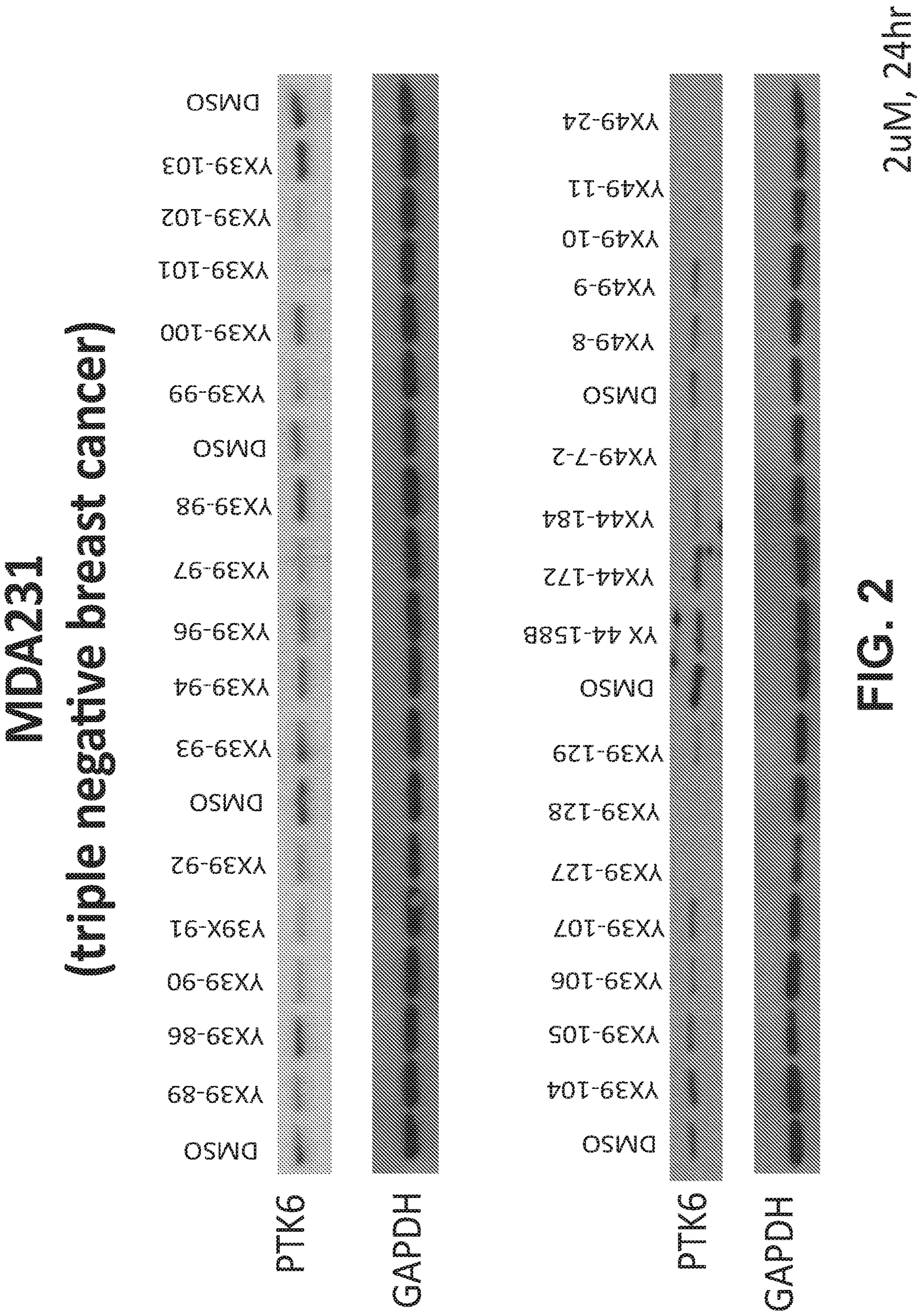
FIGS. 2-5. Effects of exemplary compounds on reducing PTK6 protein levels in breast cancer cells. Triple negative MDA-MB231 cells were treated for 24 hours with 500 nM, 2 uM or 2.5 uM of test compound and lysed. Proteins were resolved by SDS/PAGE and immunoblotted with antibody to PTK6 (Santa Cruz, Cell Signaling) or GAPDH loading control (Cell Signaling).
Figure 3:
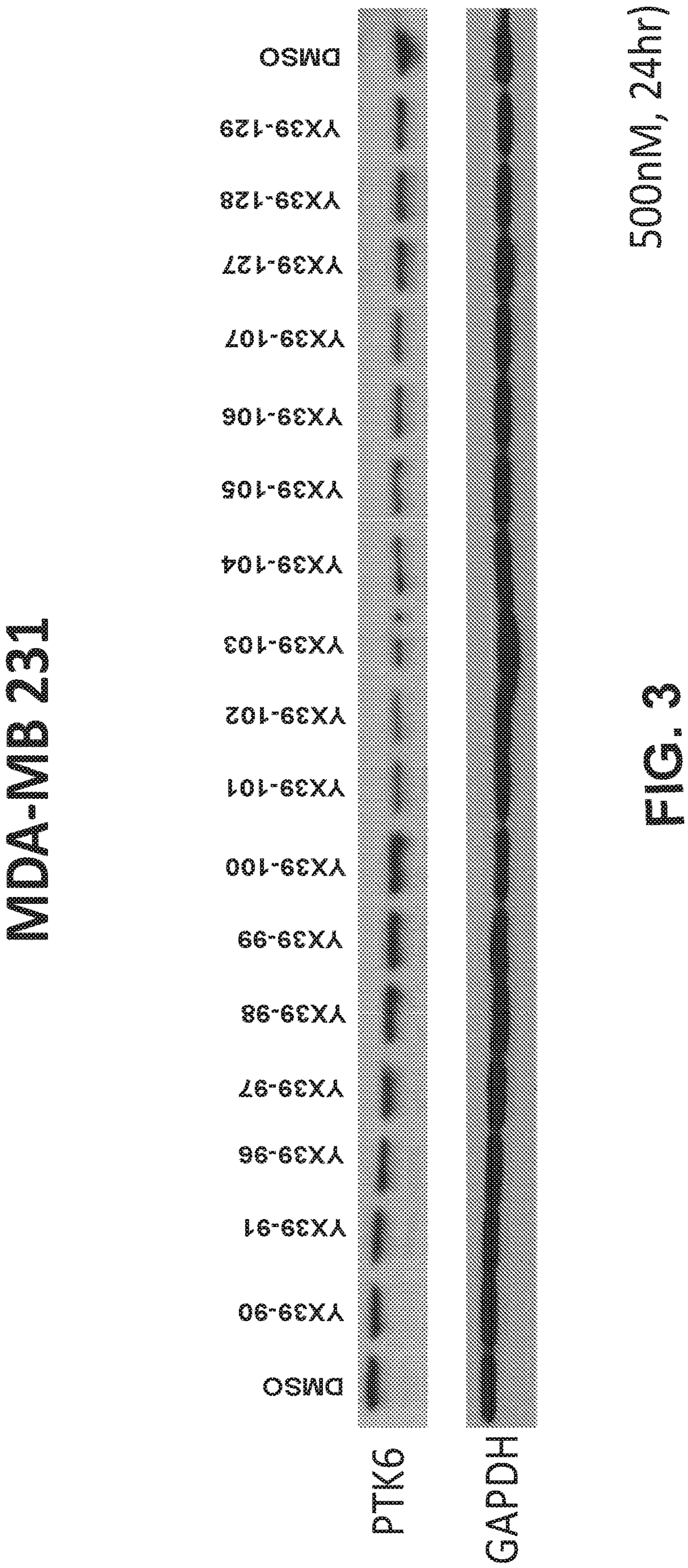
Figure 4:
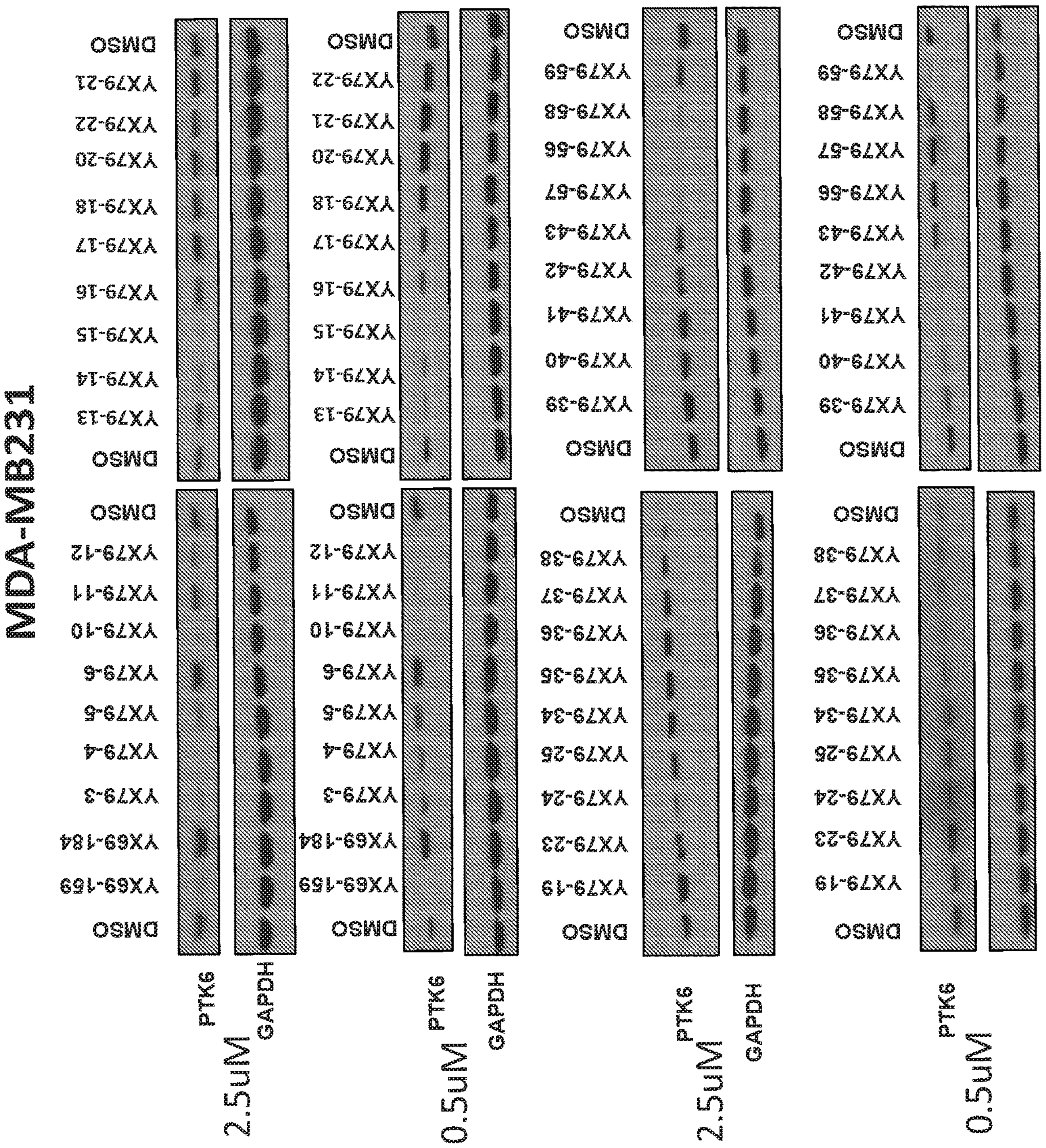
Figure 5:
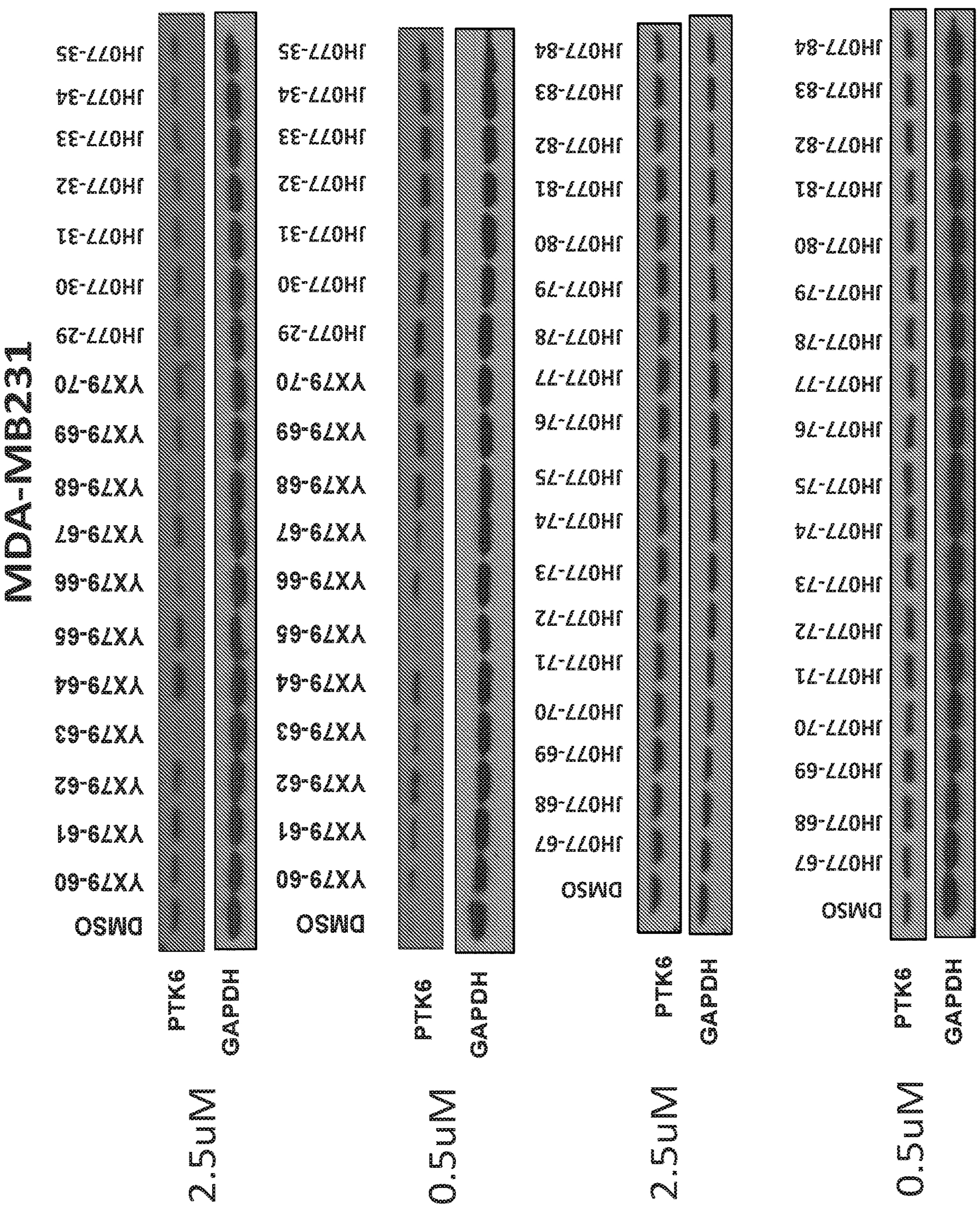

Specific exemplary PTK6 degraders/disruptors were characterized in triple negative MDA-231 breast cancer cells (Examples 83-85, FIGS. 2-5). Bifunctional compounds YX39-101, YX39-102, YX39-103, YX39-104, YX39-105, YX39-106, and YX39-107 in particular were found to be effective in reducing PTK6 protein levels in MDA-231 cells at 500 nM (FIG. 3). In addition, YX69-159, YX79-10, YX79-11, YX79-12, YX79-15, YX79-36, YX79-37, YX79-40, YX79-41, YX79-42, YX79-59, and YX79-65 were also found to potently suppress PTK6 expression in MDA-MB231 cells at 500 nM (FIGS. 4, 5).

Figure 6A:
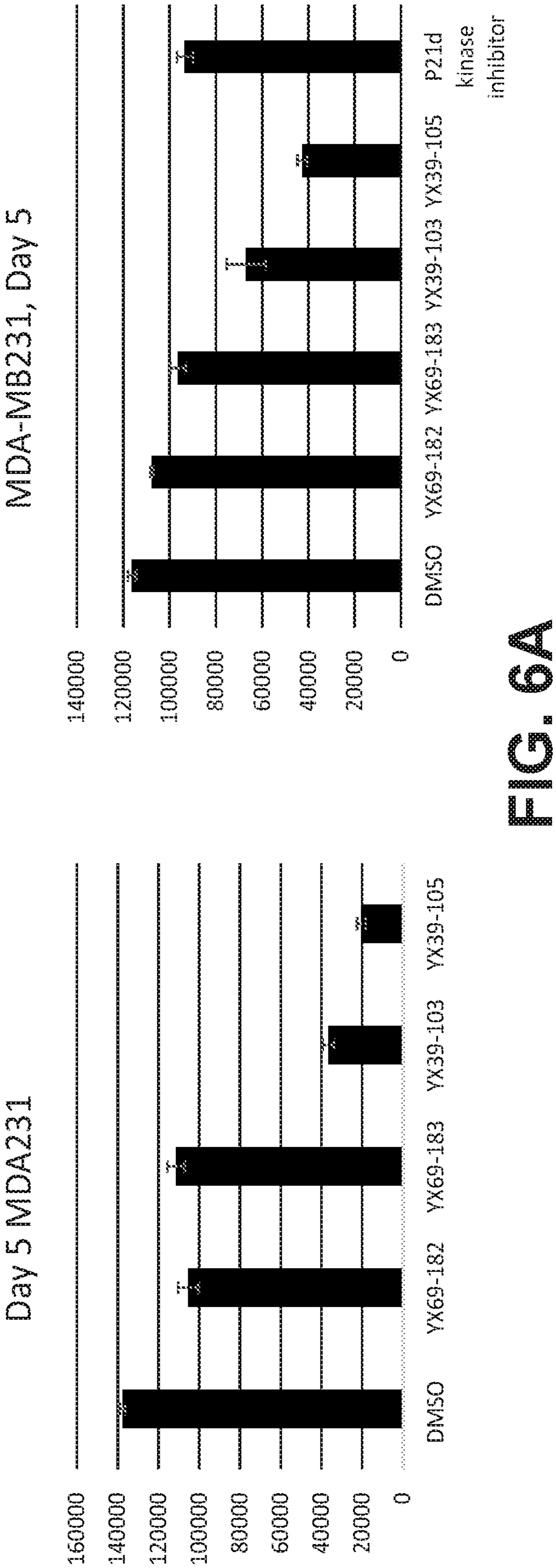
FIG. 6*a*. PTK6 degraders, but not kinase activity inhibitor suppress viability in 3D cultures. MDA-MB231 triple negative breast cancer cells were seeded into 3D Matrigel cultures (4×10^3 cells/well) and treated with indicated PTK6 degraders, negative control compounds or PTK6 kinase activity inhibitor at 1 uM for 5 days with re-feeding of compound after 3 days in culture. Viability was assessed using 3D Cell Titer glo (Promega).
Figure 6B:
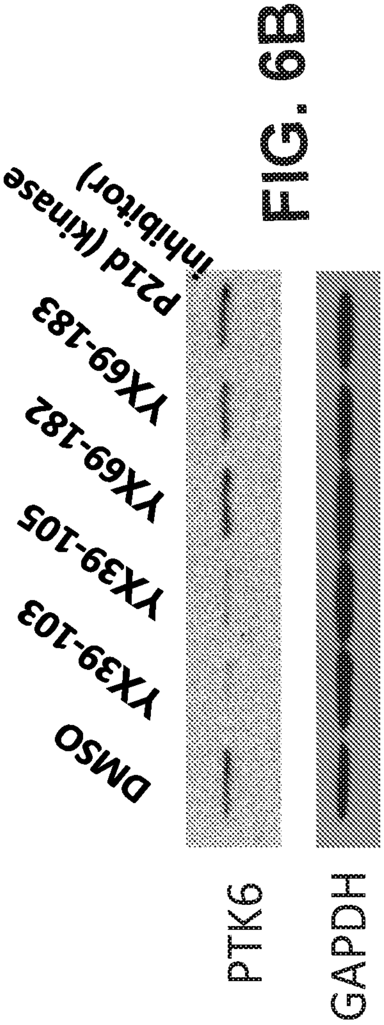
FIG. 6*b*. Expression of PTK6 in cells treated with PTK6 degraders, negative control compounds or PTK6 kinase activity inhibitor was assessed after 24 hour treatment in monolayer cultures with 1 uM of compound. Cells were lysed and proteins were resolved and probed with anti-PTK6 antibody (Cell Signaling)
Figure 7A:
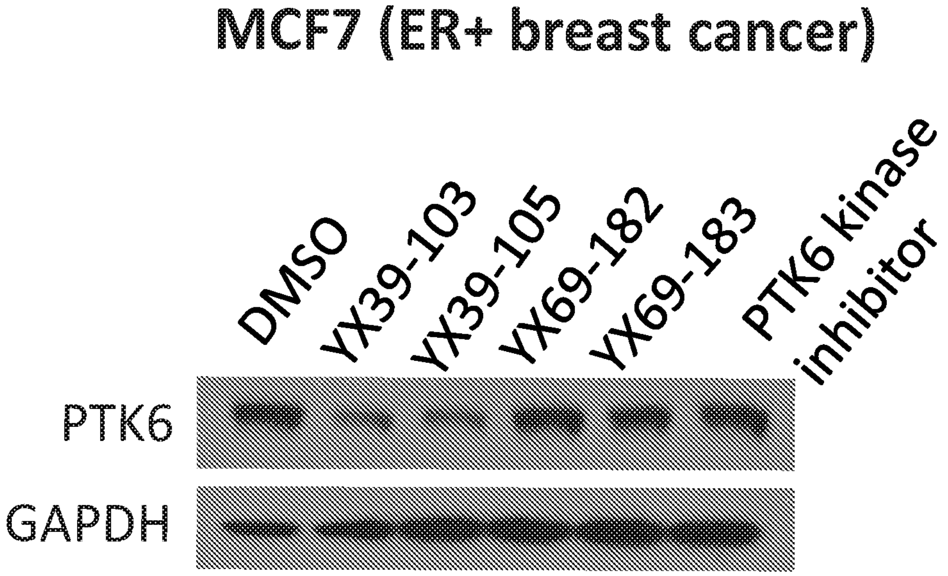
FIG. 7*a*. PTK6 degrader treatment suppresses growth of ER+ breast cancer cells. ER+ breast cancer cells (MCF-7) were treated with indicated concentrations of top candidate degraders, negative control compounds or PTK6 kinase activity inhibitor for 24 hours, lysed and proteins were resolved by SDS-PAGE. PTK6 expression was interrogated by Western analysis.
Figure 7B:
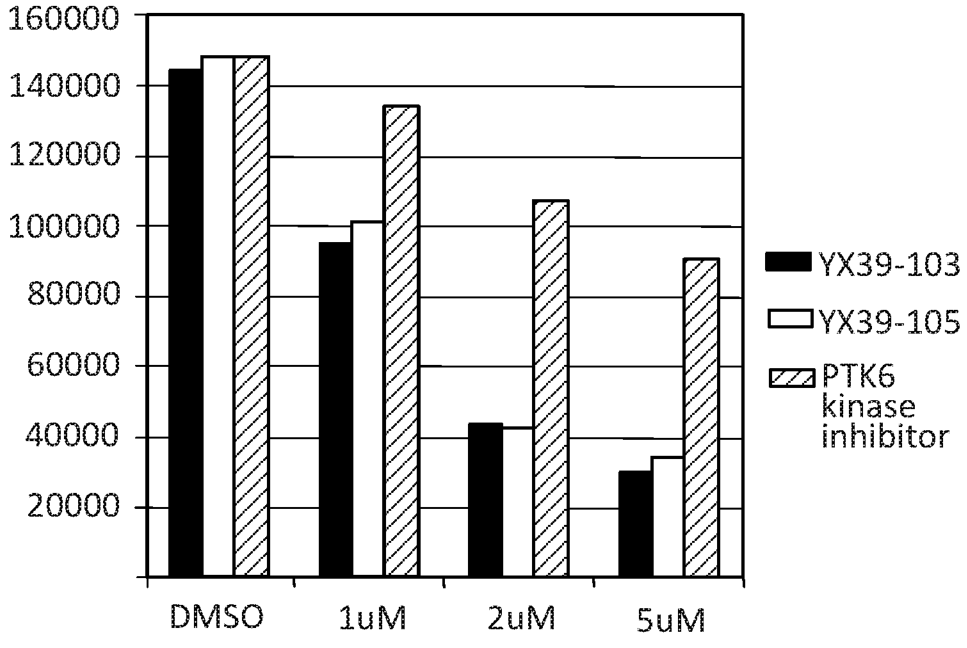
FIG. 7*b*. MCF-7 cells were seeded into 3D Matrigel cultures and treated with indicated PTK6 degraders or PTK6 kinase inhibitor for 4 days. Viability was quantified using 3-D Cell Titer glo (Promega).
Figure 8:
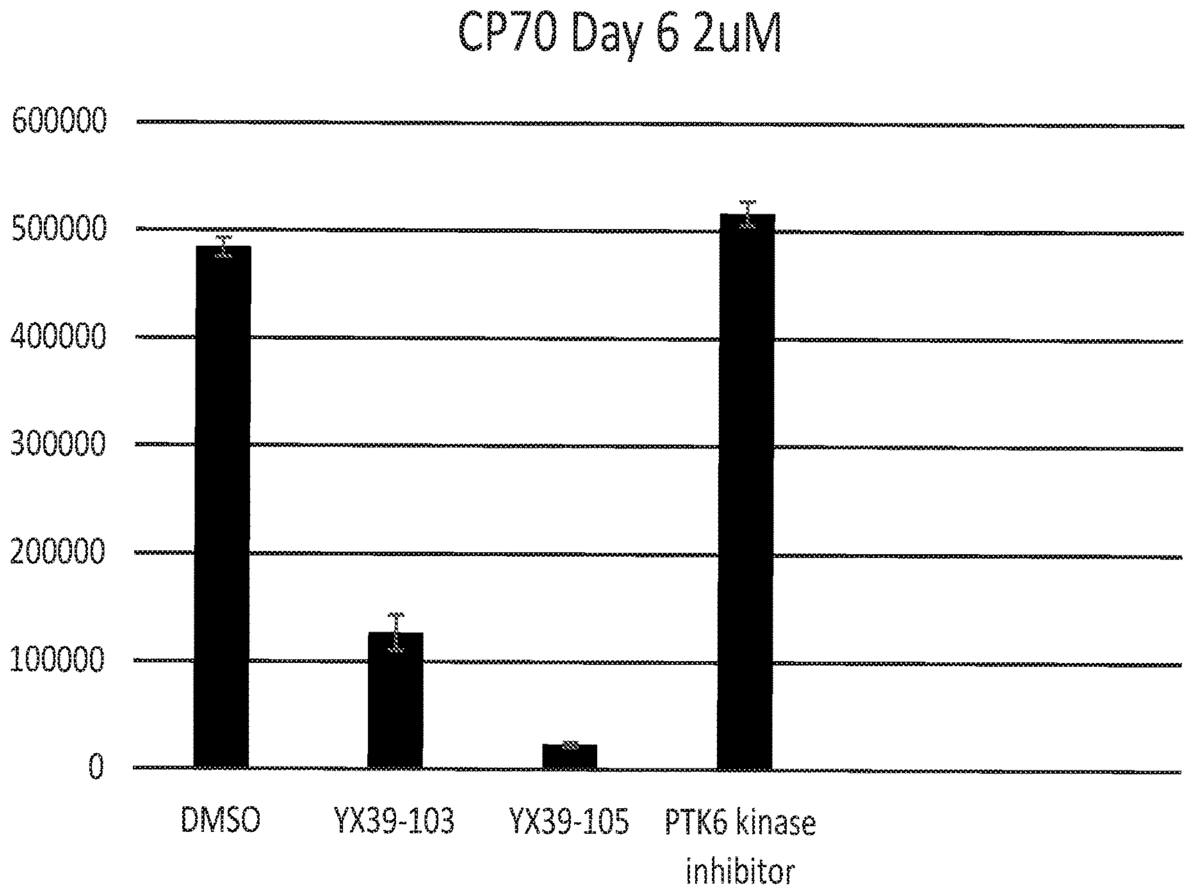
FIG. 8. Treatment with PTK6 degraders, but not kinase activity inhibitor, suppress viability of chemotherapy-resistant ovarian cancer cells (CP70). Cells were seeded into 3D Matrigel cultures and treated with compounds (2 uM) for 6 days. Viability was assessed using 3D Cell Titre glo assay (Promega)

Treatment of cells in 3D Matrigel culture assays often give better insight into the activity of compounds in in vivo (mouse) biological models than standard (2D) monolayer culture systems. Treatment of triple negative or ER+ breast cancer cells with PTK6 degraders that reduced PTK6 protein levels suppressed viability and invasive branching of triple negative MDA-MB231 breast cancer cells in 3D cultures (FIGS. 6, 7). Using 3D Cell Titer Glo (Promega), the effect of PTK6 degrader treatment on cell viability was quantified; treatment with PTK6 degraders significantly impaired viability in a concentration-dependent manner, comparable to the effects observed with the PTK6 shRNA vectors (FIGS. 6, 7). At comparable concentrations, a PTK6 kinase inhibitor (P21d) had only a modest effect on viability of cells in 3D cell culture (FIGS. 6, 7), thus supporting kinase-independent functions of PTK6 that regulate growth of some PTK6+ tumors that would be better targeted with PTK6 degraders. Similarly, treatment with top PTK6 degraders, but not PTK6 kinase activity inhibitor suppressed viability of 3D cultures of CP70 cells, a platinum chemotherapy-resistant ovarian cancer cell line (FIG. 8).

Figure 9:
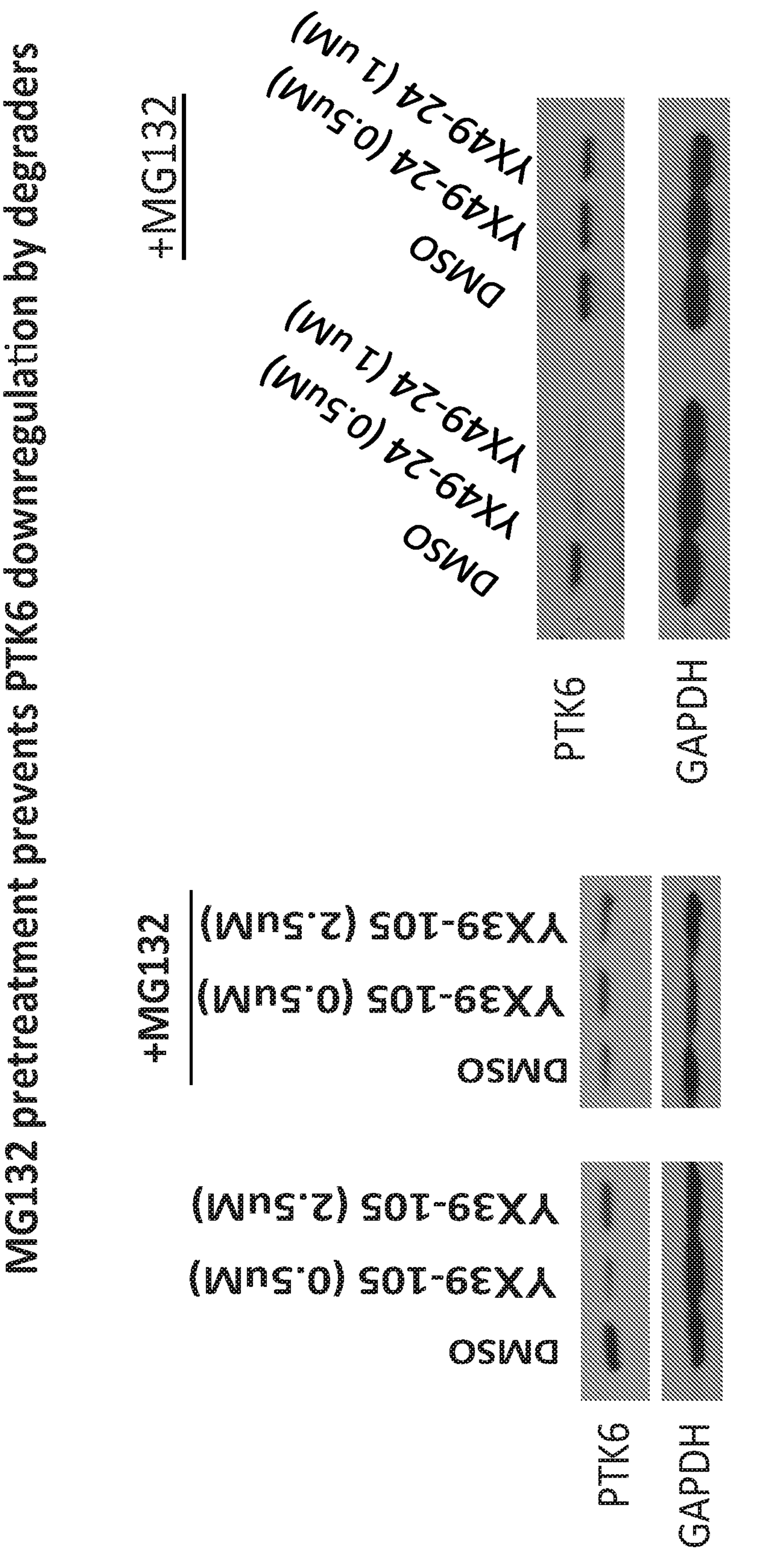
FIG. 9. PTK6 degrader suppresses PTK6 expression in a proteasome-dependent manner. MDA-MB231 cells (left) or OV2008 cells (right) were pre-treated with DMSO or MG-132 (10 uM) for two hours, then treated for an additional 4 hours with DMSO or PTK6 degrader at the indicated concentrations.
Figure 10:
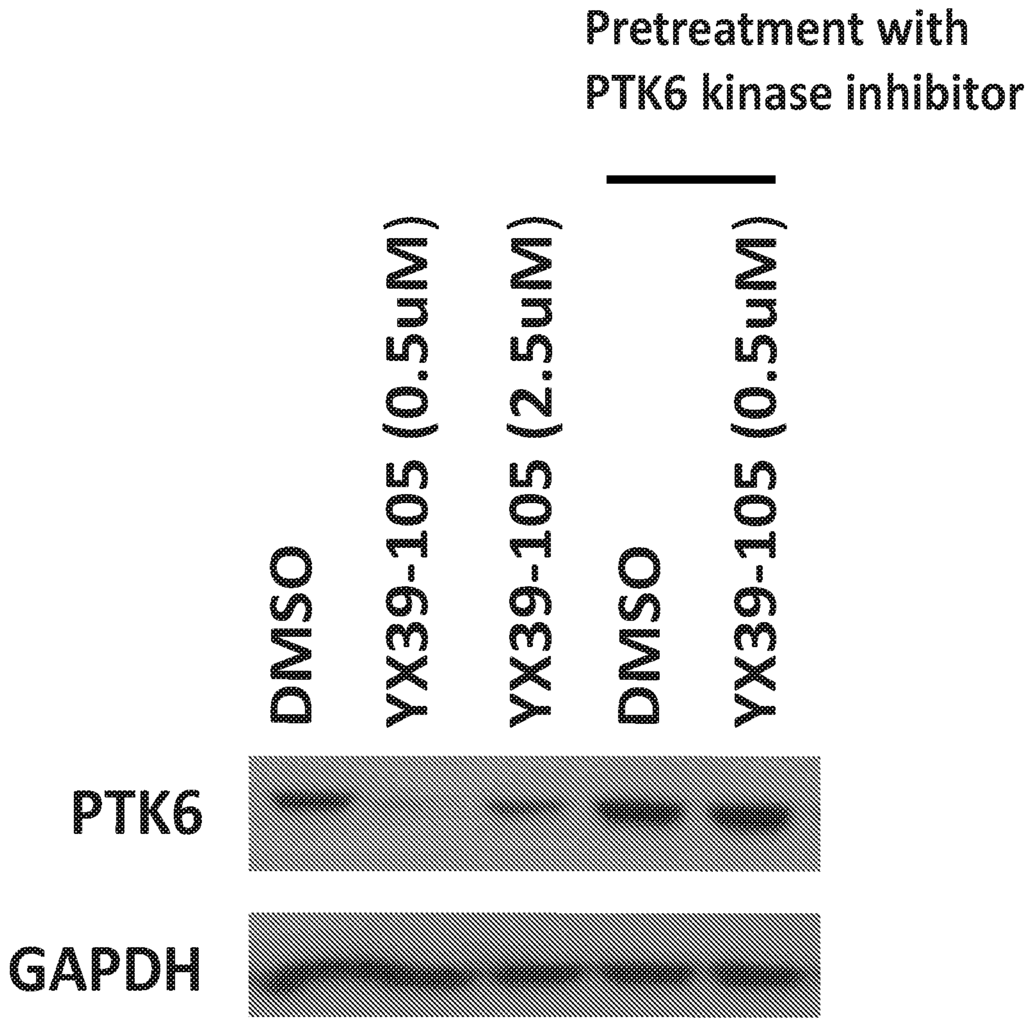
FIG. 10. PTK6 kinase activity inhibitor pre-treatment prevents PTK6 degrader-dependent suppression of PTK6 expression. MDA-MB231 cells in monolayer cultures were pre-treated with DMSO or PTK6 kinase activity inhibitor (5 uM), then treated for an additional 24 hours with PTK6 degrader, YX39-105. Cells were lysed and expression of PTK6 was assessed by Western analysis.

Mechanistically, suppression of PTK6 expression observed with degrader treatment is dependent on proteasome activity. Pre-treatment of cells with the proteasome inhibitor MG-132, prevents downregulation of PTK6 expression (FIG. 9). In addition, pre-treatment with the PTK6 kinase activity inhibitor that binds to the same binding site(s) as the PTK6 degraders rescues PTK6 protein levels in the degrader-treated cells (FIG. 10).

PTk6 degraders suppress PTK6 expression in cell lines that are resistant to current standard of care therapies. Degraders downregulate expression in ER+ breast cancer cells that are resistant to estrogen deprivation (FIG. 11), highlighting the potential utility of PTK6 degraders to target therapy resistant disease.

Definition of Terms

"Alkyl" refers to a straight or branched hydrocarbon chain radical consisting solely of carbon and hydrogen atoms, containing no unsaturation. An alkyl may comprise one, two, three, four, five, six, seven, eight, nine, ten, eleven, twelve, thirteen, fourteen, fifteen, or sixteen carbon atoms. In certain embodiments, an alkyl comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_8$-$C_{15}$ alkyl). In other embodiments, an alkyl comprises five to eight carbon atoms (e.g., $C_8$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), pentyl, 3-methylhexyl, 2-methylhexyl, and the like.

"Alkenyl" refers to a straight or branched hydrocarbon chain radical group consisting solely of carbon and hydrogen atoms, containing at least one double bond. An alkenyl may comprise two, three, four, five, six, seven, eight, nine, ten, eleven, twelve, thirteen, fourteen, fifteen, or sixteen carbon atoms. In certain embodiments, an alkenyl comprises two to twelve carbon atoms (e.g., $C_2$-$C_{12}$ alkenyl). In certain embodiments, an alkenyl comprises two to eight carbon atoms (e.g., $C_2$-$C_8$ alkenyl). In certain embodiments, an alkenyl comprises two to six carbon atoms (e.g., $C_2$-$C_6$ alkenyl). In other embodiments, an alkenyl comprises two to four carbon atoms (e.g., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

The term "allyl," as used herein, means a $-CH_2CH{=}CH_2$ group.

As used herein, the term "alkynyl" refers to a straight or branched hydrocarbon chain radical group consisting solely of carbon and hydrogen atoms, containing at least one triple bond. An alkynyl may comprise two, three, four, five, six, seven, eight, nine, ten, eleven, twelve, thirteen, fourteen, fifteen, or sixteen carbon atoms. In certain embodiments, an alkynyl comprises two to twelve carbon atoms (e.g., $C_2$-$C_{12}$ alkynyl). In certain embodiments, an alkynyl comprises two to eight carbon atoms (e.g., $C_2$-$C_8$ alkynyl). In other embodiments, an alkynyl has two to six carbon atoms (e.g., $C_2$-$C_6$ alkynyl). In other embodiments, an alkynyl has two to four carbon atoms (e.g., $C_2$-$C_4$ alkynyl). The alkynyl is attached to the rest of the molecule by a single bond. Examples of such groups include, but are not limited to, ethynyl, propynyl, 1-butynyl, 2-butynyl, 1-pentynyl, 2-pentynyl, 1-hexynyl, 2-hexynyl, 3-hexynyl, and the like.

The term "alkoxy", as used herein, means an alkyl group as defined herein which is attached to the rest of the molecule via an oxygen atom. Examples of such groups include, but are not limited to, methoxy, ethoxy, n-propyloxy, iso-propyloxy, n-butoxy, iso-butoxy, tert-butoxy, pentyloxy, hexyloxy, and the like.

The term "aryl", as used herein, "refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms. An aryl may comprise from six to eighteen carbon atoms, where at least one of the rings in the ring system is fully unsaturated, i.e., it contains a cyclic, delocalized (4n+

2) π-electron system in accordance with the Hückel theory. In certain embodiments, an aryl comprises six to fourteen carbon atoms ($C_6$-$C_{14}$ aryl). In certain embodiments, an aryl comprises six to ten carbon atoms ($C_6$-$C_{10}$ aryl). Examples of such groups include, but are not limited to, phenyl, fluorenyl and naphthyl. The terms "Ph" and "phenyl," as used herein, mean a —$C_6H_5$ group.

The term "heteroaryl", refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. In certain embodiments, a heteroaryl refers to a radical derived from a 3- to 10-membered aromatic ring radical (3-10 membered heteroaryl). In certain embodiments, a heteroaryl refers to a radical derived from 5- to 7-membered aromatic ring (5-7 membered heteroaryl). Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of such groups include, but not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. In certain embodiments, an heteroaryl is attached to the rest of the molecule via a ring carbon atom. In certain embodiments, an heteroaryl is attached to the rest of the molecule via a nitrogen atom (N-attached) or a carbon atom (C-attached). For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "heterocyclyl", as used herein, means a non-aromatic, monocyclic, bicyclic, tricyclic, or tetracyclic radical having a total of from 4, 5, 6, 7, 8, 9, 10, 11, 12, or 13 atoms in its ring system, and containing from 3 to 12 carbon atoms and from 1 to 4 heteroatoms each independently selected from O, S and N, and with the proviso that the ring of said group does not contain two adjacent O atoms or two adjacent S atoms. A heterocyclyl group may include fused, bridged or spirocyclic ring systems. In certain embodiments, a heterocyclyl group comprises 3 to ring atoms (3-10 membered heterocyclyl). In certain embodiments, a heterocyclyl group comprises 3 to 8 ring atoms (3-8 membered heterocyclyl). In certain embodiments, a heterocyclyl group comprises 4 to 8 ring atoms (4-8 membered heterocyclyl). In certain embodiments, a heterocyclyl group comprises 3 to 6 ring atoms (3-6 membered heterocyclyl). A heterocyclyl group may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocyclyl group contains a sulfur atom, said sulfur atom may be oxidized with one or two oxygen atoms to afford either a sulfoxide or sulfone. An example of a 4 membered heterocyclyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such heterocyclyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, 3-oxopiperazinyl, 4-methylpiperazinyl, 4-ethylpiperazinyl, and 1-oxo-2,8,diazaspiro[4.5]dec-8-yl. A heteroaryl group may be attached to the rest of molecular via a carbon atom (C-attached) or a nitrogen atom (N-attached). For instance, a group derived from piperazine may be piperazin-1-yl (N-attached) or piperazin-2-yl (C-attached).

The term "cycloalkyl" means a saturated, monocyclic, bicyclic, tricyclic, or tetracyclic radical having a total of from 4, 5, 6, 7, 8, 9, 10, 11, 12, or 13 carbon atoms in its ring system. A cycloalkyl may be fused, bridged or spirocyclic. In certain embodiments, a cycloalkyl comprises 3 to 8 carbon ring atoms ($C_3$-$C_8$ cycloalkyl). In certain embodiments, a cycloalkyl comprises 3 to 6 carbon ring atoms ($C_3$-$C_6$ cycloalkyl). Examples of such groups include, but are not limited to, cyclopropyl, cyclobutyl, cyclopentyl, cyclopentenyl, cyclohexyl, cycloheptyl, adamantyl, and the like.

The term "cycloalkylene" is a bidentate radical obtained by removing a hydrogen atom from a cycloalkyl ring as defined above. Examples of such groups include, but are not limited to, cyclopropylene, cyclobutylene, cyclopentylene, cyclopentenylene, cyclohexylene, cycloheptylene, and the like.

The term "spirocyclic" as used herein has its conventional meaning, that is, any ring system containing two or more rings wherein two of the rings have one ring carbon in common. Each ring of the spirocyclic ring system, as herein defined, independently comprises 3 to 20 ring atoms. Preferably, they have 3 to 10 ring atoms. Non-limiting examples of a spirocyclic system include spiro[3.3]heptane, spiro[3.4]octane, and spiro[4.5]decane.

The term cyano" refers to a —C≡N group.

An "aldehyde" group refers to a —C(O)H group.

An "alkoxy" group refers to both an —O-alkyl, as defined herein.

An "alkoxycarbonyl" refers to a —C(O)-alkoxy, as defined herein.

An "alkylaminoalkyl" group refers to an -alkyl-NR-alkyl group, as defined herein.

An "alkylsulfonyl" group refer to a —$SO_2$alkyl, as defined herein.

An "amino" group refers to an optionally substituted —$NH_2$.

An "aminoalkyl" group refers to an -alky-amino group, as defined herein.

An "aminocarbonyl" refers to a —C(O)-amino, as defined herein.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)-aryloxy, as defined herein.

An "arylsulfonyl" group refers to a —$SO_2$aryl, as defined herein.

A "carbonyl" group refers to a —C(O)— group, as defined herein.

A "carboxylic acid" group refers to a —C(O)OH group.

A "cycloalkoxy" refers to a —O-cycloalkyl group, as defined herein.

A "halo" or "halogen" group refers to fluorine, chlorine, bromine or iodine.

A "haloalkyl" group refers to an alkyl group substituted with one or more halogen atoms.

A "hydroxy" group refers to an —OH group.

A "nitro" group refers to a —$NO_2$ group.

An "oxo" group refers to the =O substituent.

A "trihalomethyl" group refers to a methyl substituted with three halogen atoms.

The term "substituted," means that the specified group or moiety bears one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "null" means the absence of an atom or moiety, and there is a bond between adjacent atoms in the structure.

The term "optionally substituted" means that the specified group may be either unsubstituted or substituted by one or more substituents as defined herein. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one at which the remainder of the compound of the present invention is attached to and an additional substituent, remaining 4 positions open). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

As used herein, the same symbol in a different FORMULA may have a different definition, for example, the definition of R1 in FORMULA 1 is as defined with respect to FORMULA 1 and the definition of R1 in FORMULA 6 is as defined with respect to FORMULA 6.

As used herein, when m (or n or o or p) is defined by a range, for example, "m is 0 to 15" or "m=0-3" mean that m is an integer from 0 to 15 (i.e. m is 0, 1, 2, 3, 4, 5, 6, 7, 8, 9, 10, 11, 12, 13, 14, or 15) or m is an integer from 0 to 3 (i.e. m is 0, 1, 2, or 3) or is any integer in the defined range.

"Pharmaceutically acceptable salt" includes both acid and base addition salts. A pharmaceutically acceptable salt of any one of the bivalent compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, the same symbol in a different FORMULA may have a different definition, for example, the definition of R' in FORMULA 1 is different from that in FORMULA 6.

As used herein, when m (or n or o or p) is defined as, for example, "m is 0 to 15" or "m=0-5" mean m is m is an integer from 0 to 15 (or 0 to 5).

Pharmaceutical Compositions

In some aspects, the compositions and methods described herein include the manufacture and use of pharmaceutical compositions and medicaments that include one or more bivalent compounds as disclosed herein. Also included are the pharmaceutical compositions themselves.

In some aspects, the compositions disclosed herein can include other compounds, drugs, or agents used for the treatment of cancer. For example, in some instances, pharmaceutical compositions disclosed herein can be combined with one or more (e.g., one, two, three, four, five, or less than ten) compounds. Such additional compounds can include, e.g., conventional chemotherapeutic agents known in the art. When co-administered, PTK6 degraders/disruptors disclosed herein can operate in conjunction with conventional chemotherapeutic agents to produce mechanistically additive or synergistic therapeutic effects.

In some aspects, the pH of the compositions disclosed herein can be adjusted with pharmaceutically acceptable acids, bases, or buffers to enhance the stability of the PTK6 degraders/disruptor or its delivery form.

Pharmaceutical compositions typically include a pharmaceutically acceptable carrier, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable carrier, adjuvant, or vehicle is a composition that can be administered to a patient, together with a compound of the invention, and which does not destroy the pharmacological activity thereof and is nontoxic when administered in doses sufficient to deliver a therapeutic amount of the compound. Exemplary conventional nontoxic pharmaceutically acceptable carriers, adjuvants, and vehicles include saline, solvents, dispersion media, coatings, antibacterial and antifungal agents, isotonic and absorption delaying agents, and the like, compatible with pharmaceutical administration.

In particular, pharmaceutically acceptable carriers, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

As used herein, the PTK6 degraders/disruptors disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Particularly favored derivatives and prodrugs are those that increase the bioavailability of the compounds disclosed herein when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. Such derivatives are recognizable to those skilled in the art without undue experimentation. Nevertheless, reference is made to the teaching of Burger's Medicinal Chemistry and Drug Discovery, $5^{th}$ Edition, Vol. 1: Principles and Practice, which is incorporated herein by reference to the extent of teaching such derivatives.

The PTK6 degraders/disruptors disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivatives thereof.

In particular, pharmaceutically acceptable salts of the PTK6 degraders/disruptors disclosed herein include, e.g., those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include, e.g., alkali metal (e.g., sodium), alkaline earth metal (e.g., magnesium), ammonium and N-(alkyl)4+ salts. The invention also envisions the quaternization of any basic nitrogen-containing groups of the PTK6 degraders/disruptors disclosed herein. Water or oil-soluble or dispersible products can be obtained by such quaternization.

In some aspects, the pharmaceutical compositions disclosed herein can include an effective amount of one or more PTK6 degraders/disruptors. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of cell growth, cell proliferation, or cancer). In some aspects, pharmaceutical compositions can further include one or more additional compounds, drugs, or agents used for the treatment of cancer (e.g., conventional chemotherapeutic agents) in amounts effective for causing an intended effect or physiological outcome (e.g., treatment or prevention of cell growth, cell proliferation, or cancer).

In some aspects, the pharmaceutical compositions disclosed herein can be formulated for sale in the United States, import into the United States, or export from the United States.

Administration of Pharmaceutical Compositions

The pharmaceutical compositions disclosed herein can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/Forms-SubmissionRequirements/ElectronicSubmissions/DataStandardsManualmonographs). In particular, the pharmaceutical compositions can be formulated for and administered via oral, parenteral, or transdermal delivery. The term "parenteral" as used herein includes subcutaneous, intracutaneous, intravenous, intramuscular, intraperitoneal, intra-articular, intra-arterial, intrasynovial, intrasternal, intrathecal, intralesional, and intracranial injection or infusion techniques.

For example, the pharmaceutical compositions disclosed herein can be administered, e.g., topically, rectally, nasally (e.g., by inhalation spray or nebulizer), buccally, vaginally, subdermally (e.g., by injection or via an implanted reservoir), or ophthalmically.

For example, pharmaceutical compositions of this invention can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening, flavoring, or coloring agents can be added.

For example, the pharmaceutical compositions of this invention can be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

For example, the pharmaceutical compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, or other solubilizing or dispersing agents known in the art.

For example, the pharmaceutical compositions of this invention can be administered by injection (e.g., as a solution or powder). Such compositions can be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, e.g., as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium. For this purpose, any bland fixed oil can be employed, including synthetic mono- or diglycerides. Fatty acids, such as oleic acid and its glyceride derivatives are useful in the preparation of injectables, as are natural pharmaceutically-acceptable oils, e.g., olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, or other similar emulsifying agents or bioavailability enhancers which are commonly used in the manufacture of pharmaceutically acceptable solid, liquid, or other dosage forms can also be used for the purposes of formulation.

In some aspects, an effective dose of a pharmaceutical composition of this invention can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day, or according to the requirements of the particular pharmaceutical composition.

When the pharmaceutical compositions disclosed herein include a combination of a compound of the formulae described herein (e.g., an PTK6 degraders/disruptors) and one or more additional compounds (e.g., one or more additional compounds, drugs, or agents used for the treatment of cancer or any other condition or disease, including conditions or diseases known to be associated with or caused by cancer), both the compound and the additional compound should be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day or, alternately or in addition, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, the present disclosure provides methods for using a composition comprising a PTK6 degrader/disruptor, including pharmaceutical compositions (indicated below as 'X') disclosed herein in the following methods: Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of cancer.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had or having a condition or disease. In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the in the methods disclosed herein. Samples can include, e.g., cells or populations of cells.

In some aspects, methods of treatment can include a single administration, multiple administrations, and repeating administration of one or more compounds disclosed herein as required for the prevention or treatment of the disease or condition from which the subject is suffering (e.g., an PTK6-mediated disease). In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The terms "treat", "treating," or "treatment," as used herein, refer to partially or completely alleviating, inhibiting, ameliorating, or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the compositions and methods of the present invention. In some embodiments, treatment can promote or result in, for example, a decrease in the number of tumor cells (e.g., in a subject) relative to the number of tumor cells prior to treatment; a decrease in the viability (e.g., the average/mean viability) of tumor cells (e.g., in a subject) relative to the viability of tumor cells prior to treatment; a decrease in the rate of growth of tumor cells; a decrease in the rate of local or distant tumor metastasis; or reductions in one or more symptoms associated with one or more tumors in a subject relative to the subject's symptoms prior to treatment.

As used herein, the term "treating cancer" means causing a partial or complete decrease in the rate of growth of a tumor, and/or in the size of the tumor and/or in the rate of local or distant tumor metastasis, and/or the overall tumor burden in a subject, and/or any decrease in tumor survival, in the presence of a degrader/disruptor (e.g., an PTK6 degrader/disruptor) described herein.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention. Exemplary PTK6-mediated diseases that can be treated with PTK6 degraders/disruptors include, for example, breast cancer, ovarian cancer, prostate cancer, colon cancer, pancreatic cancer, bladder cancer, liver cancer and cervical cancer.

As used herein, the term "preventing a disease" (e.g., preventing cancer) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms.

The present disclosure is also described and demonstrated by way of the following examples. However, the use of these and other examples anywhere in the specification is illustrative only and in no way limits the scope and meaning of the invention or of any exemplified term. Likewise, the invention is not limited to any particular preferred embodiment or aspect described herein. Indeed, many modifications and variations may be apparent to those skilled in the art upon reading this specification, and such variations can be made without departing from the invention in spirit or in scope. The invention is therefore to be limited only by the terms of the appended claims along with the full scope of equivalents to which those claims are entitled.

EXAMPLES

Procedures for the Synthesis of Intermediates for PTK6 PROTACs

Scheme 1. Synthesis of Intermediate 1

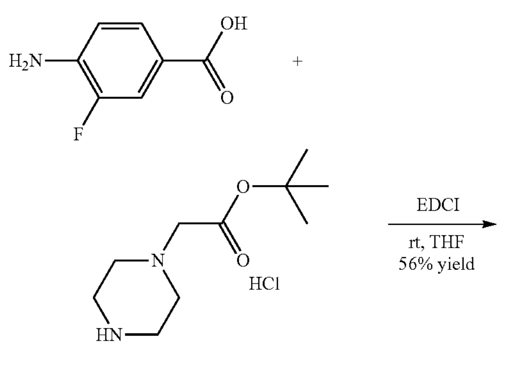

-continued

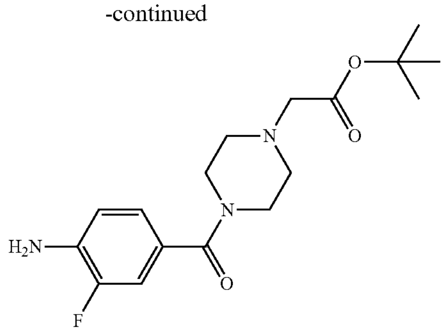

Intermediate 1

Intermediate 1: tert-Butyl 2-(4-(4-amino-3-fluorobenzoyl)piperazin-1-yl)acetate. To a mixture of 4-amino-3-fluorobenzoic acid (613 mg, 3.9 mmol) and tert-butyl 2-(piperazin-1-yl)acetate hydrochloride (908 mg, 3.3 mmol) in THF (20 mL) were added DIEA (2.3 mL, 13.2 mmol) and EDCI (762 mg, 4.0 mmol). The resulting solution was stirred at room temperature ("rt"). After being stirred for 12 hours ("h"), the reaction was quenched with water. After concentration under reduced pressure, the resulting residue was purified by reverse-phase chromatography to yield the title compound (740 mg, 56% yield) as brown oil. $^1$H NMR (600 MHz, $CDCl_3$) δ 7.13 (dd, J=11.4, 1.5 Hz, 1H), 7.07 (d, J=8.1 Hz, 1H), 6.77 (t, J=8.5 Hz, 1H), 3.95 (s, 2H), 3.68 (br, 4H), 2.62 (br, 4H), 1.48 (s, 9H).

Scheme 2. Synthesis of Intermediate 4

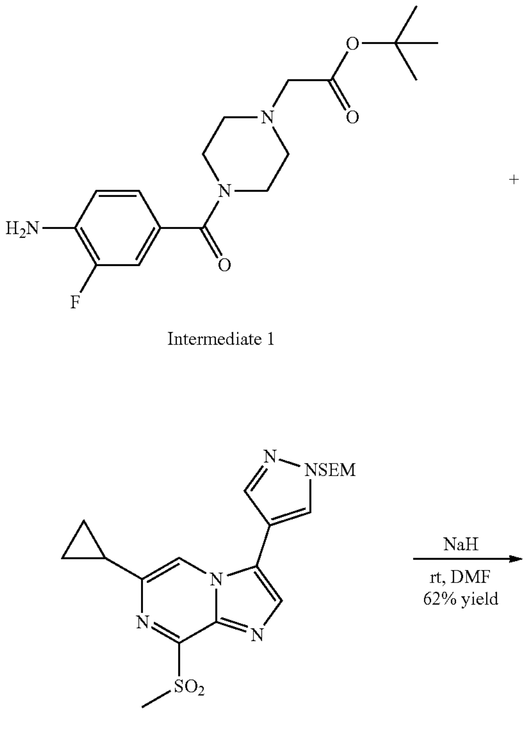

Intermediate 1

Intermediate 2

-continued

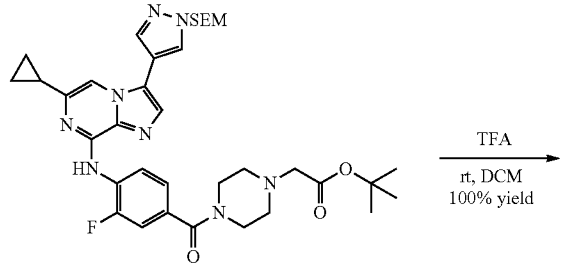

Intermediate 3

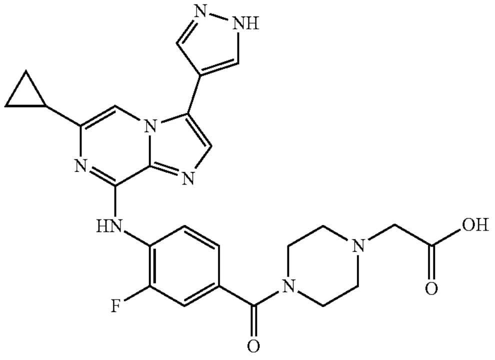

Intermediate 4

Intermediate 4: 2-(4-(4-((6-Cyclopropyl-3-(1H-pyrazol-4-yl)imidazo[1,2-a]pyrazin-8-yl)amino)-3-fluorobenzoyl)piperazin-1-yl)acetic acid. To a solution of intermediate 1 (298 mg, 0.88 mmol) and intermediate 2 (Zeng et al., 2011) (170 mg, 0.39 mmol) in DMF (6 mL) was added NaH (39 mg, 0.98 mmol). The reaction solution was stirred at rt for 3 h before being quench with water. After concentration under reduced pressure, the resulting residue was purified by reverse-phase chromatography to yield intermediate 3 (160 mg, 59% yield) as brown oil. Intermediate 3 (160 mg, 0.23 mmol) was dissolved in DCM/TFA (2:1, 3 mL). The resulting solution was stirred at rt for 1 h before being concentrated under reduced pressure to yield the title compound (170 mg, 0.23 mmol) as brown oil. $^{1}$H NMR (600 MHz, $CD_3OD$) δ 8.45 (q, J=7.8 Hz, 1H), 8.18 (s, 2H), 8.06 (s, 1H), 8.01 (s, 1H), 7.43 (dd, J=11.1, 1.5 Hz, 1H), 7.38 (dd, J=8.5, 1.3 Hz, 1H), 4.21 (s, 2H), 3.98 (br, 4H), 3.55 (br, 4H), 2.19-2.08 (m, 1H), 1.06-0.91 (m, 4H).

Scheme 3. Synthesis of Intermediate 5

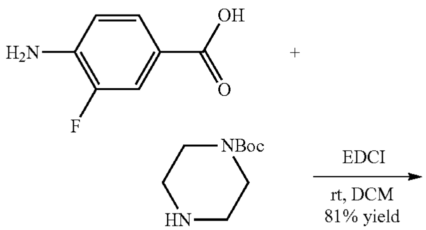

-continued

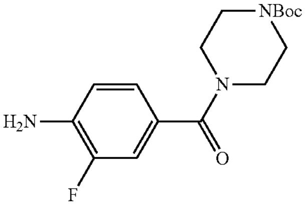

Intermediate 5

Intermediate 5: tert-Butyl 4-(4-amino-3-fluorobenzoyl)piperazine-1-carboxylate. To a mixture of 4-amino-3-fluorobenzoic acid (182 mg, 1.1 mmol) and tert-butyl piperazine-1-carboxylate (228 mg, 1.2 mmol) in DCM (5 mL) were added DIEA (0.26 mL, 1.5 mmol) and EDCI (236 mg, 1.2 mmol). The resulting solution was stirred at rt for 12 h before being quenched with water. After concentration under reduced pressure, the resulting residue was purified by reverse-phase chromatography to yield the title compound (306 mg, 81% yield) as white solid. $^{1}$H NMR (600 MHz, $CDCl_3$) δ 7.13 (d, J=11.3 Hz, 1H), 7.06 (d, J=8.0 Hz, 1H), 6.78 (t, J=8.4 Hz, 1H), 3.99 (s, 2H), 3.60 (br, 4H), 3.47 (br, 4H), 1.49 (s, 9H).

Scheme 4. Synthesis of Intermediate 7

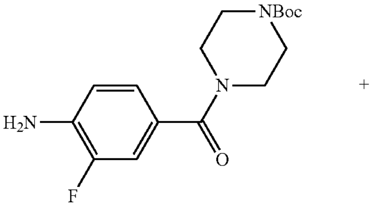

Intermediate 5

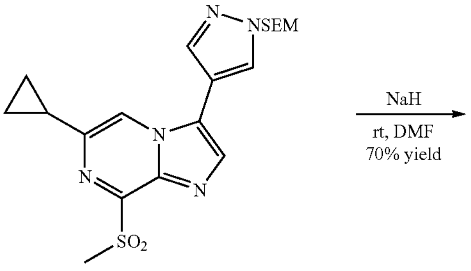

Intermediate 2

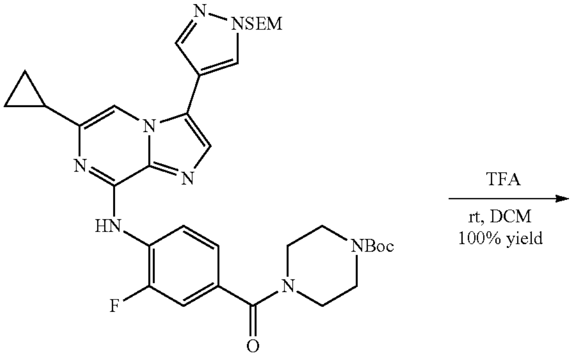

Intermediate 6

-continued

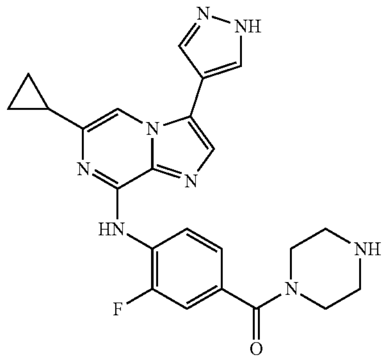

Intermediate 7

-continued

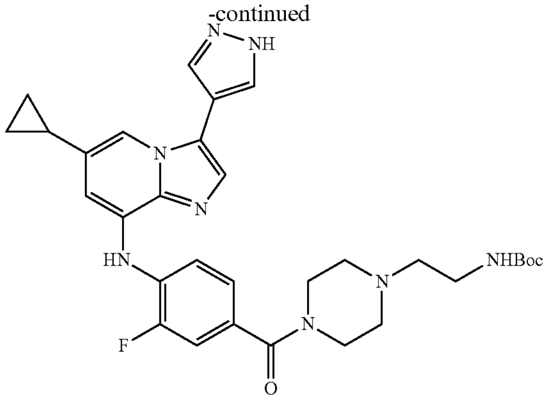

Intermediate 8

Intermediate 7: (4-((6-Cyclopropyl-3-(1H-pyrazol-4-yl)imidazo[1,2-a]pyrazin-8-yl)amino)-3-fluorophenyl)(piperazin-1-yl)methanone. Intermediate 7 was synthesized according to the procedures for the preparation of intermediate 4 as brown oil. $^{1}$H NMR (600 MHz, $CD_3OD$) δ 8.47 (t, J=8.1 Hz, 1H), 8.17 (s, 2H), 8.03 (s, 1H), 8.01 (s, 1H), 7.43 (dd, J=11.2, 1.6 Hz, 1H), 7.38 (dd, J=8.4, 1.5 Hz, 1H), 3.92 (s, 4H), 3.45-3.26 (m, 4H), 2.19-2.07 (m, 1H), 1.09-0.92 (m, 4H).

Scheme 5. Synthesis of Intermediate 8

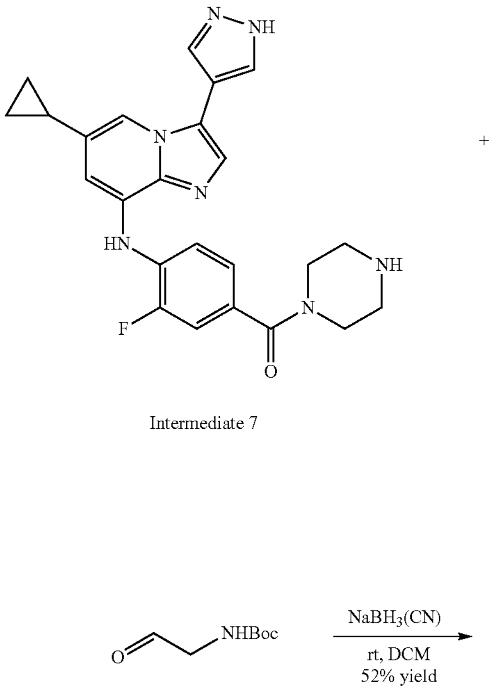

Intermediate 8: tert-Butyl (2-(4-(4-((6-cyclopropyl-3-(1H-pyrazol-4-yl)imidazo[1,2-a]pyrazin-8-yl)amino)-3-fluorobenzoyl)piperazin-1-yl)ethyl)carbamate. To a solution of intermediate 7 (10 mg, 0.018 mmol) and tert-butyl (2-oxoethyl)carbamate (4.3 mg 0.027 mmol) in DCM (1 mL) was added sodium cyanoborohydride (5.9 mg, 0.1 mmol). After being stirred at rt for 12 h, the solution was concentrated under reduced pressure. The resulting residue was purified by HPLC to yield the title compound (5.5 mg, 52%) as brown oil. $^{1}$H NMR (600 MHz, $CD_3OD$) δ 8.76 (t, J=8.2 Hz, 1H), 8.15 (s, 2H), 7.98 (s, 1H), 7.84 (s, 1H), 7.47 (dd, J=11.2, 1.7 Hz, 1H), 7.41 (dd, J=9.3, 7.9 Hz, 1H), 3.86-3.39 (m, 12H), 2.18-2.08 (m, 1H), 1.49 (s, 9H), 1.11-1.02 (m, 2H), 1.02-0.91 (m, 2H).

Scheme 6. Synthesis of intermediate 9

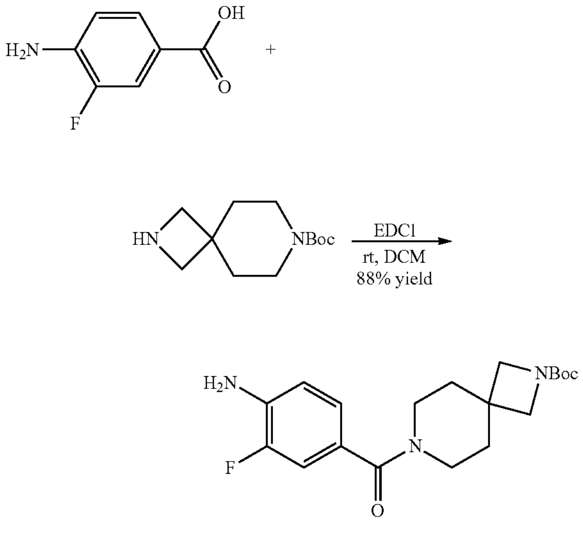

intermediate 9

Intermediate 9: tert-Butyl 7-(4-amino-3-fluorobenzoyl)-2,7-diazaspiro[3.5]nonane-2-carboxylate. Intermediate 9 was synthesized according to the procedure for the preparation of Intermediate 5 as a white solid. $^{1}$H NMR (500 MHz, $CD_3OD$) δ 7.09 (dd, J=11.7, 1.7 Hz, 1H), 7.03 (dd, J=8.2, 1.6 Hz, 1H), 6.85 (t, J=8.5 Hz, 1H), 3.72 (br, 4H), 3.58 (br, 4H), 1.81 (br, 4H), 1.46 (s, 9H).

Scheme 7. Synthesis of intermediate 11

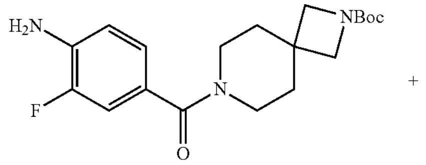

intermediate 9

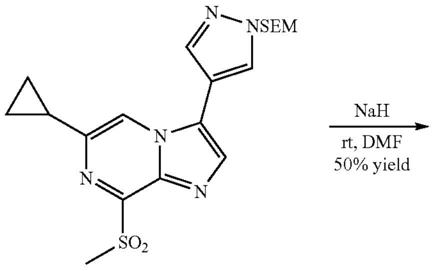

intermediate 2

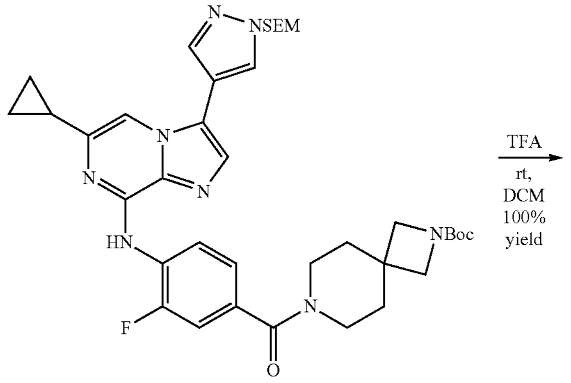

intermediate 10

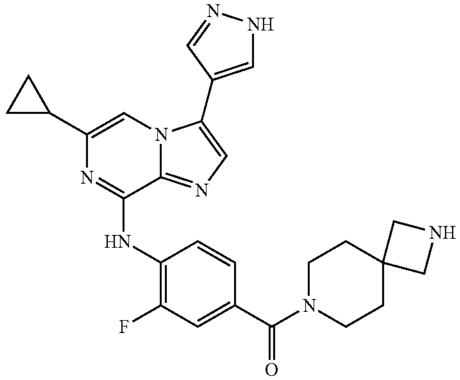

intermediate 11

Intermediate 11: (4-((6-Cyclopropyl-3-(1H-pyrazol-4-yl)imidazo[1,2-a]pyrazin-8-yl)amino)-3-fluorophenyl)(2,7-diazaspiro[3.5]nonan-7-yl)methanone. Intermediate 11 was synthesized according to the procedures for the preparation of intermediate 4. $^1$H NMR (600 MHz, $CD_3OD$) δ 8.47 (t, J=8.0 Hz, 1H), 8.18 (s, 2H), 8.03 (s, 1H), 8.01 (s, 1H), 7.36 (d, J=11.1 Hz, 1H), 7.31 (d, 1=8.3 Hz, 1H), 3.96 (br, 4H), 3.80-3.44 (m, 4H), 2.20-2.09 (m, 1H), 1.95 (br, 4H), 1.06-0.94 (m, 4H).

Scheme 8. Synthesis of intermediate 14

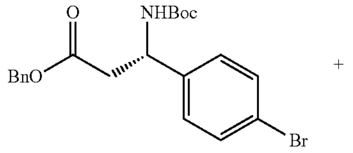

intermediate 12

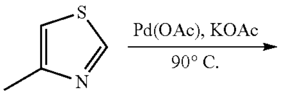

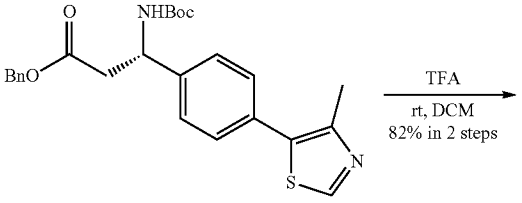

intermediate 13

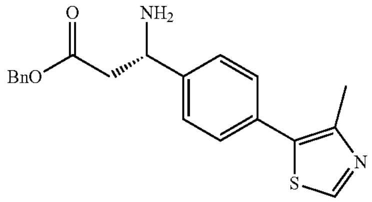

intermediate 14

Intermediate 14: Benzyl (S)-3-amino-3-(4-(4-methylthiazol-5-yl)phenyl)propanoate Intermediated 14 was synthesized from a commercial available intermediate 12, in 2 steps 82% yield, according to a known procedure (Han et al., 2019).

Scheme 9. Synthesis of intermediate 17

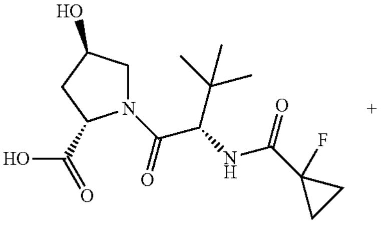

intermediate 15

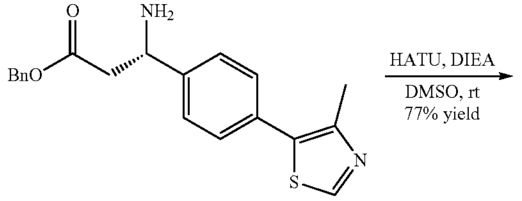

intermediate 14

-continued

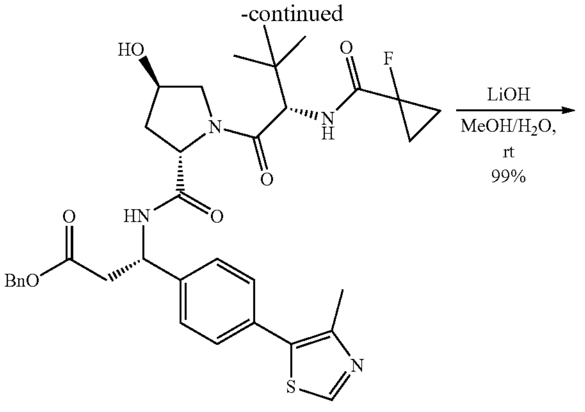

intermediate 16

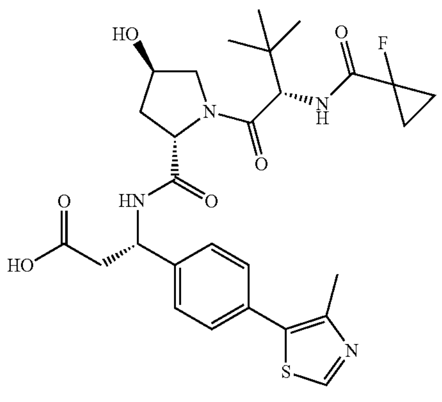

intermediate 17

Intermediate 17: (S)-3-((2S,4R)-1-((S)-2-(1-Fluorocyclopropane-1-carboxamido)-3,3-dimethylbutanoyl)-4-hydroxypyrrolidine-2-carboxamido)-3-(4-(4-methylthiazol-5-yl)phenyl)propanoic acid. Intermediate 17 was synthesized according to a known procedure (Han et al., 2019). $^1$H NMR (600 MHz, $CD_3OD$) δ 9.31 (s, 1H), 7.52 (d, J=8.2 Hz, 1H), 7.49-7.44 (m, 2H), 5.42-5.27 (m, 1H), 4.77-4.69 (m, 1H), 4.62-4.37 (m, 2H), 3.97-3.81 (m, 1H), 3.78-3.72 (m, 1H), 3.05-2.97 (m, 1H), 2.94-2.83 (m, 1H), 2.51 (s, 3H), 2.30-2.14 (m, 1H), 2.13-1.90 (m, 1H), 1.41-1.22 (m, 3H), 1.11 (s, 3H), 1.05 (s, 6H).

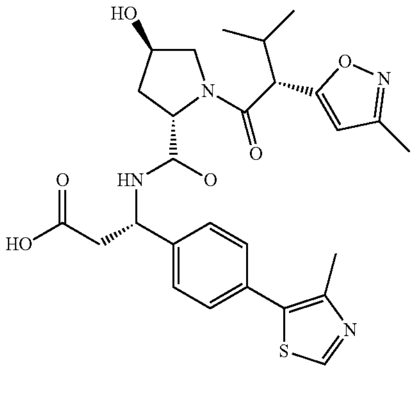 [SMILES: Cc1cc([C@H](C(=O)N2C[C@H](O)C[C@H]2C(O)N[C@@H](CC(=O)O)c2ccc(-c3scnc3C)cc2)C(C)C)on1]

Intermediate 18: (S)-3-((2S,4R)-4-Hydroxy-1-((R)-3-methyl-2-(3-methylisoxazol-5-yl)butanoyl)pyrrolidine-2-carboxamido)-3-(4-(4-methylthiazol-5-yl)phenyl)propanoic acid. Intermediate 18 was synthesized according to the procedures for the preparation of Intermediate 17. δ 9.22-9.08 (m, 1H), 7.62-7.39 (m, 4H), 6.29-6.13 (m, 1H), 5.47-5.31 (m, 1H), 4.63-4.34 (m, 2H), 3.93-3.84 (m, 1H), 3.76 (dd, J=29.5, 10.4 Hz, 1H), 3.69-3.57 (m, 1H), 3.08-2.83 (m, 2H), 2.53 (s, 3H), 2.47-2.36 (m, 1H), 2.30-2.23 (m, 3H), 2.23-2.13 (m, 1H), 2.03-1.94 (m, 1H), 1.11-1.02 (m, 3H), 0.93-0.86 (m, 3H).

Scheme 10. Synthesis of intermediate 19

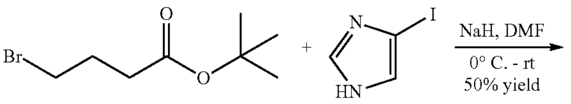

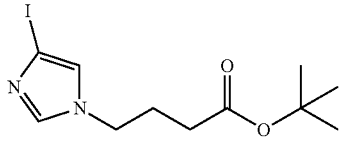

intermediate 19

Intermediate 19: tert-Butyl 4-(4-iodo-1H-imidazol-1-yl) butanoate. To a solution of 4-iodo-1H-imidazole (1.5 g, 7.73 mmol) in DMF (10 mL) at 0° C., was added NaH (0.93 g, 23.19 mmol). After being stirred at 0° C. for 0.5 h, tert-butyl 4-bromobutanoate (3.45 g, 15.46 mmol) was added. The mixture was allowed to warm up to rt and stirred for 16 h, before water (100 mL) was poured into the reaction mixture at 0° C., and extracted with EtOAc (3-100 mL). The combined organic layers were dried over $Na_2SO_4$, filtered, and concentrated. The resulting residue was purified by reverse-phase column to provide title compound (1.3 g, 50% yield) as yellow oil. $^1$H NMR (600 MHz, $CD_3OD$) δ 8.12 (d, J=1.4 Hz, 1H), 7.46 (d, J=1.4 Hz, 1H), 4.14 (t, J=7.1 Hz, 2H), 2.26 (t, J=7.2 Hz, 2H), 2.06 (p, J=7.1 Hz, 2H), 1.44 (s, 9H).

Scheme 11. Synthesis of intermediate 22

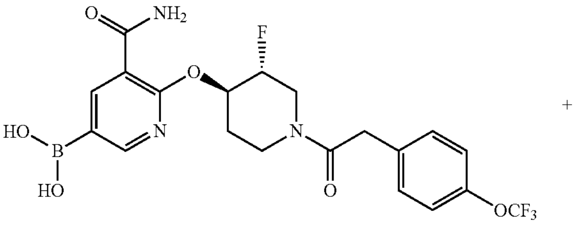

intermediate 20

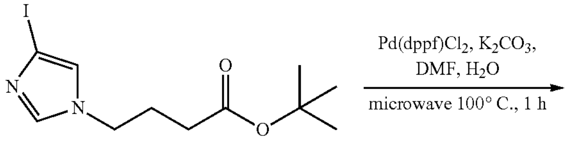

intermediate 19

-continued

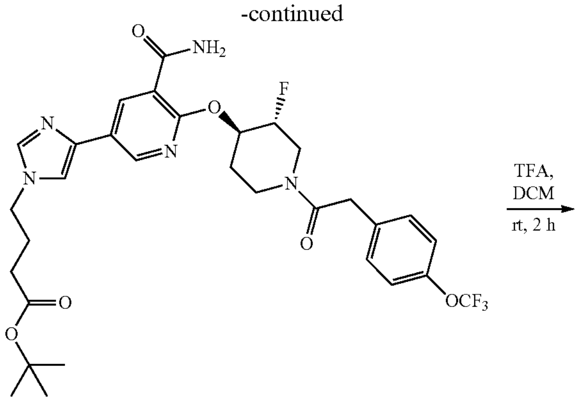

intermediate 21

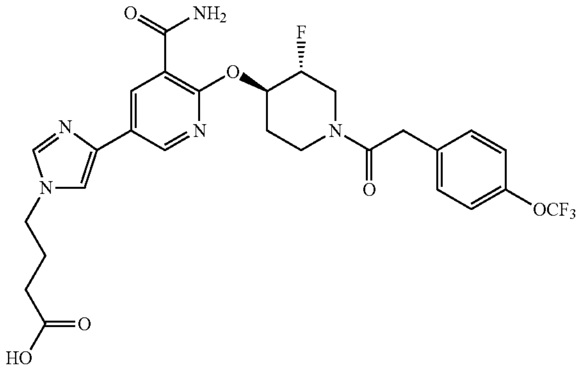

intermediate 22

Intermediate 22: 4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butanoic acid. To a solution of intermediate 20 (1.0 g, 2.06 mmol) in DMF (5 mL) and $H_2O$ (1 mL), were added intermediate 19 (0.76 g, 2.27 mmol), $K_2CO_3$ (1.14 g, 8.24 mmol), and Pd(dppf)$Cl_2$ (151 mg, 0.21 mmol). The reaction mixture was purged with nitrogen for 5 min before being irradiated by microwave at 100° C. for 1 h. The solvent was evaporated and purified by reverse-phase column to provide intermediate 21 (0.7 g, 52%) as yellow solid. $^1$H NMR (800 MHz, $CD_3OD$) δ 9.03 (s, 1H), 8.66 (dd, J=6.5, 2.6 Hz, 1H), 8.57 (dd, J=8.5, 2.6 Hz, 1H), 8.07 (d, 0.1=3.2 Hz, 1H), 7.37 (d, J=8.0 Hz, 2H), 7.29-7.19 (m, 2H), 5.70-5.61 (m, 1H), 4.32 (t, J=7.3 Hz, 2H), 4.14-4.00 (m, 1H), 3.95-3.85 (m, 3H), 3.83-3.77 (m, 2H), 3.63-3.58 (m, 1H), 2.39 (t, J=7.1 Hz, 2H), 2.21 (p, J=7.1 Hz, 3H), 1.96-1.76 (m, 1H), 1.44 (s, 9H). To a solution of intermediate 21 (0.7 g, 1.08 mmol) in DCM (2 mL), was added TFA (2 mL). After being stirred at rt for 2 h, the solvent was evaporated to yield the title compound (0.7 g, 92% yield) as yellow solid, which was used in the next step without further purification.

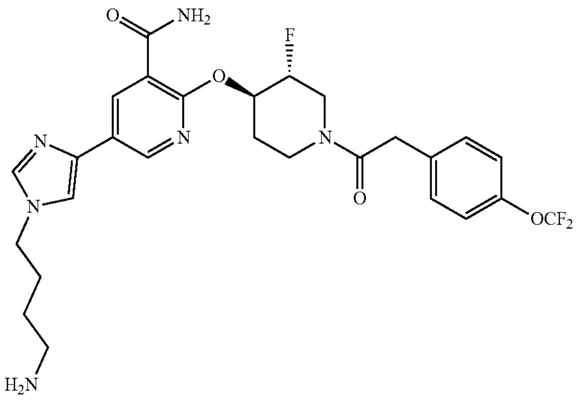

Intermediate 23: 5-(1-(4-Aminobutyl)-1H-imidazol-4-yl)-2-(((3R,4R)-3-fluoro-1-(2-(4-(trifluoromethoxy)phenyl)acetyl)piperidin-4-yl)oxy)nicotinamide Intermediate 23 was synthesized according to the procedures for the preparation of intermediate 22.

Procedures for the Synthesis of Linkers

Scheme 12. Synthesis of linker 1

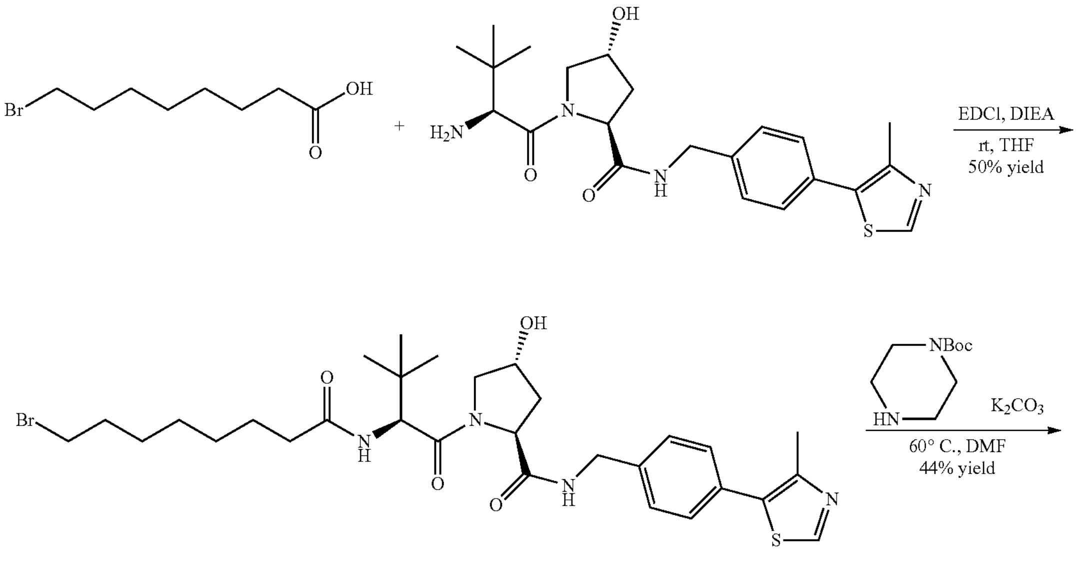

intermediate 10

-continued

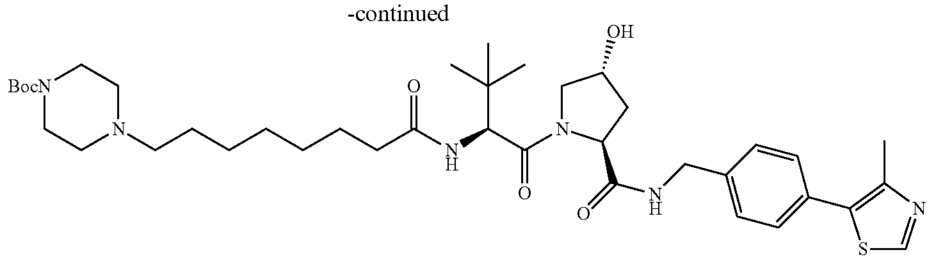

linker 1

Intermediate 10: (2S,4R)-1-((S)-2-(8-Bromooctanamido)-3,3-dimethylbutanoyl)-4-hydroxy-N-(4-(4-methylthiazol-5-yl)benzyl)pyrrolidine-2-carboxamide To a mixture of 8-bromooctanoic acid (24 mg, 0.11 mmol) and VHL-1 (48 mg, 0.11 mmol) in THF (1 mL) were added DIEA (0.05 mL, 0.29 mmol) and EDCI (23.5 mg, 0.12 mmol). After being stirred at rt for 12 h, the reaction was concentrated under reduced pressure. The resulting residue was purified by HPLC to obtain the title compound (32 mg, 50% yield) as brown oil. $^1$H NMR (600 MHz, $CD_3OD$) δ 9.01 (s, 1H), 7.49 (d, J=6.8 Hz, 2H), 7.45 (d, J=8.1 Hz, 2H), 4.66 (s, 1H), 4.63-4.48 (m, 3H), 4.38 (dd, J=15.3, 6.8 Hz, 1H), 3.93 (d, J=11.1 Hz, 1H), 3.83 (dd, J=10.9, 3.9 Hz, 1H), 3.60-3.54 (m, 2H), 2.51 (s, 3H), 2.38-2.16 (m, 3H), 2.17-2.04 (m, 1H), 1.80-1.73 (m, 2H), 1.64 (dt, J=13.5, 7.1 Hz, 2H), 1.51-1.43 (m, 2H), 1.42-1.33 (m, 4H), 1.06 (s, 9H).

Linker 1: tert-Butyl 4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)piperazine-1-carboxylate To a solution of intermediate 10 (28 mg, 0.043 mmol) and tert-butyl piperazine-1-carboxylate (17 mg, 0.092 mmol) in DMF (1 mL) was added $K_2CO_3$ (14 mg, 0.1 mmol). After being heated at 60° C. for 4 h, the reaction mixture was cooled to rt. The insoluble materials were filtered off. And the filtrate was concentrated under reduced pressure. The resulting residue was purified by HPLC to obtain the title compound (30 mg, 44% yield) as brown oil. $^1$H NMR (600 MHz, $CD_3OD$) δ 9.20 (s, 1H), 7.51 (d, J=8.1 Hz, 2H), 7.46 (d, J=8.1 Hz, 2H), 4.66 (s, 1H), 4.61-4.49 (m, 3H), 4.40 (d, J=15.6 Hz, 1H), 4.23 (d, J=13.1 Hz, 2H), 3.93 (d, J=11.0 Hz, 1H), 3.83 (dd, J=10.9, 3.8 Hz, 1H), 3.60-3.51 (m, 2H), 3.28-3.10 (m, 4H), 3.02 (t, J=11.1 Hz, 2H), 2.53 (s, 3H), 2.37-2.21 (m, 3H), 2.14-2.06 (m, 1H), 1.82-1.71 (m, 2H), 1.68-1.57 (m, 2H), 1.49 (s, 9H), 1.45-1.33 (m, 6H), 1.06 (s, 9H).

Linker 2, linker 3, linker 4 and linker 5 were synthesized according to the procedure for the preparation of linker 1

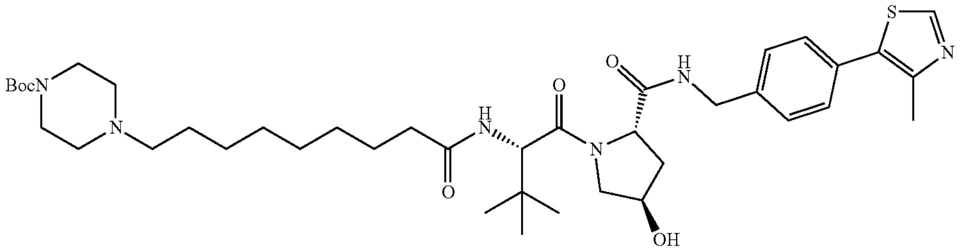 [SMILES: Cc1ncsc1-c1ccc(CNC(=O)[C@@H]2C[C@@H](O)CN2C(=O)[C@@H](NC(=O)CCCCCCCCN2CCN(C(=O)OC(C)(C)C)CC2)C(C)(C)C)cc1]

Linker 2: tert-Butyl 4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)piperazine-1-carboxylate. White solid 67% yield. $^1$H NMR (600 MHz, $CD_3OD$) δ 9.15 (s, 1H), 7.51 (d, J=7.9 Hz, 2H), 7.46 (d, J=8.0 Hz, 2H), 4.66 (s, 1H), 4.63-4.49 (m, 3H), 4.40 (d, J=15.5 Hz, 1H), 4.23 (d, J=12.9 Hz, 2H), 3.93 (d, J=11.0 Hz, 1H), 3.83 (dd, J=10.9, 3.6 Hz, 1H), 3.63-3.51 (m, 2H), 3.29-3.08 (m, 4H), 3.02 (t, J=10.5 Hz, 2H), 2.53 (s, 3H), 2.37-2.21 (m, 3H), 2.17-2.04 (m, 1H), 1.82-1.72 (m, 2H), 1.70-1.56 (m, 2H), 1.49 (s, 9H), 1.46-1.31 (m, 8H), 1.05 (s, 9H).

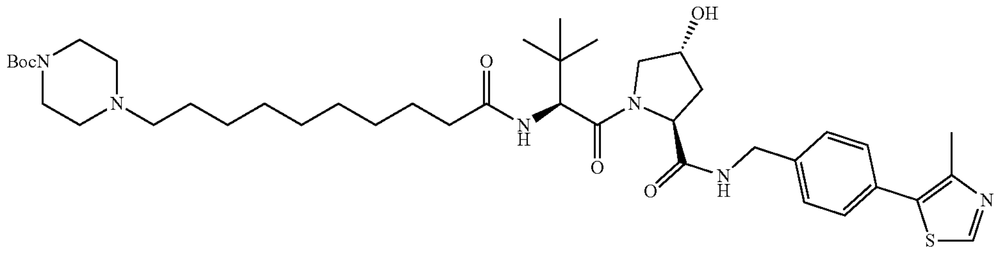 [SMILES: Cc1ncsc1-c1ccc(CNC(=O)[C@@H]2C[C@@H](O)CN2C(=O)[C@@H](NC(=O)CCCCCCCCCN2CCN(C(=O)OC(C)(C)C)CC2)C(C)(C)C)cc1]

Linker 3: tert-Butyl 4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)piperazine-1-carboxylate. White solid 60% yield. $^1$H NMR (600 MHz, $CD_3OD$) δ 9.14 (s, 1H), 7.51 (d, J=8.1 Hz, 2H), 7.45 (d, J=7.6 Hz, 2H), 4.66 (s, 1H), 4.63-4.50 (m, 3H), 4.39 (d, J=15.5 Hz, 1H), 4.23 (d, J=13.1 Hz, 2H), 3.93 (d, J=11.0 Hz, 1H), 3.83 (dd, J=10.9, 3.9 Hz, 1H), 3.68-3.48 (m, 2H), 3.28-3.10 (m, 4H), 3.02 (t, J=10.6 Hz, 2H), 2.53 (s, 3H), 2.41-2.18 (m, 3H), 2.17-2.04 (m, 1H), 1.82-1.70 (m, 2H), 1.70-1.58 (m, 2H), 1.49 (s, 9H), 1.44-1.28 (m, 10H), 1.06 (s, 9H).

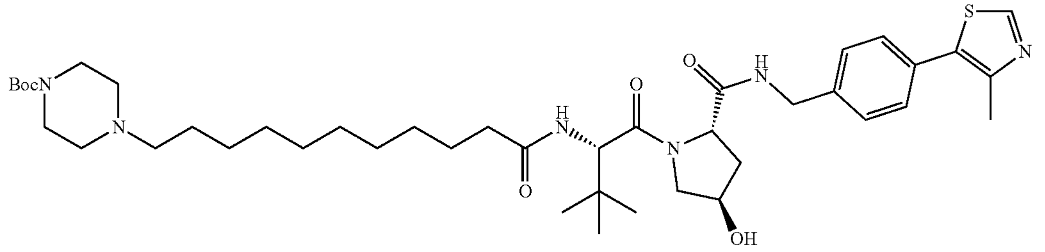 [SMILES: Cc1ncsc1-c1ccc(CNC(=O)[C@@H]2C[C@@H](O)CN2C(=O)[C@@H](NC(=O)CCCCCCCCCCN2CCN(C(=O)OC(C)(C)C)CC2)C(C)(C)C)cc1]

Linker 4: tert-Butyl 4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)piperazine-1-carboxylate. White solid 62% yield. $^1$H NMR (600 MHz, $CD_3OD$) S 9.17 (s, 1H), 7.51 (d, J=7.5 Hz, 2H), 7.46 (d, J=7.8 Hz, 2H), 4.66 (s, 1H), 4.63-4.49 (m, 3H), 4.39 (d, J=15.4 Hz, 1H), 4.23 (d, J=12.6 Hz, 2H), 3.93 (d, J=10.8 Hz, 1H), 3.87-3.78 (m, 1H), 3.72-3.45 (m, 2H), 3.28-3.11 (m, 4H), 3.06-2.97 (m, 2H), 2.53 (s, 3H), 2.36-2.19 (m, 3H), 2.15-2.04 (m, 1H), 1.85-1.71 (m, 2H), 1.72-1.56 (m, 2H), 1.49 (s, 9H), 1.45-1.26 (m, 12H), 1.04 (s, 9H).

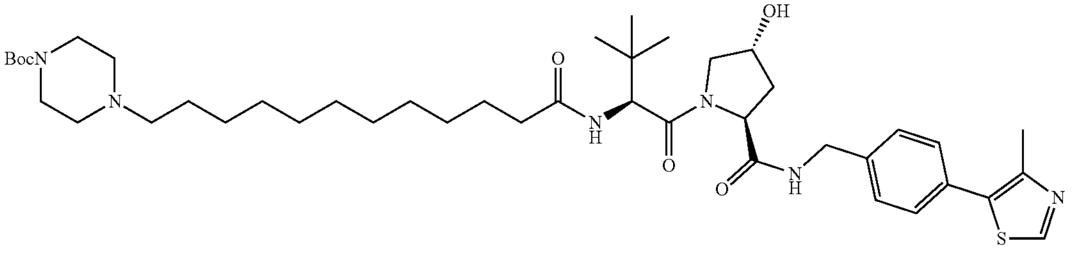 [SMILES: Cc1ncsc1-c1ccc(CNC(=O)[C@@H]2C[C@@H](O)CN2C(=O)[C@@H](NC(=O)CCCCCCCCCCCN2CCN(C(=O)OC(C)(C)C)CC2)C(C)(C)C)cc1]

Linker 5: tert-Butyl 4-(12-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-12-oxododecyl)piperazine-1-carboxylate. White solid 56% yield. $^1$H NMR (600 MHz, $CD_3OD$) δ 9.16 (s, 1H), 7.51 (t, J=6.6 Hz, 2H), 7.46 (d, J=8.1 Hz, 2H), 4.66 (s, 1H), 4.62-4.49 (m, 3H), 4.38 (d, J=9.7 Hz, 1H), 4.23 (d, J=13.2 Hz, 2H), 3.93 (d, J=11.0 Hz, 1H), 3.83 (dd, J=10.9, 3.7 Hz, 1H), 3.71-3.46 (m, 2H), 3.28-3.08 (m, 4H), 3.09-2.90 (m, 2H), 2.53 (s, 3H), 2.39-2.18 (m, 3H), 2.15-2.02 (m, 1H), 1.76 (s, 2H), 1.71-1.55 (m, 2H), 1.49 (s, 9H), 1.44-1.27 (m, 14H), 1.04 (s, 9H).

Scheme 13. Synthesis of linker 6

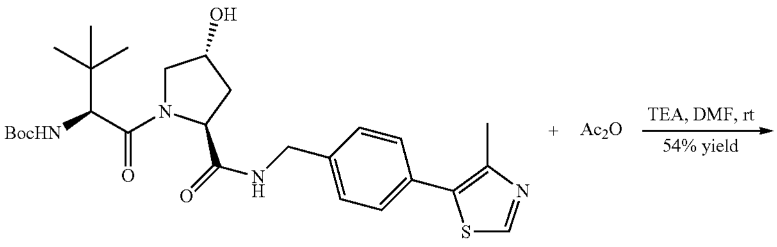

-continued

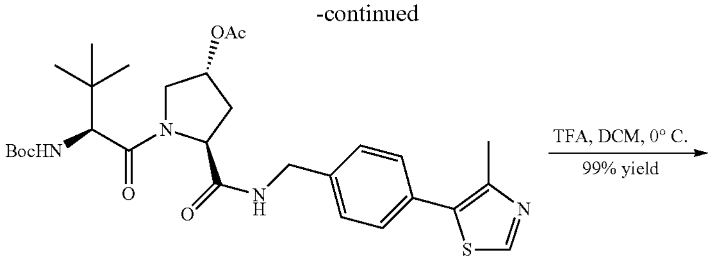

intermediate 25

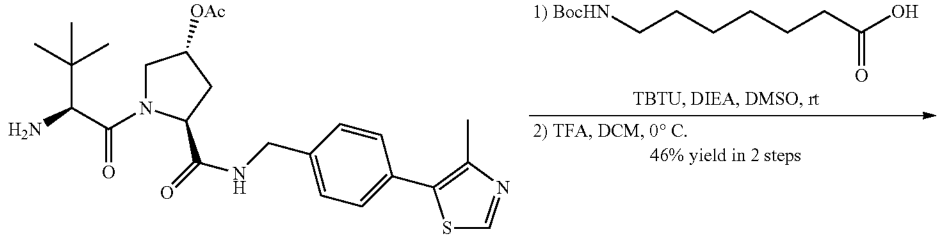

intermediate 26

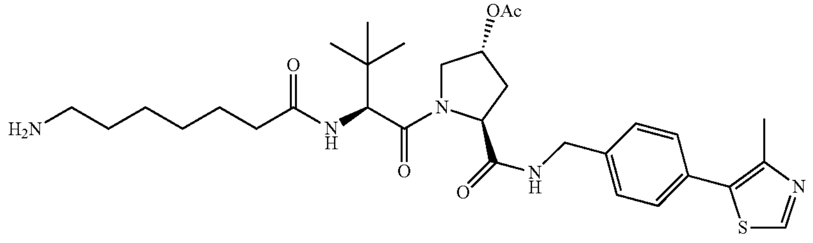

Linker 6

Intermediate 26: (3R,5S)-1-((S)-2-Amino-3,3-dimethylbutanoyl)-5-((4-(4-methylthiazol-5-yl)benzyl)carbamoyl) pyrrolidin-3-yl acetate. To a solution of Boc protected VHL-1 (600 mg, 1.1 mmol) in DCM (6 mL), were added $Ac_2O$ (0.2 mL, 2.1 mmol) and TEA (0.32 mL, 2.3 mmol). The solution was stirred at rt for 3 d, before being quenched with water, and extracted with DCM (3×5 mL). The combined organic layers were dried over $Na_2SO_4$, filtered, and concentrated. The resulting residue was purified by reverse-phase column to yield intermediate 25 as white oil (340 mg, 54% yield). Intermediate 25 was dissolved in DCM and TFA (7:2, 9 mL) in ice-water bath. The resulting solution was stirred at 0° C. for 30 min, before being concentrated to yield the title compound as oil (556 mg, 99% yield).

Linker 6: (3R,5S)-1-((S)-2-(7-Aminoheptanamido)-3,3-dimethylbutanoyl)-5-((4-(4-methylthiazol-5-yl)benzyl)carbamoyl)pyrrolidin-3-yl acetate. To a solution of Intermediate 26 (29 mg. 0.05 mmol) in DMSO (0.5 mL), were added the Boc protected amino acid (12 mg, 0.05 mmol), TBTU (17 mg, 0.05 mmol) and DIEA (0.1 mL, 0.57 mmol). The solution was stirred at rt for 1 h. After being quenched with MeOH, the reaction was diluted with DCM (2 mL) and TFA (0.5 mL). The resulting solution was stirred at 0° C. for 30 min before being concentrated. The resulting residue was purified by prep-HPLC to yield the title compound (17 mg, 49% yield). $^1H$ NMR (600 MHz, $CD_3OD$) δ 9.21 (s, 1H), 7.53-7.45 (m, 4H), 5.44-5.36 (m, 1H), 4.62-4.50 (m, 3H), 4.40 (d, J=15.5 Hz, 1H), 4.19 (d, J=11.8 Hz, 1H), 3.94 (dd, J=11.7, 4.0 Hz, 1H), 2.93 (t, J=7.6 Hz, 2H), 2.53 (s, 3H), 2.42 (dd, J=13.9, 7.6 Hz, 1H), 2.38-2.23 (m, 3H), 2.07 (s, 3H), 1.73-1.60 (m, 4H), 1.50-1.36 (m, 4H), 1.06 (s, 10H).

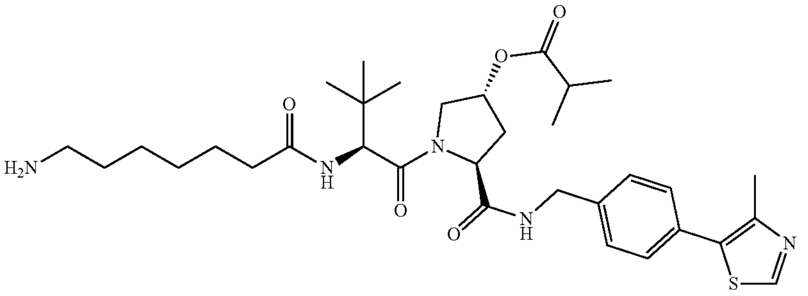 [SMILES: Cc1ncsc1-c1ccc(CNC(=O)[C@@H]2C[C@@H](OC(=O)C(C)C)CN2C(=O)[C@@H](NC(=O)CCCCCCN)C(C)(C)C)cc1]

Linker 7: (3R,5S)-1-((S)-2-(7-Aminoheptanamido)-3,3-dimethylbutanoyl)-5-((4-(4-methylthiazol-5-yl)benzyl)carbamoyl)pyrrolidin-3-yl isobutyrate. Linker 7 was synthesized according to the procedures for the preparation of linker 6 with 57% yield. $^1$H NMR (600 MHz, $CD_3OD$) δ 9.31 (s, 1H), 7.50 (dd, J=26.4, 8.1 Hz, 4H), 5.42-5.35 (m, 1H), 4.61-4.54 (m, 3H), 4.41 (d, J=15.6 Hz, 1H), 4.16 (d, J=11.8 Hz, 1H), 3.95 (dd, J=11.7, 3.9 Hz, 1H), 2.93 (t, J=7.6 Hz, 2H), 2.58-2.53 (m, 4H), 2.44-2.38 (m, 1H), 2.37-2.23 (m, 3H), 1.73-1.60 (m, 4H), 1.47-1.34 (m, 4H), 1.16 (d, J=7.0 Hz, 6H) 1.06 (s, 9H).

Scheme 14. Synthesis of linker 8

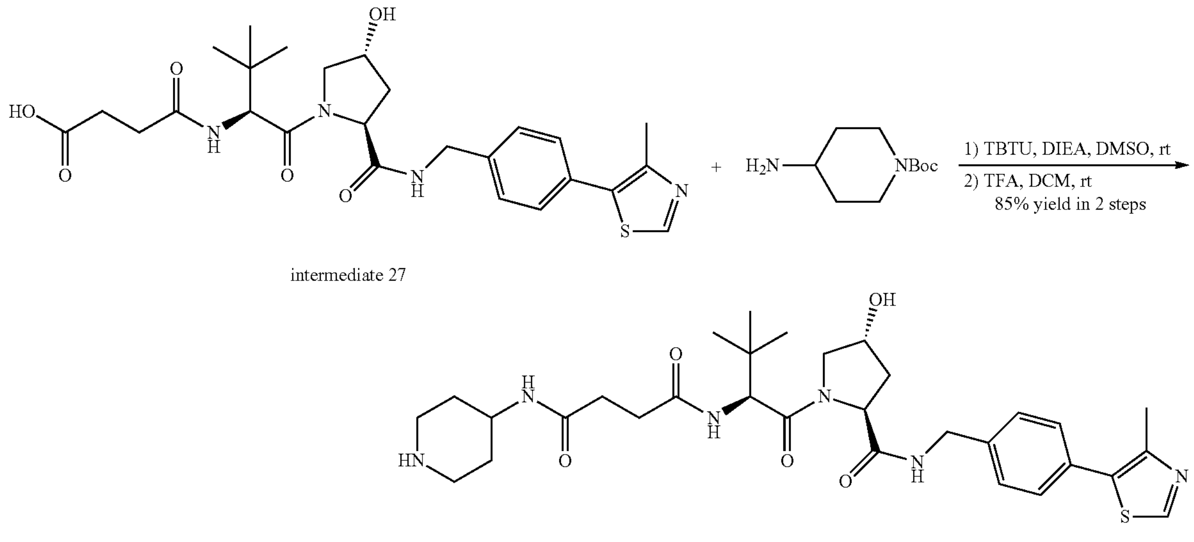

intermediate 27

Linker 8

Linker 8: (2S,4R)-1-((S)-2-(4-(4-Aminopiperidin-1-yl)-4-oxobutanamido)-3,3-dimethylbutanoyl)-4-hydroxy-N-(4-(4-methylthiazol-5-yl)benzyl)pyrrolidine-2-carboxamide. Linker 8 was synthesized according to the procedures for the preparation of linker 6 with 86% yield. $^1$H NMR (500 MHz, $CD_3OD$) δ 9.14 (s, 1H), 7.51 (d, J=8.3 Hz, 2H), 7.49-7.42 (m, 2H), 4.65-4.50 (m, 4H), 4.39 (d, J=15.5 Hz, 1H), 3.98-3.86 (m, 2H), 3.81 (dd, J=11.0, 3.9 Hz, 1H), 3.47-3.37 (m, 2H), 3.11 (td, J=12.9, 3.0 Hz, 2H), 2.64 (dd, J=14.9, 7.5 Hz, 1H), 2.58-2.45 (m, 6H), 2.29-2.20 (m, 1H), 2.10 (ddd, J=13.2, 9.0, 4.4 Hz, 3H), 1.78-1.65 (m, 2H), 1.05 (s, 9H).

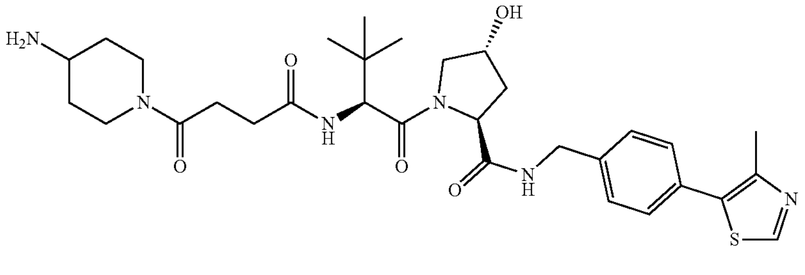 [SMILES: Cc1ncsc1-c1ccc(CNC(=O)[C@@H]2C[C@@H](O)CN2C(=O)[C@@H](NC(=O)CCC(=O)N2CCC(N)CC2)C(C)(C)C)cc1]

Linker 9: (2S,4R)-1-((S)-2-(4-(4-Aminopiperidin-1-yl)-4-oxobutanamido)-3,3-dimethylbutanoyl)-4-hydroxy-N-(4-(4-methylthiazol-5-yl)benzyl)pyrrolidine-2-carboxamide. Linker 9 was synthesized according to the procedures for the preparation of linker 6 in 73% yield. δ 9.28 (s, 1H), 7.51 (dd, J=10.2, 5.7 Hz, 2H), 7.46 (d, J=8.2 Hz, 2H), 4.68-4.49 (m, 5H), 4.41 (dd, J=15.6, 2.1 Hz, 1H), 4.10 (d, J=13.8 Hz, 1H), 3.91 (d, J=11.0 Hz, 1H), 3.81 (dd, J=11.0, 3.8 Hz, 1H), 3.39 (t, J=11.5 Hz, 1H), 3.18 (t, J=13.3 Hz, 1H), 2.79-2.60 (m, 4H), 2.60-2.49 (m, 4H), 2.26 (dd, J=13.1, 7.7 Hz, 1H), 2.17-2.00 (m, 3H), 1.61 (dt, J=12.1, 8.1 Hz, 1H, 1.55-1.41 (m, 1H, 1.05 (s, 9H).

Scheme 15. Synthesis of linker 10

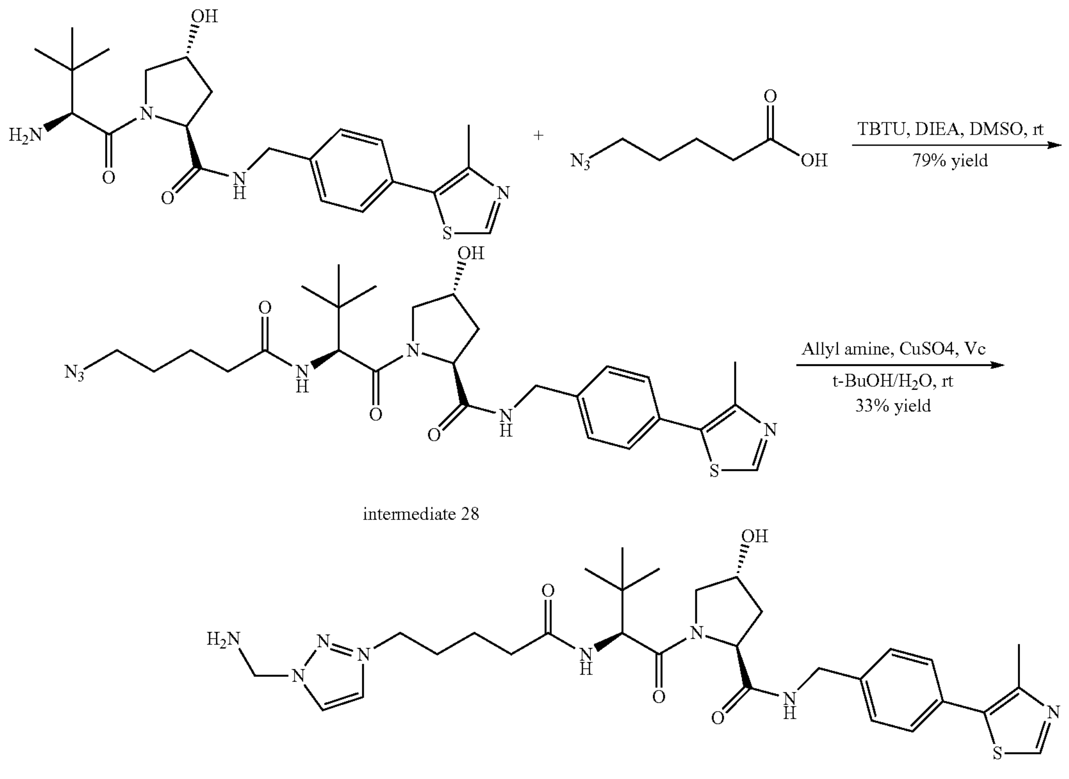

intermediate 28

Linker 10

Intermediate 28: (2S,4R)-1-((S)-2-(5-Azidopentanamido)-3,3-dimethylbutanoyl)-4-hydroxy-N-(4-(4-methylthiazol-5-yl)benzyl)pyrrolidine-2-carboxamide. Intermediate 28 was synthesized according to the procedures for the preparation of linker 6 in 79% yield. $^1H$ NMR (500 MHz, $CD_3OD$) δ 8.88 (s, 1H), 7.50-7.38 (m, 4H), 4.66 (s, 1H), 4.62 (t, J=8.3 Hz, 1H), 4.59-4.50 (m, 2H), 4.38 (d, J=15.5 Hz, 1H), 3.93 (d, J=11.1 Hz, 1H), 3.82 (dd, J=10.9, 3.9 Hz, 1H), 3.31 (t, J=6.7 Hz, 2H), 2.49 (s, 3H), 2.41-2.20 (m, 4H), 2.14-2.07 (m, 1H), 1.77-1.56 (m, 4H), 1.06 (s, 9H).

Linker 10: (2S,4R)-1-((S)-2-(5-(1-(Aminomethyl)-1H-1,2,314-triazol-3-yl)pentanamido)-3,3-dimethylbutanoyl)-4-hydroxy-N-(4-(4-methylthiazol-5-yl)benzyl)pyrrolidine-2-carboxamide. Intermediate 28 (35 mg, 0.06 mmol) was dissolved in t-BuOH and water (5:1, 0.5 mL), followed by allyl amine (3.4 mg, 0.06 mmol), $CuSO_4$ (20 mg, 0.08 mmol) and Vc (1 mg, 0.004 mmol). The mixture was stirred at room temperature. After 24 h, the solvent concentrated, the resulted residue was purified by prep-HPLC to yield the title compound (15 mg, 33% yield). $^1H$ NMR (500 MHz, $CD_3OD$) δ 9.13 (s, 1H), 8.06 (s, 1H), 7.48 (dd, J=24.2, 8.2 Hz, 4H), 4.64 (s, 1H), 4.60-4.51 (m, 3H), 4.47 (t, J=6.9 Hz, 2H), 4.40 (d, J=15.5 Hz, 1H), 4.26 (s, 2H), 3.92 (d, J=11.0 Hz, 1H), 3.83 (dd, J=10.9, 3.9 Hz, 1H), 2.52 (s, 3H), 2.40-2.30 (m, 2H), 2.28-2.21 (m, 1H), 2.16-2.07 (m, 1H), 1.98-1.90 (m, 2H), 1.66-1.56 (m, 2H), 1.05 (s, 9H).

Scheme 16. Synthesis of linker 11

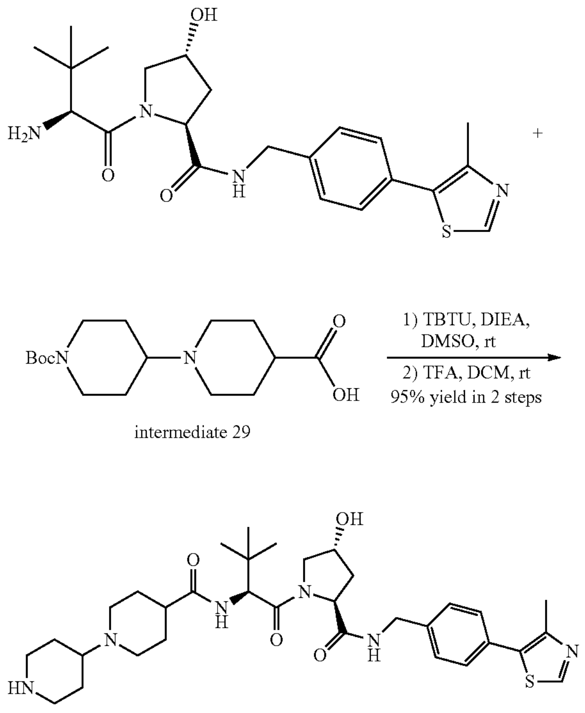

intermediate 29

Linker 11

Linker 11: Linker 11 was synthesized according to the procedures for the preparation of linker 6 in 95% yield. $^1$H NMR (500 MHz, $CD_3OD$) δ 9.28 (s, 1H), 7.51 (d, J=8.1 Hz, 2H), 7.44 (d, J=8.1 Hz, 2H), 4.70-4.50 (m, 4H), 4.39 (d, J=15.6 Hz, 1H), 3.92 (d, J=10.1 Hz, 1H), 3.82 (dd, J=10.9, 3.6 Hz, 1H), 3.74-3.53 (m, 5H), 3.14 (t, J=12.2 Hz, 4H), 2.79-2.65 (m, 1H), 2.52 (s, 3H), 2.40 (d, J=12.7 Hz, 2H), 2.31-2.22 (m, 1H), 2.20-1.93 (m, 8H), 1.06 (s, 9H).

Scheme 17. Synthesis of linker 12

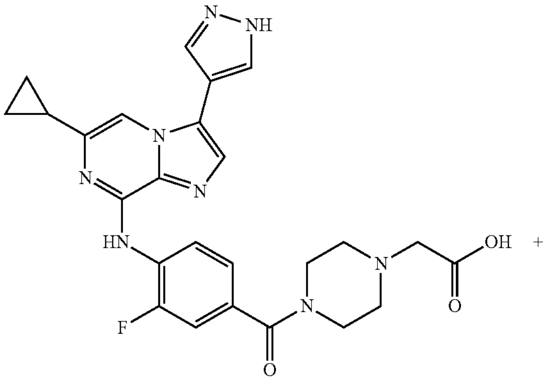

intermediate 4

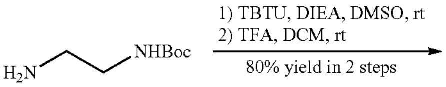

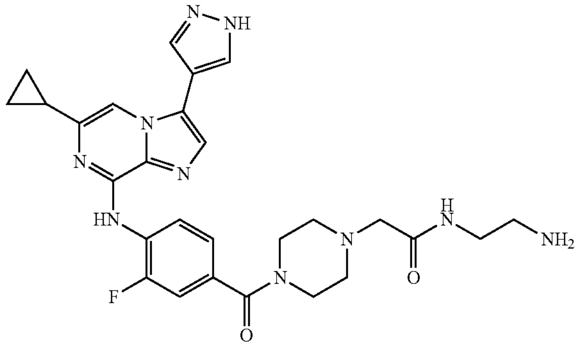

Linker 12

Linker 12: N-(2-Aminoethyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. Linker 12 was synthesized according to the procedures for the preparation of linker 6 in 80% yield. $^1$H NMR (500 MHz, $CD_3OD$) δ 9.28 (s, 1H), 7.51 (d, J=8.1 Hz, 2H), 7.44 (d, J=8.1 Hz, 2H), 4.70-4.50 (m, 4H), 4.39 (d, J=15.6 Hz, 1H), 3.92 (d, J=10.1 Hz, 1H), 3.82 (dd, J=10.9, 3.6 Hz, 1H), 3.74-3.53 (m, 5H), 3.14 (t, J=12.2 Hz, 4H), 2.79-2.65 (m, 1H), 2.52 (s, 3H), 2.40 (d, J=12.7 Hz, 2H), 2.31-2.22 (m, 1H), 2.20-1.93 (m, 8H), 1.06 (s, 9H).

Linkers 13-23 were synthesized according to the procedures for the preparation of Linker 12.

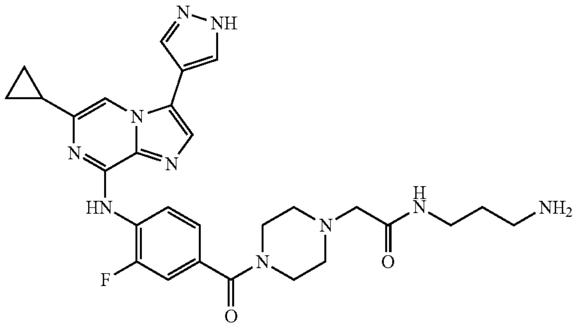 [SMILES: NCCCNC(=O)CN1CCN(C(=O)c2ccc(Nc3nc(C4CC4)cn4c(-c5cn[nH]c5)cnc34)c(F)c2)CC1]

Linker 13: N-(3-Aminopropyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 82% yield. $^1$H NMR (500 MHz, $CD_3OD$) δ 8.60 (t, J=8.2 Hz, 1H), 8.14 (s, 2H), 7.95 (s, 1H), 7.90 (s, 1H), 7.43 (dd, J=11.2, 1.6 Hz, 1H), 7.39 (d, J=8.5 Hz, 1H), 4.12-3.85 (m, 6H), 3.49 (br, 4H), 3.40 (t, J=6.7 Hz, 2H), 3.01 (t, J=7.4 Hz, 2H), 2.21-2.04 (m, 1H), 1.97-1.84 (m, 2H), 1.07-0.92 (m, 4H).

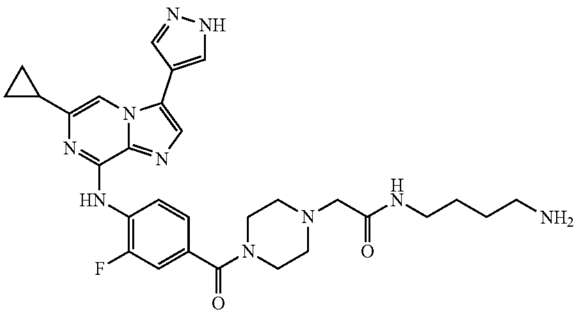 [SMILES: NCCCCNC(=O)CN1CCN(C(=O)c2ccc(Nc3nc(C4CC4)cn4c(-c5cn[nH]c5)cnc34)c(F)c2)CC1]

Linker 14: N-(4-Aminobutyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 86% yield. $^1$H NMR (500 MHz, $CD_3OD$) δ 8.73 (t, J=8.1 Hz, 1H), 8.14 (s, 2H), 7.90 (s, 1H), 7.77 (s, 1H), 7.42 (d, J=11.3 Hz, 1H), 7.38 (d, J=8.4 Hz, 1H), 3.96 (br, 6H), 3.41 (br, 4H), 2.97 (t, J=7.3 Hz, 2H), 2.14-2.03 (m, 1H), 1.79-1.58 (m, 4H), 1.07-1.00 (m, 2H), 1.00-0.89 (m, 2H).

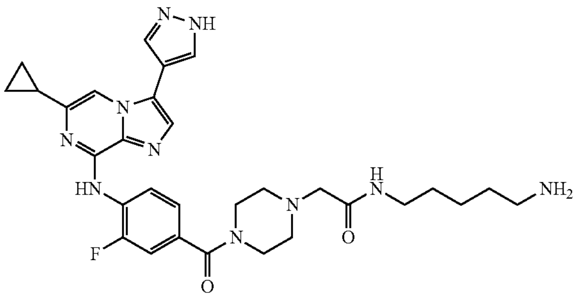 [SMILES: NCCCCCNC(=O)CN1CCN(C(=O)c2ccc(Nc3nc(C4CC4)cn4c(-c5cn[nH]c5)cnc34)c(F)c2)CC1]

Linker 15: N-(5-Aminopentyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 80% yield. $^1$H NMR (500 MHz, $CD_3OD$) δ 8.66 (t, J=8.2 Hz, 1H), 8.14 (s, 2H), 7.94 (s, 1H), 7.85 (s, 1H), 7.44 (dd, J=11.3, 1.8 Hz, 1H), 7.39 (d, J=8.4 Hz, 1H), 4.21-3.77 (m, 6H), 3.48 (br, 4H), 3.30 (t, J=7.1 Hz, 2H), 2.95 (t, J=7.6 Hz, 2H), 2.15-2.04 (m, 1H), 1.79-1.66 (m, 2H), 1.66-1.55 (m, 2H), 1.51-1.41 (m, 2H), 1.09-0.92 (m, 4H).

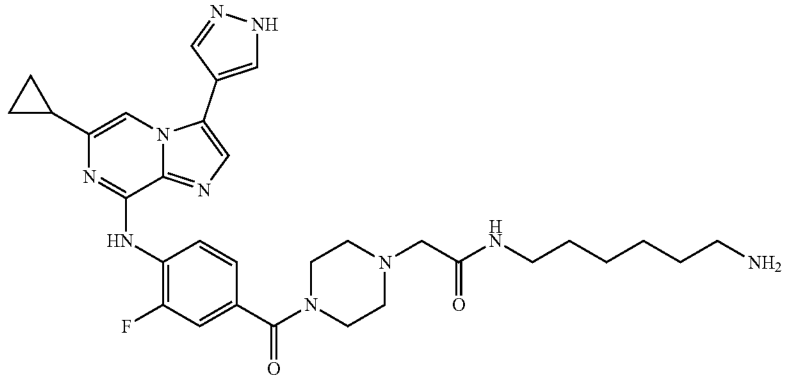 [SMILES: NCCCCCCNC(=O)CN1CCN(C(=O)c2ccc(Nc3nc(C4CC4)cn4c(-c5cn[nH]c5)cnc34)c(F)c2)CC1]

Linker 16: N-(6-Aminohexyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 79% yield. $^1$H NMR (500 MHz, $CD_3OD$) δ 8.73 (t, J=8.2 Hz, 1H), 8.12 (s, 2H), 7.90 (s, 1H), 7.76 (s, 1H), 7.46-7.40 (m, 1H), 7.38 (d, J=8.5 Hz, 1H), 4.13-3.86 (m, 6H), 3.43 (br, 4H), 3.29 (t, J=7.1 Hz, 2H), 2.94 (t, J=7.5 Hz, 2H), 2.14-2.04 (m, 1H), 1.74-1.64 (m, 2H), 1.64-1.54 (m, 2H), 1.49-1.39 (m, 4H), 1.07-1.00 (m, 2H), 1.00-0.92 (m, 2H).

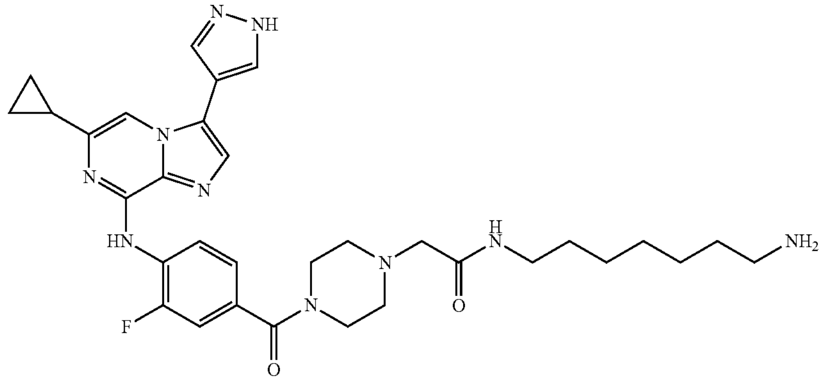 [SMILES: NCCCCCCCNC(=O)CN1CCN(C(=O)c2ccc(Nc3nc(C4CC4)cn4c(-c5cn[nH]c5)cnc34)c(F)c2)CC1]

Linker 17: N-(7-Aminoheptyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 83% yield. $^1$H NMR (500 MHz, $CD_3OD$) δ 8.74 (t, J=8.2 Hz, 1H), 8.12 (s, 2H), 7.91 (s, 1H), 7.76 (s, 1H), 7.43 (dd, J=11.3, 1.7 Hz, 1H), 7.38 (d, J=8.5 Hz, 1H), 4.05-3.86 (m, 6H), 3.43 (br, 4H), 3.28 (t, J=7.2 Hz, 2H), 3.00-2.86 (m, 2H), 2.21-2.00 (m, 1H), 1.73-1.63 (m, 2H), 1.63-1.53 (m, 2H), 1.47-1.33 (m, 6H), 1.07-0.99 (m, 2H), 0.99-0.91 (m, 2H).

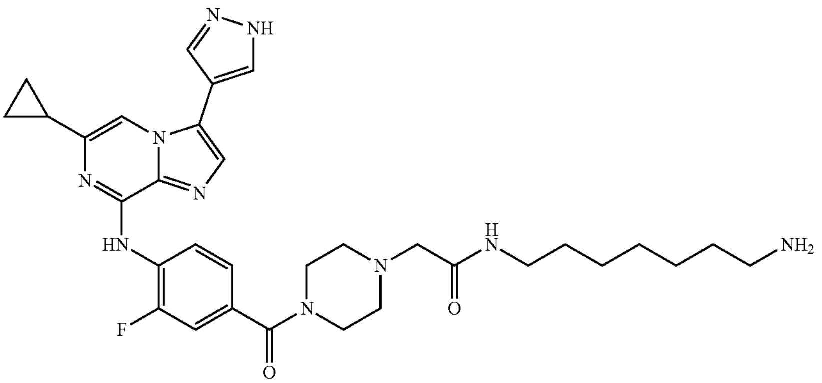 [SMILES: NCCCCCCCNC(=O)CN1CCN(C(=O)c2ccc(Nc3nc(C4CC4)cn4c(-c5cn[nH]c5)cnc34)c(F)c2)CC1]

Linker 18: N-(7-Aminoheptyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 83% yield. $^1$H NMR (500 MHz, $CD_3OD$) δ 8.74 (t, J=8.2 Hz, 1H), 8.12 (s, 2H), 7.91 (s, 1H), 7.76 (s, 1H), 7.43 (dd, J=11.3, 1.7 Hz, 1H), 7.38 (d, J=8.5 Hz, 1H), 4.05-3.86 (m, 6H), 3.43 (br, 4H), 3.28 (t, J=7.2 Hz, 2H), 3.00-2.86 (m, 2H), 2.21-2.00 (m, 1H), 1.73-1.63 (m, 2H), 1.63-1.53 (m, 2H), 1.47-1.33 (m, 6H), 1.07-0.99 (m, 2H), 0.99-0.91 (m, 2H).

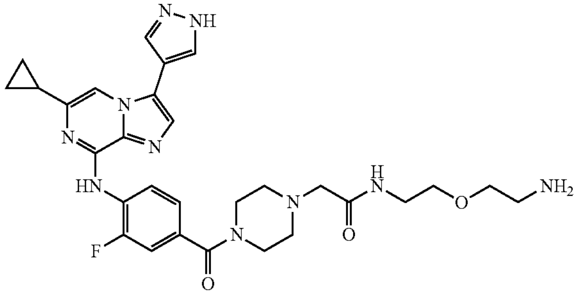 [SMILES: NCCOCCNC(=O)CN1CCN(C(=O)c2ccc(Nc3nc(C4CC4)cn4c(-c5cn[nH]c5)cnc34)c(F)c2)CC1]

Linker 19: N-(2-(2-Aminoethoxy)ethyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 82% yield. $^1$H NMR (500 MHz, $CD_3OD$) δ 8.65 (t, J=8.2 Hz, 1H), 8.16 (s, 2H), 7.98 (s, 1H), 7.92 (s, 1H), 7.46 (dd, J=11.3, 1.6 Hz, 1H), 7.41 (d, J=8.5 Hz, 1H), 4.13-3.89 (m, 6H), 3.76-3.68 (m, 2H), 3.63 (t, J=5.4 Hz, 2H), 3.56-3.44 (m, 6H), 3.18-3.12 (m, 2H), 2.18-2.09 (m, 1H), 1.09-1.02 (m, 2H), 1.01-0.96 (m, 2H).

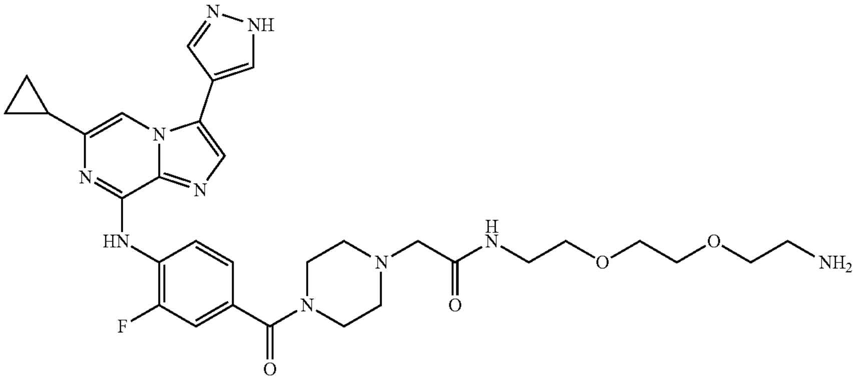 [SMILES: NCCOCCOCCNC(=O)CN1CCN(C(=O)c2ccc(Nc3nc(C4CC4)cn4c(-c5cn[nH]c5)cnc34)c(F)c2)CC1]

Linker 20: N-(2-(2-(2-Aminoethoxy)ethoxy)ethyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 85% yield. $^1$H NMR (500 MHz, $CD_3OD$) δ 8.75 (t, J=8.2 Hz, 1H), 8.12 (s, 2H), 7.91 (s, 1H), 7.76 (s, 1H), 7.43 (dd, J=11.3, 1.7 Hz, 1H), 7.39 (d, J=8.5 Hz, 1H), 4.04-3.86 (m, 6H), 3.77-3.71 (m, 2H), 3.69 (s, 4H), 3.62 (t, J=5.6 Hz, 2H), 3.49 (t, J=5.5 Hz, 2H), 3.40 (br, 4H), 3.20-3.11 (m, 2H), 2.16-2.04 (m, 1H), 1.06-1.01 (m, 2H), 1.00-0.91 (m, 2H).

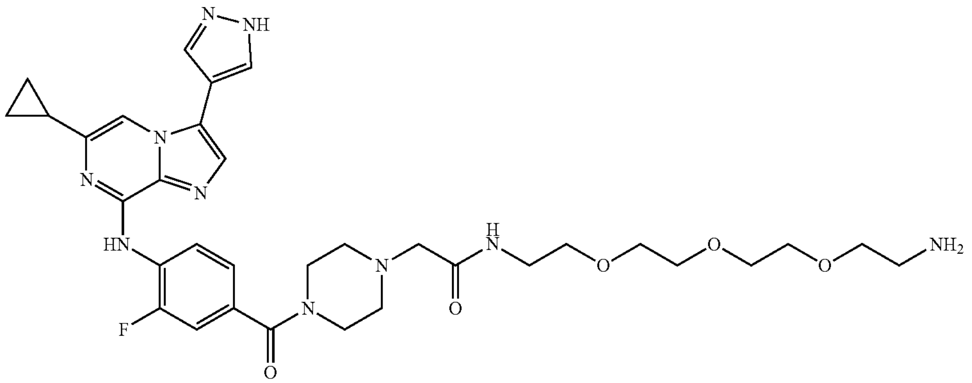 [SMILES: NCCOCCOCCOCCNC(=O)CN1CCN(C(=O)c2ccc(Nc3nc(C4CC4)cn4c(-c5cn[nH]c5)cnc34)c(F)c2)CC1]

Linker 21: N-(2-(2-(2-(2-Aminoethoxy)ethoxy)ethoxy)ethyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 84% yield. $^1$H NMR (500 MHz, $CD_3OD$) δ 8.66 (t, J=8.2 Hz, 1H), 8.16 (s, 2H), 7.99 (s, 1H), 7.93 (s, 1H), 7.46 (d, J=12.7 Hz, 1H), 7.42 (d, J=8.4 Hz, 1H), 4.09-3.95 (m, 6H), 3.78-3.64 (m, 12H), 3.64-3.58 (m, 2H), 3.52-3.45 (m, 4H), 3.19-3.12 (m, 2H), 2.15 (t, J=6.3 Hz, 1H), 1.13-0.93 (m, 4H).

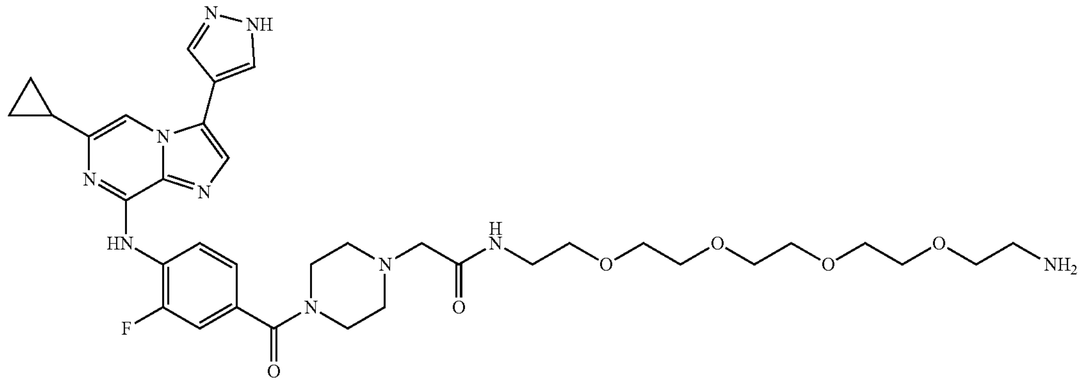 [SMILES: NCCOCCOCCOCCOCCNC(=O)CN1CCN(C(=O)c2ccc(Nc3nc(C4CC4)cn4c(-c5cn[nH]c5)cnc34)c(F)c2)CC1]

Linker 22: N-(14-Amino-3,6,9,12-tetraoxatetradecyl)-2-(4-(4-((6-cyclopropyl-3-(1H-pyrazol-4-yl)imidazo[1,2-a]pyrazin-8-yl)amino)-3-fluorobenzoyl)piperazin-t-yl)acetamide. 81% yield. H NMR (500 MHz, $CD_3OD$) δ 8.66 (t, J=8.2 Hz, 1H), 8.15 (s, 2H), 7.97 (s, 1H), 7.89 (s, 1H), 7.45 (dd, J=11.3, 1.7 Hz, 1H), 7.41 (d, J=8.4 Hz, 1H), 4.14-3.88 (m, 6H), 3.78-3.72 (m, 2H), 3.72-3.64 (m, 12H), 3.61 (t, J=5.4 Hz, 2H), 3.53-3.42 (m, 6H), 3.20-3.12 (m, 2H), 2.17-2.08 (m, 1H), 1.08-1.01 (m, 2H), 1.01-0.93 (m, 2H).

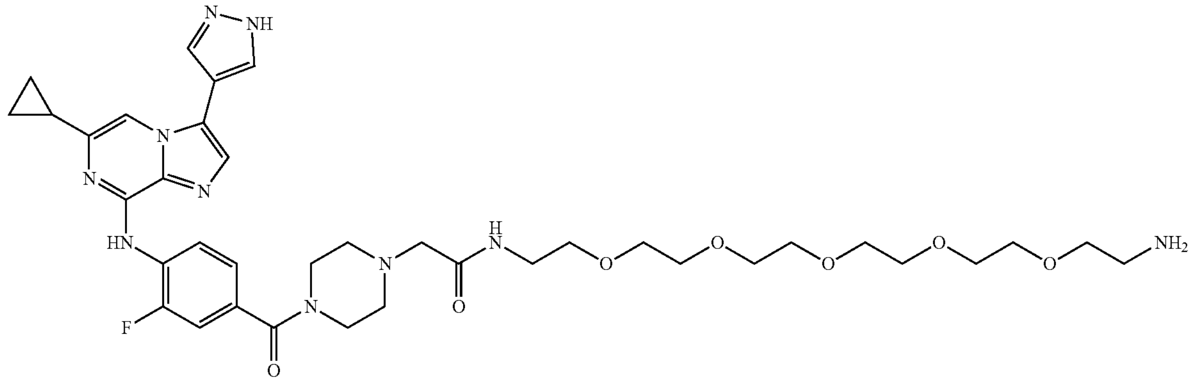 [SMILES: NCCOCCOCCOCCOCCOCCNC(=O)CN1CCN(C(=O)c2ccc(Nc3nc(C4CC4)cn4c(-c5cn[nH]c5)cnc34)c(F)c2)CC1]

Linker 23: N-(17-Amino-3,6,9,12,15-pentaoxaheptadecyl)-2-(4-(4-((6-cyclopropyl-3-(1H-pyrazol-4-yl)imidazo[1,2-a]pyrazin-8-yl)amino)-3-fluorobenzoyl)piperazin-1-yl)acetamide. 78% yield. $^1$H NMR (500 MHz, $CD_3OD$) δ 8.66 (t, J=8.2 Hz, 1H), 8.15 (s, 2H), 7.97 (s, 1H), 7.89 (s, 1H), 7.45 (dd, J=11.2, 1.7 Hz, 1H), 7.41 (d, J=8.5 Hz, 1H), 4.12-3.94 (m, 6H), 3.77-3.73 (m, 2H), 3.73-3.65 (m, 16H), 3.62-3.60 (m, 2H), 3.52-3.44 (m, 6H), 3.18-3.10 (m, 2H), 2.19-2.07 (m, 1H), 1.08-0.92 (m, 4H).

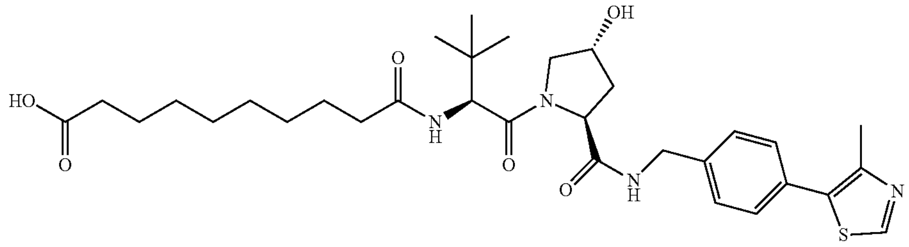 [SMILES: Cc1ncsc1-c1ccc(CNC(=O)[C@@H]2C[C@@H](O)CN2C(=O)[C@@H](NC(=O)CCCCCCCCC(=O)O)C(C)(C)C)cc1]

Linker 24: 10-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-10-oxodecanoic acid Linker 24 was synthesized in a reported method (Galdeano et al., 2014; Maniaci et al., 2017).

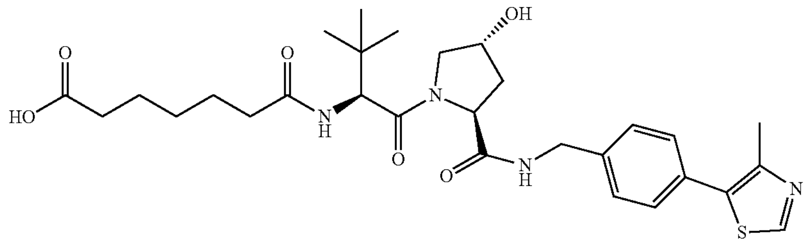 [SMILES: Cc1ncsc1-c1ccc(CNC(=O)[C@@H]2C[C@@H](O)CN2C(=O)[C@@H](NC(=O)CCCCCC(=O)O)C(C)(C)C)cc1]

Linker 25: 7-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid Linker 25 was synthesized in a reported method (Galdeano et al., 2014; Maniaci et al., 2017).

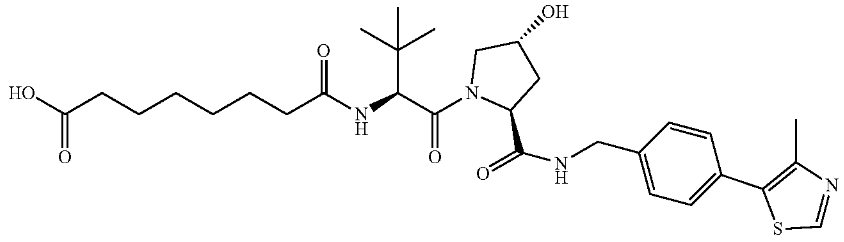 [SMILES: Cc1ncsc1-c1ccc(CNC(=O)[C@@H]2C[C@@H](O)CN2C(=O)[C@@H](NC(=O)CCCCCCC(=O)O)C(C)(C)C)cc1]

Linker 26: 8-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-8-oxooctanoic acid Linker 24 was synthesized in a reported method (Galdeano et al., 2014; Maniaci et al., 2017).

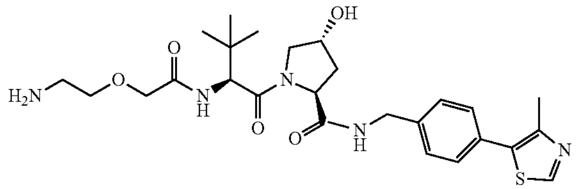

Linker 27: (2S,4R)-1-((S)-2-(2-(2-Aminoethoxy)acetamido)-3,3-dimethylbutanoyl)-4-hydroxy-N-(4-(4-methylthiazol-5-yl)benzyl)pyrrolidine-2-carboxamide Linker 26 was synthesized in a reported method (Galdeano et al., 2014; Maniaci et al., 2017).

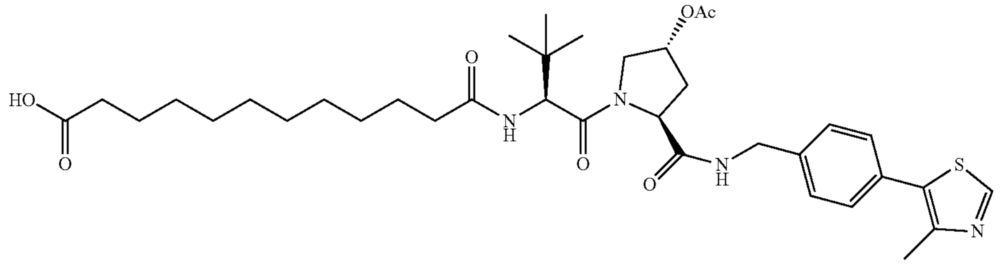 [SMILES: CC(=O)O[C@@H]1C[C@@H](C(=O)NCc2ccc(-c3scnc3C)cc2)N(C(=O)[C@@H](NC(=O)CCCCCCCCCCC(=O)O)C(C)(C)C)C1]

Linker 28: 12-(((S)-1-((2S,4R)-4-acetoxy-2-((4-(4-methylthiazol-5-yl)benzyl)carbamoyl)pyrrolidin-1-yl)-3,3-dimethyl-1-oxobutan-2-yl)amino)-12-oxododecanoic acid Linker 28 was synthesized in the same procedure as linker 6.

Scheme 18. Synthesis of linker 29

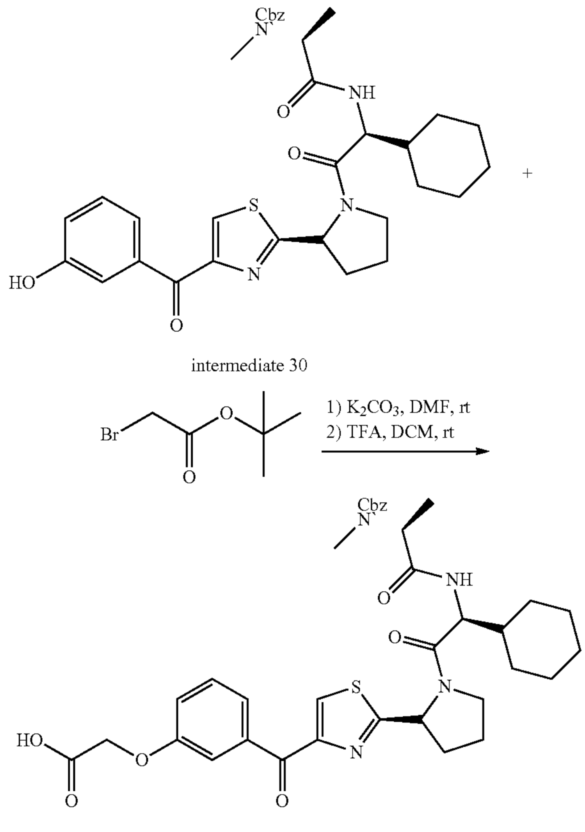

intermediate 30

Linker 29

Linker 29: 2-(3-(2-((R)-1-((S)-2-((S)-2-(((Benzyloxy)carbonyl)(methyl)amino)propanamido)-2-cyclohexylacetyl)pyrrolidin-2-yl)thiazole-4-carbonyl)phenoxy)acetic acid. The title compound can be synthesized according to the following procedures: To a solution of intermediate 30 (1 equive.) in DMF, will be added $K_2CO_3$ (1.5 equiv.), followed by tert-butyl 2-bromoacetate (1.5 equiv.). After being stirred at rt for 12 h, the mixture will be filtered. And the filtrate will be collected and concentrated. The resulting residue will be purified by HPLC. The purified compound will be dissolved in DCM and TFA (1:1). After being stirred at 1 h for 1 h, the solvent will be removed to yield the title compound.

Scheme 19. Synthesis of linker 30

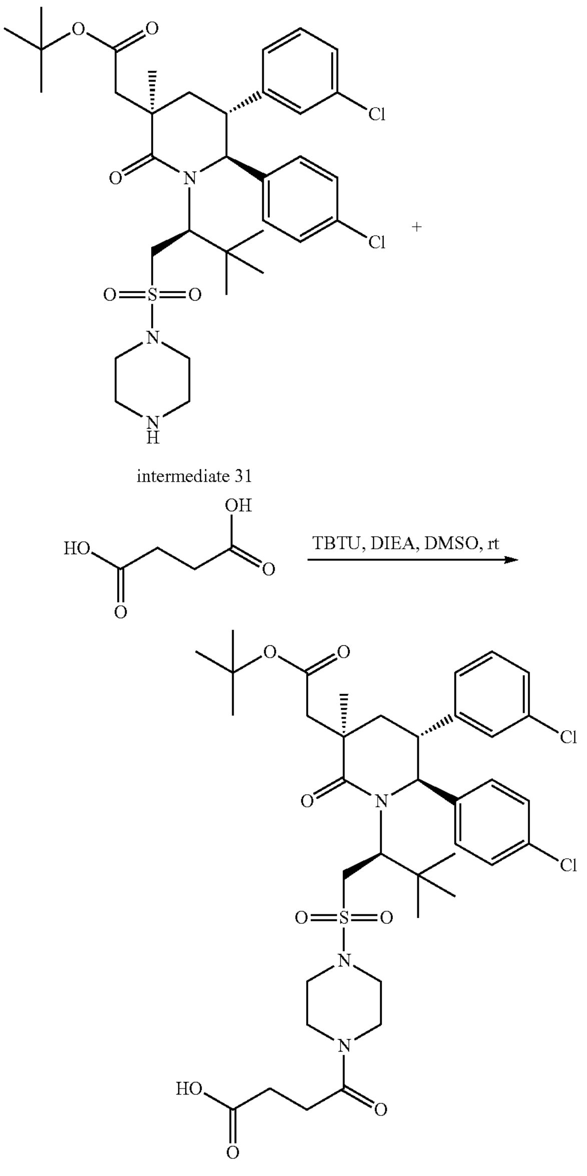

intermediate 31 linker 30

Linker 30: 4-(4-(((S)-2-((3R,5R,6S)-3-(2-(tert-Butoxy)-2-oxoethyl)-5-(3-chlorophenyl)-6-(4-chlorophenyl)-3-methyl-2-oxopiperidin-1-yl)-3,3-dimethylbutyl)sulfonyl) piperazin-1-yl)-4-oxobutanoic acid. The title compound can be synthesized according to the following procedures: To a solution of intermediate 31 (1 equiv.) in DMSO, will be added succinic acid (5 equiv.), followed by TBTU (1.1 equiv.) and DIEA (1.5 equiv.). After being stirred at rt for 1 h, the mixture will be concentrated. The resulting residue will be purified by HPLC to yield the title compound.

Scheme 20. Synthesis of linker 31

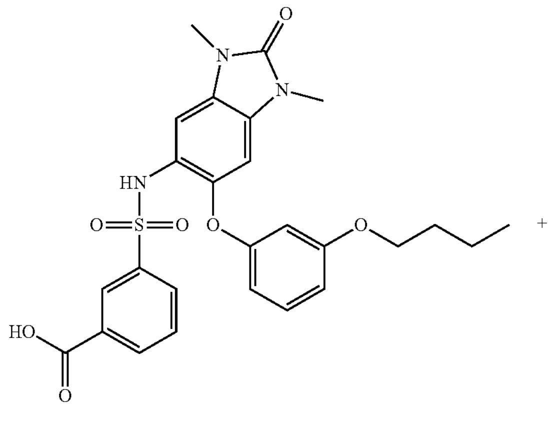

intermediate 32

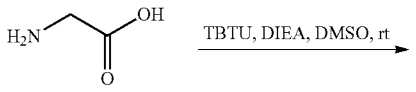

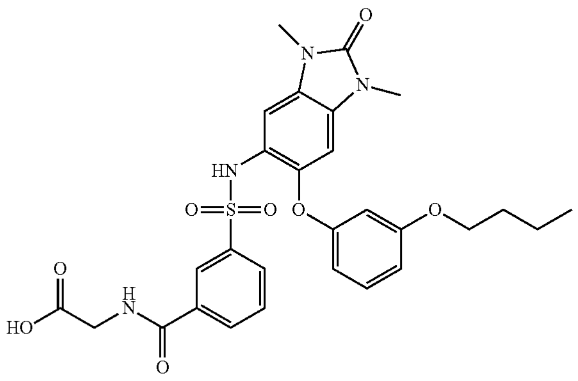

linker 31

Linker 31: (3-(N-(6-(3-Butoxyphenoxy)-1,3-dimethyl-2-oxo-2,3-dihydro-1H-benzo[d]imidazol-5-yl)sulfamoyl)benzoyl)glycine. The title compound can be synthesized according to the following procedures: To a solution of intermediate 32 (1 equiv.) in DMSO will be added glycine (1.1 equiv.), followed by TBTU (1.1 equiv.) and DIEA (1.5 equiv.). After being stirred at rt for 1 h, the mixture will be concentrated. The resulted residue will be purified by HPLC to yield the title compound.

Scheme 21. Synthesis of linker 32

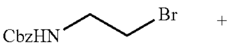

Intermediate 33

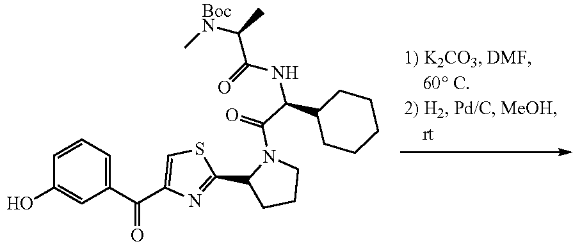

Intermediate 34

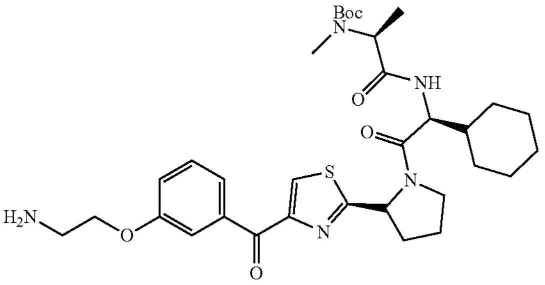

linker 32

Linker 32: tert-Butyl ((S)-1-(((S)-2-((R)-2-(4-(3-(2-aminoethoxy)benzoyl)thiazol-2-yl)pyrrolidin-1-yl)-1-cyclohexyl-2-oxoethyl)amino)-1-oxopropan-2-yl)(methyl)carbamate. The title compound can be synthesized according to the following procedures: To a mixture of intermediate 33 (1.2 equiv.) and intermediate 34 (1 equiv.) in DMF, will be added $K_2CO_3$ (1.5 equiv.). After being heated at 60° C. for 12 h, the mixture will be filtered. The filtrate will be collected and concentrated. The resulting residue will be purified by HPLC. The purified compound will be dissolved in MeOH, followed by Pd/C (0.1 equiv.). After being stirred at rt for 2 h under $H_2$ atmosphere, the mixture will be filtered. The filtrate will be collected and concentrated to yield the title compound.

Scheme 22. Synthesis of linker 33

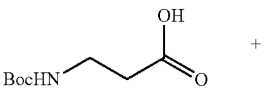

intermediate 35

-continued

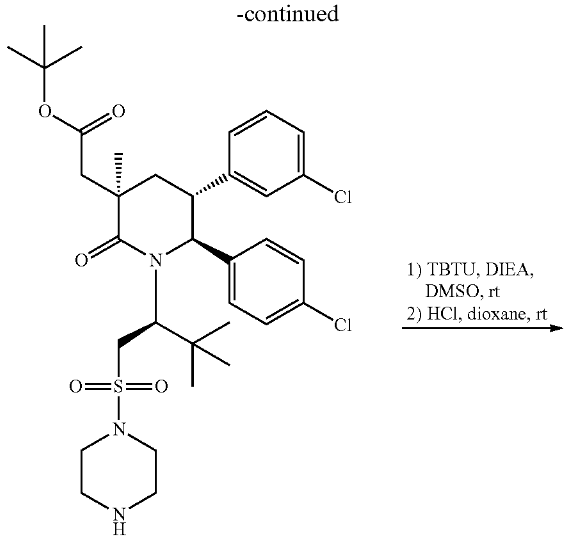

intermediate 36

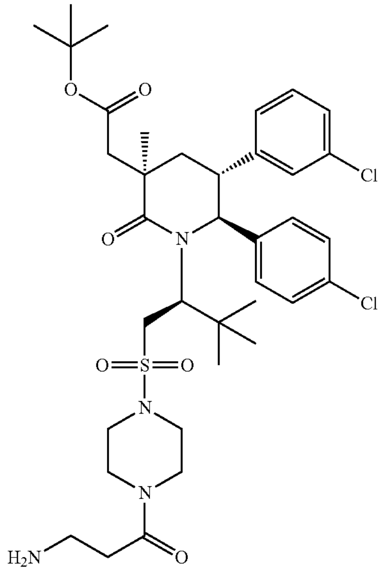

linker 33

Linker 33: tert-Butyl 2-((3R,5R,6S)-1-((S)-1-((4-(3-aminopropanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetate. The title compound can be synthesized according to the following procedures: To a mixture of intermediate 35 (1 equiv.) and intermediate 36 (1.1 equiv.) in DMSO, will be added TBTU (1.1 equiv.) and DIEA (1.5 equiv.). After being stirred at rt for 1 h, the solution will be concentrated. The resulting residue will be diluted with HCl in dioxane (4 N). The resulting mixture will be stirred at rt for 2 h, before being concentrated. The resulting residue will be purified by HPLC to yield the title compound.

Scheme 23. Synthesis of linker 34

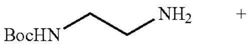

Intermediate 37

-continued

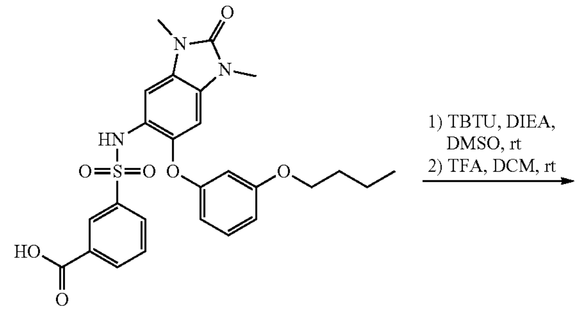

intermediate 38

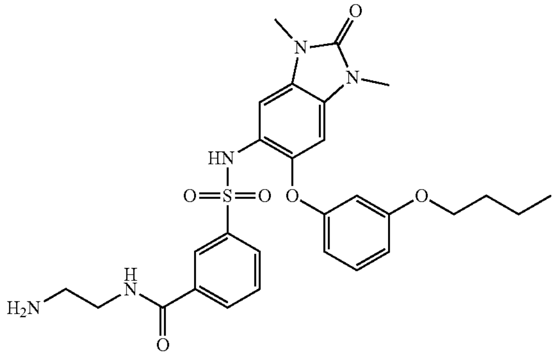

linker 34

Linker 34: N-(2-Aminoethyl)-3-(N-(6-(3-butoxyphenoxy)-1,3-dimethyl-2-oxo-2,3-dihydro-1H-benzo[d]imidazol-5-yl)sulfamoyl)benzamide. Linker 34 will be synthesized according to the procedures for the synthesis of linker 33.

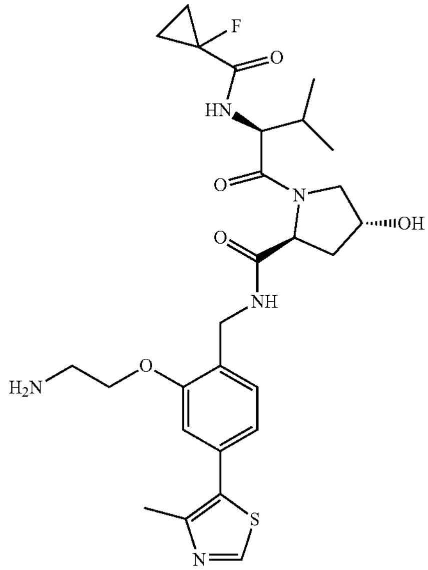 [SMILES: Cc1ncsc1-c1ccc(CNC(=O)[C@@H]2C[C@@H](O)CN2C(=O)[C@@H](NC(=O)C2(F)CC2)C(C)C)c(OCCN)c1]

Linker 35: (2S,4R)—N-(2-(2-Aminoethoxy)-4-(4-methylthiazol-5-yl)benzyl)-1-((1-fluorocyclopropane-1-carbonyl)-L-valyl)-4-hydroxypyrrolidine-2-carboxamide. Linker 35 will be synthesized using a known method (Farnaby et al., 2019).

Procedures for the Synthesis of Examples

Scheme 24. Synthesis of Example 1

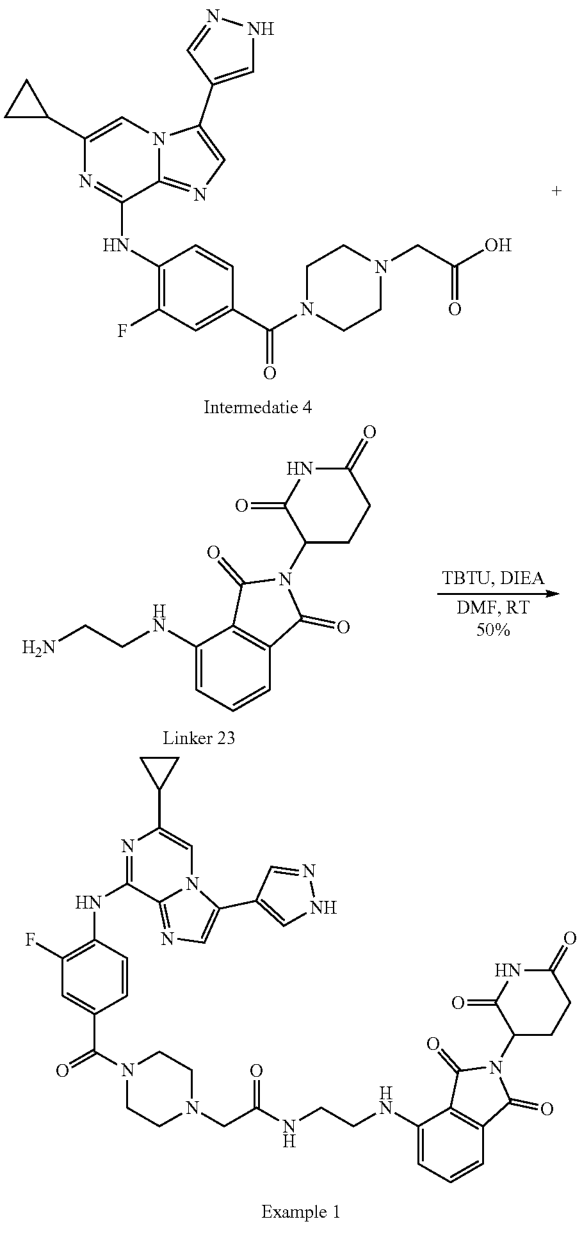

Example 1: 2-(4-(4-((6-Cyclopropyl-3-(1H-pyrazol-4-yl) imidazo[1,2-a]pyrazin-8-yl)amino)-3-fluorobenzoyl)piperazin-1-yl)-N-(2-((2-(2,6-dioxopiperidin-3-yl)-1,3-dioxoisoindolin-4-yl)amino)ethyl)acetamide. To a solution of intermediate 4 (7 mg, 0.011 mmol) and linker 6 (5 mg, 0.012 mmol) in DMF (0.5 mL) were added DIEA (17 μL, 0.1 mmol) and TBTU (6 mg, 0.02 mmol). After being stirred at rt for 12 h, the mixture was purified by HPLC to yield the title compound (6 mg, 50% yield) as brown oil. $^1$H NMR (600 MHz, $CD_3OD$) δ 8.82 (t, J=8.2 Hz, 1H), 8.13 (s, 2H), 7.93 (s, 1H), 7.75 (s, 1H), 7.64-7.55 (m, 1H), 7.40 (dd, J=26.8, 9.8 Hz, 2H), 7.17 (d, J=8.6 Hz, 1H), 7.09 (d, J=7.0 Hz, 1H), 5.04 (dd, J=12.8, 5.3 Hz, 1H), 4.14-3.71 (m, 6H), 3.66-3.46 (m, 4H), 3.27-3.12 (m, 2H), 2.84 (dd, J=25.0, 11.5 Hz, 1H), 2.81-2.63 (m, 2H), 2.18-2.01 (m, 2H), 1.11-1.02 (m, 2H), 1.01-0.90 (m, 2H). HRMS(ESI-TOF) m/z: $[M+H]^+$ calcd for $C_{40}H_{40}FN_{12}O_6^+$, 803.3172; found 803.3190.

Example compounds 2-22, 37-45, 63, 64, 102-107, and 130-134 were synthesized according to the procedure for the preparation of example compound 1.

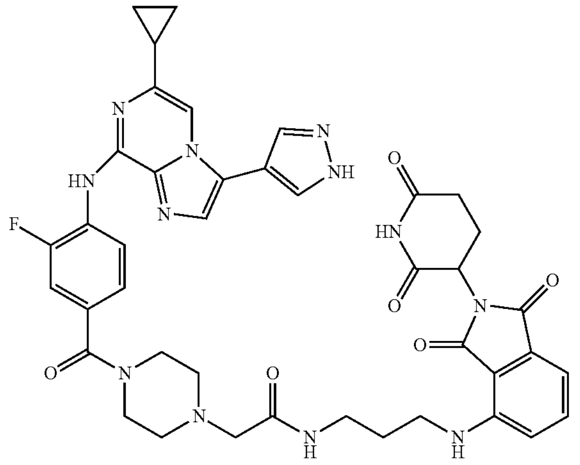 [SMILES: O=C(CN1CCN(C(=O)c2ccc(Nc3nc(C4CC4)cn4c(-c5cn[nH]c5)cnc34)c(F)c2)CC1)NCCCNc1cccc2c1C(=O)N(C1CCC(=O)NC1=O)C2=O]

Example 2: 2-(4-(4-((6-Cyclopropyl-3-(1H-pyrazol-4-yl) imidazo[1,2-a]pyrazin-8-yl)amino)-3-fluorobenzoyl)piperazin-1-yl)-N-(3-((2-(2,6-dioxopiperidin-3-yl)-1,3-dioxoisoindolin-4-yl)amino)propyl)acetamide. 55% yield. $^1$H NMR (600 MHz, $CD_3OD$) δ 8.77 (t, J=8.1 Hz, 1H), 8.11 (s, 2H), 7.92 (s, 1H), 7.80 (s, 1H), 7.56 (t, J=7.7 Hz, 1H), 7.40 (dd, J=27.8, 9.8 Hz, 2H), 7.06 (t, J=8.7 Hz, 2H), 5.08 (dd, J=12.7, 5.2 Hz, 1H), 3.96 (br, 6H), 3.53-3.36 (m, 6H), 2.91-2.53 (m, 3H), 2.22-2.00 (m, 2H), 2.00-1.82 (m, 2H), 1.12-1.01 (m, 2H), 1.00-0.92 (m, 2H). HRMS (ESI-TOF) m/z: $[M+H]^+$ calcd for $C_{41}H_{42}FN_{12}O_6^+$, 817.3329; found 817.3310.

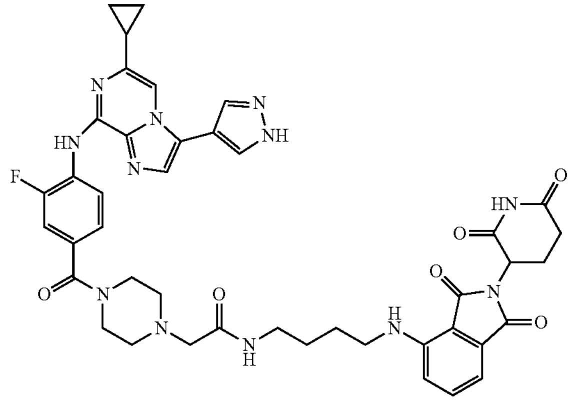 [SMILES: O=C(CN1CCN(C(=O)c2ccc(Nc3nc(C4CC4)cn4c(-c5cn[nH]c5)cnc34)c(F)c2)CC1)NCCCCNc1cccc2c1C(=O)N(C1CCC(=O)NC1=O)C2=O]

Example 3: 2-(4-(4-((6-Cyclopropyl-3-(1H-pyrazol-4-yl) imidazo[1,2-a]pyrazin-8-yl)amino)-3-fluorobenzoyl)piperazin-1-yl)-N-(4-((2-(2,6-dioxopiperidin-3-yl)-1,3-dioxoisoindolin-4-yl)amino)butyl)acetamide. 48% yield. $^1$H NMR (600 MHz, $CD_3OD$) δ 8.80 (t, J=8.2 Hz, 1H), 8.14 (s, 2H), 7.94 (s, 1H), 7.78 (s, 1H), 7.57 (dd, J=13.9, 6.5 Hz, 1H), 7.44 (d, J=11.1 Hz, 1H), 7.40 (d, J=8.5 Hz, 1H), 7.11-7.02 (m, 2H), 5.07 (dd, J=12.8, 5.4 Hz, 1H), 3.95 (br, 6H), 3.45-3.34 (m, 6H), 2.92-2.82 (m, 2H), 2.80-2.66 (m, 2H), 2.17-2.05 (m, 3H), 1.78-1.61 (m, 4H), 1.08-1.02 (m, 2H), 0.99-0.91

(m, 2H). HRMS (ESI-TOF) m/z: $[M+H]^+$ calcd for $C_{42}H_{44}FNO_6^+$, 831.3485; found 831.3502.

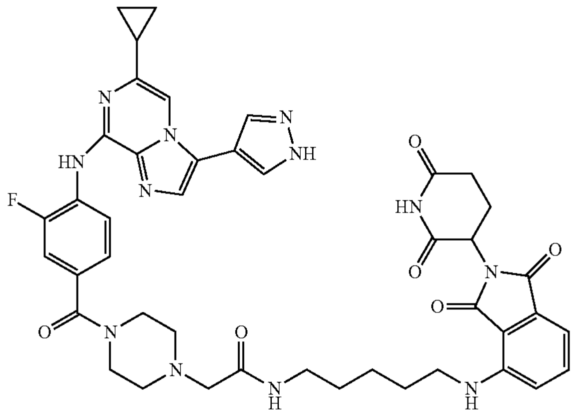 [SMILES: O=C(CN1CCN(C(=O)c2ccc(Nc3nc(C4CC4)cn4c(-c5cn[nH]c5)cnc34)c(F)c2)CC1)NCCCCCNc1cccc2c1C(=O)N(C1CCC(=O)NC1=O)C2=O]

Example 4: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(5-((2-(2,6-dioxopiperidin-3-yl)-1,3-dioxoisoindolin-4-yl)amino)pentyl)acetamide. 60% yield. $^1H$ NMR (600 MHz, $CD_3OD$) δ 8.82 (t, J=8.2 Hz, 1H), 8.13 (s, 2H), 7.93 (s, 1H), 7.74 (s, 1H), 7.59-7.53 (m, 1H), 7.44 (d, J=12.5 Hz, 1H), 7.40 (d, J=8.5 Hz, 1H), 7.10-7.03 (m, 2H), 5.09 (dd, J=12.6, 5.5 Hz, 2H), 3.80 (br, 6H), 3.43-3.35 (m, 4H), 2.94-2.81 (m, 2H), 2.81-2.65 (m, 3H), 2.18-2.04 (m, 2H), 1.79-1.67 (m, 2H), 1.68-1.56 (m, 2H), 1.56-1.43 (m, 2H), 1.05 (dd, J=7.4, 3.0 Hz, 2H), 0.97-0.90 (m, 2H). HRMS (ESI-TOF) m/z: $[M+H]^+$ calcd for $C_{43}H_{46}FN_{12}O_6^+$, 845.3642; found 845.3620.

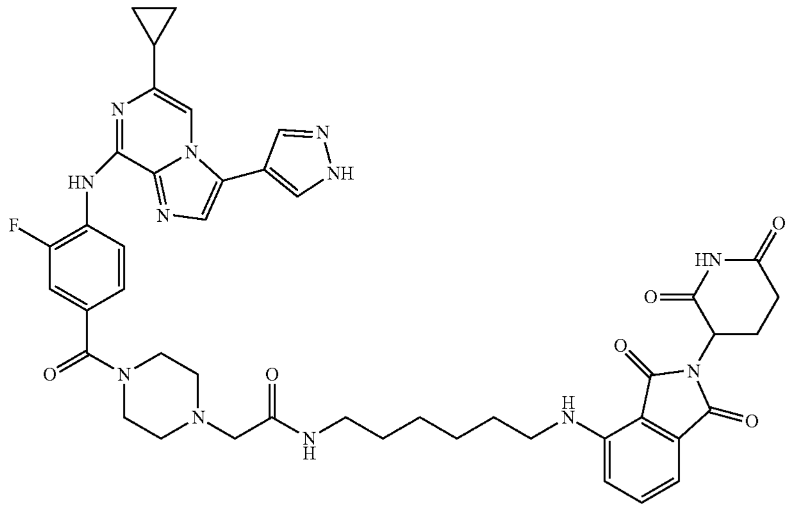 [SMILES: O=C(CN1CCN(C(=O)c2ccc(Nc3nc(C4CC4)cn4c(-c5cn[nH]c5)cnc34)c(F)c2)CC1)NCCCCCCNc1cccc2c1C(=O)N(C1CCC(=O)NC1=O)C2=O]

Example 5: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(6-((2-(2,6-dioxopiperidin-3-yl)-1,3-dioxoisoindolin-4-yl)amino)hexyl)acetamide. 50% yield. $^1H$ NMR (600 MHz, $CD_3OD$ δ 8.76 (t, J=8.1 Hz, 1H), 8.08 (s, 2H), 7.89 (s, 1H), 7.80 (s, 1H), 7.56-7.51 (m, 1H), 7.44-7.33 (m, 2H), 7.08-6.96 (m, 2H), 5.04 (dd, J=12.5, 4.9 Hz, 2H), 4.09-3.77 (m, 6H), 3.41 (br, 4H), 3.30-3.22 (m, 2H), 2.93-2.70 (m, 5H), 2.16-2.05 (m, 2H), 1.76-1.67 (m, 2H), 1.63-1.54 (m, 2H), 1.53-1.38 (m, 4H), 1.08-1.00 (m, 2H), 1.00-0.91 (m, 2H). HRMS (ESI-TOF) m/z: $[M+H]^+$ calcd for $C_{44}H_{48}FN_{12}O_6^+$, 859.3798; found 859.3810.

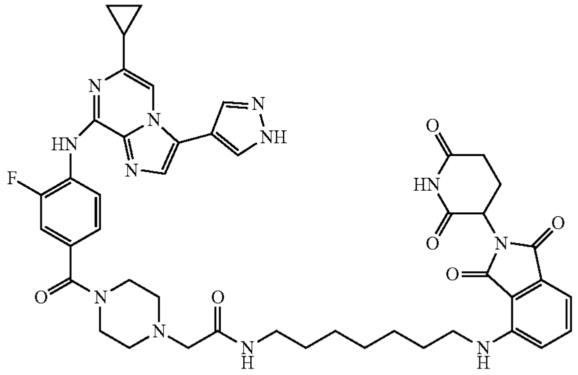 [SMILES: O=C(CN1CCN(C(=O)c2ccc(Nc3nc(C4CC4)cn4c(-c5cn[nH]c5)cnc34)c(F)c2)CC1)NCCCCCCCNc1cccc2c1C(=O)N(C1CCC(=O)NC1=O)C2=O]

Example 6: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(7-((2-(2,6-dioxopiperidin-3-yl)-1,3-dioxoisoindolin-4-yl)amino)heptyl)acetamide. 49% yield. $^1H$ NMR (600 MHz, $CD_3OD$) δ 8.81 (t, J=8.2 Hz, 1H), 8.09 (s, 2H), 7.88 (s, 1H), 7.72 (s, 1H), 7.56-7.50 (m, 1H), 7.44-7.34 (m, 2H), 7.08-6.96 (m, 2H), 5.10-4.96 (m, 1H), 4.13-3.68 (m, 6H), 3.41 (br, 4H), 3.30-3.22 (m, 2H), 2.92-2.81 (m, 2H), 2.81-2.67 (m, 3H), 2.17-2.04 (m, 2H), 1.75-1.64 (m, 2H), 1.61-1.50 (m, 2H), 1.50-1.34 (m, 6H), 1.07-0.99 (m, 2H), 0.99-0.91 (m, 2H). HRMS (ESI-TOF) m/z: $[M+H]^+$ calcd for $C_{45}H_{50}FN_{12}O_6^+$, 873.3955; found 873.3543.

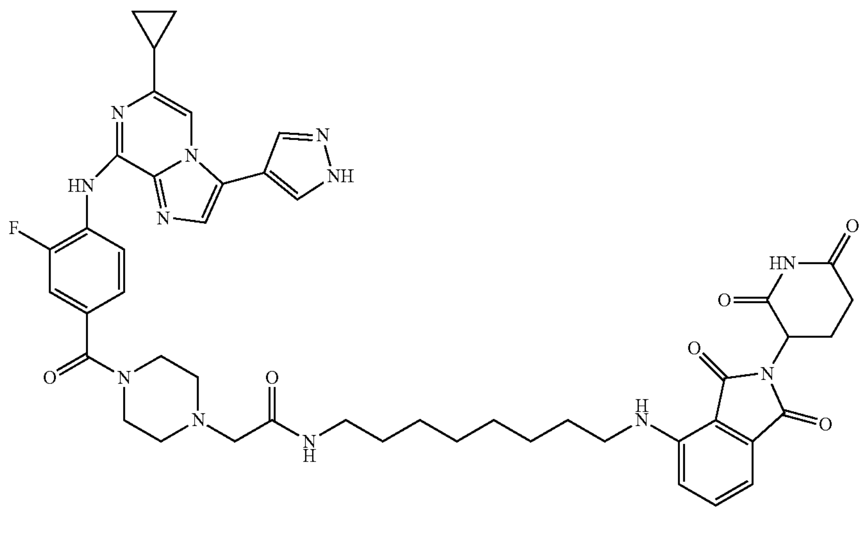 [SMILES: O=C(CN1CCN(C(=O)c2ccc(Nc3nc(C4CC4)cn4c(-c5cn[nH]c5)cnc34)c(F)c2)CC1)NCCCCCCCCNc1cccc2c1C(=O)N(C1CCC(=O)NC1=O)C2=O]

Example 7: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(8-((2-(2,6-dioxopiperidin-3-yl)-1,3-dioxoisoindolin-4-yl)amino)octyl)acetamide. 51% yield. $^1$H NMR (600 MHz, $CD_3OD$) δ 8.79 (t, J=8.2 Hz, 1H), 8.14 (s, 2H), 7.93 (s, 1H), 7.78 (s, 1H), 7.55-7.48 (m, 1H), 7.48-7.33 (m, 2H), 7.09-6.97 (m, 2H), 5.13-5.01 (m, 1H), 4.07-3.77 (m, 6H), 3.42 (br, 4H), 3.30-3.18 (m, 2H), 2.94-2.82 (m, 2H), 2.82-2.64 (m, 3H), 2.17-2.03 (m, 2H), 1.74-1.61 (m, 2H), 1.62-1.50 (m, 2H), 1.50-1.27 (m, 8H), 1.09-1.00 (m, 2H), 0.97-0.91 (m, 2H). HRMS (ESI-TOF) m/z: $[M+H]^+$ calcd for $C_{46}H_{52}FN_{12}O_6^+$, 887.4111; found 887.4119.

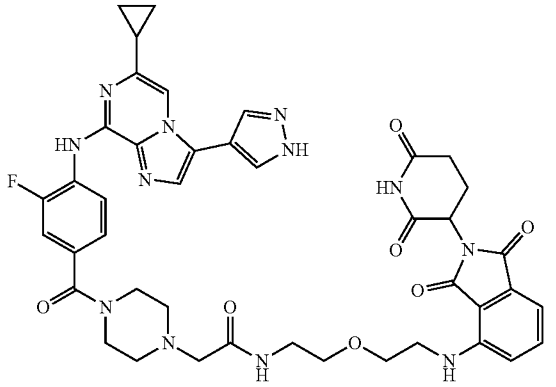 [SMILES: O=C(CN1CCN(C(=O)c2ccc(Nc3nc(C4CC4)cn4c(-c5cn[nH]c5)cnc34)c(F)c2)CC1)NCCOCCNc1cccc2c1C(=O)N(C1CCC(=O)NC1=O)C2=O]

Example 8: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(2-(2-((2-(2,6-dioxopiperidin-3-yl)-1,3-dioxoisoindolin-4-yl)amino)ethoxy)ethyl)acetamide. 65% yield. $^1$H NMR (600 MHz, $CD_3OD$) δ 8.80 (t, J=8.3 Hz, 11H), 8.10 (s, 2H), 7.90 (s, 1H), 7.74 (s, 11H), 7.55 (d, J=7.4 Hz, 11H), 7.37 (dd, J=23.0, 9.9 Hz, 2H), 7.11-7.00 (m, 2H), 5.09 (dd, J=12.8, 5.5 Hz, 1H), 4.03-3.80 (m, 6H), 3.80-3.70 (m, 2H), 3.70-3.58 (m, 2H), 3.58-3.41 (m, 6H), 2.93-2.83 (m, 1H), 2.82-2.68 (m, 3H), 2.56-2.35 (m, 1H), 2.19-2.13 (m, 1H), 2.11-2.05 (m, 1H), 1.10-1.00 (m, 2H), 0.97-0.89 (m, 2H). HRMS ESI-TOF m/z: M+H calcd for $C_{42}H_{44}FN_{12}O_7^+$, 847.3434; found 847.3455.

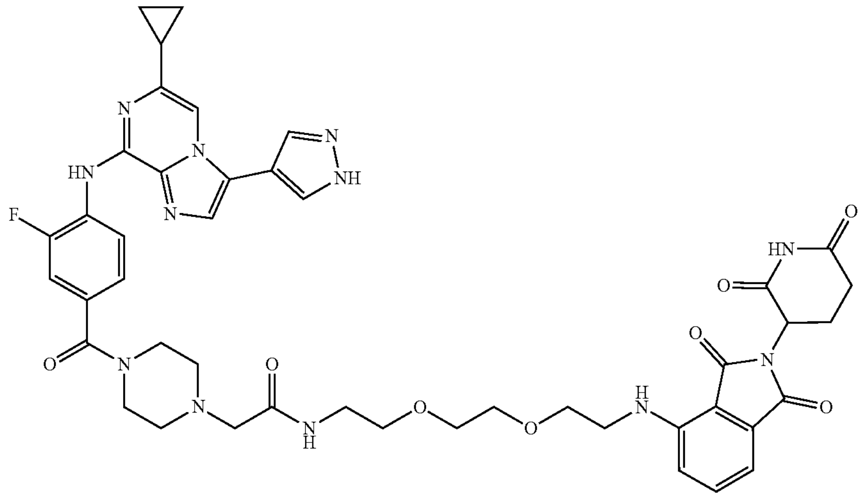 [SMILES: O=C(CN1CCN(C(=O)c2ccc(Nc3nc(C4CC4)cn4c(-c5cn[nH]c5)cnc34)c(F)c2)CC1)NCCOCCOCCNc1cccc2c1C(=O)N(C1CCC(=O)NC1=O)C2=O]

Example 9: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(2-(2-(2-((2-(2,6-dioxopiperidin-3-yl)-1,3-dioxoisoindolin-4-yl)amino)ethoxy)ethoxy)ethyl)acetamide. 62% yield. $^1$H NMR (600 MHz, $CD_3OD$) δ 8.80 (t, J=8.1 Hz, 1H), 7.97 (s, 2H), 7.73 (s, 1H), 7.61 (s, 1H), 7.50 (dd, J=8.4, 7.2 Hz, 1H), 7.29 (t, J=10.1 Hz, 2H), 7.06-7.02 (m, 1H), 6.98 (d, J=8.5 Hz, 1H), 4.98 (dd, J=12.4, 5.4 Hz, 1H), 3.86-3.70 (m, 6H), 3.67 (d, J=4.6 Hz, 4H), 3.61 (t, J=5.2 Hz, 2H), 3.52-3.39 (m, 6H), 3.07-2.86 (m, 4H), 2.87-2.68 (m, 3H), 2.19-2.09 (m, 1H), 2.05-1.97 (m, 1H), 1.07-1.00 (m, 2H), 0.99-0.90 (m, 2H). HRMS (ESI-TOF) m/z: $[M+H]^+$ calcd for $C_{44}H_{48}FN_{12}O_8^+$, 891.3697; found 891.3682.

Example 10: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(2-(2-(2-(2-((2-(2,6-dioxopiperidin-3-yl)-1,3-dioxoisoindolin-4-yl)amino)ethoxy)ethoxy)ethoxy)ethyl)acetamide. 59% yield. $^1$H NMR (600 MHz, $CD_3OD$) δ 8.82 (t, J=8.2 Hz, 1H), 7.98 (s, 2H), 7.75 (s, 1H), 7.60 (s, 1H), 7.56-7.47 (m, 1H), 7.31 (t, J=9.5 Hz, 2H), 7.09-6.90 (m, 2H), 5.02-4.96 (m, 1H), 3.86-3.70 (m, 6H), 3.67-3.61 (m, 8H), 3.50-3.30 (m, 8H), 3.09-2.89 (m, 4H), 2.87-2.68 (m, 3H), 2.16-2.05 (m, 11H), 2.04-1.97 ((m, 1H), 1.07-0.98 (m, 2H), 0.96-0.91 (m, 2H). HRMS (ESI-TOF) m/z: $[M+H]^+$ calcd for $C_{46}H_{52}FN_{12}O_9^+$, 835.3959; found 935.3966.

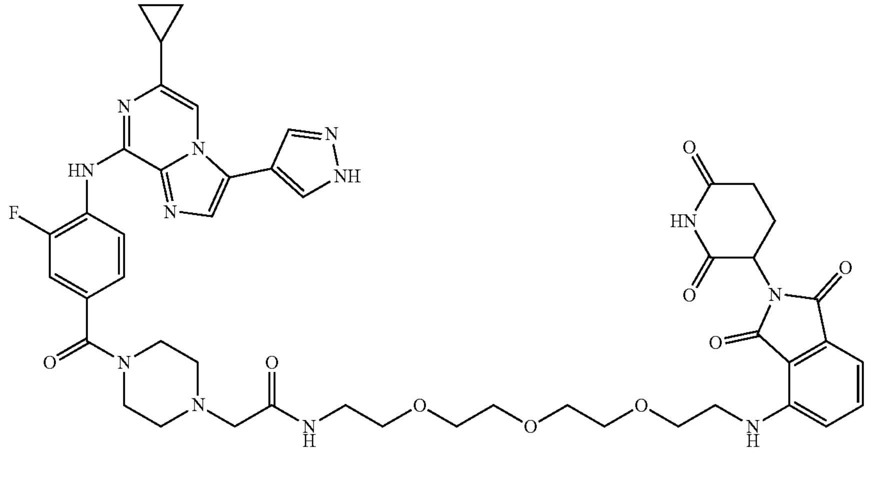 [SMILES: O=C(CN1CCN(C(=O)c2ccc(Nc3nc(C4CC4)cn4c(-c5cn[nH]c5)cnc34)c(F)c2)CC1)NCCOCCOCCOCCNc1cccc2c1C(=O)N(C1CCC(=O)NC1=O)C2=O]

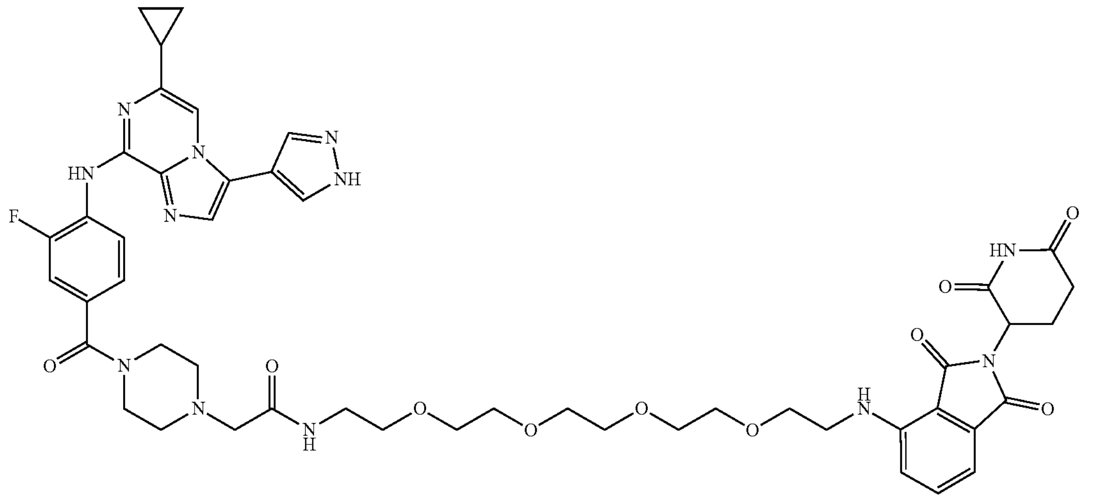 [SMILES: O=C(CN1CCN(C(=O)c2ccc(Nc3nc(C4CC4)cn4c(-c5cn[nH]c5)cnc34)c(F)c2)CC1)NCCOCCOCCOCCOCCNc1cccc2c1C(=O)N(C1CCC(=O)NC1=O)C2=O]

Example 11: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(17-((2-(2,6-dioxopiperidin-3-yl)-1,3-dioxoisoindolin-4-yl)amino)-3,6,9,12,15-pentaoxaheptadecyl)acetamide. 51% yield. $^1$H NMR (600 MHz, $CD_3OD$) δ 8.80 (t, J=8.2 Hz, 1H), 8.03 (s, 2H), 7.82 (s, 1H), 7.69 (s, 1H), 7.54-7.46 (m, 1H), 7.41-7.30 (m, 2H), 7.06-6.97 (m, 2H), 5.02 (dd, J=12.6, 5.4 Hz, 1H), 4.04-3.79 (m, 6H), 3.72 (dd, J=14.2, 9.0 Hz, 2H), 3.71-3.60 (m, 14H), 3.58 (t, J=5.2 Hz, 2H), 3.46 (ddd, J=15.6, 12.3, 7.9 Hz, 4H), 3.33 (br, 2H), 2.88-2.67 (m, 3H), 2.19-2.08 (m, 1H), 2.08-1.98 (m, 1H), 1.09-1.00 (m, 2H), 1.00-0.90 (m, 2H). HRMS (ESI-TOF) m/z: $[M+H]^+$ calcd for $C_{48}H_{56}FN_{12}O_{10}{}^+$, 979.4221; found 979.4241.

Example 12: 2-(4-(4-((6-Cyclopropyl-3-(1H-pyrazol-4-yl)imidazo[1,2-a]pyrazin-8-yl)amino)-3-fluorobenzoyl)piperazin-1-yl)-N-(17-((2-(2,6-dioxopiperidin-3-yl)-1,3-dioxoisoindolin-4-yl)amino)-3,6,9,12,15-pentaoxaheptadecyl)acetamide. 56% yield. $^1$H NMR (600 MHz, $CD_3OD$ δ 8.81 (t, J=8.2 Hz, 1H), 8.01 (s, 2H), 7.80 (s, 1H), 7.66 (s, 1H), 7.53-7.47 (m, 1H), 7.40-7.28 (m, 2H), 7.02 (dd, J=22.3, 7.8 Hz, 2H), 5.06-4.95 (m, 1H), 3.92 (br, 4H), 3.83-3.53 (m, 22H), 3.52-3.36 (m, 4H), 3.26 (br, 4H), 2.89-2.66 (m, 3H), 2.18-2.06 (m, 1H), 2.08-1.96 (m, 1H), 1.09-0.98 (m, 2H), 0.99-0.88 (m, 2H). HRMS (ESI-TOF) m/z: $[M+H]^+$ calcd for $C_{50}H_{60}FN_{12}O_{11}{}^+$, 1023.4483; found 1023.4509

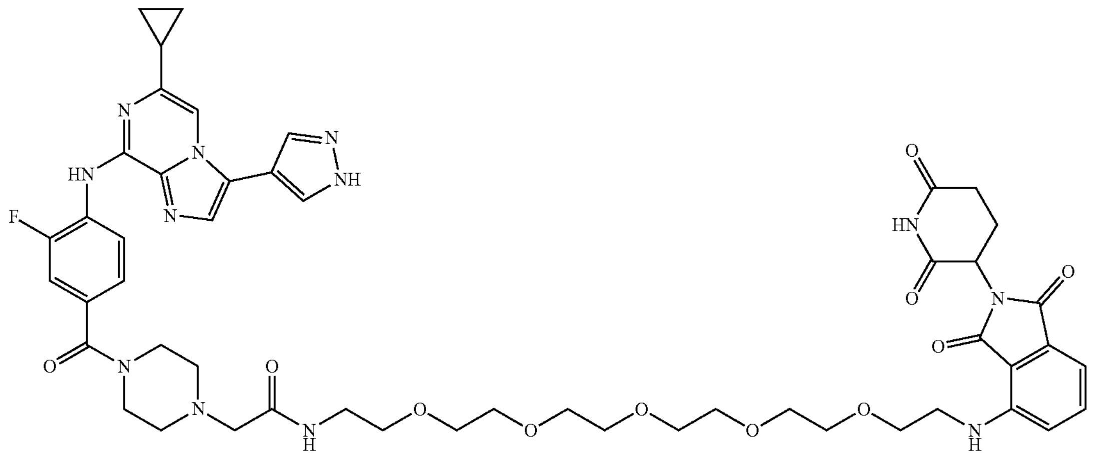 [SMILES: O=C(CN1CCN(C(=O)c2ccc(Nc3nc(C4CC4)cn4c(-c5cn[nH]c5)cnc34)c(F)c2)CC1)NCCOCCOCCOCCOCCOCCNc1cccc2c1C(=O)N(C1CCC(=O)NC1=O)C2=O]

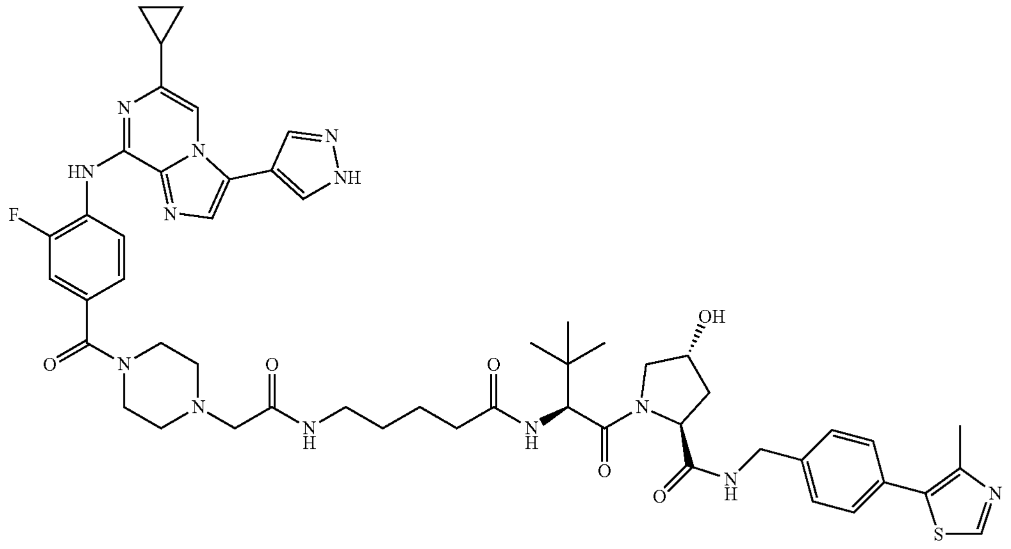 [SMILES: Cc1ncsc1-c1ccc(CNC(=O)[C@@H]2C[C@@H](O)CN2C(=O)[C@@H](NC(=O)CCCCNC(=O)CN2CCN(C(=O)c3ccc(Nc4nc(C5CC5)cn5c(-c6cn[nH]c6)cnc45)c(F)c3)CC2)C(C)(C)C)cc1]

Example 13: (2S,4R)-1-((S)-2-(5-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)pentanamido)-3,3-dimethylbutanoyl)-4-hydroxy-N-(4-(4-methylthiazol-5-yl)benzyl)pyrrolidine-2-carboxamide. 60% yield. $^{1}H$ NMR (600 MHz, $CD_3OD$) δ 8.94 (s, 1H), 8.74 (t, J=8.0 Hz, 1H), 8.15 (s, 2H), 7.97 (s, 1H), 7.85 (s, 1H), 7.52-7.35 (m, 6H), 4.65 (s, 1H), 4.61-4.32 (m, 4H), 4.12-3.87 (m, 7H), 3.82 (dd, J=10.9, 3.7 Hz, 1H), 3.48 (br, 4H), 3.31-3.21 (m, 2H), 2.48 (s, 3H), 2.40-2.18 (m, 3H), 2.16-2.03 (m, 2H), 1.74-1.49 (m, 4H), 1.08-1.00 (m, 11H), 1.01-0.92 (m, 2H). HRMS (ESI-TOF) m/z: $[M+H]^+$ calcd for $C_{52}H_{63}FN_{13}O_6S^+$, 1016.4724; found 1016.4701.

Example 14: (2S,4R)-1-((S)-2-(6-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)hexanamido)-3,3-dimethylbutanoyl)-4-hydroxy-N-(4-(4-methylthiazol-5-yl)benzyl)pyrrolidine-2-carboxamide. 70% yield. $^{1}H$ NMR (600 MHz, $CD_3OD$) δ 8.96 (s, 1H), 8.73 (t, J=8.1 Hz, 1H), 8.15 (s, 2H), 7.98 (s, 1H), 7.86 (s, 1H), 7.54-7.34 (m, 6H), 4.65 (s, 1H), 4.64-4.43 (m, 3H), 4.42-4.35 (m, 1H), 4.15-3.86 (m, 7H), 3.83 (dd, J=10.9, 3.4 Hz, 1H), 3.47 (br, 4H), 3.29 (t, J=6.9 Hz, 2H), 2.49 (s, 3H), 2.37-2.19 (m, 3H), 2.19-2.00 (m, 2H), 1.75-1.48 (m, 4H), 1.46-1.32 (m, 2H), 1.10-1.00 (m, 11H), 1.00-0.91 (m, 2H). HRMS (ESI-TOF) m/z: $[M+H]^+$ calcd for $C_{53}H_{65}FN_3O_6S^+$, 1030.4880; found 1030.4855.

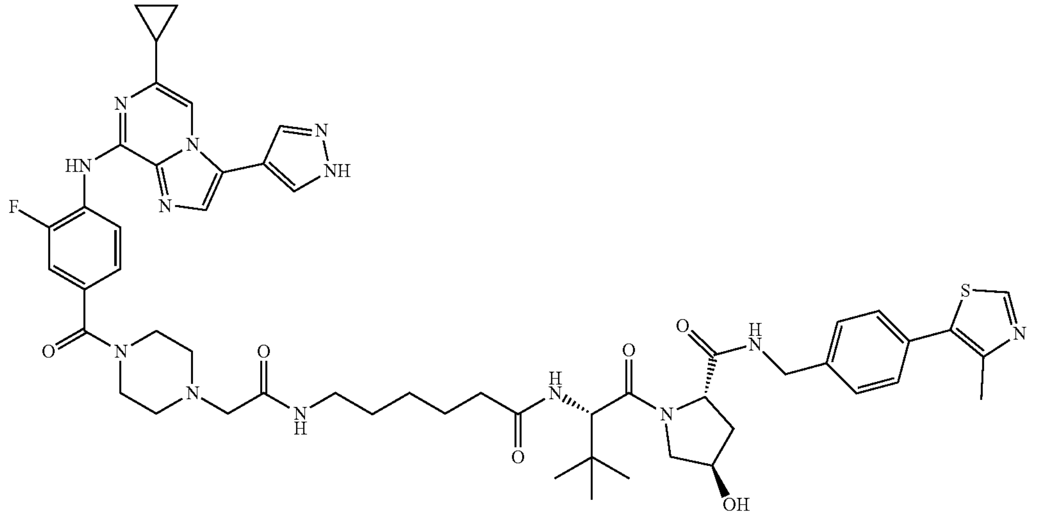 [SMILES: Cc1ncsc1-c1ccc(CNC(=O)[C@@H]2C[C@@H](O)CN2C(=O)[C@@H](NC(=O)CCCCCNC(=O)CN2CCN(C(=O)c3ccc(Nc4nc(C5CC5)cn5c(-c6cn[nH]c6)cnc45)c(F)c3)CC2)C(C)(C)C)cc1]

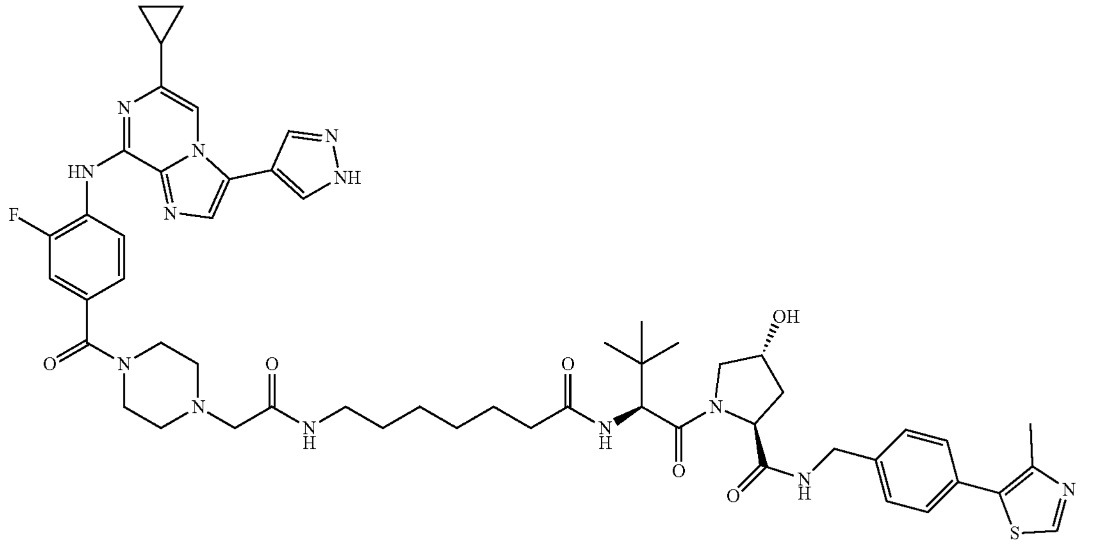 [SMILES: Cc1ncsc1-c1ccc(CNC(=O)[C@@H]2C[C@@H](O)CN2C(=O)[C@@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)cc1]

Example 15: (2S,4R)-1-((S)-2-(7-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-4-hydroxy-N-(4-(4-methylthiazol-5-yl)benzyl)pyrrolidine-2-carboxamide. 55% yield. $^1H$ NMR (600 MHz, $CD_3OD$) δ 9.00 (s, 1H), 8.70 (t, J=8.2 Hz, 1H), 8.14 (s, 2H), 8.01 (s, 1H), 7.89 (s, 1H), 7.51-7.39 (m, 6H), 4.66 (s, 1H), 4.63-4.48 (m, 3H), 4.39 (d, J=15.6 Hz, 1H), 4.06-3.86 (m, 7H), 3.83 (dd, J=10.9, 3.8 Hz, 1H), 3.47 (br, 4H), 3.30-3.23 (m, 2H), 2.49 (s, 3H), 2.36-2.18 (m, 3H), 2.12 (dddd, J=17.4, 13.2, 8.6, 4.6 Hz, 2H), 1.72-1.49 (m, 4H), 1.43-1.32 (m, 4H), 1.10-1.01 (m, 11H), 1.00-0.93 (m, 2H). HRMS (ESI-TOF) m/z: $[M+H]^+$ calcd for $C_{54}H_{67}FN_{13}O_6S^+$, 1044.5037; found 1044.5020.

Example 16: (2S,4R)-1-((S)-2-(8-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)octanamido)-3,3-dimethylbutanoyl)-4-hydroxy-N-(4-(4-methylthiazol-5-yl)benzyl)pyrrolidine-2-carboxamide. 65% yield. $^1H$ NMR (600 MHz, $CD_3OD$) δ 8.97 (s, 1H), 8.73 (t, J=8.2 Hz, 1H), 8.15 (s, 2H), 7.98 (s, 1H), 7.87 (s, 1H), 7.50-7.37 (m, 6H), 4.66 (s, 1H), 4.62-4.49 (m, 3H), 4.39 (d, J=15.4 Hz, 1H), 3.97 (br, 6H), 3.92 (d, J=11.0 Hz, 1H), 3.83 (dd, J=10.9, 3.9 Hz, 1H), 3.47 (br, 4H), 3.28 (t, J=7.0 Hz, 2H), 2.49 (s, 3H), 2.35-2.18 (m, 3H), 2.18-2.03 (m, 2H), 1.68-1.51 (m, 4H), 1.37 (br, 6H), 1.10-1.00 (m, 11H), 0.99-0.94 (m, 2H). HRMS (ESI-TOF) m/z: $[M+H]^+$ calcd for $C_{55}H_{69}FN_3O_6S^+$, 1058.5192; found 1058.5211.

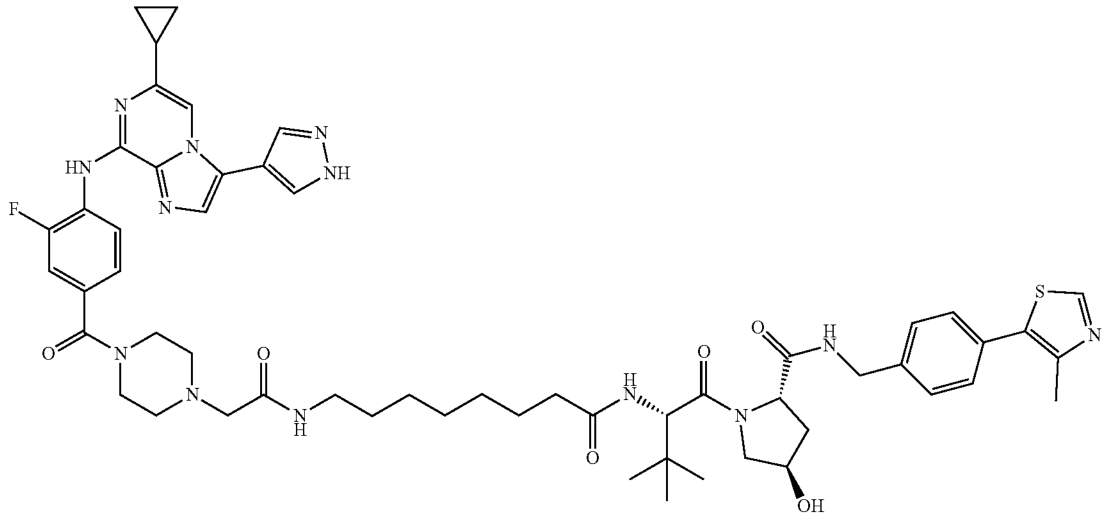 [SMILES: Cc1ncsc1-c1ccc(CNC(=O)[C@@H]2C[C@@H](O)CN2C(=O)[C@@H](NC(=O)CCCCCCCNC(=O)CN2CCN(C(=O)c3ccc(Nc4nc(C5CC5)cn5c(-c6cn[nH]c6)cnc45)c(F)c3)CC2)C(C)(C)C)cc1]

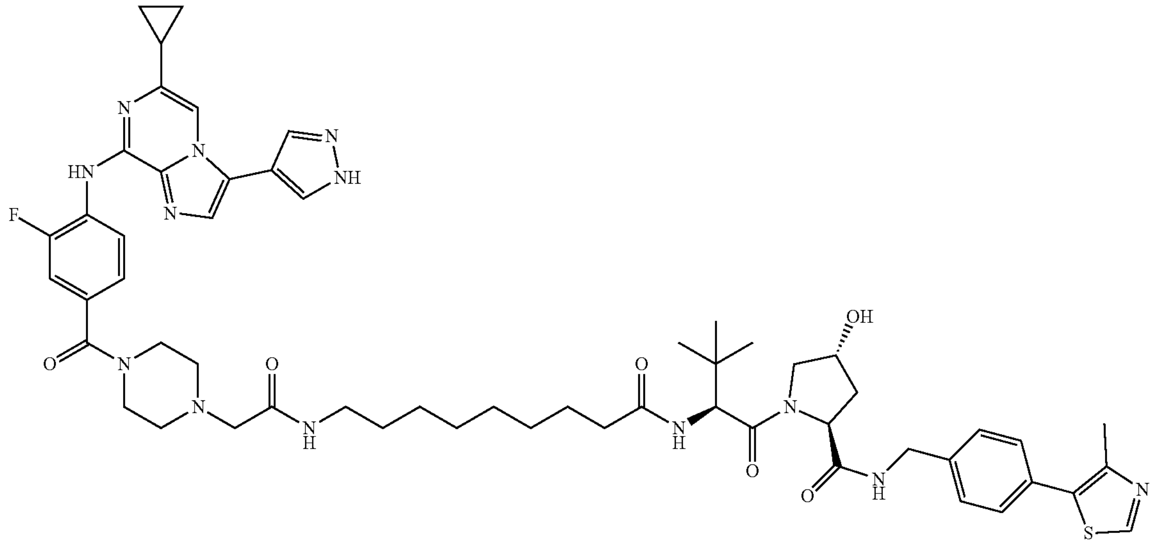 [SMILES: Cc1ncsc1-c1ccc(CNC(=O)[C@@H]2C[C@@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1]

Example 17: (2S,4R)-1-((S)-2-(9-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)nonanamido)-3,3-dimethylbutanoyl)-4-hydroxy-N-(4-(4-methylthiazol-5-yl)benzyl)pyrrolidine-2-carboxamide. 54% yield. $^1$H NMR (600 MHz, $CD_3OD$) δ 8.91 (s, 1H), 8.80 (t, J=8.2 Hz, 1H), 8.14 (s, 2H), 7.94 (s, 1H), 7.77 (s, 1H), 7.53-7.32 (m, 6H), 4.66 (s, 1H), 4.63-4.46 (m, 3H), 4.38 (d, J=15.5 Hz, 1H), 4.11-3.87 (m, 7H), 3.83 (dd, J=11.0, 3.4 Hz, 1H), 3.43 (br, 4H), 3.27 (t, J=6.8 Hz, 1H), 2.49 (s, 3H), 2.37-2.16 (m, 3H), 2.17-1.95 (m, 2H), 1.68-1.50 (m, 4H), 1.45-1.26 (m, 8H), 1.09-1.00 (m, 11H), 0.99-0.91 (m, 2H). HRMS (ESI-TOF) m/z: $[M+H]^+$ calcd for $C_{56}H_{71}FN_{13}O_6S^+$, 1072.5350, found 1072.5380.

Example 18: (2S,4R)-1-((S)-2-(10-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)decanamido)-3,3-dimethylbutanoyl)-4-hydroxy-N-(4-(4-methylthiazol-5-yl)benzyl)pyrrolidine-2-carboxamide. 56% yield. $^1$H NMR (600 MHz, $CD_3OD$) δ 8.87 (s, 1H), 8.83 (t, J=8.2 Hz, 1H), 8.09 (s, 2H), 7.88 (d, J=16.1 Hz, 1H), 7.71 (s, 1H), 7.50-7.34 (m, 6H), 4.65 (s, 1H), 4.62-4.42 (m, 3H), 4.37 (d, J=15.5 Hz, 1H), 4.02-3.78 (m, 8H), 3.34-3.32 (m, 4H), 3.27 (t, J=7.1 Hz, 2H), 2.50 (s, 3H), 2.35-2.19 (m, 3H), 2.14-2.00 (m, 2H), 1.70-1.38 (m, 4H), 1.40-1.23 (m, 10H), 1.08-0.99 (m, 11H), 0.99-0.88 (m, 2H). HRMS (ESI-TOF) m/z: $[M+H]^+$ calcd for $C_{57}H_{73}FN_{13}O_6S^+$, 1086.5506; found 1086.5530.

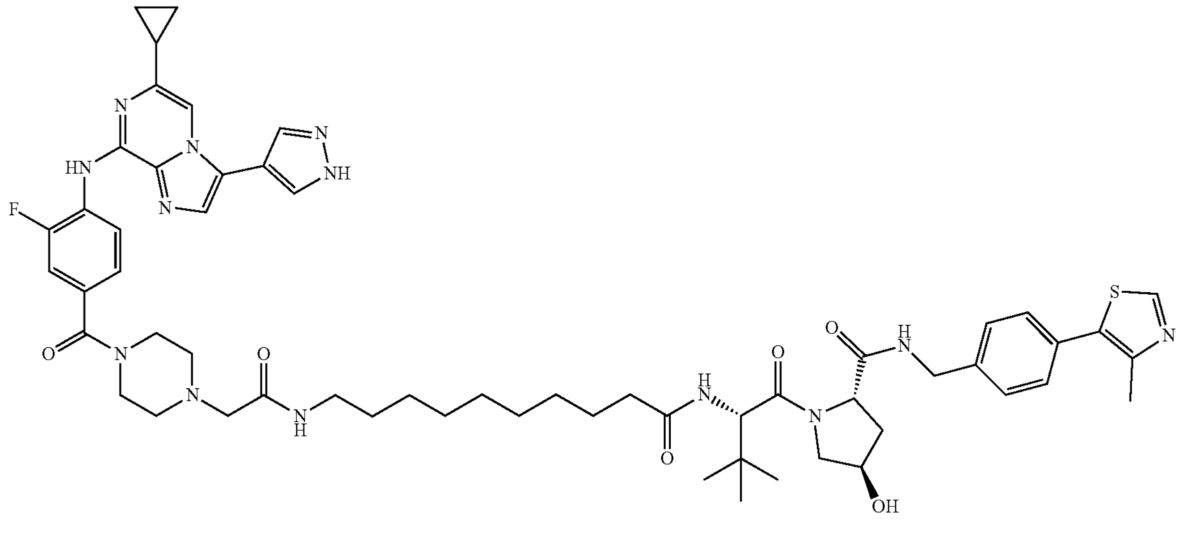 [SMILES: Cc1ncsc1-c1ccc(CNC(=O)[C@@H]2C[C@@H](O)CN2C(=O)[C@@H](NC(=O)CCCCCCCCCNC(=O)CN2CCN(C(=O)c3ccc(Nc4nc(C5CC5)cn5c(-c6cn[nH]c6)cnc45)c(F)c3)CC2)C(C)(C)C)cc1]

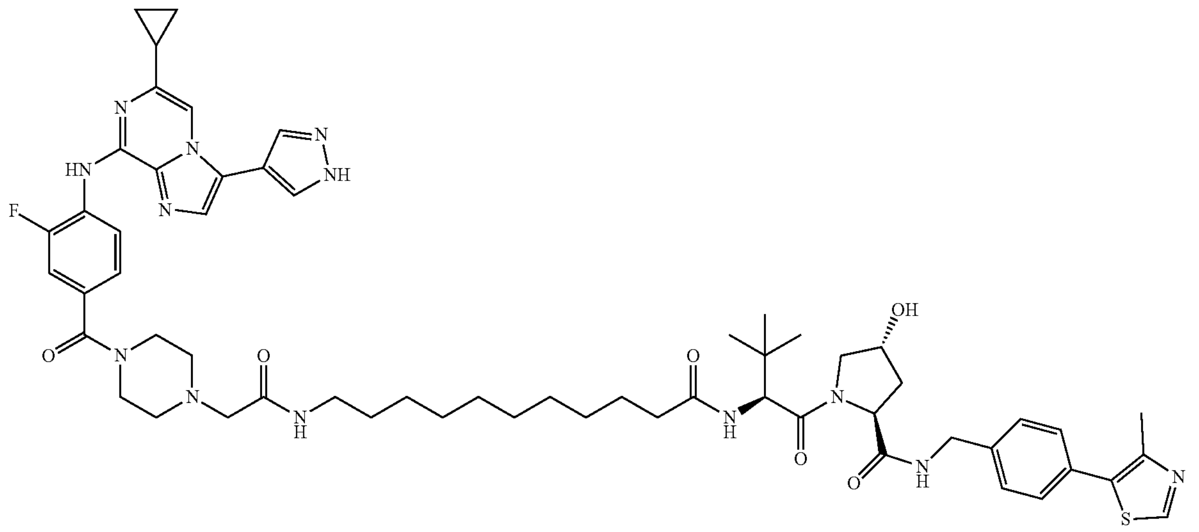 [SMILES: Cc1ncsc1-c1ccc(CNC(=O)[C@@H]2C[C@@H](O)CN2C(=O)[C@@H](NC(=O)CCCCCCCCCCNC(=O)CN2CCN(C(=O)c3ccc(Nc4nc(C5CC5)cn5c(-c6cn[nH]c6)cnc45)c(F)c3)CC2)C(C)(C)C)cc1]

Example 19: (2S,4R)-1-((S)-2-(11-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)undecanamido)-3,3-dimethylbutanoyl)-4-hydroxy-N-(4-(4-methylthiazol-5-yl)benzyl)pyrrolidine-2-carboxamide. 59% yield. $^1$H NMR (600 MHz, $CD_3OD$) δ 8.89 (s, 1H), 8.78 (t, J=8.2 Hz, 1H), 8.09 (s, 2H), 7.90 (s, 1H), 7.76 (s, 1H), 7.49-7.34 (m, 6H), 4.66 (s, 1H), 4.61-4.46 (m, 3H), 4.36 (dd, J=15.2, 8.7 Hz, 1H), 4.12-3.86 (m, 7H), 3.82 (dd, J=10.9, 3.8 Hz, 1H), 3.42 (br, 4H), 3.28-3.20 (m, 2H), 2.50 (s, 3H), 2.40-2.18 (m, 3H), 2.17-2.03 (m, 2H), 1.68-1.49 (m, 4H), 1.41-1.21 (m, 12H), 1.12-1.00 (m, 11H), 1.00-0.90 (m, 2H). HRMS (ESI-TOF) m: $[M+H]^+$ calcd for $C_{58}H_{75}FN_{13}O_6S^+$, 1100.5663; found 1100.5639.

Example 20: (2S,4R)-1-((S)-2-(2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethoxy)acetamido)-3,3-dimethylbutanoyl)-4-hydroxy-N-(4-(4-methylthiazol-5-yl)benzyl)pyrrolidine-2-carboxamide. 67% yield. $^1$H NMR (600 MHz, $CD_3OD$) δ 8.93 (s, 1H), 8.67 (t, J=8.1 Hz, 1H), 8.16 (s, 2H), 7.98 (s, 1H), 7.90 (s, 1H), 7.52-7.30 (m, 6H), 4.76 (s, 1H), 4.61-4.42 (m, 3H), 4.31 (d, J=15.3 Hz, 1H), 4.18-3.88 (m, 9H), 3.87-3.67 (m, 2H), 3.67-3.56 (m, 2H), 3.57-3.40 (m, 5H), 2.45 (s, 3H), 2.34-2.21 (m, 1H), 2.19-2.02 (m, 2H), 1.11-1.01 (m, 11H), 1.00-0.94 (m, 2H). HRMS (ESI-TOF) m/z: $[M+H]^+$ calcd for $C_{51}H_{61}FN_{13}O_7S^+$, 1018.4516; found 1018.4501.

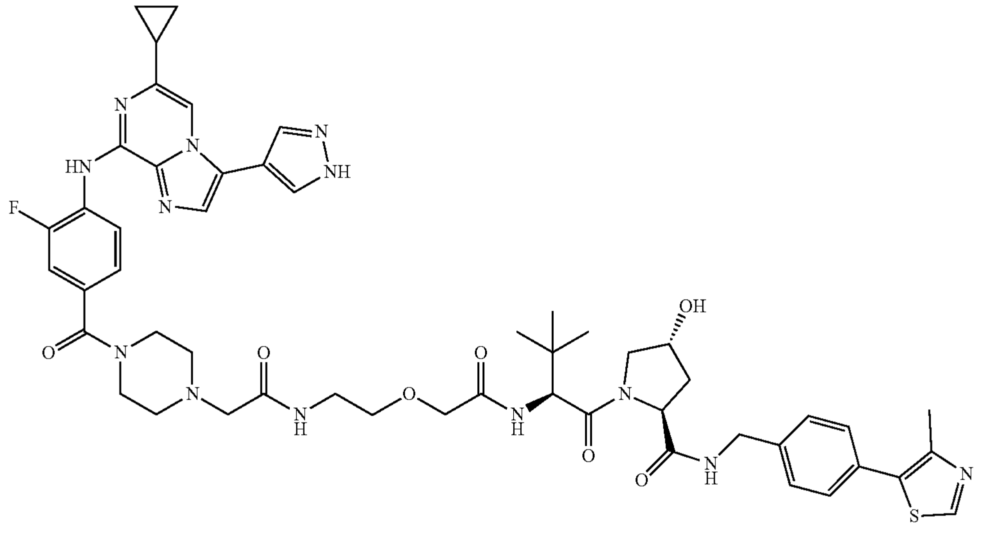 [SMILES: Cc1ncsc1-c1ccc(CNC(=O)[C@@H]2C[C@@H](O)CN2C(=O)[C@@H](NC(=O)COCCNC(=O)CN2CCN(C(=O)c3ccc(Nc4nc(C5CC5)cn5c(-c6cn[nH]c6)cnc45)c(F)c3)CC2)C(C)(C)C)cc1]

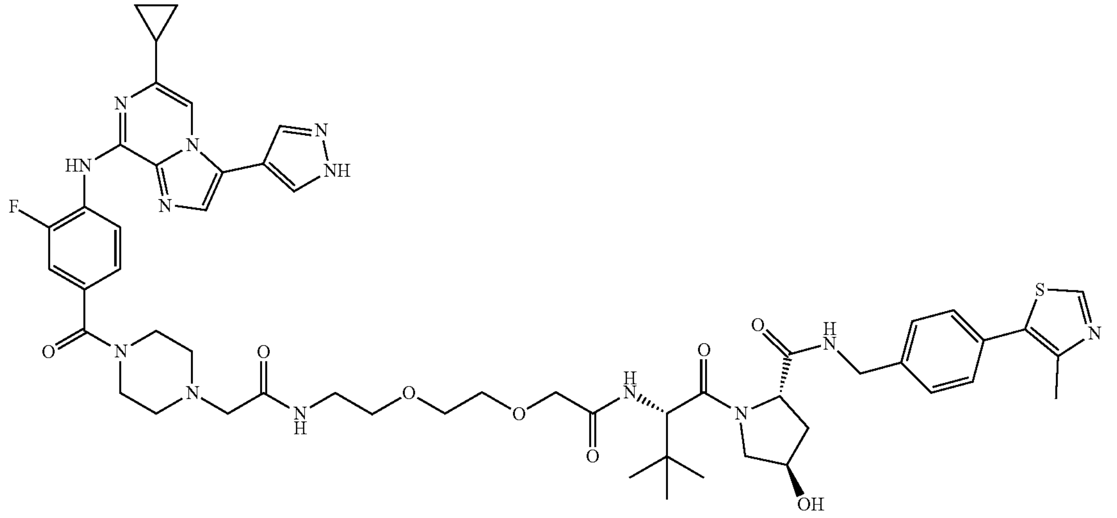 [SMILES: Cc1ncsc1-c1ccc(CNC(=O)[C@@H]2C[C@@H](O)CN2C(=O)[C@@H](NC(=O)COCCOCCNC(=O)CN2CCN(C(=O)c3ccc(Nc4nc(C5CC5)cn5c(-c6cn[nH]c6)cnc45)c(F)c3)CC2)C(C)(C)C)cc1]

Example 21: (2S,4R)-1-((S)-2-(tert-Butyl)-14-(4-(4-((6-cyclopropyl-3-(1H-pyrazol-4-yl)imidazo[1,2-a]pyrazin-8-yl)amino)-3-fluorobenzoyl)piperazin-1-yl)-4,13-dioxo-6,9-dioxa-3,12-diazatetradecanoyl)-4-hydroxy-N-(4-(4-methylthiazol-5-yl)benzyl)pyrrolidine-2-carboxamide. 65% yield. $^{1}$H NMR (600 MHz, $CD_3OD$) δ 8.94 (s, 1H), 8.70 (t, J=8.1 Hz, 1H), 8.16 (s, 2H), 7.97 (s, 1H), 7.88 (s, 1H), 7.51-7.34 (m, 6H), 4.82 (s, 1H), 4.59-4.47 (m, 3H), 4.46-4.38 (m, 1H), 4.19-3.81 (m, 10H), 3.79-3.53 (m, 8H), 3.47 (br, 4H), 2.49 (s, 3H), 2.39-2.27 (m, 1H), 2.18-2.07 (m, 2H), 1.14-1.01 (m, 11H), 1.01-0.91 (m, 2H). HRMS (ESI-TOF) m/z: $[M+H]^+$ calcd for $C_{53}H_{65}FN_{13}O_8S^+$, 1062.4778; found 1062.4790.

Example 22: (2S,4R)-1-((S)-2-(tert-Butyl)-17-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide. 70% yield. $^{1}$H NMR (600 MHz, $CD_3OD$) δ 8.93 (s, 1H), 8.77 (t, J=8.1 Hz, 1H), 8.15 (s, 2H), 7.95 (s, 1H), 7.83 (s, 1H), 7.54-7.30 (m, 6H), 4.64 (s, 1H), 4.63-4.48 (m, 3H), 4.38 (d, J=15.5 Hz, 1H), 4.15-3.88 (m, 7H), 3.82 (d, J=7.2 Hz, 1H), 3.80-3.71 (m, 2H), 3.71-3.56 (m, 10H), 3.48 (br, 4H), 2.65-2.55 (m, 1H), 2.53 (m, 4H), 2.32-2.23 (m, 1H), 2.18-2.00 (m, 2H), 1.13-1.02 (m, 11H), 1.00-0.91 (m, 2H). HRMS (ESI-TOF) m/z: $[M+H]^+$ calcd for $C_{55}H_{69}FN_{13}O_9S^+$, 1106.5040; found 1106.5018.

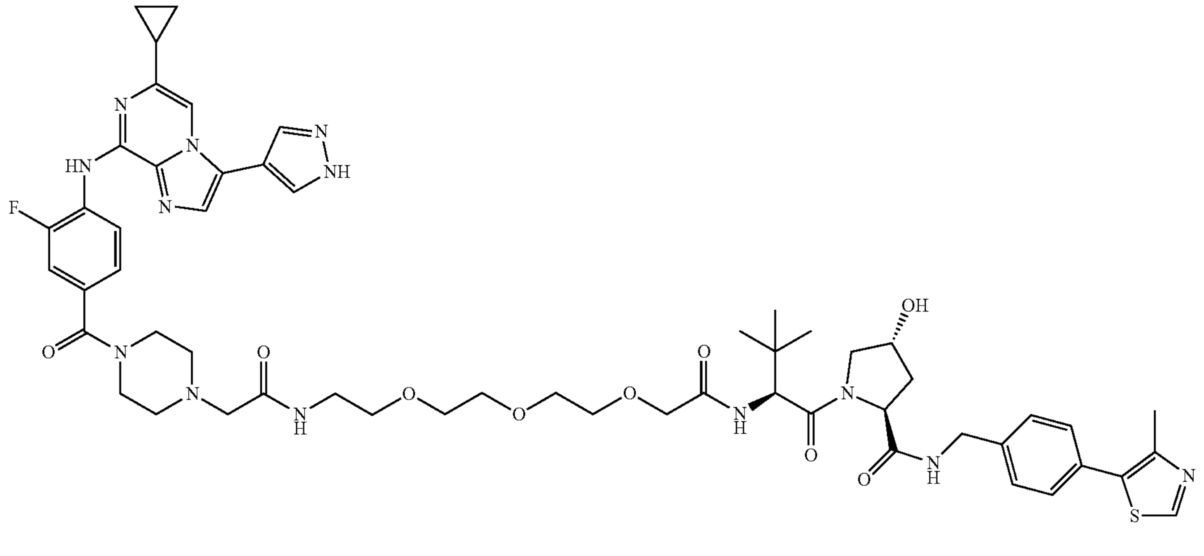 [SMILES: Cc1ncsc1-c1ccc(CNC(=O)[C@@H]2C[C@@H](O)CN2C(=O)[C@@H](NC(=O)COCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1]

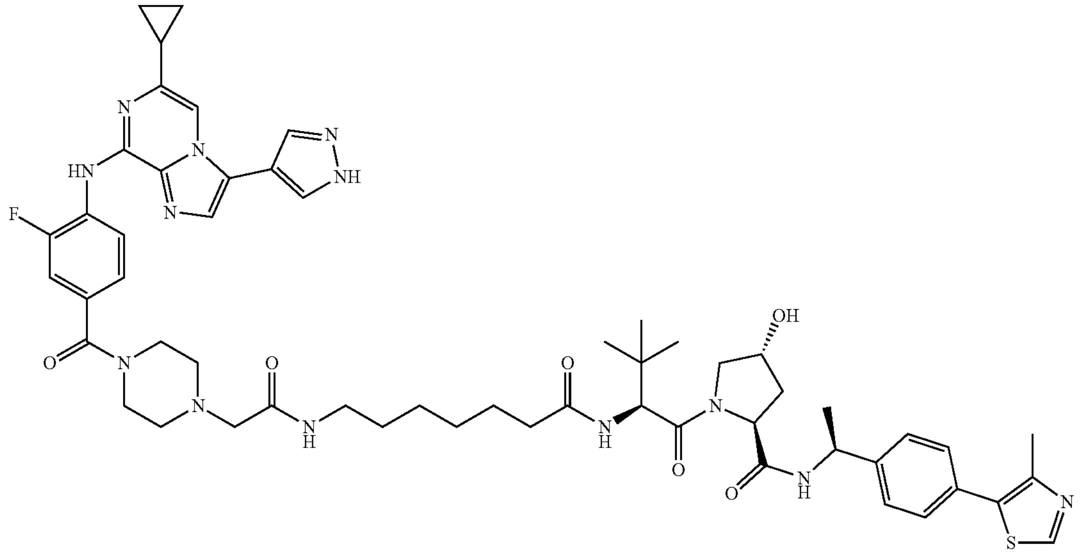 [SMILES: Cc1ncsc1-c1ccc([C@H](C)NC(=O)[C@@H]2C[C@@H](O)CN2C(=O)[C@@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)cc1]

Example 37: (2S,4R)-1-((S)-2-(7-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-4-hydroxy-N—((S)-1-(4-(4-methylthiazol-5-yl)phenyl)ethyl)pyrrolidine-2-carboxamide. 65% yield. $^1$H NMR (600 MHz, $CD_3OD$) δ 9.10 (s, 1H), 8.64 (t, J=8.2 Hz, 1H), 8.18 (s, 2H), 8.03 (s, 1H), 7.99 (s, 1H), 7.52-7.27 (m, 6H), 5.02 (q, J=7.0 Hz, 1H), 4.65 (s, 1H), 4.59 (dd, J=14.1, 5.7 Hz, 1H), 4.45 (s, 1H), 4.05-4.01 (m, 6H), 3.90 (d, J=11.0 Hz, 1H), 3.77 (dd, J=11.0, 3.9 Hz, 1H), 3.57-3.38 (m, 4H), 3.28 (t, J=7.0 Hz, 2H), 2.51 (s, 3H), 2.40-2.25 (m, 2H), 2.25-2.13 (m, 2H), 2.01-1.92 (m, 1H), 1.69-1.55 (m, 4H), 1.52 (d, J=7.0 Hz, 3H), 1.44-1.33 (m, 4H), 1.12-1.03 (m, 1H), 1.03-0.97 (m, 2H). HRMS (ESI-TOF) m/z: $[M+H]^+$ calcd for $C_{55}H_{69}FN_3O_6S^+$, 1058.5193; found 1058.5165.

Example 38: (2S,4R)-1-((S)-2-(9-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)nonanamido)-3,3-dimethylbutanoyl)-4-hydroxy-N—((S)-1-(4-(4-methylthiazol-5-yl)phenyl)ethyl)pyrrolidine-2-carboxamide. 67% yield. $^1$H NMR (600 MHz, $CD_3OD$) δ 9.01 (s, 1H), 8.72 (t, J=8.2 Hz, 1H), 8.16 (s, 2H), 8.00 (s, 1H), 7.90 (s, 1H), 7.53-7.34 (m, 6H), 5.02 (q, J=6.8 Hz, 1H), 4.65 (s, 1H), 4.62-4.54 (m, 1H), 4.47-4.42 (m, 1H), 4.20-3.82 (m, 7H), 3.77 (dd, J=11.1, 3.9 Hz, 1H), 3.58-3.38 (m, 4H), 3.28 (t, J=7.0 Hz, 2H), 2.51 (s, 3H), 2.37-2.19 (m, 3H), 2.18-2.11 (m, 1H), 2.01-1.93 (m, 1H), 1.61 (dd, J=18.7, 6.8 Hz, 4H), 1.52 (d, J=7.0 Hz, 3H), 1.39-1.34 (m, 8H), 1.10-1.01 (m, 11H), 1.01-0.95 (m, 2H). HRMS (ESI-TOF) m/z: $[M+H]^+$ calcd for $C_{57}H_{73}FN_3O_6S^+$, 1086.5506; found 1086.5545.

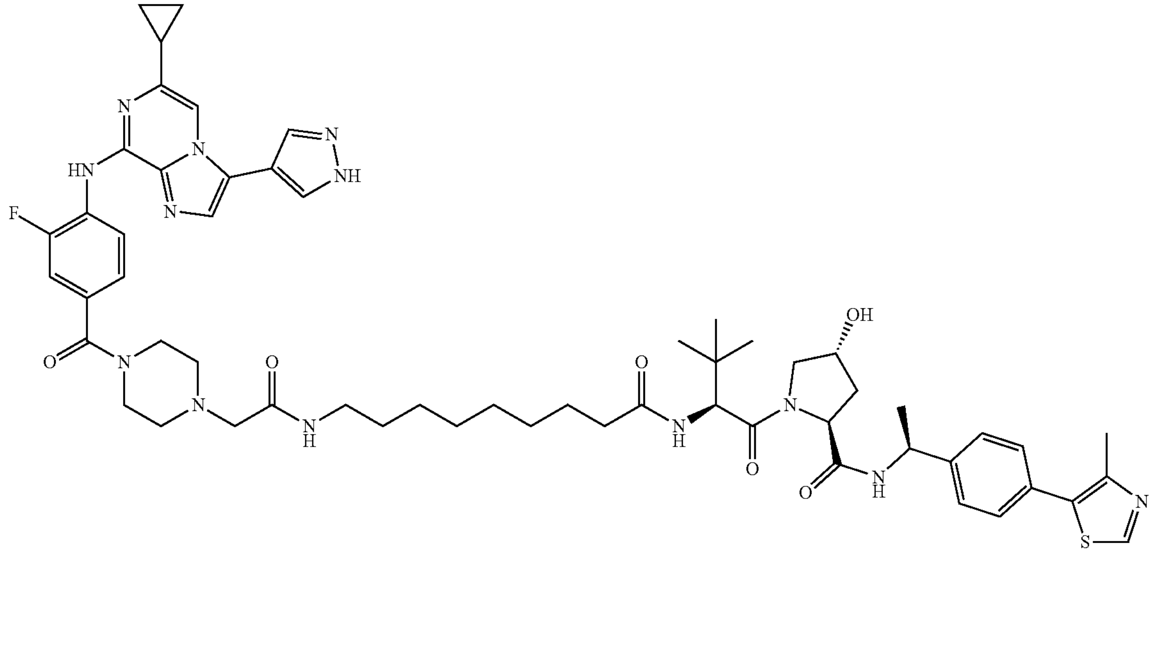 [SMILES: Cc1ncsc1-c1ccc([C@H](C)NC(=O)[C@@H]2C[C@@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1]

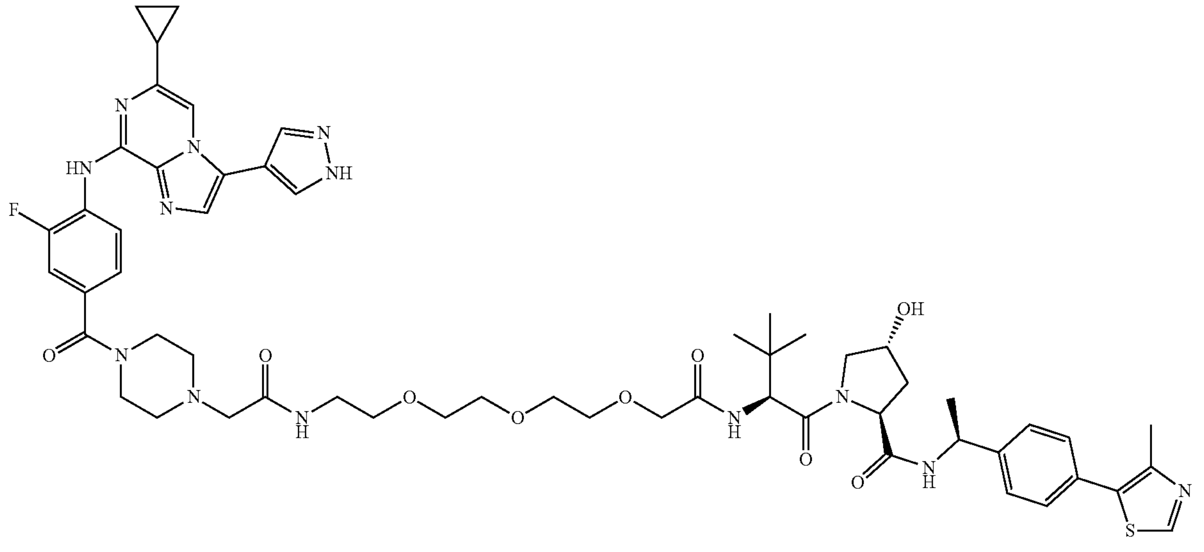 [SMILES: Cc1ncsc1-c1ccc([C@H](C)NC(=O)[C@@H]2C[C@@H](O)CN2C(=O)[C@@H](NC(=O)COCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1]

Example 39: (2S,4R)-1-((S)-2-(tert-Butyl)-17-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-6,9,12-trioxa-3,15-diazaheptadecanoyl)-4-hydroxy-N—((S)-1-(4-(4-methylthiazol-5-yl)phenyl)ethyl)pyrrolidine-2-carboxamide. 50% yield. $^{1}$H NMR (600 MHz, $CD_3OD$) δ 9.14 (s, 1H), 8.62 (t, J=8.2 Hz, 1H), 8.19 (s, 2H), 8.05 (s, 1H), 8.03 (s, 1H), 7.52-7.40 (m, 6H), 5.02 (q, J=6.9 Hz, 1H), 4.71 (s, 1H), 4.62-4.56 (m, 1H), 4.47 (s, 1H), 4.14-4.08 (m, 2H), 4.04 (s, 2H), 3.88 (d, J=11.2 Hz, 1H), 3.80-3.74 (m, 4H), 3.73-3.65 (m, 8H), 3.61 (t, J=5.2 Hz, 2H), 3.58-3.40 (m, 7H), 2.51 (s, 3H), 2.29-2.22 (m, 1H), 2.20-2.13 (m, 1H), 2.01-1.93 (m, 1H), 1.53 (d, J=7.0 Hz, 3H), 1.09-1.05 (m, 11H), 1.03-0.97 (m, 2H). HRMS (ESI-TOF) m/z: $[M+H]^+$ calcd for $C_{56}H_{71}FN_3O_9S^+$, 1120.5179; found 1120.5148.

Example 40: (2R,4S)-1-((S)-2-(7-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-4-hydroxy-N-(4-(4-methylthiazol-5-yl)benzyl)pyrrolidine-2-carboxamide. 62% yield. $^{1}$H NMR (500 MHz, $CD_3OD$) δ 8.95 (s, 1H), 8.72 (t, J=8.2 Hz, 1H), 8.15 (s, 2H), 7.97 (s, 1H), 7.86 (s, 1H), 7.50-7.37 (m, 6H), 4.59 (t, J=7.4 Hz, 1H), 4.55-4.45 (m, 3H), 4.40 (d, J=15.6 Hz, 1H), 4.10-3.85 (m, 7H), 3.74 (d, J=10.7 Hz, 1H), 3.55-3.42 (m, 4H), 3.26-3.17 (m, 2H), 2.51 (s, 3H), 2.35-2.20 (m, 2H), 2.20-2.04 (m, 3H), 1.59-1.42 (m, 4H), 1.34-1.23 (m, 4H), 1.15-1.02 (m, 11H), 1.01-0.93 (m, 2H). HRMS (ESI-TOF) m/z: $[M+H]^+$ calcd for $C_{54}H_{67}FN_3O_6S^+$, 1044.5037; found 1044.5058.

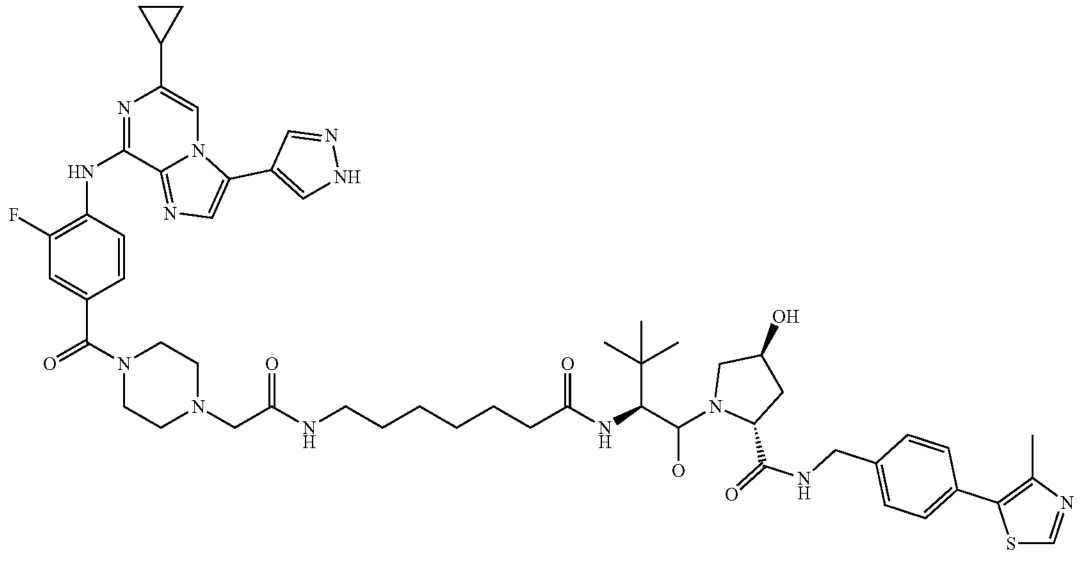 [SMILES: Cc1ncsc1-c1ccc(CNC(=O)[C@H]2C[C@H](O)CN2C(O)[C@@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)cc1]

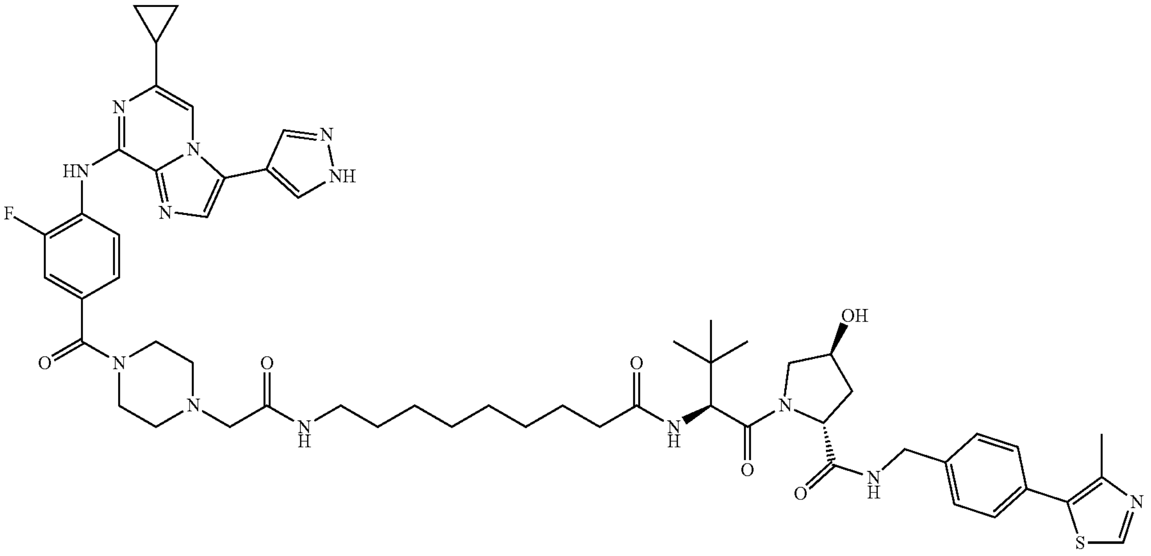 [SMILES: Cc1ncsc1-c1ccc(CNC(=O)[C@H]2C[C@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1]

Example 41: (2R,4S)-1-((S)-2-(9-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)nonanamido)-3,3-dimethylbutanoyl)-4-hydroxy-N-(4-(4-methylthiazol-5-yl)benzyl)pyrrolidine-2-carboxamide. 67% yield. $^1$H NMR (500 MHz, $CD_3OD$) δ 8.96 (s, 1H), 8.72 (t, J=8.2 Hz, 1H), 8.15 (s, 2H), 7.97 (s, 1H), 7.86 (s, 1H), 7.50-7.36 (m, 6H), 4.64-4.56 (m, 1H), 4.56-4.44 (m, 3H), 4.38 (d, J=15.6 Hz, 1H), 4.14-3.85 (m, 7H), 3.78-3.72 (m, 1H), 3.57-3.41 (m, 4H), 3.27-3.20 (m, 2H), 2.51 (s, 3H), 2.36-2.00 (m, 5H), 1.57-1.19 (m, 12H), 1.15-1.03 (m, 11H), 1.02-0.93 (m, 2H). HRMS (ESI-TOF) m/z: $[M+H]^+$ calcd for $C_{56}H_{71}FN_{13}O_6S^+$, 1072.5350; found 1072.5359.

Example 42: (2R,4S)-1-((S)-2-(tert-Butyl)-17-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide. 54% yield. $^1$H NMR (500 MHz, $CD_3OD$) δ 9.01 (s, 1H), 8.63 (t, J=8.2 Hz, 1H), 8.17 (s, 2H), 8.01 (s, 1H), 7.96 (s, 1H), 7.51-7.32 (m, 6H), 4.68-4.63 (m, 1H), 4.60-4.47 (m, 3H), 4.37 (d, J=15.6 Hz, 1H), 4.09-3.84 (m, 8H), 3.80 (d, J=10.9 Hz, 1H), 3.71-3.54 (m, 11H), 3.54-3.40 (m, 6H), 2.50 (s, 3H), 2.34-2.25 (m, 1H), 2.19-2.10 (m, 2H), 1.13-1.03 (m, 11H), 1.03-0.94 (m, 2H). HRMS (ESI-TOF) m/z: $[M+H]^+$ calcd for $C_{55}H_{69}FN_{13}O_9S^+$, 1106.5040; found 1106.5017.

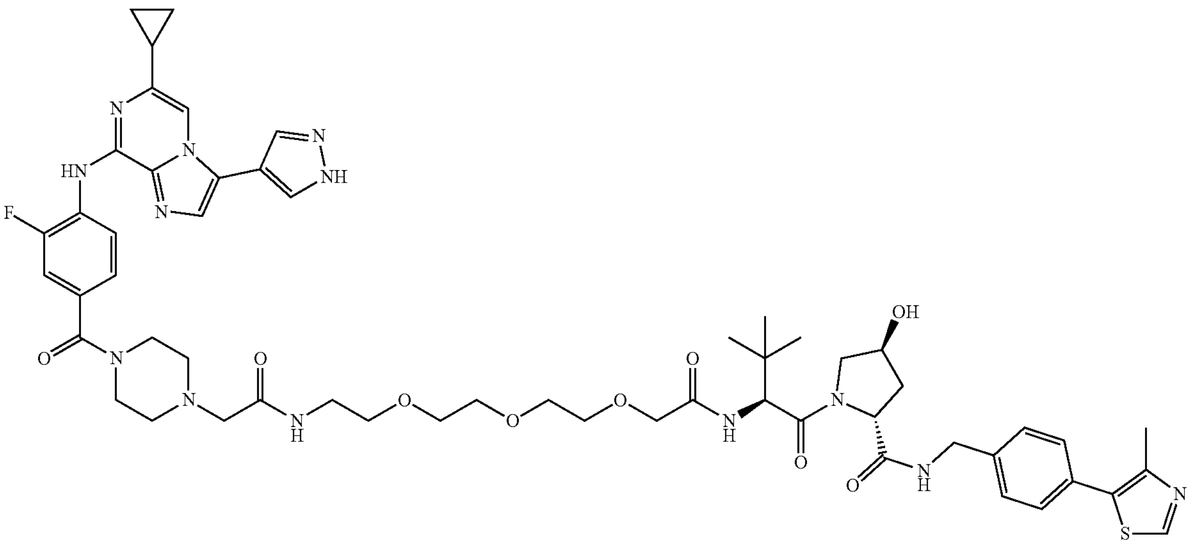 [SMILES: Cc1ncsc1-c1ccc(CNC(=O)[C@H]2C[C@H](O)CN2C(=O)[C@@H](NC(=O)COCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1]

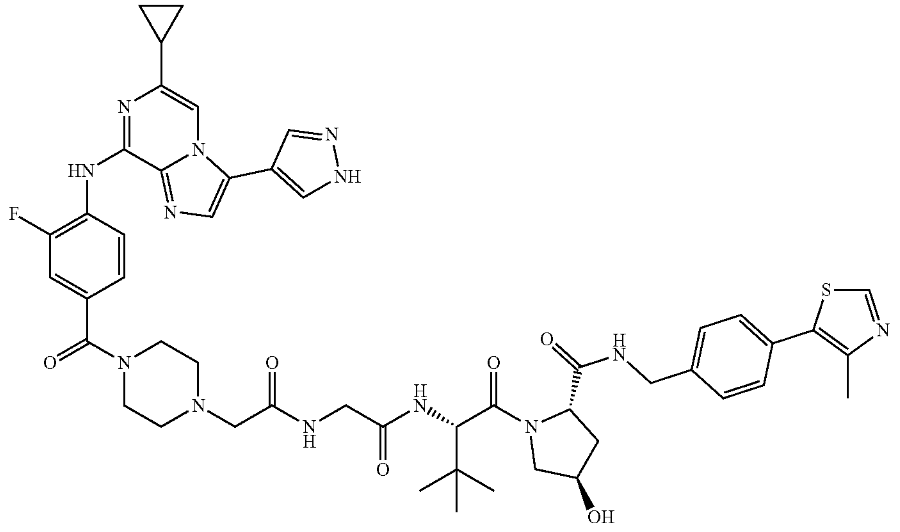 [SMILES: Cc1ncsc1-c1ccc(CNC(=O)[C@@H]2C[C@@H](O)CN2C(=O)[C@@H](NC(=O)CNC(=O)CN2CCN(C(=O)c3ccc(Nc4nc(C5CC5)cn5c(-c6cn[nH]c6)cnc45)c(F)c3)CC2)C(C)(C)C)cc1]

Example 43: (2S,4R)-1-((S)-2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)acetamido)-3,3-dimethylbutanoyl)-4-hydroxy-N-(4-(4-methylthiazol-5-yl)benzyl)pyrrolidine-2-carboxamide. 57% yield. $^1$H NMR (500 MHz, $CD_3OD$) δ 9.06 (s, 1H), 8.65 (t, J=8.2 Hz, 1H), 8.16 (s, 2H), 8.01 (s, 1H), 7.96 (s, 1H), 7.55-7.37 (m, 6H), 4.67 (s, 1H), 4.61-4.47 (m, 3H), 4.38 (d, J=15.5 Hz, 1H), 4.14-3.92 (m, 8H), 3.92-3.79 (m, 2H), 3.50 (br, 4H), 2.50 (s, 3H), 2.30-2.20 (m, 1H), 2.20-2.04 (m, 2H), 1.06 (s, 9H), 1.05-1.02 (m, 2H), 1.02-0.96 (m, 2H). HRMS (ESI-TOF) m/z: $[M+H]^+$ calcd for $C_{49}H_{57}FN_{13}O_5S^+$, 974.4254; found 974.4266.

Example 44: (2S,4R)-1-((S)-2-(3-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)propanamido)-3,3-dimethylbutanoyl)-4-hydroxy-N-(4-(4-methylthiazol-5-yl)benzyl)pyrrolidine-2-carboxamide. 53% yield. $^1$H NMR (500 MHz, $CD_3OD$) δ 8.97 (s, 1H), 8.66 (t, J=8.2 Hz, 1H), 8.16 (s, 2H), 7.99 (s, 1H), 7.92 (s, 1H), 7.53-7.33 (m, 6H), 4.64 (s, 1H), 4.62-4.47 (m, 3H), 4.42 (d, J=15.5 Hz, 1H), 3.97 (dd, J=12.8, 8.7 Hz, 6H), 3.83 (dd, J=10.9, 3.7 Hz, 1H), 3.63-3.55 (m, 1H), 3.52-3.42 (m, 4H), 2.72-2.57 (m, 2H), 2.54-2.44 (m, 5H), 2.32-2.22 (m, 1H), 2.21-2.08 (m, 2H), 1.12-1.02 (m, 11H), 1.02-0.95 (m, 2H). HRMS (ESI-TOF) m/z: $[M+H]^+$ calcd for $C_{50}H_{59}FN_{13}O_6S^+$, 988.4411; found 988.4432.

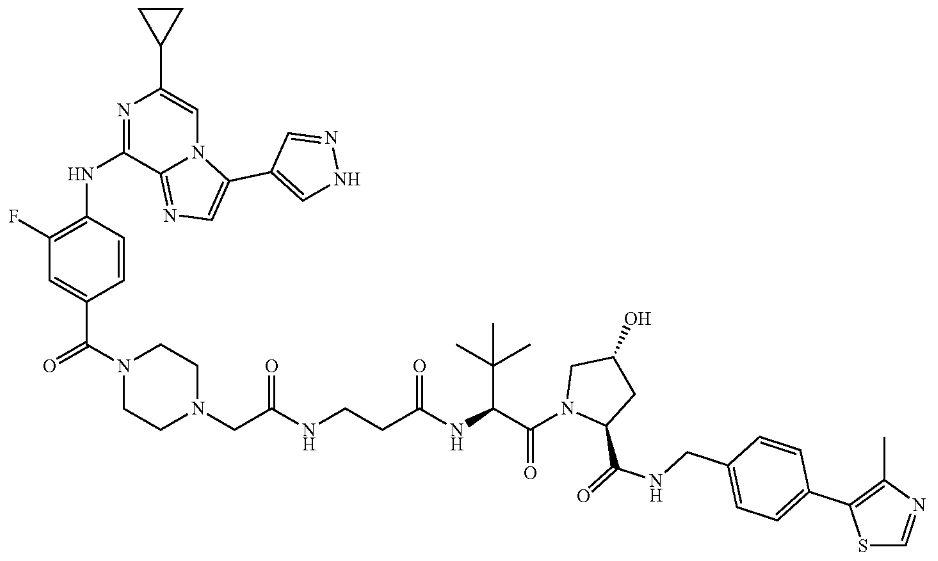 [SMILES: Cc1ncsc1-c1ccc(CNC(=O)[C@@H]2C[C@@H](O)CN2C(=O)[C@@H](NC(=O)CCNC(=O)CN2CCN(C(=O)c3ccc(Nc4nc(C5CC5)cn5c(-c6cn[nH]c6)cnc45)c(F)c3)CC2)C(C)(C)C)cc1]

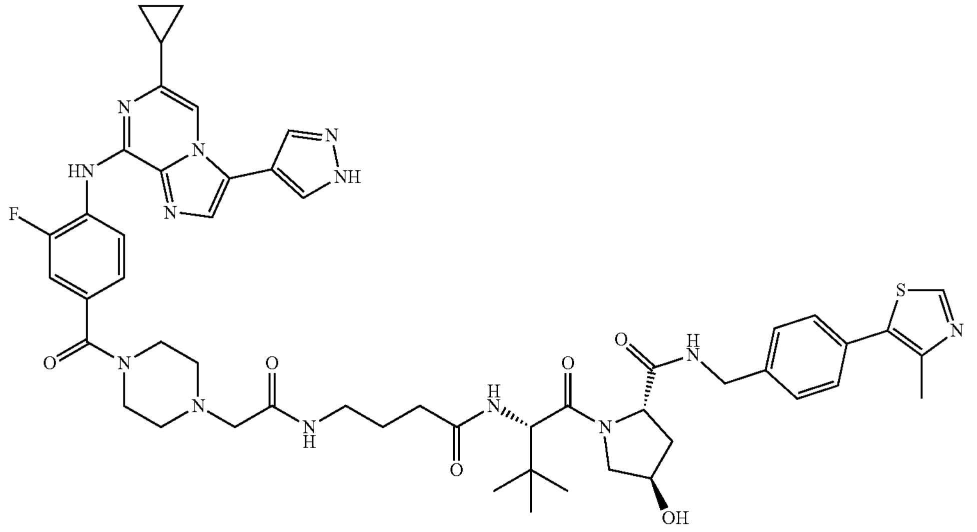 [SMILES: Cc1ncsc1-c1ccc(CNC(=O)[C@@H]2C[C@@H](O)CN2C(=O)[C@@H](NC(=O)CCCNC(=O)CN2CCN(C(=O)c3ccc(Nc4nc(C5CC5)cn5c(-c6cn[nH]c6)cnc45)c(F)c3)CC2)C(C)(C)C)cc1]

Example 45: (2S,4R)-1-((S)-2-(4-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)butanamido)-3,3-dimethylbutanoyl)-4-hydroxy-N-(4-(4-methylthiazol-5-yl)benzyl)pyrrolidine-2-carboxamide. 51% yield. $^1H$ NMR (500 MHz, $CD_3OD$) δ 8.95 (s, 1H), 8.75-8.64 (m, 1H), 8.15 (s, 2H), 7.97 (s, 1H), 7.87 (s, 1H), 7.52-7.33 (m, 6H), 4.64 (s, 1H), 4.62-4.48 (m, 3H), 4.40 (d, J=15.4 Hz, 1H), 4.12-3.89 (m, 7H), 3.83 (dd, J=10.9, 3.8 Hz, 1H), 3.64-3.36 (m, 4H), 2.48 (s, 3H), 2.42-2.30 (m, 2H), 2.30-2.21 (m, 1H), 2.19-2.06 (m, 2H), 1.97-1.77 (m, 2H), 1.14-1.02 (m, 11H), 1.02-0.93 (m, 2H). HRMS (ESI-TOF) m/z: $[M+H]^+$ calcd for $C_{51}H_{61}FN_{13}O_6S^+$, 1002.4567; found 1002.4578.

Example 63: (2R,4S)-1-((S)-2-(7-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-4-hydroxy-N—((S)-1-(4-(4-methylthiazol-5-yl)phenyl)ethyl)pyrrolidine-2-carboxamide. 59% yield. $^1H$ NMR (500 MHz, $CD_3OD$) δ 8.98 (s, 1H), 8.70 (t, J=8.2 Hz, 1H), 8.15 (s, 2H), 7.98 (s, 1H), 7.89 (s, 1H), 7.55-7.37 (m, 6H), 5.03 (q, J=6.7 Hz, 1H), 4.61-4.51 (m, 2H), 4.51-4.44 (m, 1H), 4.08-3.87 (m, 6H), 3.71 (d, J=10.9 Hz, 1H), 3.55-3.42 (m, 4H), 3.30-3.16 (m, 3H), 2.52 (s, 3H), 2.35-2.27 (m, 1H), 2.27-2.18 (m, 2H), 2.18-2.09 (m, 2H), 1.65-1.50 (m, 4H), 1.48 (d, J=7.0 Hz, 3H), 1.39-1.27 (m, 4H), 1.15-1.02 (m, 11H), 1.02-0.92 (m, 2H). HRMS (ESI-TOF) m/z: $[M+H]^+$ calcd for $C_{55}H_{69}FN_3O_6S^+$, 1058.5193; found 1058.5165.

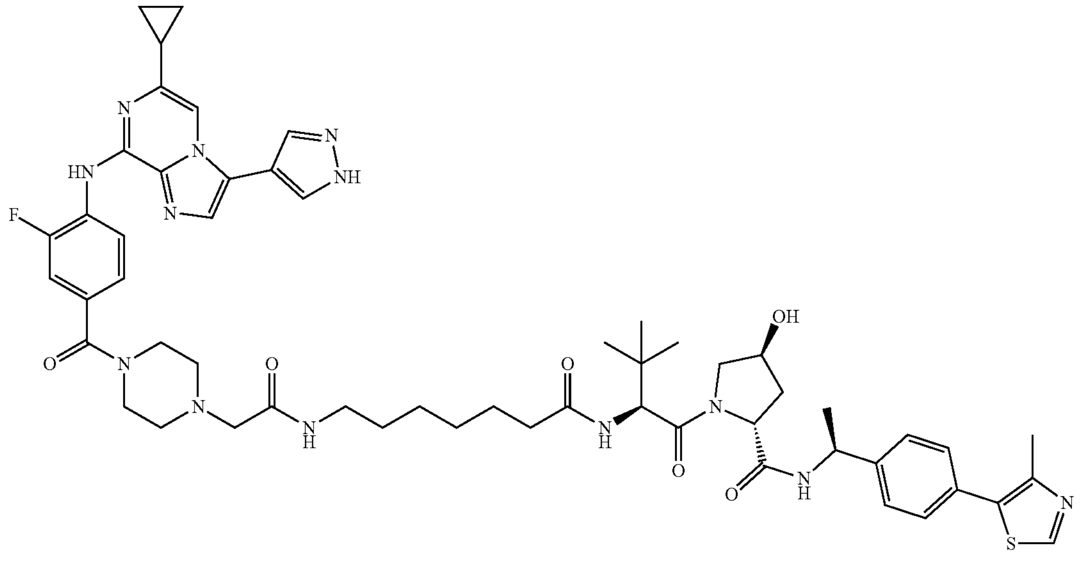 [SMILES: Cc1ncsc1-c1ccc([C@H](C)NC(=O)[C@H]2C[C@H](O)CN2C(=O)[C@@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)cc1]

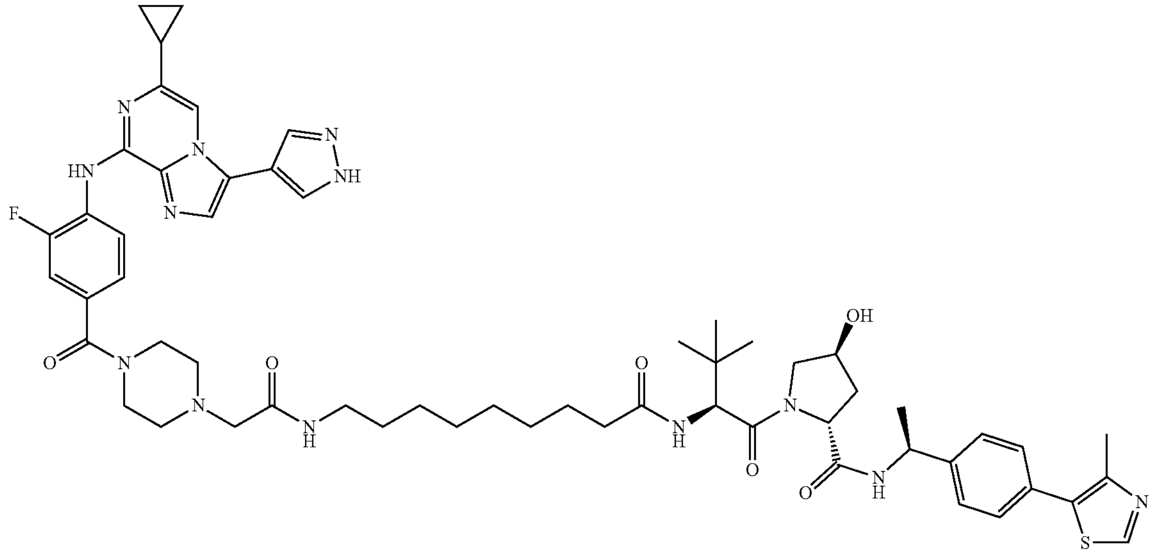 [SMILES: Cc1ncsc1-c1ccc([C@H](C)NC(=O)[C@H]2C[C@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1]

Example 64: (2R,4S)-1-((S)-2-(9-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)nonanamido)-3,3-dimethylbutanoyl)-4-hydroxy-N—((S)-1-(4-(4-methylthiazol-5-yl)phenyl)ethyl)pyrrolidine-2-carboxamide. 61% yield. $^1$H NMR (500 MHz, $CD_3OD$) δ 8.96 (s, 1H), 8.73 (t, J=8.2 Hz, 1H), 8.15 (s, 2H), 7.97 (s, 1H), 7.86 (s, 1H), 7.56-7.32 (m, 6H), 5.03 (q, J=6.8 Hz, 1H), 4.60-4.55 (m, 1H), 4.53 (s, 1H), 4.50-4.45 (m, 1H), 4.10-3.85 (m, 6H), 3.76-3.67 (m, 1H), 3.56-3.40 (m, 4H), 3.30-3.21 (m, 3H), 2.51 (s, 3H), 2.35-2.26 (m, 1H), 2.26-2.17 (m, 2H), 2.17-2.08 (m, 2H), 1.65-1.50 (m, 4H), 1.47 (d, J=7.0 Hz, 3H), 1.37-1.28 (m, 8H), 1.11-1.03 (m, 11H), 1.00-0.94 (m, 2H). HRMS (ESI-TOF) m/z: $[M+H]^+$ calcd for $C_{57}H_{73}FN_{13}O_6S^+$, 1086.5506; found 1086.5545.

Example 102: (2S,4R)-1-((S)-2-(4-(4-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)piperidin-1-yl)-4-oxobutanamido)-3,3-dimethylbutanoyl)-4-hydroxy-N-(4-(4-methylthiazol-5-yl)benzyl)pyrrolidine-2-carboxamide. 70% yield. $^1$H NMR (500 MHz, $CD_3OD$) δ 8.97 (s, 1H), 8.71 (t, J=8.2 Hz, 1H), 8.14 (s, 2H), 7.96 (s, 1H), 7.85 (s, 1H), 7.54-7.29 (m, 6H), 4.64-4.48 (m, 4H), 4.44-4.35 (m, 2H), 4.10-3.93 (m, 6H), 3.90 (d, J=10.6 Hz, 1H), 3.81 (dd, J=11.0, 3.8 Hz, 1H), 3.57-3.42 (m, 4H), 3.28-3.20 (m, 1H), 2.87 (t, J=12.2 Hz, 1H), 2.79-2.52 (m, 4H), 2.50 (s, 3H), 2.29-2.19 (m, 1H), 2.17-2.06 (m, 2H), 2.04-1.89 (m, 2H), 1.58-1.34 (m, 2H), 1.11-1.01 (m, 11H), 1.01-0.94 (m, 2H).

HRMS (ESI-TOF) m/z: $[M+H]^+$ calcd for $C_{56}H_{68}FN_{14}O_7S^+$, 1099.5095; found 1099.5107.

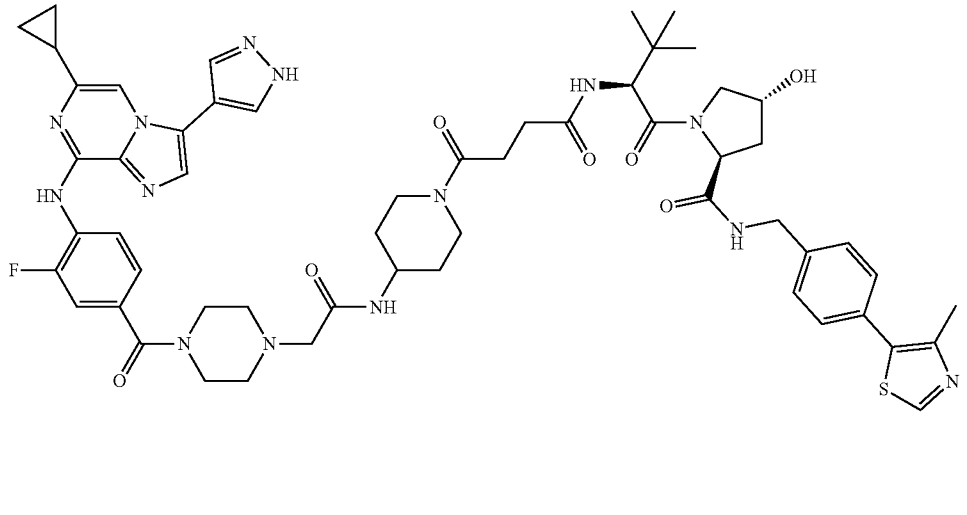 [SMILES: Cc1ncsc1-c1ccc(CNC(=O)[C@@H]2C[C@@H](O)CN2C(=O)[C@@H](NC(=O)CCC(=O)N2CCC(NC(=O)CN3CCN(C(=O)c4ccc(Nc5nc(C6CC6)cn6c(-c7cn[nH]c7)cnc56)c(F)c4)CC3)CC2)C(C)(C)C)cc1]

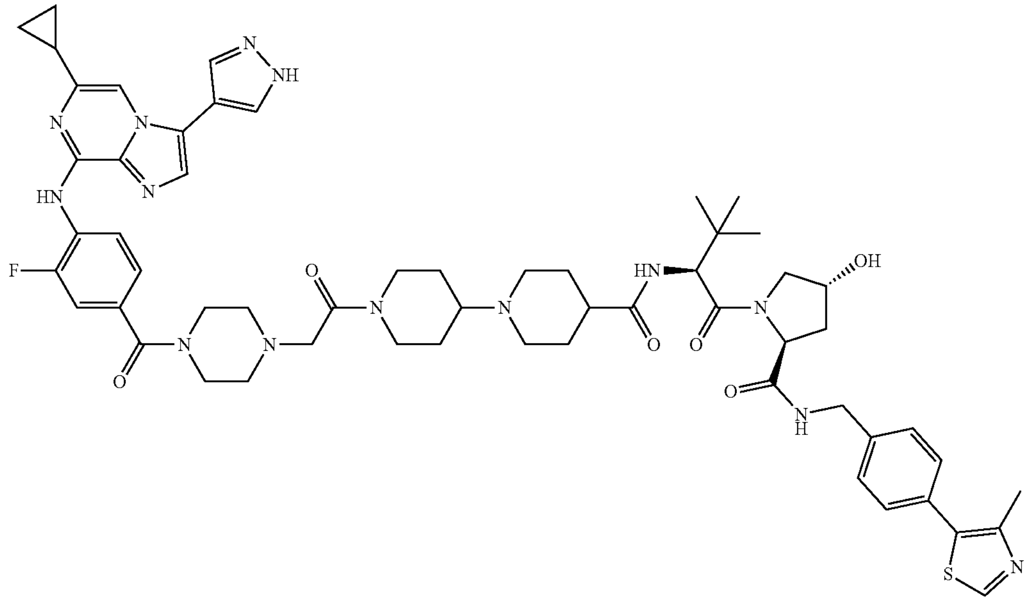 [SMILES: Cc1ncsc1-c1ccc(CNC(=O)[C@@H]2C[C@@H](O)CN2C(=O)[C@@H](NC(=O)C2CCN(C3CCN(C(=O)CN4CCN(C(=O)c5ccc(Nc6nc(C7CC7)cn7c(-c8cn[nH]c8)cnc67)c(F)c5)CC4)CC3)CC2)C(C)(C)C)cc1]

Example 103: 1'-(2-(4-(4-((6-Cyclopropyl-3-(1H-pyrazol-4-yl)imidazo[1,2-a]pyrazin-8-yl)amino)-3-fluorobenzoyl)piperazin-1-yl)acetyl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-[1,4'-bipiperidine]-4-carboxamide. 66% yield. $^1$H NMR (600 MHz, $CD_3OD$) δ 9.00 (s, 1H), 8.69 (t, J=8.2 Hz, 1H), 8.16 (s, 2H), 7.99 (s, 1H), 7.90 (s, 1H), 7.52-7.39 (m, 6H), 4.73 (d, J=12.8 Hz, 1H), 4.65 (d, J=8.8 Hz, 1H), 4.61-4.50 (m, 3H), 4.46 (d, J=16.2 Hz, 1H), 4.41-4.32 (m, 2H), 4.14-3.94 (m, 2H), 3.90-3.88 (m, 1H), 3.83 (dd, J=10.9, 3.7 Hz, 1H), 3.69-3.61 (m, 2H), 3.59-3.41 (m, 4H), 3.22 (t, J=12.4 Hz, 1H), 3.11-3.06 (m, 1H), 2.79 (t, J=12.4 Hz, 1H), 2.74-2.65 (m, 1H), 2.50 (s, 3H), 2.31-2.18 (m, 3H), 2.18-2.06 (m, 4H), 2.06-1.93 (m, 2H), 1.91-1.78 (m, 1H), 1.76-1.62 (m, 1H), 1.11-1.01 (m, 11H), 1.01-0.94 (m, 2H). HRMS (ESI-TOF) m/z: $[M+H]^+$ calcd for $C_{56}H_{68}FN_{14}O_7S^+$, 1099.5095; found 1099.5088.

Example 104: $N^1$-(1-(2-(4-(4-((6-Cyclopropyl-3-(1H-pyrazol-4-yl)imidazo[1,2-a]pyrazin-8-yl)amino)-3-fluorobenzoyl)piperazin-1-yl)acetyl)piperidin-4-yl)-$N^4$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide. 60% yield. $^1$H NMR (600 MHz, $CD_3OD$) δ 9.00 (s, 1H), 8.70 (t, J=8.2 Hz, 1H), 8.16 (s, 2H), 7.99 (s, 1H), 7.89 (s, 1H), 7.52-7.39 (m, 6H), 4.63 (s, 1H), 4.60-4.49 (m, 3H), 4.44-4.30 (m, 5H), 4.27-3.76 (m, 7H), 3.76-3.63 (m, 2H), 3.65-3.36 (m, 4H), 3.23 (t, J=12.9 Hz, 1H), 2.98 (t, J=12.1 Hz, 1H), 2.66-2.59 (m, 1H), 2.57-2.52 (m, 1H), 2.52-2.47 (m, 6H), 2.29-2.20 (m, 1H), 2.17-2.06 (m, 2H), 2.03-1.89 (m, 2H), 1.57-1.28 (m, 4H), 1.09-1.01 (m, 11H), 1.01-0.93 (m, 2H). HRMS (ESI-TOF) m/z: $[M+H]^+$ calcd for $C_{56}H_{72}FN_{14}O_6S^+$, 1111.5499; found 1111.5483.

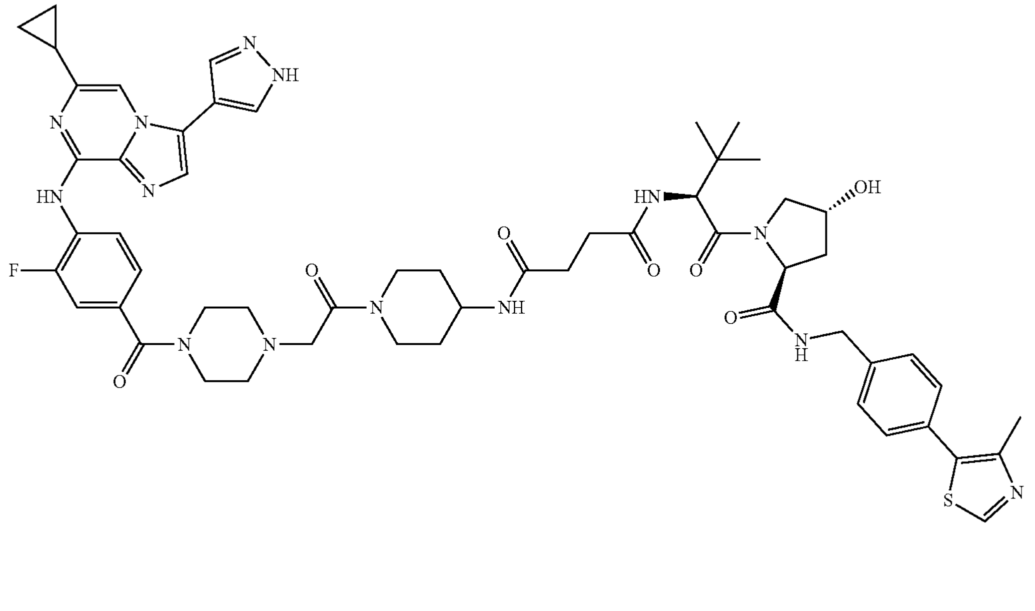 [SMILES: Cc1ncsc1-c1ccc(CNC(=O)[C@@H]2C[C@@H](O)CN2C(=O)[C@@H](NC(=O)CCC(=O)NC2CCN(C(=O)CN3CCN(C(=O)c4ccc(Nc5nc(C6CC6)cn6c(-c7cn[nH]c7)cnc56)c(F)c4)CC3)CC2)C(C)(C)C)cc1]

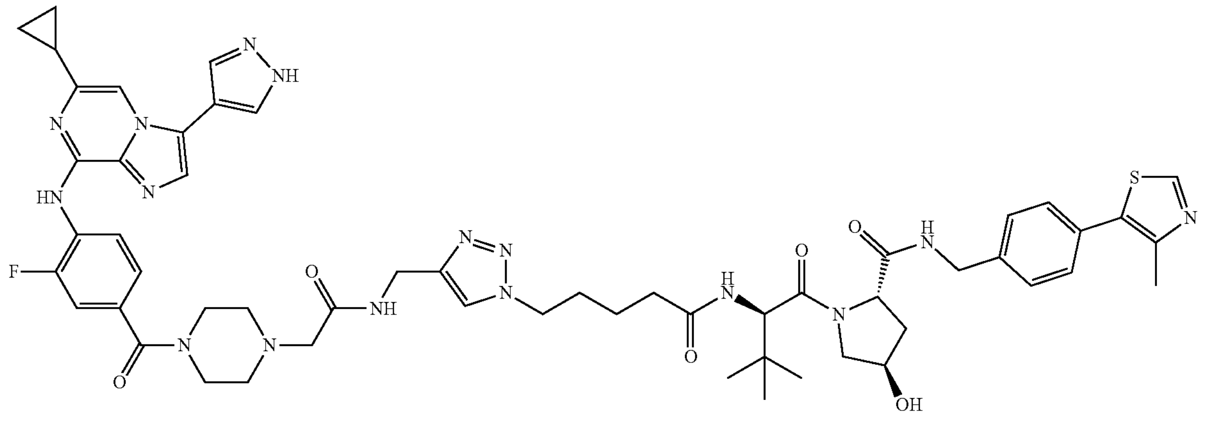 [SMILES: Cc1ncsc1-c1ccc(CNC(=O)[C@@H]2C[C@@H](O)CN2C(=O)[C@H](NC(=O)CCCCn2cc(CNC(=O)CN3CCN(C(=O)c4ccc(Nc5nc(C6CC6)cn6c(-c7cn[nH]c7)cnc56)c(F)c4)CC3)nn2)C(C)(C)C)cc1]

Example 105: (2S,4R)-1-((R)-2-(5-(4-((2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)methyl)-1H-1,2,3-triazol-1-yl)pentanamido)-3,3-dimethylbutanoyl)-4-hydroxy-N-(4-(4-methylthiazol-5-yl)benzyl)pyrrolidine-2-carboxamide. 71% yield. $^1$H NMR (600 MHz, $CD_3OD$) δ 8.97 (s, 1H), 8.69 (t, J=8.2 Hz, 1H), 8.16 (s, 2H), 7.98 (s, 1H), 7.95 (s, 1H), 7.88 (s, 1H), 7.51-7.35 (m, 6H), 4.63 (s, 1H), 4.60-4.56 (m, 1H), 4.56-4.49 (m, 4H), 4.44-4.36 (m, 3H), 4.10-3.85 (m, 7H), 3.82 (dd, J=10.9, 3.8 Hz, 1H), 3.57-3.40 (m, 4H), 2.49 (s, 3H), 2.37-2.28 (m, 2H), 2.28-2.22 (m, 1H), 2.17-2.06 (m, 2H), 1.96-1.87 (m, 2H), 1.66-1.55 (m, 2H), 1.07-1.00 (m, 1H), 1.00-0.94 (m, 2H). HRMS (ESI-TOF) m/z: $[M+H]^+$ calcd for $C_{55}H_{66}FN_{16}O_6S^+$, 1097.5050; found 1097.5059.

Example 106: (3R,5S)-1-((R)-2-(7-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-5-((4-(4-methylthiazol-5-yl)benzyl)carbamoyl)pyrrolidin-3-yl acetate. 64% yield. $^1$H NMR (600 MHz, $CD_3OD$) δ 8.95 (s, 1H), 8.72 (t, J=8.2 Hz, 1H), 8.15 (s, 2H), 7.96 (s, 1H), 7.85 (s, 1H), 7.53-7.30 (m, 6H), 5.40-5.34 (m, 1H), 4.60-4.49 (m, 3H), 4.39 (d, J=15.4 Hz, 1H), 4.19 (d, J=11.8 Hz, 1H), 4.14-3.77 (m, 7H), 3.55-3.39 (m, 4H), 3.28 (t, J=7.0 Hz, 2H), 2.49 (s, 3H), 2.44-2.37 (m, 1H), 2.37-2.22 (m, 3H), 2.16-2.10 (m, 1H), 2.06 (s, 3H), 1.69-1.60 (m, 2H), 1.60-1.51 (m, 2H), 1.44-1.33 (m, 4H), 1.10-1.00 (m, 11H), 0.99-0.94 (m, 2H). HRMS (ESI-TOF) m/z: $[M+H]^+$ calcd for $C_{55}H_{69}FN_{13}O_7S^+$, 1086.5142; found 1086.5154.

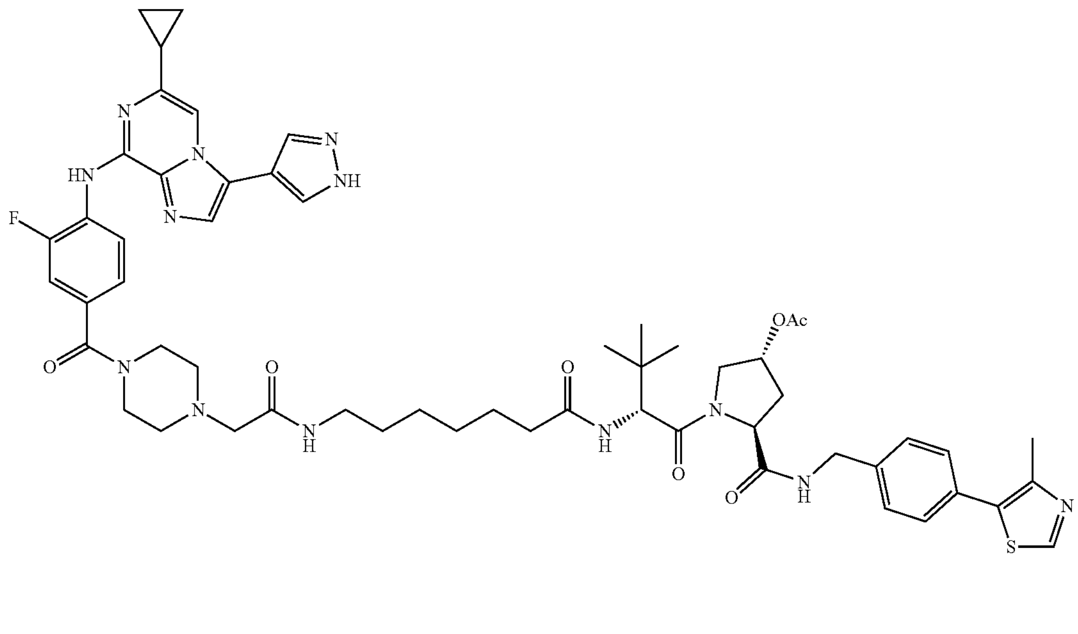 [SMILES: CC(=O)O[C@@H]1C[C@@H](C(=O)NCc2ccc(-c3scnc3C)cc2)N(C(=O)[C@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)C1]

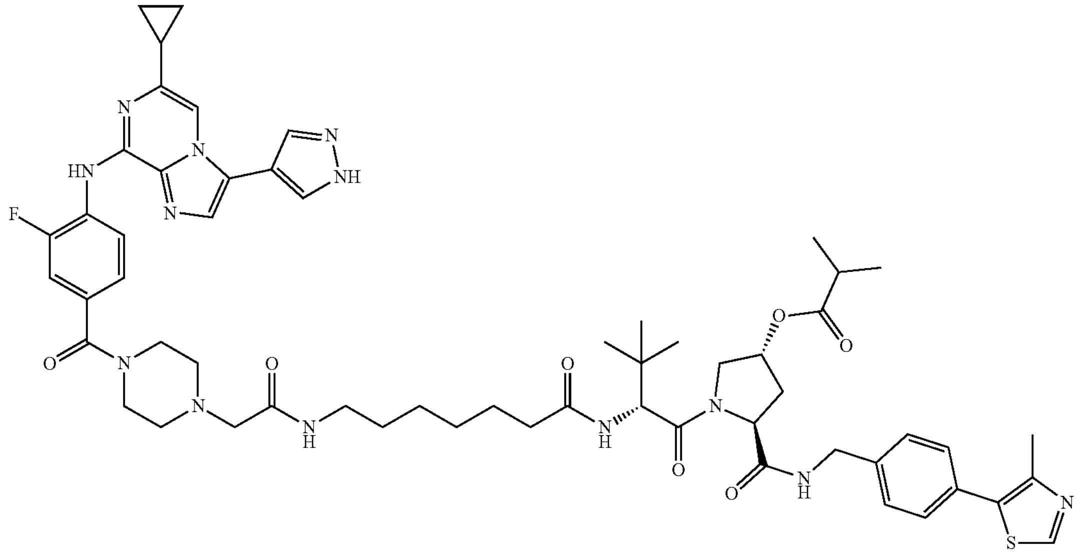 [SMILES: Cc1ncsc1-c1ccc(CNC(=O)[C@@H]2C[C@@H](OC(=O)C(C)C)CN2C(=O)[C@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)cc1]

Example 107: (3R,5S)-1-((R)-2-(7-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-5-((4-(4-methylthiazol-5-yl)benzyl)carbamoyl)pyrrolidin-3-yl isobutyrate. 68% yield. $^1$H NMR (600 MHz, $CD_3OD$) δ 8.99 (s, 1H), 8.68 (t, J=8.2 Hz, 1H), 8.16 (s, 2H), 7.98 (s, 1H), 7.89 (s, 1H), 7.50-7.36 (m, 6H), 5.41-5.35 (m, 1H), 4.63-4.51 (m, 3H), 4.39 (d, J=15.5 Hz, 1H), 4.16 (d, J=11.8 Hz, 1H), 4.11-3.81 (m, 7H), 3.42 (d, J=61.1 Hz, 4H), 3.27 (t, J=7.0 Hz, 2H), 2.59-2.52 (m, 1H), 2.49 (s, 3H), 2.43-2.36 (m, 1H), 2.36-2.20 (m, 3H), 2.17-2.08 (m, 1H), 1.68-1.50 (m, 4H), 1.44-1.30 (m, 4H), 1.15 (d, J=7.0 Hz, 6H), 1.08-1.02 (m, 11H), 1.01-0.94 (m, 2H). HRMS (ESI-TOF) m/z: $[M+H]^+$ calcd for $C_{57}H_{73}FN_{13}O_7S^+$, 1114.5455; found 1114.5437.

Example 130: (2S,4R)-1-((S)-2-(3-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethoxy)propanamido)-3,3-dimethylbutanoyl)-4-hydroxy-N-(4-(4-methylthiazol-5-yl)benzyl)pyrrolidine-2-carboxamide. 60% yield. $^1$H NMR (600 MHz, $CD_3OD$) δ 8.92 (s, 1H), 8.70 (t, J=8.1 Hz, 1H), 8.15 (s, 2H), 7.96 (d, J=1.3 Hz, 1H), 7.86 (s, 1H), 7.49-7.36 (m, 6H), 4.68 (s, 1H), 4.61-4.50 (m, 2H), 4.50-4.41 (m, 2H), 4.13-3.81 (m, 8H), 3.75 (t, J=5.7 Hz, 2H), 3.66-3.54 (m, 2H), 3.54-3.41 (m, 6H), 2.60-2.51 (m, 2H), 2.46 (s, 3H), 2.33-2.24 (m, 1H), 2.18-2.06 (m, 2H), 1.11-1.01 (m, 11H), 1.01-0.94 (m, 2H). HRMS (ESI-TOF) m/z: $[M+H]^+$ calcd for $C_{52}H_{63}FN_3O_7S^+$, 1032.4673; found 1032.4677.

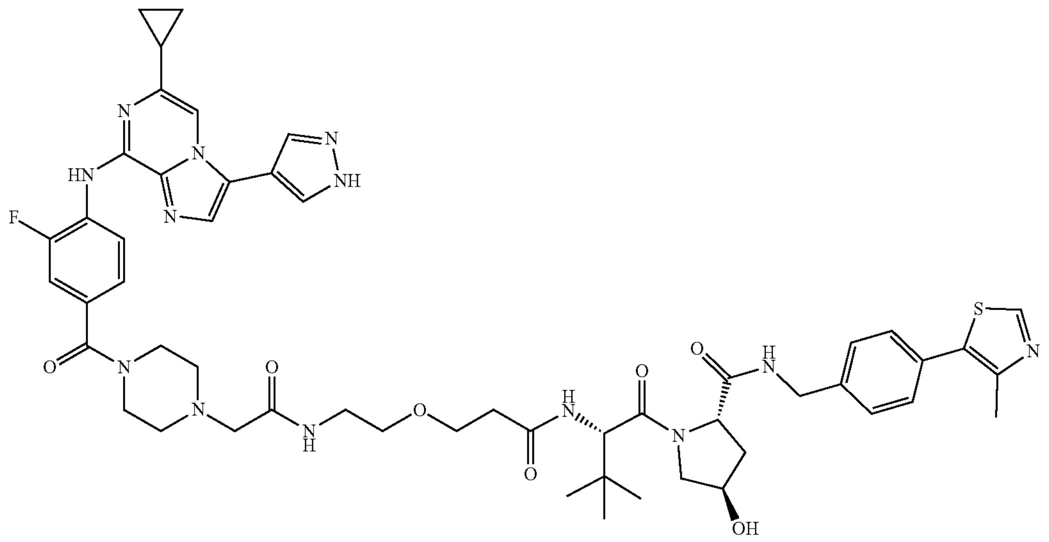 [SMILES: Cc1ncsc1-c1ccc(CNC(=O)[C@@H]2C[C@@H](O)CN2C(=O)[C@@H](NC(=O)CCOCCNC(=O)CN2CCN(C(=O)c3ccc(Nc4nc(C5CC5)cn5c(-c6cn[nH]c6)cnc45)c(F)c3)CC2)C(C)(C)C)cc1]

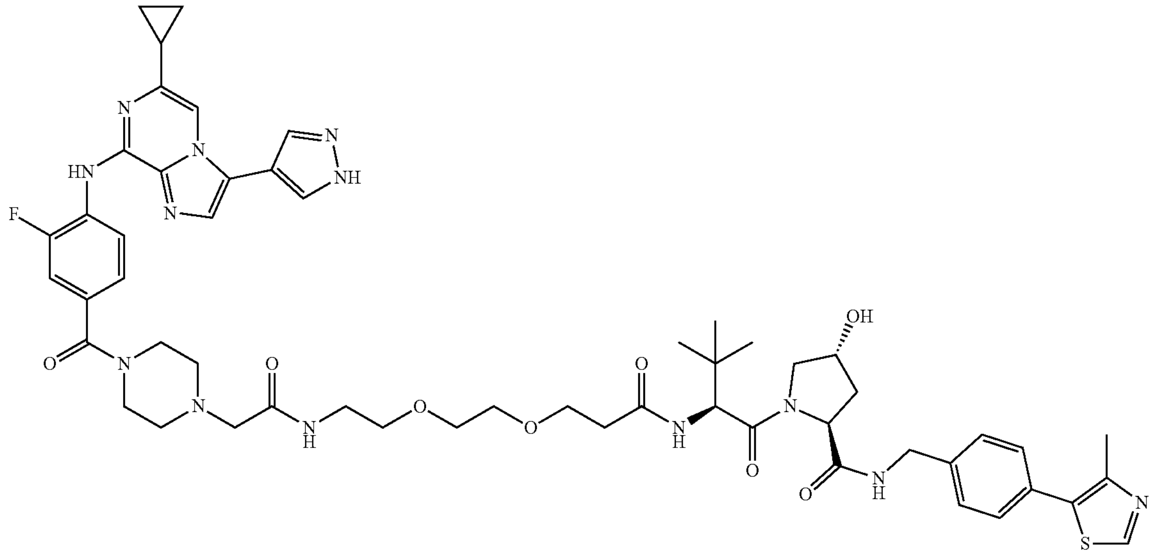 [SMILES: Cc1ncsc1-c1ccc(CNC(=O)[C@@H]2C[C@@H](O)CN2C(=O)[C@@H](NC(=O)CCOCCOCCNC(=O)CN2CCN(C(=O)c3ccc(Nc4nc(C5CC5)cn5c(-c6cn[nH]c6)cnc45)c(F)c3)CC2)C(C)(C)C)cc1]

Example 131: (2S,4R)-1-((S)-14-(tert-Butyl)-1-(4-(4-((6-cyclopropyl-3-(1H-pyrazol-4-yl)imidazo[1,2-a]pyrazin-8-yl)amino)-3-fluorobenzoyl)piperazin-1-yl)-2,12-dioxo-6,9-dioxa-3,13-diazapentadecan-15-oyl)-4-hydroxy-N-(4-(4-methylthiazol-5-yl)benzyl)pyrrolidine-2-carboxamide. 62% yield. $^1$H NMR (600 MHz, $CD_3OD$) δ 8.94 (s, 1H), 8.71 (t, J=8.2 Hz, 1H), 8.16 (s, 2H), 7.97 (s, 1H), 7.87 (s, 11H), 7.49-7.37 (m, 6H), 4.68 (s, 1H), 4.60-4.55 (m, 1H), 4.55-4.48 (m, 2H), 4.41 (d, J=15.4 Hz, 1H), 4.10-3.81 (m, 8H), 3.79-3.73 (m, 2H), 3.66-3.62 (m, 4H), 3.59 (t, J=5.3 Hz, 2H), 3.52-3.43 (m, 6H), 2.64-2.56 (m, 1H), 2.56-2.49 (m, 1H), 2.47 (s, 3H), 2.30-2.22 (m, 1H), 2.17-2.03 (m, 2H), 1.08-1.03 (m, 11H), 1.00-0.95 (m, 2H). HRMS (ESI-TOF) m/z: $[M+H]^+$ calcd for $C_{54}H_{67}FN_{13}O_8S^+$, 1076.4935; found 1076.4931.

Example 132: (2S,4R)-1-((S)-17-(tert-butyl)-1-(4-(4-((6-Cyclopropyl-3-(1H-pyrazol-4-yl)imidazo[1,2-a]pyrazin-8-yl)amino)-3-fluorobenzoyl)piperazin-1-yl)-2,15-dioxo-6,9,12-trioxa-3,16-diazaoctadecan-18-oyl)-4-hydroxy-N-(4-(4-methylthiazol-5-yl)benzyl)pyrrolidine-2-carboxamide. 61% yield. $^1$H NMR (600 MHz, $CD_3OD$) δ 8.96 (s, 1H), 8.70 (t, J=8.2 Hz, 1H), 8.16 (s, 2H), 7.98 (s, 1H), 7.88 (s, 1H), 7.51-7.37 (m, 6H), 4.67 (s, 1H), 4.58 (t, J=8.4 Hz, 1H), 4.55-4.50 (m, 2H), 4.39 (d, J=15.5 Hz, 1H), 4.10-3.85 (m, 7H), 3.82 (dd, J=11.0, 3.8 Hz, 1H), 3.80-3.72 (m, 2H), 3.66-3.62 (m, 8H), 3.59 (t, J=5.3 Hz, 2H), 3.55-3.43 (m, 6H), 2.65-2.56 (m, 1H), 2.56-2.50 (m, 1H), 2.48 (s, 3H), 2.30-2.22 (m, 1H), 2.17-2.06 (m, 2H), 1.08-1.02 (m, 11H), 0.97 (dm, J=8.0, 2.4 Hz, 2H). HRMS (ESI-TOF) m/z: $[M+H]^+$ calcd for $C_{56}H_{71}FN_{13}O_9S^+$, 1120.5197; found 1120.5190.

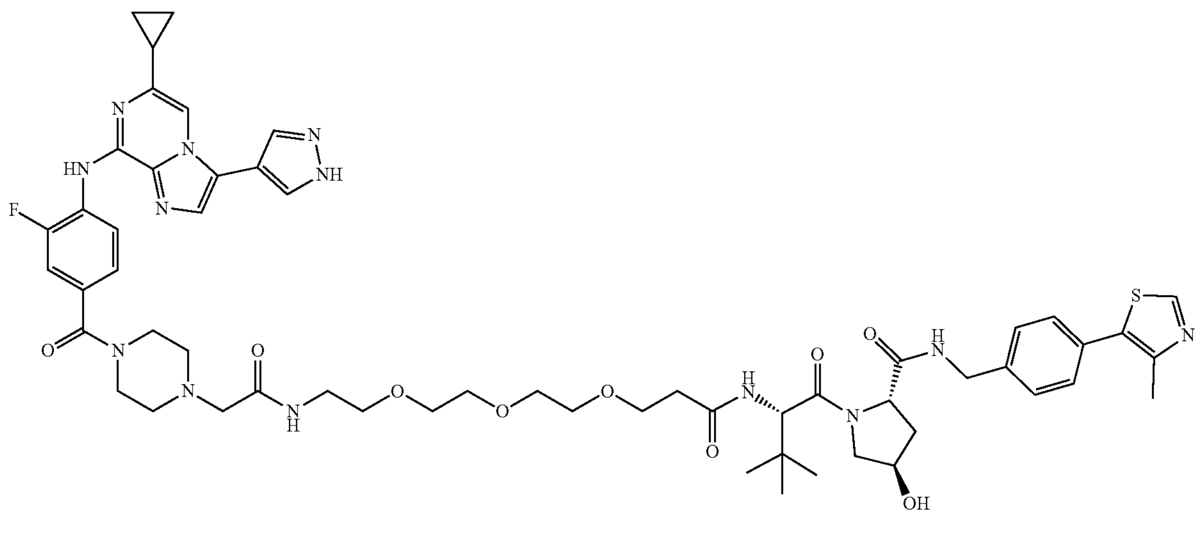 [SMILES: Cc1ncsc1-c1ccc(CNC(=O)[C@@H]2C[C@@H](O)CN2C(=O)[C@@H](NC(=O)CCOCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1]

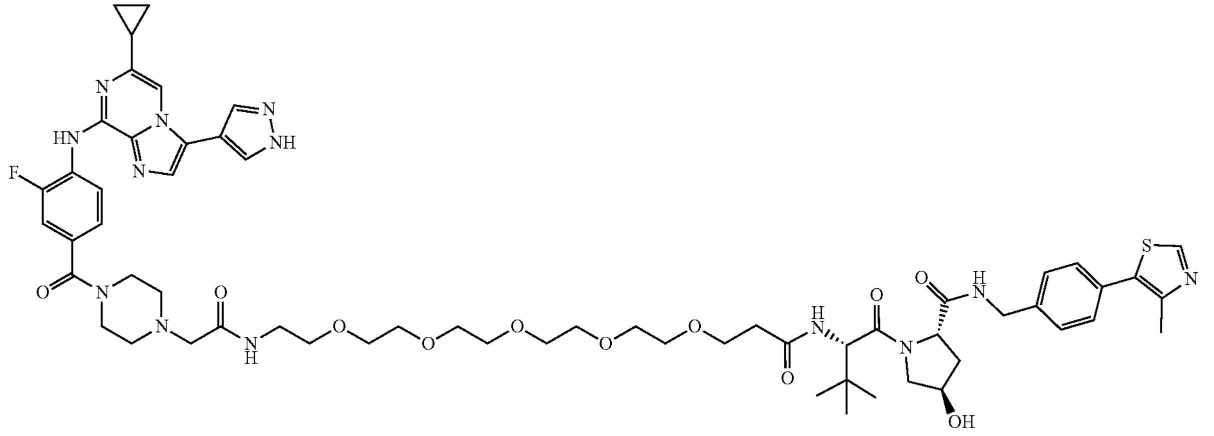 [SMILES: Cc1ncsc1-c1ccc(CNC(=O)[C@@H]2C[C@@H](O)CN2C(=O)[C@@H](NC(=O)CCOCCOCCOCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1]

Example 133: (2S,4R)-1-((S)-23-(tert-Butyl)-1-(4-(4-((6-cyclopropyl-3-(1H-pyrazol-4-yl)imidazo[1,2-a]pyrazin-8-yl)amino)-3-fluorobenzoyl)piperazin-1-yl)-2,21-dioxo-6,9,12,15,18-pentaoxa-3,22-diazatetracosan-24-oyl)-4-hydroxy-N-(4-(4-methylthiazol-5-yl)benzyl)pyrrolidine-2-carboxamide. 60% yield. $^1$H NMR (600 MHz, $CD_3OD$) δ 8.98 (s, 1H), 8.70 (t, J=8.2 Hz, 1H), 8.16 (s, 2H), 7.99 (s, 1H), 7.89 (s, 1H), 7.52-7.32 (m, 6H), 4.67 (s, 1H), 4.58 (t, J=8.4 Hz, 1H), 4.56-4.50 (m, 2H), 4.38 (d, J=15.5 Hz, 1H), 4.09-3.84 (m, 7H), 3.82 (dd, J=10.9, 3.8 Hz, 1H), 3.74 (ddd, J=13.1, 8.9, 4.7 Hz, 3H), 3.65-3.63 (m, 16H), 3.60 (t, J=5.3 Hz, 2H), 3.52-3.46 (m, 6H), 2.63-2.57 (m, 1H), 2.53-2.47 (m, 4H), 2.28-2.22 (m, 1H), 2.19-2.06 (m, 2H), 1.07-1.03 (m, 11H), 1.00-0.96 (m, 2H). HRMS (ESI-TOF) m/z: $[M+H]^+$ calcd for $C_{60}H_{79}FN_{13}O_{11}S^+$, 1208.5721; found 1208.5744.

Example 134: (2S,4R)-1-((S)-2-(tert-Butyl)-17-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide. 51% yield. $^1$H NMR (600 MHz, $CD_3OD$) δ 9.02 (s, 1H), 8.64 (t, J=8.2 Hz, 1H), 8.17 (s, 2H), 8.01 (s, 1H), 7.96 (s, 1H), 7.44 (ddd, J=16.4, 12.1, 7.9 Hz, 6H), 4.72 (s, 1H), 4.62-4.49 (m, 3H), 4.40 (d, J=15.5 Hz, 1H), 4.15-3.95 (m, 6H), 3.91 (d, J=11.0 Hz, 1H), 3.85-3.81 (m, 1H), 3.77-3.73 (m, 2H), 3.73-3.69 (m, 2H), 3.69-3.66 (m, 2H), 3.66-3.62 (m, 2H), 3.58 (t, J=5.0 Hz, 2H), 3.55-3.40 (m, 6H), 2.50 (s, 3H), 2.32-2.23 (m, 1H), 2.12 (ddd, J=22.6, 10.6, 4.4 Hz, 2H), 1.11-1.02 (m, 11H), 1.01-0.94 (m, 2H). HRMS (ESI-TOF) m/z: $[M+H]^+$ calcd for $C_{55}H_{69}FN_{13}O_9S^+$, 1106.5040: found 1106.5049.

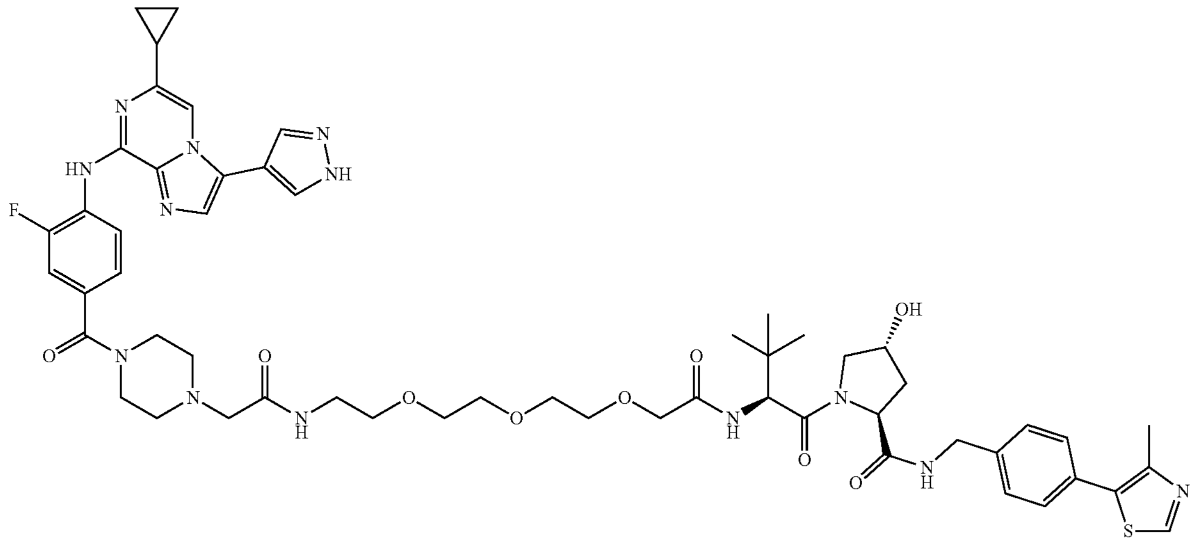 [SMILES: Cc1ncsc1-c1ccc(CNC(=O)[C@@H]2C[C@@H](O)CN2C(=O)[C@@H](NC(=O)COCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1]

Scheme 25. Synthesis of example 23

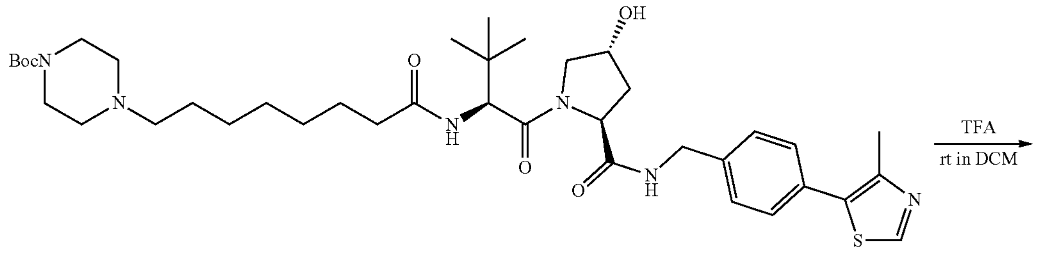

Linker 1

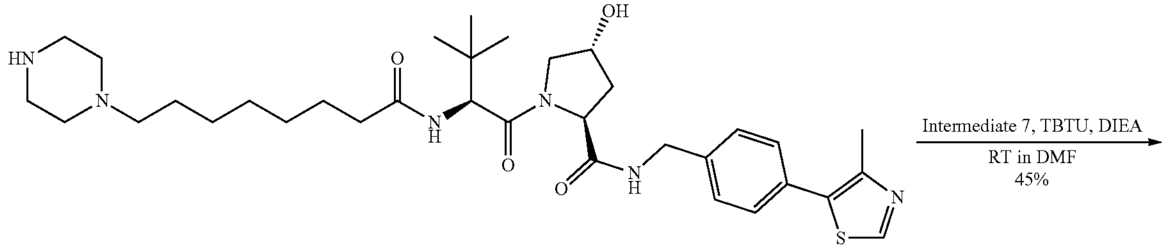

Intermediate 39

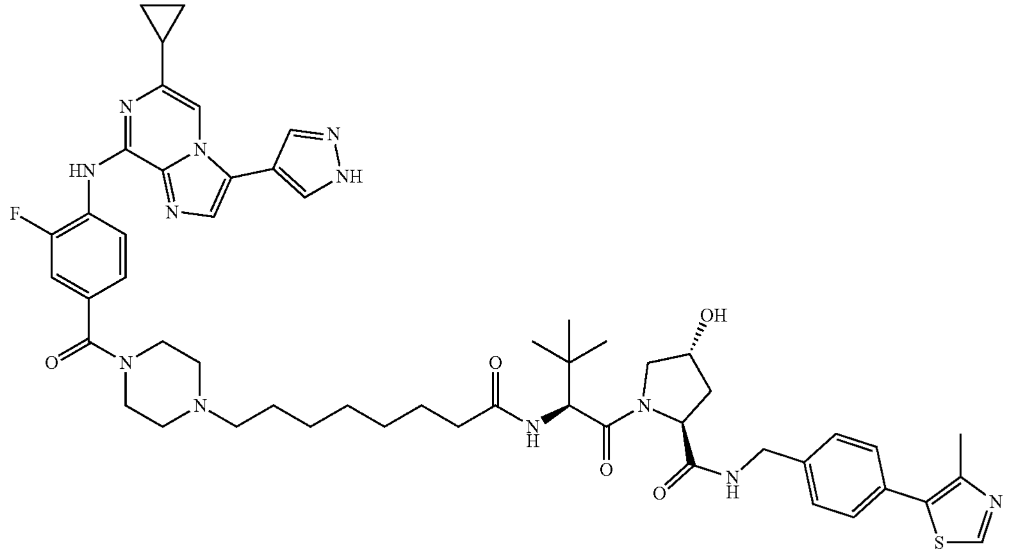

Example 23

Example 23: (2S,4R)-1-((S)-2-(8-(4-(4-((6-Cyclopropyl-3-(1H-pyrazol-4-yl)imidazo[1,2-a]pyrazin-8-yl)amino)-3-fluorobenzoyl)piperazin-1-yl)octanamido)-3,3-dimethylbutanoyl)-4-hydroxy-N-(4-(4-methylthiazol-5-yl)benzyl) pyrrolidine-2-carboxamide. A solution of linker 1 (14 mg, 0.019 mmol) in DCM/TFA (2:1, 1 mL) was stirred at rt for 2 h. After concentration under reduced pressure, the resulting crude intermediate 11 was obtained without further purification. To a solution of intermediate 11 and intermediate 7 (5.2 mg, 0.014 mmol) in DMF (1 mL) were added DIEA (17 μL, 0.1 mmol) and TBTU (7 mg, 0.02 mmol). After being stirred at rt for 12 h, the mixture was purified by HPLC to yield the title compound (6 mg, 45% yield) as brown oil. $^1$H NMR (600 MHz, $CD_3OD$) δ 8.97 (s, 1H), 8.72 (t, J=8.1 Hz, 1H), 8.16 (s, 2H), 7.99 (s, 1H), 7.88 (s, 1H), 7.52-7.38 (m, 6H), 4.67 (s, 1H), 4.61-4.48 (m, 3H), 4.39 (d, J=15.4 Hz, 1H), 3.93 (d, J=10.9 Hz, 1H), 3.83 (d, J=7.6 Hz, 1H), 3.73-3.39 (m, 6H), 3.26-3.11 (m, 4H), 2.50 (s, 3H), 2.38-2.20 (m, 3H), 2.20-2.05 (m, 2H), 1.83-1.73 (m, 2H), 1.73-1.58 (m, 2H), 1.50-1.34 (m, 6H), 1.11-0.93 (m, 13H). HRMS (ESI-TOF) m/z: $[M+H]^+$ calcd for $C_{53}H_{66}FN_{12}O_5S^+$, 1001.4978; found 1001.4999.

Example compounds 24-27 were synthesized according to the procedures for the preparation of example compound 23.

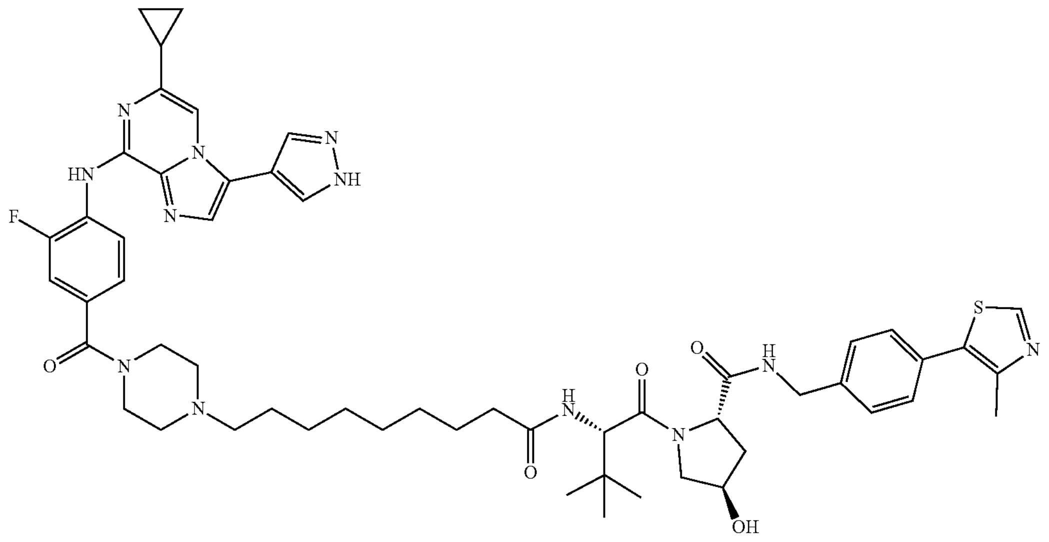 [SMILES: Cc1ncsc1-c1ccc(CNC(=O)[C@@H]2C[C@@H](O)CN2C(=O)[C@@H](NC(=O)CCCCCCCCN2CCN(C(=O)c3ccc(Nc4nc(C5CC5)cn5c(-c6cn[nH]c6)cnc45)c(F)c3)CC2)C(C)(C)C)cc1]

Example 24: (2S,4R)-1-((S)-2-(9-(4-(4-((6-Cyclopropyl-3-(1H-pyrazol-4-yl)imidazo[1,2-a]pyrazin-8-yl)amino)-3-fluorobenzoyl)piperazin-1-yl)nonanamido)-3,3-dimethylbutanoyl)-4-hydroxy-N-(4-(4-methylthiazol-5-yl)benzyl) pyrrolidine-2-carboxamide. 58% yield. $^1$H NMR (600 MHz, $CD_3OD$) δ 8.98 (s, JH), 8.72 (t, J=8.2 Hz, 1H), 8.15 (s, 2H), 7.98 (s, 1H), 7.88 (s, 1H), 7.52-7.38 (m, 6H), 4.67 (s, 1H), 4.64-4.50 (m, 3H), 4.39 (d, J=15.5 Hz, 1H), 3.92 (d, J=11.0 Hz, 1H), 3.83 (dd, J=10.9, 3.8 Hz, 1H), 3.73-3.40 (m, 6H), 3.27-3.13 (m, 4H), 2.50 (s, 3H), 2.37-2.20 (m, 3H), 2.17-2.07 (m, 2H), 1.83-1.73 (m, 2H), 1.71-1.59 (m, 2H), 1.50-1.35 (m, 8H), 1.04 (d, J=13.8 Hz, 11H), 1.00-0.92 (m, 2H). HRMS (ESI-TOF) m/z: $[M+H]^+$ calcd for $C_{54}H_{68}FN_{12}O_5S^+$, 1015.5135; found 1015.5110.

Example 25: (2S,4R)-1-((S)-2-(10-(4-(4-((6-Cyclopropyl-3-(1H-pyrazol-4-yl)imidazo[1,2-a]pyrazin-8-yl)amino)-3-fluorobenzoyl)piperazin-1-yl)decanamido)-3,3-dimethylbutanoyl)-4-hydroxy-N-(4-(4-methylthiazol-5-yl)benzyl) pyrrolidine-2-carboxamide. 67% yield. $^1$H NMR (600 MHz, $CD_3OD$) δ 8.95 (s, 1H), 8.77 (t, J=8.2 Hz, 1H), 8.16 (s, 2H), 7.98 (s, 1H), 7.83 (s, 1H), 7.52-7.34 (m, 6H), 4.66 (s, 1H), 4.62-4.48 (m, 3H), 4.38 (d, J=15.5 Hz, J H), 3.92 (d, J=11.0 Hz, 1H), 3.83 (dd, J=10.9, 3.9 Hz, 1H), 3.74-3.38 (m, 6H), 3.25-3.12 (m, 4H), 2.49 (s, 3H), 2.37-2.18 (m, 3H), 2.18-2.04 (m, 2H), 1.85-1.72 (m, 2H), 1.69-1.54 (m, 2H), 1.48-1.30 (m, 10H), 1.11-0.87 (m, 13H). HRMS (ESI-TOF) m/z: $[M+H]^+$ calcd for $C_{55}H_{70}FN_{12}O_5S^+$, 1029.5291; found 1029.5270.

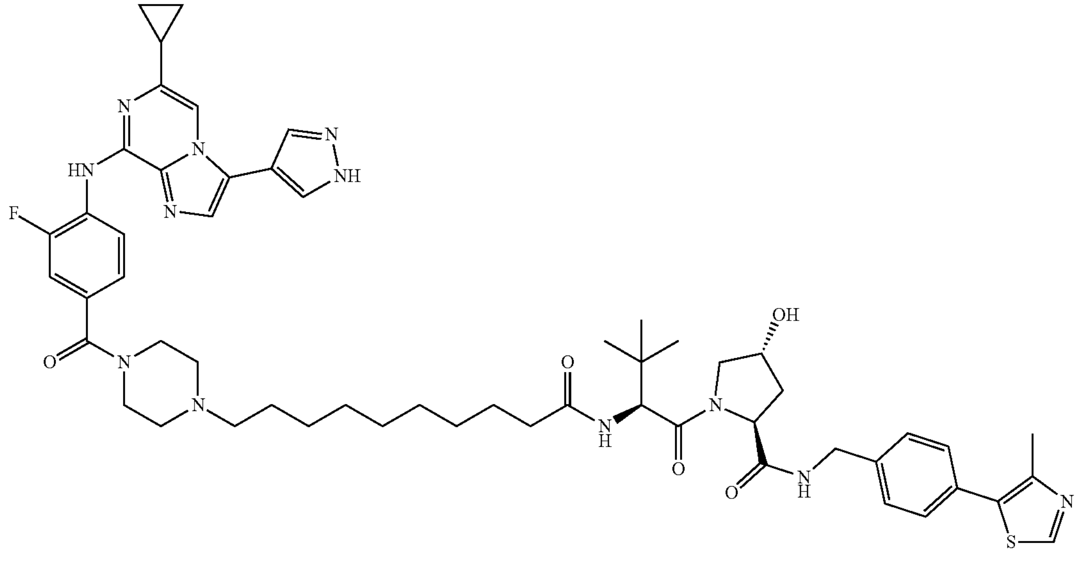 [SMILES: Cc1ncsc1-c1ccc(CNC(=O)[C@@H]2C[C@@H](O)CN2C(=O)[C@@H](NC(=O)CCCCCCCCCN2CCN(C(=O)c3ccc(Nc4nc(C5CC5)cn5c(-c6cn[nH]c6)cnc45)c(F)c3)CC2)C(C)(C)C)cc1]

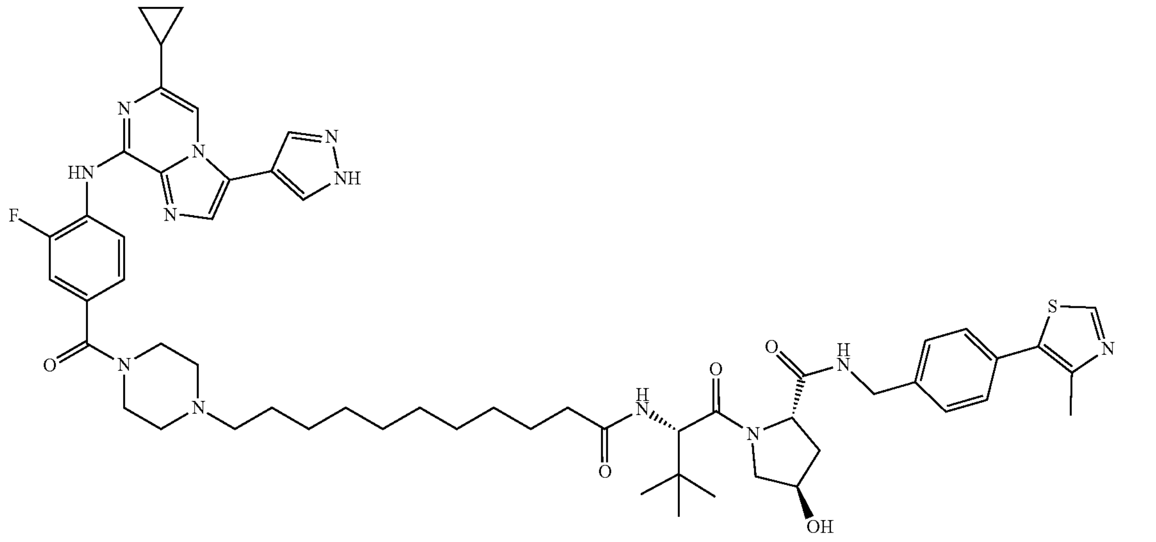 [SMILES: Cc1ncsc1-c1ccc(CNC(=O)[C@@H]2C[C@@H](O)CN2C(=O)[C@@H](NC(=O)CCCCCCCCCCN2CCN(C(=O)c3ccc(Nc4nc(C5CC5)cn5c(-c6cn[nH]c6)cnc45)c(F)c3)CC2)C(C)(C)C)cc1]

Example 26: (2S,4R)-1-((S)-2-(11-(4-(4-((6-Cyclopropyl-3-(1H-pyrazol-4-yl)imidazo[1,2-a]pyrazin-8-yl)amino)-3-fluorobenzoyl)piperazin-1-yl)undecanamido)-3,3-dimethylbutanoyl)-4-hydroxy-N-(4-(4-methylthiazol-5-yl)benzyl)pyrrolidine-2-carboxamide. 63% yield. $^1$H NMR (600 MHz, $CD_3OD$) δ 8.95 (s, 1H), 8.77 (t, J=8.2 Hz, 1H), 8.15 (s, 2H), 7.97 (s, 1H), 7.83 (s, 1H), 7.51-7.39 (m, 6H), 4.69-4.64 (m, 1H), 4.61-4.49 (m, 3H), 4.38 (dd, J=15.3, 4.8 Hz, 1H), 3.92 (d, J=11.1 Hz, 1H), 3.83 (dd, J=10.9, 3.9 Hz, 1H), 3.76-3.37 (m, 6H), 3.28-3.06 (m, 4H), 2.50 (s, 3H), 2.38-2.20 (m, 3H), 2.20-2.05 (m, 2H), 1.87-1.72 (m, 2H), 1.71-1.54 (m, 2H), 1.48-1.28 (m, 12H), 1.09-0.93 (m, 13H). HRMS (ESI-TOF) m/z: $[M+H]^+$ calcd for $C_{56}H_{72}FN_{12}O_5S^+$, 1043.5448; found 1043.5440.

Example 27: (2S,4R)-1-((S)-2-(12-(4-(4-((6-Cyclopropyl-3-(1H-pyrazol-4-yl)imidazo[1,2-a]pyrazin-8-yl)amino)-3-fluorobenzoyl)piperazin-1-yl)dodecanamido)-3,3-dimethylbutanoyl)-4-hydroxy-N-(4-(4-methylthiazol-5-yl)benzyl)pyrrolidine-2-carboxamide. 62% yield. $^1$H NMR (600 MHz, $CD_3OD$) δ 8.94 (s, 1H), 8.77 (t, J=8.2 Hz, 1H), 8.15 (s, 2H), 7.96 (s, 1H), 7.81 (s, 1H), 7.50-7.38 (m, 6H), 4.67 (s, 1H), 4.63-4.50 (m, 3H), 4.42-4.33 (m, 1H), 3.92 (d, J=11.0 Hz, 1H), 3.83 (dd, J=10.9, 3.9 Hz, 1H), 3.75-3.39 (m, 6H), 3.27-3.10 (m, 4H), 2.49 (s, 3H), 2.38-2.17 (m, 3H), 2.17-2.05 (m, 2H), 1.87-1.73 (m, 2H), 1.69-1.54 (m, 2H), 1.47-1.27 (m, 14H), 1.13-0.89 (m, 13H). HRMS (ESI-TOF) in. $[M+H]^+$ calcd for $C_{57}H_{74}FN_{12}O_5S^+$, 1057.5604; found 1057.5630.

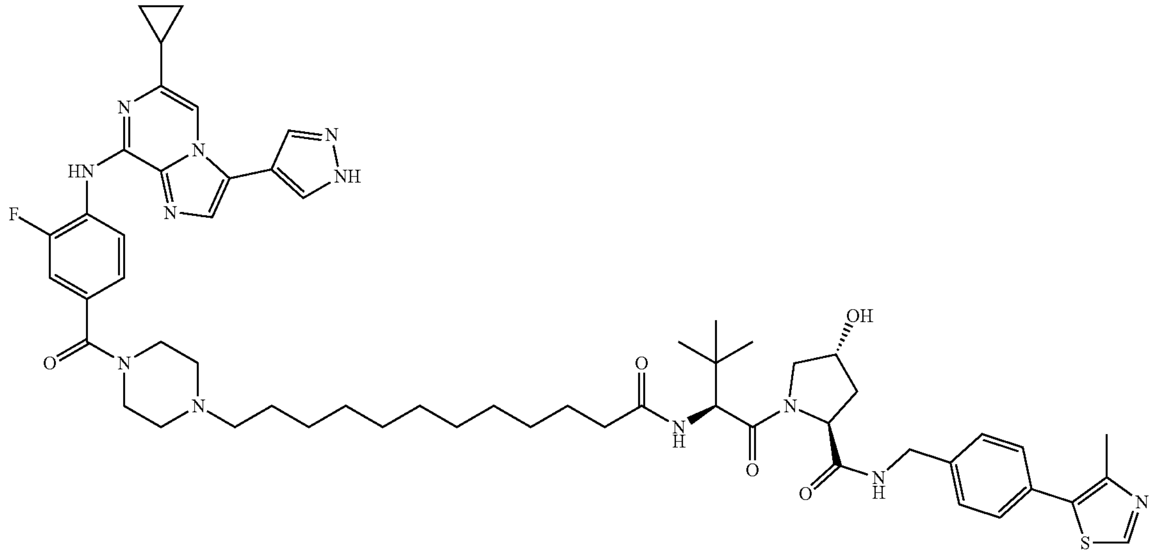 [SMILES: Cc1ncsc1-c1ccc(CNC(=O)[C@@H]2C[C@@H](O)CN2C(=O)[C@@H](NC(=O)CCCCCCCCCCCN2CCN(C(=O)c3ccc(Nc4nc(C5CC5)cn5c(-c6cn[nH]c6)cnc45)c(F)c3)CC2)C(C)(C)C)cc1]

Scheme 26. Synthesis of example 28

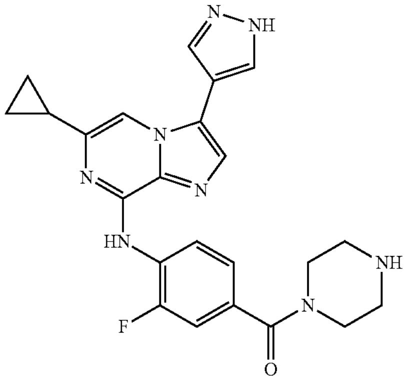

Intermediate 7

+

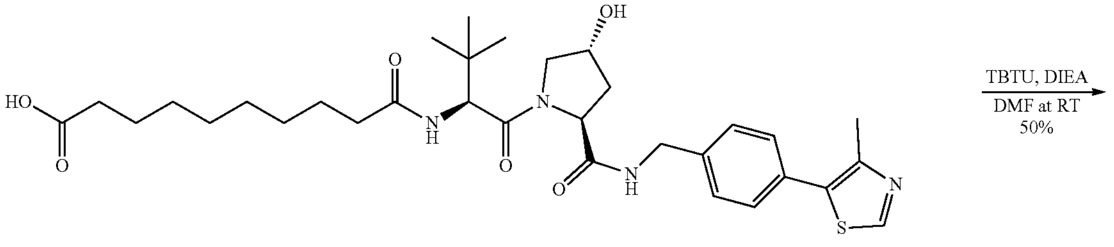

Linker 24

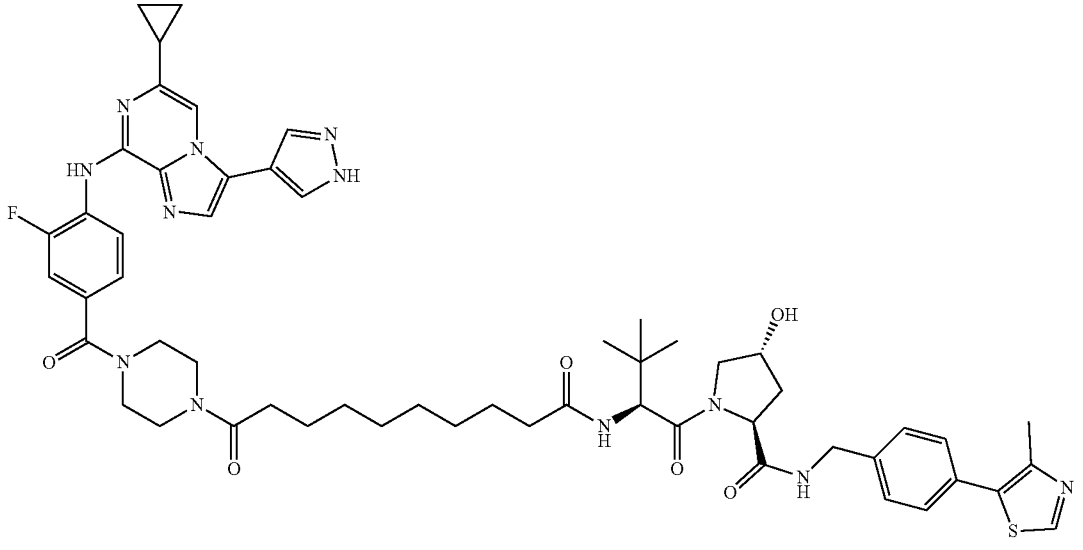

Example 28

Example 28: (2S,4R)-1-((S)-2-(10-(4-(4-((6-Cyclopropyl-3-(1H-pyrazol-4-yl)imidazo[1,2-a]pyrazin-8-yl)amino)-3-fluorobenzoyl)piperazin-1-yl)-10-oxodecanamido)-3,3-dimethylbutanoyl)-4-hydroxy-N-(4-(4-methylthiazol-5-yl)benzyl)pyrrolidine-2-carboxamide. To a solution of intermediate 7 (12 mg, 0.021 mmol) and linker 7 (11 mg, 0.018 mmol) in DMF (0.5 mL) were added DIEA (17 μL, 0.1 mmol) and TBTU (6 mg, 0.02 mmol). After being stirred at rt for 12 h, the mixture was purified by HPLC to yield the title compound (11 mg, 59%) as brown oil. $^1$H NMR (600 MHz, $CD_3OD$) δ 9.10 (s, 1H), 8.57 (t, J=8.1 Hz, 1H), 8.19 (s, 2H), 8.08-8.01 (m, 2H), 7.55-7.35 (m, 6H), 4.66 (s, 1H), 4.63-4.48 (m, 3H), 4.38 (dd, J=15.2, 6.4 Hz, 1H), 3.93 (d, J=11.0 Hz, 1H), 3.82 (dd, J=10.9, 3.8 Hz, 1H), 3.63 (br, 8H), 2.50 (s, 3H), 2.45 (s, 2H), 2.36-2.20 (m, 3H), 2.20-2.14 (m, 1H), 2.10 (ddd, J=11.2, 8.1, 3.4 Hz, 1H), 1.63 (br, 4H), 1.35 (br, J=12.8 Hz, 8H), 1.10-0.96 (m, 13H). HRMS (ESI-TOF) m/z: $[M+H]^+$ calcd for $C_{55}H_{68}FN_{12}O_6S^+$, 1043.5084; found 1043.5103.

Example compounds 29, 30, 32-36, 46-62 and 65-74 were synthesized according to the procedures for the preparation of example 28 compound.

-

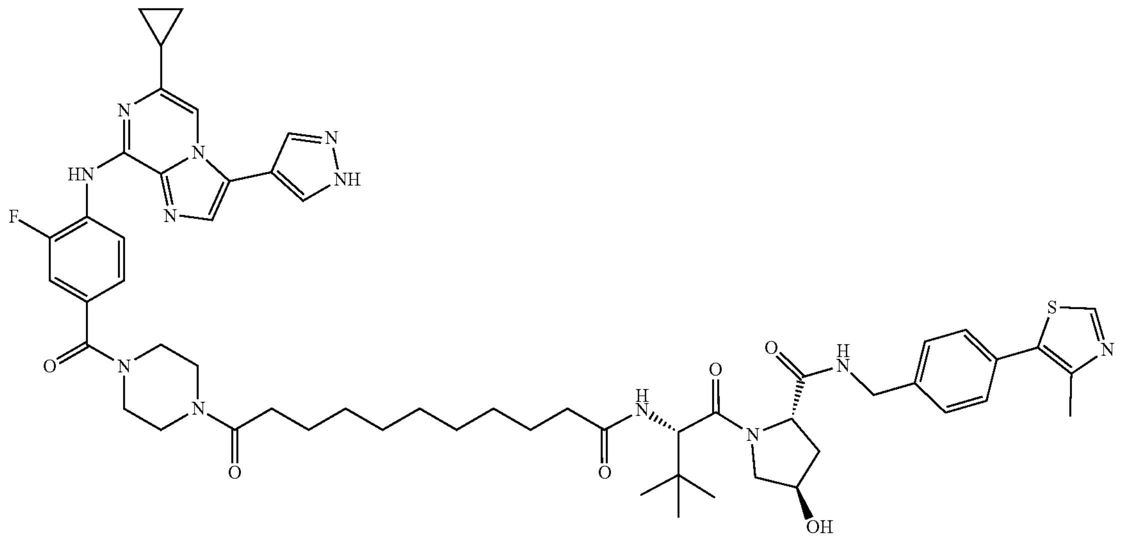 [SMILES: Cc1ncsc1-c1ccc(CNC(=O)[C@@H]2C[C@@H](O)CN2C(=O)[C@@H](NC(=O)CCCCCCCCCC(=O)N2CCN(C(=O)c3ccc(Nc4nc(C5CC5)cn5c(-c6cn[nH]c6)cnc45)c(F)c3)CC2)C(C)(C)C)cc1]

Example 29: (2S,4R)-1-((S)-2-(11-(4-(4-((6-Cyclopropyl-3-(1H-pyrazol-4-yl)imidazo[1,2-a]pyrazin-8-yl)amino)-3-fluorobenzoyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide. 60% yield. $^1$H NMR (600 MHz, $CD_3OD$) δ 9.12 (s, 1H), 8.56 (t, J=8.1 Hz, 1H), 8.20 (s, 2H), 8.07 (s, 2H), 7.55-7.33 (m, 6H), 4.66 (s, 1H), 4.63-4.48 (m, 3H), 4.38 (d, J=15.3 Hz, 1H), 3.93 (d, J=10.9 Hz, 1H), 3.82 (dd, J=10.9, 3.7 Hz, 1H), 3.78-3.47 (m, 8H), 2.53 (s, 3H), 2.49-2.38 (m, 2H), 2.35-2.21 (m, 3H), 2.21-2.14 (m, 1H), 2.14-2.06 (m, 1H), 1.63 (d, J=6.2 Hz, 4H), 1.35 (br, 10H), 1.12-0.96 (m, 13H). HRMS (ESI-TOF) m/z: $[M+H]^+$ calcd for $C_{56}H_{70}FN_{12}O_6S^+$, 1057.5241; found 1057.5269.

Example 30: (2S,4R)-1-((S)-2-(12-(4-(4-((6-Cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-4-hydroxy-N-(4-(4-methylthiazol-5-yl)benzyl)pyrrolidine-2-carboxamide. 69% yield. $^1$H NMR (600 MHz, $CD_3OD$) δ 9.04 (s, 1H), 8.60 (t, J=8.0 Hz, 1H), 8.18 (s, 2H), 8.02 (s, 1H), 7.98 (s, 1H), 7.54-7.32 (m, 6H), 4.66 (s, 1H), 4.63-4.49 (m, 3H), 4.38 (d, J=15.5 Hz, 1H), 3.92 (d, J=10.9 Hz, 1H), 3.87-3.45 (m, 9H), 2.50 (s, 3H), 2.45 (br, 2H), 2.38-2.20 (m, 3H), 2.19-2.01 (m, 2H), 1.62 (br, 4H), 1.34 (br, 12H), 1.12-0.89 (m, 13H). HRMS (ESI-TOF) m/z: $[M+H]^+$ calcd for $C_{57}H_{72}FN_{12}O_6S^+$, 1071.5397; found 1071.5420.

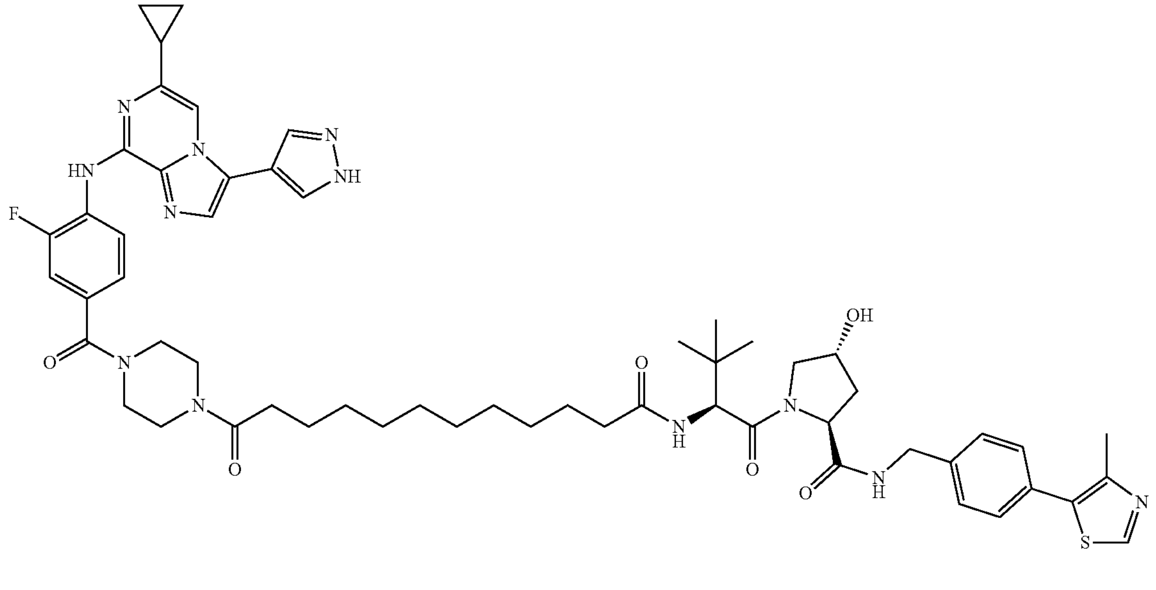 [SMILES: Cc1ncsc1-c1ccc(CNC(=O)[C@@H]2C[C@@H](O)CN2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1]

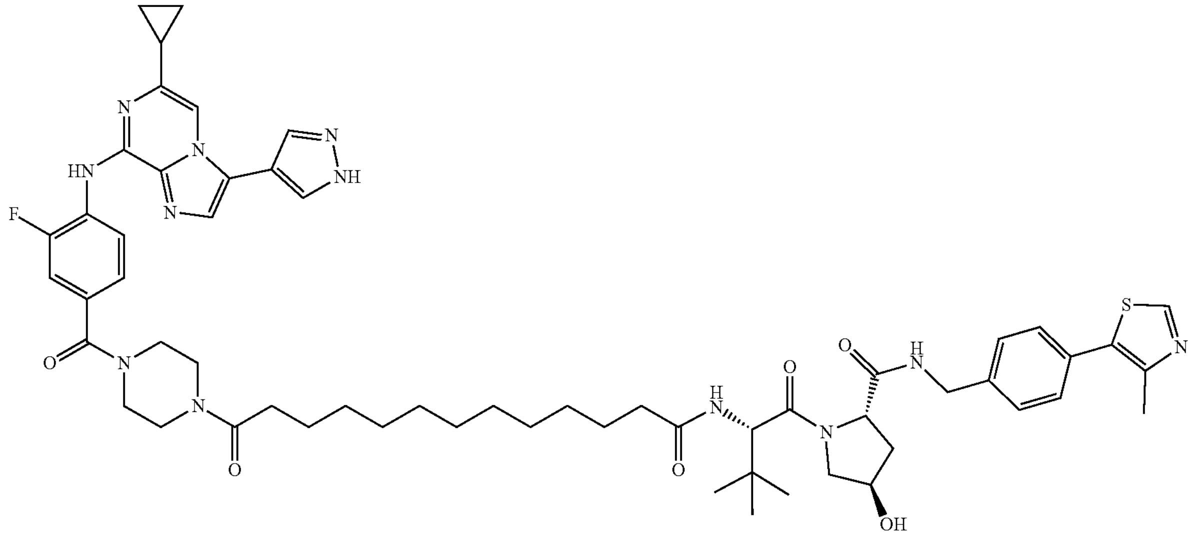 [SMILES: Cc1ncsc1-c1ccc(CNC(=O)[C@@H]2C[C@@H](O)CN2C(=O)[C@@H](NC(=O)CCCCCCCCCCCC(=O)N2CCN(C(=O)c3ccc(Nc4nc(C5CC5)cn5c(-c6cn[nH]c6)cnc45)c(F)c3)CC2)C(C)(C)C)cc1]

Example 32: (2S,4R)-1-((S)-2-(13-(4-(4-((6-Cyclopropyl-3-(1H-pyrazol-4-yl)imidazo[1,2-a]pyrazin-8-yl)amino)-3-fluorobenzoyl)piperazin-1-yl)-13-oxotridecanamido)-3,3-dimethylbutanoyl)-4-hydroxy-N-(4-(4-methylthiazol-5-yl)benzyl)pyrrolidine-2-carboxamide. 65% yield. $^1$H NMR (600 MHz, $CD_3OD$) δ 8.99 (s, 1H), 8.65 (t, J=8.0 Hz, 1H), 8.17 (s, 2H), 8.00 (s, 1H), 7.92 (s, 1H), 7.52-7.35 (m, 6H), 4.65 (s, 1H), 4.61-4.49 (m, 3H), 4.37 (d, J=15.5 Hz, 1H), 3.92 (d, J=10.8 Hz, 1H), 3.86-3.50 (m, 9H), 2.50 (s, 3H), 2.48-2.41 (m, 2H), 2.37-2.19 (m, 3H), 2.18-2.05 (m, 2H), 1.70-1.53 (m, 4H), 1.43-1.24 (m, 14H), 1.12-1.01 (m, 11H), 1.01-0.96 (m, 2H). HRMS (ESI-TOF) m/z: $[M+H]^+$ calcd for $C_{58}H_{74}FN_{12}O_6S^+$, 1085.5554; found 1085.5529.

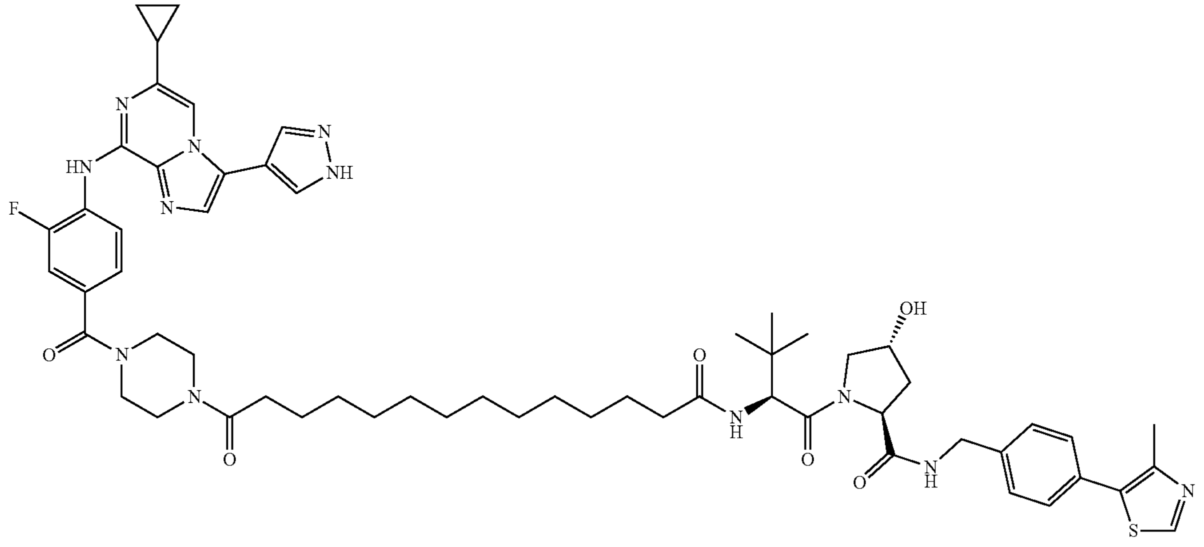 [SMILES: Cc1ncsc1-c1ccc(CNC(=O)[C@@H]2C[C@@H](O)CN2C(=O)[C@@H](NC(=O)CCCCCCCCCCCCC(=O)N2CCN(C(=O)c3ccc(Nc4nc(C5CC5)cn5c(-c6cn[nH]c6)cnc45)c(F)c3)CC2)C(C)(C)C)cc1]

Example 33: (2S,4R)-1-((S)-2-(14-(4-(4-((6-Cyclopropyl-3-(1H-pyrazol-4-yl)imidazo[1,2-a]pyrazin-8-yl)amino)-3-fluorobenzoyl)piperazin-1-yl)-14-oxotetradecanamido)-3,3-dimethylbutanoyl)-4-hydroxy-N-(4-(4-methylthiazol-5-yl)benzyl)pyrrolidine-2-carboxamide. 61% yield. $^1$H NMR (600 MHz, $CD_3OD$) δ 9.01 (s, 1H), 8.64 (t, J=7.9 Hz, 1H), 8.17 (s, 2H), 8.01 (s, 1H), 7.95 (s, 1H), 7.52-7.34 (m, 6H), 4.65 (s, 1H), 4.62-4.48 (m, 3H), 4.37 (d, J=15.5 Hz, 1H), 3.92 (d, J=10.9 Hz, 11H), 3.86-3.52 (m, 9H), 2.50 (s, 3H), 2.48-2.41 (m, 2H), 2.36-2.20 (m, 3H), 2.18-2.06 (m, 2H), 1.72-1.55 (m, 4H), 1.45-1.24 (m, 16H), 1.10-1.02 (m, 11H), 1.02-0.96 (m, 2H). HRMS (ESI-TOF) m/z: $[M+H]^+$ calcd for $C_{59}H_{76}FN_{12}O_6S^+$, 1099.5710; found 1099.5709.

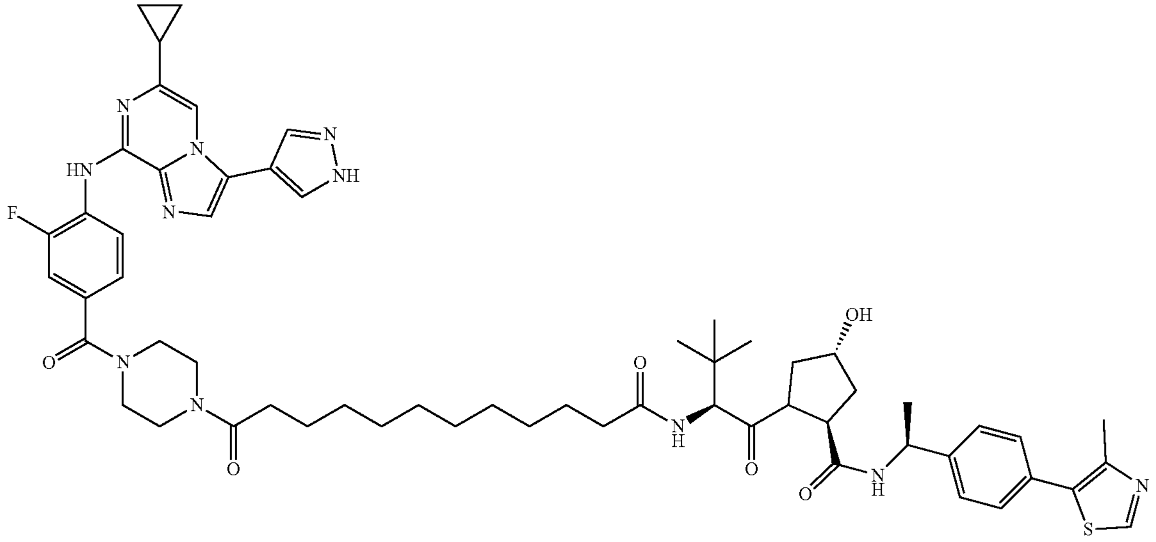 [SMILES: Cc1ncsc1-c1ccc([C@H](C)NC(=O)[C@@H]2C[C@@H](O)CC2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1]

Example 34: (2S,4R)-1-((S)-2-(12-(4-(4-((6-Cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-4-hydroxy-N—((S)-1-(4-(4-methylthiazol-5-yl)phenyl)ethyl)pyrrolidine-2-carboxamide. 63% yield. $^1$H NMR (600 MHz, $CD_3OD$) δ 9.04 (s, 1H), 8.61 (t, J=6.5 Hz, 1H), 8.18 (s, 2H), 8.02 (s, 1H), 7.97 (s, 1H), 7.50-7.35 (m, 6H), 5.02 (q, J=6.5 Hz, 1H), 4.65 (s, 1H), 4.59 (t, J=8.3 Hz, 1H), 4.45 (s, 1H), 3.90 (d, J=11.0 Hz, 1H), 3.86-3.50 (m, 9H), 2.51 (s, 3H), 2.49-2.41 (m, 2H), 2.37-2.18 (m, 3H), 2.18-2.11 (m, 1H), 2.00-1.92 (m, 1H), 1.72-1.56 (m, 5H), 1.52 (d, J=6.9 Hz, 3H), 1.44-1.28 (m, 12H), 1.11-1.02 (m, 11H), 1.02-0.96 (m, 2H). HRMS (ESI-TOF) m/z: $[M+H]^+$ calcd for $C_{55}H_{74}FN_{12}O_6S^+$, 1085.5554; found 1085.5550.

Example 35: (2S,4S)-1-((S)-2-(12-(4-(4-((6-Cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-4-hydroxy-N-(4-(4-methylthiazol-5-yl)benzyl)pyrrolidine-2-carboxamide. 70% yield. $^1$H NMR (600 MHz, $CD_3OD$) δ 9.13 (s, 1H), 8.55 (t, J=8.1 Hz, 1H), 8.20 (s, 2H), 8.06 (s, 1H), 7.52-7.36 (m, 6H), 4.61-4.49 (m, 3H), 4.41 (s, 2H), 4.07 (dd, J=10.5, 5.1 Hz, 1H), 3.88-3.50 (m, 9H), 2.51 (s, 3H), 2.48-2.39 (m, 3H), 2.34-2.22 (m, 2H), 2.20-2.13 (m, 1H), 2.01-1.96 (m, 1H), 1.70-1.52 (m, 4H), 1.44-1.29 (m, 12H), 1.10-0.97 (m, 13H). HRMS (ESI-TOF) m/z: $[M+H]^+$ calcd for $C_{57}H_{72}FN_2O_6S^+$, 1071.5397; found 1071.5388.

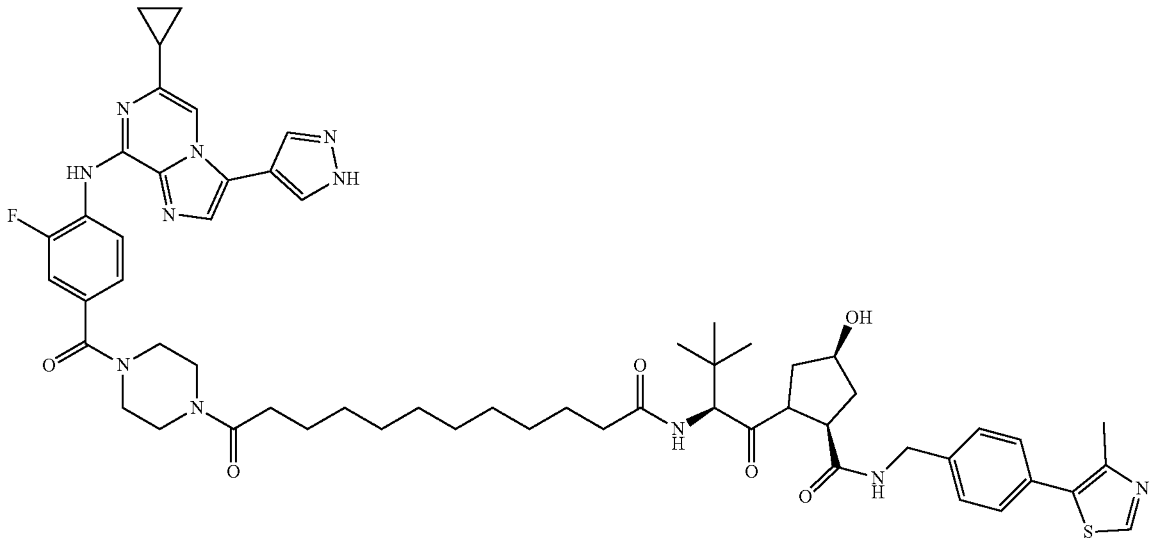 [SMILES: Cc1ncsc1-c1ccc(CNC(=O)[C@@H]2C[C@H](O)CC2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1]

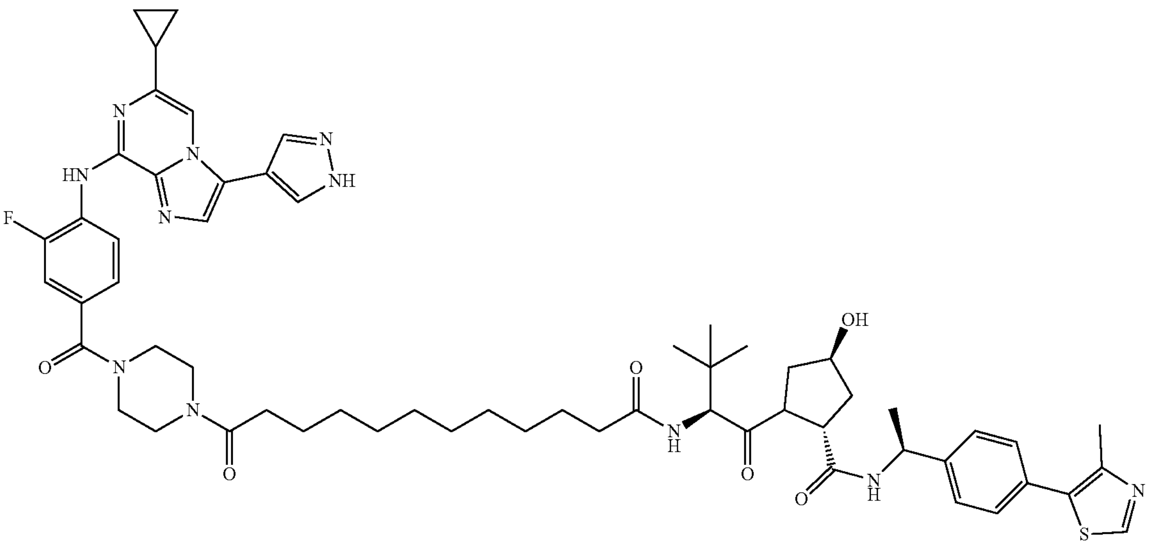 [SMILES: Cc1ncsc1-c1ccc([C@H](C)NC(=O)[C@H]2C[C@H](O)CC2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1]

Example 36: (2R,4S)-1-((S)-2-(12-(4-(4-((6-Cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-4-hydroxy-N—((S)-1-(4-(4-methylthiazol-5-yl)phenyl)ethyl)pyrrolidine-2-carboxamide. 69% yield. $^{1}$H NMR (500 MHz, $CD_3OD$) δ 8.91 (s, 1H), 8.73 (t, J=8.2 Hz, 1H), 8.13 (s, 2H), 7.91 (s, 1H), 7.77 (s, 1H), 7.52 (d, J=8.2 Hz, 2H), 7.45 (d, J=8.2 Hz, 2H), 7.43-7.38 (m, 1H), 7.35 (d, J=8.7 Hz, 1H), 5.12-4.98 (m, 1H), 4.61-4.54 (m, 1H), 4.52-4.42 (m, 2H), 3.97 (dd, J=10.7, 4.9 Hz, 1H), 3.84-3.51 (m, 9H), 2.50 (s, 3H), 2.48-2.39 (m, 2H), 2.34-2.27 (m, 1H), 2.27-2.17 (m, 2H), 2.16-2.04 (m, 2H), 1.70-1.51 (m, 4H), 1.47 (d, J=7.0 Hz, 3H), 1.31 (d, J=23.5 Hz, 14H), 1.13-1.01 (m, 11H), 0.95 (dt, J=6.8, 3.9 Hz, 2H). HRMS (ESI-TOF) m/z: $[M+H]^+$ calcd for $C_{58}H_{74}FN_{12}O_6S^+$, 1085.5554; found 1085.5561.

Example 46: (2S,4R)-1-((S)-2-(4-(4-(4-((6-Cyclopropyl-3-(1H-pyrazol-4-yl)imidazo[1,2-a]pyrazin-8-yl)amino)-3-fluorobenzoyl)piperazin-1-yl)-4-oxobutanamido)-3,3-dimethylbutanoyl)-4-hydroxy-N-(4-(4-methylthiazol-5-yl)benzyl)pyrrolidine-2-carboxamide. 63% yield. $^{1}$H NMR (500 MHz, $CD_3OD$) δ 9.03 (s, 1H), 8.59 (t, J=8.1 Hz, 1H), 8.17 (s, 2H), 8.03-7.95 (m, 2H), 7.57-7.35 (m, 6H), 4.62 (s, 1H), 4.61-4.49 (m, 3H), 4.39 (d, J=15.5 Hz, 1H), 3.91 (d, J=10.9 Hz, 1H), 3.82 (dd, J=10.9, 3.7 Hz, 1H), 3.68 (s, 8H), 2.81-2.56 (m, 4H), 2.50 (s, 3H), 2.31-2.20 (m, 1H), 2.20-2.06 (m, 2H), 1.06 (s, 111H), 1.02-0.95 (m, 2H). HRMS (ESI-TOF) m/z: $[M+H]^+$ calcd for $C_{49}H_{56}FN_{12}O_6S^+$, 959.4145; found 959.4130.

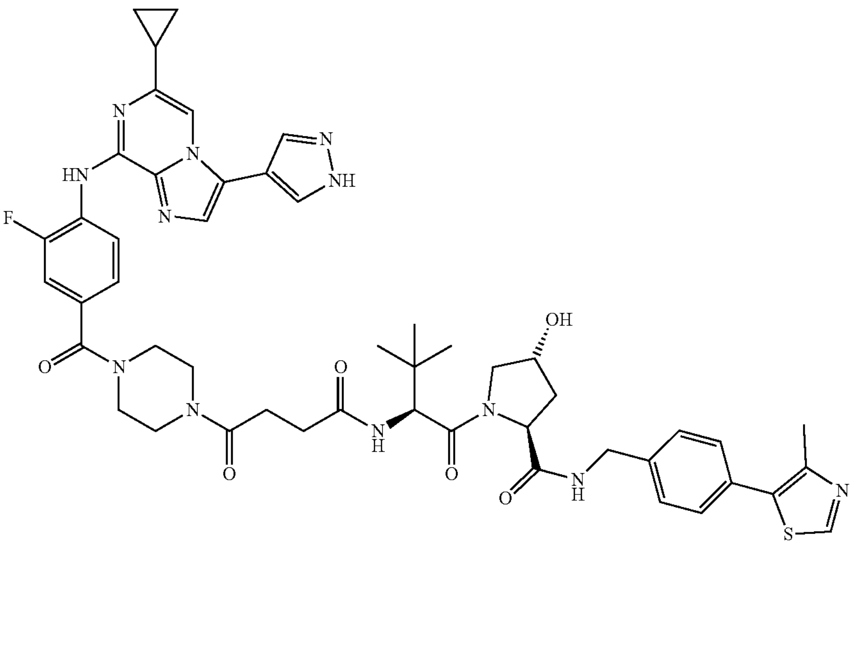

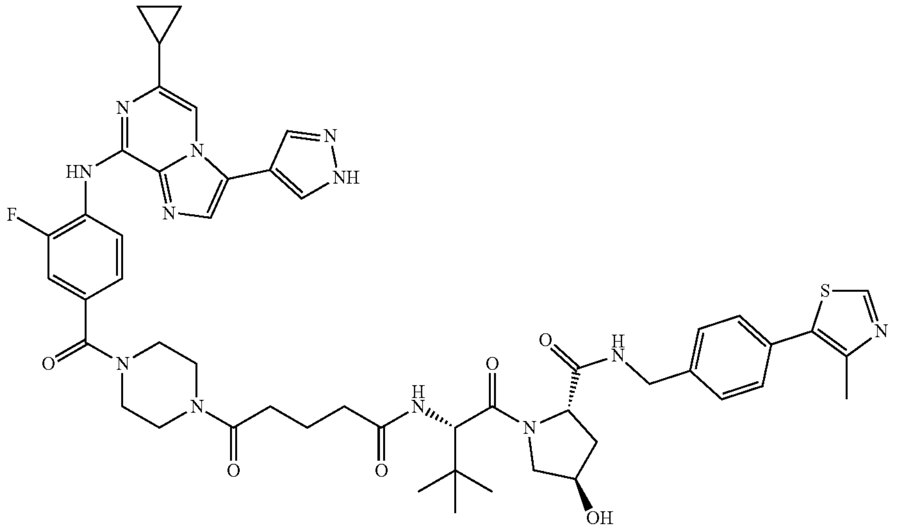 [SMILES: Cc1ncsc1-c1ccc(CNC(=O)[C@@H]2C[C@@H](O)CN2C(=O)[C@@H](NC(=O)CCCC(=O)N2CCN(C(=O)c3ccc(Nc4nc(C5CC5)cn5c(-c6cn[nH]c6)cnc45)c(F)c3)CC2)C(C)(C)C)cc1]

Example: 47: (2S,4R)-1-((S)-2-(5-(4-(4-((6-Cyclopropyl-3-(1H-pyrazol-4-yl)imidazo[1,2-a]pyrazin-8-yl)amino)-3-fluorobenzoyl)piperazin-1-yl)-5-oxopentanamido)-3,3-dimethylbutanoyl)-4-hydroxy-N-(4-(4-methylthiazol-5-yl)benzyl)pyrrolidine-2-carboxamide. 69% yield. $^1$H NMR (500 MHz, $CD_3OD$) δ 8.97 (s, 1H), 8.63 (s, 1H), 8.16 (s, 2H), 7.99 (s, 1H), 7.93 (s, 1H), 7.52-7.33 (m, 6H), 4.64 (s, 1H), 4.63-4.47 (m, 3H), 4.37 (d, J=15.5 Hz, 1H), 4.03-3.89 (m, 1H), 3.82 (d, J=8.3 Hz, 2H), 3.80-3.54 (m, 8H), 2.55-2.42 (m, 5H), 2.37 (t, J=7.0 Hz, 2H), 2.30-2.18 (m, 1H), 2.19-2.07 (m, 2H), 2.00-1.89 (m, 2H), 1.13-1.03 (m, 11H), 1.03-0.94 (m, 2H). HRMS (ESI-TOF) m/z: $[M+H]^+$ calcd for $C_{50}H_{58}FN_{12}O_6S^+$, 973.4302; found 973.4335

Example 48: (2S,4R)-1-((S)-2-(6-(4-(4-((6-Cyclopropyl-3-(1H-pyrazol-4-yl)imidazo[1,2-a]pyrazin-8-yl)amino)-3-fluorobenzoyl)piperazin-1-yl)-6-oxohexanamido)-3,3-dimethylbutanoyl)-4-hydroxy-N-(4-(4-methylthiazol-5-yl)benzyl)pyrrolidine-2-carboxamide. 68% yield. $^1$H NMR (500 MHz, $CD_3OD$) δ 8.98 (s, 1H), 8.64 (t, J=8.1 Hz, 1H), 8.17 (s, 2H), 8.00 (s, 1H), 7.93 (s, 1H), 7.53-7.34 (m, 6H), 4.66 (s, 1H), 4.62-4.49 (m, 3H), 4.38 (d, J=15.5 Hz, 1H), 3.93 (d, J=11.2 Hz, 1H), 3.87-3.80 (m, 1H), 3.78-3.54 (m, 8H), 2.56-2.41 (m, 5H), 2.41-2.29 (m, 2H), 2.28-2.20 (m, 1H), 2.19-2.07 (m, 2H), 1.80-1.54 (m, 4H), 1.12-1.02 (m, 11H), 1.02-0.94 (m, 2H). HRMS (ESI-TOF) m/z: $[M+H]^+$ calcd for $C_{51}H_{60}FN_{12}O_6S^+$, 987.4458; found 987.4440.

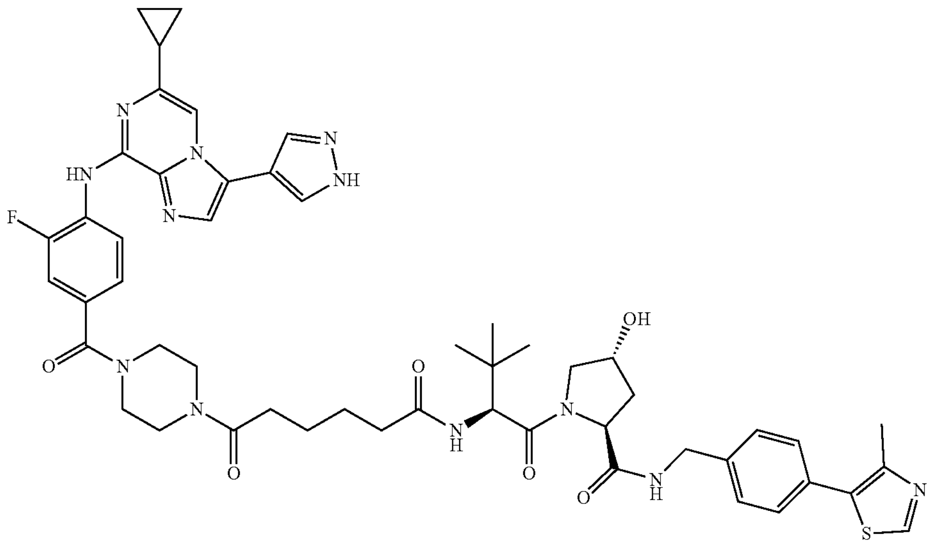 [SMILES: Cc1ncsc1-c1ccc(CNC(=O)[C@@H]2C[C@@H](O)CN2C(=O)[C@@H](NC(=O)CCCCC(=O)N2CCN(C(=O)c3ccc(Nc4nc(C5CC5)cn5c(-c6cn[nH]c6)cnc45)c(F)c3)CC2)C(C)(C)C)cc1]

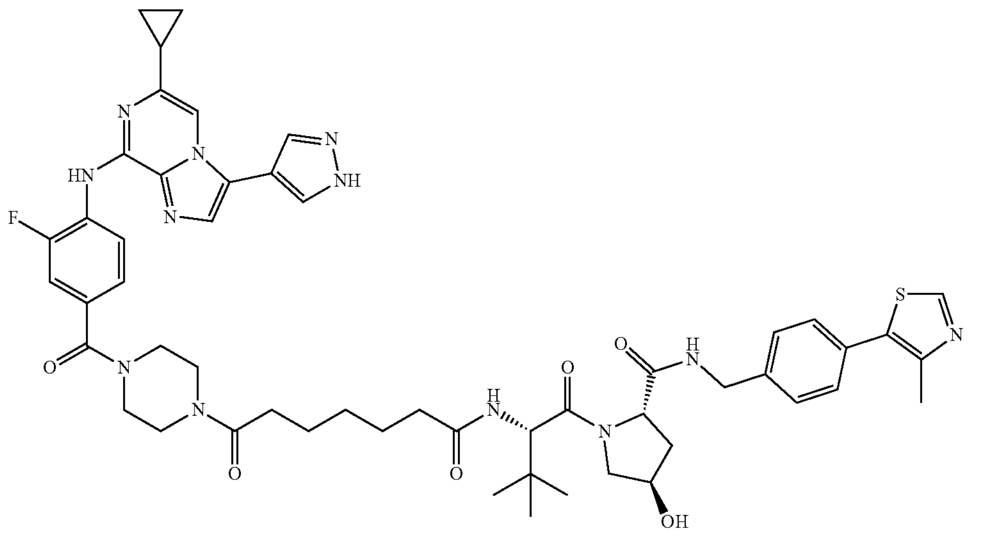 [SMILES: Cc1ncsc1-c1ccc(CNC(=O)[C@@H]2C[C@@H](O)CN2C(=O)[C@@H](NC(=O)CCCCCC(=O)N2CCN(C(=O)c3ccc(Nc4nc(C5CC5)cn5c(-c6cn[nH]c6)cnc45)c(F)c3)CC2)C(C)(C)C)cc1]

Example 49: (2S,4R)-1-((S)-2-(7-(4-(4-((6-Cyclopropyl-3-(1H-pyrazol-4-yl)imidazo[1,2-a]pyrazin-8-yl)amino)-3-fluorobenzoyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide. 61% yield. $^1$H NMR (500 MHz, $CD_3OD$) δ 9.98-9.35 (m, 1H), 9.00 (s, 1H), 8.61 (t, J=8.2 Hz, 1H), 8.16 (s, 2H), 7.99 (s, 1H), 7.94 (s, 1H), 7.42 (td, J=26.5, 8.6 Hz, 6H), 4.66 (s, 1H), 4.63-4.48 (m, 3H), 4.37 (d, J=15.5 Hz, 1H), 3.93 (d, J=11.0 Hz, 1H), 3.82 (dd, J=10.9, 3.7 Hz, 1H), 3.79-3.50 (m, 8H), 2.59-2.39 (m, 5H), 2.39-2.19 (m, 3H), 2.13 (ddd, J=13.4, 8.2, 3.7 Hz, 2H), 1.66 (d, J=6.6 Hz, 4H), 1.52-1.32 (m, 2H), 1.12-1.02 (m, 11H), 1.02-0.91 (m, 2H). HRMS (ESI-TOF) m/z: $[M+H]^+$ calcd for $C_{52}H_{62}FN_{12}O_6S^+$, 1001.4615; found 1001.4601.

Example 50: (2S,4R)-1-((S)-2-(8-(4-(4-((6-Cyclopropyl-3-(1H-pyrazol-4-yl)imidazo[1,2-a]pyrazin-8-yl)amino)-3-fluorobenzoyl)piperazin-1-yl)-8-oxooctanamido)-3,3-dimethylbutanoyl)-4-hydroxy-N-(4-(4-methylthiazol-5-yl)benzyl)pyrrolidine-2-carboxamide. 55% yield. $^1$H NMR (500 MHz, $CD_3OD$) δ 9.01 (s, 1H), 8.61 (t, J=8.2 Hz, 1H), 8.17 (s, 2H), 7.99 (s, 1H), 7.95 (s, 1H), 7.55-7.33 (m, 6H), 4.66 (s, 1H), 4.56 (dt, J=23.6, 8.2 Hz, 3H), 4.38 (d, J=15.5 Hz, 1H), 3.93 (d, J=11.0 Hz, 1H), 3.82 (dd, J=10.9, 3.7 Hz, 1H), 3.78-3.53 (m, 8H), 2.50 (s, 3H), 2.49-2.41 (m, 2H), 2.38-2.20 (m, 3H), 2.20-2.06 (m, 2H), 1.70-1.55 (m, 4H), 1.40 (d, J=3.4 Hz, 4H), 1.10-1.02 (m, 11H), 1.02-0.95 (m, 2H). HRMS (ESI-TOF) m/z: $[M+H]^+$ calcd for $C_{53}H_{64}FN_{12}O_6S^+$, 1015.4771; found 1015.4788.

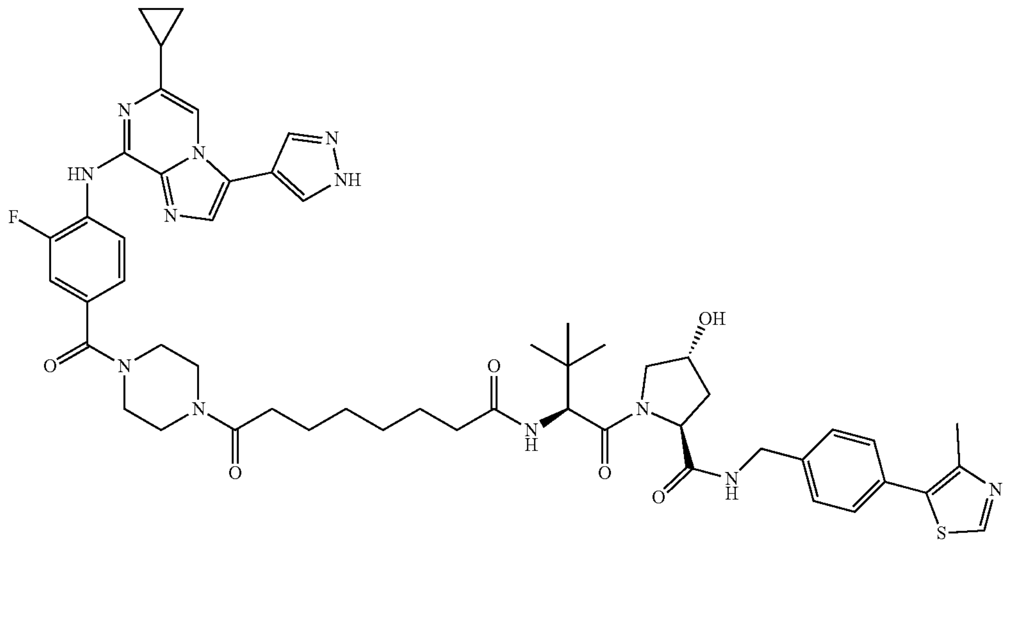 [SMILES: Cc1ncsc1-c1ccc(CNC(=O)[C@@H]2C[C@@H](O)CN2C(=O)[C@@H](NC(=O)CCCCCCC(=O)N2CCN(C(=O)c3ccc(Nc4nc(C5CC5)cn5c(-c6cn[nH]c6)cnc45)c(F)c3)CC2)C(C)(C)C)cc1]

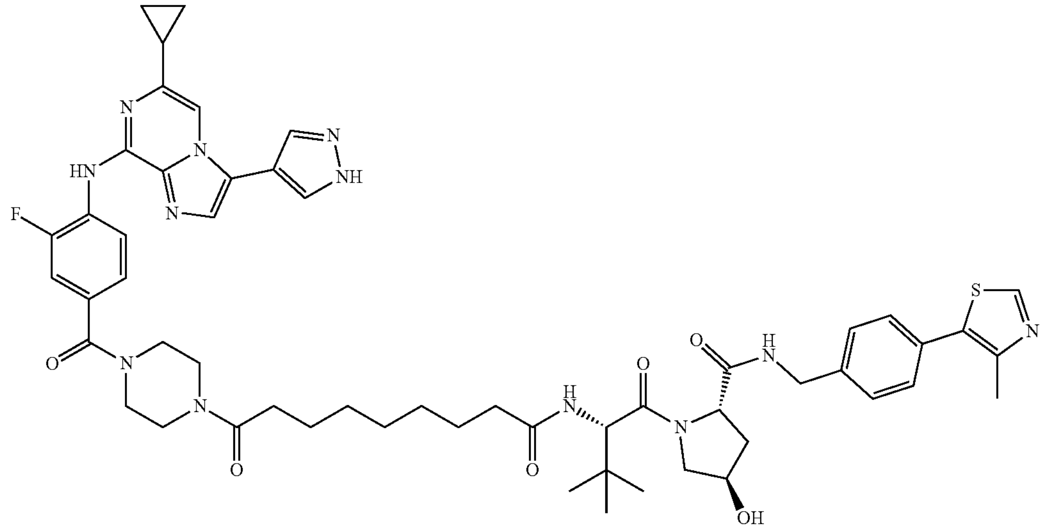 [SMILES: Cc1ncsc1-c1ccc(CNC(=O)[C@@H]2C[C@@H](O)CN2C(=O)[C@@H](NC(=O)CCCCCCCC(=O)N2CCN(C(=O)c3ccc(Nc4nc(C5CC5)cn5c(-c6cn[nH]c6)cnc45)c(F)c3)CC2)C(C)(C)C)cc1]

Example 51: (2S,4R)-1-((S)-2-(9-(4-(4-((6-Cyclopropyl-3-(1H-pyrazol-4-yl)imidazo[1,2-a]pyrazin-8-yl)amino)-3-fluorobenzoyl)piperazin-1-yl)-9-oxononanamido)-3,3-dimethylbutanoyl)-4-hydroxy-N-(4-(4-methylthiazol-5-yl)benzyl)pyrrolidine-2-carboxamide. 59% yield. $^1$H NMR (500 MHz, $CD_3OD$) δ 8.93 (s, 1H), 8.69 (t, J=8.2 Hz, 1H), 8.14 (s, 2H), 7.94 (s, 1H), 7.84 (s, 1H), 7.53-7.33 (m, 6H), 4.70-4.48 (m, 4H), 4.38 (d, J=15.5 Hz, 1H), 3.93 (d, J=11.0 Hz, 1H), 3.82 (dd, J=10.9, 3.8 Hz, 1H), 3.79-3.51 (m, 8H), 2.52-2.41 (m, 5H), 2.36-2.27 (m, 2H), 2.27-2.18 (m, 1H), 2.15-2.08 (m, 2H), 1.71-1.58 (m, 4H), 1.47-1.30 (m, 6H), 1.14-0.91 (m, 13H). HRMS (ESI-TOF) m/z: $[M+H]^+$ calcd for $C_{44}H_{66}FN_{12}O_6S^+$, 1029.4928; found 1029.4943.

Example: 52 (2S,4R)-1-((S)-2-(3-(3-(4-(4-((6-Cyclopropyl-3-(1H-pyrazol-4-yl)imidazo[1,2-a]pyrazin-8-yl)amino)-3-fluorobenzoyl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide. 66% yield. $^1$H NMR (500 MHz, $CD_3OD$) δ 8.94 (s, 1H), 8.62 (t, J=8.2 Hz, 1H), 8.17 (s, 2H), 7.98 (s, 1H), 7.92 (s, 1H), 7.48-7.31 (m, 6H), 4.70 (s, 1H), 4.65-4.42 (m, 3H), 4.36 (d, J=15.3 Hz, 1H), 3.91 (d, J=10.5 Hz, 1H), 3.86-3.54 (m, 13H), 2.83-2.66 (m, 2H), 2.59-2.49 (m, 2H), 2.46 (s, 3H), 2.31-2.20 (m, 1H), 2.12 (ddd, J=19.8, 10.8, 6.1 Hz, 2H), 1.13-0.91 (m, 13H). HRMS (ESI-TOF) m/z: $[M+H]^+$ calcd for $C_{51}H_{60}FN_{12}O_7S^+$, 1003.4407; found 1003.4427.

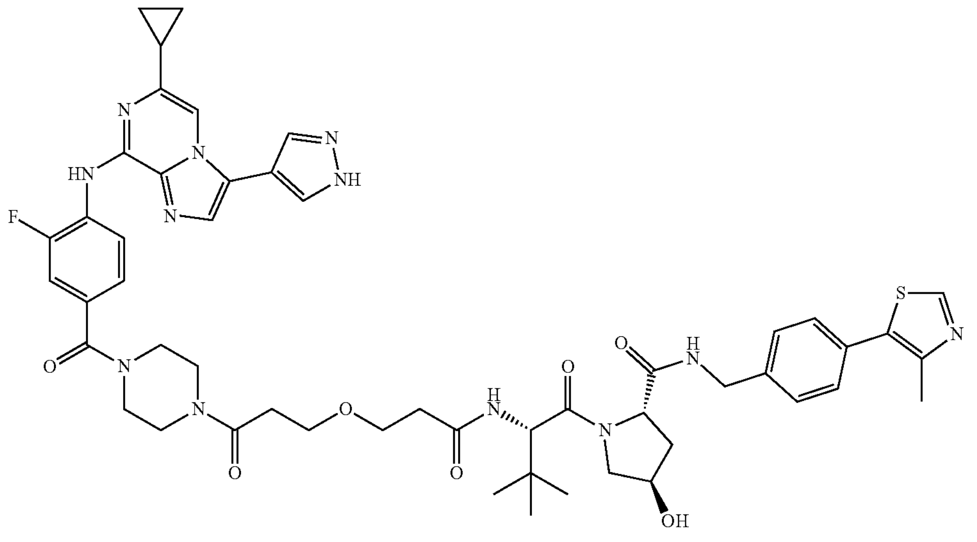

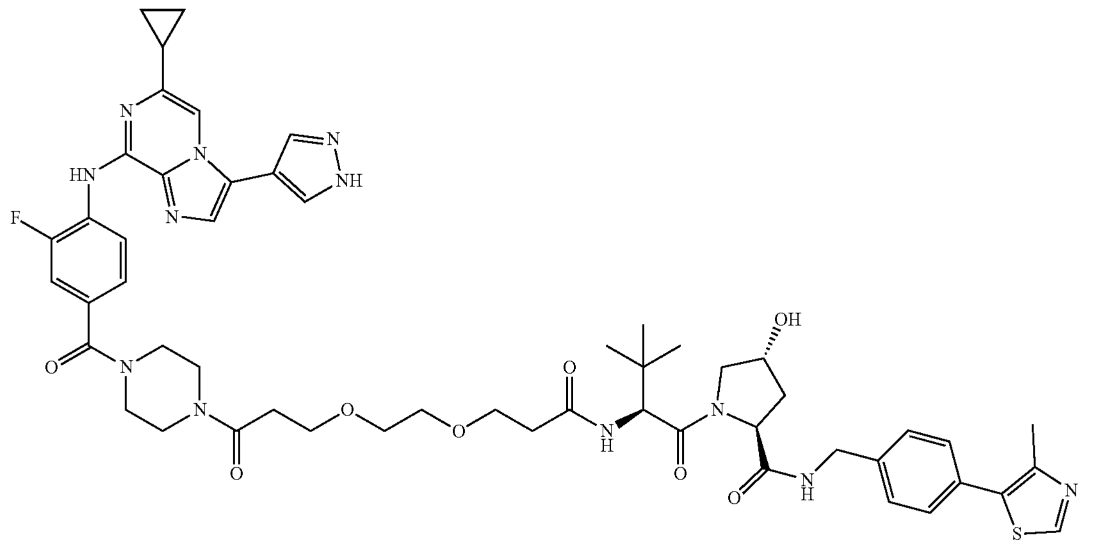 [SMILES: Cc1ncsc1-c1ccc(CNC(=O)[C@@H]2C[C@@H](O)CN2C(=O)[C@@H](NC(=O)CCOCCOCCC(=O)N2CCN(C(=O)c3ccc(Nc4nc(C5CC5)cn5c(-c6cn[nH]c6)cnc45)c(F)c3)CC2)C(C)(C)C)cc1]

Example 53: (2S,4R)-1-((S)-2-(3-(2-(3-(4-(4-((6-Cyclopropyl-3-(1H-pyrazol-4-yl)imidazo[1,2-a]pyrazin-8-yl)amino)-3-fluorobenzoyl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide. 64% yield. $^{1}H$ NMR (500 MHz, $CD_3OD$) δ 9.01 (s, 1H), 8.59 (t, J=8.2 Hz, 1H), 8.17 (s, 2H), 8.00 (s, 1H), 7.98 (s, 11H), 7.51-7.33 (m, 6H), 4.68 (s, 1H), 4.63-4.48 (m, 3H), 4.37 (d, J=15.5 Hz, 1H), 3.90 (d, J=10.9 Hz, 1H), 3.84-3.56 (m, 17H), 2.79-2.69 (m, 2H), 2.62-2.42 (m, 5H), 2.29-2.19 (m, 1H), 2.20-2.05 (m, 2H), 1.12-0.94 (m, 15H). HRMS (ESI-TOF) m/z: $[M+H]^+$ calcd for $C_{53}H_{64}FN_{12}O_8S^+$, 1047.4669; found 1047.4671.

Example 54: (2S,4R)-1-((S)-2-(tert-Butyl)-16-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide. 56% yield. $^{1}H$ NMR (500 MHz, $CD_3OD$) δ 9.04 (s, 1H), 8.57 (t, J=5.9 Hz, 1H), 8.18 (s, 2H), 8.02 (s, 1H), 8.00 (s, 1H), 7.52-7.30 (m, 6H), 4.67 (s, 1H), 4.64-4.48 (m, 3H), 4.37 (d, J=15.5 Hz, 1H), 3.91 (d, J=11.0 Hz, 1H), 3.88-3.46 (m, 21H), 2.71 (s, 2H), 2.65-2.44 (m, 5H), 2.30-2.20 (m, 1H), 2.20-2.04 (m, 2H), 1.13-0.93 (m, 13H). HRMS (ESI-TOF) m/z: $[M+H]^+$ calcd for $C_{55}H_{68}FN_{12}O_9S^+$, 1091.4931; found 1091.4933.

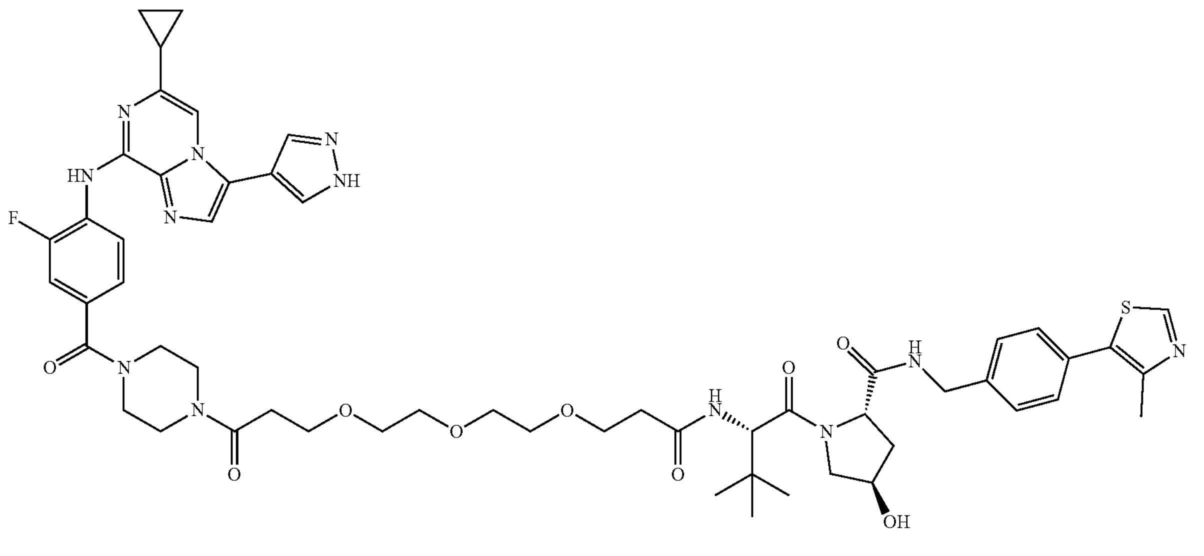 [SMILES: Cc1ncsc1-c1ccc(CNC(=O)[C@@H]2C[C@@H](O)CN2C(=O)[C@@H](NC(=O)CCOCCOCCOCCC(=O)N2CCN(C(=O)c3ccc(Nc4nc(C5CC5)cn5c(-c6cn[nH]c6)cnc45)c(F)c3)CC2)C(C)(C)C)cc1]

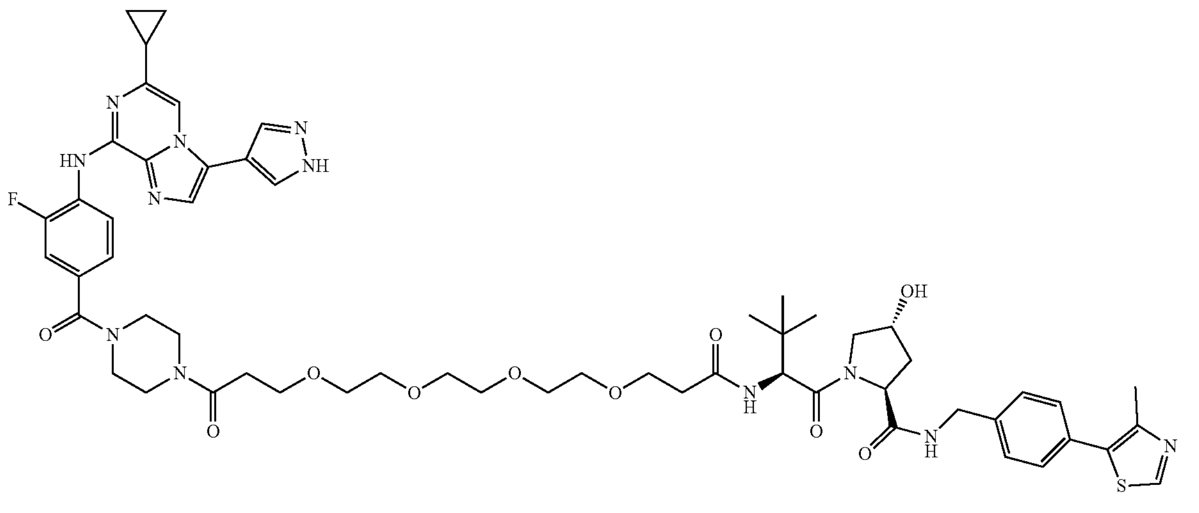 [SMILES: Cc1ncsc1-c1ccc(CNC(=O)[C@@H]2C[C@@H](O)CN2C(=O)[C@@H](NC(=O)CCOCCOCCOCCOCCC(=O)N2CCN(C(=O)c3ccc(Nc4nc(C5CC5)cn5c(-c6cn[nH]c6)cnc45)c(F)c3)CC2)C(C)(C)C)cc1]

Example 55: (2S,4R)-1-((S)-2-(tert-Butyl)-19-(4-(4-((6-cyclopropyl-3-(1H-pyrazol-4-yl)imidazo[1,2-a]pyrazin-8-yl)amino)-3-fluorobenzoyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide. 63% yield. $^1$H NMR (500 MHz, $CD_3OD$) δ 9.03 (s, 1H), 8.59 (t, J=8.1 Hz, 1H), 8.18 (s, 2H), 8.02 (s, 1H), 7.99 (s, 1H), 7.59-7.34 (m, 6H), 4.66 (s, 1H), 4.63-4.49 (m, 3H), 4.37 (d, J=15.5 Hz, 1H), 3.90 (d, J=11.0 Hz, 1H), 3.87-3.49 (m, 25H), 2.70 (d, J=19.9 Hz, 2H), 2.67-2.42 (m, 5H), 2.23 (dd, J=13.0, 7.6 Hz, 1H), 2.20-2.04 (m, 2H), 1.15-0.90 (m, 13H). HRMS (ESI-TOF) m/z: $[M+H]^+$ calcd for $C_{57}H_{72}FN_{12}O_{10}S^+$, 1135.5194; found 1135.5208.

Example 56: (2S,4R)-1-((S)-2-(tert-Butyl)-22-(4-(4-((6-cyclopropyl-3-(1H-pyrazol-4-yl)imidazo[1,2-a]pyrazin-8-yl)amino)-3-fluorobenzoyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide. 51% yield. $^1$H NMR (500 MHz, $CD_3OD$) δ 8.95 (s, 1H), 8.66 (t, J=8.2 Hz, 1H), 8.15 (s, 2H), 7.96 (s, 1H), 7.88 (s, 1H), 7.52-7.34 (m, 6H), 4.66 (s, 1H), 4.63-4.49 (m, 3H), 4.36 (d, J=15.5 Hz, 1H), 3.90 (d, J=10.9 Hz, 1H), 3.85-3.50 (m, 29H), 2.72 (s, 2H), 2.63-2.54 (m, 1H), 2.53-2.43 (m, 4H), 2.30-2.18 (m, 1H), 2.11 (m, 2H), 1.13-0.93 (m, 13H). HRMS (ESI-TOF) m/z: $[M+H]^+$ calcd for $C_{59}H_{76}FN_{12}O_{11}S^+$, 1179.5456; found 1179.5440.

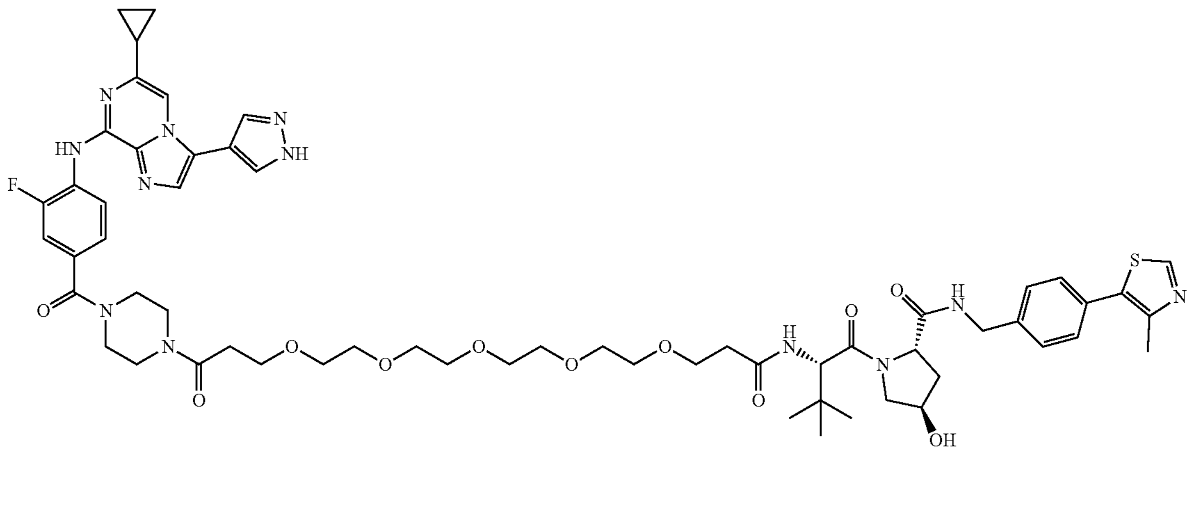 [SMILES: Cc1ncsc1-c1ccc(CNC(=O)[C@@H]2C[C@@H](O)CN2C(=O)[C@@H](NC(=O)CCOCCOCCOCCOCCOCCC(=O)N2CCN(C(=O)c3ccc(Nc4nc(C5CC5)cn5c(-c6cn[nH]c6)cnc45)c(F)c3)CC2)C(C)(C)C)cc1]

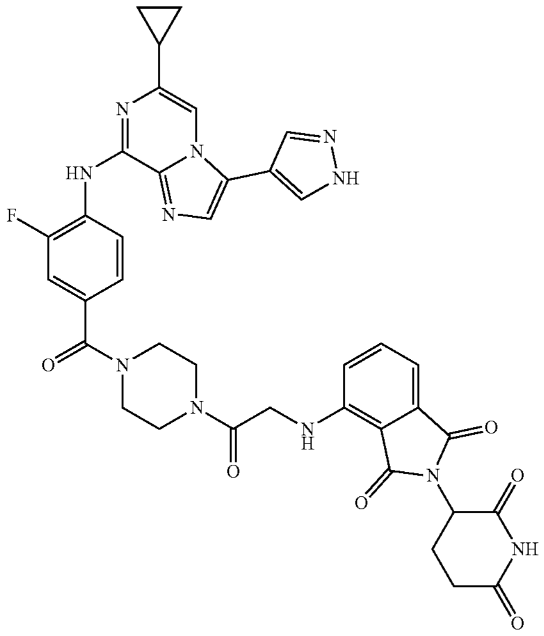 [SMILES: O=C1CCC(N2C(=O)c3cccc(NCC(=O)N4CCN(C(=O)c5ccc(Nc6nc(C7CC7)cn7c(-c8cn[nH]c8)cnc67)c(F)c5)CC4)c3C2=O)C(=O)N1]

Example 57: 4-((2-(4-(4-((6-Cyclopropyl-3-(1H-pyrazol-4-yl)imidazo[1,2-a]pyrazin-8-yl)amino)-3-fluorobenzoyl)piperazin-1-yl)-2-oxoethyl)amino)-2-(2,6-dioxopiperidin-3-yl)isoindoline-1,3-dione. 70% yield. $^1$H NMR (500 MHz, Acetone) δ 8.81 (t, J=8.4 Hz, 1H), 8.21 (s, 2H), 8.07-7.97 (m, 1H), 7.79 (d, J=8.8 Hz, 1H), 7.67-7.59 (m, 1H), 7.50-7.40 (m, 2H), 7.11 (d, J=7.3 Hz, 2H), 5.12 (dd, J=12.6, 5.4 Hz, 1H), 4.35 (s, 2H), 3.80 (s, 8H), 3.06-2.93 (m, 1H), 2.88-2.76 (m, 2H), 2.28-2.20 (m, 1H), 2.19-2.14 (m, 2H), 1.13-1.05 (m, 2H), 1.00-0.92 (m, 2H). HRMS (ESI-TOF) m/z: [M+H]$^+$ calcd for $C_{38}H_{35}FN_{11}O_6S^+$, 760.2750; found 760.2755.

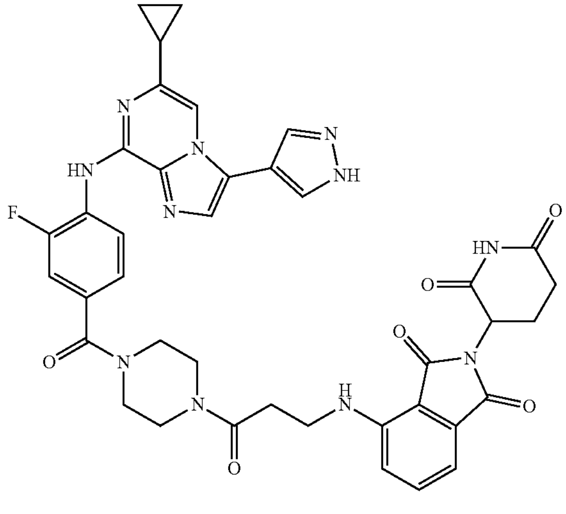 [SMILES: O=C1CCC(N2C(=O)c3cccc(NCCC(=O)N4CCN(C(=O)c5ccc(Nc6nc(C7CC7)cn7c(-c8cn[nH]c8)cnc67)c(F)c5)CC4)c3C2=O)C(=O)N1]

Example 58: 4-((3-(4-(4-((6-Cyclopropyl-3-(1H-pyrazol-4-yl)imidazo[1,2-a]pyrazin-8-yl)amino)-3-fluorobenzoyl)piperazin-1-yl)-3-oxopropyl)amino)-2-(2,6-dioxopiperidin-3-yl)isoindoline-1,3-dione. 72% yield. $^1$H NMR (500 MHz, Acetone) S 8.67-8.57 (m, 1H), 8.09 (s, 1H), 7.94-7.86 (m, 2H), 7.70 (d, J=3.8 Hz, 1H), 7.50 (dd, J=8.4, 7.2 Hz, 1H), 7.34-7.25 (m, 2H), 7.07 (d, J=8.6 Hz, 1H), 6.96 (d, J=7.0 Hz, 1H), 4.97 (dd, J=12.7, 5.5 Hz, 1H), 3.67-3.52 (m, 10H), 2.90-2.79 (m, 1H), 2.75 (s, 2H), 2.72-2.61 (m, 2H), 2.16-2.06 (m, 1H), 2.06-2.01 (m, 1H), 1.01-0.91 (m, 2H), 0.88-0.78 (m, 2H). HRMS (ESI-TOF) m/z: [M+H]$^+$ calcd for $C_{39}H_{37}FN_{11}O_6S^+$, 774.2907; found 774.2901

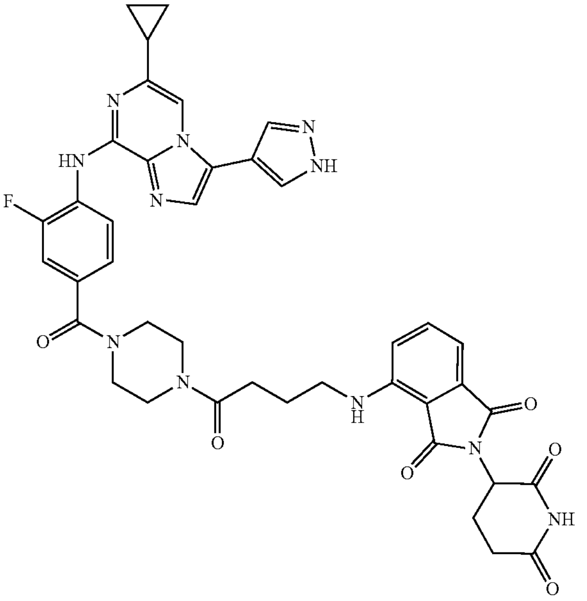 [SMILES: O=C1CCC(N2C(=O)c3cccc(NCCCC(=O)N4CCN(C(=O)c5ccc(Nc6nc(C7CC7)cn7c(-c8cn[nH]c8)cnc67)c(F)c5)CC4)c3C2=O)C(=O)N1]

Example 59: 4-((4-(4-(4-((6-Cyclopropyl-3-(1H-pyrazol-4-yl)imidazo[1,2-a]pyrazin-8-yl)amino)-3-fluorobenzoyl)piperazin-1-yl)-4-oxobutyl)amino)-2-(2,6-dioxopiperidin-3-yl)isoindoline-1,3-dione. 60% yield. $^1$H NMR (500 MHz, $CD_3OD$) δ 8.73 (t, J=8.1 Hz, 1H), 8.01 (s, 2H), 7.80 (s, 1H), 7.72 (s, 1H), 7.59-7.50 (m, 1H), 7.33 (t, J=4.9 Hz, 2H), 7.12-7.00 (m, 2H), 4.99 (dd, J=12.0, 5.5 Hz, 1H), 3.65 (d, J=30.6 Hz, 8H), 3.42 (t, J=6.7 Hz, 2H), 2.87-2.70 (m, 3H), 2.60-2.51 (m, 2H), 2.16-2.08 (m, 1H), 2.08-1.97 (m, 3H), 1.10-1.01 (m, 2H), 1.01-0.93 (m, 2H). HRMS (ESI-TOF) m/z: [M+H]$^+$ calcd for $C_{40}H_{39}FN_{11}O_6S^+$, 788.3063; found 788.3089.

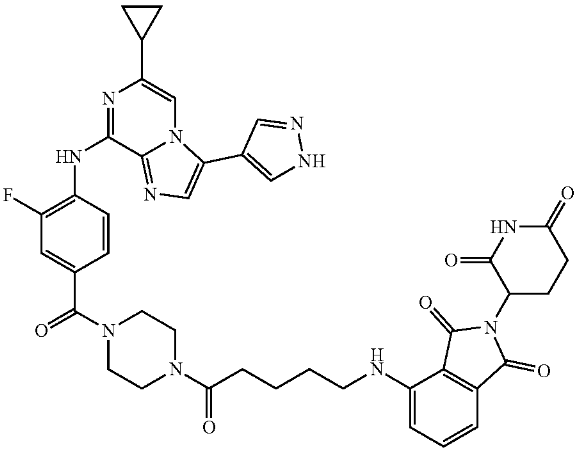 [SMILES: O=C1CCC(N2C(=O)c3cccc(NCCCCC(=O)N4CCN(C(=O)c5ccc(Nc6nc(C7CC7)cn7c(-c8cn[nH]c8)cnc67)c(F)c5)CC4)c3C2=O)C(=O)N1]

Example 60: 4-((5-(4-(4-((6-Cyclopropyl-3-(1H-pyrazol-4-yl)imidazo[1,2-a]pyrazin-8-yl)amino)-3-fluorobenzoyl)

piperazin-1-yl)-5-oxopentyl)amino)-2-(2,6-dioxopiperidin-3-yl)isoindoline-1,3-dione. 69% yield. $^1$H NMR (500 MHz, $CD_3OD$) δ 8.77 (t, J=8.3 Hz, 1H), 7.96 (s, 2H), 7.74 (s, 1H), 7.64 (s, 1H), 7.55-7.47 (m, 1H), 7.31 (t, J=8.3 Hz, 2H), 7.07 (d, J=7.1 Hz, 1H), 6.98 (d, J=8.6 Hz, 1H), 4.96 (dd, J=11.0, 6.5 Hz, 1H), 3.77-3.50 (m, 8H), 3.39-3.34 (m, 2H), 2.85-2.70 (m, 3H), 2.53-2.42 (m, 2H), 2.18-2.04 (m, 1H), 2.05-1.92 (m, 1H), 1.85-1.67 (m, 4H), 1.10-1.03 (m, 2H), 1.00-0.91 (m, 2H). HRMS (ESI-TOF) m/z: $[M+H]^+$ calcd for $C_{41}H_{41}FN_{11}O_6S^+$, 802.3220; found 802.3249.

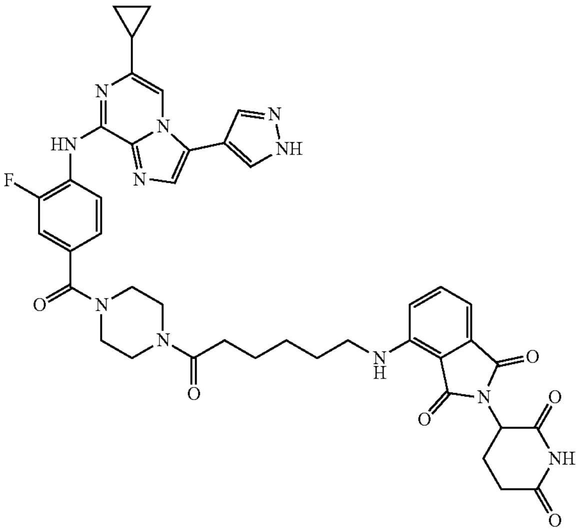

Example 61: 4-((6-(4-(4-((6-Cyclopropyl-3-(1H-pyrazol-4-yl)imidazo[1,2-a]pyrazin-8-yl)amino)-3-fluorobenzoyl) piperazin-1-yl)-6-oxohexyl)amino)-2-(2,6-dioxopiperidin-3-yl)isoindoline-1,3-dione. 65% yield. $^1$H NMR (500 MHz, $CD_3OD$) δ 8.71 (t, J=8.2 Hz, J H), 8.00 (s, 2H), 7.78 (s, 1H), 7.71 (s, 1H), 7.56-7.49 (m, 1H), 7.32 (t, J=9.6 Hz, 2H), 7.05 (d, J=7.1 Hz, 1H), 6.97 (d, J=8.6 Hz, 1H), 4.97 (dd, J=12.0, 5.5 Hz, 1H), 3.78-3.55 (m, 8H), 3.34-3.29 (m, 2H), 2.85-2.69 (m, 3H), 2.51-2.40 (m, 2H), 2.18-2.07 (m, 1H), 2.06-1.97 (m, 1H), 1.77-1.64 (m, 4H), 1.55-1.44 (m, 2H), 1.08-1.02 (m, 2H), 0.99-0.93 (m, 2H). HRMS (ESI-TOF) m/z: $[M+H]^+$ calcd for $C_{42}H_{43}FN_{11}O_6S^+$, 816.3375; found 816.3390.

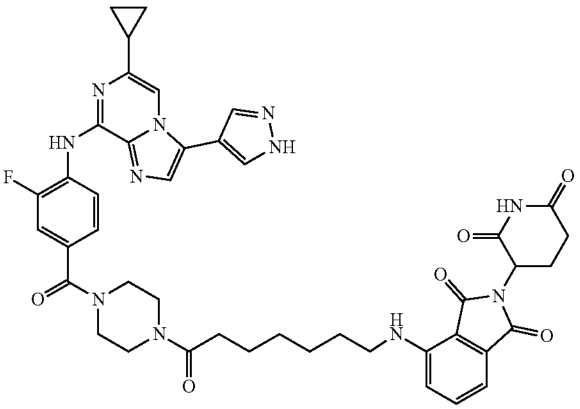 [SMILES: O=C1CCC(N2C(=O)c3cccc(NCCCCCCC(=O)N4CCN(C(=O)c5ccc(Nc6nc(C7CC7)cn7c(-c8cn[nH]c8)cnc67)c(F)c5)CC4)c3C2=O)C(=O)N1]

Example 62: 4-((7-(4-(4-((6-Cyclopropyl-3-(1H-pyrazol-4-yl)imidazo[1,2-a]pyrazin-8-yl)amino)-3-fluorobenzoyl) piperazin-1-yl)-7-oxoheptyl)amino)-2-(2,6-dioxopiperidin-3-yl)isoindoline-1,3-dione. 68% yield. $^1$H NMR (500 MHz, $CD_3OD$) δ 8.67 (t, J=8.1 Hz, 1H), 8.06 (s, 2H), 7.86 (s, 1H), 7.81 (s, 1H), 7.56-7.48 (m, 1H), 7.39-7.29 (m, 2H), 7.04 (d, J=7.0 Hz, 1H), 6.99 (d, J=8.5 Hz, 1H), 5.01 (dd, J=12.3, 5.4 Hz, 1H), 3.85-3.44 (m, 8H), 2.85-2.68 (m, 3H), 2.44 (s, 2H), 2.17-2.01 (m, 2H), 1.75-1.61 (m, 4H), 1.54-1.39 (m, 4H), 1.10-1.01 (m, 2H), 1.00-0.93 (m, 2H). HRMS (ESI-TOF) m/z: $[M+H]^+$ calcd for $C_{43}H_{45}FN_{11}O_6S^+$, 830.3533; found 830.3549.

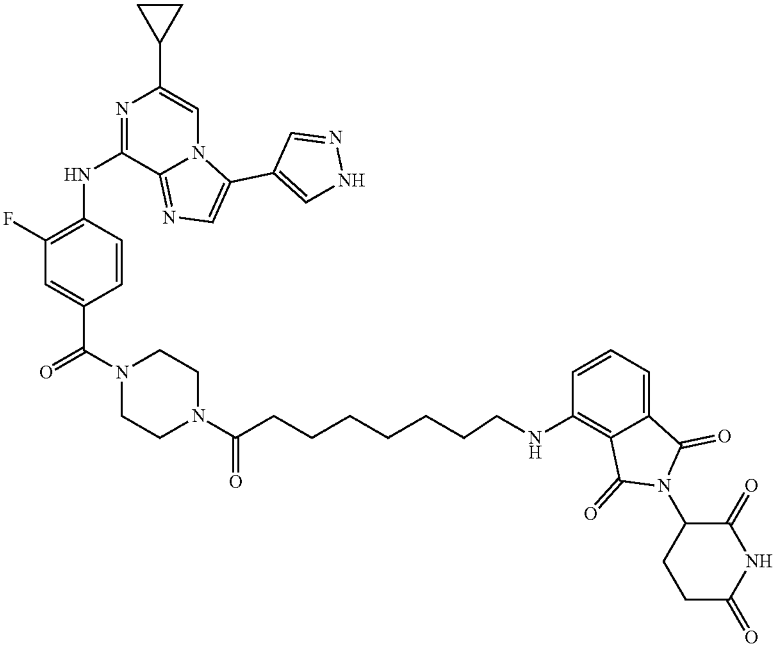 [SMILES: O=C1CCC(N2C(=O)c3cccc(NCCCCCCCC(=O)N4CCN(C(=O)c5ccc(Nc6nc(C7CC7)cn7c(-c8cn[nH]c8)cnc67)c(F)c5)CC4)c3C2=O)C(=O)N1]

Example 65: 4-((8-(4-(4-((6-Cyclopropyl-3-(1H-pyrazol-4-yl)imidazo[1,2-a]pyrazin-8-yl)amino)-3-fluorobenzoyl)piperazin-1-yl)-8-oxooctyl)amino)-2-(2,6-dioxopiperidin-3-yl)isoindoline-1,3-dione. 62% yield. $^{1}H$ NMR (500 MHz, $CD_3OD$) δ 8.75 (t, J=8.3 Hz, 1H), 8.01 (s, 2H), 7.79 (s, 1H), 7.69 (s, 1H), 7.56-7.44 (m, 1H), 7.40-7.25 (m, 2H), 7.09-7.00 (m, 1H), 6.97 (d, J=8.6 Hz, 1H), 4.99 (dd, J=12.2, 5.3 Hz, 1H), 3.82-3.49 (m, 8H), 3.31-3.27 (m, 2H), 2.86-2.69 (m, 3H), 2.46-2.36 (m, 2H), 2.19-2.08 (m, 1H), 2.06-1.98 (m, 1H), 1.78-1.53 (m, 4H), 1.52-1.33 (m, 6H), 1.10-1.00 (m, 2H), 1.00-0.92 (m, 2H). HRMS (ESI-TOF) m/z: $[M+H]^+$ calcd for $C_{44}H_{47}FN_{11}O_6S^+$, 844.3689; found 844.3671.

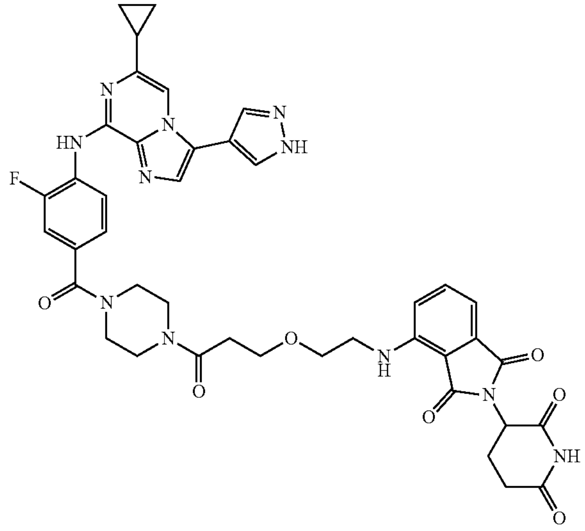 [SMILES: O=C1CCC(N2C(=O)c3cccc(NCCOCCC(=O)N4CCN(C(=O)c5ccc(Nc6nc(C7CC7)cn7c(-c8cn[nH]c8)cnc67)c(F)c5)CC4)c3C2=O)C(=O)N1]

Example 66: 4-((2-(3-(4-(4-((6-Cyclopropyl-3-(1H-pyrazol-4-yl)imidazo[1,2-a]pyrazin-8-yl)amino)-3-fluorobenzoyl)piperazin-1-yl)-3-oxopropoxy)ethyl)amino)-2-(2,6-dioxopiperidin-3-yl)isoindoline-1,3-dione. 69% yield. $^{1}H$ NMR (500 MHz, $CD_3OD$) δ 8.71 (t, J=7.6 Hz, 1H), 7.98 (s, 2H), 7.76 (s, 1H), 7.67 (s, 1H), 7.58-7.48 (m, 1H), 7.35-7.17 (m, 2H), 7.07 (d, J=7.0 Hz, 1H), 6.99 (d, J=8.5 Hz, 1H), 4.96 (dd, J=11.9, 5.2 Hz, 1H), 3.83 (t, J=5.8 Hz, 2H), 3.80-3.54 (m, 10H), 3.48 (t, J=4.9 Hz, 2H), 2.85-2.65 (m, 5H), 2.14-2.05 (m, 1H), 2.05-1.95 (m, 1H), 1.09-1.01 (m, 2H), 0.99-0.91 (m, 2H). HRMS (ESI-TOF) m/z: $[M+H]^+$ calcd for $C_{41}H_{41}FN_{11}O_7S^+$, 818.3169; found 818.3178.

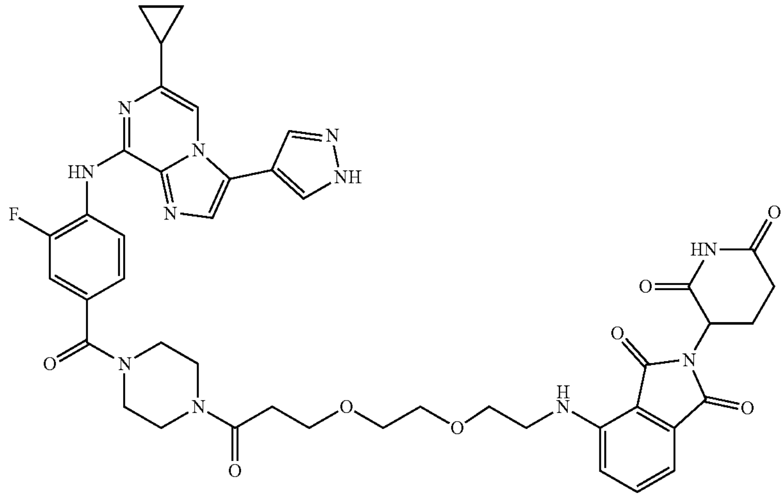 [SMILES: O=C1CCC(N2C(=O)c3cccc(NCCOCCOCCC(=O)N4CCN(C(=O)c5ccc(Nc6nc(C7CC7)cn7c(-c8cn[nH]c8)cnc67)c(F)c5)CC4)c3C2=O)C(=O)N1]

Example 67: 4-((2-(2-(3-(4-(4-((6-Cyclopropyl-3-(1H-pyrazol-4-yl)imidazo[1,2-a]pyrazin-8-yl)amino)-3-fluorobenzoyl)piperazin-1-yl)-3-oxopropoxy)ethoxy)ethyl)amino)-2-(2,6-dioxopiperidin-3-yl)isoindoline-1,3-dione. 65% yield. $^1$H NMR (500 MHz, $CD_3OD$) δ 8.69 (t, J=8.3 Hz, 1H), 8.00 (s, 2H), 7.77 (s, 1H), 7.70 (s, 1H), 7.55-7.37 (m, 1H), 7.28 (t, J=8.3 Hz, 2H), 7.10-6.84 (m, 2H), 4.96 (dd, J=12.2, 5.4 Hz, 1H), 3.79 (t, J=6.0 Hz, 2H), 3.77-3.51 (m, 14H), 3.51-3.40 (m, 2H), 2.85-2.60 (m, 5H), 2.16-2.06 (m, 1H), 2.06-1.96 (m, 1H), 1.09-1.00 (m, 2H), 0.99-0.90 (m, 2H). HRMS (ESI-TOF) m/z: $[M+H]^+$ calcd for $C_{43}H_{45}FN_{11}O_8S^+$, 862.3431; found 862.3453.

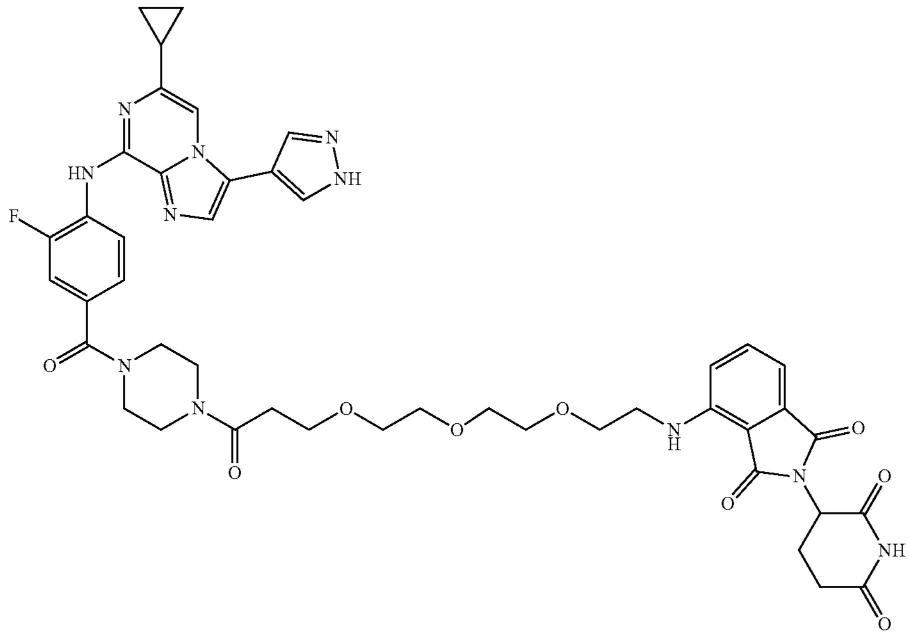 [SMILES: O=C1CCC(N2C(=O)c3cccc(NCCOCCOCCOCCC(=O)N4CCN(C(=O)c5ccc(Nc6nc(C7CC7)cn7c(-c8cn[nH]c8)cnc67)c(F)c5)CC4)c3C2=O)C(=O)N1]

Example 68: 4-((2-(2-(2-(3-(4-(4-((6-Cyclopropyl-3-(1H-pyrazol-4-yl)imidazo[1,2-a]pyrazin-8-yl)amino)-3-fluorobenzoyl)piperazin-1-yl)-3-oxopropoxy)ethoxy)ethoxy)ethyl)amino)-2-(2,6-dioxopiperidin-3-yl)isoindoline-1,3-dione. 60% yield. $^1$H NMR (500 MHz, $CD_3OD$) δ 8.66 (t, J=8.2 Hz, 1H), 8.01 (s, 2H), 7.79 (s, 1H), 7.74 (s, 1H), 7.53-7.45 (m, 1H), 7.31 (t, J=10.1 Hz, 2H), 6.99 (dd, J=21.6, 6.9 Hz, 2H), 4.97 (dd, J=12.3, 5.5 Hz, 1H), 3.78 (t, J=6.1 Hz, 2H), 3.75-3.54 (m, 18H), 3.51-3.42 (m, 2H), 2.86-2.58 (m, 5H), 2.17-2.07 (m, 1H), 2.07-1.97 (m, 1H), 1.07-1.01 (m, 2H), 0.98-0.91 (m, 2H). HRMS (ESI-TOF) m/z: $[M+H]^+$ calcd for $C_{45}H_{49}FN_{11}O_9S^+$, 906.3693; found 906.3688.

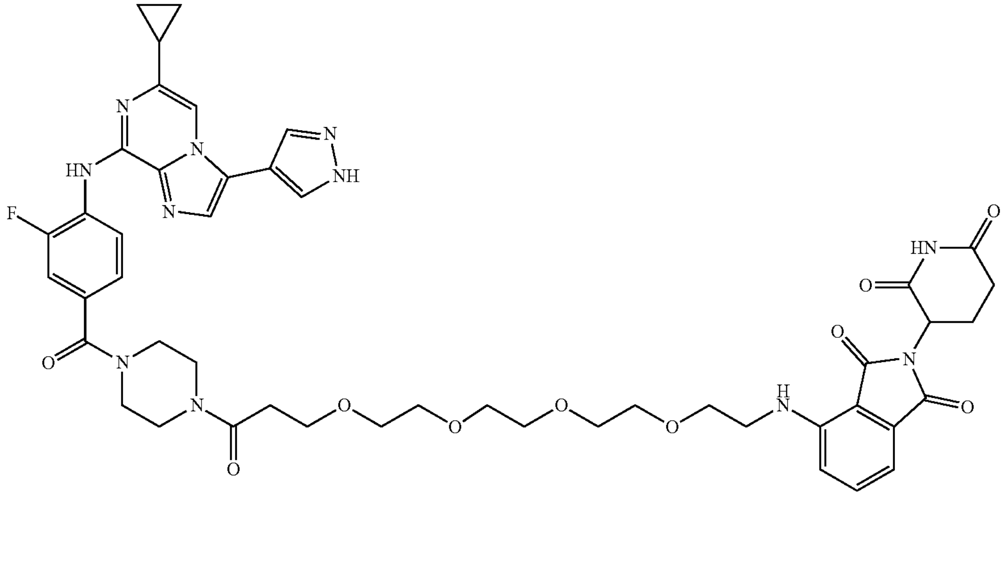 [SMILES: O=C1CCC(N2C(=O)c3cccc(NCCOCCOCCOCCOCCC(=O)N4CCN(C(=O)c5ccc(Nc6nc(C7CC7)cn7c(-c8cn[nH]c8)cnc67)c(F)c5)CC4)c3C2=O)C(=O)N1]

Example 69: 4-((15-(4-(4-((6-Cyclopropyl-3-(1H-pyrazol-4-yl)imidazo[1,2-a]pyrazin-8-yl)amino)-3-fluorobenzoyl)piperazin-1-yl)-15-oxo-3,6,9,12-tetraoxapentadecyl)amino)-2-(2,6-dioxopiperidin-3-yl)isoindoline-1,3-dione. 59% yield. $^1$H NMR (500 MHz, $CD_3OD$) δ 8.65 (t, J=8.1 Hz, 1H), 8.03 (s, 2H), 7.82 (s, 1H), 7.77 (s, 1H), 7.54-7.42 (m, 1H), 7.34 (t, J=5.0 Hz, 2H), 7.00 (dd, J=17.7, 7.8 Hz, 2H), 4.98 (dd, J=12.4, 5.4 Hz, 1H), 3.78 (t, J=6.1 Hz, 2H), 3.76-3.54 (m, 22H), 3.51-3.42 (m, 2H), 2.88-2.59 (m, 5H), 2.16-2.07 (m, 1H), 2.08-2.00 (m, 1H), 1.08-1.01 (m, 2H), 1.01-0.92 (m, 2H). HRMS (ESI-TOF) m/z: $[M+H]^+$ calcd for $C_{47}H_{53}FN_{11}O_{10}S^+$, 950.3955; found 950.3944.

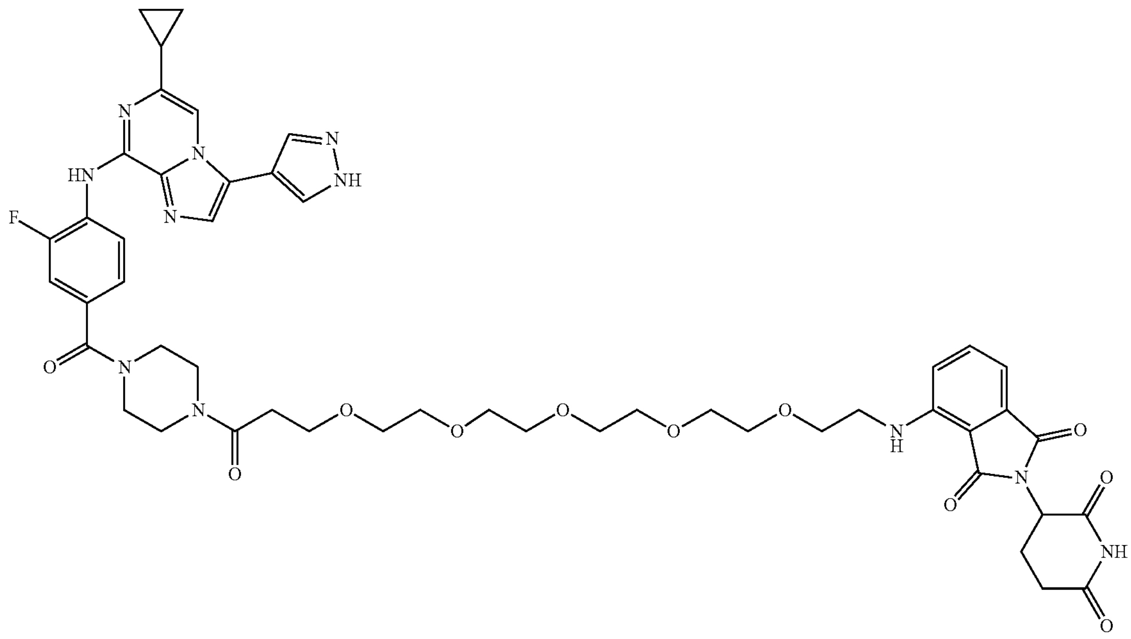 [SMILES: O=C1CCC(N2C(=O)c3cccc(NCCOCCOCCOCCOCCOCCC(=O)N4CCN(C(=O)c5ccc(Nc6nc(C7CC7)cn7c(-c8cn[nH]c8)cnc67)c(F)c5)CC4)c3C2=O)C(=O)N1]

Example 70: 4-((18-(4-(4-((6-Cyclopropyl-3-(1H-pyrazol-4-yl)imidazo[1,2-a]pyrazin-8-yl)amino)-3-fluorobenzoyl)piperazin-1-yl)-18-oxo-3,6,9,12,15-pentaoxaoctadecyl)amino)-2-(2,6-dioxopiperidin-3-yl)isoindoline-1,3-dione. 63% yield. $^1$H NMR (500 MHz, $CD_3OD$) δ 8.66 (t, J=8.3 Hz, 1H), 7.99 (s, 2H), 7.77 (s, 1H), 7.73 (s, 1H), 7.54-7.45 (m, 1H), 7.42-7.23 (m, 2H), 7.04 (d, J=7.1 Hz, 1H), 6.97 (d, J=8.6 Hz, 1H), 4.96 (dd, J=11.9, 5.6 Hz, 1H), 3.88-3.52 (m, 30H), 3.52-3.44 (m, 2H), 2.90-2.61 (m, 5H), 2.12 (dd, J=8.9, 5.2 Hz, 1H), 2.07-1.95 (m, 1H), 1.11-1.00 (m, 2H), 1.00-0.90 (m, 2H). HRMS (ESI-TOF) m/z: $[M+H]^+$ calcd for $C_{49}H_{57}FN_{11}O_{11}S^+$, 994.4218; found 994.4230.

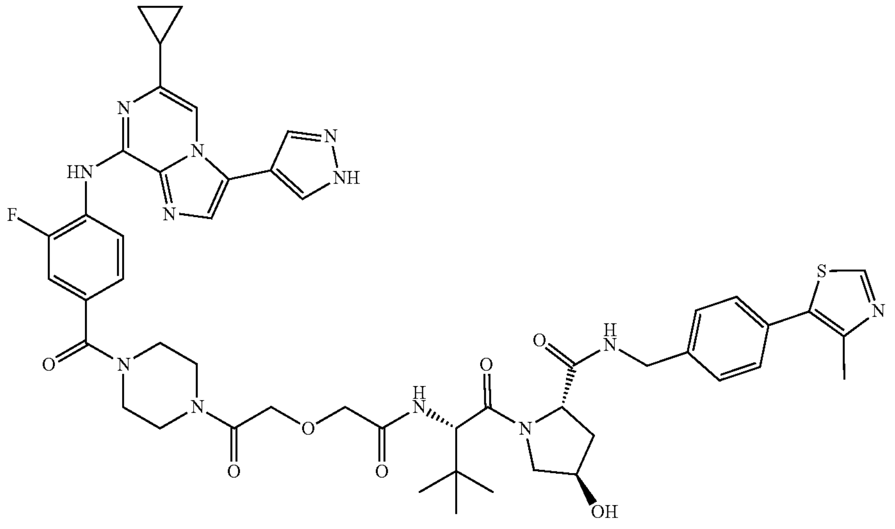 [SMILES: Cc1ncsc1-c1ccc(CNC(=O)[C@@H]2C[C@@H](O)CN2C(=O)[C@@H](NC(=O)COCC(=O)N2CCN(C(=O)c3ccc(Nc4nc(C5CC5)cn5c(-c6cn[nH]c6)cnc45)c(F)c3)CC2)C(C)(C)C)cc1]

Example 71: (2S,4R)-1-((S)-2-(2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide. 60% yield. $^1$H NMR (500 MHz, $CD_3OD$) δ 8.98 (s, 1H), 8.60 (t, J=8.2 Hz, 1H), 8.16 (s, 2H), 7.97 (s, 1H), 7.92 (s, 1H), 7.53-7.20 (m, 6H), 4.71 (s, 1H), 4.64-4.35 (m, 6H), 4.20 (d, J=15.1 Hz, 1H), 4.11 (d, J=15.1 Hz, 1H), 3.91 (d, J=10.9 Hz, 1H), 3.83 (dd, J=11.0, 3.7 Hz, 1H), 3.80-3.50 (m, 8H), 2.49 (s, 3H), 2.29-2.21 (m, 1H), 2.18-2.07 (m, 2H), 1.08 (s, 9H), 1.06-1.01 (m, 2H), 1.01-0.93 (m, 2H). HRMS (ESI-TOF) m/z: $[M+H]^+$ calcd for $C_{49}H_{56}FN_{12}O_7S^+$, 975.4094; found 975.4086.

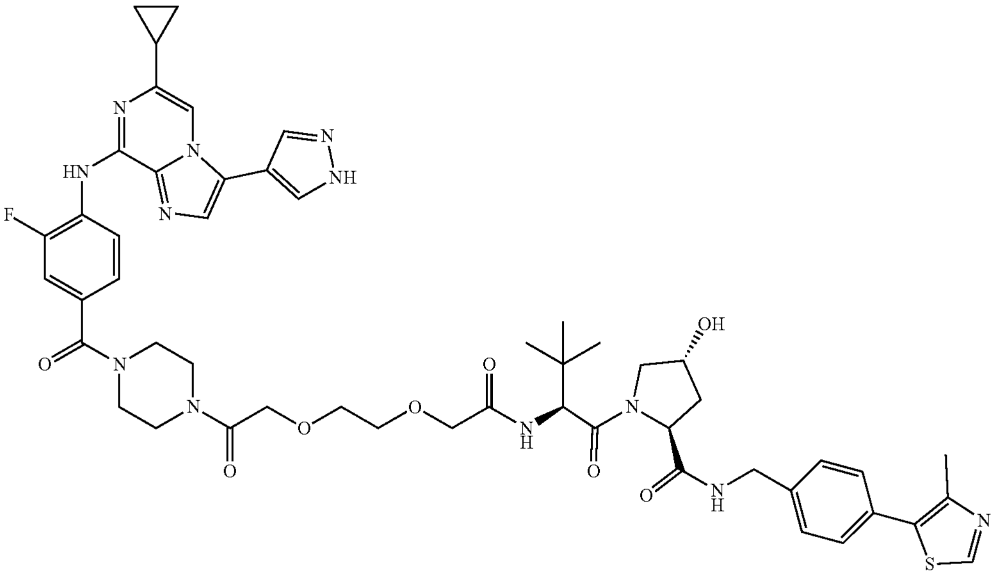 [SMILES: Cc1ncsc1-c1ccc(CNC(=O)[C@@H]2C[C@@H](O)CN2C(=O)[C@@H](NC(=O)COCCOCC(=O)N2CCN(C(=O)c3ccc(Nc4nc(C5CC5)cn5c(-c6cn[nH]c6)cnc45)c(F)c3)CC2)C(C)(C)C)cc1]

Example 72: (2S,4R)-1-((S)-2-(2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide. 66% yield. $^1$H NMR (500 MHz, $CD_3OD$) δ 8.98 (s, 1H), 8.59 (t, J=8.2 Hz, 1H), 8.16 (s, 2H), 7.98 (s, 1H), 7.94 (s, 1H), 7.40 (ddd, J=37.7, 18.3, 8.2 Hz, 6H), 4.73 (s, 1H), 4.65-4.42 (m, 3H), 4.41-4.30 (m, 3H), 4.13-4.03 (m, 2H), 3.93-3.49 (m, 14H), 2.48 (s, 3H), 2.30-2.19 (m, 1H), 2.19-2.05 (m, 2H), 1.15-0.91 (m, 13H). HRMS (ESI-TOF) m/z: $[M+H]^+$ calcd for $C_{51}H_{60}FN_{12}O_8S^+$, 1019.4356; found 1019.4377.

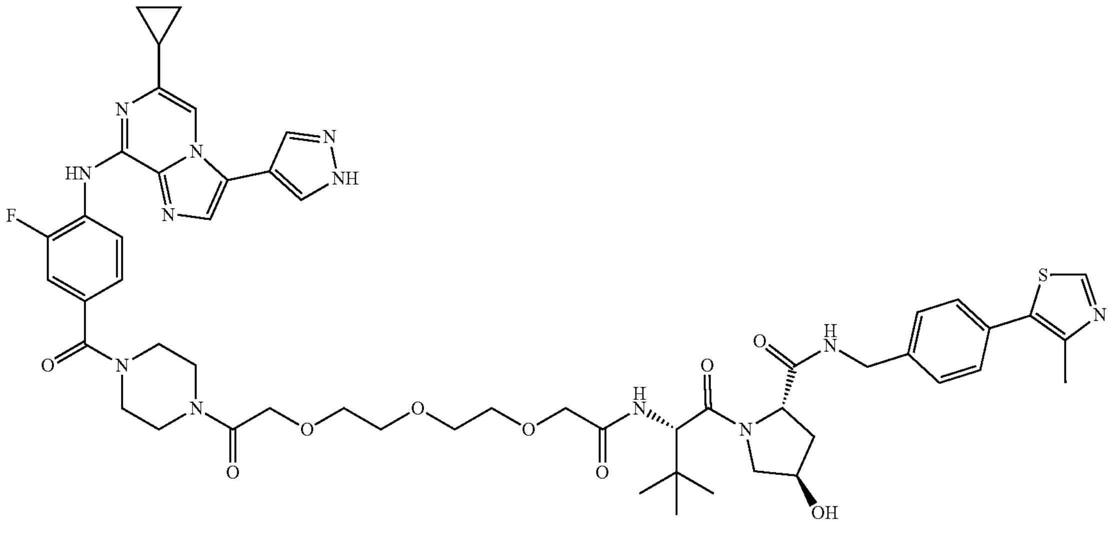 [SMILES: Cc1ncsc1-c1ccc(CNC(=O)[C@@H]2C[C@@H](O)CN2C(=O)[C@@H](NC(=O)COCCOCCOCC(=O)N2CCN(C(=O)c3ccc(Nc4nc(C5CC5)cn5c(-c6cn[nH]c6)cnc45)c(F)c3)CC2)C(C)(C)C)cc1]

Example 73: (2S,4R)-1-((S)-2-(tert-Butyl)-14-(4-(4-((6-cyclopropyl-3-(1H-pyrazol-4-yl)imidazo[1,2-a]pyrazin-8-yl)amino)-3-fluorobenzoyl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide. 67% yield. $^{1}$H NMR (500 MHz, $CD_3OD$) δ 9.03 (s, 1H), 8.58 (t, J=8.2 Hz, 1H), 8.17 (s, 2H), 8.01 (s, 1H), 7.98 (s, 1H), 7.55-7.23 (m, 6H), 4.72 (s, 1H), 4.65-4.48 (m, 3H), 4.42-4.23 (m, 3H), 4.11-3.95 (m, 2H), 3.92-3.49 (m, 18H), 2.50 (s, 3H), 2.30-2.20 (m, 1H), 2.20-2.05 (m, 2H), 1.12-0.94 (m, 13H). HRMS (ESI-TOF) m. $[M+H]^+$ calcd for $C_{53}H_{64}FN_{12}O_9S^+$, 1063.4618; found 1063.4632.

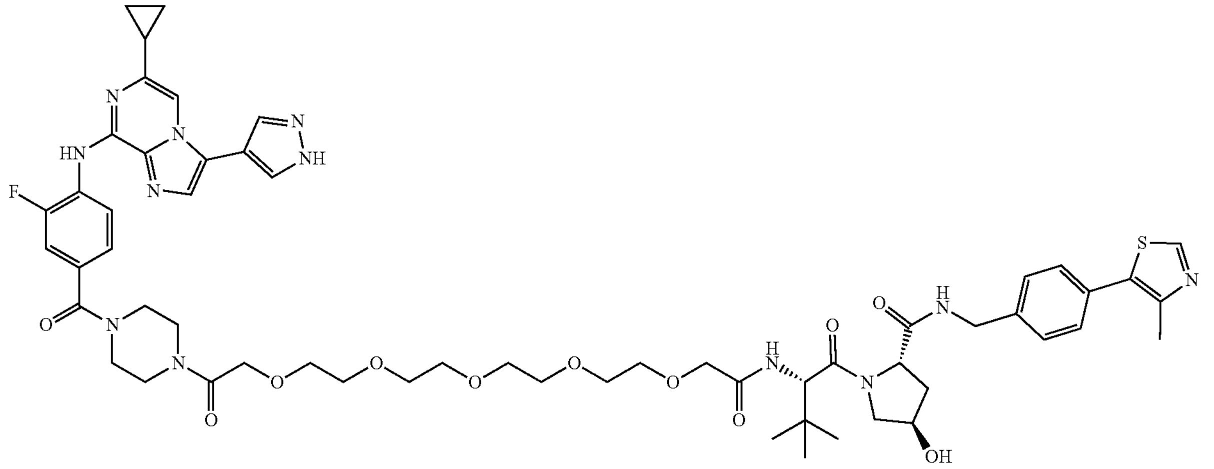 [SMILES: Cc1ncsc1-c1ccc(CNC(=O)[C@@H]2C[C@@H](O)CN2C(=O)[C@@H](NC(=O)COCCOCCOCCOCCOCC(=O)N2CCN(C(=O)c3ccc(Nc4nc(C5CC5)cn5c(-c6cn[nH]c6)cnc45)c(F)c3)CC2)C(C)(C)C)cc1]

Example 74: (2S,4R)-1-((S)-2-(tert-Butyl)-20-(4-(4-((6-cyclopropyl-3-(1H-pyrazol-4-yl)imidazo[1,2-a]pyrazin-8-yl)amino)-3-fluorobenzoyl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide. 56% yield. $^{1}$H NMR (500 MHz, $CD_3OD$) δ 9.11 (s, 1H), 8.55 (t, J=8.0 Hz, 1H), 8.18 (s, 2H), 8.03 (s, 2H), 7.56-7.32 (m, 6H), 4.71 (s, 1H), 4.64-4.49 (m, 3H), 4.37 (d, J=15.6 Hz, 1H), 4.31 (s, 2H), 4.07 (d, J=4.1 Hz, 2H), 3.94-3.48 (m, 26H), 2.51 (s, 3H), 2.29-2.20 (m, 1H), 2.20-2.06 (m, 2H), 1.13-0.93 (m, 13H). HRMS (ESI-TOF) m/z: $[M+H]^+$ calcd for $C_{57}H_{72}FN_{12}O_{11}S^+$, 1151.5143; found 1151.5117.

Scheme 27. Synthesis of example 31

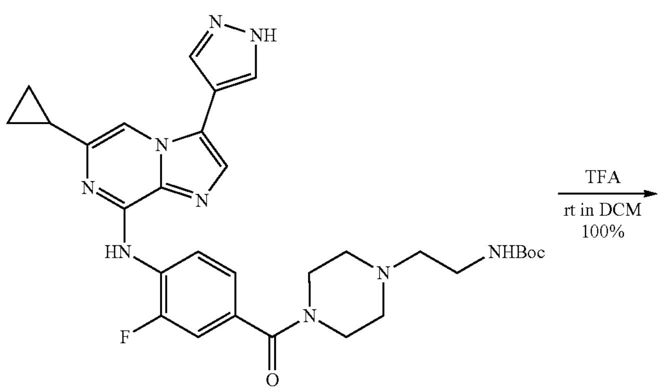

intermediate 8

-continued

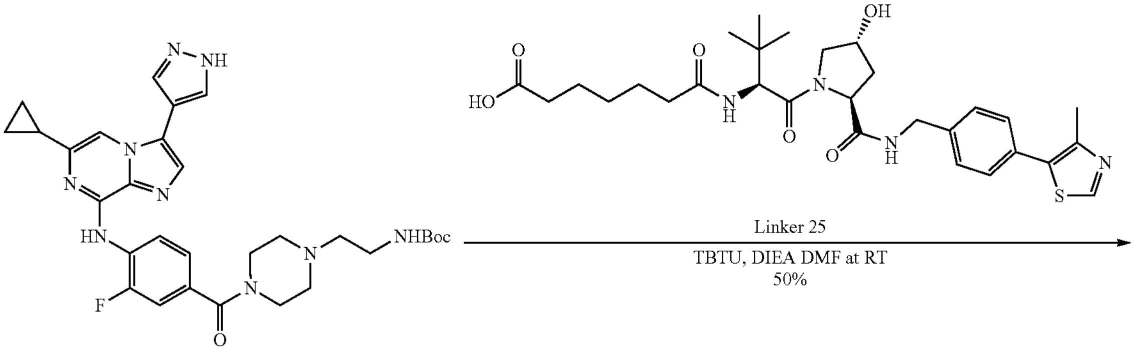

intermediate 40

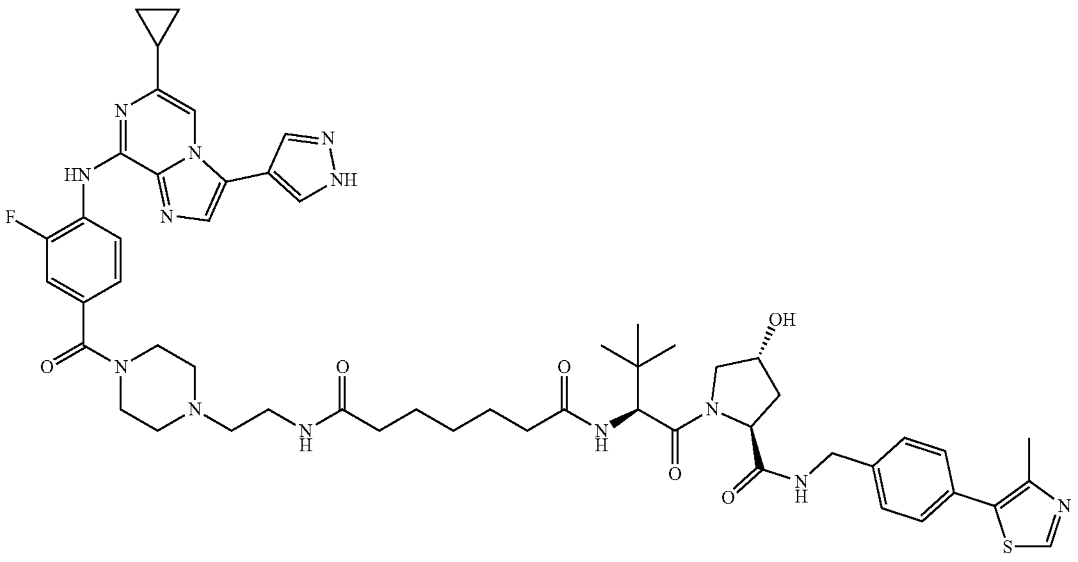

Example 31

Example 31: $N^1$-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-$N^7$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide. A solution of intermediate 8 in DCM/TFA (2:1, 1 mL) was stirred at rt. After 2 h, the solvent was removed under reduced pressure to obtain intermediate 9 as brown oil. To a solution of intermediate 9 (5 mg, 0.009 mmol) and linker 8 (5 mg, 0.008 mmol) in DMF (0.5 mL) were added DIEA (17 μL, 0.1 mmol) and TBTU (4 mg, 0.01 mmol). After being stirred at rt for 12 h, the mixture was purified by HPLC to yield the title compound (7 mg, 75%) as the brown oil. $^1H$ NMR (600 MHz, $CD_3OD$) δ 8.98-8.91 (m, 1H), 8.74 (t, J=8.2 Hz, 1H), 8.15 (s, 2H), 7.98 (s, 1H), 7.86 (s, 1H), 7.52-7.37 (m, 6H), 4.66 (s, 1H), 4.64-4.50 (m, 3H), 4.38 (d, J=15.4 Hz, 1H), 3.92 (d, J=11.0 Hz, 1H), 3.83 (dd, J=10.9, 3.8 Hz, 1H), 3.77-3.34 (m, 12H), 2.50 (s, 3H), 2.42-2.21 (m, 5H), 2.21-2.05 (m, 2H), 1.71-1.58 (m, 4H), 1.43-1.33 (m, 2H), 1.12-0.86 (m, 13H). HRMS (ESI-TOF) m/z: $[M+H]^+$ calcd for $C_{54}H_{67}FN_3O_6S^+$, 1044.5037; found 1044.5060.

Example compounds 75-101 were synthesized according to the procedures for the preparation of example compound 28.

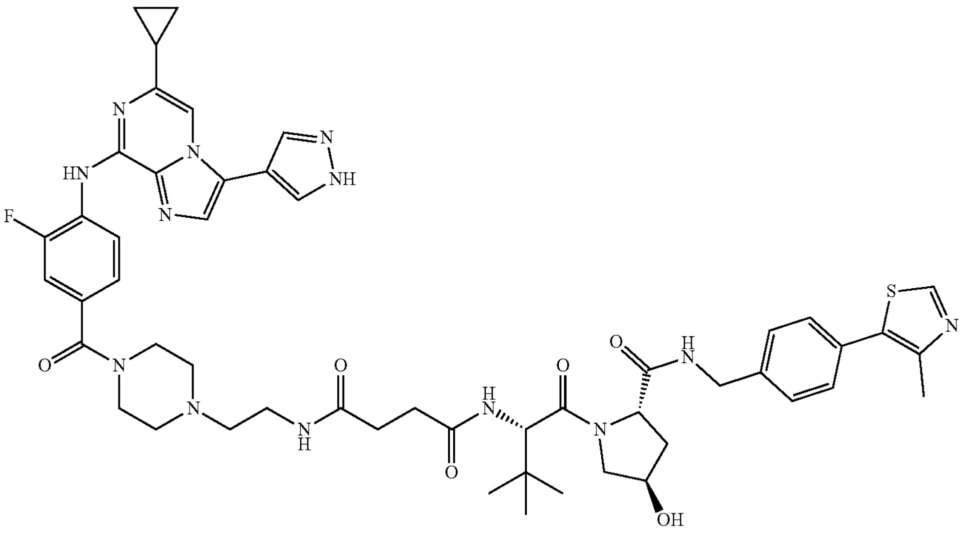 [SMILES: Cc1ncsc1-c1ccc(CNC(=O)[C@@H]2C[C@@H](O)CN2C(=O)[C@@H](NC(=O)CCC(=O)NCCN2CCN(C(=O)c3ccc(Nc4nc(C5CC5)cn5c(-c6cn[nH]c6)cnc45)c(F)c3)CC2)C(C)(C)C)cc1]

Example 75: N[1]-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-N[4]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide. 70% yield. $^1$H NMR (500 MHz, $CD_3OD$) δ 8.98 (s, 1H), 8.68 (t, J=8.2 Hz, 1H), 8.15 (s, 2H), 7.98 (s, 1H), 7.90 (s, 1H), 7.53-7.36 (m, 6H), 4.63-4.49 (m, 4H), 4.38 (d, J=15.5 Hz, 1H), 3.87-3.77 (m, 2H), 3.77-3.42 (m, 10H), 3.38 (t, J=4.8 Hz, 2H), 2.72-2.66 (m, 2H), 2.53-2.46 (m, 5H), 2.30-2.21 (m, 1H), 2.17-2.06 (m, 2H), 1.13-1.00 (m, 11H), 1.00-0.95 (m, 2H). HRMS (ESI-TOF) m/z: $[M+H]^+$ calcd for $C_{51}H_{61}FN_{13}O_6S^+$, 1002.4567; found 1002.4587.

Example 76: NM-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-N[51]—((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)glutaramide. 73% yield. $^1$H NMR (500 MHz, $CD_3OD$) δ 8.96 (s, 1H), 8.69 (t, J=8.2 Hz, 1H), 8.15 (s, 2H), 7.97 (s, 1H), 7.87 (s, 1H), 7.55-7.34 (m, 6H), 4.63 (s, 1H), 4.62-4.50 (m, 3H), 4.39 (d, J=15.5 Hz, 1H), 3.94 (d, J=11.0 Hz, 1H), 3.83 (dd, J=11.0, 3.8 Hz, 1H), 3.71-3.41 (m, 10H), 3.37 (t, J=5.8 Hz, 2H), 2.48 (s, 3H), 2.43-2.22 (m, 5H), 2.17-2.08 (m, 2H), 2.00-1.91 (m, 2H), 1.10-1.02 (m, 11H), 1.00-0.95 (m, 2H). HRMS (ESI-TOF) m/z: $[M+H]^+$ calcd for $C_{52}H_{63}FN_{13}O_6S^+$, 1016.4724; found 1016.4739.

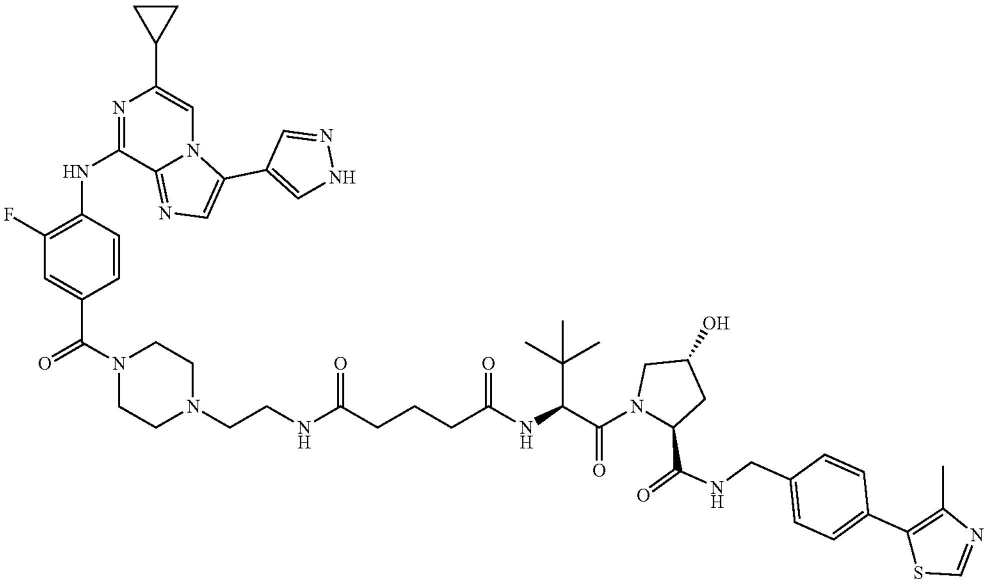 [SMILES: Cc1ncsc1-c1ccc(CNC(=O)[C@@H]2C[C@@H](O)CN2C(=O)[C@@H](NC(=O)CCCC(=O)NCCN2CCN(C(=O)c3ccc(Nc4nc(C5CC5)cn5c(-c6cn[nH]c6)cnc45)c(F)c3)CC2)C(C)(C)C)cc1]

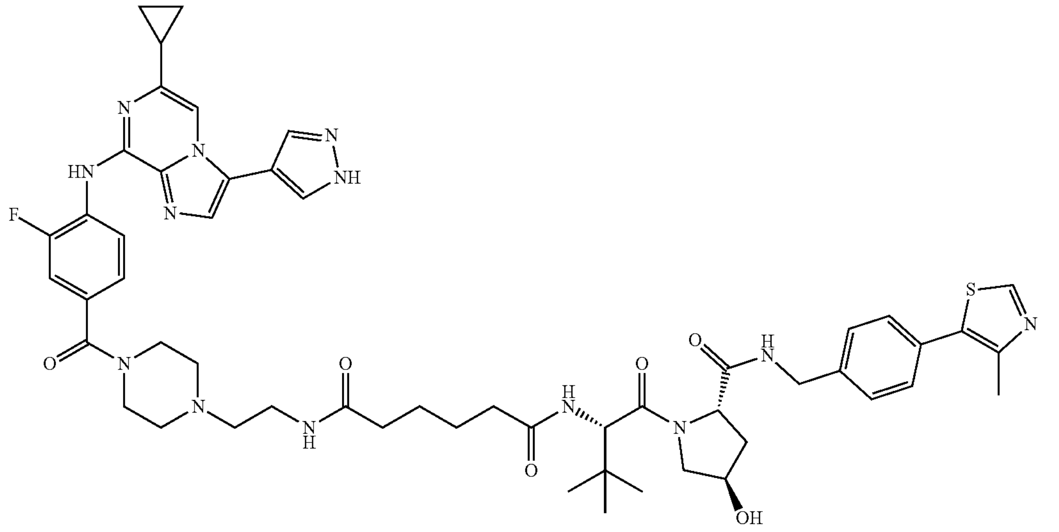 [SMILES: Cc1ncsc1-c1ccc(CNC(=O)[C@@H]2C[C@@H](O)CN2C(=O)[C@@H](NC(=O)CCCCC(=O)NCCN2CCN(C(=O)c3ccc(Nc4nc(C5CC5)cn5c(-c6cn[nH]c6)cnc45)c(F)c3)CC2)C(C)(C)C)cc1]

Example 77: $N^1$-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-$N^6$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide. 55% yield. $^1$H NMR (500 MHz, $CD_3OD$) δ 8.97 (s, 1H), 8.70 (t, J=8.2 Hz, 1H), 8.15 (s, 2H), 7.97 (s, 1H), 7.88 (s, 1H), 7.53-7.29 (m, 6H), 4.64 (s, 1H), 4.63-4.49 (m, 3H), 4.39 (d, J=15.4 Hz, 1H), 3.92 (d, J=11.1 Hz, 1H), 3.83 (dd, J=11.0, 3.8 Hz, 1H), 3.72-3.40 (m, 10H), 3.37 (t, J=5.9 Hz, 2H), 2.49 (s, 3H), 2.38-2.19 (m, 5H), 2.18-2.06 (m, 2H), 1.74-1.57 (m, 4H), 1.11-1.01 (m, 11H), 1.01-0.92 (m, 2H). HRMS (ESI-TOF) m/z: $[M+H]^+$ calcd for $C_{53}H_{65}FN_3O_6S^+$, 1030.4880; found 1030.4897.

Example 78: $N^1$-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-$N^8$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide. 73% yield. $^1$H NMR (500 MHz, $CD_3OD$) δ 8.99 (s, 1H), 8.69 (t, J=8.2 Hz, 1H), 8.15 (s, 2H), 7.98 (s, 1H), 7.90 (s, 1H), 7.59-7.25 (m, 6H), 4.65 (s, 1H), 4.63-4.49 (m, 3H), 4.38 (d, J=15.5 Hz, 1H), 3.92 (d, J=11.0 Hz, 1H), 3.83 (dd, J=10.9, 3.8 Hz, 1H), 3.71-3.40 (m, 10H), 3.39-3.35 (m, 2H), 2.49 (s, 3H), 2.38-2.19 (m, 5H), 2.19-2.05 (m, 2H), 1.76-1.56 (m, 4H), 1.47-1.31 (m, 4H), 1.11-1.01 (m, 11H), 1.01-0.93 (m, 2H). HRMS (ESI-TOF) m/z: $[M+H]^+$ calcd for $C_{55}H_{69}FN_{13}O_6S^+$, 1058.5193; found 1058.5177.

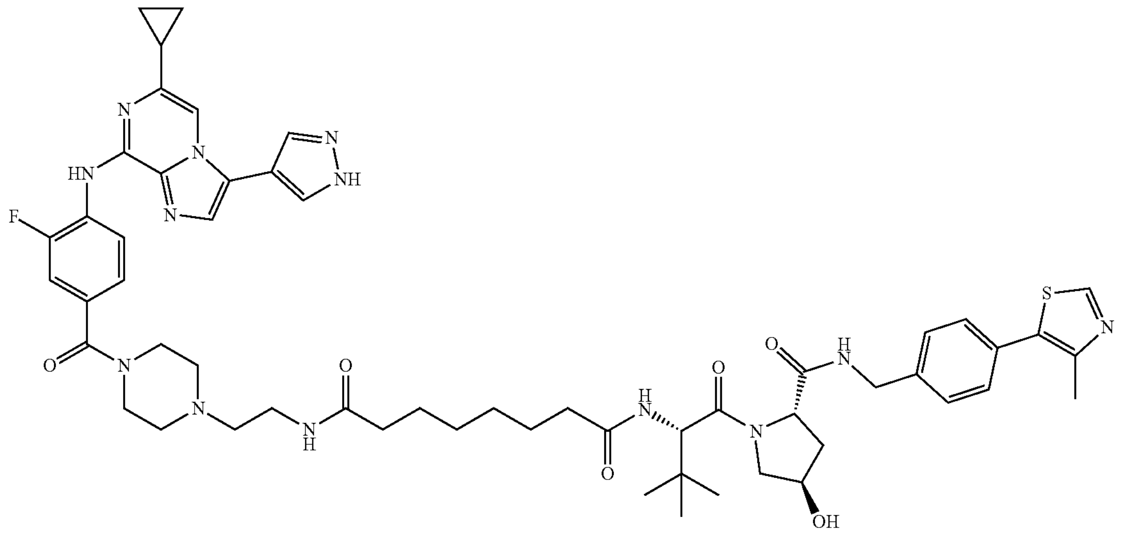 [SMILES: Cc1ncsc1-c1ccc(CNC(=O)[C@@H]2C[C@@H](O)CN2C(=O)[C@@H](NC(=O)CCCCCCC(=O)NCCN2CCN(C(=O)c3ccc(Nc4nc(C5CC5)cn5c(-c6cn[nH]c6)cnc45)c(F)c3)CC2)C(C)(C)C)cc1]

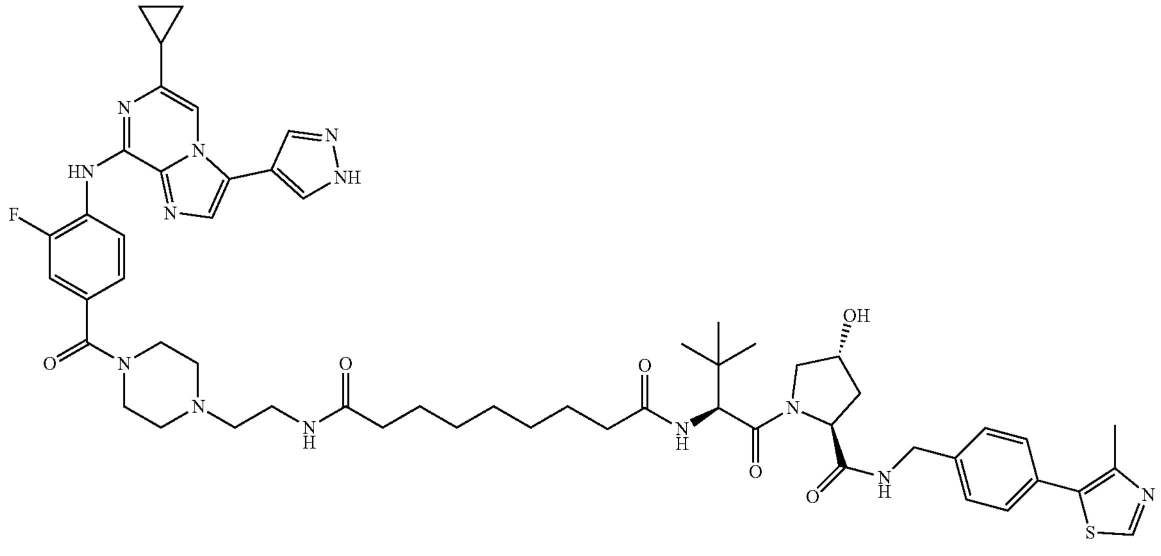 [SMILES: Cc1ncsc1-c1ccc(CNC(=O)[C@@H]2C[C@@H](O)CN2C(=O)[C@@H](NC(=O)CCCCCCCC(=O)NCCN2CCN(C(=O)c3ccc(Nc4nc(C5CC5)cn5c(-c6cn[nH]c6)cnc45)c(F)c3)CC2)C(C)(C)C)cc1]

Example 79: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-$N^9$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide. 69% yield. $^1$H NMR (500 MHz, $CD_3OD$) δ 8.95 (s, 1H), 8.73 (t, J=8.2 Hz, 1H), 8.14 (s, 2H), 7.96 (s, 1H), 7.84 (s, 1H), 7.53-7.33 (m, 6H), 4.65 (s, 1H), 4.62-4.49 (m, 3H), 4.38 (d, J=15.5 Hz, 1H), 3.92 (d, J=11.1 Hz, 1H), 3.82 (dd, J=10.9, 3.9 Hz, 1H), 3.73-3.40 (m, 10H), 3.37-3.35 (m, 2H), 2.49 (s, 3H), 2.35-2.18 (m, 5H), 2.16-2.05 (m, 2H), 1.69-1.55 (m, 4H), 1.36 (s, 6H), 1.12-1.00 (m, 11H), 1.00-0.92 (m, 2H). HRMS (ESI-TOF) m/z: $[M+H]^+$ calcd for $C_{56}H_{71}FN_{13}O_6S^+$, 1072.5350; found 1072.5371.

Example 80: NM-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-$N^{10}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide. 63% yield. $^1$H NMR (500 MHz, $CD_3OD$) δ 9.01 (s, 1H), 8.68 (t, J=8.2 Hz, 1H), 8.16 (s, 2H), 7.99 (s, 1H), 7.91 (s, 1H), 7.61-7.30 (m, 6H), 4.66 (s, 1H), 4.62-4.49 (m, 3H), 4.38 (d, J=15.5 Hz, 1H), 3.92 (d, J=11.0 Hz, 1H), 3.82 (dd, J=10.9, 3.8 Hz, 1H), 3.68-3.39 (m, 10H), 3.39-3.35 (m, 2H), 2.50 (s, 3H), 2.37-2.19 (m, 5H), 2.19-2.06 (m, 2H), 1.71-1.54 (m, 4H), 1.42-1.27 (m, 8H), 1.11-1.02 (m, 1H), 1.02-0.95 (m, 2H). HRMS (ESI-TOF) m/z: $[M+H]^+$ calcd for $C_7H_{73}FN_{13}O_6S^+$, 1086.5506; found 1086.5519.

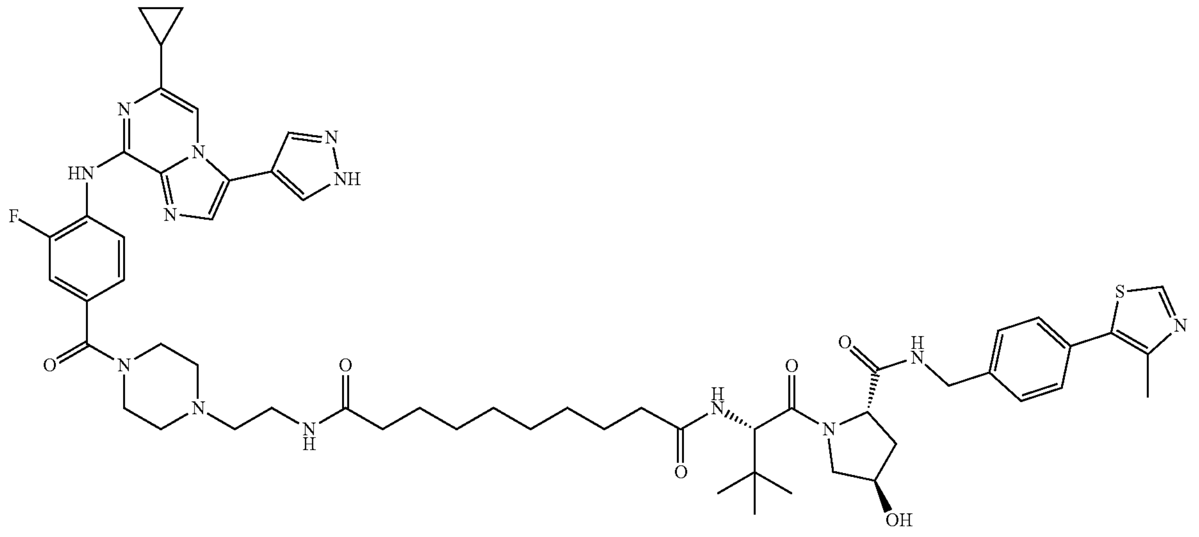 [SMILES: Cc1ncsc1-c1ccc(CNC(=O)[C@@H]2C[C@@H](O)CN2C(=O)[C@@H](NC(=O)CCCCCCCCC(=O)NCCN2CCN(C(=O)c3ccc(Nc4nc(C5CC5)cn5c(-c6cn[nH]c6)cnc45)c(F)c3)CC2)C(C)(C)C)cc1]

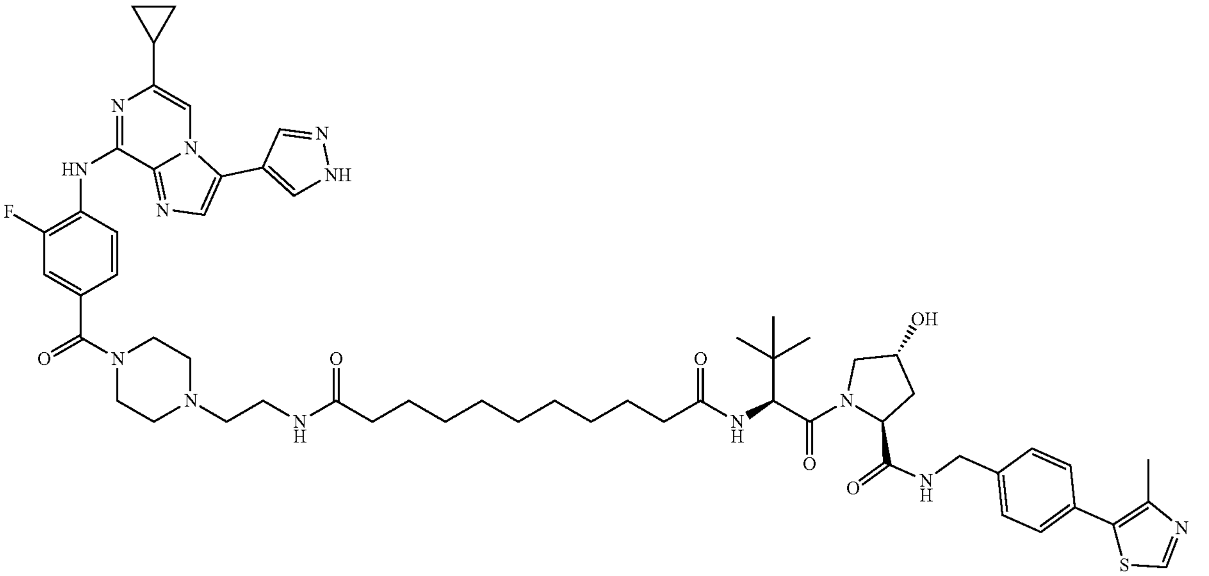 [SMILES: Cc1ncsc1-c1ccc(CNC(=O)[C@@H]2C[C@@H](O)CN2C(=O)[C@@H](NC(=O)CCCCCCCCCC(=O)NCCN2CCN(C(=O)c3ccc(Nc4nc(C5CC5)cn5c(-c6cn[nH]c6)cnc45)c(F)c3)CC2)C(C)(C)C)cc1]

Example 81: $N^1$-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-$N^{11}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide. 67% yield. $^1$H NMR (500 MHz, $CD_3OD$) δ 9.00 (s, 1H), 8.69 (t, J=8.2 Hz, 1H), 8.16 (s, 2H), 7.99 (s, 1H), 7.90 (s, 1H), 7.53-7.31 (m, 6H), 4.65 (s, 1H), 4.61-4.50 (m, 3H), 4.38 (d, J=15.5 Hz, 1H), 3.92 (d, J=11.0 Hz, 1H), 3.82 (dd, J=10.9, 3.9 Hz, 1H), 3.69-3.39 (m, 10H), 3.38-3.34 (m, 2H), 2.50 (s, 3H), 2.36-2.19 (m, 5H), 2.19-2.06 (m, 2H), 1.73-1.54 (m, 4H), 1.44-1.24 (m, 10H), 1.11-0.95 (m, 13H). HRMS (ESI-TOF) m/z: $[M+H]^+$ calcd for $C_{55}H_{75}FN_{13}O_6S^+$, 1100.5663; found 1100.5655.

Example 82: (2S,4R)-1-((S)-2-(2-(2-((2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)amino)-2-oxoethoxy)acetamido)-3,3-dimethylbutanoyl)-4-hydroxy-N-(4-(4-methylthiazol-5-yl)benzyl)pyrrolidine-2-carboxamide. 66% yield. $^1$H NMR (500 MHz, $CD_3OD$) δ 8.98 (s, 1H), 8.66 (t, J=8.2 Hz, 1H), 8.15 (s, 2H), 7.98 (s, 1H), 7.91 (s, 1H), 7.56-7.32 (m, 6H), 4.73 (s, 1H), 4.63-4.44 (m, 3H), 4.39 (d, J=15.5 Hz, 1H), 4.25-4.09 (m, 4H), 3.92 (d, J=11.0 Hz, 1H), 3.84 (dd, J=11.0, 3.7 Hz, 1H), 3.76-3.37 (m, 12H), 2.48 (s, 3H), 2.31-2.23 (m, 1H), 2.18-2.05 (m, 2H), 1.11-1.02 (m, 11H), 1.01-0.95 (m, 2H). HRMS (ESI-TOF) m/z: $[M+H]^+$ calcd for $C_{51}H_{61}FN_{13}O_7S^+$, 1018.4516; found 1018.4516.

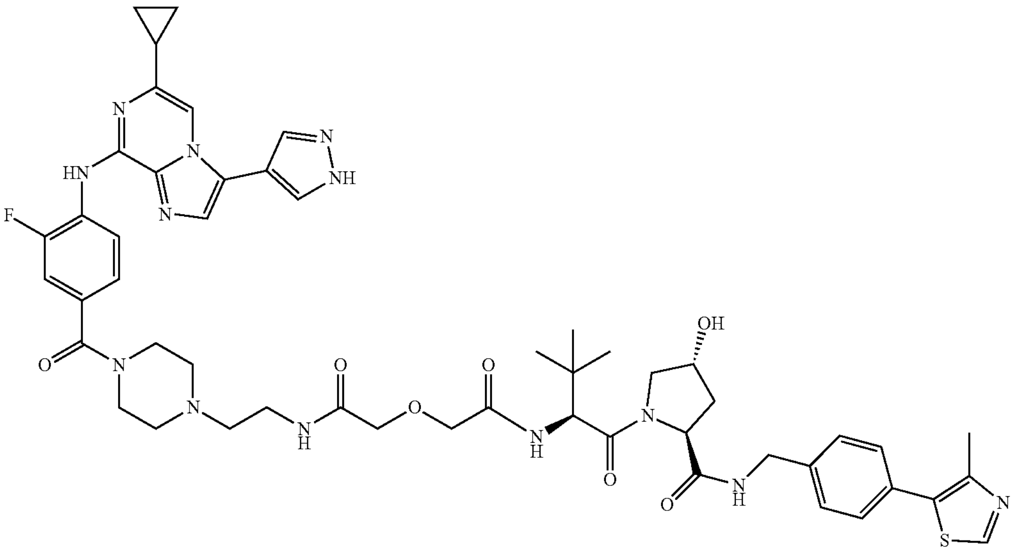 [SMILES: Cc1ncsc1-c1ccc(CNC(=O)[C@@H]2C[C@@H](O)CN2C(=O)[C@@H](NC(=O)COCC(=O)NCCN2CCN(C(=O)c3ccc(Nc4nc(C5CC5)cn5c(-c6cn[nH]c6)cnc45)c(F)c3)CC2)C(C)(C)C)cc1]

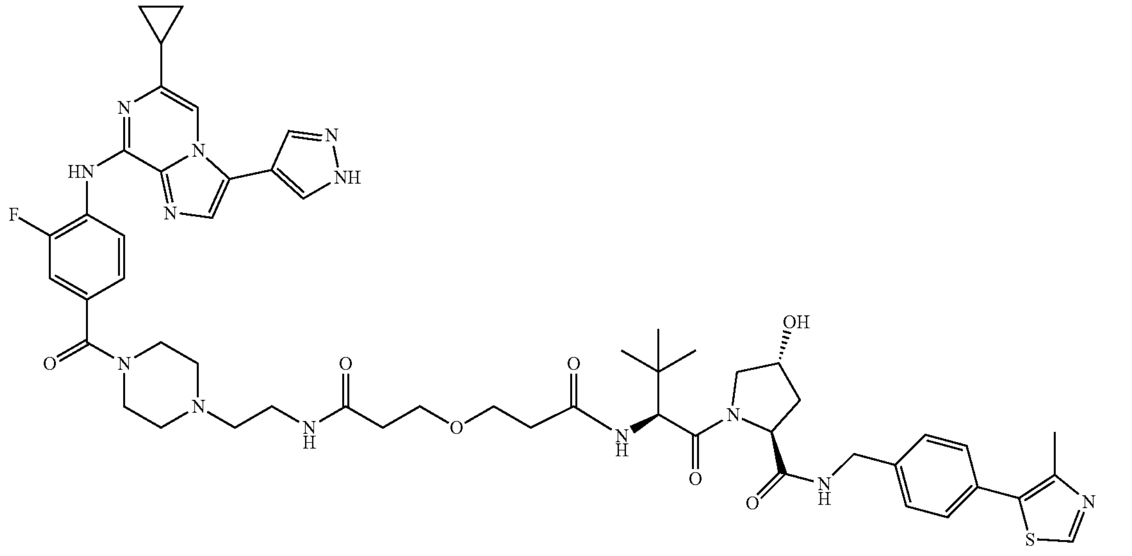 [SMILES: Cc1ncsc1-c1ccc(CNC(=O)[C@@H]2C[C@@H](O)CN2C(=O)[C@@H](NC(=O)CCOCCC(=O)NCCN2CCN(C(=O)c3ccc(Nc4nc(C5CC5)cn5c(-c6cn[nH]c6)cnc45)c(F)c3)CC2)C(C)(C)C)cc1]

Example 83: (2S,4R)-1-((S)-2-(3-(3-((2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)amino)-3-oxopropoxy)propanamido)-3,3-dimethylbutanoyl)-4-hydroxy-N-(4-(4-methylthiazol-5-yl)benzyl)pyrrolidine-2-carboxamide. 68% yield. $^1$H NMR (500 MHz, $CD_3OD$) δ 8.98 (s, 1H), 8.66 (t, J=8.2 Hz, 1H), 8.16 (s, 2H), 7.99 (s, 1H), 7.92 (s, 1H), 7.53-7.34 (m, 6H), 4.66 (s, 1H), 4.63-4.48 (m, 3H), 4.40 (d, J=15.4 Hz, 1H), 3.91 (d, J=11.1 Hz, 1H), 3.83 (dd, J=11.0, 3.8 Hz, 1H), 3.74 (dd, J=13.5, 5.9 Hz, 4H), 3.69-3.35 (m, 12H), 2.61-2.50 (m, 4H), 2.48 (s, 3H), 2.31-2.20 (m, 1H), 2.18-2.06 (m, 2H), 1.10-1.01 (m, 11H), 1.01-0.94 (m, 2H). HRMS (ESI-TOF) m/z: $[M+H]^+$ calcd for $C_{53}H_{65}FN_{13}O_7S^+$, 1046.4829; found 1046.4813.

Example 84: (2S,4R)-1-((S)-2-(tert-Butyl)-14-(4-(4-((6-cyclopropyl-3-(1H-pyrazol-4-yl)imidazo[1,2-a]pyrazin-8-yl)amino)-3-fluorobenzoyl)piperazin-1-yl)-4,11-dioxo-6,9-dioxa-3,12-diazatetradecanoyl)-4-hydroxy-N-(4-(4-methylthiazol-5-yl)benzyl)pyrrolidine-2-carboxamide. 61% yield. $^1$H NMR (500 MHz, $CD_3OD$) δ 8.98 (s, 1H), 8.67 (t, J=8.2 Hz, 1H), 8.16 (s, 2H), 7.99 (s, 1H), 7.91 (s, 1H), 7.52-7.33 (m, 6H), 4.72 (s, 1H), 4.61-4.55 (m, 1H), 4.55-4.51 (m, 1H), 4.46 (s, 2H), 4.16 (d, J=15.6 Hz, 1H), 4.12-4.05 (m, 3H), 3.91 (d, J=11.1 Hz, 1H), 3.84 (dd, J=11.1, 3.6 Hz, 1H), 3.82-3.72 (m, 14H), 3.69 (t, J=5.6 Hz, 2H), 3.40 (dd, J=11.0, 5.3 Hz, 2H), 2.49 (s, 3H), 2.34-2.24 (m, 1H), 2.21-2.03 (m, 2H), 1.13-1.01 (m, 13H), 1.01-0.94 (m, 2H). HRMS (ESI-TOF) m/z: $[M+H]^+$ calcd for $C_{53}H_{65}FN_{13}O_8S^+$, 1062.4778; found 1062.4753.

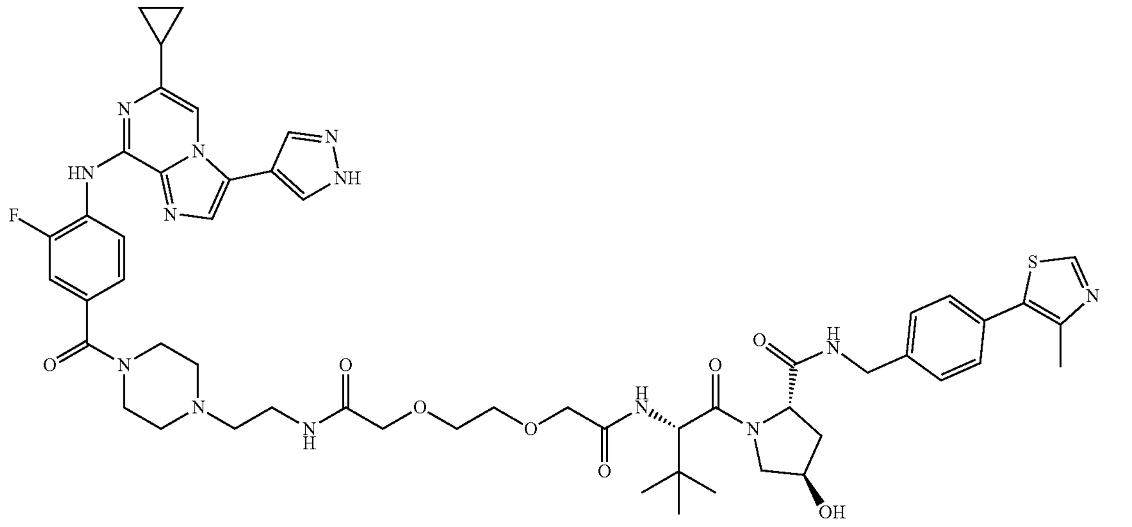 [SMILES: Cc1ncsc1-c1ccc(CNC(=O)[C@@H]2C[C@@H](O)CN2C(=O)[C@@H](NC(=O)COCCOCC(=O)NCCN2CCN(C(=O)c3ccc(Nc4nc(C5CC5)cn5c(-c6cn[nH]c6)cnc45)c(F)c3)CC2)C(C)(C)C)cc1]

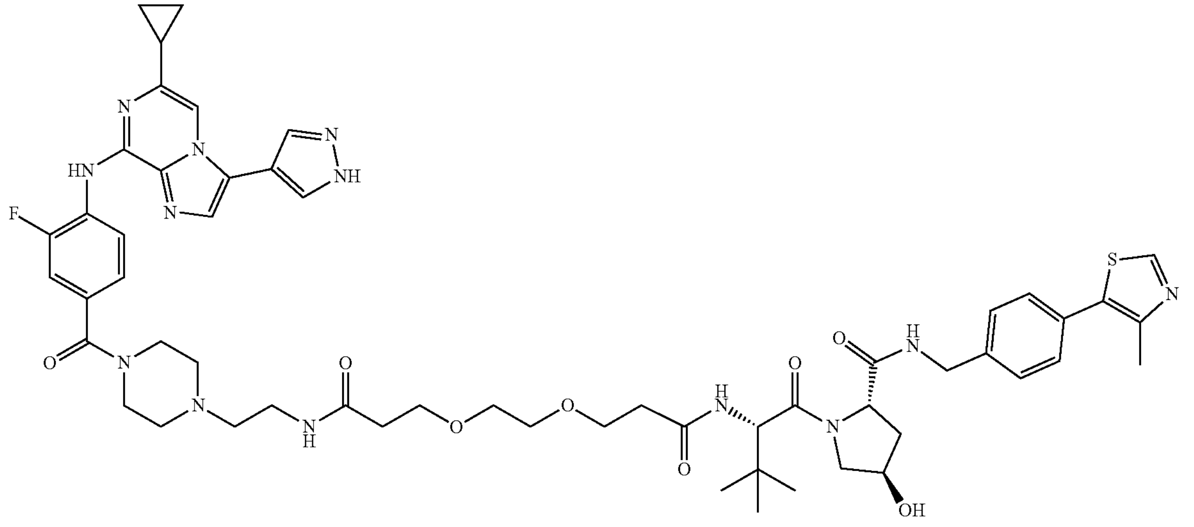 [SMILES: Cc1ncsc1-c1ccc(CNC(=O)[C@@H]2C[C@@H](O)CN2C(=O)[C@@H](NC(=O)CCOCCOCCC(=O)NCCN2CCN(C(=O)c3ccc(Nc4nc(C5CC5)cn5c(-c6cn[nH]c6)cnc45)c(F)c3)CC2)C(C)(C)C)cc1]

Example 85: (2S,4R)-1-((S)-2-(tert-Butyl)-16-(4-(4-((6-cyclopropyl-3-(1H-pyrazol-4-yl)imidazo[1,2-a]pyrazin-8-yl)amino)-3-fluorobenzoyl)piperazin-1-yl)-4,13-dioxo-7,10-dioxa-3,14-diazahexadecanoyl)-4-hydroxy-N-(4-(4-methylthiazol-5-yl)benzyl)pyrrolidine-2-carboxamide. 61% yield. $^1$H NMR (500 MHz, $CD_3OD$) δ 8.99 (s, 1H), 8.66 (t, J=8.2 Hz, 1H), 8.16 (s, 2H), 7.98 (s, 1H), 7.91 (s, 1H), 7.57-7.34 (m, 6H), 4.67 (s, 1H), 4.63-4.49 (m, 3H), 4.39 (d, J=15.5 Hz, 1H), 3.91 (d, J=10.1 Hz, 1H), 3.88-3.70 (m, 7H), 3.70-3.42 (m, 12H), 3.42-3.36 (m, 2H), 2.65-2.44 (m, 7H), 2.30-2.20 (m, 1H), 2.20-2.06 (m, 2H), 1.13-0.90 (m, 13H). HRMS (ESI-TOF) m/z: $[M+H]^+$ calcd for $C_{55}H_{69}FN_3O_8S^+$, 1090.5091; found 1062.4753.

Example 86: (2S,4R)-1-((S)-2-(tert-Butyl)-17-(4-(4-((6-cyclopropyl-3-(1H-pyrazol-4-yl)imidazo[1,2-a]pyrazin-8-yl)amino)-3-fluorobenzoyl)piperazin-1-yl)-4,14-dioxo-6,9,12-trioxa-3,15-diazaheptadecanoyl)-4-hydroxy-N-(4-(4-methylthiazol-5-yl)benzyl)pyrrolidine-2-carboxamide. 67% yield. $^1$H NMR (500 MHz, $CD_3OD$) δ 8.99 (s, 1H), 8.66 (t, J=8.2 Hz, 1H), 8.16 (s, 2H), 7.99 (s, 1H), 7.92 (s, 1H), 7.54-7.38 (m, 6H), 4.69 (s, 1H), 4.61-4.50 (m, 3H), 4.39 (d, J=15.5 Hz, 1H), 4.18-4.10 (m, 2H), 4.09-3.99 (m, 2H), 3.90 (d, J=11.0 Hz, 1H), 3.86-3.80 (m, 1H), 3.80-3.44 (m, 18H), 3.40 (t, J=5.6 Hz, 2H), 2.49 (s, 3H), 2.26 (dd, J=13.1, 7.6 Hz, 1H), 2.19-2.04 (m, 2H), 1.18-1.00 (m, 11H), 1.01-0.94 (m, 2H). HRMS (ESI-TOF) m/z: $[M+H]^+$ calcd for $C_{55}H_{69}FN_{13}O_9S^+$, 1106.5040; found 1106.5071.

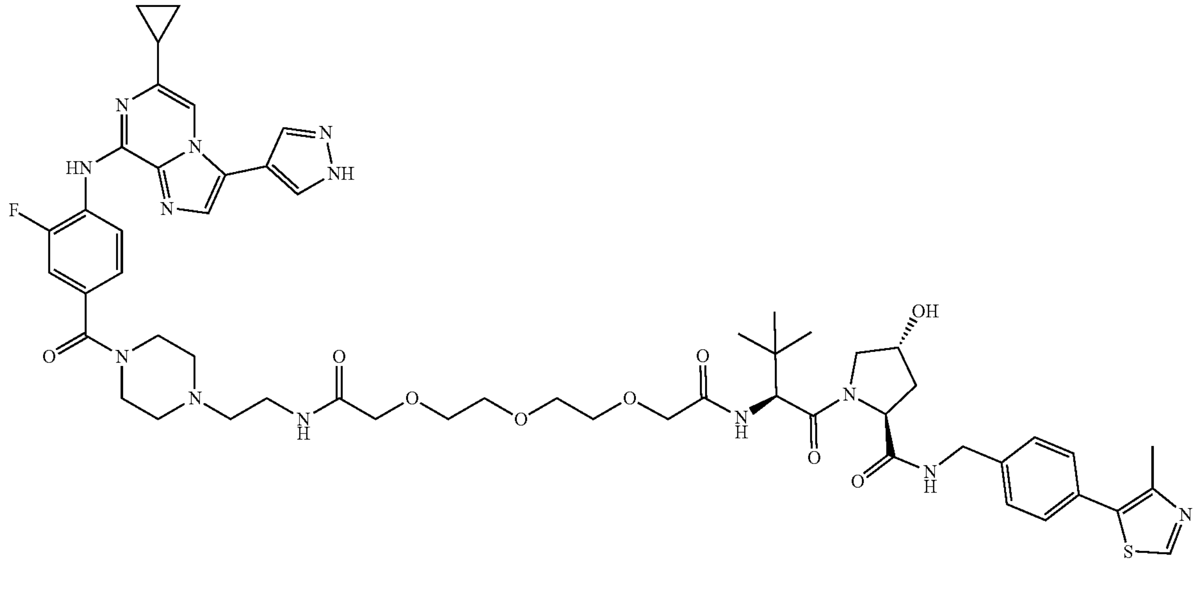 [SMILES: Cc1ncsc1-c1ccc(CNC(=O)[C@@H]2C[C@@H](O)CN2C(=O)[C@@H](NC(=O)COCCOCCOCC(=O)NCCN2CCN(C(=O)c3ccc(Nc4nc(C5CC5)cn5c(-c6cn[nH]c6)cnc45)c(F)c3)CC2)C(C)(C)C)cc1]

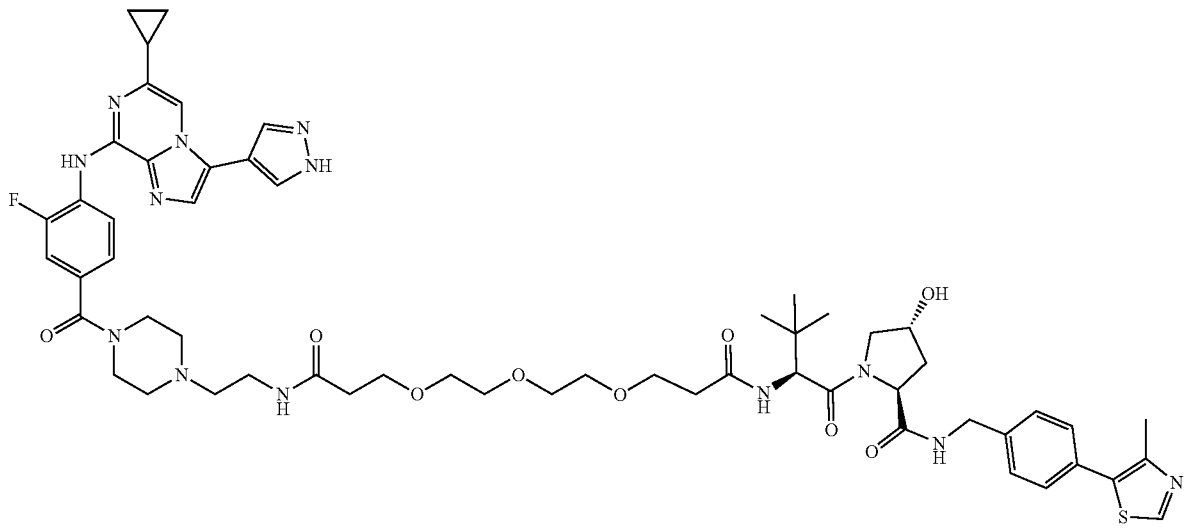 [SMILES: Cc1ncsc1-c1ccc(CNC(=O)[C@@H]2C[C@@H](O)CN2C(=O)[C@@H](NC(=O)CCOCCOCCOCCC(=O)NCCN2CCN(C(=O)c3ccc(Nc4nc(C5CC5)cn5c(-c6cn[nH]c6)cnc45)c(F)c3)CC2)C(C)(C)C)cc1]

Example 87: (2S,4R)-1-((S)-2-(tert-Butyl)-19-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-7,10,13-trioxa-3,17-diazanonadecanoyl)-4-hydroxy-N-(4-(4-methylthiazol-5-yl)benzyl)pyrrolidine-2-carboxamide. 64% yield. $^1$H NMR (500 MHz, $CD_3OD$) δ 9.07 (s, 1H), 8.61 (t, J=8.2 Hz, 1H), 8.18 (s, 2H), 8.03 (s, 1H), 8.00 (s, 1H), 7.54-7.28 (m, 6H), 4.66 (s, 1H), 4.63-4.49 (m, 3H), 4.39 (d, J=15.5 Hz, 1H), 3.91 (d, J=11.0 Hz, 1H), 3.82 (dd, J=11.0, 3.8 Hz, 1H), 3.80-3.70 (m, 6H), 3.70-3.42 (m, 16H), 3.41-3.36 (m, 2H), 2.65-2.44 (m, 7H), 2.29-2.21 (m, 1H), 2.20-2.06 (m, 2H), 1.10-1.02 (m, 11H), 1.02-0.96 (m, 1H). HRMS (ESI-TOF) m/z: $[M+H]^+$ calcd for $C_{57}H_{73}FN_{13}O_9S^+$, 1134.5353; found 1134.5370.

Example 88: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-$N^{16}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide. 60% yield. $^1$H NMR (500 MHz, $CD_3OD$) δ 9.03 (s, 1H), 8.65 (t, J=8.2 Hz, 1H), 8.17 (s, 2H), 8.01 (s, 1H), 7.96 (s, 1H), 7.52-7.39 (m, 6H), 4.66 (s, 1H), 4.62-4.49 (m, 3H), 4.38 (d, J=15.5 Hz, 1H), 3.91 (d, J=11.0 Hz, 1H), 3.82 (dd, J=11.0, 3.8 Hz, 1H), 3.80-3.69 (m, 6H), 3.69-3.42 (m, 20H), 3.42-3.36 (m, 2H), 2.65-2.43 (m, 7H), 2.29-2.19 (m, 1H), 2.19-2.06 (m, 2H), 1.11-1.01 (m, 11H), 1.01-0.94 (m, 2H). HRMS (ESI-TOF) m/z: $[M+H]^+$ calcd for $C_{19}H_{77}FN_{13}O_{10}S^+$, 1178.5616; found 1178.5627.

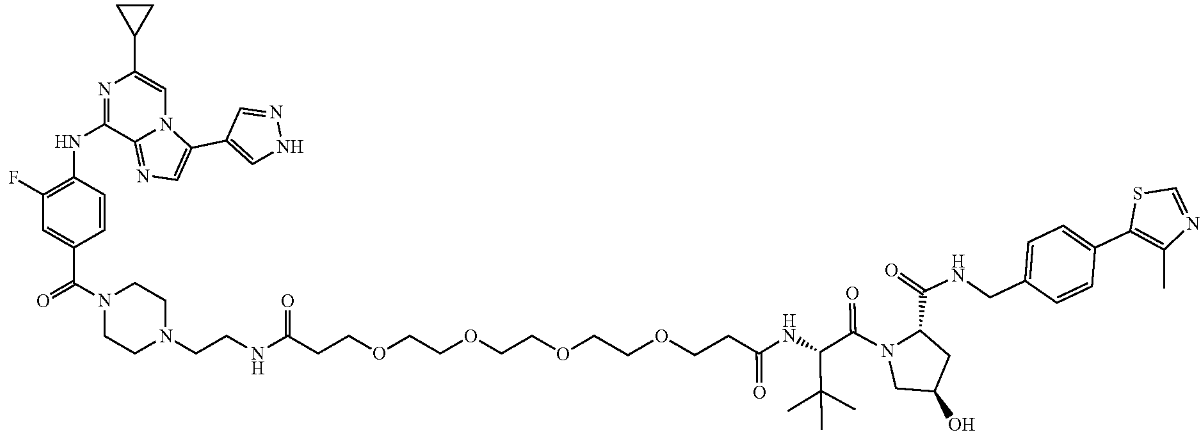 [SMILES: Cc1ncsc1-c1ccc(CNC(=O)[C@@H]2C[C@@H](O)CN2C(=O)[C@@H](NC(=O)CCOCCOCCOCCOCCC(=O)NCCN2CCN(C(=O)c3ccc(Nc4nc(C5CC5)cn5c(-c6cn[nH]c6)cnc45)c(F)c3)CC2)C(C)(C)C)cc1]

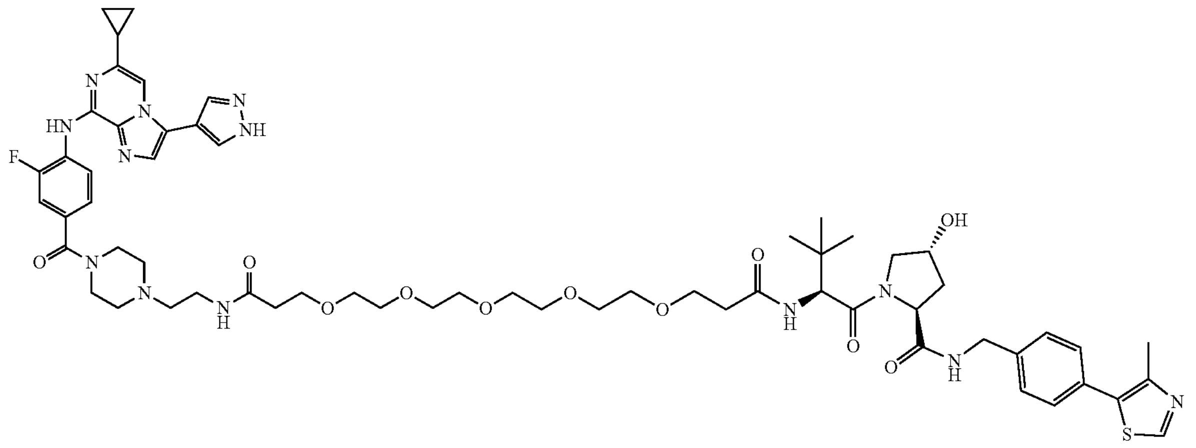 [SMILES: Cc1ncsc1-c1ccc(CNC(=O)[C@@H]2C[C@@H](O)CN2C(=O)[C@@H](NC(=O)CCOCCOCCOCCOCCOCCC(=O)NCCN2CCN(C(=O)c3ccc(Nc4nc(C5CC5)cn5c(-c6cn[nH]c6)cnc45)c(F)c3)CC2)C(C)(C)C)cc1]

Example 89: N[1]-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-N[19]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide. 62% yield. $^1$H NMR (500 MHz, $CD_3OD$) δ 9.06 (s, 1H), 8.63 (t, J=8.2 Hz, 1H), 8.17 (s, 2H), 8.02 (s, 1H), 7.98 (s, 1H), 7.61-7.34 (m, 6H), 4.66 (s, 1H), 4.62-4.49 (m, 3H), 4.38 (d, J=15.5 Hz, 1H), 3.91 (d, J=10.8 Hz, 1H), 3.85-3.71 (m, 7H), 3.70-3.41 (m, 24H), 3.41-3.37 (m, 2H), 2.63-2.46 (m, 7H), 2.29-2.20 (m, 1H), 2.20-2.07 (m, 2H), 1.14-0.95 (m, 13H). HRMS (ESI-TOF) m/z: $[M+H]^+$ calcd for $C_{61}H_{81}FN_{13}O_{11}S^+$, 1222.5878; found 1222.5899.

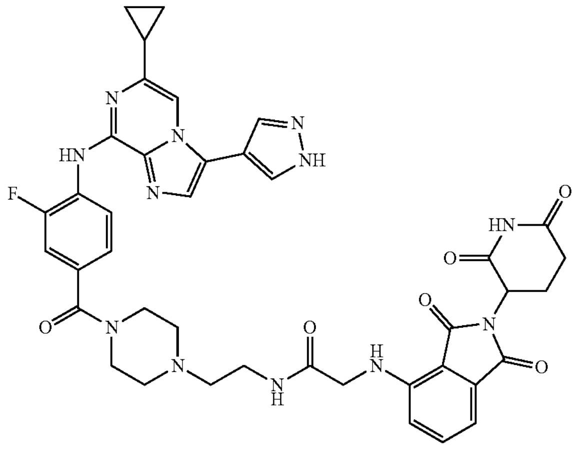 [SMILES: O=C(CNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 90: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-2-((2-(2,6-dioxopiperidin-3-yl)-1,3-dioxoisoindolin-4-yl)amino)acetamide. 70% yield. $^1$H NMR (500 MHz, $CD_3OD$) δ 8.78 (t, J=8.2 Hz, 1H), 7.98 (s, 2H), 7.77 (s, 1H), 7.67 (s, 1H), 7.55 (t, J=7.5 Hz, 1H), 7.36 (m, 2H), 7.14 (d, J=7.1 Hz, 1H), 6.88 (d, J=8.5 Hz, 1H), 5.00 (dd, J=12.0, 5.6 Hz, 1H), 4.14-3.78 (m, 6H), 3.65 (t, J=5.5 Hz, 2H), 3.49-3.35 (m, 4H), 3.32-3.29 (m, 2H), 2.86-2.70 (m, 3H), 2.17-2.08 (m, 1H), 2.06-1.97 (m, 1H), 1.08-1.00 (m, 2H), 0.99-0.91 (m, 2H). HRMS (ESI-TOF) m/z: $[M+H]^+$ calcd for $C_{40}H_{40}FN_{12}O_6S^+$, 803.3172; found 803.3178.

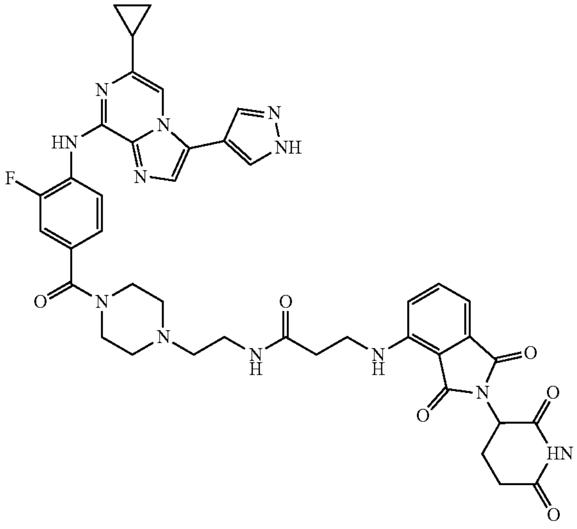 [SMILES: O=C(CCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 91: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-3-((2-(2,6-dioxopiperidin-3-yl)-1,3-dioxoisoindolin-4-yl)amino)propenamide. 71% yield. $^1$H NMR (500 MHz, $CD_3OD$) δ 8.69 (t, J=8.1 Hz, 1H), 7.99 (s, 2H), 7.79 (s, 1H), 7.74 (s, 1H), 7.57-7.50 (m, 1H), 7.41-7.29 (m, 2H), 7.06 (dd, J=17.8, 7.8 Hz, 2H), 4.98 (dd, J=12.3, 5.6 Hz, 1H), 4.20-3.70 (m, 4H), 3.70-3.54 (m, 4H), 3.53-3.37 (m, 4H), 3.28 (t, J=5.6 Hz, 2H), 2.89-2.67 (m, 3H), 2.64-2.53 (m, 2H), 2.18-2.08 (m, 1H), 2.07-1.97 (m, 1H), 1.08-0.99 (m, 2H), 1.00-0.90 (m, 2H). HRMS (ESI-TOF) m/z: $[M+H]^+$ calcd for $C_4H_{42}FN_{12}O_6S^+$, 817.3329: found 817.3311.

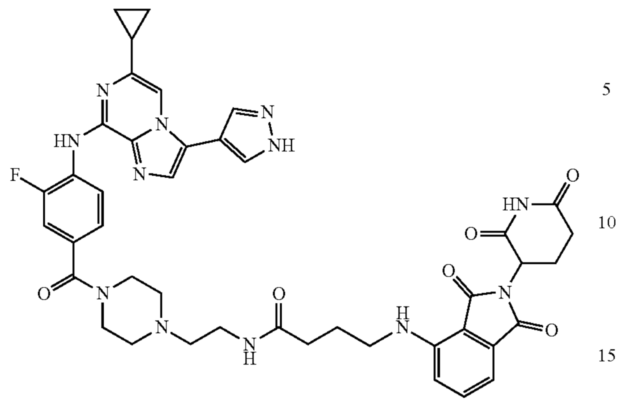

Example 92: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-4-((2-(2,6-dioxopiperidin-3-yl)-1,3-dioxoisoindolin-4-yl)amino)butanamide. 73% yield. $^1$H NMR (500 MHz, $CD_3OD$) δ 8.73 (t, J=8.1 Hz, 1H), 7.99 (s, 2H), 7.77 (s, 1H), 7.71 (s, 1H), 7.56-7.47 (m, 1H), 7.35 (dd, J=13.2, 10.5 Hz, 2H), 7.05 (d, J=7.1 Hz, 1H), 7.00 (d, J=8.6 Hz, 1H), 4.98 (dd, J=12.2, 5.6 Hz, 1H), 4.19-3.62 (m, 4H), 3.56 (t, J=5.6 Hz, 2H), 3.49-3.34 (m, 4H), 3.28 (t, J=5.6 Hz, 2H), 2.85-2.68 (m, 3H), 2.37 (t, J=7.0 Hz, 2H), 2.17-2.08 (m, 1H), 2.07-1.95 (m, 3H), 1.09-1.02 (m, 2H), 0.99-0.91 (m, 2H). HRMS (ESI-TOF) m/z: $[M+H]^+$ calcd for $C_{42}H_{44}FN_{12}O_6S^+$, 831.3485; found 831.3499.

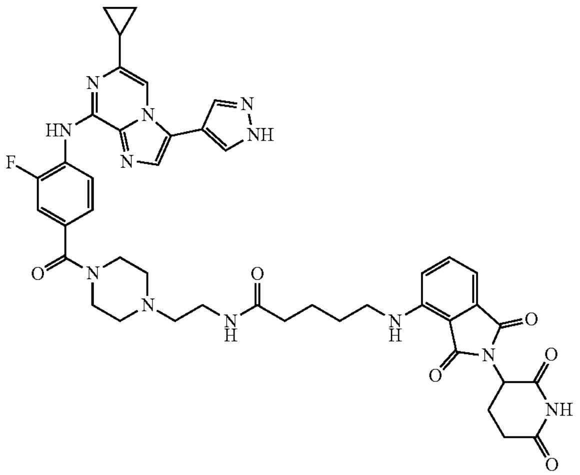 [SMILES: O=C(CCCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 93: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-5-((2-(2,6-dioxopiperidin-3-yl)-1,3-dioxoisoindolin-4-yl)amino)pentanamide. 69% yield. $^1$H NMR (500 MHz, $CD_3OD$) δ 8.69 (t, J=8.1 Hz, 1H), 8.00 (s, 2H), 7.79 (s, 1H), 7.75 (s, 1H), 7.54-7.46 (m, 1H), 7.41-7.30 (m, 2H), 7.04 (d, J=7.1 Hz, 1H), 6.96 (d, J=8.6 Hz, 1H), 4.97 (dd, J=12.2, 5.7 Hz, 1H), 4.19-3.68 (m, 4H), 3.59 (t, J=5.5 Hz, 2H), 3.52-3.36 (m, 4H), 3.32-3.23 (m, 2H), 2.87-2.68 (m, 3H), 2.30 (t, J=7.1 Hz, 2H), 2.18-2.06 (m, 1H), 2.06-1.97 (m, 1H), 1.72 (ddd, J=20.9, 12.7, 7.6 Hz, 4H), 1.09-1.01 (m, 2H), 1.01-0.92 (m, 2H). HRMS (ESI-TOF) m/z: $[M+H]^+$ calcd for $C_{43}H_4(FN_{12}O_6S^+$, 845.3642; found 845.3655.

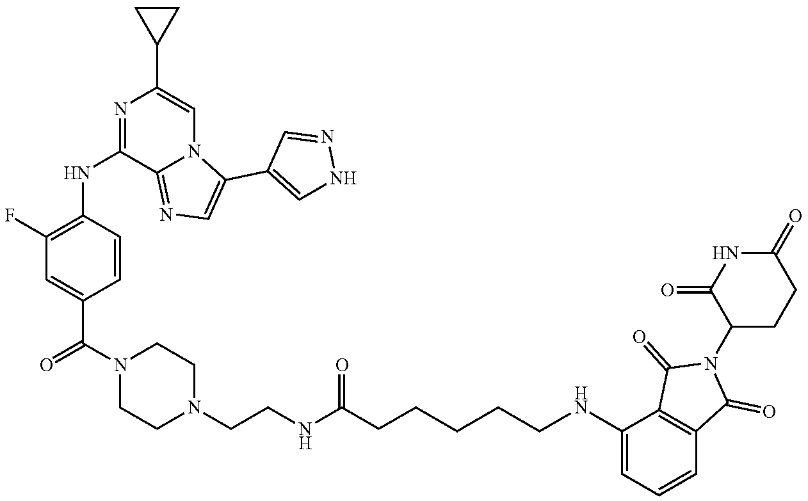 [SMILES: O=C(CCCCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 94: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-6-((2-(2,6-dioxopiperidin-3-yl)-1,3-dioxoisoindolin-4-yl)amino)hexanamide. 64% yield. HRMS (ESI-TOF) m/z: $[M+H]^+$ calcd for $C_{44}H_{46}FN_{12}O_6S^+$, 859.3798; found 859.3811.

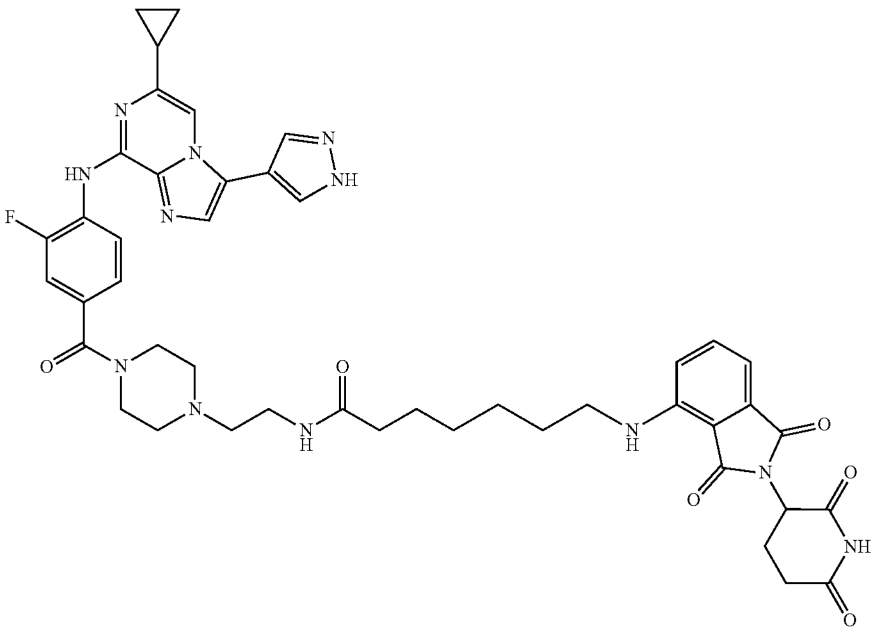 [SMILES: O=C(CCCCCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 95: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-7-((2-(2,6-dioxopiperidin-3-yl)-1,3-dioxoisoindolin-4-yl)amino)heptanamide. 70% yield. $^1H$ NMR (500 MHz, $CD_3OD$) δ 8.73 (t, J=8.1 Hz, 1H), 7.98 (s, 2H), 7.77 (s, 1H), 7.71 (s, 1H), 7.50 (dd, J=8.5, 7.2 Hz, 1H), 7.43-7.30 (m, 2H), 7.04 (d, J=7.1 Hz, 1H), 6.94 (d, J=8.6 Hz, 1H), 4.97 (dd, J=12.1, 5.6 Hz, 1H), 4.17-3.69 (m, 4H), 3.59 (t, J=5.7 Hz, 2H), 3.51-3.37 (m, 4H), 3.32-3.26 (m, 4H), 2.90-2.69 (m, 3H), 2.24 (t, J=7.6 Hz, 2H), 2.17-2.09 (m, 1H), 2.05-1.98 (m, 1H), 1.73-1.57 (m, 4H), 1.50-1.33 (m, 4H), 1.08-1.01 (m, 2H), 0.99-0.92 (m, 2H). HRMS (ESI-TOF) m/z: $[M+H]^+$ calcd for $C_{45}H_{50}FN_{12}O_6S^+$, 873.3955; found 873.3928.

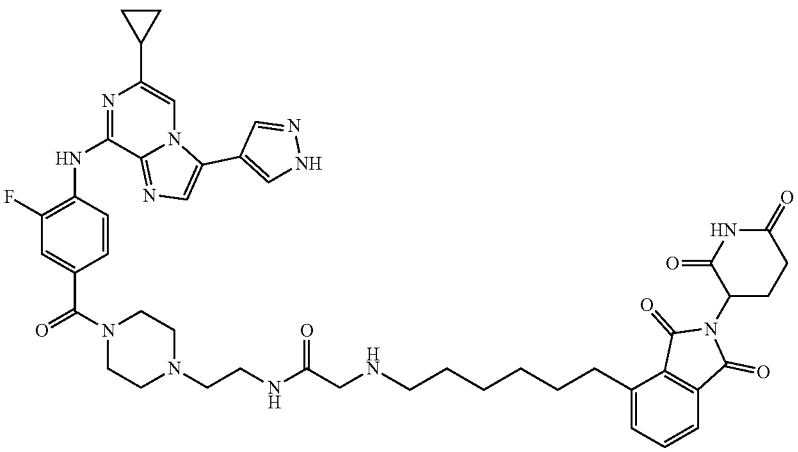 [SMILES: O=C(CNCCCCCCc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 96: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-8-((2-(2,6-dioxopiperidin-3-yl)-1,3-dioxoisoindolin-4-yl)amino)octanamide. 71% yield. $^1$H NMR (500 MHz, $CD_3OD$) δ 8.67 (t, J=8.1 Hz, 1H), 8.01 (s, 2H), 7.80 (s, 1H), 7.76 (s, 1H), 7.54-7.46 (m, 1H), 7.41-7.31 (m, 2H), 7.04 (t, J=7.9 Hz, 1H), 6.93 (d, J=8.6 Hz, 1H), 4.97 (dd, J=12.1, 5.6 Hz, 1H), 4.17-3.66 (m, 4H), 3.59 (t, J=5.6 Hz, 2H), 3.54-3.37 (m, 4H), 3.33-3.21 (m, 4H), 2.86-2.68 (m, 3H), 2.22 (t, J=7.6 Hz, 2H), 2.17-2.07 (m, 1H), 2.08-1.96 (m, 1H), 1.73-1.52 (m, 4H), 1.49-1.29 (m, 6H), 1.09-1.00 (m, 2H), 1.01-0.90 (m, 2H). HRMS (ESI-TOF) m/z: $[M+H]^+$ calcd for $C_{46}H_{52}FN_{12}O_6S^+$, 887.4111; found 887.4114.

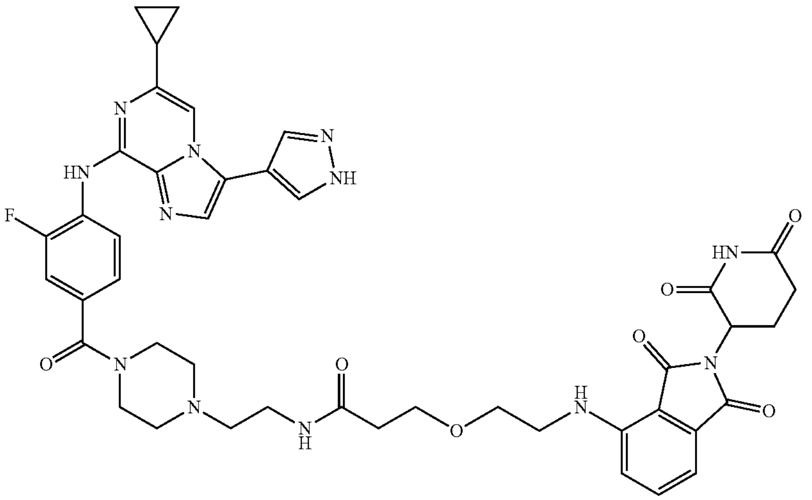

Example 97: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-3-(2-((2-(2,6-dioxopiperidin-3-yl)-1,3-dioxoisoindolin-4-yl)amino)ethoxy)propenamide. 73% yield. HRMS (ESI-TOF) m/z: $[M+H]^+$ calcd for $C_{43}H_{46}FN_{12}O_7S^+$, 861.3591; found 861.3588.

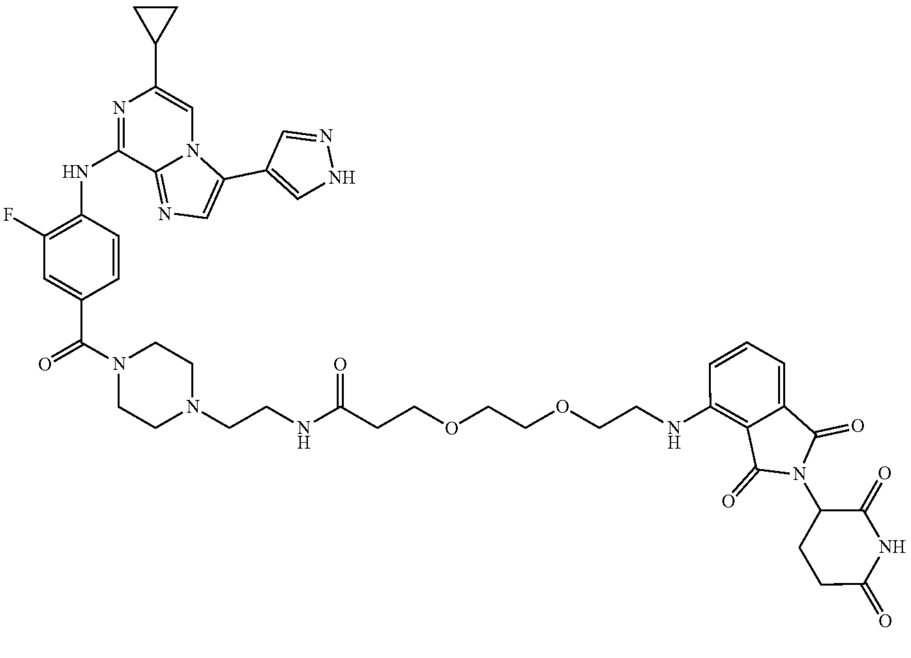 [SMILES: O=C(CCOCCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 98: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-3-(2-(2-((2-(2,6-dioxopiperidin-3-yl)-1,3-dioxoisoindolin-4-yl)amino)ethoxy)ethoxy)propenamide. 70% yield. $^1$H NMR (500 MHz, $CD_3OD$) δ 8.75 (t, J=8.2 Hz, 1H), 7.98 (s, 2H), 7.76 (s, 1H), 7.67 (s, 1H), 7.54-7.46 (m, 1H), 7.41-7.25 (m, 2H), 7.05 (d, J=7.0 Hz, 1H), 6.98 (d, J=8.6 Hz, 1H), 4.99 (dd, J=12.3, 5.6 Hz, 1H), 4.21-3.83 (m, 4H), 3.77 (t, J=5.8 Hz, 2H), 3.72 (t, J=5.1 Hz, 2H), 3.65 (s, 4H), 3.61-3.52 (m, 2H), 3.52-3.36 (m, 6H), 3.31-3.23 (m, 2H), 2.90-2.70 (m, 3H), 2.50 (t, J=5.8 Hz, 2H), 2.18-2.09 (m, 1H), 2.01 (ddd, J=12.9, 8.3, 4.2 Hz, 1H), 1.06-1.00 (m, 2H), 1.00-0.90 (m, 2H). HRMS (ESI-TOF) m/z: $[M+H]^+$ calcd for $C_{45}H_{50}FN_{12}O_8S^+$, 905.3853; found 905.3829.

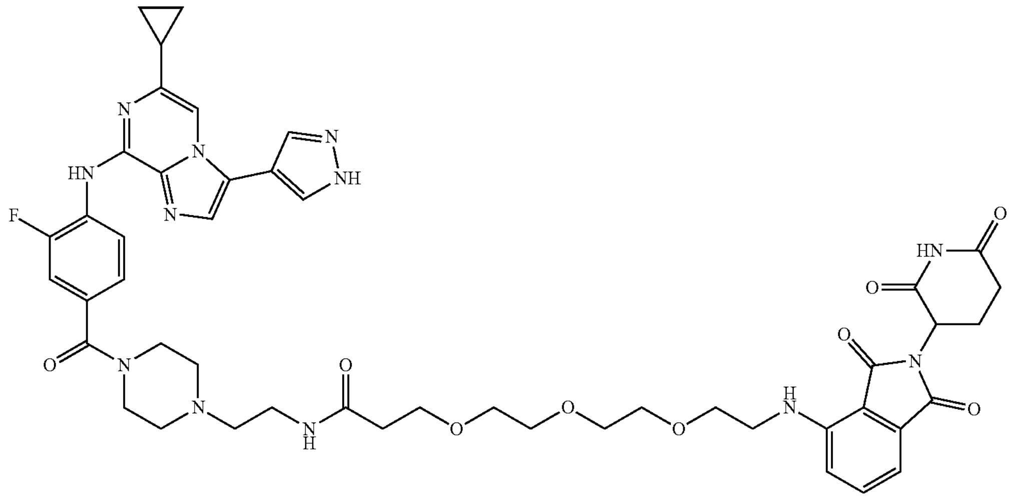 [SMILES: O=C(CCOCCOCCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 99: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-3-(2-(2-(2-((2-(2,6-dioxopiperidin-3-yl)-1,3-dioxoisoindolin-4-yl)amino)ethoxy)ethoxy)ethoxy)propenamide. 68% yield. $^1$H NMR (500 MHz, $CD_3OD$) δ 8.72 (t, J=8.1 Hz, 1H), 7.96 (s, 2H), 7.74 (s, 1H), 7.66 (d, J=12.2 Hz, 1H), 7.49 (dd, J=8.4, 7.2 Hz, 1H), 7.34 (dd, J=17.0, 5.7 Hz, 2H), 7.05 (d, J=7.1 Hz, 1H), 6.97 (t, J=8.8 Hz, 1H), 4.97 (dd, J=12.3, 5.6 Hz, 1H), 4.12-3.80 (m, 4H), 3.79-3.69 (m, 4H), 3.69-3.53 (m, 10H), 3.53-3.35 (m, 6H), 3.31-3.27 (m, 2H), 2.85-2.69 (m, 3H), 2.48 (t, J=5.8 Hz, 2H), 2.17-2.09 (m, 1H), 2.02-1.95 (m, 1H), 1.05-0.99 (m, 2H), 0.98-0.92 (m, 2H). HRMS (ESI-TOF) m/z: $[M+H]^+$ calcd for $C_{47}H_{54}FN_{12}O_9S^+$, 949.4115: found 949.4133.

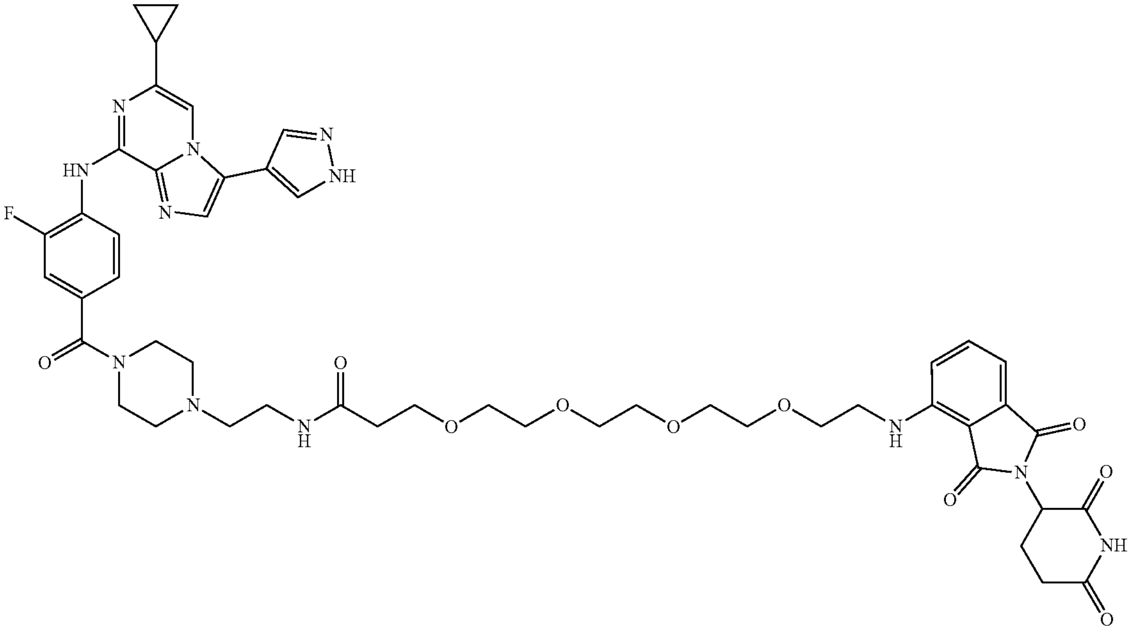 [SMILES: O=C(CCOCCOCCOCCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Example 100: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-1-(2-(2,6-dioxopiperidin-3-yl)-1,3-dioxoisoindolin-4-yl)amino)-3,6,9,12-tetraoxapentadecan-15-amide. 66% yield. $^1$H NMR (500 MHz, $CD_3OD$) δ 8.71 (t, J=8.1 Hz, 1H), 7.99 (s, 2H), 7.78 (s, 1H), 7.72 (s, 1H), 7.54-7.44 (m, 1H), 7.36 (dd, J=17.1, 5.9 Hz, 2H), 7.04 (d, J=7.1 Hz, 1H), 6.98 (d, J=8.6 Hz, 1H), 4.98 (dd, J=12.4, 5.6 Hz, 1H), 4.15-3.80 (m, 4H), 3.80-3.70 (m, 4H), 3.70-3.53 (m, 14H), 3.52-3.36 (m, 6H), 3.32-3.29 (m, 2H), 2.87-2.68 (m, 3H), 2.49 (t, J=5.8 Hz, 2H), 2.19-2.08 (m, 1H), 2.08-1.97 (m, 1H), 1.09-0.99 (m, 2H), 1.00-0.90 (m, 2H). HRMS (ESI-TOF) m/z: $[M+H]^+$ calcd for $C_{49}H_{58}FN_{12}O_{10}S^+$, 993.4377; found 993.4369.

Example 101: N-(2-(4-(4-((6-Cyclopropyl-3-(1H-pyrazol-4-yl)imidazo[1,2-a]pyrazin-8-yl)amino)-3-fluorobenzoyl)piperazin-1-yl)ethyl)-1-((2-(2,6-dioxopiperidin-3-yl)-1,3-dioxoisoindolin-4-yl)amino)-3,6,9,12,15-pentaoxaoctadecan-18-amide. 72% yield. $^1$H NMR (500 MHz, $CD_3OD$) δ 8.74 (t, J=8.1 Hz, 1H), 7.97 (s, 2H), 7.73 (s, 1H), 7.66 (s, 1H), 7.52-7.47 (m, 1H), 7.39-7.29 (m, 2H), 7.05 (d, J=7.1 Hz, 1H), 6.98 (d, J=8.6 Hz, 1H), 4.96 (dd, J=12.2, 5.6 Hz, 1H), 4.13-3.77 (m, 4H), 3.79-3.69 (m, 4H), 3.69-3.54 (m, 18H), 3.52-3.35 (m, 6H), 3.32-3.28 (m, 2H), 2.86-2.68 (m, 3H), 2.49 (t, J=5.8 Hz, 2H), 2.13 (dd, J=9.6, 5.9 Hz, 1H), 2.04-1.92 (m, 1H), 1.07-1.00 (m, 2H), 1.00-0.92 (m, 2H). HRMS (ESI-TOF) m/z: $[M+H]^+$ calcd for $C_{51}H_{62}FN_{12}O_{11}S^+$, 1037.4640; found 1037.4655.

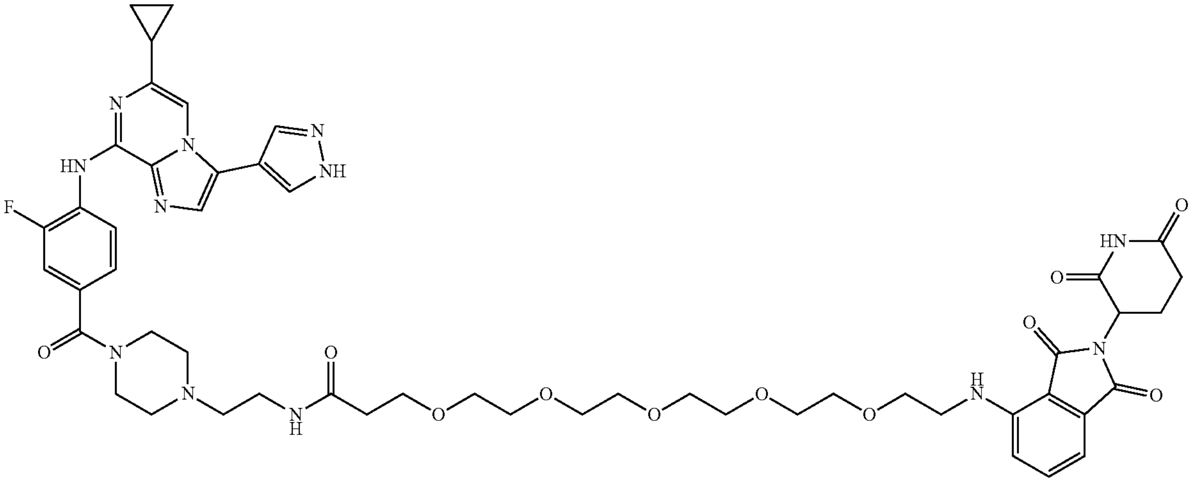 [SMILES: O=C(CCOCCOCCOCCOCCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

Scheme 28. Synthesis of example 108

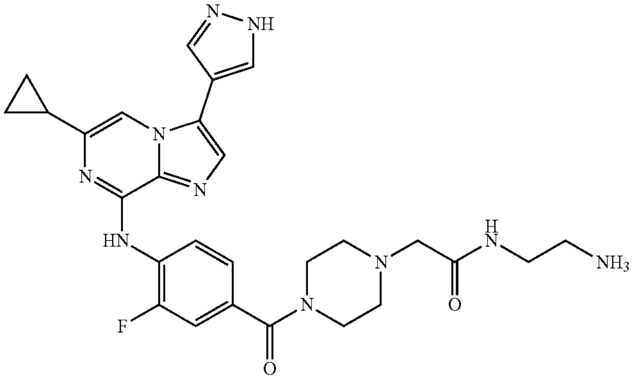

Linker 12

+

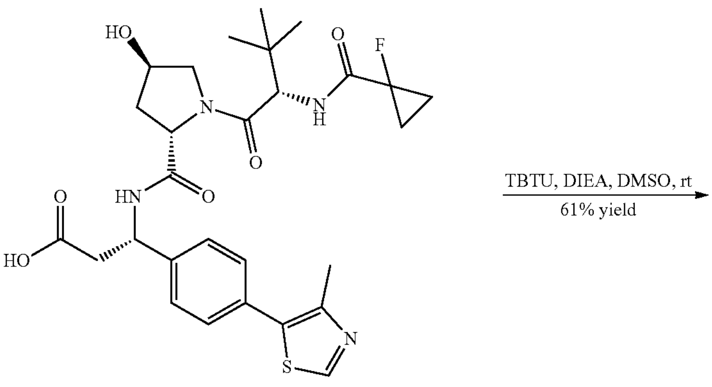

Intermediate 17

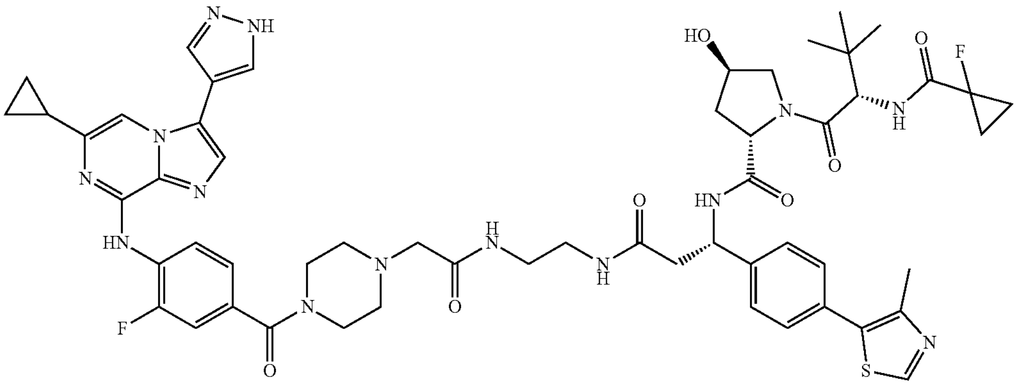

Example 108

Example 108: (2S,4R)—N—((S)-3-((2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide. Example 108 was synthesized according to the procedures for the preparation of example 1. 61% yield. $^1$H NMR (500 MHz, $CD_3OD$) δ 8.99-8.92 (m, 1H), 8.75-8.65 (m, 1H), 8.16 (s, 2H), 7.97 (s, 1H), 7.91 (s, 1H), 7.55-7.36 (m, 6H), 5.43-5.29 (m, 1H), 4.77-4.66 (m, 1H), 4.64-4.55 (m, 1H), 4.53-4.45 (m, 1H), 4.10-3.91 (m, 6H), 3.87 (d, J=11.2 Hz, 1H), 3.78 (dd, J=11.1, 3.5 Hz, 1H), 3.57-3.40 (m, 6H), 3.32-3.26 (m, 2H), 2.88-2.70 (m, 2H), 2.49 (s, 3H), 2.25 (dd, J=13.1, 7.6 Hz, 1H), 2.17-2.07 (m, 1H), 1.97 (ddd, J=13.5, 9.5, 4.4 Hz, 1H), 1.44-1.27 (m, 4H), 1.12 (s, 3H), 1.10-1.02 (m, 9H), 0.99-0.94 (m, 2H). HRMS (ESI-TOF) m/z: $[M+H]^+$ calcd for $C_{55}H_{65}F_2N_{14}O_7S^+$, 1103.4844; found 1103.4856.

Example compounds 109-129 were synthesized according to the procedures for the preparation of example compound 108.

1H), 4.66-4.53 (m, 1H), 4.47 (s, 1H), 4.13-3.89 (m, 6H), 3.85 (d, J=11.2 Hz, 1H), 3.78 (dd, J=11.1, 3.6 Hz, 1H), 3.55-3.41 (m, 4H), 3.27-3.09 (m, 4H), 2.93-2.84 (m, 1H), 2.82-2.70 (m, 1H), 2.49 (s, 3H), 2.30-2.17 (m, 1H), 2.17-2.05 (m, 1H), 2.02-1.91 (m, 1H), 1.71-1.55 (m, 2H), 1.45-1.25 (m, 4H), 1.12 (s, 2H), 1.10-1.00 (m, 9H), 0.97 (dd, J=8.1, 2.4 Hz, 2H). HRMS (ESI-TOF) m/z: $[M+H]^+$ calcd for $C_{56}H_{67}F_2N_{14}O_7S^+$, 1117.5000; found 1117.4977.

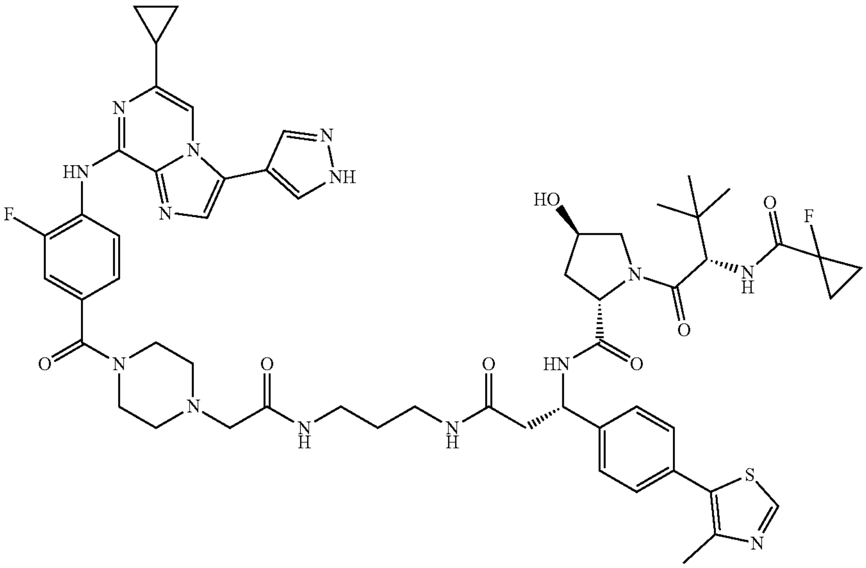 [SMILES: Cc1ncsc1-c1ccc([C@H](CC(=O)NCCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

Example 109: (2S,4R)—N—((S)-3-((3-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)propyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide.

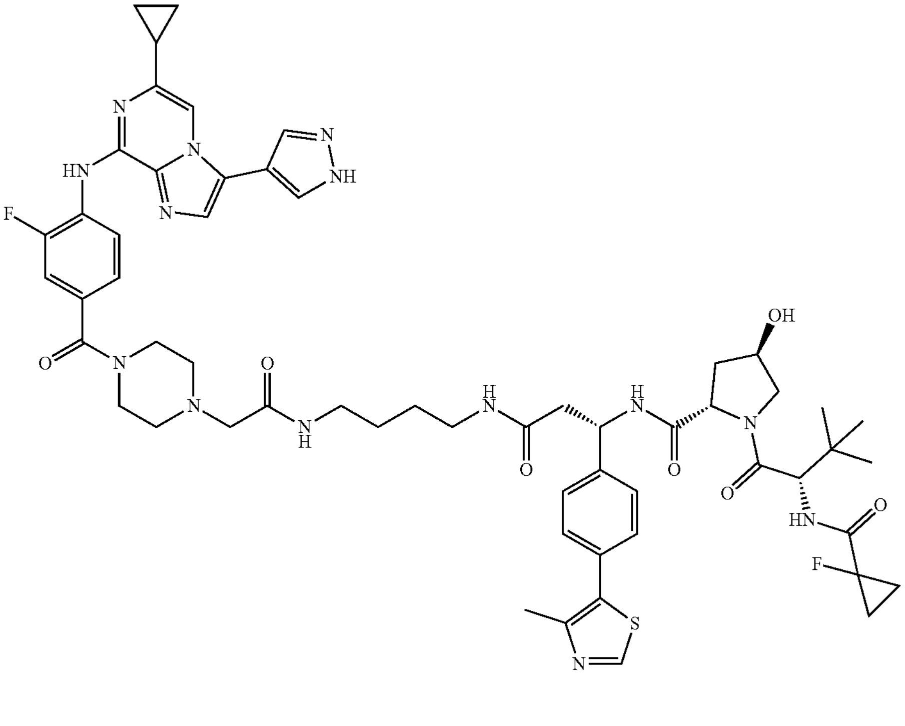 [SMILES: Cc1ncsc1-c1ccc([C@H](CC(=O)NCCCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

68% yield. $^1H$ NMR (500 MHz, $CD_3OD$) δ 8.96 (s, 1H), 8.75-8.63 (m, 1H), 8.15 (s, 2H), 7.98 (s, 1H), 7.89 (s, 1H), 7.54-7.36 (m, 6H), 5.41-5.29 (m, 1H), 4.75 (d, J=9.1 Hz, Example 110: (2S,4R)—N—((S)-3-((4-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)butyl)

amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide. 63% yield. $^1$H NMR (600 MHz, $CD_3OD$) δ 8.99-8.86 (m, 1H), 8.76-8.65 (m, 1H), 8.15 (s, 2H), 8.00-7.93 (m, 1H), 7.85 (s, 1H), 7.52-7.36 (m, 6H), 5.40-5.21 (m, 1H), 4.78-4.71 (m, 1H), 4.66-4.53 (m, 2H), 4.51-4.37 (m, 1H), 4.16-3.87 (m, 6H), 3.85 (d, J=11.3 Hz, 1H), 3.80-3.73 (m, 1H), 3.58-3.37 (m, 4H), 3.29-3.18 (m, 2H), 3.18-3.09 (m, 2H), 2.89-2.66 (m, 2H), 2.49 (s, 3H), 2.28-2.18 (m, 1H), 2.16-2.05 (m, 1H), 2.02-1.90 (m, 1H), 1.55-1.25 (m, 8H), 1.13 (s, 3H), 1.10-1.01 (m, 8H), 0.99-0.93 (m, 2H). HRMS (ESI-TOF) m/z: $[M+H]^+$ calcd for $C_{57}H_{69}F_2N_{14}O_7S^+$, 1131.5157; found 1131.5131.

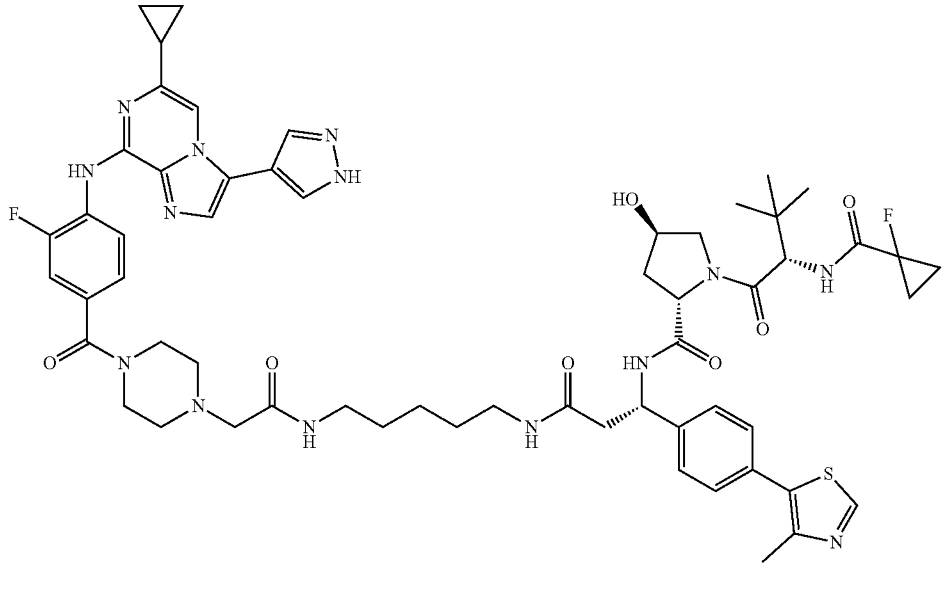

Example 111: (2S,4R)—N—((S)-3-((5-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)pentyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide. 59% yield. $^1$H NMR (600 MHz, $CD_3OD$) δ 8.92 (s, 1H), 8.72 (t, J=8.3 Hz, 1H), 8.15 (s, 2H), 7.95 (s, 1H), 7.84 (s, 1H), 7.53-7.36 (m, 6H), 5.42-5.23 (m, 1H), 4.75 (d, J=9.2 Hz, 1H), 4.67-4.53 (m, 2H), 4.52-4.42 (m, 1H), 4.17-3.89 (m, 6H), 3.86 (d, J=11.1 Hz, 1H), 3.80-3.73 (m, 1H), 3.58-3.38 (m, 4H), 3.28-3.04 (m, 4H), 2.89-2.66 (m, 2H), 2.48 (s, 3H), 2.28-2.17 (m, 1H), 2.15-2.06 (m, 1H), 2.04-1.91 (m, 1H), 1.57-1.19 (m, 10H), 1.13 (s, 3H), 1.10-1.00 (m, 8H), 1.00-0.93 (m, 2H). HRMS (ESI-TOF) m/z: $[M+H]^+$ calcd for $C_{55}H_{71}F_2N_{14}O_7S^+$, 1145.5313; found 1145.5335.

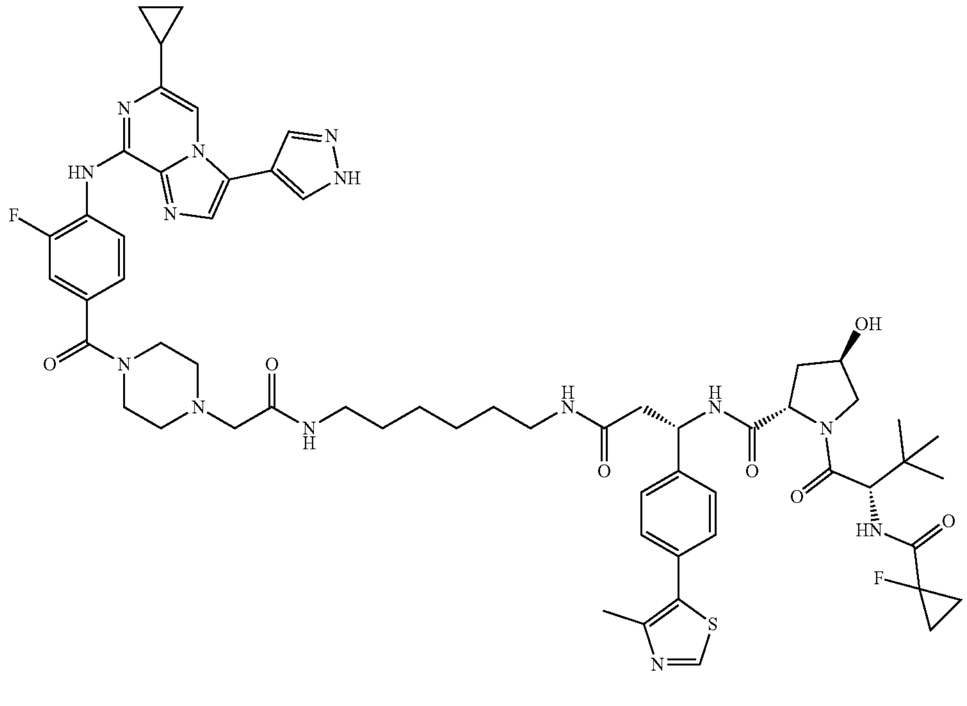 [SMILES: Cc1ncsc1-c1ccc([C@H](CC(=O)NCCCCCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

Example 112: (2S,4R)—N—((S)-3-((6-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)hexyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide. 70% yield. $^1$H NMR (600 MHz, $CD_3OD$) δ 8.93 (s, 1H), 8.76-8.70 (m, 1H), 8.15 (s, 2H), 7.96 (d, J=1.6 Hz, 1H), 7.84 (s, 1H), 7.52-7.37 (m, 6H), 5.38-5.24 (m, 1H), 4.76 (d, J=8.9 Hz, 1H), 4.66-4.53 (m, 2H), 4.51-4.38 (m, 1H), 4.15-3.88 (m, 6H), 3.85 (d, J=11.2 Hz, 1H), 3.78 (dd, J=11.1, 3.6 Hz, 1H), 3.57-3.39 (m, 4H), 3.27-3.04 (m, 4H), 2.91-2.67 (m, 2H), 2.49 (d, J=2.2 Hz, 3H), 2.28-2.17 (m, 1H), 2.17-2.06 (m, 1H), 2.05-1.94 (m, 1H), 1.57-1.16 (m, 12H), 1.13 (s, 2H), 1.10-1.01 (m, 9H), 0.98-0.93 (m, 2H). HRMS (ESI-TOF) m/z: [M+H]$^+$ calcd for $C_{59}H_{73}F_2N_4O_7S^+$, 1159.5470; found 1159.5439.

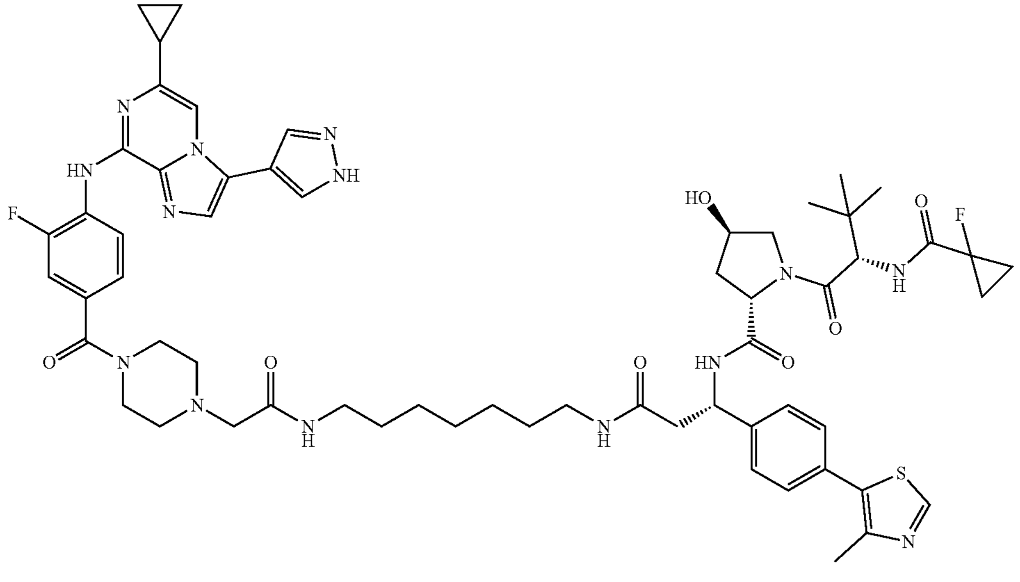 [SMILES: Cc1ncsc1-c1ccc([C@H](CC(=O)NCCCCCCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

Example 113: (2S,4R)—N—((S)-3-((7-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)heptyl)amino)-1-(4-(4-methylthiazol-5-yl)phenyl)-3-oxopropyl)-1-((S)-2-(l-fluorocyclopropane-1-carboxamido)-3,3-dimethylbutanoyl)-4-hydroxypyrrolidine-2-carboxamide. 60% yield. $^1$H NMR (600 MHz, $CD_3OD$) δ 8.96-8.88 (m, 1H), 8.79-8.69 (m, 1H), 8.15 (s, 2H), 7.96 (s, 1H), 7.82 (s, 1H), 7.52-7.31 (m, 6H), 5.41-5.22 (m, 1H), 4.76 (d, J=9.1

Hz, 1H), 4.67-4.52 (m, 2H), 4.48 (d, J=13.4 Hz, 1H), 4.16-3.88 (m, 6H), 3.85 (d, J=11.1 Hz, 1H), 3.82-3.71 (m, 1H), 3.57-3.38 (m, 4H), 3.29-3.00 (m, 4H), 2.88-2.66 (m, 2H), 2.49 (s, 3H), 2.28-2.17 (m, 1H), 2.17-2.06 (m, 1H), 2.02-1.91 (m, 1H), 1.56-1.15 (m, 14H), 1.13 (s, 2H), 1.09-1.01 (m, 9H), 0.99-0.93 (m, 2H). HRMS (ESI-TOF) m/z: $[M+H]^+$ calcd for $C_{60}H_{75}F_2N_{14}O_7S^+$, 1173.5626; found 1173.5644.

carboxamido)-3,3-dimethylbutanoyl)-4-hydroxypyrrolidine-2-carboxamide. 66% yield. $^1H$ NMR (600 MHz, $CD_3OD$) δ 8.93-8.87 (m, 1H), 8.77-8.66 (m, 1H), 8.16 (s, 2H), 7.97 (s, 1H), 7.85 (d, J=2.8 Hz, 1H), 7.53-7.35 (m, 6H), 5.43-5.33 (m, 1H), 4.76 (d, J=9.0 Hz, 1H), 4.65-4.56 (m, 2H), 4.52-4.45 (m, 1H), 4.12-3.89 (m, 6H), 3.87 (d, J 15=11.3 Hz, 1H), 3.78 (dd, J=11.1, 3.6 Hz, 1H), 3.62-3.36 (m, 12H), 2.93-2.82 (m, 1H), 2.82-2.72 (m, 1H), 2.48 (s, 3H), 2.30-2.20 (m, 1H), 2.17-2.08 (m, 1H), 2.02-1.94 (m, 1H), 1.46-1.26 (m, 4H), 1.14 (s, 2H), 1.09-1.02 (m, 9H), 0.99-0.94 (m, 2H). HRMS (ESI-TOF) m/z: $[M+H]^+$ calcd for $C_{57}H_{69}F_2N_{14}O_8S^+$, 1147.5106; found 1147.5124.

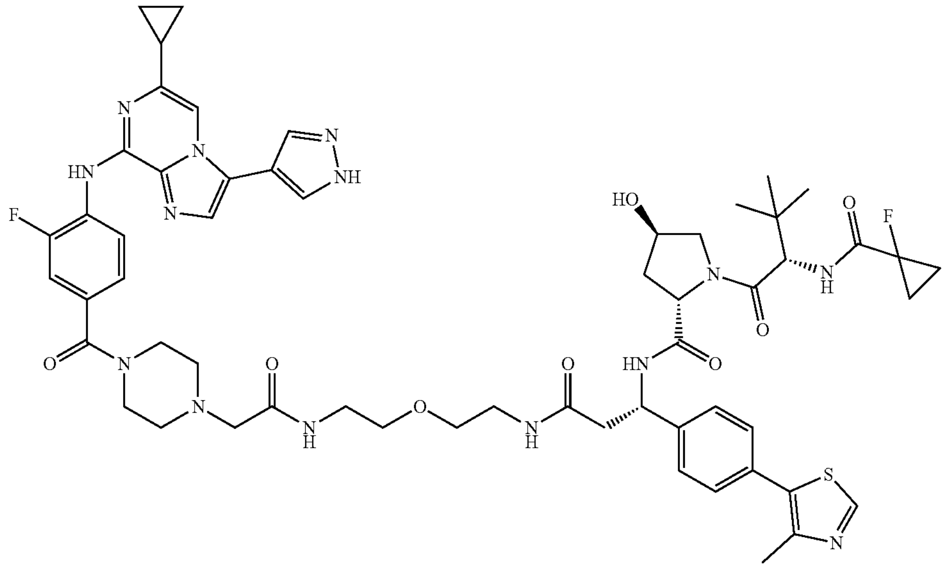 [SMILES: Cc1ncsc1-c1ccc([C@H](CC(=O)NCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

Example 114: (2S,4R)—N—((S)-3-((2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethoxy)ethyl)amino)-1-(4-(4-methylthiazol-5-yl)phenyl)-3-oxopropyl)-1-((S)-2-(1-fluorocyclopropane-1-

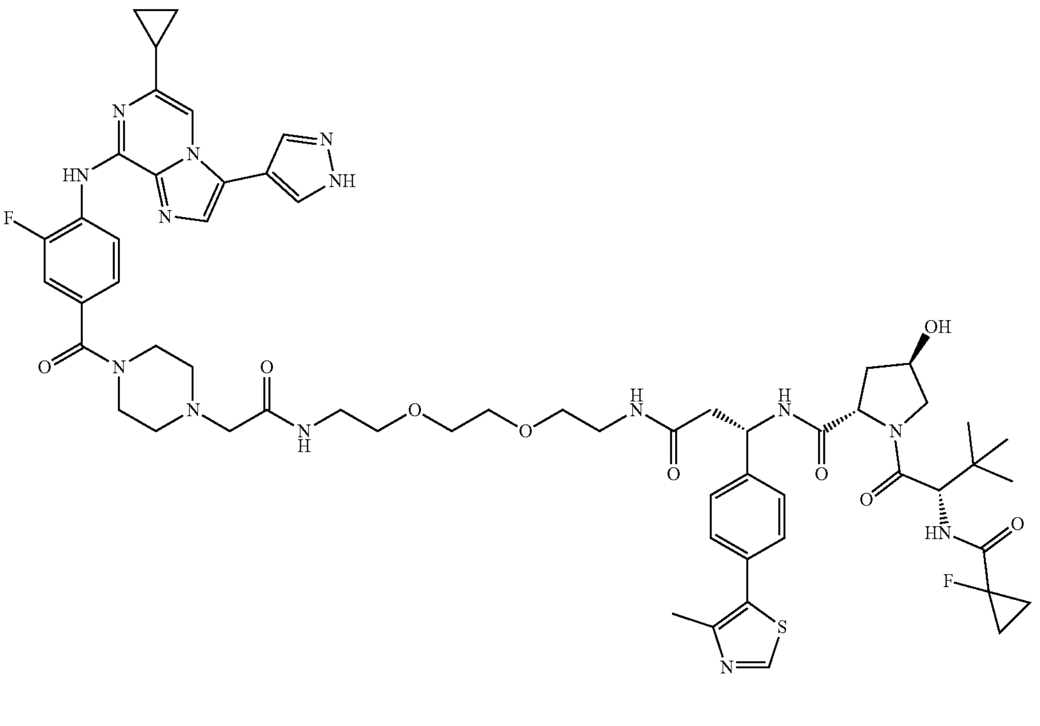 [SMILES: Cc1ncsc1-c1ccc([C@H](CC(=O)NCCOCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

Example 115: (2S,4R)—N—((S)-1-(4-(4-((6-Cyclopropyl-3-(1H-pyrazol-4-yl)imidazo[1,2-a]pyrazin-8-yl)amino)-3-fluorobenzoyl)piperazin-1-yl)-15-(4-(4-methylthiazol-5-yl)phenyl)-2,13-dioxo-6,9-dioxa-3,12-diazapentadecan-15-yl)-1-((S)-2-(1-fluorocyclopropane-1-carboxamido)-3,3-dimethylbutanoyl)-4-hydroxypyrrolidine-2-carboxamide. 65% yield. $^{1}H$ NMR (600 MHz, $CD_3OD$) δ 8.91-8.88 (m, 1H), 8.76-8.68 (m, 1H), 8.15 (s, 2H), 7.96 (s, 1H), 7.84 (s, 1H), 7.53-7.37 (m, 6H), 5.45-5.32 (m, 1H), 4.75 (d, J=9.0 Hz, 1H), 4.63-4.54 (m, 2H), 4.51-4.42 (m, 1H), 4.12-3.88 (m, 6H), 3.85 (d, J=11.2 Hz, 1H), 3.78 (dd, J=10.9, 3.5 Hz, 1H), 3.65-3.54 (m, 7H), 3.54-3.39 (m, 9H), 2.91-2.70 (m, 2H), 2.48 (s, 3H), 2.28-2.18 (m, 1H), 2.16-2.06 (m, 1H), 2.03-1.93 (m, 1H), 1.42-1.26 (m, 4H), 1.13 (s, 2H), 1.10-1.01 (m, 9H), 0.99-0.92 (m, 2H). HRMS (ESI-TOF) m/z: $[M+H]^+$ calcd for $C_{59}H_{73}F_2N_{14}O_9S^+$, 1191.5368; found 1191.5355.

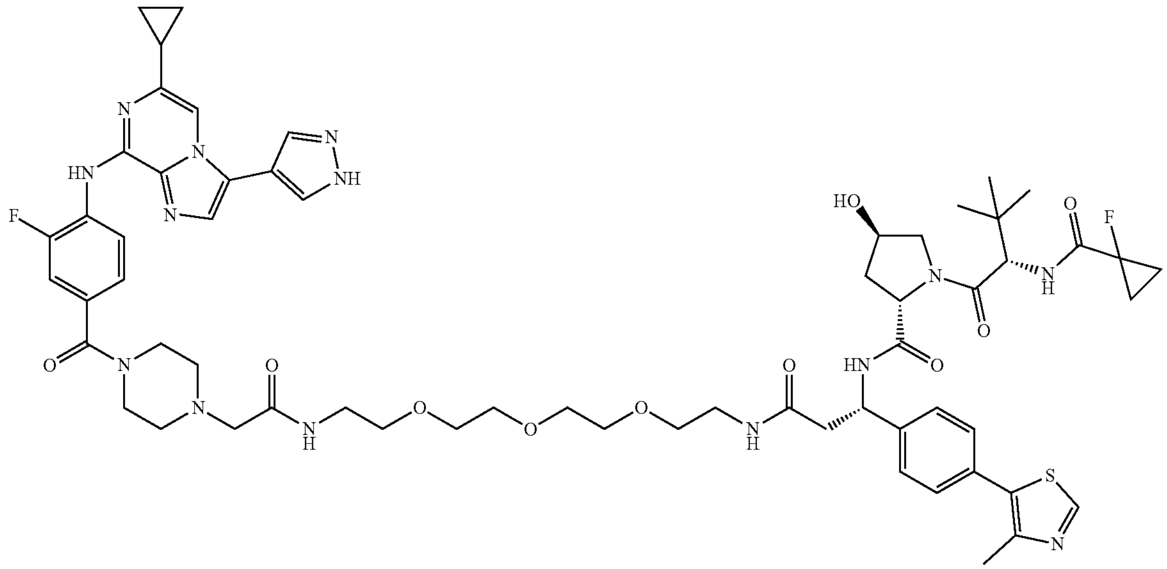 [SMILES: Cc1ncsc1-c1ccc([C@H](CC(=O)NCCOCCOCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

Example 116: (2S,4R)—N—((S)-1-(4-(4-((6-Cyclopropyl-3-(1H-pyrazol-4-yl)imidazo[1,2-a]pyrazin-8-yl)amino)-3-fluorobenzoyl)piperazin-1-yl)-18-(4-(4-methylthiazol-5-yl)phenyl)-2,16-dioxo-6,9,12-trioxa-3,15-diazaoctadecan-18-yl)-1-((S)-2-(1-fluorocyclopropane-1-carboxamido)-3,3-dimethylbutanoyl)-4-hydroxypyrrolidine-2-carboxamide. 63% yield. $^{1}H$ NMR (600 MHz, $CD_3OD$) δ 8.94 (s, 1H), 8.68 (t, J=8.1 Hz, 1H), 8.17 (s, 2H), 7.99 (s, 1H), 7.91 (s, 1H), 7.48-7.38 (m, 6H), 5.41-5.31 (m, 1H), 4.76 (d, J=8.7 Hz, 1H), 4.62-4.48 (m, 2H), 4.47-4.38 (m, 1H), 4.12-3.88 (m, 6H), 3.85 (d, J=11.2 Hz, 1H), 3.80-3.72 (m, 1H), 3.69-3.54 (m, 11H), 3.54-3.39 (m, 9H), 2.90-2.70 (m, 2H), 2.49 (s, 3H), 2.29-2.18 (m, 1H), 2.18-2.07 (m, 1H), 2.01-1.94 (m, 1H), 1.43-1.27 (m, 6H), 1.15-1.11 (m, 2H), 1.10-1.02 (m, 9H), 0.99-0.95 (m, 2H). HRMS (ESI-TOF) m/z: $[M+H]^+$ calcd for $C_{61}H_{77}F_2N_4O_{10}S^+$, 1235.5630; found 1235.5641.

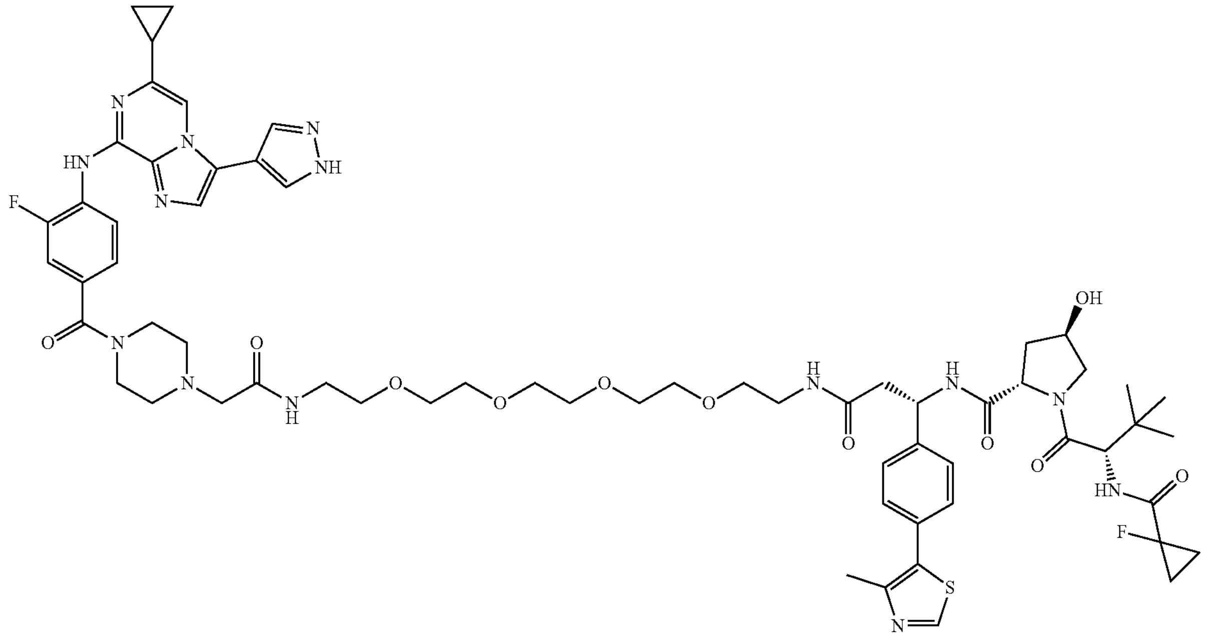 [SMILES: Cc1ncsc1-c1ccc([C@H](CC(=O)NCCOCCOCCOCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

Example 117: (2S,4R)—N—((S)-1-(4-(4-((6-Cyclopropyl-3-(1H-pyrazol-4-yl)imidazo[1,2-a]pyrazin-8-yl)amino)-3-fluorobenzoyl)piperazin-1-yl)-21-(4-(4-methylthiazol-5-yl)phenyl)-2,19-dioxo-6,9,12,15-tetraoxa-3,18-diazahenicosan-21-yl)-1-((S)-2-(1-fluorocyclopropane-1-carboxamido)-3,3-dimethylbutanoyl)-4-hydroxypyrrolidine-2-carboxamide. 61% yield. $^1$H NMR (600 MHz, $CD_3OD$) δ 8.91 (s, 1H), 8.77-8.71 (m, 1H), 8.15 (s, 2H), 7.96 (s, 1H), 7.83 (s, 1H), 7.48-7.38 (m, 6H), 5.40-5.30 (m, 1H), 4.76 (d, J=9.0 Hz, 1H), 4.63-4.49 (m, 2H), 4.47-4.38 (m, 1H), 4.13-3.88 (m, 6H), 3.85 (d, J=11.2 Hz, 1H), 3.78 (dd, J=11.2, 3.8 Hz, 1H), 3.68-3.52 (m, 16H), 3.52-3.38 (m, 8H), 2.90-2.68 (m, 2H), 2.49 (s, 3H), 2.30-2.20 (m, 1H), 2.18-2.07 (m, 1H), 2.06-1.91 (m, 1H), 1.44-1.25 (m, 4H), 1.13 (s, 2H), 1.10-1.01 (m, 9H), 0.99-0.93 (m, 2H). HRMS (ESI-TOF) m/z: $[M+H]^+$ calcd for $C_{63}H_{81}F_2N_{14}O_{11}S^+$, 1279.5893; found 1279.5870.

Example 118: (2S,4R)—N—((S)-1-(4-(4-((6-Cyclopropyl-3-(1H-pyrazol-4-yl)imidazo[1,2-a]pyrazin-8-yl)amino)-3-fluorobenzoyl)piperazin-1-yl)-24-(4-(4-methylthiazol-5-yl)phenyl)-2,22-dioxo-6,9,12,15,18-pentaoxa-3,21-diazatetracosan-24-yl)-1-((S)-2-(1-fluorocyclopropane-1-carboxamido)-3,3-dimethylbutanoyl)-4-hydroxypyrrolidine-2-carboxamide. 60% yield. $^1$H NMR (600 MHz, $CD_3OD$) δ 8.93 (s, 1H), 8.76-8.67 (m, 1H), 8.15 (s, 2H), 7.97 (s, 1H), 7.85 (s, 1H), 7.49-7.38 (m, 6H), 5.42-5.30 (m, 1H), 4.76 (d, J=9.2 Hz, 1H), 4.66-4.48 (m, 2H), 4.48-4.39 (m, 1H), 4.14-3.89 (m, 6H), 3.85 (d, J=11.3 Hz, 1H), 3.81-3.72 (m, 1H), 3.67-3.52 (m, 22H), 3.52-3.36 (m, 6H), 2.90-2.69 (m, 2H), 2.49 (s, 3H), 2.28-2.19 (m, 1H), 2.15-2.07 (m, 1H), 2.06-1.93 (m, 1H), 1.35 (ddt, J=19.9, 15.9, 6.4 Hz, 4H), 1.13 (s, 2H), 1.10-1.01 (m, 9H), 0.98-0.93 (m, 2H). HRMS (ESI-TOF) m/z: $[M+H]^+$ calcd for $C_{65}H_{85}F_2N_{14}O_2S^+$, 1323.6155; found 1323.6170.

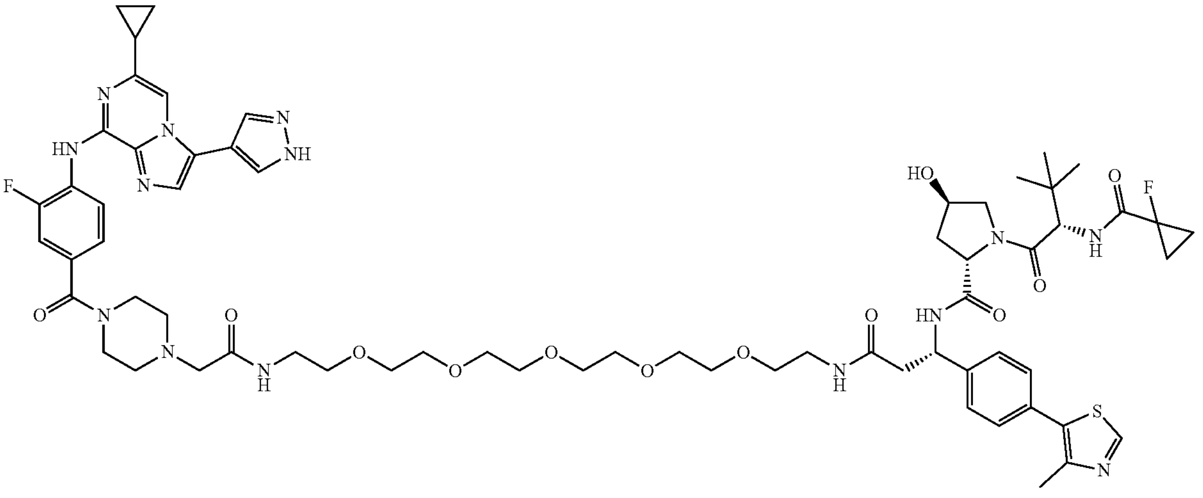 [SMILES: Cc1ncsc1-c1ccc([C@H](CC(=O)NCCOCCOCCOCCOCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

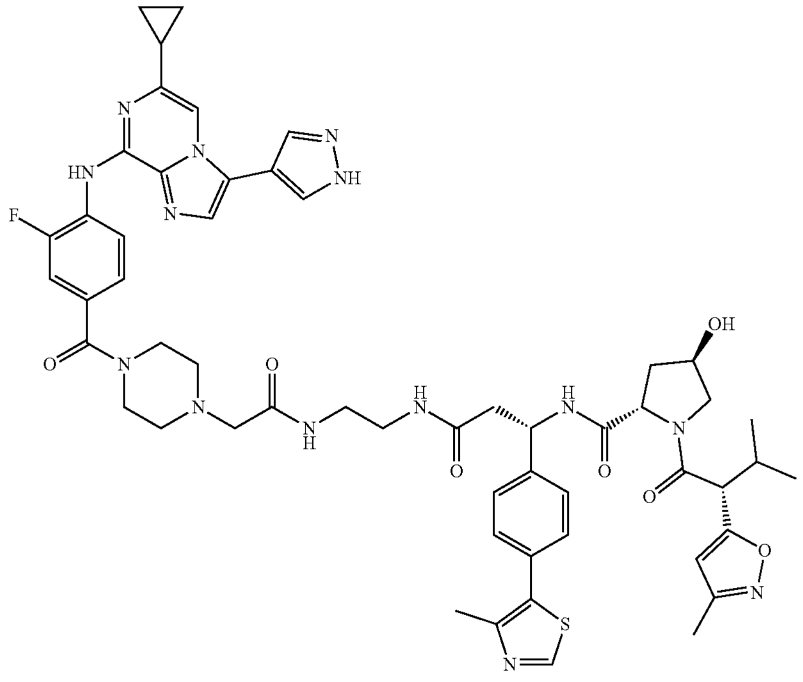 [SMILES: Cc1cc([C@H](C(=O)N2C[C@H](O)C[C@H]2C(=O)N[C@@H](CC(=O)NCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

Example 119: (2S,4R)—N—((S)-3-((2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethyl) 1H), 2.00-1.89 (m, 1H), 1.12-1.05 (m, 3H), 1.05-0.90 (m, 4H), 0.90-0.84 (m, 3H). HRMS (ESI-TOF) m/z: $[M+H]^+$ calcd for $C_{54}H_{62}FN_{14}O_7S^+$, 1069.4625; found 1069.4635.

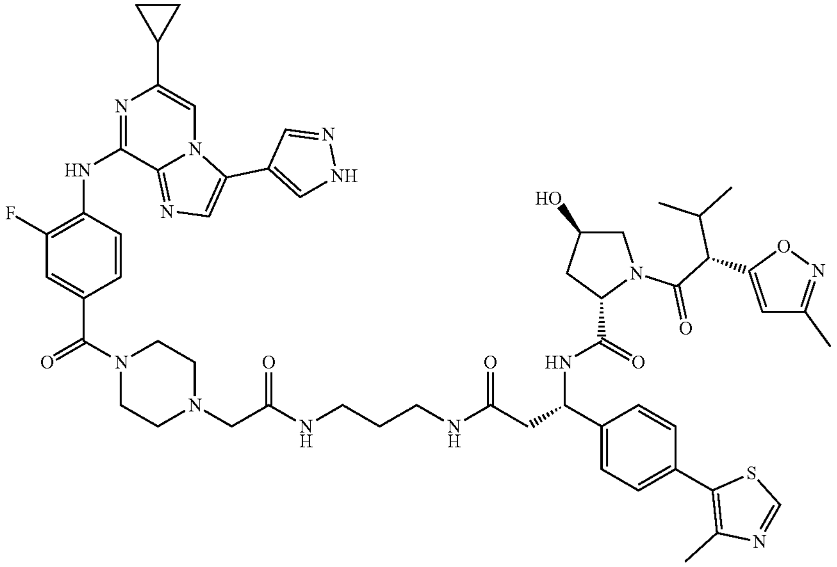 [SMILES: Cc1cc([C@H](C(=O)N2C[C@H](O)C[C@H]2C(=O)N[C@@H](CC(=O)NCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide. 68% yield. $^1$H NMR (500 MHz, $CD_3OD$) δ 8.93 (s, 1H), 8.74-8.59 (m, 1H), 8.15 (s, 2H), 7.94 (s, 1H), 7.86 (s, 1H), 7.48-7.36 (m, 6H), 6.28 (s, 1H), 5.40-5.24 (m, 1H), 4.62-4.57 (m, 1H), 4.56-4.51 (m, 1H), 4.47 (s, 1H), 4.16-3.91 (m, 5H), 3.89-3.77 (m, 2H), 3.72-3.64 (m, 1H), 3.64-3.41 (m, 6H), 3.19-3.05 (m, 1H), 2.84-2.61 (m, 2H), 2.46 (s, 3H), 2.27 (s, 3H), 2.15-2.05 (m, Example 120: (2S,4R)—N—((S)$_3$-((3-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)propyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide. 60% yield. $^1$H NMR (600 MHz, $CD_3OD$) δ 8.99-8.93 (nm, 1H), 8.72-8.66 (m, 1H), 8.16 (s, 2H), 7.99 (d, J=2.7 Hz, 1H), 7.91 (s, 1H), 7.53-7.36 (m, 6H), 6.26 (d, J=10.3 Hz, 1H), 5.40-5.27 (m, 1H), 4.62-4.49 (m, 1H), 4.45 (s, 1H), 4.10-3.61 (m, 9H), 3.57-3.40 (m, 4H), 3.27-3.13 (m, 4H), 2.91-2.71 (m, 2H), 2.49 (d, J=5.3 Hz, 3H), 2.46-2.36 (m, 1H), 2.31-2.23 (m, 3H), 2.17-2.10 (m, 1H), 2.02-1.91 (m, 1H), 1.73-1.61 (m, 2H), 1.12-1.02 (m, 5H), 1.00-0.95 (m, 2H), 0.91-0.85 (m, 3H). HRMS (ESI-TOF) m/z: $[M+H]^+$ calcd for $C_{55}H_{64}FN_{14}O_7S^+$, 1083.4782; found 1083.4781.

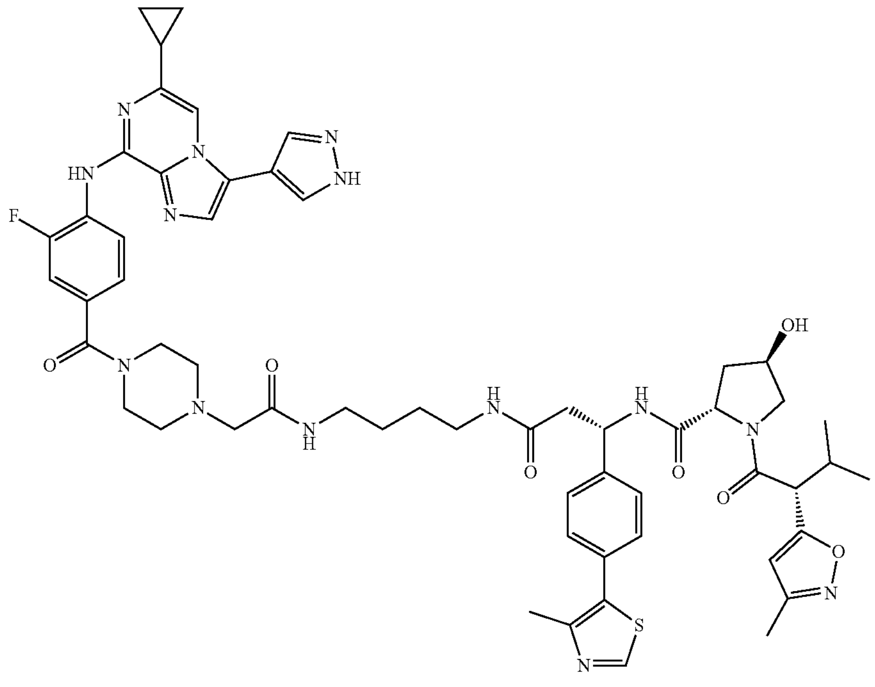 [SMILES: Cc1cc([C@H](C(=O)N2C[C@H](O)C[C@H]2C(=O)N[C@@H](CC(=O)NCCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

Example 121: (2S,4R)—N—((S)-3-((4-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)butyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide. 59% yield. $^1H$ NMR (600 MHz, $CD_3OD$) δ 8.91 (d, J=16.4 Hz, 1H), 8.78-8.68 (m, 1H), 8.15 (s, 2H), 7.97-7.92 (m, 1H), 7.83 (s, 1H), 7.49-7.34 (m, 6H), 6.25 (d, J=12.4 Hz, 1H), 5.39-5.25 (m, 1H), 4.61-4.48 (m, 1H), 4.45 (s, 1H), 4.18-3.57 (m, 9H), 3.57-3.40 (m, 4H), 3.28-3.07 (m, 4H), 2.87-2.65 (m, 2H), 2.47 (d, J=11.2 Hz, 3H), 2.46-2.38 (m, 1H), 2.26 (d, J=16.8 Hz, 3H), 2.15-2.08 (m, 1H), 2.01-1.94 (m, 1H), 1.56-1.42 (m, 4H), 1.12-0.99 (m, 5H), 0.99-0.92 (m, 2H), 0.88 (dd, J=13.1, 6.7 Hz, 3H). HRMS (ESI-TOF) m/z: $[M+H]^+$ calcd for $C_{56}H_{66}FN_{14}O_7S^+$, 1097.4938; found 1097.4928.

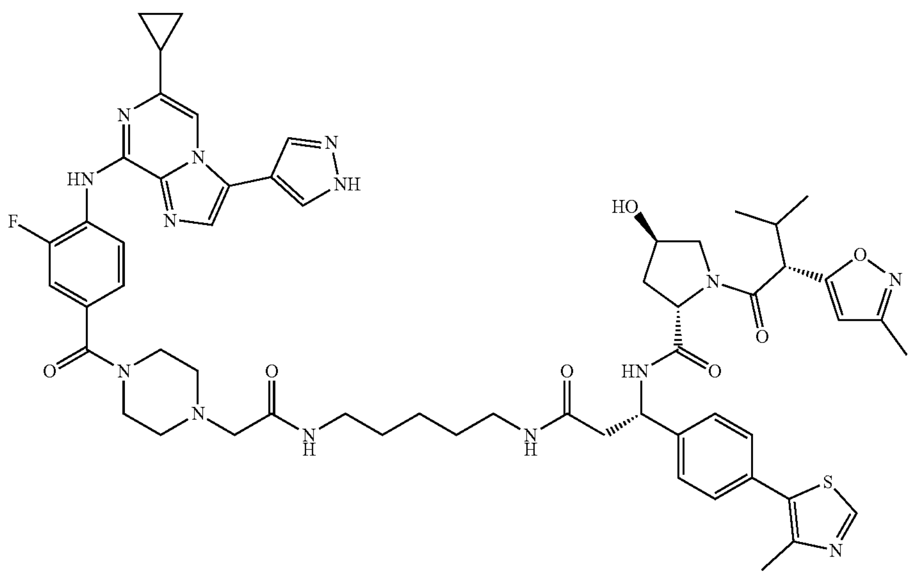 [SMILES: Cc1cc([C@H](C(=O)N2C[C@H](O)C[C@H]2C(=O)N[C@@H](CC(=O)NCCCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

Example 122: (2S,4R)—N—((S)-3-((5-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)pentyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide. 70% yield. $^1$H NMR (600 MHz, $CD_3OD$) δ 8.92-8.86 (m, 1H), 8.78-8.69 (m, 1H), 8.15 (s, 2H), 7.94 (d, J=3.4 Hz, 1H), 7.82 (s, 1H), 7.50-7.34 (m, 6H), 6.26 (d, J=27.8 Hz, 1H), 5.37-5.27 (m, 1H), 4.60-4.48 (m, 1H), 4.46 (s, 1H), 4.09-3.56 (m, 9H), 3.55-3.41 (m, 4H), 3.28-3.02 (m, 4H), 2.87-2.65 (m, 2H), 2.47 (d, J=10.7 Hz, 3H), 2.45-2.38 (m, 1H), 2.26 (d, J=11.4 Hz, 3H), 2.18-2.09 (m, 1H), 2.02-1.93 (m, 1H), 1.61-1.23 (m, 6H), 1.10-1.06 (m, 3H), 1.05-0.99 (m, 2H), 0.99-0.92 (m, 2H), 0.91-0.85 (m, 3H). HRMS (ESI-TOF) m/z: $[M+H]^+$ calcd for $C_{57}H_{68}FN_{14}O_7S^+$, 1111.5095; found 1111.5078.

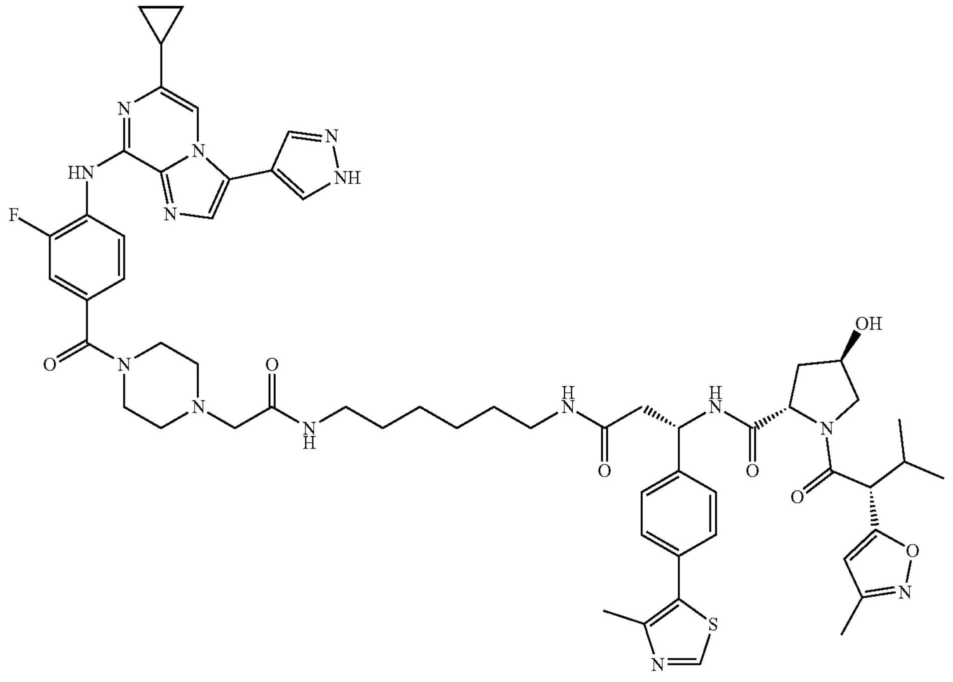 [SMILES: Cc1cc([C@H](C(=O)N2C[C@H](O)C[C@H]2C(=O)N[C@@H](CC(=O)NCCCCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

Example 123: (2S,4R)—N—((S)-3-((6-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)hexyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide. 73% yield. $^1$H NMR (600 MHz, $CD_3OD$) δ 8.95-8.86 (m, 1H), 8.78-8.69 (m, 1H), 8.14 (s, 2H), 7.94 (d, J=2.2 Hz, 1H), 7.80 (s, 1H), 7.49-7.37 (m, 6H), 6.25 (d, J=21.7 Hz, 1H), 5.38-5.25 (m, 1H), 4.62-4.48 (m, 1H), 4.46 (s, 1H), 4.11-3.56 (m, 9H), 3.55-3.38 (m, 4H), 3.24 (dd, J=16.7, 9.9 Hz, 2H), 3.18-3.06 (m, 2H), 2.91-2.68 (m, 2H), 2.52-2.46 (m, 3H), 2.46-2.36 (m, 1H), 2.30-2.23 (m, 3H), 2.21-2.06 (m, 1H), 2.01-1.92 (m, 1H), 1.52-1.45 (m, 2H), 1.45-1.35 (m, 2H), 1.35-1.28 (m, 2H), 1.28-1.18 (m, 2H), 1.11-1.00 (m, 5H), 0.99-0.92 (m, 2H), 0.92-0.85 (m, 3H). HRMS (ESI-TOF) m/z: $[M+H]^+$ calcd for $C_{58}H_{70}FN_{14}O_7S^+$, 1125.5251; found 1125.5270.

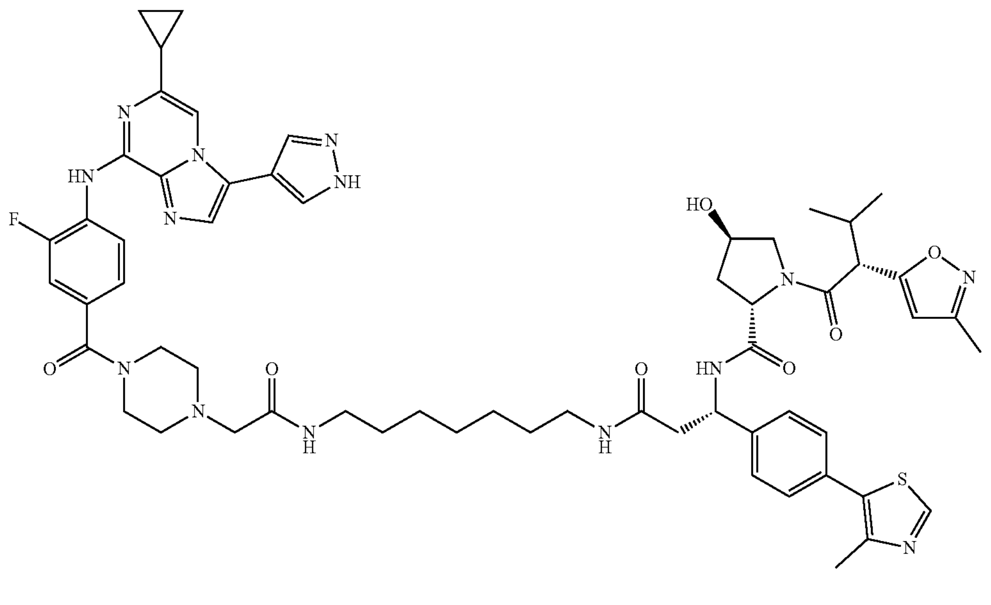 [SMILES: Cc1cc([C@H](C(=O)N2C[C@H](O)C[C@H]2C(=O)N[C@@H](CC(=O)NCCCCCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

Example 124: (2S,4R)—N—((S)-3-((7-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)heptyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide. 63% yield. $^{1}H$ NMR (600 MHz, $CD_3OD$) δ 8.97-8.86 (m, 1H), 8.77-8.66 (m, 1H), 8.15 (s, 2H), 7.97 (d, J=3.1 Hz, 1H), 7.86 (s, 1H), 7.51-7.36 (m, 6H), 6.26 (d, J=24.9 Hz, 11H), 5.38-5.27 (m, 1H), 4.60-4.48 (m, 1H), 4.46 (s, 1H), 4.13-3.57 (m, 9H), 3.57-3.40 (m, 4H), 3.27-3.18 (m, 2H), 3.18-3.04 (m, 2H), 2.88-2.68 (m, 2H), 2.49 (d, J=9.4 Hz, 3H), 2.46-2.34 (m, 1H), 2.26 (d, J=12.3 Hz, 3H), 2.22-2.09 (m, 1H), 2.02-1.91 (m, 1H), 1.55-1.44 (m, 2H), 1.44-1.34 (m, 2H), 1.34-1.25 (m, 4H), 1.25-1.16 (m, 2H), 1.10-1.01 (m, 5H), 0.99-0.93 (m, 2H), 0.93-0.85 (m, 3H). HRMS (ESI-TOF) m/z: $[M+H]^+$ Example 125: (2S,4R)—N—((S)-3-((2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethoxy)ethyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide. 65% yield. $^{1}H$ NMR (600 MHz, $CD_3OD$) δ 8.89-8.81 (m, 1H), 8.78-8.66 (m, 1H), 8.15 (d, J=1.9 Hz, 2H), 7.95 (d, J=3.1 Hz, 1H), 7.82 (s, 1H), 7.50-7.32 (m, 6H), 6.26 (d, J=31.5 Hz, 1H), 5.40-5.28 (m, 1H), 4.62-4.49 (m, 1H), 4.47 (s, 1H), 4.12-3.67 (m, 9H), 3.67-3.38 (m, 12H), 2.92-2.70 (m, 2H), 2.48-2.37 (m, 4H), 2.29-2.23 (m, 3H), 2.15-2.06 (m, 1H), 2.03-1.94 (m, 1H), 1.11-0.99 (m, 5H), 0.99-0.92 (m, 2H), 0.89 (dd, J=20.6, 6.7 Hz, 3H). HRMS (ESI-TOF) m/z: $[M+H]^+$ calcd for $C_{56}H_{66}FN_{14}O_8S^+$, 1113.4887; found 1113.4899.

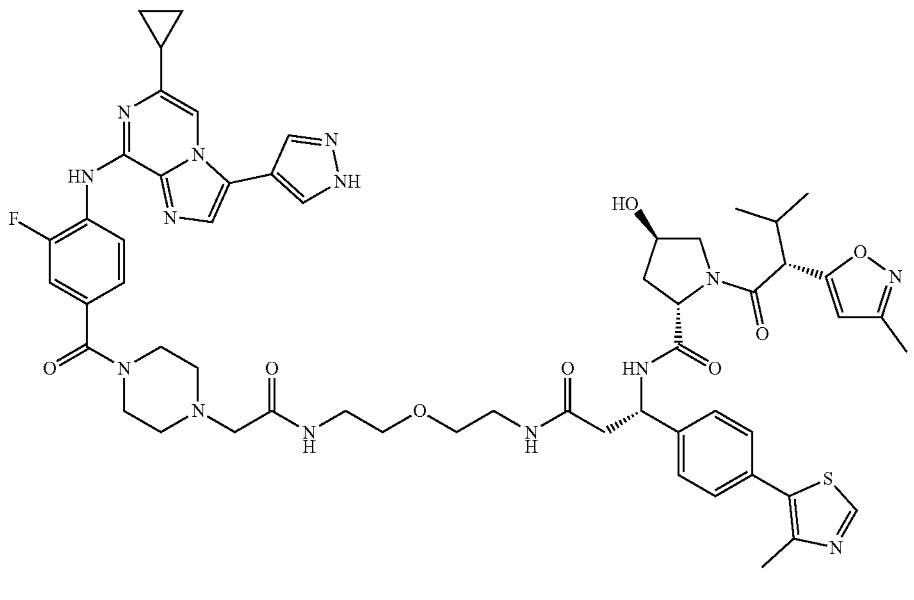 [SMILES: Cc1cc([C@H](C(=O)N2C[C@H](O)C[C@H]2C(=O)N[C@@H](CC(=O)NCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

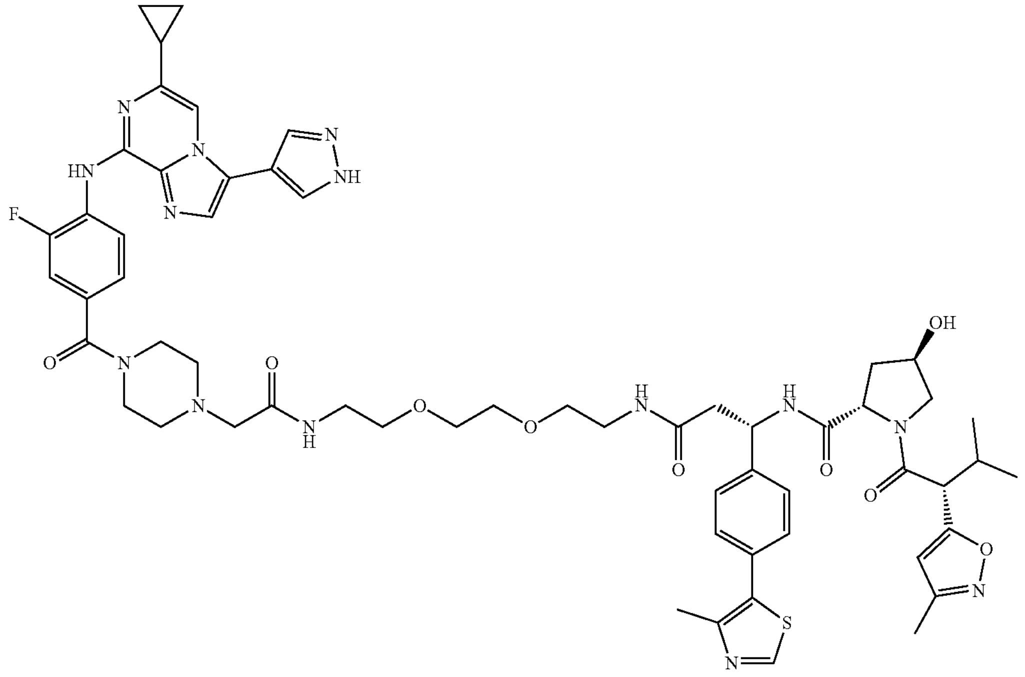 [SMILES: Cc1cc([C@H](C(=O)N2C[C@H](O)C[C@H]2C(=O)N[C@@H](CC(=O)NCCOCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

Example 126: (2S,4R)—N—((S)-1-(4-(4-((6-Cyclopropyl-3-(1H-pyrazol-4-yl)imidazo[1,2-a]pyrazin-8-yl)amino)-3-fluorobenzoyl)piperazin-1-yl)-15-(4-(4-methylthiazol-5-yl)phenyl)-2,13-dioxo-6,9-dioxa-3,12-diazapentadecan-15-yl)-4-hydroxy-1-((R)-3-methyl-2-(3-methylisoxazol-5-yl)butanoyl)pyrrolidine-2-carboxamide. 60% yield. HRMS (ESI-TOF) m/z: $[M+H]^+$ calcd for $C_{55}H_{70}FN_{14}O_9S^+$, 1157.5149; found 1157.5177.

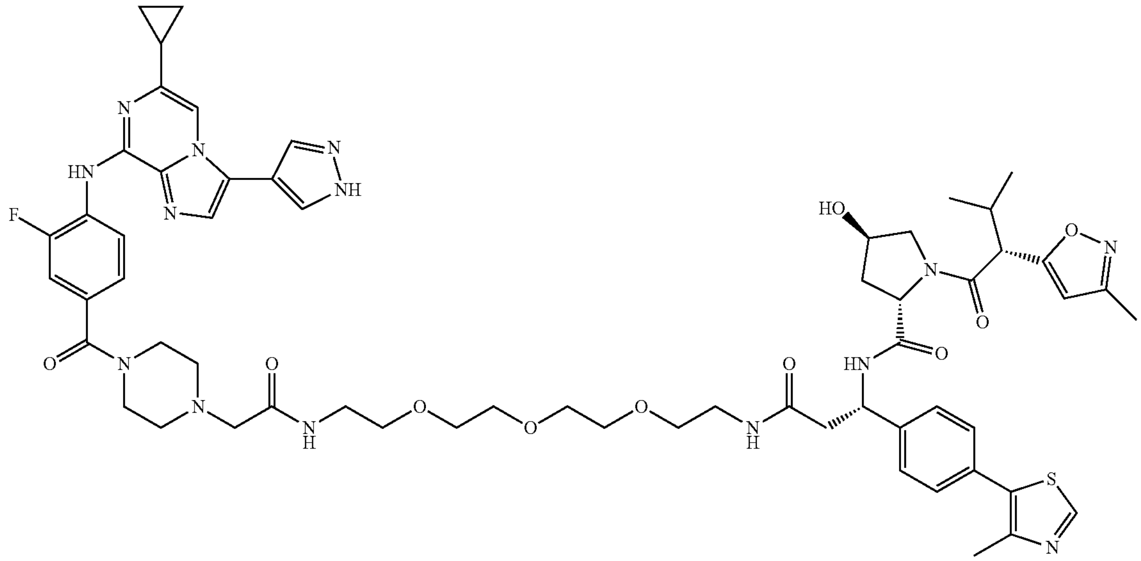 [SMILES: Cc1cc([C@H](C(=O)N2C[C@H](O)C[C@H]2C(=O)N[C@@H](CC(=O)NCCOCCOCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

Example 127: (2S,4R)—N—((S)-1-(4-(4-((6-Cyclopropyl-3-(1H-pyrazol-4-yl)imidazo[1,2-a]pyrazin-8-yl)amino)-3-fluorobenzoyl)piperazin-1-yl)-18-(4-(4-methylthiazol-5-yl)phenyl)-2,16-dioxo-6,9,12-trioxa-3,15-diazaoctadecan-18-yl)-4-hydroxy-1-((R)-3-methyl-2-(3-methylisoxazol-5-yl)butanoyl)pyrrolidine-2-carboxamide. 63% yield. $^1$H NMR (600 MHz, $CD_3OD$) δ 8.89 (d, J=15.4 Hz, 1H), 8.75-8.65 (m, 1H), 8.15 (s, 2H), 7.96 (d, J=2.5 Hz, 1H), 7.85 (s, 1H), 7.52-7.34 (m, 6H), 6.32-6.21 (m, 1H), 5.41-5.30 (m, 1H), 4.61-4.48 (m, 1H), 4.46 (s, 1H), 4.12-3.68 (m, 9H), 3.68-3.54 (m, 8H), 3.54-3.41 (m, 8H), 2.90-2.71 (m, 2H), 2.53-2.45 (m, 3H), 2.45-2.37 (m, 1H), 2.31-2.22 (m, 3H), 2.16-2.09 (m, 1H), 2.02-1.94 (m, 1H), 1.12-0.99 (m, 5H), 0.99-0.93 (m, 2H), 0.93-0.84 (m, 3H). HRMS (ESI-TOF) m/z: $[M+H]^+$ calcd for $C_{60}H_{74}FN_{14}O_{10}S^+$, 1201.5412; found 1201.5431.

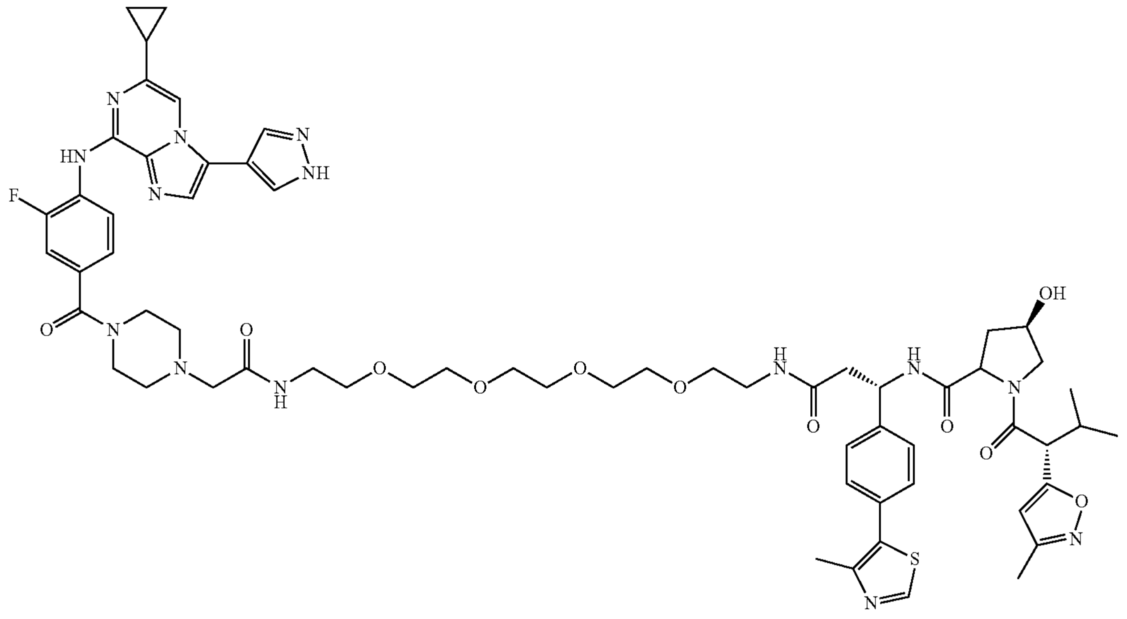 [SMILES: Cc1cc([C@H](C(=O)N2C[C@H](O)CC2C(=O)N[C@@H](CC(=O)NCCOCCOCCOCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

Example 128: (2S,4R)—N—((S)-1-(4-(4-((6-Cyclopropyl-3-(1H-pyrazol-4-yl)imidazo[1,2-a]pyrazin-8-yl)amino)-3-fluorobenzoyl)piperazin-1-yl)-21-(4-(4-methylthiazol-5-yl)phenyl)-2,19-dioxo-6,9,12,15-tetraoxa-3,18-diazahenicosan-21-yl)-4-hydroxy-1-((R)-3-methyl-2-(3-methylisoxazol-5-yl)butanoyl)pyrrolidine-2-carboxamide. 60% yield. $^1$H NMR (600 MHz, $CD_3OD$) δ 8.95-8.88 (m, 1H), 8.76-8.65 (m, 1H), 8.16 (s, 2H), 7.97 (d, J=4.0 Hz, 1H), 7.87 (s, 1H), 7.52-7.31 (m, 6H), 6.25 (d, J=22.2 Hz, 1H), 5.40-5.27 (m, 1H), 4.60-4.48 (m, 1H), 4.46 (s, 1H), 4.11-3.69 (m, 9H), 3.68-3.55 (m, 12H), 3.55-3.43 (m, 8H), 2.90-2.72 (m, 2H), 2.54-2.45 (m, 3H), 2.45-2.35 (m, 1H), 2.33-2.22 (m, 3H), 2.18-2.09 (m, 1H), 2.03-1.90 (m, 1H), 1.15-1.00 (m, 5H), 1.00-0.92 (m, 2H), 0.92-0.84 (m, 3H). HRMS (ESI-TOF) m/z: $[M+H]^+$ calcd for $C_{62}H_{78}FN_{14}O_{11}S^+$, 1245.5674; found 1245.5677.

Example 129: (2S,4R)—N—((S)-1-(4-(4-((6-Cyclopropyl-3-(1H-pyrazol-4-yl)imidazo[1,2-a]pyrazin-8-yl)amino)-3-fluorobenzoyl)piperazin-1-yl)-24-(4-(4-methylthiazol-5-yl)phenyl)-2,22-dioxo-6,9,12,15,18-pentaoxa-3,21-diazatetracosan-24-yl)-4-hydroxy-1-((R)-3-methyl-2-(3-methylisoxazol-5-yl)butanoyl)pyrrolidine-2-carboxamide. 67% yield. $^1$H NMR (600 MHz, $CD_3OD$) δ 8.94-8.87 (m, 1H), 8.77-8.68 (m, 1H), 8.16 (s, 2H), 7.96 (d, J=3.3 Hz, 1H), 7.85 (d, J=2.1 Hz, 1H), 7.51-7.34 (m, 6H), 6.26 (d, J=22.2 Hz, 1H), 5.39-5.27 (m, 1H), 4.60-4.48 (m, 1H), 4.46 (s, 1H), 4.12-3.68 (m, 9H), 3.68-3.53 (m, 16H), 3.53-3.41 (m, 8H), 2.92-2.70 (m, 2H), 2.52-2.46 (m, 3H), 2.46-2.35 (m, 1H), 2.31-2.23 (m, 3H), 2.23-2.09 (m, 1H), 2.03-1.92 (m, 1H), 1.12-1.00 (m, 5H), 1.00-0.93 (m, 2H), 0.93-0.84 (m, 2H). HRMS (ESI-TOF) m/z: $[M+H]^+$ calcd for $C_{64}H_{82}FN_{14}O_{12}S^+$, 1289.5636; found 1289.5661.

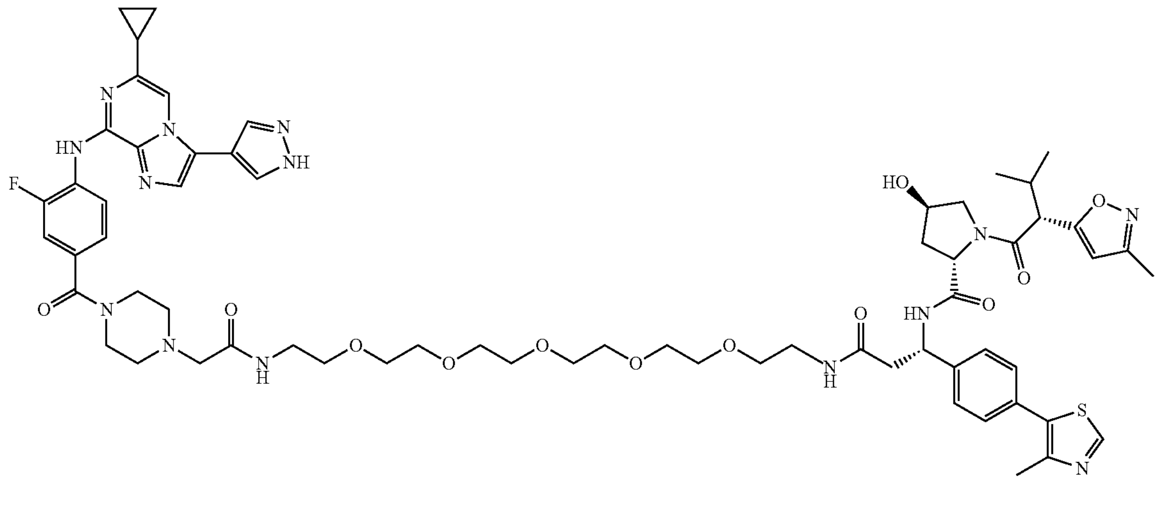

Scheme 29. Synthesis of example 135

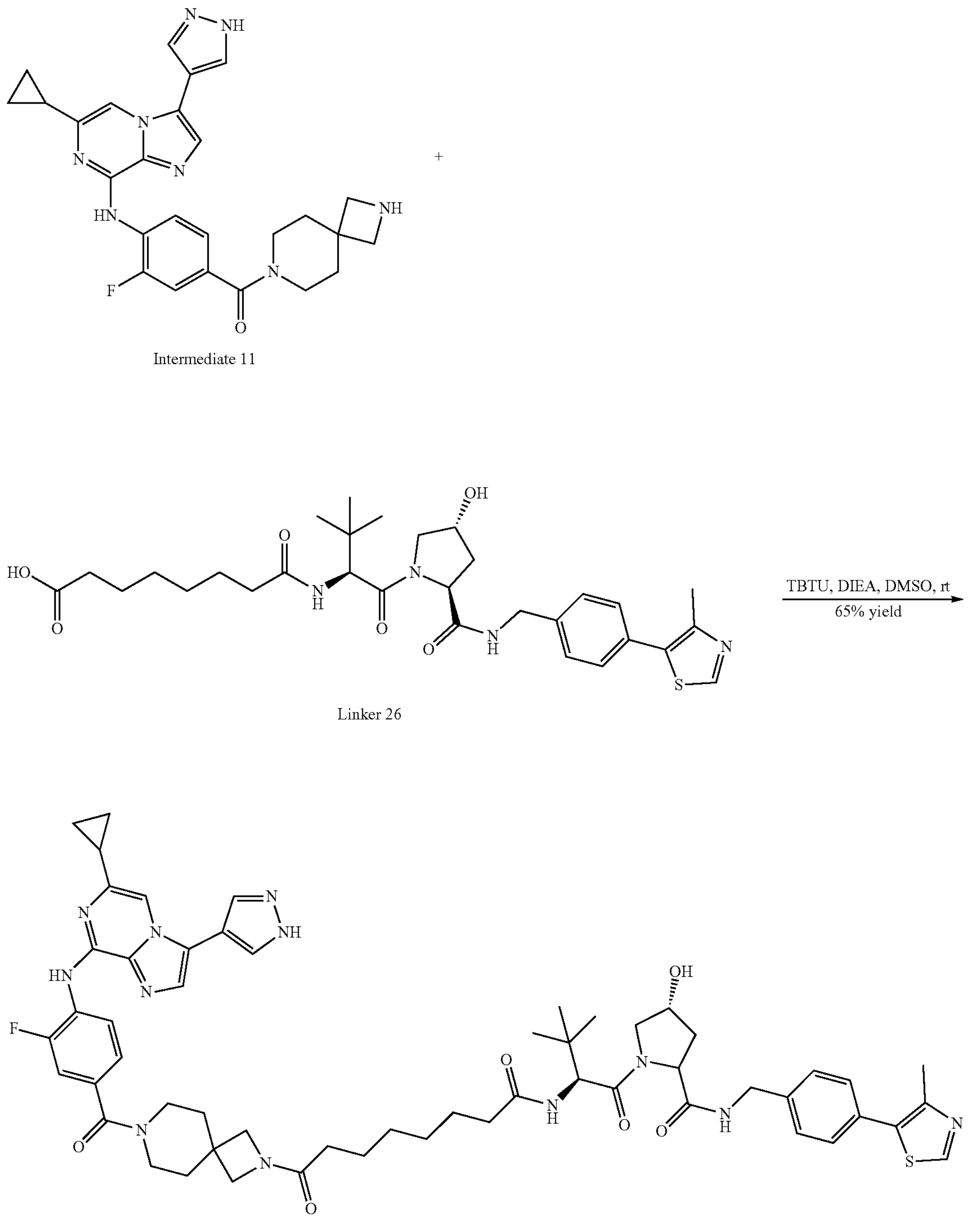

Intermediate 11

Linker 26

Example 135

Example 135: (2S,4R)-1-((S)-2-(8-(7-(4-((6-Cyclopropyl-3-(1H-pyrazol-4-yl)imidazo[1,2-a]pyrazin-8-yl)amino)-3-fluorobenzoyl)-2,7-diazaspiro[3.5]nonan-2-yl)-8-oxooctanamido)-3,3-dimethylbutanoyl)-4-hydroxy-N-(4-(4-methylthiazol-5-yl)benzyl)pyrrolidine-2-carboxamide. Example 135 was synthesized according to the procedures for the preparation of example 1. 63% yield. $^1$H NMR (600 MHz, $CD_3OD$) δ 9.03 (s, 1H), 8.58 (t, J=8.1 Hz, 1H), 8.18 (s, 2H), 8.02 (s, 1H), 7.98 (s, 1H), 7.49 (d, J=8.1 Hz, 2H), 7.44 (d, J=8.0 Hz, 2H), 7.39 (d, J=11.3 Hz, 1H), 7.34 (d, J=8.4 Hz, 1H), 4.66 (s, 1H), 4.63-4.49 (m, 3H), 4.38 (d, J=15.5 Hz, 1H), 4.06-3.96 (m, 2H), 3.92 (d, J=10.9 Hz, J H), 3.82 (dd, J=10.9, 3.8 Hz, 1H), 3.80-3.67 (m, 4H), 3.62-3.42 (m, 2H), 2.50 (s, 3H), 2.36-2.20 (m, 3H), 2.20-2.13 (m, 3H), 2.13-2.07 (m, 1H), 1.97-1.75 (m, 4H), 1.69-1.57 (m, 4H), 1.43-1.33 (m, 4H), 1.11-1.03 (m, 11 H), 1.01-0.97 (m, 2H). HRMS (ESI-TOF) m/z: $[M+H]^+$ calcd for $C_{56}H_{67}FN_{12}O_6S^+$, 1055.5084; found 1055.5099.

Example compound 136 was synthesized according to the procedures for the preparation of example compound 135.

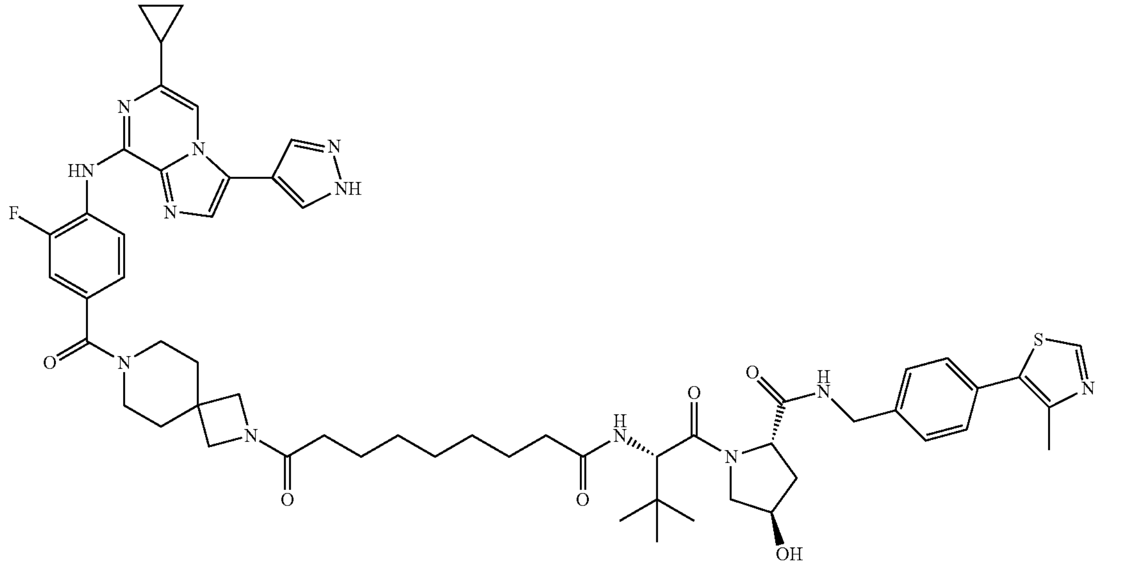 [SMILES: Cc1ncsc1-c1ccc(CNC(=O)[C@@H]2C[C@@H](O)CN2C(=O)[C@@H](NC(=O)CCCCCCCC(=O)N2CC3(CCN(C(=O)c4ccc(Nc5nc(C6CC6)cn6c(-c7cn[nH]c7)cnc56)c(F)c4)CC3)C2)C(C)(C)C)cc1]

Example 136: (2S,4R)-1-((S)-2-(9-(7-(4-((6-Cyclopropyl-3-(1H-pyrazol-4-yl)imidazo[1,2-a]pyrazin-8-yl)amino)-3-fluorobenzoyl)-2,7-diazaspiro[3.5]nonan-2-yl)-9-oxononanamido)-3,3-dimethylbutanoyl)-4-hydroxy-N-(4-(4-methylthiazol-5-yl)benzyl)pyrrolidine-2-carboxamide. 66% yield. $^{1}$H NMR (600 MHz, $CD_3OD$) δ 9.00 (s, 1H), 8.61 (t, J=8.2 Hz, 1H), 8.17 (s, 2H), 8.01 (s, 1H), 7.96 (s, 1H), 7.49 (d, J=8.2 Hz, 2H), 7.44 (d, J=8.3 Hz, 2H), 7.39 (dd, J=11.2, 1.8 Hz, 1H), 7.34 (d, J=9.7 Hz, 1H), 4.66 (s, 1H), 4.61-4.50 (m, 3H), 4.38 (d, J=15.5 Hz, 1H), 4.05-3.96 (m, 2H), 3.92 (d, J=11.2 Hz, 1H), 3.82 (dd, J=10.9, 3.9 Hz, 1H), 3.80-3.63 (m, 4H), 3.62-3.43 (m, 2H), 2.50 (s, 3H), 2.35-2.21 (m, 3H), 2.20-2.12 (m, 3H), 2.12-2.07 (m, 1H), 1.97-1.75 (m, 4H), 1.68-1.57 (m, 4H), 1.41-1.31 (m, 6H), 1.09-1.04 (m, 11H), 1.01-0.96 (m, 2H). HRMS (ESI-TOF) m/z: $[M+H]^+$ calcd for $C_{57}H_{67}FN_{12}O_6S^+$, 1055.5084; found 1055.5099.

Scheme 30. Synthesis of Example 137

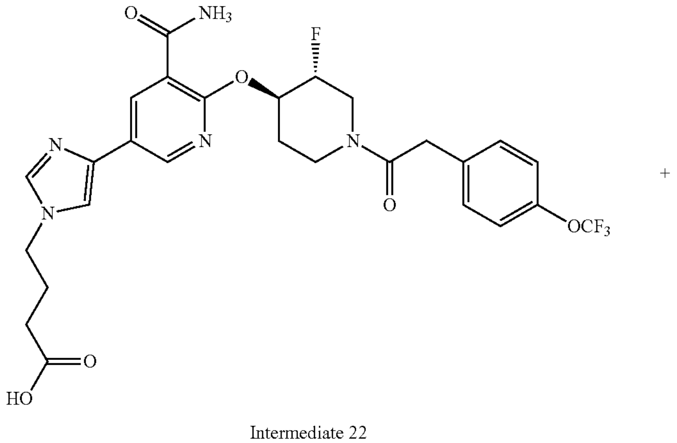

Intermediate 22

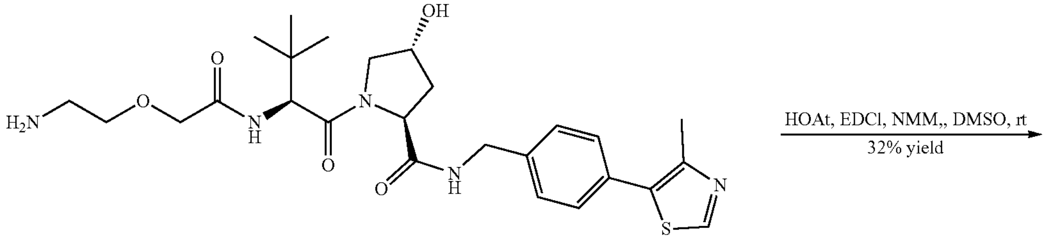

Linker 27

-continued

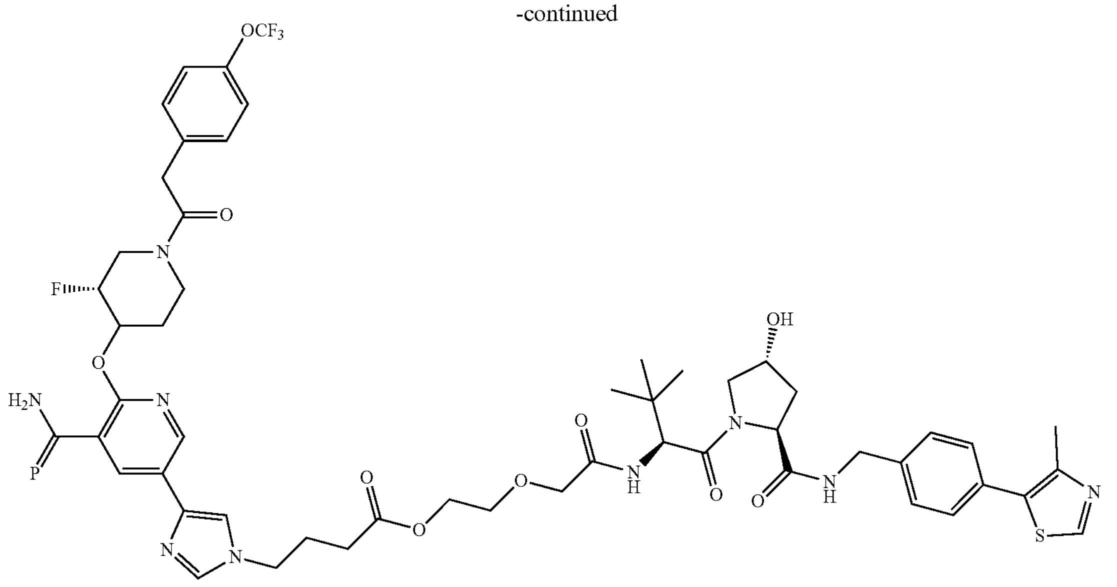

Example 137

Example 137: 2-(((3R,4R)-3-Fluoro-1-(2-(4-(trifluoromethoxy)phenyl)acetyl)piperidin-4-yl)oxy)-5-(l-(4-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-4-oxobutyl)-1H-imidazol-4-yl)nicotinamide. To a solution of intermediate 22 (10 mg, 0.017 mmol) and linker 27 (9 mg, 0.017 mmol) in DMSO (0.5 mL), were added NMM (10 μL, 0.085 mmol), EDCI (5 mg, 0.026 mmol), and HOAt (3.5 mg, 0.026 mmol). After being stirred at rt for 12 h, the mixture was concentrated and purified by HPLC to yield the title compound (6 mg, 32% yield) as the brown oil. $^1$H NMR (600 MHz, $CD_3OD$) δ 9.01 (s, 1H), 8.90 (s, 1H), 8.65 (s, 1H), 8.57 (s, 1H), 8.04 (s, 1H), 7.43 (d, J=8.3 Hz, 2H), 7.40 (d, J=8.2 Hz, 2H), 7.37 (d, J=7.9 Hz, 2H), 7.25 (d, J=8.2 Hz, 2H), 5.69-5.59 (m, 1H), 4.83-4.76 (m, 1H), 4.71 (s, 1H), 4.59-4.53 (m, 1H), 4.52-4.46 (m, 2H), 4.38 (d, J=15.5 Hz, 1H), 4.30 (t, J=7.0 Hz, 2H), 4.07 (d, J=15.2 Hz, 1H), 4.04-3.97 (m, 2H), 3.92-3.86 (m, 3H), 3.83-3.76 (m, 3H), 3.68-3.56 (m, 3H), 3.46-3.34 (m, 2H), 2.46 (s, 3H), 2.34 (t, J=7.0 Hz, 2H), 2.29-2.17 (m, 4H), 2.13-2.04 (m, 1H), 1.91-1.75 (m, 1H), 1.03 (s, 9H). HRMS (ESI-TOF) m/z: $[M+H]^+$ calcd for $C_{53}H_{63}F_4N_{10}O_{10}S^+$, 1107.4380; found 1107.4449.

Example compounds 138-189 were synthesized according to the procedures for the preparation of example compound 137.

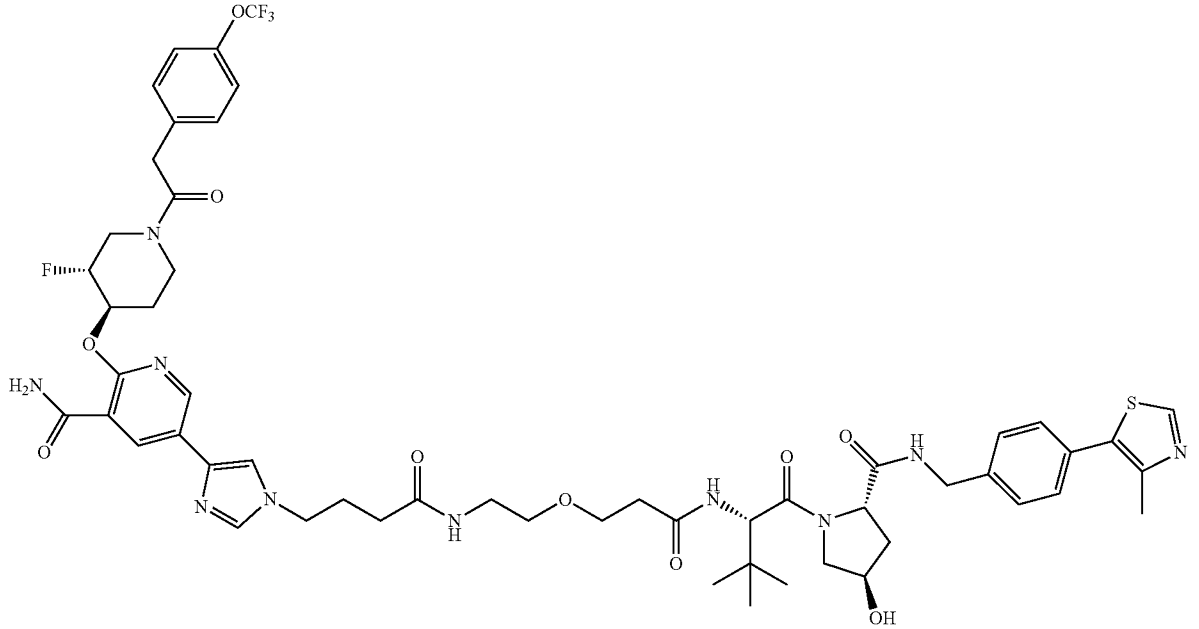 [SMILES: Cc1ncsc1-c1ccc(CNC(=O)[C@@H]2C[C@@H](O)CN2C(=O)[C@@H](NC(=O)CCOCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 138: 2-(((3R,4R)-3-Fluoro-1-(2-(4-(trifluoromethoxy)phenyl)acetyl)piperidin-4-yl)oxy)-5-(1-(4-((2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl)amino)-4-oxobutyl)-1H-imidazol-4-yl)nicotinamide. 40% yield. $^1$H NMR (500 MHz, $CD_3OD$) δ 9.03 (s, 1H), 8.91 (s, 1H), 8.71-8.63 (m, 1H), 8.58 (dd, J=4.9, 2.5 Hz, 1H), 8.05 (t, J=1.6 Hz, 1H), 7.44 (d, J=8.3 Hz, 2H), 7.41-7.39 (m, 2H), 7.37 (d, J=8.4 Hz, 2H), 7.24 (d, J=8.2 Hz, 2H), 5.70-5.58 (m, 1H), 4.57 (dd, J=9.1, 7.6 Hz, 2H), 4.52-4.47 (m, 2H), 4.38 (d, J=15.5 Hz, 1H), 4.31 (t, J=7.0 Hz, 2H), 4.18-3.98 (m, 1H), 3.94-3.84 (m, 3H), 3.83-3.76 (m, 3H), 3.75-3.68 (m, 3H), 3.64-3.56 (td, J=12.1, 11.6, 4.4 Hz, 1H), 3.52 (t, J=5.4 Hz, 2H), 3.38-3.33 (m, 2H), 2.59-2.50 (m, 2H), 2.46 (s, 3H), 2.32 (t, J=7.4 Hz, 2H), 2.28-2.17 (m, 4H), 2.09 (ddd, J=13.3, 9.2, 4.5 Hz, 1H), 1.92-1.75 (m, 1H), 1.03 (s, 9H). HRMS (ESI-TOF) m/z: $[M+H]^+$ calcd for $C_{54}H_{65}F_4N_{10}O_{10}S^+$, 1121.4536; found 1121.4535.

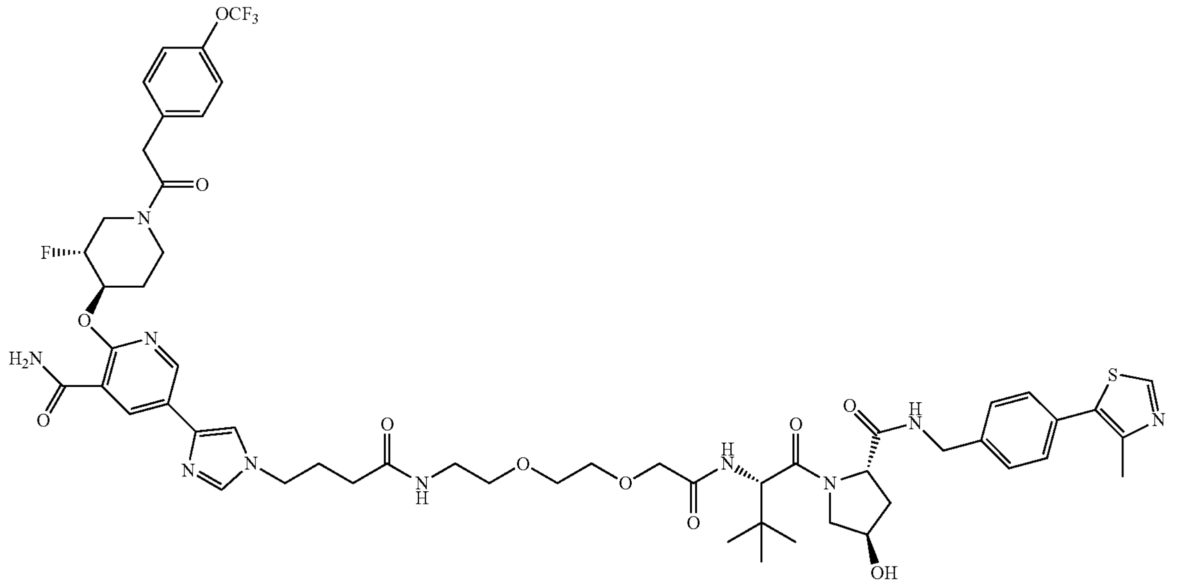 [SMILES: Cc1ncsc1-c1ccc(CNC(=O)[C@@H]2C[C@@H](O)CN2C(=O)[C@@H](NC(=O)COCCOCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 139: 2-(((3R,4R)-3-Fluoro-1-(2-(4-(trifluoromethoxy)phenyl)acetyl)piperidin-4-yl)oxy)-5-(1-((S)-3-

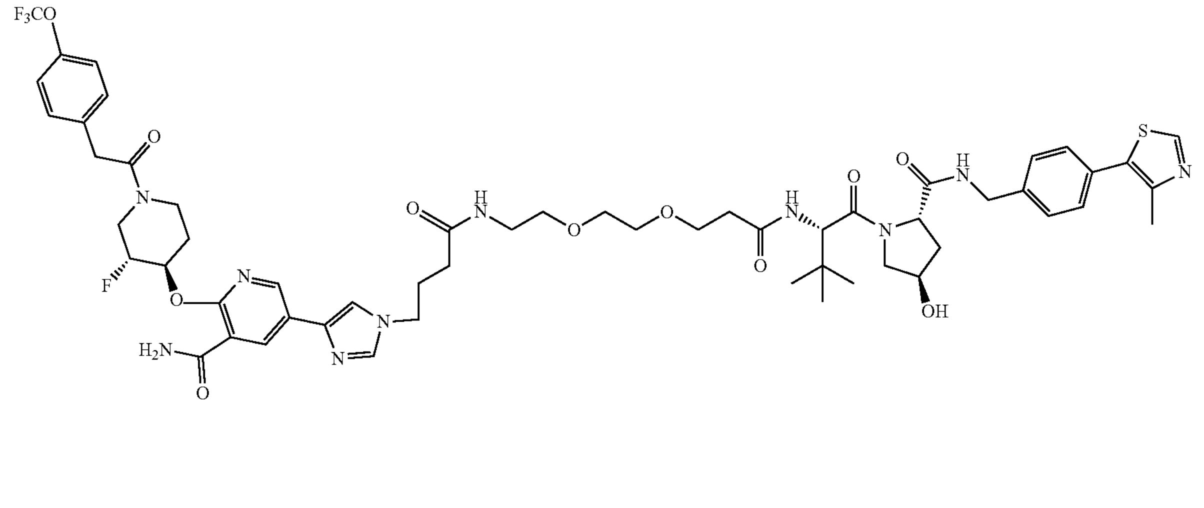

((2S,4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaheptadecan-17-yl)-1H-imidazol-4-yl)nicotinamide. 33% yield. $^1$H NMR (600 MHz, $CD_3OD$) δ 9.01 (s, 1H), 8.90 (s, 1H), 8.65 (s, 1H), 8.58 (s, 1H), 8.04 (s, 1H), 7.43 (d, J=11.3 Hz, 2H), 7.40 (d, J=8.1 Hz, 2H), 7.37 (d, J=8.1 Hz, 2H), 7.25 (d, J=8.1 Hz, 2H), 5.68-5.59 (m, 1H), 4.83-4.78 (m, 1H), 4.75 (d, J=8.1 Hz, 1H), 4.55 (t, J=8.5 Hz, 1H), 4.52-4.46 (m, 2H), 4.39 (d, J=15.5 Hz, 1H), 4.28 (t, J=7.0 Hz, 2H), 4.16-4.08 (m, 1H), 4.06-3.98 (m, 2H), 3.88 (t, J=5.7 Hz, 3H), 3.84-3.77 (m, 3H), 3.73-3.69 (m, 3H), 3.66-3.60 (m, 3H), 3.58-3.54 (m, 2H), 3.49-3.43 (m, 1H), 2.46 (s, 3H), 2.33 (dt, J=14.7, 7.1 Hz, 2H), 2.29-2.23 (m, 2H), 2.20 (t, J=7.1 Hz, 2H), 2.13-2.04 (m, 1H), 1.91-1.77 (m, 1H), 1.04 (s, 9H). HRMS (ESI-TOF) m/z: $[M+H]^+$ calcd for $C_{55}H_{67}F_4N_{10}O_{11}S^+$, 1151.4642; found 1151.4634.

Example 140: 2-(((3R,4R)-3-Fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,15-dioxo-8,11-dioxa-4,14-diazaoctadecan-18-yl)-1H-imidazol-4-yl)nicotinamide. 41% yield. $^{1}H$ NMR (600 MHz, $CD_3OD$) δ 9.06 (s, 1H), 8.93 (s, 1H), 8.67 (dd, J=4.7, 2.6 Hz, 1H), 8.60-8.54 (m, 1H), 8.08 (s, 1H), 7.46 (d, J=8.0 Hz, 2H), 7.41 (d, J=8.1 Hz, 2H), 7.37 (d, J=8.0 Hz, 2H), 7.24 (d, J=8.2 Hz, 2H), 5.69-5.61 (m, 1H), 4.83-4.77 (m, 1H), 4.65 (s, 1H), 4.56 (t, J=8.4 Hz, 1H), 4.53-4.48 (m, 2H), 4.37 (d, J=15.4 Hz, 1H), 4.31 (t, J=6.9 Hz, 2H), 4.16-3.99 (m, 1H), 3.94-3.84 (m, 3H), 3.84-3.76 (m, 3H), 3.75-3.69 (m, 2H), 3.65-3.57 (m, 5H), 3.53 (t, J=5.3 Hz, 2H), 3.34 (t, J=5.4 Hz, 2H), 2.61-2.52 (m, 1H), 2.50-2.44 (d, J=3.8 Hz, 4H), 2.31 (t, J=6.9 Hz, 2H), 2.23 (p, J=7.2 Hz, 4H), 2.08 (ddd, J=13.3, 9.4, 4.5 Hz, 1H), 1.91-1.75 (m, 1H), 1.03 (s, 9H). HRMS (ESI-TOF) m/z: $[M+H]^+$ calcd for $CH_{19}F_4N_{10}O_{11}S^+$, 1165.4799, found 1165.4808.

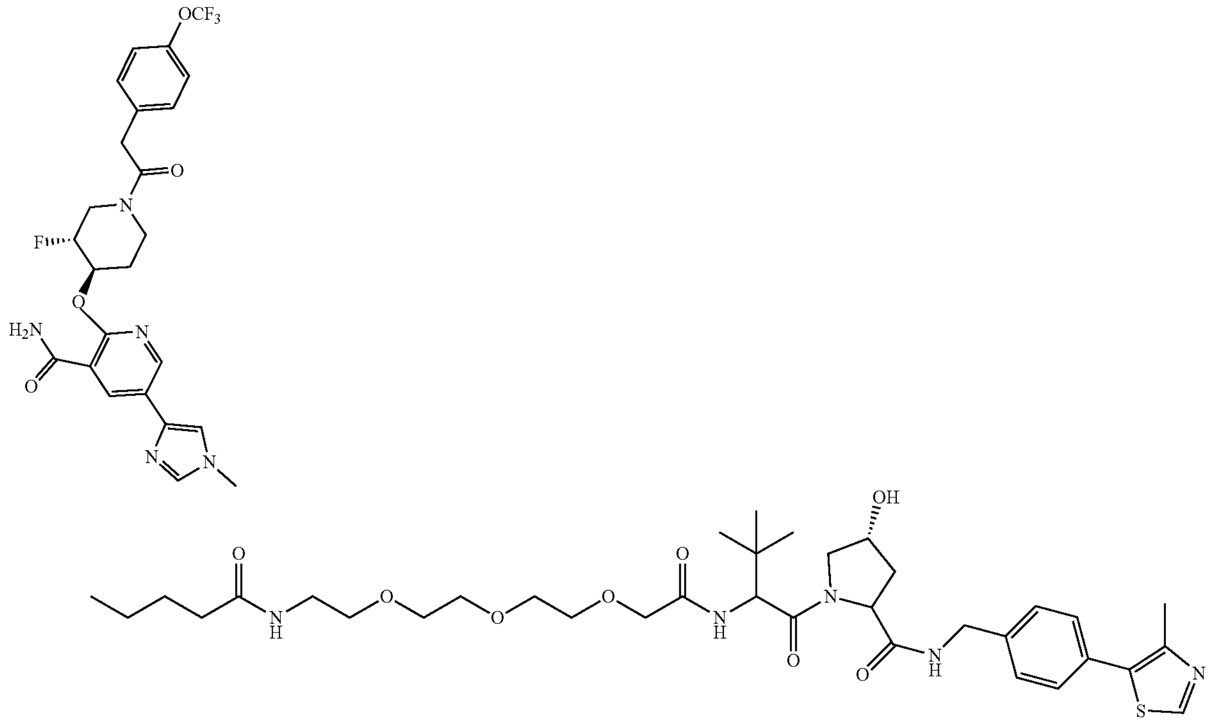

Example 141: 2-(((3R,4R)-3-Fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,17-dioxo-7,10,13-trioxa-4,16-diazaicosan-20-yl)-1H-imidazol-4-yl)nicotinamide. 31% yield. $^{1}H$ NMR (600 MHz, $CD_3OD$) δ 9.07 (s, 1H), 8.96 (s, 1H), 8.67 (dd, J=4.8, 2.7 Hz, 1H), 8.59 (dd, J=6.0, 2.6 Hz, 1H), 8.08 (s, 1H), 7.45 (t, J=7.7 Hz, 2H), 7.42 (d, J=8.1 Hz, 2H), 7.37 (d, J=8.1 Hz, 2H), 7.24 (d, J=8.1 Hz, 2H), 5.69-5.60 (s, 1H), 4.83-4.77 (m, 1H), 4.69 (s, 1H), 4.59-4.55 (m, 1H), 4.54-4.48 (m, 2H), 4.37 (d, J=15.5 Hz, 1H), 4.31 (t, J=6.9 Hz, 2H), 4.16-4.06 (m, 1H), 4.04-3.98 (m, 2H), 3.92-3.84 (m, 3H), 3.80 (dd, J=11.1, 3.9 Hz, 3H), 3.72-3.64 (m, 7H), 3.62 (q, J=5.1, 4.6 Hz, 2H), 3.55-3.48 (m, 2H), 3.37-3.32 (m, 2H), 2.48 (s, 3H), 2.29 (d, J=6.6 Hz, 2H), 2.27-2.18 (m, 4H), 2.13-2.04 (m, 1H), 1.92-1.76 (m, 1H), 1.04 (s, 9H). HRMS (ESI-TOF) m/z: $[M+H]^+$ calcd for $C_{57}H_{71}F_4N_{10}O_{12}S^+$, 1195.4904; found 1195.4888.

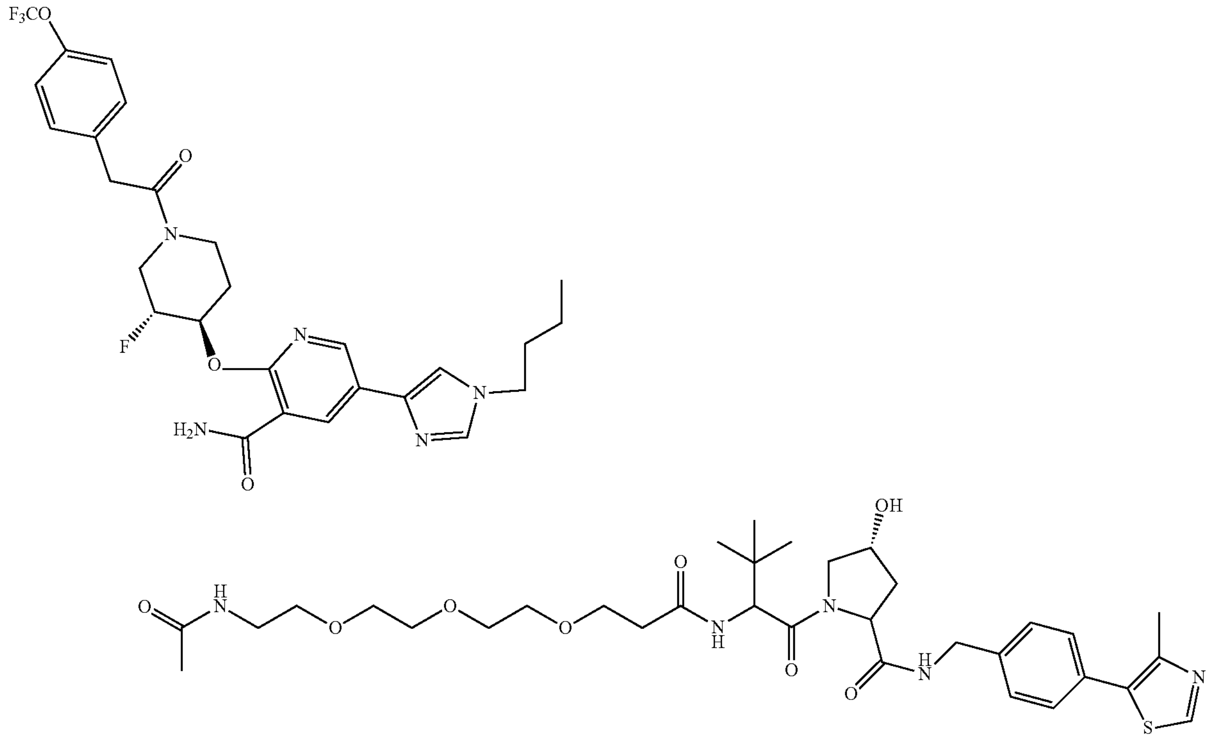

Example 142: 2-(((3R,4R)-3-Fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,18-dioxo-8,11,14-trioxa-4,17-diazahenicosan-21-yl)-1H-imidazol-4-yl)nicotinamide. 35% yield. $^1$H NMR (500 MHz, $CD_3OD$) δ 8.97 (s, 1H), 8.89 (d, J=4.9 Hz, 1H), 8.66 (q, J=4.3, 3.8 Hz, 1H), 8.60-8.54 (m, 1H), 8.04 (s, 1H), 7.45 (td, J=7.9, 6.9, 3.1 Hz, 2H), 7.40 (dt, J=6.2, 1.9 Hz, 2H), 7.36 (dd, J=7.9, 4.8 Hz, 2H), 7.24 (d, J=7.9 Hz, 2H), 5.64 (brs, 1H), 4.60-4.52 (m, 2H), 4.51-4.46 (m, 2H), 4.40-4.34 (m, 1H), 4.32-4.27 (m, 2H), 4.19-3.97 (m, 1H), 3.92-3.82 (m, 3H), 3.81-3.76 (m, 3H), 3.74-3.66 (m, 3H), 3.65-3.55 (m, 9H), 3.52 (q, J=5.1 Hz, 2H), 3.38-3.33 (m, 2H), 2.59-2.50 (m, 1H), 2.49-2.42 (m, 4H), 2.30 (p, J=5.6, 5.2 Hz, 2H), 2.27-2.17 (m, 4H), 2.09 (ddd, J=13.3, 9.0, 4.5 Hz, 1H), 1.91-1.73 (d, J=41.5 Hz, 1H), 1.03 (s, 9H). HRMS (ESI-TOF) m/z: $[M+H]^+$ calcd for $C_{58}H_{73}F_4N_{10}O_{12}S^+$, 1209.5061; found 1209.5067.

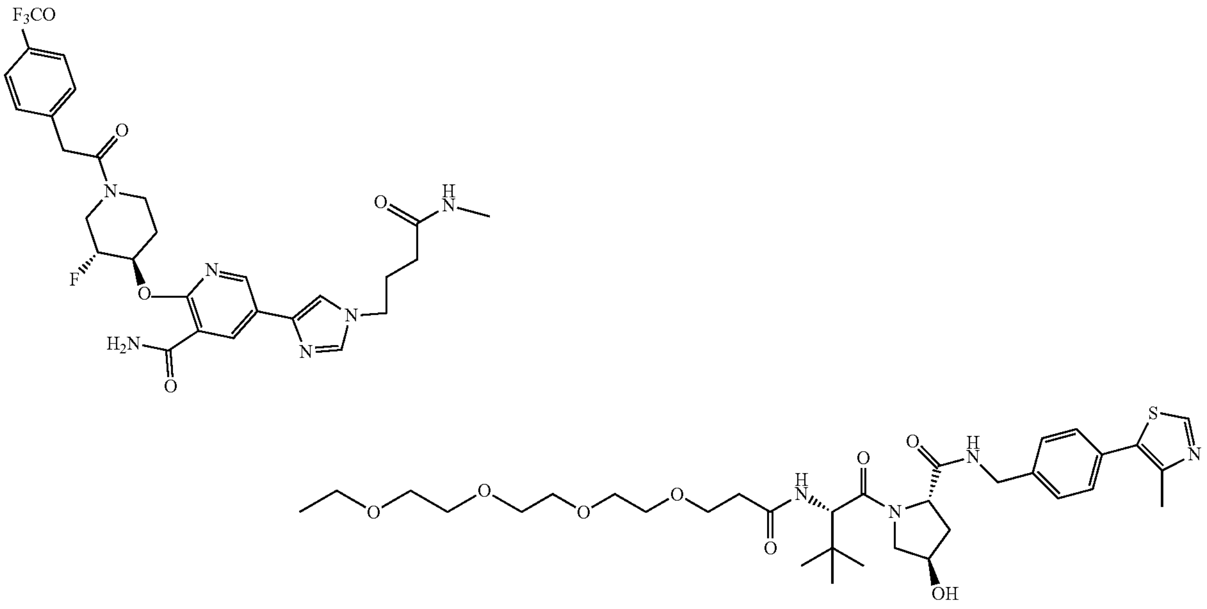

Example 143: 2-(((3R,4R)-3-Fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,18-dioxo-8,11,14-trioxa-4,17-diazahenicosan-21-yl)-1H-imidazol-4-yl)nicotinamide. 45% yield. $^1$H NMR (500 MHz, $CD_3OD$) δ 9.07 (d, J=3.5 Hz, 1H), 8.96 (d, J=3.5 Hz, 1H), 8.67 (q, J=3.3 Hz, 1H), 8.59 (dt, J=6.3, 3.0 Hz, 1H), 8.09 (d, J=3.8 Hz, 1H), 7.46 (dd, J=8.2, 3.4 Hz, 2H), 7.43-7.39 (m, 2H), 7.37 (dd, J=8.5, 3.3 Hz, 2H), 7.24 (d, J=8.1 Hz, 2H), 5.65 (brs, 1H), 4.60-4.53 (m, 2H), 4.52-4.47 (m, 2H), 4.40-4.29 (m, 3H), 4.17-3.98 (m, 1H), 3.91-3.85 (m, 3H), 3.83-3.76 (m, 3H), 3.75-3.66 (m, 3H), 3.64-3.56 (m, 14H), 3.53 (td, J=5.4, 3.5 Hz, 3H), 2.60-2.51 (m, 1H), 2.49-2.42 (m, 4H), 2.34-2.29 (m, 2H), 2.28-2.17 (m, 4H), 2.12-2.05 (m, 1H), 1.92-1.76 (m, 1H), 1.03 (s, 9H). HRMS (ESI-TOF) m/z: $[M+H]^+$ calcd for $C_{60}H_{77}F_4N_{10}O_{13}S^+$, 1253.5323; found 1253.5312.

((2S,4R)-4-hydroxy-2-((4-(4-methylthiazol-5-yl)benzyl)carbamoyl)pyrrolidine-1-carbonyl)-2,2-dimethyl-5,24-dioxo-8,11,14,17,20-pentaoxa-4,23-diazaheptacosan-27-yl)-1H-imidazol-4-yl)nicotinamide. 34% yield. $^1$H NMR (600 MHz, $CD_3OD$) δ 9.07 (s, 1H), 8.93 (s, 1H), 8.67 (s, 1H), 8.60 (d, J=5.9 Hz, 1H), 8.09 (s, 1H), 7.47 (d, J=8.0 Hz, 2H), 7.41 (d, J=8.0 Hz, 2H), 7.37 (d, J=8.1 Hz, 2H), 7.25 (d, J=8.1 Hz, 2H), 5.70-5.60 (m, 1H), 4.83-4.77 (m, 2H), 4.65 (s, 1H), 4.57 (dd, J=16.9, 8.6 Hz, 1H), 4.53-4.47 (m, 1H), 4.40-4.30 (m, 3H), 4.17-4.00 (s, 1H), 3.93-3.84 (m, 3H), 3.83-3.77 (m, 3H), 3.75-3.67 (m, 3H), 3.65-3.56 (m, 16H), 3.53 (t, J=5.3 Hz, 2H), 3.34 (t, J=5.4 Hz, 2H), 2.60-2.53 (m, 1H), 2.51-2.43 (m, 4H), 2.32 (t, J=6.9 Hz, 2H), 2.29-2.17 (m, 4H), 2.12-2.02 (m, 1H), 1.91-1.75 (m, 1H), 1.03 (s, 9H). HRMS (ESI-TOF) m/z: $[M+H]^+$ calcd for $C_{62}H_{81}F_4N_{10}O_{14}S^+$, 1297.5585; found 1297.5596.

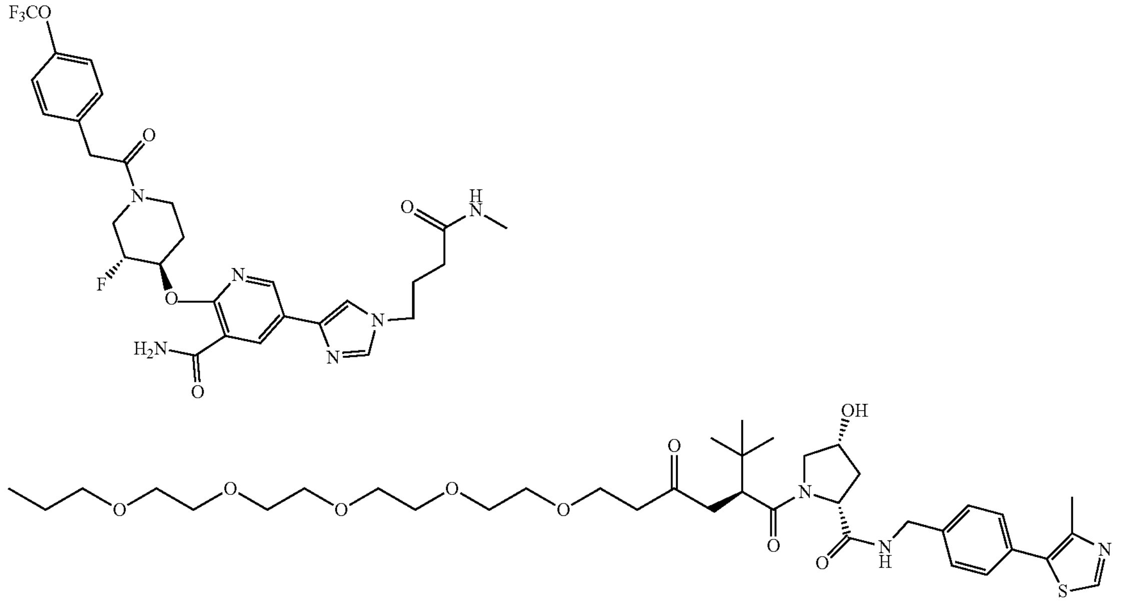

Example 144: 2-(((3R,4R)-3-Fluoro-1-(2-(4-(trifluoromethoxy)phenyl)acetyl)piperidin-4-yl)oxy)-5-(1-((S)-3-

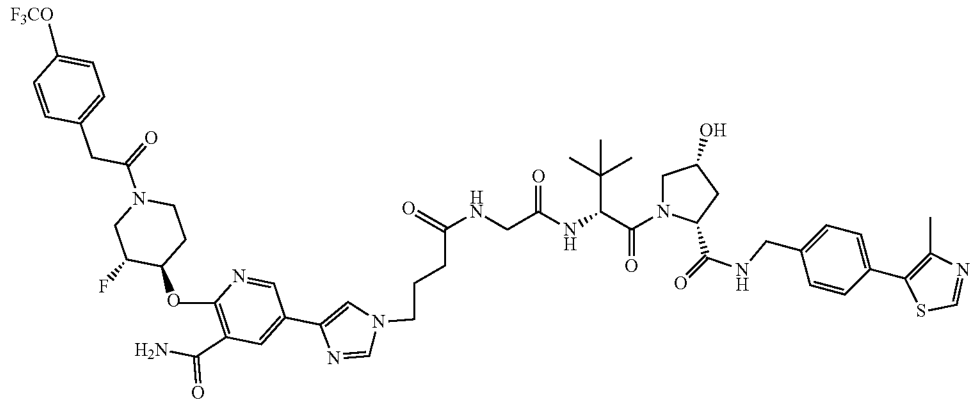

Example 145: 2-(((3R,4R)-3-fluoro-1-(2-(4-(trifluoromethoxy)phenyl)acetyl)piperidin-4-yl)oxy)-5-(1-(4-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)amino)-4-oxobutyl)-1H-imidazol-4-yl)nicotinamide 39% yield. $^1H$ NMR (500 MHz, $CD_3OD$) δ 9.10 (s, 1H), 8.93 (s, 1H), 8.66 (t, J=3.4 Hz, 1H), 8.58 (dd, J=4.7, 2.7 Hz, 1H), 8.11 (s, 1H), 7.45 (dt, J=8.2, 3.0 Hz, 2H), 7.41-7.35 (m, 4H), 7.24 (d, J=7.8 Hz, 2H), 5.64 (brs, 1H), 4.66-4.62 (m, 1H), 4.59-4.52 (m, 2H), 4.50 (d, J=4.2 Hz, 2H), 4.39-4.32 (m, 3H), 4.20-3.98 (m, 1H), 3.94-3.84 (m, 5H), 3.83-3.75 (m, 3H), 3.71-3.54 (m, 1H), 2.52-2.42 (m, 3H), 2.40-2.34 (m, 2H), 2.32-2.17 (m, 4H), 2.09 (ddd, J=13.3, 9.0, 4.4 Hz, 1H), 1.93-1.73 (m, 11H), 1.04 (s, 9H). HRMS (ESI-TOF) m/z: $[M+H]^+$ calcd for $C_{51}H_{59}F_4N_{10}O_9S^+$, 1063.4118; found 1063.4128.

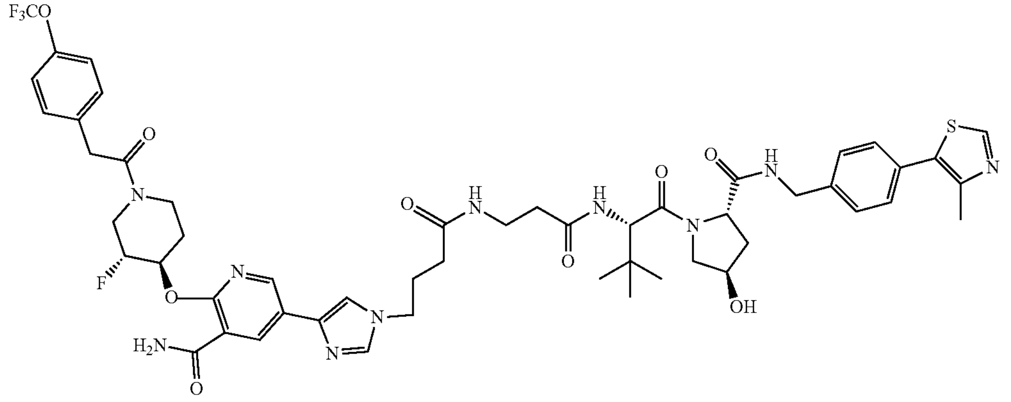

Example 146 2-(((3R,4R)-3-Fluoro-1-(2-(4-(trifluoromethoxy)phenyl)acetyl)piperidin-4-yl)oxy)-5-(l-(4-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)amino)-4-oxobutyl)-1H-imidazol-4-yl)nicotinamide. 37% yield. $^1H$ NMR (600 MHz, $CD_3OD$) δ 8.97 (s, 1H), 8.89 (s, 1H), 8.66 (s, 1H), 8.57 (s, 1H), 8.05 (s, 1H), 7.44 (d, J=7.5 Hz, 2H), 7.41-7.34 (m, 4H), 7.25 (d, J=8.2 Hz, 2H), 5.69-5.59 (m, 1H), 4.60 (s, 1H), 4.56-4.54 (m, 1H), 4.52 (d, J=6.4 Hz, 1H), 4.51-4.48 (m, 1H), 4.37 (d, J=15.6 Hz, 1H), 4.29 (t, J=7.0 Hz, 2H), 4.15-3.99 (m, 1H), 3.94 (d, J=11.1 Hz, 1H), 3.90-3.86 (m, 2H), 3.83-3.76 (m 3H), 3.65-3.56 (m, 1H), 3.48-3.42 (m, 1H), 3.42-3.35 (m, 1H), 2.60-2.43 (m, 5H), 2.29-2.25 (m, 3H), 2.24-2.17 (m, 4H), 2.11-2.05 (m, 1H), 1.91-1.76 (m, 1H), 1.03 (s, 9H). HRMS (ESI-TOF) m/z: $[M+H]^+$ calcd for $C_{52}H_{61}F_4N_{10}O_9S^+$, 1077.4274; found 1077.4290.

Example 147: 2-(((3R,4R)-3-Fluoro-1-(2-(4-(trifluoromethoxy)phenyl)acetyl)piperidin-4-yl)oxy)-5-(1-(4-((4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)amino)-4-oxobutyl)-1H-imidazol-4-yl)nicotinamide. 41% yield. $^1H$ NMR (600 MHz, $CD_3OD$) δ 9.09 (s, 1H), 8.96 (s, 1H), 8.66 (dd, J=4.6, 2.6 Hz, 1H), 8.57 (dd, J=6.0, 2.6 Hz, 1H), 8.09 (s, 1H), 7.46 (d, J=8.0 Hz, 2H), 7.41 (d, J=8.0 Hz, 2H), 7.37 (d, J=8.1 Hz, 2H), 7.24 (d, J=8.1 Hz, 2H), 5.69-5.60 (m, 1H), 4.82-4.73 (m, 1H), 4.62 (s, 1H), 4.57 (d, J=8.4 Hz, 1H), 4.55 (d, J=7.1 Hz, 1H), 4.52-4.48 (m, 1H), 4.36 (d, J=15.5 Hz, 1H), 4.33 (t, J=7.1 Hz, 2H), 4.18-3.99 (m, 1H), 3.94-3.87 (m, 3H), 3.85-3.76 (m, 3H), 3.64-3.57 (m, 1H), 3.18 (t, J=6.9 Hz, 2H), 2.47 (s, 3H), 2.31 (q, J=7.3 Hz, 3H), 2.29-2.19 (m, 5H), 2.09 (ddd, J=13.4, 9.3, 4.6 Hz, 1H), 1.92-1.79 (m, 1H), 1.76

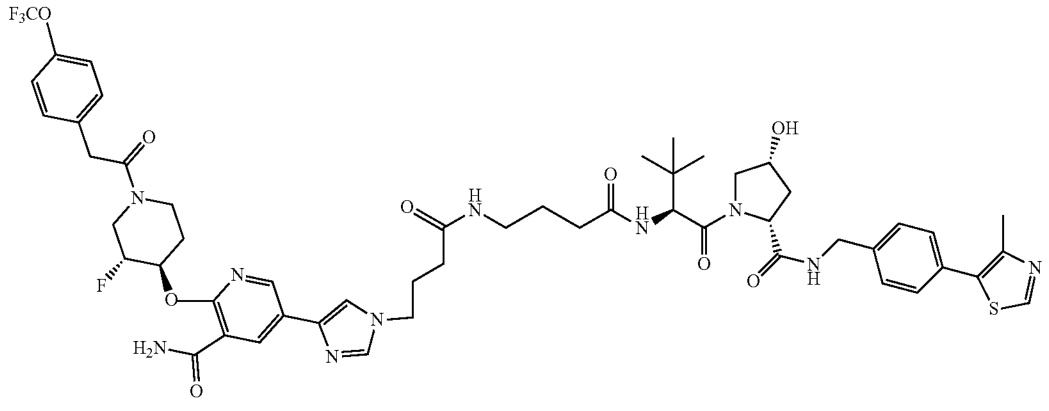

(p, J=7.2 Hz, 2H), 1.04 (s, 9H). HRMS (ESI-TOF) m/z: $[M+H]^+$ calcd for $C_{53}H_{63}F_4N_{10}O_9S^+$, 1091.4431; found 1091.4445.

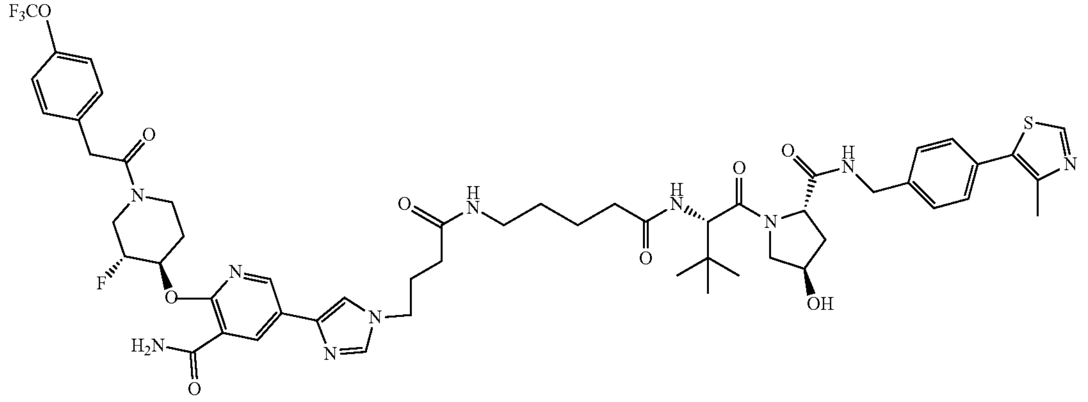

Example 148: 2-(((3R,4R)-3-Fluoro-1-(2-(4-(trifluoromethoxy)phenyl)acetyl)piperidin-4-yl)oxy)-5-(1-(4-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-4-oxobutyl)-1H-imidazol-4-yl)nicotinamide 33% yield. $^1$H NMR (600 MHz, $CD_3OD$) δ 9.04 (s, 1H), 8.90 (s, 1H), 8.67 (s, 1H), 8.59 (s, 1H), 8.07 (s, 1H), 7.46 (d, J=8.0 Hz, 2H), 7.40 (d, J=8.2 Hz, 2H), 7.37 (d, J=7.9 Hz, 2H), 7.25 (d, J=8.4 Hz, 2H), 5.68-5.61 (m, 1H), 4.62 (s, 1H), 4.56 (d, J=8.4 Hz, 1H), 4.55-4.53 (m, 1H), 4.52-4.48 (m, 2H), 4.36 (d, J=15.5 Hz, 1H), 4.32 (t, J=7.0 Hz, 3H), 3.92-3.86 (m, 4H), 3.83-3.76 (m, 3H), 3.66-3.57 (m, 1H), 3.21-3.09 (m, 3H), 2.48-2.45 (m, 5H), 2.32-2.27 (m, 4H), 2.26-2.19 (m, 3H), 1.91-1.76 (m, 1H), 1.64-1.57 (m, 1H), 1.53-1.46 (m, 1H), 1.03 (s, 9H). HRMS (ESI-TOF) m/z: $[M+H]^+$ calcd for $C_{54}H_{65}F_4N_{10}O_9S^+$, 1105.4587; found 1105.4638.

Example 149: 2-(((3R,4R)-3-Fluoro-1-(2-(4-(trifluoromethoxy)phenyl)acetyl)piperidin-4-yl)oxy)-5-(1-(4-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)amino)-4-oxobutyl)-1H-imidazol-4-yl)nicotinamide. 39% yield. $^1$H NMR (600 MHz, $CD_3OD$) δ 9.03 (s, 1H), 8.90 (s, 1H), 8.66 (s, 1H), 8.58 (d, J=5.8 Hz, 1H), 8.06 (s, 1H), 7.46 (d, J=8.0 Hz, 2H), 7.41 (d, J=8.0 Hz, 2H), 7.37 (d, J=8.0 Hz, 2H), 7.25 (d, J=8.2 Hz, 2H), 5.69-5.60 (m, 1H), 4.64-4.62 (m, 1H), 4.59-4.53 (m, 1H), 4.52-4.48 (m, 1H), 4.39-4.33 (m, 1H), 4.32-4.26 (m, 3H), 3.92-3.87 (m, 4H), 3.83-3.77 (m, 3H), 3.66-3.62 (m, 1H), 3.43-3.41 (m, 1H), 3.21-3.18 (m, 1H), 3.14 (t, J=7.1 Hz, 3H), 2.48-2.45 (m, 4H), 2.29 (d, J=7.0 Hz, 4H), 2.25-2.19 (m, 4H), 2.11-2.06 (m, 1H), 1.62-1.57 (m, 1H), 1.51-1.47 (m, 1H), 1.36-1.30 (m, 2H), 1.03 (s, 9H). HRMS (ESI-TOF) m/z: $[M+H]^+$ calcd for $C_{55}H_{67}F_4N_{10}O_9S^+$, 1119.4744; found 1119.4838.

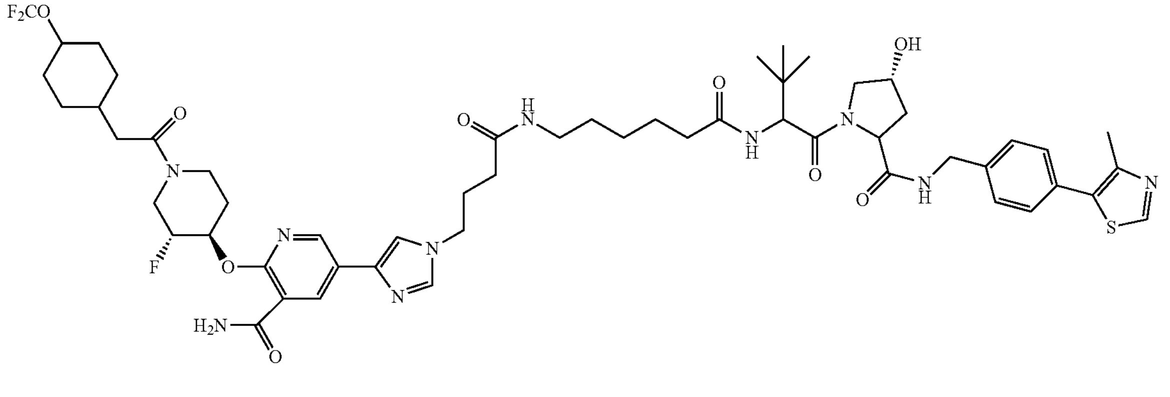

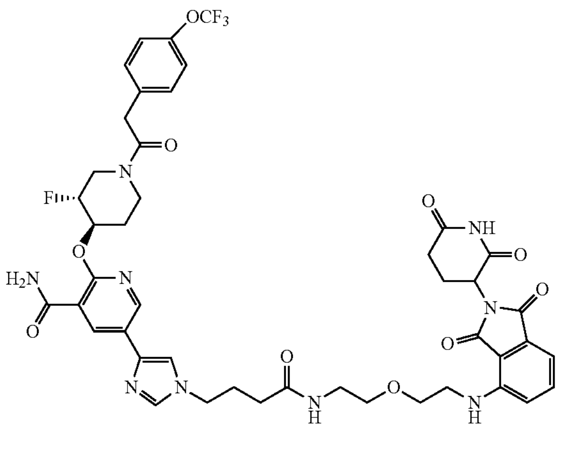 [SMILES: NC(=O)c1cc(-c2cn(CCCC(=O)NCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 150: 5-(1-(4-((2-(2-((2-(2,6-Dioxopiperidin-3-yl)-1,3-dioxoisoindolin-4-yl)amino)ethoxy)ethyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy) nicotinamide. 33% yield. $^1$H NMR (600 MHz, $CD_3OD$) δ 8.81 (s, 1H), 8.60 (s, 1H), 8.52 (s, 1H), 7.92 (s, 1H), 7.50 (s, 1H), 7.38 (d, J=7.7 Hz, 2H), 7.25 (d, J=8.2 Hz, 2H), 7.03 (d, J=8.4 Hz, 1H), 6.99 (d, J=7.8 Hz, 1H), 5.67-5.57 (m, 1H), 5.04 (dd, J=12.8, 5.4 Hz, 1H), 4.23 (t, J=7.0 Hz, 2H), 3.89 (d, J=5.5 Hz, 2H), 3.84-3.77 (m, 2H), 3.72 (t, J=5.2 Hz, 3H), 3.61 (t, J=5.2 Hz, 3H), 3.50-3.46 (m, 2H), 3.44-3.37 (m, 2H), 2.89-2.81 (m, 1H), 2.76-2.70 (m, 1H), 2.68-2.64 (m, 1H), 2.29 (t, J=6.8 Hz, 2H), 2.22-2.17 (m, 2H), 2.12-2.06 (m, 1H), 1.92-1.84 (m, 1H), 1.83-1.75 (m, 1H). HRMS (ESI-TOF) m/z: $[M+H]^+$ calcd for $C_{44}H_{46}F_4N_9O_{10}^+$, 936.3298; found 936.3292.

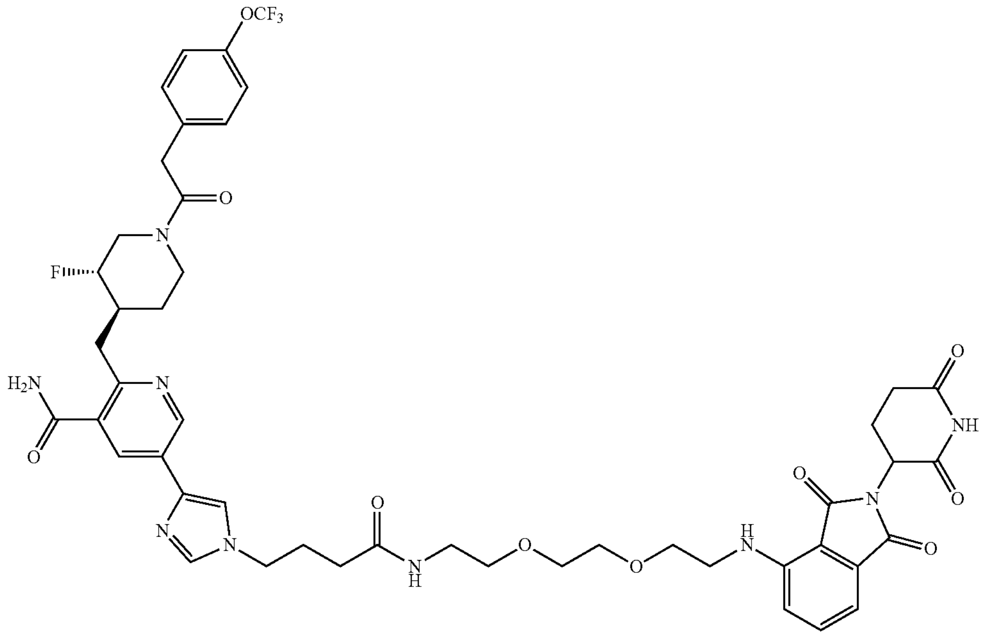

Example 151: 5-(1-(4-((2-(2-(2-((2-(2,6-Dioxopiperidin-3-yl)-1,3-dioxoisoindolin-4-yl)amino)ethoxy)ethoxy)ethyl) amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide. 37% yield. $^1$H NMR (600 MHz, $CD_3OD$) δ 9.01 (s, 1H), 8.59 (dd, J=5.1, 2.6 Hz, 1H), 8.52 (dd, J=6.0, 2.6 Hz, 1H), 8.01 (s, 1H), 7.54-7.45 (m, 1H), 7.37 (d, J=8.0 Hz, 2H), 7.25 (d, J=8.1 Hz, 2H), 7.06-6.88 (m, 1H), 5.68-5.57 (m, 1H), 5.04 (dd, J=12.8, 5.4 Hz, 1H), 4.27 (t, J=6.6 Hz, 2H), 4.19-3.99 (m, 1H), 3.94-3.85 (m, 2H), 3.84-3.76 (m, 2H), 3.72 (t, J=5.0 Hz, 2H), 3.69 (dd, J=6.3, 2.7 Hz, 2H), 3.66 (dd, J=6.2, 2.8 Hz, 2H), 3.63-3.58 (m, 1H), 3.57 (t, J=5.3 Hz, 2H), 3.45 (t, J=5.3 Hz, 2H), 3.35 (td, J=5.2, 2.3 Hz, 2H), 2.85 (ddd, J=18.7, 13.9, 5.4 Hz, 1H), 2.74 (dt, J=17.4, 3.2 Hz, 1H), 2.67 (qd, J=13.2, 4.6 Hz, 1H), 2.31-2.18 (m, 5H), 2.12-2.05 (m, 1H), 1.92-1.76 (m, 1H). HRMS (ESI-TOF) m/z: $[M+H]^+$ calcd for $C_{46}H_{50}F_4N_9O_{11}^+$, 980.3560; found 980.3641.

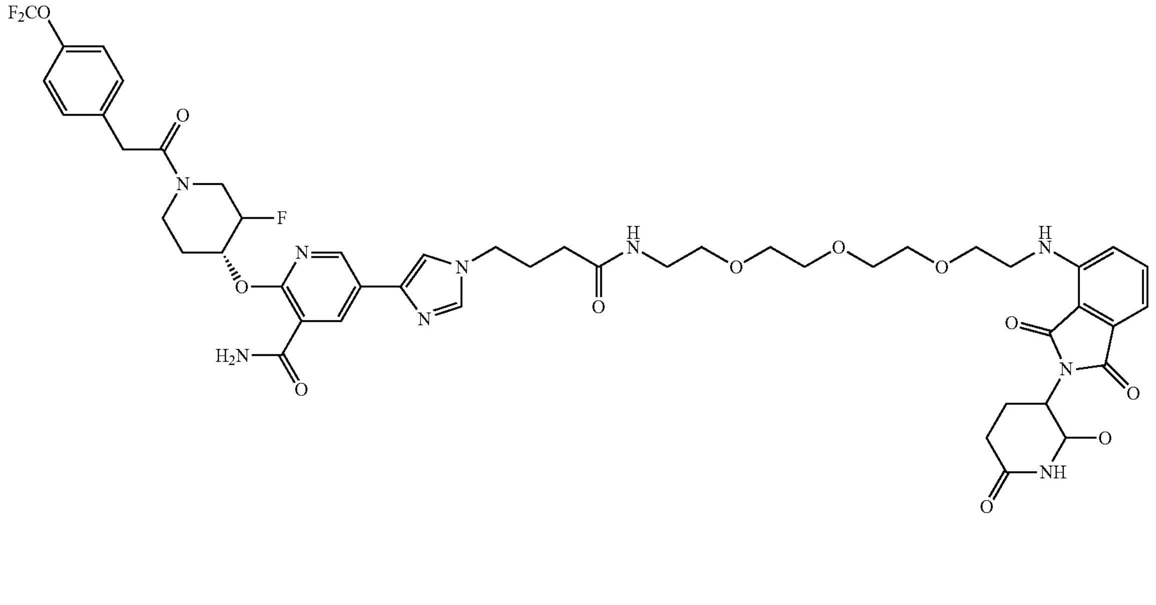

Example 152: 5-(1-(1-((2-(2,6-Dioxopiperidin-3-yl)-1,3-dioxoisoindolin-4-yl)amino)-13-oxo-3,6,9-trioxa-12-aza-hexadecan-16-yl)-1H-imidazol-4-yl)-2-(((3R,4R)-3-fluoro-1-(2-(4-(trifluoromethoxy)phenyl)acetyl)piperidin-4-yl)oxy)nicotinamide. 36% yield. $^1$H NMR (600 MHz, $CD_3OD$) δ 8.99 (s, 1H), 8.60 (dd, J=5.6, 2.6 Hz, 1H), 8.55-8.50 (m, 1H), 8.00 (s, 1H), 7.59-7.44 (m, 1H), 7.37 (d, J=8.1 Hz, 2H), 7.25 (d, J=8.1 Hz, 2H), 7.12-6.87 (m, 2H), 5.67-5.57 (m, 1H), 5.05 (dd, J=12.7, 5.5 Hz, 1H), 4.83-4.78 (m, 1H), 4.27 (t, J=6.7 Hz, 2H), 4.19-4.00 (m, 1H), 3.94-3.85 (m, 2H), 3.84-3.75 (m, 2H), 3.73-3.65 (m, 10H), 3.63-3.58 (m, 2H), 3.52 (t, J=5.2 Hz, 2H), 3.45-3.40 (m, 2H), 2.87 (ddd, J=18.8, 14.0, 5.4 Hz, 1H), 2.77-2.71 (m, 1H), 2.71-2.61 (m, 1H), 2.30-2.26 (m, 2H), 2.25-2.19 (m, 3H), 2.14-2.07 (m, 1H), 1.92-1.75 (m, 1H). HRMS (ESI-TOF) m/z: $[M+H]^+$ calcd for $C_{48}H_{54}F_4N_9O_{12}^+$, 1024.3823; found 1024.3845.

Example 153: 5-(1-(1-((2-(2,6-Dioxopiperidin-3-yl)-1,3-dioxoisoindolin-4-yl)amino)-19-oxo-3,6,9,12,15-pentaoxa-18-azadocosan-22-yl)-1H-imidazol-4-yl)-2-(((3R,4R)-3-fluoro-1-(2-(4-(trifluoromethoxy)phenyl)acetyl)piperidin-4-yl)oxy)nicotinamide. 34% yield. $^1$H NMR (500 MHz, $CD_3OD$) δ 9.02 (s, 1H), 8.63 (dd, J=4.0, 2.5 Hz, 1H), 8.56 (dd, J=4.9, 2.6 Hz, 1H), 8.04 (s, 1H), 7.51 (dd, J=8.6, 7.1 Hz, 1H), 7.40-7.33 (m, 2H), 7.24 (d, J=8.2 Hz, 2H), 7.04 (d, J=8.6 Hz, 1H), 7.01 (d, J=7.1 Hz, 1H), 5.68-5.57 (m, 1H), 5.03 (dd, J=12.8, 5.4 Hz, 1H), 4.30 (t, J=6.9 Hz, 2H), 4.20-3.98 (m, 1H), 3.93-3.84 (m, 2H), 3.83-3.75 (m, 2H), 3.71 (t, J=5.2 Hz, 2H), 3.67-3.64 (m, 4H), 3.63-3.59 (m, 5H), 3.58-3.55 (m, 6H), 3.53 (t, J=5.3 Hz, 2H), 3.46 (t, J=5.1 Hz, 2H), 3.34 (t, J=5.3 Hz, 2H), 2.85 (ddd, J=17.7, 14.0, 5.3 Hz, 1H), 2.77-2.71 (m, 1H), 2.70-2.62 (m, 1H), 2.29 (t, J=6.4 Hz, 2H), 2.23 (t, J=6.6 Hz, 3H), 2.10 (ddt, J=13.1, 5.5, 2.7 Hz, 1H), 1.95-1.84 (m, 1H), 1.83-1.74 (m, 1H). HRMS (ESI-TOF) m/z: $[M+H]^+$ calcd for $C_{52}H_{62}F_4N_9O_{14}^+$, 1112.4347; found 1112.4816.

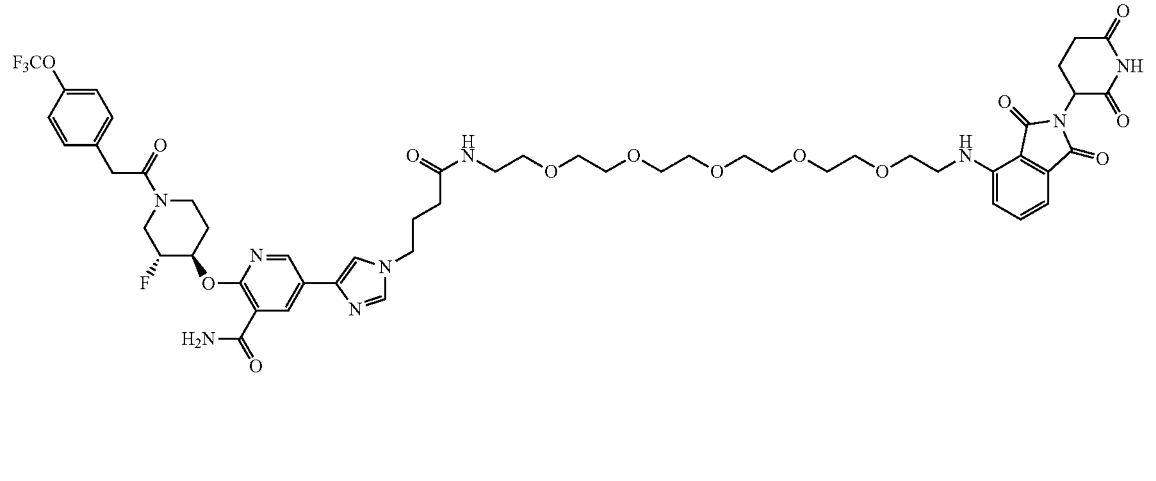 [SMILES: NC(=O)c1cc(-c2cn(CCCC(=O)NCCOCCOCCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

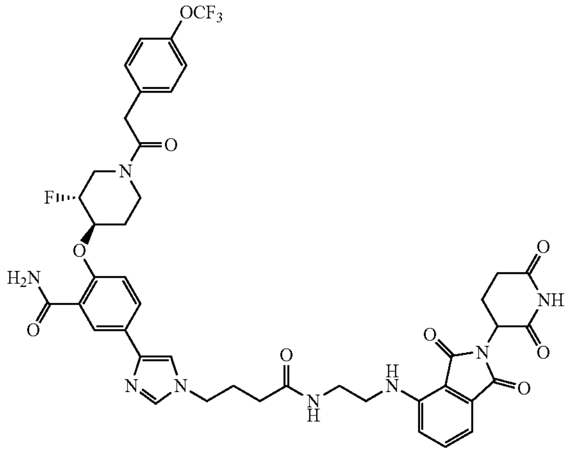 [SMILES: NC(=O)c1cc(-c2cn(CCCC(=O)NCCNc3cccc4c3C(=O)N(C3CCC(=O)NC3=O)C4=O)cn2)ccc1O[C@@H]1CCN(C(=O)Cc2ccc(OC(F)(F)F)cc2)C[C@H]1F]

Example 154: 5-(1-(4-((2-((2-(2,6-Dioxopiperidin-3-yl)-1,3-dioxoisoindolin-4-yl)amino)ethyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)benzamide. 40% yield. $^1$H NMR (500 MHz, $CD_3OD$) δ 8.85 (s, 1H), 8.63 (dd, J=4.8, 2.5 Hz, 1H), 8.55 (dd, J=4.8, 2.5 Hz, 1H), 7.95 (s, 1H), 7.59-7.50 (m, 1H), 7.41-7.33 (m, 2H), 7.24 (d, J=8.2 Hz, 2H), 7.10 (d, J=8.6 Hz, 1H), 7.02 (d, J=7.1 Hz, 1H), 5.69-5.58 (m, 1H), 5.01 (dd, J=12.4, 5.4 Hz, 1H), 4.23 (t, J=7.1 Hz, 2H), 4.16-3.98 (m, 1H), 3.94-3.85 (m, 3H), 3.83-3.73 (m, 2H), 3.65-3.57 (m, 1H), 3.48-3.43 (m, 4H), 2.81 (ddd, J=18.0, 14.2, 5.4 Hz, 1H), 2.73-2.70 (m, 1H), 2.68-2.61 (m, 1H), 2.29 (t, J=7.0 Hz, 2H), 2.21-2.16 (m, 2H), 2.12-2.04 (m, 1H), 1.93-1.74 (m, 1H). HRMS (ESI-TOF) m/z: $[M+H]^+$ calcd for $C_{42}H_{42}F_4N_9O_9^+$, 892.3036: found 892.3066.

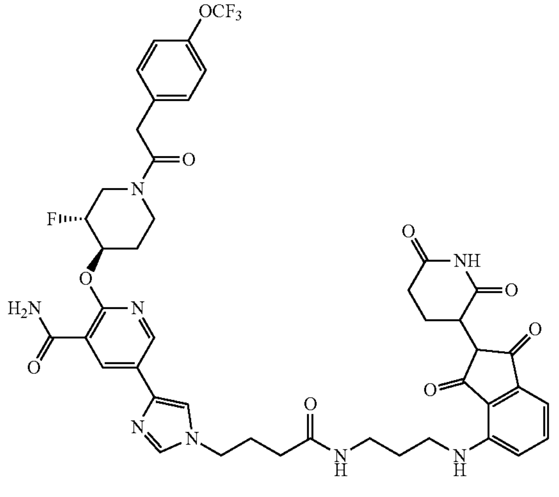 [SMILES: NC(=O)c1cc(-c2cn(CCCC(=O)NCCCNc3cccc4c3C(=O)C(C3CCC(=O)NC3=O)C4=O)cn2)cnc1O[C@@H]1CCN(C(=O)Cc2ccc(OC(F)(F)F)cc2)C[C@H]1F]

Example 155: 5-(1-(4-((3-((2-(2,6-Dioxopiperidin-3-yl)-1,3-dioxoisoindolin-4-yl)amino)propyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy) nicotinamide 33% yield. $^1$H NMR (600 MHz, $CD_3OD$) δ 9.00 (s, 1H), 8.75-8.62 (m, 1H), 8.60-8.52 (m, 1H), 8.04 (s, 1H), 7.53 (t, J=7.8 Hz, 1H), 7.37 (d, J=7.9 Hz, 2H), 7.25 (d, J=8.1 Hz, 2H), 7.07-6.96 (m, 2H), 5.68-5.57 (m, 1H), 5.05 (dd, J=12.7, 5.5 Hz, 1H), 4.30 (t, J=7.1 Hz, 2H), 4.16-3.99 (m, 1H), 3.94-3.84 (m, 3H), 3.82-3.72 (m, 2H), 3.63-3.57 (m, 1H), 3.37-3.34 (m, 2H), 2.85 (ddd, J=18.1, 13.9, 5.3 Hz, 1H), 2.79-2.63 (m, 2H), 2.32 (t, J=7.1 Hz, 2H), 2.22 (q, J=7.2 Hz, 3H), 2.13-2.06 (m, 1H), 1.95-1.85 (m, 1H), 1.82 (t, J=6.5 Hz, 3H). HRMS (ESI-TOF) m/z: $[M+H]^+$ calcd for $C_{43}H_{44}F_4N_9O_9^+$, 906.3193; found 906.3197.

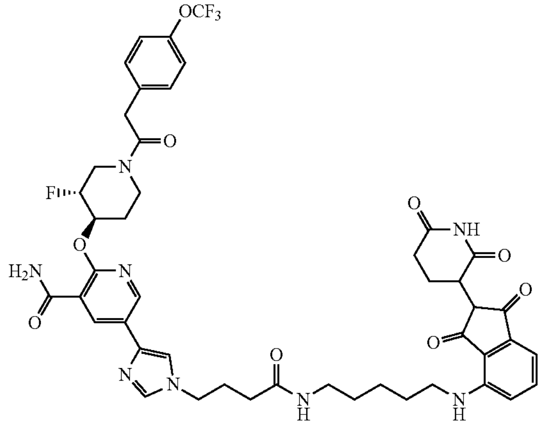 [SMILES: NC(=O)c1cc(-c2cn(CCCC(=O)NCCCCCNc3cccc4c3C(=O)C(C3CCC(=O)NC3=O)C4=O)cn2)cnc1O[C@@H]1CCN(C(=O)Cc2ccc(OC(F)(F)F)cc2)C[C@H]1F]

Example 157: 5-(1-(4-((5-((2-(2,6-Dioxopiperidin-3-yl)-1,3-dioxoisoindolin-4-yl)amino)pentyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy) nicotinamide. 37% yield. $^1$H NMR (600 MHz, $CD_3OD$) δ 9.02 (s, 1H), 8.65 (dd, J=4.4, 2.6 Hz, 1H), 8.57 (dd, J=6.5, 2.6 Hz, 1H), 8.03 (s, 1H), 7.61-7.48 (m, 1H), 7.37 (d, J=8.2 Hz, 2H), 7.24 (d, J=8.1 Hz, 2H), 7.03 (d, J=8.6 Hz, 1H), 7.00 (d, J=7.1 Hz, 1H), 5.69-5.60 (m, 1H), 5.04 (dd, J=12.8, 5.5 Hz, 1H), 4.83-4.76 (m, 1H), 4.28 (t, J=7.1 Hz, 2H), 4.17-3.98 (m, 1H), 3.93-3.84 (m, 3H), 3.83-3.70 (m, 2H), 3.63-3.56 (m, 1H), 3.18 (t, J=6.9 Hz, 2H), 2.93-2.79 (m, 1H), 2.76-2.71 (m, 1H), 2.71-2.64 (m, 1H), 2.29 (t, J=7.0 Hz, 2H), 2.22 (q, J=6.9 Hz, 3H), 2.13-2.04 (m, 1H), 1.92-1.75 (m, 1H), 1.69-1.63 (m, 2H), 1.57-1.51 (m, 2H), 1.47-1.40 (m, 2H). HRMS (ESI-TOF) m/z: $[M+H]^+$ calcd for $C_{45}H_{48}F_4N_9O_9^+$, 934.3506; found 934.3521.

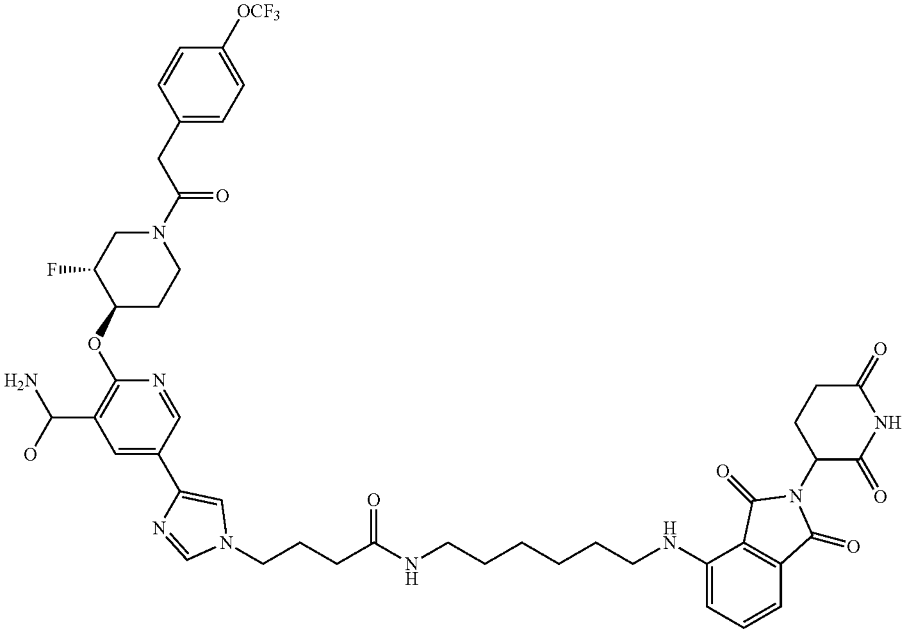 [SMILES: NC(O)c1cc(-c2cn(CCCC(=O)NCCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 158: 5-(1-(4-((6-((2-(2,6-Dioxopiperidin-3-yl)-1,3-dioxoisoindolin-4-yl)amino)hexyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide.

36% yield. $^1$H NMR (600 MHz, $CD_3OD$) δ 8.98 (s, 1H), 8.65 (d, J=3.7 Hz, 1H), 8.58 (d, J=6.3 Hz, 1H), 8.03 (s, 1H), 7.54 (dd, J=8.6, 7.1 Hz, 1H), 7.37 (d, J=8.3 Hz, 2H), 7.24 (d, J=8.2 Hz, 2H), 7.03 (d, J=4.2 Hz, 1H), 7.02 (d, J=2.6 Hz, 1H), 5.69-5.60 (m, 1H), 5.05 (dd, J=12.9, 5.4 Hz, 1H), 4.82-4.78 (m, 1H), 4.30 (t, J=7.0 Hz, 2H), 4.17-3.98 (m, 1H), 3.94-3.84 (m, 3H), 3.83-3.73 (m, 2H), 3.62-3.56 (m, 1H), 3.15 (t, J=7.0 Hz, 2H), 2.93-2.81 (m, 1H), 2.79-2.64 (m, 2H), 2.29 (t, J=7.1 Hz, 2H), 2.25-2.17 (m, 3H), 2.13-2.07 (m, 1H), 1.92-1.76 (m, 1H), 1.65 (t, J=7.5 Hz, 2H), 1.50 (t, J=7.3 Hz, 2H), 1.46-1.40 (m, 2H), 1.39-1.35 (m, 2H). HRMS (ESI-TOF) m/z: $[M+H]^+$ calcd for $C_{46}H_{50}F_4N_9O_9{}^+$, 948.3662; found 948.3695.

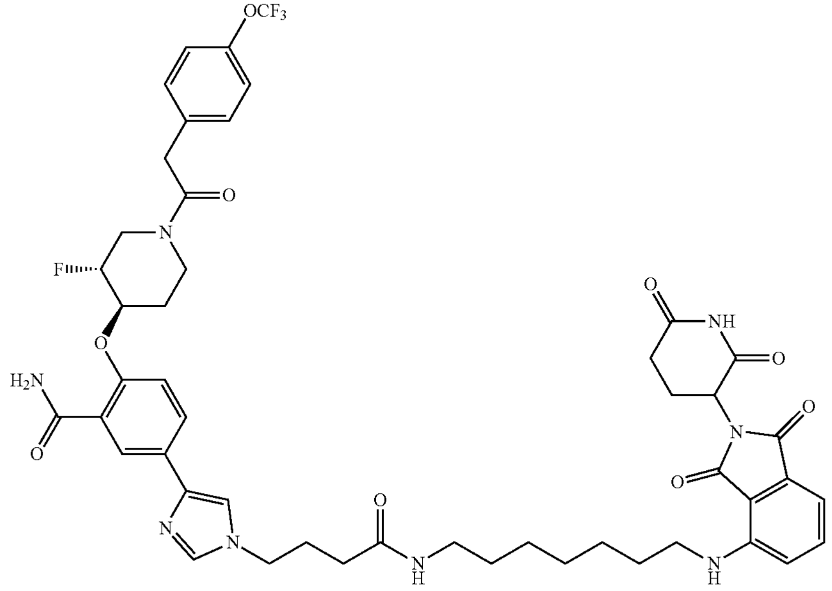 [SMILES: NC(=O)c1cc(-c2cn(CCCC(=O)NCCCCCCCNc3cccc4c3C(=O)N(C3CCC(=O)NC3=O)C4=O)cn2)ccc1O[C@@H]1CCN(C(=O)Cc2ccc(OC(F)(F)F)cc2)C[C@H]1F]

Example 159: 5-(1-(4-((7-((2-(2,6-Dioxopiperidin-3-yl)-1,3-dioxoisoindolin-4-yl)amino)heptyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy) nicotinamide. 34% yield. $^1$H NMR (600 MHz, $CD_3OD$) δ 9.00 (s, 1H), 8.65 (d, J=3.7 Hz, 1H), 8.60-8.53 (m, 1H), 8.04 (s, 1H), 7.54 (dd, J=8.6, 7.1 Hz, 1H), 7.37 (d, J=8.2 Hz, 2H), 7.24 (d, J=8.2 Hz, 2H), 7.03 (d, J=5.1 Hz, 1H), 7.01 (d, J=3.5 Hz, 1H), 5.69-5.60 (m, 1H), 5.05 (dd, J=12.8, 5.5 Hz, 1H), 4.30 (t, J=7.0 Hz, 2H), 4.18-3.95 (m, 1H), 3.95-3.84 (m, 3H), 3.83-3.73 (m, 2H), 3.62-3.55 (m, 1H), 3.13 (t, J=7.0 Hz, 2H), 2.91-2.80 (m, 1H), 2.77-2.64 (m, 2H), 2.29 (t, J=6.9 Hz, 2H), 2.23 (q, J=7.1 Hz, 3H), 2.13-2.06 (m, 1H), 1.95-1.75 (m, 1H), 1.69-1.58 (m, 2H), 1.50-1.45 (m, 2H), 1.44-1.39 (m, 2H), 1.38-1.28 (s, 5H). HRMS (ESI-TOF) m/z: $[M+H]^+$ calcd for $C_{47}H_{52}F_4N_9O_9^+$, 962.3819; found 962.3863.

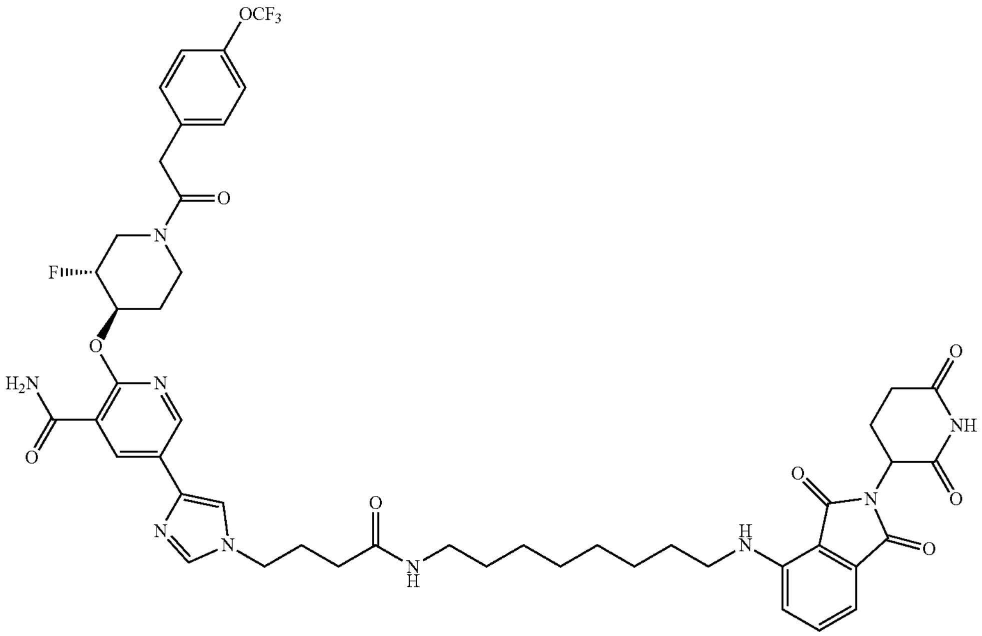 [SMILES: NC(=O)c1cc(-c2cn(CCCC(=O)NCCCCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 160: 5-(1-(4-((8-((2-(2,6-Dioxopiperidin-3-yl)-1,3-dioxoisoindolin-4-yl)amino)octyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide. 38% yield. $^1H$ NMR (600 MHz, $CD_3OD$) δ 9.05 (s, 1H), 8.65 (dd, J=4.6, 2.6 Hz, 1H), 8.57 (dd, J=6.2, 2.5 Hz, 1H), 8.06 (s, 1H), 7.53 (dd, J=9.1, 6.8 Hz, 1H), 7.37 (d, J=8.1 Hz, 2H), 7.24 (d, J=8.0 Hz, 2H), 7.02 (d, J=7.7 Hz, 2H), 5.71-5.60 (m, 1H), 5.08-4.97 (m, 2H), 4.31 (t, J=7.0 Hz, 2H), 4.17-3.99 (m, 1H), 3.92-3.84 (m, 3H), 3.83-3.74 (m, 2H), 3.62-3.49 (m, 1H), 3.13 (t, J=7.1 Hz, 2H), 2.90-2.80 (m, 1H), 2.77-2.64 (m, 2H), 2.35-2.27 (m, 2H), 2.26-2.18 (m, 3H), 2.13-2.08 (m, 1H), 1.98-1.84 (m, 1H), 1.68-1.61 (m, 3H), 1.52-1.38 (m, 4H), 1.37-1.31 (m, 5H). HRMS (ESI-TOF) m/z: $[M+H]^+$ calcd for $C_{48}H_{54}F_4N_9O_9^+$, 976.3975; found 976.4135.

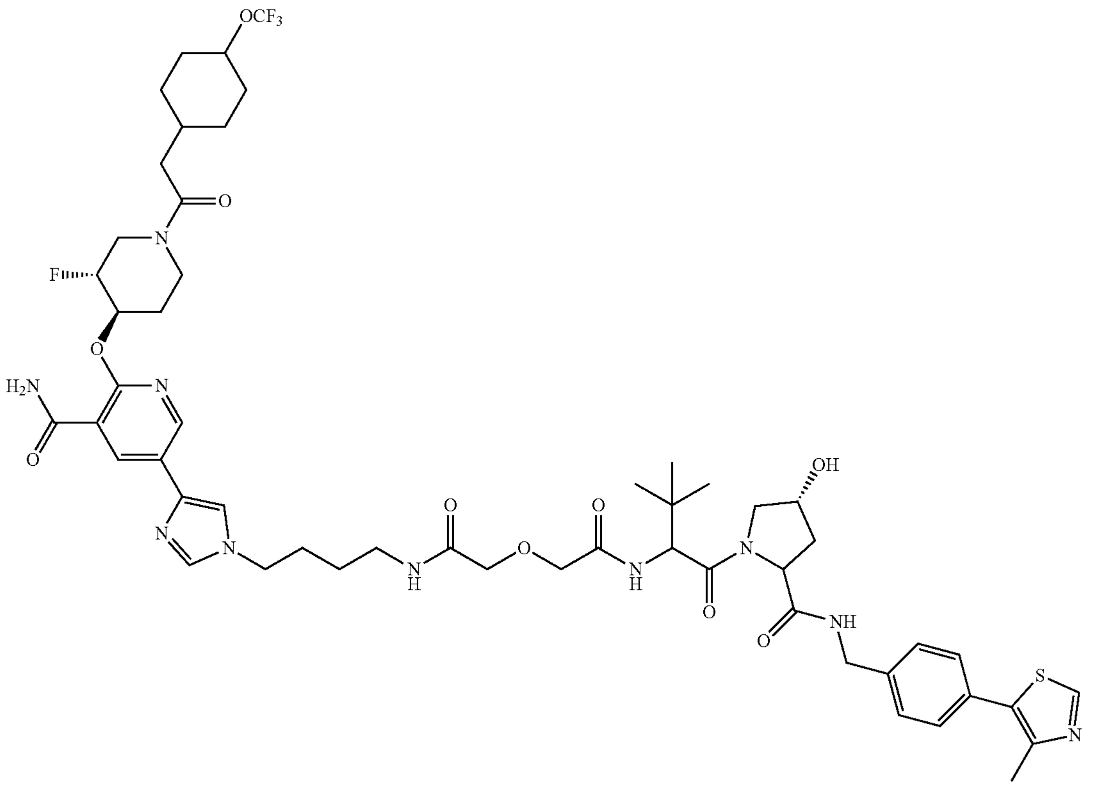 [SMILES: Cc1ncsc1-c1ccc(CNC(=O)C2C[C@@H](O)CN2C(=O)C(NC(=O)COCC(=O)NCCCCn2cnc(-c3cnc(O[C@@H]4CCN(C(=O)CC5CCC(OC(F)(F)F)CC5)C[C@H]4F)c(C(N)=O)c3)c2)C(C)(C)C)cc1]

Example 161: 2-(((3R,4R)-3-Fluoro-1-(2-(4-(trifluoromethoxy)phenyl)acetyl)piperidin-4-yl)oxy)-5-(I-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetamido)butyl)-1H-imidazol-4-yl)nicotinamide. 35% yield. $^1$H NMR (600 MHz, $CD_3OD$) δ 9.09 (s, 1H), 9.01 (s, 1H), 8.66 (dd, J=4.8, 2.5 Hz, 1H), 8.57 (dd, J=6.1, 2.6 Hz, 1H), 8.09 (d, J=2.0 Hz, 1H), 7.46 (d, J=8.3 Hz, 2H), 7.41 (d, J=8.2 Hz, 2H), 7.39-7.34 (m, 2H), 7.24 (d, J=8.0 Hz, 2H), 5.64 (brs, 1H), 4.83-4.76 (m, 1H), 4.71 (d, J=6.9 Hz, 1H), 4.61-4.55 (m, 1H), 4.54-4.47 (m, 2H), 4.38-4.34 (m, 1H), 4.35-4.27 (m, 2H), 4.16-4.11 (m, 3H), 4.10-4.05 (m, 2H), 3.93-3.85 (m, 3H), 3.84-3.75 (m, 3H), 3.66-3.55 (m, 1H), 3.36-3.31 (m, 2H), 2.48 (s, 3H), 2.31-2.16 (m, 2H), 2.12-2.05 (m, 1H), 2.02-1.93 (m, 2H), 1.91-1.76 (m, 1H), 1.62 (p, J=7.0 Hz, 2H), 1.04 (s, 9H). HRMS (ESI-TOF) m/z: $[M+H]^+$ calcd for $C_3H_{63}F_4N_{10}O_{10}S^+$, 1107.4380; found 1107.4389.

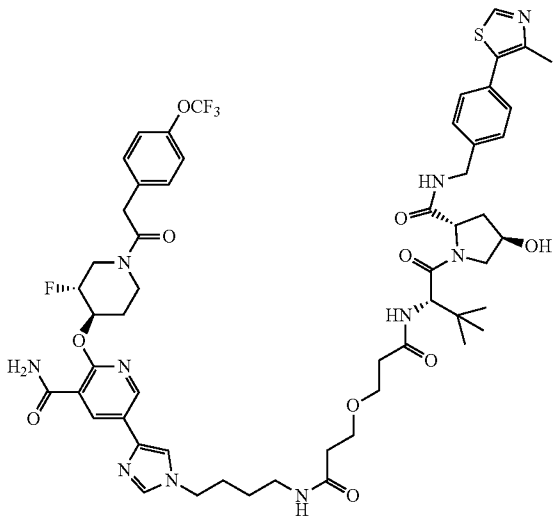 [SMILES: Cc1ncsc1-c1ccc(CNC(=O)[C@@H]2C[C@@H](O)CN2C(=O)[C@@H](NC(=O)CCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 162: 2-(((3R,4R)-3-Fluoro-1-(2-(4-(trifluoromethoxy)phenyl)acetyl)piperidin-4-yl)oxy)-5-(1-(4-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanamido)butyl)-1H-imidazol-4-yl)nicotinamide. 31% yield. $^1$H NMR (600 MHz, $CD_3OD$) δ 9.07 (s, 1H), 8.94 (s, 1H), 8.66 (dd, J=4.7, 2.6 Hz, 1H), 8.58 (dd, J=6.0, 2.6 Hz, 1H), 8.09 (s, 1H), 7.46 (d, J=8.1 Hz, 2H), 7.41 (d, J=8.2 Hz, 2H), 7.37 (d, J=7.8 Hz, 2H), 7.24 (d, J=8.0 Hz, 2H), 5.69-5.61 (m, 1H), 4.84-4.75 (m, 1H), 4.64 (s, 1H), 4.60-4.54 (m, 1H), 4.54-4.48 (m, 2H), 4.36 (d, J=15.5 Hz, 1H), 4.31 (t, J=7.3 Hz, 2H), 4.22-3.94 (m, 1H), 3.93-3.84 (m, 3H), 3.83-3.75 (m, 3H), 3.74-3.64 (ddq, J=18.5, 10.1, 4.9, 4.4 Hz, 5H), 3.62-3.56 (m, 1H), 3.28-3.20 (h, J=6.7 Hz, 2H), 2.57-2.49 (m, 1H), 2.47 (s, 3H), 2.45-2.41 (m, 2H), 2.29-2.17 (m, 2H), 2.11-2.05 (m, 1H), 1.94 (q, J=7.5 Hz, 2H), 1.91-1.76 (m, 1H), 1.57 (p, J=7.1 Hz, 2H), 1.03 (s, 9H). HRMS (ESI-TOF) m/z: $[M+H]^+$ calcd for $C_{55}H_{67}F_4N_{10}O_{10}S^+$, 1135.4693; found 1135.4730.

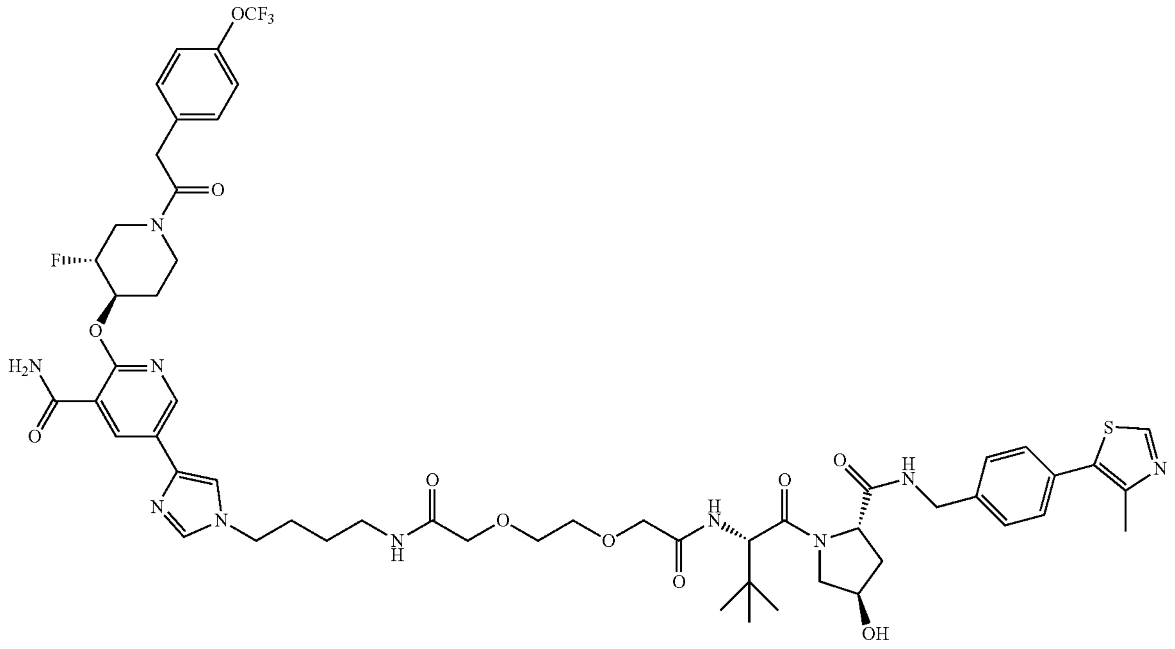 [SMILES: Cc1ncsc1-c1ccc(CNC(=O)[C@@H]2C[C@@H](O)CN2C(=O)[C@@H](NC(=O)COCCOCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 163: 2-(((3R,4R)-3-Fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,12-dioxo-7,10-dioxa-4,13-diazaheptadecan-17-yl)-1H-imidazol-4-yl)nicotinamide. 39% yield. $^1$H NMR (600 MHz, $CD_3OD$) δ 9.06 (s, 1H), 8.92 (s, 1H), 8.65 (dd, J=4.8, 2.7 Hz, 1H), 8.57 (dd, J=5.9, 2.6 Hz, 1H), 8.08 (s, 1H), 7.45-7.39 (m, 4H), 7.38-7.36 (m, 2H), 7.25 (d, J=8.1 Hz, 2H), 5.68-5.59 (m, 1H), 4.83-4.76 (m, 1H), 4.73-4.66 (m, 1H), 4.57 (t, J=8.5 Hz, 1H), 4.52-4.46 (m, 1H), 4.45-4.38 (m, 2H), 4.34-4.27 (m, 2H), 4.15-4.07 (m, 2H), 4.07-3.97 (m, 4H), 3.93-3.83 (m, 3H), 3.82-3.77 (m, 3H), 3.76-3.69 (m, 5H), 3.64-3.54 (m, 1H), 2.47 (s, 3H), 2.26 (dd, J=13.2, 7.6 Hz, 1H), 2.22-2.12 (m, 1H), 2.08 (ddd, J=13.4, 9.4, 4.3 Hz, 1H), 2.00-1.91 (m, 2H), 1.90-1.75 (m, 1H), 1.66-1.53 (m, 2H), 1.02 (s, 9H). HRMS (ESI-TOF) m/z: $[M+H]^+$ calcd for $C_{55}H_{67}F_4N_{10}O_{11}S^+$, 1151.4642, found 1151.4645.

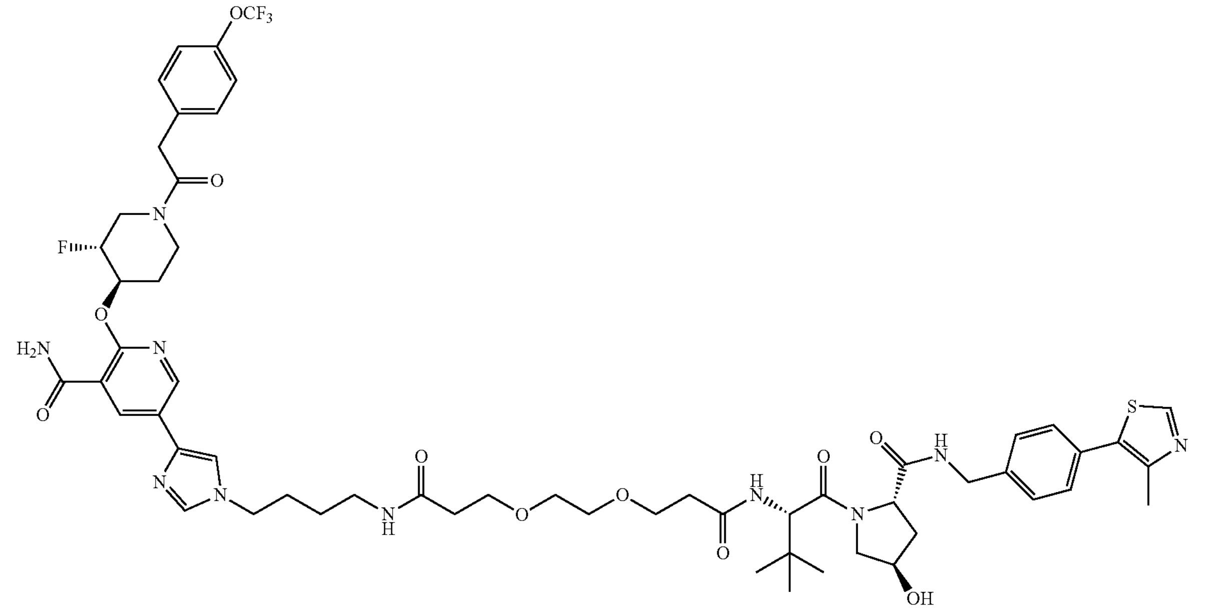 [SMILES: Cc1ncsc1-c1ccc(CNC(=O)[C@@H]2C[C@@H](O)CN2C(=O)[C@@H](NC(=O)CCOCCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 164: 2-(((3R,4R)-3-Fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,14-dioxo-8,11-dioxa-4,15-diazanonadecan-19-yl)-1H-imidazol-4-yl)nicotinamide. 38% yield. $^1$H NMR (600 MHz, $CD_3OD$) δ 9.07 (s, 1H), 8.96 (s, 1H), 8.67 (dd, J=4.7, 2.6 Hz, 1H), 8.59 (dd, J=6.1, 2.6 Hz, 1H), 8.09 (d, J=2.0 Hz, 1H), 7.46 (d, J=8.0 Hz, 2H), 7.41 (d, J=8.2 Hz, 2H), 7.38-7.35 (m, 2H), 7.24 (d, J=8.0 Hz, 2H), 5.69-5.60 (m, 1H), 4.83-4.77 (m, 1H), 4.64 (s, 1H), 4.60-4.52 (m, 1H), 4.52-4.47 (m, 2H), 4.36 (d, J=15.5 Hz, 1H), 4.31 (t, J=7.3 Hz, 2H), 4.15-3.99 (m, 1H), 3.93-3.84 (m, 3H), 3.80 (dd, J=11.0, 4.0 Hz, 3H), 3.75-3.64 (m, 5H), 3.61-3.51 (m, 5H), 3.26 (t, J=6.8 Hz, 2H), 2.57-2.51 (m, 1H), 2.47 (s, 4H), 2.44-2.39 (m, 2H), 2.28-2.17 (m, 11H), 2.08 (ddd, J=13.4, 9.3, 4.4 Hz, 1H), 1.97 (p, J=7.5 Hz, 2H), 1.84 (d, J=49.2 Hz, 1H), 1.57 (p, J=7.0 Hz, 2H), 1.03 (s, 9H). HRMS (ESI-TOF) m/z: $[M+H]^+$ calcd for $C_{57}H_{71}F_4N_{10}O_{11}S^+$, 1179.4955; found 1179.5066.

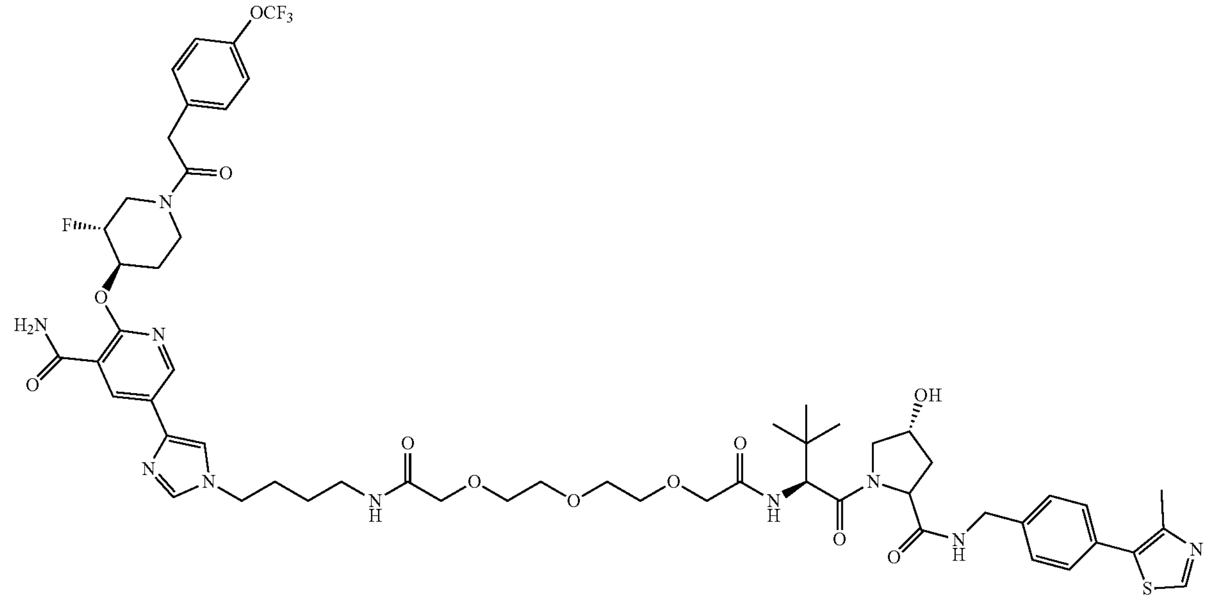 [SMILES: Cc1ncsc1-c1ccc(CNC(=O)C2C[C@@H](O)CN2C(=O)[C@@H](NC(=O)COCCOCCOCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 165: 2-(((3R,4R)-3-Fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,15-dioxo-7,10,13-trioxa-4,16-diazaicosan-20-yl)-1H-imidazol-4-yl)nicotinamide. 30% yield. $^1H$ NMR (600 MHz, $CD_3OD$) S 9.07 (s, 1H), 8.95 (s, 1H), 8.66 (dd, J=4.7, 2.6 Hz, 1H), 8.58 (dd, J=6.1, 2.6 Hz, 1H), 8.09 (d, J=2.1 Hz, 1H), 7.46 (d, J=8.1 Hz, 2H), 7.42 (t, J=7.6 Hz, 2H), 7.39-7.35 (m, 2H), 7.24 (d, J=8.0 Hz, 2H), 5.64 (brs, 1H), 4.82-4.73 (m, 1H), 4.70 (s, 1H), 4.60-4.54 (m, 2H), 4.53-4.47 (m, 2H), 4.36 (d, J=15.5 Hz, 1H), 4.33-4.27 (m, 2H), 4.11-3.98 (m, 3H), 3.98-3.91 (m, 2H), 3.91-3.84 (m, 3H), 3.83-3.76 (m, 3H), 3.75-3.65 (m, 9H), 3.30-3.28 (m, 1H), 2.47 (s, 3H), 2.29-2.17 (m, 2H), 2.09 (ddd, J=13.4, 9.4, 4.4 Hz, 1H), 1.95 (p, J=7.4 Hz, 2H), 1.90-1.76 (m, 1H), 1.58 (p, J=7.2 Hz, 2H), 1.03 (s, 9H). HRMS (ESI-TOF) m/z: $[M+H]^+$ calcd for $C_{57}H_{71}F_4N_{10}O_{12}S^+$, 1195.4904; found 1195.5010.

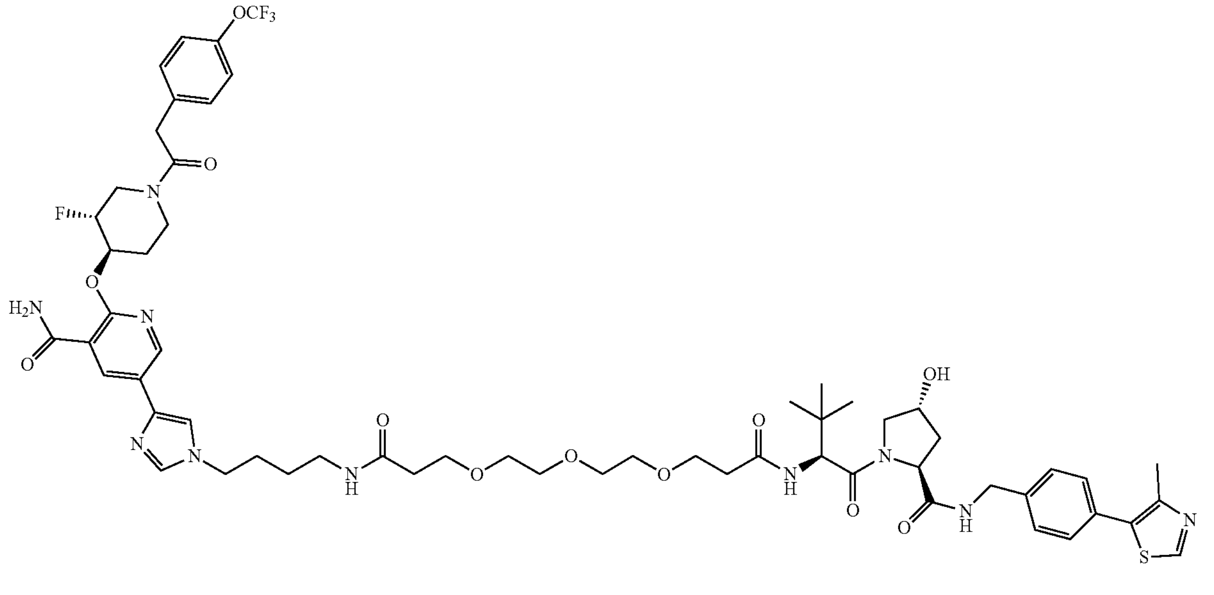 [SMILES: Cc1ncsc1-c1ccc(CNC(=O)[C@@H]2C[C@@H](O)CN2C(=O)[C@@H](NC(=O)CCOCCOCCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 166: 2-(((3R,4R)-3-Fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,17-dioxo-8,11,14-trioxa-4,18-diazadocosan-22-yl)-1H-imidazol-4-yl)nicotinamide. 30% yield. $^1H$ NMR (600 MHz, $CD_3OD$) δ 9.05 (s, 1H), 8.91 (s, 1H), 8.67 (dd, J=4.7, 2.5 Hz, 1H), 8.59 (dd, J=6.0, 2.6 Hz, 1H), 8.09 (t, J=1.9 Hz, 1H), 7.46 (d, J=8.0 Hz, 2H), 7.40 (d, J=8.1 Hz, 2H), 7.39-7.34 (m, 2H), 7.24 (d, J=8.5 Hz, 2H), 5.65 (brs, 1H), 4.85-4.76 (m, 1H), 4.64 (s, 1H), 4.60-4.54 (m, 1H), 4.52-4.47 (m, 1H), 4.36 (d, J=15.5 Hz, 1H), 4.31 (t, J=7.3 Hz, 2H), 4.15-3.99 (m, 1H), 3.93-3.83 (m, 3H), 3.80 (dd, J=11.0, 4.0 Hz, 2H), 3.70 (dt, J=13.7, 6.0 Hz, 4H), 3.63-3.51 (m, 8H), 3.35 (s, 4H), 3.27 (t, J=6.7 Hz, 2H), 2.56 (ddd, J=15.0, 7.3, 5.3 Hz, 1H), 2.47 (s, 3H), 2.42 (t, J=6.0 Hz, 2H), 2.29-2.18 (m, 2H), 2.08 (ddd, J=13.3, 9.3, 4.5 Hz, 1H), 1.97 (p, J=7.4 Hz, 2H), 1.91-1.76 (m, 1H), 1.57 (p, J=7.0 Hz, 2H), 1.03 (s, 9H). HRMS (ESI-TOF) m/z: $[M+H]^+$ calcd for $C_{59}H_{75}F_4N_{10}O_{12}S^+$, 1223.5217; found 1223.5263.

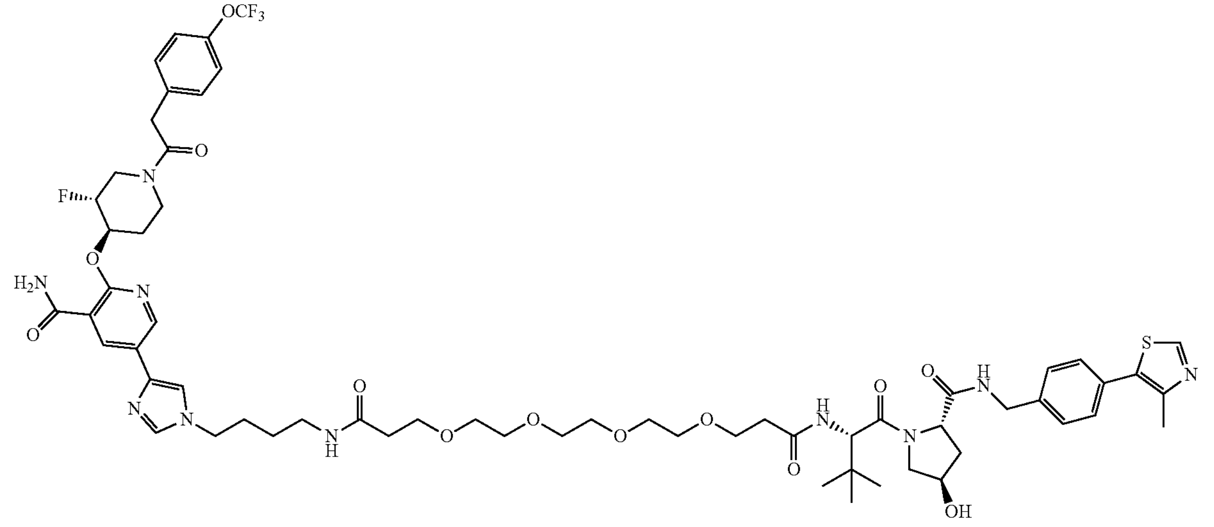 [SMILES: Cc1ncsc1-c1ccc(CNC(=O)[C@@H]2C[C@@H](O)CN2C(=O)[C@@H](NC(=O)CCOCCOCCOCCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 167: M-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{16}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide. 31% yield. $^{1}H$ NMR (600 MHz, $CD_3OD$) δ 9.06 (s, 1H), 8.91 (s, 1H), 8.67 (dd, J=4.6, 2.5 Hz, 1H), 8.59 (dd, J=6.2, 2.6 Hz, 1H), 8.10 (d, J=2.1 Hz, 1H), 7.46 (d, J=8.1 Hz, 2H), 7.41 (d, J=8.2 Hz, 2H), 7.38-7.34 (m, 2H), 7.27-7.20 (m, 2H), 5.75-5.58 (m, 1H), 4.84-4.75 (m, 1H), 4.64 (s, 1H), 4.60-4.54 (m, 1H), 4.53-4.47 (m, 1H), 4.36 (d, J=15.5 Hz, 1H), 4.32 (t, J=7.3 Hz, 2H), 4.17-3.97 (m, 1H), 3.94-3.84 (m, 3H), 3.80 (dd, J=11.0, 3.9 Hz, 2H), 3.75-3.66 (m, 5H), 3.65-3.52 (m, 13H), 3.35 (s, 2H), 3.27 (t, J=6.7 Hz, 2H), 2.59-2.52 (m, 1H), 2.47 (s, 3H), 2.42 (t, J=6.0 Hz, 2H), 2.32-2.18 (m, 2H), 2.08 (ddd, J=13.3, 9.2, 4.4 Hz, 1H), 1.97 (p, J=7.4 Hz, 2H), 1.91-1.76 (m, 1H), 1.58 (p, J=6.9 Hz, 2H), 1.03 (s, 9H). HRMS (ESI-TOF) m/z: $[M+H]^+$ calcd for $C_{61}H_{79}F_4N_{10}O_{13}S^+$, 1267.5479; found 1267.5484.

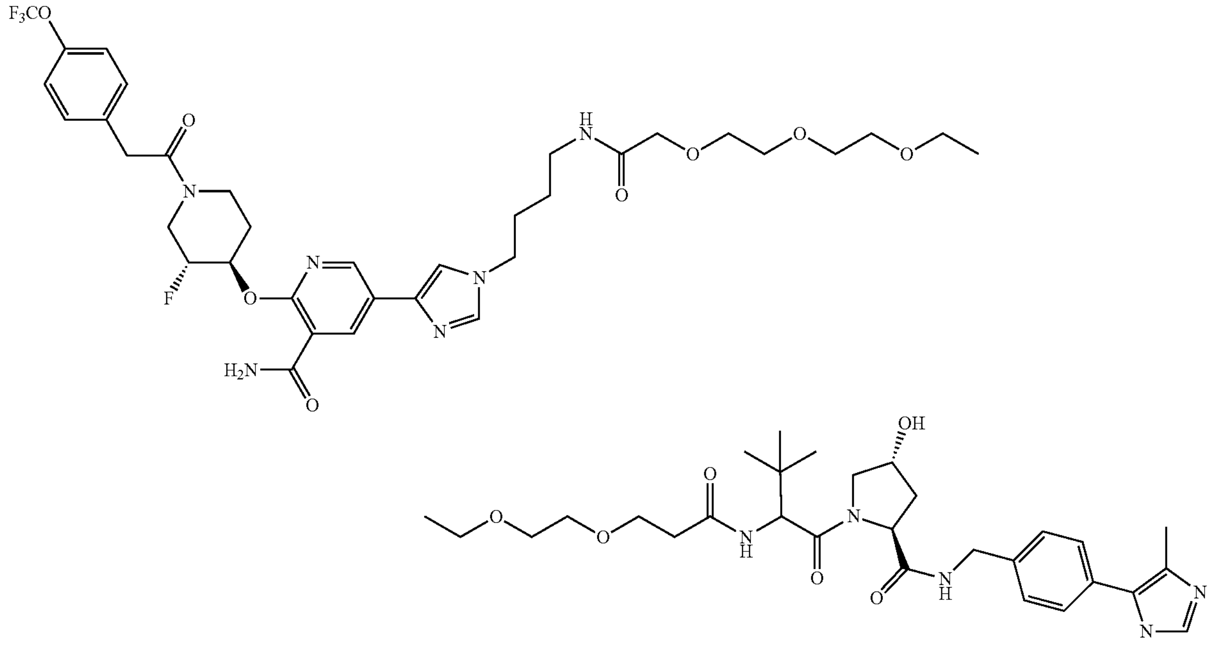

Example 168: $N^1$-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{18}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaoctadecanediamide. 31% yield. $^{1}H$ NMR (600 MHz, $CD_3OD$) δ 9.09 (s, 1H), 8.95 (s, 1H), 8.67 (dd, J=4.7, 2.6 Hz, 1H), 8.59 (dd, J=5.8, 2.6 Hz, 2H), 8.10 (s, 1H), 7.46 (d, J=8.1 Hz, 3H), 7.44-7.40 (m, 4H), 7.37 (d, J=8.0 Hz, 4H), 7.24 (d, =8.1 Hz, 4H), 5.69-5.61 (m, 1H), 4.84-4.76 (m, 1H), 4.69 (s, 1H), 4.59-4.56 (m, 1H), 4.55 (d, J=5.4 Hz, 1H), 4.53-4.48 (m, 2H), 4.36 (d, J=15.6 Hz, 1H), 4.32 (t, J=7.3 Hz, 2H), 4.09-4.00 (m, 3H), 3.97 (s, 2H), 3.91-3.84 (m, 3H), 3.83-3.76 (m, 3H), 3.71-3.67 (m, 5H), 3.66-3.62 (m, 10H), 3.61-3.57 (m, 5H), 2.48 (s, 3H), 2.36-2.16 (m, 2H), 2.08 (ddd, J=13.2, 9.3, 4.3 Hz, 1H), 1.97 (p, J=7.4 Hz, 2H), 1.91-1.76 (m, 1H), 1.61 (q, J=7.5 Hz, 2H), 1.04 (s, 9H). HRMS (ESI-TOF) m/z: $[M+H]^+$ calcd for $C_{62}H_{81}F_4N_{10}O_{14}S^+$, 1297.5585; found 1297.5586.

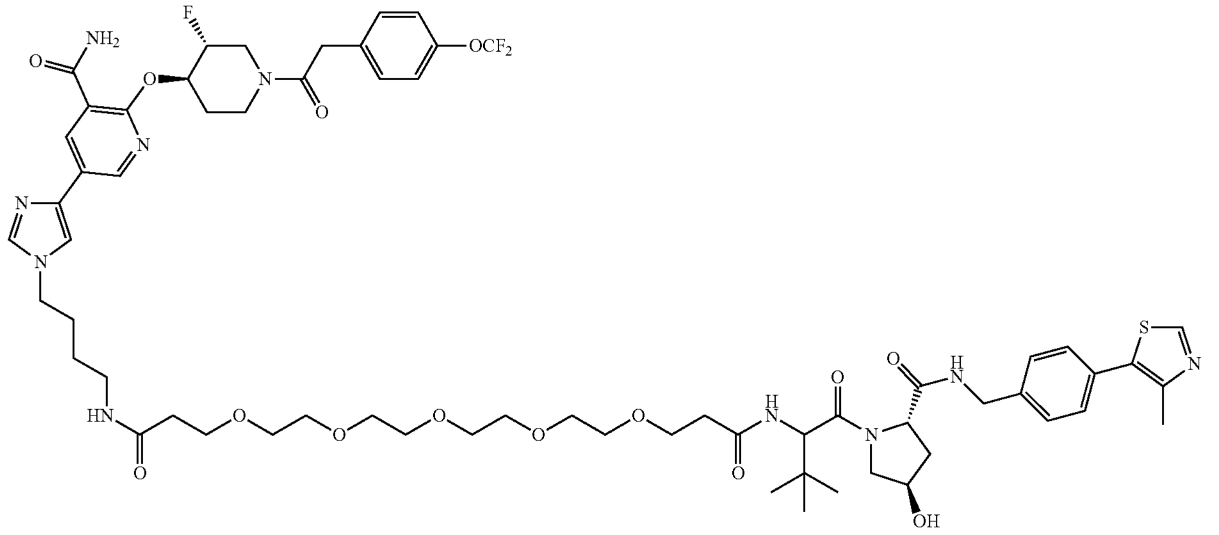

Example 169: $N^1$-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{19}$—((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)-4,7,10,13,16-pentaoxanonadecanediamide. 33% yield. $^1H$ NMR (600 MHz, $CD_3OD$) δ 9.08 (s, 1H), 8.94 (s, 1H), 8.68 (dd, J=4.5, 2.5 Hz, 1H), 8.60 (dd, J=6.3, 2.6 Hz, 1H), 8.11 (t, J=1.8 Hz, 1H), 7.47 (d, J=8.1 Hz, 2H), 7.41 (d, J=8.2 Hz, 2H), 7.37 (dd, J=8.6, 1.9 Hz, 2H), 7.28-7.15 (m, 2H), 5.70-5.61 (m, J H), 4.83-4.75 (m, 1H), 4.65 (s, 1H), 4.60-4.54 (m, 1H), 4.53-4.48 (m, 1H), 4.36 (d, J=15.5 Hz, 1H), 4.32 (t, J=7.3 Hz, 2H), 4.18-3.97 (m, 1H), 3.94-3.83 (m, 3H), 3.80 (dd, J=11.0, 3.8 Hz, 3H), 3.74-3.66 (m, 5H), 3.61-3.58 (m, 8H), 3.57-3.54 (m, 9H), 3.28 (t, J=6.7 Hz, 2H), 2.56 (ddd, J=14.9, 7.4, 5.1 Hz, 1H), 2.47 (s, 4H), 2.42 (t, J=5.9 Hz, 2H), 2.29-2.18 (m, 2H), 2.08 (ddd, J=13.3, 9.2, 4.5 Hz, 1H), 1.98 (p, J=7.4 Hz, 2H), 1.91-1.76 (m, 1H), 1.58 (p, J=6.9 Hz, 2H), 1.03 (s, 9H). HRMS (ESI-TOF) m/z: $[M+H]^+$ calcd for $C_{63}H_{83}F_4N_{10}O_{14}S^+$, 1311.5742; found 1311.5700.

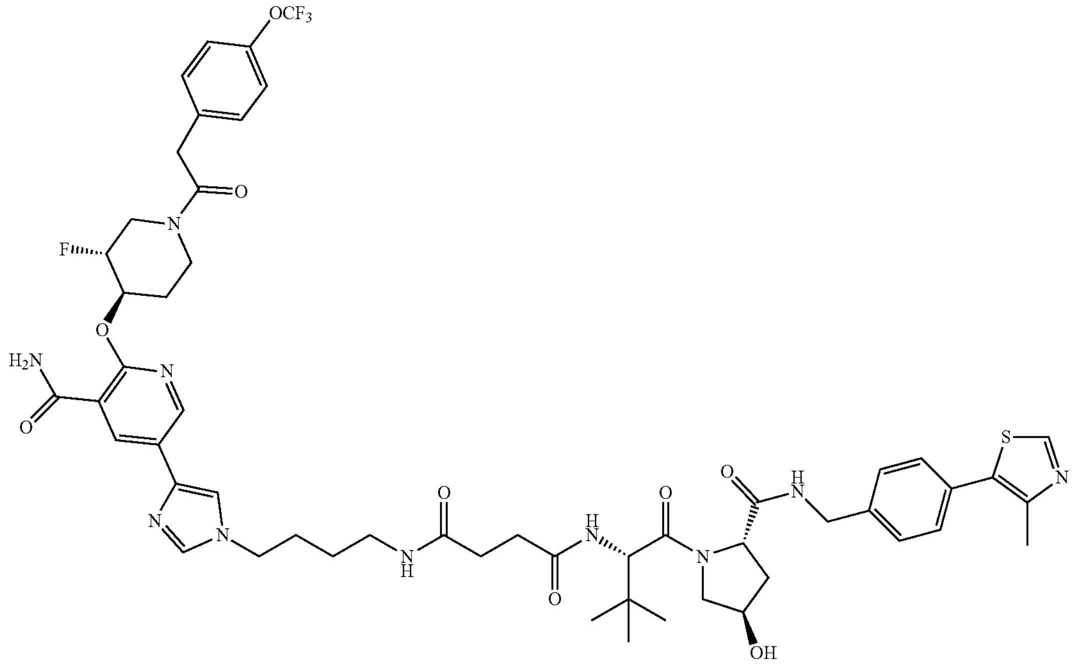 [SMILES: Cc1ncsc1-c1ccc(CNC(=O)[C@@H]2C[C@@H](O)CN2C(=O)[C@@H](NC(=O)CCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 170: N[1]-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-N[4]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide. 37% yield. $^1$H NMR (600 MHz, $CD_3OD$) δ 9.07 (s, 1H), 8.91 (s, 1H), 8.67 (dd, J=4.7, 2.6 Hz, 1H), 8.59 (dd, J=6.3, 2.5 Hz, 1H), 8.12 (d, J=2.9 Hz, 1H), 7.46 (d, J=8.0 Hz, 2H), 7.40 (d, J=8.1 Hz, 2H), 7.38-7.35 (m, 2H), 7.24 (d, J=8.1 Hz, 2H), 5.69-5.60 (m, 1H), 4.82-4.72 (m, 1H), 4.59 (s, 1H), 4.57-4.53 (m, 1H), 4.52-4.46 (m, 1H), 4.36 (d, J=15.5 Hz, 1H), 4.31 (t, J=7.3 Hz, 2H), 4.21-3.96 (m, 1H), 3.94-3.83 (m, 4H), 3.82-3.74 (m, 3H), 3.66-3.55 (m, 1H), 3.24 (t, J=6.8 Hz, 2H), 2.66-2.59 (m, 1H), 2.56-2.50 (m, 1H), 2.49-2.45 (m, 5H), 2.31-2.17 (m, 2H), 2.07 (ddd, J=13.3, 9.2, 4.4 Hz, 1H), 1.96 (p, J=7.5 Hz, 2H), 1.90-1.74 (m, 1H), 1.56 (p, J=7.1 Hz, 2H), 1.01 (s, 9H). HRMS (ESI-TOF) m/z: $[M+H]^+$ calcd for $C_{53}H_{63}F_4N_{10}O_9S^+$, 1091.4431; found 1091.4437.

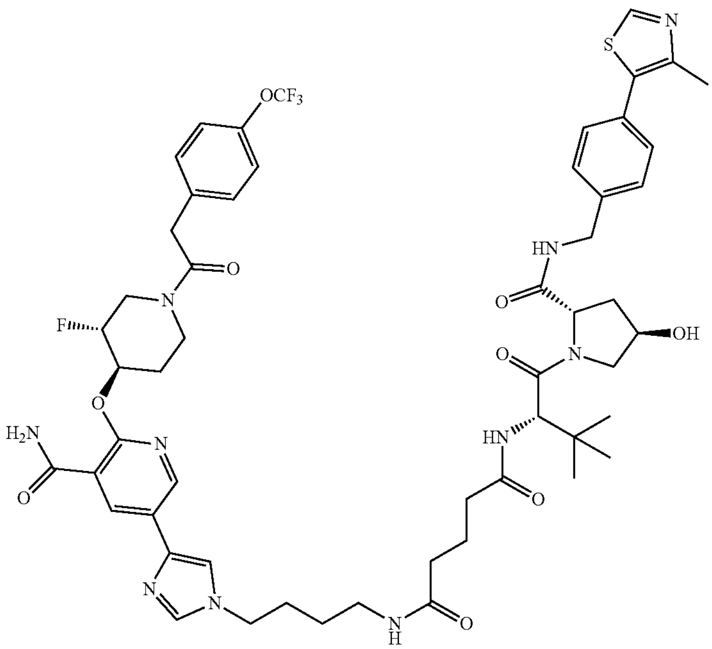 [SMILES: Cc1ncsc1-c1ccc(CNC(=O)[C@@H]2C[C@@H](O)CN2C(=O)[C@@H](NC(=O)CCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 171: $N^1$-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^5$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide. 35% yield. $^1$H NMR (600 MHz, $CD_3OD$) δ 9.09 (s, 1H), 8.96 (s, 1H), 8.67 (dd, J=4.7, 2.6 Hz, 1H), 8.58 (dd, J=6.2, 2.6 Hz, 1H), 8.09 (d, J=2.3 Hz, 1H), 7.46 (d, J=8.1 Hz, 2H), 7.41 (d, J=8.1 Hz, 2H), 7.38-7.33 (m, 2H), 7.24 (d, J=8.1 Hz, 2H), 5.69-5.60 (m, 1H), 4.83-4.76 (m, 1H), 4.61 (s, 1H), 4.59-4.55 (m, 1H), 4.55-4.52 (m, 1H), 4.51-4.48 (m, 1H), 4.36 (d, J=15.5 Hz, 1H), 4.31 (t, J=7.3 Hz, 2H), 4.16-3.97 (m, 1H), 3.92 (d, J=10.8 Hz, 1H), 3.90-3.87 (d, J=9.3 Hz, 2H), 3.84-3.76 (m, 2H), 3.65-3.55 (m, 1H), 3.24 (t, J=6.9 Hz, 2H), 2.47 (s, 3H), 2.38-2.25 (m, 3H), 2.25-2.18 (m, 3H), 2.16 (s, 2H), 2.08 (ddd, J=13.3, 9.2, 4.4 Hz, 1H), 1.99-1.92 (m, 2H), 1.91-1.85 (m, 2H), 1.57 (p, J=7.1 Hz, 2H), 1.03 (s, 9H). HRMS (ESI-TOF) m/z: $[M+H]^+$ calcd for $C_{54}H_{65}F_4N_{10}O_9S^+$, 1105.4587; found 1105.4619.

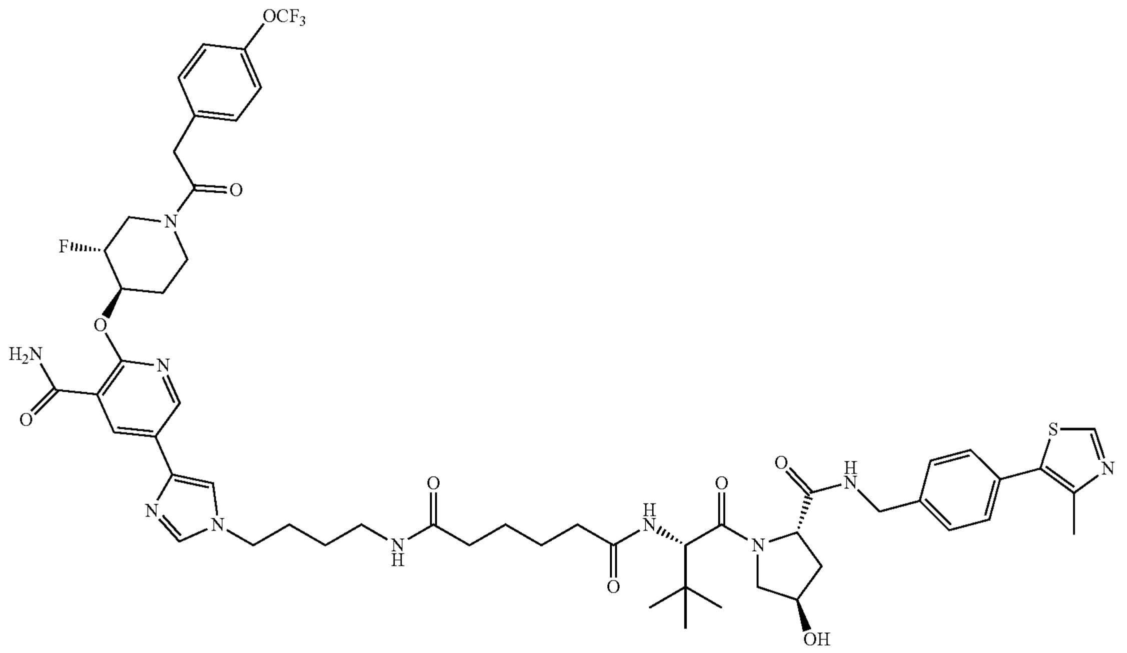 [SMILES: Cc1ncsc1-c1ccc(CNC(=O)[C@@H]2C[C@@H](O)CN2C(=O)[C@@H](NC(=O)CCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 172: $N^1$-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^6$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide. 39% yield. $^1$H NMR (600 MHz, $CD_3OD$) δ 9.10 (s, 1H), 8.97 (s, 1H), 8.67 (dd, J=4.6, 2.5 Hz, 1H), 8.58 (dd, J=6.2, 2.6 Hz, 1H), 8.10 (t, J=1.9 Hz, 1H), 7.47 (d, J=8.0 Hz, 2H), 7.41 (d, J=8.1 Hz, 2H), 7.38-7.35 (m, 2H), 7.24 (d, J=8.1 Hz, 2H), 5.69-5.60 (m, 1H), 4.83-4.76 (m, 1H), 4.62 (s, 1H), 4.60-4.54 (m, 1H), 4.53 (d, J=15.8 Hz, 1H), 4.51-4.48 (m, 1H), 4.36 (d, J=15.5 Hz, 1H), 4.32 (t, J=7.2 Hz, 2H), 4.19-3.96 (m, 1H), 3.93-3.83 (m, 3H), 3.80 (dd, J=11.1, 4.1 Hz, 3H), 3.64-3.54 (m, 1H), 3.24 (t, J=6.8 Hz, 2H), 2.47 (s, 3H), 2.37-2.24 (m, 3H), 2.23-2.18 (m, 3H), 2.08 (ddd, J=13.3, 9.1, 4.4 Hz, 1H), 1.96 (p, J=7.3 Hz, 2H), 1.91-1.76 (m, 1H), 1.67-1.59 (m, 4H), 1.56 (q, J=7.5 Hz, 2H), 1.03 (s, 9H). HRMS (ESI-TOF) m/z: $[M+H]^+$ calcd for $C_{55}H_{67}F_4N_{10}O_9S^+$, 1119.4744; found 1119.4723.

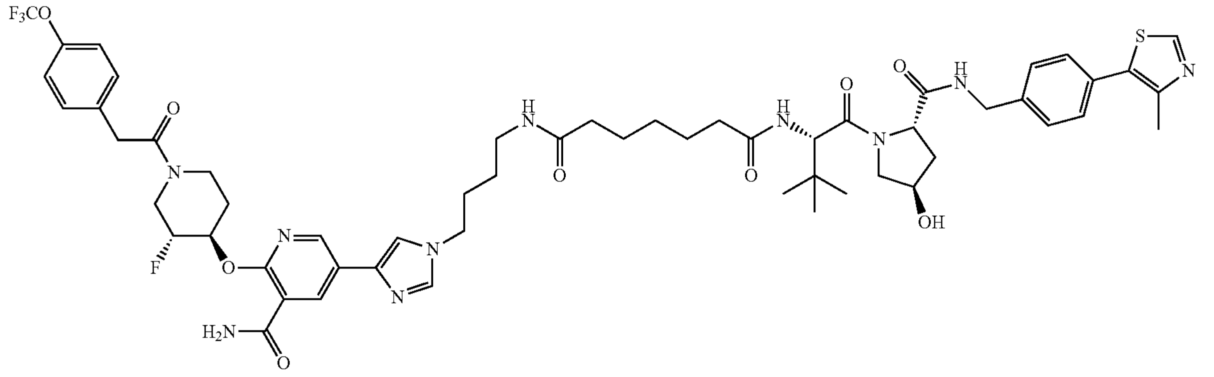 [SMILES: Cc1ncsc1-c1ccc(CNC(=O)[C@@H]2C[C@@H](O)CN2C(=O)[C@@H](NC(=O)CCCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 173: N-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^7$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide. 30% yield. $^1$H NMR (600 MHz, $CD_3OD$) o 9.10 (s, 1H), 9.02 (s, 1H), 8.67 (dd, J=4.7, 2.6 Hz, 1H), 8.58 (dd, J=6.3, 2.6 Hz, 1H), 8.10 (d, J=1.9 Hz, 1H), 7.47 (d, J=8.0 Hz, 2H), 7.42 (d, J=8.2 Hz, 2H), 7.39-7.34 (m, 2H), 7.29-7.16 (m, 2H), 5.69-5.60 (m, 1H), 4.83-4.75 (m, 1H), 4.63 (s, 1H), 4.59-4.56 (m, 1H), 4.53 (d, J=16.2 Hz, 1H), 4.51-4.48 (m, 1H), 4.36 (d, J=15.5 Hz, 1H), 4.32 (t, J=7.1 Hz, 2H), 4.17-3.97 (m, 1H), 3.93-3.83 (m, 3H), 3.80 (dd, J=11.0, 4.0 Hz, 3H), 3.66-3.55 (m, 1H), 3.23 (t, J=7.0 Hz, 2H), 2.48 (s, 3H), 2.33-2.25 (m, 1H), 2.26-2.20 (m, 3H), 2.18 (t, J=7.5 Hz, 2H), 2.08 (ddd, J=13.4, 9.2, 4.5 Hz, 1H), 1.96 (p, J=7.3 Hz, 2H), 1.91-1.76 (m, 1H), 1.66-1.53 (m, 6H), 1.33 (p, J=7.7 Hz, 2H), 1.03 (s, 9H). HRMS (ESI-TOF) m/z: $[M+H]^+$ calcd for $C_{56}H_{69}F_4N_{10}O_9S^+$, 1133.4900; found 1133.4889.

Example 174: $N^1$-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^7$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide. 38% yield. $^1$H NMR (600 MHz, $CD_3OD$) S 9.05 (s, 1H), 8.91 (s, 1H), 8.67 (dd, J=4.6, 2.6 Hz, 1H), 8.58 (dd, J=6.2, 2.6 Hz, 1H), 8.08 (d, J=1.8 Hz, 1H), 7.46 (d, J=8.0 Hz, 2H), 7.41 (d, J=8.2 Hz, 2H), 7.38-7.34 (m, 2H), 7.29-7.20 (m, 2H), 5.78-5.57 (m, 1H), 4.83-4.76 (d, J=17.3 Hz, 1H), 4.63 (s, 1H), 4.60-4.55 (m, 1H), 4.53 (d, J=15.5 Hz, 1H), 4.51-4.48 (m, 1H), 4.36 (d, J=15.5 Hz, 1H), 4.31 (t, J=7.3 Hz, 2H), 4.19-3.95 (m, 1H), 3.94-3.84 (m, 3H), 3.80 (dd, J=11.0, 4.0 Hz, 3H), 3.66-3.55 (m, 1H), 3.24 (t, J=7.0 Hz, 2H), 2.47 (s, 3H), 2.31-2.27 (m, 1H), 2.26-2.19 (m, 3H), 2.17 (t, J=7.5 Hz, 2H), 2.08 (ddd, J=13.2, 9.2, 4.5 Hz, 1H), 1.95 (p, J=7.3 Hz, 2H), 1.91-1.76 (m, 1H), 1.64-1.52 (m, 6H), 1.43-1.23 (m, 4H), 1.03 (s, 9H). HRMS (ESI-TOF) mi: $[M+H]^+$ calcd for $C_{55}H_{71}F_4N_{10}O_9S^+$, 1147.5057; found 1147.5161.

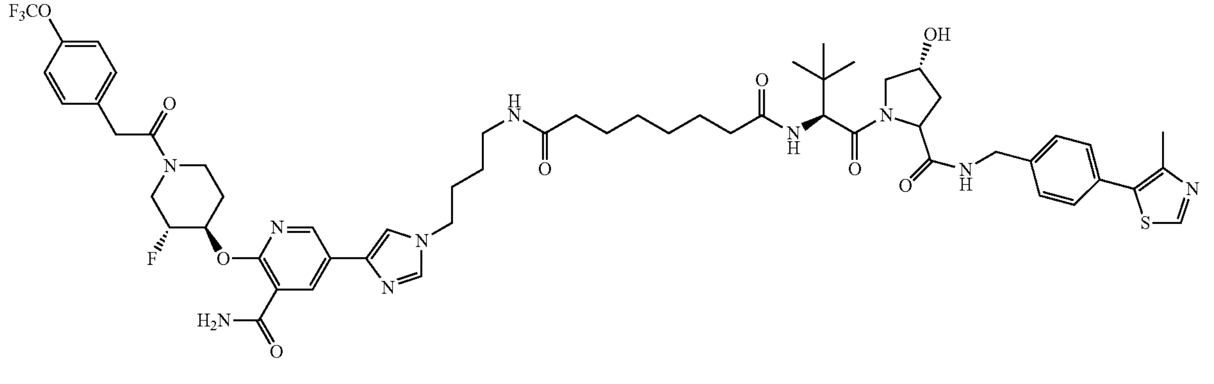 [SMILES: Cc1ncsc1-c1ccc(CNC(=O)C2C[C@@H](O)CN2C(=O)[C@@H](NC(=O)CCCCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

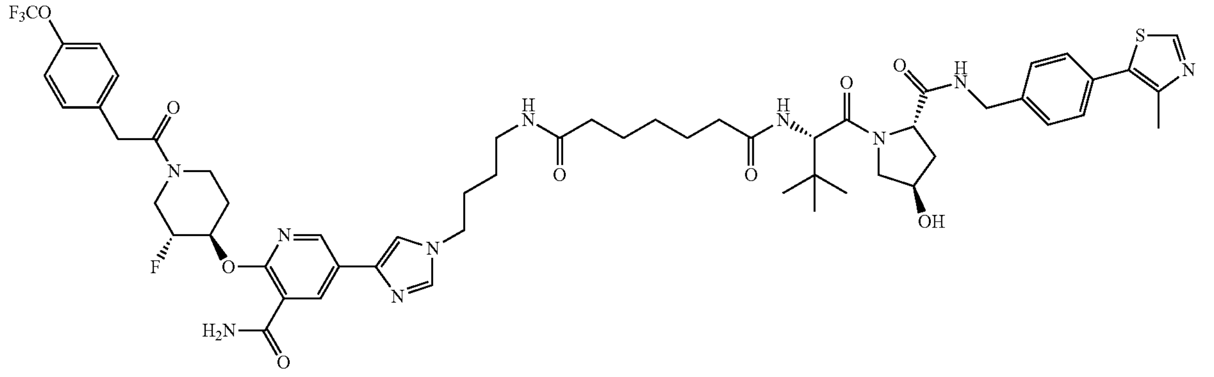 [SMILES: Cc1ncsc1-c1ccc(CNC(=O)[C@@H]2C[C@@H](O)CN2C(=O)[C@@H](NC(=O)CCCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 175: N[1]-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-N[1]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide. 37% yield. $^1$H NMR (600 MHz, $CD_3OD$) S 9.12 (s, 1H), 9.05 (s, 1H), 8.69 (dd, J=4.6, 2.6 Hz, 1H), 8.60 (dd, J=6.3, 2.6 Hz, 1H), 8.11 (d, J=2.0 Hz, 1H), 7.49 (d, J=8.0 Hz, 2H), 7.44 (d, J=8.2 Hz, 2H), 7.40-7.35 (m, 2H), 7.26 (d, J=8.0 Hz, 2H), 5.71-5.62 (m, 1H), 4.85-4.77 (m, 1H), 4.65 (s, 1H), 4.61-4.57 (m, 1H), 4.55 (d, J=15.5 Hz, 1H), 4.52-4.50 (m, 1H), 4.38 (d, J=15.5 Hz, 1H), 4.34 (t, =7.2 Hz, 2H), 4.20-4.00 (m, 1H), 3.96-3.85 (m, 3H), 3.82 (dd, J=11.0, 4.0 Hz, 2H), 3.66-3.58 (m, 1H), 3.25 (t, J=6.9 Hz, 2H), 2.50 (s, 3H), 2.30 (dq, J=15.3, 7.6 Hz, 2H), 2.24 (dd, J=13.6, 7.4 Hz, 2H), 2.20-2.16 (m, 4H), 2.10 (ddd, J=13.3, 9.2, 4.5 Hz, 1H), 1.97 (p, J=7.3 Hz, 2H), 1.93-1.78 (m, 1H), 1.67-1.51 (m, 6H), 1.38-1.26 (m, 5H), 1.05 (s, 9H). HRMS (ESI-TOF) m/z: $[M+H]^+$ calcd for $C_{58}H_{73}F_4N_{10}O_9S^+$, 1161.5213; found 1161.5303.

Example 176: N[1]-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-N[10]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide. 30% yield. $^1$H NMR (600 MHz, $CD_3OD$) S 9.07 (s, 1H), 8.92 (s, 1H), 8.67 (dd, J=4.6, 2.6 Hz, 1H), 8.58 (dd, J=6.2, 2.6 Hz, 1H), 8.09 (t, J=2.0 Hz, 1H), 7.47 (d, J=8.0 Hz, 2H), 7.41 (d, J=8.2 Hz, 2H), 7.39-7.35 (m, 2H), 7.24 (d, J=8.1 Hz, 2H), 5.69-5.60 (m, 1H), 4.83-4.76 (m, 1H), 4.64 (s, 1H), 4.59-4.55 (m, 1H), 4.55-4.52 (s, 1H), 4.51-4.48 (m, 1H), 4.36 (d, J=15.5 Hz, 1H), 4.32 (t, J=7.3 Hz, 2H), 4.21-3.96 (m, 1H), 3.95-3.84 (m, 3H), 3.80 (dd, J=11.0, 4.1 Hz, 3H), 3.68-3.56 (m, 1H), 3.24 (t, J=6.9 Hz, 2H), 2.47 (s, 3H), 2.28 (dq, J=15.6, 7.8 Hz, 2H), 2.22 (dd, J=13.4, 7.1 Hz, 2H), 2.17 (t, J=7.5 Hz, 2H), 2.08 (ddd, J=13.3, 9.1, 4.5 Hz, 1H), 1.96 (p, J=7.4 Hz, 2H), 1.91-1.76 (m, 1H), 1.64-1.52 (m, 6H), 1.34-1.25 (m, 8H), 1.03 (s, 9H). HRMS (ESI-TOF) m/z: $[M+H]^+$ calcd for $C_{59}H_{75}F_4N_{10}O_9S^+$, 1175.5370; found 1175.5453.

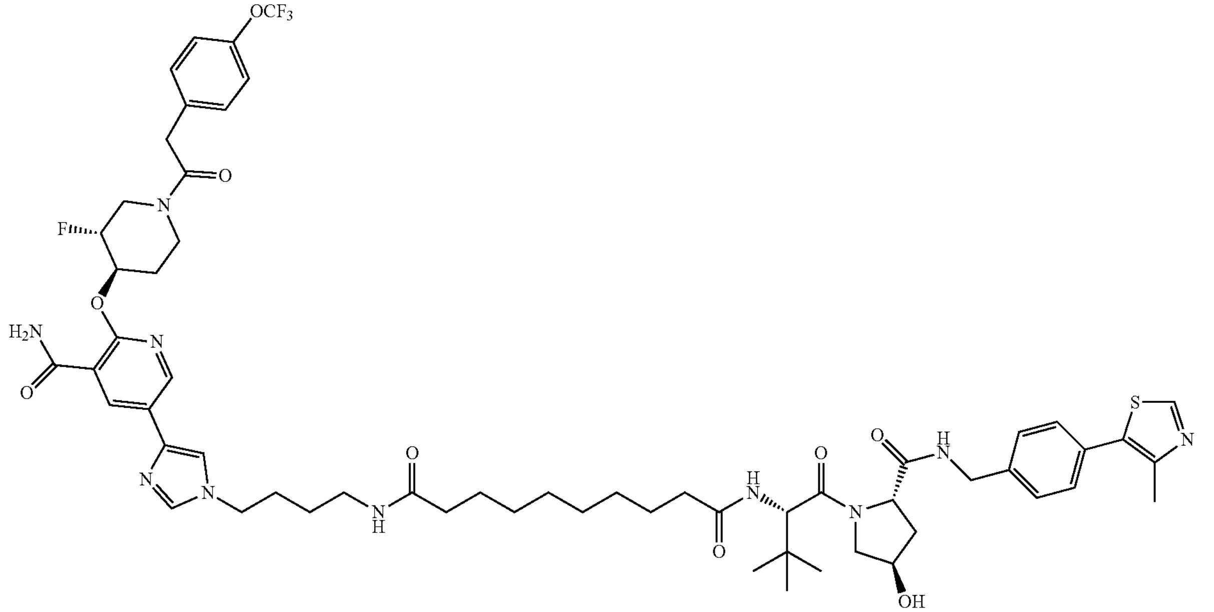 [SMILES: Cc1ncsc1-c1ccc(CNC(=O)[C@@H]2C[C@@H](O)CN2C(=O)[C@@H](NC(=O)CCCCCCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

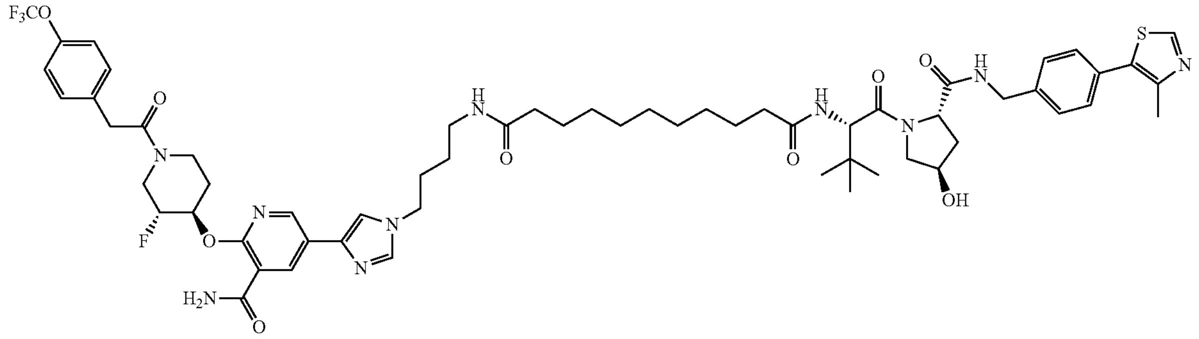 [SMILES: Cc1ncsc1-c1ccc(CNC(=O)[C@@H]2C[C@@H](O)CN2C(=O)[C@@H](NC(=O)CCCCCCCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

Example 177: N-(4-(4-(5-Carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{11}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide. 31% yield. $^{1}$H NMR (600 MHz, $CD_3OD$) δ 9.02 (s, 1H), 8.90 (s, 1H), 8.67 (dd, J=4.6, 2.6 Hz, 1H), 8.58 (dd, J=6.3, 2.6 Hz, 1H), 8.07 (t, J=1.9 Hz, 1H), 7.46 (d, J=8.1 Hz, 2H), 7.41 (d, J=8.2 Hz, 2H), 7.39-7.34 (m, 2H), 7.24 (d, J=8.5 Hz, 2H), 5.69-5.60 (m, 1H), 4.83-4.75 (m, 1H), 4.63 (s, 1H), 4.60-4.55 (m, 1H), 4.54-4.51 (m, 1H), 4.51-4.47 (m, 1H), 4.35 (d, J=15.5 Hz, 1H), 4.31 (t, J=7.3 Hz, 2H), 4.16-3.99 (m, 1H), 3.94-3.84 (m, 3H), 3.83-3.76 (m, 3H), 3.65-3.56 (m, 1H), 3.24 (t, J=6.9 Hz, 2H), 2.47 (s, 3H), 2.28 (td, J=15.3, 14.9, 7.7 Hz, 2H), 2.23-2.19 (m, 2H), 2.17 (t, J=7.5 Hz, 2H), 2.08 (ddd, J=13.3, 9.1, 4.5 Hz, 1H), 1.95 (p, J=7.4 Hz, 2H), 1.91-1.76 (m, 1H), 1.57 (q, J=7.4 Hz, 6H), 1.35-1.22 (m, 10H), 1.03 (s, 9H). HRMS (ESI-TOF) m/z: $[M+H]^+$ calcd for $C_{60}H_{77}F_4N_{10}O_9S^+$, 1189.5526; found 1189.5613.

Example 178: 5-(1-(4-(2-((2-(2,6-Dioxopiperidin-3-yl)-1,3-dioxoisoindolin-4-yl)amino)acetamido)butyl)-1H-imidazol-4-yl)-2-(((3R,4R)-3-fluoro-1-(2-(4-(trifluoromethoxy)phenyl)acetyl)piperidin-4-yl)oxy)nicotinamide. 35% yield. $^{1}$H NMR (600 MHz, $CD_3OD$) δ 9.05 (s, 1H), 8.62 (dd, J=5.2, 2.6 Hz, 1H), 8.55 (dd, J=6.5, 2.6 Hz, 1H), 8.00 (d, J=1.8 Hz, 1H), 7.52 (t, J=7.8 Hz, 1H), 7.37 (dd, J=8.5, 2.0 Hz, 2H), 7.25 (d, J=8.1 Hz, 2H), 7.05 (d, J=7.1 Hz, 1H), 6.86 (d, J=8.5 Hz, 1H), 5.69-5.60 (m, 1H), 5.05 (dd, J=12.9, 5.5 Hz, 1H), 4.28 (t, J=7.3 Hz, 2H), 4.17-4.02 (m, 1H), 4.00 (s, 2H), 3.94-3.84 (m, 3H), 3.84-3.72 (m, 2H), 3.64-3.58 (m, 1H), 2.85 (ddd, J=17.7, 14.0, 5.3 Hz, 1H), 2.77-2.72 (m, 1H), 2.72-2.65 (m, 1H), 2.31-2.17 (m, 1H), 2.10 (ddt, J=12.3, 6.9, 3.9 Hz, 1H), 1.90 (p, J=7.4 Hz, 3H), 1.84-1.77 (m, 1H), 1.57 (p, J=7.0 Hz, 2H). HRMS (ESI-TOF) m/z: $[M+H]^+$ calcd for $C_{42}H_{42}F_4N_9O_9^+$, 892.3036; found 892.4059.

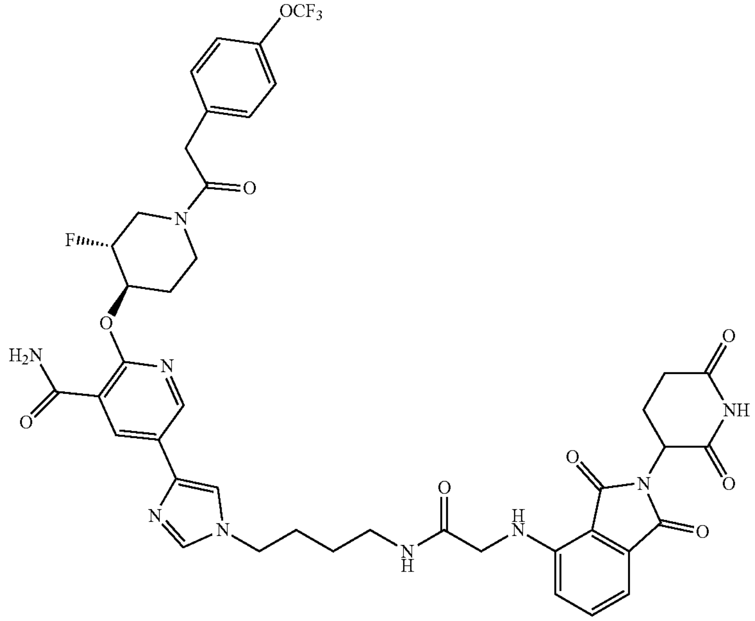 [SMILES: NC(=O)c1cc(-c2cn(CCCCNC(=O)CNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

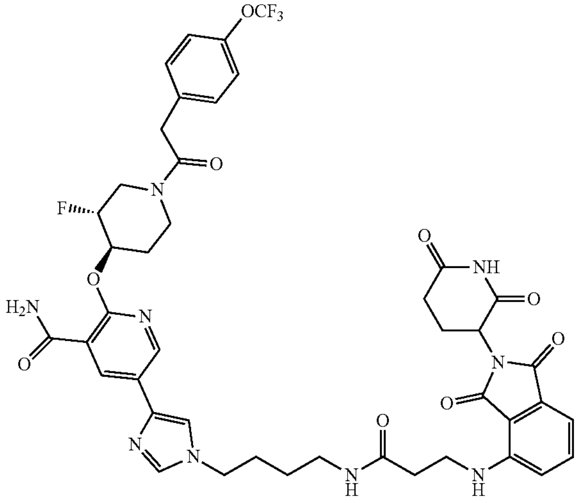 [SMILES: NC(=O)c1cc(-c2cn(CCCCNC(=O)CCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 179: 5-(1-(4-(3-((2-(2,6-Dioxopiperidin-3-yl)-1,3-dioxoisoindolin-4-yl)amino)propanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide. 33% yield. $^1$H NMR (600 MHz, $CD_3OD$) δ 8.96 (s, 1H), 8.61 (dd, J=5.1, 2.5 Hz, 1H), 8.53 (dd, J=5.6, 2.5 Hz, 1H), 7.96 (s, 1H), 7.58-7.46 (m, 1H), 7.42-7.34 (m, 2H), 7.28-7.21 (m, 2H), 7.09 (d, J=8.6 Hz, 1H), 6.96 (dd, J=7.1, 2.2 Hz, 1H), 5.69-5.59 (m, 1H), 4.99 (dd, J=12.7, 5.5 Hz, 1H), 4.24 (t, J=7.4 Hz, 2H), 4.17-3.97 (m, 1H), 3.95-3.84 (m, 2H), 3.84-3.71 (m, 2H), 3.67-3.58 (m, 3H), 3.27 (dt, J=8.2, 4.0 Hz, 2H), 2.80 (ddd, J=17.1, 13.7, 5.3 Hz, 1H), 2.72-2.58 (m, 2H), 2.54 (q, J=5.6 Hz, 2H), 2.33-2.18 (m, 1H), 2.06 (ddd, J=12.6, 7.0, 4.3 Hz, 1H), 1.92-1.78 (m, 3H), 1.52 (p, J=6.9 Hz, 2H). HRMS (ESI-TOF) m/z: $[M+H]^+$ calcd for $C_{43}H_{44}F_4N_9O_9^+$, 906.3193; found 906.4594.

dazol-4-yl)-2-(((3R,4R)-3-fluoro-1-(2-(4-(trifluoromethoxy)phenyl)acetyl)piperidin-4-yl)oxy)nicotinamide. 34% yield. $^1$H NMR (600 MHz, $CD_3OD$) δ 9.06 (s, 1H), 8.63 (dd, J=5.0, 2.5 Hz, 1H), 8.58-8.51 (m, 1H), 8.06 (s, 1H), 7.54-7.44 (m, 1H), 7.40-7.33 (m, 2H), 7.24 (d, J=8.1 Hz, 2H), 7.09-7.00 (m, 1H), 6.98 (dd, J=7.1, 2.7 Hz, 1H), 5.77-5.50 (m, 1H), 5.04 (dd, J=12.8, 5.5 Hz, 1H), 4.29 (t, J=7.2 Hz, 2H), 4.17-3.99 (m, 1H), 3.93-3.84 (m, 2H), 3.84-3.69 (m, 2H), 3.63-3.55 (m, 1H), 3.34 (t, J=6.9 Hz, 2H), 3.23 (t, J=6.9 Hz, 2H), 2.85 (ddd, J=17.6, 14.0, 5.4 Hz, 1H), 2.76-2.61 (m, 2H), 2.31 (t, J=7.1 Hz, 2H), 2.28-2.17 (m, 1H), 2.13-2.06 (m, 1H), 1.94 (h, J=7.8, 7.3 Hz, 4H), 1.90-1.74 (m, 1H), 1.54 (p, J=7.1 Hz, 2H). HRMS (ESI-TOF) m/z: $[M+H]^+$ calcd for $C_{44}H_{46}F_4N_9O_9^+$, 920.3349; found 920.3956.

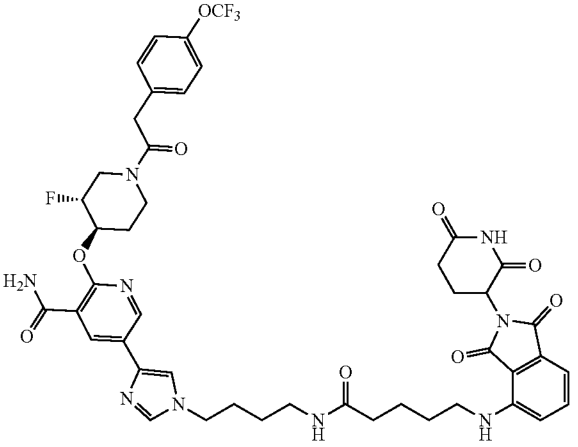

Example 181: 5-(1-(4-(5-((2-(2,6-Dioxopiperidin-3-yl)-1,3-dioxoisoindolin-4-yl)amino)pentanamido)butyl)-1H-imi-

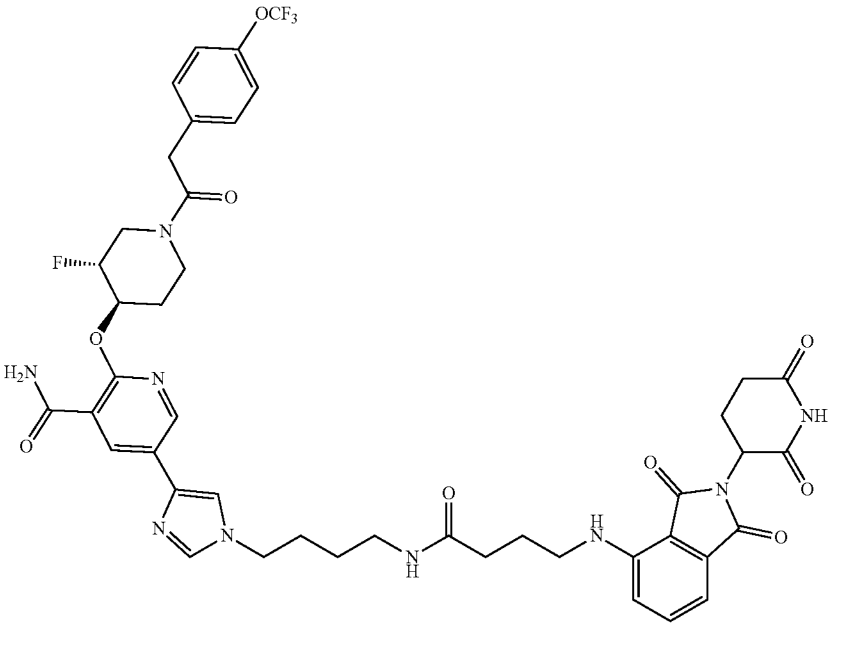 [SMILES: NC(=O)c1cc(-c2cn(CCCCNC(=O)CCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 180: 5-(1-(4-(4-((2-(2,6-Dioxopiperidin-3-yl)-1,3-dioxoisoindolin-4-yl)amino)butanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide.

35% yield. $^1$H NMR (600 MHz, $CD_3OD$) δ 8.96 (s, 1H), 8.63 (dd, J=4.7, 2.6 Hz, 1H), 8.55 (dd, J=5.9, 2.5 Hz, 1H), 8.01 (d, J=2.2 Hz, 1H), 7.51 (t, J=7.8 Hz, 1H), 7.37 (d, J=8.1 Hz, 2H), 7.24 (d, J=7.9 Hz, 2H), 7.00 (d, J=7.4 Hz, 2H), 5.67-5.58 (m, 1H), 5.03 (dd, J=12.7, 5.5 Hz, 1H), 4.82-4.75 (m, 1H), 4.28 (t, J=7.2 Hz, 2H), 4.18-3.98 (m, 1H), 3.93-3.83 (m, 3H), 3.82-3.69 (m, 2H), 3.63-3.56 (m, 1H), 3.25 (t, J=6.8 Hz, 2H), 2.84 (ddd, J=18.2, 13.8, 5.2 Hz, 1H), 2.76-2.61 (m, 2H), 2.32-2.17 (m, 3H), 2.12-2.06 (m, 1H), 1.94 (p, J=7.4 Hz, 2H), 1.90-1.77 (m, 1H), 1.73 (p, J=7.1 Hz, 2H), 1.69-1.62 (m, 2H), 1.56 (p, J=7.0 Hz, 2H). HRMS (ESI-TOF) m/z: $[M+H]^+$ calcd for $C_{45}H_{48}F_4N_9O_9^+$, 934.3506; found 934.4065.

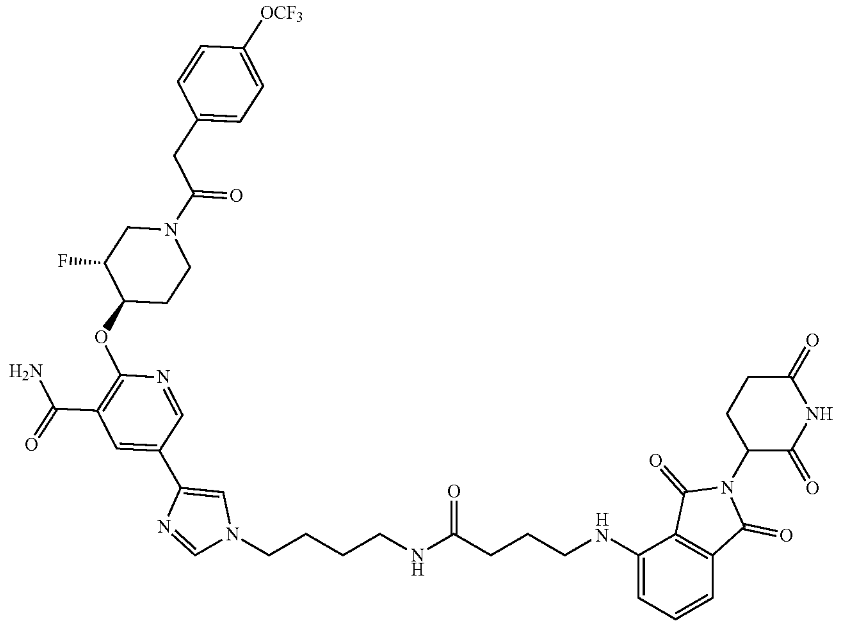 [SMILES: NC(=O)c1cc(-c2cn(CCCCNC(=O)CCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 182: 5-(1-(4-(6-((2-(2,6-Dioxopiperidin-3-yl)-1,3-dioxoisoindolin-4-yl)amino)hexanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide. 38% yield. $^1$H NMR (600 MHz, $CD_3OD$) δ 9.06 (s, 1H), 8.64 (dd, J=5.2, 2.5 Hz, 1H), 8.55 (dd, J=6.3, 2.6 Hz, 1H), 8.06 (d, J=2.1 Hz, 1H), 7.49 (td, J=7.8, 3.3 Hz, 1H), 7.39-7.35 (m, 2H), 7.24 (d, J=8.1 Hz, 2H), 6.98 (ddd, J=13.3, 7.7, 3.6 Hz, 2H), 5.68-5.58 (m, 1H), 5.05 (dd, J=12.9, 5.5 Hz, 1H), 4.29 (t, J=7.3 Hz, 2H), 4.19-3.97 (m, 1H), 3.95-3.83 (m, 2H), 3.83-3.67 (m, 2H), 3.62-3.56 (m, 1H), 3.30-3.26 (m, 2H), 3.24 (t, J=6.9 Hz, 2H), 2.85 (ddd, J=18.8, 14.0, 5.3 Hz, 1H), 2.77-2.63 (m, 2H), 2.22 (t, J=7.2 Hz, 3H), 2.12-2.06 (m, 1H), 1.94 (p, J=7.5 Hz, 2H), 1.89-1.75 (m, 1H), 1.66 (dt, J=12.4, 6.8 Hz, 4H), 1.55 (p, J=7.1 Hz, 2H), 1.46-1.38 (m, 2H). HRMS (ESI-TOF) m/z: $[M+H]^+$ calcd for $C_{46}H_{50}F_4N_9O_9^+$, 948.3662; found 948.4017.

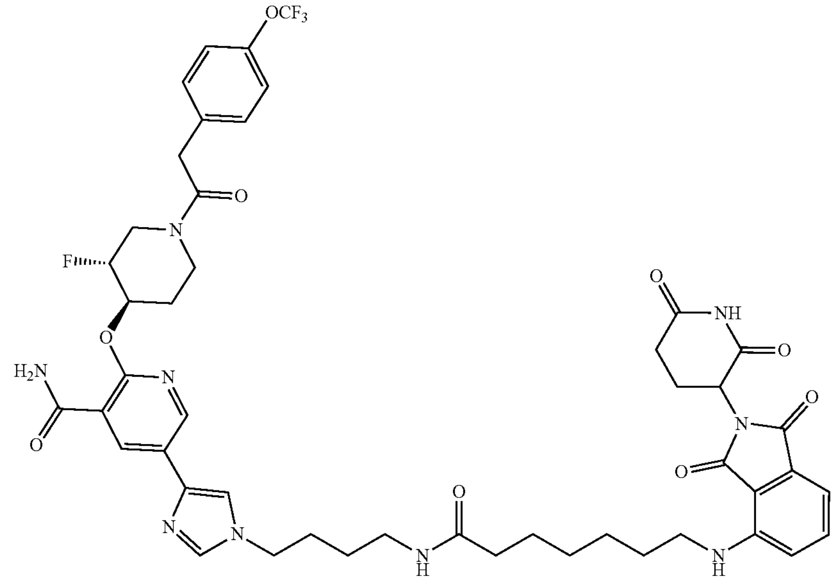 [SMILES: NC(=O)c1cc(-c2cn(CCCCNC(=O)CCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 183: 5-(1-(4-(7-((2-(2,6-Dioxopiperidin-3-yl)-1,3-dioxoisoindolin-4-yl)amino)heptanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide. 39% yield. $^1$H NMR (600 MHz, $CD_3OD$) δ 9.05 (s, 1H), 8.65 (dd, J=4.6, 2.6 Hz, 1H), 8.56 (dd, J=6.3, 2.5 Hz, 1H), 8.06 (s, 1H), 7.52 (t, J=7.8 Hz, 1H), 7.37 (d, J=8.1 Hz, 2H), 7.24 (d, J=8.1 Hz, 2H), 7.00 (dd, J=11.0, 7.9 Hz, 2H), 5.68-5.57 (m, 1H), 5.05 (dd, J=12.8, 5.5 Hz, 1H), 4.30 (t, J=7.3 Hz, 2H), 4.18-3.96 (m, 1H), 3.93-3.83 (m, 3H), 3.82-3.68 (m, 2H), 3.28 (t, J=6.7 Hz, 2H), 3.23 (t, J=6.9 Hz, 2H), 2.85 (ddd, J=18.9, 14.1, 5.3 Hz, 1H), 2.77-2.61 (m, 2H), 2.19 (t, J=7.3 Hz, 3H), 2.13-2.07 (m, 1H), 1.95 (p, J=7.5 Hz, 2H), 1.90-1.75 (m, 1H), 1.62 (p, J=7.3 Hz, 4H), 1.56 (p, J=7.1 Hz, 2H), 1.43 (p, J=7.4 Hz, 2H), 1.37 (q, J=7.6 Hz, 2H). HRMS (ESI-TOF) m/z: $[M+H]^+$ calcd for $C_{47}H_{52}F_4N_9O_9^+$, 962.3819: found 962.4877.

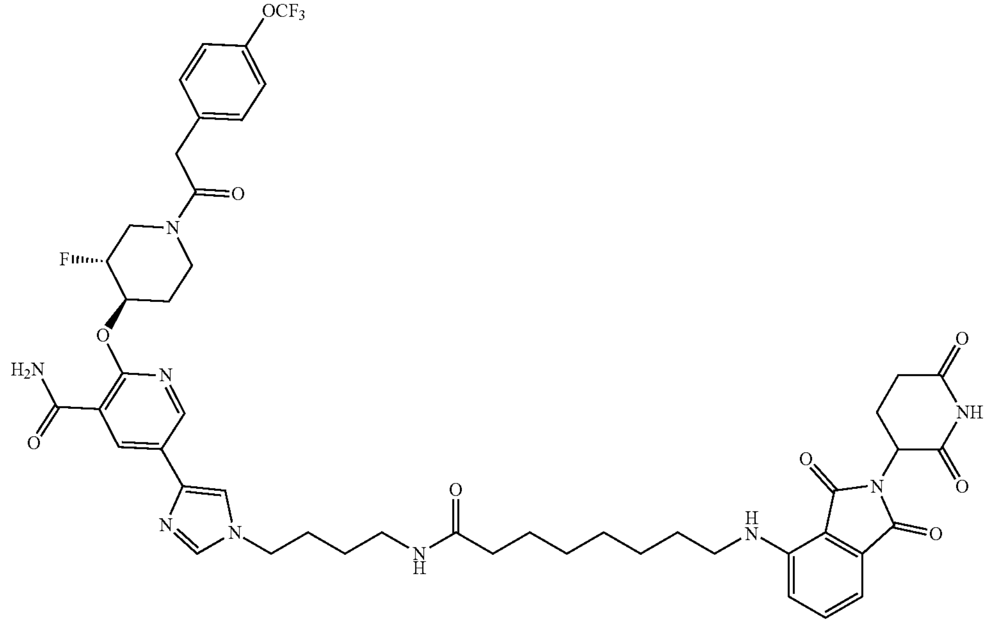 [SMILES: NC(=O)c1cc(-c2cn(CCCCNC(=O)CCCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 184: 5-(1-(4-(8-((2-(2,6-Dioxopiperidin-3-yl)-1,3-dioxoisoindolin-4-yl)amino)octanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide. 31% yield. $^1$H NMR (600 MHz, $CD_3OD$) δ 9.07 (s, 1H), 8.65 (dd, J=4.6, 2.6 Hz, 11H), 8.57 (dd, J=6.4, 2.6 Hz, 1H), 8.06 (d, J=2.2 Hz, 1H), 7.53 (t, J=7.8 Hz, 1H), 7.37 (d, J=8.2 Hz, 2H), 7.24 (d, J=8.1 Hz, 2H), 7.04-6.90 (m, 2H), 5.63 (brs, 1H), 5.05 (dd, J=12.8, 5.5 Hz, 1H), 4.30 (t, J=7.3 Hz, 2H), 4.19-3.97 (m, 1H), 3.93-3.82 (m, 2H), 3.82-3.66 (m, 2H), 3.64-3.49 (m, 1H), 3.29-3.26 (m, 2H), 3.24 (t, J=7.0

Hz, 2H), 2.91-2.80 (m, 1H), 2.78-2.64 (m, 2H), 2.30-2.20 (s, 1H), 2.18 (t, J=7.3 Hz, 2H), 2.14-2.06 (m, 1H), 1.95 (p, J=7.4 Hz, 2H), 190-1.75 (m, 1H), 1.65-1.58 (m, 4H), 1.55 (q, J=7.3 Hz, 2H), 1.43-1.35 (s, 4H), 1.35-1.31 (m, 2H). HRMS (ESI-TOF) m/z: $[M+H]^+$ calcd for $C_{48}H_{54}F_4N_9O_9^+$, 976.3975; found 976.4222.

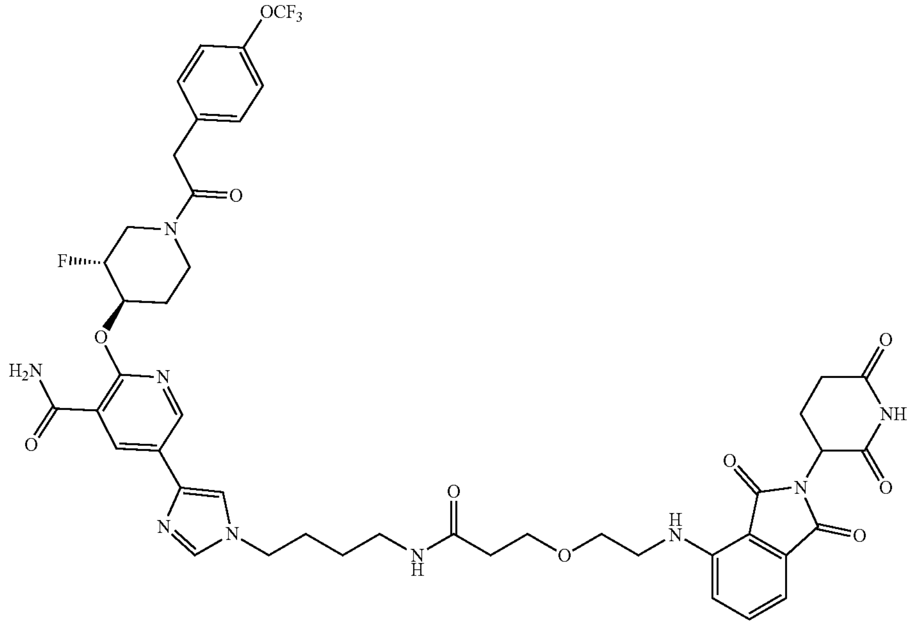 [SMILES: NC(=O)c1cc(-c2cn(CCCCNC(=O)CCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 186: 5-(1-(4-(3-(2-((2-(2,6-Dioxopiperidin-3-yl)-1,3-dioxoisoindolin-4-yl)amino)ethoxy)propanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide. 40% yield. $^1H$ NMR (600 MHz, $CD_3OD$) δ 8.97 (s, 1H), 8.58 (dd, J=5.3, 2.6 Hz, 1H), 8.51 (dd, J=5.5, 2.5 Hz, 1H), 7.99 (s, 1H), 7.48-7.43 (m, 1H), 7.41-7.34 (m, 2H), 7.25 (d, J=8.0 Hz, 2H), 7.00-6.94 (m, 2H), 5.68-5.58 (m, 1H), 5.04 (dd, J=12.7, 5.5 Hz, 1H), 4.25 (t, J=7.4 Hz, 2H), 4.19-4.00 (m, 1H), 3.96-3.82 (m, 3H), 3.78 (t, J=5.8 Hz, 3H), 3.67 (t, J=5.2 Hz, 2H), 3.63-3.56 (m, 1H), 3.42 (s, 2H), 3.25 (q, J=6.7 Hz, 2H), 2.85 (ddd, J=18.6, 13.9, 5.4 Hz, 1H), 2.76-2.61 (m, 2H), 2.46 (t J=5.7 Hz, 2H), 2.35-2.16 (m, 1H), 2.13-2.05 (m, 1H), 1.91 (p, J=7.5 Hz, 2H), 1.84-1.75 (m, 1H), 1.53 (p, J=7.0 Hz, 2H). HRMS (ESI-TOF) m/z: $[M+H]^+$ calcd for $C_{45}H_{48}F_4N_9O_{10}^+$, 950.3455; found 950.3895.

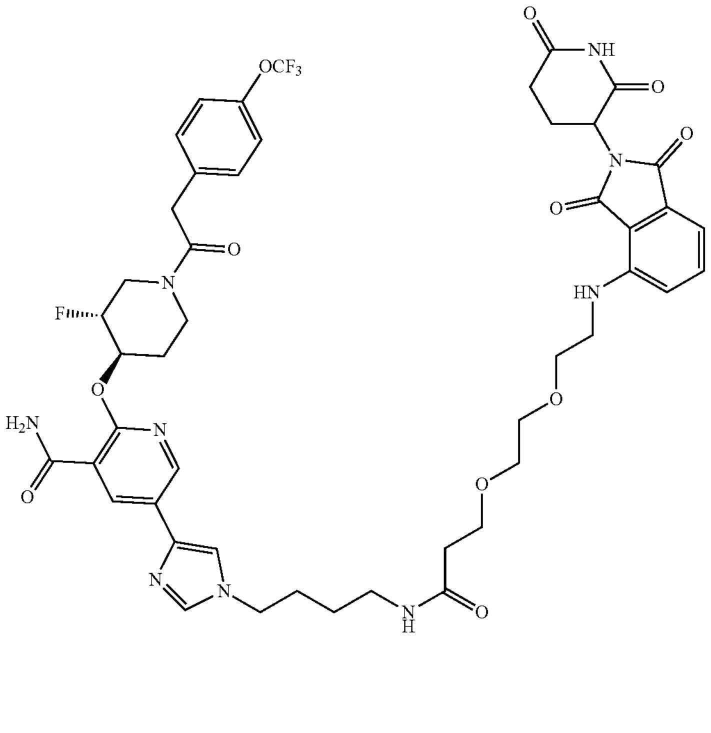 [SMILES: NC(=O)c1cc(-c2cn(CCCCNC(=O)CCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 186: 5-(1-(4-(3-(2-(2-((2-(2,6-Dioxopiperidin-3-yl)-1,3-dioxoisoindolin-4-yl)amino)ethoxy)ethoxy)propanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide. 29% yield. $^1$H NMR (600 MHz, $CD_3OD$) δ 9.01 (s, 1H), 8.60 (dd, J=5.0, 2.6 Hz, 1H), 8.53 (dd, J=6.4, 2.5 Hz, 1H), 8.02 (s, 1H), 7.49 (td, J=7.8, 3.1 Hz, 1H), 7.40-7.32 (m, 2H), 7.25 (d, J=8.0 Hz, 2H), 7.02-6.95 (m, 2H), 5.68-5.57 (m, 1H), 5.03 (dd, J=12.8, 5.5 Hz, 1H), 4.26 (t, J=7.3 Hz, 2H), 4.18-3.96 (m, 1H), 3.95-3.84 (m, 2H), 3.84-3.76 (m, 2H), 3.74 (t, J=5.8 Hz, 2H), 3.69 (t, J=5.2 Hz, 2H), 3.64 (q, J=5.2 Hz, 4H), 3.62-3.56 (m, 1H), 3.42 (q, J=4.2, 3.6 Hz, 2H), 3.24 (t, J=6.7 Hz, 2H), 2.85 (ddd, J=17.3, 13.8, 5.4 Hz, 1H), 2.77-2.70 (m, 1H), 2.66 (td, J=13.4, 4.5 Hz, 1H), 2.42 (t, J=5.8 Hz, 2H), 2.31-2.18 (m, 1H), 2.12-2.06 (m, 1H), 1.93 (p, J=7.5 Hz, 2H), 1.90-1.76 (m, 1H), 1.53 (p, J=6.9 Hz, 2H). HRMS (ESI-TOF) m/z: $[M+H]^+$ calcd for $C_{47}H_{52}F_4N_9O_{11}{}^+$, 994.3717; found 994.4232.

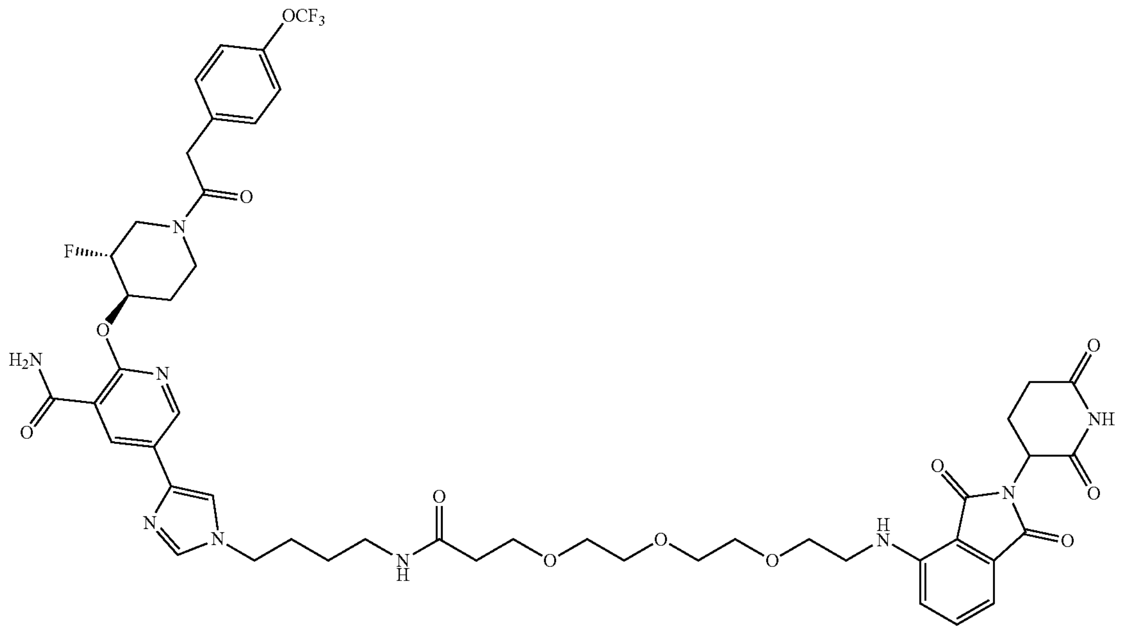 [SMILES: NC(=O)c1cc(-c2cn(CCCCNC(=O)CCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 187: 5-(1-(1-((2-(2,6-Dioxopiperidin-3-yl)-1,3-dioxoisoindolin-4-yl)amino)-12-oxo-3,6,9-trioxa-13-azaheptadecan-17-yl)-H-imidazol-4-yl)-2-(((3R,4R)-3-fluoro-1-(2-(4-(trifluoromethoxy)phenyl)acetyl)piperidin-4-yl)oxy)nicotinamide. 36% yield. $^1$H NMR (600 MHz, $CD_3OD$) δ 8.99 (s, 1H), 8.60 (dd, J=5.1, 2.5 Hz, 1H), 8.53 (dd, J=6.1, 2.5 Hz, 1H), 8.02 (s, 1H), 7.49 (ddd, J=9.6, 7.4, 2.7 Hz, 1H), 7.37 (d, J=8.0 Hz, 2H), 7.25 (d, J=8.1 Hz, 2H), 6.99 (ddd, J=10.6, 7.9, 2.7 Hz, 2H), 5.67-5.57 (m, 1H), 5.04 (dd, J=12.7, 5.5 Hz, 1H), 4.27 (t, 1=7.3 Hz, 2H), 4.19-3.97 (m, 1H), 3.94-3.84 (m, 2H), 3.83-3.75 (m, 2H), 3.70 (t, J=5.6 Hz, 5H), 3.68-3.63 (m, 4H), 3.61 (dd, J=6.2, 3.1 Hz, 2H), 3.58 (dd, J=5.9, 3.1 Hz, 2H), 3.48-3.40 (m, 2H), 3.25 (t, J=6.6 Hz, 2H), 2.86 (ddd, J=18.5, 13.8, 5.3 Hz, 1H), 2.78-2.70 (m, 1H), 2.67 (td, J=13.1, 4.3 Hz, 1H), 2.40 (t, J=5.8 Hz, 2H), 2.30-2.18 (m, 1H), 2.10 (td, J=7.8, 7.2, 3.3 Hz, 1H), 1.94 (p, J=7.3 Hz, 2H), 1.90-1.74 (m, 1H), 1.55 (p, J=6.9 Hz, 2H). HRMS (ESI-TOF) m/z: $[M+H]^+$ calcd for $C_{49}H_{56}F_4N_9O_{11}{}^+$, 1038.3979; found 1038.4780.

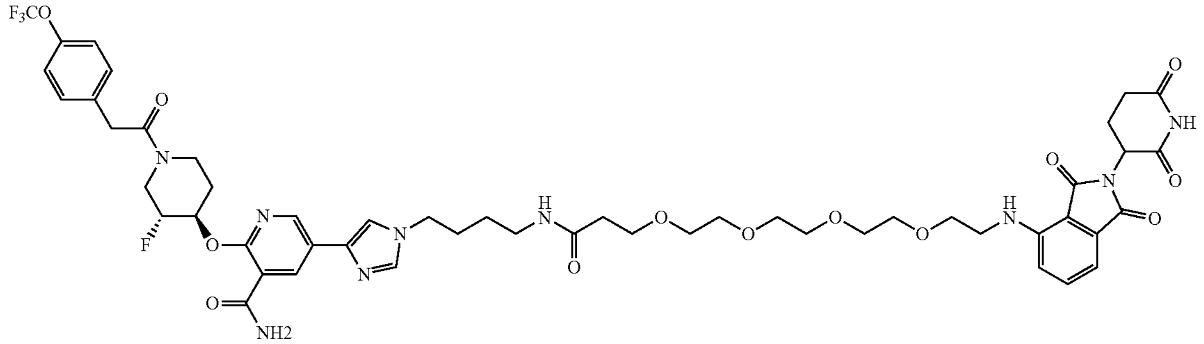 [SMILES: NC(=O)c1cc(-c2cn(CCCCNC(=O)CCOCCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Example 188: 5-(1-(1-((2-(2,6-Dioxopiperidin-3-yl)-1,3-dioxoisoindolin-4-yl)amino)-15-oxo-3,6,9,12-tetraoxa-16-azaicosan-20-yl)-1H-imidazol-4-yl)-2-(((3R,4R)-3-fluoro-1-(2-(4-(trifluoromethoxy)phenyl)acetyl)piperidin-4-yl)oxy)nicotinamide. 29% yield. $^1$H NMR (600 MHz, $CD_3OD$) δ 9.04 (s, 1H), 8.61 (dd, J=5.0, 2.5 Hz, 1H), 8.54 (dd, J=6.5, 2.5 Hz, 1H), 8.04 (s, 1H), 7.49 (ddd, J=9.9, 7.3, 2.8 Hz, 1H), 7.37 (d, J=8.0 Hz, 2H), 7.24 (d, J=8.1 Hz, 2H), 7.06-6.93 (m, 2H), 5.68-5.58 (m, 1H), 5.04 (dd, J=12.7, 5.5 Hz, 1H), 4.28 (t, J=7.3 Hz, 2H), 4.22-3.96 (m, 1H), 3.94-3.84 (m, 2H), 3.83-3.74 (m, 2H), 3.72-3.68 (m, 5H), 3.67-3.64 (m, 4H), 3.63-3.60 (m, 2H), 3.59-3.56 (m, 2H), 3.55-3.52 (m, 4H), 3.46-3.41 (m, 2H), 3.26 (t, J=6.6 Hz, 2H), 2.86 (ddd, J=17.3, 13.8, 5.3 Hz, 1H), 2.74 (dt, J=17.6, 3.2 Hz, 1H), 2.67 (td, J=13.2, 4.4 Hz, 1H), 2.41 (t, J=5.8 Hz, 2H), 2.31-2.18 (m, 1H), 2.12-2.07 (m, 1H), 1.95 (p, J=7.4 Hz, 2H), 1.92-1.74 (m, 1H), 1.56 (p, J=6.9 Hz, 2H). HRMS (ESI-TOF) m/z: $[M+H]^+$ calcd for $C_{51}H_{60}F_4N_9O_3{}^+$, 1082.4241; found 1082.4686.

Example 189: 5-(1-(1-((2-(2,6-Dioxopiperidin-3-yl)-1,3-dioxoisoindolin-4-yl)amino)-18-oxo-3,6,9,12,15-pentaoxa-19-azatricosan-23-yl)-1H-imidazol-4-yl)-2-(((3R,4R)-3-fluoro-1-(2-(4-(trifluoromethoxy)phenyl)acetyl)piperidin-4-yl)oxy)nicotinamide. 30% yield. $^1$H NMR (600 MHz, $CD_3OD$) δ 9.04 (s, 1H), 8.62 (dd, J=5.0, 2.5 Hz, 1H), 8.56 (dd, J=5.5, 2.6 Hz, 1H), 8.05 (s, 1H), 7.50 (t, J=7.9 Hz, 1H), 7.37 (d, J=8.1 Hz, 2H), 7.25 (d, J=8.1 Hz, 2H), 7.01 (t, J=9.4 Hz, 2H), 5.62 (brs, 1H), 5.05 (dd, J=12.7, 5.5 Hz, 1H), 4.29 (t, J=7.4 Hz, 2H), 4.19-4.00 (m, 1H), 3.93-3.84 (m, 2H), 3.84-3.75 (m, 2H), 3.70 (q, J=5.0, 4.4 Hz, 5H), 3.66 (s, 4H), 3.63 (dd, J=6.1, 3.3 Hz, 2H), 3.59 (dd, J=6.1, 3.4 Hz, 2H), 3.55-3.51 (m, 8H), 3.44 (t, J=4.9 Hz, 2H), 3.27 (t, J=6.7 Hz, 2H), 2.86 (ddd, J=18.2, 13.9, 5.4 Hz, 1H), 2.77-2.72 (m, 1H), 2.71-2.64 (m, 1H), 2.41 (t, J=5.8 Hz, 2H), 2.31-2.18 (m, 1H), 2.12-2.06 (m, 1H), 1.96 (p, J=7.4 Hz, 2H), 1.90-1.76 (m, 1H), 1.56 (p, J=7.0 Hz, 2H). HRMS (ESI-TOF) m/z: $[M+H]^+$ calcd for $C_{53}H_{64}F_4N_9O_{14}{}^+$, 1126.4503; found 1126.5436.

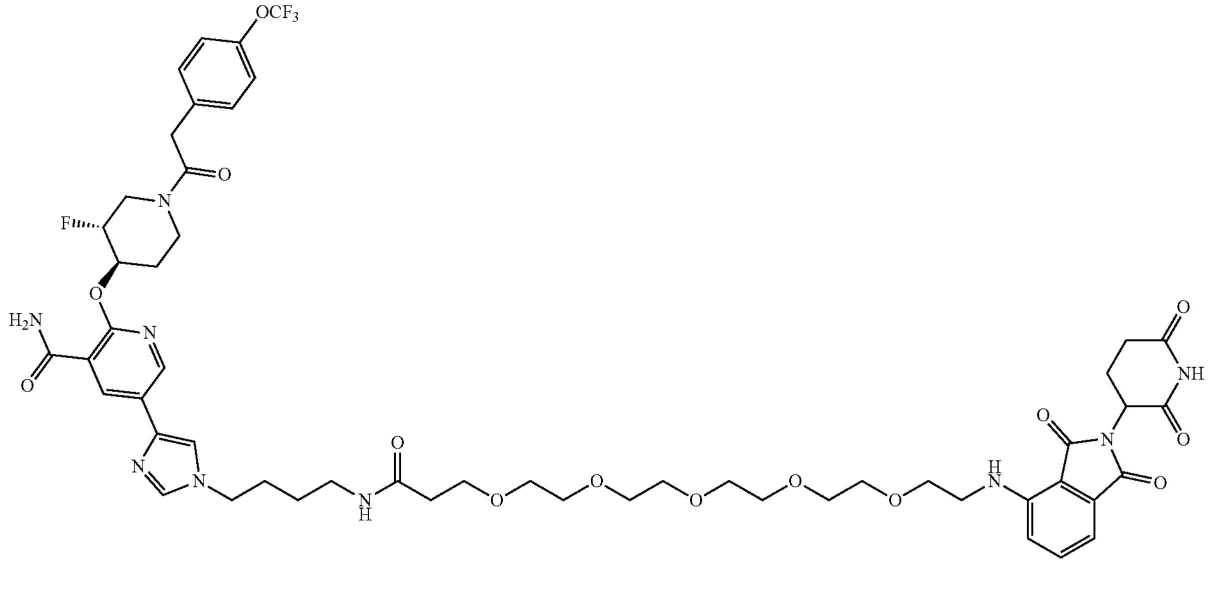 [SMILES: NC(=O)c1cc(-c2cn(CCCCNC(=O)CCOCCOCCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

Scheme 31. Synthesis of Example 190

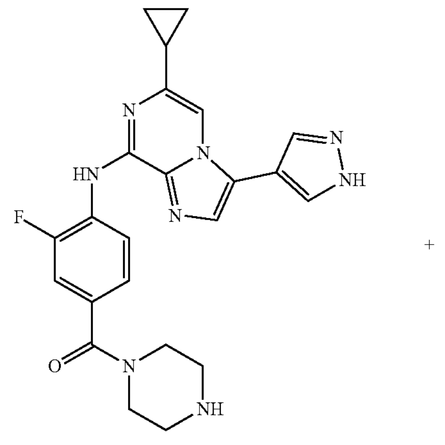

Intermediate 7

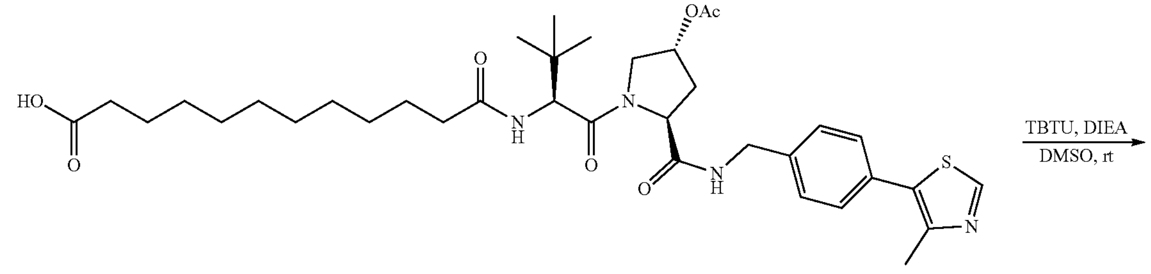

linker 38

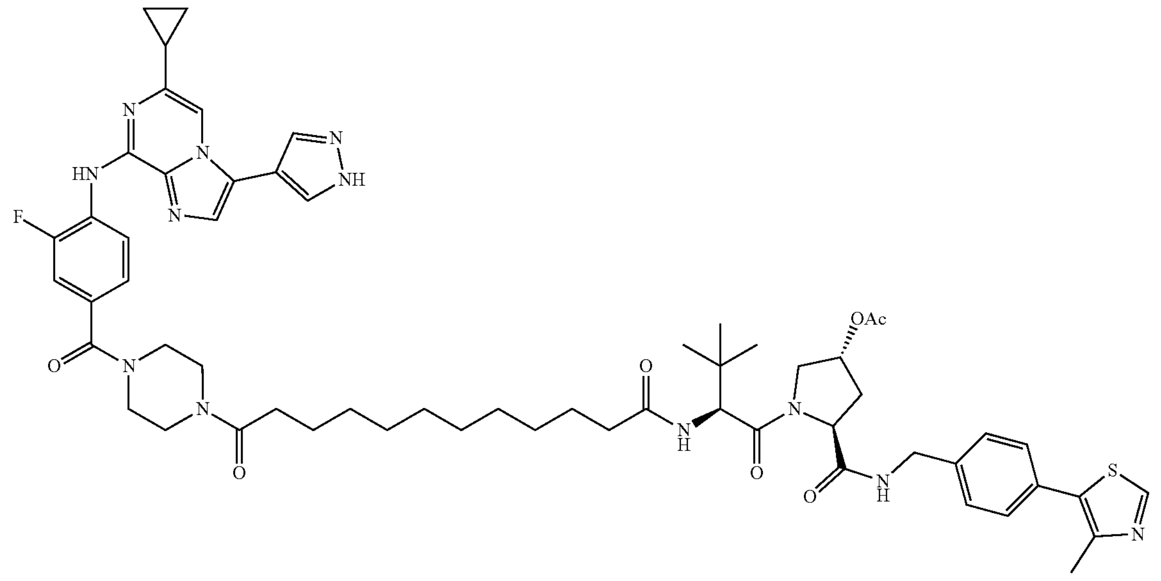

example 190

Example 190: (3R,5S)-1-((S)-2-(12-(4-(4-((6-Cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-5-((4-(4-methylthiazol-5-yl)benzyl)carbamoyl)pyrrolidin-3-yl acetate. The title compound can be synthesized according to the following procedures: To a solution of intermediate 7 (1 equiv.) and linker 28 (1.1 equiv.) in DMSO will be added DIEA (7 equiv.) and TBTU (1.1 equiv.). After being stirred at rt for 1 h, the mixture will be purified by HPLC to yield the title compound.

Example compounds 191 and 192 will be synthesized from intermediate 7 and corresponding linkers according to the procedures for the preparation of example compound 190.

Scheme 32. Synthesis of Example 193

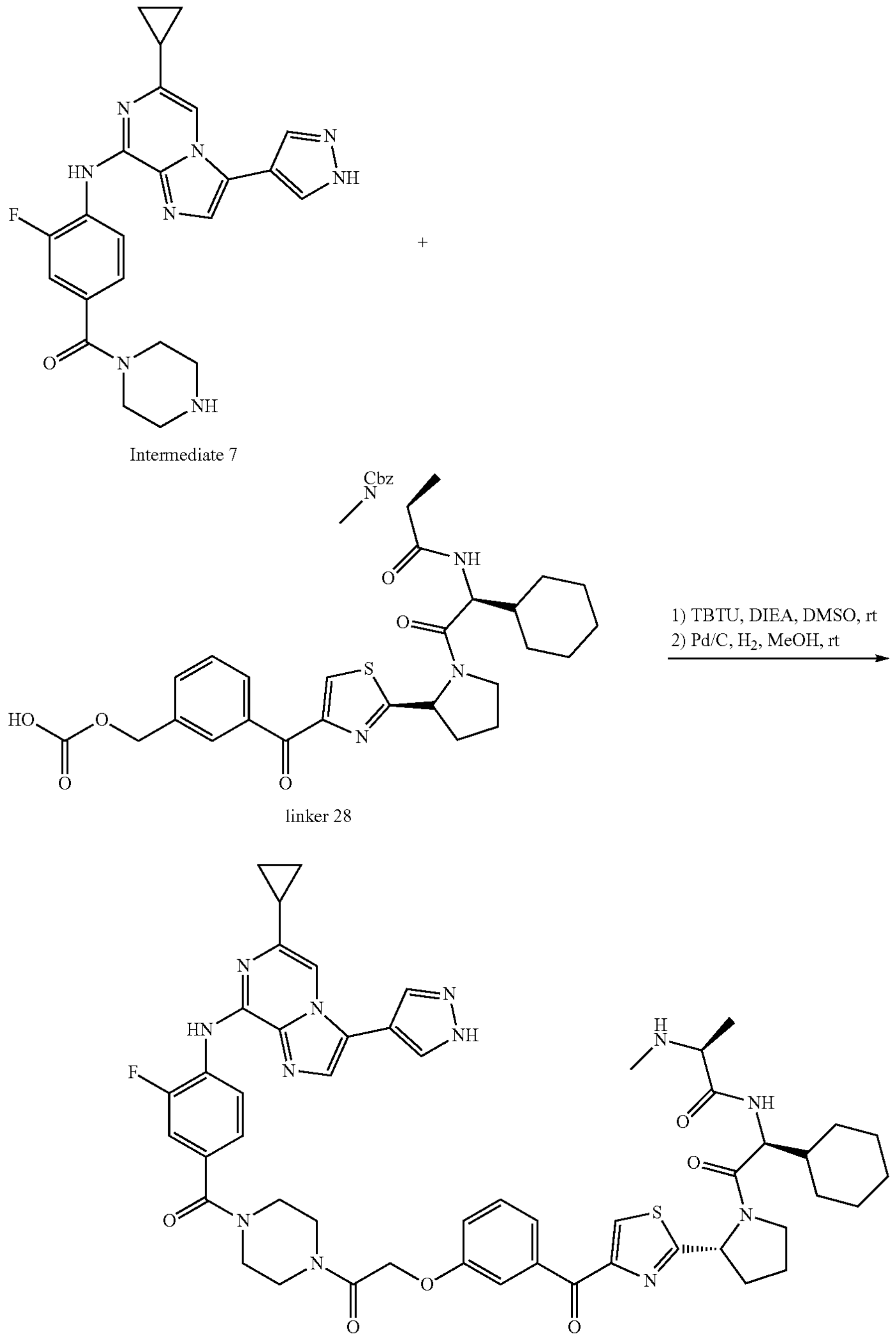

Intermediate 7 linker 28 example 193

Example 193: (S)—N—((S)-1-Cyclohexyl-2-((S)-2-(4-(3-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)benzoyl)thiazol-2-yl)pyrrolidin-1-yl)-2-oxoethyl)-2-(methylamino)propenamide. The title compound can be synthesized according to the following procedures: To a solution of intermediate 7 (1 equiv.) and linker 29 (1.1 equiv.) in DMSO will be added DIEA (7 equiv.) and TBTU (1.1 equiv.). After being stirred at rt for 1 h, the mixture will be purified by HPLC. The purified compound will be dissolved in MeOH, followed by Pd/C (0.1 equiv.), and stirred under $H_2$ atmosphere for another 2 h. Then, the mixture will be filtered, and the filtrate will be concentrated to yield the title compound.

Example compounds 194-208 will be synthesized from intermediate 7 and corresponding linkers according to the procedures for the preparation of example compound 193.
Scheme 33. Synthesis of Example 209
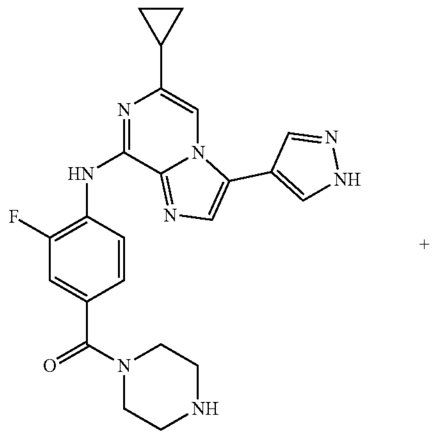
Intermediate 7
+
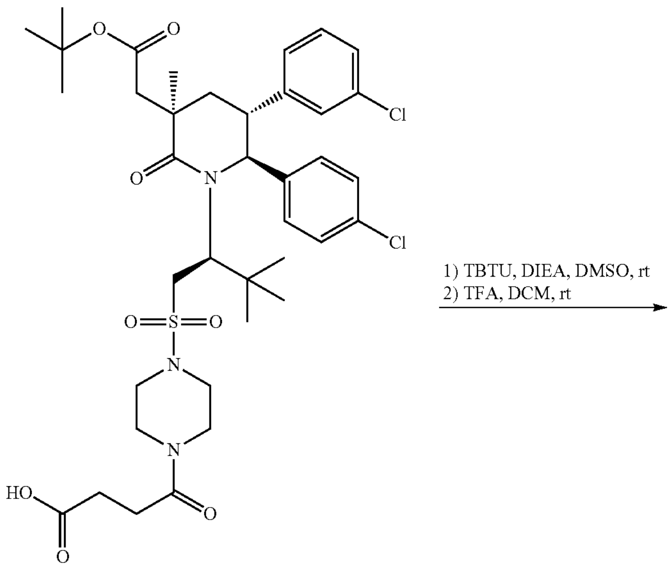
linker 30
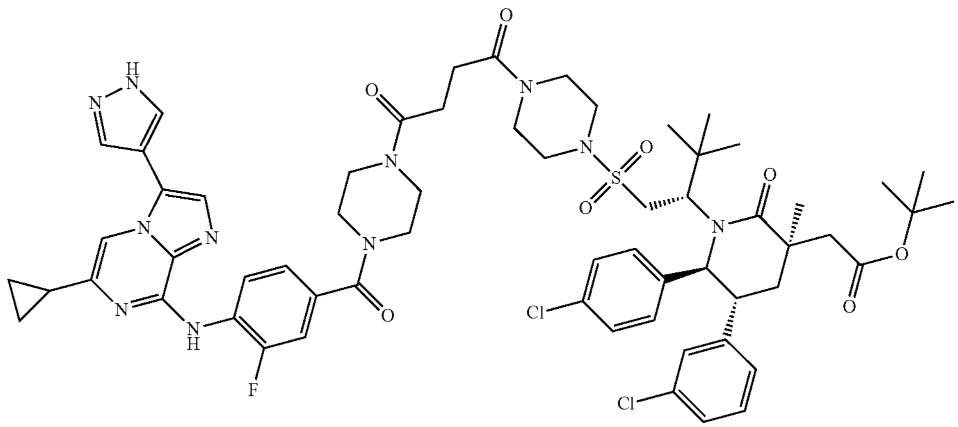
example 209

Example 209: 2-((3R,5R,6S)-5-(3-Chlorophenyl)-6-(4-chlorophenyl)-1-((S)-1-((4-(4-(4-(4-((6-cyclopropyl-3-(1H-pyrazol-4-yl)imidazo[1,2-a]pyrazin-8-yl)amino)-3-fluorobenzoyl)piperazin-1-yl)-4-oxobutanoyl)piperazin-1-yl)sulfonyl)-3,3-dimethylbutan-2-yl)-3-methyl-2-oxopiperidin-3-yl)acetic acid. The title compound can be synthesized according to the following procedures: To a solution of intermediate 7 (1 equiv.) and linker 30 (1.1 equiv.) in DMSO were added DIEA (7 equiv.) and TBTU (1.1 equiv.). After being stirred at rt for 1 h, the mixture will be diluted with DCM and TFA. The resulting solution will be stirred at rt for another 1 h. After concentrated, the residue will be purified by HPLC to yield the title compound.

Example compounds 210-223 will be synthesized from intermediate 7 and corresponding linkers according to the procedures for the preparation of example compound 209.

Scheme 34. Synthesis of Example 224

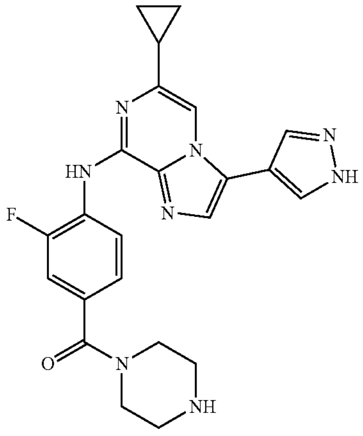

Intermediate 7

+

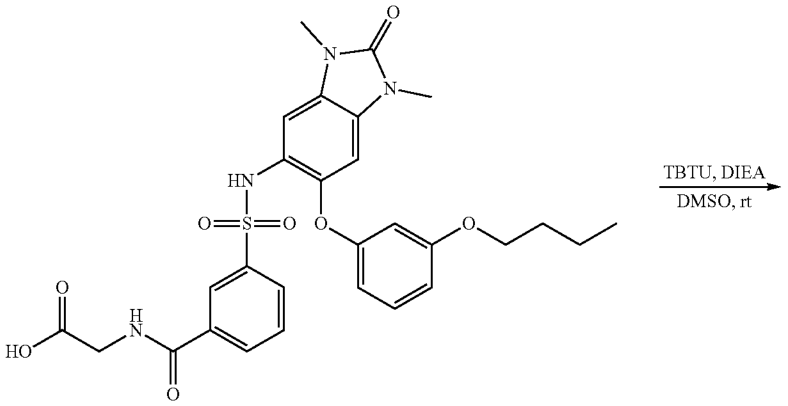

linker 31

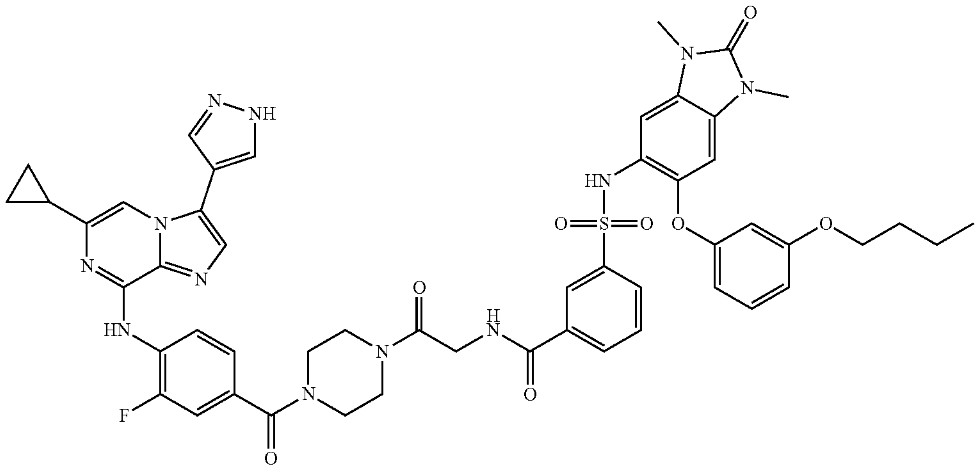

example 224

Example 224: N-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethyl)-3-(N-(1,3-dimethyl-2-oxo-6-(3-propoxyphenoxy)-2,3-dihydro-1H-benzo[d]imidazol-5-yl)sulfamoyl)benzamide. The title compound can be synthesized according to the following procedures: To a solution of intermediate 7 (1 equiv.) and linker 31 (1.1 equiv.) in DMSO will be added DIEA (7 equiv.) and TBTU (1.1 equiv.). After being stirred at rt for 1 h, the mixture will be purified by HPLC to yield the title compound.

Example compounds 225-239 will be synthesized from intermediate 7 and corresponding linkers according to the procedures for the preparation of example compound 209.

Scheme 35. Synthesis of Example 240

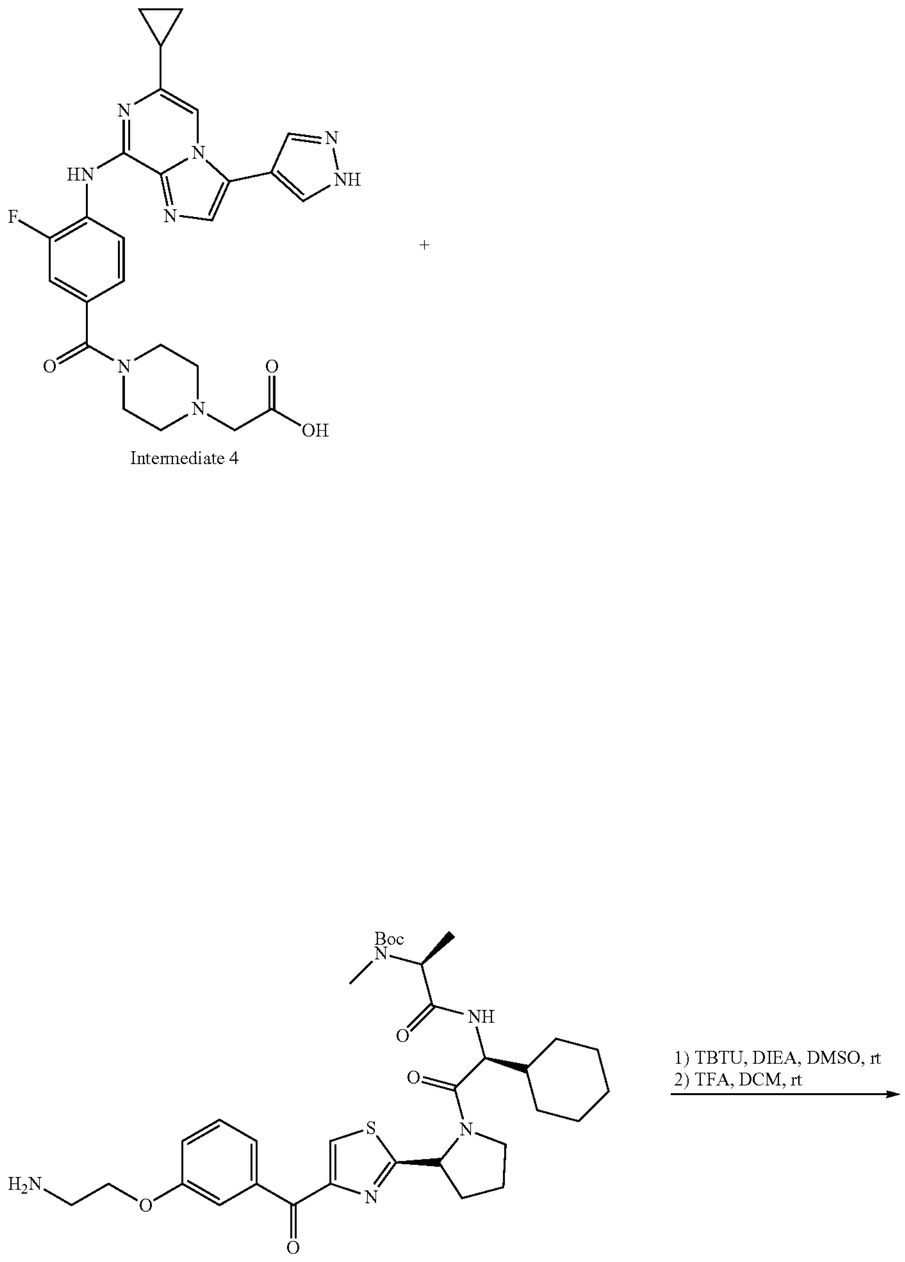

Intermediate 4

+ linker 32

-continued

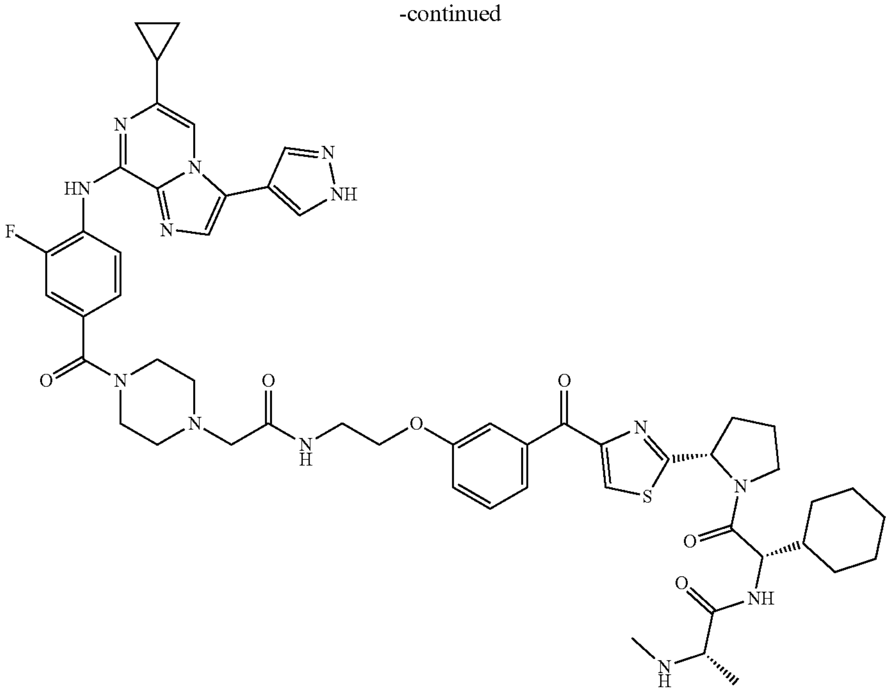

example 240

Example 240: (S)—N—((S)-1-Cyclohexyl-2-((S)-2-(4-(3-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)benzoyl)thiazol-2-yl)pyrrolidin-1-yl)-2-oxoethyl)-2-(methylamino)propenamide. The title compound can be synthesized according to the following procedures: To a solution of intermediate 4 (1 equiv.) and linker 32 (1.1 equiv.) in DMSO will be added DIEA (7 equiv.) and TBTU (1.1 equiv.). After being stirred at rt for 1 h, the mixture will be diluted with DCM and TFA. The resulting solution will be stirred at rt for another 1 h. After concentrated, the residue will be purified by HPLC to yield the title compound.

Example compounds 241-250 will be synthesized from intermediate 4 and corresponding linkers according to the procedures for the preparation of example compound 240.

Scheme 36. Synthesis of Example 251

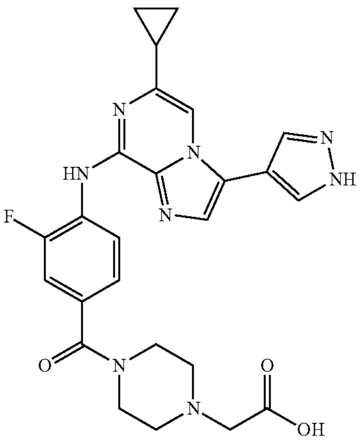

Intermediate 4

+

-continued

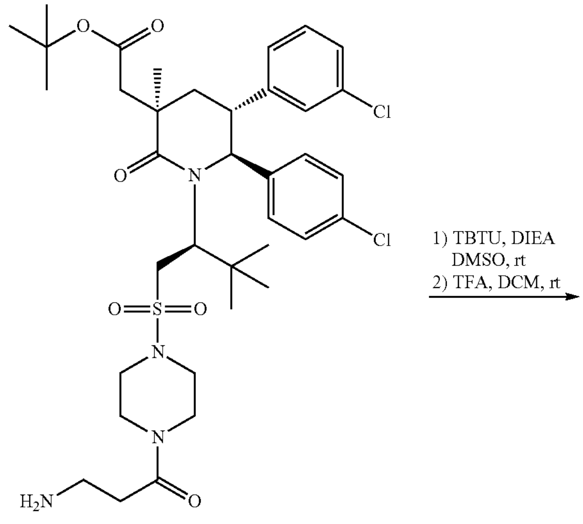

linker 32

-continued

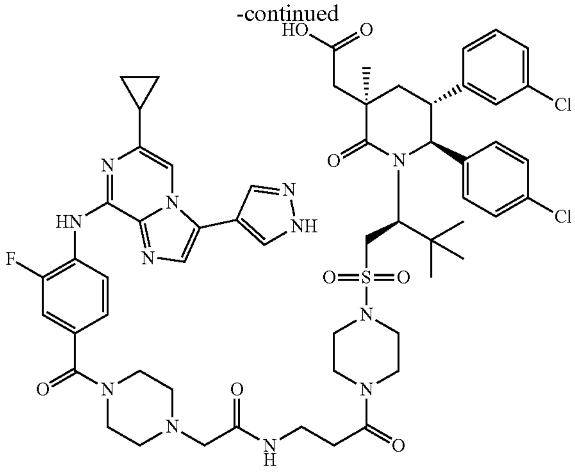

example 251

Example 251: 2-((3R,5R,6S)5-(3-Chlorophenyl)-6-(4-chlorophenyl)-1-((S)-1-((4-(3-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)propanoyl) piperazin-1-yl)sulfonyl)-3,3-dimethylbutan-2-yl)-3-methyl-2-oxopiperidin-3-yl)acetic acid. The title compound can be synthesized according to the following procedures: To a solution of intermediate 4 (1 equiv.) and linker 33 (1.1 equiv.) in DMSO will be added DIEA (7 equiv.) and TBTU (1.1 equiv.). After being stirred at rt for 1 h, the mixture will be diluted with DCM and TFA. The resulting solution will be stirred at rt for another 1 h. After concentration, the residue will be purified by HPLC to yield the title compound.

Example compounds 252-259 will be synthesized from intermediate 4 and corresponding linkers according to the procedures for the preparation of example compound 251.

Scheme 37. Synthesis of Example 260

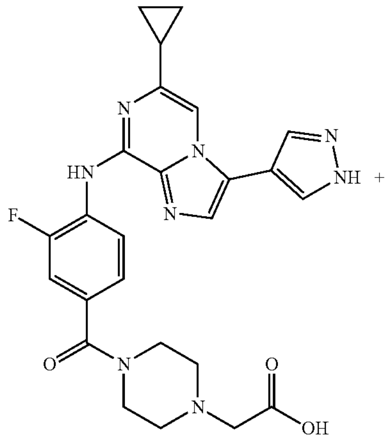

intermediate 4

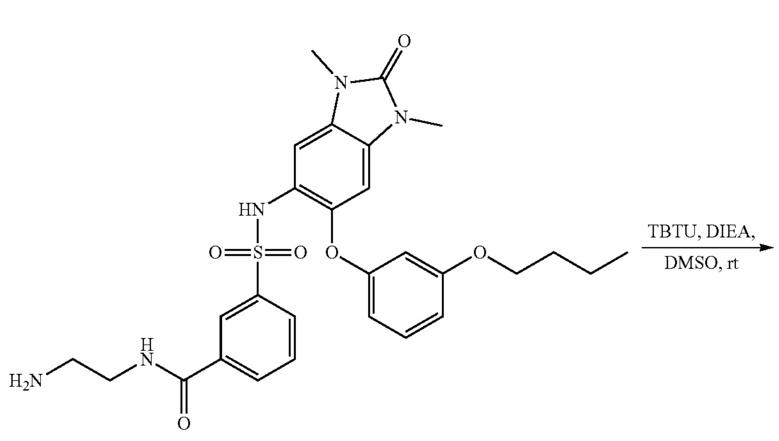

linker 34

-continued

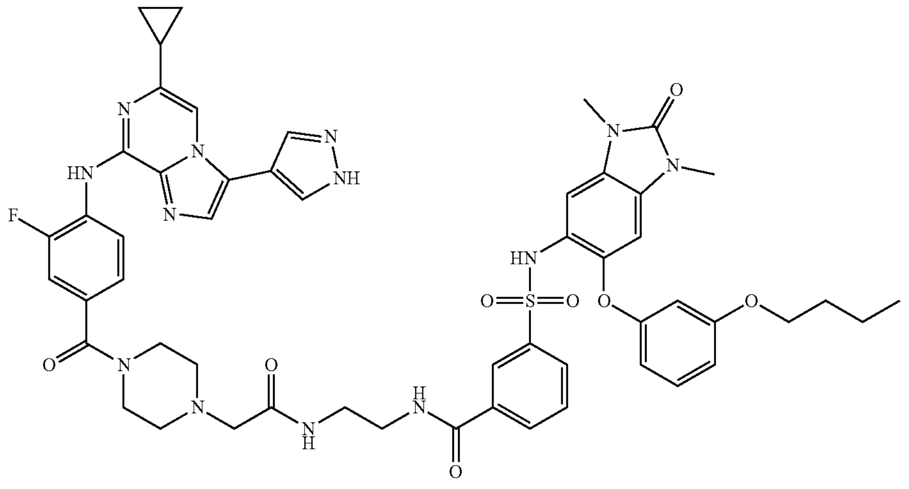

example 260

Example 260: 3-(N-(6-(3-Butoxyphenoxy)-1,3-dimethyl-2-oxo-2,3-dihydro-1H-benzo[d]imidazol-5-yl)sulfamoyl)-N-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethyl)benzamide. The title compound can be synthesized according to the following procedures: To a solution of intermediate 4 (1 equiv.) and linker 34 (1.1 equiv.) in DMSO will be added DIEA (7 equiv.) and TBTU (1.1 equiv.). After being stirred at it for 1 h, the mixture will be purified by HPLC to yield the title compound.

Example compounds 261-269 will be synthesized from intermediate 4 and corresponding linkers according to the procedures for the preparation of example compound 260.

Scheme 38. Synthesis of Example 270

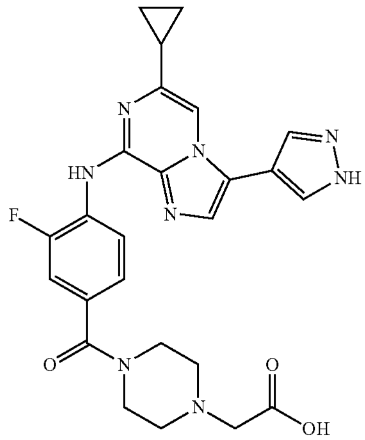

Intermediate 4

+

-continued

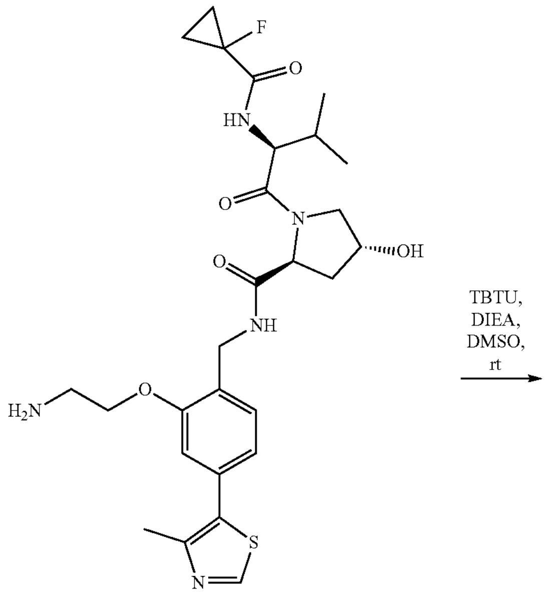

linker 35

-continued

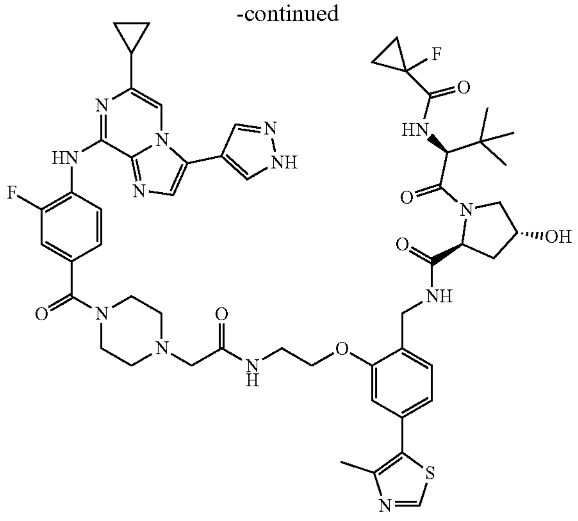

example 270

Example 270: (2S,4R)—N-(2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide. To a solution of intermediate 4 (1 equiv.) and linker 35 (1.1 equiv.) in DMSO will be added DIEA (7 equiv.) and TBTU (1.1 equiv.). After being stirred at rt for 1 h, the mixture will be purified by HPLC to yield the title compound. Example compounds 271-280 will be synthesized from intermediate 4 and corresponding linkers according to the procedures for the preparation of example compound 270.

Example compounds are set forth in Table 1 below.

TABLE 1

| Cpd. Example Number | Cpd. Code | Structure |
|---|---|---|
| 1 | YX39-89 | 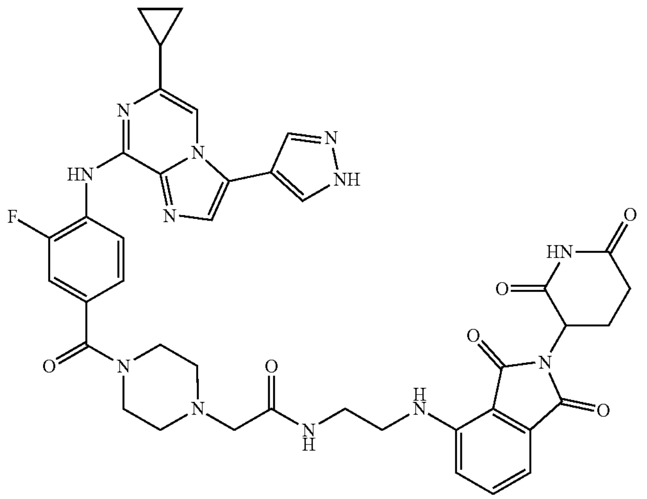 [SMILES: O=C(CN1CCN(C(=O)c2ccc(Nc3nc(C4CC4)cn4c(-c5cn[nH]c5)cnc34)c(F)c2)CC1)NCCNc1cccc2c1C(=O)N(C1CCC(=O)NC1=O)C2=O] |

TABLE 1-continued
| | | |
|---|---|---|
| 2 | YX39-86 | 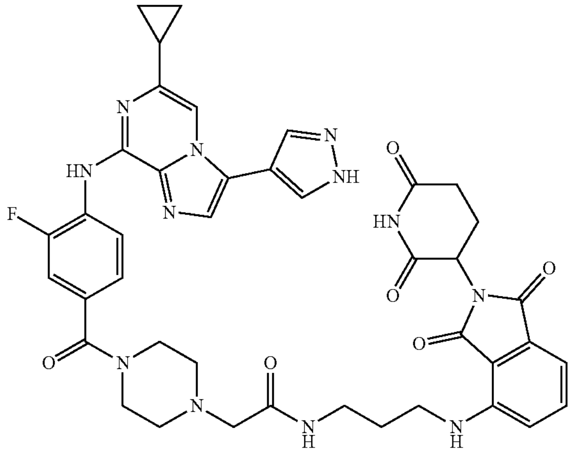 [SMILES: O=C(CN1CCN(C(=O)c2ccc(Nc3nc(C4CC4)cn4c(-c5cn[nH]c5)cnc34)c(F)c2)CC1)NCCCNc1cccc2c1C(=O)N(C1CCC(=O)NC1=O)C2=O] |
| 3 | YX39-90 | 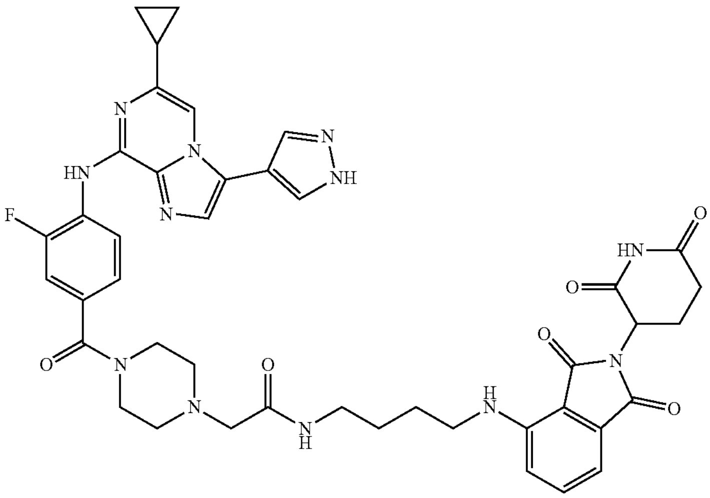 [SMILES: O=C(CN1CCN(C(=O)c2ccc(Nc3nc(C4CC4)cn4c(-c5cn[nH]c5)cnc34)c(F)c2)CC1)NCCCCNc1cccc2c1C(=O)N(C1CCC(=O)NC1=O)C2=O] |
| 4 | YX39-91 | 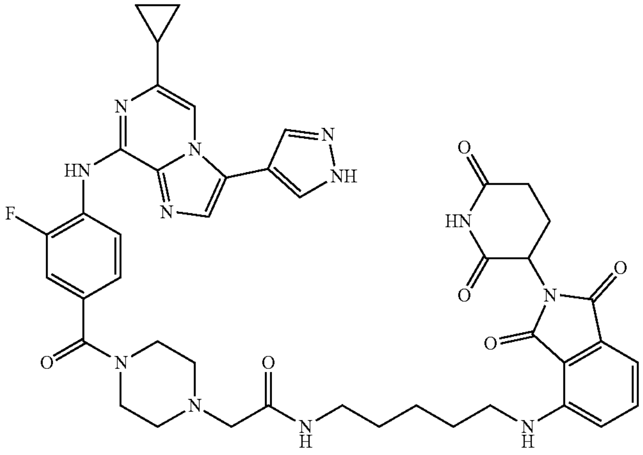 [SMILES: O=C(CN1CCN(C(=O)c2ccc(Nc3nc(C4CC4)cn4c(-c5cn[nH]c5)cnc34)c(F)c2)CC1)NCCCCCNc1cccc2c1C(=O)N(C1CCC(=O)NC1=O)C2=O] |

TABLE 1-continued
| | | |
|---|---|---|
| 5 | YX39-92 | 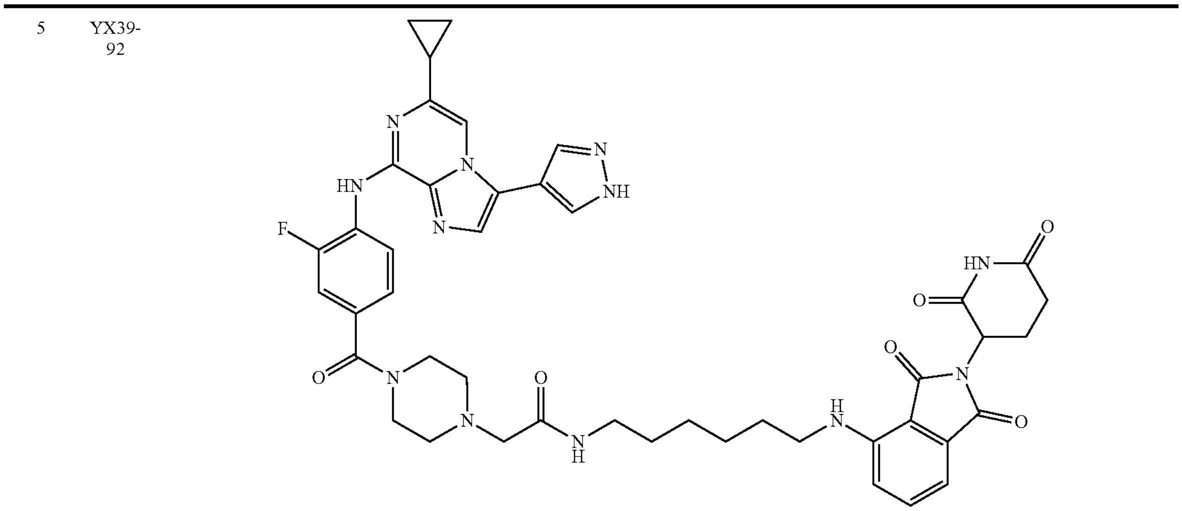 |
| 6 | YX39-93 | 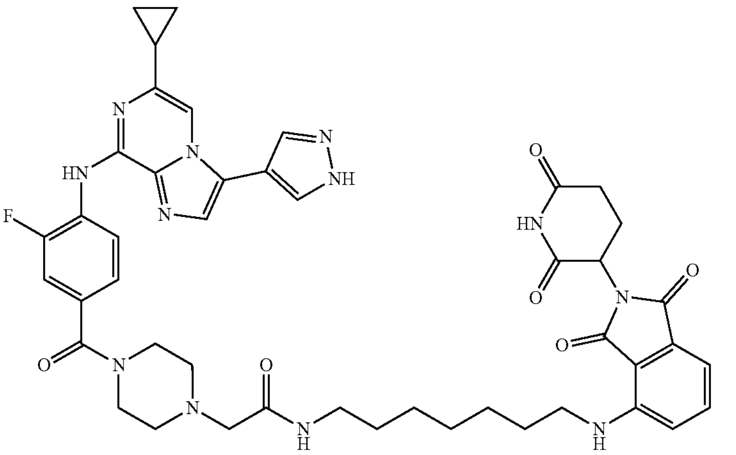 [SMILES: O=C(CN1CCN(C(=O)c2ccc(Nc3nc(C4CC4)cn4c(-c5cn[nH]c5)cnc34)c(F)c2)CC1)NCCCCCCCNc1cccc2c1C(=O)N(C1CCC(=O)NC1=O)C2=O] |
| 7 | YX39-94 | 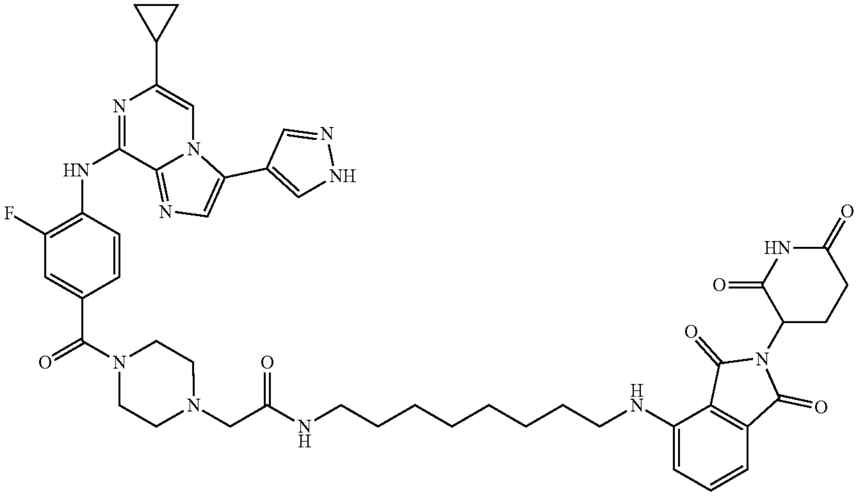 |

TABLE 1-continued
| | | |
|---|---|---|
| 8 | YX39-96 | 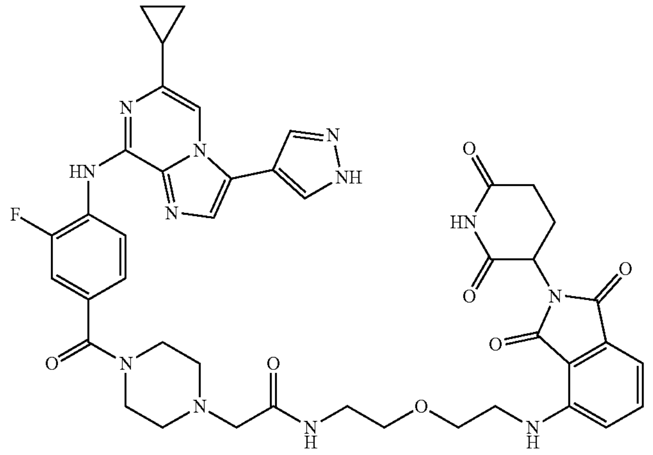 [SMILES: O=C(CN1CCN(C(=O)c2ccc(Nc3nc(C4CC4)cn4c(-c5cn[nH]c5)cnc34)c(F)c2)CC1)NCCOCCNc1cccc2c1C(=O)N(C1CCC(=O)NC1=O)C2=O] |
| 9 | YX39-97 | 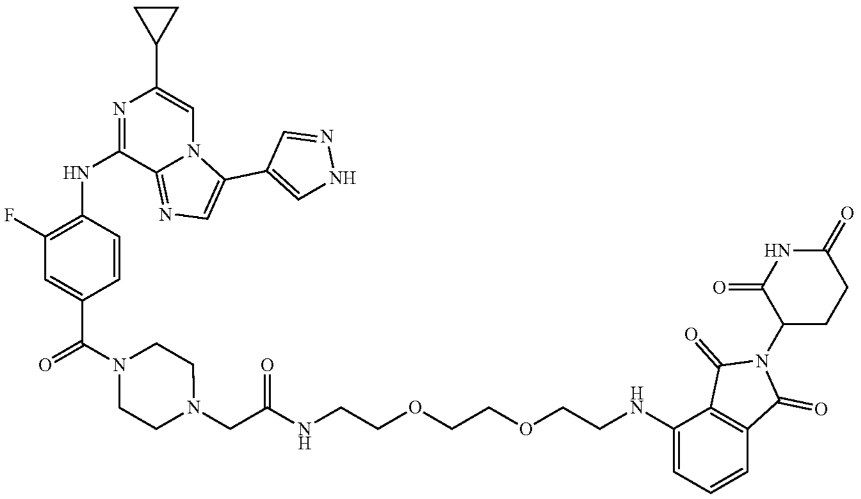 [SMILES: O=C(CN1CCN(C(=O)c2ccc(Nc3nc(C4CC4)cn4c(-c5cn[nH]c5)cnc34)c(F)c2)CC1)NCCOCCOCCNc1cccc2c1C(=O)N(C1CCC(=O)NC1=O)C2=O] |
| 10 | YX39-98 | 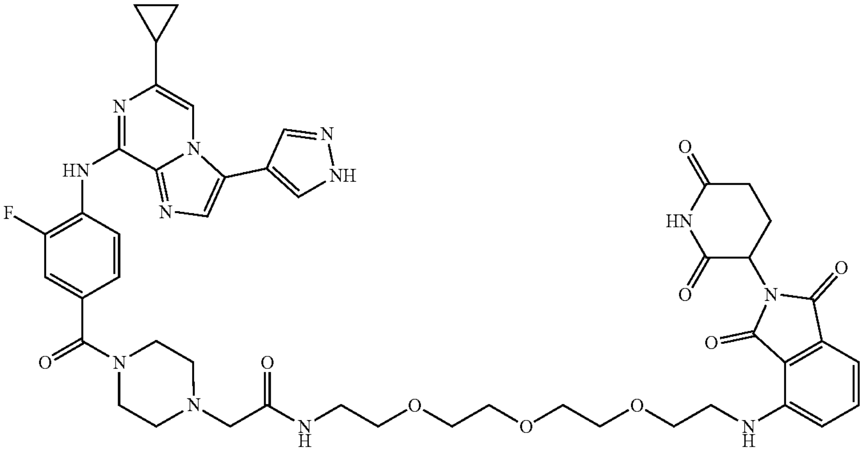 [SMILES: O=C(CN1CCN(C(=O)c2ccc(Nc3nc(C4CC4)cn4c(-c5cn[nH]c5)cnc34)c(F)c2)CC1)NCCOCCOCCOCCNc1cccc2c1C(=O)N(C1CCC(=O)NC1=O)C2=O] |

TABLE 1-continued
| | | |
|---|---|---|
| 11 | YX39-99 | 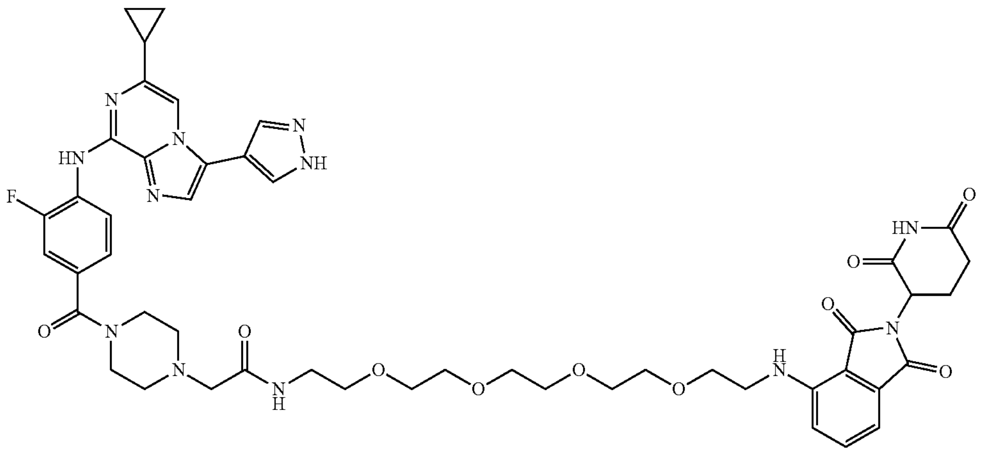 [SMILES: O=C(CN1CCN(C(=O)c2ccc(Nc3nc(C4CC4)cn4c(-c5cn[nH]c5)cnc34)c(F)c2)CC1)NCCOCCOCCOCCOCCNc1cccc2c1C(=O)N(C1CCC(=O)NC1=O)C2=O] |
| 12 | YX39-100 | 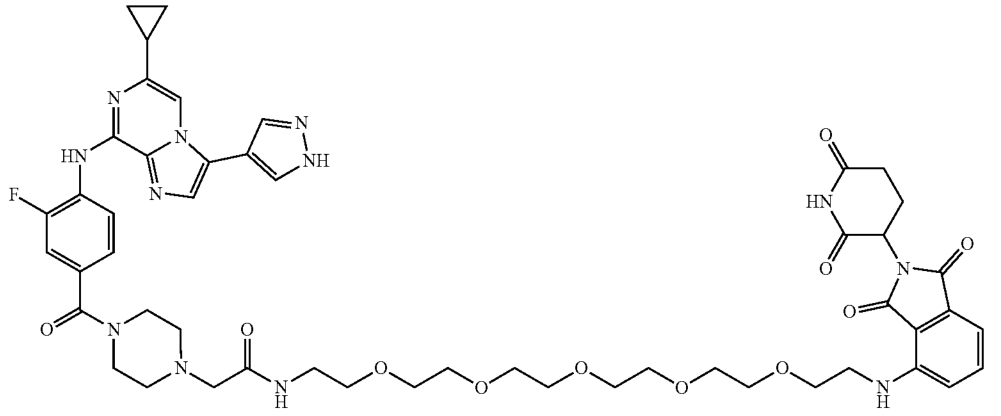 [SMILES: O=C(CN1CCN(C(=O)c2ccc(Nc3nc(C4CC4)cn4c(-c5cn[nH]c5)cnc34)c(F)c2)CC1)NCCOCCOCCOCCOCCOCCNc1cccc2c1C(=O)N(C1CCC(=O)NC1=O)C2=O] |
| 13 | YX39-101 | 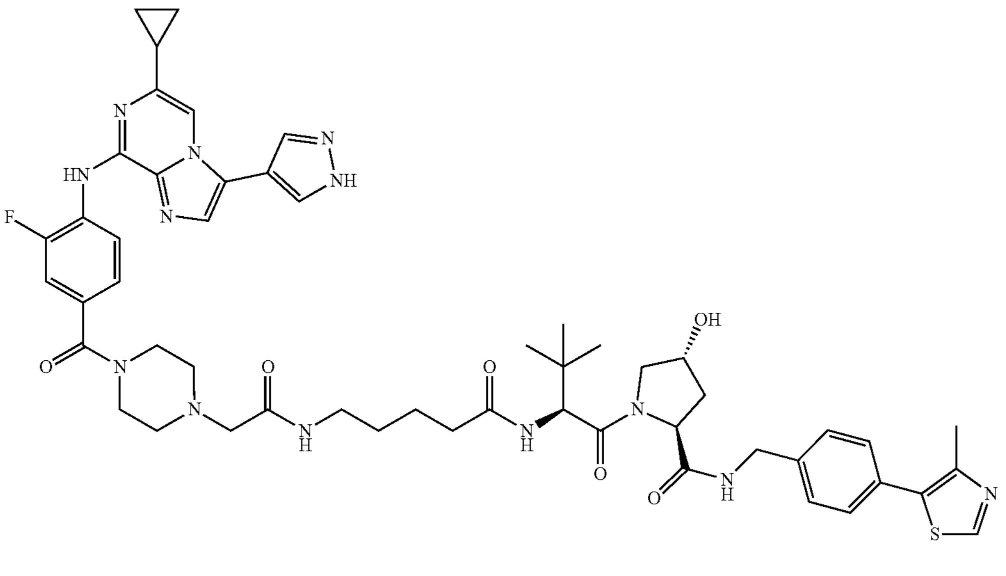 [SMILES: Cc1ncsc1-c1ccc(CNC(=O)[C@@H]2C[C@@H](O)CN2C(=O)[C@@H](NC(=O)CCCCNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 14 | YX39-102 | 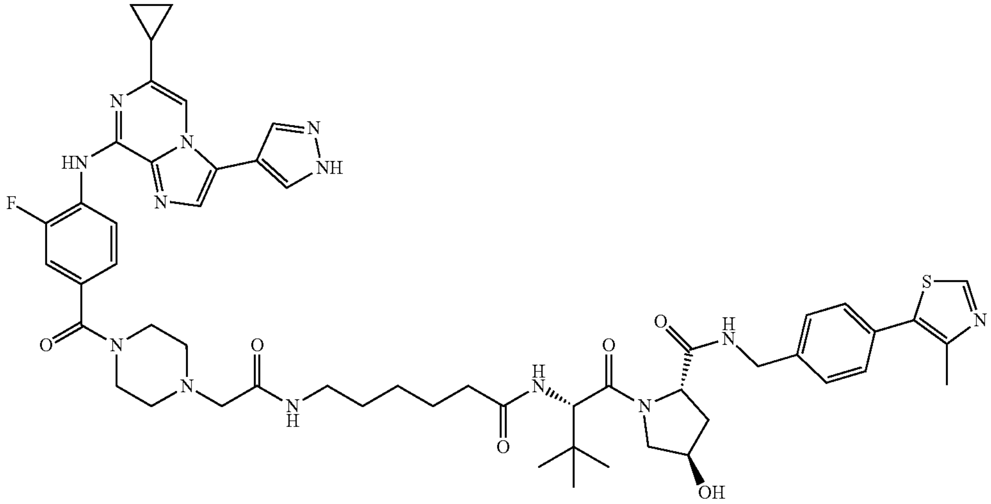 [SMILES: Cc1ncsc1-c1ccc(CNC(=O)[C@@H]2C[C@@H](O)CN2C(=O)[C@@H](NC(=O)CCCCCNC(=O)CN2CCN(C(=O)c3ccc(Nc4nc(C5CC5)cn5c(-c6cn[nH]c6)cnc45)c(F)c3)CC2)C(C)(C)C)cc1] |
| 15 | YX39-103 | 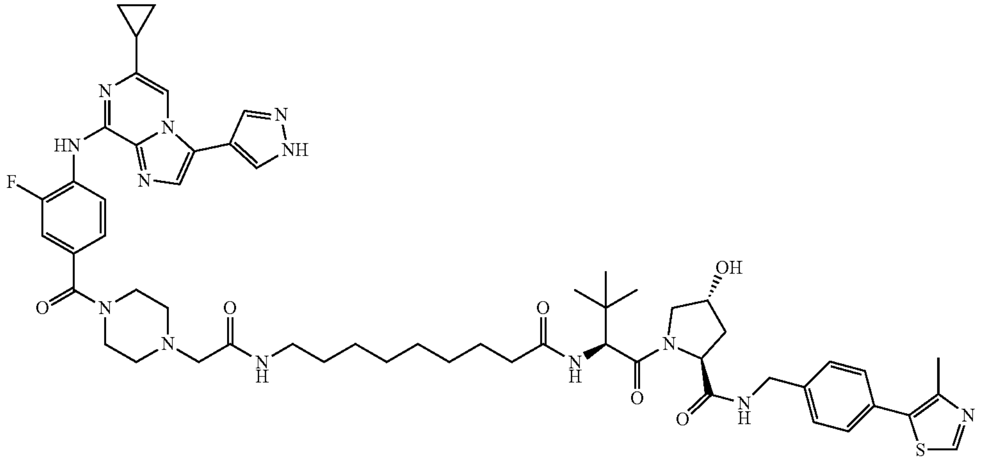 [SMILES: Cc1ncsc1-c1ccc(CNC(=O)[C@@H]2C[C@@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1] |
| 16 | YX39-104 | 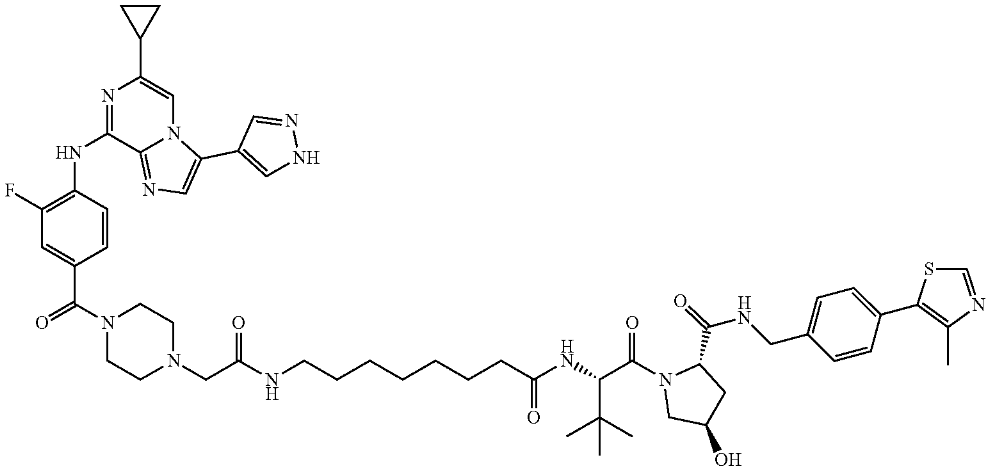 [SMILES: Cc1ncsc1-c1ccc(CNC(=O)[C@@H]2C[C@@H](O)CN2C(=O)[C@@H](NC(=O)CCCCCCCNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 17 | YX39-105 | 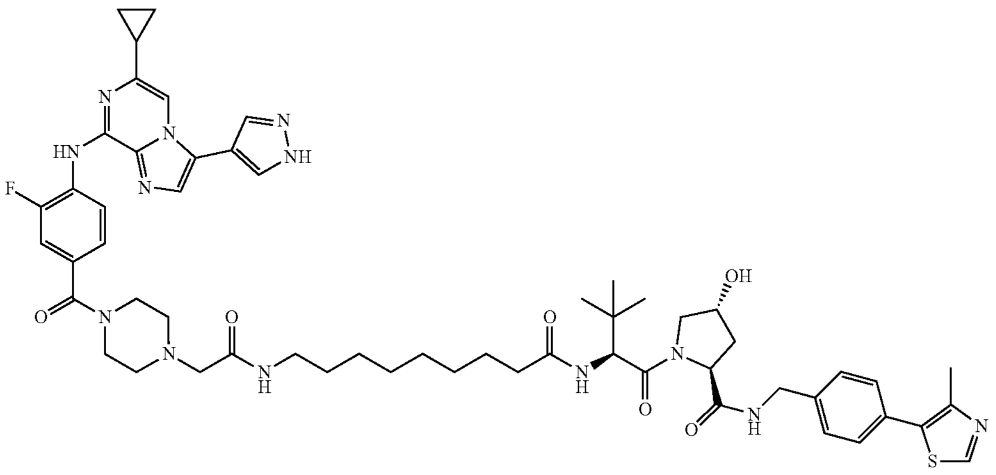 [SMILES: Cc1ncsc1-c1ccc(CNC(=O)[C@@H]2C[C@@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1] |
| 18 | YX39-106 | 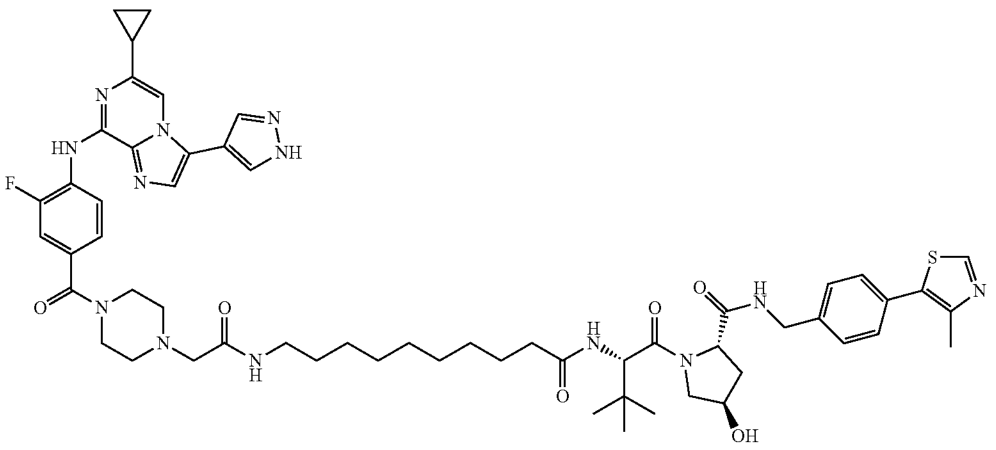 [SMILES: Cc1ncsc1-c1ccc(CNC(=O)[C@@H]2C[C@@H](O)CN2C(=O)[C@@H](NC(=O)CCCCCCCCCNC(=O)CN2CCN(C(=O)c3ccc(Nc4nc(C5CC5)cn5c(-c6cn[nH]c6)cnc45)c(F)c3)CC2)C(C)(C)C)cc1] |
| 19 | YX39-107 | 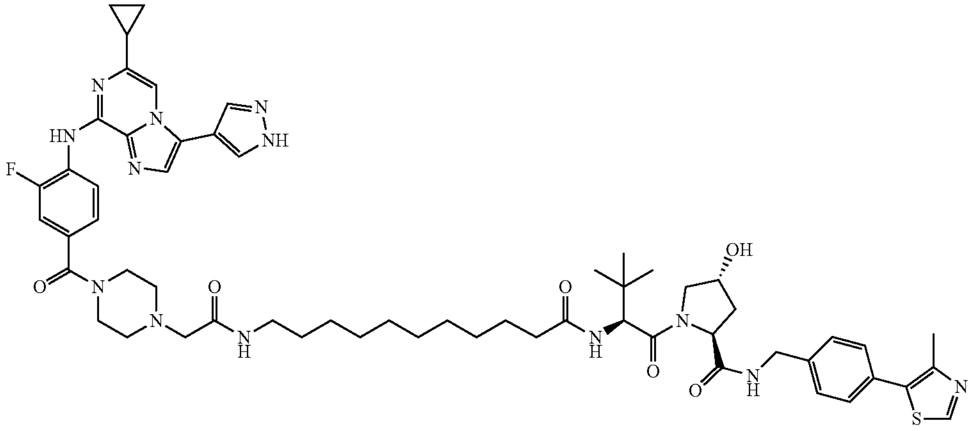 [SMILES: Cc1ncsc1-c1ccc(CNC(=O)[C@@H]2C[C@@H](O)CN2C(=O)[C@@H](NC(=O)CCCCCCCCCCNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 20 | YX39-127 | 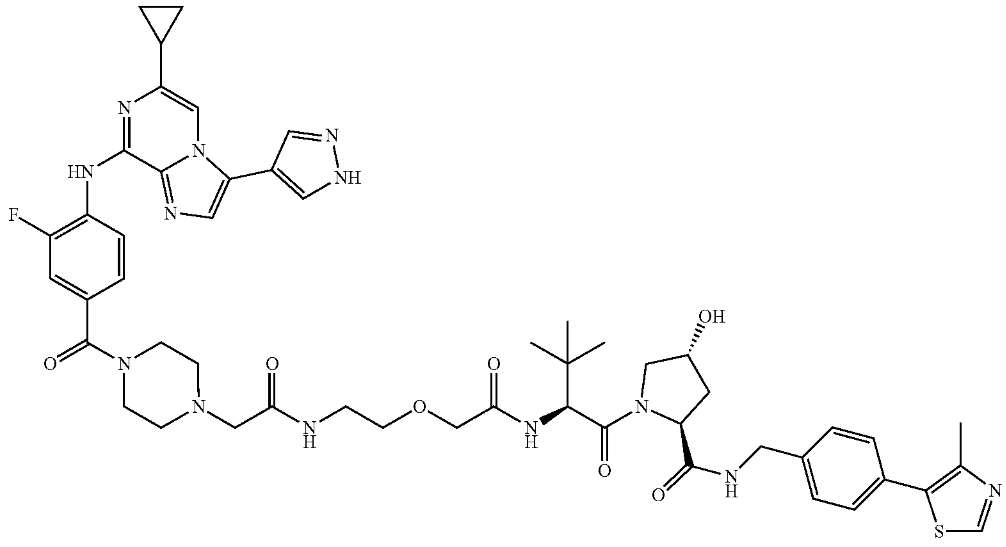 |
| 21 | YX39-128 | 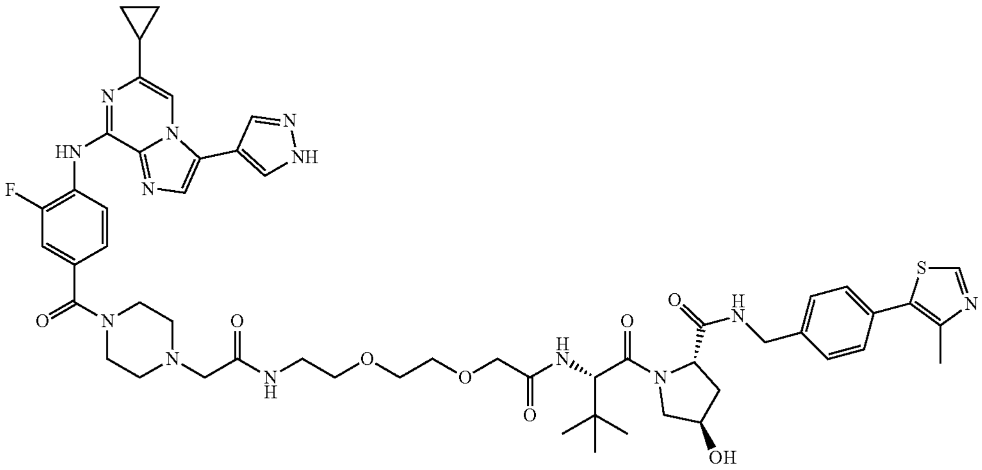 [SMILES: Cc1ncsc1-c1ccc(CNC(=O)[C@@H]2C[C@@H](O)CN2C(=O)[C@@H](NC(=O)COCCOCCNC(=O)CN2CCN(C(=O)c3ccc(Nc4nc(C5CC5)cn5c(-c6cn[nH]c6)cnc45)c(F)c3)CC2)C(C)(C)C)cc1] |
| 22 | YX39-129 | 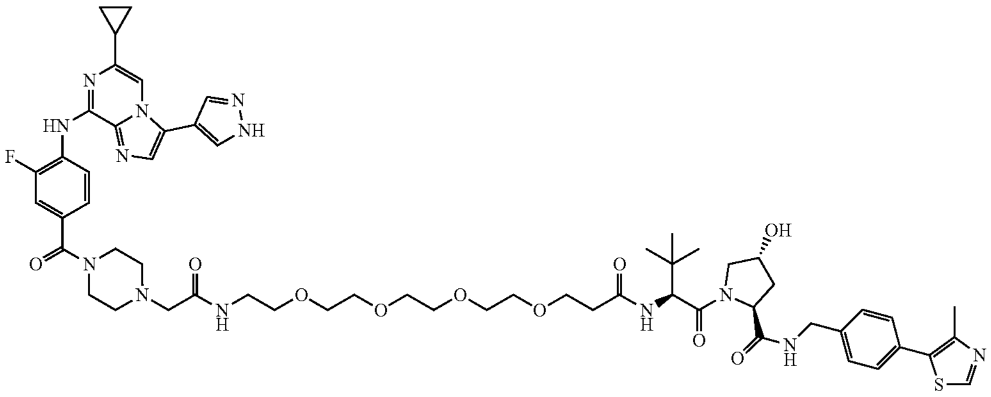 [SMILES: Cc1ncsc1-c1ccc(CNC(=O)[C@@H]2C[C@@H](O)CN2C(=O)[C@@H](NC(=O)CCOCCOCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 23 | YX49-8 | 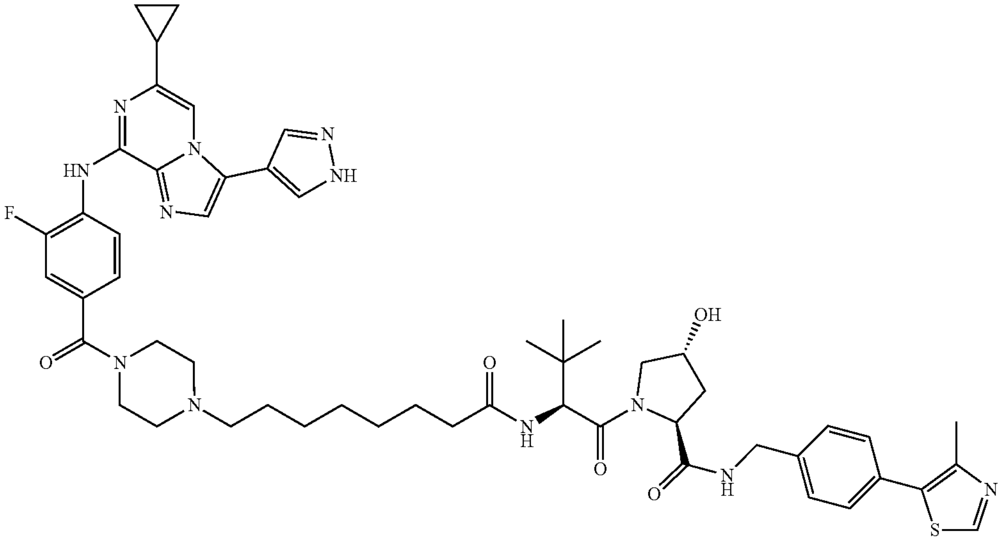 [SMILES: Cc1ncsc1-c1ccc(CNC(=O)[C@@H]2C[C@@H](O)CN2C(=O)[C@@H](NC(=O)CCCCCCCN2CCN(C(=O)c3ccc(Nc4nc(C5CC5)cn5c(-c6cn[nH]c6)cnc45)c(F)c3)CC2)C(C)(C)C)cc1] |
| 24 | YX49-7-2 | 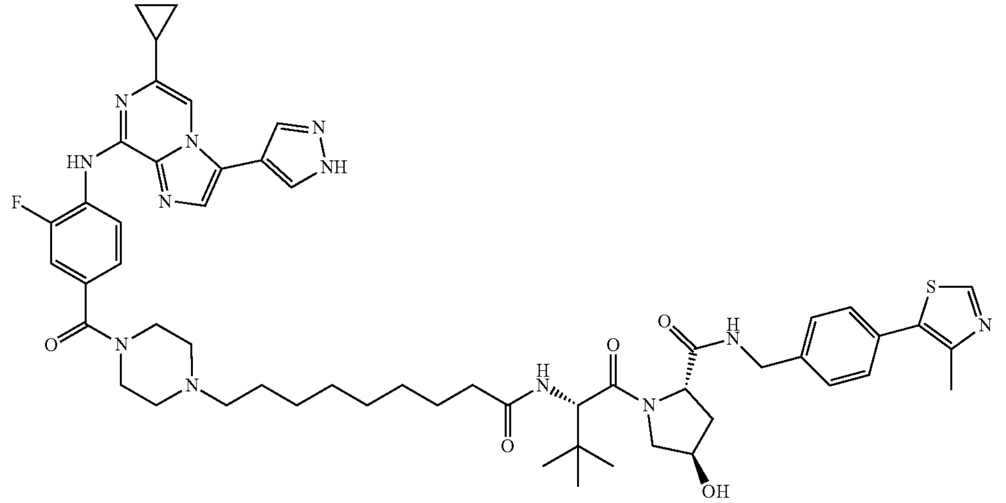 [SMILES: Cc1ncsc1-c1ccc(CNC(=O)[C@@H]2C[C@@H](O)CN2C(=O)[C@@H](NC(=O)CCCCCCCCN2CCN(C(=O)c3ccc(Nc4nc(C5CC5)cn5c(-c6cn[nH]c6)cnc45)c(F)c3)CC2)C(C)(C)C)cc1] |
| 25 | YX49-9 | 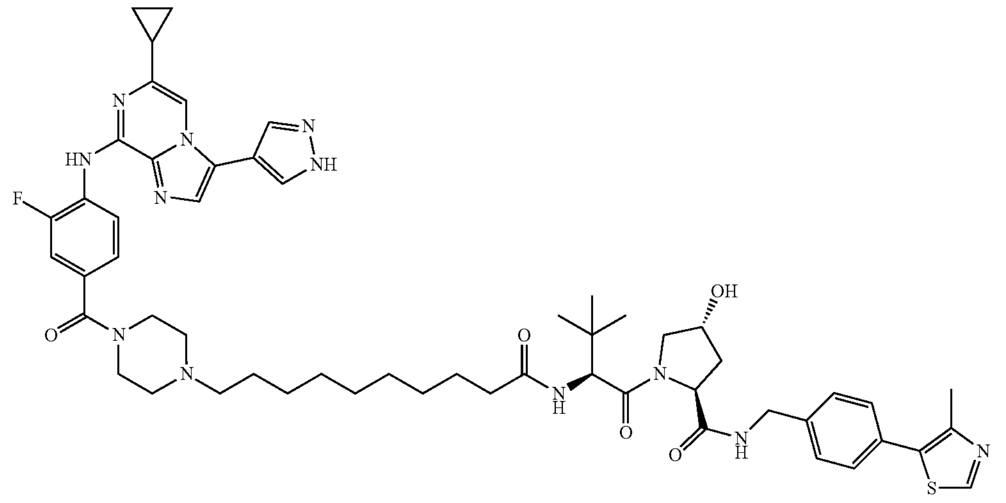 [SMILES: Cc1ncsc1-c1ccc(CNC(=O)[C@@H]2C[C@@H](O)CN2C(=O)[C@@H](NC(=O)CCCCCCCCCN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 26 | YX49-10 | 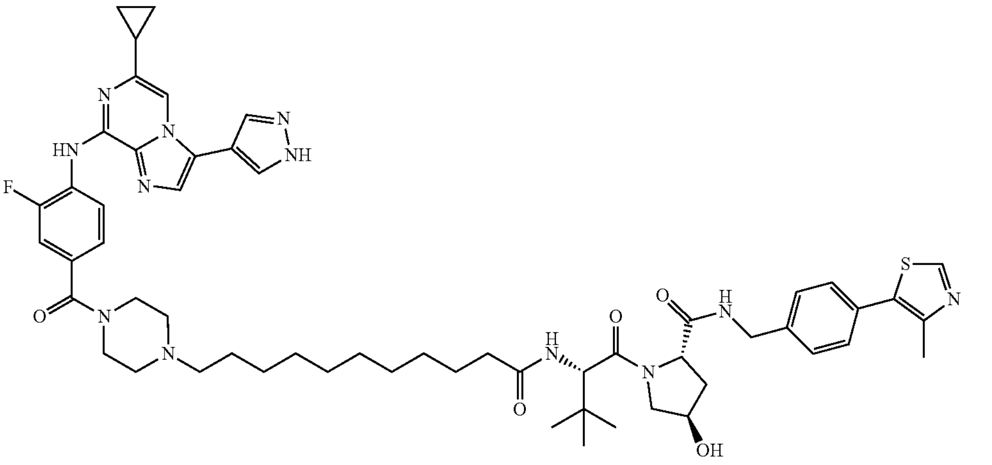 [SMILES: Cc1ncsc1-c1ccc(CNC(=O)[C@@H]2C[C@@H](O)CN2C(=O)[C@@H](NC(=O)CCCCCCCCCCN2CCN(C(=O)c3ccc(Nc4nc(C5CC5)cn5c(-c6cn[nH]c6)cnc45)c(F)c3)CC2)C(C)(C)C)cc1] |
| 27 | YX49-11 | 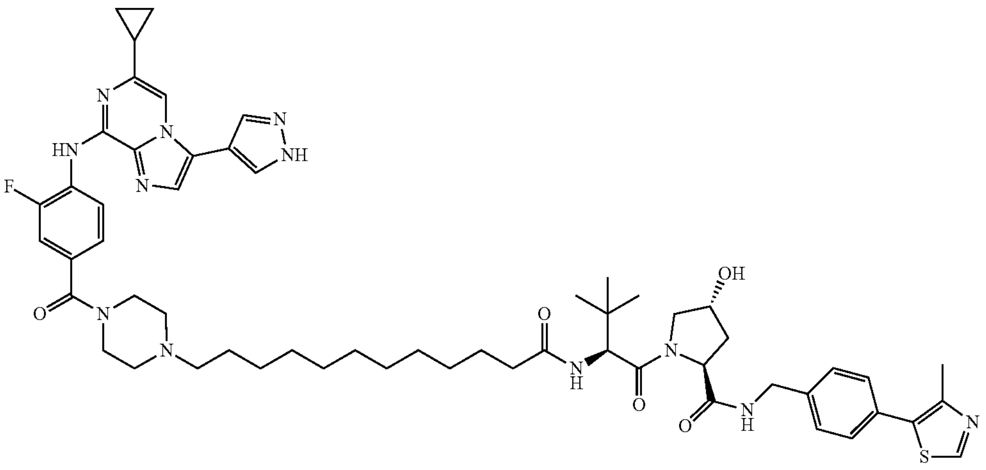 [SMILES: Cc1ncsc1-c1ccc(CNC(=O)[C@@H]2C[C@@H](O)CN2C(=O)[C@@H](NC(=O)CCCCCCCCCCCN2CCN(C(=O)c3ccc(Nc4nc(C5CC5)cn5c(-c6cn[nH]c6)cnc45)c(F)c3)CC2)C(C)(C)C)cc1] |
| 28 | YX44-158 | 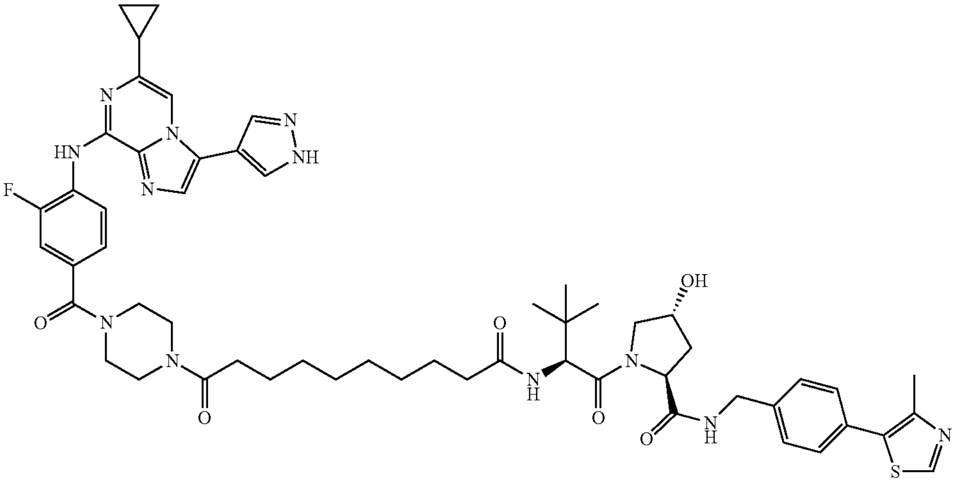 |

TABLE 1-continued
| | | |
|---|---|---|
| 29 | YX44-184 | 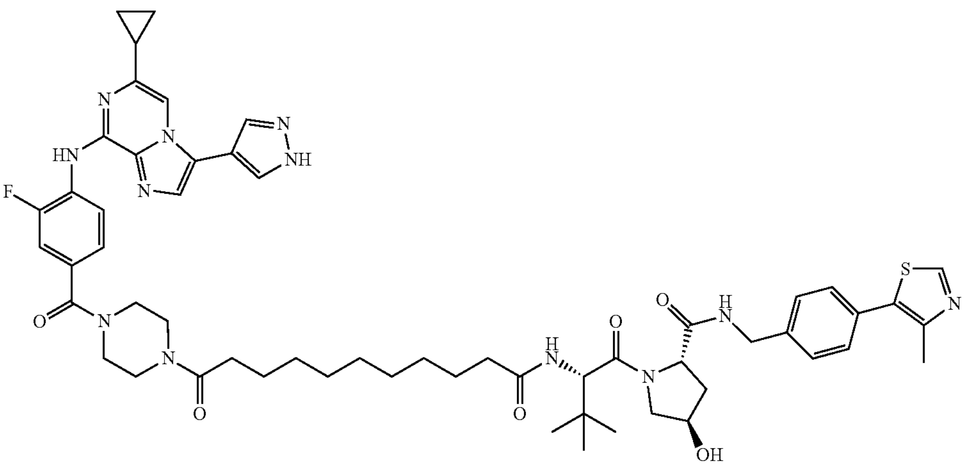 |
| 30 | YX49-24 | 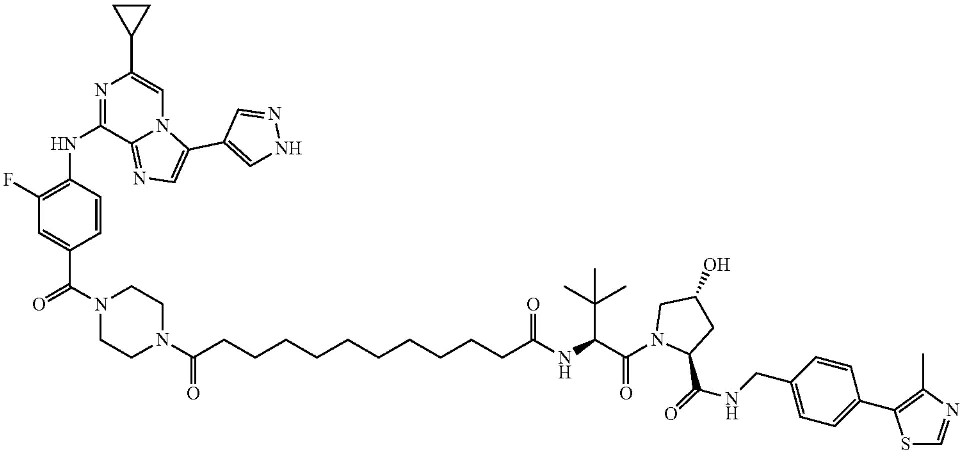 [SMILES: Cc1ncsc1-c1ccc(CNC(=O)[C@@H]2C[C@@H](O)CN2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1] |
| 31 | YX44-172 | 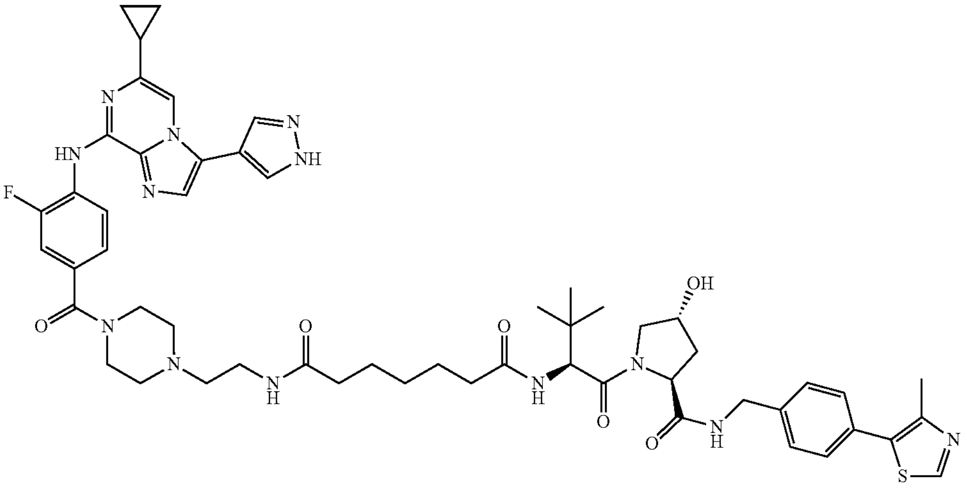 [SMILES: Cc1ncsc1-c1ccc(CNC(=O)[C@@H]2C[C@@H](O)CN2C(=O)[C@@H](NC(=O)CCCCCC(=O)NCCN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 32 | YX49-100 | 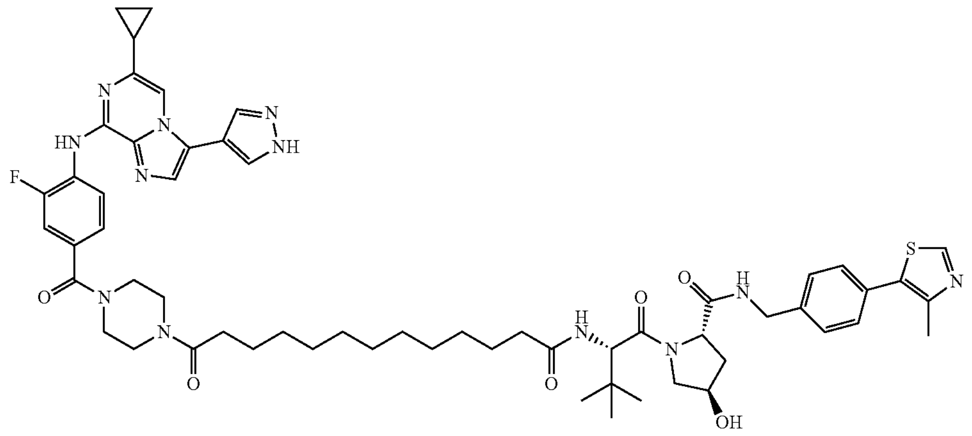 |
| 33 | YX49-101 | 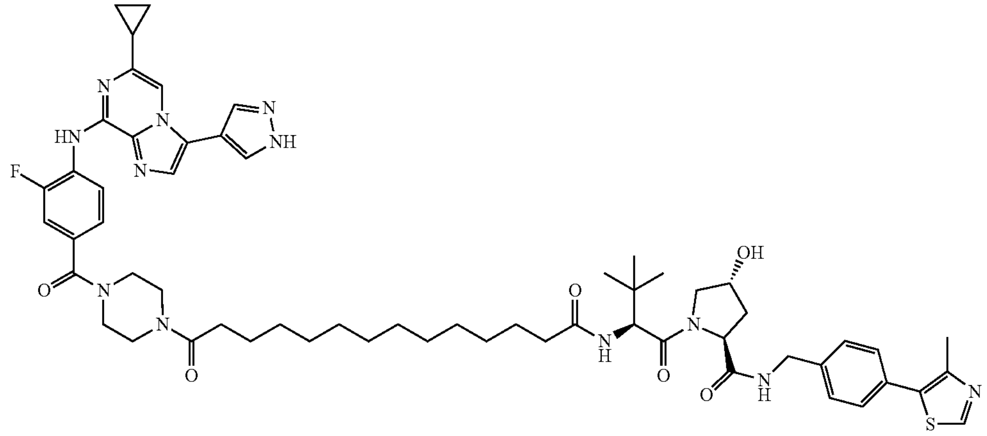 [SMILES: Cc1ncsc1-c1ccc(CNC(=O)[C@@H]2C[C@@H](O)CN2C(=O)[C@@H](NC(=O)CCCCCCCCCCCCC(=O)N2CCN(C(=O)c3ccc(Nc4nc(C5CC5)cn5c(-c6cn[nH]c6)cnc45)c(F)c3)CC2)C(C)(C)C)cc1] |
| 34 | YX49-99 | 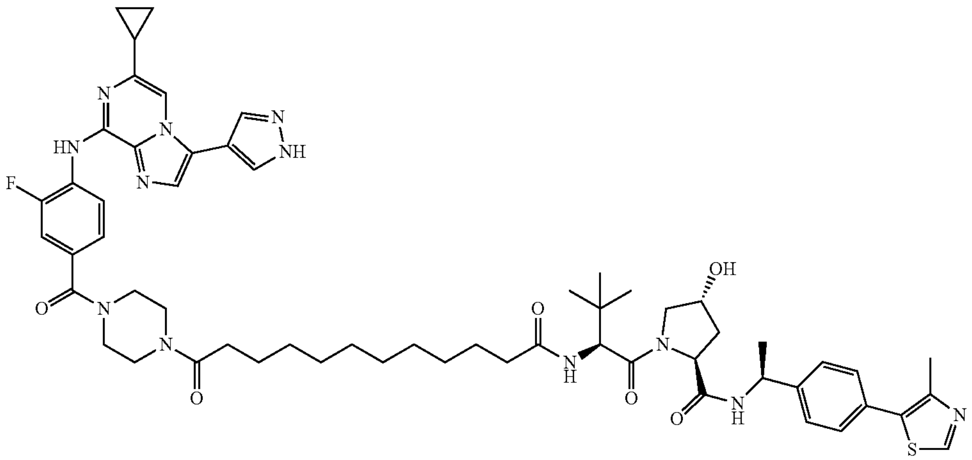 [SMILES: Cc1ncsc1-c1ccc([C@H](C)NC(=O)[C@@H]2C[C@@H](O)CN2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 35 | YX59-122 | 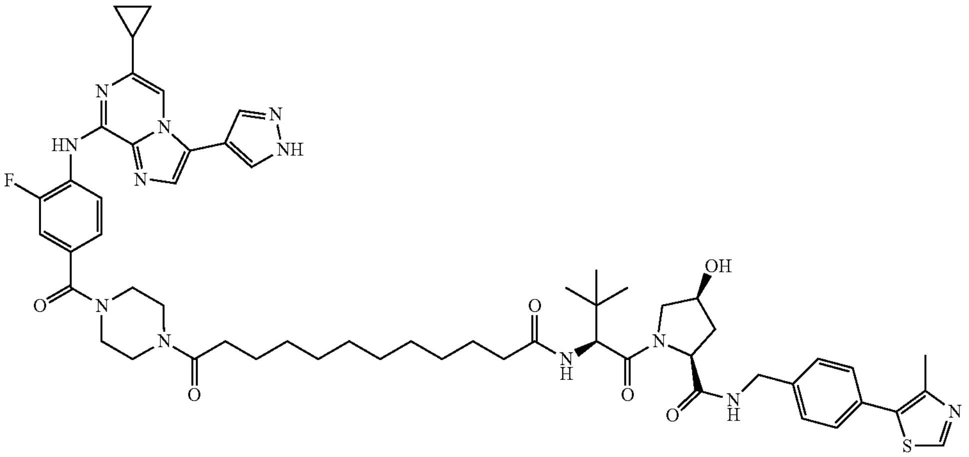 [SMILES: Cc1ncsc1-c1ccc(CNC(=O)[C@@H]2C[C@H](O)CN2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1] |
| 36 | YX69-5 | 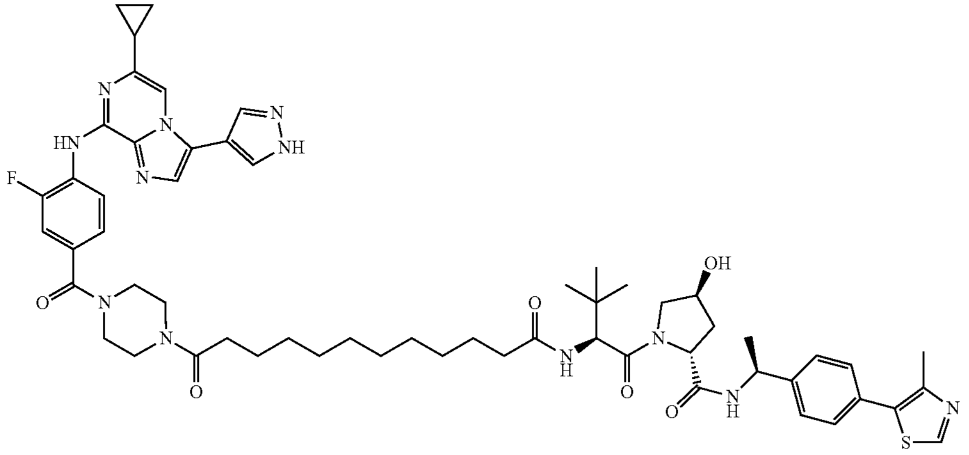 [SMILES: Cc1ncsc1-c1ccc([C@H](C)NC(=O)[C@H]2C[C@H](O)CN2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1] |
| 37 | YX69-157 | 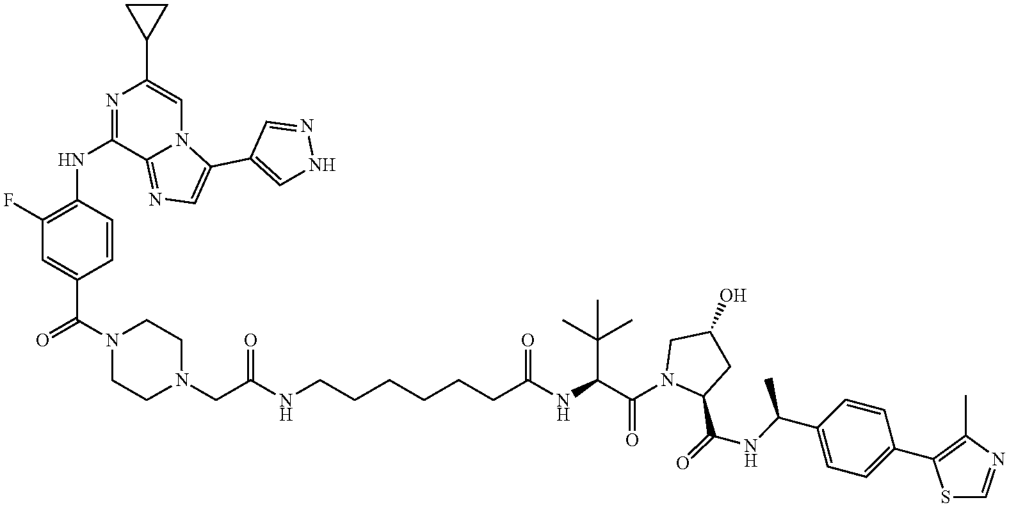 [SMILES: Cc1ncsc1-c1ccc([C@H](C)NC(=O)[C@@H]2C[C@@H](O)CN2C(=O)[C@@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 38 | YX69-158 | 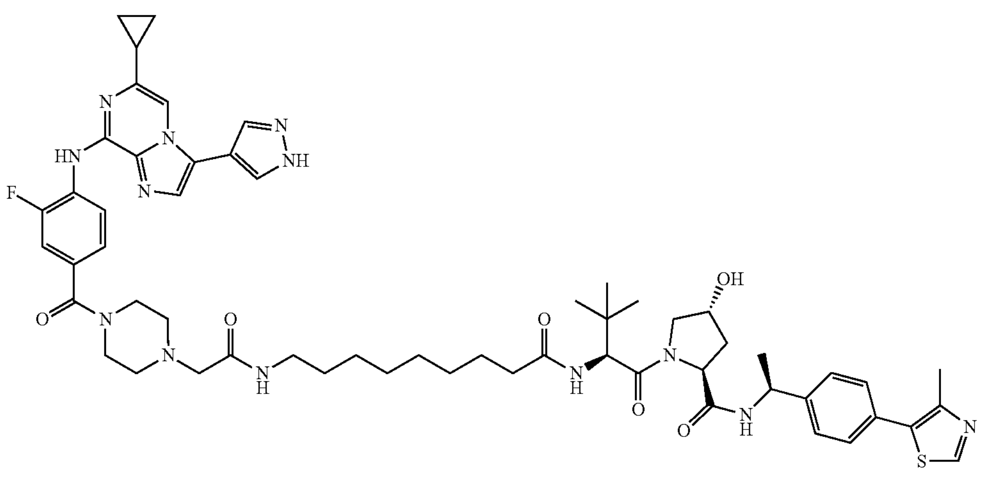 [SMILES: Cc1ncsc1-c1ccc([C@H](C)NC(=O)[C@@H]2C[C@@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1] |
| 39 | YX69-159 | 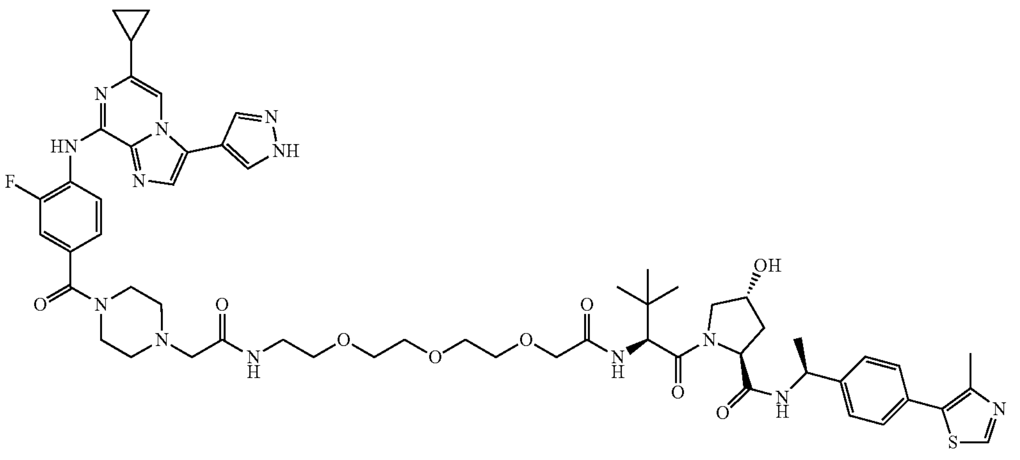 [SMILES: Cc1ncsc1-c1ccc([C@H](C)NC(=O)[C@@H]2C[C@@H](O)CN2C(=O)[C@@H](NC(=O)COCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1] |
| 40 | YX69-182 | 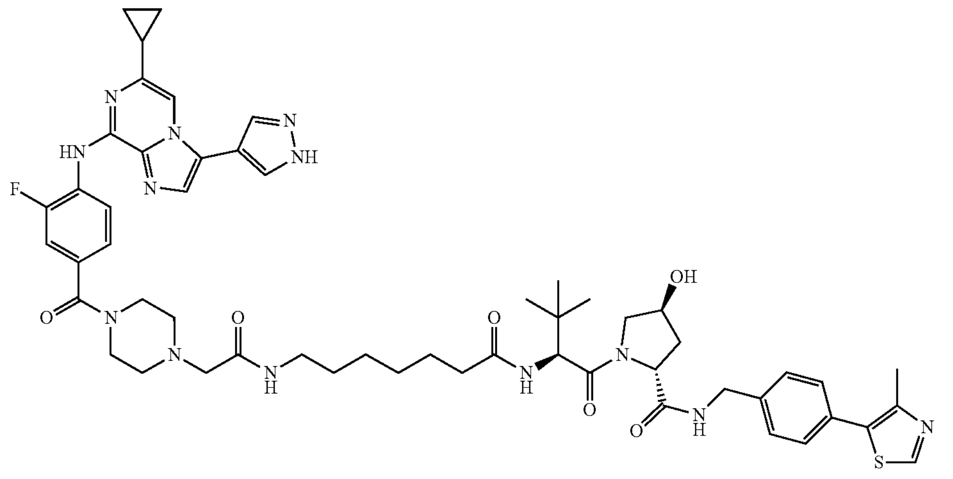 [SMILES: Cc1ncsc1-c1ccc(CNC(=O)[C@H]2C[C@H](O)CN2C(=O)[C@@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 41 | YX69-183 | 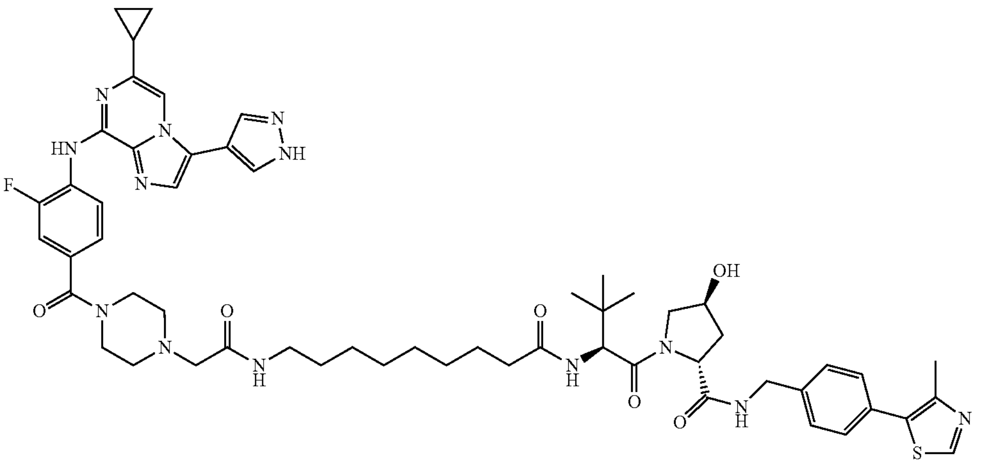 [SMILES: Cc1ncsc1-c1ccc(CNC(=O)[C@H]2C[C@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1] |
| 42 | YX69-184 | 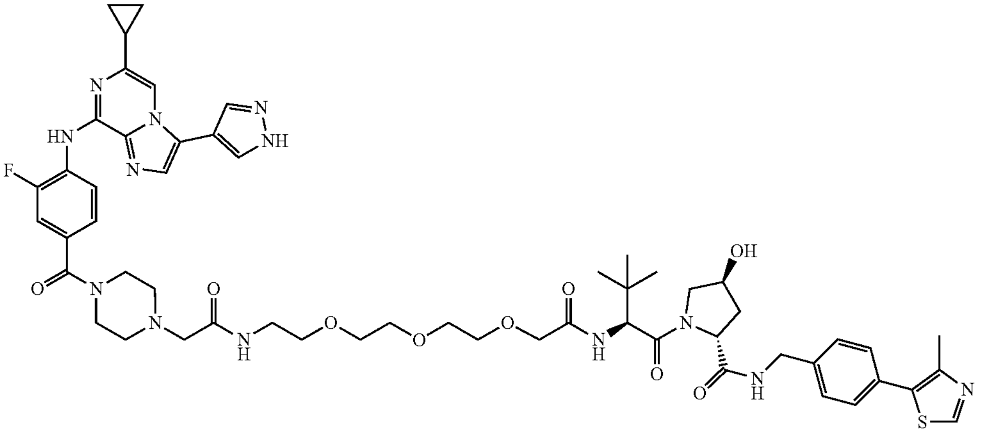 [SMILES: Cc1ncsc1-c1ccc(CNC(=O)[C@H]2C[C@H](O)CN2C(=O)[C@@H](NC(=O)COCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1] |
| 43 | YX79-3 | 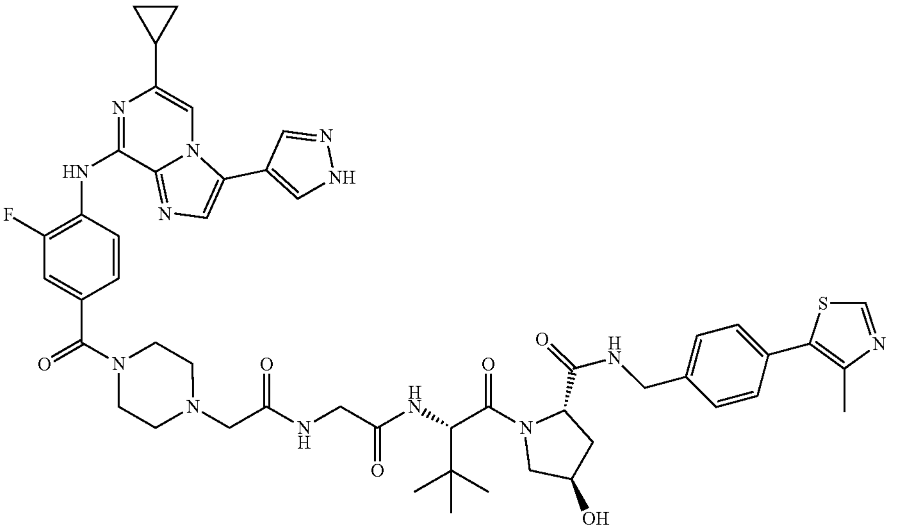 [SMILES: Cc1ncsc1-c1ccc(CNC(=O)[C@@H]2C[C@@H](O)CN2C(=O)[C@@H](NC(=O)CNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 44 | YX79-4 | 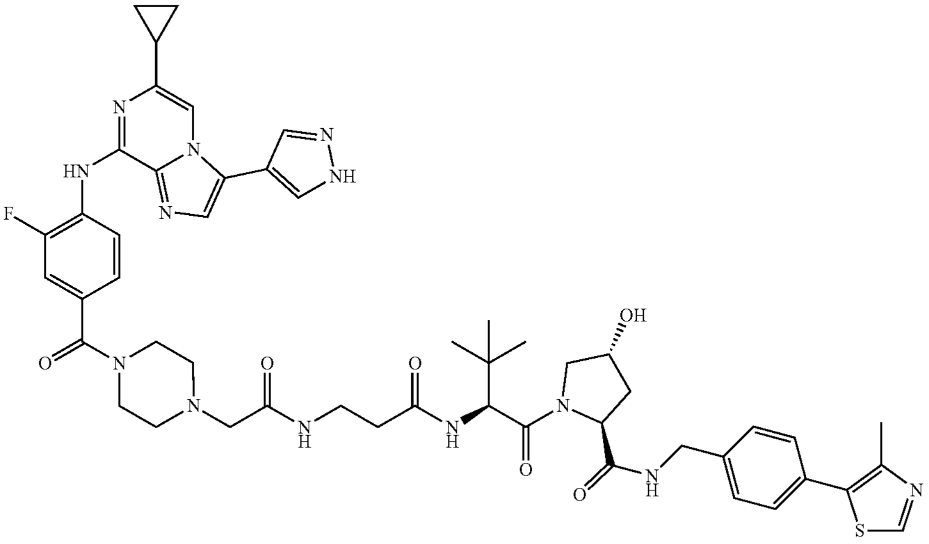 [SMILES: Cc1ncsc1-c1ccc(CNC(=O)[C@@H]2C[C@@H](O)CN2C(=O)[C@@H](NC(=O)CCNC(=O)CN2CCN(C(=O)c3ccc(Nc4nc(C5CC5)cn5c(-c6cn[nH]c6)cnc45)c(F)c3)CC2)C(C)(C)C)cc1] |
| 45 | YX79-5 | 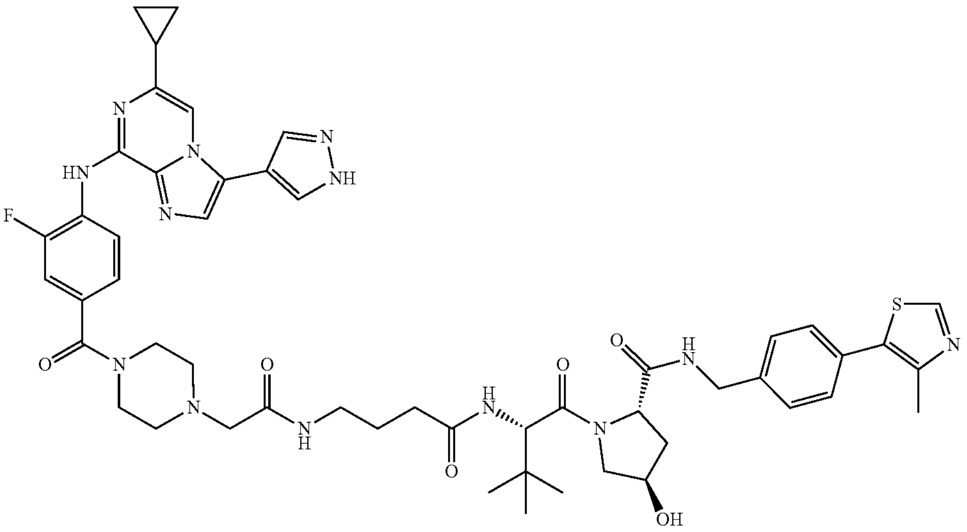 [SMILES: Cc1ncsc1-c1ccc(CNC(=O)[C@@H]2C[C@@H](O)CN2C(=O)[C@@H](NC(=O)CCCNC(=O)CN2CCN(C(=O)c3ccc(Nc4nc(C5CC5)cn5c(-c6cn[nH]c6)cnc45)c(F)c3)CC2)C(C)(C)C)cc1] |
| 46 | YX79-6 | 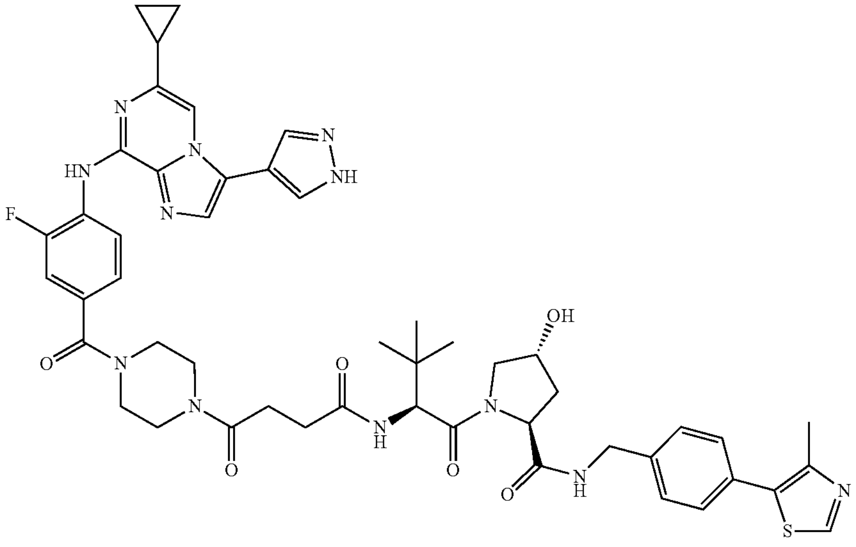 |

TABLE 1-continued
47 YX79-10
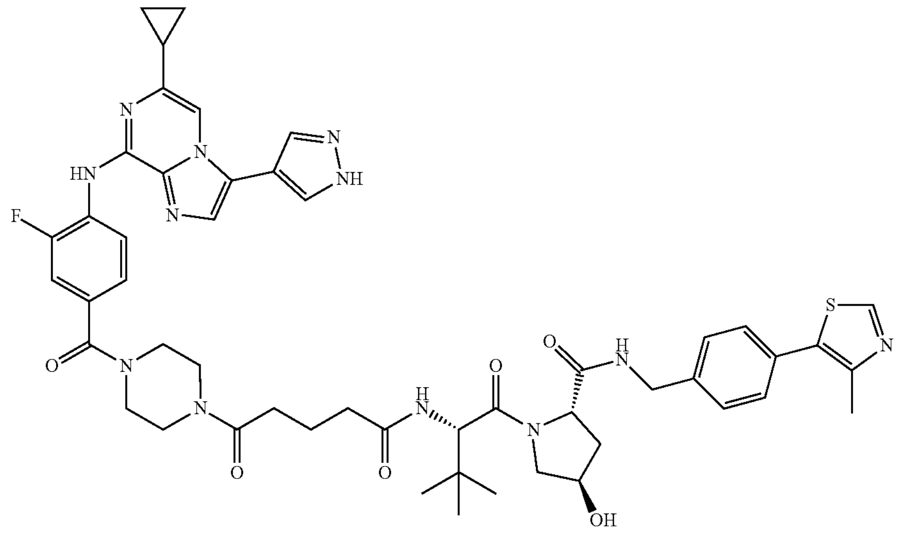 [SMILES: Cc1ncsc1-c1ccc(CNC(=O)[C@@H]2C[C@@H](O)CN2C(=O)[C@@H](NC(=O)CCCC(=O)N2CCN(C(=O)c3ccc(Nc4nc(C5CC5)cn5c(-c6cn[nH]c6)cnc45)c(F)c3)CC2)C(C)(C)C)cc1]
48 YX79-11
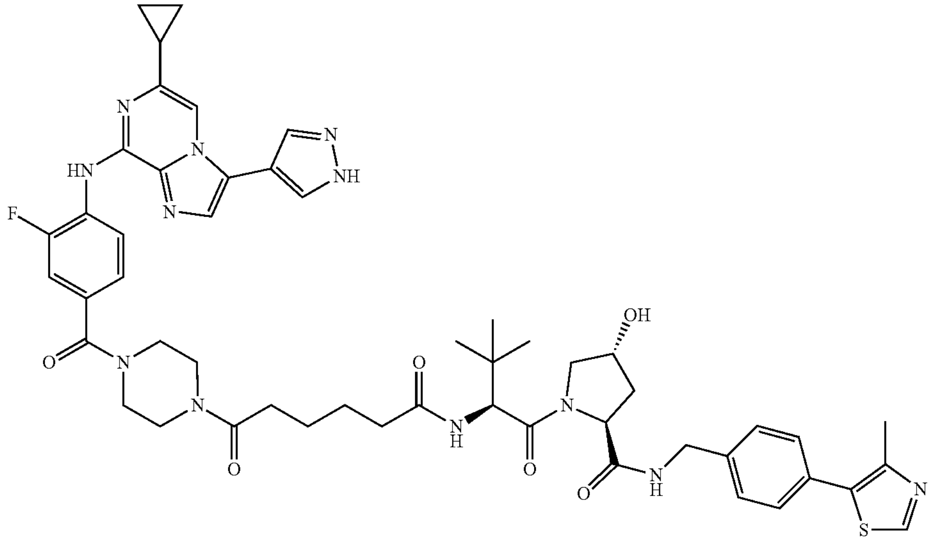 [SMILES: Cc1ncsc1-c1ccc(CNC(=O)[C@@H]2C[C@@H](O)CN2C(=O)[C@@H](NC(=O)CCCCC(=O)N2CCN(C(=O)c3ccc(Nc4nc(C5CC5)cn5c(-c6cn[nH]c6)cnc45)c(F)c3)CC2)C(C)(C)C)cc1]
49 YX79-12
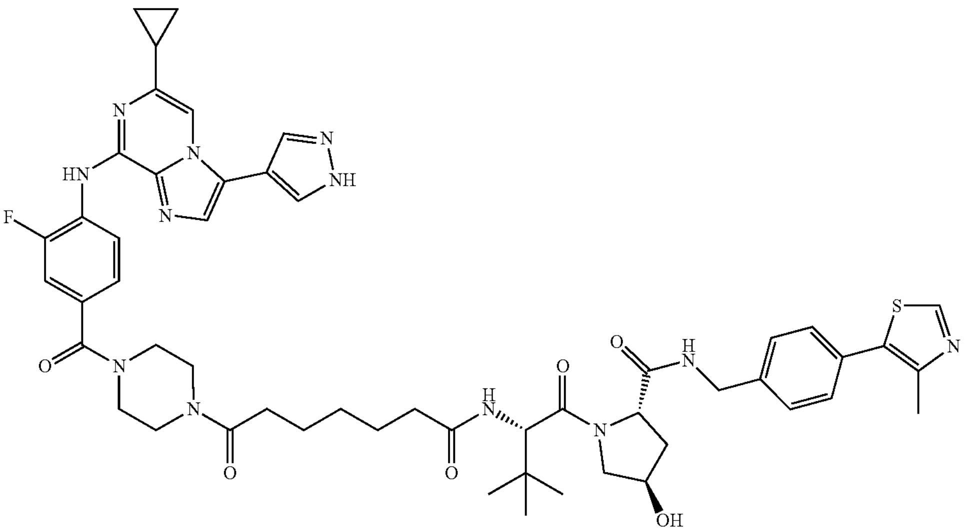 [SMILES: Cc1ncsc1-c1ccc(CNC(=O)[C@@H]2C[C@@H](O)CN2C(=O)[C@@H](NC(=O)CCCCCC(=O)N2CCN(C(=O)c3ccc(Nc4nc(C5CC5)cn5c(-c6cn[nH]c6)cnc45)c(F)c3)CC2)C(C)(C)C)cc1]

TABLE 1-continued
| | | |
|---|---|---|
| 50 | YX79-13 | 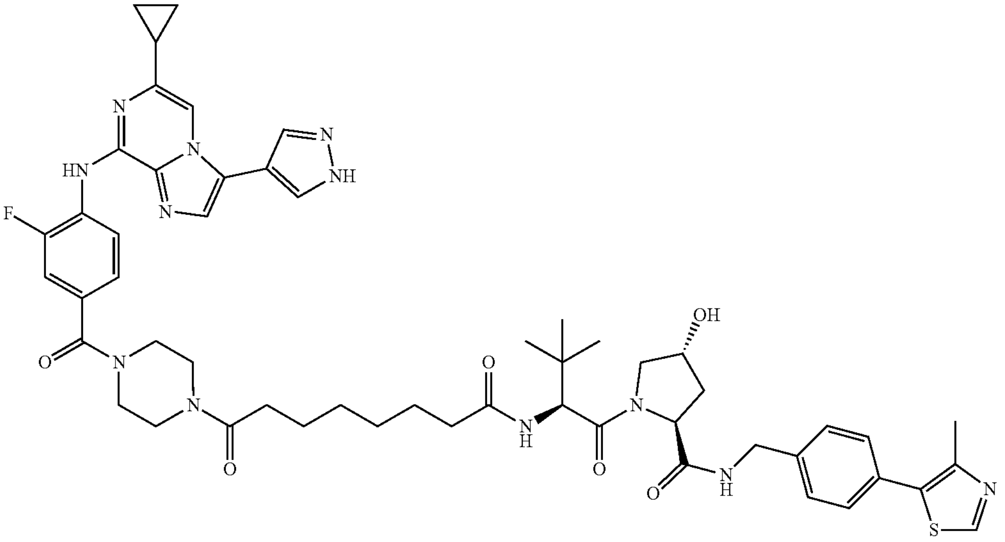 [SMILES: Cc1ncsc1-c1ccc(CNC(=O)[C@@H]2C[C@@H](O)CN2C(=O)[C@@H](NC(=O)CCCCCCC(=O)N2CCN(C(=O)c3ccc(Nc4nc(C5CC5)cn5c(-c6cn[nH]c6)cnc45)c(F)c3)CC2)C(C)(C)C)cc1] |
| 51 | YX79-14 | 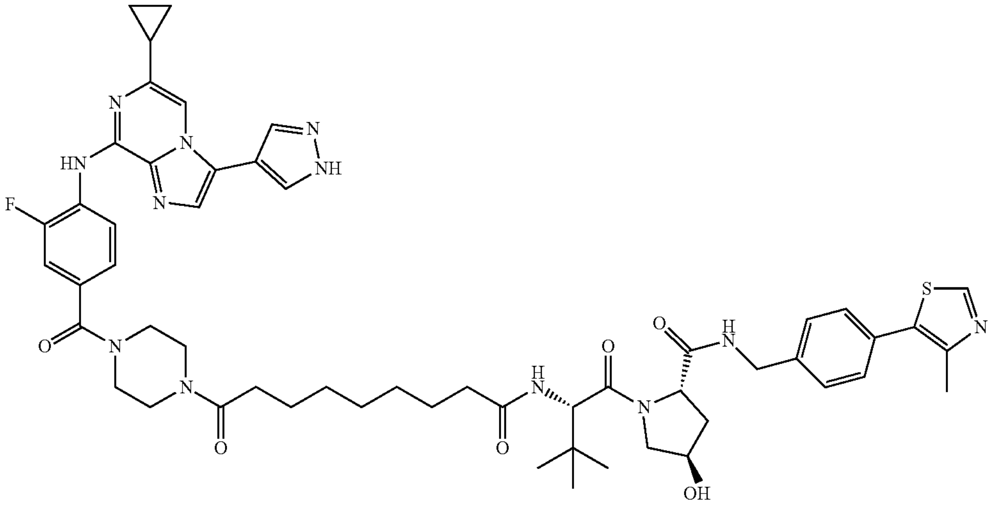 [SMILES: Cc1ncsc1-c1ccc(CNC(=O)[C@@H]2C[C@@H](O)CN2C(=O)[C@@H](NC(=O)CCCCCCCC(=O)N2CCN(C(=O)c3ccc(Nc4nc(C5CC5)cn5c(-c6cn[nH]c6)cnc45)c(F)c3)CC2)C(C)(C)C)cc1] |
| 52 | YX79-15 | 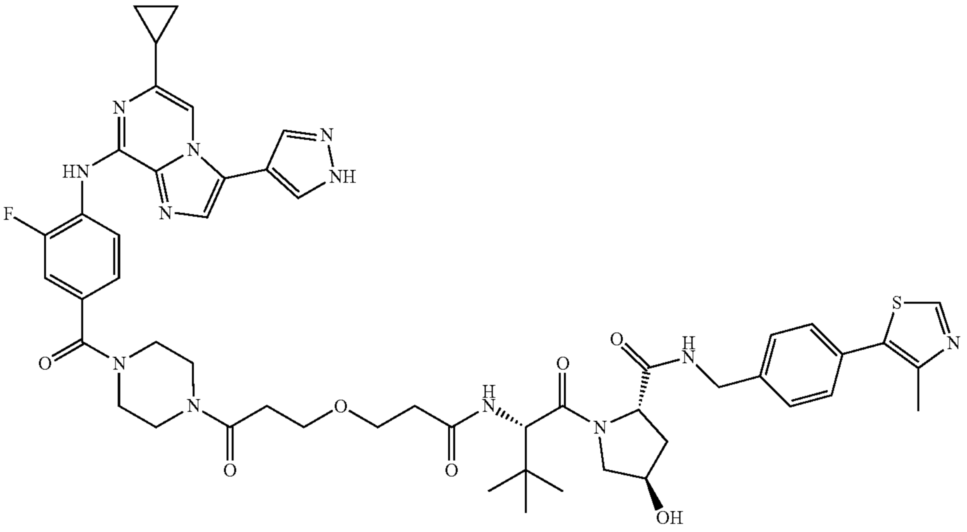 [SMILES: Cc1ncsc1-c1ccc(CNC(=O)[C@@H]2C[C@@H](O)CN2C(=O)[C@@H](NC(=O)CCOCCC(=O)N2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 53 | YX79-16 | 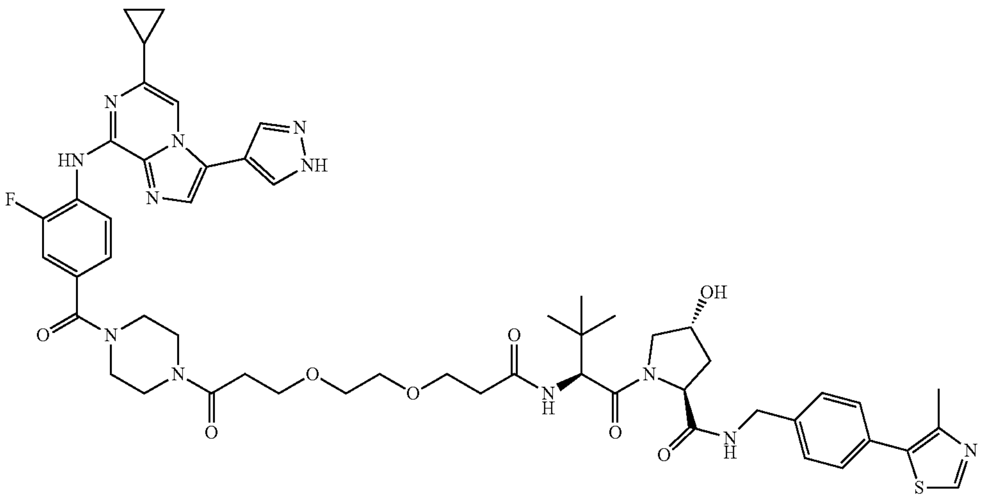 [SMILES: Cc1ncsc1-c1ccc(CNC(=O)[C@@H]2C[C@@H](O)CN2C(=O)[C@@H](NC(=O)CCOCCOCCC(=O)N2CCN(C(=O)c3ccc(Nc4nc(C5CC5)cn5c(-c6cn[nH]c6)cnc45)c(F)c3)CC2)C(C)(C)C)cc1] |
| 54 | YX79-17 | 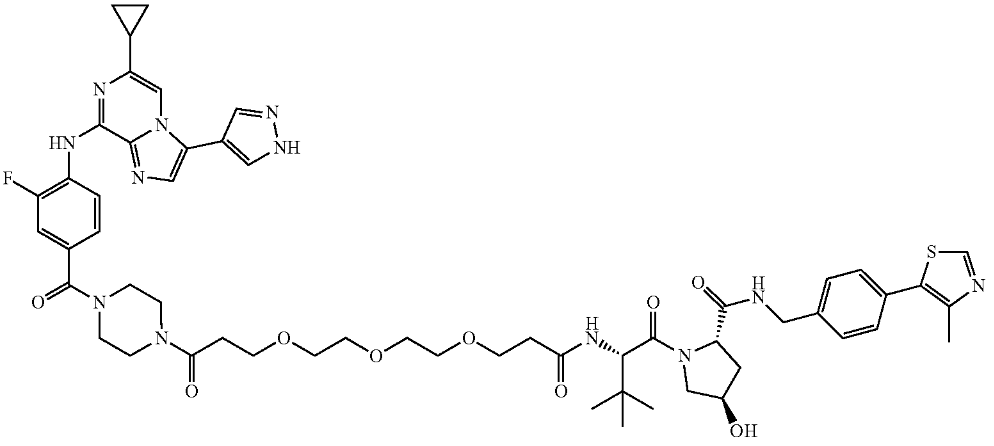 [SMILES: Cc1ncsc1-c1ccc(CNC(=O)[C@@H]2C[C@@H](O)CN2C(=O)[C@@H](NC(=O)CCOCCOCCOCCC(=O)N2CCN(C(=O)c3ccc(Nc4nc(C5CC5)cn5c(-c6cn[nH]c6)cnc45)c(F)c3)CC2)C(C)(C)C)cc1] |
| 55 | YX79-18 | 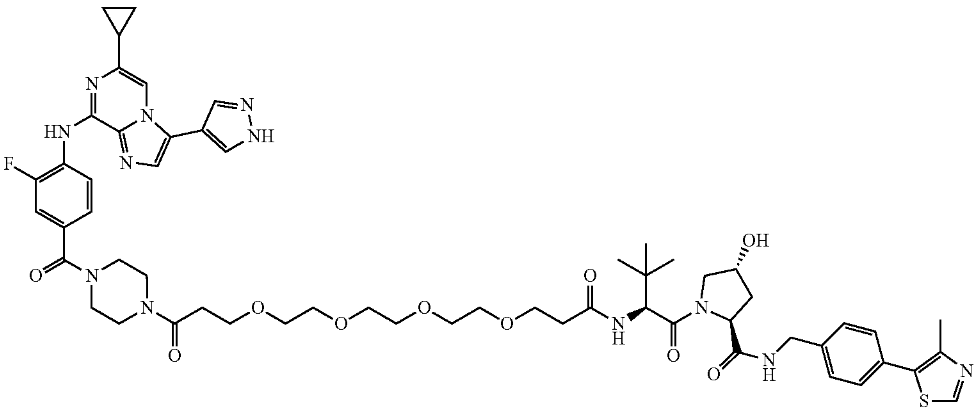 [SMILES: Cc1ncsc1-c1ccc(CNC(=O)[C@@H]2C[C@@H](O)CN2C(=O)[C@@H](NC(=O)CCOCCOCCOCCOCCC(=O)N2CCN(C(=O)c3ccc(Nc4nc(C5CC5)cn5c(-c6cn[nH]c6)cnc45)c(F)c3)CC2)C(C)(C)C)cc1] |

TABLE 1-continued
56 YX79-19
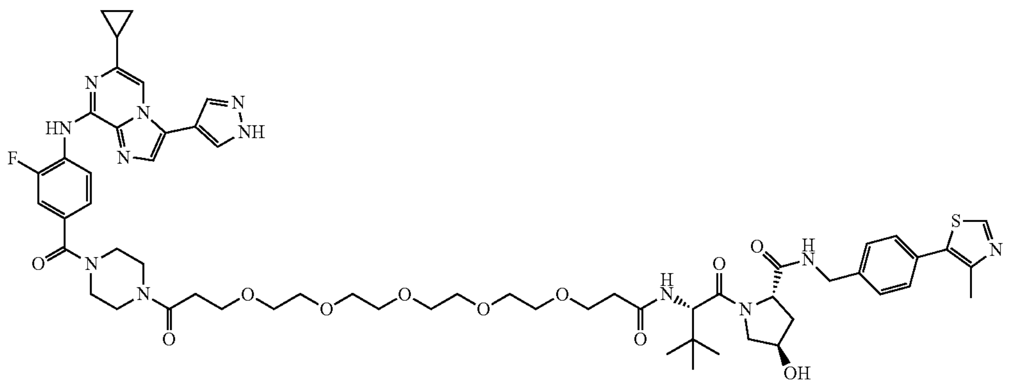 [SMILES: Cc1ncsc1-c1ccc(CNC(=O)[C@@H]2C[C@@H](O)CN2C(=O)[C@@H](NC(=O)CCOCCOCCOCCOCCOCCC(=O)N2CCN(C(=O)c3ccc(Nc4nc(C5CC5)cn5c(-c6cn[nH]c6)cnc45)c(F)c3)CC2)C(C)(C)C)cc1]
57 YX79-20
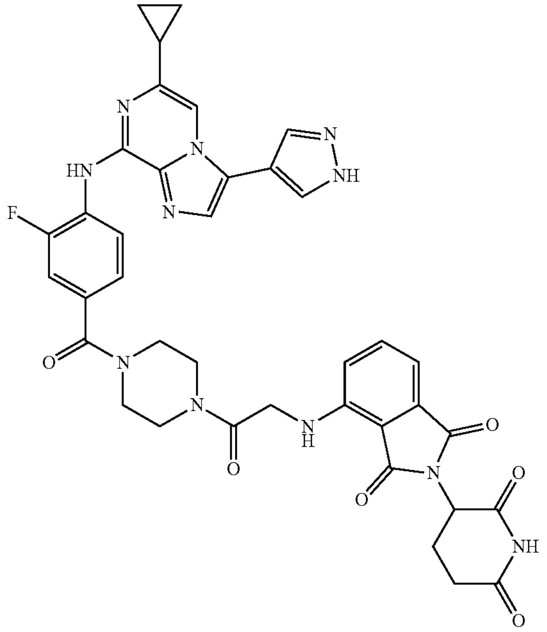 [SMILES: O=C1CCC(N2C(=O)c3cccc(NCC(=O)N4CCN(C(=O)c5ccc(Nc6nc(C7CC7)cn7c(-c8cn[nH]c8)cnc67)c(F)c5)CC4)c3C2=O)C(=O)N1]
58 YX79-21
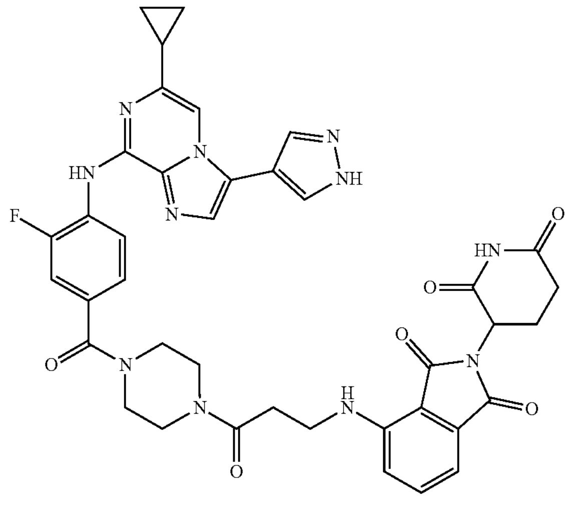 [SMILES: O=C1CCC(N2C(=O)c3cccc(NCCC(=O)N4CCN(C(=O)c5ccc(Nc6nc(C7CC7)cn7c(-c8cn[nH]c8)cnc67)c(F)c5)CC4)c3C2=O)C(=O)N1]

TABLE 1-continued
| | | |
|---|---|---|
| 59 | YX79-22 | 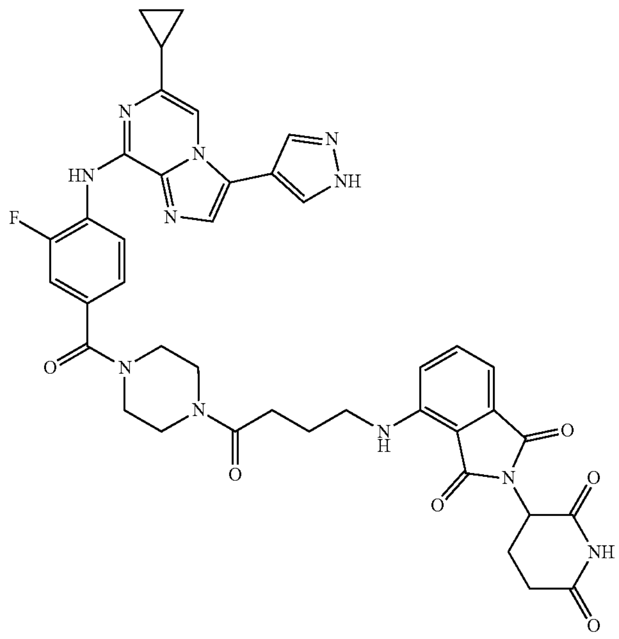 [SMILES: O=C1CCC(N2C(=O)c3cccc(NCCCC(=O)N4CCN(C(=O)c5ccc(Nc6nc(C7CC7)cn7c(-c8cn[nH]c8)cnc67)c(F)c5)CC4)c3C2=O)C(=O)N1] |
| 60 | YX79-23 | 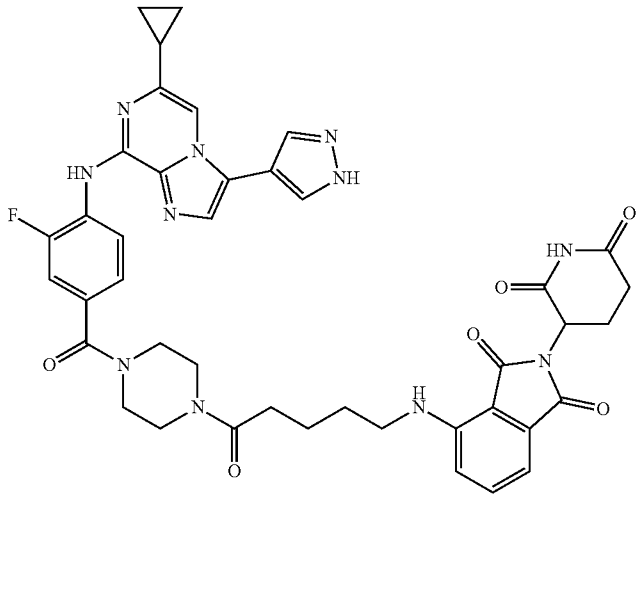 [SMILES: O=C1CCC(N2C(=O)c3cccc(NCCCCC(=O)N4CCN(C(=O)c5ccc(Nc6nc(C7CC7)cn7c(-c8cn[nH]c8)cnc67)c(F)c5)CC4)c3C2=O)C(=O)N1] |

TABLE 1-continued
| | | |
|---|---|---|
| 61 | YX79-24 | 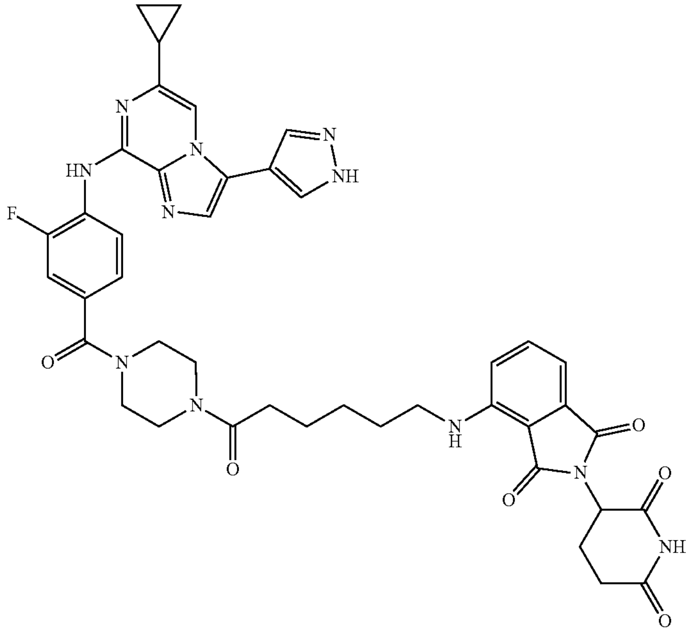 [SMILES: O=C1CCC(N2C(=O)c3cccc(NCCCCCC(=O)N4CCN(C(=O)c5ccc(Nc6nc(C7CC7)cn7c(-c8cn[nH]c8)cnc67)c(F)c5)CC4)c3C2=O)C(=O)N1] |
| 62 | YX79-25 | 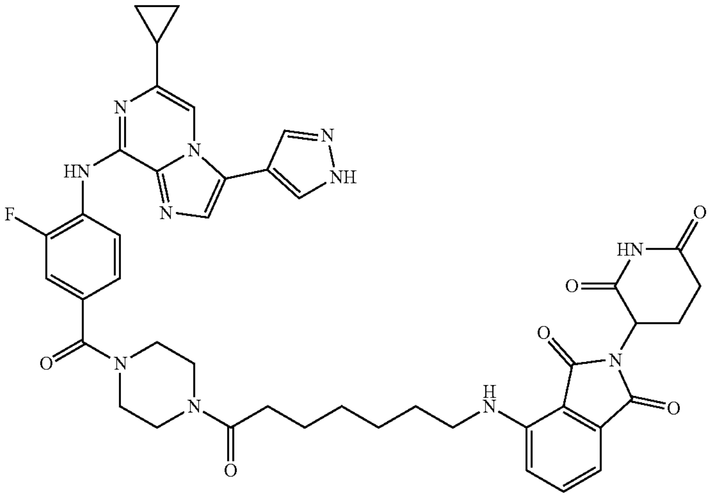 [SMILES: O=C1CCC(N2C(=O)c3cccc(NCCCCCCC(=O)N4CCN(C(=O)c5ccc(Nc6nc(C7CC7)cn7c(-c8cn[nH]c8)cnc67)c(F)c5)CC4)c3C2=O)C(=O)N1] |
| 63 | YX79-29 | 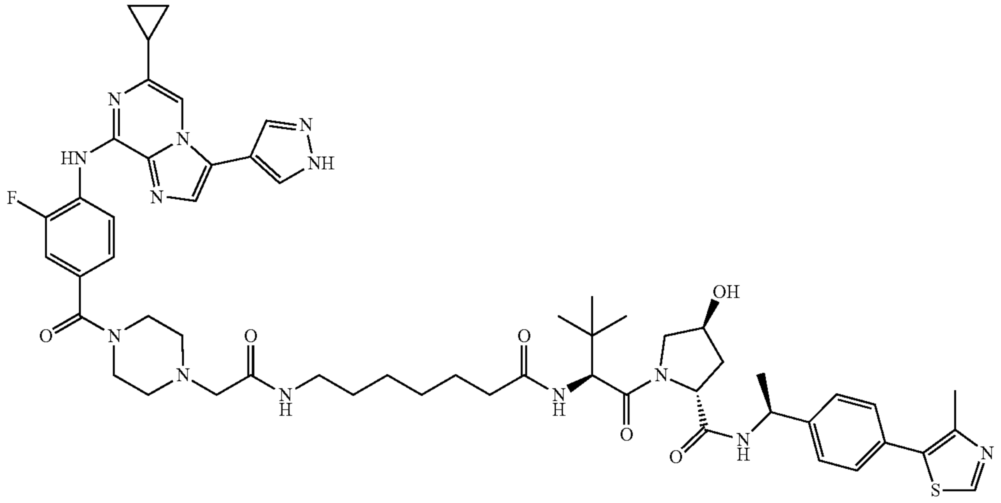 [SMILES: Cc1ncsc1-c1ccc([C@H](C)NC(=O)[C@H]2C[C@H](O)CN2C(=O)[C@@H](NC(=O)CCCCCCNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
64 YX79-30
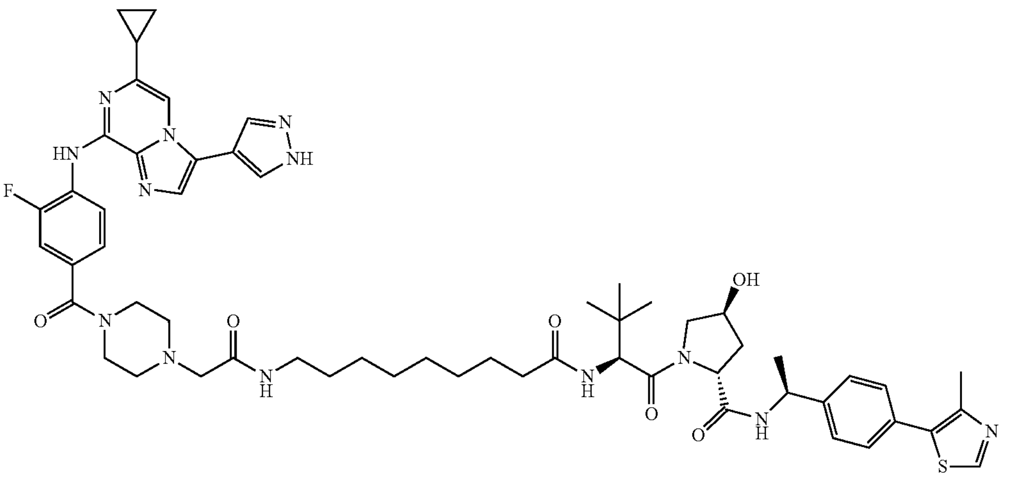 [SMILES: Cc1ncsc1-c1ccc([C@H](C)NC(=O)[C@H]2C[C@H](O)CN2C(=O)[C@@H](NC(=O)CCCCCCCCNC(=O)CN2CCN(C(=O)c3ccc(Nc4nc(C5CC5)cn5c(-c6cn[nH]c6)cnc45)c(F)c3)CC2)C(C)(C)C)cc1]
65 YX79-34
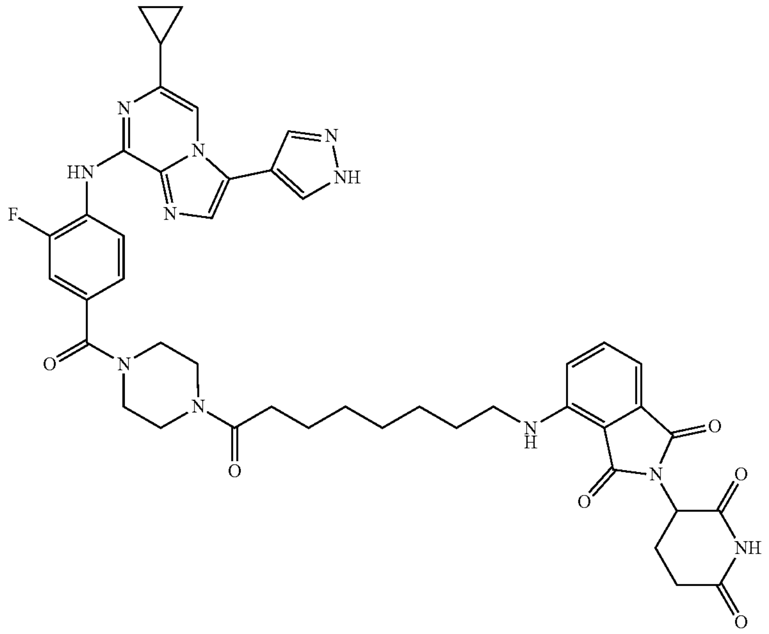 [SMILES: O=C1CCC(N2C(=O)c3cccc(NCCCCCCCC(=O)N4CCN(C(=O)c5ccc(Nc6nc(C7CC7)cn7c(-c8cn[nH]c8)cnc67)c(F)c5)CC4)c3C2=O)C(=O)N1]

TABLE 1-continued
66 YX79-35
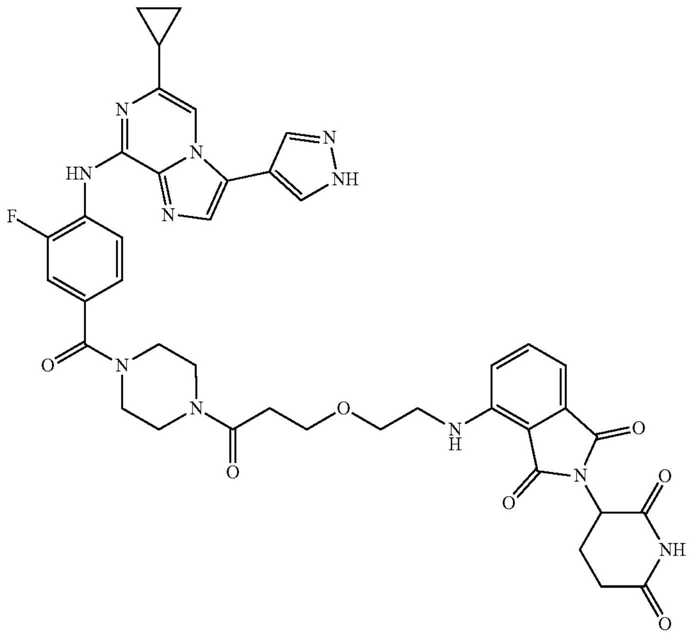
67 YX79-36
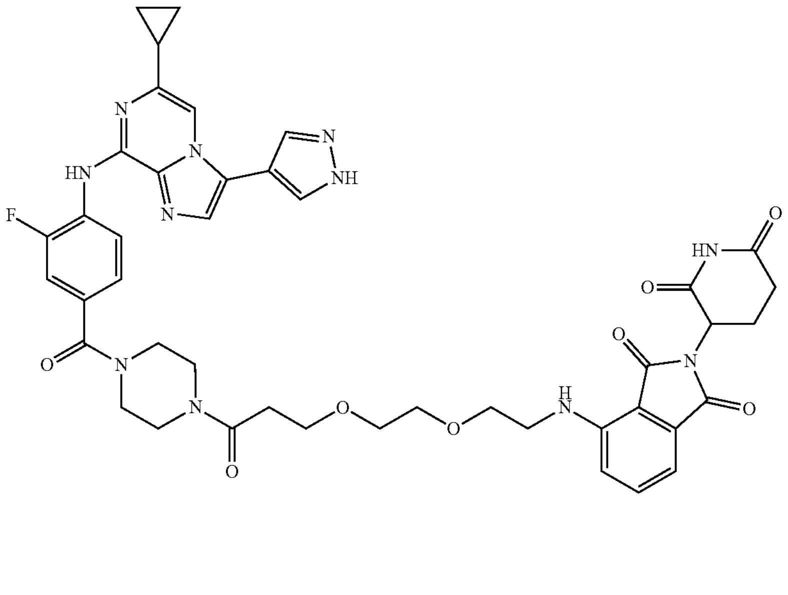 [SMILES: O=C1CCC(N2C(=O)c3cccc(NCCOCCOCCC(=O)N4CCN(C(=O)c5ccc(Nc6nc(C7CC7)cn7c(-c8cn[nH]c8)cnc67)c(F)c5)CC4)c3C2=O)C(=O)N1]

TABLE 1-continued
68 YX79-37
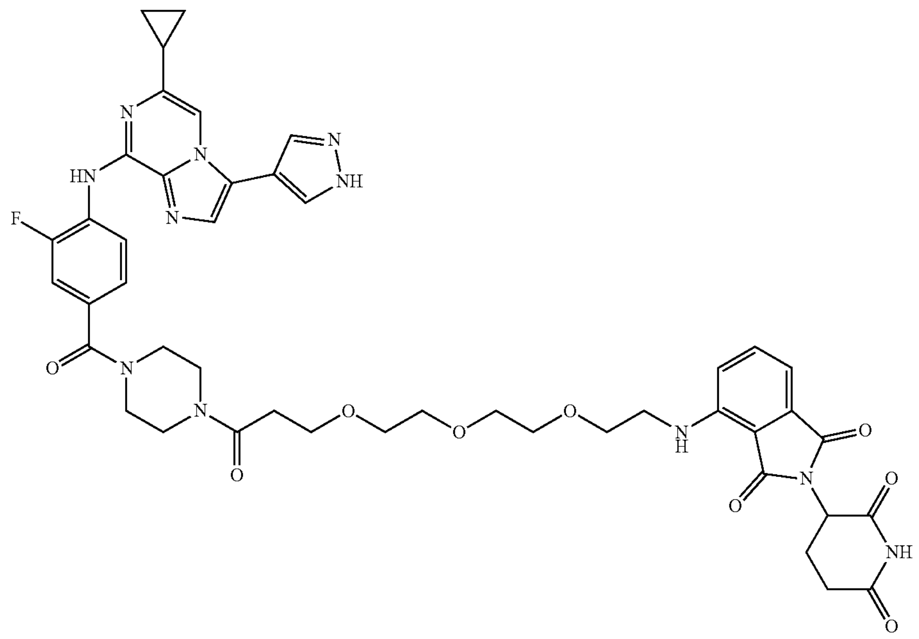 [SMILES: O=C1CCC(N2C(=O)c3cccc(NCCOCCOCCOCCC(=O)N4CCN(C(=O)c5ccc(Nc6nc(C7CC7)cn7c(-c8cn[nH]c8)cnc67)c(F)c5)CC4)c3C2=O)C(=O)N1]
69 YX79-38
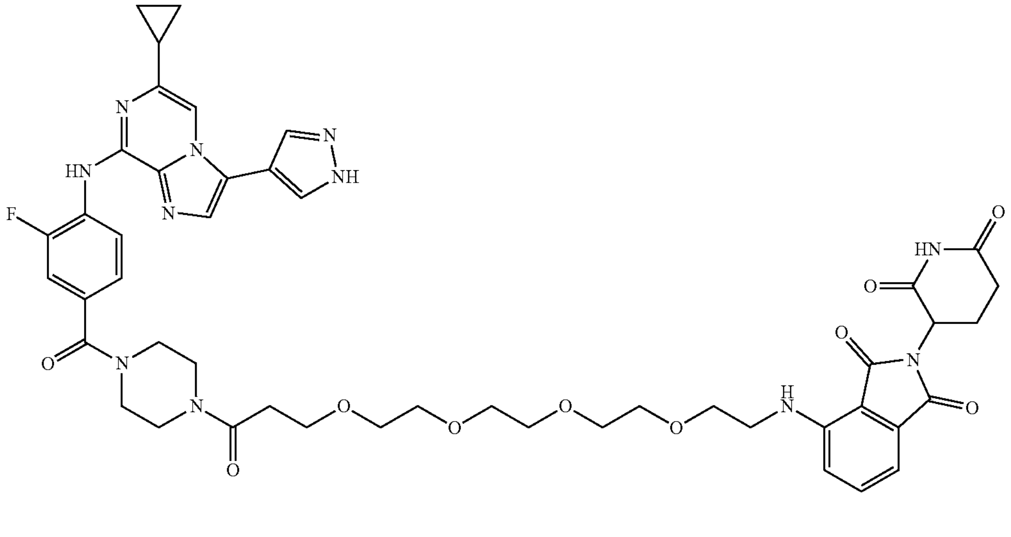 [SMILES: O=C1CCC(N2C(=O)c3cccc(NCCOCCOCCOCCOCCC(=O)N4CCN(C(=O)c5ccc(Nc6nc(C7CC7)cn7c(-c8cn[nH]c8)cnc67)c(F)c5)CC4)c3C2=O)C(=O)N1]

TABLE 1-continued
| | | |
|---|---|---|
| 70 | YX79-39 | 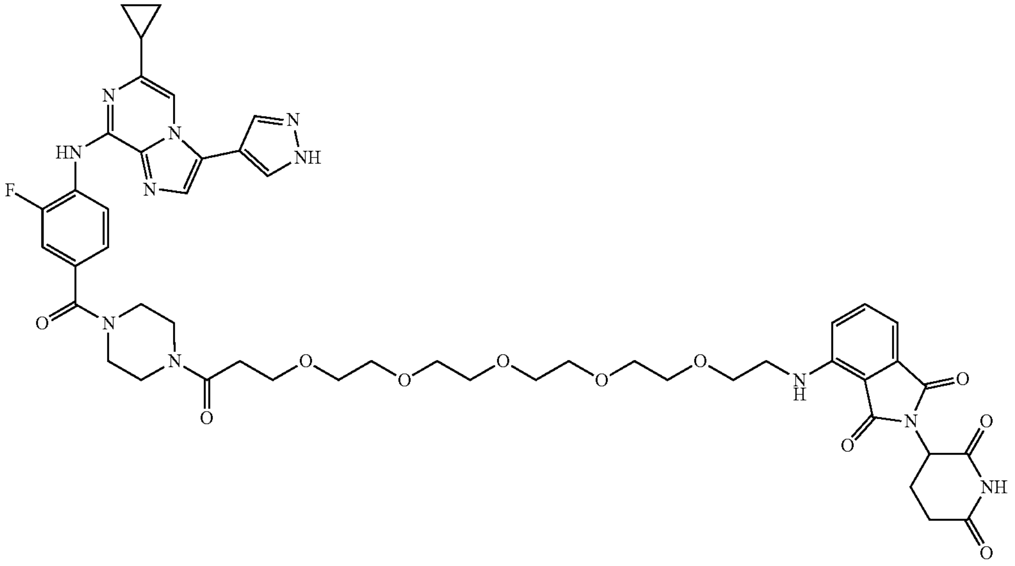 [SMILES: O=C1CCC(N2C(=O)c3cccc(NCCOCCOCCOCCOCCOCCC(=O)N4CCN(C(=O)c5ccc(Nc6nc(C7CC7)cn7c(-c8cn[nH]c8)cnc67)c(F)c5)CC4)c3C2=O)C(=O)N1] |
| 71 | YX79-40 | 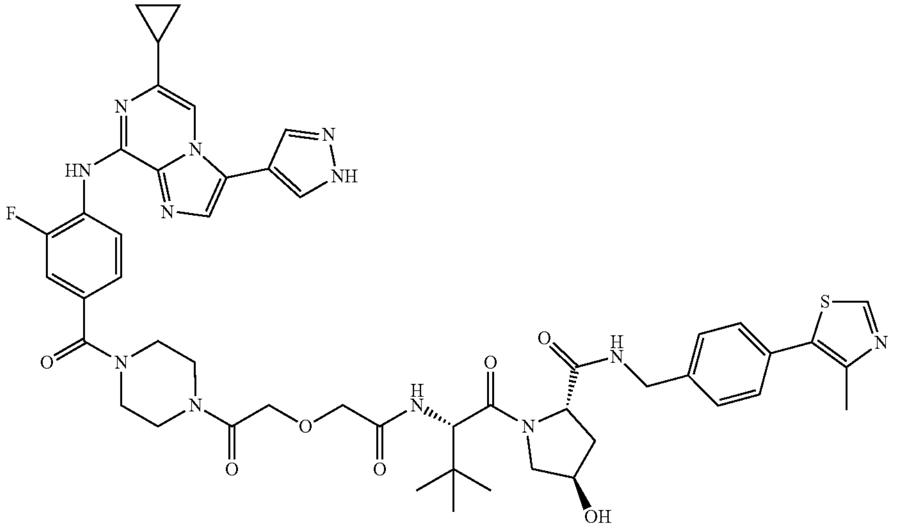 |
| 72 | YX79-41 | 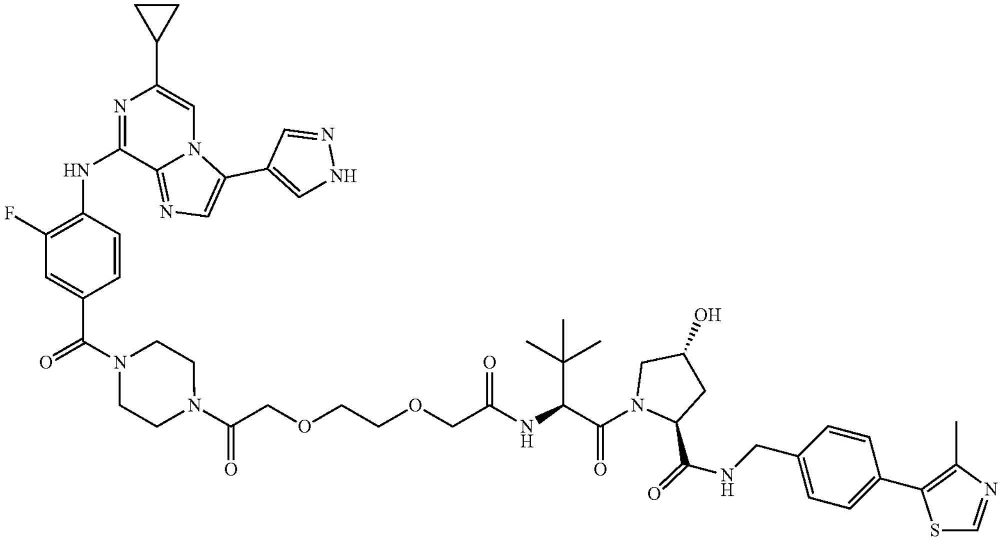 |

TABLE 1-continued
73 YX79-42
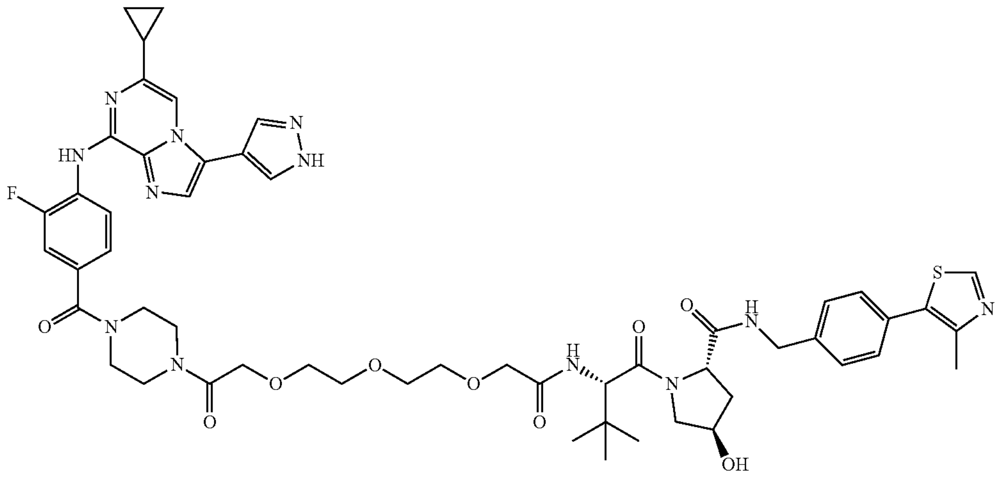 [SMILES: Cc1ncsc1-c1ccc(CNC(=O)[C@@H]2C[C@@H](O)CN2C(=O)[C@@H](NC(=O)COCCOCCOCC(=O)N2CCN(C(=O)c3ccc(Nc4nc(C5CC5)cn5c(-c6cn[nH]c6)cnc45)c(F)c3)CC2)C(C)(C)C)cc1]
74 YX79-43
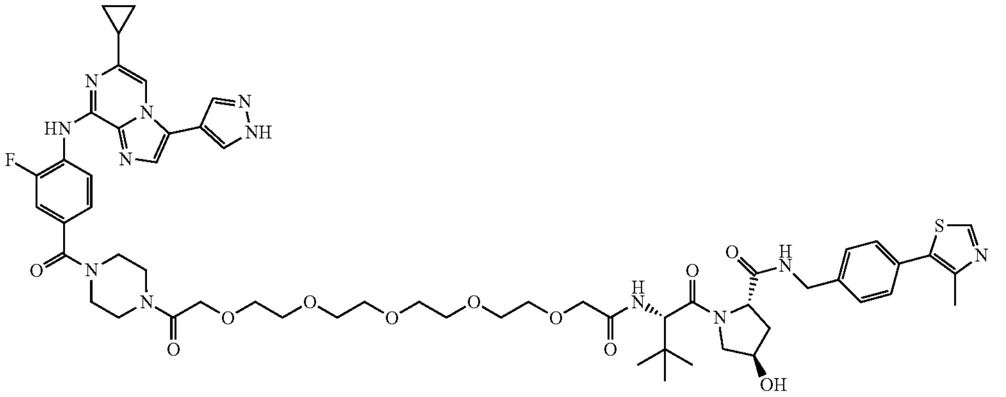 [SMILES: Cc1ncsc1-c1ccc(CNC(=O)[C@@H]2C[C@@H](O)CN2C(=O)[C@@H](NC(=O)COCCOCCOCCOCCOCC(=O)N2CCN(C(=O)c3ccc(Nc4nc(C5CC5)cn5c(-c6cn[nH]c6)cnc45)c(F)c3)CC2)C(C)(C)C)cc1]
75 YX79-56
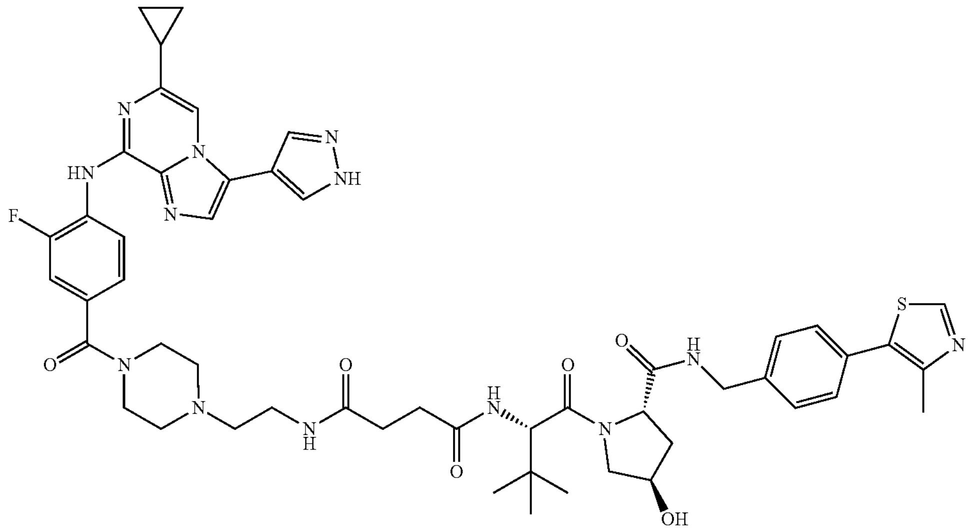 [SMILES: Cc1ncsc1-c1ccc(CNC(=O)[C@@H]2C[C@@H](O)CN2C(=O)[C@@H](NC(=O)CCC(=O)NCCN2CCN(C(=O)c3ccc(Nc4nc(C5CC5)cn5c(-c6cn[nH]c6)cnc45)c(F)c3)CC2)C(C)(C)C)cc1]

TABLE 1-continued
| | | |
|---|---|---|
| 76 | YX79-57 | 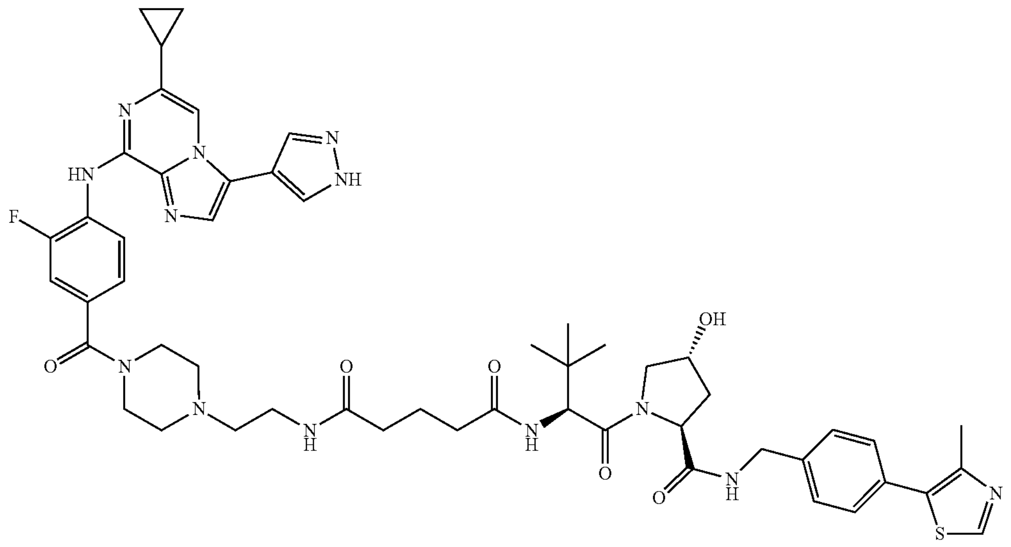 [SMILES: Cc1ncsc1-c1ccc(CNC(=O)[C@@H]2C[C@@H](O)CN2C(=O)[C@@H](NC(=O)CCCC(=O)NCCN2CCN(C(=O)c3ccc(Nc4nc(C5CC5)cn5c(-c6cn[nH]c6)cnc45)c(F)c3)CC2)C(C)(C)C)cc1] |
| 77 | YX79-58 | 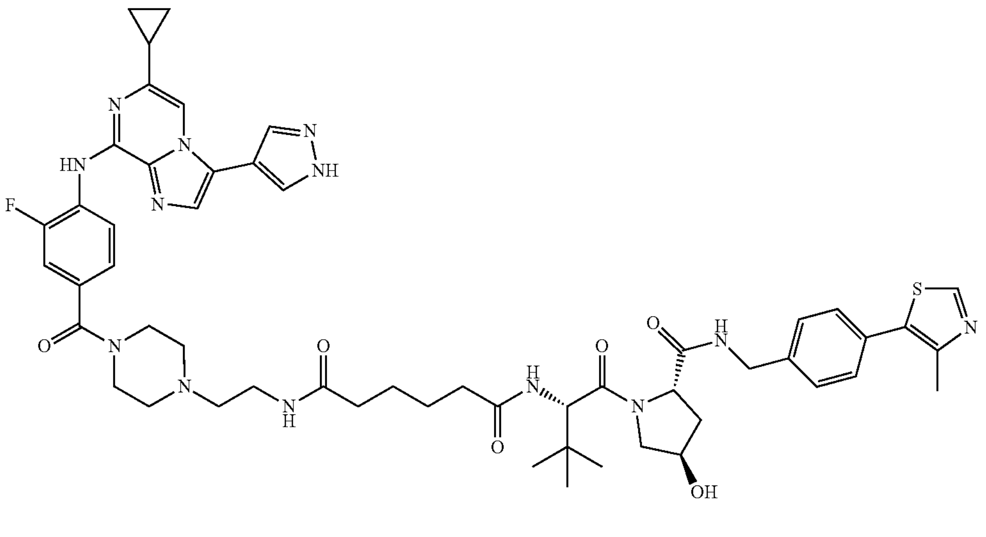 [SMILES: Cc1ncsc1-c1ccc(CNC(=O)[C@@H]2C[C@@H](O)CN2C(=O)[C@@H](NC(=O)CCCCC(=O)NCCN2CCN(C(=O)c3ccc(Nc4nc(C5CC5)cn5c(-c6cn[nH]c6)cnc45)c(F)c3)CC2)C(C)(C)C)cc1] |
| 78 | YX79-59 | 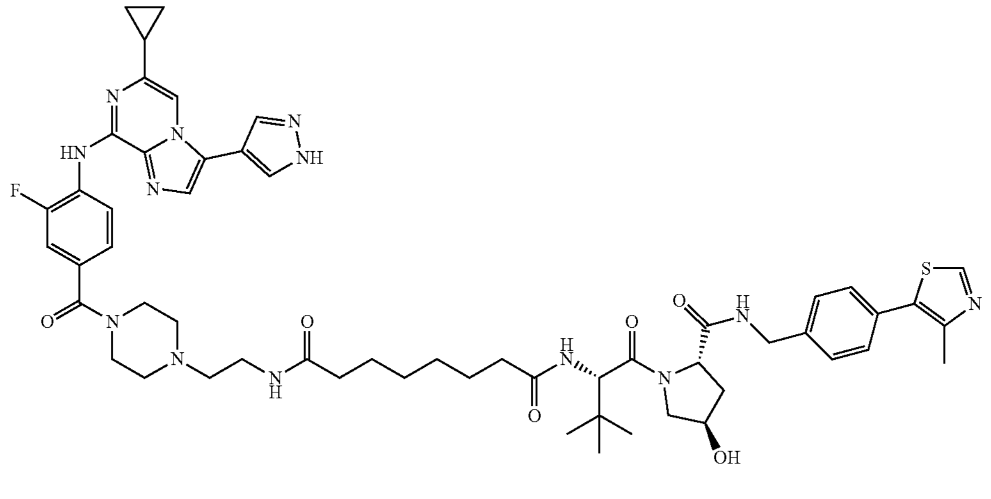 [SMILES: Cc1ncsc1-c1ccc(CNC(=O)[C@@H]2C[C@@H](O)CN2C(=O)[C@@H](NC(=O)CCCCCCC(=O)NCCN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 79 | YX79-60 | 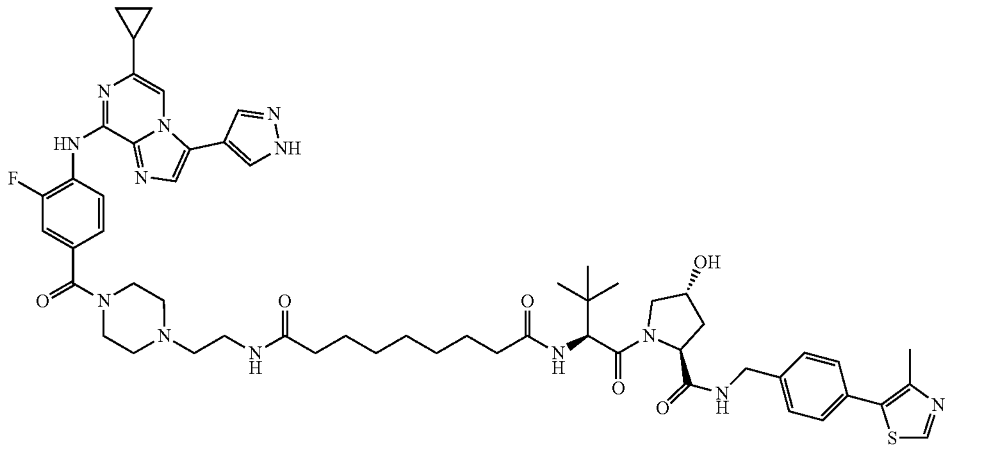 [SMILES: Cc1ncsc1-c1ccc(CNC(=O)[C@@H]2C[C@@H](O)CN2C(=O)[C@@H](NC(=O)CCCCCCCC(=O)NCCN2CCN(C(=O)c3ccc(Nc4nc(C5CC5)cn5c(-c6cn[nH]c6)cnc45)c(F)c3)CC2)C(C)(C)C)cc1] |
| 80 | YX79-61 | 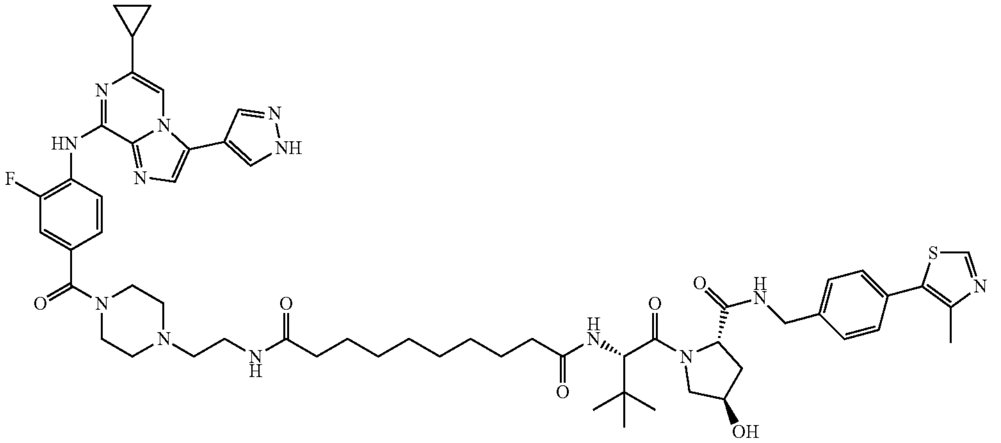 [SMILES: Cc1ncsc1-c1ccc(CNC(=O)[C@@H]2C[C@@H](O)CN2C(=O)[C@@H](NC(=O)CCCCCCCCC(=O)NCCN2CCN(C(=O)c3ccc(Nc4nc(C5CC5)cn5c(-c6cn[nH]c6)cnc45)c(F)c3)CC2)C(C)(C)C)cc1] |
| 81 | YX79-62 | 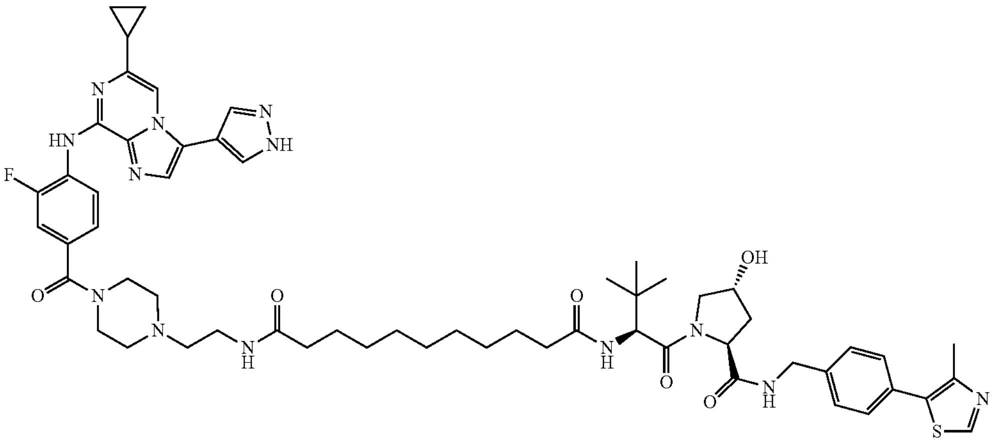 [SMILES: Cc1ncsc1-c1ccc(CNC(=O)[C@@H]2C[C@@H](O)CN2C(=O)[C@@H](NC(=O)CCCCCCCCCC(=O)NCCN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 82 | YX79-63 | 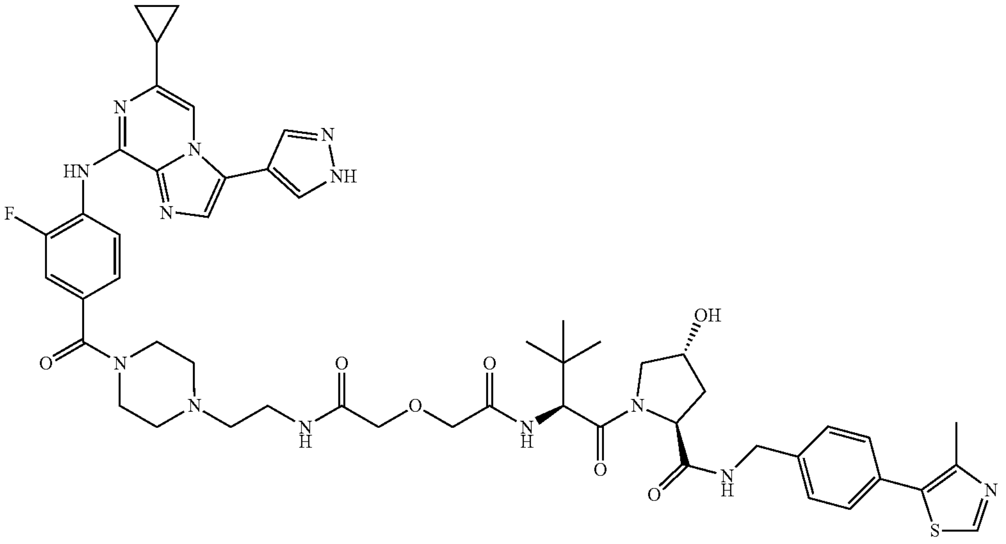 [SMILES: Cc1ncsc1-c1ccc(CNC(=O)[C@@H]2C[C@@H](O)CN2C(=O)[C@@H](NC(=O)COCC(=O)NCCN2CCN(C(=O)c3ccc(Nc4nc(C5CC5)cn5c(-c6cn[nH]c6)cnc45)c(F)c3)CC2)C(C)(C)C)cc1] |
| 83 | YX79-64 | 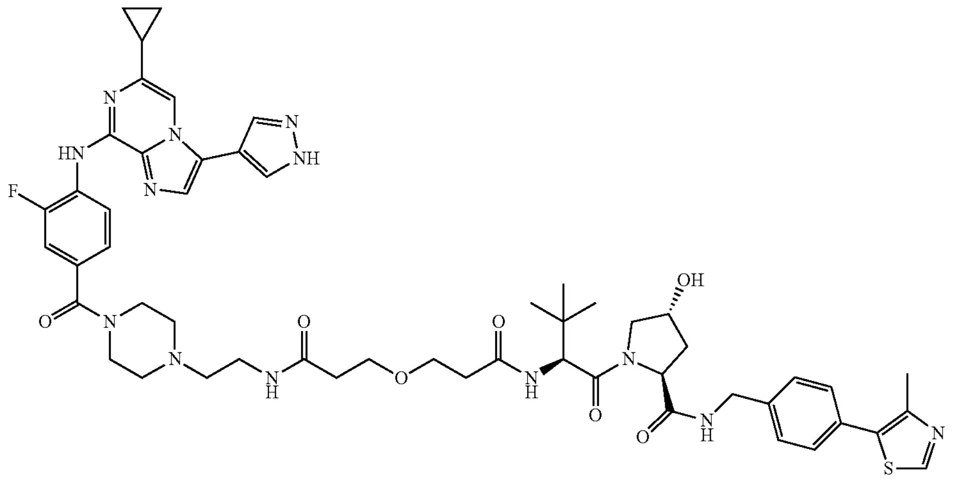 |
| 84 | YX79-65 | 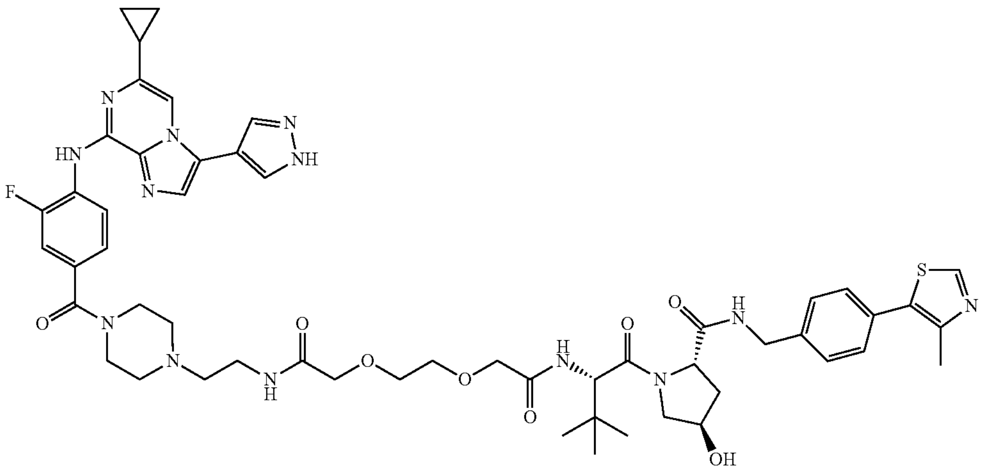 [SMILES: Cc1ncsc1-c1ccc(CNC(=O)[C@@H]2C[C@@H](O)CN2C(=O)[C@@H](NC(=O)COCCOCC(=O)NCCN2CCN(C(=O)c3ccc(Nc4nc(C5CC5)cn5c(-c6cn[nH]c6)cnc45)c(F)c3)CC2)C(C)(C)C)cc1] |

TABLE 1-continued
85 YX79-66
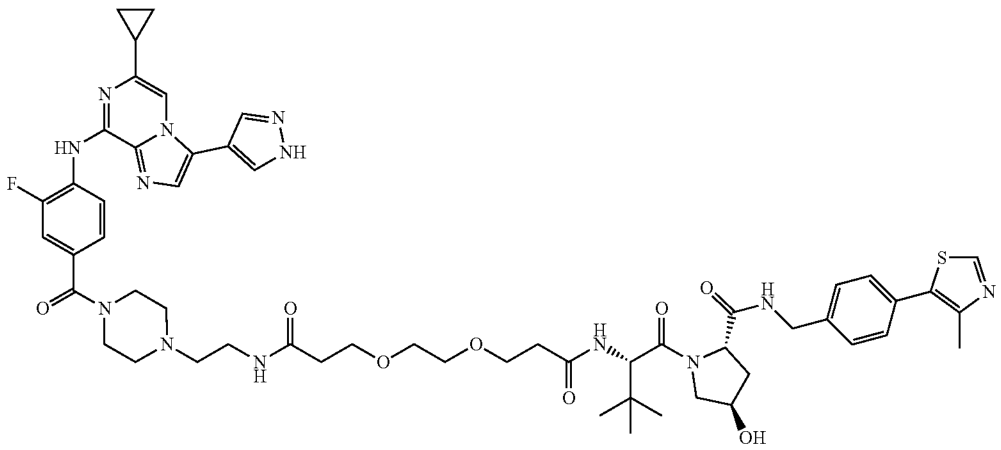 [SMILES: Cc1ncsc1-c1ccc(CNC(=O)[C@@H]2C[C@@H](O)CN2C(=O)[C@@H](NC(=O)CCOCCOCCC(=O)NCCN2CCN(C(=O)c3ccc(Nc4nc(C5CC5)cn5c(-c6cn[nH]c6)cnc45)c(F)c3)CC2)C(C)(C)C)cc1]
86 YX79-67
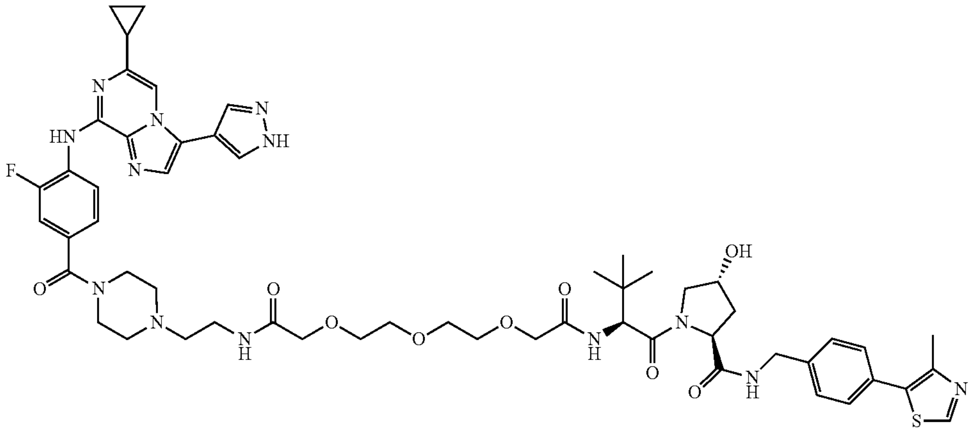
87 YX79-68
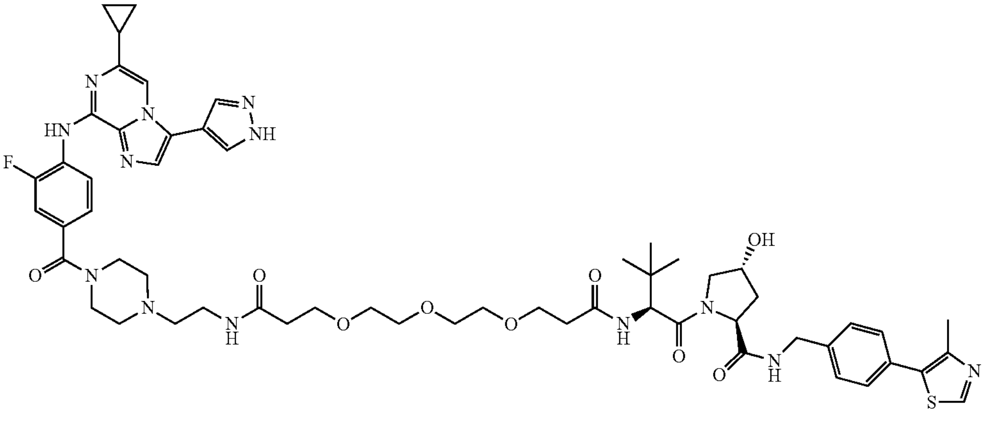 [SMILES: Cc1ncsc1-c1ccc(CNC(=O)[C@@H]2C[C@@H](O)CN2C(=O)[C@@H](NC(=O)CCOCCOCCOCCC(=O)NCCN2CCN(C(=O)c3ccc(Nc4nc(C5CC5)cn5c(-c6cn[nH]c6)cnc45)c(F)c3)CC2)C(C)(C)C)cc1]

TABLE 1-continued
| | | |
|---|---|---|
| 88 | YX79-69 | 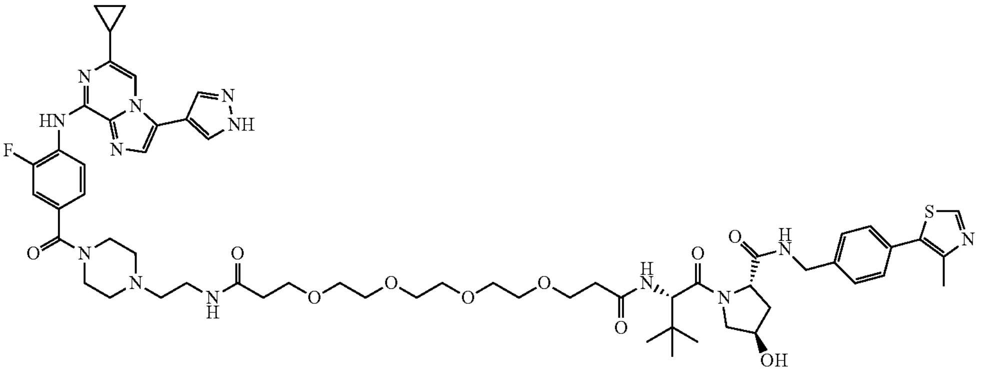 [SMILES: Cc1ncsc1-c1ccc(CNC(=O)[C@@H]2C[C@@H](O)CN2C(=O)[C@@H](NC(=O)CCOCCOCCOCCOCCC(=O)NCCN2CCN(C(=O)c3ccc(Nc4nc(C5CC5)cn5c(-c6cn[nH]c6)cnc45)c(F)c3)CC2)C(C)(C)C)cc1] |
| 89 | YX79-70 | 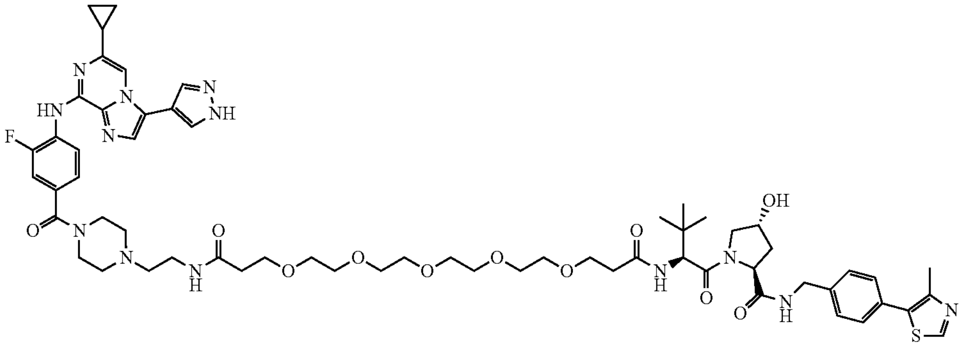 [SMILES: Cc1ncsc1-c1ccc(CNC(=O)[C@@H]2C[C@@H](O)CN2C(=O)[C@@H](NC(=O)CCOCCOCCOCCOCCOCCC(=O)NCCN2CCN(C(=O)c3ccc(Nc4nc(C5CC5)cn5c(-c6cn[nH]c6)cnc45)c(F)c3)CC2)C(C)(C)C)cc1] |
| 90 | YX79-86 | 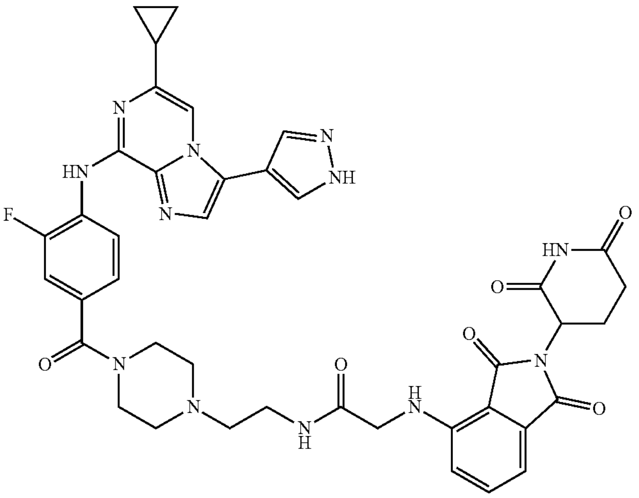 [SMILES: O=C(CNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1] |

TABLE 1-continued
91 YX79-87
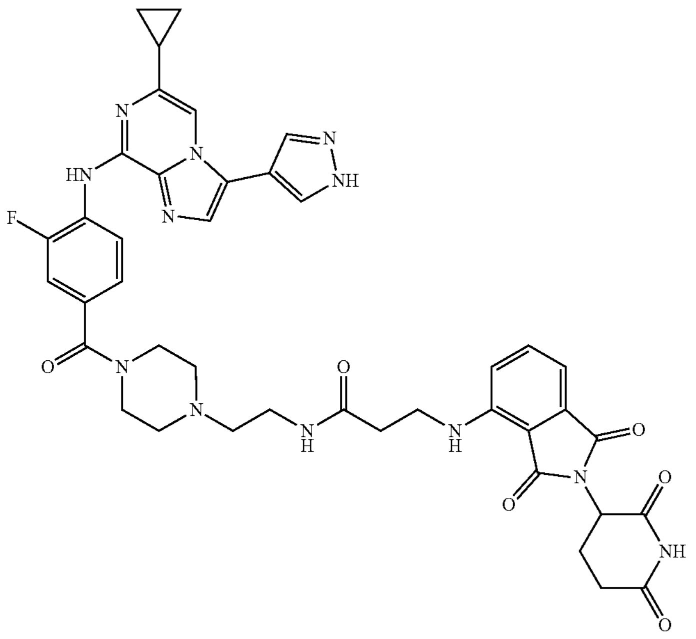 [SMILES: O=C(CCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]
92 YX79-88
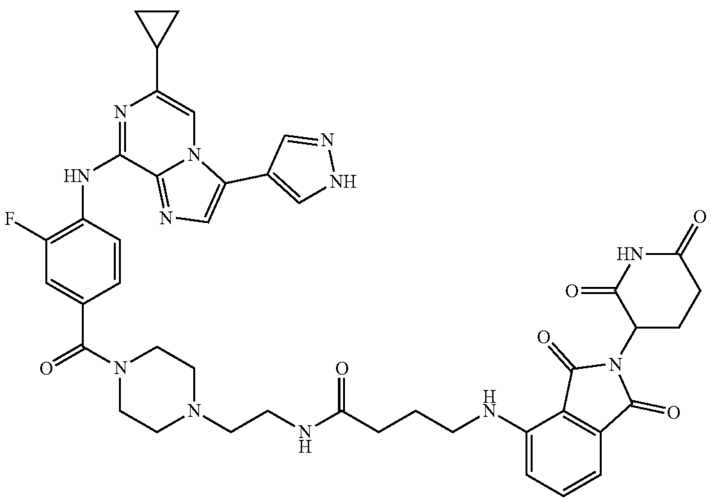 [SMILES: O=C(CCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

TABLE 1-continued
| | | |
|---|---|---|
| 93 | YX79-89 | 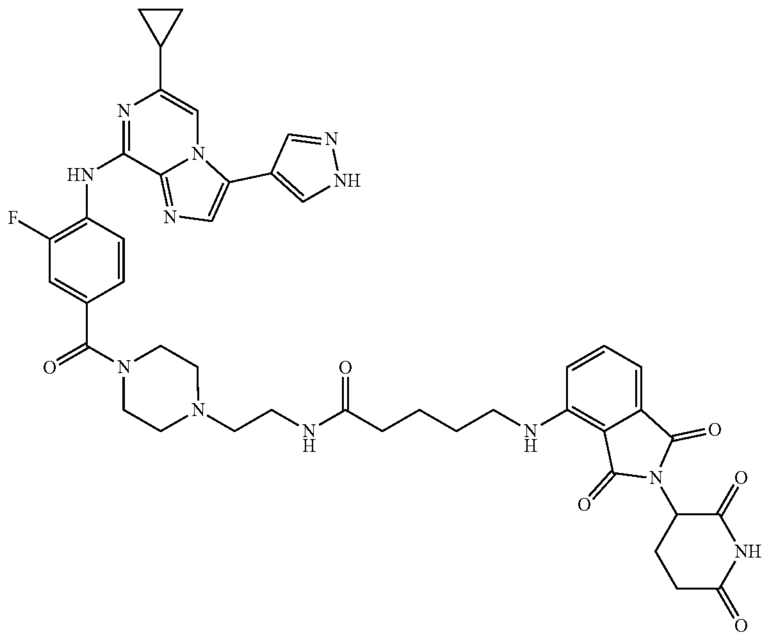 [SMILES: O=C(CCCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1] |
| 94 | YX79-90 | 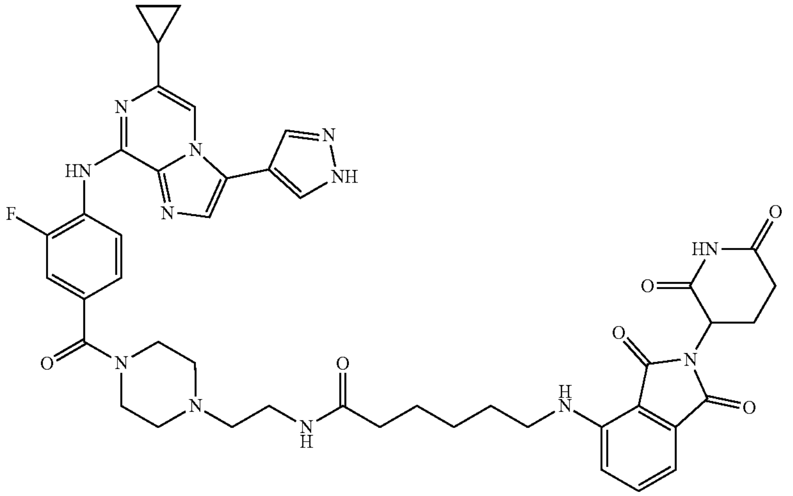 [SMILES: O=C(CCCCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1] |

TABLE 1-continued
95 YX79-91
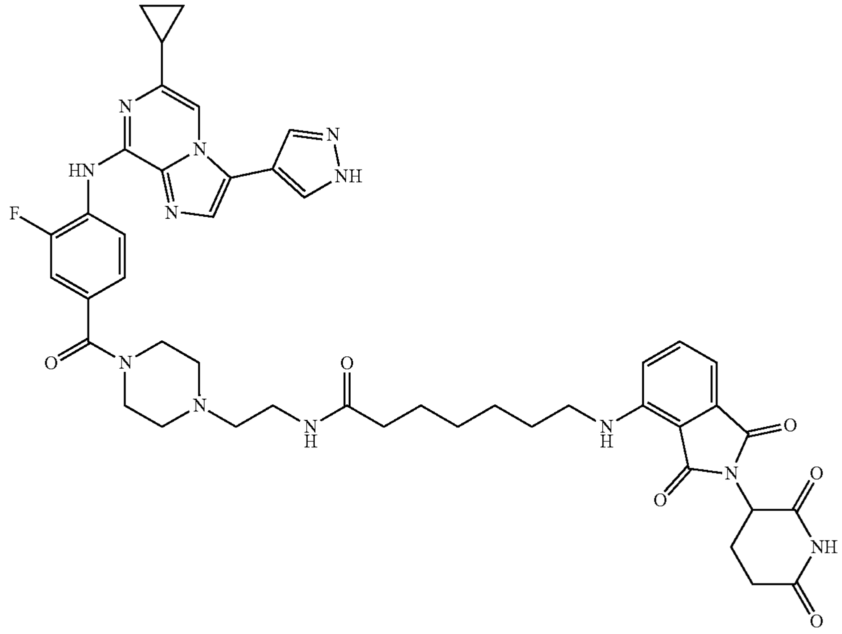 [SMILES: O=C(CCCCCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]
96 YX79-92
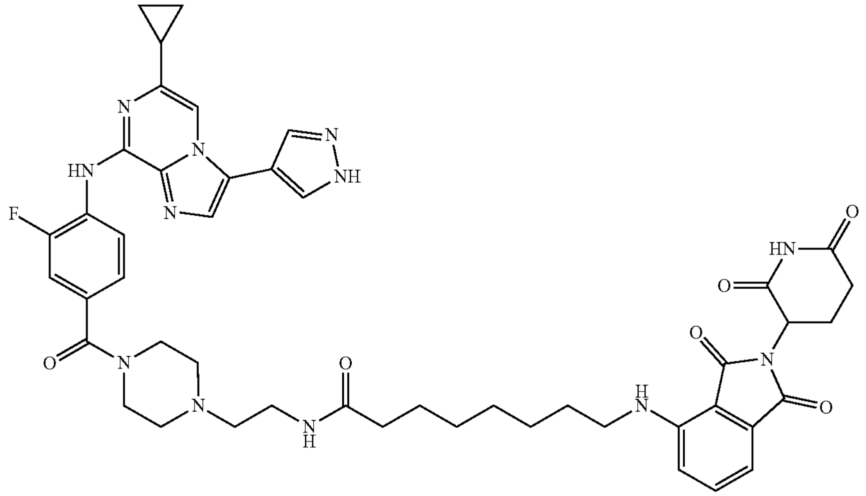 [SMILES: O=C(CCCCCCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]
97 YX79-93
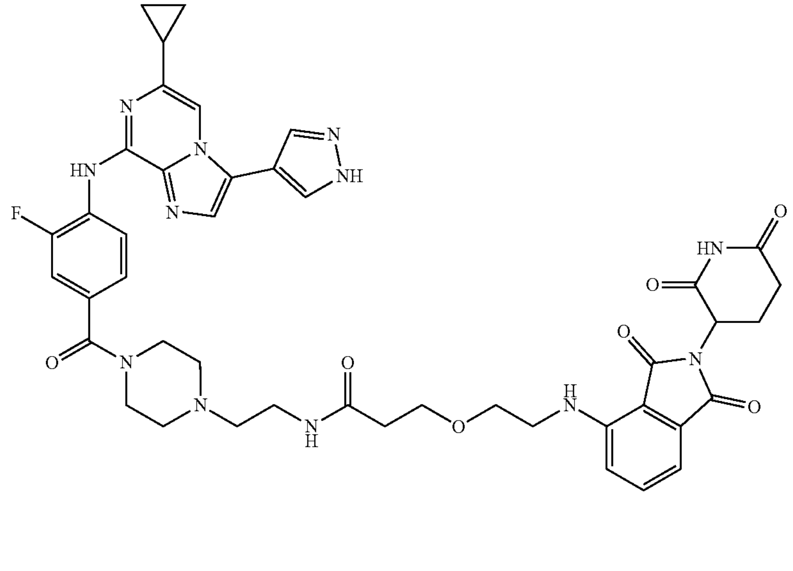 [SMILES: O=C(CCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

TABLE 1-continued
98 YX79-94
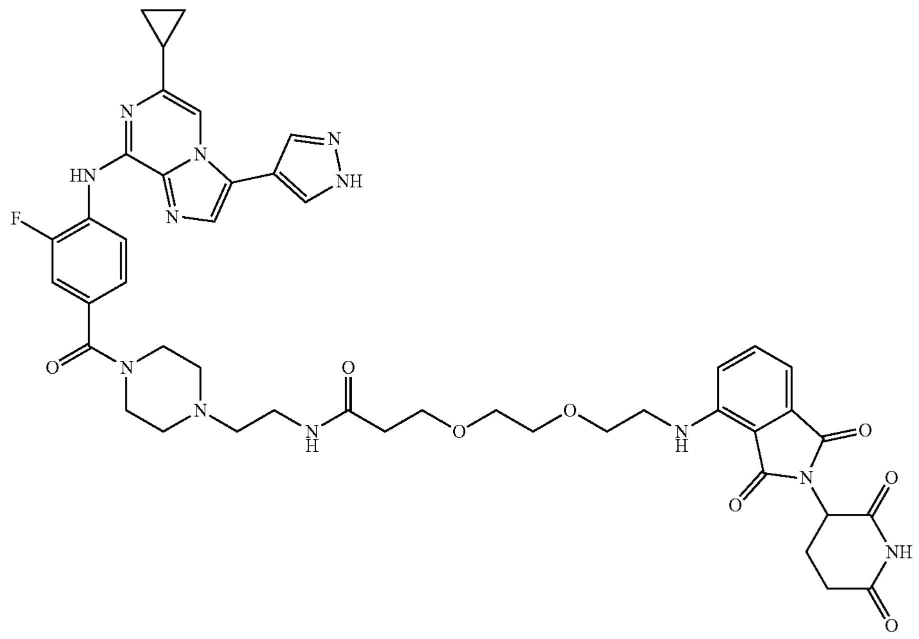 [SMILES: O=C(CCOCCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]
99 YX79-95
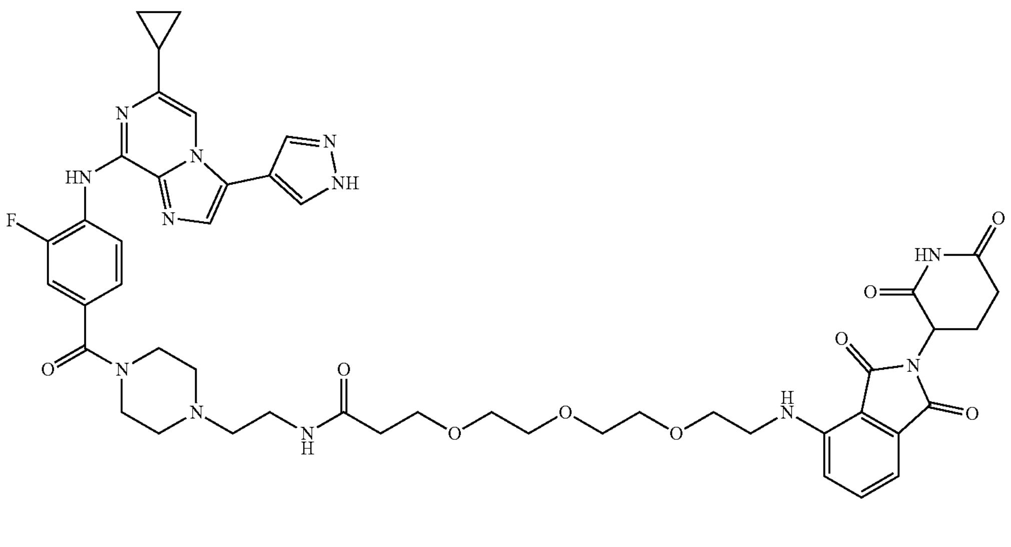 [SMILES: O=C(CCOCCOCCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1]

TABLE 1-continued
| | | |
|---|---|---|
| 100 | YX79-96 | 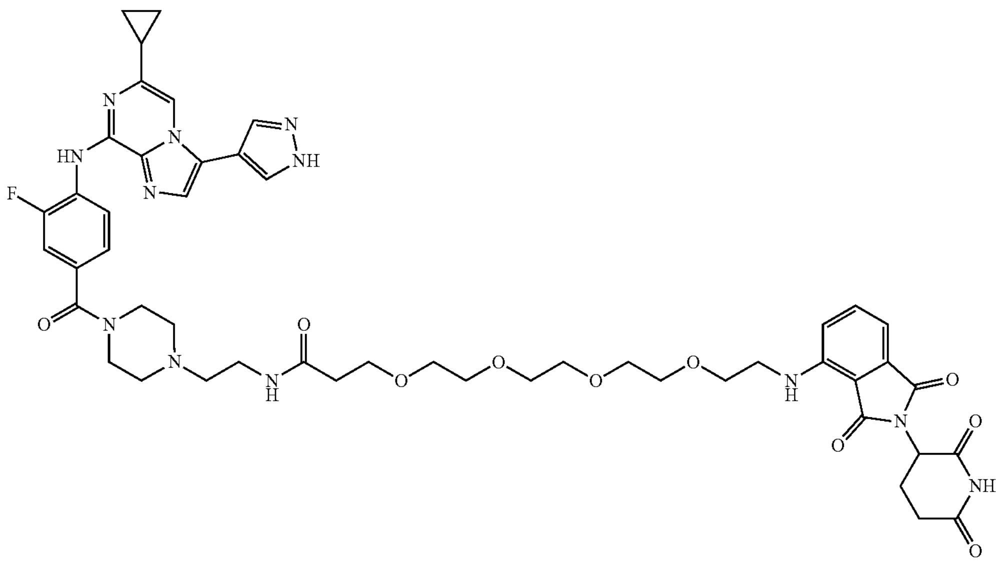 [SMILES: O=C(CCOCCOCCOCCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1] |
| 101 | YX79-97 | 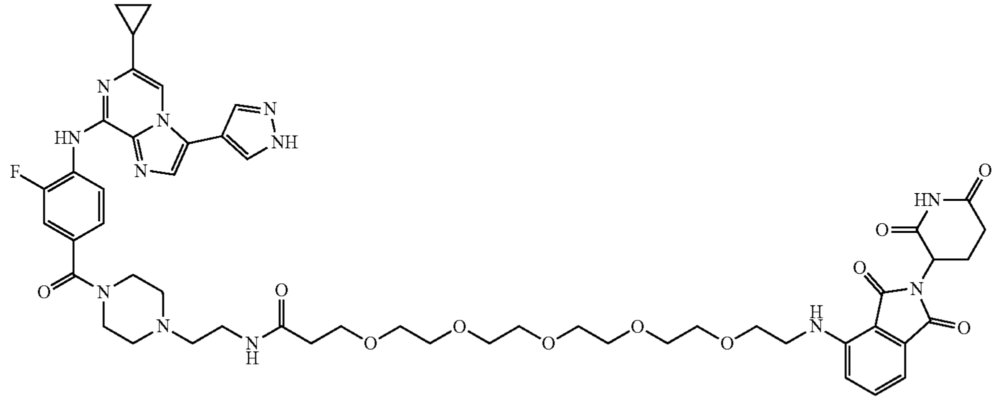 [SMILES: O=C(CCOCCOCCOCCOCCOCCNc1cccc2c1C(=O)N(C1CCC(=O)NC1=O)C2=O)NCCN1CCN(C(=O)c2ccc(Nc3nc(C4CC4)cn4c(-c5cn[nH]c5)cnc34)c(F)c2)CC1] |
| 102 | YX79-132 | 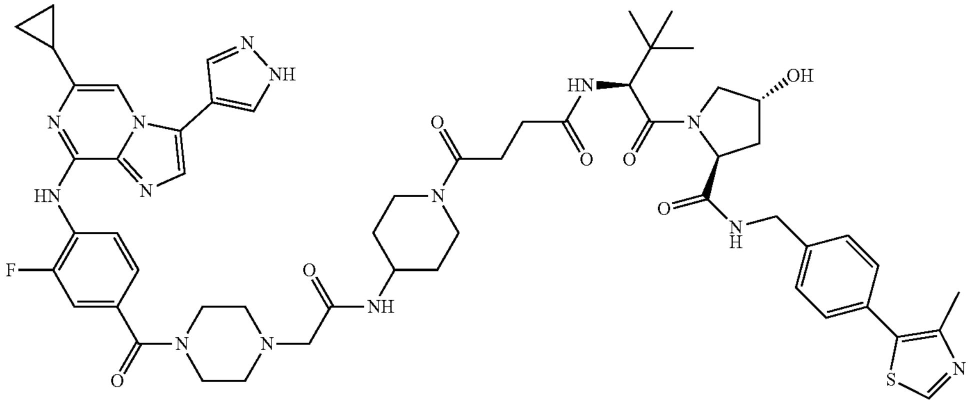 [SMILES: Cc1ncsc1-c1ccc(CNC(=O)[C@@H]2C[C@@H](O)CN2C(=O)[C@@H](NC(=O)CCC(=O)N2CCC(NC(=O)CN3CCN(C(=O)c4ccc(Nc5nc(C6CC6)cn6c(-c7cn[nH]c7)cnc56)c(F)c4)CC3)CC2)C(C)(C)C)cc1] |

TABLE 1-continued
| | | |
|---|---|---|
| 103 | YX79-133 | 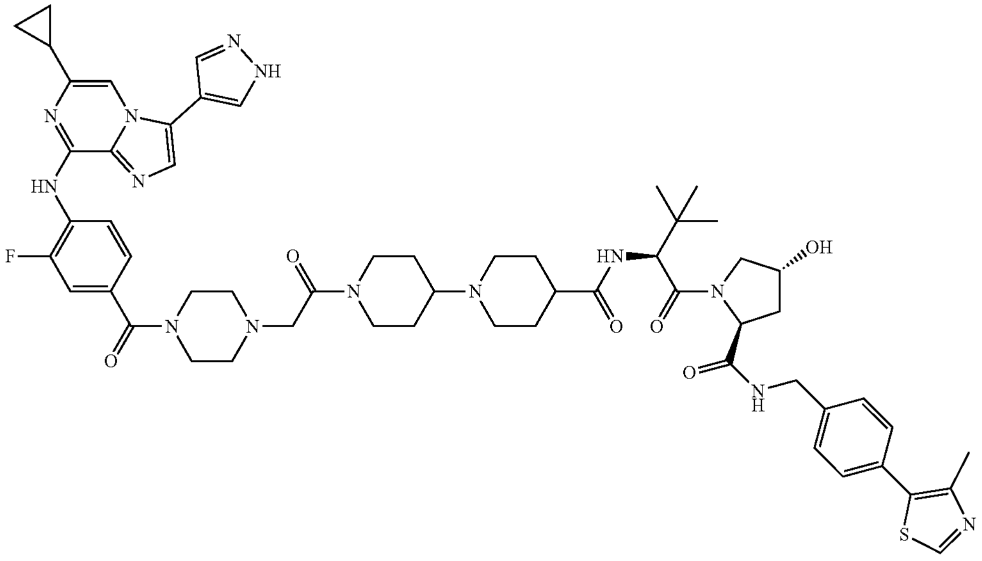 [SMILES: Cc1ncsc1-c1ccc(CNC(=O)[C@@H]2C[C@@H](O)CN2C(=O)[C@@H](NC(=O)C2CCN(C3CCN(C(=O)CN4CCN(C(=O)c5ccc(Nc6nc(C7CC7)cn7c(-c8cn[nH]c8)cnc67)c(F)c5)CC4)CC3)CC2)C(C)(C)C)cc1] |
| 104 | YX79-134 | 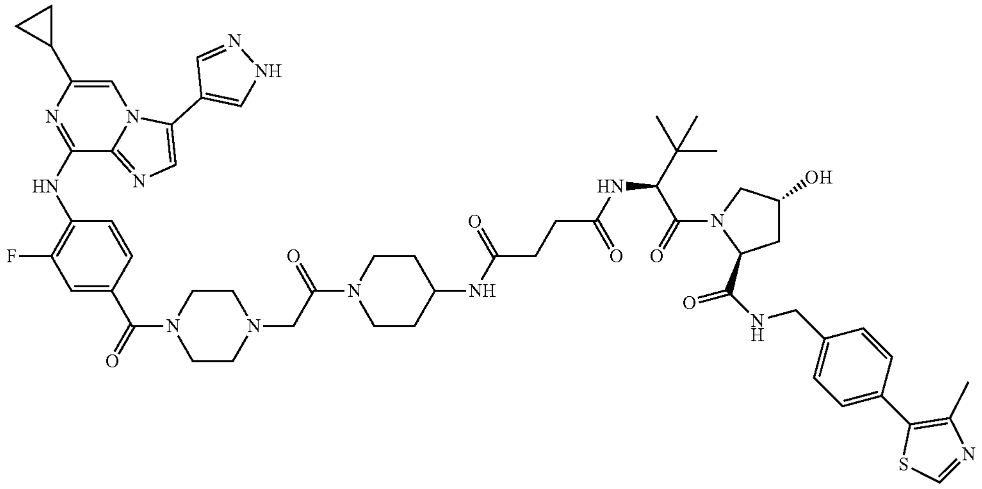 [SMILES: Cc1ncsc1-c1ccc(CNC(=O)[C@@H]2C[C@@H](O)CN2C(=O)[C@@H](NC(=O)CCC(=O)NC2CCN(C(=O)CN3CCN(C(=O)c4ccc(Nc5nc(C6CC6)cn6c(-c7cn[nH]c7)cnc56)c(F)c4)CC3)CC2)C(C)(C)C)cc1] |
| 105 | YX79-135 | 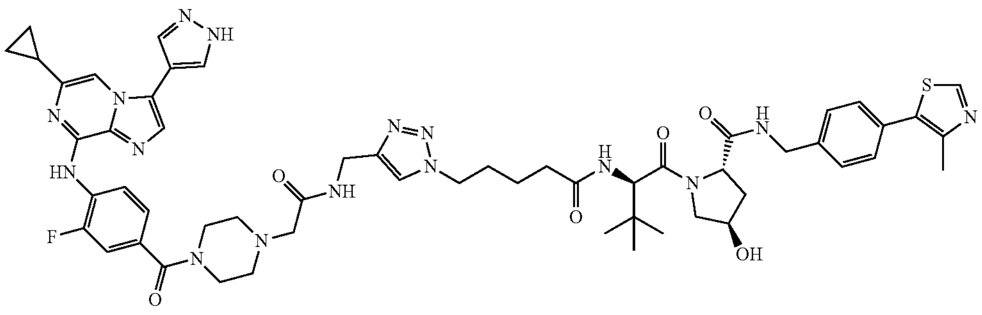 [SMILES: Cc1ncsc1-c1ccc(CNC(=O)[C@@H]2C[C@@H](O)CN2C(=O)[C@H](NC(=O)CCCCn2cc(CNC(=O)CN3CCN(C(=O)c4ccc(Nc5nc(C6CC6)cn6c(-c7cn[nH]c7)cnc56)c(F)c4)CC3)nn2)C(C)(C)C)cc1] |

TABLE 1-continued
| | | |
|---|---|---|
| 106 | YX79-136 | 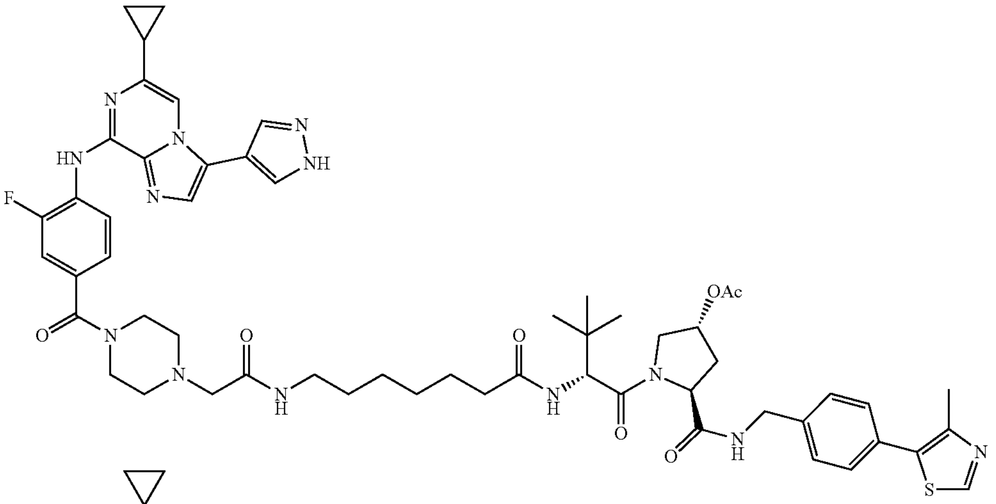 |
| 107 | YX79-137 | 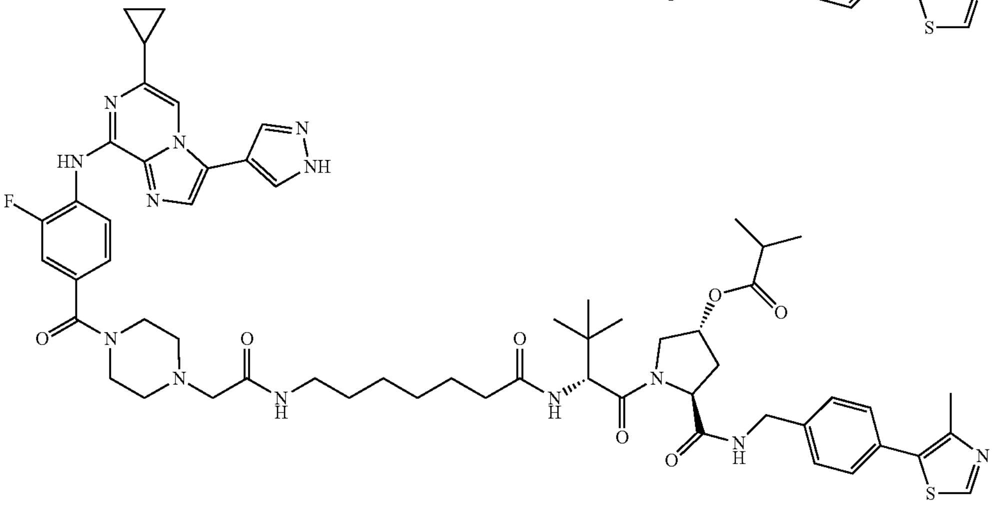 |
| 108 | YX79-131 | 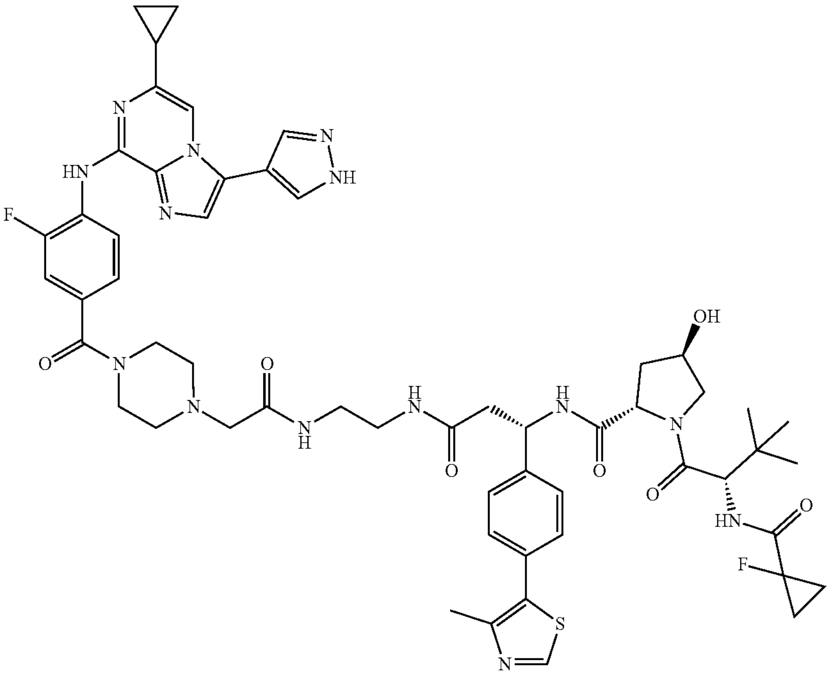 [SMILES: Cc1ncsc1-c1ccc([C@H](CC(=O)NCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1] |

TABLE 1-continued
109 YX79-139
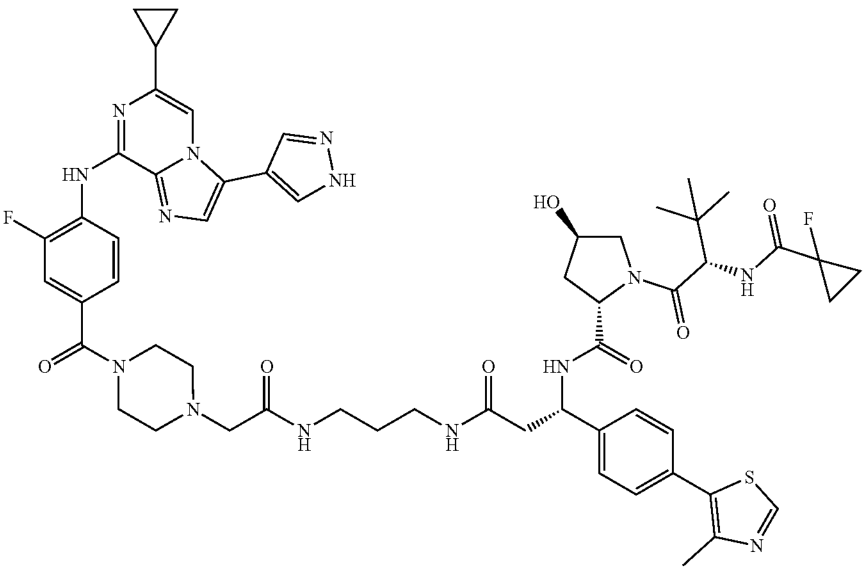 [SMILES: Cc1ncsc1-c1ccc([C@H](CC(=O)NCCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]
110 YX79-140
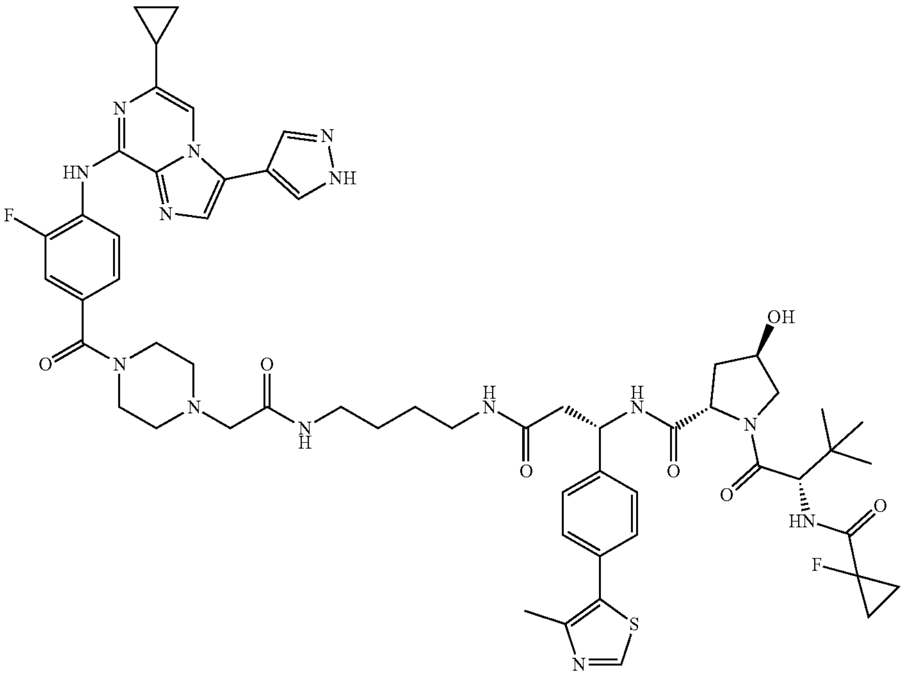 [SMILES: Cc1ncsc1-c1ccc([C@H](CC(=O)NCCCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

TABLE 1-continued
111 YX79-141
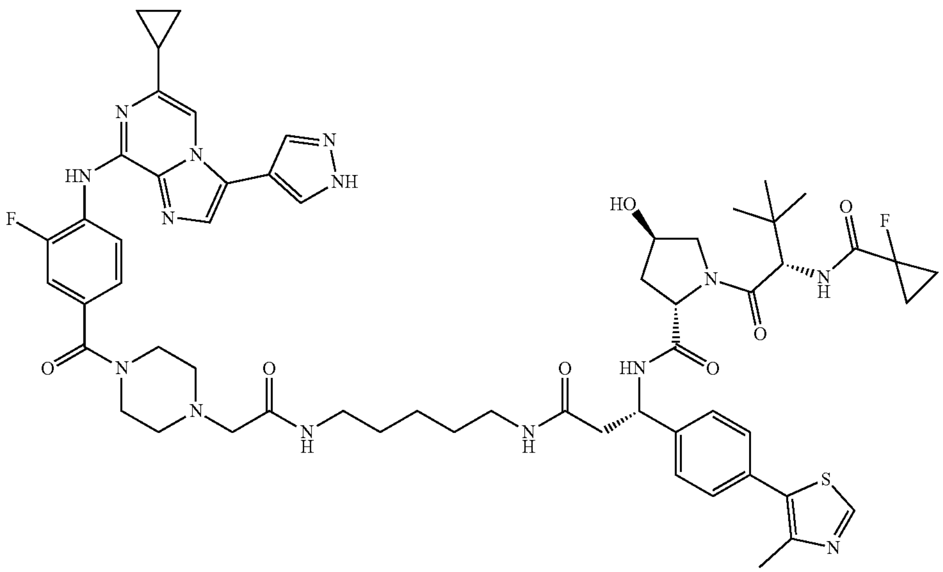
112 YX79-142
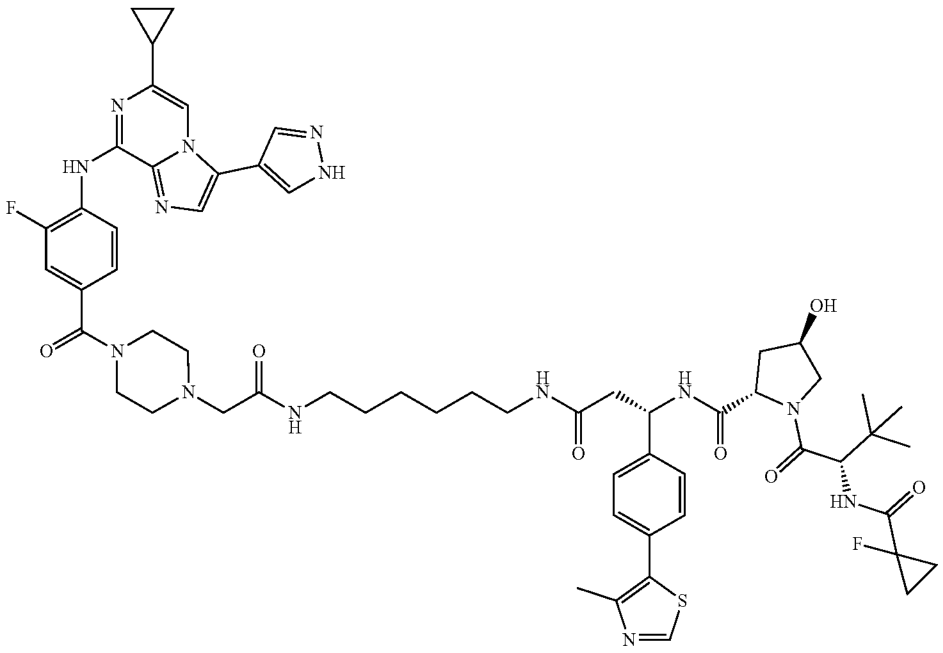 [SMILES: Cc1ncsc1-c1ccc([C@H](CC(=O)NCCCCCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

TABLE 1-continued
113 YX79-143
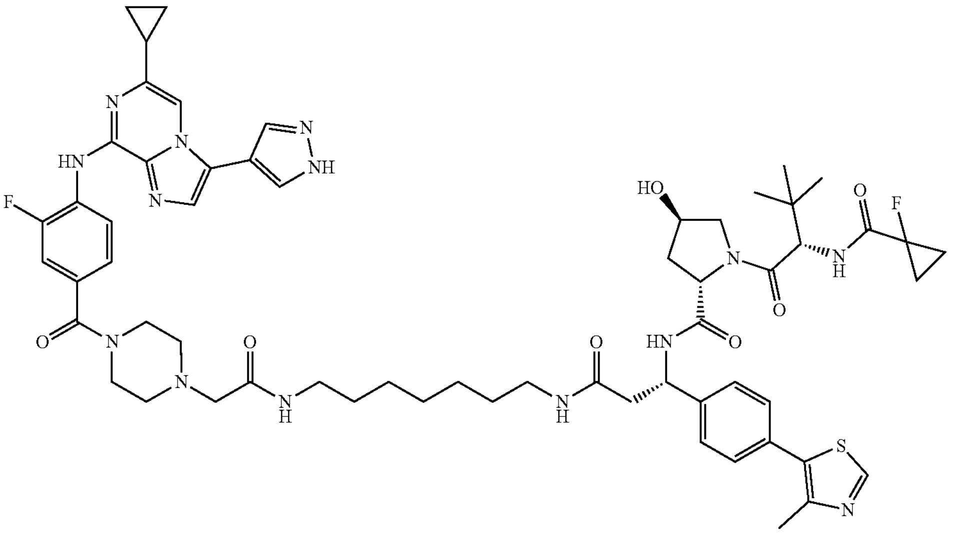 [SMILES: Cc1ncsc1-c1ccc([C@H](CC(=O)NCCCCCCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]
114 YX79-144
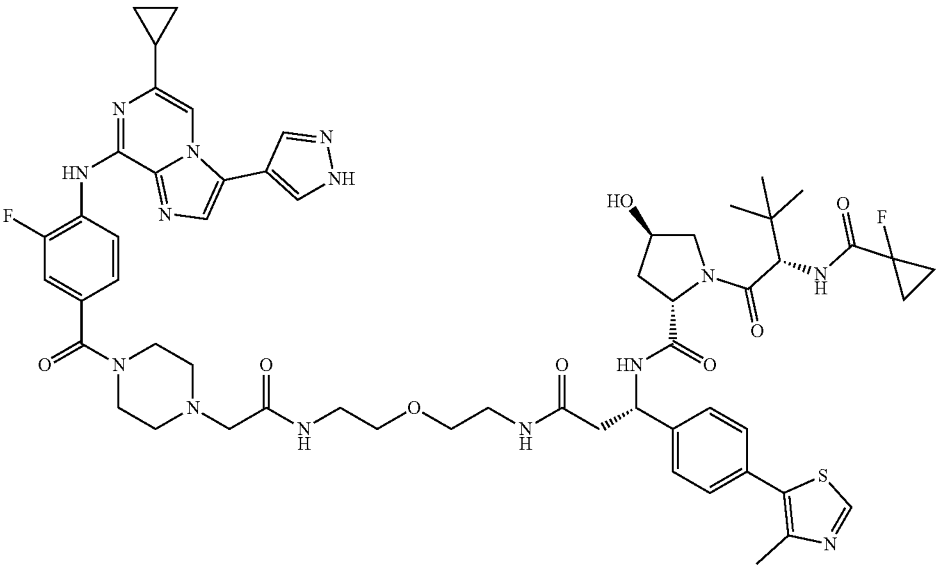 [SMILES: Cc1ncsc1-c1ccc([C@H](CC(=O)NCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

TABLE 1-continued
115 YX79-145
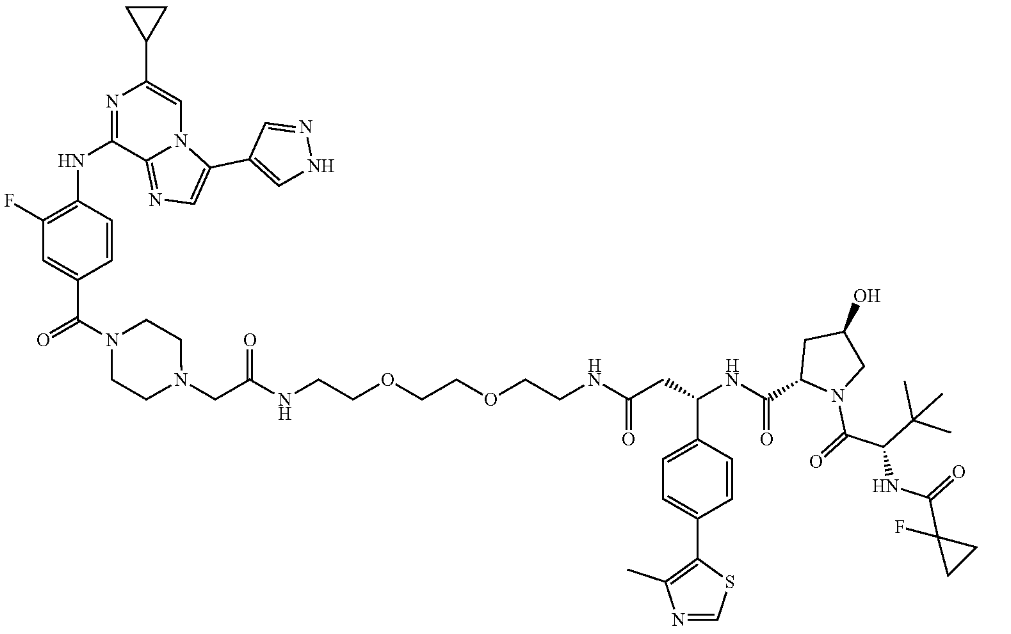 [SMILES: Cc1ncsc1-c1ccc([C@H](CC(=O)NCCOCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]
116 YX79-146
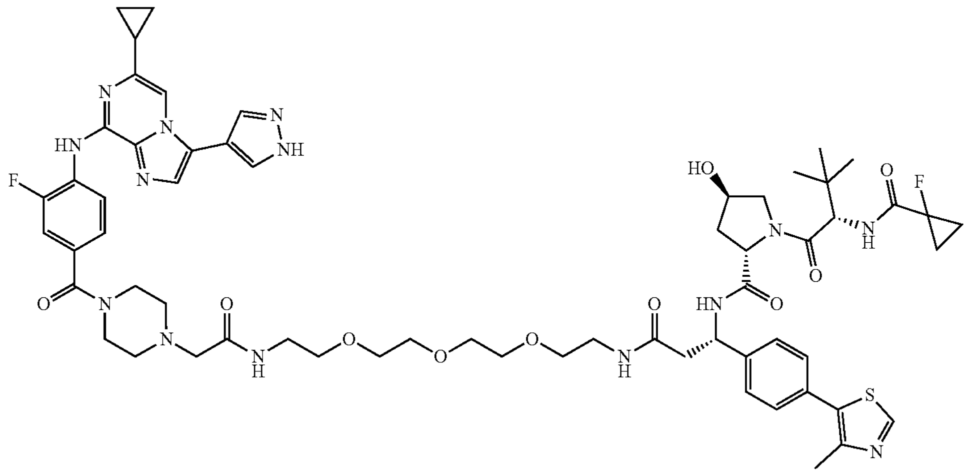 [SMILES: Cc1ncsc1-c1ccc([C@H](CC(=O)NCCOCCOCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]
117 YX79-147
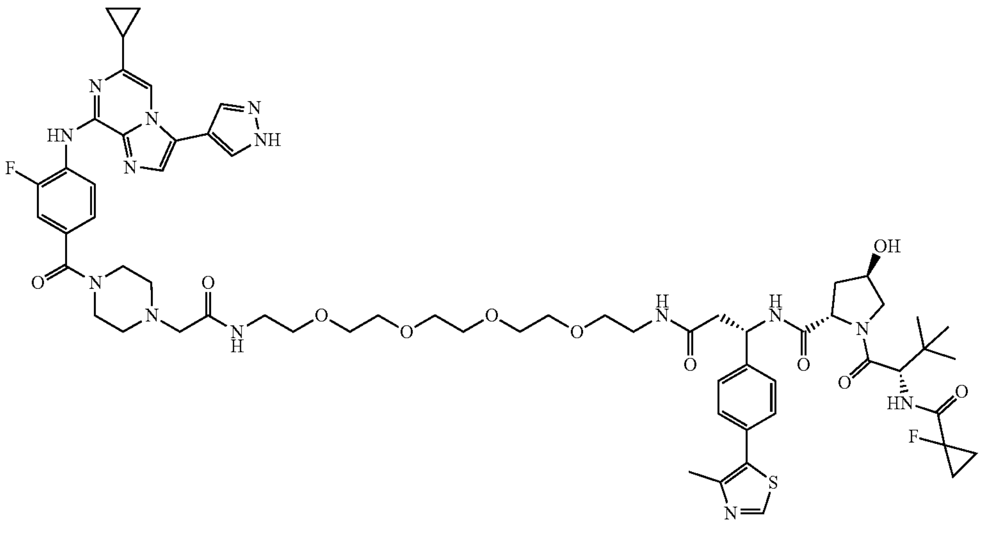 [SMILES: Cc1ncsc1-c1ccc([C@H](CC(=O)NCCOCCOCCOCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]

TABLE 1-continued
118 YX79-148
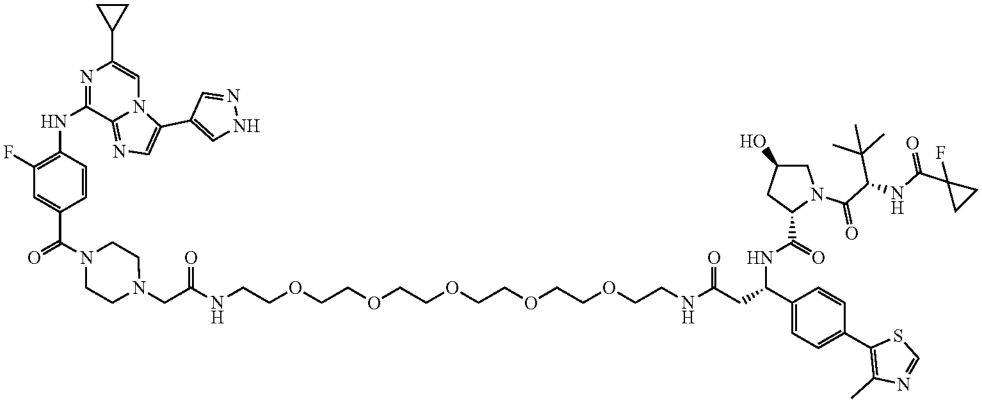 [SMILES: Cc1ncsc1-c1ccc([C@H](CC(=O)NCCOCCOCCOCCOCCOCCNC(=O)CN2CCN(C(=O)c3ccc(Nc4nc(C5CC5)cn5c(-c6cn[nH]c6)cnc45)c(F)c3)CC2)NC(=O)[C@@H]2C[C@@H](O)CN2C(=O)[C@@H](NC(=O)C2(F)CC2)C(C)(C)C)cc1]
119 YX79-138
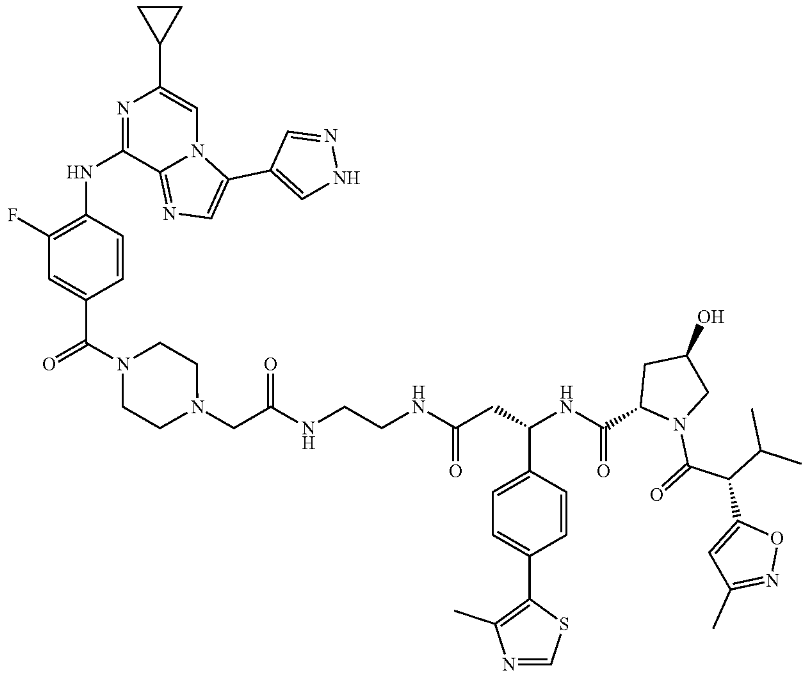 [SMILES: Cc1cc([C@H](C(=O)N2C[C@H](O)C[C@H]2C(=O)N[C@@H](CC(=O)NCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]
120 YX79-149
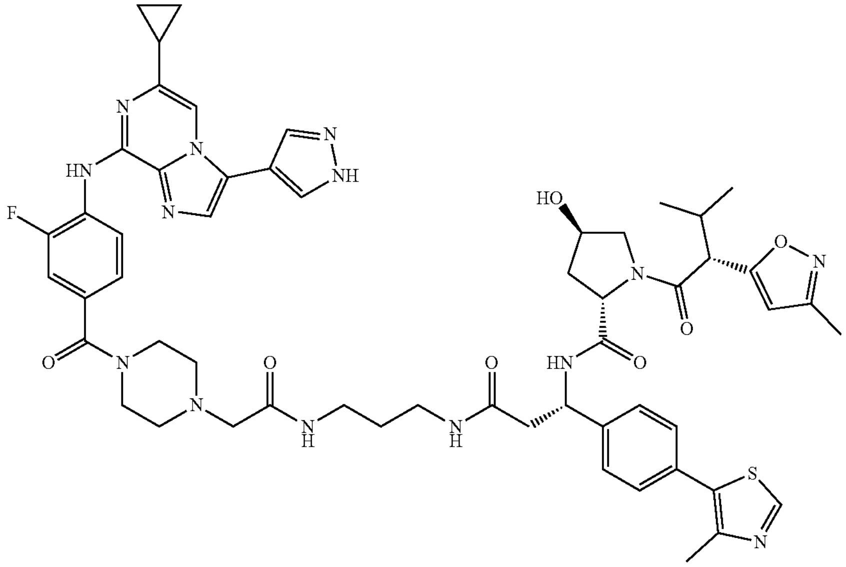 [SMILES: Cc1cc([C@H](C(=O)N2C[C@H](O)C[C@H]2C(=O)N[C@@H](CC(=O)NCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1]

TABLE 1-continued
| | | |
|---|---|---|
| 121 | YX79-150 | 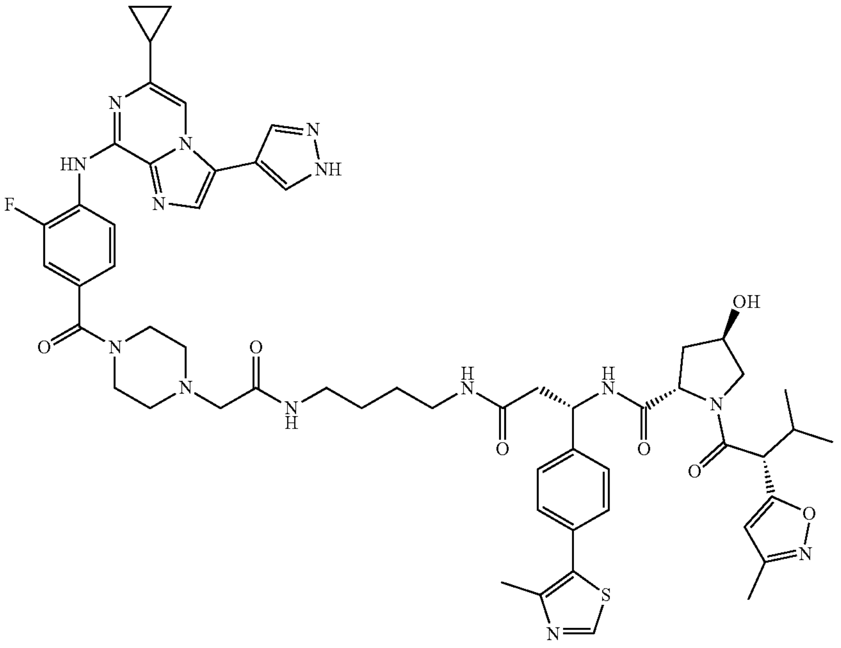 [SMILES: Cc1cc([C@H](C(=O)N2C[C@H](O)C[C@H]2C(=O)N[C@@H](CC(=O)NCCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1] |
| 122 | YX79-151 | 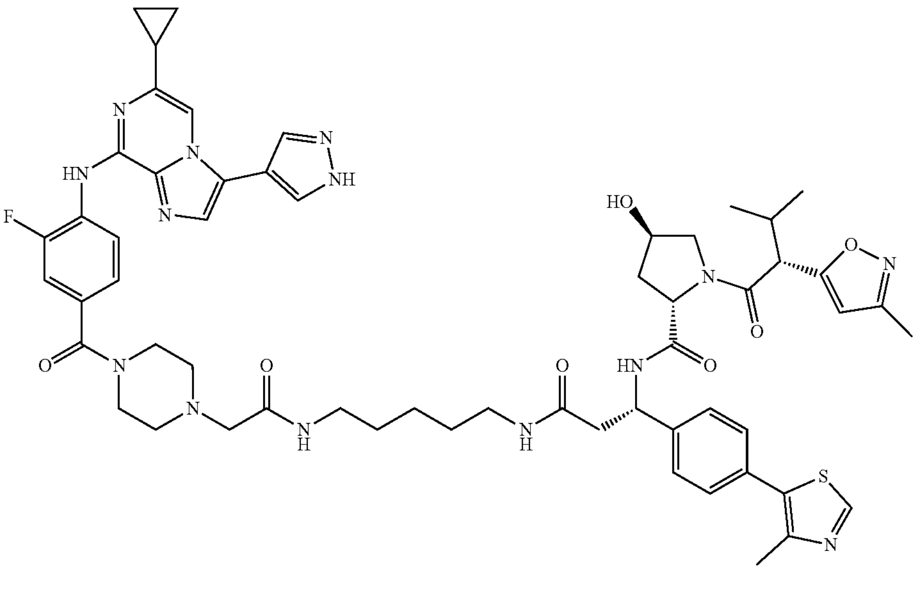 [SMILES: Cc1cc([C@H](C(=O)N2C[C@H](O)C[C@H]2C(=O)N[C@@H](CC(=O)NCCCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1] |

TABLE 1-continued
| | | |
|---|---|---|
| 123 | YX79-152 | 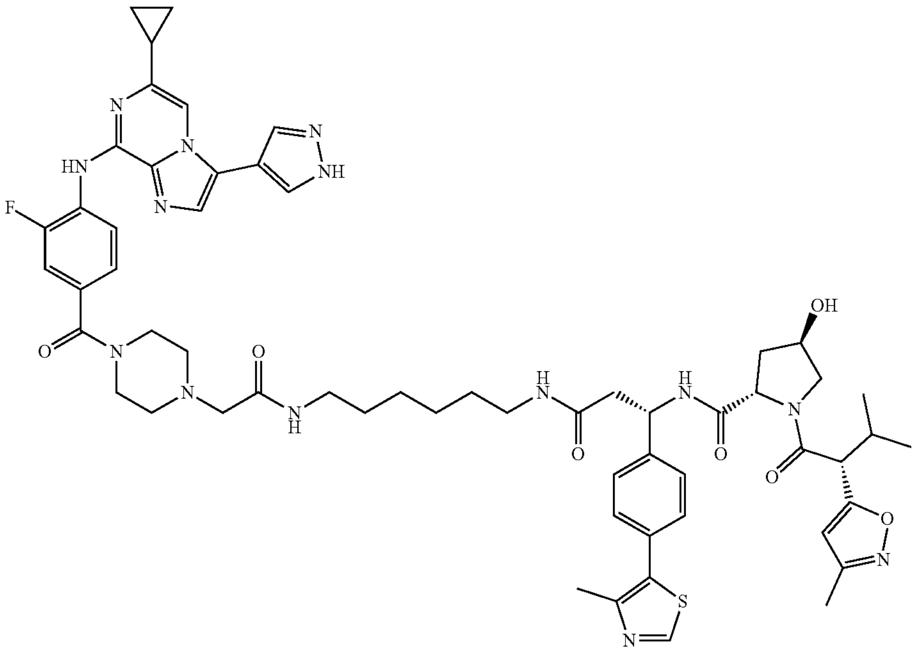 [SMILES: Cc1cc([C@H](C(=O)N2C[C@H](O)C[C@H]2C(=O)N[C@@H](CC(=O)NCCCCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1] |
| 124 | YX79-153 | 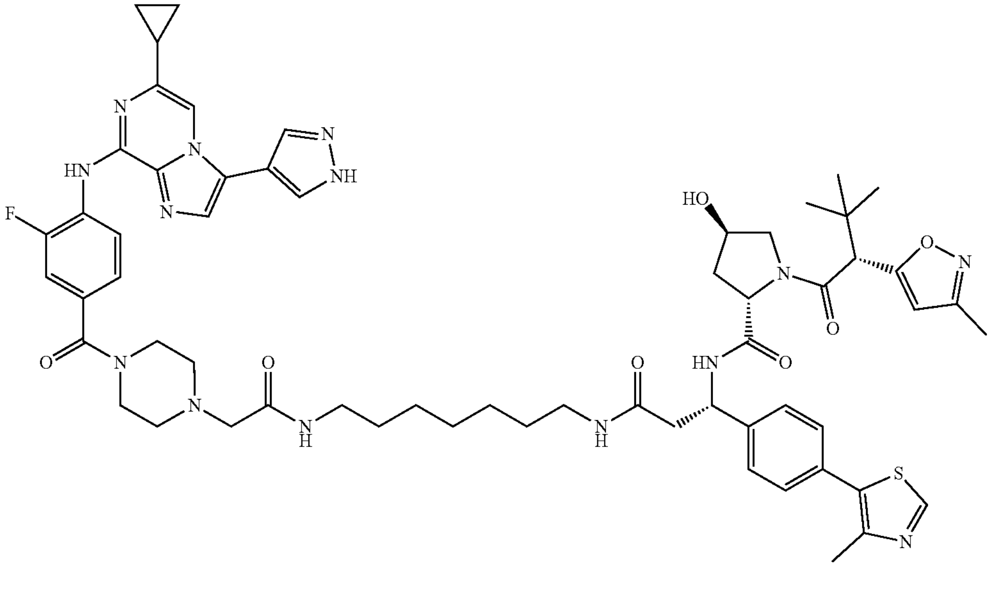 [SMILES: Cc1cc([C@H](C(=O)N2C[C@H](O)C[C@H]2C(=O)N[C@@H](CC(=O)NCCCCCCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)(C)C)on1] |

TABLE 1-continued
| | | |
|---|---|---|
| 125 | YX79-154 | 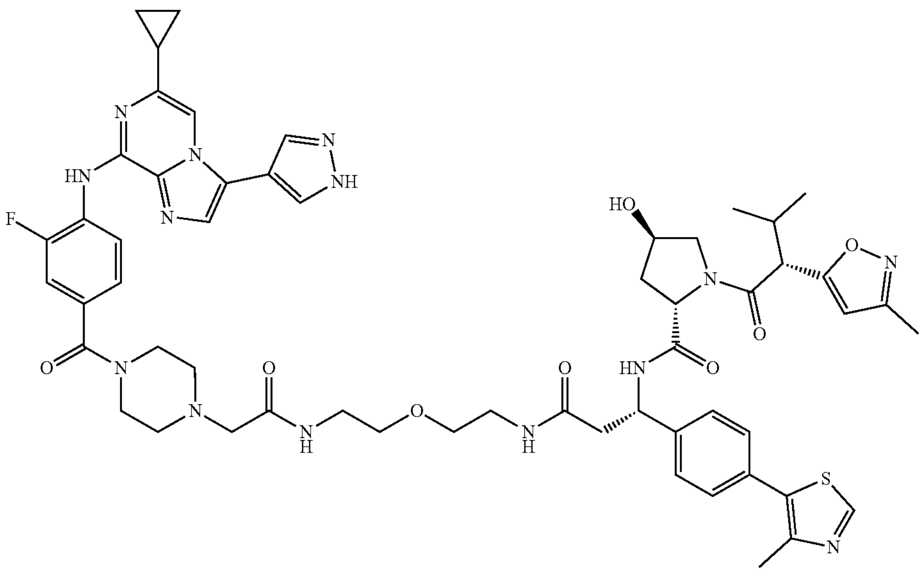 [SMILES: Cc1cc([C@H](C(=O)N2C[C@H](O)C[C@H]2C(=O)N[C@@H](CC(=O)NCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1] |
| 126 | YX79-155 | 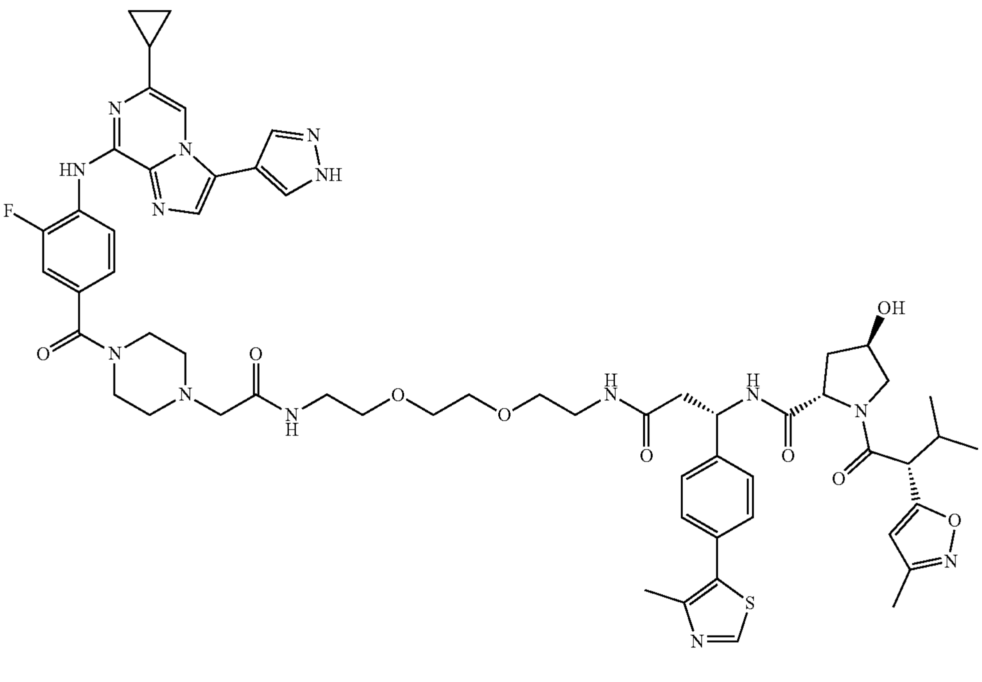 [SMILES: Cc1cc([C@H](C(=O)N2C[C@H](O)C[C@H]2C(=O)N[C@@H](CC(=O)NCCOCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1] |

TABLE 1-continued
| | | |
|---|---|---|
| 127 | YX79-156 | 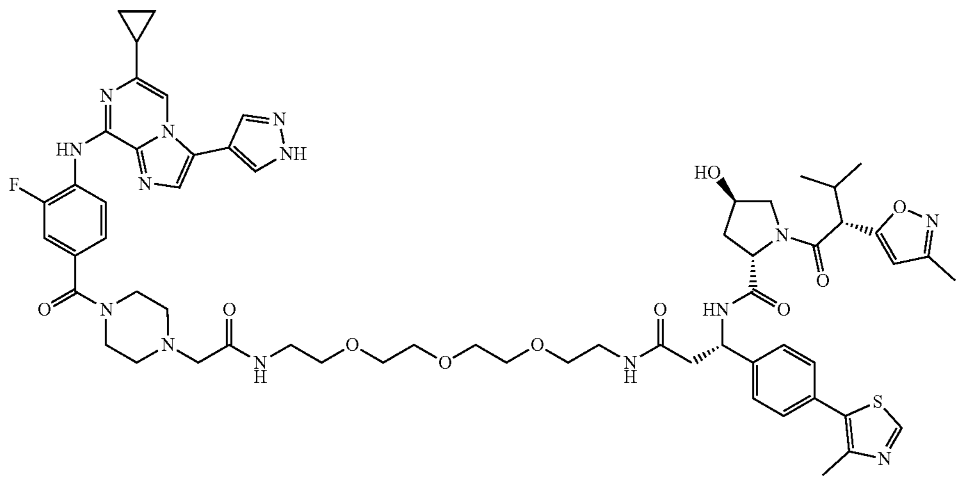 [SMILES: Cc1cc([C@H](C(=O)N2C[C@H](O)C[C@H]2C(=O)N[C@@H](CC(=O)NCCOCCOCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1] |
| 128 | YX79-157 | 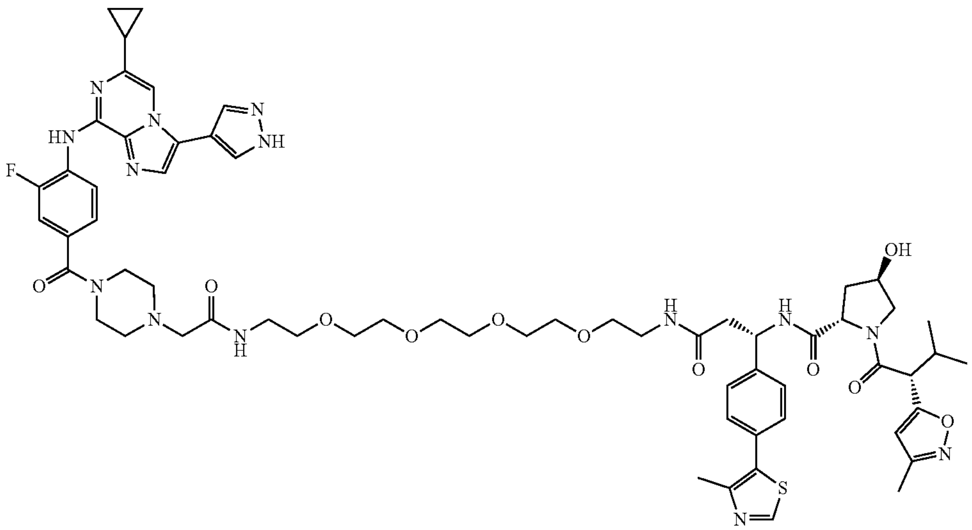 [SMILES: Cc1cc([C@H](C(=O)N2C[C@H](O)C[C@H]2C(=O)N[C@@H](CC(=O)NCCOCCOCCOCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1] |
| 129 | YX79-158 | 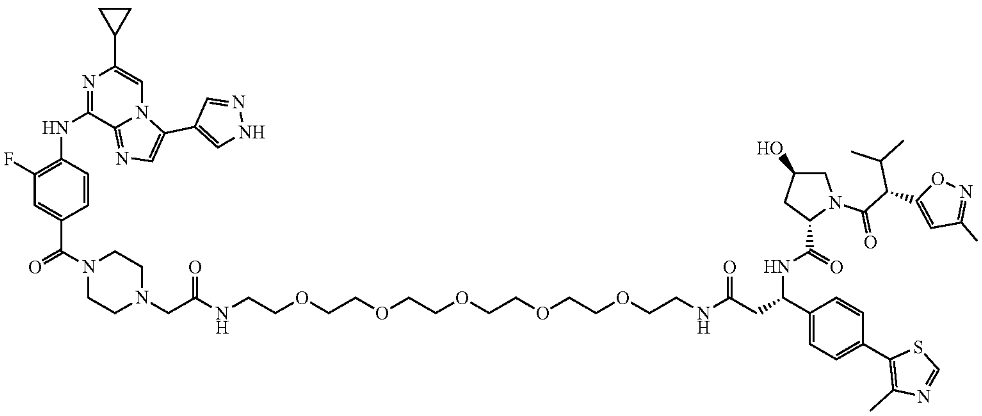 [SMILES: Cc1cc([C@H](C(=O)N2C[C@H](O)C[C@H]2C(=O)N[C@@H](CC(=O)NCCOCCOCCOCCOCCOCCNC(=O)CN2CCN(C(=O)c3ccc(Nc4nc(C5CC5)cn5c(-c6cn[nH]c6)cnc45)c(F)c3)CC2)c2ccc(-c3scnc3C)cc2)C(C)C)on1] |

TABLE 1-continued
| | | |
|---|---|---|
| 130 | YX79-159 | 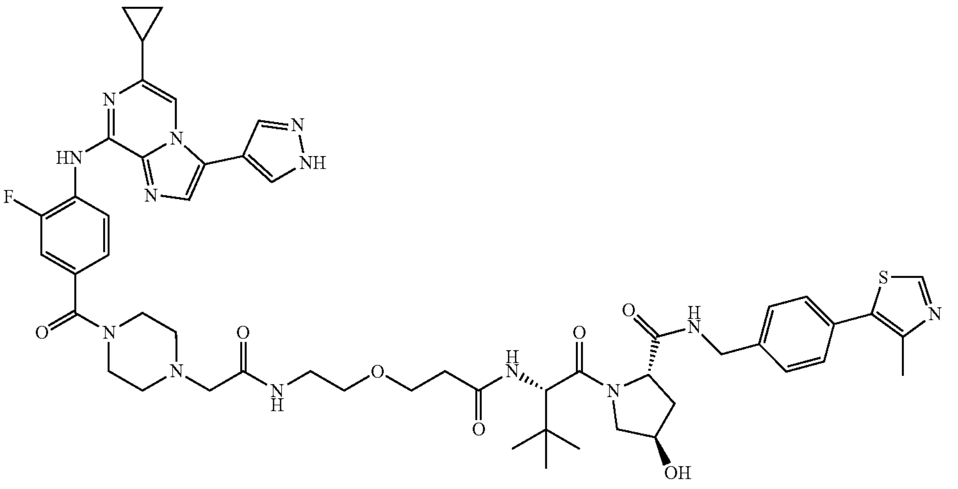 [SMILES: Cc1ncsc1-c1ccc(CNC(=O)[C@@H]2C[C@@H](O)CN2C(=O)[C@@H](NC(=O)CCOCCNC(=O)CN2CCN(C(=O)c3ccc(Nc4nc(C5CC5)cn5c(-c6cn[nH]c6)cnc45)c(F)c3)CC2)C(C)(C)C)cc1] |
| 131 | YX79-160 | 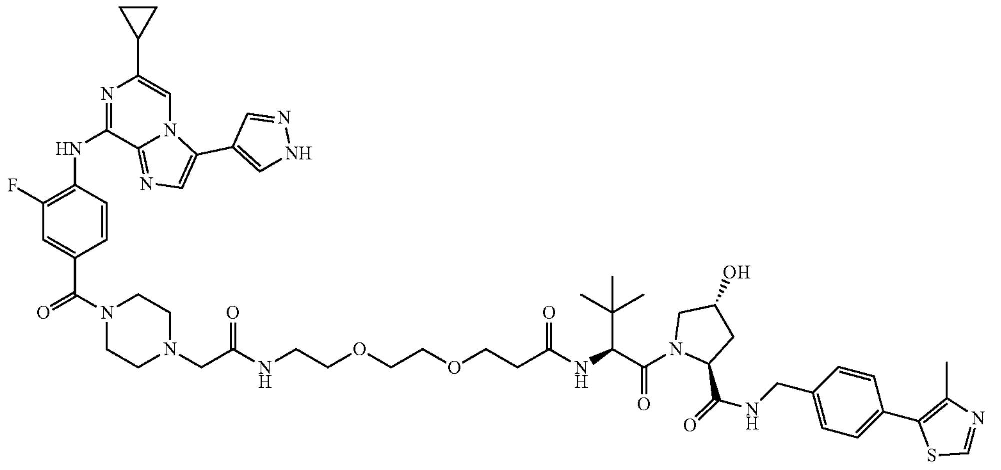 |
| 132 | YX79-161 | 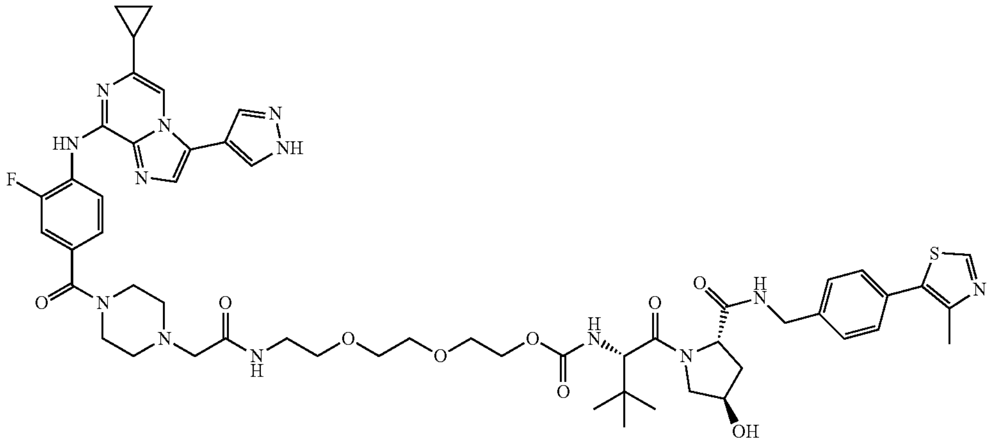 [SMILES: Cc1ncsc1-c1ccc(CNC(=O)[C@@H]2C[C@@H](O)CN2C(=O)[C@@H](NC(=O)OCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1] |

TABLE 1-continued
| | | |
|---|---|---|
| 133 | YX79-162 | 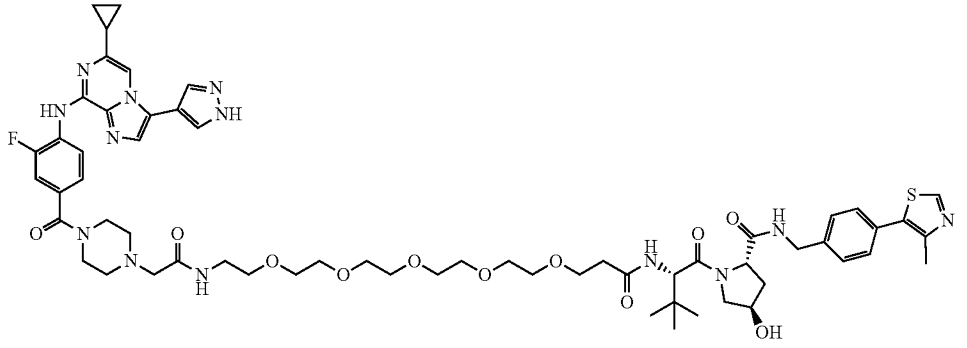 [SMILES: Cc1ncsc1-c1ccc(CNC(=O)[C@@H]2C[C@@H](O)CN2C(=O)[C@@H](NC(=O)CCOCCOCCOCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1] |
| 134 | YX49-102 | 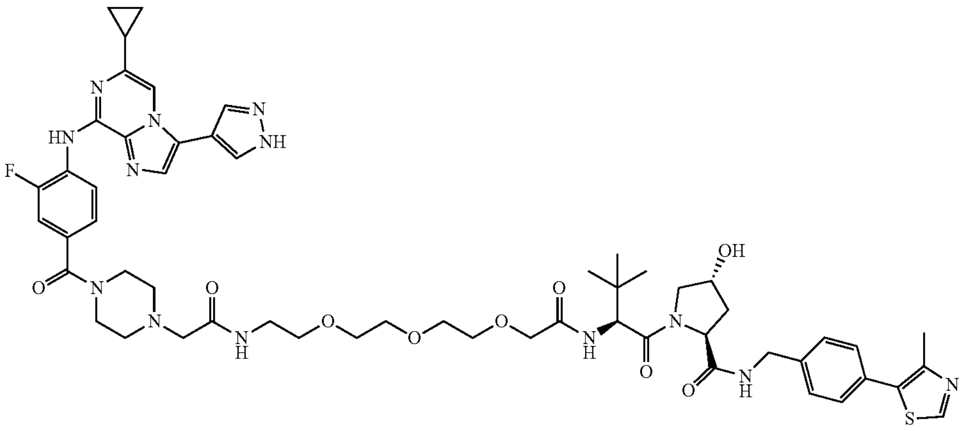 [SMILES: Cc1ncsc1-c1ccc(CNC(=O)[C@@H]2C[C@@H](O)CN2C(=O)[C@@H](NC(=O)COCCOCCOCCNC(=O)CN2CCN(C(=O)c3ccc(Nc4nc(C5CC5)cn5c(-c6cn[nH]c6)cnc45)c(F)c3)CC2)C(C)(C)C)cc1] |
| 135 | YX79-164 | 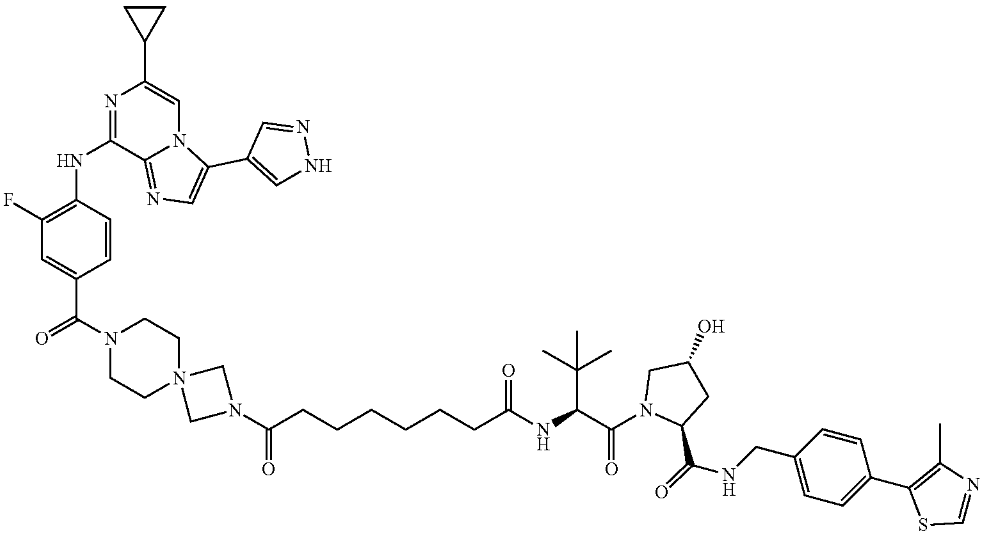 |

TABLE 1-continued
| | | |
|---|---|---|
| 136 | YX79-165 | 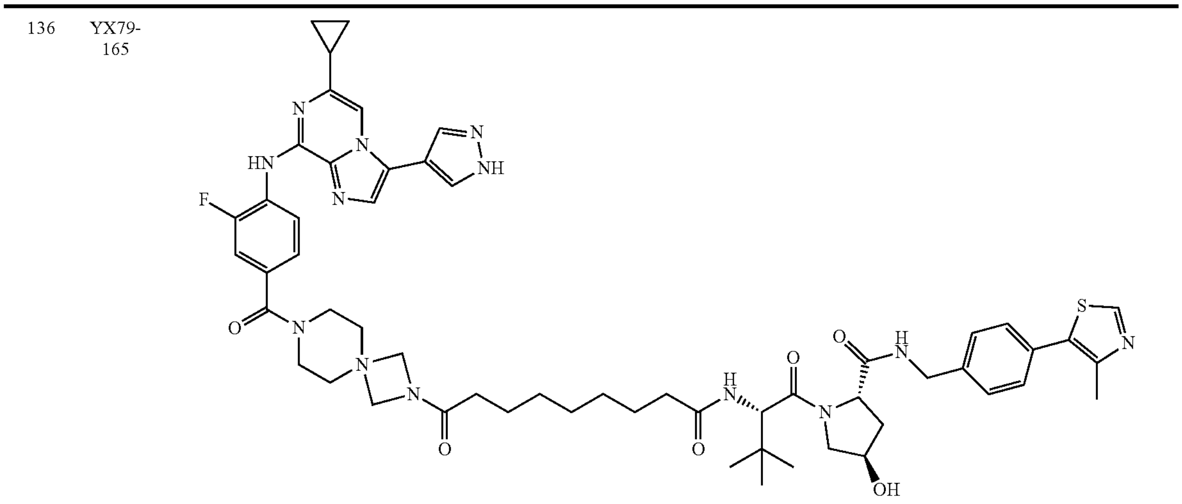 |
| 137 | JH077-29 | 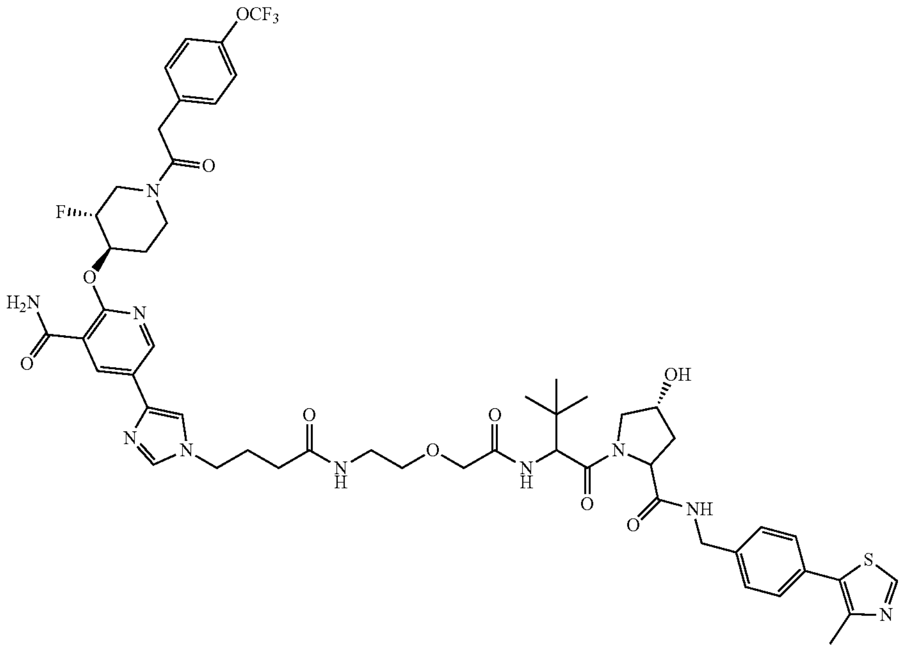 [SMILES: Cc1ncsc1-c1ccc(CNC(=O)C2C[C@@H](O)CN2C(=O)C(NC(=O)COCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 138 | JH077-30 | 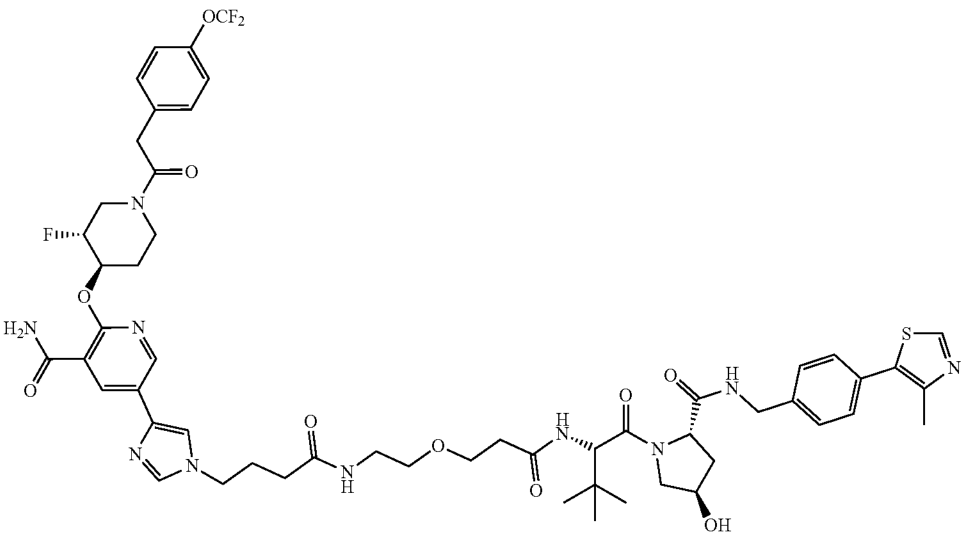 |

TABLE 1-continued
139 JH077-31
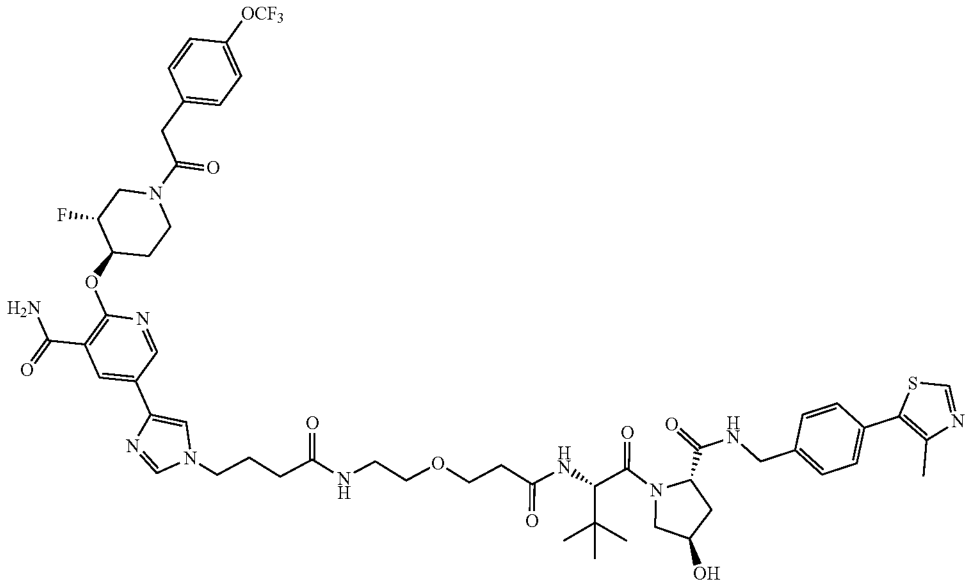 [SMILES: Cc1ncsc1-c1ccc(CNC(=O)[C@@H]2C[C@@H](O)CN2C(=O)[C@@H](NC(=O)CCOCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]
140 JH077-32
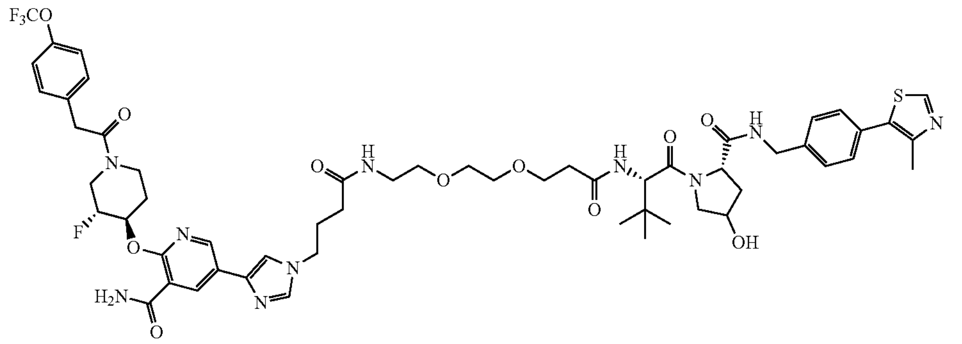
141 JH077-33
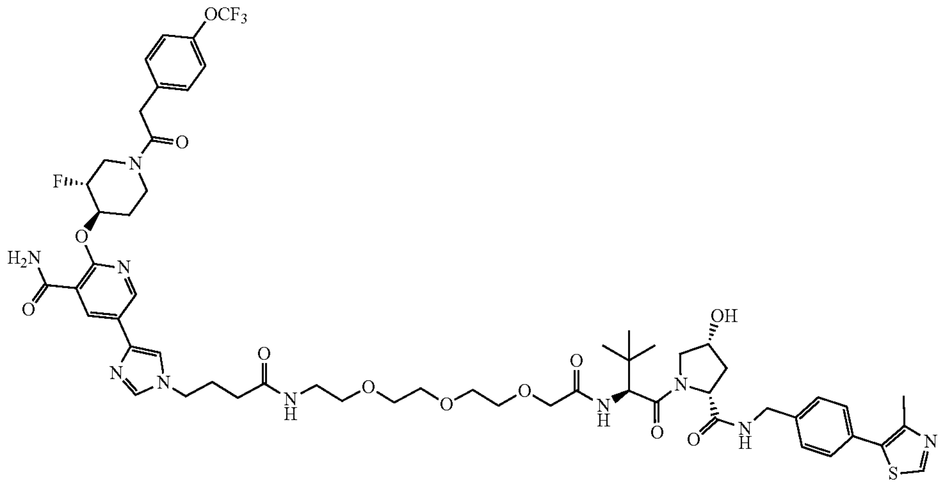 [SMILES: Cc1ncsc1-c1ccc(CNC(=O)[C@H]2C[C@@H](O)CN2C(=O)[C@@H](NC(=O)COCCOCCOCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

TABLE 1-continued
| | | |
|---|---|---|
| 142 | JH077-34 | 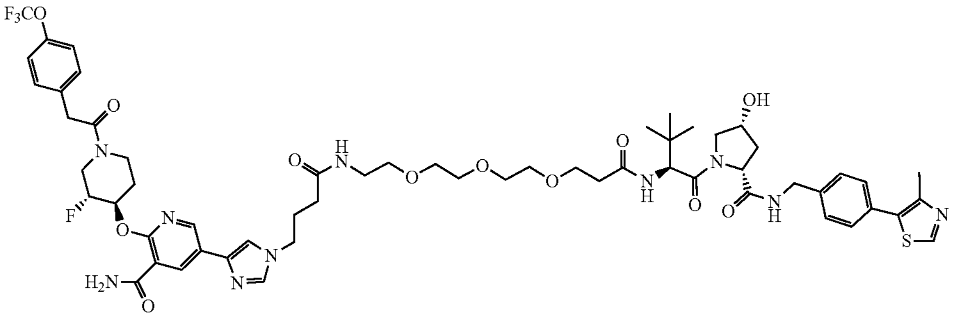 [SMILES: Cc1ncsc1-c1ccc(CNC(=O)[C@H]2C[C@@H](O)CN2C(=O)[C@@H](NC(=O)CCOCCOCCOCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 143 | JH077-35 | 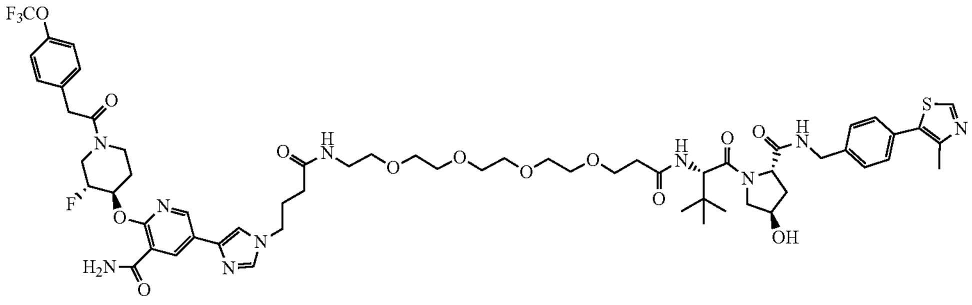 [SMILES: Cc1ncsc1-c1ccc(CNC(=O)[C@@H]2C[C@@H](O)CN2C(=O)[C@@H](NC(=O)CCOCCOCCOCCOCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 144 | JH077-36 | 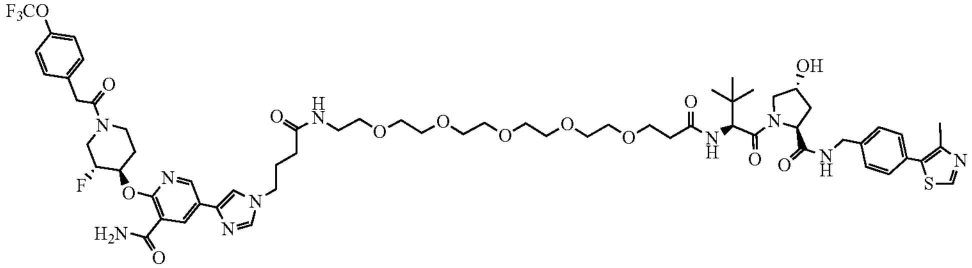 [SMILES: Cc1ncsc1-c1ccc(CNC(=O)[C@@H]2C[C@@H](O)CN2C(=O)[C@@H](NC(=O)CCOCCOCCOCCOCCOCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 145 | JH077-37 | 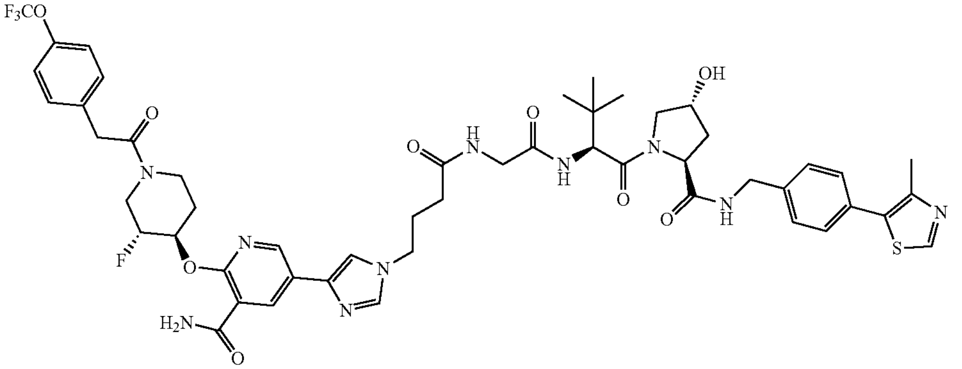 [SMILES: Cc1ncsc1-c1ccc(CNC(=O)[C@@H]2C[C@@H](O)CN2C(=O)[C@@H](NC(=O)CNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 146 | JH077-38 | 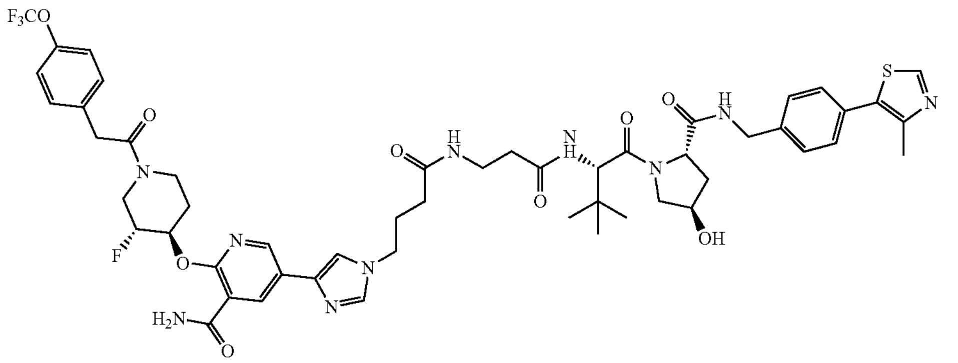 [SMILES: Cc1ncsc1-c1ccc(CNC(=O)[C@@H]2C[C@@H](O)CN2C(=O)[C@@H](NC(=O)CCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |

TABLE 1-continued
147 JH077-39
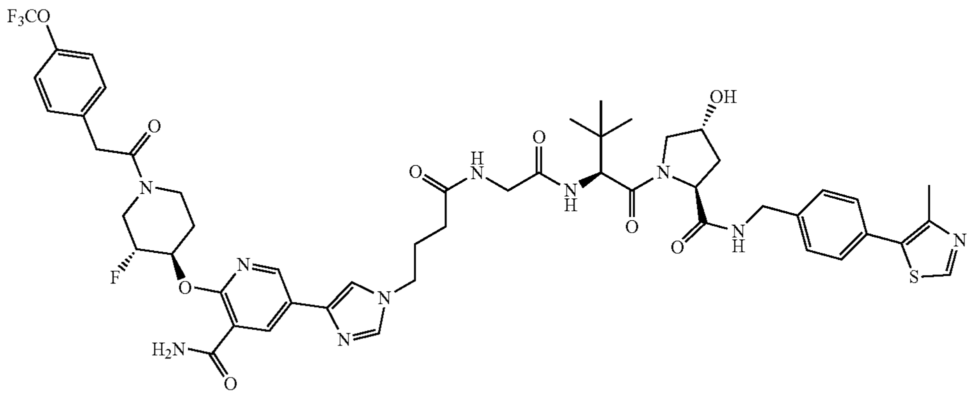 [SMILES: Cc1ncsc1-c1ccc(CNC(=O)[C@@H]2C[C@@H](O)CN2C(=O)[C@@H](NC(=O)CNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]
148 JH077-40
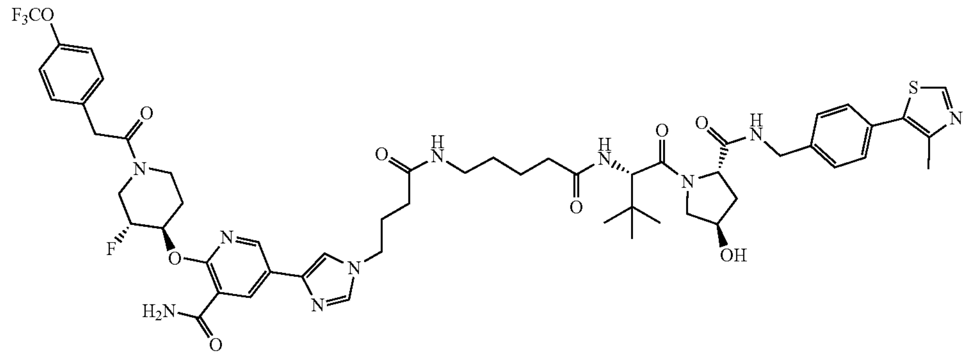 [SMILES: Cc1ncsc1-c1ccc(CNC(=O)[C@@H]2C[C@@H](O)CN2C(=O)[C@@H](NC(=O)CCCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]
149 JH077-41
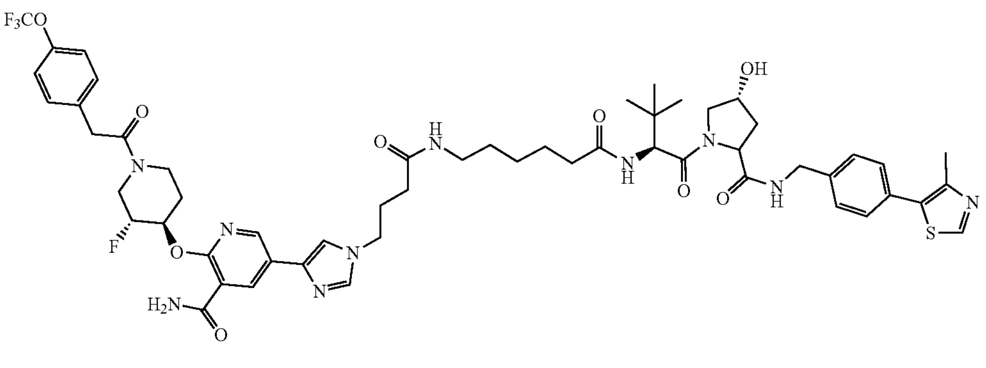 [SMILES: Cc1ncsc1-c1ccc(CNC(=O)C2C[C@@H](O)CN2C(=O)[C@@H](NC(=O)CCCCCNC(=O)CCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

TABLE 1-continued
| | | |
|---|---|---|
| 150 | JH077-47 | 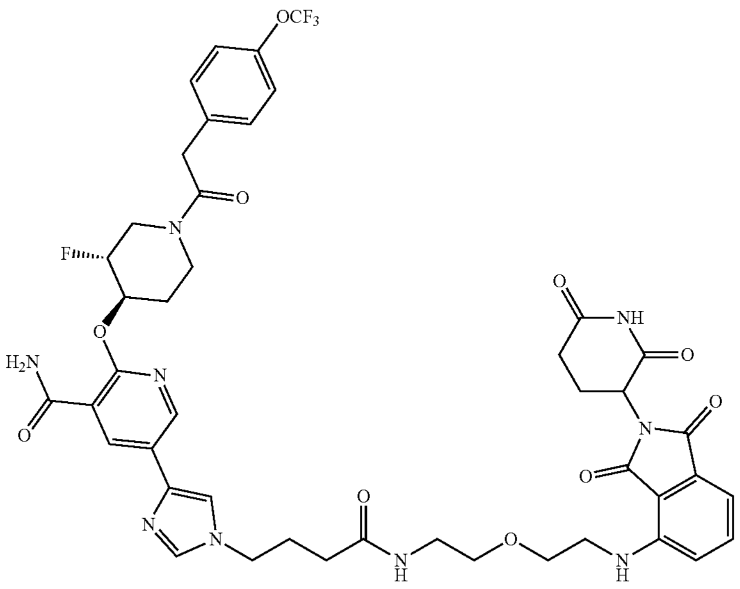 |
| 151 | JH077-48 | 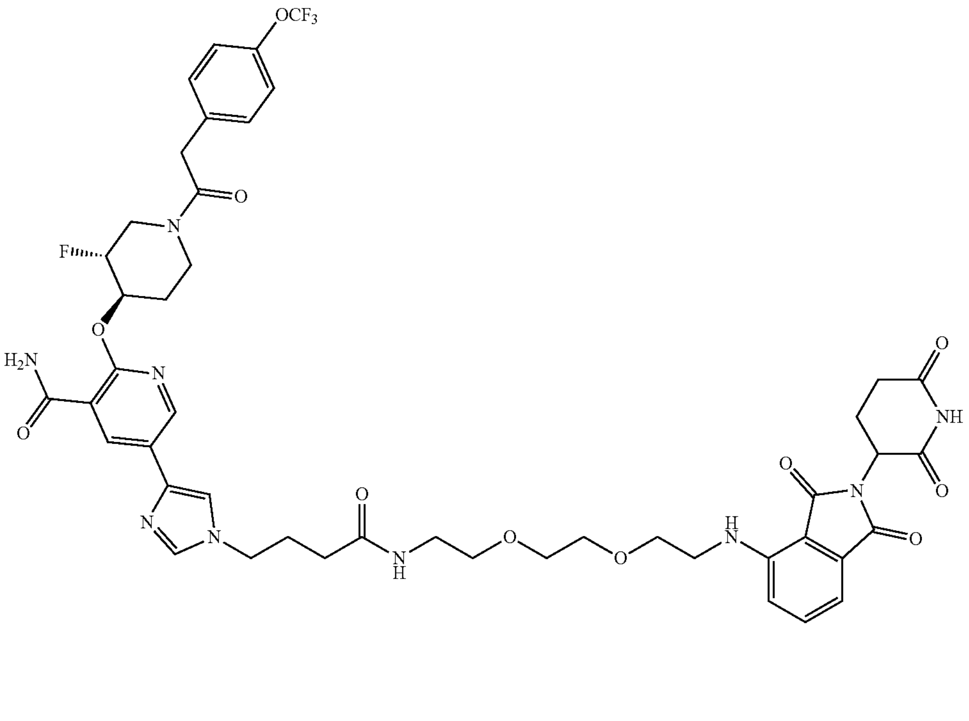 |

TABLE 1-continued
152 JH077-49
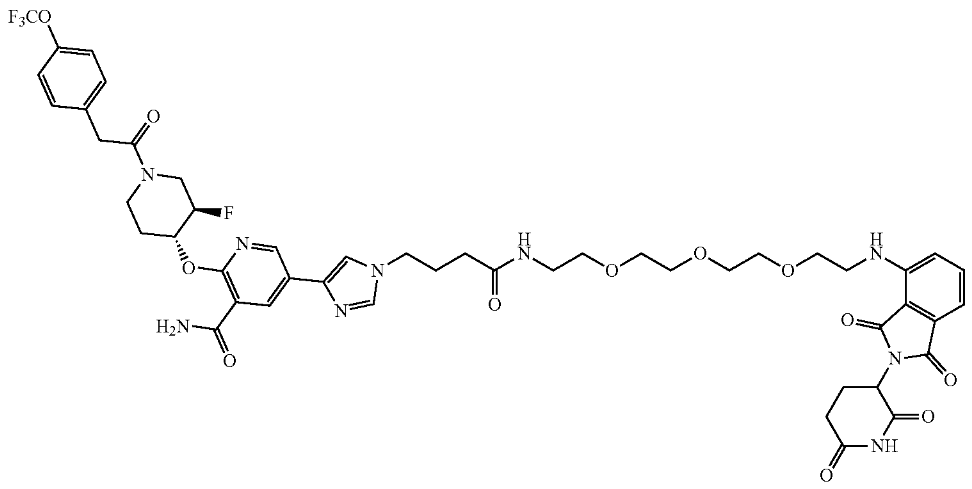 [SMILES: NC(=O)c1cc(-c2cn(CCCC(=O)NCCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]
153 JH077-51
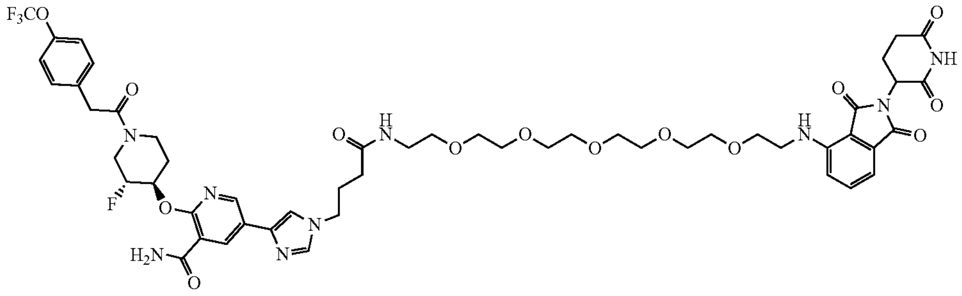 [SMILES: NC(=O)c1cc(-c2cn(CCCC(=O)NCCOCCOCCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]
154 JH077-52
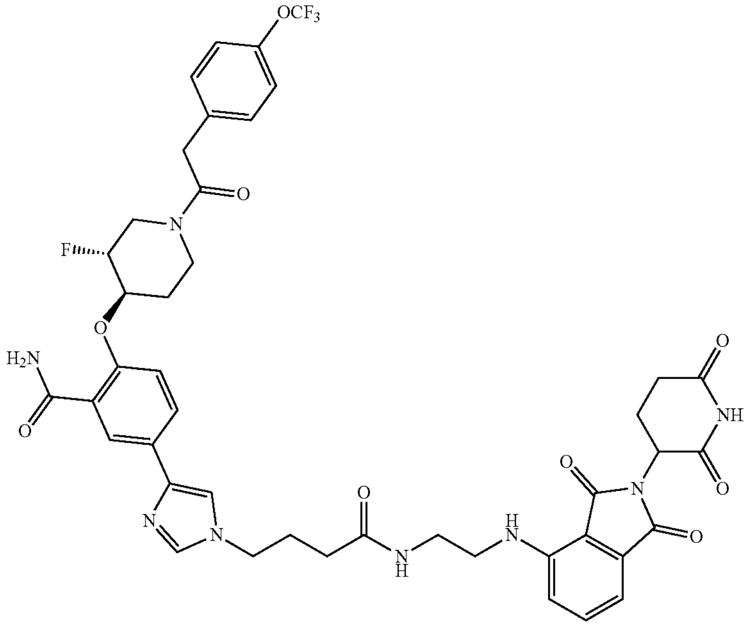 [SMILES: NC(=O)c1cc(-c2cn(CCCC(=O)NCCNc3cccc4c3C(=O)N(C3CCC(=O)NC3=O)C4=O)cn2)ccc1O[C@@H]1CCN(C(=O)Cc2ccc(OC(F)(F)F)cc2)C[C@H]1F]

TABLE 1-continued
155 JH077-53
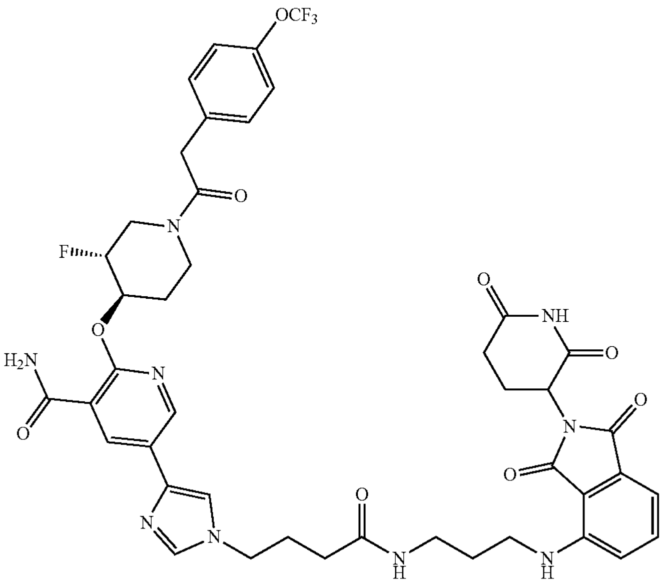 [SMILES: NC(=O)c1cc(-c2cn(CCCC(=O)NCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]
156 JH077-54
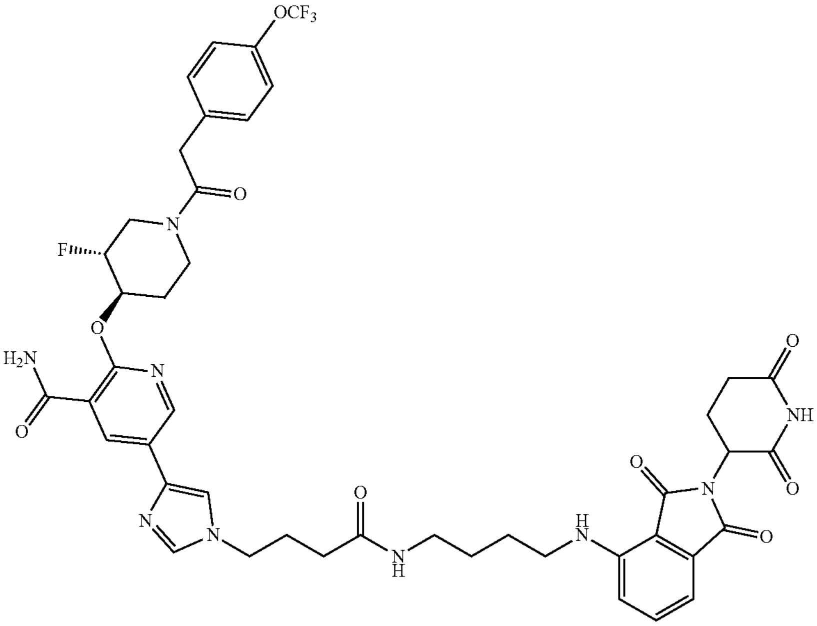 [SMILES: NC(=O)c1cc(-c2cn(CCCC(=O)NCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

TABLE 1-continued
157 JH077-55
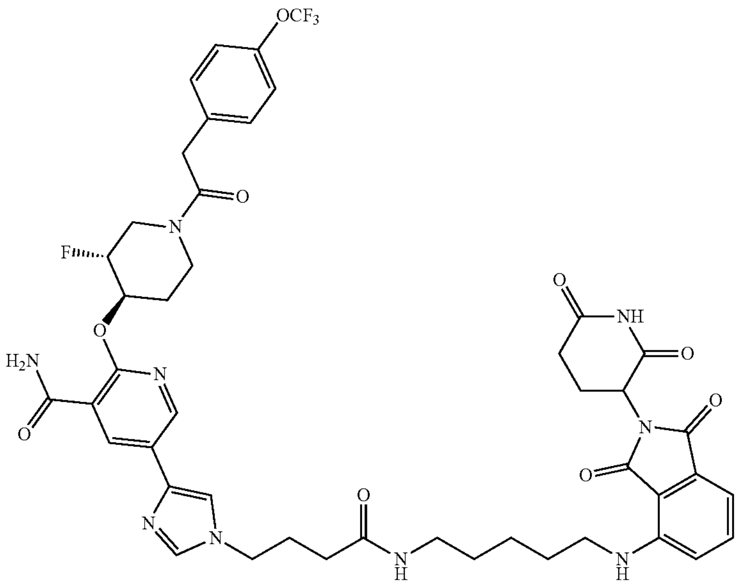 [SMILES: NC(=O)c1cc(-c2cn(CCCC(=O)NCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]
158 JH077-56
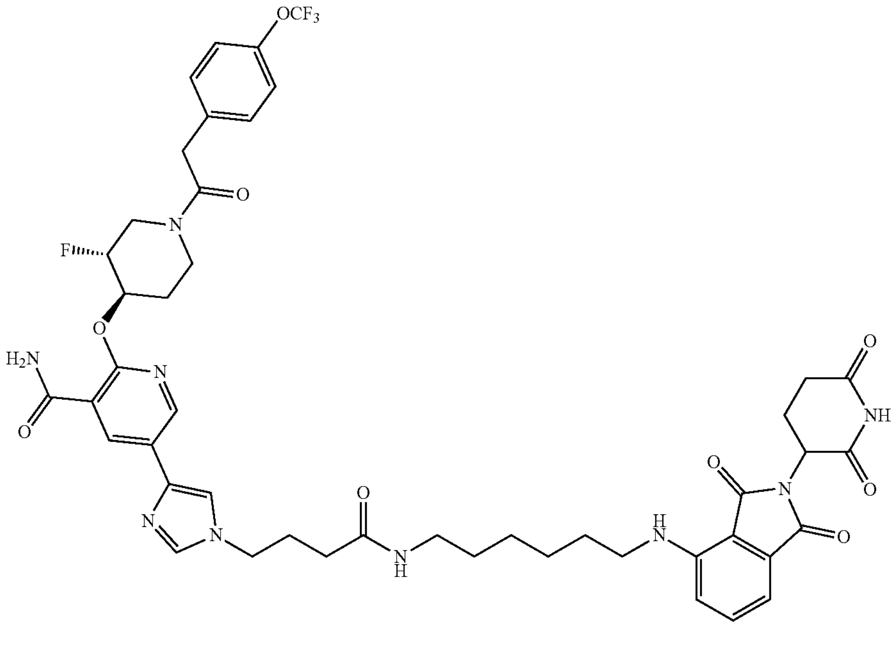 [SMILES: NC(=O)c1cc(-c2cn(CCCC(=O)NCCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

TABLE 1-continued
159 JH077-57
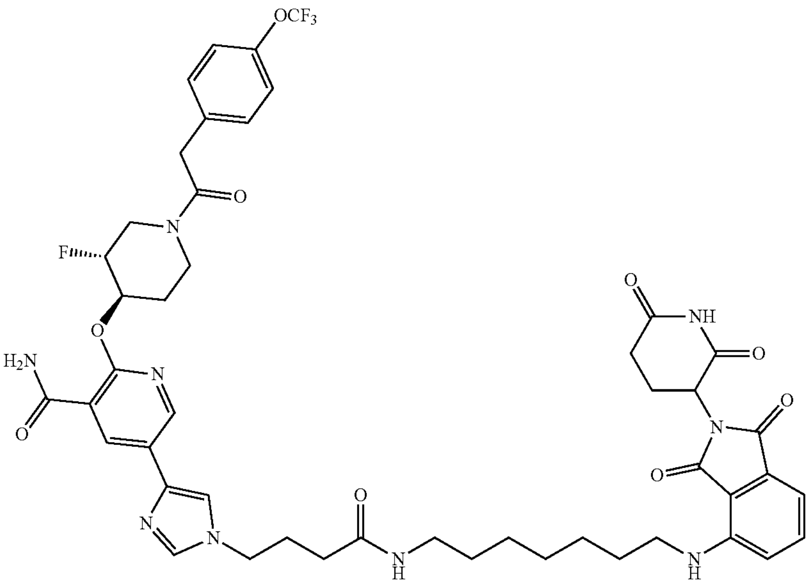 [SMILES: NC(=O)c1cc(-c2cn(CCCC(=O)NCCCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]
160 JH077-58
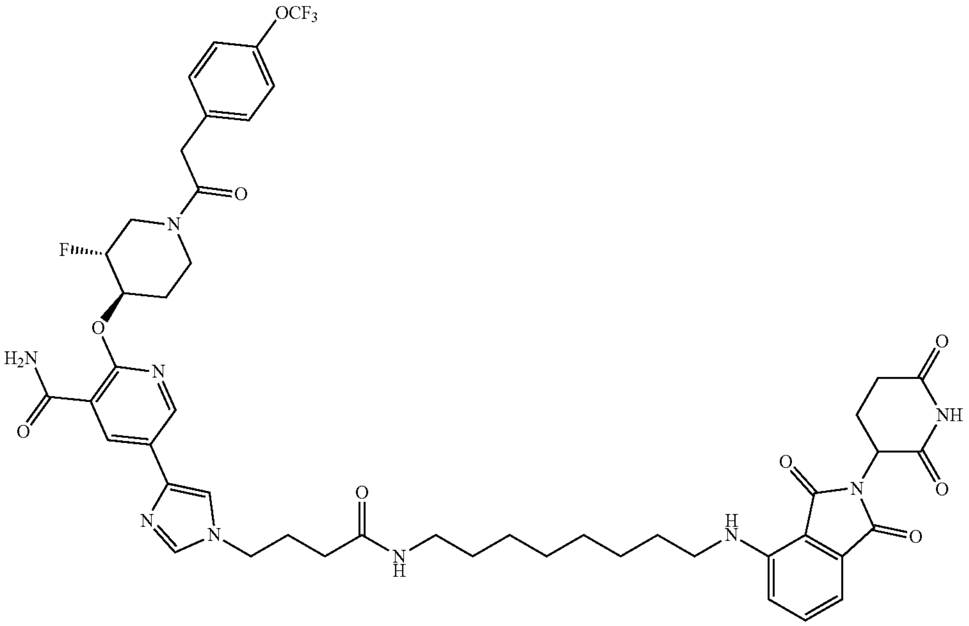 [SMILES: NC(=O)c1cc(-c2cn(CCCC(=O)NCCCCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

TABLE 1-continued
| | | |
|---|---|---|
| 161 | JH077-65 | 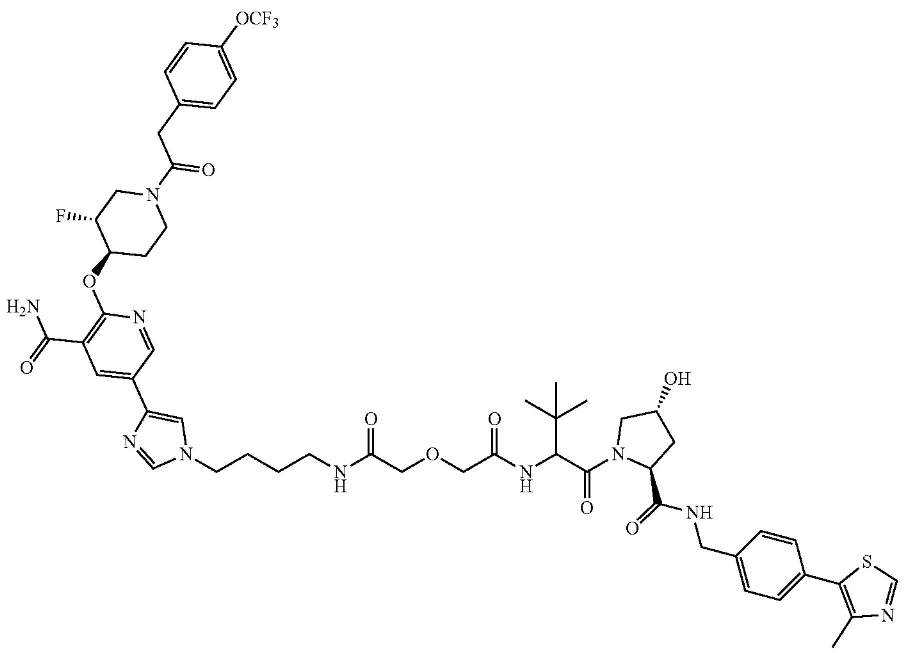 [SMILES: Cc1ncsc1-c1ccc(CNC(=O)[C@@H]2C[C@@H](O)CN2C(=O)C(NC(=O)COCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 162 | JH077-66 | 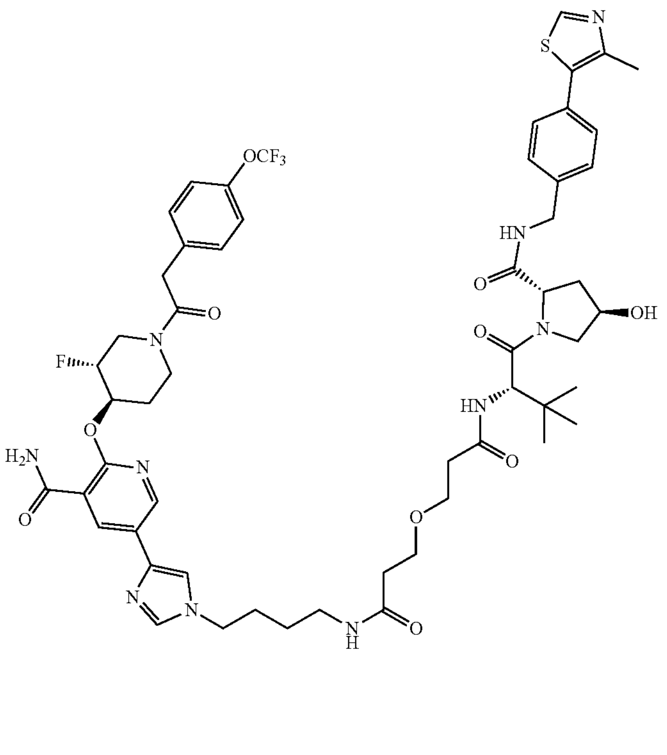 [SMILES: Cc1ncsc1-c1ccc(CNC(=O)[C@@H]2C[C@@H](O)CN2C(=O)[C@@H](NC(=O)CCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |

TABLE 1-continued
163 JH077-67
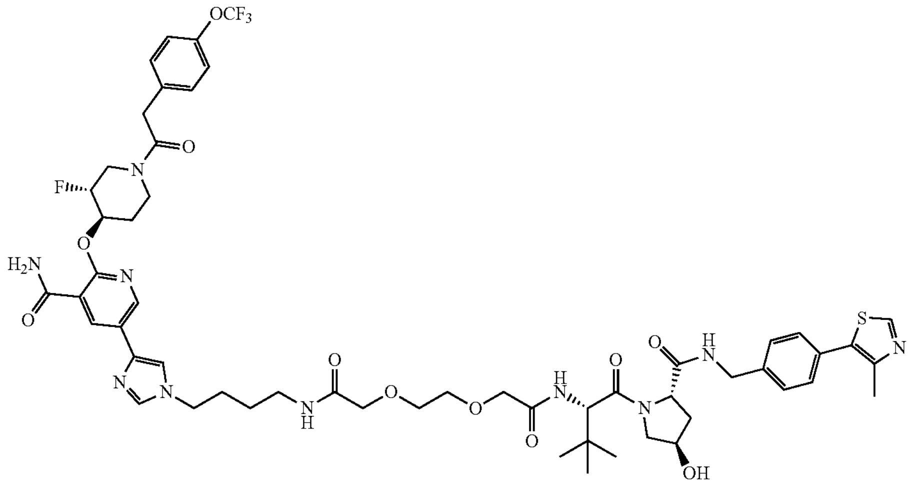 [SMILES: Cc1ncsc1-c1ccc(CNC(=O)[C@@H]2C[C@@H](O)CN2C(=O)[C@@H](NC(=O)COCCOCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]
164 JH077-68
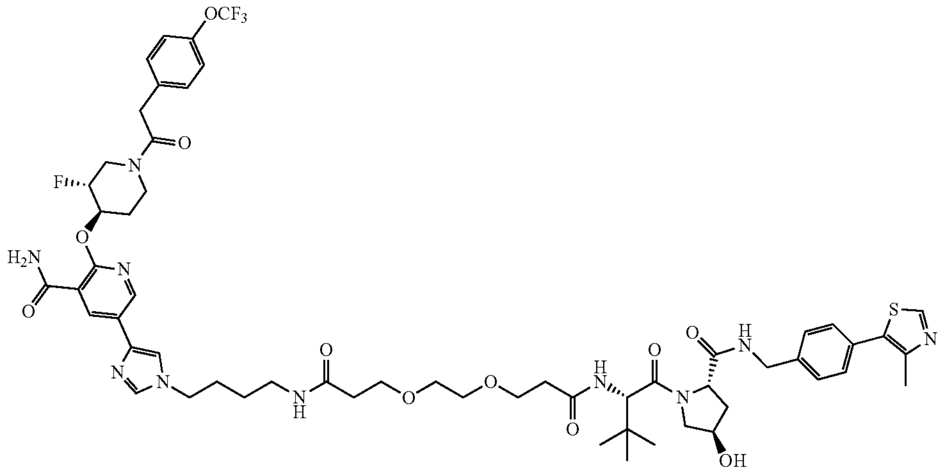 [SMILES: Cc1ncsc1-c1ccc(CNC(=O)[C@@H]2C[C@@H](O)CN2C(=O)[C@@H](NC(=O)CCOCCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]
165 JH077-69
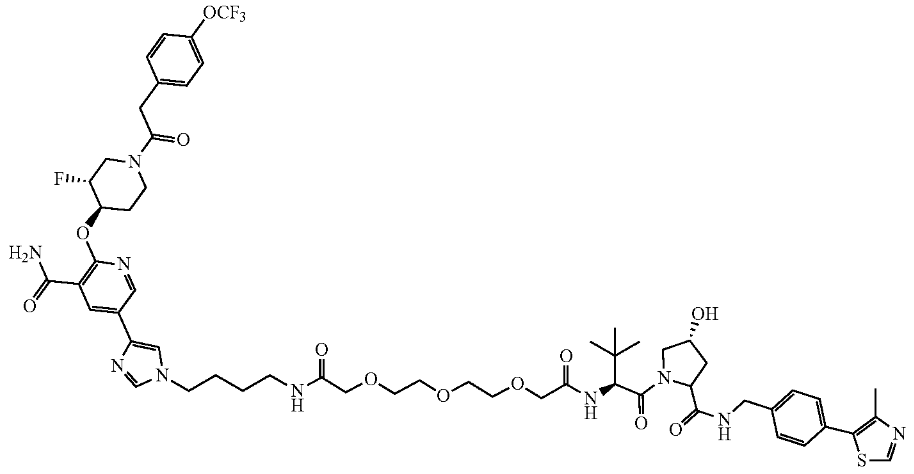 [SMILES: Cc1ncsc1-c1ccc(CNC(=O)C2C[C@@H](O)CN2C(=O)[C@@H](NC(=O)COCCOCCOCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

TABLE 1-continued
| | | |
|---|---|---|
| 166 | JH077-70 | 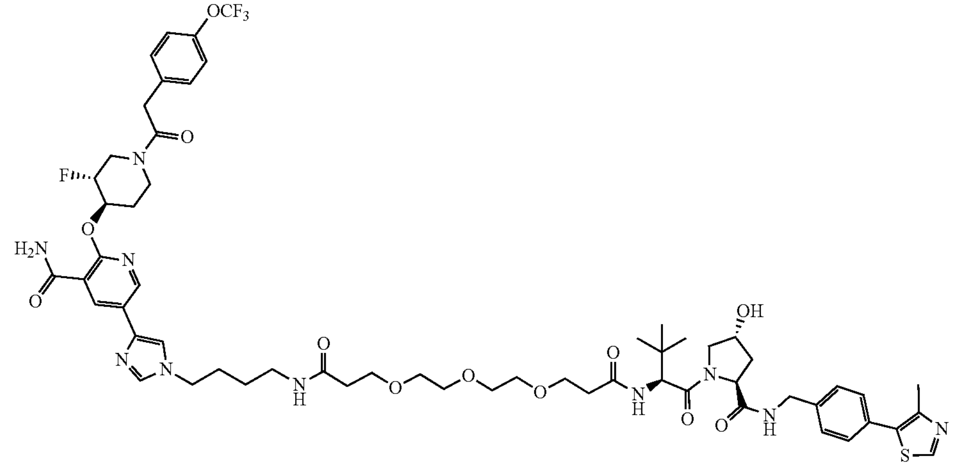 [SMILES: Cc1ncsc1-c1ccc(CNC(=O)[C@@H]2C[C@@H](O)CN2C(=O)[C@@H](NC(=O)CCOCCOCCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 167 | JH077-71 | 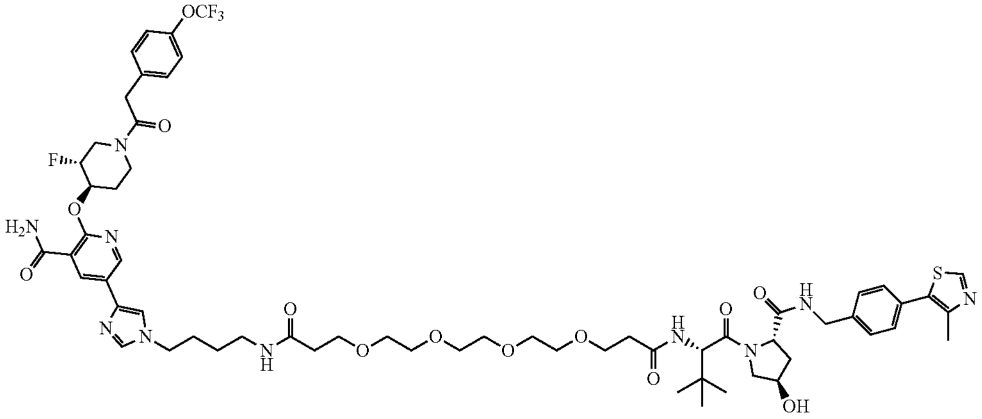 [SMILES: Cc1ncsc1-c1ccc(CNC(=O)[C@@H]2C[C@@H](O)CN2C(=O)[C@@H](NC(=O)CCOCCOCCOCCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 168 | JH077-72 | 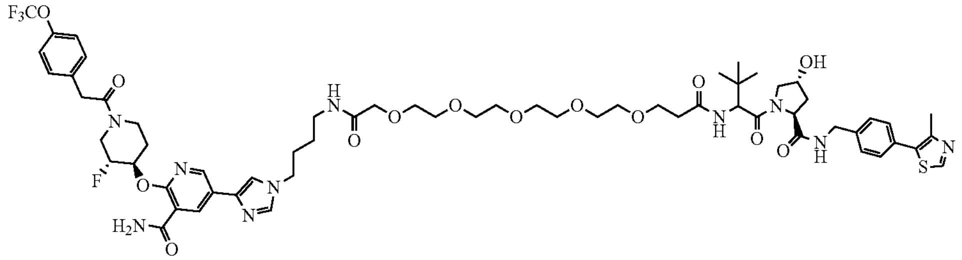 [SMILES: Cc1ncsc1-c1ccc(CNC(=O)[C@@H]2C[C@@H](O)CN2C(=O)C(NC(=O)CCOCCOCCOCCOCCOCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 169 | JH077-73 | 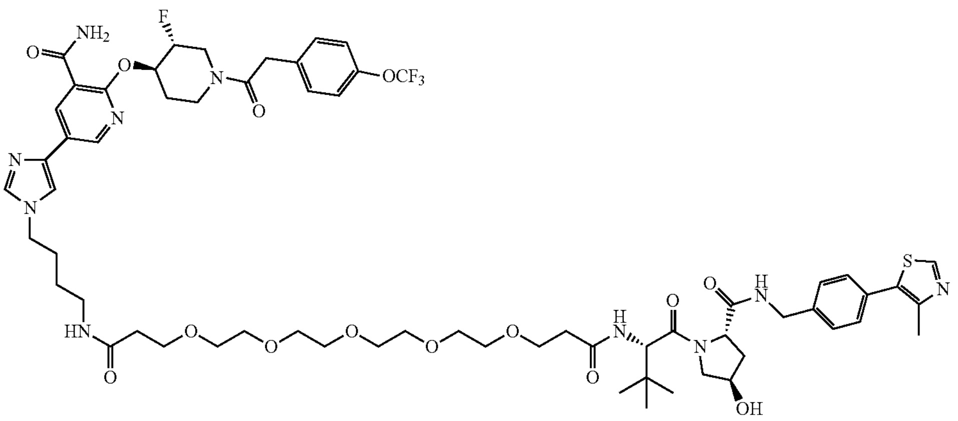 [SMILES: Cc1ncsc1-c1ccc(CNC(=O)[C@@H]2C[C@@H](O)CN2C(=O)[C@@H](NC(=O)CCOCCOCCOCCOCCOCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |

TABLE 1-continued
170 JH077-74
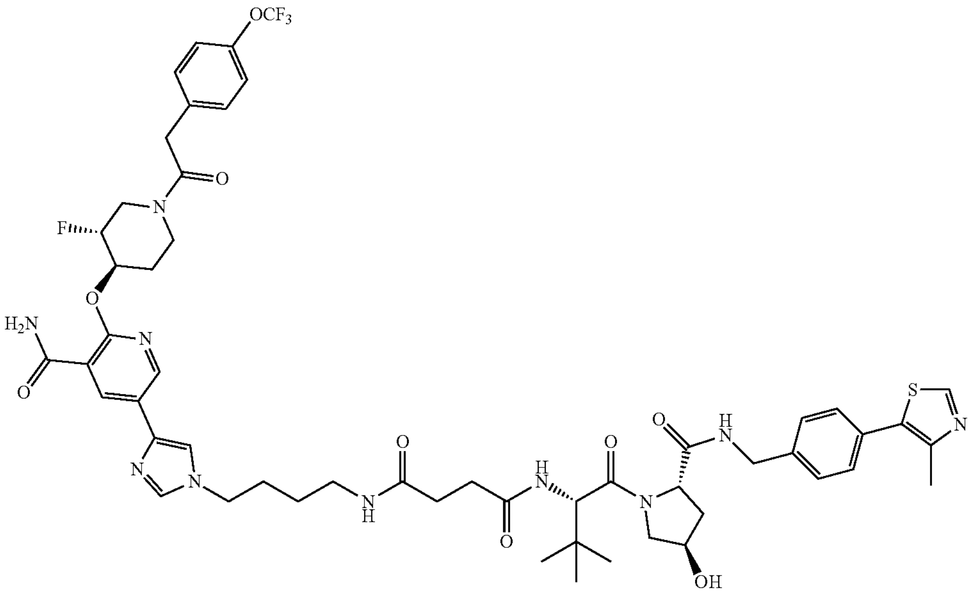 [SMILES: Cc1ncsc1-c1ccc(CNC(=O)[C@@H]2C[C@@H](O)CN2C(=O)[C@@H](NC(=O)CCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]
171 JH077-75
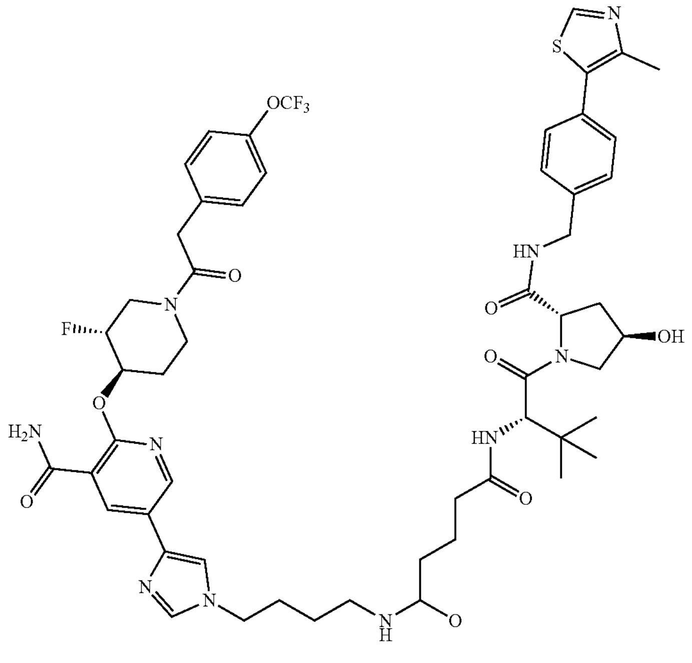 [SMILES: Cc1ncsc1-c1ccc(CNC(=O)[C@@H]2C[C@@H](O)CN2C(=O)[C@@H](NC(=O)CCCC(O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1]

TABLE 1-continued
| | | |
|---|---|---|
| 172 | JH077-76 | 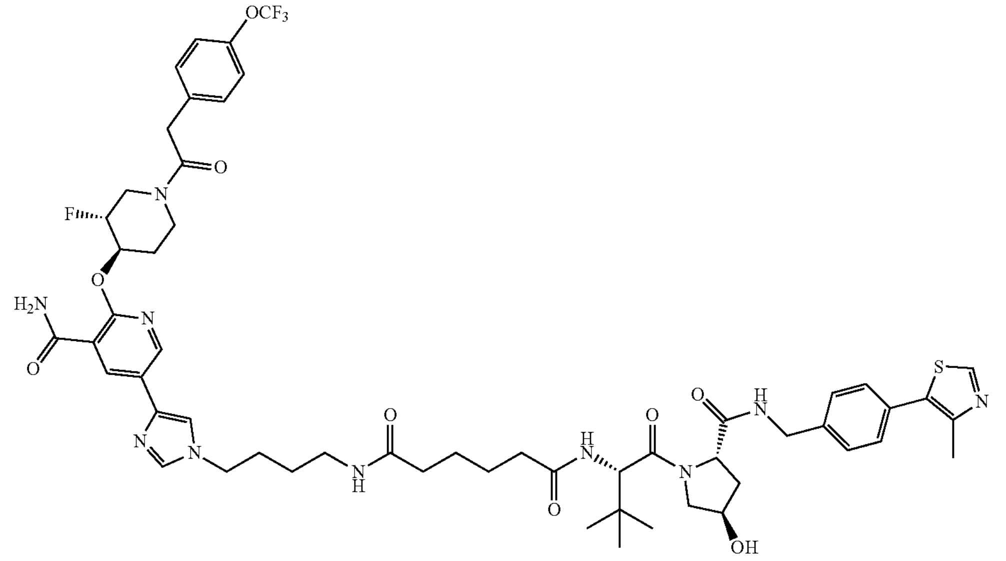 [SMILES: Cc1ncsc1-c1ccc(CNC(=O)[C@@H]2C[C@@H](O)CN2C(=O)[C@@H](NC(=O)CCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 173 | JH077-77 | 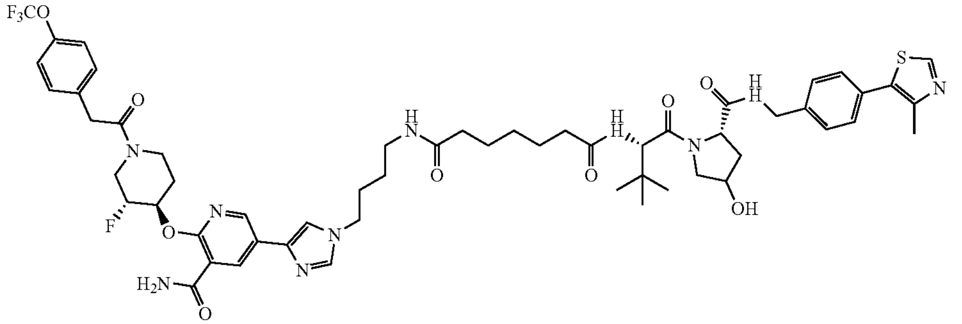 |
| 174 | JH077-78 | 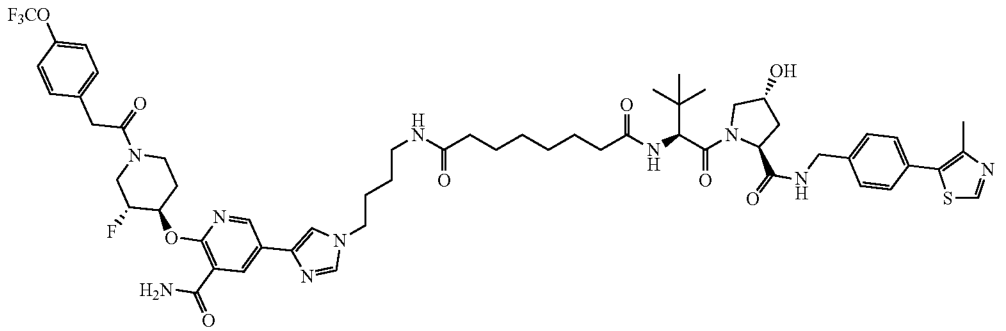 [SMILES: Cc1ncsc1-c1ccc(CNC(=O)[C@@H]2C[C@@H](O)CN2C(=O)[C@@H](NC(=O)CCCCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 175 | JH077-79 | 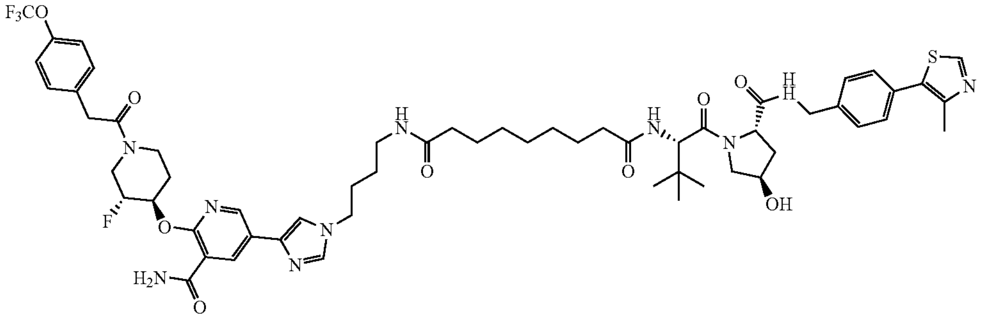 |

TABLE 1-continued
| | | |
|---|---|---|
| 176 | JH077-80 | 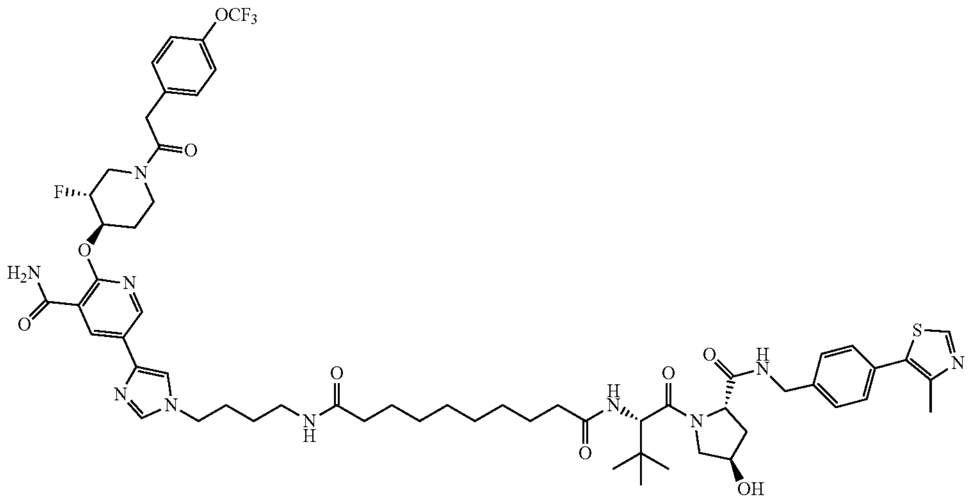 [SMILES: Cc1ncsc1-c1ccc(CNC(=O)[C@@H]2C[C@@H](O)CN2C(=O)[C@@H](NC(=O)CCCCCCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 177 | JH077-81 | 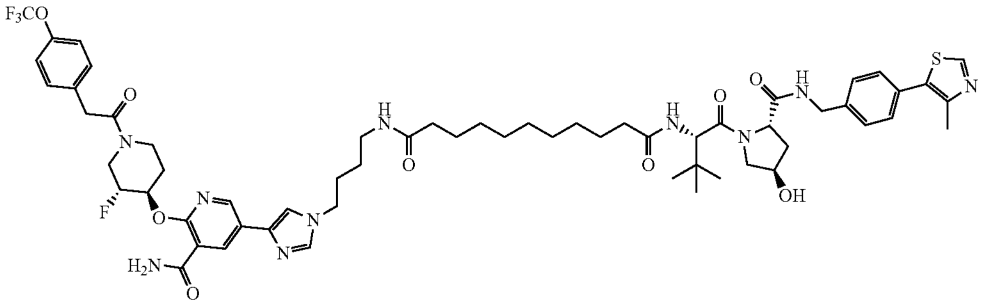 [SMILES: Cc1ncsc1-c1ccc(CNC(=O)[C@@H]2C[C@@H](O)CN2C(=O)[C@@H](NC(=O)CCCCCCCCCC(=O)NCCCCn2cnc(-c3cnc(O[C@@H]4CCN(C(=O)Cc5ccc(OC(F)(F)F)cc5)C[C@H]4F)c(C(N)=O)c3)c2)C(C)(C)C)cc1] |
| 178 | JH077-82 | 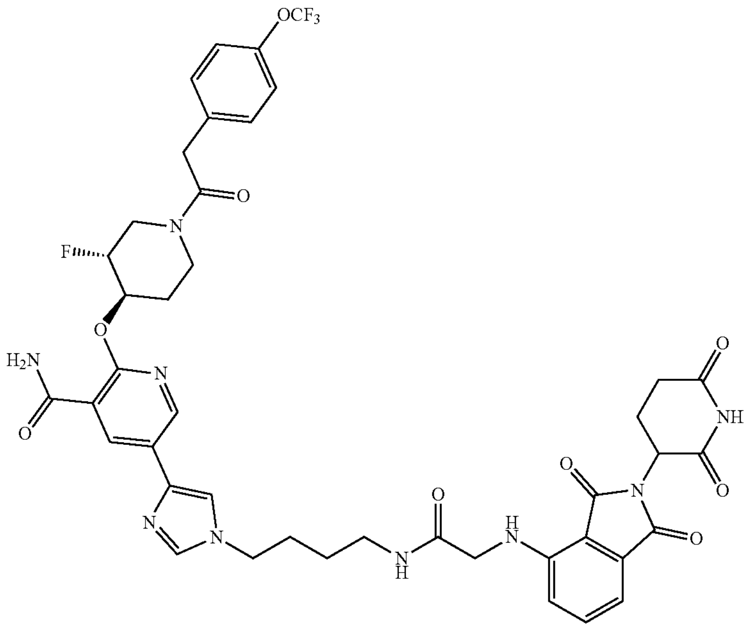 [SMILES: NC(=O)c1cc(-c2cn(CCCCNC(=O)CNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F] |

TABLE 1-continued
179 JH077-83
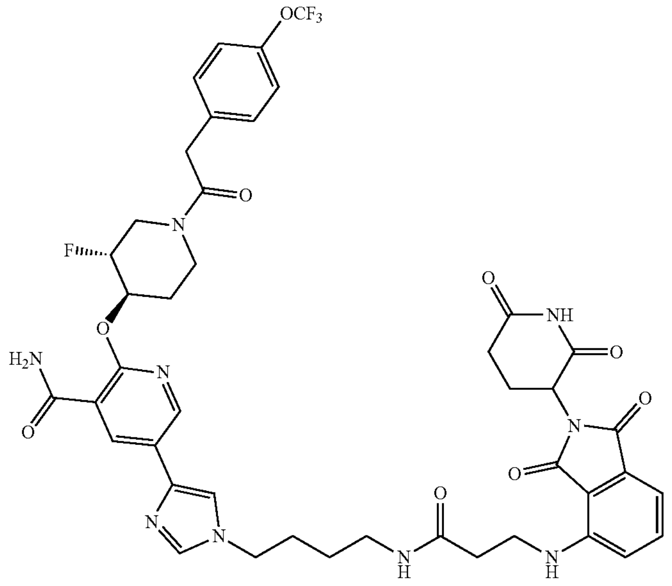 [SMILES: NC(=O)c1cc(-c2cn(CCCCNC(=O)CCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]
180 JH077-84
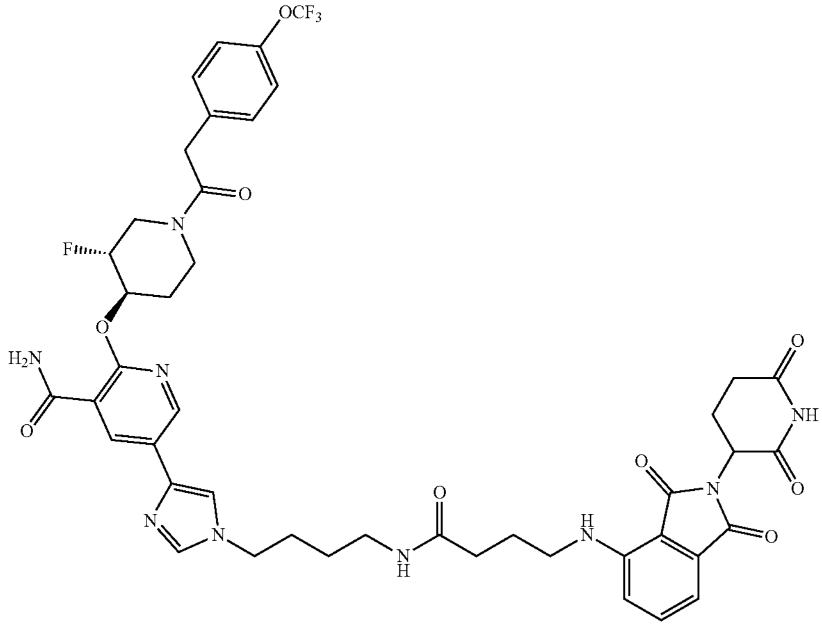 [SMILES: NC(=O)c1cc(-c2cn(CCCCNC(=O)CCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

TABLE 1-continued
| | | |
|---|---|---|
| 181 | JH077-85 | 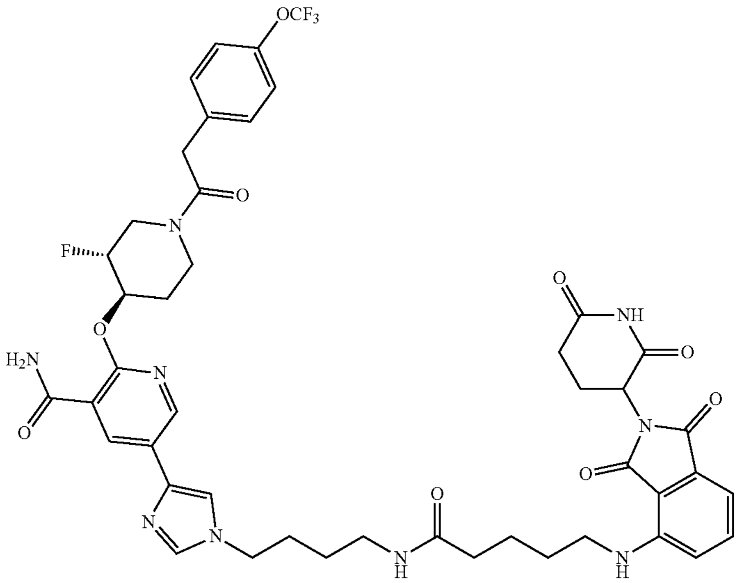 [SMILES: NC(=O)c1cc(-c2cn(CCCCNC(=O)CCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F] |
| 182 | JH077-86 | 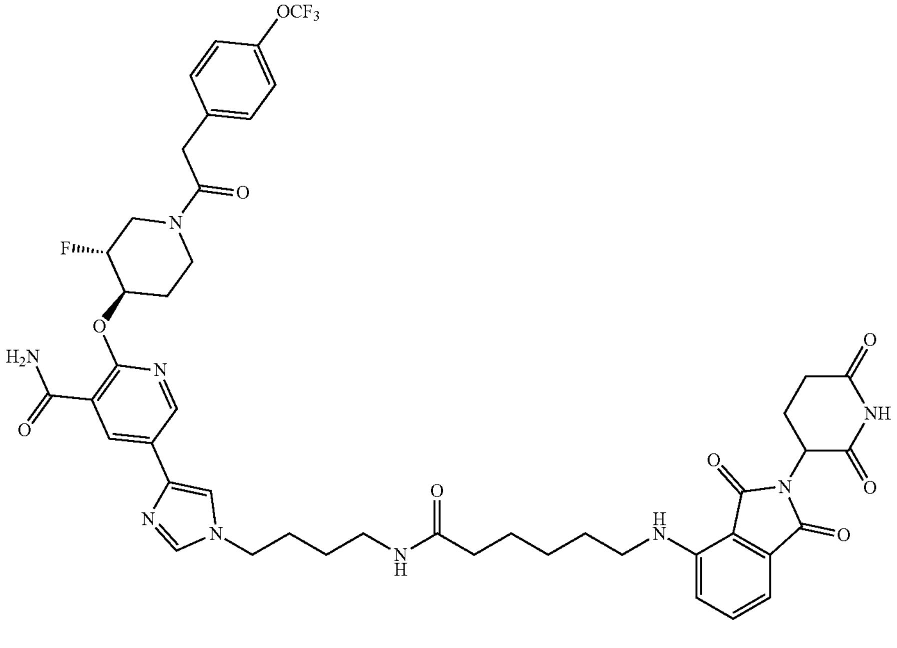 [SMILES: NC(=O)c1cc(-c2cn(CCCCNC(=O)CCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F] |

TABLE 1-continued
183 JH077-87
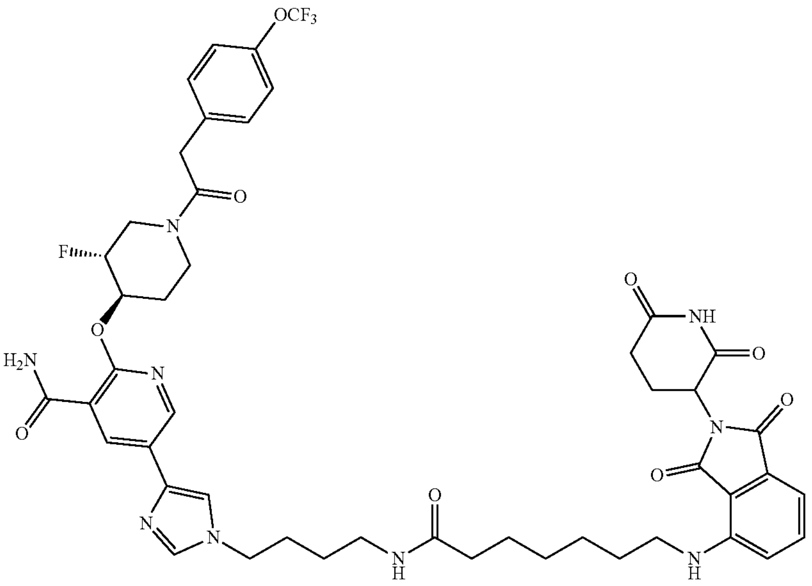 [SMILES: NC(=O)c1cc(-c2cn(CCCCNC(=O)CCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]
184 JH077-88
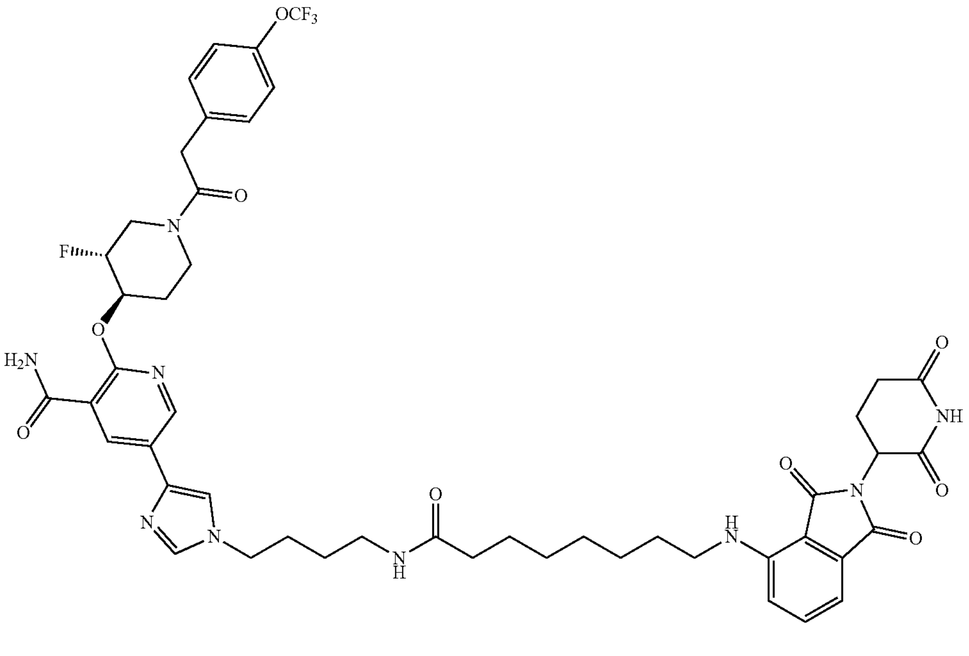 [SMILES: NC(=O)c1cc(-c2cn(CCCCNC(=O)CCCCCCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

TABLE 1-continued
185 JH077-89
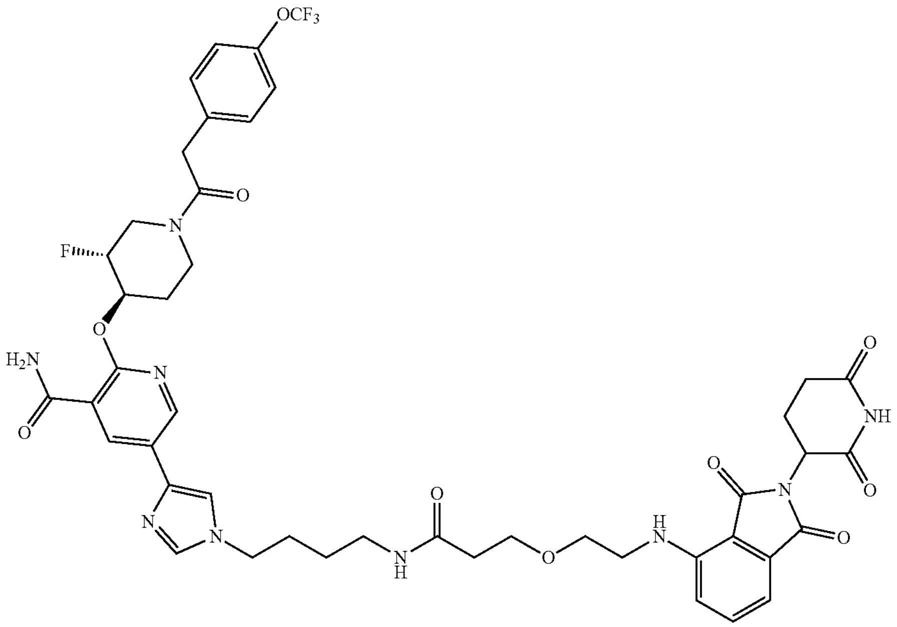 [SMILES: NC(=O)c1cc(-c2cn(CCCCNC(=O)CCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]
186 JH077-90
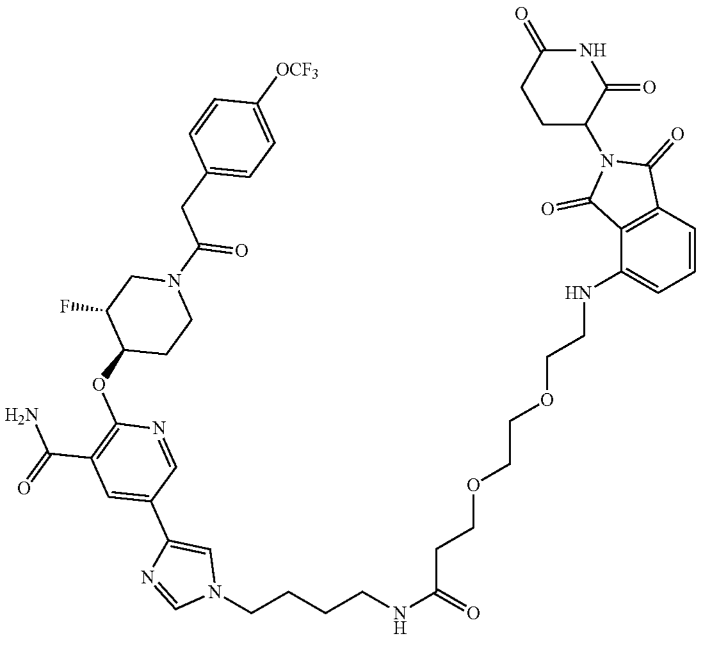 [SMILES: NC(=O)c1cc(-c2cn(CCCCNC(=O)CCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F]

TABLE 1-continued
| | | |
|---|---|---|
| 187 | JH077-91 | 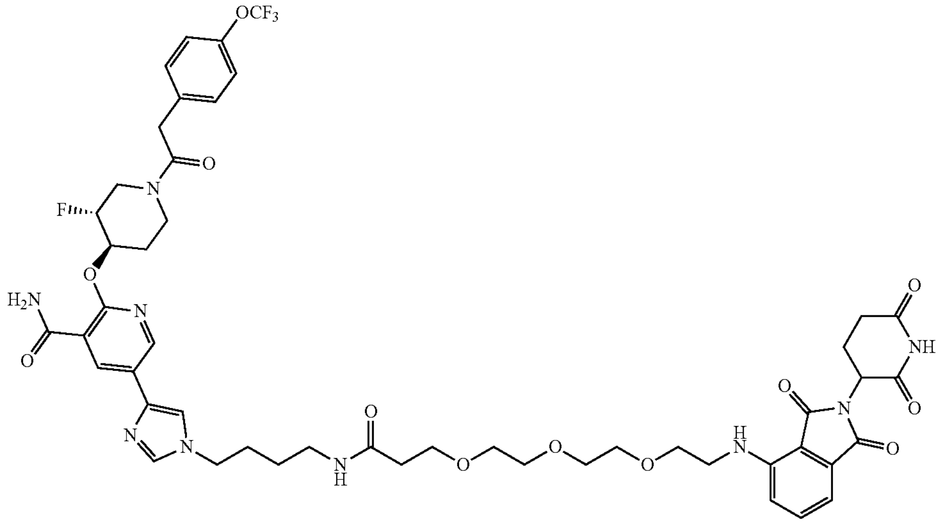 [SMILES: NC(=O)c1cc(-c2cn(CCCCNC(=O)CCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F] |
| 188 | JH077-92 | 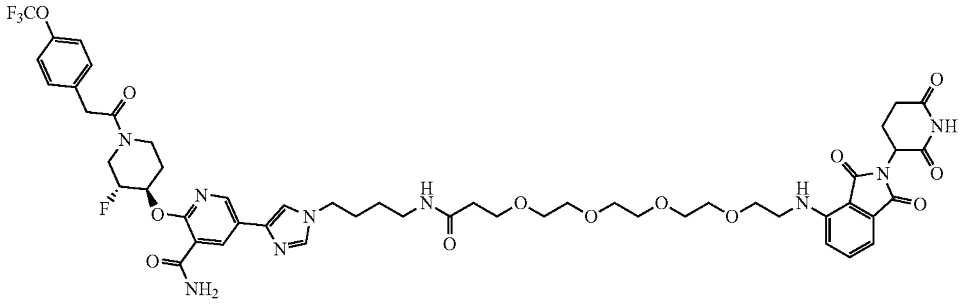 [SMILES: NC(=O)c1cc(-c2cn(CCCCNC(=O)CCOCCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F] |
| 189 | JH077-93 | 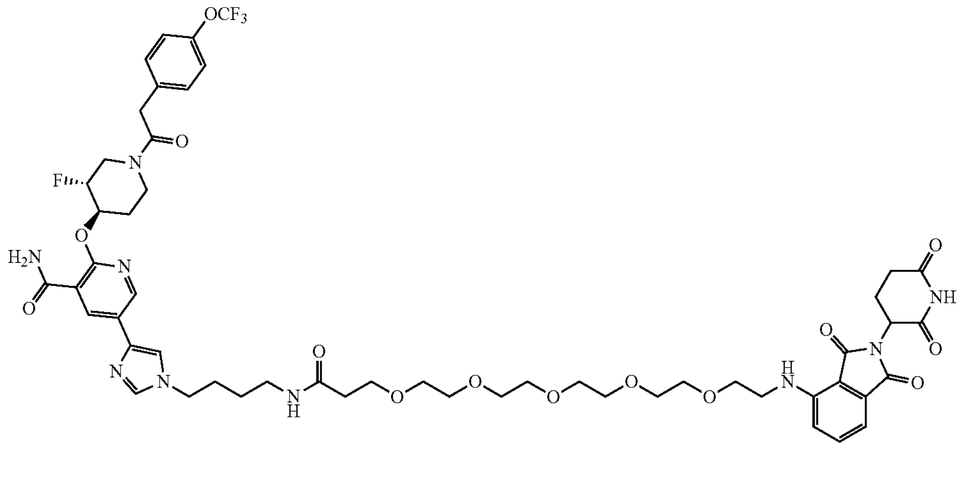 [SMILES: NC(=O)c1cc(-c2cn(CCCCNC(=O)CCOCCOCCOCCOCCOCCNc3cccc4c3C(=O)N(C3CCC(=O)NC3=O)C4=O)cn2)cnc1O[C@@H]1CCN(C(=O)Cc2ccc(OC(F)(F)F)cc2)C[C@H]1F] |

TABLE 1-continued
190
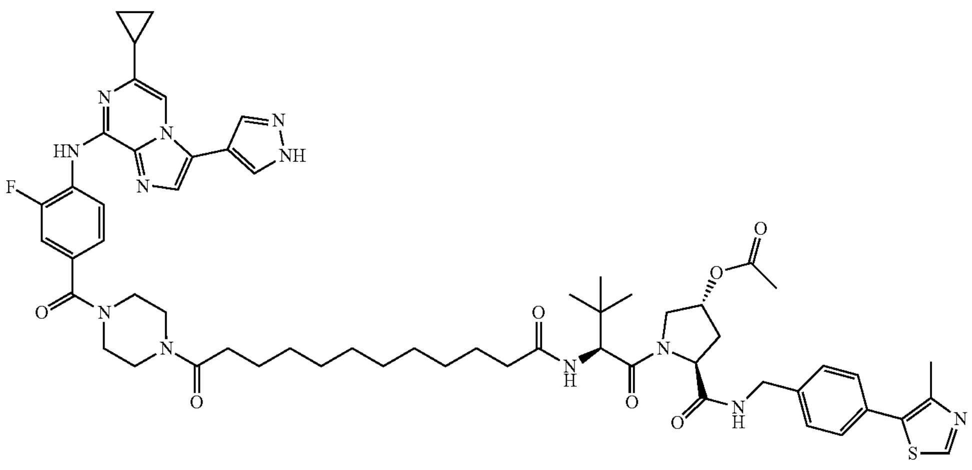 [SMILES: CC(=O)O[C@@H]1C[C@@H](C(=O)NCc2ccc(-c3scnc3C)cc2)N(C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)C1]
191
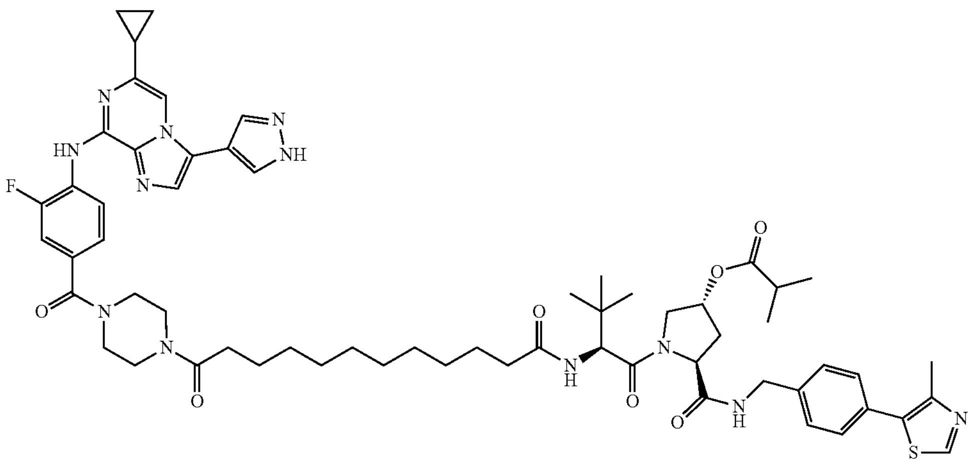 [SMILES: Cc1ncsc1-c1ccc(CNC(=O)[C@@H]2C[C@@H](OC(=O)C(C)C)CN2C(=O)[C@@H](NC(=O)CCCCCCCCCCC(=O)N2CCN(C(=O)c3ccc(Nc4nc(C5CC5)cn5c(-c6cn[nH]c6)cnc45)c(F)c3)CC2)C(C)(C)C)cc1]
192
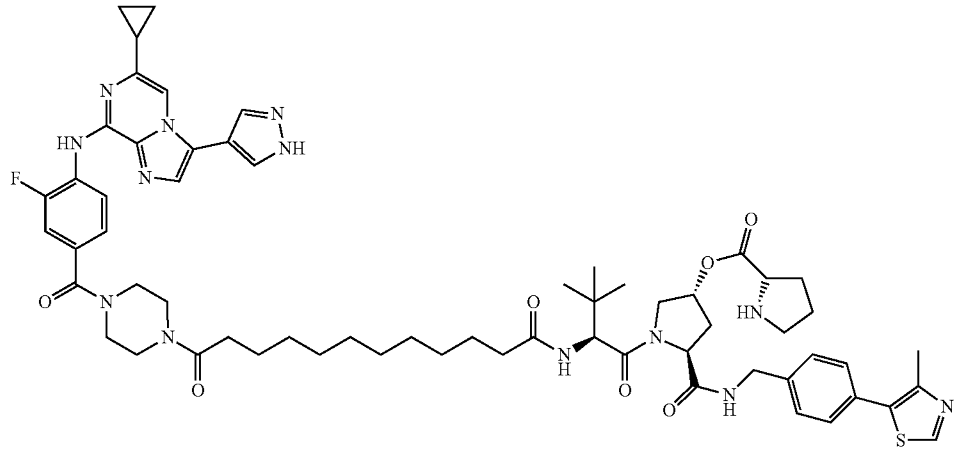

TABLE 1-continued
193
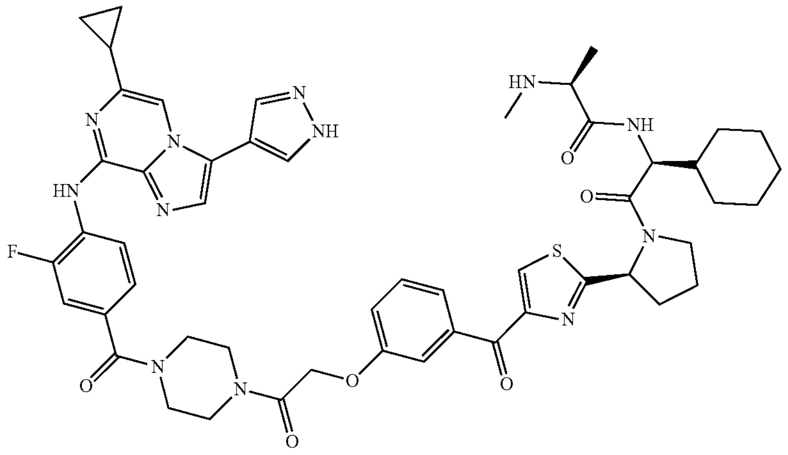 [SMILES: CN[C@@H](C)C(=O)N[C@H](C(=O)N1CCC[C@H]1c1nc(C(=O)c2cccc(OCC(=O)N3CCN(C(=O)c4ccc(Nc5nc(C6CC6)cn6c(-c7cn[nH]c7)cnc56)c(F)c4)CC3)c2)cs1)C1CCCCC1]
194
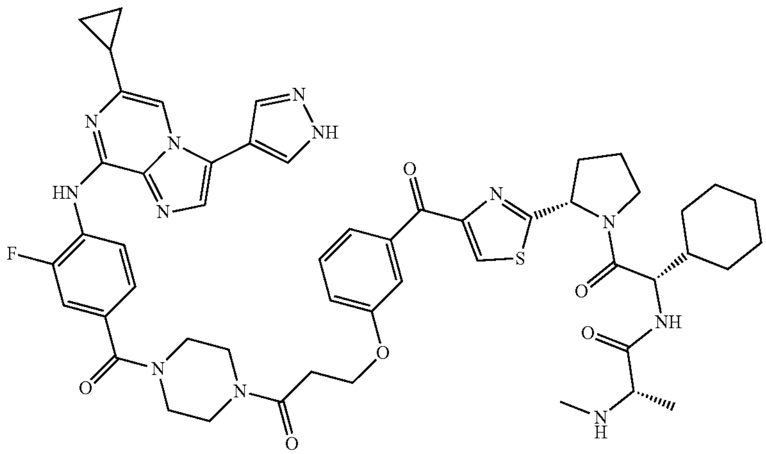 [SMILES: CN[C@@H](C)C(=O)N[C@H](C(=O)N1CCC[C@H]1c1nc(C(=O)c2cccc(OCCC(=O)N3CCN(C(=O)c4ccc(Nc5nc(C6CC6)cn6c(-c7cn[nH]c7)cnc56)c(F)c4)CC3)c2)cs1)C1CCCCC1]
195
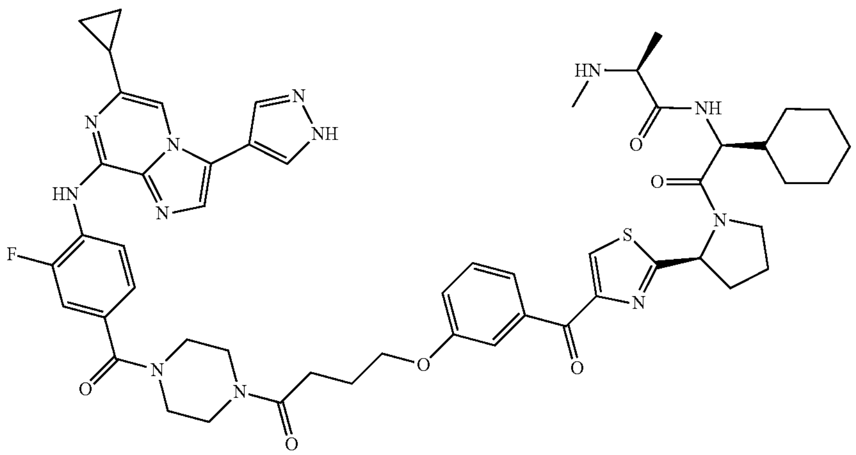 [SMILES: CN[C@@H](C)C(=O)N[C@H](C(=O)N1CCC[C@H]1c1nc(C(=O)c2cccc(OCCCC(=O)N3CCN(C(=O)c4ccc(Nc5nc(C6CC6)cn6c(-c7cn[nH]c7)cnc56)c(F)c4)CC3)c2)cs1)C1CCCCC1]

TABLE 1-continued
196
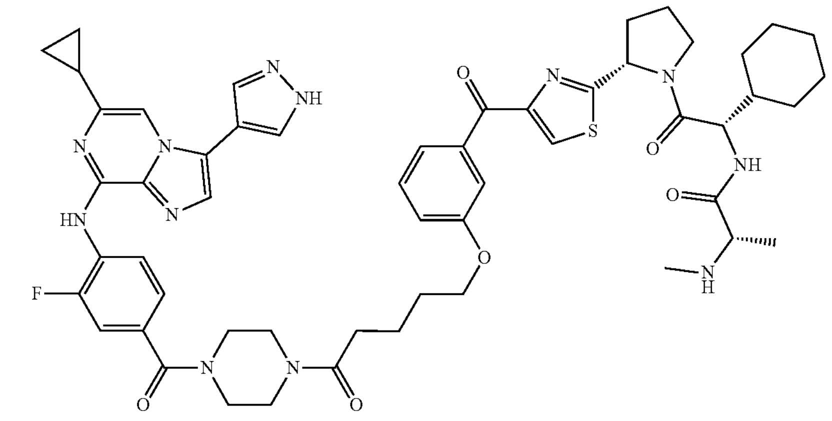 [SMILES: CN[C@@H](C)C(=O)N[C@H](C(=O)N1CCC[C@H]1c1nc(C(=O)c2cccc(OCCCCC(=O)N3CCN(C(=O)c4ccc(Nc5nc(C6CC6)cn6c(-c7cn[nH]c7)cnc56)c(F)c4)CC3)c2)cs1)C1CCCCC1]
197
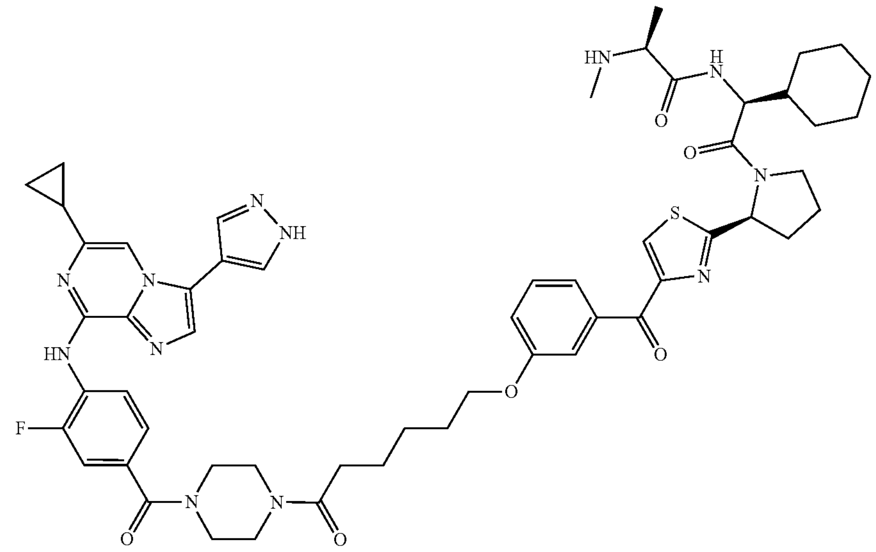 [SMILES: CN[C@@H](C)C(=O)N[C@H](C(=O)N1CCC[C@H]1c1nc(C(=O)c2cccc(OCCCCCC(=O)N3CCN(C(=O)c4ccc(Nc5nc(C6CC6)cn6c(-c7cn[nH]c7)cnc56)c(F)c4)CC3)c2)cs1)C1CCCCC1]
198
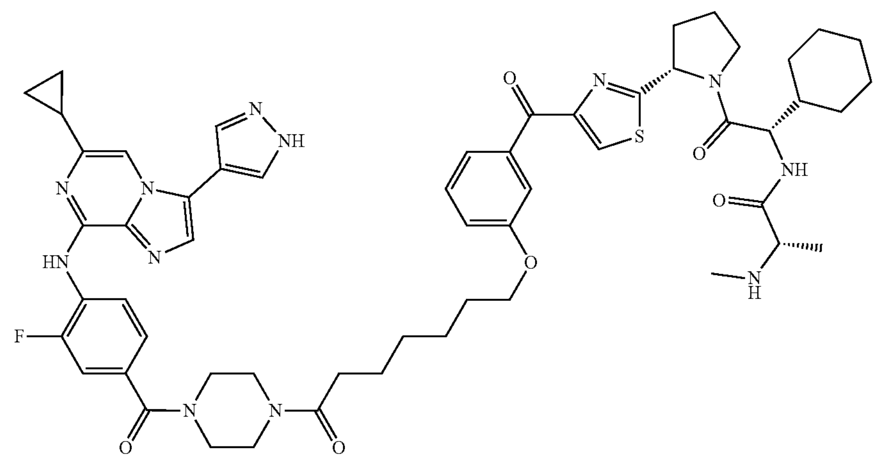 [SMILES: CN[C@@H](C)C(=O)N[C@H](C(=O)N1CCC[C@H]1c1nc(C(=O)c2cccc(OCCCCCCC(=O)N3CCN(C(=O)c4ccc(Nc5nc(C6CC6)cn6c(-c7cn[nH]c7)cnc56)c(F)c4)CC3)c2)cs1)C1CCCCC1]

TABLE 1-continued
199
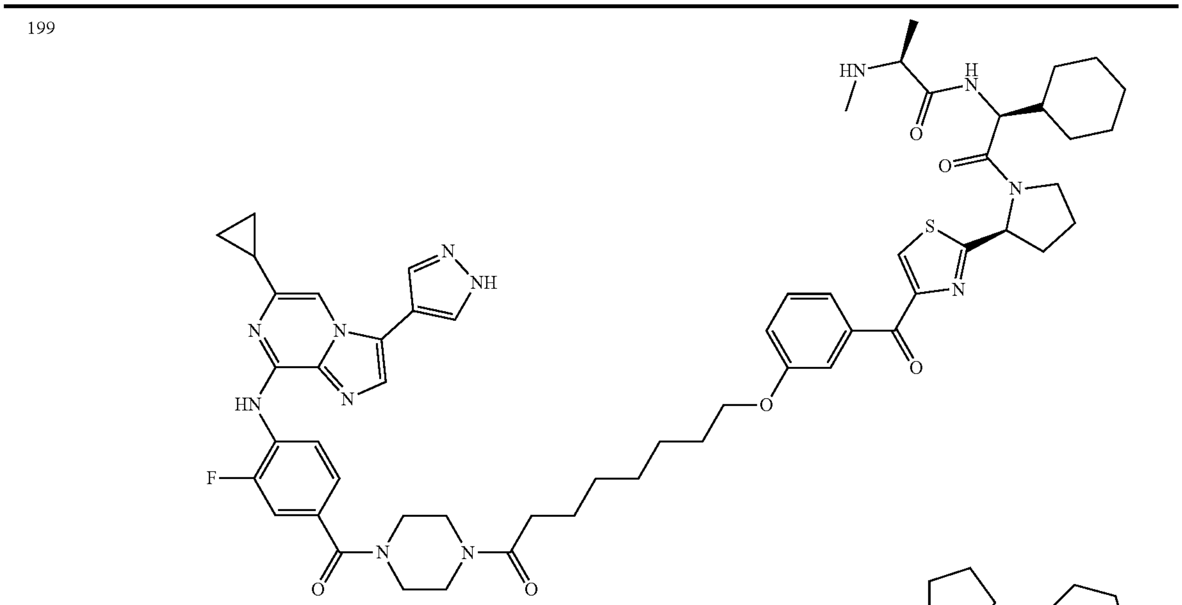
200
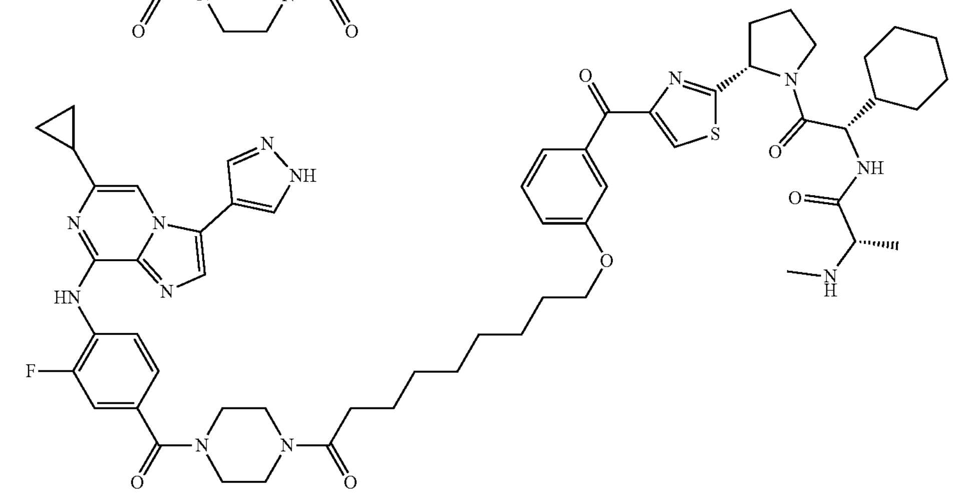
201
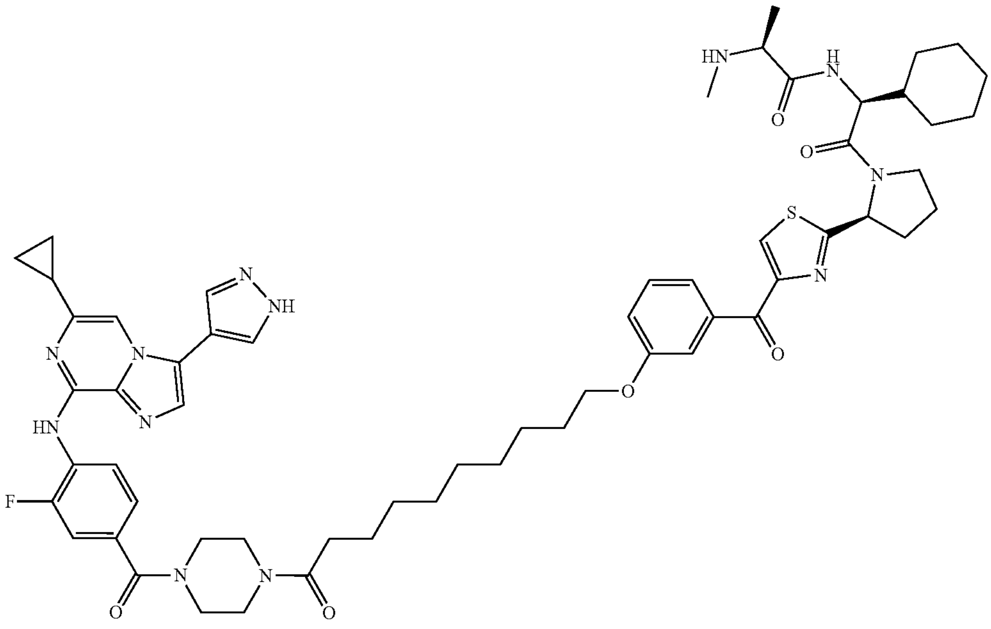 [SMILES: CN[C@@H](C)C(=O)N[C@H](C(=O)N1CCC[C@H]1c1nc(C(=O)c2cccc(OCCCCCCCCCC(=O)N3CCN(C(=O)c4ccc(Nc5nc(C6CC6)cn6c(-c7cn[nH]c7)cnc56)c(F)c4)CC3)c2)cs1)C1CCCCC1]

TABLE 1-continued
202
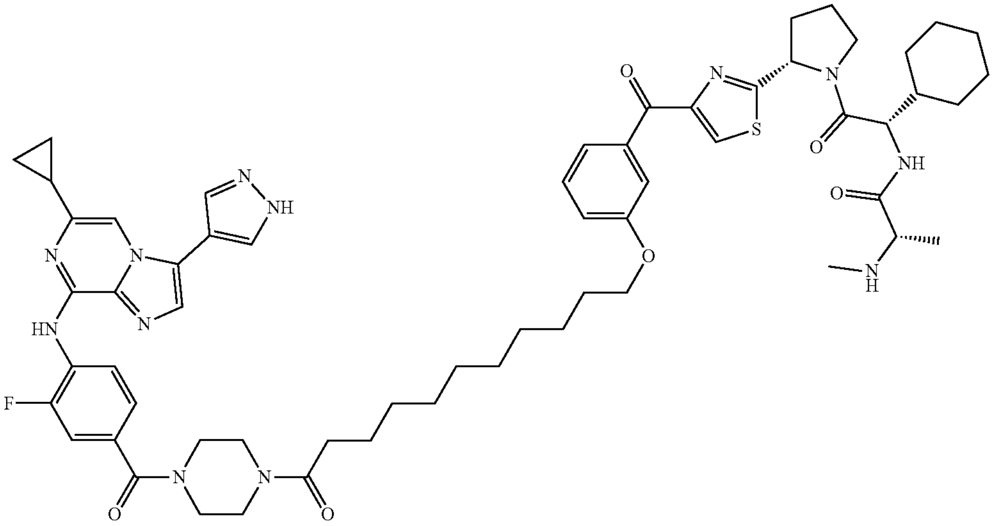 [SMILES: CN[C@@H](C)C(=O)N[C@H](C(=O)N1CCC[C@H]1c1nc(C(=O)c2cccc(OCCCCCCCCCCC(=O)N3CCN(C(=O)c4ccc(Nc5nc(C6CC6)cn6c(-c7cn[nH]c7)cnc56)c(F)c4)CC3)c2)cs1)C1CCCCC1]
203
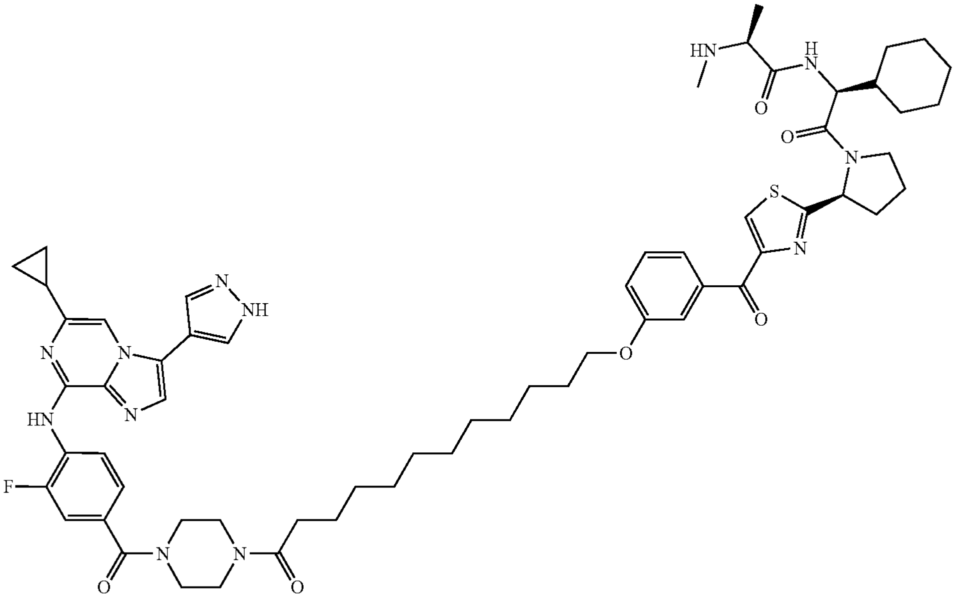 [SMILES: CN[C@@H](C)C(=O)N[C@H](C(=O)N1CCC[C@H]1c1nc(C(=O)c2cccc(OCCCCCCCCCCCC(=O)N3CCN(C(=O)c4ccc(Nc5nc(C6CC6)cn6c(-c7cn[nH]c7)cnc56)c(F)c4)CC3)c2)cs1)C1CCCCC1]
204
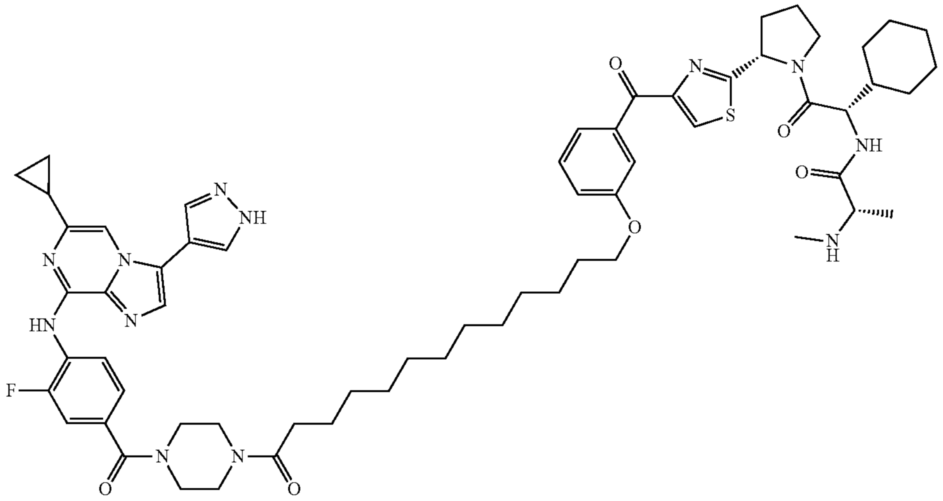 [SMILES: CN[C@@H](C)C(=O)N[C@H](C(=O)N1CCC[C@H]1c1nc(C(=O)c2cccc(OCCCCCCCCCCCCC(=O)N3CCN(C(=O)c4ccc(Nc5nc(C6CC6)cn6c(-c7cn[nH]c7)cnc56)c(F)c4)CC3)c2)cs1)C1CCCCC1]

TABLE 1-continued
205
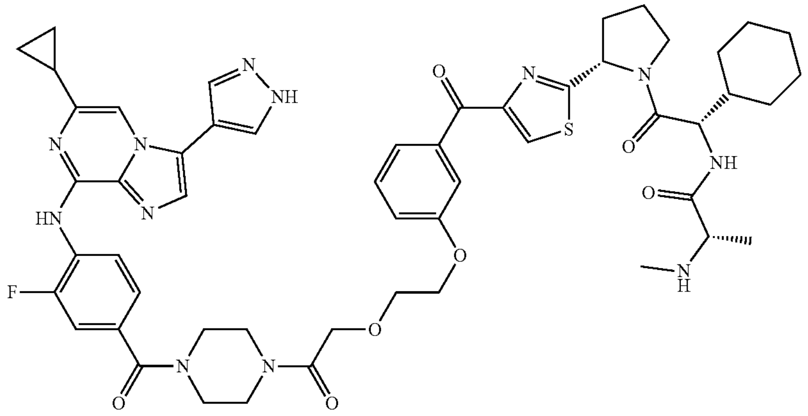
206
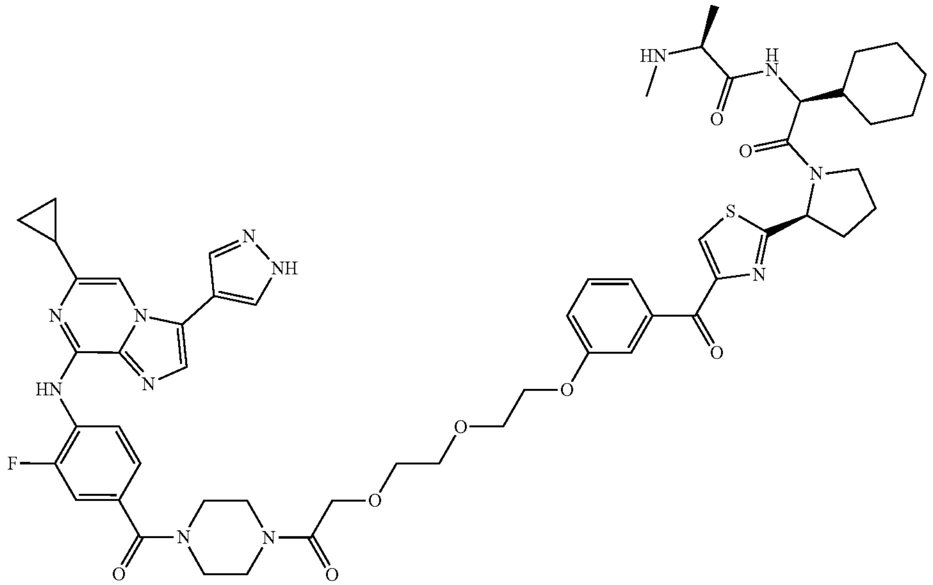
207
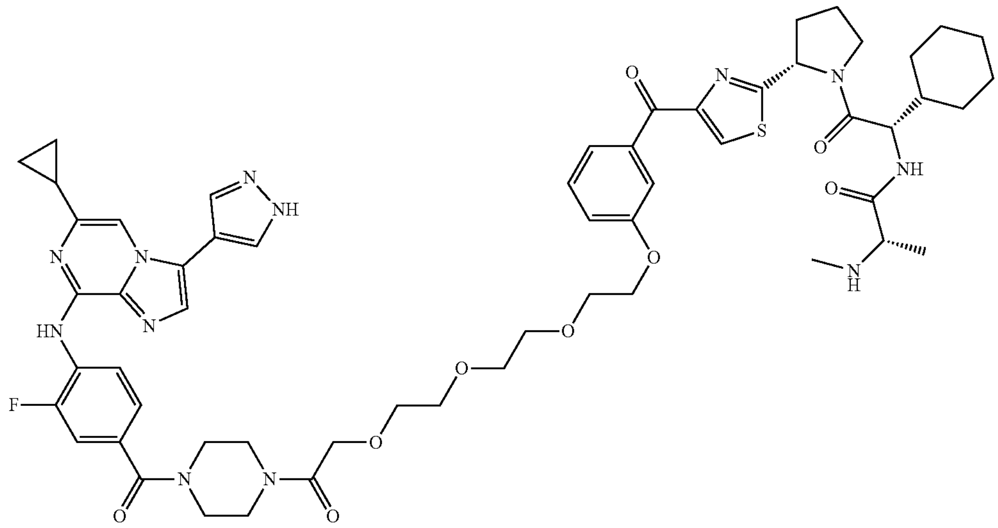 [SMILES: CN[C@@H](C)C(=O)N[C@H](C(=O)N1CCC[C@H]1c1nc(C(=O)c2cccc(OCCOCCOCCOCC(=O)N3CCN(C(=O)c4ccc(Nc5nc(C6CC6)cn6c(-c7cn[nH]c7)cnc56)c(F)c4)CC3)c2)cs1)C1CCCCC1]

TABLE 1-continued
208
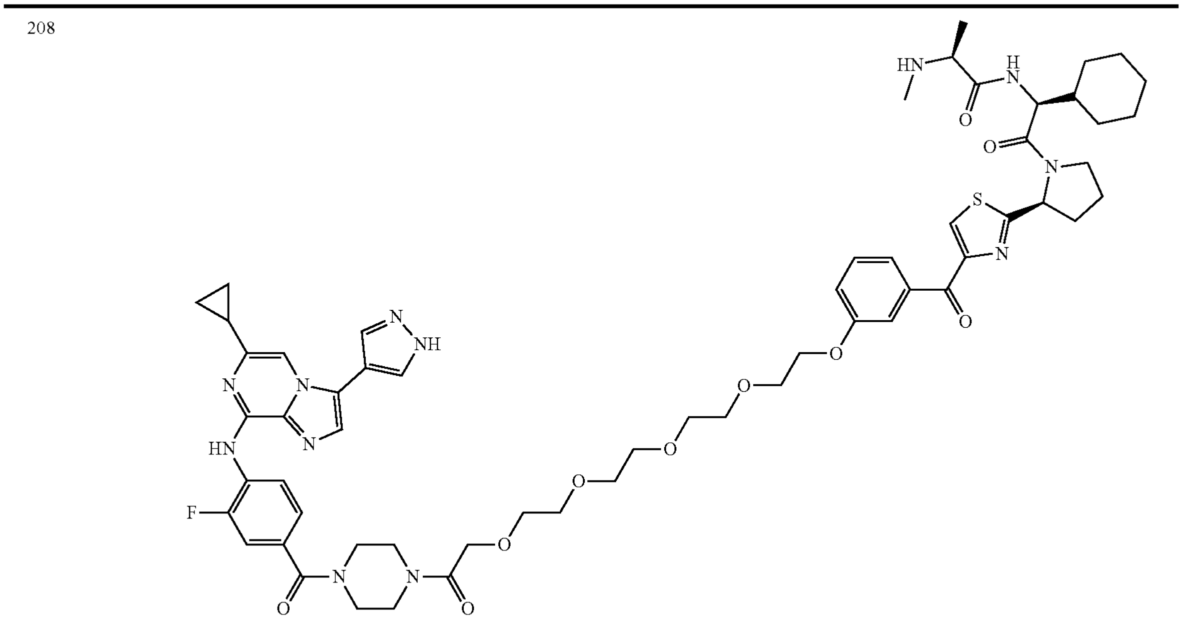
209
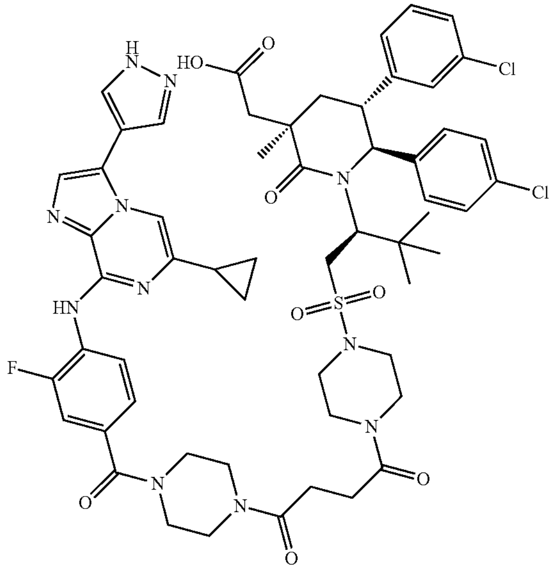 [SMILES: CC(C)(C)[C@@H](CS(=O)(=O)N1CCN(C(=O)CCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
210
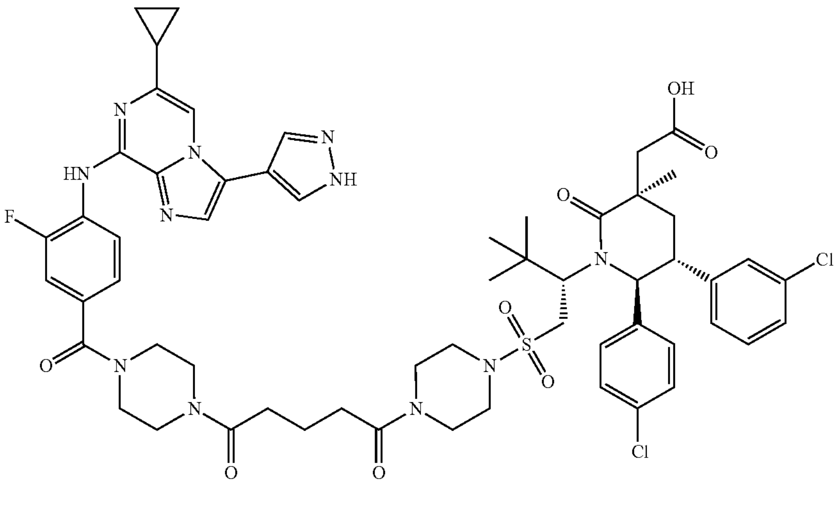 [SMILES: CC(C)(C)[C@@H](CS(=O)(=O)N1CCN(C(=O)CCCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]

TABLE 1-continued
211
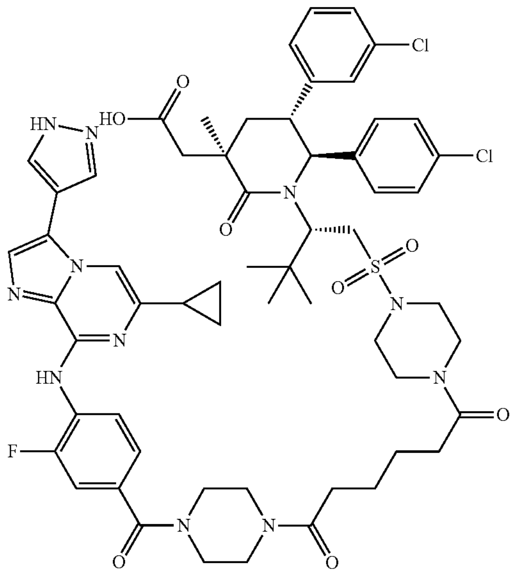 [SMILES: CC(C)(C)[C@@H](CS(=O)(=O)N1CCN(C(=O)CCCCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
212
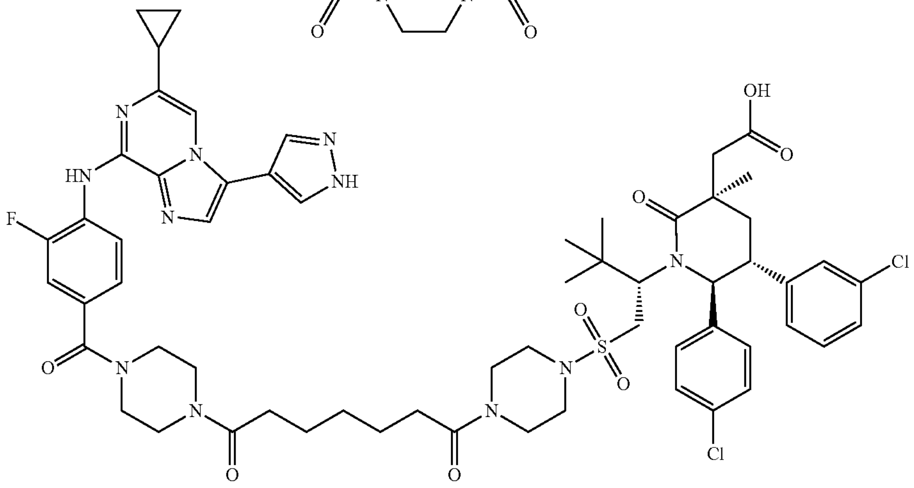
213
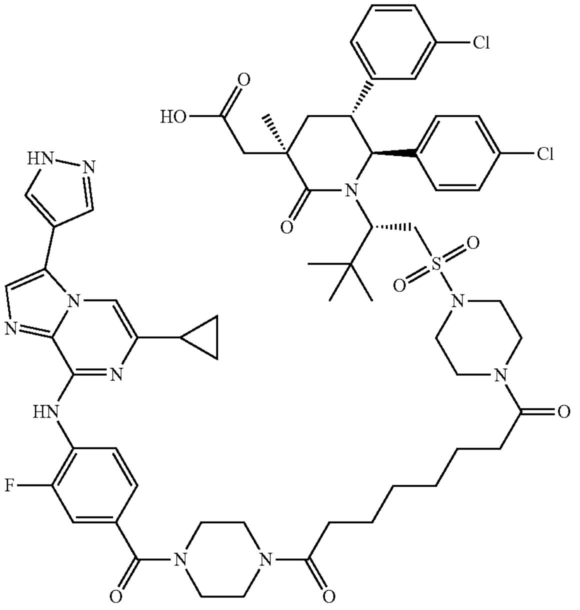

TABLE 1-continued
214
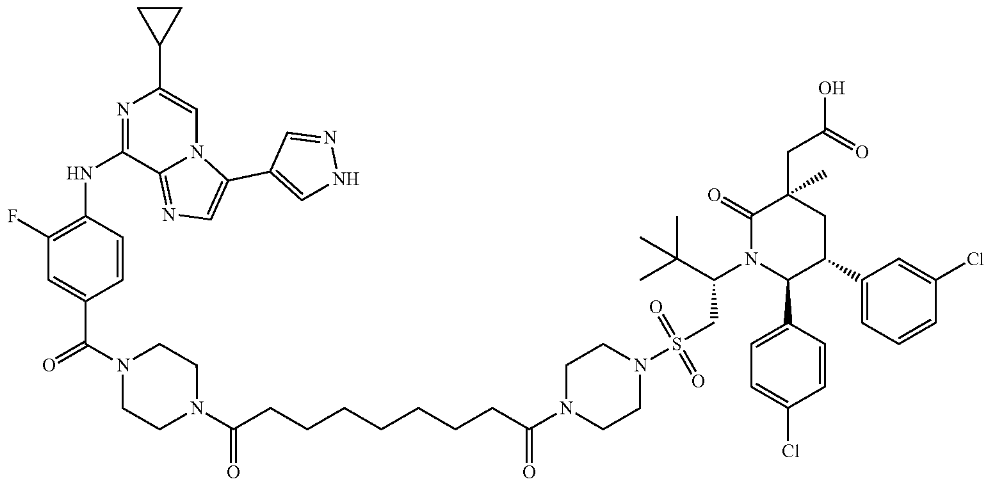 [SMILES: CC(C)(C)[C@@H](CS(=O)(=O)N1CCN(C(=O)CCCCCCCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
215
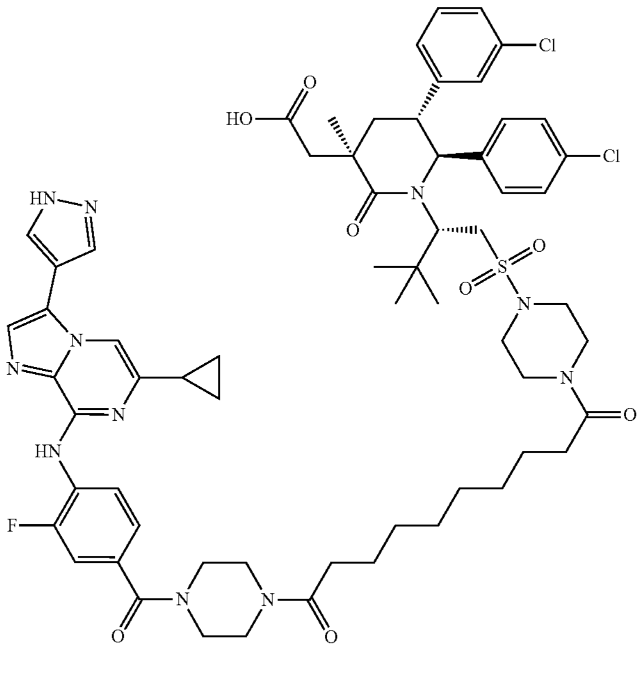 [SMILES: CC(C)(C)[C@@H](CS(=O)(=O)N1CCN(C(=O)CCCCCCCCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
216
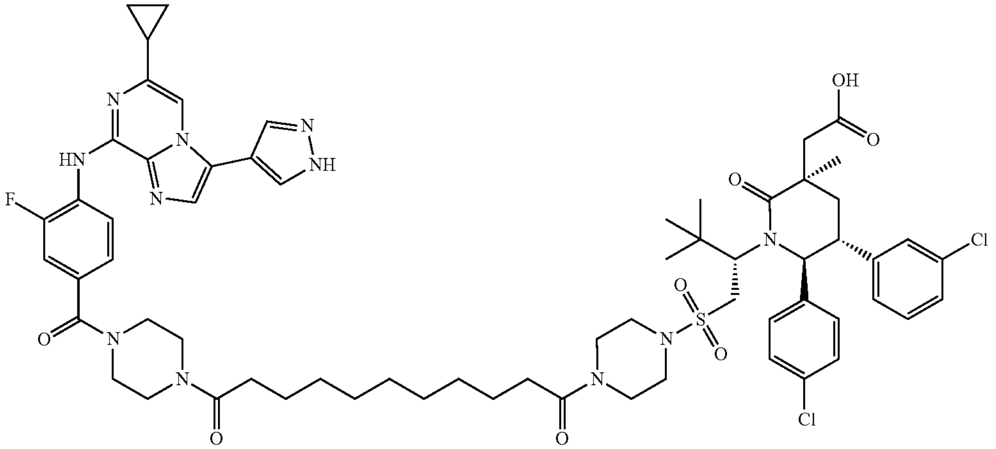 [SMILES: CC(C)(C)[C@@H](CS(=O)(=O)N1CCN(C(=O)CCCCCCCCCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]

TABLE 1-continued
217
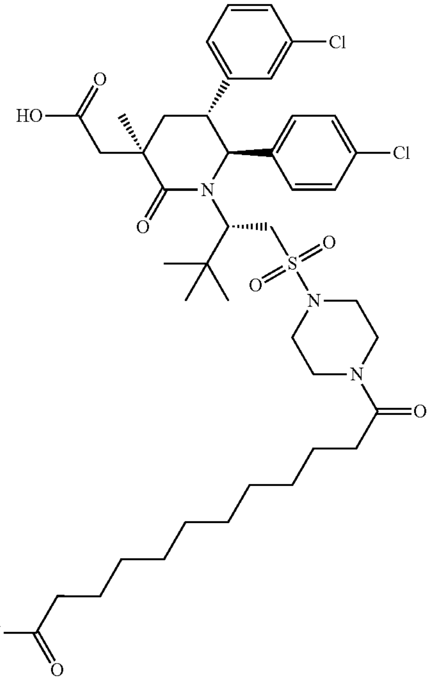
218
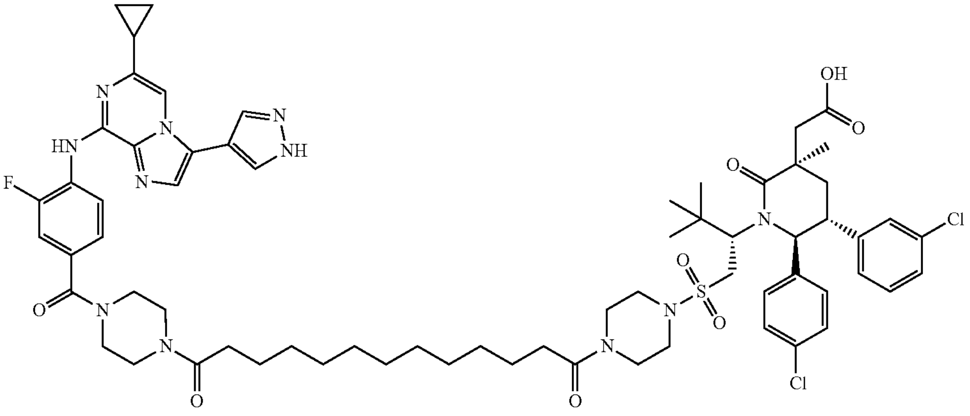 [SMILES: CC(C)(C)[C@@H](CS(=O)(=O)N1CCN(C(=O)CCCCCCCCCCCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]

TABLE 1-continued
219
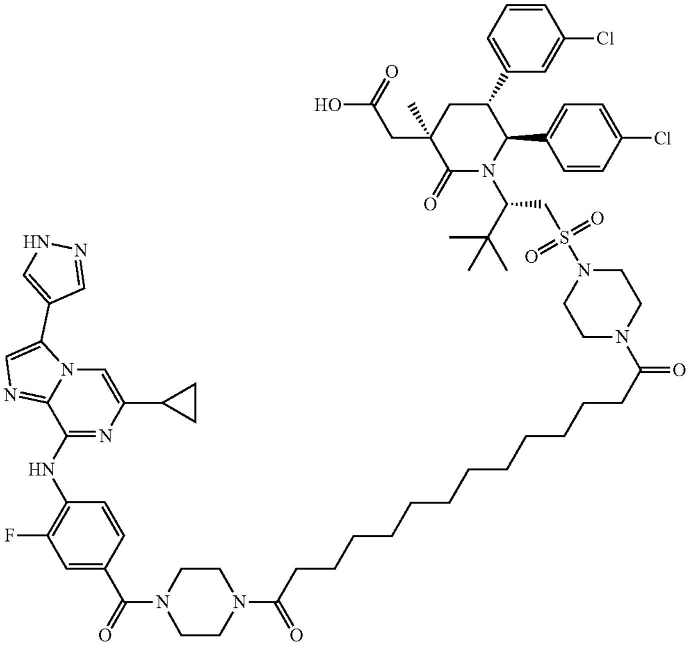
220
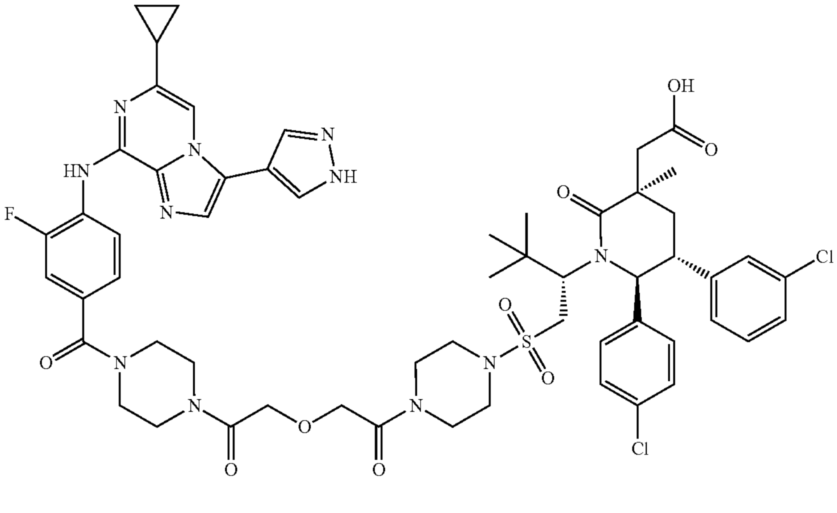 [SMILES: CC(C)(C)[C@@H](CS(=O)(=O)N1CCN(C(=O)COCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]

TABLE 1-continued
221
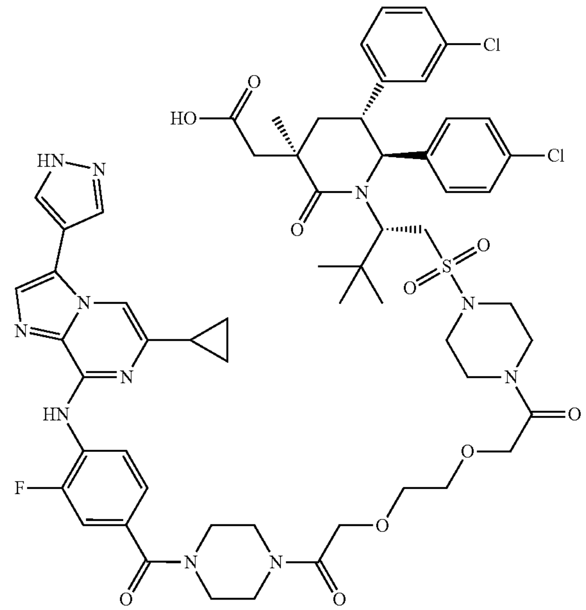 [SMILES: CC(C)(C)[C@@H](CS(=O)(=O)N1CCN(C(=O)COCCOCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
222
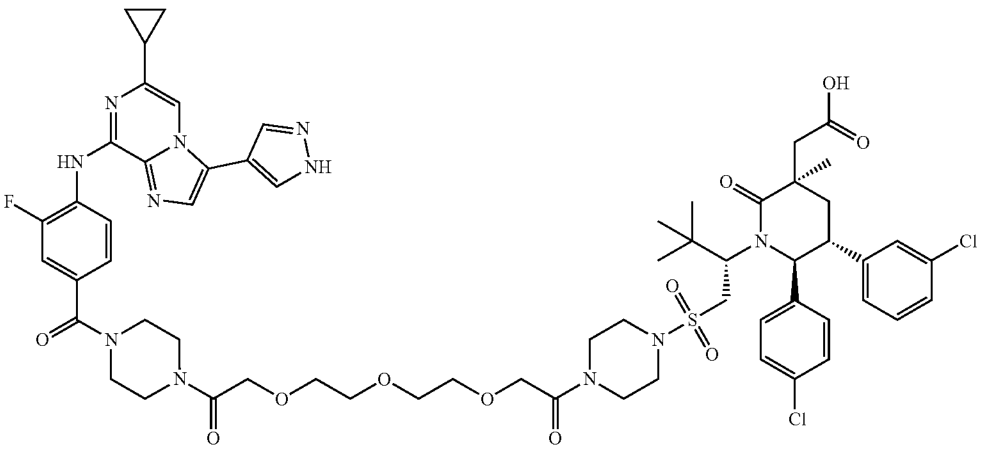

TABLE 1-continued
223
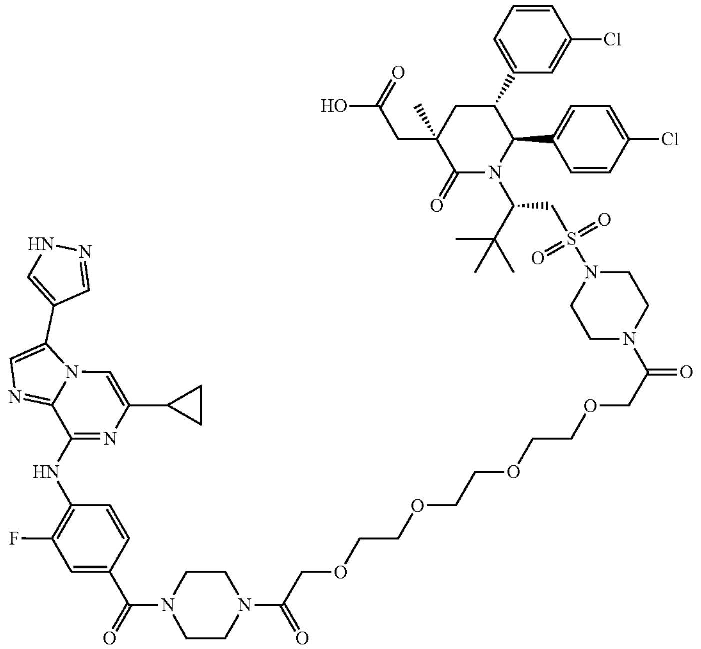 [SMILES: CC(C)(C)[C@@H](CS(=O)(=O)N1CCN(C(=O)COCCOCCOCCOCC(=O)N2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
224
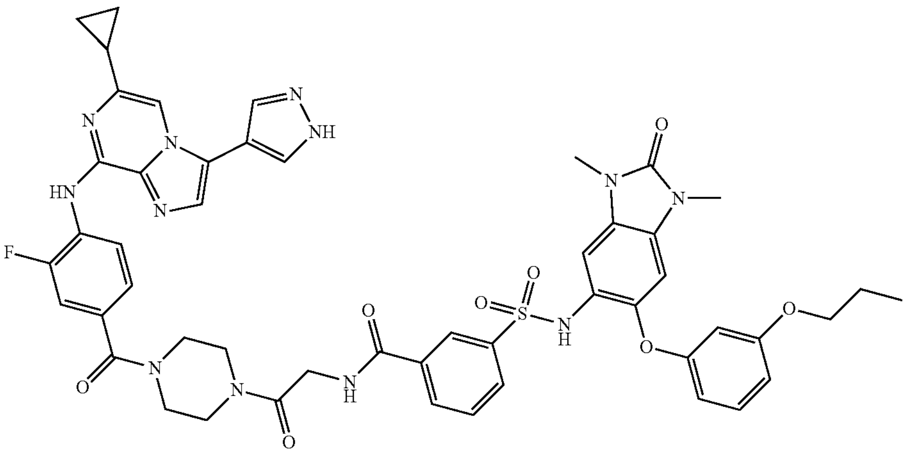 [SMILES: CCCOc1cccc(Oc2cc3c(cc2NS(=O)(=O)c2cccc(C(=O)NCC(=O)N4CCN(C(=O)c5ccc(Nc6nc(C7CC7)cn7c(-c8cn[nH]c8)cnc67)c(F)c5)CC4)c2)n(C)c(=O)n3C)c1]
225
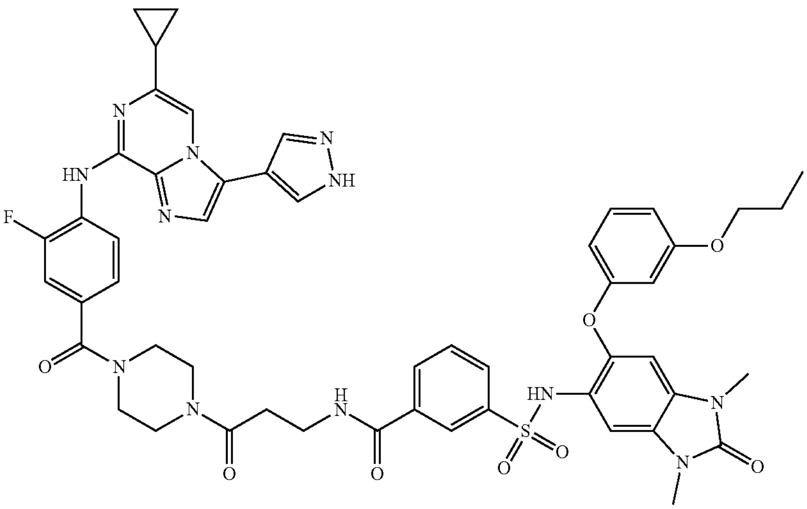 [SMILES: CCCOc1cccc(Oc2cc3c(cc2NS(=O)(=O)c2cccc(C(=O)NCCC(=O)N4CCN(C(=O)c5ccc(Nc6nc(C7CC7)cn7c(-c8cn[nH]c8)cnc67)c(F)c5)CC4)c2)n(C)c(=O)n3C)c1]

TABLE 1-continued
226
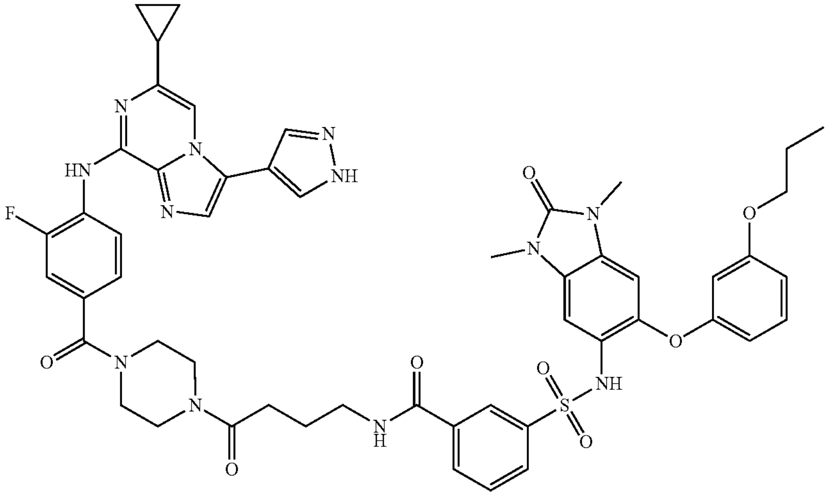 [SMILES: CCCOc1cccc(Oc2cc3c(cc2NS(=O)(=O)c2cccc(C(=O)NCCCC(=O)N4CCN(C(=O)c5ccc(Nc6nc(C7CC7)cn7c(-c8cn[nH]c8)cnc67)c(F)c5)CC4)c2)n(C)c(=O)n3C)c1]
227
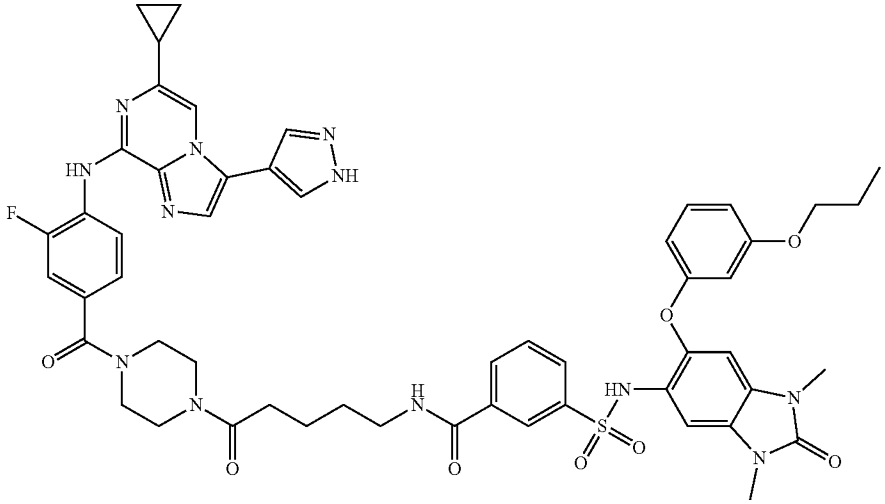 [SMILES: CCCOc1cccc(Oc2cc3c(cc2NS(=O)(=O)c2cccc(C(=O)NCCCCC(=O)N4CCN(C(=O)c5ccc(Nc6nc(C7CC7)cn7c(-c8cn[nH]c8)cnc67)c(F)c5)CC4)c2)n(C)c(=O)n3C)c1]
228
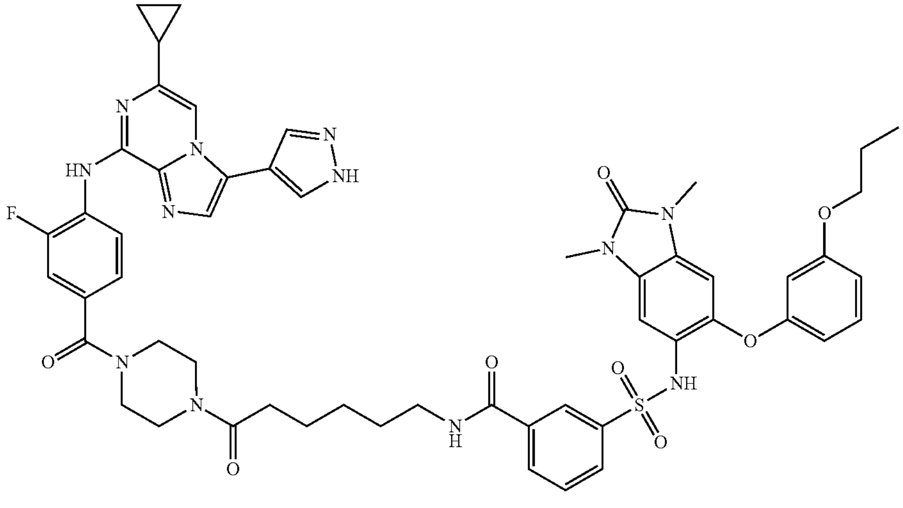 [SMILES: CCCOc1cccc(Oc2cc3c(cc2NS(=O)(=O)c2cccc(C(=O)NCCCCCC(=O)N4CCN(C(=O)c5ccc(Nc6nc(C7CC7)cn7c(-c8cn[nH]c8)cnc67)c(F)c5)CC4)c2)n(C)c(=O)n3C)c1]

TABLE 1-continued
229
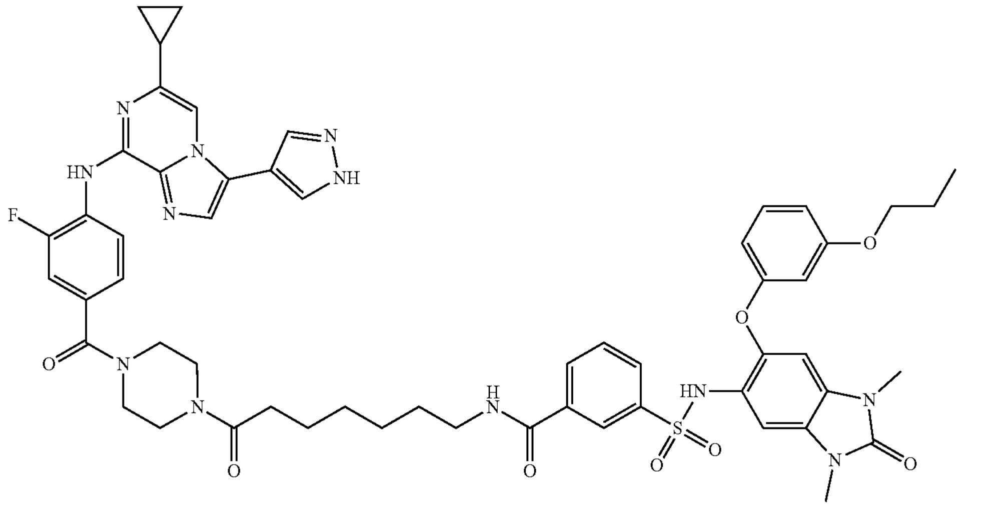 [SMILES: CCCOc1cccc(Oc2cc3c(cc2NS(=O)(=O)c2cccc(C(=O)NCCCCCCC(=O)N4CCN(C(=O)c5ccc(Nc6nc(C7CC7)cn7c(-c8cn[nH]c8)cnc67)c(F)c5)CC4)c2)n(C)c(=O)n3C)c1]
230
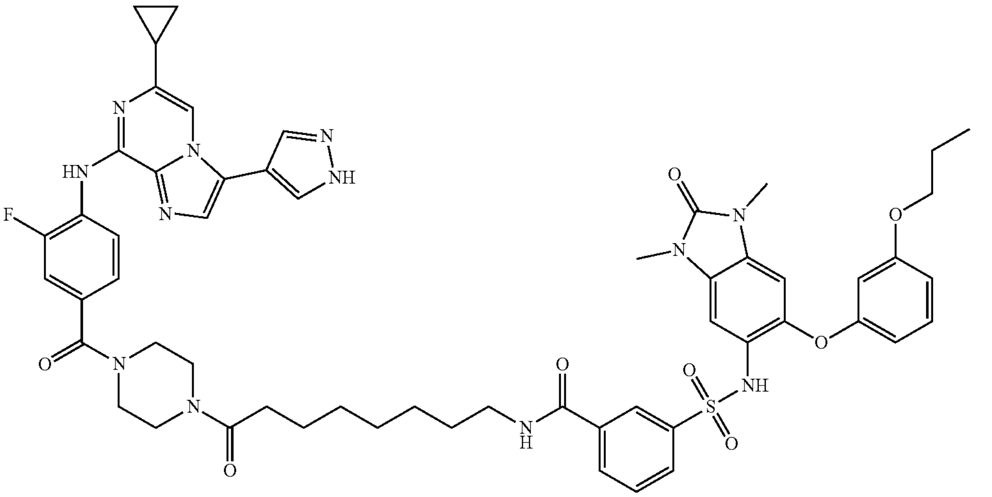
231
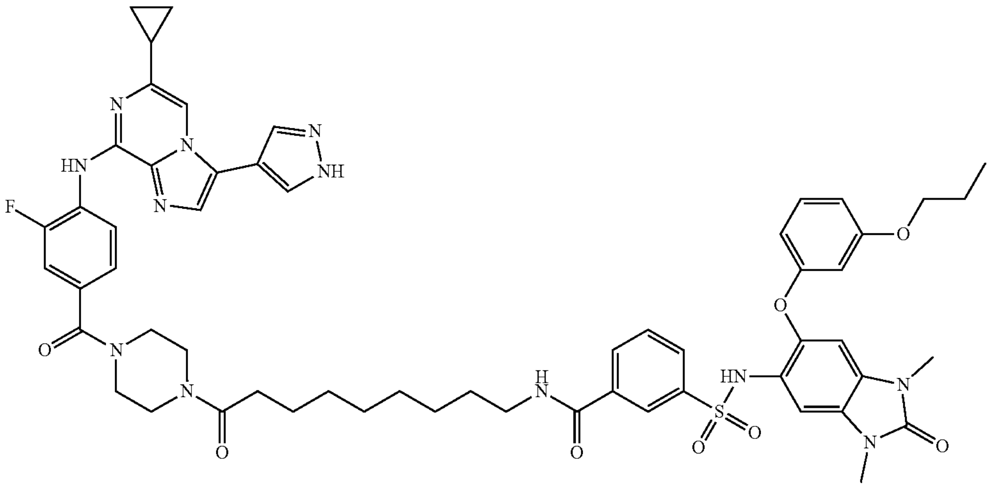 [SMILES: CCCOc1cccc(Oc2cc3c(cc2NS(=O)(=O)c2cccc(C(=O)NCCCCCCCCC(=O)N4CCN(C(=O)c5ccc(Nc6nc(C7CC7)cn7c(-c8cn[nH]c8)cnc67)c(F)c5)CC4)c2)n(C)c(=O)n3C)c1]

TABLE 1-continued
232
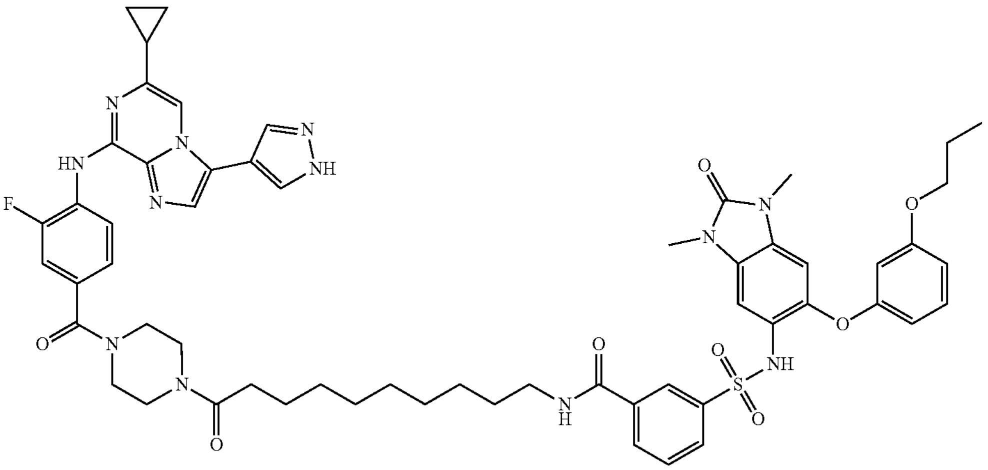 [SMILES: CCCOc1cccc(Oc2cc3c(cc2NS(=O)(=O)c2cccc(C(=O)NCCCCCCCCCC(=O)N4CCN(C(=O)c5ccc(Nc6nc(C7CC7)cn7c(-c8cn[nH]c8)cnc67)c(F)c5)CC4)c2)n(C)c(=O)n3C)c1]
233
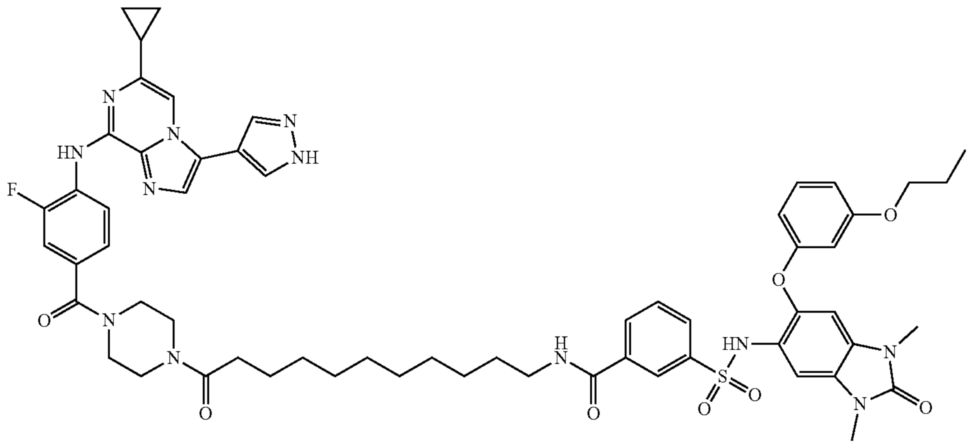
234
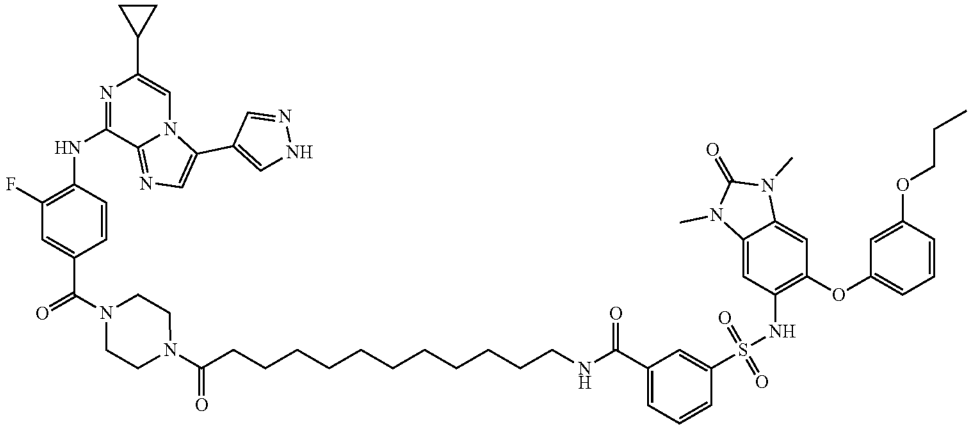 [SMILES: CCCOc1cccc(Oc2cc3c(cc2NS(=O)(=O)c2cccc(C(=O)NCCCCCCCCCCCC(=O)N4CCN(C(=O)c5ccc(Nc6nc(C7CC7)cn7c(-c8cn[nH]c8)cnc67)c(F)c5)CC4)c2)n(C)c(=O)n3C)c1]

TABLE 1-continued
235
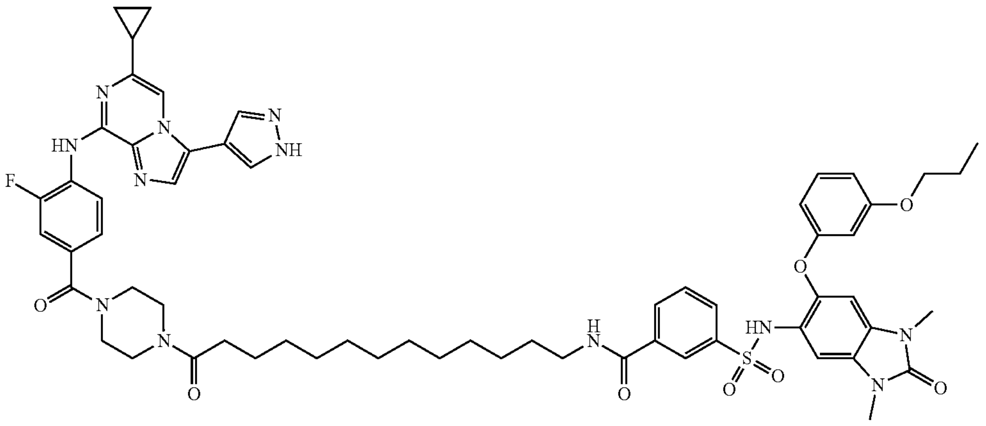 [SMILES: CCCOc1cccc(Oc2cc3c(cc2NS(=O)(=O)c2cccc(C(=O)NCCCCCCCCCCCCC(=O)N4CCN(C(=O)c5ccc(Nc6nc(C7CC7)cn7c(-c8cn[nH]c8)cnc67)c(F)c5)CC4)c2)n(C)c(=O)n3C)c1]
236
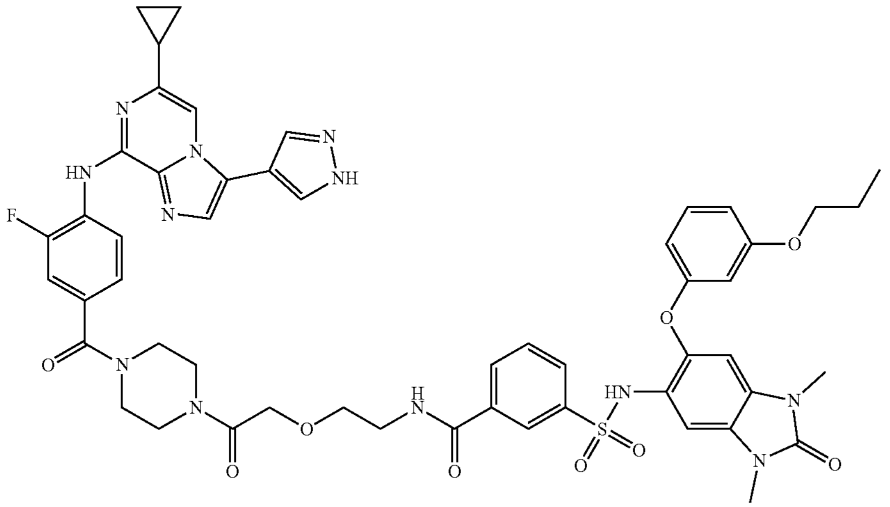 [SMILES: CCCOc1cccc(Oc2cc3c(cc2NS(=O)(=O)c2cccc(C(=O)NCCOCC(=O)N4CCN(C(=O)c5ccc(Nc6nc(C7CC7)cn7c(-c8cn[nH]c8)cnc67)c(F)c5)CC4)c2)n(C)c(=O)n3C)c1]
237
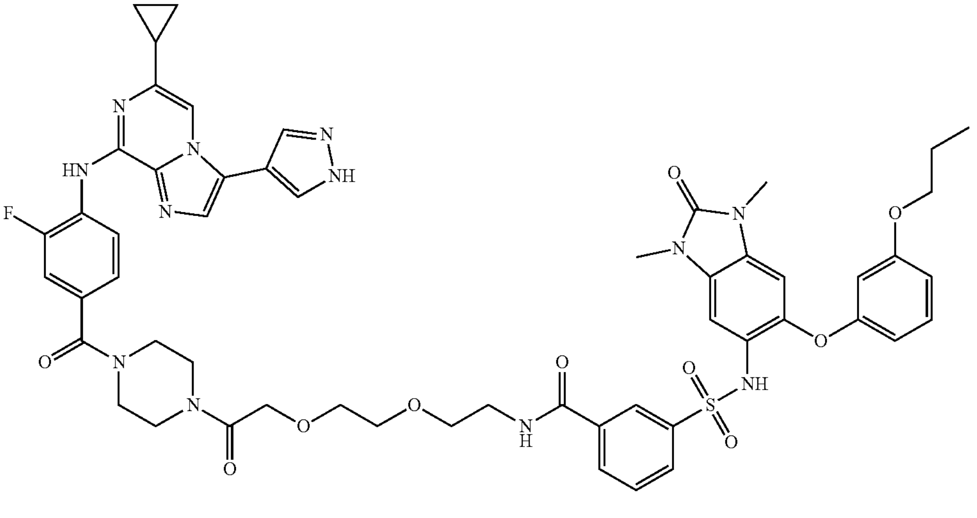 [SMILES: CCCOc1cccc(Oc2cc3c(cc2NS(=O)(=O)c2cccc(C(=O)NCCOCCOCC(=O)N4CCN(C(=O)c5ccc(Nc6nc(C7CC7)cn7c(-c8cn[nH]c8)cnc67)c(F)c5)CC4)c2)n(C)c(=O)n3C)c1]

TABLE 1-continued
238
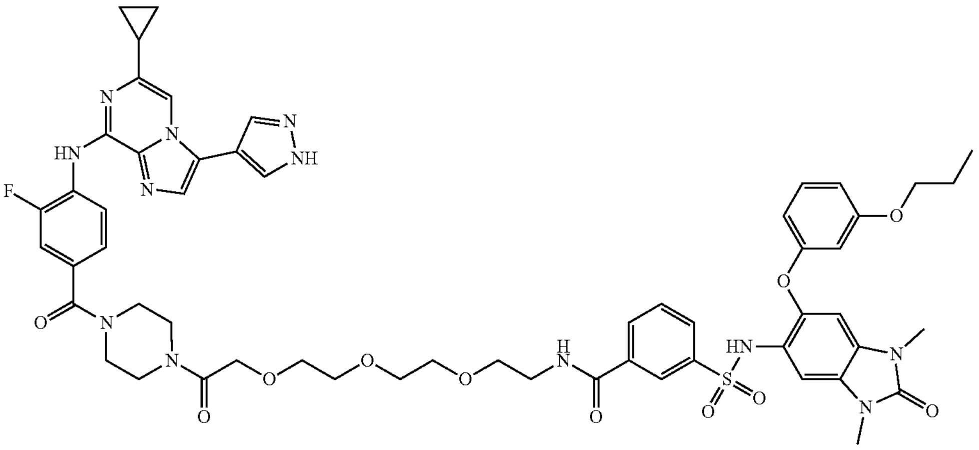 [SMILES: CCCOc1cccc(Oc2cc3c(cc2NS(=O)(=O)c2cccc(C(=O)NCCOCCOCCOCC(=O)N4CCN(C(=O)c5ccc(Nc6nc(C7CC7)cn7c(-c8cn[nH]c8)cnc67)c(F)c5)CC4)c2)n(C)c(=O)n3C)c1]
239
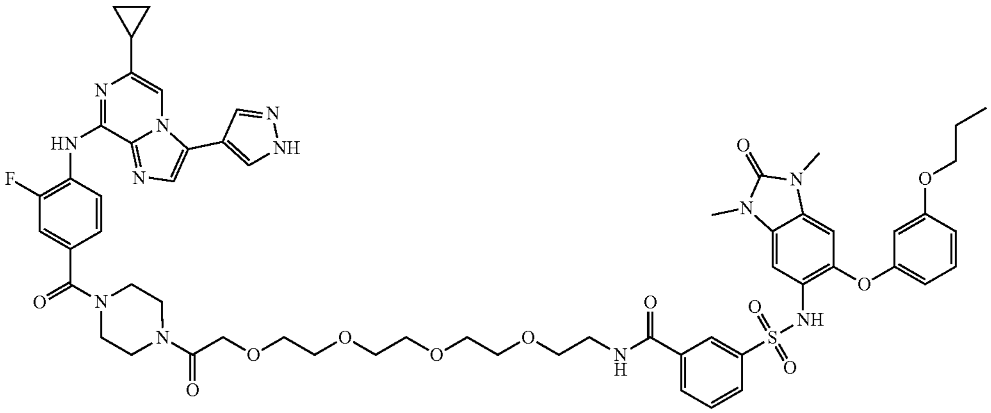 [SMILES: CCCOc1cccc(Oc2cc3c(cc2NS(=O)(=O)c2cccc(C(=O)NCCOCCOCCOCCOCC(=O)N4CCN(C(=O)c5ccc(Nc6nc(C7CC7)cn7c(-c8cn[nH]c8)cnc67)c(F)c5)CC4)c2)n(C)c(=O)n3C)c1]
240
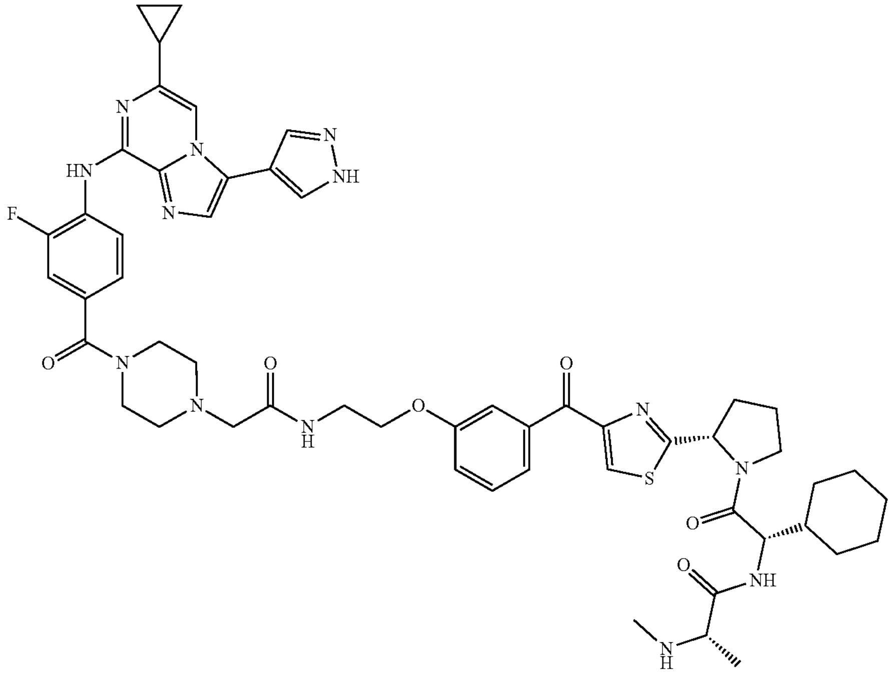 [SMILES: CN[C@@H](C)C(=O)N[C@H](C(=O)N1CCC[C@H]1c1nc(C(=O)c2cccc(OCCNC(=O)CN3CCN(C(=O)c4ccc(Nc5nc(C6CC6)cn6c(-c7cn[nH]c7)cnc56)c(F)c4)CC3)c2)cs1)C1CCCCC1]

TABLE 1-continued
241
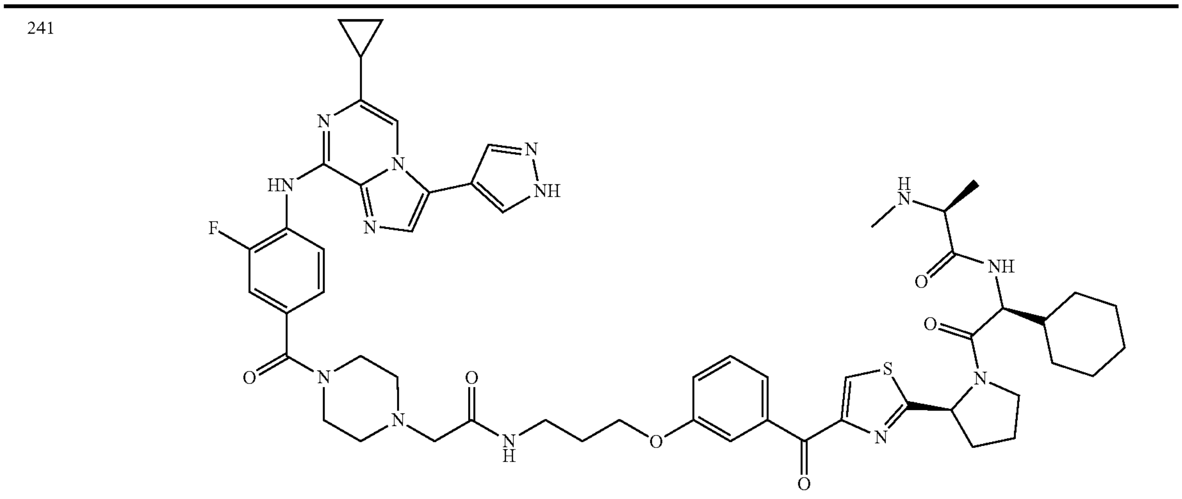
242
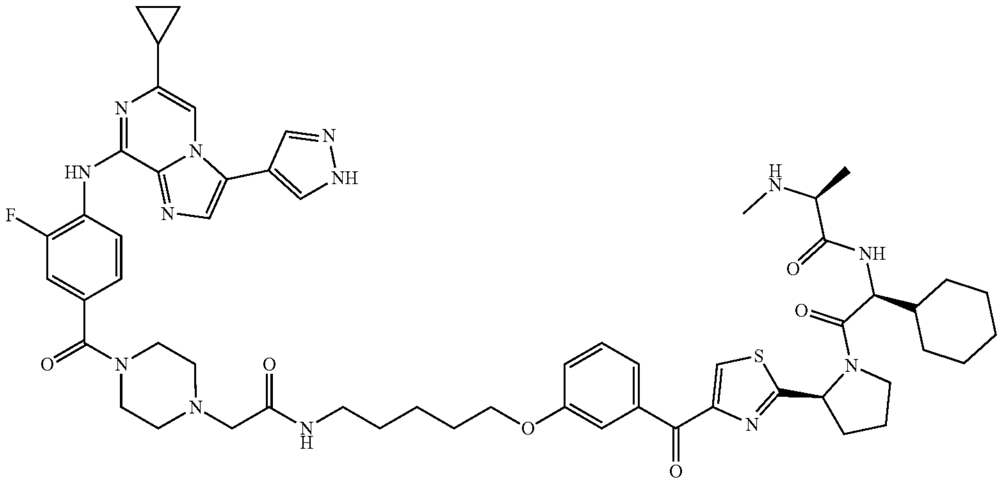
243
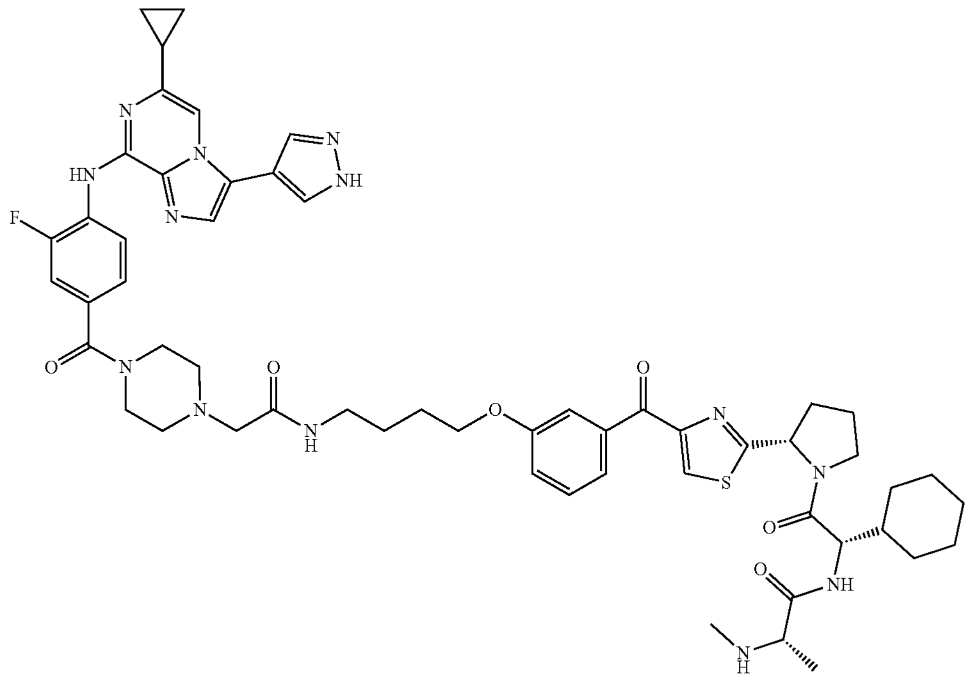 [SMILES: CN[C@@H](C)C(=O)N[C@H](C(=O)N1CCC[C@H]1c1nc(C(=O)c2cccc(OCCCCNC(=O)CN3CCN(C(=O)c4ccc(Nc5nc(C6CC6)cn6c(-c7cn[nH]c7)cnc56)c(F)c4)CC3)c2)cs1)C1CCCCC1]

TABLE 1-continued
244
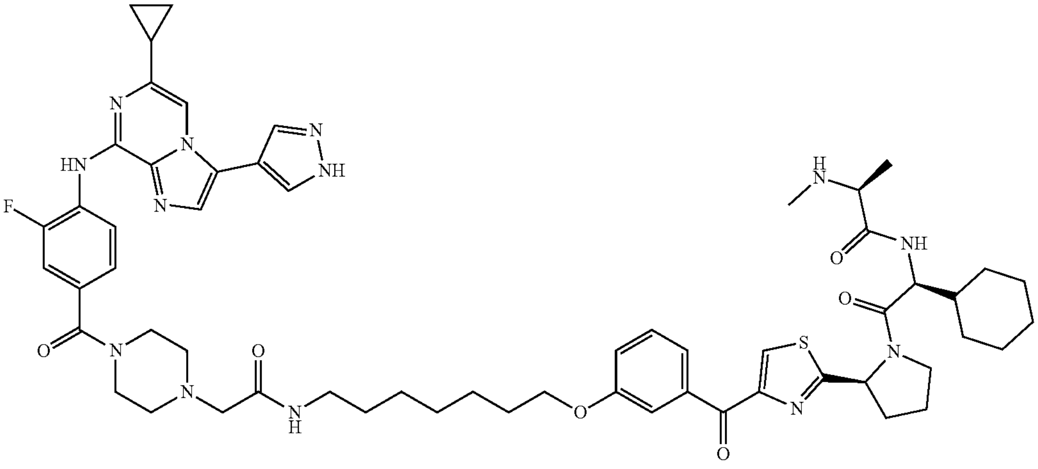 [SMILES: CN[C@@H](C)C(=O)N[C@H](C(=O)N1CCC[C@H]1c1nc(C(=O)c2cccc(OCCCCCCCNC(=O)CN3CCN(C(=O)c4ccc(Nc5nc(C6CC6)cn6c(-c7cn[nH]c7)cnc56)c(F)c4)CC3)c2)cs1)C1CCCCC1]
245
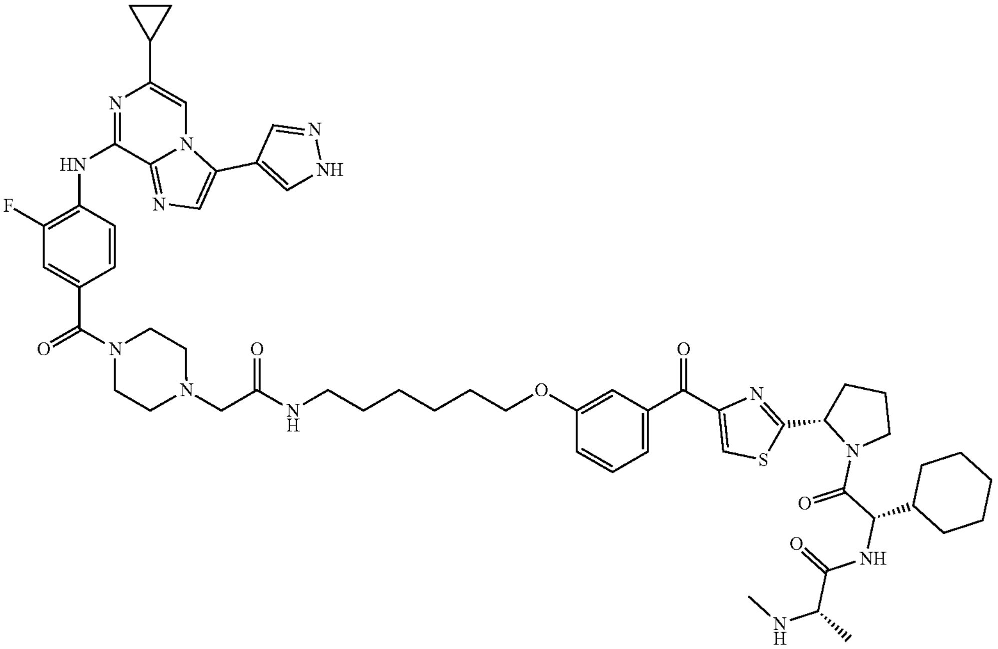 [SMILES: CN[C@@H](C)C(=O)N[C@H](C(=O)N1CCC[C@H]1c1nc(C(=O)c2cccc(OCCCCCCNC(=O)CN3CCN(C(=O)c4ccc(Nc5nc(C6CC6)cn6c(-c7cn[nH]c7)cnc56)c(F)c4)CC3)c2)cs1)C1CCCCC1]
246
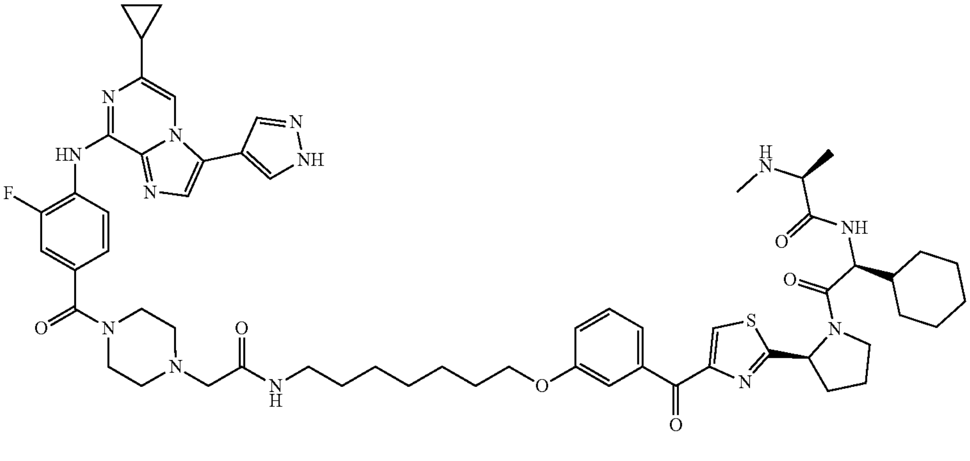 [SMILES: CN[C@@H](C)C(=O)N[C@H](C(=O)N1CCC[C@H]1c1nc(C(=O)c2cccc(OCCCCCCCNC(=O)CN3CCN(C(=O)c4ccc(Nc5nc(C6CC6)cn6c(-c7cn[nH]c7)cnc56)c(F)c4)CC3)c2)cs1)C1CCCCC1]

TABLE 1-continued
247
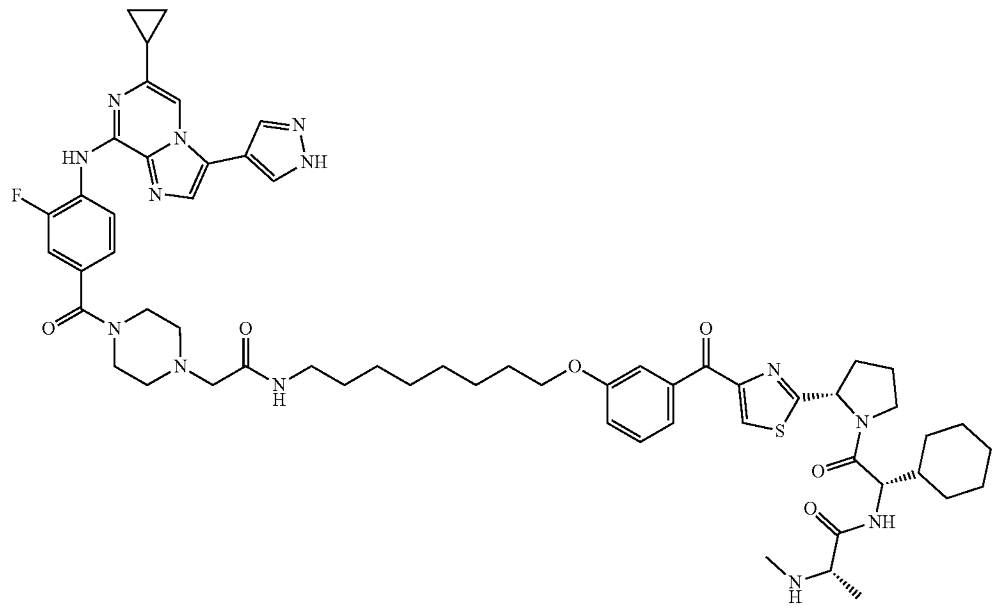 [SMILES: CN[C@@H](C)C(=O)N[C@H](C(=O)N1CCC[C@H]1c1nc(C(=O)c2cccc(OCCCCCCCCNC(=O)CN3CCN(C(=O)c4ccc(Nc5nc(C6CC6)cn6c(-c7cn[nH]c7)cnc56)c(F)c4)CC3)c2)cs1)C1CCCCC1]
248
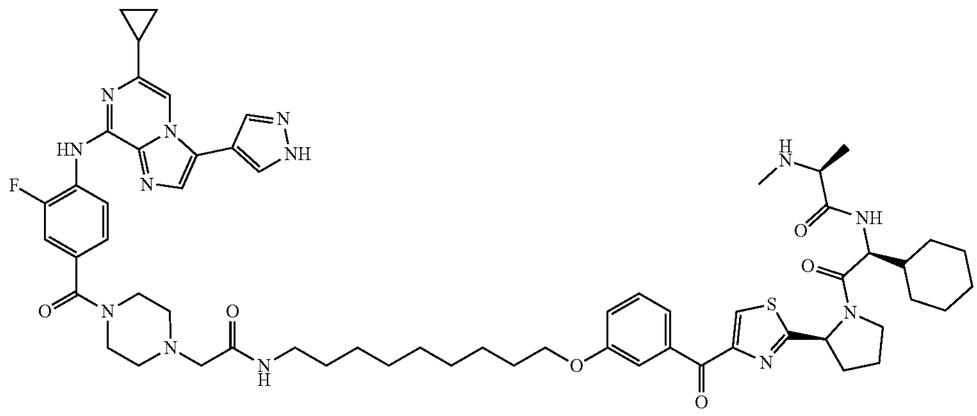 [SMILES: CN[C@@H](C)C(=O)N[C@H](C(=O)N1CCC[C@H]1c1nc(C(=O)c2cccc(OCCCCCCCCCNC(=O)CN3CCN(C(=O)c4ccc(Nc5nc(C6CC6)cn6c(-c7cn[nH]c7)cnc56)c(F)c4)CC3)c2)cs1)C1CCCCC1]
249
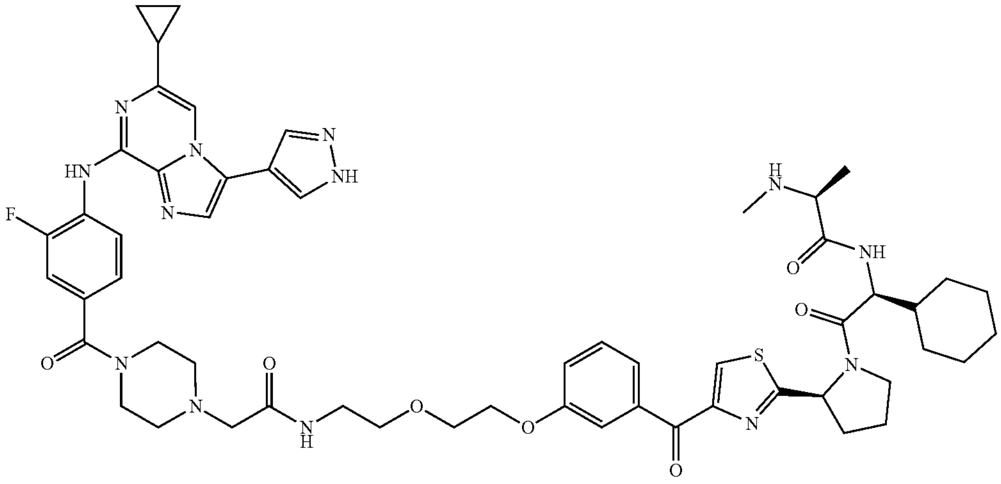 [SMILES: CN[C@@H](C)C(=O)N[C@H](C(=O)N1CCC[C@H]1c1nc(C(=O)c2cccc(OCCOCCNC(=O)CN3CCN(C(=O)c4ccc(Nc5nc(C6CC6)cn6c(-c7cn[nH]c7)cnc56)c(F)c4)CC3)c2)cs1)C1CCCCC1]

TABLE 1-continued
250
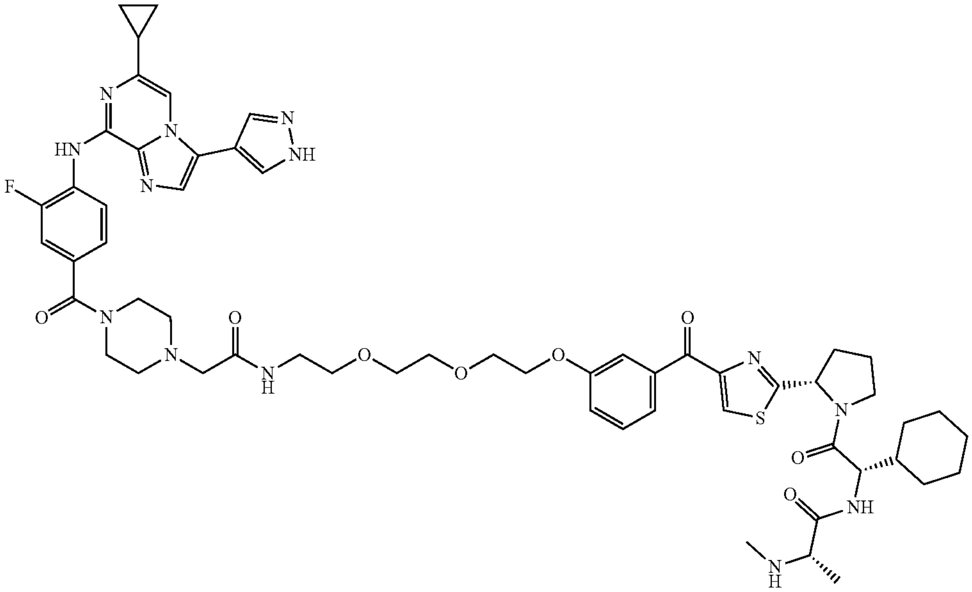 [SMILES: CN[C@@H](C)C(=O)N[C@H](C(=O)N1CCC[C@H]1c1nc(C(=O)c2cccc(OCCOCCOCCNC(=O)CN3CCN(C(=O)c4ccc(Nc5nc(C6CC6)cn6c(-c7cn[nH]c7)cnc56)c(F)c4)CC3)c2)cs1)C1CCCCC1]
251
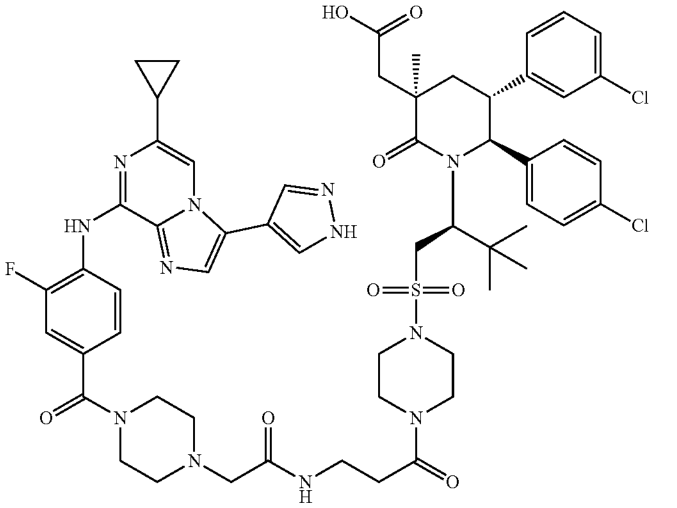 [SMILES: CC(C)(C)[C@@H](CS(=O)(=O)N1CCN(C(=O)CCNC(=O)CN2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
252
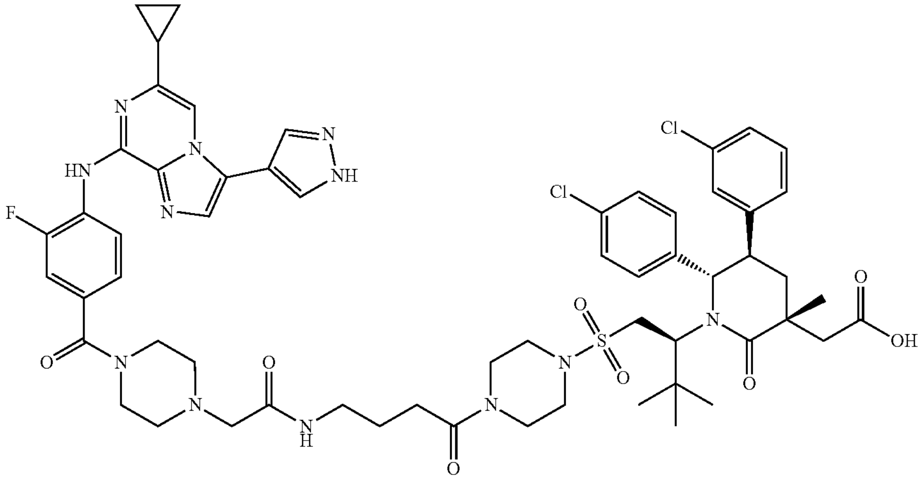 [SMILES: CC(C)(C)[C@@H](CS(=O)(=O)N1CCN(C(=O)CCCNC(=O)CN2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]

TABLE 1-continued
253
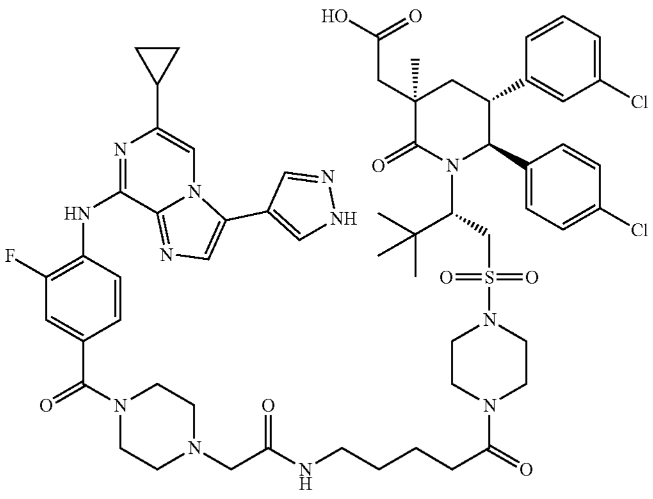 [SMILES: CC(C)(C)[C@@H](CS(=O)(=O)N1CCN(C(=O)CCCCNC(=O)CN2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
254
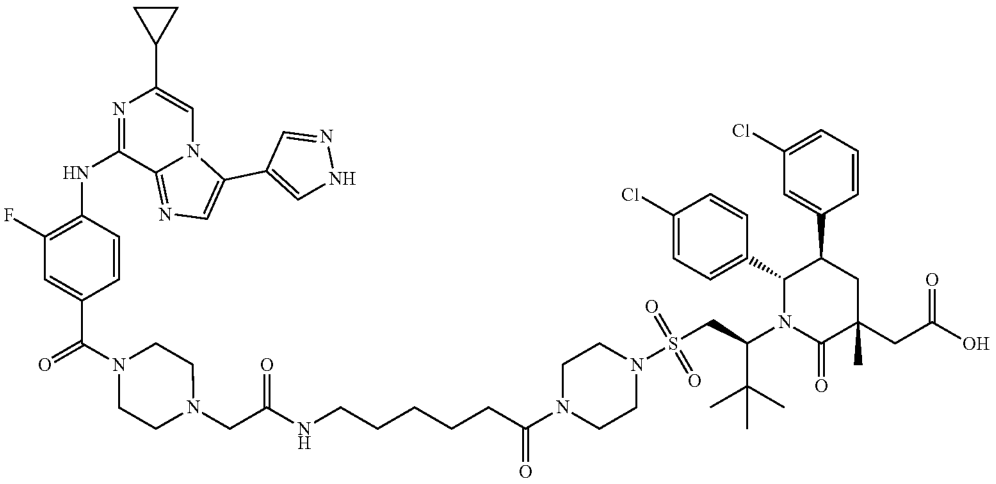 [SMILES: CC(C)(C)[C@@H](CS(=O)(=O)N1CCN(C(=O)CCCCCNC(=O)CN2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
255
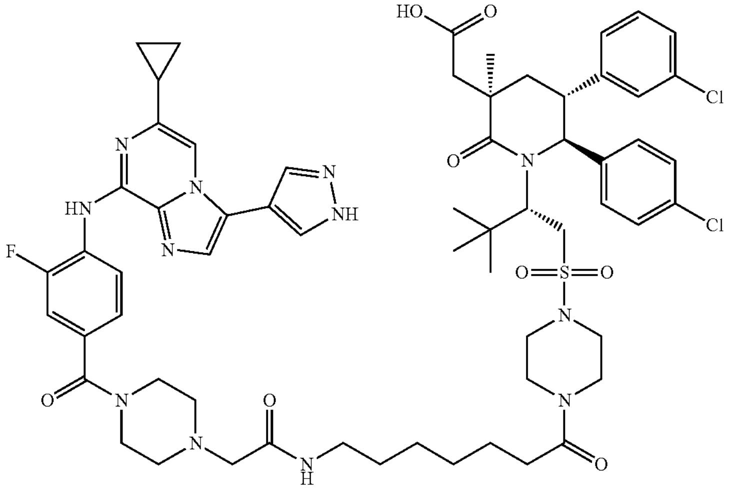 [SMILES: CC(C)(C)[C@@H](CS(=O)(=O)N1CCN(C(=O)CCCCCCNC(=O)CN2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]

TABLE 1-continued
256
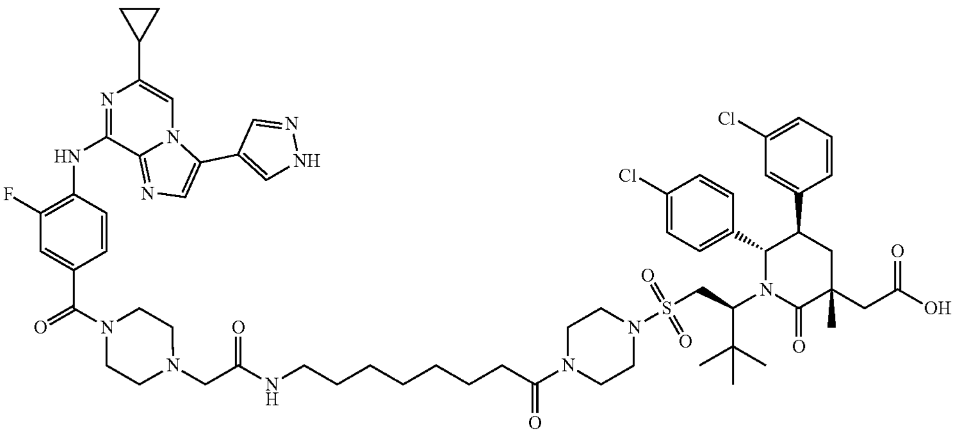 [SMILES: CC(C)(C)[C@@H](CS(=O)(=O)N1CCN(C(=O)CCCCCCCNC(=O)CN2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
257
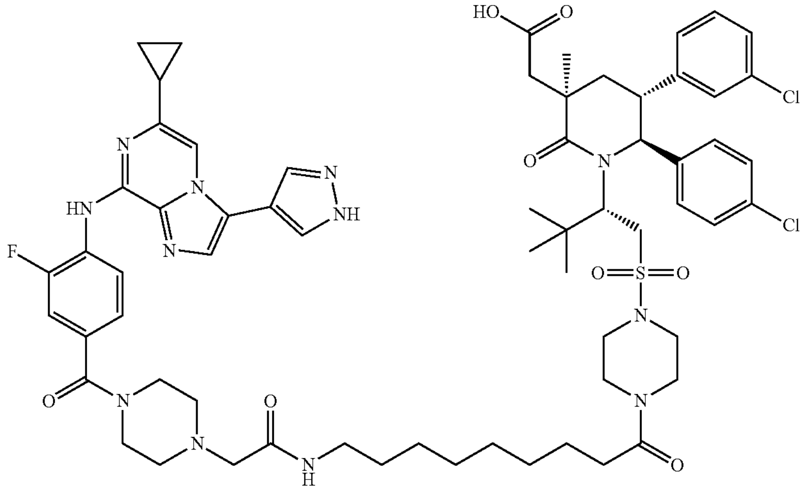 [SMILES: CC(C)(C)[C@@H](CS(=O)(=O)N1CCN(C(=O)CCCCCCCCNC(=O)CN2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
258
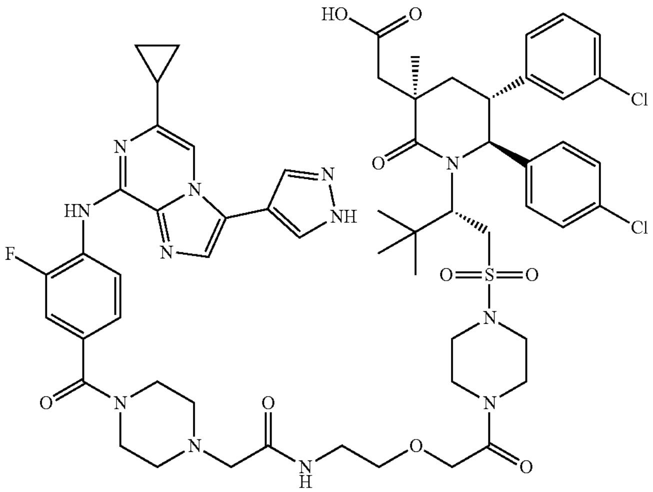

TABLE 1-continued
259
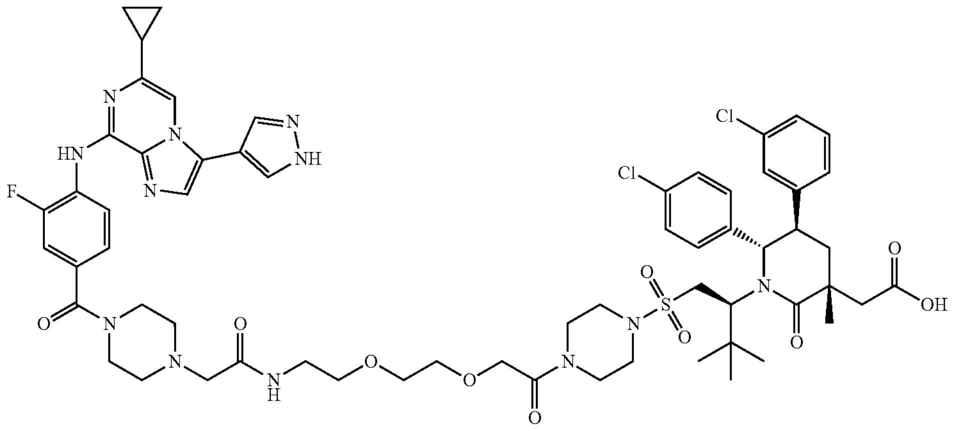 [SMILES: CC(C)(C)[C@@H](CS(=O)(=O)N1CCN(C(=O)COCCOCCNC(=O)CN2CCN(C(=O)c3ccc(Nc4nc(C5CC5)cn5c(-c6cn[nH]c6)cnc45)c(F)c3)CC2)CC1)N1C(=O)[C@@](C)(CC(=O)O)C[C@H](c2cccc(Cl)c2)[C@H]1c1ccc(Cl)cc1]
260
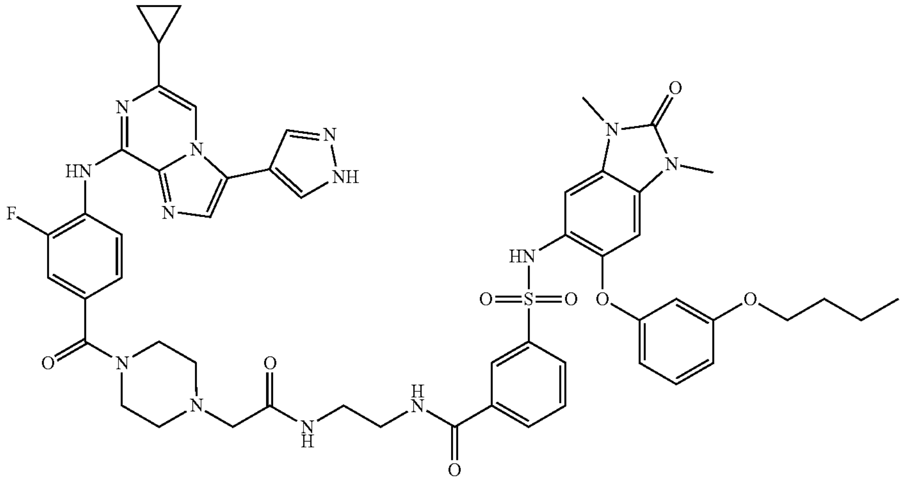 [SMILES: CCCCOc1cccc(Oc2cc3c(cc2NS(=O)(=O)c2cccc(C(=O)NCCNC(=O)CN4CCN(C(=O)c5ccc(Nc6nc(C7CC7)cn7c(-c8cn[nH]c8)cnc67)c(F)c5)CC4)c2)n(C)c(=O)n3C)c1]
261
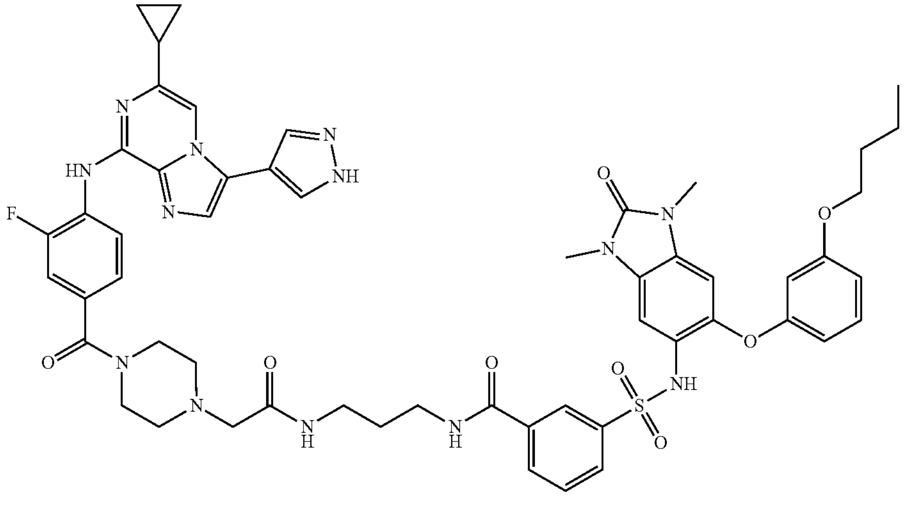 [SMILES: CCCCOc1cccc(Oc2cc3c(cc2NS(=O)(=O)c2cccc(C(=O)NCCCNC(=O)CN4CCN(C(=O)c5ccc(Nc6nc(C7CC7)cn7c(-c8cn[nH]c8)cnc67)c(F)c5)CC4)c2)n(C)c(=O)n3C)c1]

TABLE 1-continued
262
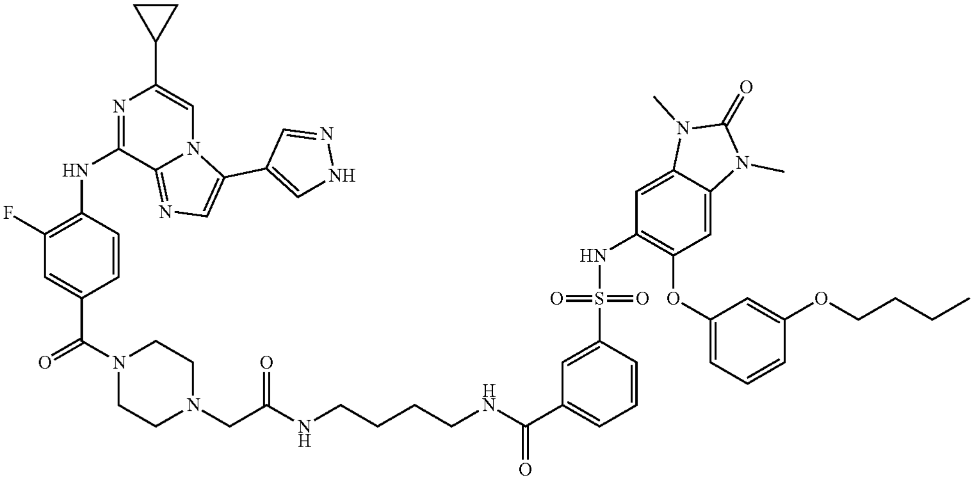 [SMILES: CCCCOc1cccc(Oc2cc3c(cc2NS(=O)(=O)c2cccc(C(=O)NCCCCNC(=O)CN4CCN(C(=O)c5ccc(Nc6nc(C7CC7)cn7c(-c8cn[nH]c8)cnc67)c(F)c5)CC4)c2)n(C)c(=O)n3C)c1]
263
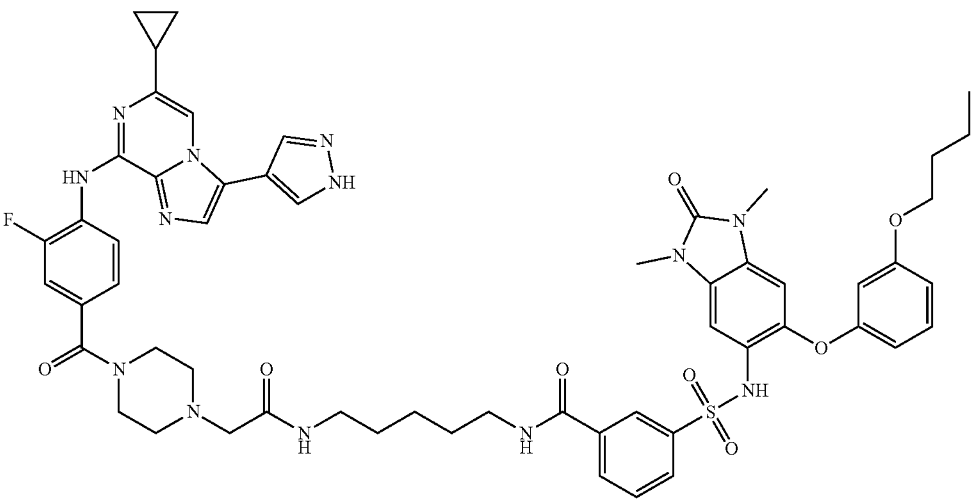 [SMILES: CCCCOc1cccc(Oc2cc3c(cc2NS(=O)(=O)c2cccc(C(=O)NCCCCCNC(=O)CN4CCN(C(=O)c5ccc(Nc6nc(C7CC7)cn7c(-c8cn[nH]c8)cnc67)c(F)c5)CC4)c2)n(C)c(=O)n3C)c1]
264
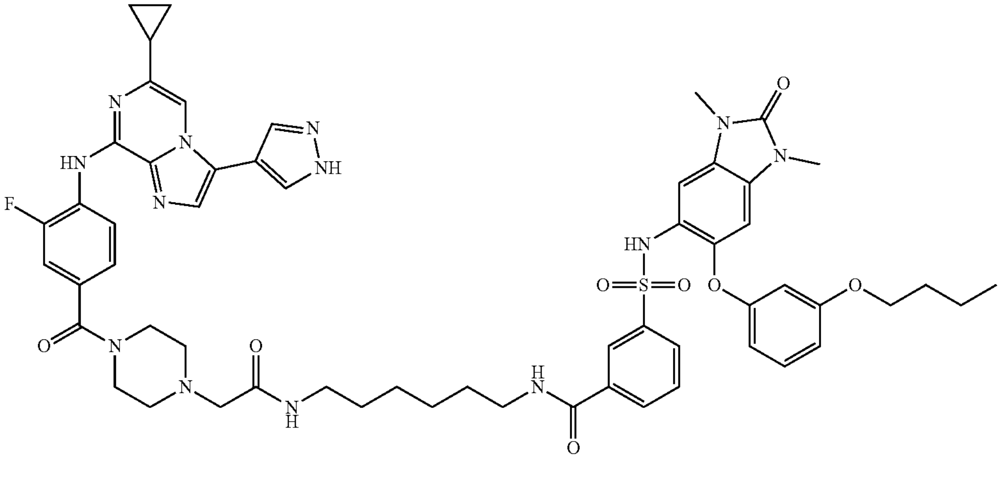 [SMILES: CCCCOc1cccc(Oc2cc3c(cc2NS(=O)(=O)c2cccc(C(=O)NCCCCCCNC(=O)CN4CCN(C(=O)c5ccc(Nc6nc(C7CC7)cn7c(-c8cn[nH]c8)cnc67)c(F)c5)CC4)c2)n(C)c(=O)n3C)c1]

TABLE 1-continued
265
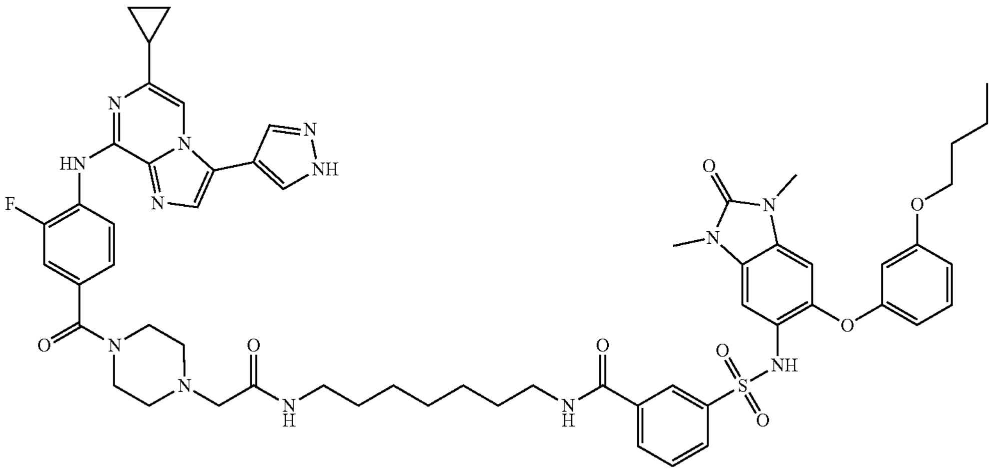 [SMILES: CCCCOc1cccc(Oc2cc3c(cc2NS(=O)(=O)c2cccc(C(=O)NCCCCCCCNC(=O)CN4CCN(C(=O)c5ccc(Nc6nc(C7CC7)cn7c(-c8cn[nH]c8)cnc67)c(F)c5)CC4)c2)n(C)c(=O)n3C)c1]
266
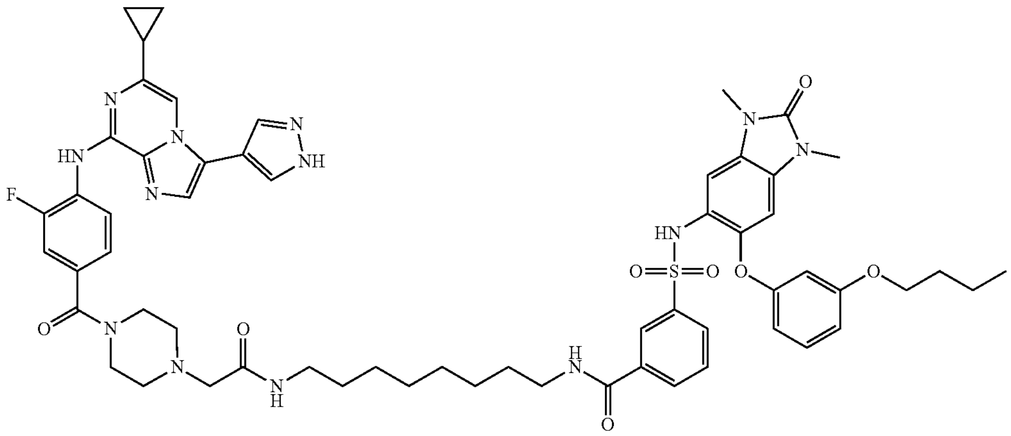 [SMILES: CCCCOc1cccc(Oc2cc3c(cc2NS(=O)(=O)c2cccc(C(=O)NCCCCCCCCNC(=O)CN4CCN(C(=O)c5ccc(Nc6nc(C7CC7)cn7c(-c8cn[nH]c8)cnc67)c(F)c5)CC4)c2)n(C)c(=O)n3C)c1]
267
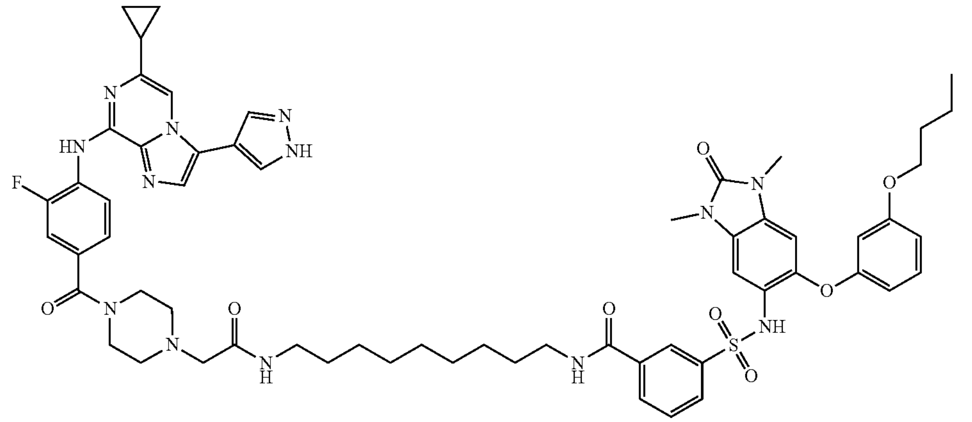 [SMILES: CCCCOc1cccc(Oc2cc3c(cc2NS(=O)(=O)c2cccc(C(=O)NCCCCCCCCCNC(=O)CN4CCN(C(=O)c5ccc(Nc6nc(C7CC7)cn7c(-c8cn[nH]c8)cnc67)c(F)c5)CC4)c2)n(C)c(=O)n3C)c1]

TABLE 1-continued
268
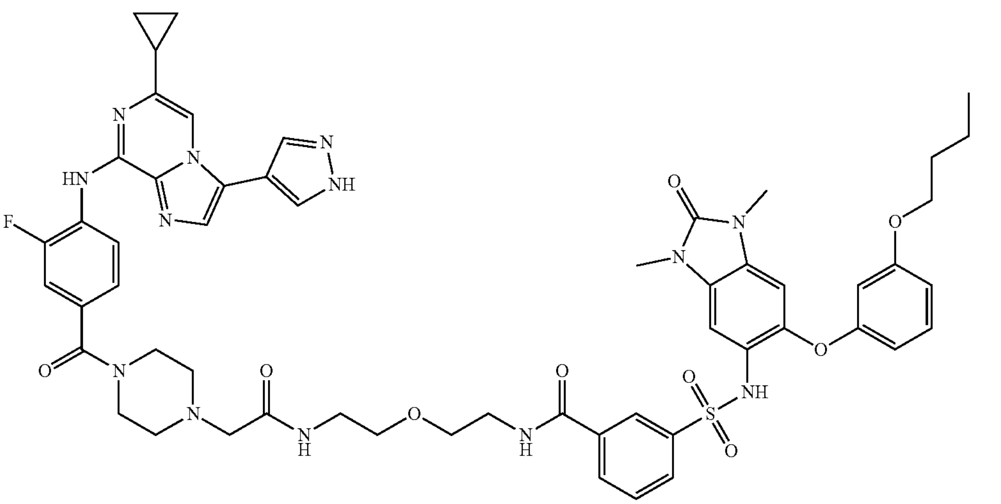
269
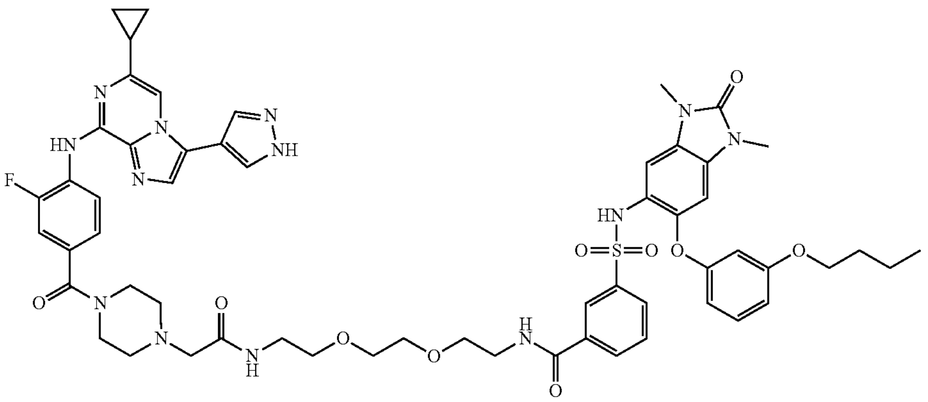
270
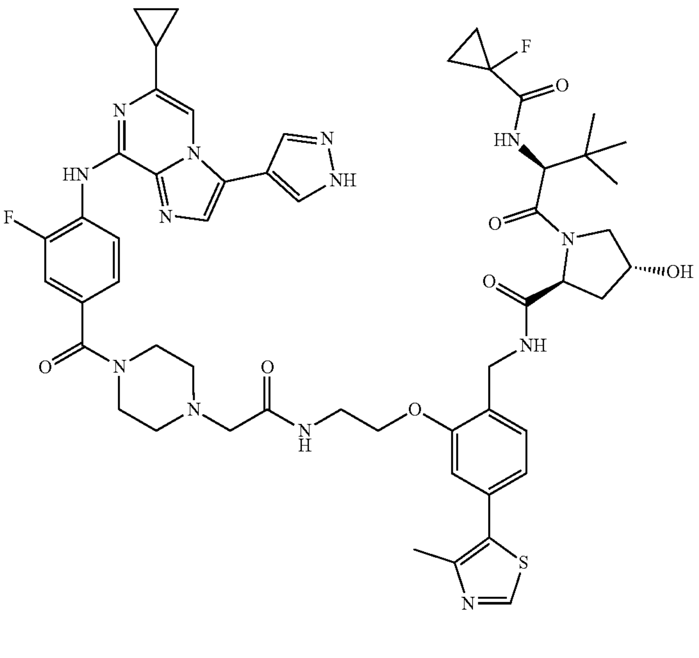 [SMILES: Cc1ncsc1-c1ccc(CNC(=O)[C@@H]2C[C@@H](O)CN2C(=O)[C@@H](NC(=O)C2(F)CC2)C(C)(C)C)c(OCCNC(=O)CN2CCN(C(=O)c3ccc(Nc4nc(C5CC5)cn5c(-c6cn[nH]c6)cnc45)c(F)c3)CC2)c1]

TABLE 1-continued
271
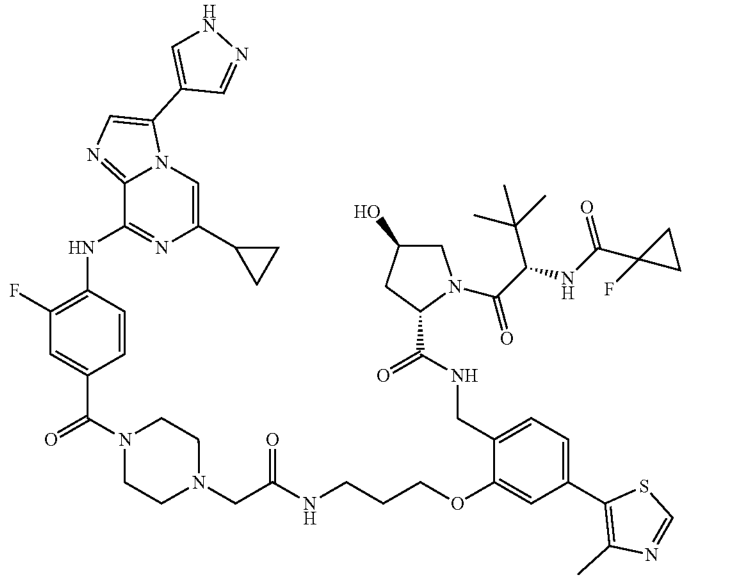 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCNC(=O)CN2CCN(C(=O)c3ccc(Nc4nc(C5CC5)cn5c(-c6cn[nH]c6)cnc45)c(F)c3)CC2)c1]
272
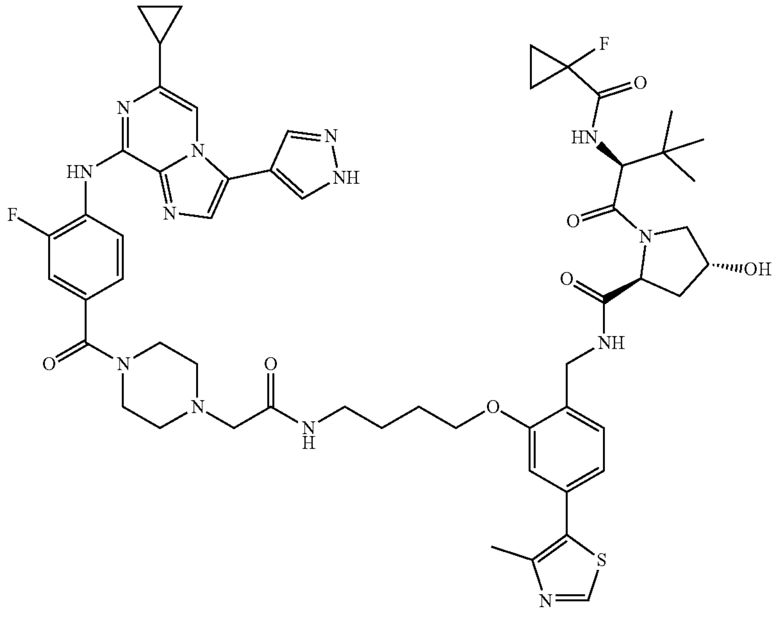 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCNC(=O)CN2CCN(C(=O)c3ccc(Nc4nc(C5CC5)cn5c(-c6cn[nH]c6)cnc45)c(F)c3)CC2)c1]

TABLE 1-continued
273
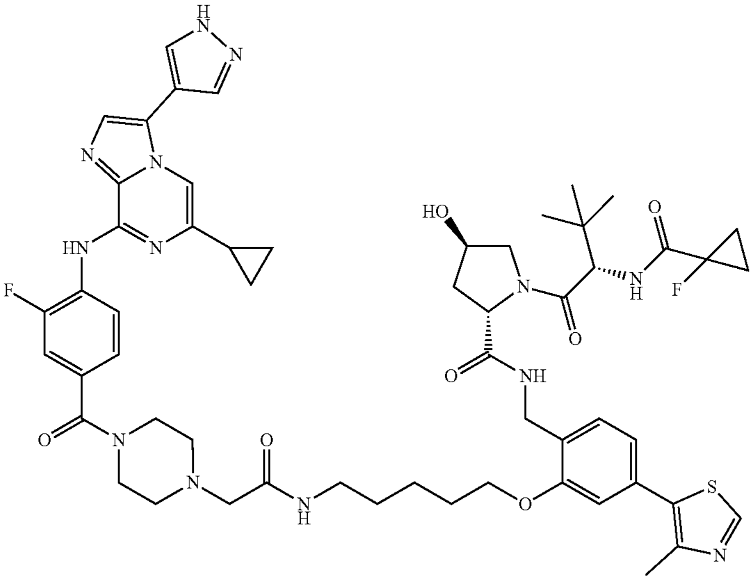 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCNC(=O)CN2CCN(C(=O)c3ccc(Nc4nc(C5CC5)cn5c(-c6cn[nH]c6)cnc45)c(F)c3)CC2)c1]
274
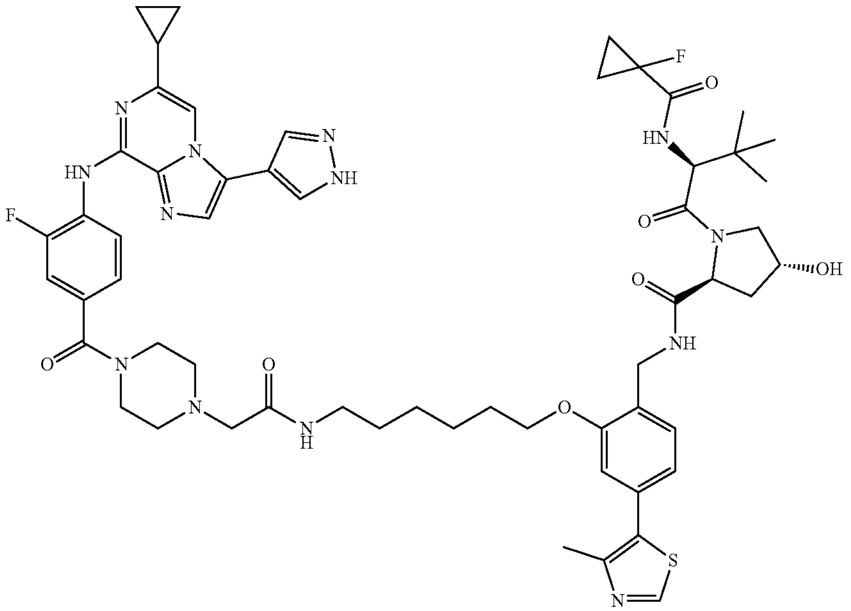 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCNC(=O)CN2CCN(C(=O)c3ccc(Nc4nc(C5CC5)cn5c(-c6cn[nH]c6)cnc45)c(F)c3)CC2)c1]

TABLE 1-continued
275
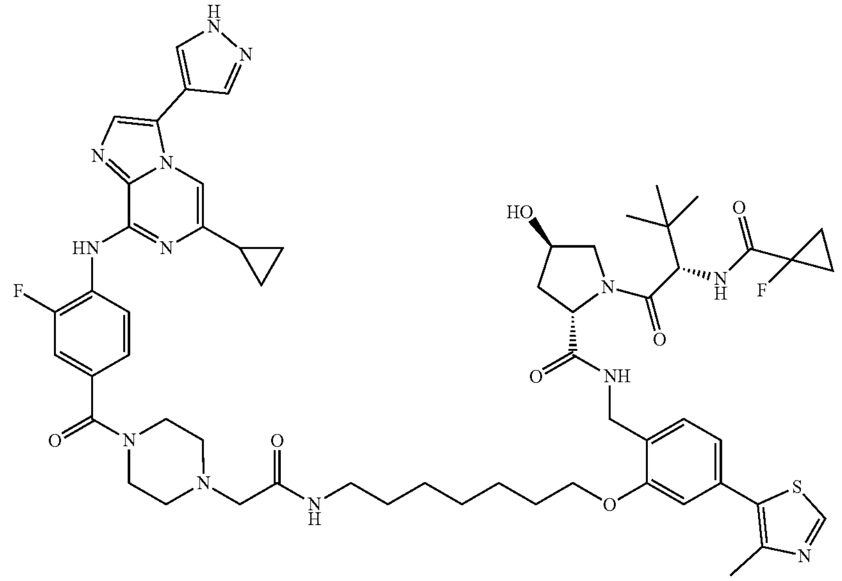 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCNC(=O)CN2CCN(C(=O)c3ccc(Nc4nc(C5CC5)cn5c(-c6cn[nH]c6)cnc45)c(F)c3)CC2)c1]
276
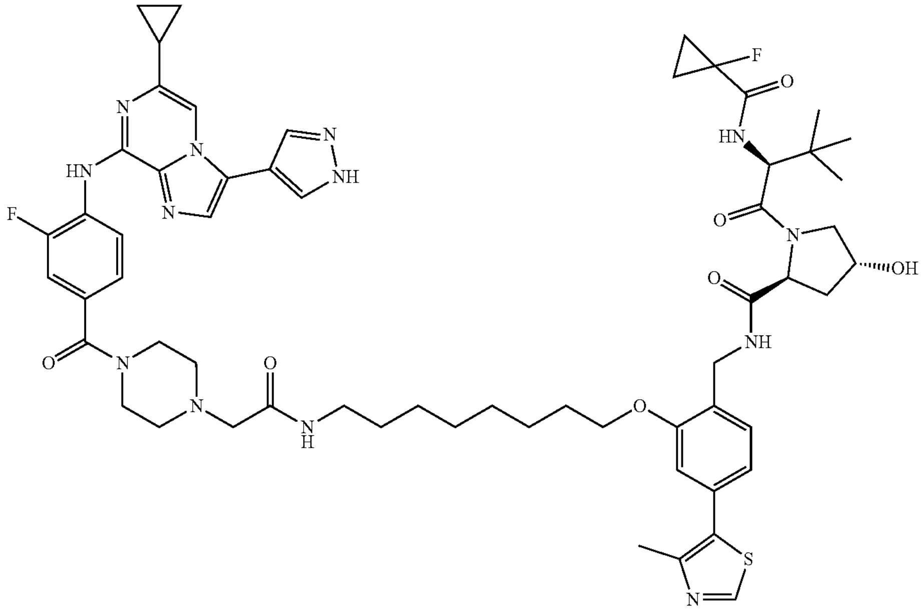 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCCNC(=O)CN2CCN(C(=O)c3ccc(Nc4nc(C5CC5)cn5c(-c6cn[nH]c6)cnc45)c(F)c3)CC2)c1]

TABLE 1-continued
277
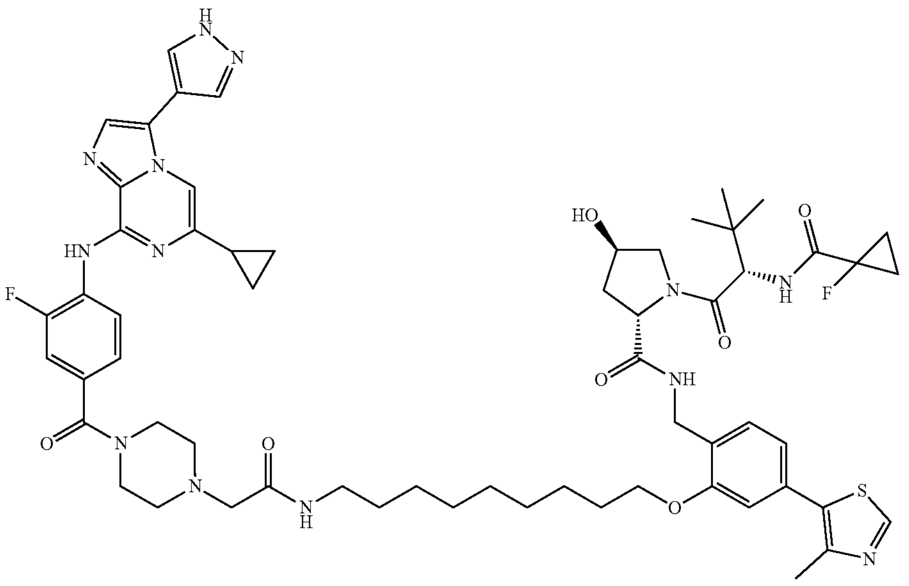 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCCCNC(=O)CN2CCN(C(=O)c3ccc(Nc4nc(C5CC5)cn5c(-c6cn[nH]c6)cnc45)c(F)c3)CC2)c1]
278
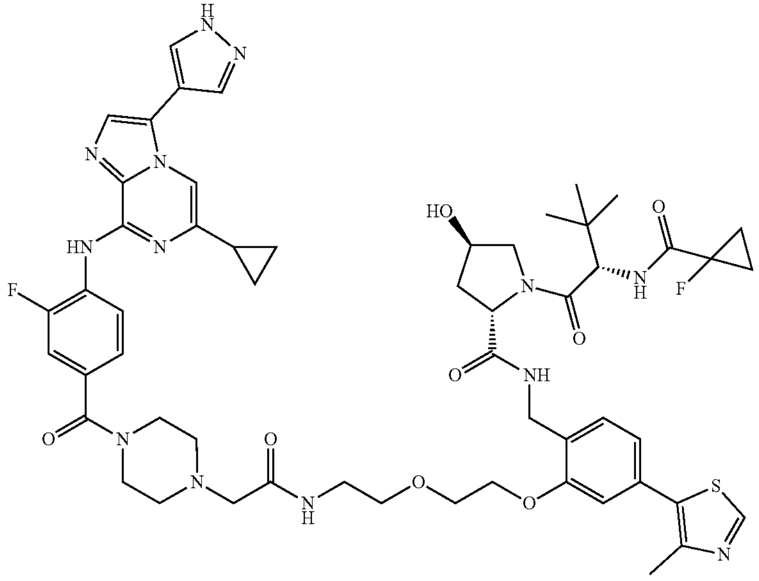

TABLE 1-continued

279

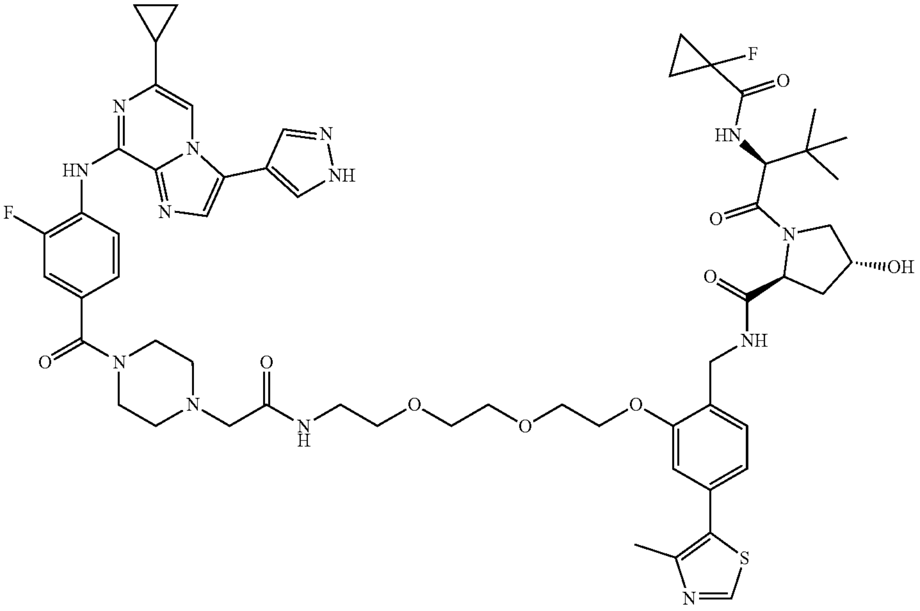 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCNC(=O)CN2CCN(C(=O)c3ccc(Nc4nc(C5CC5)cn5c(-c6cn[nH]c6)cnc45)c(F)c3)CC2)c1]

280

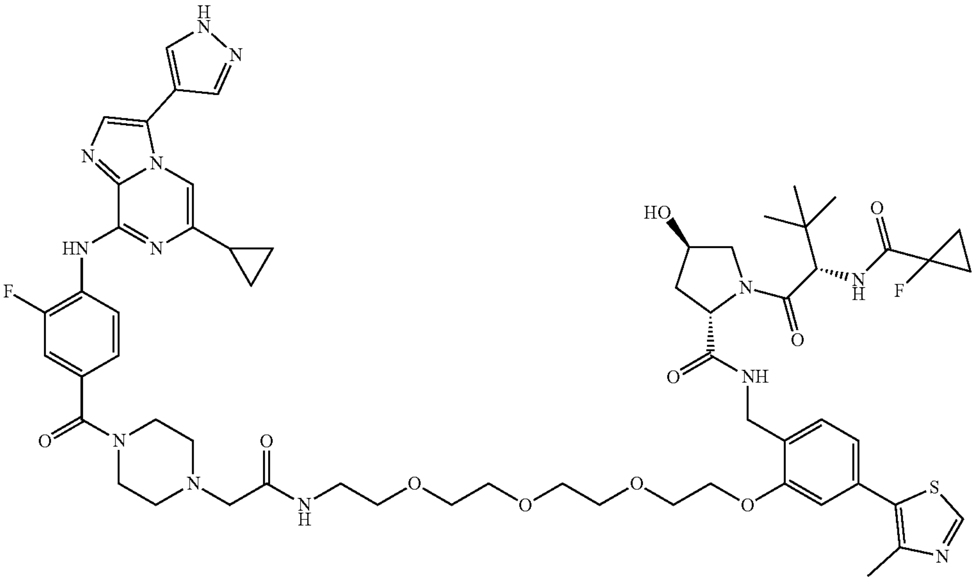 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCNC(=O)CN2CCN(C(=O)c3ccc(Nc4nc(C5CC5)cn5c(-c6cn[nH]c6)cnc45)c(F)c3)CC2)c1]

| Cpd. Example Number | Chemical Name |
|---|---|
| 1 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(2-((2-(2,6-dioxopiperidin-3-yl)-1,3-dioxoisoindolin-4-yl)amino)ethyl)acetamide |
| 2 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(3-((2-(2,6-dioxopiperidin-3-yl)-1,3-dioxoisoindolin-4-yl)amino)propyl)acetamide |
| 3 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(4-((2-(2,6-dioxopiperidin-3-yl)-1,3-dioxoisoindolin-4-yl)amino)butyl)acetamide |
| 4 | 2-(4-(4-((6-cyclopropyl-3-(1H-pyrazol-4-yl)imidazo[1,2-a]pyrazin-8-yl)amino)-3-fluorobenzyl)piperazin-1-yl)-N-(5-((2-(2,6-dioxopiperidin-3-yl)-1,3-dioxoisoindolin-4-yl)amino)pentyl)acetamide |
| 5 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(6-((2-(2,6-dioxopiperidin-3-yl)-1,3-dioxoisoindolin-4-yl)amino)hexyl)acetamide |
| 6 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(7-((2-(2,6-dioxopiperidin-3-yl)-1,3-dioxoisoindolin-4-yl)amino)heptyl)acetamide |
| 7 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(8-((2-(2,6-dioxopiperidin-3-yl)-1,3-dioxoisoindolin-4-yl)amino)octyl)acetamide |
| 8 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(2-(2-((2-(2,6-dioxopiperidin-3-yl)-1,3-dioxoisoindolin-4-yl)amino)ethoxy)ethyl)acetamide |

TABLE 1-continued

| | |
|---|---|
| 9 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(2-(2-(2-((2-(2,6-dioxopiperidin-3-yl)-1,3-dioxoisoindolin-4-yl)amino)ethoxy)ethoxy)ethyl)acetamide |
| 10 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(2-(2-(2-(2-((2-(2,6-dioxopiperidin-3-yl)-1,3-dioxoisoindolin-4-yl)amino)ethoxy)ethoxy)ethoxy)ethyl)acetamide |
| 11 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(14-((2-(2,6-dioxopiperidin-3-yl)-1,3-dioxoisoindolin-4-yl)amino)-3,6,9,12-tetraoxatetradecyl)acetamide |
| 12 | 2-(4-(4-((6-cyclopropyl-3-(1H-pyrazol-4-yl)imidazo[1,2-a]pyrazin-8-yl)amino)-3-fluorobenzoyl)piperazin-1-yl)-N-(17-((2-(2,6-dioxopiperidin-3-yl)-1,3-dioxoisoindolin-4-yl)amino)-3,6,9,12,15-pentaoxaheptadecyl)acetamide |
| 13 | (2S,4R)-1-((S)-2-(5-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)pentanamido)-3,3-dimethylbutanoyl)-4-hydroxy-N-(4-(4-methylthiazol-5-yl)benzyl)pyrrolidine-2-carboxamide |
| 14 | (2S,4R)-1-((S)-2-(6-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)hexanamido)-3,3-dimethylbutanoyl)-4-hydroxy-N-(4-(4-methylthiazol-5-yl)benzyl)pyrrolidine-2-carboxamide |
| 15 | (2S,4R)-1-((S)-2-(7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-4-hydroxy-N-(4-(4-methylthiazol-5-yl)benzyl)pyrrolidine-2-carboxamide |
| 16 | (2S,4R)-1-((S)-2-(8-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)octanamido)-3,3-dimethylbutanoyl)-4-hydroxy-N-(4-(4-methylthiazol-5-yl)benzyl)pyrrolidine-2-carboxamide |
| 17 | (2S,4R)-1-((S)-2-(9-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)nonanamido)-3,3-dimethylbutanoyl)-4-hydroxy-N-(4-(4-methylthiazol-5-yl)benzyl)pyrrolidine-2-carboxamide |
| 18 | (2S,4R)-1-((S)-2-(10-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)decanamido)-3,3-dimethylbutanoyl)-4-hydroxy-N-(4-(4-methylthiazol-5-yl)benzyl)pyrrolidine-2-carboxamide |
| 19 | (2S,4R)-1-((S)-2-(11-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)undecanamido)-3,3-dimethylbutanoyl)-4-hydroxy-N-(4-(4-methylthiazol-5-yl)benzyl)pyrrolidine-2-carboxamide |
| 20 | (2S,4R)-1-((S)-2-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)acetamido)-3,3-dimethylbutanoyl)-4-hydroxy-N-(4-(4-methylthiazol-5-yl)benzyl)pyrrolidine-2-carboxamide |
| 21 | (2S,4R)-1-((S)-2-(tert-butyl)-14-(4-(4-((6-cyclopropyl-3-(1H-pyrazol-4-yl)imidazo[1,2-a]pyrazin-8-yl)amino)-3-fluorobenzoyl)piperazin-1-yl)-4,13-dioxo-6,9-dioxa-3,12-diazatetradecanoyl)-4-hydroxy-N-(4-(4-methylthiazol-5-yl)benzyl)pyrrolidine-2-carboxamide |
| 22 | (2S,4R)-1-((S)-2-(tert-butyl)-20-(4-(4-((6-cyclopropyl-3-(1H-pyrazol-4-yl)imidazo[1,2-a]pyrazin-8-yl)amino)-3-fluorobenzoyl)piperazin-1-yl)-4,19-dioxo-6,9,12,15-tetraoxa-3,18-diazaicosanoyl)-4-hydroxy-N-(4-(4-methylthiazol-5-yl)benzyl)pyrrolidine 2-carboxamide |
| 23 | (2S,4R)-1-((S)-2-(8-(4-(4-((6-cyclopropyl-3-(1H-pyrazol-4-yl)imidazo[1,2-a]pyrazin-8-yl)amino)-3-fluorobenzoyl)piperazin-1-yl)octanamido)-3,3-dimethylbutanoyl)-4-hydroxy-N-(4-(4-methylthiazol-5-yl)benzyl)pyrrolidine-2-carboxamide |
| 24 | (2S,4R)-1-((S)-2-(9-(4-(4-((6-cyclopropyl-3-(1H-pyrazol-4-yl)imidazo[1,2-a]pyrazin-8-yl)amino)-3-fluorobenzoyl)piperazin-1-yl)nonanamido)-3,3-dimethylbutanoyl)-4-hydroxy-N-(4-(4-methylthiazol-5-yl)benzyl)pyrrolidine-2-carboxamide |
| 25 | (2S,4R)-1-((S)-2-(10-(4-(4-((6-cyclopropyl-3-(1H-pyrazol-4-yl)imidazo[1,2-a]pyrazin-8-yl)amino)-3-fluorobenzoyl)piperazin-1-yl)decanamido)-3,3-dimethylbutanoyl)-4-hydroxy-N-(4-(4-methylthiazol-5-yl)benzyl)pyrrolidine-2-carboxamide |
| 26 | (2S,4R)-1-((S)-2-(11-(4-(4-((6-cyclopropyl-3-(1H-pyrazol-4-yl)imidazo[1,2-a]pyrazin-8-yl)amino)-3-fluorobenzoyl)piperazin-1-yl)undecanamido)-3,3-dimethylbutanoyl)-4-hydroxy-N-(4-(4-methylthiazol-5-yl)benzyl)pyrrolidine-2-carboxamide |
| 27 | (2S,4R)-1-((S)-2-(12-(4-(4-((6-cyclopropyl-3-(1H-pyrazol-4-yl)imidazo[1,2-a]pyrazin-8-yl)amino)-3-fluorobenzoyl)piperazin-1-yl)dodecanamido)-3,3-dimethylbutanoyl)-4-hydroxy-N-(4-(4-methylthiazol-5-yl)benzyl)pyrrolidine-2-carboxamide |
| 28 | (2S,4R)-1-((S)-2-(10-(4-(4-((6-cyclopropyl-3-(1H-pyrazol-4-yl)imidazo[1,2-a]pyrazin-8-yl)amino)-3-fluorobenzoyl)piperazin-1-yl)-10-oxodecanamido)-3,3-dimethylbutanoyl)-4-hydroxy-N-(4-(4-methylthiazol-5-yl)benzyl)pyrrolidine-2-carboxamide |
| 29 | (2S,4R)-1-((S)-2-(11-(4-(4-((6-cyclopropyl-3-(1H-pyrazol-4-yl)imidazo[1,2-a]pyrazin-8-yl)amino)-3-fluorobenzoyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |
| 30 | (2S,4R)-1-((S)-2-(12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-4-hydroxy-N-(4-(4-methylthiazol-5-yl)benzyl)pyrrolidine-2-carboxamide |
| 31 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^7$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |
| 32 | (2S,4R)-1-((S)-2-(13-(4-(4-((6-cyclopropyl-3-(1H-pyrazol-4-yl)imidazo[1,2-a]pyrazin-8-yl)amino)-3-fluorobenzoyl)piperazin-1-yl)-13-oxotridecanamido)-3,3-dimethylbutanoyl)-4-hydroxy-N-(4-(4-methylthiazol-5-yl)benzyl)pyrrolidine-2-carboxamide |
| 33 | (2S,4R)-1-((S)-2-(14-(4-(4-((6-cyclopropyl-3-(1H-pyrazol-4-yl)imidazo[1,2-a]pyrazin-8-yl)amino)-3-fluorobenzoyl)piperazin-1-yl)-14-oxotetradecanamido)-3,3-dimethylbutanoyl)-4-hydroxy-N-(4-(4-methylthiazol-5-yl)benzyl)pyrrolidine-2-carboxamide |
| 34 | (2S,4R)-1-((S)-2-(12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-4-hydroxy-N-((S)-1-(4-(4-methylthiazol-5-yl)phenyl)ethyl)pyrrolidine-2-carboxamide |
| 35 | (2S,4S)-1-((S)-2-(12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-4-hydroxy-N-(4-(4-methylthiazol-5-yl)benzyl)pyrrolidine-2-carboxamide |
| 36 | (2R,4S)-1-((S)-2-(12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-4-hydroxy-N-((S)-1-(4-(4-methylthiazol-5-yl)phenyl)ethyl)pyrrolidine-2-carboxamide |
| 37 | (2S,4R)-1-((S)-2-(7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-4-hydroxy-N-((S)-1-(4-(4-methylthiazol-5-yl)phenyl)ethyl)pyrrolidine-2-carboxamide |
| 38 | (2S,4R)-1-((S)-2-(9-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)nonanamido)-3,3-dimethylbutanoyl)-4-hydroxy-N-((S)-1-(4-(4-methylthiazol-5-yl)phenyl)ethyl)pyrrolidine-2-carboxamide |
| 39 | (2S,4R)-1-((S)-2-(tert-butyl)-17-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-6,9,12-trioxa-3,15-diazaheptadecanoyl)-4-hydroxy-N-((S)-1-(4-(4-methylthiazol-5-yl)phenyl)ethyl)pyrrolidine-2-carboxamide |
| 40 | (2R,4S)-1-((S)-2-(7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-4-hydroxy-N-(4-(4-methylthiazol-5-yl)benzyl)pyrrolidine-2-carboxamide |
| 41 | (2R,4S)-1-((S)-2-(9-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)nonanamido)-3,3-dimethylbutanoyl)-4-hydroxy-N-(4-(4-methylthiazol-5-yl)benzyl)pyrrolidine-2-carboxamide |
| 42 | (2R,4S)-1-((S)-2-(tert-butyl)-17-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide |
| 43 | (2S,4R)-1-((S)-2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)acetamido)-3,3-dimethylbutanoyl)-4-hydroxy-N-(4-(4-methylthiazol-5-yl)benzyl)pyrrolidine-2-carboxamide |
| 44 | (2S,4R)-1-((S)-2-(3-(2-(4-(4-((6-cyclopropyl-3-(1H-pyrazol-4-yl)imidazo[1,2-a]pyrazin-8-yl)amino)-3-fluorobenzyl)piperazin-1-yl)acetamido)propanamido)-3,3-dimethylbutanoyl)-4-hydroxy-N-(4-(4-methylthiazol-5-yl)benzyl)pyrrolidine-2-carboxamide |

TABLE 1-continued

| | |
|---|---|
| 45 | (2S,4R)-1-((S)-2-(4-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)butanamido)-3,3-dimethylbutanoyl)-4-hydroxy-N-(4-(4-methylthiazol-5-yl)benzyl)pyrrolidine-2-carboxamide |
| 46 | (2S,4R)-1-((S)-2-(4-(4-(4-((6-cyclopropyl-3-(1H-pyrazol-4-yl)imidazo[1,2-a]pyrazin-8-yl)amino)-3-fluorobenzoyl)piperazin-1-yl)-4-oxobutanamido)-3,3-dimethylbutanoyl)-4-hydroxy-N-(4-(4-methylthiazol-5-yl)benzyl)pyrrolidine-2-carboxamide |
| 47 | (2S,4R)-1-((S)-2-(5-(4-(4-((6-cyclopropyl-3-(1H-pyrazol-4-yl)imidazo[1,2-a]pyrazin-8-yl)amino)-3-fluorobenzoyl)piperazin-1-yl)-5-oxopentanamido)-3,3-dimethylbutanoyl)-4-hydroxy-N-(4-(4-methylthiazol-5-yl)benzyl)pyrrolidine-2-carboxamide |
| 48 | (2S,4R)-1-((S)-2-(6-(4-(4-((6-cyclopropyl-3-(1H-pyrazol-4-yl)imidazo[1,2-a]pyrazin-8-yl)amino)-3-fluorobenzoyl)piperazin-1-yl)-6-oxohexanamido)-3,3-dimethylbutanoyl)-4-hydroxy-N-(4-(4-methylthiazol-5-yl)benzyl)pyrrolidine-2-carboxamide |
| 49 | (2S,4R)-1-((S)-2-(7-(4-(4-((6-cyclopropyl-3-(1H-pyrazol-4-yl)imidazo[1,2-a]pyrazin-8-yl)amino)-3-fluorobenzoyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| 50 | (2S,4R)-1-((S)-2-(8-(4-(4-((6-cyclopropyl-3-(1H-pyrazol-4-yl)imidazo[1,2-a]pyrazin-8-yl)amino)-3-fluorobenzoyl)piperazin-1-yl)-8-oxooctanamido)-3,3-dimethylbutanoyl)-4-hydroxy-N-(4-(4-methylthiazol-5-yl)benzyl)pyrrolidine-2-carboxamide |
| 51 | (2S,4R)-1-((S)-2-(9-(4-(4-((6-cyclopropyl-3-(1H-pyrazol-4-yl)imidazo[1,2-a]pyrazin-8-yl)amino)-3-fluorobenzoyl)piperazin-1-yl)-9-oxononanamido)-3,3-dimethylbutanoyl)-4-hydroxy-N-(4-(4-methylthiazol-5-yl)benzyl)pyrrolidine-2-carboxamide |
| 52 | (2S,4R)-1-((S)-2-(3-(3-(4-(4-((6-cyclopropyl-3-(1H-pyrazol-4-yl)imidazo[1,2-a]pyrazin-8-yl)amino)-3-fluorobenzoyl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide |
| 53 | (2S,4R)-1-((S)-2-(3-(2-(3-(4-(4-((6-cyclopropyl-3-(1H-pyrazol-4-yl)imidazo[1,2-a]pyrazin-8-yl)amino)-3-fluorobenzoyl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |
| 54 | (2S,4R)-1-((S)-2-(tert-butyl)-16-(4-(4-((6-cyclopropyl-3-(1H-pyrazol-4-yl)imidazo[1,2-a]pyrazin-8-yl)amino)-3-fluorobenzoyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |
| 55 | (2S,4R)-1-((S)-2-(tert-butyl)-19-(4-(4-((6-cyclopropyl-3-(1H-pyrazol-4-yl)imidazo[1,2-a]pyrazin-8-yl)amino)-3-fluorobenzoyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |
| 56 | (2S,4R)-1-((S)-2-(tert-butyl)-22-(4-(4-((6-cyclopropyl-3-(1H-pyrazol-4-yl)imidazo[1,2-a]pyrazin-8-yl)amino)-3-fluorobenzoyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |
| 57 | 4-((2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethyl)amino)-2-(2,6-dioxopiperidin-3-yl)isoindoline-1,3-dione |
| 58 | 4-((3-(4-(4-((6-cyclopropyl-3-(1H-pyrazol-4-yl)imidazo[1,2-a]pyrazin-8-yl)amino)-3-fluorobenzoyl)piperazin-1-yl)-3-oxopropyl)amino)-2-(2,6-dioxopiperidin-3-yl)isoindoline-1,3-dione |
| 59 | 4-((4-(4-(4-((6-cyclopropyl-3-(1H-pyrazol-4-yl)imidazo[1,2-a]pyrazin-8-yl)amino)-3-fluorobenzyl)piperazin-1-yl)-4-oxobutyl)amino)-2-(2,6-dioxopiperidin-3-yl)isoindoline-1,3-dione |
| 60 | 4-((5-(4-(4-((6-cyclopropyl-3-(1H-pyrazol-4-yl)imidazo[1,2-a]pyrazin-8-yl)amino)-3-fluorobenzoyl)piperazin-1-yl)-5-oxopentyl)amino)-2-(2,6-dioxopiperidin-3-yl)isoindoline-1,3-dione |
| 61 | 4-((6-(4-(4-((6-cyclopropyl-3-(1H-pyrazol-4-yl)imidazo[1,2-a]pyrazin-8-yl)amino)-3-fluorobenzoyl)piperazin-1-yl)-6-oxohexyl)amino)-2-(2,6-dioxopiperidin-3-yl)isoindoline-1,3-dione |
| 62 | 4-((7-(4-(4-((6-cyclopropyl-3-(1H-pyrazol-4-yl)imidazo[1,2-a]pyrazin-8-yl)amino)-3-fluorobenzoyl)piperazin-1-yl)-7-oxoheptyl)amino)-2-(2,6-dioxopiperidin-3-yl)isoindoline-1,3-dione |
| 63 | (2S,4S)-1-((S)-2-(7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptanamido)-3,3-dimethylbutanoyl)-4-hydroxy-N-((S)-1-(4-(4-methylthiazol-5-yl)phenyl)ethyl)pyrrolidine-2-carboxamide |
| 64 | (2R,4S)-1-((S)-2-(9-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)nonanamido)-3,3-dimethylbutanoyl)-4-hydroxy-N-((S)-1-(4-(4-methylthiazol-5-yl)phenyl)ethyl)pyrrolidine-2-carboxamide |
| 65 | 4-((8-(4-(4-((6-cyclopropyl-3-(1H-pyrazol-4-yl)imidazo[1,2-a]pyrazin-8-yl)amino)-3-fluorobenzoyl)piperazin-1-yl)-8-oxooctyl)amino)-2-(2,6-dioxopiperidin-3-yl)isoindoline-1,3-dione |
| 66 | 4-((2-(3-(4-(4-((6-cyclopropyl-3-(1H-pyrazol-4-yl)imidazo[1,2-a]pyrazin-8-yl)amino)-3-fluorobenzoyl)piperazin-1-yl)-3-oxopropoxy)ethyl)amino)-2-(2,6-dioxopiperidin-3-yl)isoindoline-1,3-dione |
| 67 | 4-((2-(2-(3-(4-(4-((6-cyclopropyl-3-(1H-pyrazol-4-yl)imidazo[1,2-a]pyrazin-8-yl)amino)-3-fluorobenzoyl)piperazin-1-yl)-3-oxopropoxy)ethoxy)ethyl)amino)-2-(2,6-dioxopiperidin-3-yl)isoindoline-1,3-dione |
| 68 | 4-((2-(2-(2-(3-(4-(4-((6-cyclopropyl-3-(1H-pyrazol-4-yl)imidazo[1,2-a]pyrazin-8-yl)amino)-3-fluorobenzoyl)piperazin-1-yl)-3-oxopropoxy)ethoxy)ethoxy)ethyl)amino)-2-(2,6-dioxopiperidin-3-yl)isoindoline-1,3-dione |
| 69 | 4-((15-(4-(4-((6-cyclopropyl-3-(1H-pyrazol-4-yl)imidazo[1,2-a]pyrazin-8-yl)amino)-3-fluorobenzoyl)piperazin-1-yl)-15-oxo-3,6,9,12-tetraoxapentadecyl)amino)-2-(2,6-dioxopiperidin-3-yl)isoindoline-1,3-dione |
| 70 | 4-((18-(4-(4-((6-cyclopropyl-3-(1H-pyrazol-4-yl)imidazo[1,2-a]pyrazin-8-yl)amino)-3-fluorobenzoyl)piperazin-1-yl)-18-oxo-3,6,9,12,15-pentaoxaoctadecyl)amino)-2-(2,6-dioxopiperidin-3-yl)isoindoline-1,3-dione |
| 71 | (2S,4R)-1-((S)-2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide |
| 72 | (2S,4R)-1-((S)-2-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
| 73 | (2S,4R)-1-((S)-2-(tert-butyl)-14-(4-(4-((6-cyclopropyl-3-(1H-pyrazol-4-yl)imidazo[1,2-a]pyrazin-8-yl)amino)-3-fluorobenzoyl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide |
| 74 | (2S,4R)-1-((S)-2-(tert-butyl)-20-(4-(4-((6-cyclopropyl-3-(1H-pyrazol-4-yl)imidazo[1,2-a]pyrazin-8-yl)amino)-3-fluorobenzoyl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide |
| 75 | $N^1$-(2-(4-(4-((6-cyclopropyl-3-(1H-pyrazol-4-yl)imidazo[1,2-a]pyrazin-8-yl)amino)-3-fluorobenzyl)piperazin-1-yl)ethyl)-$N^4$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |
| 76 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^5$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |
| 77 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^6$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |
| 78 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^8$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |
| 79 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^9$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |

TABLE 1-continued

| | |
|---|---|
| 80 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^{10}$-((S)-1-((2S,4R)-4-hydroxy-2-((4-(4-methylthiazol-5-yl)benzyl)carbamoyl)pyrrolidin-1-yl)-3,3-diimethyl-1-oxobutan-2-yl) decanediamide |
| 81 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^{11}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| 82 | (2S,4R)-1-((S)-2-(2-(2-((2-(4-(4-((6-cyclopropyl-3-(1H-pyrazol-4-yl)imidazo[1,2-a]pyrazin-8-yl)amino)-3-fluorobenzoyl)piperazin-1-yl)ethyl)amino)-2-oxoethoxy)acetamido)-3,3-dimethybutanoyl)-4-hydroxy-N-(4-(4-methylthiazol-5-yl)benzyl)pyrrolidine-2-carboxamide |
| 83 | (2S,4R)-1-((S)-2-(3-(3-((2-(4-(4-((6-cyclopropyl-3-(1H-pyrazol-4-yl)imidazo[1,2-a]pyrazin-8-yl)amino)-3-fluorobenzoyl) piperazin-1-yl)ethyl)amino)-3-oxopropoxy)propanamido)-3,3-dimethylbutanoyl)-4-hydroxy-N-(4-(4-methylthiazol-5-yl)benzyl) pyrrolidine-2-carboxamide |
| 84 | (2S,4R)-1-((S)-2-(tert-butyl)-14-(4-(4-((6-cyclopropyl-3-(1H-pyrazol-4-yl)imidazo[1,2-a]pyrazin-8-yl)amino)-3-fluorobenzoyl) piperazin-1-yl)-4,11-dioxo-6,9-dioxa-3,12-diazatetradecanoyl)-4-hydroxy-N-(4-(4-methylthiazol-5-yl)benzyl)pyrrolidine-2-carboxamide |
| 85 | (2S,4R)-1-((S)-2-(tert-butyl)-16-(4-(4-((6-cyclopropyl-3-(1H-pyrazol-4-yl)imidazo[1,2-a]pyrazin-8-yl)amino-3-fluorobenzoyl) piperazin-1-yl)-4,13-dioxo-7,10-dioxa-3,14-diazahexadecanoyl)-4-hydroxy-N-(4-(4-methylthiazol-5-yl)benzyl)pyrrolidine-2-carboxamide |
| 86 | (2S,4R)-1-((S)-2-(tert-butyl)-17-(4-(4-((6-cyclopropyl-3-(1H-pyrazol-4-yl)imidazo[1,2-a]pyrazin-8-yl)amino)-3-fluorobenzoyl) piperazin-1-yl)-4,14-dioxo-6,9,12-trioxa-3,15-diazaheptadecanoyl)-4-hydroxy-N-(4-(4-methylthiazol-5-yl)benzyl)pyrrolidine-2-carboxamide |
| 87 | (2S,4R)-1-((S)-2-(tert-butyl)-19-(4-(4-((6-cyclopropyl-3-(1H-pyrazol-4-yl)imidazo[1,2-a]pyrazin-8-yl)amino)-3-fluorobenzoyl) piperazin-1-yl)-4,16-dioxo-7,10,13-trioxa-3,17-diazanonadecanoyl)-4-hydroxy-N-(4-(4-methylthiazol-5-yl)benzyl)pyrrolidine-2-carboxamide |
| 88 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^{16}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide |
| 89 | $N^1$-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-$N^{19}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| 90 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-2-((2-(2,6-dioxopiperidin-3-yl)-1,3-dioxoisoindolin-4-yl)amino)acetamide |
| 91 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)piperazin-1-yl)ethyl)-3-((2-(2,6-dioxopiperidin-3-yl)-1,3-dioxoisoindolin-4-yl)amino)propanamide |
| 92 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-4-((2-(2,6-dioxopiperidin-3-yl)-1,3-dioxoisoindolin-4-yl)amino)butanamide |
| 93 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-5-((2-(2,6-dioxopiperidin-3-yl)-1,3-dioxoisoindolin-4-yl)amino)pentanamide |
| 94 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-6-((2-(2,6-dioxopiperidin-3-yl)-1,3-dioxoisoindolin-4-yl)amino)hexanamide |
| 95 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-7-((2-(2,6-dioxopiperidin-3-yl)-1,3-dioxoisoindolin-4-yl)amino)heptanamide |
| 96 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-8-((2-(2,6-dioxopiperidin-3-yl)-1,3-dioxoisoindolin-4-yl)amino)octanamide |
| 97 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-3-(2-((2-(2,6-dioxopiperidin-3-yl)-1,3-dioxoisoindolin-4-yl)amino)ethoxy)propanamide |
| 98 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-3-(2-(2-((2-(2,6-dioxopiperidin-3-yl)-1,3-dioxoisoindolin-4-yl)amino)ethoxy)ethoxy)propanamide |
| 99 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-3-(2-(2-(2-((2-(2,6-dioxopiperidin-3-yl)-1,3-dioxoisoindolin-4-yl)amino)ethoxy)ethoxy)ethoxy)propanamide |
| 100 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-1-((2-(2,6-dioxopiperidin-3-yl)-1,3-dioxoisoindolin-4-yl)amino)-3,6,9,12-tetraoxapentadecan-15-amide |
| 101 | N-(2-(4-(4-((6-cyclopropyl-3-(1H-pyrazol-4-yl)imidazo[1,2-a]pyrazin-8-yl)amino)-3-fluorobenzoyl)piperazin-1-yl)ethyl)-1-((2-(2,6-dioxopiperidin-3-yl)-1,3-dioxoisoindolin-4-yl)amino)-3,6,9,12,15-pentaoxaoctadecan-18-amide |
| 102 | (2S,4R)-1-((S)-2-(4-(4-(2-(4-(4-((6-cyclopropyl-3-(1H-pyrazol-4-yl)imidazo[1,2-a]pyrazin-8-yl)amino)-3-fluorobenozyl)piperazin-1-yl)acetamido)piperidin-1-yl)-4-oxobutanamido)-3,3-dimethylbenzoyl)-4-hydroxy-N-(4-(4-methylthiazol-5-yl)benzyl)pyrrolidine-2-carboxamide |
| 103 | 1'-(2-(4-(4-((6-cyclopropyl-3-(1H-pyrazol-4-yl)imidazo[1,2-a]pyrazin-8-yl)amino)-3-fluorobenzoyl)piperazin-1-yl)acetyl)-N-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-[1,4'-bipiperidine]-4-carboxamide |
| 104 | $N^1$-(1-(2-(4-(4-((6-cyclopropyl-3-(1H-pyrazol-4-yl)imidazo[1,2-a]pyrazin-8-yl)amino)-3-fluorobenzyl)piperazin-1-yl)acetyl) piperidin-4-yl)-$N^4$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |
| 105 | (2S,4R)-1-((R)-2-(5-(4-((2-(4-(4-((6-cyclopropyl-3-(1H-pyrazol-4-yl)imidazo[1,2-a]pyrazin-8-yl)amino)-3-fluorobenzoyl)piperazin-1-yl)acetamido)methyl)-1H-1,2,3-triazol-1-yl)pentanamido)-3,3-dimethylbutanoyl)-4-hydroxy-N-(4-(4-methylthiazol-5-yl)benzyl)pyrrolidine-2-carboxamide |
| 106 | (3R,5S)-1-((R)-2-(7-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)heptanamido)-3,3-dimethylbutanoyl)-5-((4-(4-methylthiazol-5-yl)benzyl)carbamoyl)pyrrolidin-3-yl acetate |
| 107 | (3R,5S)-1-((R)-(7-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)heptanamido)-3,3-dimethylbutanoyl)-5-((4-(4-methylthiazol-5-yl)benzyl)carbamoyl)pyrrolidin-3-yl isobutyrate |
| 108 | (2S,4R)-N-((S)-3-((2-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)ethyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide |
| 109 | (2S,4R)-N-((S)-3-((3-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)propyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide |
| 110 | (2S,4R)-N-((S)-3-((4-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)butyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide |

TABLE 1-continued

| | |
|---|---|
| 111 | (2S,4R)-N-((S)-3-((5-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)pentyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide |
| 112 | (2S,4R)-N-((S)-3-((6-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)hexyl)amino)-1-(4-(4-methylthiazol-5-yl)phenyl)-3-oxopropyl-1-((S)-2-(1-fluorocyclopropane-1-carboxamido)-3,3-dimethylbutanoyl)-4-hydroxypyrrolidine-2-carboxamide |
| 113 | (2S,4R)-N-((S)-3-((7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide |
| 114 | (2S,4R)-N-((S)-3-((2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)ethyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide |
| 115 | (2S,4R)-N-((S)-1-(4-(4-((6-cyclopropyl-3-(1H-pyrazol-4-yl)imidazo[1,2-a]pyrazin-8-yl)amino)-3-fluorobenzoyl)piperazin-1-yl)-15-(4-(4-methylthiazol-5-yl)phenyl)-2,13-dioxo-6,9-dioxa-3,12-diazapentadecan-15-yl)-1-((S)-2-(1-fluorocyclopropane-1-carboxamido)-3,3-dimethylbutanoyl)-4-hydroxypyrrolidine-2-carboxamide |
| 116 | (2S,4R)-N-((S)-1-(4-(4-((6-cyclopropyl-3-(1H-pyrazol-4-yl)imidazo[1,2-a]pyrazin-8-yl)amino)-3-fluorobenzoyl)piperazin-1-yl)-18-(4-(4-methylthiazol-5-yl)phenyl)-2,16-dioxo-6,9,12-trioxa-3,15-diazaoctadecan-18-yl)-1-((S)-2-(1-fluorocyclopropane-1-carboxamido)-3,3-dimethylbutanoyl)-4-hydroxypyrrolidine-2-carboxamide |
| 117 | (2S,4R)-N-((S)-1-(4-(4-((6-cyclopropyl-3-(1H-pyrazol-4-yl)imidazo[1,2-a]pyrazin-8-yl)amino)-3-fluorobenzoyl)piperazin-1-yl)-21-(4-(4-methylthiazol-5-yl)phenyl)-2,19-dioxo-6,9,12,15-tetraoxa-3,18-diazahenicosan-21-yl)-1-((S)-2-(1-fluorocyclopropane-1-carboxamido)-3,3-dimethylbutanoyl)-4-hydroxypyrrolidine-2-carboxamide |
| 118 | (2S,4R)-N-((S)-1-(4-(4-((6-cyclopropyl-3-(1H-pyrazol-4-yl)imidazo[1,2-a]pyrazin-8-yl)amino)-3-fluorobenzoyl)piperazin-1-yl)-24-(4-(4-methylthiazol-5-yl)phenyl)-2,22-dioxo-6,9,12,15,18-pentaoxa-3,21-diazatetracosan-24-yl)-1-((S)-2-(1-fluorocyclopropane-1-carboxamido)-3,3-dimethylbutanoyl)-4-hydroxypyrrolidine-2-carboxamide |
| 119 | (2S,4R)-N-((S)-3-((2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide |
| 120 | (2S,4R)-N-((S)-3-((3-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)propyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide |
| 121 | (2S,4R)-N-((S)-3-((4-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)butyl)amino)-1-(4-(4-methylthiazol-5-yl)phenyl)-3-oxopropyl)-4-hydroxy-1-((R)-3-methyl-2-(3-methylisoxazol-5-yl) butanoyl)pyrrolidine-2-carboxamide |
| 122 | (2S,4R)-N-((S)-3-((5-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)pentyl)amino)-1-(4-(4-methylthiazol-5-yl)phenyl)-3-oxopropyl)-4-hydroxy-1-((R)-3-methyl-2-(3-methylisoxazol-5-yl) butanoyl)pyrrolidine-2-carboxamide |
| 123 | (2S,4R)-N-((S)-3-((6-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)hexyl)amino)-1-(4-(4-methylthiazol-5-yl)phenyl)-3-oxopropyl)-4-hydroxy-1-((R)-3-methyl-2-(3-methylisoxazol-5-yl) butanoyl)pyrrolidine-2-carboxamide |
| 124 | (2S,4R)-N-((S)-3-((7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide |
| 125 | (2S,4R)-N-((S)-3-((2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)ethyl)amino)-1-(4-(4-methylthiazol-5-yl)phenyl)-3-oxopropyl)-4-hydroxy-1-((R)-3-methyl-2-(3-methylisoxazol-5-yl)butanoyl)pyrrolidine-2-carboxamide |
| 126 | (2S,4R)-N-((S)-1-(4-(4-((6-cyclopropyl-3-(1H-pyrazol-4-yl)imidazo[1,2-a]pyrazin-8-yl)amino)-3-fluorobenzoyl)piperazin-1-yl)-15-(4-(4-methylthiazol-5-yl)phenyl)-2,13-dioxo-6,9-dioxa-3,12-diazapentadecan-15-yl)-4-hydroxy-1-((R)-3-methyl-2-(3-methylisoxazol-5-yl)butanoyl)pyrrolidine-2-carboxamide |
| 127 | (2S,4R)-N-((S)-1-(4-(4-((6-cyclopropyl-3-(1H-pyrazol-4-yl)imidazo[1,2-a]pyrazin-8-yl)amino)-3-fluorobenzoyl)piperazin-1-yl)-18-(4-(4-methylthiazol-5-yl)phenyl)-2,16-dioxo-6,9,12-trioxa-3,15-diazaoctadecan-18-yl)-4-hydroxy-1-((R)-3-methyl-2-(3-methylisoxazol-5-yl)butanoyl)pyrrolidine-2-carboxamide |
| 128 | (2S,4R)-N-((S)-1-(4-(4-((6-cyclopropyl-3-(1H-pyrazol-4-yl)imidazo[1,2-a]pyrazin-8-yl)amino)-3-fluorobenzoyl)piperazin-1-yl)-21-(4-(4-methylthiazol-5-yl)phenyl)-2,19-dioxo-6,9,12,15-tetraoxa-3,18-diazahenicosan-21-yl)-4-hydroxy-1-((R)-3-methyl-2-(3-methylisoxazol-5-yl)butanoyl)pyrrolidine-2-carboxamide |
| 129 | (2S,4R)-N-((S)-1-(4-(4-((6-cyclopropyl-3-(1H-pyrazol-4-yl)imidazo[1,2-a]pyrazin-8-yl)amino)-3-fluorobenzoyl)piperazin-1-yl)-24-(4-(4-methylthiazol-5-yl)phenyl)-2,22-dioxo-6,9,12,15,18-pentaoxa-3,21-diazatetracosan-24-yl)-4-hydroxy-1-((R)-3-methyl-2-(3-methylisoxazol-5-yl)butanoyl)pyrrolidine-2-carboxamide |
| 130 | (2S,4R)-1-((S)-2-(3-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)propanamido)-3,3-dimethylbutanoyl)-4-hydroxy-N-(4-(4-methylthiazol-5-yl)benzyl)pyrrolidine-2-carboxamide |
| 131 | (2S,4R)-1-((S)-14-(tert-butyl)-1-(4-(4-((6-cyclopropyl-3-(1H-pyrazol-4-yl)imidazo[1,2-a]pyrazin-8-yl)amino)-3-fluorobenzoyl) piperazin-1-yl)-2,12-dioxo-6,9-dioxa-3,13-diazapentadecan-15-oyl)-4-hydroxy-N-(4-(4-methylthiazol-5-yl)benzyl)pyrrolidine-2-carboxamide |
| 132 | (2S,4R)-1-((S)-17-(tert-butyl)-1-(4-(4-((6-cyclopropyl-3-(1H-pyrazol-4-yl)imidazo[1,2-a]pyrazin-8-yl)amino)-3-fluorobenzoyl) piperazin-1-yl)-2,15-dioxo-6,9,12-trioxa-3,16-diazaoctadecan-18-oyl)-4-hydroxy-N-(4-(4-methylthiazol-5-yl)benzyl)pyrrolidine-2-carboxamide |
| 133 | (2S,4R)-1-((S)-23-(tert-butyl)-1-(4-(4-((6-cyclopropyl-3-(1H-pyrazol-4-yl)imidazo[1,2-a]pyrazin-8-yl)amino)-3-fluorobenzoyl) piperazin-1-yl)-2,21-dioxo-6,9,12,15,18-pentaoxa-3,22-diazatetracosan-24-oyl)-4-hydroxy-N-(4-(4-methylthiazol-5-yl)benzyl) pyrrolidine-2-carboxamide |
| 134 | (2S,4R)-1-((S)-2-(tert-butyl)-17-(4-(4-((6-cyclopropyl-3-(1H-pyrazol-4-yl)imidazo[1,2-a]pyrazin-8-yl)amino)-3-fluorobenzoyl) piperazin-1-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide |
| 135 | (2S,4R)-1-((S)-2-(8-(7-(4-((6-cyclopropyl-3-(1H-pyrazol-4-yl)imidazo[1,2-a]pyrazin-8-yl)amino)-3-fluorobenzoyl)-2,7-diazaspiro [3.5]nonan-2-yl)-8-oxooctanamido)-3,3-dimethylbutanoyl)-4-hydroxy-N-(4-(4-methylthiazol-5-yl)benzyl)pyrrolidine-2-carboxamide |
| 136 | (2S,4R)-1-((S)-2-(9-(7-(4-((6-cyclopropyl-3-(1H-pyrazol-4-yl)imidazo[1,2-a]pyrazin-8-yl)amino)-3-fluorobenzoyl)-2,7-diazaspiro [3.5]nonan-2-yl)-9-oxononanamido)-3,3-dimethylbutanoyl)-4-hydroxy-5-yl)benzyl)pyrrolidine-2-carboxamide |
| 137 | 2-(((3R,4R)-3-fluoro-1-(2-(4-(trifluoromethoxy)phenyl)acetyl)piperidin-4-yl)oxy)-5-(1-(4-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-4-oxobutyl)-1H-imidazol-4-yl)nicotinamide |

TABLE 1-continued

| | |
|---|---|
| 138 | 2-(((3R,4R)-3-fluoro-1-(2-(4-(trifluoromethoxy)phenyl)acetyl)piperidin-4-yl)oxy)-5-(1-(4-((2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl)amino)-4-oxobutyl)-1H-imidazol-4-yl)nicotinamide |
| 139 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaheptadecan-17-yl)-1H-imidazol-4-yl)nicotinamide |
| 140 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,15-dioxo-8,11-dioxa-4,14-diazaoctadecan-18-yl)-1H-imidazol-4-yl)nicotinamide |
| 141 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,17-dioxo-7,10,13-trioxa-4,16-diazaicosan-20-yl)-1H-imidazol-4-yl)nicotinamide |
| 142 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,18-dioxo-8,11,14-trioxa-4,17-diazahenicosan-21-yl)-1H-imidazol-4-yl)nicotinamide |
| 143 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,21-dioxo-8,11,14,17-tetraoxa-4,20-diazatetracosan-24-yl)-1H-imidazol-4-yl)nicotinamide |
| 144 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,24-dioxo-8,11,14,17,20-pentaoxa-4,23-diazaheptacosan-27-yl)-1H-imidazol-4-yl)nicotinamide |
| 145 | 2-(((3R,4R)-3-fluoro-1-(2-(4-(trifluoromethoxy)phenyl)acetyl)piperidin-4-yl)oxy)-5-(1-(4-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)amino)-4-oxobutyl)-1H-imidazol-4-yl)nicotinamide |
| 146 | 2-(((3R,4R)-3-fluoro-1-(2-(4-(trifluoromethoxy)phenyl)acetyl)piperidin-4-yl)oxy)-5-(1-(4-((3-(((S)-1-((2S,4R)-4-hydroxy-2-((4-(4-methylthiazol-5-yl)benzyl)carbamooyl)pyrrolidin-1-yl)-3,3-dimethyl-1-oxobutan-2-yl)amino)-3-oxopropyl)amino)-4-oxobutyl)-1H-imidazol-4-yl)nicotinamide |
| 147 | 2-(((3R,4R)-3-fluoro-1-(2-(4-(trifluoromethoxy)phenyl)acetyl)piperidin-4-yl)oxy)-5-(1-(4-((4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)amino)-4-oxobutyl)-1H-imidazol-4-yl)nicotinamide |
| 148 | 2-(((3R,4R)-3-fluoro-1-(2-(4-(trifluoromethoxy)phenyl)acetyl)piperidin-4-yl)oxy)-5-(1-(4-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-4-oxobutyl)-1H-imidazol-4-yl)nicotinamide |
| 149 | 2-(((3R,4R)-3-fluoro-1-(2-(4-(trifluoromethoxy)phenyl)acetyl)piperidin-4-yl)oxy)-5-(1-(4-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)amino)-4-oxobutyl)-1H-imidazol-4-yl)nicotinamide |
| 150 | 5-(1-(4-((2-(2-((2-(2,6-dioxopiperidin-3-yl)-1,3-dioxoisoindolin-4-yl)amino)ethoxy)ethyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide |
| 151 | 5-(1-(4-((2-(2-(2-((2-(2,6-dioxopiperidin-3-yl)-1,3-dioxoisoindolin-4-yl)amino)ethoxy)ethoxy)ethyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide |
| 152 | 5-(1-(1-((2-(2,6-dioxopiperidin-3-yl)-1,3-dioxoisoindolin-4-yl)amino)-13-oxo-3,6,9-trioxa-12-azahexadecan-16-yl)-1H-imidazol-4-yl)-2-(((3R,4R)-3-fluoro-1-(2-(4-(trifluoromethoxy)phenyl)acetyl)piperidin-4-yl)oxy)nicotinamide |
| 153 | 5-(1-(1-((2-(2,6-dioxopiperidin-3-yl)-1,3-dioxoisoindolin-4-yl)amino)-19-oxo-3,6,9,12,15-pentaoxa-18-azadocosan-22-yl)-1H-imidazol-4-yl)-2-(((3R,4R)-3-fluoro-1-(2-(4-(trifluoromethoxy)phenyl)acetyl)piperidin-4-yl)oxy)nicotinamide |
| 154 | 5-(1-(4-((2-((2-(2,6-dioxopiperidin-3-yl)-1,3-dioxoisoindolin-4-yl)amino)ethyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)benzamide |
| 155 | 5-(1-(4-((3-((2-(2,6-dioxopiperidin-3-yl)-1,3-dioxoisoindolin-4-yl)amino)propyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide |
| 156 | 5-(1-(4-((4-((2-(2,6-dioxopiperidin-3-yl)-1,3-dioxoisoindolin-4-yl)amino)butyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide |
| 157 | 5-(1-(4-((5-((2-(2,6-dioxopiperidin-3-yl)-1,3-dioxoisoindolin-4-yl)amino)pentyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide |
| 158 | 5-(1-(4-((6-((2-(2,6-dioxopiperidin-3-yl)-1,3-dioxoisoindolin-4-yl)amino)hexyl)amino)-4-oxobutyl)-1H-imdiazol-4-yl)-2-(((3R,4R)-3-fluoro-1-(2-(4-(trifluoromethoxy)phenyl)acetyl)piperidin-4-yl)oxy)nicotinamide |
| 159 | 5-(1-(4-((7-((2-(2,6-dioxopiperidin-3-yl)-1,3-dioxoisoindolin-4-yl)amino)heptyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide |
| 160 | 5-(1-(4-((8-((2-(2,6-dioxopiperidin-3-yl)-1,3-dioxoisoindolin-4-yl)amino)octyl)amino)-4-oxobutyl)-1H-imidazol-4-yl)-2-(((3R,4R)-3-fluoro-1-(2-(4-(trifluoromethoxy)phenyl)acetyl)piperidin-4-yl)oxy)nicotinamide |
| 161 | 2-(((3R,4R)-3-fluoro-1-(2-(4-(trifluoromethoxy)phenyl)acetyl)piperidin-4-yl)oxy)-5-(1-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetamido)butyl)-1H-imidazol-4-yl)nicotinamide |
| 162 | 2-(((3R,4R)-3-fluoro-1-(2-(4-(trifluoromethoxy)phenyl)acetyl)piperidin-4-yl)oxy)-5-(1-(4-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxopropoxy)propanamido)butyl)-1H-imidazol-4-yl)nicotinamide |
| 163 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,12-dioxo-7,10-dioxa-4,13-diazaheptadecan-17-yl)-1H-imidazol-4-yl)nicotinamide |
| 164 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,14-dioxo-8,11-dioxa-4,15-diazanonadecan-19-yl)-1H-imidazol-4-yl)nicotinamide |
| 165 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,15-dioxo-7,10,13-trioxa-4,16-diazaicosan-20-yl)-1H-imidazol-4-yl)nicotinamide |
| 166 | 2-(((3R,4R)-3-fluoro-1-(2-(4-(trifluoromethoxy)phenyl)acetyl)piperidin-4-yl)oxy)-5-(1-((S)-3-((2S,4R)-4-hydroxy-2-((4-(4-methylthiazol-5-yl)benzyl)carbamoyl)pyrrolidine-1-carbonyl)-2,2-dimethyl-5,17-dioxo-8,11,14-trioxa-4,18-diazadocosan-22-yl)-1H-imidazol-4-yl)nicotinamide |
| 167 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{16}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamine |

TABLE 1-continued

| | |
|---|---|
| 168 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{18}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaoctadecanediamide |
| 169 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{19}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| 170 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |
| 171 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^5$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |
| 172 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^6$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |
| 173 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^7$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamine |
| 174 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^8$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |
| 175 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^9$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |
| 176 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{10}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |
| 177 | $N^1$-(4-(4-(5-carbamoyl-6-(((3R,4R)-3-fluoro-1-(2-(4-(trifluoromethoxy)phenyl)acetyl)piperidin-4-yl)oxy)pyridin-3-yl)-1H-imidazol-1-yl)butyl)-$N^{11}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| 178 | 5-(1-(4-(2-((2-(2,6-dioxopiperidin-3-yl)-1,3-dioxoisoindolin-4-yl)amino)acetamido)butyl)-1H-imidazol-4-yl)-2-(((3R,4R)-3-fluoro-1-(2-(4-(trifluoromethoxy)phenyl)acetyl)piperidin-4-yl)oxy)nicotinamide |
| 179 | 5-(1-(4-(3-((2-(2,6-dioxopiperidin-3-yl)-1,3-dioxoisoindolin-4-yl)amino)propanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide |
| 180 | 5-(1-(4-(4-((2-(2,6-dioxopiperidin-3-yl)-1,3-dioxoisoindolin-4-yl)amino)butanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide |
| 181 | 5-(1-(4-(5-((2-(2,6-dioxopiperidin-3-yl)-1,3-dioxoisoindolin-4-yl)amino)pentanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide |
| 182 | 5-(1-(4-(6-((2-(2,6-dioxopiperidin-3-yl)-1,3-dioxoisoindolin-4-yl)amino)hexanamido)butyl)-1H-imidazol-4-yl)-2-((3R,4R)-3-fluoro-1-(2-(4-(trifluoromethoxy)phenyl)acetyl)piperidin-4-yl)oxy)nicotinamide |
| 183 | 5-(1-(4-(7-((2-(2,6-dioxopiperidin-3-yl)-1,3-dioxoisoindolin-4-yl)amino)heptanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide |
| 184 | 5-(1-(4-(8-((2-(2,6-dioxopiperidin-3-yl)-1,3-dioxoisoindolin-4-yl)amino)octanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide |
| 185 | 5-(1-(4-(3-(2-((2-(2,6-dioxopiperidin-3-yl)-1,3-dioxoisoindolin-4-yl)amino)ethoxy)propanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide |
| 186 | 5-(1-(4-(3-(2-(2-((2-(2,6-dioxopiperidin-3-yl)-1,3-dioxoisoindolin-4-yl)amino)ethoxy)ethoxy)propanamido)butyl)-1H-imidazol-4-yl)-2-(((3R,4R)-3-fluoro-1-(2-(4-(trifluoromethoxy)phenyl)acetyl)piperidin-4-yl)oxy)nicotinamide |
| 187 | 5-(1-(1-((2-(2,6-dioxopiperidin-3-yl)-1,3-dioxoisoindolin-4-yl)amino)-12-oxo-3,6,9-trioxa-13-azaheptadecan-17-yl)-1H-imidazol-4-yl)-2-(((3R,4R)-3-fluoro-1-(2-(4-(trifluoromethoxy)phenyl)acetyl)piperidin-4-yl)oxy)nicotinamide |
| 188 | 5-(1-(1-((2-(2,6-dioxopiperidin-3-yl)-1,3-dioxoisoindolin-4-yl)amino)-15-oxo-3,6,9,12-tetraoxa-16-azaicosan-20-yl)-1H-imidazol-4-yl)-2-(((3R,4R)-3-fluoro-1-(2-(4-(trifluoromethoxy)phenyl)acetyl)piperidin-4-yl)oxy)nicotinamide |
| 189 | 5-(1-(1-((2-(2,6-dioxopiperidin-3-yl)-1,3-dioxoisoindolin-4-yl)amino)-18-oxo-3,9,12,15-pentaoxa-19-azatricosan-23-yl)-1H-imidazol-4-yl)-2-(((3R,4R)-3-fluoro-1-(2-(4-(trifluoromethoxy)phenyl)acetyl)piperidin-4-yl)oxy)nicotinamide |
| 190 | (3R,5S)-1-((S)-2-(12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-5-((4-(4-methylthiazol-5-yl)benzyl)carbamoyl)pyrrolidin-3-yl acetate |
| 191 | (3R,5S)-1-((S)-2-(12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-5-((4-(4-methylthiazol-5-yl)benzyl)carbamoyl)pyrrolidin-3-yl isobutyrate |
| 192 | (3R,5S)-1-((S)-2-(12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecanamido)-3,3-dimethylbutanoyl)-5-((4-(4-methylthiazol-5-yl)benzyl)carbamoyl)pyrrolidin-3-yl L-prolinate |
| 193 | (S)-N-((S)-1-cyclohexyl-2-((S)-2-(4-(3-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)benzoyl)thiazol-2-yl)pyrrolidn-1-yl)-2-oxoethyl)-2-(methylamino)propanamide |
| 194 | (S)-N-((S)-1-cyclohexyl-2-((S)-2-(4-(3-(3-(4-(4-((6-cyclopropyl-3-(1H-pyrazol-4-yl)imidazo[1,2-a]pyrazin-8-yl)amino)-3-fluorobenzoyl)piperazin-1-yl)-3-oxopropoxy)benzoyl)thiazol-2-yl)pyrrolidin-1-yl)-2-oxoethyl)-2-(methylamino)propanamide |
| 195 | (S)-N-((S)-1-cyclohexyl-2-((S)-2-(4-(3-(4-(4-(4-((6-cyclopropyl-3-(1H-pyrazol-4-yl)imidazo[1,2-a]pyrazin-8-yl)amino)-3-fluorobenzoyl)piperazin-1-yl)-4-oxobutoxy)benzoyl)thiazol-2-yl)pyrrolidin-1-yl)-2-oxoethyl)-2-(methylamino)propanamide |
| 196 | (S)-N-((S)-1-cyclohexyl-2-((S)-2-(4-(3-((5-(4-(4-((6-cyclopropyl-3-(1H-pyrazol-4-yl)imidazo[1,2-a]pyrazin-8-yl)amino)-3-fluorobenzoyl)piperazin-1-yl)-5-oxopentyl)oxy)benzoyl)thiazol-2-yl)pyrrolidin-1-yl)-2-oxoethyl)-2-(methylamino)propanamide |
| 197 | (S)-N-((S)-1-cyclohexyl-2-((S)-2-(4-(3-((6-(4-(4-((6-cyclopropyl-3-(1H-pyrazol-4-yl)imidazo[1,2-a]pyrazin-8-yl)amino)-3-fluorobenzoyl)piperazin-1-yl)-6-oxohexyl)oxy)benzoyl)thiazol-2-yl)pyrrolidin-1-yl)-2-oxoethyl)-2-(methylamino)propanamide |
| 198 | (S)-N-((S)-1-cyclohexyl-2-((S)-2-(4-(3-((7-(4-(4-((6-cyclopropyl-3-(1H-pyrazol-4-yl)imidazo[1,2-a]pyrazin-8-yl)amino)-3-fluorobenzoyl)piperazin-1-yl)-7-oxoheptyl)oxy)benzoyl)thiazol-2-yl)pyrrolidin-1-yl)-2-oxoethyl)-2-(methylamino)propanamide |
| 199 | (S)-N-((S)-1-cyclohexyl-2-((S)-2-(4-(3-((8-(4-(4-((6-cyclopropyl-3-(1H-pyrazol-4-yl)imidazo[1,2-a]pyrazin-8-yl)amino)-3-fluorobenzoyl)piperazin-1-yl)-8-oxooctyl)oxy)benzoyl)thiazol-2-yl)pyrrolidin-1-yl)-2-oxoethyl)-2-(methylamino)propanamide |
| 200 | (S)-N-((S)-1-cyclohexyl-2-((S)-2-(4-(3-((9-(4-(4-((6-cyclopropyl-3-(1H-pyrazol-4-yl)imidazo[1,2-a]pyrazin-8-yl)amino)-3-fluorobenzoyl)piperazin-1-yl)-9-oxononyl)oxy)benzoyl)thiazol-2-yl)pyrrolidin-1-yl)-2-oxoethyl)-2-(methylamino)propanamide |
| 201 | (S)-N-((S)-1-cyclohexyl-2-((S)-2-(4-(3-((10-(4-(4-((6-cyclopropyl-3-(1H-pyrazol-4-yl)imidazo[1,2-a]pyrazin-8-yl)amino)-3-fluorobenzoyl)piperazin-1-yl)-10-oxodecyl)oxy)benzoyl)thiazol-2-yl)pyrrolidin-1-yl)-2-oxoethyl)-2-(methylamino)propanamide |
| 202 | (S)-N-((S)-1-cyclohexyl-2-((S)-2-(4-(3-((11-(4-(4-((6-cyclopropyl-3-(1H-pyrazol-4-yl)imidazo[1,2-a]pyrazin-8-yl)amino)-3-flurobenzoyl)piperazin-1-yl)-11-oxoundecyl)oxy)benzoyl)thiazol-2-yl)pyrrolidin-1-yl)-2-oxoethyl)-2-(methylamino)propanamide |

TABLE 1-continued

| | |
|---|---|
| 203 | (S)-N-((S)-1-cyclohexyl-2-((S)-2-(4-(3-((12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecyl)oxy)benzoyl)thiazol-2-yl)pyrrolidin-1-yl)-2-oxoethyl)-2-(methylamino)propanamide |
| 204 | (S)-N-((S)-1-cyclohexyl-2-((S)-2-(4-(3-((13-(4-(4-((6-cyclopropyl-3-(1H-pyrazol-4-yl)imidazo[1,2-a]pyrazin-8-yl)amino)-3-fluorobenzoyl)piperazin-1-yl)-13-oxotridecyl)oxy)benzoyl)thiazol-2-yl)pyrrolidin-1-yl)-2-oxoethyl)-2-(methylamino)propanamide |
| 205 | (S)-N-((S)-1-cyclohexyl-2-((S)-2-(4-(3-(2-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)ethoxy)benzoyl)thiazol-2-yl)pyrrolidin-1-yl)-2-oxoethyl)-2-(methylamino)propanamide |
| 206 | (S)-N-((S)-1-cyclohexyl-2-((S)-2-(4-(3-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)ethoxy)ethoxy)benzoyl)thiazol-2-yl)pyrrolidin-1-yl)-2-oxoethyl)-2-(methylamino) propanamide |
| 207 | (S)-N-((S)-1-cyclohexyl-2-((S)-2-(4-(3-(2-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)ethoxy)ethoxy)ethoxy)benzoyl)thiazol-2-yl)pyrrolidin-1-yl)-2-oxoethyl)-2-(methylamino)propanamide |
| 208 | (S)-N-((S)-1-cyclohexyl-2-((S)-2-(4-(3-((14-(4-(4-((6-cyclopropyl-3-(1H-pyrazol-4-yl)imidazo[1,2-a]pyrazin-8-yl)amino)-3-fluorobenzoyl)piperazin-1-yl)-14-oxo-3,6,9,12-tetraoxatetradecyl)oxy)benzoyl)thiazol-2-yl)pyrrolidin-1-yl)-2-oxoethyl)-2-(methylamino)propanamide |
| 209 | 2-((3R,5R,6S)-5-(3-chlorophenyl)-6-(4-chlorophenyl)-1-((S)-1-((4-(4-(4-(4-((6-cyclopropyl-(1H-pyrazol-4-yl)imidazo[1,2-a] pyrazin-8-yl)amino)-3-fluorobenzoyl)piperazin-1-yl)-4-oxobutanoyl)piperazin-1-yl)sulfonyl)-3,3-dimethylbutan-2-yl)-3-methyl-2-oxopiperidin-3-yl)acetic acid |
| 210 | 2-((3R,5R,6S)-5-(3-chlorophenyl)-6-(4-chlorophenyl)-1-((S)-1-((4-(5-(4-(4-((6-cyclopropyl-3-(1H-pyrazol-4-yl)imidazo[1,2-a] pyrazin-8-yl)amino)-3-fluorobenzoyl)piperazin-1-yl)sulfonyl)-3,3-dimethylbutan-2-yl)-3-methyl-2-oxopiperidine-3-yl)acetic acid |
| 211 | 2-((3R,5R,6S)-5-(3-chlorophenyl)-6-(4-chlorophenyl)-1-((S)-1-((4-(6-(4-(4-((6-cyclopropyl-3-(1H-pyrazol-4-yl)imidazo[1,2-a] pyrazin-8-yl)amino)-3-fluorobenzoyl)piperazin-1-yl)-6-oxohexanoyl)piperazin-1-yl)sulfonyl)-3,3-dimethylbutan-2-yl)-3-methyl-2-oxopiperidin-3-yl)acetic acid |
| 212 | 2-((3R,5R,6S)-5-(3-chlorophenyl)-6-(4-chlorophenyl)-1-((S)-1-((4-(7-(4-(4-((6-cyclopropyl-3-(1H-pyrazol-4-yl)imidazo[1,2-a] pyrazin-8-yl)amino)-3-fluorobenzoyl)piperazin-1-yl)-7-oxoheptanoyl)piperazin-1-yl)sulfonyl)-3,3-dimethylbutan-2-yl)-3-methyl-2-oxopiperidin-3-yl)acetic acid |
| 213 | 2-((3R,5R,6S)-5-(3-chlorophenyl)-6-(4-chlorophenyl)-1-((S)-1-((4-(8-(4-(4-((6-cyclopropyl-3-(1H-pyrazol-4-yl)imidazo[1,2-a] pyrazin-8-yl)amino)-3-fluorobenzoyl)piperazin-1-yl)-8-oxooctanoyl)piperazin-1-yl)sulfonyl)-3,3-dimethylbutan-2-yl)-3-methyl-2-oxopiperidin-3-yl)acetic acid |
| 214 | 2-((3R,5R,6S)-5-(3-chlorophenyl)-6-(4-chlorophenyl)-1-((S)-1-((4-(9-(4-(4-((6-cyclopropyl-3-(1H-pyrazol-4-yl)imidazo[1,2-a] pyrazin-8-yl)amino)-3-fluorobenzoyl)piperazin-1-yl)-9-oxononanoyl)piperazin-1-yl)sulfonyl)-3,3-dimethylbutan-2-yl)-3-methyl-2-oxopiperidin-3-yl)acetic acid |
| 215 | 2-((3R,5R,6S)-5-(3-chlorophenyl)-6-(4-chlorophenyl)-1-((S)-1-((4-(10-(4-(4-((6-cyclopropyl-3-(1H-pyrazol-4-yl)imidazo[1,2-a] pyrazin-8-yl)amino)-3-fluorobenzoyl)piperazin-1-yl)-10-oxodecanoyl)piperazin-1-yl)sulfonyl)-3,3-dimethylbutan-2-yl)-3-methyl-2-oxopiperidin-3-yl)acetic acid |
| 216 | 2-((3R,5R,6S)-5-(3-chlorophenyl)-6-(4-chlorophenyl)-1-((S)-1-((4-(11-(4-(4-((6-cyclopropyl-3(1H-pyrazol-4-yl)imidazo[1,2-a] pyrazin-8-yl)amino)-3-fluorobenzoyl)piperazin-1-yl)-11-oxoundecanoyl)piperazin-1-yl)sulfonyl)-3,3-dimethylbutan-2-yl)-3-methyl-2-oxopiperidin-3-yl)acetic acid |
| 217 | 2-((3R,5R,6S)-5-(3-chlorophenyl)-6-(4-chlorophenyl)-1-((S)-1-((4-(12-(4-(4-((6-cyclopropyl-3-(1H-pyrazol-4-yl)imidazo[1,2-a] pyrazin-8-yl)amino)-3-fluorobenzoyl)piperazin-1-yl)-12-oxododecanoyl)piperazin-1-yl)sulfonyl)-3,3-dimethylbutan-2-yl)-3-methyl-2-oxopiperidin-3-yl)acetic acid |
| 218 | 2-((3R,5R,6S)-5-(3-chlorophenyl)-6-(4-chlorophenyl)-1-((S)-1-((4-(13-(4-(4-((6-cyclopropyl-3-(1H-pyrazol-4-yl)imidazo[1,2-a] pyrazin-8-yl)amino)-3-fluorobenzoyl)piperazin-1-yl)-13-oxotridecanoyl)piperazin-1-yl)sulfonyl)-3,3-dimethylbutan-2-yl)-3-methyl-2-oxopiperidin-3-yl)acetic acid |
| 219 | 2-((3R,5R,6S)-5-(3-chlorophenyl)-6-(4-chlorophenyl)-1-((S)-1-((4-(14-(4-(4-((6-cyclopropyl-3-(1H-pyrazol-4-yl)imidazo[1,2-a] pyrazin-8-yl)amino)-3-fluorobenzoyl)piperazin-1-yl)-14-oxotetradecanoyl)piperazin-1-yl)sulfonyl)-3,3-dimethylbutan-2-yl)-3-methyl-2-oxopiperidin-3-yl)acetic acid |
| 220 | 2-((3R,5R,6S)-5-(3-chlorophenyl)-6-(4-chlorophenyl)-1-((S)-1-((4-(2-(2-(4-(4-((6-cyclopropyl-3-(1H-pyrazol-4-yl)imidazo[1,2-a] pyrazin-8-yl)amino)-3-fluorobenzoyl)piperazin-1-yl)-2-oxoethoxy)acetyl)piperazin-1-yl)sulfonyl)-3,3-dimethylbutan-2-yl)-3-methyloxopiperidin-3-yl)acetic acid |
| 221 | 2-((3R,5R,6S)-5-(3-chlorophenyl)-6-(4-chlorophenyl)-1-((S)-1-((4-(2-(2-(2-(4-(4-((6-cyclopropyl-3-(1H-pyrazol-4-yl)imidazo [1,2-a]pyrazin-8-yl)amino)-3-fluorobenzoyl)piperazin-1-yl)-2-oxoethoxy)ethoxy)acetyl)piperazin-1-yl)sulfonyl)-3,3-dimethylbutan-2-yl)-3-methyl-2-oxopiperidin-3-yl)acetic acid |
| 222 | 2-((3R,5R,6S)-5-(3-chlorophenyl)-6-(4-chlorophenyl)-1-((S)-1-((4-(2-(2-(2-(2-(4-(4-((6-cyclopropyl-3-(1H-pyrazol-4-yl)imidazo [1,2-a]pyrazin-8-yl)amino)-3-fluorobenzoyl)piperazin-1-yl)-2-oxoethoxy)ethoxy)ethoxy)acetyl)piperazin-1-yl)sulfonyl)-3,3-dimethylbutan-2-yl)-3-methyl-2-oxopiperidin-3-yl)acetic acid |
| 223 | 2-((3R,5R,6S)-5-(3-chlorophenyl)-6-(4-chlorophenyl)-1-((S)-1-((4-(14-(4-(4-((6-cyclopropyl-3-(1H-pyrazol-4-yl)imidazo[1,2-a] pyrazin-8-yl)amino)-3-fluorobenzoyl)piperazin-1-yl)-14-oxo-3,6,9,12-tetraoxatetradecanoyl)piperazin-1-yl)sulfonyl)-3,3-dimethylbutan-2-yl)-3-methyl-2-oxopiperidin-3-yl)acetic acid |
| 224 | N-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethyl)-3-(N-(1,3-dimethyl-2-oxo-6-(3-propoxyphenoxy)-2,3-dihydro-1H-benzo[d]imidazol-5-yl)sulfamoyl)benzamide |
| 225 | N-(3-(4-(4-((6-cyclopropyl-3-(1H-pyrazol-4-yl)imidazo[1,2-a]pyrazin-8-yl)amino)-3-fluorobenzoyl)piperazin-1-yl)-3-oxopropyl)-3-(N-(1,3-dimethyl-2-oxo-6-(3-propoxyphenoxy)-2,3-dihydro-1H-benzo[d]imidazol-5-yl)sulfamoyl)benzamide |
| 226 | N-(4-(4-(4-((6-cyclopropyl-3-(1H-pyrazol-4-yl)imidazo[1,2-a]pyrazin-8-yl)amino)-3-fluorobenzoyl)piperazin-1-yl)-4-oxobutyl)-3-(N-(1,3-dimethyl-2-oxo-6-(3-propoxyphenoxy)-2,3-dihydro-1H-benzo[d]imidazol-5-yl)sulfamoyl)benzamide |
| 227 | N-(5-(4-(4-((6-cyclopropyl-3-(1H-pyrazol-4-yl)imidazo[1,2-a]pyrazin-8-yl)amino)-3-fluorobenzoyl)piperazin-1-yl)-5-oxopentyl)-3-N-(1,3-dimethyl-2-oxo-6-(3-propoxyphenoxy)-2,3-dihydro-1H-benzo[d]imidazol-5-yl)sulfamoyl)benzamide |
| 228 | N-(6-(4-(4-((6-cyclopropyl-3-(1H-pyrazol-4-yl)imidazo[1,2-a]pyrazin-8-yl)amino)-3-fluorobenzoyl)piperazin-1-yl)-6-oxohexyl)-3-(N-(1,3-dimethyl-2-oxo-6-(3-propoxyphenoxy)-2,3-dihydro-1H-benzo[d]imidazol-5-yl)sulfamoyl)benzamide |
| 229 | N-(7-(4-(4-((6-cyclopropyl-3-(1H-pyrazol-4-yl)imidazo[1,2-a]pyrazin-8-yl)amino)-3-fluorobenzoyl)piperazin-1-yl)-7-oxoheptyl)-3-(N-(1,3-dimethyl-2-oxo-6-(3-propoxyphenoxy)-2,3-dihydro-1H-benzo[d]imidazol-5-yl)sulfamoyl)benzamide |
| 230 | N-(8-(4-(4-((6-cyclopropyl-3-(1H-pyrazol-4-yl)imidazo[1,2-a]pyrazin-8-yl)amino)-3-fluorobenzoyl)piperazin-1-yl)-8-oxooctyl)-3-(N-(1,3-dimethyl-2-oxo-6-(3-propoxyphenoxy)-2,3-dihydro-1H-benzo[d]imidazol-5-yl)sulfamoyl)benzamide |
| 231 | N-(9-(4-(4-((6-cyclopropyl-3-(1H-pyrazol-4-yl)imidazo[1,2-a]pyrazin-8-yl)amino)-3-fluorobenzoyl)piperazin-1-yl)-9-oxononyl)-3-(N-(1,3-dimethyl-2-oxo-6-(3-propoxyphenoxy)-2,3-dihydro-1H-benzo[d]imidazol-5-yl)sulfamoyl)benzamide |
| 232 | N-(10-(4-(4-((6-cyclopropyl-3-(1H-pyrazol-4-yl)imidazo[1,2-a]pyrazin-8-yl)amino)-3-fluorobenzoyl)piperazin-1-yl)-10-oxodecyl)-3-(N-(1,3-dimethyl-2-oxo-6-(3-propoxyphenoxy)-2,3-dihydro-1H-benzo[d]imidazol-5-yl)sulfamoyl)benzamide |
| 233 | N-(11-(4-(4-((6-cyclopropyl-3-(1H-pyrazol-4-yl)imidazo[1,2-a]pyrazin-8-yl)amino)-3-fluorobenzoyl)piperazin-1-yl)-11-oxoundecyl)-3-(N-(1,3-dimethyl-2-oxo-6-(3-propoxyphenoxy)-2,3-dihydro-1H-benzo[d]imidazol-5-yl)sulfamoyl)benzamide |

TABLE 1-continued

| | |
|---|---|
| 234 | N-(12-(4-(4-((6-cyclopropyl-3-(1H-pyrazol-4-yl)imidazo[1,2-a]pyrazin-8-yl)amino)-3-fluorobenzoyl)piperazin-1-yl)-12-oxododecyl)-3-(N-(1,3-dimethyl-2-oxo-6-(3-propoxyphenxoy)-2,3-dihydro-1H-benzo[d]imidazol-5-yl)sulfamoyl)benzamide |
| 235 | N-(13-(4-(4-((6-cyclopropyl-3-(1H-pyrazol-4-yl)imidazo[1,2-a]pyrazin-8-yl)amino)-3-fluorobenzoyl)piperazin-1-yl)-13-oxotridecyl)-3-(N-(1,3-dimethyl-2-oxo-6-(3-propoxyphenoxy)-2,3-dihydro-1H-benzo[d]imidazol-5-yl)sulfamoyl)benzamide |
| 236 | N-(2-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)ethyl)-3-(N-(1,3-dimethyl-2-oxo-6-(3-propoxyphenoxy)-2,3-dihydro-1H-benzo[d]imidazol-5-yl)sulfamoyl)benzamide |
| 237 | N-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)ethoxy)ethyl)-3-(N-(1,3-dimethyl-2-oxo-6-(3-propoxyphenoxy)-2,3-dihydro-1H-benzo[d]imidazol-5-yl)sulfamoyl)benzamide |
| 238 | N-(2-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)-2-oxoethoxy)ethoxy)ethoxy)ethyl)-3-(N-(1,3-dimethyl-2-oxo-6-(3-propoxyphenoxy)-2,3-dihydro-1H-benzo[d]imidazol-5-yl)sulfamoyl)benzamide |
| 239 | N-(14-(4-(4-((6-cyclopropyl-3-(1H-pyrazol-4-yl)imidazo[1,2-a]pyrazin-8-yl)amino)-3-fluorobenzoyl)piperazin-1-yl)-14-oxo-3,6,9,12-tetraoxatetradecyl)-3-(N-(1,3-dimethyl-2-oxo-6-(3-propoxyphenoxy)-2,3-dihydro-1H-benzo[d]imidazol-5-yl)sulfamoyl)benzamide |
| 240 | (S)-N-((S)-1-cyclohexyl-2-((S)-2-(4-(3-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)benzoyl)thiazol-2-yl)pyrrolidin-1-yl)-2-oxoethyl)-2-(methylamino)propanamide |
| 241 | (S)-N-((S)-1-cyclohexyl-2-((S)-2-(4-(3-(3-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)propoxy)benzoyl)thiazol-2-yl)pyrrolidin-1-yl)-2-oxoethyl)-2-(methylamino)propanamide |
| 242 | (S)-N-((S)-1-cyclohexyl-2-((S)-2-(4-(3-((5-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)pentyl)oxy)benzoyl)thiazol-2-yl)pyrrolidin-1-yl)-2-oxoethyl)-2-(methylamino)propanamide |
| 243 | (S)-N-((S)-1-cyclohexyl-2-((S)-2-(4-(3-(4-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)butoxy)benzoyl)thiazol-2-yl)pyrrolidin-1-yl)-2-oxoethyl)-2-(methylamino)propanamide |
| 244 | (S)-N-((S)-1-cyclohexyl-2-((S)-2-(4-(3-((7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptyl)oxy)benzoyl)thiazol-2-yl)pyrrolidin-1-yl)-2-oxoethyl)-2-(methylamino)propanamide |
| 245 | (S)-N-((S)-1-cyclohexyl-2-((S)-2-(4-(3-((6-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)hexyl)oxy)benzoyl)thiazol-2-yl)pyrrolidin-1-yl)-2-oxoethyl)-2-(methylamino)propanamide |
| 246 | (S)-N-((S)-1-cyclohexyl-2-((S)-2-(4-(3-((7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptyl)oxy)benzoyl)thiazol-2-yl)pyrrolidin-1-yl)-2-oxoethyl)-2-(methylamino)propanamide |
| 247 | (S)-N-((S)-1-cyclohexyl-2-((S)-2-(4-(3-((8-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)octyl)oxy)benzoyl)thiazol-2-yl)pyrrolidin-1-yl)-2-oxoethyl)-2-(methylamino)propanamide |
| 248 | (S)-N-((S)-1-cyclohexyl-2-((S)-2-(4-(3-((9-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)nonyl)oxy)benzoyl)thiazol-2-yl)pyrrolidin-1-yl)-2-oxoethyl)-2-(methylamino)propanamide |
| 249 | (S)-N-((S)-1-cyclohexyl-2-((S)-2-(4-(3-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)ethoxy)benzoyl)thiazol-2-yl)pyrrolidin-1-yl)-2-oxoethyl)-2-(methylamino)propanamide |
| 250 | (S)-N-((S)-1-cyclohexyl-2-((S)-2-(4-(3-(2-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)ethoxy)ethoxy)benzoyl)thiazol-2-yl)pyrrolidin-1-yl)-2-oxoethyl)-2-(methylamino)propanamide |
| 251 | 2-((3R,5R,6S)-5-(2-chlorophenyl)-6-(4-chlorophenyl)-1-((S)-1-((4-(3-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)propanoyl)piperazin-1-yl)acetamido)propanoyl)piperazin-1-yl)sulfonyl)-3,3-dimethylbutan-2-yl)-3-methyl-2-oxopiperidin-3-yl)acetic acid |
| 252 | 2-((3R,5R,6S)-5-(3-chlorophenyl)-6-(4-chlorophenyl)-1-((S)-1-((4-(4-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)butanoyl)piperazin-1-yl)sulfonyl)-3,3-dimethylbutan-2-yl)-3-methyl-2-oxopiperidin-3-yl)acetic acid |
| 253 | 2-((3R,5R,6S)-5-(3-chlorophenyl)-6-(4-chlorophenyl)-1-((S)-1-((4-(5-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)pentanoyl)piperazin-1-yl)sulfonyl)-3,3-dimethylbutan-2-yl)-3-methyl-2-oxopiperidin-3-yl)acetic acid |
| 254 | 2-((3R,5R,6S)-5-(3-chlorophenyl)-6-(4-chlorophenyl)-1-((S)-1-((4-(6-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)hexanoyl)piperazin-1-yl)sulfonyl)-3,3-dimethylbutan-2-yl)-3-methyl-2-oxopiperidin-3-yl)acetic acid |
| 255 | 2-((3R,5R,6S)-5-(3-chlorophenyl)-6-(4-chlorophenyl)-1-((S)-1-((4-(7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptanoyl)piperazin-1-yl)sulfonyl)-3,3-dimethylbutan-2-yl)-3-methyl-2-oxopiperidin-3-yl)acetic acid |
| 256 | 2-((3R,5R,6S)-5-(3-chlorophenyl)-6-(4-chlorophenyl)-1-((S)-1-((4-(8-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)octanoyl)piperazin-1-yl)sulfonyl)-3,3-dimethylbutan-2-yl)-3-methyl-2-oxopiperidin-3-yl)acetic acid |
| 257 | 2-((3R,5R,6S)-5-(3-chlorophenyl)-6-(4-chlorophenyl)-1-((S)-1-((4-(9-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)nonanyl)piperazin-1-yl)sulfonyl)-3,3-dimethylbutan-2-yl)-3-methyl-2-oxopiperidin-3-yl)acetic acid |
| 258 | 2-((3R,5R,6S)-5-(3-chlorophenyl)-6-(4-chlorophenyl)-1-((S)-1-((4-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)acetyl)piperazin-1-yl)sulfonyl)-3,3-dimethylbutan-2-yl)-3-methyl-2-oxopiperidin-3-yl)acetic acid |
| 259 | 2-((3R,5R,6S)-5-(3-chlorophenyl)-6-(4-chlorophenyl)-1-((S)-1-((4-(2-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)ethoxy)acetyl)piperazin-1-yl)sulfonyl)-3,3-dimethylbutan-2-yl)-3-methyl-2-oxopiperidin-3-yl)acetic acid |
| 260 | 3-(N-(6-(3-butoxyphenoxy)-1,3-dimethyl-2-oxo-2,3-dihydro-1H-benzo[d]imidazol-5-yl)sulfamoyl)-N-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethyl)benzamide |
| 261 | 3-(N-(6-(3-butoxyphenoxy)-1,3-dimetjhyl-2-oxo-2,3-dihydro-1H-benzo[d]imidazol-5-yl)sulfamoyl)-N-(3-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)propyl)benzamide |
| 262 | 3-(N-(6-(3-butoxyphenoxy)-1,3-dimethyl-2-oxo-2,3-dihydro-1H-benzo[d]imidazol-5-yl)sulfamoyl)-N-(4-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)butyl)benzamide |
| 263 | 3-(N-(6-(3-butoxyphenoxy)-1,3-dimethyl-2-oxo-2,3-dihydro-1H-benzo[d]imidazol-5-yl)sulfamoyl)-N-(5-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)pentyl)benzamide |
| 264 | 3-(N-(6-(3-butoxyphenoxy)-1,3-dimethyl-2-oxo-2,3-dihydro-1H-benzo[d]imidazol-5-yl)sulfamoyl)-N-(6-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)hexyl)benzamide |
| 265 | 3-(N-(6-(3-butoxyphenoxy)-1,3-dimethyl-2-oxo-2,3-dihydro-1H-benzo[d]imidazol-5-yl)sulfamoyl)-N-(7-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)heptyl)benzamide |
| 266 | 3-(N-(6-(3-butoxyphenoxy)-1,3-dimethyl-2-oxo-2,3-dihydro-1H-benzo[d]imidazol-5-yl)sulfamoyl)-N-(8-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)octyl)benzamide |
| 267 | 3-(N-(6-(3-butoxyphenoxy)-1,3-dimethyl-2-oxo-2,3-dihydro-1H-benzo[d]imidazol-5-yl)sulfamoyl)-N-(9-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)nonyl)benzamide |

TABLE 1-continued

| | |
|---|---|
| 268 | 3-(N-(6-(3-butoxyphenoxy)-1,3-dimethyl-2-oxo-2,3-dihydro-1H-benzo[d]imidazol-5-yl)sulfamoyl)-N-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)ethyl)benzamide |
| 269 | 3-(N-(6-(3-butoxyphenoxy)-1,3-dimethyl-2-oxo-2,3-dihydro-1H-benzo[d]imidazol-5-yl)sulfamoyl)-N-(2-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)ethoxy)ethyl) benzamide |
| 270 | (2S,4R)-N-(2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethoxy)-4-(4-methylthiazol-5-yl)benzyl)-1-((S)-2-(1-fluorocyclopropane-1-carboxamido)-3,3-dimethybutanoyl)-4-hydroxypyrrolidine-2-carboxamide |
| 271 | (2S,4R)-N-(2-(3-(2-(4-(4-((6-Cyclopropyl-3-(1H-pyrazol-4-yl)imidazo[1,2-a]pyrazin-8-yl)amino)-3-fluorobenzoyl)piperazin-1-yl) acetamido)propoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| 272 | (2S,4R)-N-(2-(4-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)butoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| 273 | (2S,4R)-N-(2-((5-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)pentyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| 274 | (2S,4R)-N-(2-((6-(2-(4-(4-((6-Cyclopropyl-3-(1H-pyrazol-4-yl)imidazo[1,2-a]pyrazin-8-yl)amino)-3-fluorobenzoyl)piperazin-1-yl) acetamido)hexyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| 275 | (2S,4R)-N-(2-((7-(2-(4-(4-((6-cyclopropyl-3-(1H-pyrazol-4-yl)imidazo[1,2-a]pyrazin-8-yl)amino)-3-fluorobenzoyl)piperazin-1-yl) acetamido)heptyl)oxy)-4-(4-methylthiazol-5-yl)benzyl)-1-((S)-2-(1-fluorocyclopropane-1-carboxamido)-3,3-dimethylbutan)-4-hydroxypyrrolidine-2-carboxamide |
| 276 | (2S,4R)-N-(2-((8-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)octyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| 277 | (2S,4R)-N-(2-((9-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)nonyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| 278 | (2S,4R)-N-(2-(2-(2-(2-(4-(4-((6-Cyclopropyl-3-(1H-pyrazol-4-yl)imidazo[1,2-a]pyrazin-8-yl)amino)-3-fluorobenzoyl)piperazin-1-yl)acetamido)ethoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| 279 | (2S,4R)-N-(2-(2-(2-(2-(2-(2-(4-(4-((6-cyclopropyl-3-(1H-pyrazol-4-yl)imidazo[1,2-a]pyrazin-8-yl)amino)-3-fluorobenzoyl)piperazin-1-yl)acetamido)ethoxy)ethoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| 280 | (2S,4R)-N-(2-((1-(4-(4-((6-Cyclopropyl-3-(1H-pyrazol-4-yl)imidazo[1,2-a]pyrazin-8-yl)amino)-3-fluorobenzoyl)piperazin-1-yl)-2-oxo-6,9,12-trioxa-3-azatetradecan-14-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |

In Table 1, the left portion of the structure of the PTK6 disruptors/degraders binds to PTK6 (as, e.g. compound 21d (Zeng et al., 2011), compound 4f (Mahmoud et al., 2014), compound 1 (Yamamoto, 2016), XMU-MP-2 (Jiang et al., 2017), and compound 3s (Cardenas et al., 2018), and analogs thereof), and the right portion of the structure recruits the ubiquitination machinery to PTK6, which induces polyubiquitination and degradation of PTK6 at the proteasome.

Compounds corresponding to Examples 1-189 have been synthesized and are provided with a Compound Code in Table 1. Compounds in Table 1 corresponding to Examples 190-280 have not been synthesized and are not provided with a Compound Code. These compounds may be synthesized according to the schemes set forth above.

As used herein, in case of discrepancy between the structure and chemical name provided for a particular compound, the structure shall control.

Example 281. Assessing the Effect of Selected Compounds on Reducing PTK6 Protein Levels in Cancer Cells (FIG. 2-5)

MDA-MB231 cells were treated with DMSO or indicated compounds at 2.5 uM, 2 uM or 500 nM for 24 hours. The Western blot results showed that multiple compounds significantly reduced PTK6 protein levels.

Example 282. PTK6 Degraders Suppressed Growth and Invasive Branching of Triple Negative MDA-MiB231 Breast Cancer Cells in 3-D Cultures (FIG. 6)

MDA-MB231 cells were treated with indicated compounds at 1 μM for 3 days in 3D cultures. YX39-103 and YX39-105 significantly suppressed growth and invasive branching of these cells, whereas negative control compounds and PTK6 kinase activity inhibitor did not.

Example 283. YX39-103 and YX39-105 Suppressed Viability of MCF7 ER+ Breast Cancer Cells in 3-D Cultures (FIG. 7)

MCF7 cells were treated with YX39-103, YX39-105, and compound 21d at 0, 1, 2 and 5 μM for 4 days using 3D Cell Titer Glo (Promega) assay conditions. YX39-103 and YX39-105 significantly impaired viability of MCF7 cells in a dose-dependent manner, while the effect of PTK6 kinase inhibitor compound 21 is less pronounced.

Example 284. YX39-103 and YX39-105 Suppressed Viability of Chemotherapy-Resistant Ovarian Cells (CP70) (FIG. 8)

Platinum resistant ovarian cancer cells CP70 were treated with PTK6 degrader or kinase inhibitor P21d (2 uM) for 6 days in 3D culture. Viability after 6 days was assessed by 3D Cell Titer glo.

Example 285. MG132 Pretreatment Prevents PTK6 from being Degraded by YX39-105 in MDA-MB231 Cells (FIG. 9)

MDA-MB231 cells were pre-treated with MG132 (10 uM) or DMSO for 2 hours, then treated for additional 4 hours with PTK6 degrader YX39-105 or DMSO. Cells were lysed and expression of PTK6 was assessed by Western analysis.

Example 286. PTK6 Inhibitor Pretreatment Prevents PTK6 from being Degraded by YX39-105 in MDA-MB231 Cells (FIG. 10)

MDA-MB231 cells pretreated with DMSO or PTK6 kinase activity inhibitor, P21d, (5 uM) for 2 hours were subsequently treated with PTK6 degrader YX39-105 for 24 hours. Expression of PTK6 was assessed by Western analysis.

Example 287. PTK6 Degraders Downregulate PTK6 in Endocrine Therapy Resistant ER+ MCF7/EDR Cells (FIG. 11)

MCF7EDR cells in monolayer cultures were treated with PTK6 degraders for 24 hours at the indicated concentrations. Cells were lysed and expression of PTK6 was assessed.

Example 288. PTK6 Degraders, but not Kinase Activity Inhibitor, Suppress Viability in 3D Cultures (FIG. 12)

Expression of PTK6 in cells treated with PTK6 degraders, negative control compounds or PTK6 kinase activity inhibitor was assessed after 24 hour treatment in monolayer cultures with 1 uM of compound (FIG. 12A). Cells were lysed and proteins were resolved and probed with anti-PTK6 antibody (Cell Signaling).

MDA-MB231 triple negative breast cancer cells were seeded into 3D Matrigel cultures (4×10^3 cells/well) and treated with indicated PTK6 degraders, negative control compounds or PTK6 kinase activity inhibitor at 1 uM for 6 days with re-feeding of compound after 3 days in culture (FIG. 12B). Viability was assessed using 3D Cell Titer glo (Promega).

Example 289. PTK6 Degraders Suppress PTK6 Protein Levels in MDA-MB231 Cells (FIG. 13)

MDA-MB231 cells were treated with compounds (500 nM or 1 uM) for 24 hours in monolayer cultures. Cells were lysed and lysates were probed with anti-PTK6 antibody.

Materials and Methods

General Chemistry Methods:

All chemicals and reagents were purchased from commercial suppliers and used without further purification. HPLC spectra for all compounds were acquired using an Agilent 1200 Series system with DAD detector. Chromatography was performed on a 2.1×150 mm Zorbax 300SB-C18 5 μm column with water containing 0.1% formic acid as solvent A and acetonitrile containing 0.1% formic acid as solvent B at a flow rate of 0.4 ml/min. The linear gradient was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI) source. Proton Nuclear Magnetic Resonance ($^1$H-NMR) spectra were recorded on a Bruker DRX-600 spectrometer, and Carbon Nuclear Magnetic ($^{13}$C NMR) were recorded at 150 MHz. Chemical shifts are expressed in parts per million (ppm) and reported as S value (chemical shift 8). Coupling constants are reported in units of hertz (J value, Hz; Integration and splitting patterns: where s=singlet, d=double, t=triplet, q=quartet, brs=broad singlet, m=multiple). Preparative HPLC was performed on Agilent Prep 1200 series with UV detector set to 254 nm. Samples were injected onto a Phenomenex Luna 75×30 mm, 5 μm, C18 column at room temperature. The flow rate was 40 ml/min. A linear gradient was used with 10% (or 50%) of MeOH (A) in $H_2O$ (with 0.1% TFA) (B) to 100% of MeOH (A). HPLC was used to establish the purity of target compounds. All compounds showed >95% purity using the HPLC methods described above.

Antibodies and Reagents

Antibodies purchased from Cell Signaling Technology are: GAPDH (14C10), β-tubulin ($9F_3$), E-Cadherin (24E10), and PTK6. Antibodies obtained from Santa Cruz Biotechnology are: BRK antibodies (C-18 and D-7), goat anti-rabbit IgG-HRP and goat anti-mouse IgG-HRP. PTK6 inhibitor (Pyrazin-21d, P21d) was synthesized according to published description [24]. MDA231, MCF7, UACC893 and MCFA-10A cells were obtained from ATCC. OV2008 was purchased from ThermoFisher Scientific. HeyC2 was purchased from Cellutions Biosystems, Inc. All cell lines were cultured according to ATCC recommended media guidelines or individual provider specifications. MDA-MB231 cells (ATCC) were cultured in RPMI-1640 supplemented with 10% FBS. MCF7TamR, EDR, FulvR and MMTV-myc cells were cultured according to published protocols (Ito et al., 2017; Ito et al., 2016)

RNAi Knockdown siRNAs targeting PTK6 were obtained from GE Healthcare Dharmacon. Transfection was performed using Oligofectamine (Life Technologies), following the manufacturer's protocol. Short hairpin-RNAs targeting PTK6 were purchased from Sigma-Aldrich. Lentivirus was generated by co-transfecting 293T cells with shRNA vector and packaging plasmids (Delta 8.9 and pCMV-VSV-G) using Lipofectamine 2000 and Plus reagent (Life Technologies). The supernatants were collected and stored at −80° C. Cells were infected with viral supernatants.

Immunoblotting

Cells were lysed in 1% NP-40 lysis buffer containing NaF, $Na_3VO_4$, Leupeptin, PMSF, aprotinin, and phosphatase inhibitor (PhosSTOP, Roche) as described previously (Irie et al., 2010). Cleared cell lysates were stored at −80° C. and were analyzed by western analysis as described previously (Irie et al., 2010).

3D Cell Growth Assays

MDA-MB231, MCF-7, OV2008 and Hey $C_2$ cells (3,000 cells) were added to 8-well chamber slides (BD Biosciences) coated with 50 μl of growth factor-reduced Matrigel™ Matrix basement membrane (Corning). Treatment with degrader was begun later the same day. Media was replaced every 3 days. Cells were imaged using the Axiovert 25 inverted microscope (Carl Zeiss AB). CellTiter-Glo 3D Cell Viability Assay (Promega) was used to quantitate viability of cells grown in Matrigel™ in 96-well plates.

Apoptosis Assay

Culture medium containing floating cells was transferred to 15 ml conical tubes. Attached cells were collected by trypsinization at 37° C. in the same tubes followed by spinning at 360×g for 3 min. Cell pellets were washed with ice-cold PBS once and resuspended in 250 μl of 1× binding buffer containing 5 μl of FITC-AnnexinV and PI (BD Biosciences, #556547). After 15 min incubation at room temperature in the dark, 250 μl of 1× binding buffer was added and flow cytometry analysis was performed as described (Park et al., 2015).

Tumor Xenograft Studies

Six-week-old female nude (nu/nu) mice (Charles River Laboratories) were subcutaneously injected with MCF-7 or UACC893R cells infected with control or PTK6 shRNA lentivirus. Cancer cells expressing PTK6 shRNA or vector control shRNA were generated in vitro prior to subcutaneous injection into nude mice. Mice from the combined purchased cages were randomly assigned to injection with PTK6 or control shRNA expressing cells. Tumor growth was monitored twice weekly, and tumor volume was determined [$V=\frac{1}{2}(L\times W^2)$]. Tumor measurements were performed by a second investigator who was blinded to the shRNA treatment. The mice were euthanized when the tumor diameters reached 10 mm in any direction according to approved IACUC protocol. All procedures and studies with mice were performed in accordance with protocols approved by the Institutional Animal Care and Use Committee of Icahn School of Medicine at Mount Sinai.

Lung Colonization Assay

MDA-MB231 or MMTV-myc cells were transduced with PTK6 shRNA virus for 72 hours. For PTK6 inhibitor experiments, MMTV-myc cells were treated with PTK6 inhibitor P21d for 48 h in vitro. shRNA-infected or inhibitor-treated cells were washed with PBS three times. MDA-MB231 cells ($2\times10^6$ per mouse) or MMTV-myc cells ($5\times10^4$ per mouse) in 100 μl of PBS were injected into the tail veins of 6-week old NOD-SCID or FVB female mice (Charles River Labs), respectively. Lung tissues were harvested after four weeks for MDA-MB231 and three weeks for MMTV-myc, and fixed in Bouin's solution. The number of surface lung metastases (size greater than 0.5 mm diameter for MDA-MB231 and 1 mm for MMTV-myc cells) was counted. All animal procedures were conducted in compliance with the guidelines of the IACUC Committees of Mount Sinai School of Medicine.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Aguilar, A., Lu, J., Liu, L., Du, D., Bernard, D., McEachern, D., Przybranowski, S., Li, X., Luo, R., Wen, B., et al. (2017). Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido) bicyclo[2.2.2]octane-1-carboxylic Acid (AA-115/APG-115). A Potent and Orally Active Murine Double Minute 2 (MDM2) Inhibitor in Clinical Development. J Med Chem 60, 2819-2839.

Bondeson, D. P., Mares, A., Smith, I. E., Ko, E., Campos, S., Miah, A. H., Mulholland, K. E., Routly, N., Buckley, D. L., Gustafson, J. L., et al. (2015). Catalytic in vivo protein knockdown by small-molecule PROTACs. Nat Chem Biol 11, 611-617.

Brauer, P. M., and Tyner, A. L. (2010). Building a better understanding of the intracellular tyrosine kinase PTK6—BRK by BRK. Biochim Biophys Acta 1806, 66-73.

Buckley, D. L., and Crews, C. M. (2014). Small-molecule control of intracellular protein levels through modulation of the ubiquitin proteasome system. Angew Chem Int Ed Engl 53, 2312-2330.

Buckley, D. L., Gustafson, J. L., Van Molle, I., Roth, A. G., Tae, H. S., Gareiss, P. C., Jorgensen, W. L., Ciulli, A., and Crews, C. M. (2012a). Small-molecule inhibitors of the interaction between the E3 ligase VHL and HIFl alpha. Angew Chem Int Ed Engl 51, 11463-11467.

Buckley, D. L., Raina, K., Darricarrere, N., Hines, J., Gustafson, J. L., Smith, I. E., Miah, A. H., Harling, J. D., and Crews, C. M. (2015). HaloPROTACS: Use of Small Molecule PROTACs to Induce Degradation of HaloTag Fusion Proteins. ACS Chem Biol 10, 1831-1837.

Buckley, D. L., Van Molle, I., Gareiss, P. C., Tae, H. S., Michel, J., Noblin, D. J., Jorgensen, W. L., Ciulli, A., and Crews, C. M. (2012b). Targeting the von Hippel-Lindau E3 ubiquitin ligase using small molecules to disrupt the VHL/HIF-1alpha interaction. J Am Chem Soc 134, 4465-4468.

Cardenas, M. M., Toenjes, S. T., Nalbandian, C. J., and Gustafson, J. L. (2018). Enantioselective Synthesis of Pyrrolopyrimidine Scaffolds through Cation-Directed Nucleophilic Aromatic Substitution. Org Lett 20, 2037-2041.

Castro, N. E., and Lange, C. A. (2010). Breast tumor kinase and extracellular signal-regulated kinase 5 mediate Met receptor signaling to cell migration in breast cancer cells. Breast Cancer Res 12, R60.

Chamberlain, P. P., Lopez-Girona, A., Miller, K., Carmel, G., Pagarigan, B., Chie-Leon, B., Rychak, E., Corral, L. G., Ren, Y. J., Wang, M., et al. (2014). Structure of the human Cereblon-DDB1-lenalidomide complex reveals basis for responsiveness to thalidomide analogs. Nat Struct Mol Biol 21, 803-809.

Chen, X., Song, B., Lin, Y., Cao, L., Feng, S., Zhang, L., and Wang, F. (2016). PTK6 promotes hepatocellular carcinoma cell proliferation and invasion. Am J Transl Res 8, 4354-4361.

Davies, T. G., Wixted, W. E., Coyle, J. E., Griffiths-Jones, C., Hearn, K., McMenamin, R., Norton, D., Rich, S. J., Richardson, C., Saxty, G., et al. (2016). Monoacidic Inhibitors of the Kelch-like ECH-Associated Protein 1: Nuclear Factor Erythroid 2-Related Factor 2 (KEAP1: NRF2) Protein-Protein Interaction with High Cell Potency Identified by Fragment-Based Discovery. J Med Chem 59, 3991-4006.

Derry, J. J., Prins, G. S., Ray, V., and Tyner, A. L. (2003). Altered localization and activity of the intracellular tyrosine kinase BRK/Sik in prostate tumor cells. Oncogene 22, 4212-4220.

E. Wakeling, A. (1995). Use of pure antioestrogens to elucidate the mode of action of oestrogens. Biochem Pharmacol 49, 1545-1549.

Fan, Q., Aksoy, O., Wong, R. A., Ilkhanizadeh, S., Novotny, C. J., Gustafson, W. C., Truong, A. Y., Cayanan, G., Simonds, E. F., Haas-Kogan, D., et al. (2017). A Kinase Inhibitor Targeted to mTORC1 Drives Regression in Glioblastoma. Cancer Cell 31, 424-435.

Fischer, E. S., Bohm, K., Lydeard, J. R., Yang, H., Stadler, M. B., Cavadini, S., Nagel, J., Serluca, F., Acker, V., Lingaraju, G. M., et al. (2014). Structure of the DDB1-CRBN E3 ubiquitin ligase in complex with thalidomide. Nature 512, 49-53.

Galdeano, C., Gadd, M. S., Soares, P., Scaffidi, S., Van Molle, I., Birced, I., Hewitt, S., Dias, D. M., and Ciulli, A. (2014). Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem 57, 8657-8663.

Haegebarth, A., Bie, W., Yang, R., Crawford, S. E., Vasioukhin, V., Fuchs, E., and Tyner, A. L. (2006). Protein tyrosine kinase 6 negatively regulates growth and promotes enterocyte differentiation in the small intestine. Mol Cell Biol 26, 4949-4957.

Han, X., Wang, C., Qin, C., Xiang, W. G., Fernandez-Salas, E., Yang, C. Y., Wang, M., Zhao, L. J., Xu, T. F., Chinnaswamy, K., et al. (2019). Discovery of ARD-69 as a Highly Potent Proteolysis Targeting Chimera (PROTAC) Degrader of Androgen Receptor (AR) for the Treatment of Prostate Cancer. J Med Chem 62, 941-964.

Harvey, A. J., and Crompton, M. R. (2003). Use of RNA interference to validate Brk as a novel therapeutic target in breast cancer: Brk promotes breast carcinoma cell proliferation. Oncogene 22, 5006-5010.

Harvey, A. J., Pennington, C. J., Porter, S., Burmi, R. S., Edwards, D. R., Court, W., Eccles, S. A., and Crompton, M. R. (2009). Brk protects breast cancer cells from autophagic cell death induced by loss of anchorage. Am J Pathol 175, 1226-1234.

Hiroyuki Suda, Tomohisa Takita, Takaaki Aoyagi, and Umezawa, H. (1976). The structure of bestatin. The Journal of Antibiotic 20, 100-101.

Irie, H. Y., Shrestha, Y., Selfors, L. M., Frye, F., Iida, N., Wang, Z., Zou, L., Yao, J., Lu, Y., Epstein, C. B., et al. (2010). PTK6 regulates IGF-1-induced anchorage-independent survival. PLoS One 5, e11729.

Ito, K., Park, S. H., Katsyv, I., Zhang, W., De Angelis, C., Schiff, R., and Irie, H. Y. (2017). PTK6 regulates growth and survival of endocrine therapy-resistant ER+ breast cancer cells. NPJ Breast Cancer 3, 45.

Ito, K., Park, S. H., Nayak, A., Byerly, J. H., and Irie, H. Y. (2016). PTK6 Inhibition Suppresses Metastases of Triple-Negative Breast Cancer via SNAIL-Dependent E-Cadherin Regulation. Cancer Res 76, 4406-4417.

Ito, T., Ando, H., Suzuki, T., Ogura, T., Hotta, K., Imamura, Y., Yamaguchi, Y., and Handa, H. (2010). Identification of a primary target of thalidomide teratogenicity. Science 327, 1345-1350.

Jiang, J., Gui, F., He, Z., Li, L., Li, Y., Li, S., Wu, X., Deng, Z., Sun, X., Huang, X., et al. (2017). Targeting BRK-Positive Breast Cancers with Small-Molecule Kinase Inhibitors. Cancer Res 77, 175-186.

Lai, A. C., Toure, M., Hellerschmied, D., Salami, J., Jaime-Figueroa, S., Ko, E., Hines, J., and Crews, C. M. (2016). Modular PROTAC Design for the Degradation of Oncogenic BCR-ABL. Angew Chem Int Ed Engl 55, 807-810.

Liu, J., Farmer, J. D., Jr., Lane, W. S., Friedman, J., Weissman, I., and Schreiber, S. L. (1991). Calcineurin is a common target of cyclophilin-cyclosporin A and FKBP-FK506 complexes. Cell 66, 807-815.

Lu, J., Qian, Y., Altieri, M., Dong, H., Wang, J., Raina, K., Hines, J., Winkler, J. D., Crew, A. P., Coleman, K., et al. (2015). Hijacking the E3 Ubiquitin Ligase Cereblon to Efficiently Target BRD4. Chemistry & biology 22, 755-763.

Mahmoud, K. A., Krug, M., Wersig, T., Slynko, I., Schachtele, C., Totzke, F., Sippl, W., and Hilgeroth, A. (2014). Discovery of 4-anilino alpha-carbolines as novel Brk inhibitors. Bioorg Med Chem Lett 24, 1948-1951.

Maniaci, C., Hughes, S. J., Testa, A., Chen, W., Lamont, D. J., Rocha, S., Alessi, D. R., Romeo, R., and Ciulli, A. (2017). Homo-PROTACs: bivalent small-molecule dimerizers of the VHL E3 ubiquitin ligase to induce self-degradation. Nat Commun 8, 830.

Mitchell, P. J., Barker, K. T., Martindale, J. E., Kamalati, T., Lowe, P. N., Page, M. J., Gusterson, B. A., and Crompton, M. R. (1994). Cloning and characterisation of cDNAs encoding a novel non-receptor tyrosine kinase, brk, expressed in human breast tumours. Oncogene 9, 2383-2390.

Ohoka, N., Okuhira, K., Ito, M., Nagai, K., Shibata, N., Hattori, T., Ujikawa, O., Shimokawa, K., Sano, O., Koyama, R., et al. (2017). In Vivo Knockdown of Pathogenic Proteins via Specific and Nongenetic Inhibitor of Apoptosis Protein (IAP)-dependent Protein Erasers (SNIPERs). J Biol Chem 292, 4556-4570.

Okuhira, K., Ohoka, N., Sai, K., Nishimaki-Mogami, T., Itoh, Y., Ishikawa, M., Hashimoto, Y., and Naito, M. (2011). Specific degradation of CRABP-II via cIAP1-mediated ubiquitylation induced by hybrid molecules that crosslink cIAP1 and the target protein. FEBS Lett 585, 1147-1152.

Ono, H., Basson, M. D., and Ito, H. (2014). PTK6 promotes cancer migration and invasion in pancreatic cancer cells dependent on ERK signaling. PLoS One 9, e96060.

Ostrander, J. H., Daniel, A. R., and Lange, C. A. (2010). Brk/PTK6 signaling in normal and cancer cell models. Curr Opin Pharmacol 10, 662-669.

Park, S. H., Ito, K., Olcott, W., Katsyv, I., Halstead-Nussloch, G., and Irie, H. Y. (2015). PTK6 inhibition promotes apoptosis of Lapatinib-resistant Her2(+) breast cancer cells by inducing Bim. Breast Cancer Res 17, 86.

Peng, M., Ball-Kell, S. M., and Tyner, A. L. (2015). Protein tyrosine kinase 6 promotes ERBB2-induced mammary gland tumorigenesis in the mouse. Cell Death Dis 6, e1848.

Rodrik-Outmezguine, V. S., Okaniwa, M., Yao, Z., Novotny, C. J., McWhirter, C., Banaji, A., Won, H., Wong, W., Berger, M., de Stanchina, E., et al. (2016). Overcoming mTOR resistance mutations with a new-generation mTOR inhibitor. Nature 534, 272-276.

Schmandt, R. E., Bennett, M., Clifford, S., Thornton, A., Jiang, F., Broaddus, R. R., Sun, C. C., Lu, K. H., Sood, A. K., and Gershenson, D. M. (2006). The BRK tyrosine kinase is expressed in high-grade serous carcinoma of the ovary. Cancer Biol Ther 5, 1136-1141.

Shibata, N., Miyamoto, N., Nagai, K., Shimokawa, K., Sameshima, T., Ohoka, N., Hattori, T., Imaeda, Y., Nara, H., Cho, N., et al. (2017). Development of protein degradation inducers of oncogenic BCR-ABL protein by conjugation of ABL kinase inhibitors and IAP ligands. Cancer Sci 108, 1657-1666.

Sun, D., Li, Z., Rew, Y., Gribble, M., Bartberger, M. D., Beck, H. P., Canon, J., Chen, A., Chen, X., Chow, D., et al. (2014). Discovery of AMG 232, a potent, selective, and orally bioavailable MDM2-p53 inhibitor in clinical development. J Med Chem 57, 1454-1472.

Varfolomeev, E., Blankenship, J. W., Wayson, S. M., Fedorova, A. V., Kayagaki, N., Garg, P., Zobel, K., Dynek, J. N., Elliott, L. O., Wallweber, H. J., et al. (2007). IAP antagonists induce autoubiquitination of c-IAPs, NF-kappaB activation, and TNFalpha-dependent apoptosis. Cell 131, 669-681.

Vassilev, L. T., Vu, B. T., Graves, B., Carvajal, D., Podlaski, F., Filipovic, Z., Kong, N., Kammlott, U., Lukacs, C., Klein, C., et al. (2004). In vivo activation of the p53 pathway by small-molecule antagonists of MDM2. Science 303, 844-848.

Vu, B., Wovkulich, P., Pizzolato, G., Lovey, A., Ding, Q., Jiang, N., Liu, J. J., Zhao, C., Glenn, K., Wen, Y., et al. (2013). Discovery of RG7112: A Small-Molecule MDM2 Inhibitor in Clinical Development. ACS Med Chem Lett 4, 466-469.

Weisberg, E., Ray, A., Barrett, R., Nelson, E., Christie, A. L., Porter, D., Straub, C., Zawel, L., Daley, J. F., Lazo-Kallanian, S., et al. (2010). Smac mimetics: implications for enhancement of targeted therapies in leukemia. Leukemia 24, 2100-2109.

Winter, G. E., Buckley, D. L., Paulk, J., Roberts, J. M., Souza, A., Dhe-Paganon, S., and Bradner, J. E. (2015). Phthalimide conjugation as a strategy for in vivo target protein degradation. Science 348, 1376-1381.

Xie, T., Lim, S. M., Westover, K. D., Dodge, M. E., Ercan, D., Ficarro, S. B., Udayakumar, D., Gurbani, D., Tae, H. S., Riddle, S. M., et al. (2014). Pharmacological targeting of the pseudokinase Her3. Nat Chem Biol 10, 1006-1012.

Yamamoto, S. T., Hiroshi; Kurono, Masakuni; Nomura, Yoshinori; Hotta, Shingo (2016). BRK INHIBITORY COMPOUND (ONO PHARMACEUTICAL CO., LTD. (1-5 Doshomachi 2-chome, Chuo-ku Osaka-sh, Osaka 26, T5418526, JP)).

Zeng, H., Belanger, D. B., Curran, P. J., Shipps, G. W., Jr., Miao, H., Bracken, J. B., Arshad Siddiqui, M., Malkowski, M., and Wang, Y. (2011). Discovery of novel imidazo[1,2-a]pyrazin-8-amines as Brk/PTK6 inhibitors. Bioorg Med Chem Lett 21, 5870-5875.

Zengerle, M., Chan, K. H., and Ciulli, A. (2015). Selective Small Molecule Induced Degradation of the BET Bromodomain Protein BRD4. ACS Chem Biol 10, 1770-1777.

Zheng, Y., Wang, Z., Bie, W., Brauer, P. M., Perez White, B. E., Li, J., Nogueira, V., Raychaudhuri, P., Hay, N., Tonetti, D. A., et al. (2013). PTK6 activation at the membrane regulates epithelial-mesenchymal transition in prostate cancer. Cancer Res 73, 5426-5437.

What is claimed is:

1. Bivalent compound YX39-105 having the following structure:

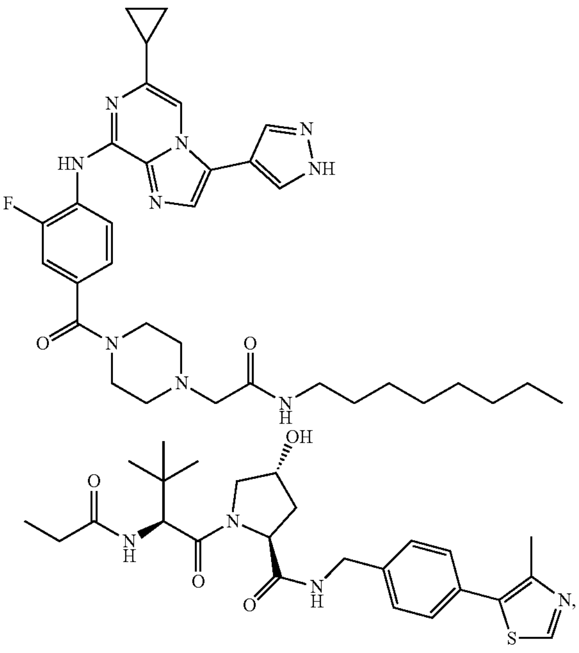

and pharmaceutically acceptable salts and enantiomers thereof.

* * * * *